(12) United States Patent
Lauffer et al.

(10) Patent No.: US 11,572,364 B2
(45) Date of Patent: *Feb. 7, 2023

(54) PTERIDINONE COMPOUNDS AND USES THEREOF

(71) Applicant: Vertex Pharmaceuticals Incorporated, Boston, MA (US)

(72) Inventors: David Lauffer, Stow, MA (US); Guy Bemis, Boston, MA (US); Michael Boyd, Boston, MA (US); David Deininger, Boston, MA (US); Hongbo Deng, Southborough, MA (US); Warren Dorsch, Boston, MA (US); Wenxin Gu, Concord, MA (US); Russell R. Hoover, Harvard, MA (US); Mac Arthur Johnson, Jr., Derry, NH (US); Mark Willem Ledeboer, Boston, MA (US); Brian Ledford, Boston, MA (US); Francois Maltais, Boston, MA (US); Marina Penney, Acton, MA (US); Darin Takemoto, Belmont, MA (US); Nathan D. Waal, Cambridge, MA (US); Tiansheng Wang, Concord, MA (US); Pan Li, Lexington, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/188,132

(22) Filed: Mar. 1, 2021

(65) Prior Publication Data

US 2022/0363685 A1 Nov. 17, 2022

Related U.S. Application Data

(63) Continuation of application No. 16/391,407, filed on Apr. 23, 2019, now Pat. No. 11,059,826.

(60) Provisional application No. 62/661,744, filed on Apr. 24, 2018.

(51) Int. Cl.
| | | |
|---|---|---|
| C07D 471/04 | (2006.01) | |
| C07D 487/04 | (2006.01) | |
| C07D 491/20 | (2006.01) | |
| C07D 487/14 | (2006.01) | |
| C07D 519/00 | (2006.01) | |
| C07D 471/14 | (2006.01) | |
| C07D 498/04 | (2006.01) | |

(52) U.S. Cl.
CPC ......... *C07D 487/04* (2013.01); *C07D 471/04* (2013.01); *C07D 471/14* (2013.01); *C07D 487/14* (2013.01); *C07D 491/20* (2013.01); *C07D 498/04* (2013.01); *C07D 519/00* (2013.01)

(58) Field of Classification Search
CPC .. C07D 471/04; C07D 471/14; C07D 475/04; A61K 31/505; A61P 35/00
USPC ....................................... 544/258; 514/262.1
See application file for complete search history.

(56) References Cited

U.S. PATENT DOCUMENTS

| 6,806,272 B2 | 10/2004 | Bauer et al. |
| 11,059,826 B2 * | 7/2021 | Lauffer ............... C07D 475/04 |
| 2013/0225593 A1 | 8/2013 | Eickmeier et al. |
| 2019/0322673 A1 | 10/2019 | Lauffer et al. |

FOREIGN PATENT DOCUMENTS

| CN | 105801582 A | 7/2016 |
| WO | WO-2003020722 A1 | 3/2003 |
| WO | WO-2005123736 A1 | 12/2005 |
| WO | WO-2006018182 A1 | 2/2006 |
| WO | WO-2006021378 A1 | 3/2006 |
| WO | WO-2014127815 A1 | 8/2014 |
| WO | WO-2014127816 A1 | 8/2014 |
| WO | 2015117055 A1 | 8/2015 |
| WO | WO-2015193229 A1 | 12/2015 |
| WO | 2016201370 A1 | 12/2016 |
| WO | WO-2019209757 A1 | 10/2019 |

OTHER PUBLICATIONS

Koblan et al., "Assessment of Bromodomain Target Engagement by a Series of BI2536 Analogues with Miniaturized BET-BRET,"ChemMedChem. 2016;11(23):2575-2581.
Li et al., "Design, synthesis and antiproliferative activity of novel substituted 2-amino-7,8-dihydropteridin-6(5H)-one derivatives," Bioorg. Med. Chem. Lett. 2017;27(17):3954-3958.
PCT International Search Report and Written Opinion from PCT/US2019/028604 dated Apr. 23, 2019.

* cited by examiner

*Primary Examiner* — Deepak R Rao
(74) *Attorney, Agent, or Firm* — Dechert LLP; Andrea L. C. Reid; Gang Wang

(57) ABSTRACT

The present invention provides compounds of Formula I, or pharmaceutically acceptable salts thereof, pharmaceutical compositions thereof, and methods of use thereof for treating cellular proliferative disorders (e.g., cancer).

48 Claims, 12 Drawing Sheets

Specification includes a Sequence Listing.

SEQUENCE LISTING

<160> NUMBER OF SEQ ID NOS: 2

<210> SEQ ID NO 1
<211> LENGTH: 40
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 1
tccgcggccc caagcttatc gccatggact ccaacactgc                             40

<210> SEQ ID NO 2
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
gatgggccca gatctcgagt caggccgccg acaggaatg                              39
```

PTERIDINONE COMPOUNDS AND USES THEREOF

This application is a Continuation of U.S. patent application Ser. No. 16/391,407 filed on Apr. 23, 2019, which claims the benefit of U.S. Provisional Application No. 62/661,744 filed on Apr. 24, 2018, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 23, 2019, is named 394927-020WO_SL.txt and is 788 bytes in size.

TECHNICAL FIELD OF THE INVENTION

The present invention relates to compounds and methods useful for treating cellular proliferative disorders (e.g., cancer). The invention also provides pharmaceutically acceptable compositions comprising compounds of the present invention and methods of using said compositions in the treatment of various proliferative disorders.

BACKGROUND OF THE INVENTION

Cellular proliferative disorders comprise malignant and non-malignant cell populations which differ from the surround tissue morphologically and/or genotypically. Examples of cellular proliferative disorders include, for example, solid tumors, cancer, diabetic retinopathy, intraocular neovascular syndromes, macular degeneration, rheumatoid arthritis, psoriasis, and endometriosis. Cancer is a group of diseases involving abnormal cell proliferation with the potential to invade or spread to other parts of the body. According to Centers for Disease Control and Prevention (CDC), Cancer is the second leading cause of death in the United States. Therefore, additional treatments for cellular proliferative disorders are desired to provide patients with more options.

SUMMARY OF THE INVENTION

It has now been found that compounds of the present invention, and pharmaceutically acceptable compositions thereof, are useful for treating proliferative disorders (e.g., cancer). In one aspect, the present invention provides a compound of Formula I.

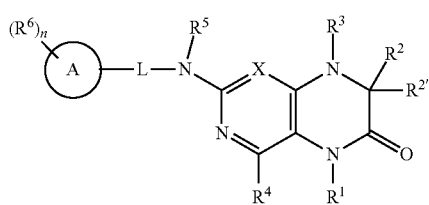

or a pharmaceutically acceptable salt thereof, wherein each variable is as defined and described herein.

Compounds of the present invention, and pharmaceutically acceptable compositions thereof, are useful for treating a variety of proliferative disorders (e.g., cancer) as described herein.

DETAILED DESCRIPTION OF CERTAIN EMBODIMENTS

Figure 1:
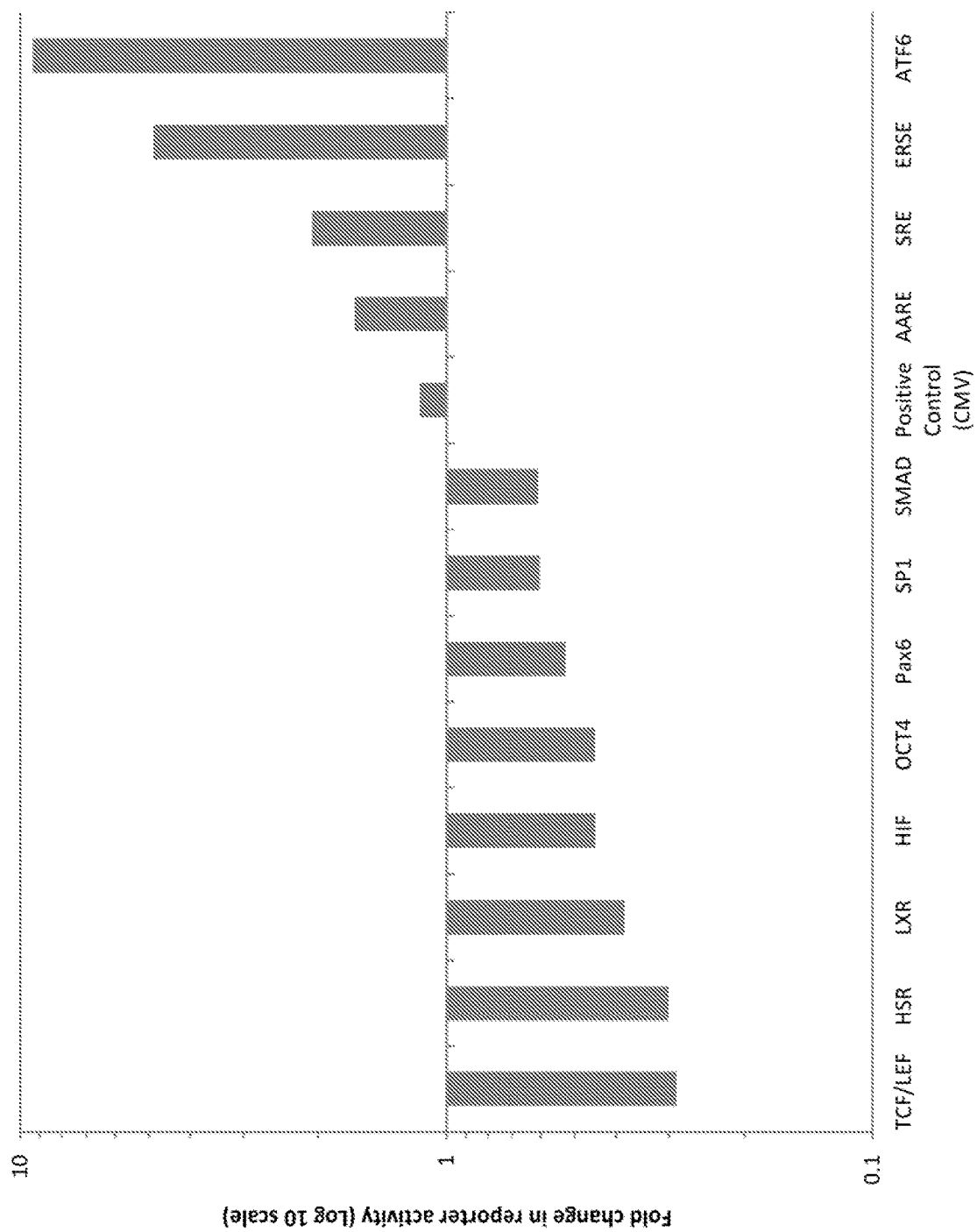
FIG. 1 is a graph showing the effect of Compound 136 on several transcriptional reporters and shows the fold change in reporter activity (p<0.01) in HepG2 cells treated with 1 μM of Compound 136 for six hours.

1. General Description of Certain Embodiments of the Invention

It has been found that the compounds of the present invention, or salts thereof, exhibit pronounced efficacy in multiple cell-line-derived and patient-derived xenograft models. For example, the compounds of the invention, or salts thereof, are found to lead to complete and durable regression in models of non-small cell lung cancer (NSCLC), myeloma, hepatocellular carcinoma (HCC), breast cancer, and melanoma. It has also been found that the compounds of the invention result in enhanced inhibition of cell viability, particularly the cells where Wolframin (WFS1) is overexpressed. Without wishing to be bound by any specific theory, it is believed that the compounds of the invention cause calcium release from the endoplasmic reticulum (ER) via a putative $Ca^{2+}$ channel known as Wolframin (WFS1), which induces ER stress and the "unfolded protein response" (UPR) and leads to cell death.

In one aspect, the present invention provides a compound of formula I.

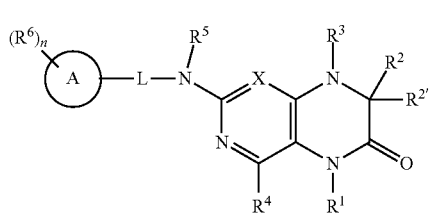

or a pharmaceutically acceptable salt thereof, wherein:

Ring A is selected from a 3-8 membered saturated or partially unsaturated monocyclic carbocyclic ring, phenyl, indanyl, a 4-8 membered saturated or partially unsaturated monocyclic heterocyclic ring having 1-2 heteroatoms independently selected from nitrogen, oxygen, or sulfur, a 8-12 membered saturated or partially unsaturated bicyclic heterocyclic ring having 1-2 heteroatoms independently selected from nitrogen, oxygen, or sulfur, a 5-8 membered saturated or partially unsaturated bridged bicyclic carbocyclic ring, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

L is a covalent bond or a $C_{1-6}$ bivalent straight or branched saturated or unsaturated hydrocarbon chain wherein one to three methylene units of the chain are independently and optionally replaced with -Cy-, —O—, —C(R)$_2$—, —CH(R)—, —CH(OR)—, —CR(OR)—, —C(D)$_2$-, —C(F)$_2$—, —N(R)—, —N(R)C(O)—, —C(O)N(R)—, —N(R)C(O)O—, —OC(O)N(R)—, —N(R)C(O)N(R)—, —N(R)S(O)$_2$—, —S(O)$_2$N(R)—, —C(O)—, —OC(O)—, —C(O)O—, —S—, —S(O)—, —S(O)$_2$—, or —Si(R)$_2$—, wherein -Cy- is an optionally substituted bivalent group selected from phenylenyl, cyclopropylenyl, cyclobutylenyl, cyclopentylenyl, cyclohexylenyl, furylenyl, tetrahydrofurylenyl, azetidylenyl, pyrrolidylenyl, piperidylenyl, triazolylenyl, pyrrolylenyl, pyrazolylenyl, pyridylenyl, 2,4,5,6-tetrahydrocyclopenta[c]pyrazolylenyl, or thiazolylenyl;

$R^1$ is hydrogen, $R^D$, or an optionally substituted group selected from $C_{1-3}$ aliphatic or a 4-8 membered saturated or partially unsaturated monocyclic heterocyclic ring having 1-2 heteroatoms independently selected from nitrogen, oxygen, or sulfur;

each of $R^2$ and $R^{2'}$ is independently hydrogen, $R^D$, or an optionally substituted group selected from $C_{1-6}$ aliphatic, a 3-8 membered saturated or partially unsaturated monocyclic carbocyclic ring, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or $R^2$ and $R^{2'}$ are optionally taken together to form =$CH_2$ or =CH—($C_{1-3}$ aliphatic); or $R^2$ and $R^{2'}$ are optionally taken together with their intervening atoms to form an optionally substituted 3-6 membered saturated or partially unsaturated spirocyclic ring having 0-2 heteroatoms independently selected from nitrogen, oxygen or sulfur;

$R^3$ is hydrogen, $R^D$, or an optionally substituted $C_{1-6}$ aliphatic group; or $R^2$ and $R^3$ are optionally taken together with their intervening atoms to form an optionally substituted 5-8 membered saturated or partially unsaturated fused ring comprising the nitrogen atom to which $R^3$ attaches and 0-2 additional heteroatoms independently selected from nitrogen, oxygen or sulfur; or $R^2$, $R^{2'}$, and $R^3$ are optionally taken together with their intervening atoms to form an optionally substituted 5-8 membered saturated or partially unsaturated fused ring comprising the nitrogen atom to which $R^3$ attaches and 0-2 additional heteroatoms independently selected from nitrogen, oxygen or sulfur;

$R^4$ is hydrogen, $R^D$, —$CD_2OH$, or an optionally substituted $C_{1-3}$ aliphatic group;

$R^5$ is hydrogen, —C(O)R, —C(O)OR, —C(O)NR$_2$, an optionally substituted 3-8 membered saturated or partially unsaturated monocyclic carbocyclic ring, or a $C_{1-3}$ aliphatic group;

each of $R^6$ is independently halogen, —CN, —NO$_2$, —C(O)R, —C(O)OR, —C(O)NR$_2$, —NR$_2$, —NRC(O)R, —NRC(O)OR, —NRS(O)$_2$R, —OR, —P(O)R$_2$, —SR, —SF$_5$, —S(CF$_3$)$_5$, —S(O)R, —S(O)$_2$R, —S(O)(NH)R, —C(=NR)—OR, —O—C(=NR)—R, or R; or two $R^6$ groups are optionally taken together to form =O;

each R is independently hydrogen or an optionally substituted group selected from $C_{1-6}$ aliphatic, a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur;

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups;

$R^D$ is a $C_{1-4}$ aliphatic group wherein one or more hydrogens are replaced by deuterium;

X is N or CH; and n is 0, 1, 2, 3, 4 or 5.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

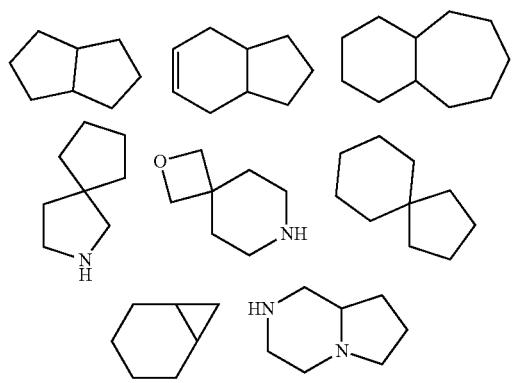

Exemplary bridged bicyclics include:

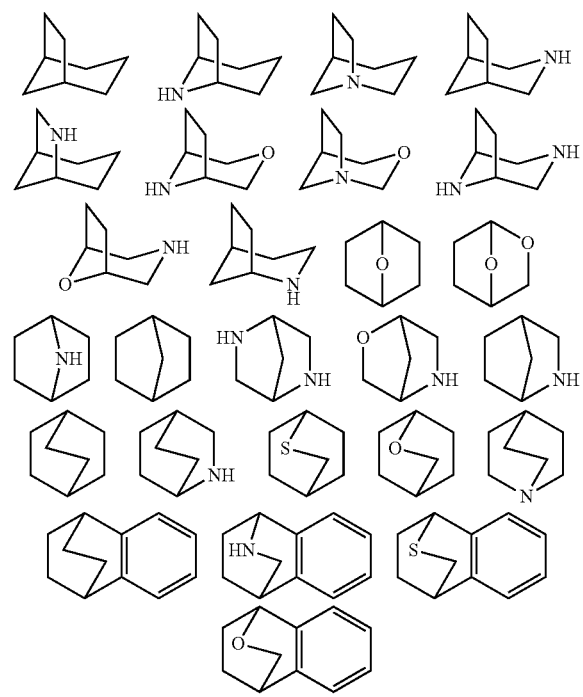

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for exampleN(as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

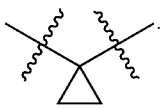 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$;—

$-(CH_2)_{0-4}SR^o$; $-(CH_2)_{0-4}Ph$, which may be substituted with $R^o$; $-(CH_2)_{0-4}O(CH_2)_{0-1}Ph$ which may be substituted with $R^o$; $-CH=CHPh$, which may be substituted with $R^o$; $-(CH_2)_{0-4}O(CH_2)_{0-1}$-pyridyl which may be substituted with $R^o$; $-NO_2$; $-CN$; $-N_3$; $-(CH_2)_{0-4}N(R^o)_2$; $-(CH_2)_{0-4}N(R^o)C(O)R^o$; $-N(R^o)C(S)R^o$; $-(CH_2)_{0-4}N(R^o)C(O)NR^o_2$; $-N(R^o)C(S)NR^o_2$; $-(CH_2)_{0-4}N(R^o)C(O)OR^o$; $-N(R^o)N(R^o)C(O)R^o$; $-N(R^o)N(R^o)C(O)NR^o_2$; $-N(R^o)N(R^o)C(O)OR^o$; $-(CH_2)_{0-4}C(O)R^o$; $-C(S)R^o$; $-(CH_2)_{0-4}C(O)OR^o$; $-(CH_2)_{0-4}C(O)SR^o$; $-(CH_2)_{0-4}C(O)OSiR^o_3$; $-(CH_2)_{0-4}OC(O)R^o$; $-OC(O)(CH_2)_{0-4}SR-$, $SC(S)SR^o$; $-(CH_2)_{0-4}SC(O)R^o$; $-(CH_2)_{0-4}C(O)NR^o_2$; $-C(S)NR^o_2$; $-C(S)SR^o$; $-SC(S)SR^o$, $-(CH_2)_{0-4}OC(O)NR^o_2$; $-C(O)N(OR^o)R^o$; $-C(O)C(O)R^o$; $-C(O)CH_2C(O)R^o$; $-C(NOR^o)R^o$; $-(CH_2)_{0-4}SSR^o$; $-(CH_2)_{0-4}S(O)_2R^o$; $-(CH_2)_{0-4}S(O)_2OR^o$; $-(CH_2)_{0-4}OS(O)_2R^o$; $-S(O)_2NR^o_2$; $-S(O)(NR^o)R^o$; $-S(O)_2N=C(NR^o_2)_2$; $-(CH_2)_{0-4}S(O)R^o$; $-N(R^o)S(O)_2NR^o_2$; $-N(R^o)S(O)_2R^o$; $-N(OR^o)R^o$; $-C(NH)NR^o_2$; $-P(O)_2R^o$; $-P(O)R^o_2$; $-OP(O)R^o_2$; $-OP(O)(OR^o)_2$; $SiR^o_3$; $-(C_{1-4}$ straight or branched alkylene)$O-N(R^o)_2$; or $-(C_{1-4}$ straight or branched alkylene)$C(O)O-N(R^o)_2$.

Each $R^o$ is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^o$ selected from $=O$ and $=S$; or each $R^o$ is optionally substituted with a monovalent substituent independently selected from halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$.

Each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, or a divalent substituent bound to vicinal substitutable carbons of an "optionally substituted" group is $-O(CR^*_2)_{2-3}O-$, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

An optional substituent on a substitutable nitrogen is independently $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic, unsubstituted $-OPh$, or an unsubstituted 5-6-membered saturated, partially unsaturated, or aryl ring having 0-4 heteroatoms independently selected from nitrogen, oxygen, or sulfur, or, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^\dagger$ is $C_{1-6}$ aliphatic, $R^\dagger$ is optionally substituted with halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

3. Description of Exemplary Embodiments

In one aspect, the present invention provides a compound of formula I.

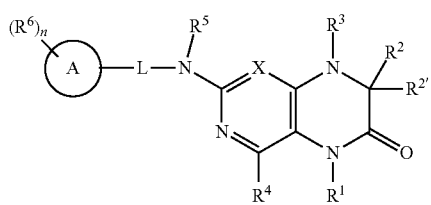

or a pharmaceutically acceptable salt thereof, wherein:

Ring A is selected from a 3-8 membered saturated or partially unsaturated monocyclic carbocyclic ring, phenyl, indanyl, a 4-8 membered saturated or partially unsaturated monocyclic heterocyclic ring having 1-2 heteroatoms independently selected from nitrogen, oxygen, or sulfur, a 8-12 membered saturated or partially unsaturated bicyclic heterocyclic ring having 1-2 heteroatoms independently selected from nitrogen, oxygen, or sulfur, a 5-8 membered saturated or partially unsaturated bridged bicyclic carbocyclic ring, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; L is a covalent bond or a $C_{1-6}$ bivalent straight or branched saturated or unsaturated hydrocarbon chain wherein one to three methylene units of the chain are independently and optionally replaced with -Cy-, —O—, —C(R)$_2$—, —CH(R)—, —CH(OR)—, —CR(OR)—, —C(D)$_2$-, —C(F)$_2$—, —N(R)—, —N(R)C(O)—, —C(O)N(R)—, —N(R)C(O)O—, —OC(O)N(R)—, —N(R)C(O)N(R)—, —N(R)S(O)$_2$—, —S(O)$_2$N(R)—, —C(O)—, —OC(O)—, —C(O)O—, —S—, —S(O)—, —S(O)$_2$—, or —Si(R)$_2$—, wherein -Cy- is an optionally substituted bivalent group selected from phenylenyl, cyclopropylenyl, cyclobutylenyl, cyclopentylenyl, cyclohexylenyl, furylenyl, tetrahydrofurylenyl, azetidylenyl, pyrrolidylenyl, piperidylenyl, triazolylenyl, pyrrolylenyl, pyrazolylenyl, pyridylenyl, 2,4,5,6-tetrahydrocyclopenta[c]pyrazolylenyl, or thiazolylenyl;

$R^1$ is hydrogen, $R^D$, or an optionally substituted group selected from $C_{1-3}$ aliphatic or a 4-8 membered saturated or partially unsaturated monocyclic heterocyclic ring having 1-2 heteroatoms independently selected from nitrogen, oxygen, or sulfur;

each of $R^2$ and $R^{2'}$ is independently hydrogen, $R^D$, or an optionally substituted group selected from $C_{1-6}$ aliphatic, a 3-8 membered saturated or partially unsaturated monocyclic carbocyclic ring, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or $R^2$ and $R^{2'}$ are optionally taken together to form =CH$_2$ or =CH—(C$_{1-3}$ aliphatic); or $R^2$ and $R^{2'}$ are optionally taken together with their intervening atoms to form an optionally substituted 3-6 membered saturated or partially unsaturated spirocyclic ring having 0-2 heteroatoms independently selected from nitrogen, oxygen or sulfur;

$R^3$ is hydrogen, $R^D$, or an optionally substituted $C_{1-6}$ aliphatic group; or $R^2$ and $R^3$ are optionally taken together with their intervening atoms to form an optionally substituted 5-8 membered saturated or partially unsaturated fused ring comprising the nitrogen atom to which $R^3$ attaches and 0-2 additional heteroatoms independently selected from nitrogen, oxygen or sulfur; or $R^2$, $R^{2'}$, and $R^3$ are optionally taken together with their intervening atoms to form an optionally substituted 5-8 membered saturated or partially unsaturated fused ring comprising the nitrogen atom to which $R^3$ attaches and 0-2 additional heteroatoms independently selected from nitrogen, oxygen or sulfur;

$R^4$ is hydrogen, $R^D$, —CD$_2$OH, or an optionally substituted $C_{1-3}$ aliphatic group;

$R^5$ is hydrogen, —C(O)R, —C(O)OR, —C(O)NR$_2$, an optionally substituted 3-8 membered saturated or partially unsaturated monocyclic carbocyclic ring, or a $C_{1-3}$ aliphatic group;

each of $R^6$ is independently halogen, —CN, —NO$_2$, —C(O)R, —C(O)OR, —C(O)NR$_2$, —NR$_2$, —NRC(O)R, —NRC(O)OR, —NRS(O)$_2$R, —OR, —P(O)R$_2$, —SR, —SF$_5$, —S(CF$_3$)$_5$, —S(O)R, —S(O)$_2$R, —S(O)(NH)R, —C(=NR)—OR, —O—C(=NR)—R, or R; or two $R^6$ groups are optionally taken together to form =O;

each R is independently hydrogen or an optionally substituted group selected from $C_{1-6}$ aliphatic, a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur;

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups;

$R^D$ is a $C_{1-4}$ aliphatic group wherein one or more hydrogens are replaced by deuterium;

X is N or CH; and n is 0, 1, 2, 3, 4 or 5.

As defined generally above, Ring A is selected from a 3-8 membered saturated or partially unsaturated monocyclic carbocyclic ring, phenyl, indanyl, a 4-8 membered saturated or partially unsaturated monocyclic heterocyclic ring having 1-2 heteroatoms independently selected from nitrogen, oxygen, or sulfur, a 8-12 membered saturated or partially unsaturated bicyclic heterocyclic ring having 1-2 heteroatoms independently selected from nitrogen, oxygen, or sulfur, a 5-8 membered saturated or partially unsaturated bridged bicyclic carbocyclic ring, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, Ring A is a 3-8 membered saturated or partially unsaturated monocyclic carbocyclic ring. In some embodiments, Ring A is phenyl. In some embodiments, Ring A is indanyl. In some embodiments, Ring A is a 4-8 membered saturated or partially unsaturated monocyclic heterocyclic ring having 1-2 heteroatoms independently selected from nitrogen, oxygen, or sulfur. In some embodiments, Ring A is a 8-12 membered saturated or partially unsaturated bicyclic heterocyclic ring having 1-2 heteroatoms independently selected from nitrogen, oxygen, or sulfur. In some embodiments, Ring A is a 5-8 membered saturated or partially unsaturated bridged bicyclic carbocyclic ring. In some embodiments, Ring A is a 5-6 membered monocyclic heteroaromatic ring having 1-4 heteroatoms independently selected from nitrogen, oxygen, or sulfur. In some embodiments, Ring A is an 8-10 membered bicyclic heteroaromatic ring having 1-5 heteroatoms independently selected from nitrogen, oxygen, or sulfur.

In some embodiments, Ring A is a 3 membered saturated or partially unsaturated monocyclic carbocyclic ring. In some embodiments, Ring A is a 4 membered saturated or partially unsaturated monocyclic carbocyclic ring. In some embodiments, Ring A is a 5 membered saturated or partially unsaturated monocyclic carbocyclic ring. In some embodiments, Ring A is a 6 membered saturated or partially unsaturated monocyclic carbocyclic ring. In some embodiments, Ring A is a 7 membered saturated or partially unsaturated monocyclic carbocyclic ring. In some embodiments, Ring A is an 8 membered saturated or partially unsaturated monocyclic carbocyclic ring. In some embodiments, Ring A is

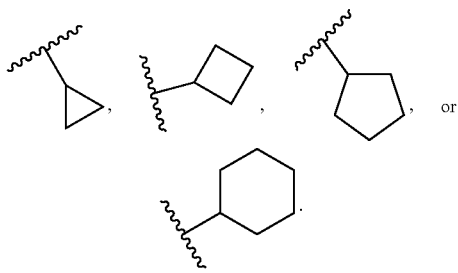

In some embodiments, Ring A is

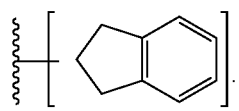

In some embodiments, Ring A is

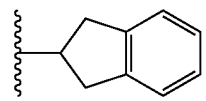 [SMILES: *C1Cc2ccccc2C1]

or

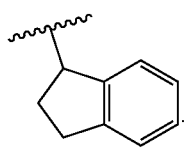 [SMILES: *C1CCc2ccccc21]

In some embodiments, Ring A is a 4 membered saturated or partially unsaturated monocyclic heterocyclic ring having 1-2 heteroatoms independently selected from nitrogen, oxygen, or sulfur. In some embodiments, Ring A is a 5 membered saturated or partially unsaturated monocyclic heterocyclic ring having 1-2 heteroatoms independently selected from nitrogen, oxygen, or sulfur. In some embodiments, Ring A is a 6 membered saturated or partially unsaturated monocyclic heterocyclic ring having 1-2 heteroatoms independently selected from nitrogen, oxygen, or sulfur. In some embodiments, Ring A is a 7 membered saturated or partially unsaturated monocyclic heterocyclic ring having 1-2 heteroatoms independently selected from nitrogen, oxygen, or sulfur. In some embodiments, Ring A is a 8 membered saturated or partially unsaturated monocyclic heterocyclic ring having 1-2 heteroatoms independently selected from nitrogen, oxygen, or sulfur. In some embodiments, Ring A is a 4-8 membered saturated or partially unsaturated monocyclic heterocyclic ring having 1-2 heteroatoms independently selected from nitrogen or oxygen. In some embodiments, Ring A is a 4-8 membered saturated or partially unsaturated monocyclic heterocyclic ring having 1 heteroatom selected from nitrogen, oxygen, or sulfur. In some embodiments, Ring A is

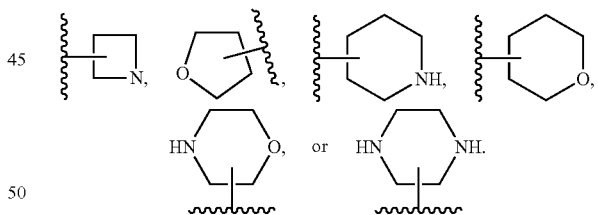

In some embodiments, Ring A is:

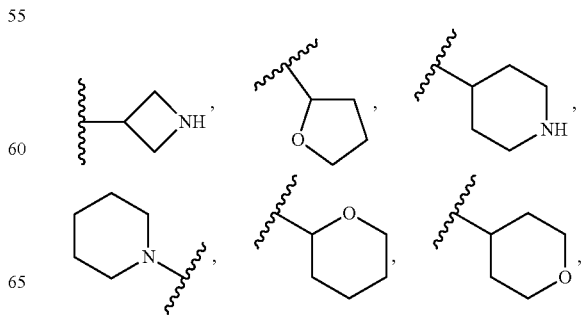

-continued

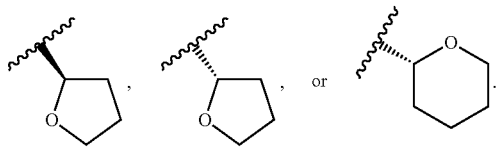 [SMILES: *[C@H]1CCCO1 ; *[C@@H]1CCCO1 ; *[C@H]1CCCCO1]

In some embodiments, Ring A is

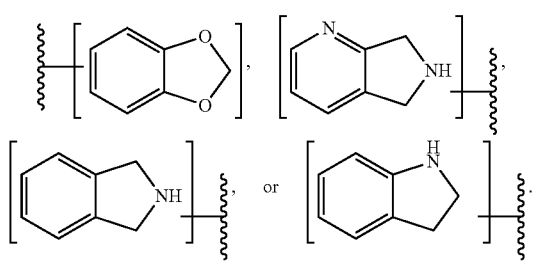

In some embodiments, Ring A is a 8 membered saturated or partially unsaturated bicyclic heterocyclic ring having 1-2 heteroatoms independently selected from nitrogen, oxygen, or sulfur. In some embodiments, Ring A is a 9 membered saturated or partially unsaturated bicyclic heterocyclic ring having 1-2 heteroatoms independently selected from nitrogen, oxygen, or sulfur. In some embodiments, Ring A is a 10 membered saturated or partially unsaturated bicyclic heterocyclic ring having 1-2 heteroatoms independently selected from nitrogen, oxygen, or sulfur. In some embodiments, Ring A is a 11 membered saturated or partially unsaturated bicyclic heterocyclic ring having 1-2 heteroatoms independently selected from nitrogen, oxygen, or sulfur. In some embodiments, Ring A is a 12 membered saturated or partially unsaturated bicyclic heterocyclic ring having 1-2 heteroatoms independently selected from nitrogen, oxygen, or sulfur. In some embodiments, Ring A is a 8-12 membered saturated or partially unsaturated bicyclic heterocyclic ring having 1-2 heteroatoms independently selected from nitrogen or oxygen. In some embodiments, Ring A is a 8-12 membered saturated or partially unsaturated bicyclic heterocyclic ring having 1 heteroatom selected from nitrogen, oxygen, or sulfur. In some embodiments, Ring A is

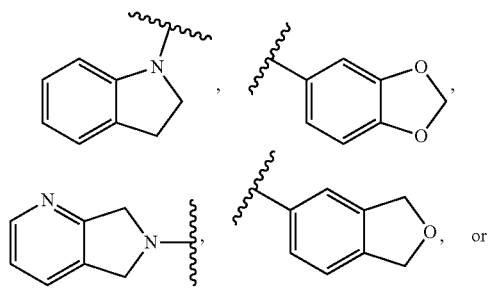

In some embodiments, Ring A is

In some embodiments, Ring A is a 5 membered saturated or partially unsaturated bridged bicyclic carbocyclic ring. In some embodiments, Ring A is a 6 membered saturated or partially unsaturated bridged bicyclic carbocyclic ring. In some embodiments, Ring A is a 7 membered saturated or partially unsaturated bridged bicyclic carbocyclic ring. In some embodiments, Ring A is a 8 membered saturated or partially unsaturated bridged bicyclic carbocyclic ring. In some embodiments, Ring A is

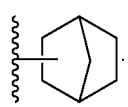

or

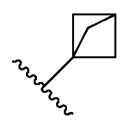

In some embodiments, Ring A is

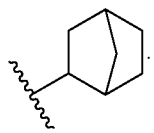

or

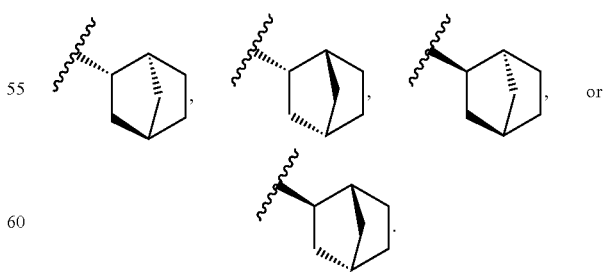

In some embodiments, Ring A is

In some embodiments, Ring A is a 5 membered monocyclic heteroaromatic ring having 1-4 heteroatoms independently selected from nitrogen, oxygen, or sulfur. In some embodiments, Ring A is a 6 membered monocyclic heteroaromatic ring having 1-4 heteroatoms independently selected from nitrogen, oxygen, or sulfur. In some embodiments, Ring A is a 5-6 membered monocyclic heteroaromatic ring having 1-3 heteroatoms independently selected from nitrogen, oxygen, or sulfur. In some embodiments, Ring A is a 5-6 membered monocyclic heteroaromatic ring having 1-2 heteroatoms independently selected from nitrogen, oxygen, or sulfur. In some embodiments, Ring A is a 5-6 membered monocyclic heteroaromatic ring having 1 heteroatom selected from nitrogen, oxygen, or sulfur. In some embodiments, Ring A is a 5 membered monocyclic heteroaromatic ring having 1-2 heteroatoms independently selected from nitrogen or oxygen. In some embodiments, Ring A is a 5 membered monocyclic heteroaromatic ring having 1-2 heteroatoms independently selected from nitrogen or sulfur. In some embodiments, Ring A is a 6 membered monocyclic heteroaromatic ring having 1-2 heteroatoms independently selected from nitrogen or oxygen. In some embodiments, Ring A is a 6 membered monocyclic heteroaromatic ring having 1-2 heteroatoms independently selected from nitrogen or sulfur. In some embodiments, Ring A is

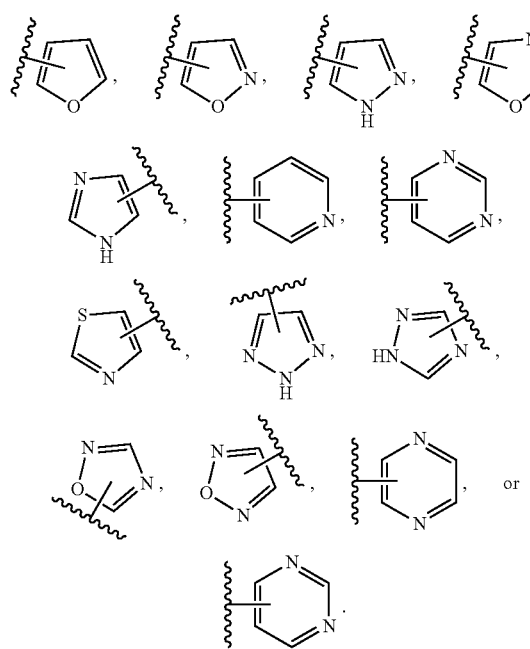

In some embodiments, Ring A is:

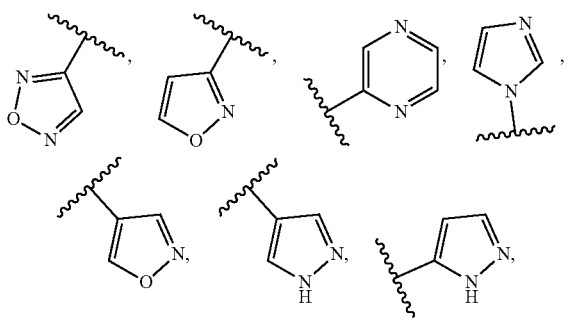

-continued

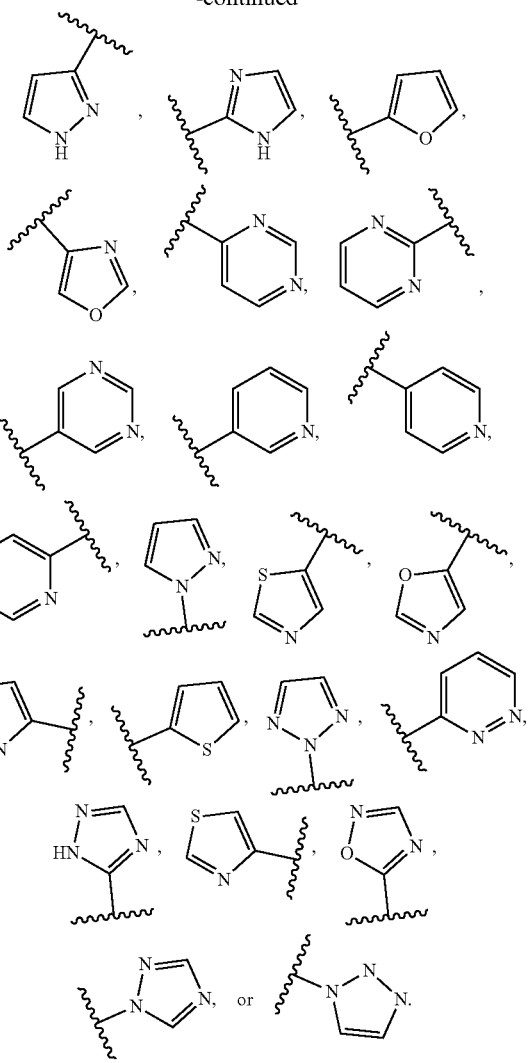

In some embodiments, Ring A is a 8 membered bicyclic heteroaromatic ring having 1-5 heteroatoms independently selected from nitrogen, oxygen, or sulfur. In some embodiments, Ring A is a 9 membered bicyclic heteroaromatic ring having 1-5 heteroatoms independently selected from nitrogen, oxygen, or sulfur. In some embodiments, Ring A is a 10 membered bicyclic heteroaromatic ring having 1-5 heteroatoms independently selected from nitrogen, oxygen, or sulfur. In some embodiments, Ring A is an 8-10 membered bicyclic heteroaromatic ring having 1-4 heteroatoms independently selected from nitrogen, oxygen, or sulfur. In some embodiments, Ring A is an 8-10 membered bicyclic heteroaromatic ring having 1-3 heteroatoms independently selected from nitrogen, oxygen, or sulfur. In some embodiments, Ring A is an 8-10 membered bicyclic heteroaromatic ring having 1-2 heteroatoms independently selected from nitrogen, oxygen, or sulfur. In some embodiments, Ring A is

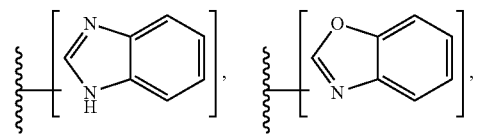

-continued
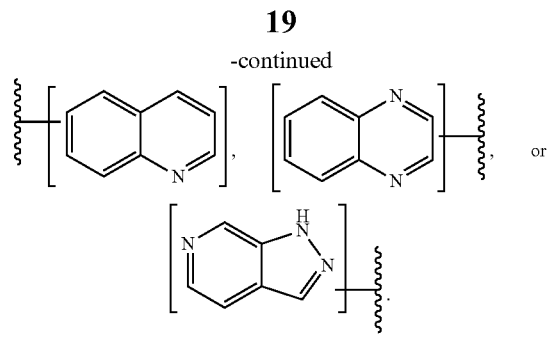
In some embodiments, Ring A is
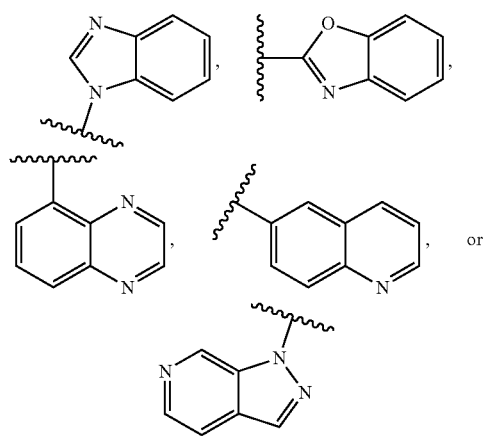
In some embodiments, Ring A is selected from:
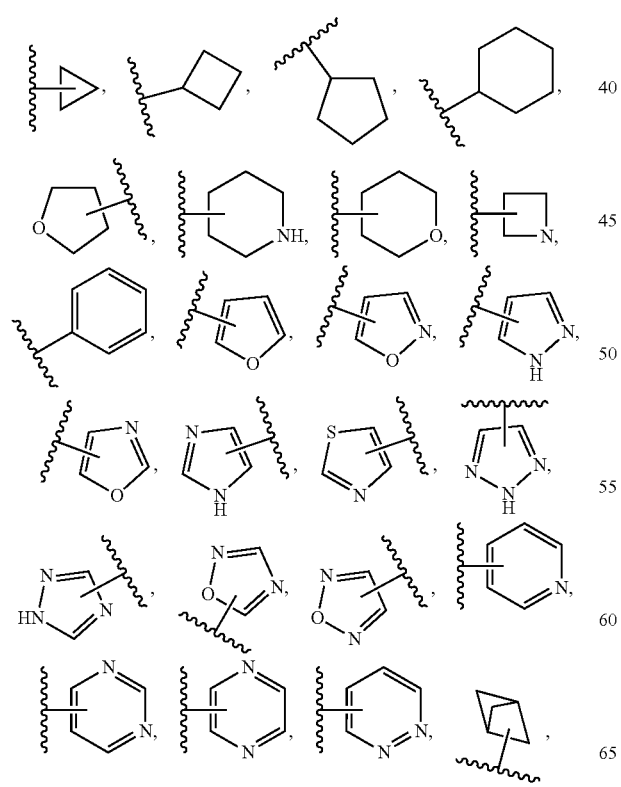
-continued
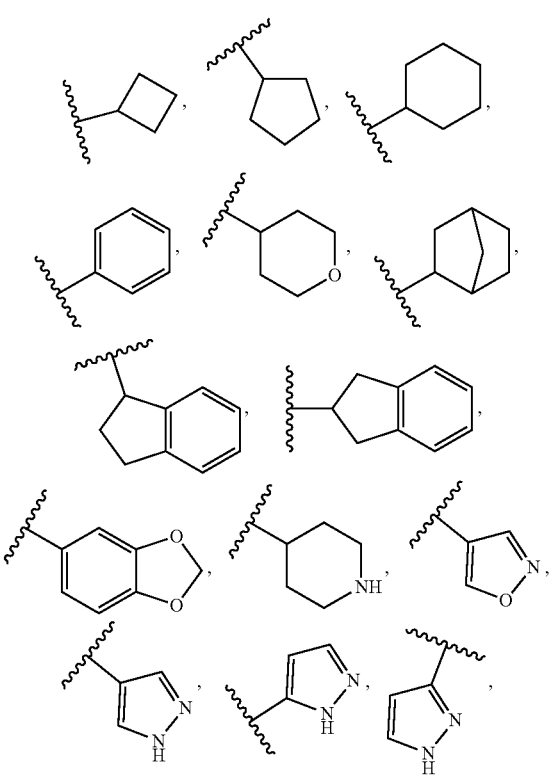
In some embodiments, Ring A is selected from:

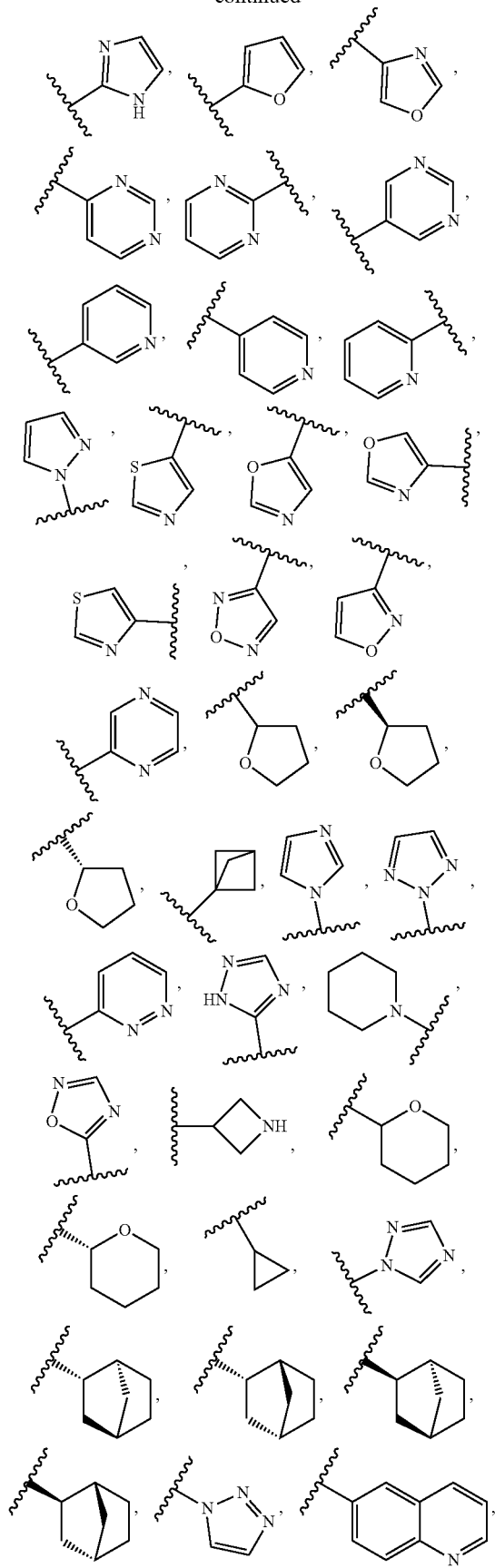
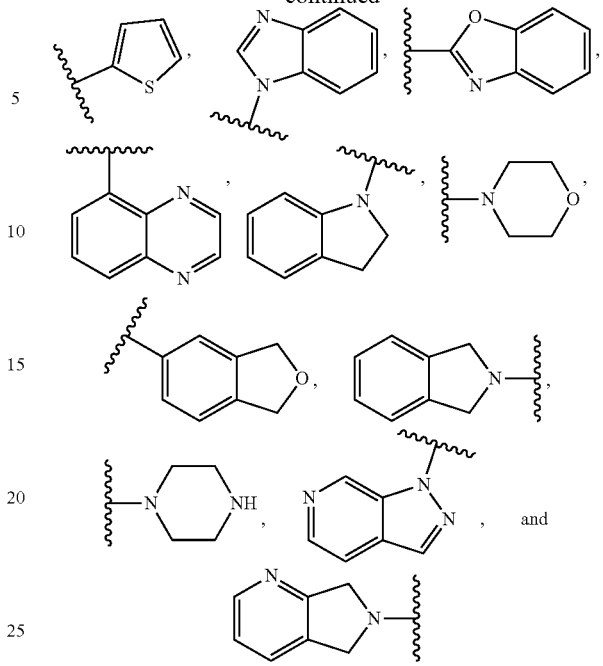
In some embodiments, Ring A is:
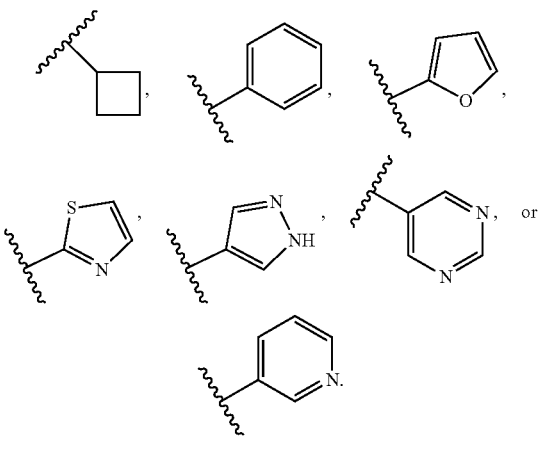
In some embodiments, Ring A is
In some embodiments, Ring A is

In some embodiments, Ring A is selected from those depicted in Tables A-C, below.

As defined generally above, L is a covalent bond or a $C_{1-6}$ bivalent straight or branched saturated or unsaturated hydrocarbon chain wherein one to three methylene units of the chain are independently and optionally replaced with -Cy-, —O—, —C(R)$_2$—, —CH(R)—, —CH(OR)—, —CR(OR)—, —C(D)$_2$-, —C(F)$_2$—, —N(R)—, —N(R)C(O)—, —C(O)N(R)—, —N(R)C(O)O—, —OC(O)N(R)—, —N(R)C(O)N(R)—, —N(R)S(O)$_2$—, —S(O)$_2$N(R)—, —C(O)—, —OC(O)—, —C(O)O—, —S—, —S(O)—, —S(O)$_2$—, or —Si(R)$_2$—, wherein -Cy- is an optionally substituted bivalent group selected from phenylenyl, cyclopropylenyl, cyclobutylenyl, cyclopentylenyl, cyclohexylenyl, furylenyl, tetrahydrofurylenyl, azetidylenyl, pyrrolidylenyl, piperidylenyl, triazolylenyl, pyrrolylenyl, pyrazolylenyl, pyridylenyl, 2,4,5,6-tetrahydrocyclopenta[c]pyrazolylenyl, or thiazolylenyl.

In some embodiments, L is a covalent bond. In some embodiments, L is a $C_{1-6}$ bivalent straight or branched saturated or unsaturated hydrocarbon chain wherein one to three methylene units of the chain are independently and optionally replaced with -Cy-, —O—, —C(R)$_2$—, —CH(R)—, —CH(OR)—, —CR(OR)—, —C(D)$_2$-, —C(F)$_2$—, —N(R)—, —N(R)C(O)—, —C(O)N(R)—, —N(R)C(O)O—, —OC(O)N(R)—, —N(R)C(O)N(R)—, —N(R)S(O)$_2$—, —S(O)$_2$N(R)—, —C(O)—, —OC(O)—, —C(O)O—, —S—, —S(O)—, —S(O)$_2$—, or —Si(R)$_2$—, wherein -Cy- is an optionally substituted bivalent group selected from phenylenyl, cyclopropylenyl, cyclobutylenyl, cyclopentylenyl, cyclohexylenyl, furylenyl, tetrahydrofurylenyl, azetidylenyl, pyrrolidylenyl, piperidylenyl, triazolylenyl, pyrrolylenyl, pyrazolylenyl, pyridylenyl, 2,4,5,6-tetrahydrocyclopenta[c]pyrazolylenyl, or thiazolylenyl.

In some embodiments, L is a $C_{1-6}$ bivalent straight or branched saturated or unsaturated hydrocarbon chain wherein one to two methylene units of the chain are independently and optionally replaced with -Cy-, —O—, —C(R)$_2$—, —CH(R)—, —CH(OR)—, —CR(OR)—, —C(D)$_2$-, —C(F)$_2$—, —N(R)—, —N(R)C(O)—, —C(O)N(R)—, —N(R)C(O)O—, —OC(O)N(R)—, —N(R)C(O)N(R)—, —N(R)S(O)$_2$—, —S(O)$_2$N(R)—, —C(O)—, —OC(O)—, —C(O)O—, —S—, —S(O)—, —S(O)$_2$—, or —Si(R)$_2$—, wherein -Cy- is an optionally substituted bivalent group selected from phenylenyl, cyclopropylenyl, cyclobutylenyl, cyclopentylenyl, cyclohexylenyl, furylenyl, tetrahydrofurylenyl, azetidylenyl, pyrrolidylenyl, piperidylenyl, triazolylenyl, pyrrolylenyl, pyrazolylenyl, pyridylenyl, 2,4,5,6-tetrahydrocyclopenta[c]pyrazolylenyl, or thiazolylenyl.

In some embodiments, L is a $C_{1-6}$ bivalent straight or branched saturated or unsaturated hydrocarbon chain wherein one methylene unit of the chain is optionally replaced with -Cy-, —O—, —C(R)$_2$—, —CH(R)—, —CH(OR)—, —CR(OR)—, —C(D)$_2$-, —C(F)$_2$—, —N(R)—, —N(R)C(O)—, —C(O)N(R)—, —N(R)C(O)O—, —OC(O)N(R)—, —N(R)C(O)N(R)—, —N(R)S(O)$_2$—, —S(O)$_2$N(R)—, —C(O)—, —OC(O)—, —C(O)O—, —S—, —S(O)—, —S(O)$_2$—, or —Si(R)$_2$—, wherein -Cy- is an optionally substituted bivalent group selected from phenylenyl, cyclopropylenyl, cyclobutylenyl, cyclopentylenyl, cyclohexylenyl, furylenyl, tetrahydrofurylenyl, azetidylenyl, pyrrolidylenyl, piperidylenyl, triazolylenyl, pyrrolylenyl, pyrazolylenyl, pyridylenyl, 2,4,5,6-tetrahydrocyclopenta[c]pyrazolylenyl, or thiazolylenyl.

In some embodiments, L is an unsubstituted $C_{1-6}$ bivalent straight or branched saturated or unsaturated hydrocarbon chain. In some embodiments, L is —CH$_2$—. In some embodiments, L is —CH$_2$CH$_2$—. In some embodiments, L is —CH$_2$CH$_2$CH$_2$—. In some embodiments, L is —CH$_2$CH$_2$CH$_2$CH$_2$—. In some embodiments, L is —CH$_2$CH$_2$CH$_2$CH$_2$CH$_2$—. In some embodiments, L is —CH$_2$CH$_2$CH$_2$CH$_2$CH$_2$CH$_2$—.

In some embodiments, L is a $C_{1-6}$ bivalent straight or branched saturated or unsaturated hydrocarbon chain wherein one methylene unit of the chain is optionally replaced with -Cy-, wherein -Cy- is an optionally substituted bivalent group selected from phenylenyl, cyclopropylenyl, cyclobutylenyl, cyclopentylenyl, cyclohexylenyl, furylenyl, tetrahydrofurylenyl, azetidylenyl, pyrrolidylenyl, piperidylenyl, triazolylenyl, pyrrolylenyl, pyrazolylenyl, pyridylenyl, 2,4,5,6-tetrahydrocyclopenta[c]pyrazolylenyl, or thiazolylenyl. In some embodiments, -Cy- is an optionally substituted bivalent group selected from cyclopropylenyl, cyclobutylenyl, cyclopentylenyl, or cyclohexylenyl. In some embodiments, -Cy- is an optionally substituted bivalent group selected from tetrahydrofurylenyl, azetidylenyl, pyrrolidylenyl, or piperidylenyl. In some embodiments, -Cy- is an optionally substituted bivalent group selected from furylenyl, triazolylenyl, pyrrolylenyl, pyrazolylenyl, pyridylenyl, or thiazolylenyl. In some embodiments, —Cy- is an optionally substituted bivalent group 2,4,5,6-tetrahydrocyclopenta[c]pyrazolylenyl.

In some embodiments, L is a $C_{1-6}$ bivalent straight or branched saturated or unsaturated hydrocarbon chain wherein one to three methylene units of the chain are independently and optionally replaced with —O—. In some embodiments, L is a $C_{1-6}$ bivalent straight or branched saturated or unsaturated hydrocarbon chain wherein one to three methylene units of the chain are independently and optionally replaced with —C(R)$_2$—. In some embodiments, L is a $C_{1-6}$ bivalent straight or branched saturated or unsaturated hydrocarbon chain wherein one to three methylene units of the chain are independently and optionally replaced with —CH(R)—. In some embodiments, L is a $C_{1-6}$ bivalent straight or branched saturated or unsaturated hydrocarbon chain wherein one to three methylene units of the chain are independently and optionally replaced with —CH(OR)—. In some embodiments, L is a $C_{1-6}$ bivalent straight or branched saturated or unsaturated hydrocarbon chain wherein one to three methylene units of the chain are independently and optionally replaced with —CR(OR)—. In some embodiments, L is a $C_{1-6}$ bivalent straight or branched saturated or unsaturated hydrocarbon chain wherein one to three methylene units of the chain are independently and optionally replaced with —C(D)$_2$-. In some embodiments, L is a $C_{1-6}$ bivalent straight or branched saturated or unsaturated hydrocarbon chain wherein one to three methylene units of the chain are independently and optionally replaced with —C(F)$_2$-. In some embodiments, L is a $C_{1-6}$ bivalent straight or branched saturated or unsaturated hydrocarbon chain wherein one to three methylene units of the chain are independently and optionally replaced with —N(R)—. In some embodiments, L is a $C_{1-6}$ bivalent straight or branched saturated or unsaturated hydrocarbon chain wherein one to three methylene units of the chain are independently and optionally replaced with —N(R)C(O)— or —C(O)N(R)—. In some embodiments, L is a $C_{1-6}$ bivalent straight or branched saturated or unsaturated hydrocarbon chain wherein one to three methylene units of the chain are independently and optionally replaced with —N(R)C(O)O— or —OC(O)N(R). In some embodiments, L is a $C_{1-6}$ bivalent straight or branched saturated or unsaturated hydrocarbon chain wherein one to three methylene units of the chain are independently and optionally replaced with —N(R)C(O)N(R)—. In some embodiments, L is a C$_{1-6}$ bivalent straight or branched saturated or unsaturated hydrocarbon chain wherein one to three methylene units of the chain are independently and optionally replaced with —N(R)S(O)$_2$— or —S(O)$_2$N(R)—. In some embodiments, L is a C$_{1-6}$ bivalent straight or branched saturated or unsaturated hydrocarbon chain wherein one to three methylene units of the chain are independently and optionally replaced with —C(O)—. In some embodiments, L is a C$_{1-6}$ bivalent straight or branched saturated or unsaturated hydrocarbon chain wherein one to three methylene units of the chain are independently and optionally replaced with —OC(O)— or —C(O)O—. In some embodiments, L is a C$_{1-6}$ bivalent straight or branched saturated or unsaturated hydrocarbon chain wherein one to three methylene units of the chain are independently and optionally replaced with —S—. In some embodiments, L is a C$_{1-6}$ bivalent straight or branched saturated or unsaturated hydrocarbon chain wherein one to three methylene units of the chain are independently and optionally replaced with —S(O)—. In some embodiments, L is a C$_{1-6}$ bivalent straight or branched saturated or unsaturated hydrocarbon chain wherein one to three methylene units of the chain are independently and optionally replaced with —S(O)$_2$—. In some embodiments, L is a C$_{1-6}$ bivalent straight or branched saturated or unsaturated hydrocarbon chain wherein one to three methylene units of the chain are independently and optionally replaced with —Si(R)$_2$—.

In some embodiments, L is:

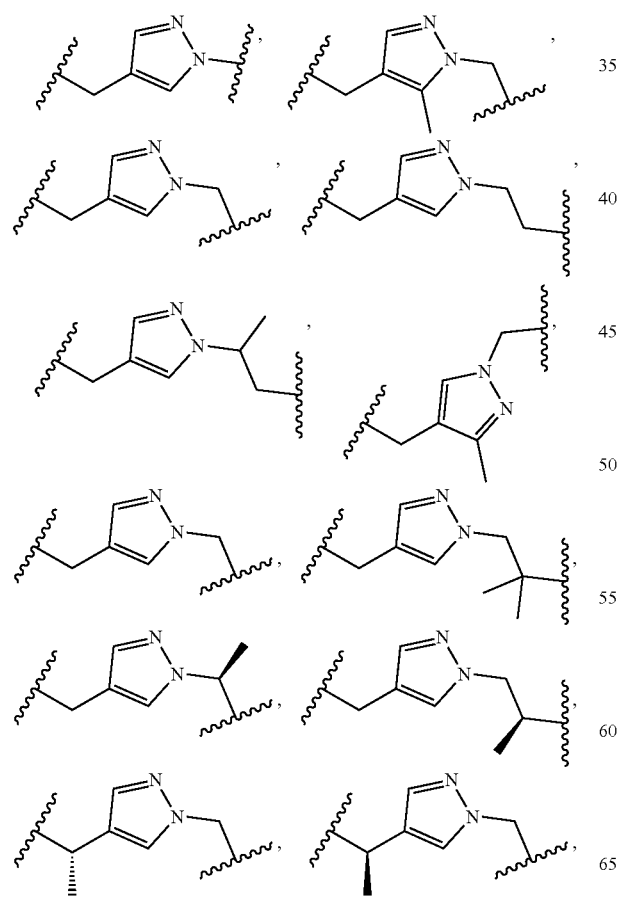

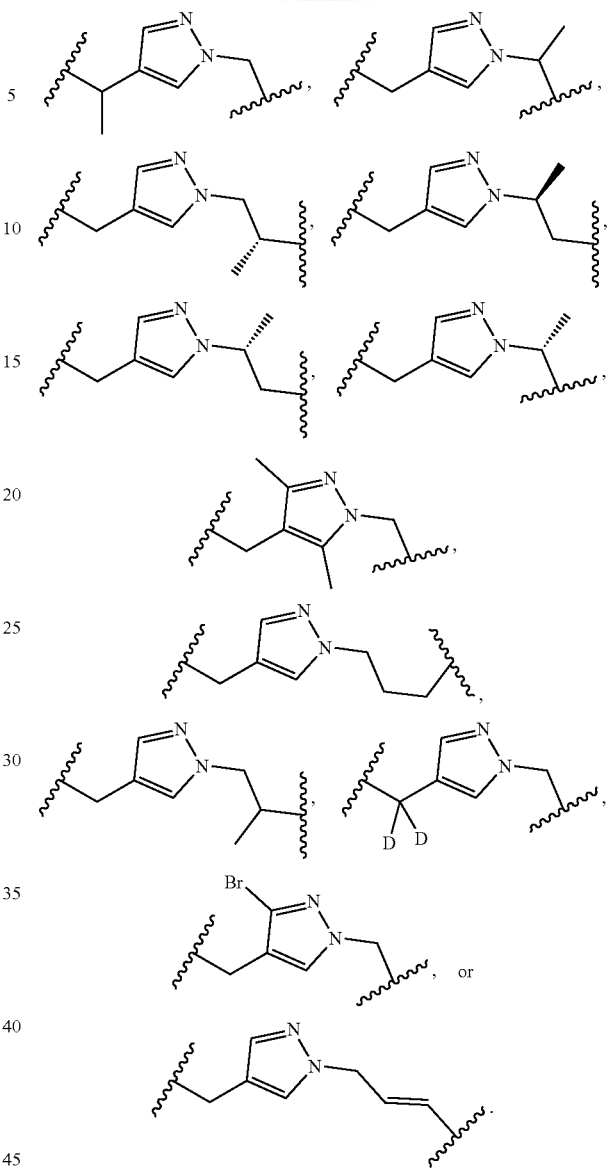

In some embodiments, L is:

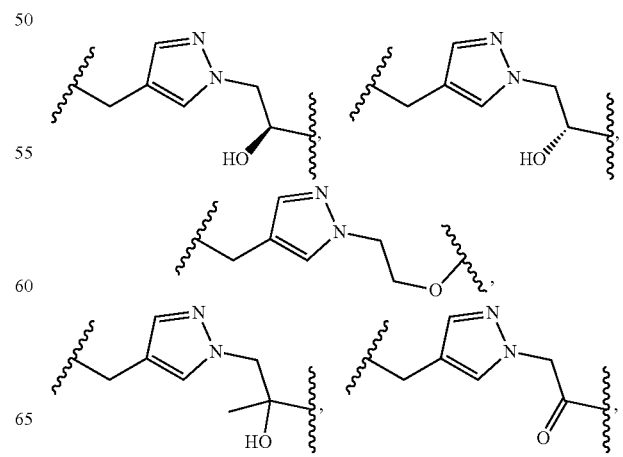

-continued
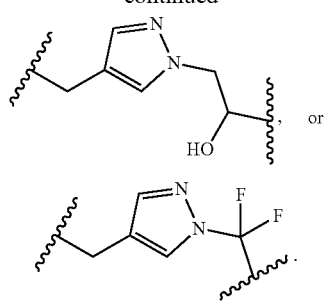, or
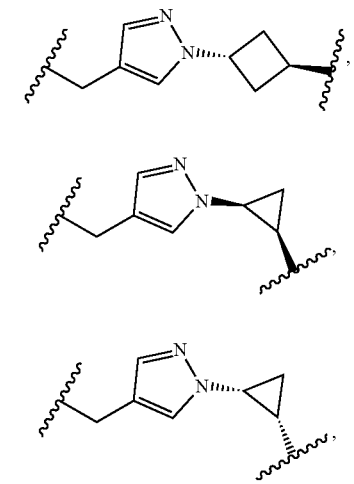
In some embodiments, L is:
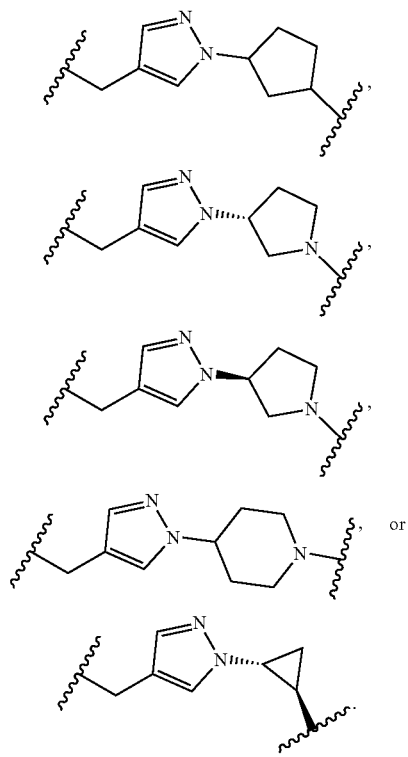
In some embodiments, L is:
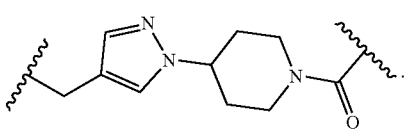 [SMILES: *Cc1cnn(C2CCN(C(*)=O)CC2)c1]
In some embodiments, L is:
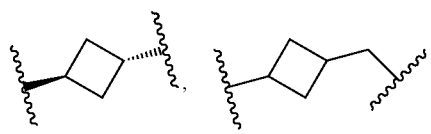
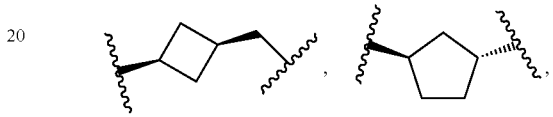
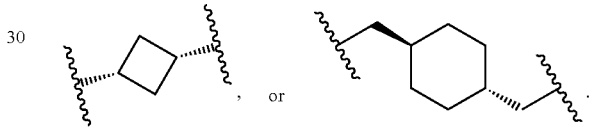
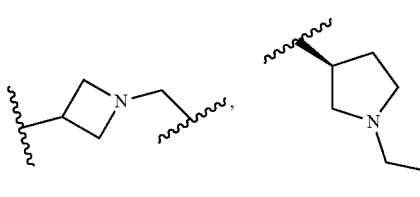, or
In some embodiments, L is:
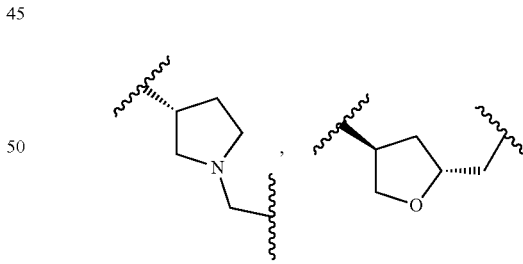
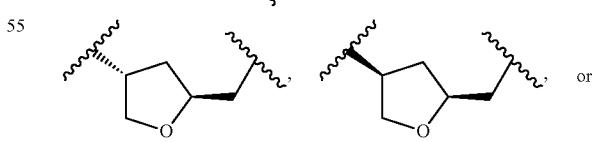
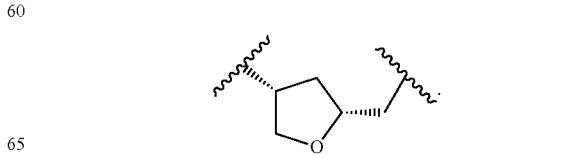

In some embodiments, L is:
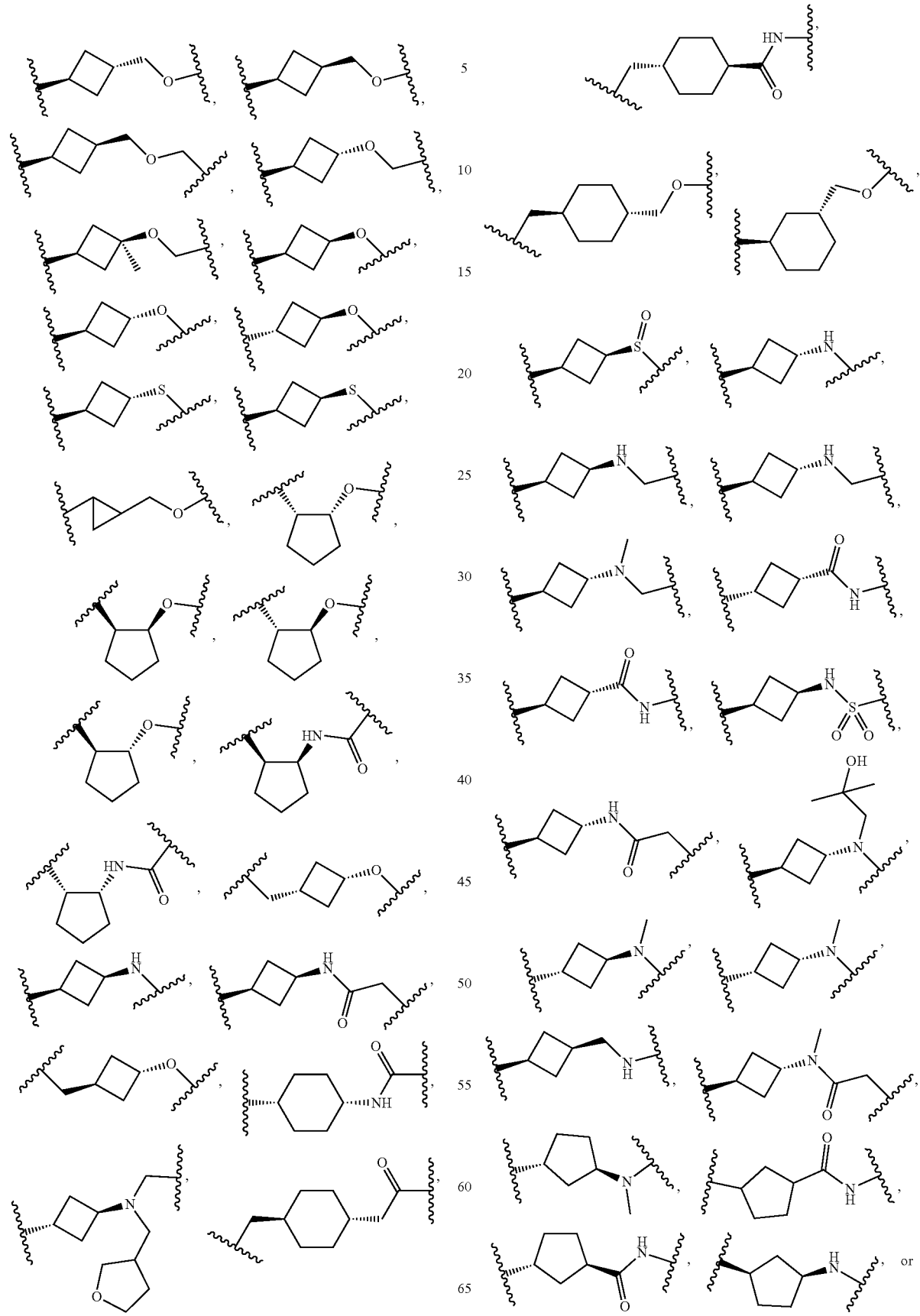

-continued
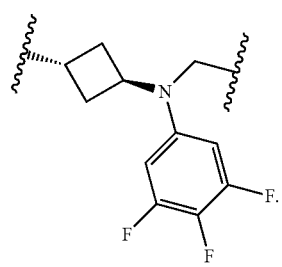
In some embodiments, L is:
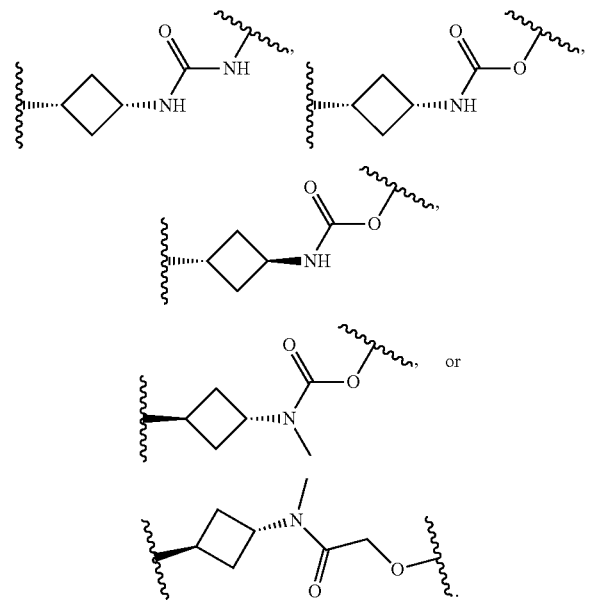
In some embodiments, L is:
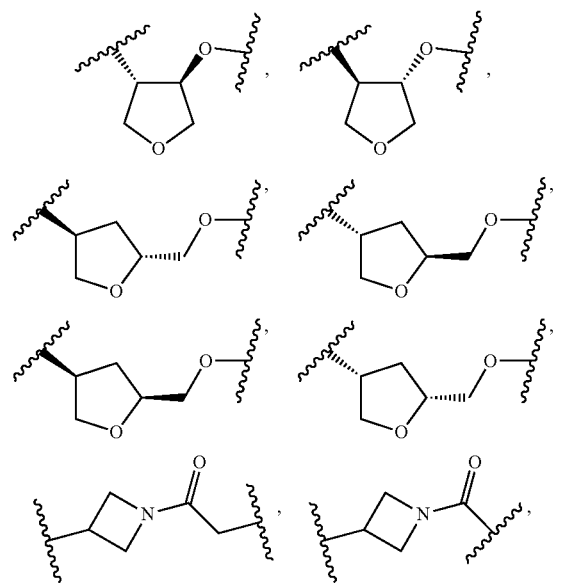
-continued
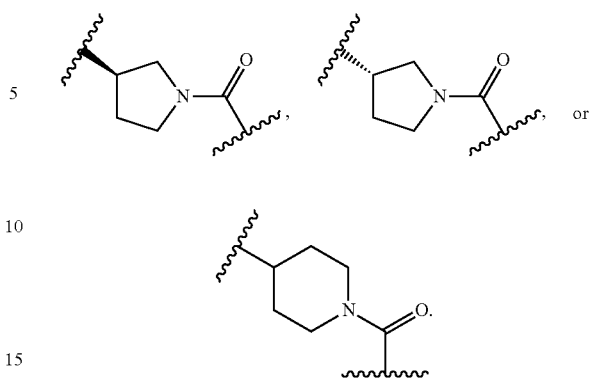
In some embodiments, L is:
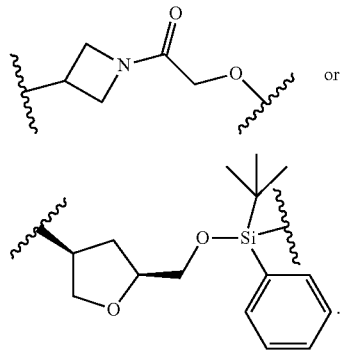
In some embodiments, L is:
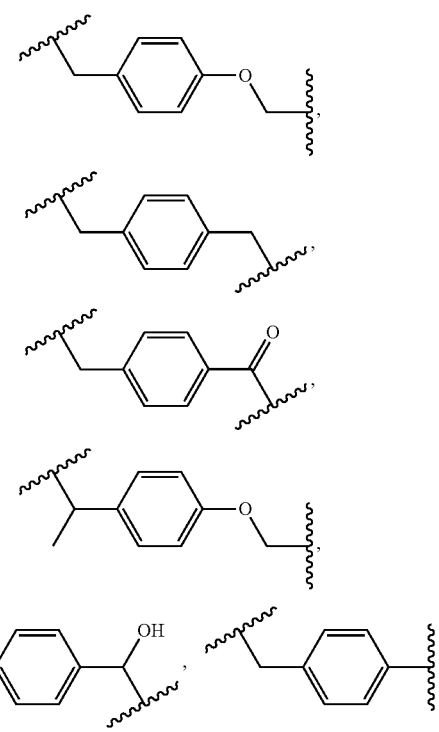

-continued
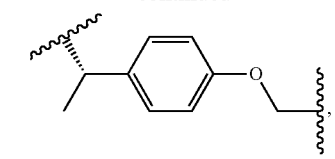
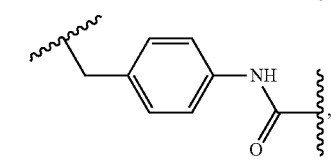
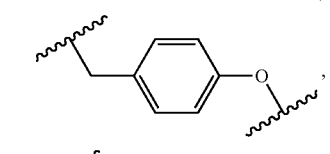
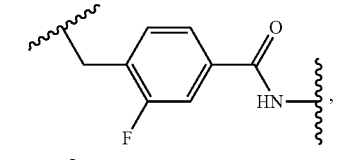
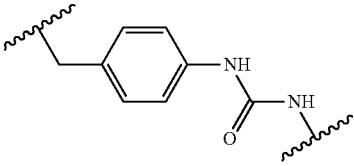
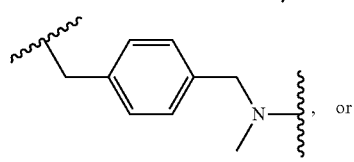
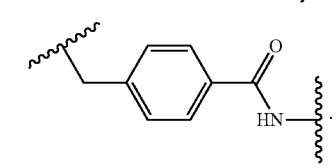
In some embodiments, L is:
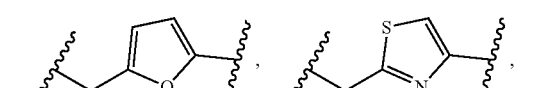
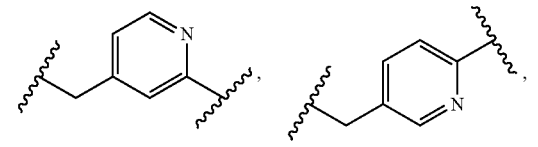
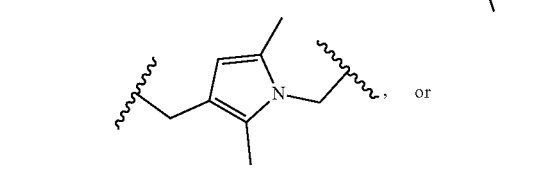
-continued
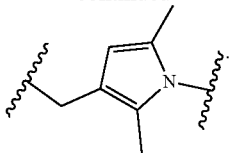
In some embodiments, L is:
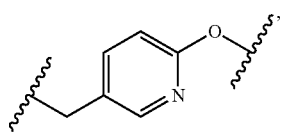
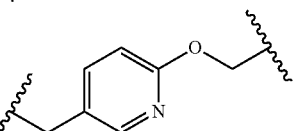
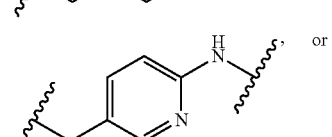
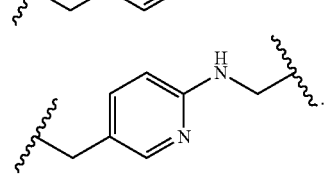
In some embodiments, L is
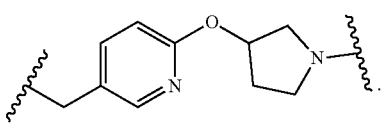 [SMILES: *Cc1ccc(OC2CCN(*)C2)nc1]
In some embodiments, L is
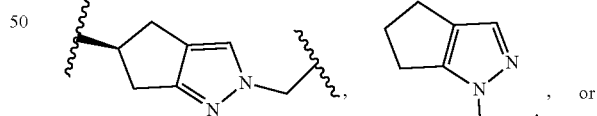
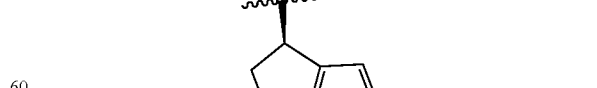
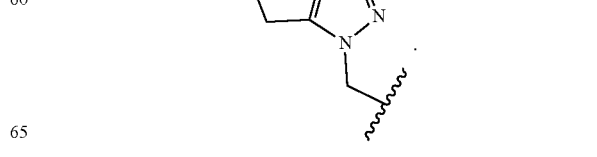

In some embodiments, L is selected from those depicted in Tables A-C below.

As defined generally above, $R^1$ is hydrogen, $R^D$, or an optionally substituted group selected from $C_{1-3}$ aliphatic or a 4-8 membered saturated or partially unsaturated monocyclic heterocyclic ring having 1-2 heteroatoms independently selected from nitrogen, oxygen, or sulfur.

In some embodiments, $R^1$ is hydrogen. In some embodiments, $R^1$ is $R^D$, or an optionally substituted group selected from $C_{1-3}$ aliphatic or a 4-8 membered saturated or partially unsaturated monocyclic heterocyclic ring having 1-2 heteroatoms independently selected from nitrogen, oxygen, or sulfur. In some embodiments, $R^1$ is hydrogen, $R^D$, or an optionally substituted $C_{1-3}$ aliphatic group.

In some embodiments, $R^1$ is $R^D$. In some embodiments, $R^1$ is —$CD_3$. In some embodiments, $R^1$ is —$CD_2CD_3$.

In some embodiments, $R^1$ is optionally substituted $C_{1-3}$ aliphatic. In some embodiments, $R^1$ is $C_{1-3}$ aliphatic optionally substituted by 1-3 halogen, —OH, —$OCH_3$, or —$C(O)N(CH_3)_2$. In some embodiments, $R^1$ is unsubstituted $C_{1-3}$ aliphatic. In some embodiments, $R^1$ is $C_{1-3}$ aliphatic substituted by 1-3 halogen. In some embodiments, $R^1$ is $C_{1-3}$ aliphatic substituted by 1-3 —OH. In some embodiments, $R^1$ is $C_{1-3}$ aliphatic substituted by 1-3 —$OCH_3$. In some embodiments, $R^1$ is $C_{1-3}$ aliphatic substituted by 1-3 —$C(O)N(CH_3)_2$.

In some embodiments, $R^1$ is an optionally substituted 4-8 membered saturated or partially unsaturated monocyclic heterocyclic ring having 1-2 heteroatoms independently selected from nitrogen, oxygen, or sulfur. In some embodiments, $R^1$ is an optionally substituted 4 membered saturated or partially unsaturated monocyclic heterocyclic ring having 1-2 heteroatoms independently selected from nitrogen, oxygen, or sulfur. In some embodiments, $R^1$ is an optionally substituted 5 membered saturated or partially unsaturated monocyclic heterocyclic ring having 1-2 heteroatoms independently selected from nitrogen, oxygen, or sulfur. In some embodiments, $R^1$ is an optionally substituted 6 membered saturated or partially unsaturated monocyclic heterocyclic ring having 1-2 heteroatoms independently selected from nitrogen, oxygen, or sulfur. In some embodiments, $R^1$ is an optionally substituted 7 membered saturated or partially unsaturated monocyclic heterocyclic ring having 1-2 heteroatoms independently selected from nitrogen, oxygen, or sulfur. In some embodiments, $R^1$ is an optionally substituted 8 membered saturated or partially unsaturated monocyclic heterocyclic ring having 1-2 heteroatoms independently selected from nitrogen, oxygen, or sulfur.

In some embodiments, $R^1$ is:

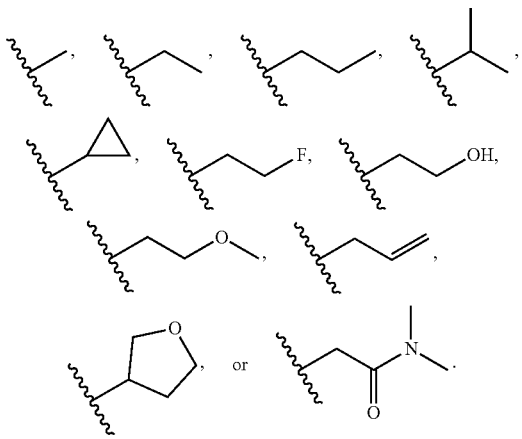

In some embodiments, $R^1$ is selected from those depicted in Tables A-C, below.

As defined generally above, each of $R^2$ and $R^{2'}$ is independently hydrogen, $R^D$, or an optionally substituted group selected from $C_{1-6}$ aliphatic, a 3-8 membered saturated or partially unsaturated monocyclic carbocyclic ring, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or $R^2$ and $R^{2'}$ are optionally taken together to form =$CH_2$ or =CH—($C_{1-3}$ aliphatic); or $R^2$ and $R^{2'}$ are optionally taken together with their intervening atoms to form an optionally substituted 3-6 membered saturated or partially unsaturated spirocyclic ring having 0-2 heteroatoms independently selected from nitrogen, oxygen or sulfur.

In some embodiments, each of $R^2$ and $R^{2'}$ is independently hydrogen, $R^D$, or an optionally substituted group selected from $C_{1-6}$ aliphatic, a 3-8 membered saturated or partially unsaturated monocyclic carbocyclic ring, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur.

In some embodiments, $R^2$ is hydrogen. In some embodiments, $R^2$ is $R^D$. In some embodiments, $R^2$ is optionally substituted $C_{1-6}$ aliphatic. In some embodiments, $R^2$ is an optionally substituted 3-8 membered saturated or partially unsaturated monocyclic carbocyclic ring. In some embodiments, $R^2$ is an optionally substituted 4-8 membered saturated or partially unsaturated monocyclic heterocyclic ring having 1-2 heteroatoms independently selected from nitrogen, oxygen, or sulfur. In some embodiments, $R^2$ is an optionally substituted 5-6 membered monocyclic heteroaromatic ring having 1-4 heteroatoms independently selected from nitrogen, oxygen, or sulfur.

In some embodiments, $R^2$ is $C_{1-6}$ aliphatic optionally substituted by 1-4 halogen or —OR. In some embodiments, $R^2$ is a 3-8 membered saturated or partially unsaturated monocyclic carbocyclic ring optionally substituted by 1-4 halogen or —OR. In some embodiments, $R^2$ is a 4-8 membered saturated or partially unsaturated monocyclic heterocyclic ring having 1-2 heteroatoms independently selected from nitrogen, oxygen, or sulfur, optionally substituted by 1-4 halogen or —OR. In some embodiments, $R^2$ is a 5-6 membered monocyclic heteroaromatic ring having 1-4 heteroatoms independently selected from nitrogen, oxygen, or sulfur, optionally substituted by 1-4 halogen or —OR.

In some embodiments, $R^2$ is $C_{1-6}$ aliphatic optionally substituted by 1-3 halogen, —OH, —$OCH_3$, or —$OC(CH_3)_3$. In some embodiments, $R^2$ is a 3-8 membered saturated or partially unsaturated monocyclic carbocyclic ring substituted by 1-3 halogen, —OH, —$OCH_3$, or —$OC(CH_3)_3$. In some embodiments, $R^2$ is a 4-8 membered saturated or partially unsaturated monocyclic heterocyclic ring having 1-2 heteroatoms independently selected from nitrogen, oxygen, or sulfur, substituted by 1-3 halogen, —OH, —$OCH_3$, or —$OC(CH_3)_3$. In some embodiments, $R^2$ is unsubstituted $C_{1-6}$ aliphatic.

In some embodiments, $R^{2'}$ is hydrogen. In some embodiments, $R^{2'}$ is $R^D$. In some embodiments, $R^{2'}$ is optionally substituted $C_{1-6}$ aliphatic. In some embodiments, $R^{2'}$ is an optionally substituted 3-8 membered saturated or partially unsaturated monocyclic carbocyclic ring. In some embodiments, $R^{2'}$ is an optionally substituted 4-8 membered saturated or partially unsaturated monocyclic heterocyclic ring having 1-2 heteroatoms independently selected from nitrogen, oxygen, or sulfur. In some embodiments, $R^{2'}$ is an optionally substituted 5-6 membered monocyclic heteroaromatic ring having 1-4 heteroatoms independently selected from nitrogen, oxygen, or sulfur.

In some embodiments, $R^{2'}$ is $C_{1-6}$ aliphatic optionally substituted by 1-4 halogen or —OR. In some embodiments, $R^{2'}$ is a 3-8 membered saturated or partially unsaturated monocyclic carbocyclic ring optionally substituted by 1-4 halogen or —OR. In some embodiments, $R^{2'}$ is a 4-8 membered saturated or partially unsaturated monocyclic heterocyclic ring having 1-2 heteroatoms independently selected from nitrogen, oxygen, or sulfur, optionally substituted by 1-4 halogen or —OR. In some embodiments, $R^{2'}$ is a 5-6 membered monocyclic heteroaromatic ring having 1-4 heteroatoms independently selected from nitrogen, oxygen, or sulfur, optionally substituted by 1-4 halogen or —OR.

In some embodiments, $R^{2'}$ is $C_{1-6}$ aliphatic optionally substituted by 1-3 halogen, —OH, —OCH$_3$, or —OC(CH$_3$)$_3$. In some embodiments, $R^{2'}$ is a 3-8 membered saturated or partially unsaturated monocyclic carbocyclic ring substituted by 1-3 halogen, —OH, —OCH$_3$, or —OC(CH$_3$)$_3$. In some embodiments, $R^{2'}$ is a 4-8 membered saturated or partially unsaturated monocyclic heterocyclic ring having 1-2 heteroatoms independently selected from nitrogen, oxygen, or sulfur, substituted by 1-3 halogen, —OH, —OCH$_3$, or —OC(CH$_3$)$_3$. In some embodiments, $R^{2'}$ is unsubstituted $C_{1-6}$ aliphatic.

In some embodiments, each of $R^2$ and $R^{2'}$ is independently:

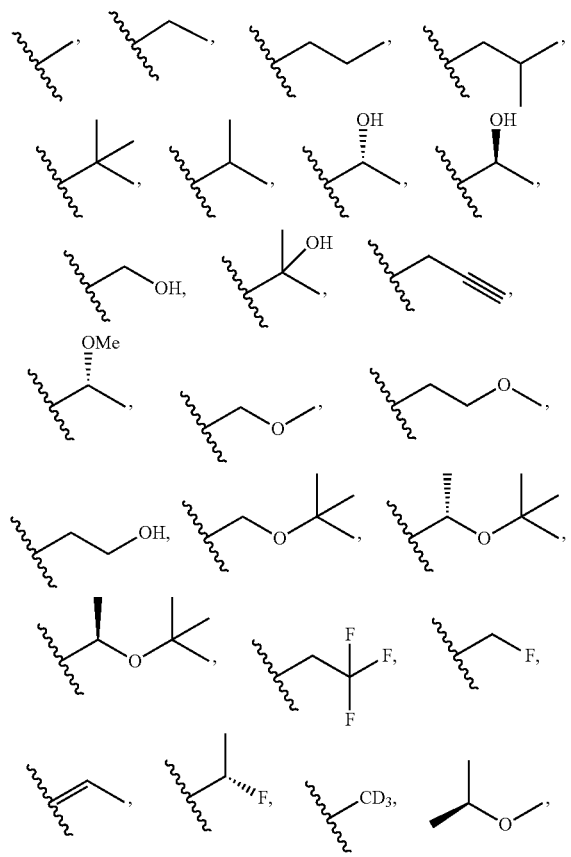

In some embodiments, each of $R^2$ and $R^{2'}$ is independently:

In some embodiments, $R^2$ is

In some embodiments, $R^2$ is

In some embodiments, $R^2$ or $R^{2'}$ is

In some embodiments, $R^{2'}$ is

In some embodiments, $R^2$ and $R^{2'}$ are taken together to form =CH$_2$ or =CH—(C$_{1-3}$ aliphatic). In some embodiments, $R^2$ and $R^{2'}$ are taken together to form =CH$_2$. In some embodiments, $R^2$ and $R^{2'}$ are taken together to form =CH—CH$_3$.

In some embodiments, $R^2$ and $R^{2'}$ are taken together with their intervening atoms to form an optionally substituted 3-6 membered saturated or partially unsaturated spirocyclic ring having 0-2 heteroatoms independently selected from nitrogen, oxygen or sulfur. In some embodiments, $R^2$ and $R^{2'}$ are taken together with their intervening atoms to form an optionally substituted 3 membered saturated or partially unsaturated spirocyclic ring having 0-2 heteroatoms independently selected from nitrogen, oxygen or sulfur. In some embodiments, $R^2$ and $R^{2'}$ are taken together with their intervening atoms to form an optionally substituted 4 membered saturated or partially unsaturated spirocyclic ring having 0-2 heteroatoms independently selected from nitrogen, oxygen or sulfur. In some embodiments, $R^2$ and $R^{2'}$ are taken together with their intervening atoms to form an optionally substituted 5 membered saturated or partially unsaturated spirocyclic ring having 0-2 heteroatoms independently selected from nitrogen, oxygen or sulfur. In some embodiments, $R^2$ and $R^{2'}$ are taken together with their intervening atoms to form an optionally substituted 6 membered saturated or partially unsaturated spirocyclic ring having 0-2 heteroatoms independently selected from nitrogen, oxygen or sulfur.

In some embodiments, $R^2$ and $R^{2'}$ are taken together with their intervening atoms to form a 3-6 membered saturated or partially unsaturated spirocyclic carbocyclic ring optionally substituted by 1-3 halogen. In some embodiments, $R^2$ and $R^{2'}$ are taken together with their intervening atoms to form spirocyclic cyclopropane optionally substituted by 1-3 halogen. In some embodiments, $R^2$ and $R^{2'}$ are taken together with their intervening atoms to form unsubstituted spirocyclic cyclopropane. In some embodiments, $R^2$ and $R^{2'}$ are taken together with their intervening atoms to form spirocyclic cyclobutane optionally substituted by 1-3 halogen. In some embodiments, $R^2$ and $R^{2'}$ are taken together with their intervening atoms to form unsubstituted spirocyclic cyclobutane. In some embodiments, $R^2$ and $R^{2'}$ are taken together with their intervening atoms to form

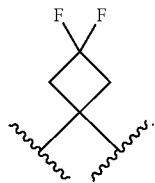 [SMILES: *C1(*)CC(F)(F)C1]

In some embodiments, $R^2$ and $R^{2'}$ are taken together with their intervening atoms to form optionally substituted spirocyclic oxetane. In some embodiments, $R^2$ and $R^{2'}$ are taken together with their intervening atoms to form

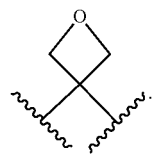

In some embodiments, $R^2$ and $R^{2'}$ are taken together with their intervening atoms to form optionally substituted spirocyclic tetrahydrofuran. In some embodiments, $R^2$ and $R^{2'}$ are taken together with their intervening atoms to form.
D-4C

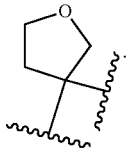

In some embodiments, each of $R^2$ and $R^{2'}$ is selected from those depicted in Tables A-C, below.

As defined generally above, $R^3$ is hydrogen, $R^D$, or an optionally substituted $C_{1-6}$ aliphatic group.

In some embodiments, $R^3$ is hydrogen. In some embodiments, $R^3$ is $R^D$. In some embodiments, $R^3$ is optionally substituted $C_{1-6}$ aliphatic. In some embodiments, $R^3$ is unsubstituted $C_{1-6}$ aliphatic. In some embodiments, $R^3$ is $C_{1-6}$ aliphatic substituted by 1-4 halogen. In some embodiments, $R^3$ is $C_{1-6}$ aliphatic substituted by

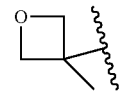

or —$OCH_3$.

In some embodiments, $R^3$ is:

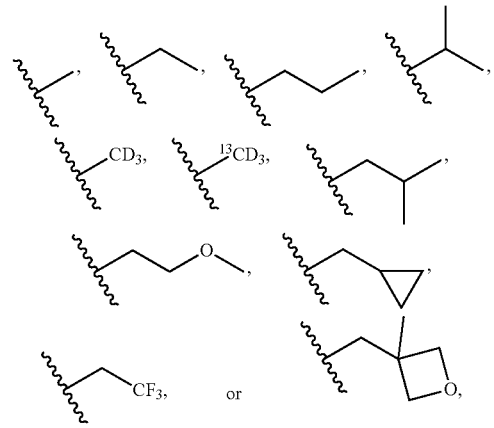

In some embodiments, $R^3$ is selected from those depicted in Tables A-C, below.

As defined generally above, $R^2$ and $R^3$ are optionally taken together with their intervening atoms to form an optionally substituted 5-8 membered saturated or partially unsaturated fused ring comprising the nitrogen atom to which $R^3$ attaches and 0-2 additional heteroatoms independently selected from nitrogen, oxygen or sulfur, or $R^2$, $R^{2'}$, and $R^3$ are optionally taken together with their intervening atoms to form an optionally substituted 5-8 membered saturated or partially unsaturated fused ring comprising the nitrogen atom to which $R^3$ attaches and 0-2 additional heteroatoms independently selected from nitrogen, oxygen or sulfur.

In some embodiments, $R^2$ and $R^3$ are taken together with their intervening atoms to form an optionally substituted 5-8 membered saturated or partially unsaturated fused ring comprising the nitrogen atom to which $R^3$ attaches and 0-2 additional heteroatoms independently selected from nitrogen, oxygen or sulfur. In some embodiments, $R^2$, $R^{2'}$, and $R^3$ are taken together with their intervening atoms to form an optionally substituted 5-8 membered saturated or partially unsaturated fused ring comprising the nitrogen atom to which R³ attaches and 0-2 additional heteroatoms independently selected from nitrogen, oxygen or sulfur.

In some embodiments, R² and R³ are taken together with their intervening atoms to form a 5-8 membered saturated or partially unsaturated fused ring substituted by 1-3 halogen, —OH, or C₁₋₆ aliphatic. In some embodiments, R², R²', and R³ are taken together with their intervening atoms to form an 5-8 membered saturated or partially unsaturated fused ring comprising the nitrogen atom to which R³ attaches and 0-2 additional heteroatoms independently selected from nitrogen, oxygen or sulfur.

In some embodiments, R² and R³ are taken together with their intervening atoms to form an optionally substituted fused ring:

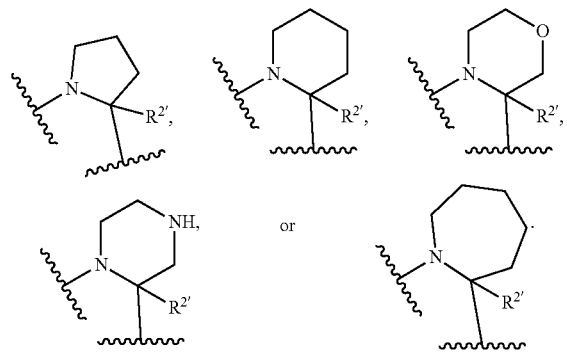

In some embodiments, R² and R³ are taken together with their intervening atoms to form a fused ring:

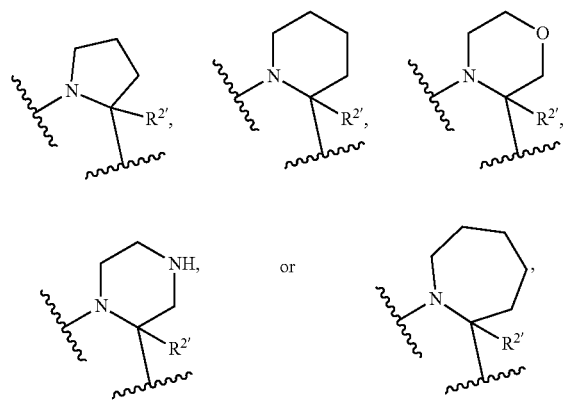

each of which is optionally substituted by 1-3 halogen, —OH, or C₁₋₆ aliphatic.

In some embodiments, R² and R³ are taken together with their intervening atoms to form a fused ring:

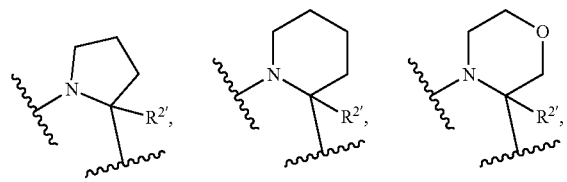

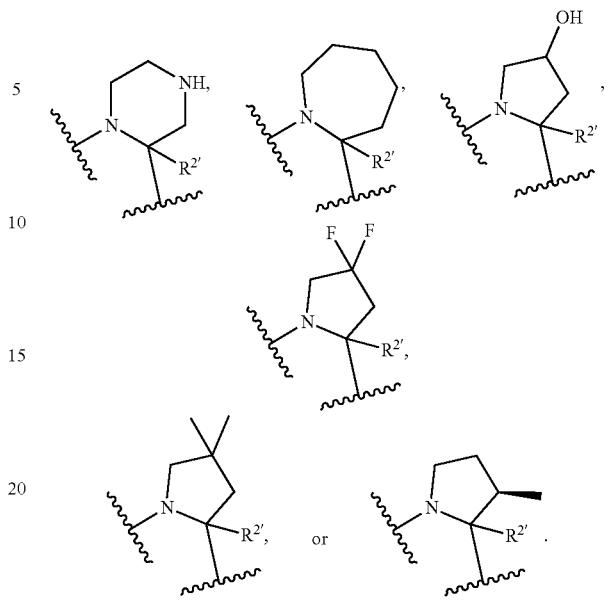

In some embodiments, R², R²', and R³ are taken together with their intervening atoms to form an optionally substituted fused ring:

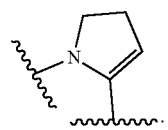

In some embodiments, R², R²', and R³ are taken together with their intervening atoms to form a fused ring

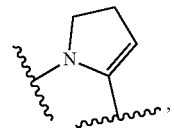 [SMILES: *C1=CCCN1*]

which is optionally substituted by 1-3 halogen, —OH, or C₁₋₆ aliphatic. In some embodiments, R², R²', and R³ are taken together with their intervening atoms to form a fused ring

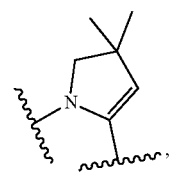 [SMILES: *C1=CC(C)(C)CN1*]

In some embodiments, R² and R³ are taken together with their intervening atoms to form an optionally substituted 5-8 membered saturated or partially unsaturated fused ring selected from those depicted in Tables A-C, below. In some embodiments, R², R²', and R³ are taken together with their intervening atoms to form an optionally substituted 5-8 membered saturated or partially unsaturated fused ring selected from those depicted in Tables A-C, below.

As defined generally above, $R^4$ is hydrogen, $R^D$, —CD$_2$OH, or an optionally substituted $C_{1-3}$ aliphatic group.

In some embodiments, $R^4$ is hydrogen.

In some embodiments, $R^4$ is $R^D$. In some embodiments, $R^4$ is —CD$_3$.

In some embodiments, $R^4$ is —CD$_2$OH.

In some embodiments, $R^4$ is optionally substituted $C_{1-3}$ aliphatic. In some embodiments, $R^4$ is unsubstituted $C_{1-3}$ aliphatic. In some embodiments, $R^4$ is methyl. In some embodiments, $R^4$ is ethyl. In some embodiments, $R^4$ is propyl. In some embodiments, $R^4$ is $C_{1-3}$ aliphatic substituted by 1-3 halogen and OR. In some embodiments, $R^4$ is $C_{1-3}$ aliphatic substituted by 1-3 halogen or —OH. In some embodiments, $R^4$ is —CH$_2$OH.

In some embodiments, $R^4$ is selected from those depicted in Tables A-C, below.

As defined generally above, $R^5$ is hydrogen, —C(O)R, —C(O)OR, —C(O)NR$_2$, a 3-8 membered saturated or partially unsaturated monocyclic carbocyclic ring, or a $C_{1-3}$ aliphatic group.

In some embodiments, $R^5$ is hydrogen, —C(O)R, —C(O)OR, or a $C_{1-3}$ aliphatic group.

In some embodiments, $R^5$ is hydrogen.

In some embodiments, $R^5$ is —C(O)R. In some embodiments, $R^5$ is —C(O)R, wherein R is optionally substituted $C_{1-6}$ aliphatic. In some embodiments, $R^5$ is —C(O)R, wherein R is $C_{1-6}$ aliphatic optionally substituted by 1-3 —NH$_2$ or —NHC(O)CH$_3$. In some embodiments, $R^5$ is

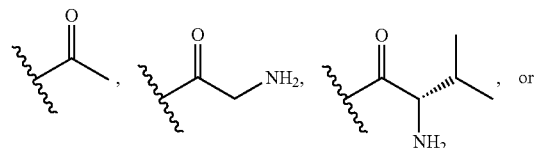

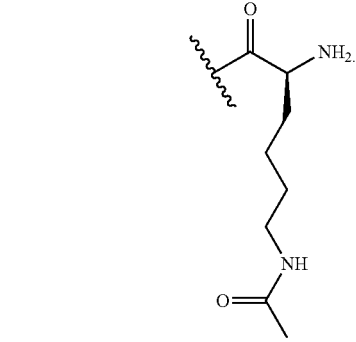

In some embodiments, $R^5$ is —C(O)OR. In some embodiments, $R^5$ is —C(O)OR, wherein R is optionally substituted $C_{1-6}$ aliphatic. In some embodiments, $R^5$ is —C(O)OR, wherein R is $C_{1-6}$ aliphatic optionally substituted by 1-3 —OC(O)CH(CH$_3$)$_2$. In some embodiments, $R^5$ is

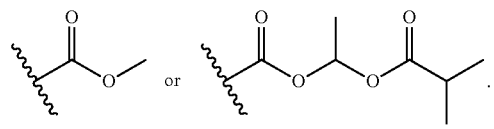

In some embodiments, $R^5$ is —C(O)NR$_2$. In some embodiments, $R^5$ is —C(O)NR$_2$, wherein R is independently hydrogen or an optionally substituted 3-8 membered saturated or partially unsaturated monocyclic carbocyclic ring. In some embodiments, $R^5$ is —C(O)NR$_2$, wherein R is independently hydrogen or an optionally substituted 6 membered saturated or partially unsaturated monocyclic carbocyclic ring. In some embodiments, $R^5$ is

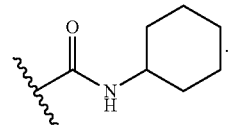 [SMILES: *C(=O)NC1CCCCC1]

In some embodiments, $R^5$ is an optionally substituted 3-8 membered saturated or partially unsaturated monocyclic carbocyclic ring. In some embodiments, $R^5$ is a 3-8 membered saturated or partially unsaturated monocyclic carbocyclic ring optionally substituted by 1-3 halogen, —OH, or NH$_2$. In some embodiments, $R^5$ is a 5 membered saturated or partially unsaturated monocyclic carbocyclic ring optionally substituted by 1-3 halogen, —OH, or NH$_2$. In some embodiments, $R^5$ is

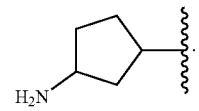

In some embodiments, $R^5$ is

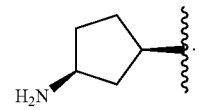

In some embodiments, $R^5$ is $C_{1-3}$ aliphatic. In some embodiments, $R^5$ is methyl.

In some embodiments, $R^5$ is selected from those depicted in Tables A-C, below.

As defined generally above, each of $R^6$ is independently halogen, —CN, —NO$_2$, —C(O)R, —C(O)OR, —C(O)NR$_2$, —NR$_2$, —NRC(O)R, —NRC(O)OR, —NRS(O)$_2$R, —OR, —P(O)R$_2$, —SR, —SF$_5$, —S(O)R, —S(O)$_2$R, —S(O)(NH)R, —C(=NR)—OR, —O—C(=NR)—R, or R; or two $R^6$ groups are optionally taken together to form =O.

In some embodiments, $R^6$ is halogen. In some embodiments, $R^6$ is —CN. In some embodiments, $R^6$ is —NO$_2$. In some embodiments, $R^6$ is —C(O)R. In some embodiments, $R^6$ is —C(O)OR. In some embodiments, $R^6$ is —C(O)NR$_2$. In some embodiments, $R^6$ is —NR$_2$. In some embodiments, $R^6$ is —NRC(O)R. In some embodiments, $R^6$ is —NRC(O)OR. In some embodiments, $R^6$ is —NRS(O)$_2$R. In some embodiments, $R^6$ is —OR. In some embodiments, $R^6$ is —P(O)R$_2$. In some embodiments, $R^6$ is —SR. In some embodiments, $R^6$ is —SF$_5$. In some embodiments, $R^6$ is —S(CF$_3$)$_5$. In some embodiments, $R^6$ is —S(O)R. In some embodiments, $R^6$ is —S(O)$_2$R. In some embodiments, $R^6$ is —S(O)(NH)R. In some embodiments, $R^6$ is —C(=NR)—OR. In some embodiments, $R^6$ is —O—C(=NR)—R. In some embodiments, $R^6$ is R. In some embodiments, two $R^6$ groups are taken together to form =O.

In some embodiments, $R^6$ is F. In some embodiments, $R^6$ is Cl. In some embodiments, $R^6$ is I.

In some embodiments, $R^6$ is optionally substituted $C_{1-6}$ aliphatic. In some embodiments, $R^6$ is unsubstituted $C_{1-6}$ aliphatic. In some embodiments, $R^6$ is $C_{1-6}$ aliphatic substituted by 1-5 halogen, —CN, or —OR. In some embodiments, $R^6$ is $C_{1-6}$ aliphatic substituted by 1-5 halogen, —CN, or —OH. In some embodiments, $R^6$ is $C_{1-6}$ aliphatic substituted by 1-5 halogen or —OH.

In some embodiments, $R^6$ is —C(O)R, wherein R is optionally substituted $C_{1-6}$ aliphatic. In some embodiments, $R^6$ is —C(O)R, wherein R is unsubstituted $C_{1-6}$ aliphatic. In some embodiments, $R^6$ is —C(O)R, wherein R is $C_{1-6}$ aliphatic substituted by 1-4 halogen or —O—($C_{1-6}$ aliphatic optionally substituted by 1-3 halogen). In some embodiments, $R^6$ is —C(O)R, wherein R is $C_{1-6}$ aliphatic substituted by —O—($C_{1-6}$ aliphatic optionally substituted by 1-3 halogen). In some embodiments, $R^6$ is —C(O)R, wherein R is $C_{1-6}$ aliphatic substituted by —OCH$_2$CF$_3$. In some embodiments, $R^6$ is —C(O)—CH$_2$OCH$_2$CF$_3$ or —C(O)—CH$_2$CH$_2$OCH$_2$CF$_3$.

In some embodiments, $R^6$ is —NR$_2$, wherein each R is independently Hydrogen or optionally substituted $C_{1-6}$ aliphatic. In some embodiments, $R^6$ is —NR$_2$, wherein R is independently Hydrogen or unsubstituted $C_{1-6}$ aliphatic. In some embodiments, $R^6$ is —NR$_2$, wherein R is independently Hydrogen or $C_{1-6}$ aliphatic substituted by 1-4 halogen. In some embodiments, $R^6$ is —NR$_2$, wherein R is independently $C_{1-6}$ aliphatic substituted by optionally substituted phenyl or a 4-8 membered saturated or partially unsaturated monocyclic heterocyclic ring having 1-2 heteroatoms independently selected from nitrogen, oxygen, or sulfur. In some embodiments, $R^6$ is —NR$_2$, wherein R is independently $C_{1-6}$ aliphatic substituted by phenyl or a 4-6 membered saturated monocyclic heterocyclic ring having 1-2 heteroatoms independently selected from nitrogen, oxygen, or sulfur, wherein the phenyl and heterocyclic ring is optionally and independently substituted by 1-3 halogen. In some embodiments, $R^6$ is

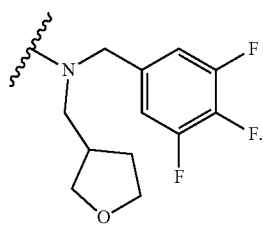 [SMILES: *N(Cc1cc(F)c(F)c(F)c1)CC1CCOC1]

In some embodiments, $R^6$ is —OR, wherein R is Hydrogen or optionally substituted $C_{1-6}$ aliphatic. In some embodiments, $R^6$ is —OR, wherein R is Hydrogen or unsubstituted $C_{1-6}$ aliphatic. In some embodiments, $R^6$ is —OR, wherein R is Hydrogen or $C_{1-6}$ aliphatic substituted by 1-4 halogen.

In some embodiments, $R^6$ is —C(=NR)—OR, wherein each R is independently Hydrogen or optionally substituted $C_{1-6}$ aliphatic. In some embodiments, $R^6$ is —C(=NR)—OR, wherein R is independently Hydrogen or unsubstituted $C_{1-6}$ aliphatic. In some embodiments, $R^6$ is —C(=NH)—OR, wherein R is optionally substituted $C_{1-6}$ aliphatic. In some embodiments, $R^6$ is —C(=NH)—OR, wherein R is unsubstituted $C_{1-6}$ aliphatic. In some embodiments, $R^6$ is —C(=NH)—OC(CH$_3$)$_3$.

In some embodiments, $R^6$ is:

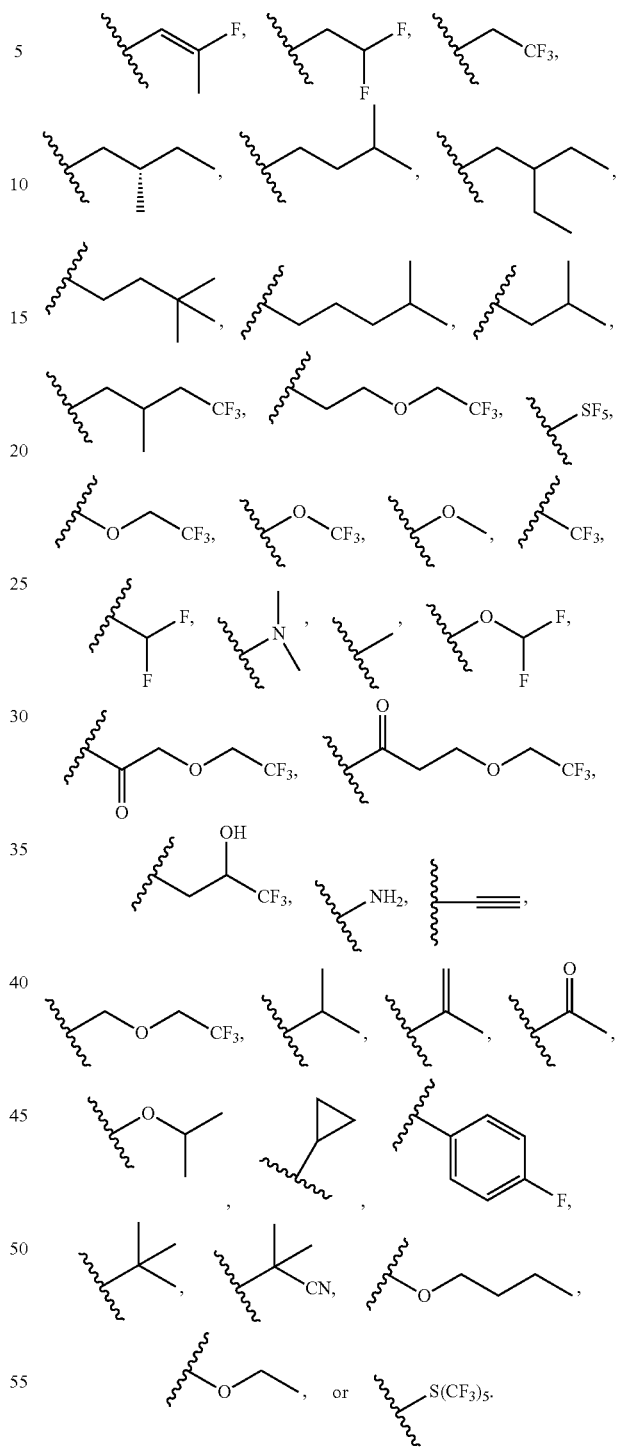

In some embodiments, two $R^6$ are attached to the same position on Ring A.

In some embodiments, $R^6$ is selected from those depicted in Tables A-C, below.

As defined generally above, each R is independently hydrogen or an optionally substituted group selected from $C_{1-6}$ aliphatic, a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups.

In some embodiments, R is hydrogen. In some embodiments, R is optionally substituted $C_{1-6}$ aliphatic. In some embodiments, R is an optionally substituted 3-8 membered saturated or partially unsaturated monocyclic carbocyclic ring. In some embodiments, R is optionally substituted phenyl. In some embodiments, R is an optionally substituted 4-8 membered saturated or partially unsaturated monocyclic heterocyclic ring having 1-2 heteroatoms independently selected from nitrogen, oxygen, or sulfur. In some embodiments, R is an optionally substituted 5-6 membered monocyclic heteroaromatic ring having 1-4 heteroatoms independently selected from nitrogen, oxygen, or sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups.

In some embodiments, R is $C_{1-6}$ aliphatic optionally substituted by 1-4 halogen, —CN, —NO$_2$, —OH, —NH$_2$, —OCH$_3$, or —C(O)N(CH$_3$)$_2$. In some embodiments, R is unsubstituted $C_{1-6}$ aliphatic.

In some embodiments, each R is selected from those depicted in Tables A-C, below.

As defined generally above, $R^D$ is a $C_{1-4}$ aliphatic group wherein one or more hydrogens are replaced by deuterium.

In some embodiments, $R^D$ is a $C_{1-3}$ aliphatic group wherein one or more hydrogens are replaced by deuterium. In some embodiments, $R^D$ is a $C_{1-2}$ aliphatic group wherein one or more hydrogens are replaced by deuteriumn. In some embodiments, $R^D$ is a methyl group wherein one or more hydrogens are replaced by deuteriumn. In some embodiments, $R^D$ is —CD$_3$. In some embodiments, $R^D$ is —CD$_2$CD$_3$.

In some embodiments, $R^D$ is selected from those depicted in Tables A-C, below.

As defined generally above, X is N or CH.

In some embodiments, X is N. In some embodiments, X is CH.

In some embodiments, X is selected from those depicted in Tables A-C, below.

As defined generally above, n is 0, 1, 2, 3, 4 or 5.

In some embodiments, n is 0. In some embodiments, n is 1, 2, 3, 4 or 5. In some embodiments, n is 1, 2, 3, or 4. In some embodiments, n is 1, 2, or 3. In some embodiments, n is 1. In some embodiments, n is 2. In some embodiments, n is 3. In some embodiments, n is 4. In some embodiments, n is 5.

In some embodiments, n is selected from those depicted in Tables A-C, below.

In some embodiments, the present invention provides a compound of Formula I':

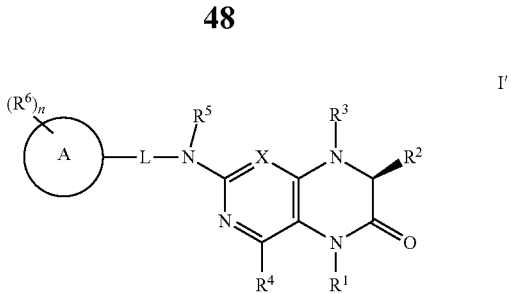

or a pharmaceutically acceptable salt thereof, wherein each of Ring A, L, $R^1$, $R^2$, $R^3$, $R^4$, $R^6$, and n is as defined above and described in embodiments herein, both singly and in combination.

In some embodiments, the present invention provides a compound of Formula II:

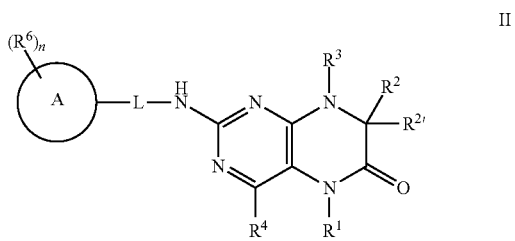

or a pharmaceutically acceptable salt thereof, wherein each of Ring A, L, $R^1$, $R^2$, $R^{2'}$, $R^3$, $R^4$, $R^6$, and n is as defined above and described in embodiments herein, both singly and in combination.

In some embodiments, the present invention provides a compound of Formula II':

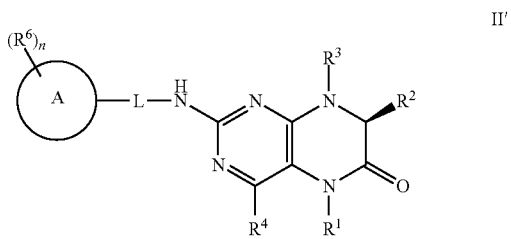

or a pharmaceutically acceptable salt thereof, wherein each of Ring A, L, $R^1$, $R^2$, $R^3$, $R^4$, $R^6$, and n is as defined above and described in embodiments herein, both singly and in combination.

In some embodiments, the present invention provides a compound of Formula III:

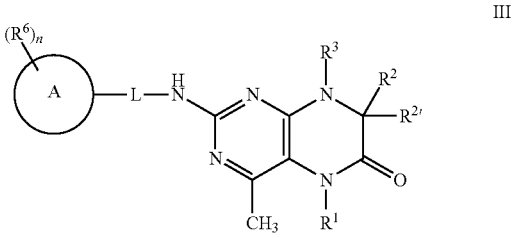

or a pharmaceutically acceptable salt thereof, wherein each of Ring A, L, R$^1$, R$^2$, R$^{2'}$, R$^3$, R$^6$, and n is as defined above and described in embodiments herein, both singly and in combination.

In some embodiments, the present invention provides a compound of Formula III':

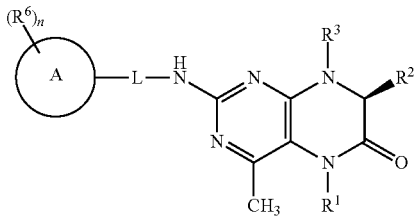

III' or a pharmaceutically acceptable salt thereof, wherein each of Ring A, L, R$^1$, R$^2$, R$^3$, R$^6$, and n is as defined above and described in embodiments herein, both singly and in combination.

In some embodiments, the present invention provides a compound of Formula IV:

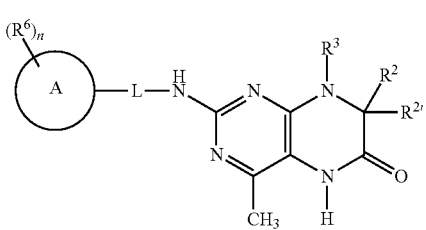

IV or a pharmaceutically acceptable salt thereof, wherein each of Ring A, L, R$^2$, R$^{2'}$, R$^3$, R$^6$, and n is as defined above and described in embodiments herein, both singly and in combination.

In some embodiments, the present invention provides a compound of Formula IV':

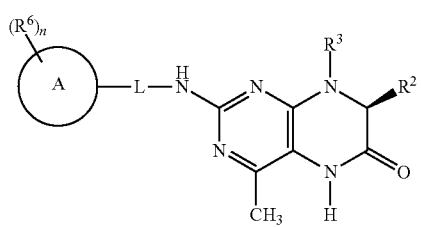

IV' or a pharmaceutically acceptable salt thereof, wherein each of Ring A, L, R$^2$, R$^3$, R$^6$, and n is as defined above and described in embodiments herein, both singly and in combination.

In some embodiments, the present invention provides a compound of Formula V:

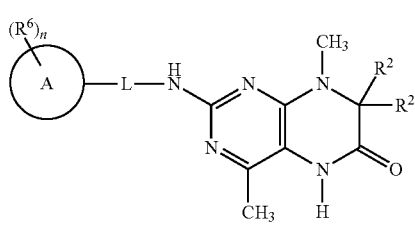

V or a pharmaceutically acceptable salt thereof, wherein each of Ring A, L, R$^2$, R$^{2'}$, R$^6$, and n is as defined above and described in embodiments herein, both singly and in combination.

In some embodiments, the present invention provides a compound of Formula V':

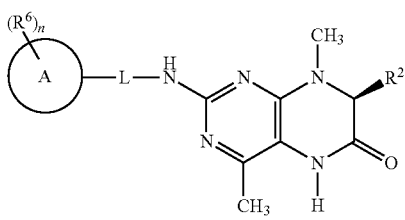

V' or a pharmaceutically acceptable salt thereof, wherein each of Ring A, L, R$^2$, R$^6$, and n is as defined above and described in embodiments herein, both singly and in combination.

In some embodiments, the present invention provides a compound of Formula VI-a, VI-b, VI-c, or VI-d:

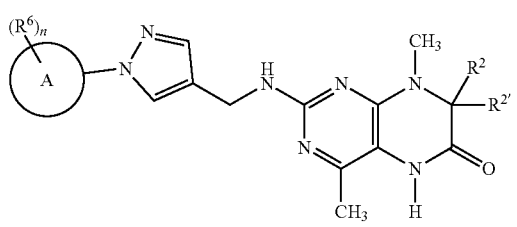

VI-a

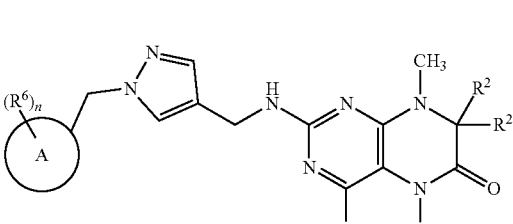

VI-b

VI-c

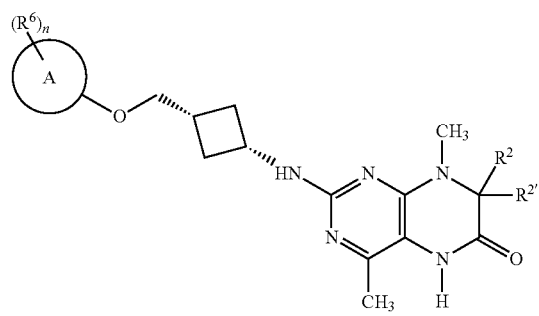

VI-d

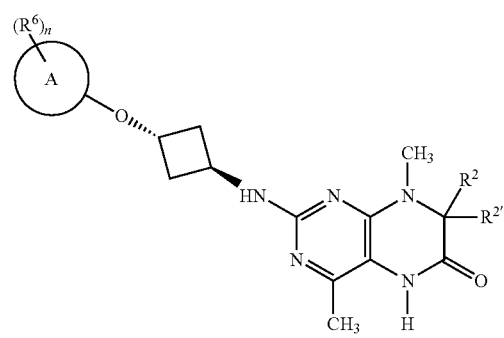

or a pharmaceutically acceptable salt thereof, wherein each of Ring A, $R^2$, $R^{2'}$, $R^6$, and n is as defined above and described in embodiments herein, both singly and in combination.

In some embodiments, the present invention provides a compound of Formula VI'-a, VI'-a

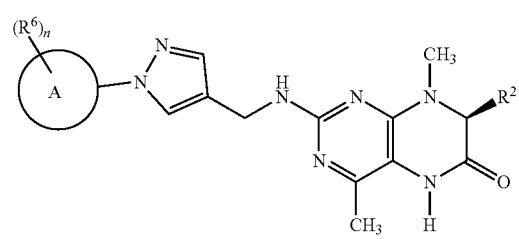

VI'-b

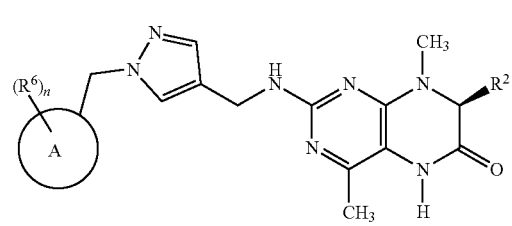

VI'-c

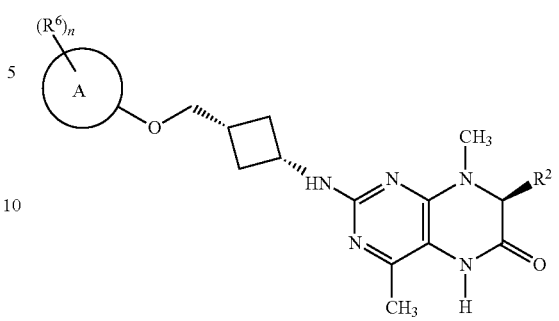

VI'-d or a pharmaceutically acceptable salt thereof, wherein each of Ring A, $R^2$, $R^6$, and n is as defined above and described in embodiments herein, both singly and in combination.

In some embodiments, the present invention provides a compound of Formula VII:

VII or a pharmaceutically acceptable salt thereof, wherein each of Ring A, L, $R^2$, $R^{2'}$, $R^4$, $R^6$, and n is as defined above and described in embodiments herein, both singly and in combination.

In some embodiments, the present invention provides a compound of Formula VII':

VII' or a pharmaceutically acceptable salt thereof, wherein each of Ring A, L, $R^2$, $R^4$, $R^6$, and n is as defined above and described in embodiments herein, both singly and in combination.

In some embodiments, the present invention provides a compound of Formula VI'-a, VI'-b, VI'-c, or VI'-d, or a pharmaceutically acceptable salt thereof, wherein $R^2$ is unsubstituted $C_{1-6}$ aliphatic, or $R^D$;

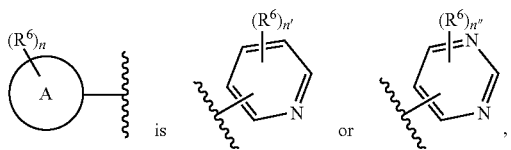

wherein one of $R^6$ is —$CF_3$; n' is 1, 2, 3, or 4; and n" is 1, 2, or 3;

or

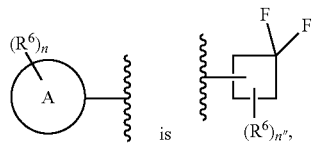

wherein n'" is 0, 1, 2, or 3; and each of $R^6$ and $R^D$ is as defined above and described in embodiments herein.

In some embodiments,

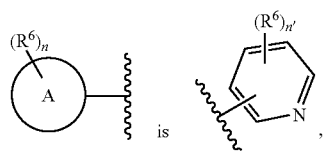

wherein one of $R^6$ is —$CF_3$; each of the other $R^{6'}$ is as defined above and described in embodiments herein; and n' is 1, 2, 3, or 4.

In some embodiments,

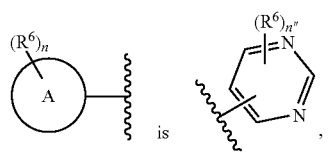

wherein one of $R^6$ is —$CF_3$; each of the other $R^6$ is as defined above and described in embodiments herein; and n" is 1, 2, or 3.

In some embodiments,

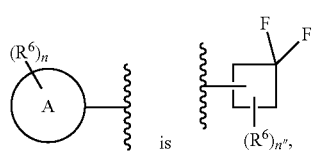

wherein each $R^6$ is as defined above and described in embodiments herein; and n'" is 0, 1, 2, or 3.

In some embodiments, n' is 1. In some embodiments, n' is 2. In some embodiments, n' is 3. In some embodiments, n' is 4. In some embodiments, n" is 1. In some embodiments, n" is 2. In some embodiments, n" is 3. In some embodiments, n'" is 0. In some embodiments, n'" is 1. In some embodiments, n'" is 2. In some embodiments, n'" is 3.

In some embodiments, is N

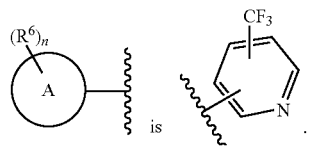

In some embodiments, is

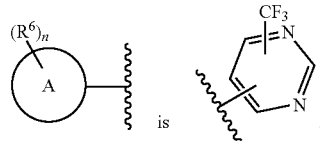

In some embodiments, is

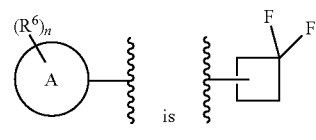

In some embodiments, the present invention provides a compound of Formula VIII'-a, VIII'-b, or VIII'-c:

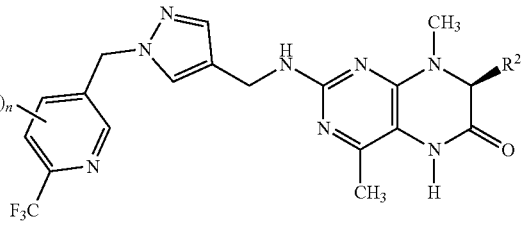

VIII'-a

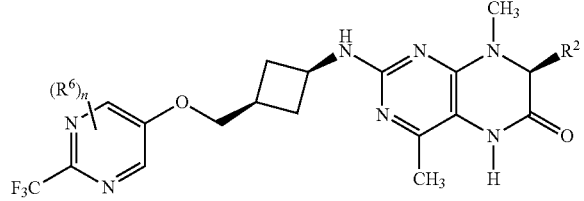

VIII'-b

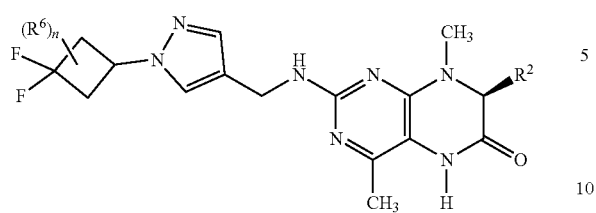

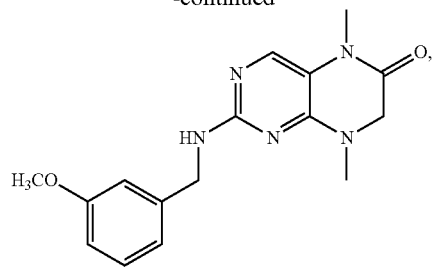

or a pharmaceutically acceptable salt thereof, wherein $R^2$ is unsubstituted $C_{1-6}$ aliphatic, or $R^D$;

n is 0, 1, 2, 3, or 4 in formulas VIII'-a and VIII'-b, and 0, 1, 2, or 3 in formula VIII'-c; and each of $R^6$ and $R^D$ is as defined above and described in embodiments herein, both singly and in combination.

In some embodiments, the present invention provides a compound of formula I wherein said compound is other than a compound selected from:

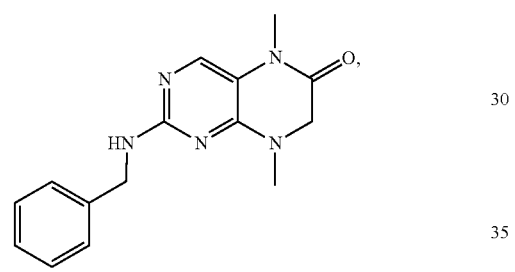

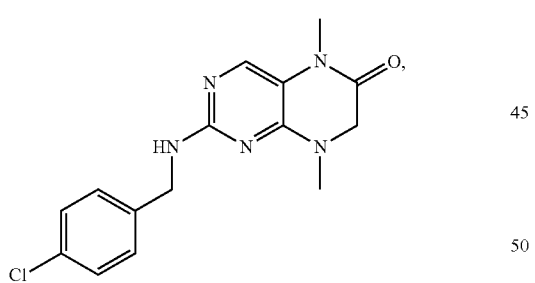

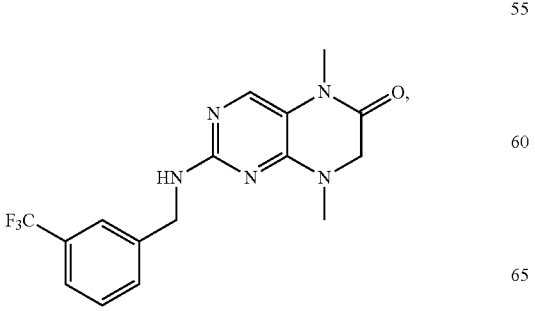

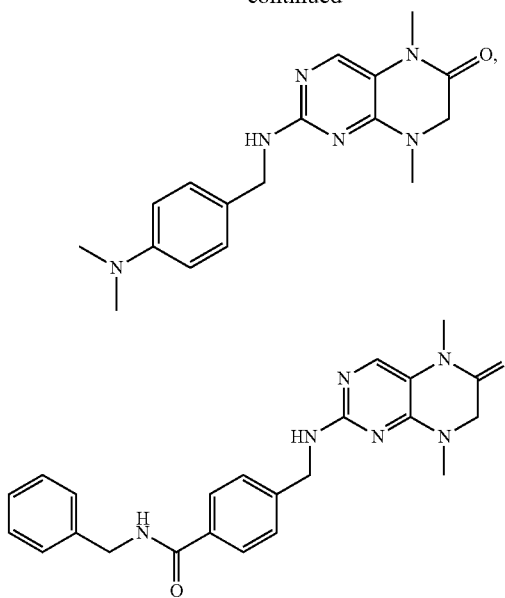
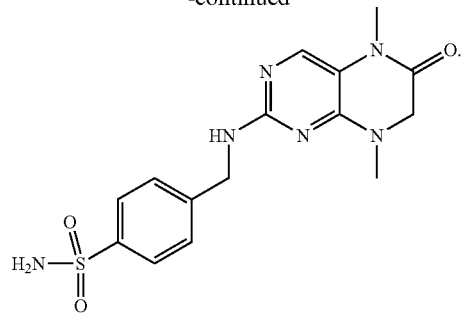
Exemplary compounds of the invention are set forth in Tables A-C, below.
TABLE A
Exemplary Compounds
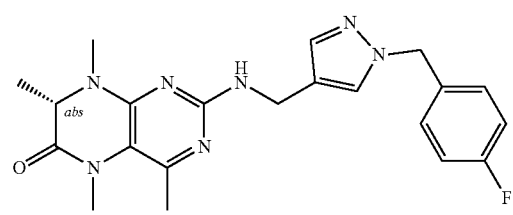 [SMILES: Cc1nc(NCc2cnn(Cc3ccc(F)cc3)c2)nc2c1N(C)C(=O)[C@H](C)N2C]
I-1
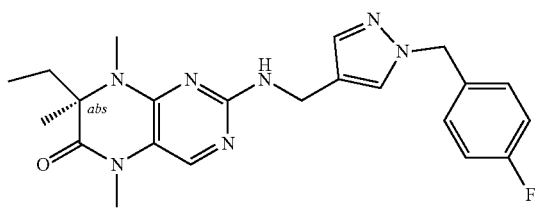 [SMILES: CC[C@]1(C)C(=O)N(C)c2cnc(NCc3cnn(Cc4ccc(F)cc4)c3)nc2N1C]
I-2
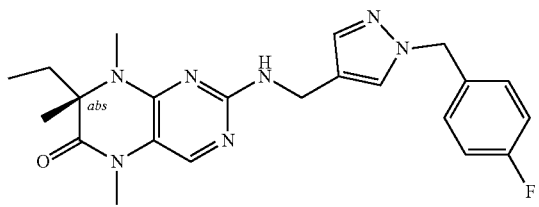 [SMILES: CC[C@@]1(C)C(=O)N(C)c2cnc(NCc3cnn(Cc4ccc(F)cc4)c3)nc2N1C]
I-3
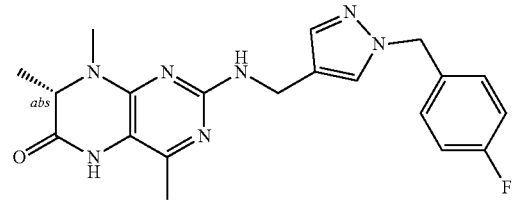 [SMILES: Cc1nc(NCc2cnn(Cc3ccc(F)cc3)c2)nc2c1NC(=O)[C@H](C)N2C]
I-4

TABLE A-continued
Exemplary Compounds
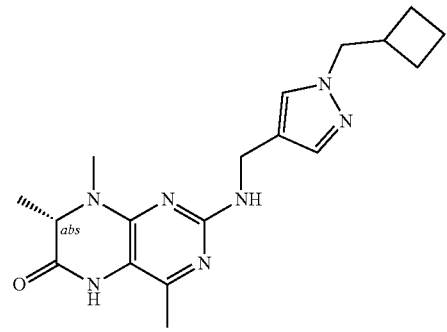 [SMILES: Cc1nc(NCc2cnn(CC3CCC3)c2)nc2c1NC(=O)[C@H](C)N2C]
I-5
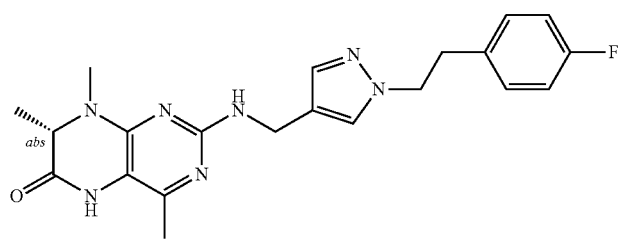 [SMILES: Cc1nc(NCc2cnn(CCc3ccc(F)cc3)c2)nc2c1NC(=O)[C@H](C)N2C]
I-6
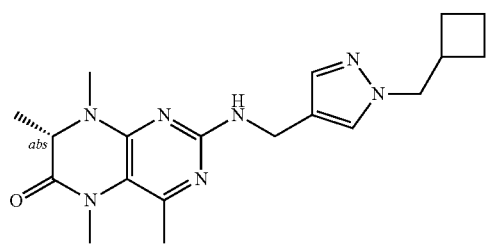 [SMILES: Cc1nc(NCc2cnn(CC3CCC3)c2)nc2c1N(C)C(=O)[C@H](C)N2C]
I-7
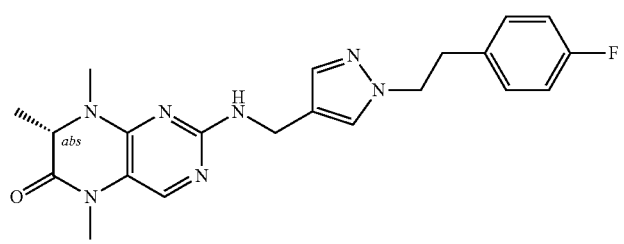 [SMILES: C[C@H]1C(=O)N(C)c2cnc(NCc3cnn(CCc4ccc(F)cc4)c3)nc2N1C]
I-8
I-9
I-10
I-11
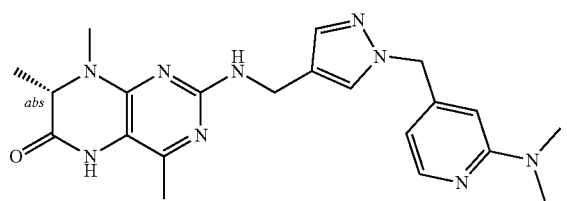 [SMILES: Cc1nc(NCc2cnn(Cc3ccnc(N(C)C)c3)c2)nc2c1NC(=O)[C@H](C)N2C]
I-12

TABLE A-continued
Exemplary Compounds
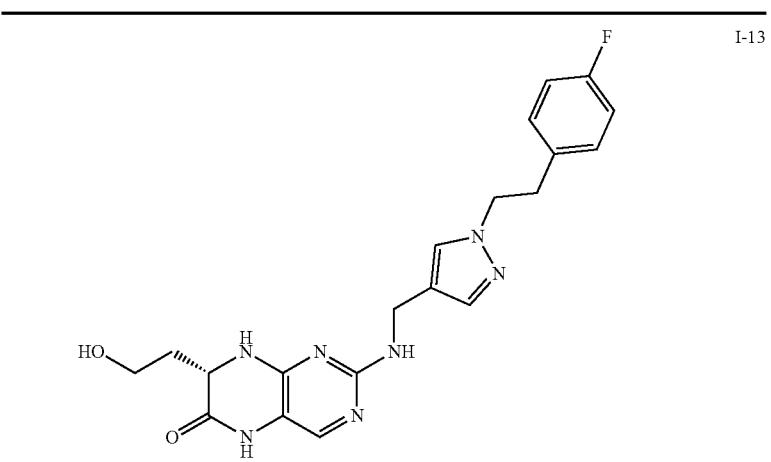
I-13
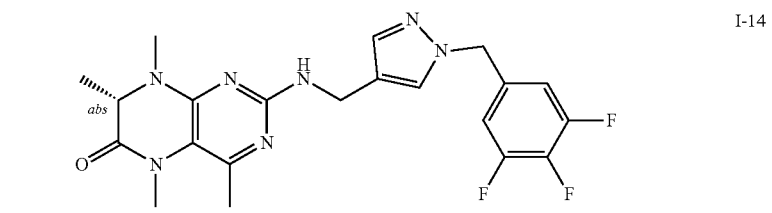
I-14
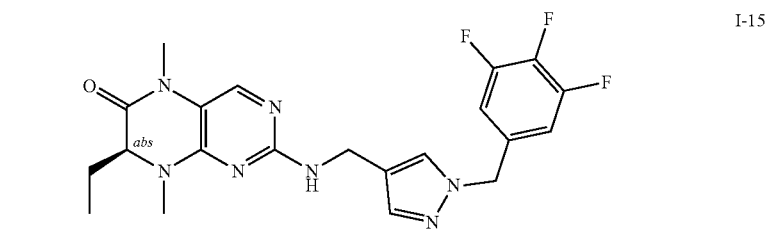
I-15
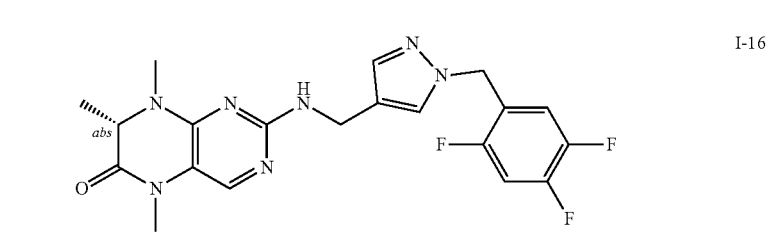
I-16
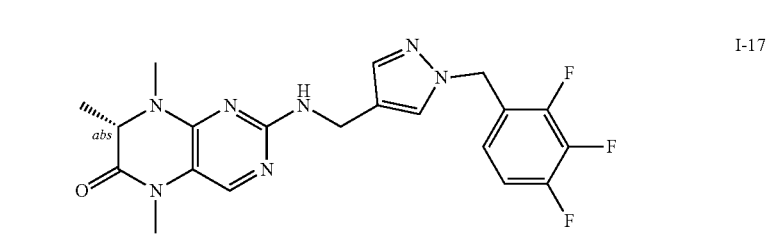
I-17
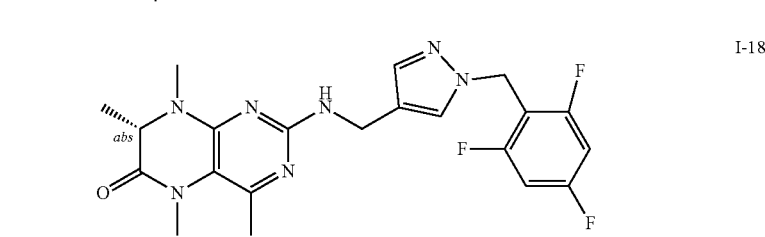
I-18

TABLE A-continued

Exemplary Compounds

TABLE A-continued

Exemplary Compounds

| Compound ID |
|---|
| I-26 |
| I-27 |
| I-28 |
| I-29 |
| I-30 |
| I-31 |
| I-32 |

TABLE A-continued

Exemplary Compounds

| | |
|---|---|
| (structure) | I-33 |
| (structure) | I-34 |
| (structure) | I-35 |
| (structure) | I-36 |
| (structure) | I-37 |
| (structure) | I-38 |

TABLE A-continued

Exemplary Compounds

| Compound | ID |
|---|---|
| (structure) | I-39 |
| (structure) | I-40 |
| (structure) | I-41 |
| (structure) | I-42 |
| (structure) | I-43 |
| (structure) | I-44 |

TABLE A-continued

Exemplary Compounds

I-45

I-46

I-47

I-48

I-49

TABLE A-continued
Exemplary Compounds
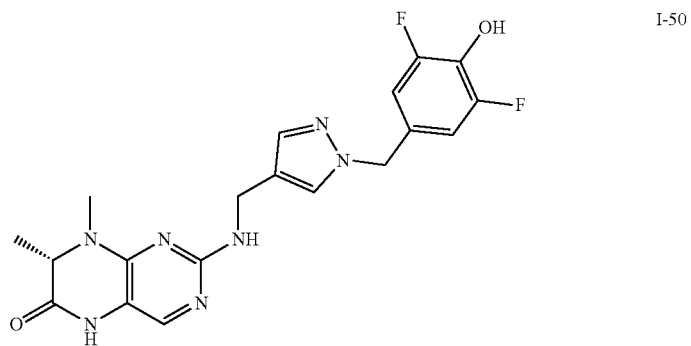
I-50
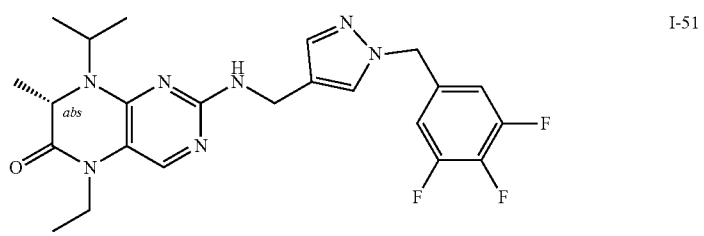
I-51
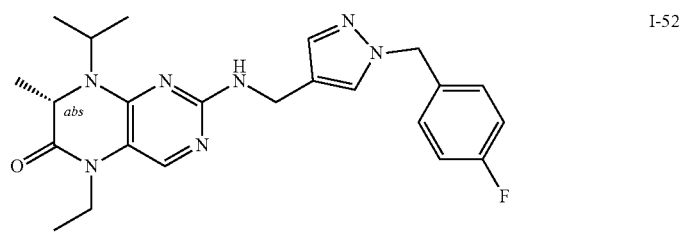
I-52
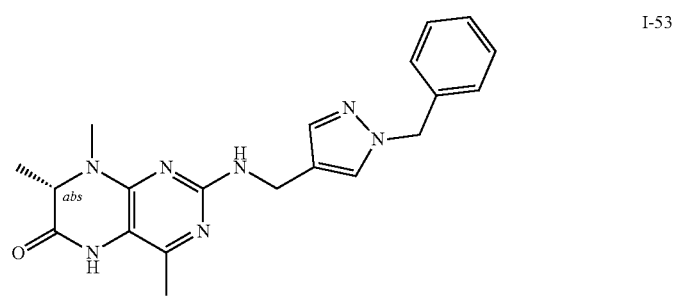
I-53
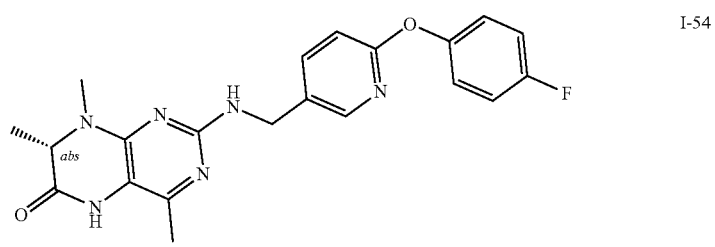
I-54

TABLE A-continued
Exemplary Compounds
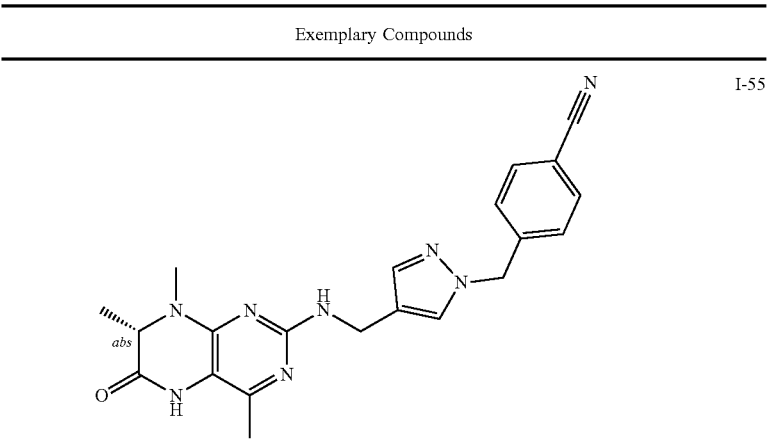
I-55
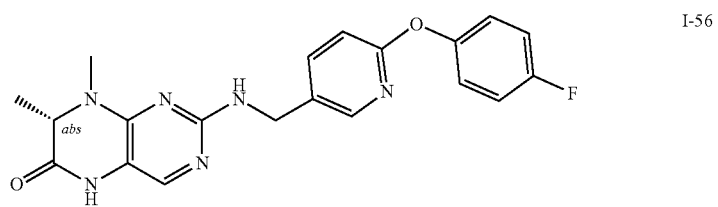
I-56
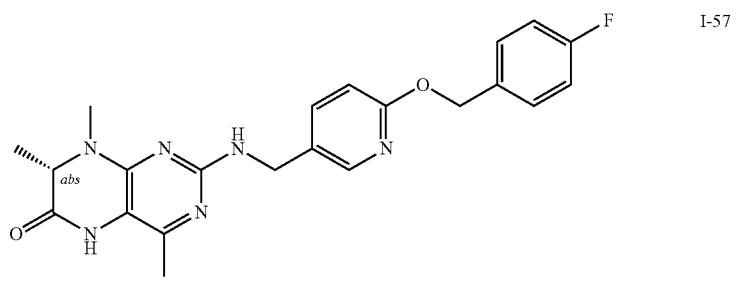
I-57
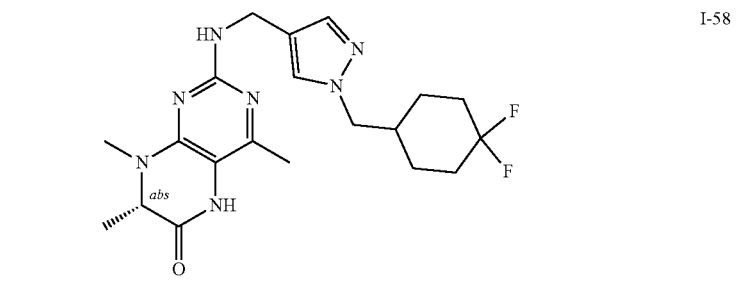
I-58
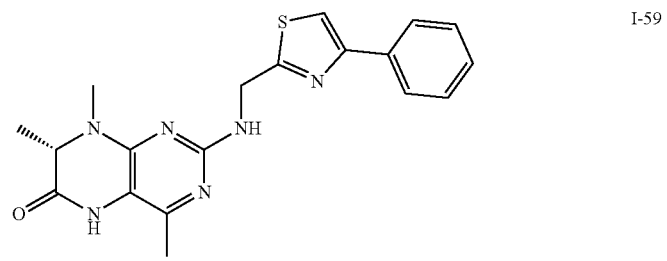
I-59

TABLE A-continued
Exemplary Compounds
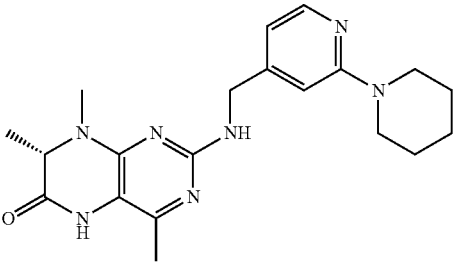 [SMILES: Cc1nc(NCc2ccnc(N3CCCCC3)c2)nc2c1NC(=O)[C@H](C)N2C] I-60
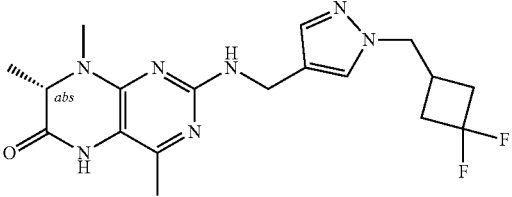 [SMILES: Cc1nc(NCc2cnn(CC3CC(F)(F)C3)c2)nc2c1NC(=O)[C@H](C)N2C] I-61
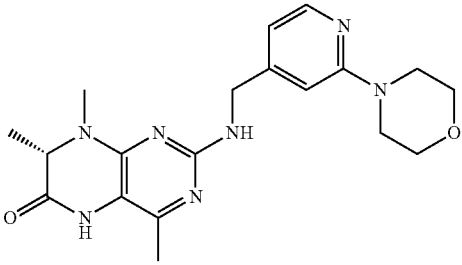 [SMILES: Cc1nc(NCc2ccnc(N3CCOCC3)c2)nc2c1NC(=O)[C@H](C)N2C] I-62
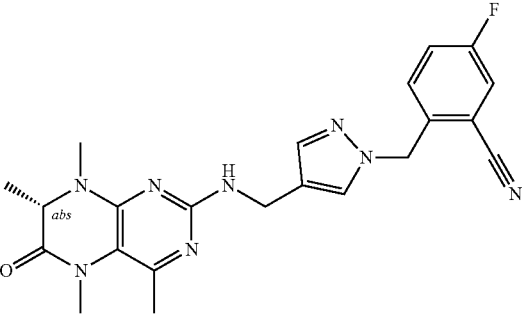 [SMILES: Cc1nc(NCc2cnn(Cc3ccc(F)cc3C#N)c2)nc2c1N(C)C(=O)[C@H](C)N2C] I-63
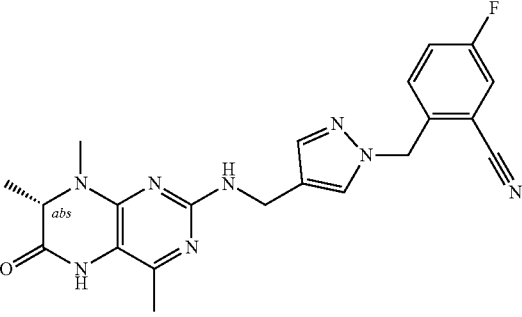 [SMILES: Cc1nc(NCc2cnn(Cc3ccc(F)cc3C#N)c2)nc2c1NC(=O)[C@H](C)N2C] I-64

TABLE A-continued

Exemplary Compounds

| Compound | 
|---|
| I-65 |
| I-66 |
| I-67 |
| I-68 |
| I-69 |
| I-70 |
| I-71 |

TABLE A-continued
Exemplary Compounds
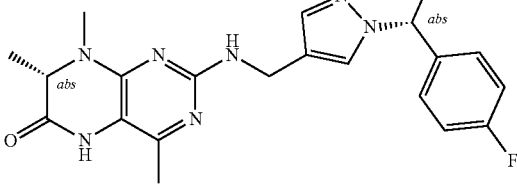
I-72
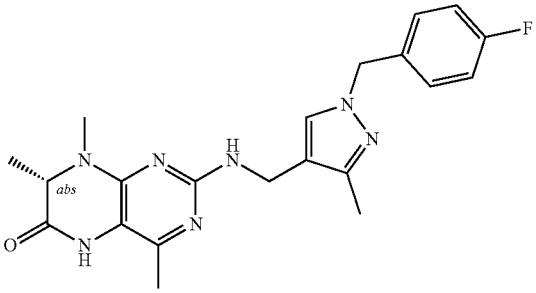 [SMILES: Cc1nn(Cc2ccc(F)cc2)cc1CNc1nc(C)c2c(n1)N(C)[C@@H](C)C(=O)N2]
I-73
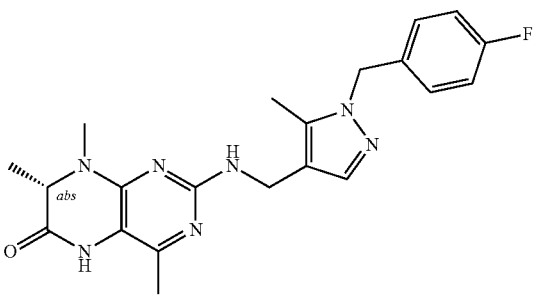 [SMILES: Cc1nc(NCc2cnn(Cc3ccc(F)cc3)c2C)nc2c1NC(=O)[C@H](C)N2C]
I-74
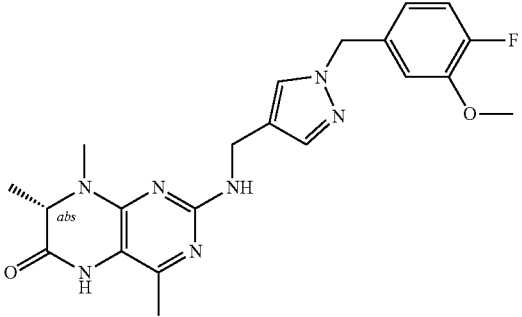 [SMILES: COc1cc(Cn2cc(CNc3nc(C)c4c(n3)N(C)[C@@H](C)C(=O)N4)cn2)ccc1F]
I-75
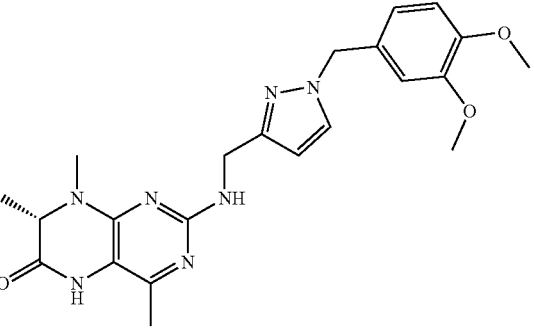 [SMILES: COc1ccc(Cn2ccc(CNc3nc(C)c4c(n3)N(C)[C@@H](C)C(=O)N4)n2)cc1OC]
I-76

TABLE A-continued
Exemplary Compounds
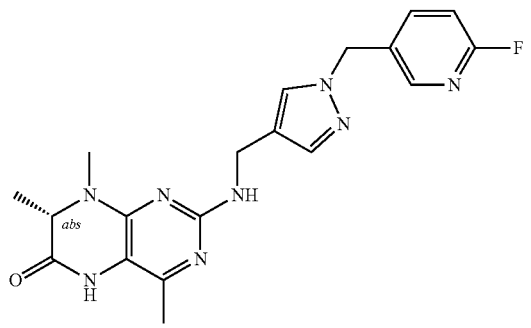 [SMILES: Cc1nc(NCc2cnn(Cc3ccc(F)nc3)c2)nc2c1NC(=O)[C@H](C)N2C]
I-77
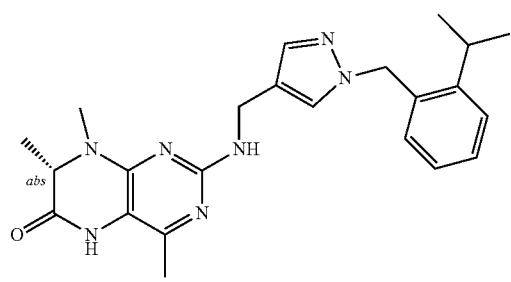 [SMILES: Cc1nc(NCc2cnn(Cc3ccccc3C(C)C)c2)nc2c1NC(=O)[C@H](C)N2C]
I-78
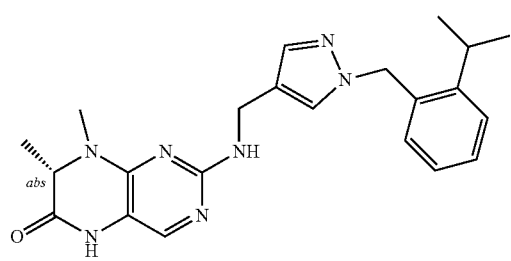 [SMILES: CC(C)c1ccccc1Cn1cc(CNc2ncc3c(n2)N(C)[C@@H](C)C(=O)N3)cn1]
I-79
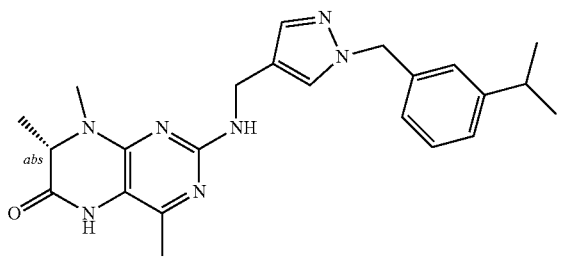 [SMILES: Cc1nc(NCc2cnn(Cc3cccc(C(C)C)c3)c2)nc2c1NC(=O)[C@H](C)N2C]
I-80
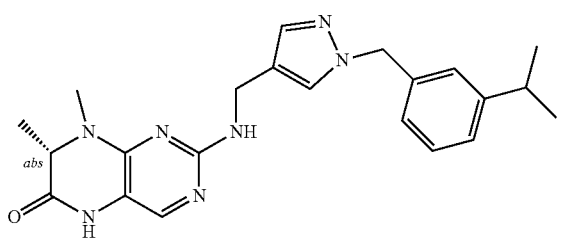 [SMILES: CC(C)c1cccc(Cn2cc(CNc3ncc4c(n3)N(C)[C@@H](C)C(=O)N4)cn2)c1]
I-81

TABLE A-continued
Exemplary Compounds
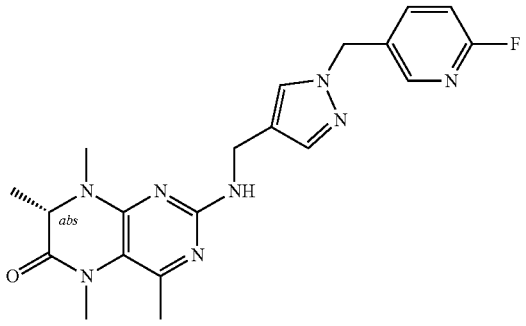 [SMILES: Cc1nc(NCc2cnn(Cc3ccc(F)nc3)c2)nc2c1N(C)C(=O)[C@H](C)N2C]
I-82
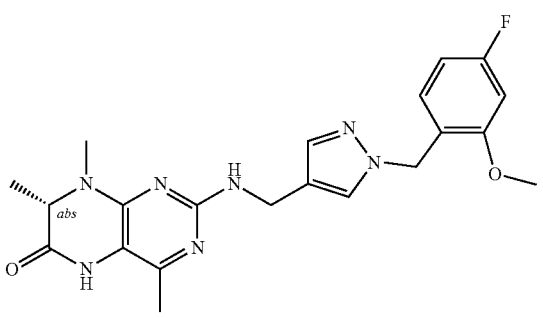 [SMILES: COc1cc(F)ccc1Cn1cc(CNc2nc(C)c3c(n2)N(C)[C@@H](C)C(=O)N3)cn1]
I-83
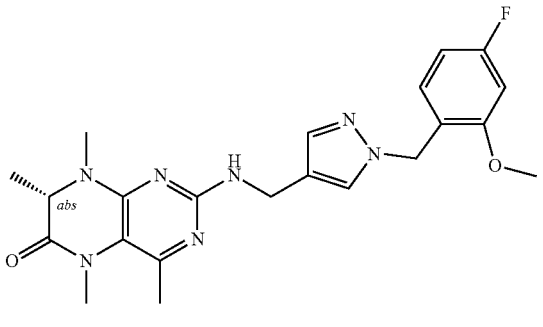 [SMILES: COc1cc(F)ccc1Cn1cc(CNc2nc(C)c3c(n2)N(C)[C@@H](C)C(=O)N3C)cn1]
I-84
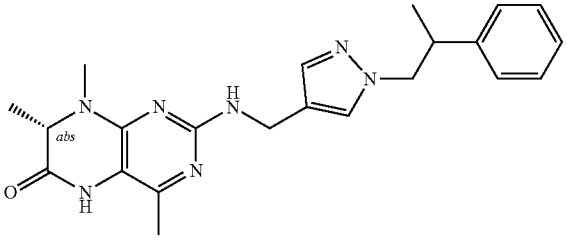 [SMILES: Cc1nc(NCc2cnn(CC(C)c3ccccc3)c2)nc2c1NC(=O)[C@H](C)N2C]
I-85
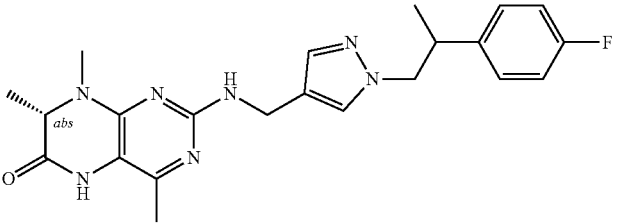 [SMILES: Cc1nc(NCc2cnn(CC(C)c3ccc(F)cc3)c2)nc2c1NC(=O)[C@H](C)N2C]
I-86

TABLE A-continued

Exemplary Compounds

I-87

I-88

I-89

I-90

I-91

TABLE A-continued
Exemplary Compounds
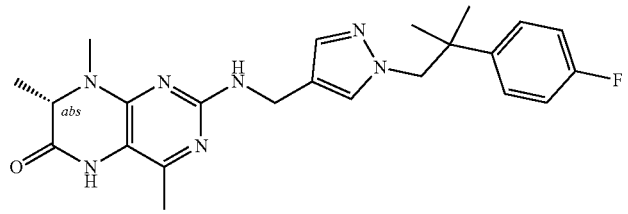 [SMILES: Cc1nc(NCc2cnn(CC(C)(C)c3ccc(F)cc3)c2)nc2c1NC(=O)[C@H](C)N2C]
I-92
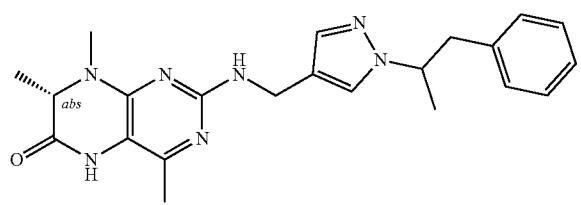 [SMILES: Cc1nc(NCc2cnn(C(C)Cc3ccccc3)c2)nc2c1NC(=O)[C@H](C)N2C]
I-93
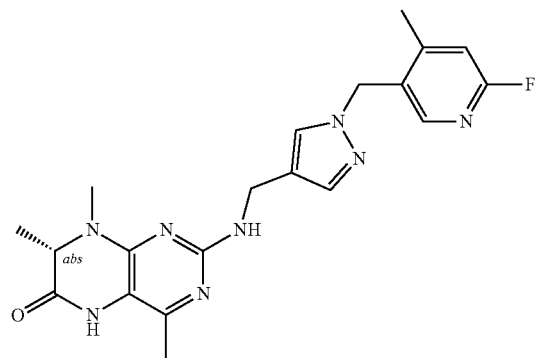 [SMILES: Cc1cc(F)ncc1Cn1cc(CNc2nc(C)c3c(n2)N(C)[C@@H](C)C(=O)N3)cn1]
I-94
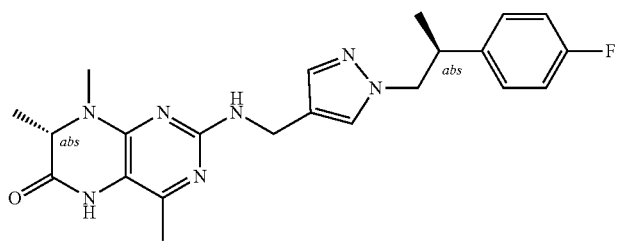 [SMILES: Cc1nc(NCc2cnn(C[C@@H](C)c3ccc(F)cc3)c2)nc2c1NC(=O)[C@H](C)N2C]
I-95
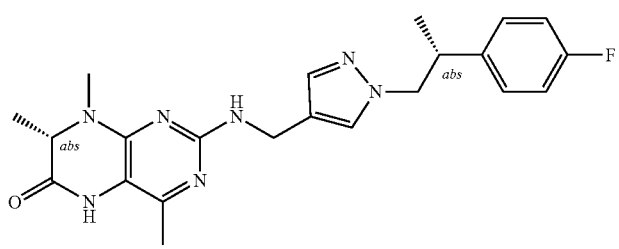 [SMILES: Cc1nc(NCc2cnn(C[C@H](C)c3ccc(F)cc3)c2)nc2c1NC(=O)[C@H](C)N2C]
I-96

TABLE A-continued

Exemplary Compounds

I-97

I-98

I-99

I-100

TABLE A-continued
Exemplary Compounds
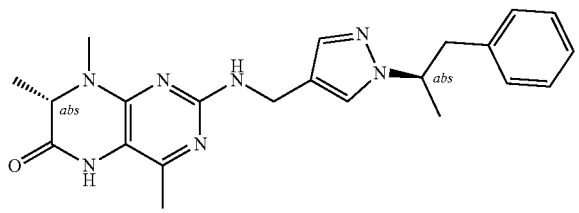 [SMILES: Cc1nc(NCc2cnn([C@H](C)Cc3ccccc3)c2)nc2c1NC(=O)[C@H](C)N2C] I-101
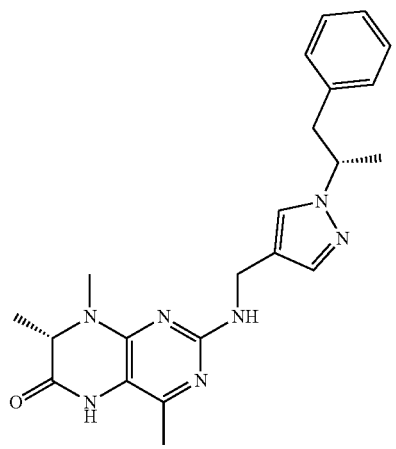 [SMILES: Cc1nc(NCc2cnn([C@@H](C)Cc3ccccc3)c2)nc2c1NC(=O)[C@H](C)N2C] I-102
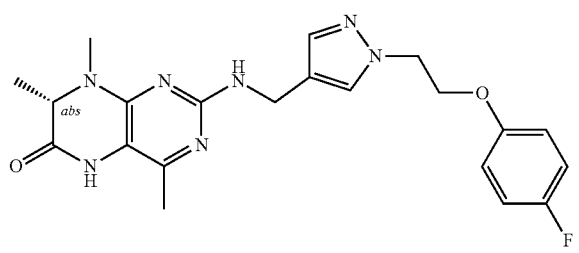 [SMILES: Cc1nc(NCc2cnn(CCOc3ccc(F)cc3)c2)nc2c1NC(=O)[C@H](C)N2C] I-103
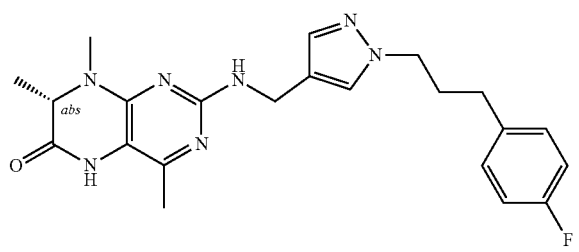 [SMILES: Cc1nc(NCc2cnn(CCCc3ccc(F)cc3)c2)nc2c1NC(=O)[C@H](C)N2C] I-104
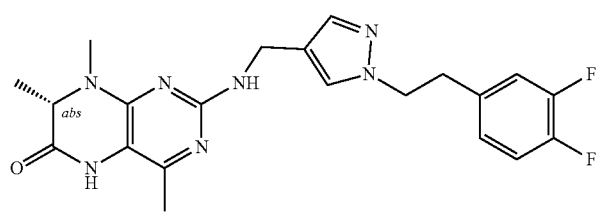 [SMILES: Cc1nc(NCc2cnn(CCc3ccc(F)c(F)c3)c2)nc2c1NC(=O)[C@H](C)N2C] I-105

TABLE A-continued
Exemplary Compounds
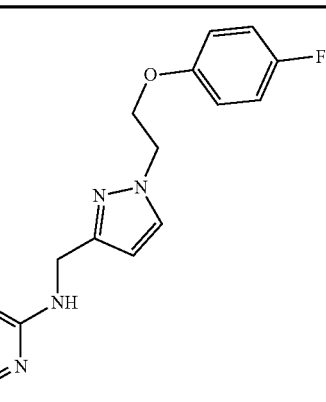
I-106
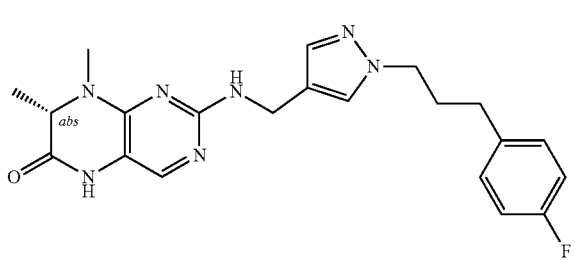 [SMILES: C[C@H]1C(=O)Nc2cnc(NCc3cnn(CCCc4ccc(F)cc4)c3)nc2N1C]
I-107
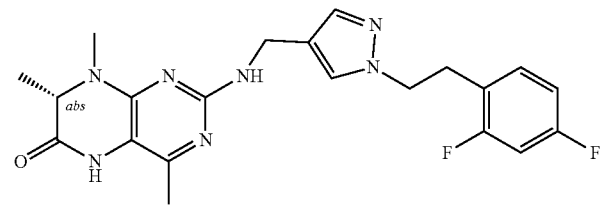 [SMILES: Cc1nc(NCc2cnn(CCc3ccc(F)cc3F)c2)nc2c1NC(=O)[C@H](C)N2C]
I-108
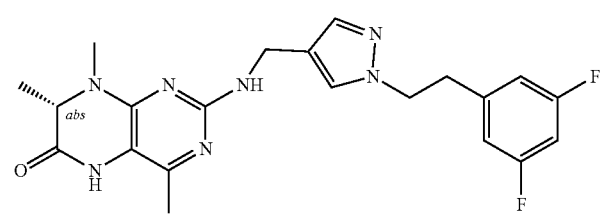 [SMILES: Cc1nc(NCc2cnn(CCc3cc(F)cc(F)c3)c2)nc2c1NC(=O)[C@H](C)N2C]
I-109
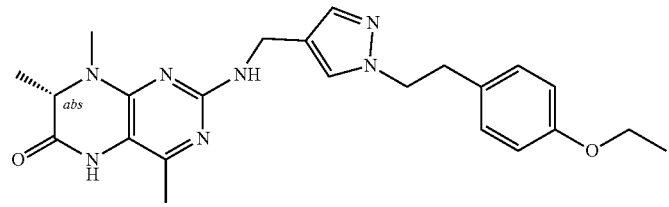 [SMILES: CCOc1ccc(CCn2cc(CNc3nc(C)c4c(n3)N(C)[C@@H](C)C(=O)N4)cn2)cc1]
I-110
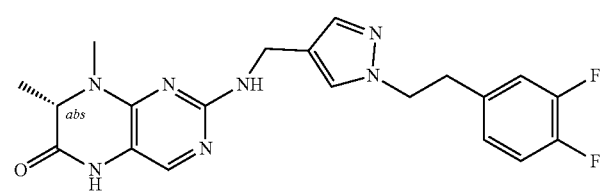 [SMILES: C[C@H]1C(=O)Nc2cnc(NCc3cnn(CCc4ccc(F)c(F)c4)c3)nc2N1C]
I-111

TABLE A-continued
Exemplary Compounds
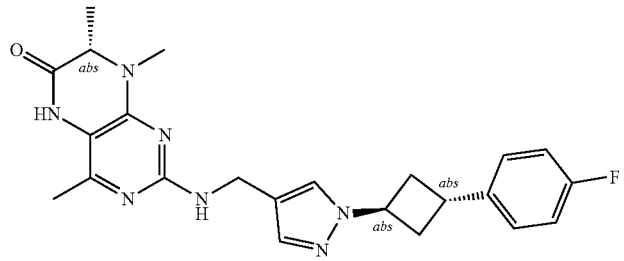 [SMILES: Cc1nc(NCc2cnn([C@H]3C[C@H](c4ccc(F)cc4)C3)c2)nc2c1NC(=O)[C@H](C)N2C]
I-112
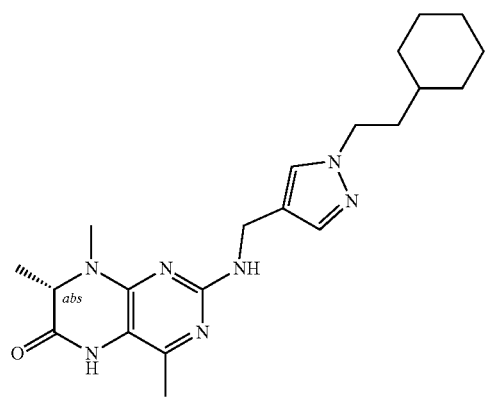 [SMILES: Cc1nc(NCc2cnn(CCC3CCCCC3)c2)nc2c1NC(=O)[C@H](C)N2C]
I-113
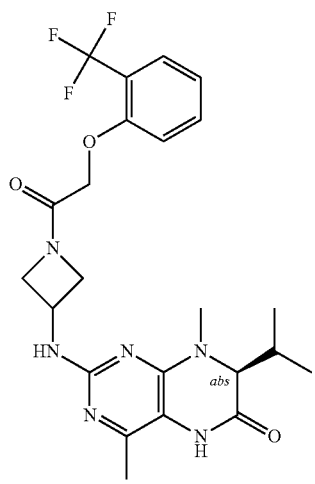 [SMILES: Cc1nc(NC2CN(C(=O)COc3ccccc3C(F)(F)F)C2)nc2c1NC(=O)[C@H](C(C)C)N2C]
I-115
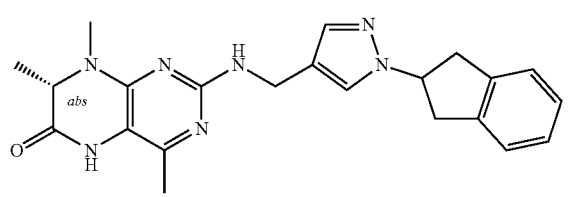 [SMILES: Cc1nc(NCc2cnn(C3Cc4ccccc4C3)c2)nc2c1NC(=O)[C@H](C)N2C]
I-116

TABLE A-continued
Exemplary Compounds
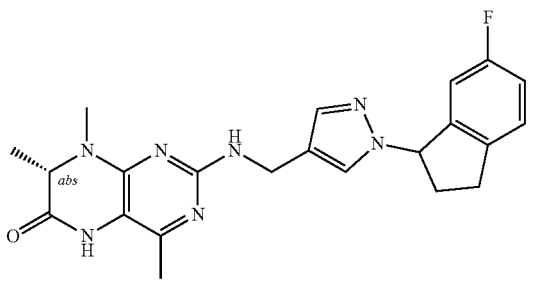 [SMILES: Cc1nc(NCc2cnn(C3CCc4ccc(F)cc43)c2)nc2c1NC(=O)[C@H](C)N2C]
I-117
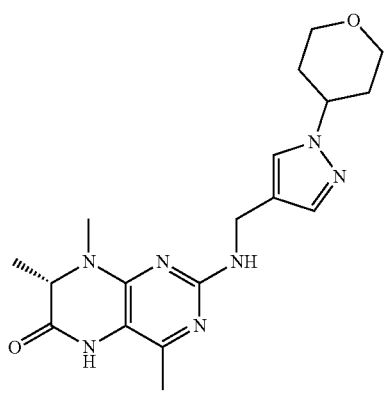 [SMILES: Cc1nc(NCc2cnn(C3CCOCC3)c2)nc2c1NC(=O)[C@H](C)N2C]
I-118
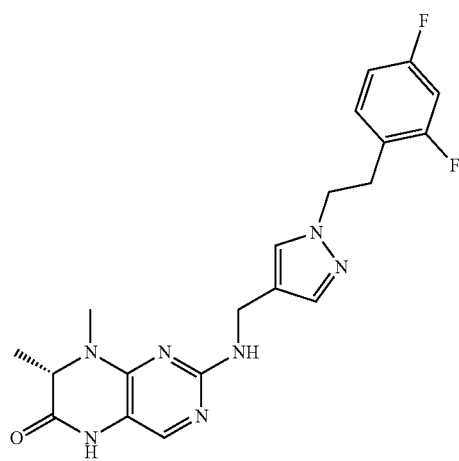 [SMILES: C[C@H]1C(=O)Nc2cnc(NCc3cnn(CCc4ccc(F)cc4F)c3)nc2N1C]
I-119
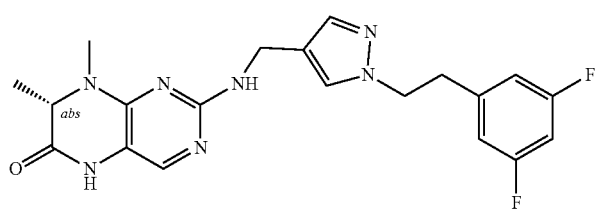 [SMILES: C[C@H]1C(=O)Nc2cnc(NCc3cnn(CCc4cc(F)cc(F)c4)c3)nc2N1C]
I-120

TABLE A-continued
Exemplary Compounds
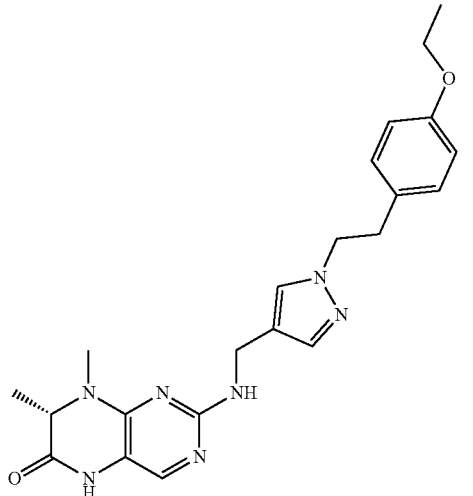 [SMILES: CCOc1ccc(CCn2cc(CNc3ncc4c(n3)N(C)[C@@H](C)C(=O)N4)cn2)cc1]
I-121
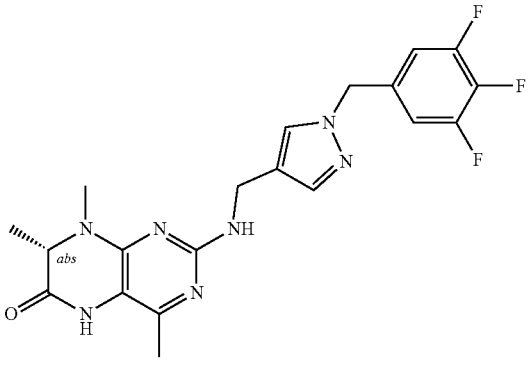 [SMILES: Cc1nc(NCc2cnn(Cc3cc(F)c(F)c(F)c3)c2)nc2c1NC(=O)[C@H](C)N2C]
I-122
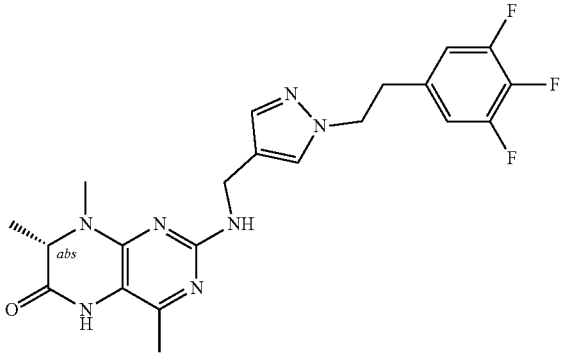 [SMILES: Cc1nc(NCc2cnn(CCc3cc(F)c(F)c(F)c3)c2)nc2c1NC(=O)[C@H](C)N2C]
I-123
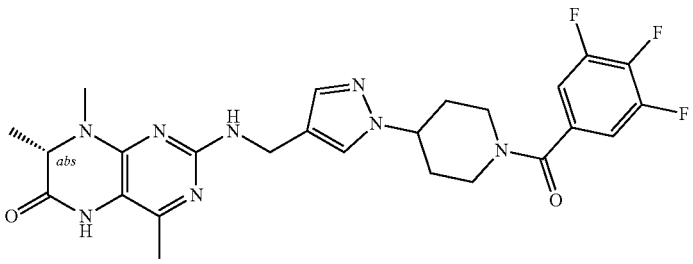 [SMILES: Cc1nc(NCc2cnn(C3CCN(C(=O)c4cc(F)c(F)c(F)c4)CC3)c2)nc2c1NC(=O)[C@H](C)N2C]
I-124

103
TABLE A-continued
Exemplary Compounds
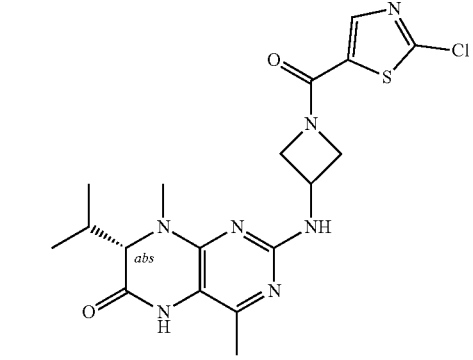 [SMILES: Cc1nc(NC2CN(C(=O)c3cnc(Cl)s3)C2)nc2c1NC(=O)[C@H](C(C)C)N2C]
I-125
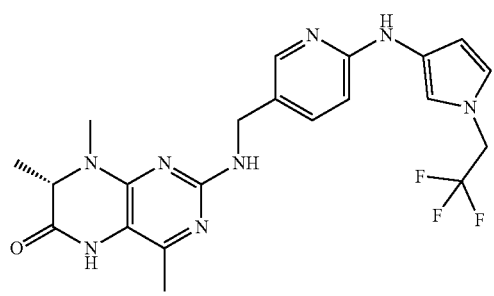 [SMILES: Cc1nc(NCc2ccc(Nc3ccn(CC(F)(F)F)c3)nc2)nc2c1NC(=O)[C@H](C)N2C]
I-126
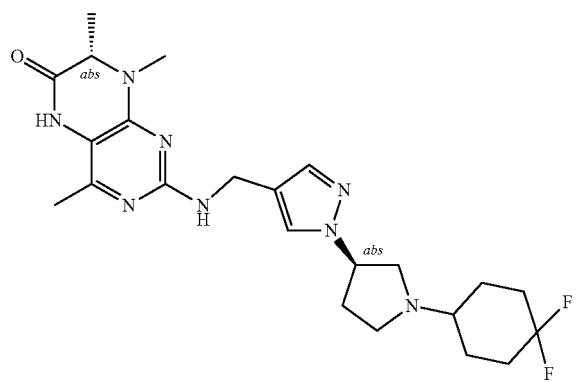 [SMILES: Cc1nc(NCc2cnn([C@@H]3CCN(C4CCC(F)(F)CC4)C3)c2)nc2c1NC(=O)[C@H](C)N2C]
I-127
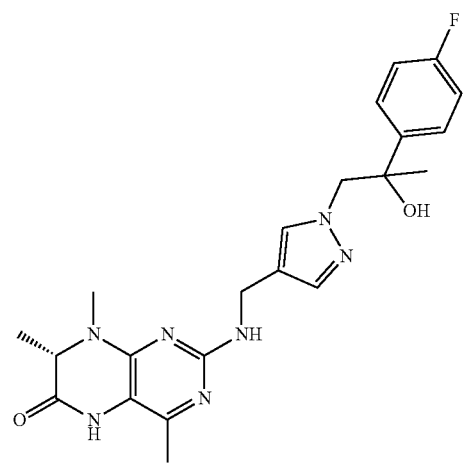 [SMILES: Cc1nc(NCc2cnn(CC(C)(O)c3ccc(F)cc3)c2)nc2c1NC(=O)[C@H](C)N2C]
I-128

TABLE A-continued
Exemplary Compounds
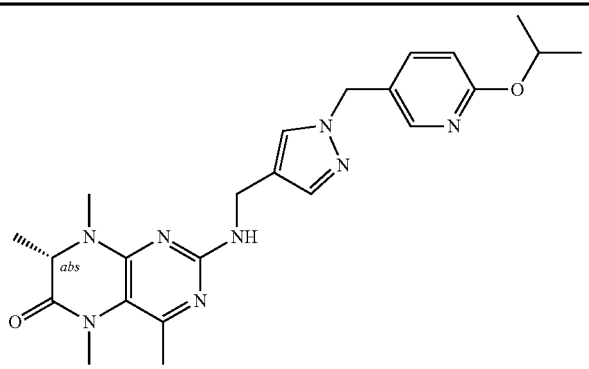
I-129
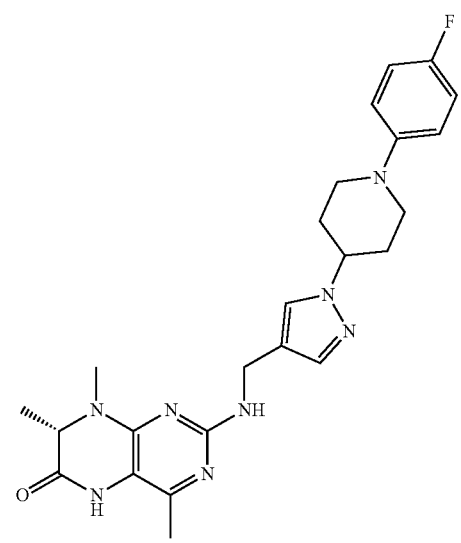 [SMILES: Cc1nc(NCc2cnn(C3CCN(c4ccc(F)cc4)CC3)c2)nc2c1NC(=O)[C@H](C)N2C]
I-130
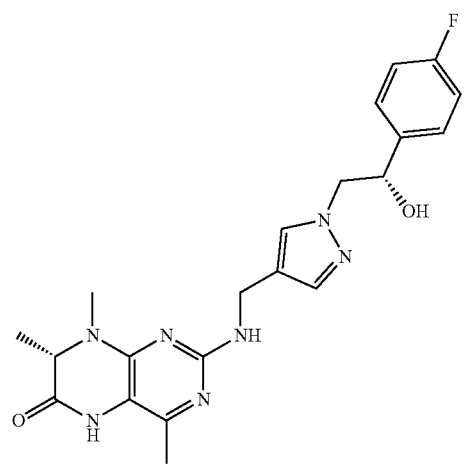 [SMILES: Cc1nc(NCc2cnn(C[C@@H](O)c3ccc(F)cc3)c2)nc2c1NC(=O)[C@H](C)N2C]
I-131
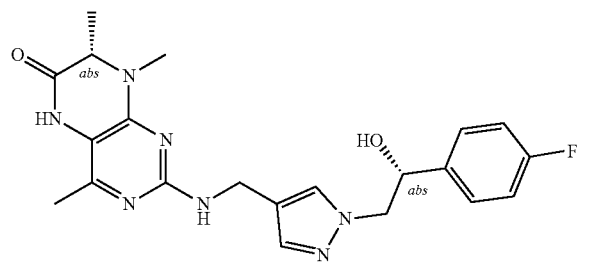 [SMILES: Cc1nc(NCc2cnn(C[C@H](O)c3ccc(F)cc3)c2)nc2c1NC(=O)[C@H](C)N2C]
I-132

TABLE A-continued
Exemplary Compounds
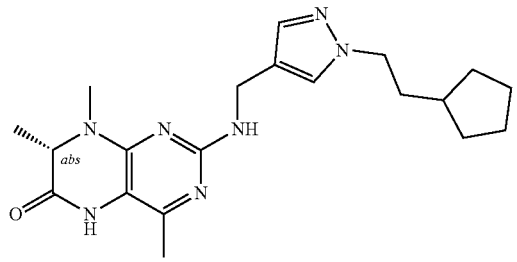 [SMILES: Cc1nc(NCc2cnn(CCC3CCCC3)c2)nc2c1NC(=O)[C@H](C)N2C]
I-133
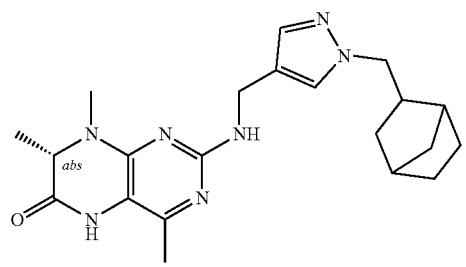 [SMILES: Cc1nc(NCc2cnn(CC3CC4CCC3C4)c2)nc2c1NC(=O)[C@H](C)N2C]
I-134
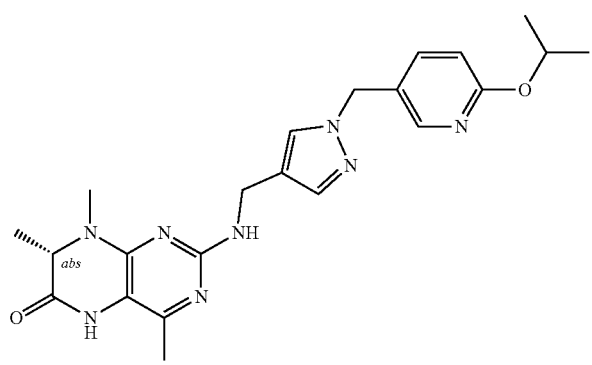 [SMILES: Cc1nc(NCc2cnn(Cc3ccc(OC(C)C)nc3)c2)nc2c1NC(=O)[C@H](C)N2C]
I-135
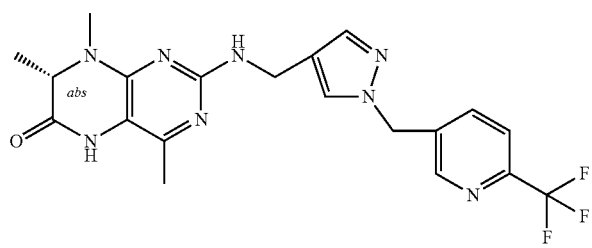 [SMILES: Cc1nc(NCc2cnn(Cc3ccc(C(F)(F)F)nc3)c2)nc2c1NC(=O)[C@H](C)N2C]
I-136
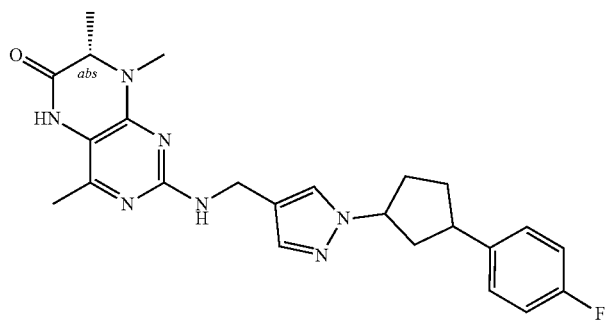 [SMILES: Cc1nc(NCc2cnn(C3CCC(c4ccc(F)cc4)C3)c2)nc2c1NC(=O)[C@H](C)N2C]
I-137

TABLE A-continued
Exemplary Compounds
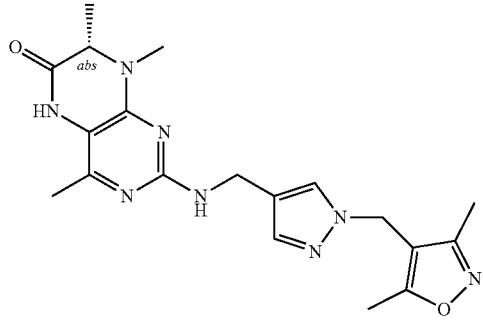 [SMILES: Cc1noc(C)c1Cn1cc(CNc2nc(C)c3c(n2)N(C)[C@@H](C)C(=O)N3)cn1]
I-138
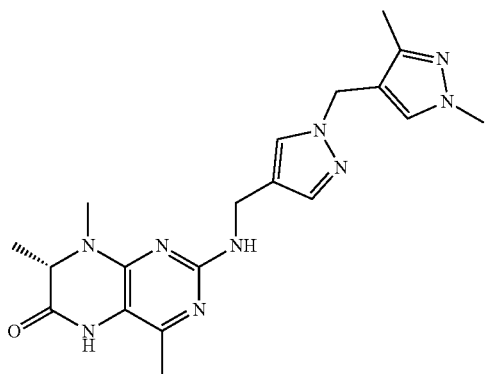 [SMILES: Cc1nn(C)cc1Cn1cc(CNc2nc(C)c3c(n2)N(C)[C@@H](C)C(=O)N3)cn1]
I-139
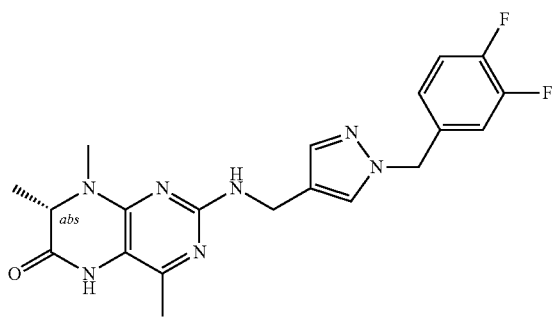 [SMILES: Cc1nc(NCc2cnn(Cc3ccc(F)c(F)c3)c2)nc2c1NC(=O)[C@H](C)N2C]
I-140
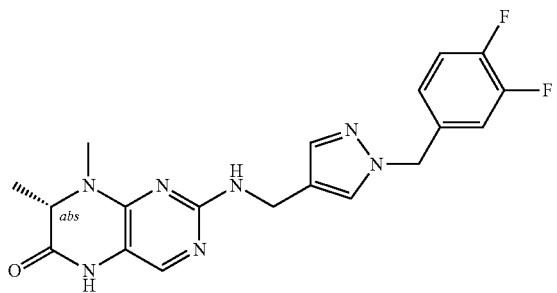 [SMILES: C[C@H]1C(=O)Nc2cnc(NCc3cnn(Cc4ccc(F)c(F)c4)c3)nc2N1C]
I-141

TABLE A-continued

Exemplary Compounds

I-142

I-143

I-144

I-145

TABLE A-continued
Exemplary Compounds
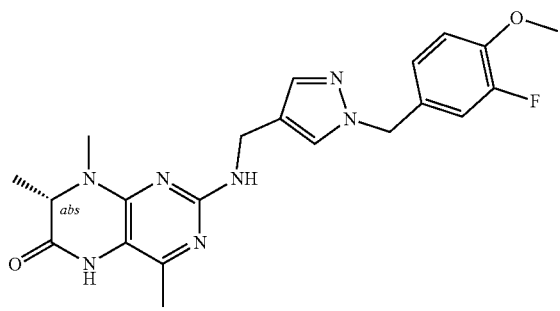 [SMILES: COc1ccc(Cn2cc(CNc3nc(C)c4c(n3)N(C)[C@@H](C)C(=O)N4)cn2)cc1F]
I-146
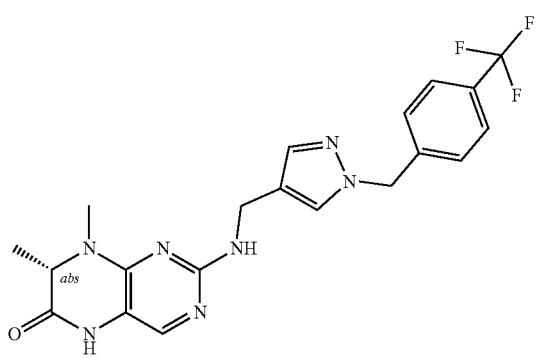 [SMILES: C[C@H]1C(=O)Nc2cnc(NCc3cnn(Cc4ccc(C(F)(F)F)cc4)c3)nc2N1C]
I-147
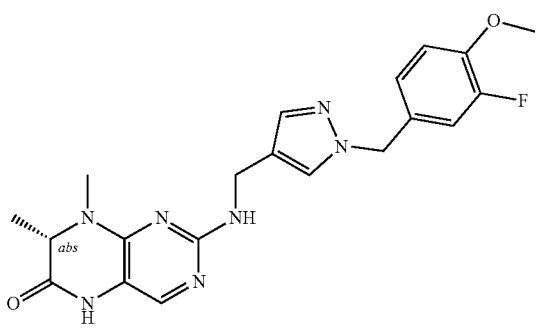 [SMILES: COc1ccc(Cn2cc(CNc3ncc4c(n3)N(C)[C@@H](C)C(=O)N4)cn2)cc1F]
I-148
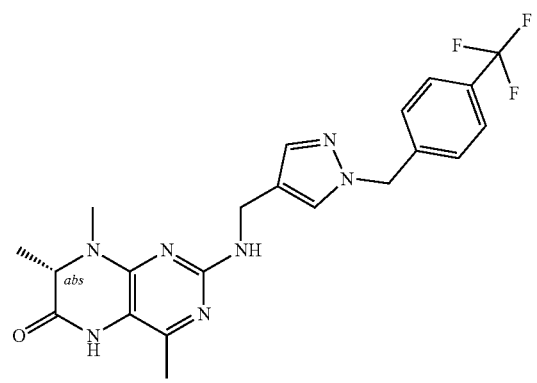 [SMILES: Cc1nc(NCc2cnn(Cc3ccc(C(F)(F)F)cc3)c2)nc2c1NC(=O)[C@H](C)N2C]
I-149

TABLE A-continued

Exemplary Compounds

I-150
I-151
I-152
I-153
I-154
I-155
I-156

TABLE A-continued
Exemplary Compounds
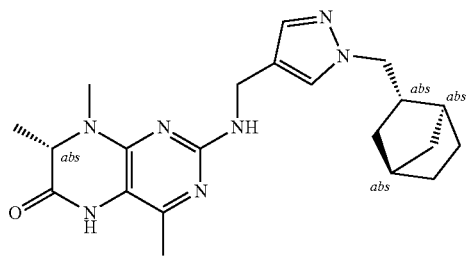 [SMILES: Cc1nc(NCc2cnn(C[C@H]3C[C@@H]4CC[C@H]3C4)c2)nc2c1NC(=O)[C@H](C)N2C]
I-157
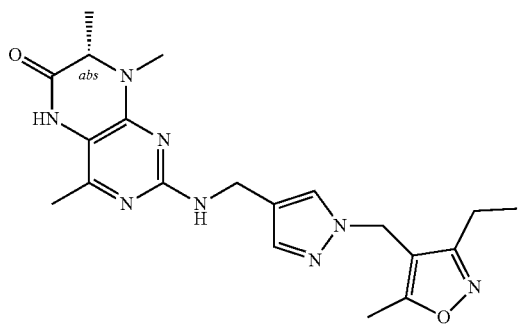 [SMILES: CCc1noc(C)c1Cn1cc(CNc2nc(C)c3c(n2)N(C)[C@@H](C)C(=O)N3)cn1]
I-158
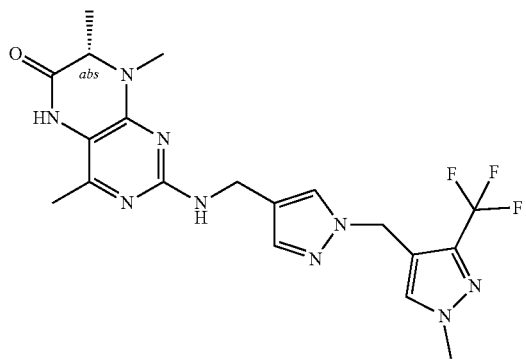 [SMILES: Cc1nc(NCc2cnn(Cc3cn(C)nc3C(F)(F)F)c2)nc2c1NC(=O)[C@H](C)N2C]
I-159
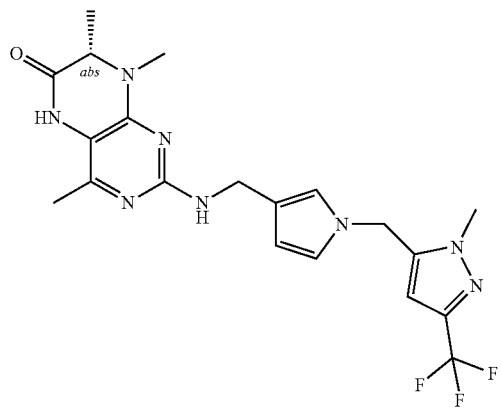 [SMILES: Cc1nc(NCc2ccn(Cc3cc(C(F)(F)F)nn3C)c2)nc2c1NC(=O)[C@H](C)N2C]
I-160

TABLE A-continued
Exemplary Compounds
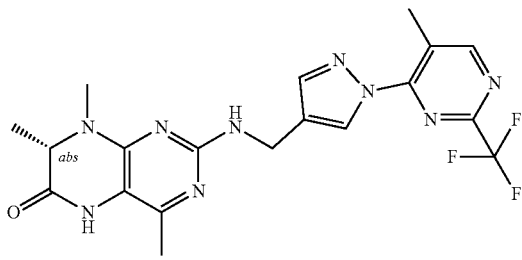 [SMILES: Cc1cnc(C(F)(F)F)nc1-n1cc(CNc2nc(C)c3c(n2)N(C)[C@@H](C)C(=O)N3)cn1]
I-161
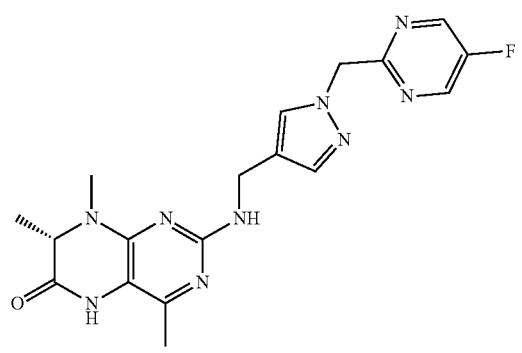 [SMILES: Cc1nc(NCc2cnn(Cc3ncc(F)cn3)c2)nc2c1NC(=O)[C@H](C)N2C]
I-162
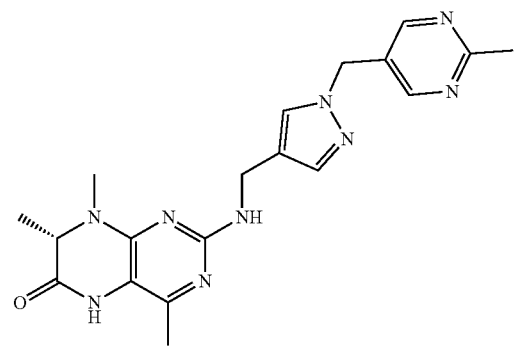 [SMILES: Cc1ncc(Cn2cc(CNc3nc(C)c4c(n3)N(C)[C@@H](C)C(=O)N4)cn2)cn1]
I-163
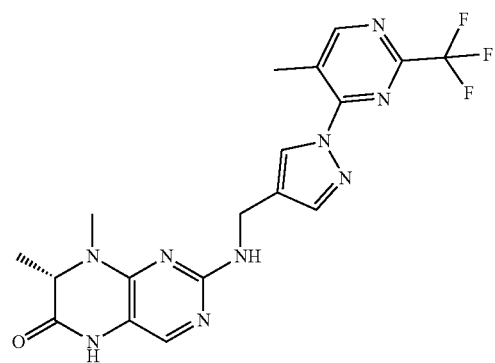 [SMILES: Cc1cnc(C(F)(F)F)nc1-n1cc(CNc2ncc3c(n2)N(C)[C@@H](C)C(=O)N3)cn1]
I-164

TABLE A-continued
Exemplary Compounds
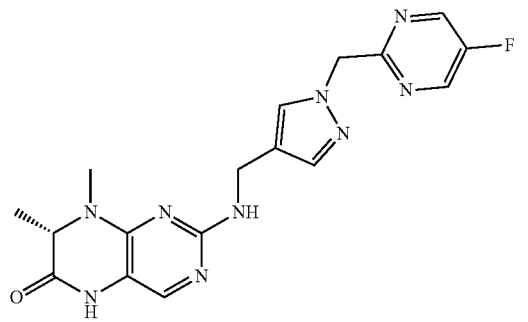 [SMILES: C[C@H]1C(=O)Nc2cnc(NCc3cnn(Cc4ncc(F)cn4)c3)nc2N1C]
I-165
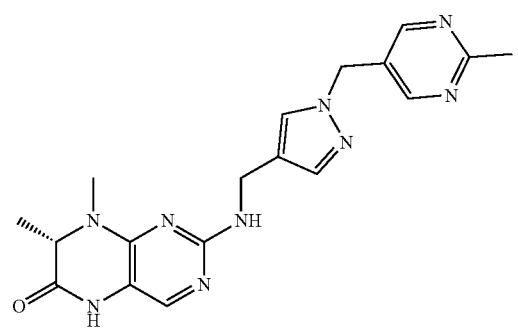 [SMILES: Cc1ncc(Cn2cc(CNc3ncc4c(n3)N(C)[C@@H](C)C(=O)N4)cn2)cn1]
I-166
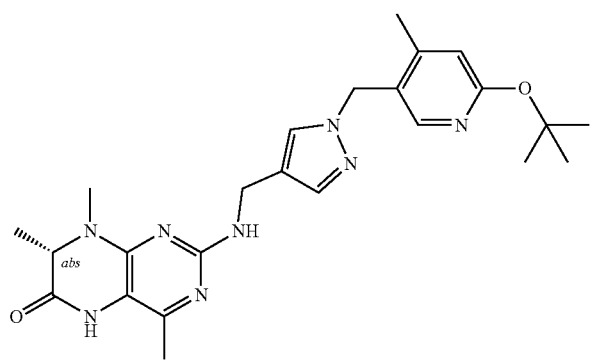 [SMILES: Cc1cc(OC(C)(C)C)ncc1Cn1cc(CNc2nc(C)c3c(n2)N(C)[C@@H](C)C(=O)N3)cn1]
I-167
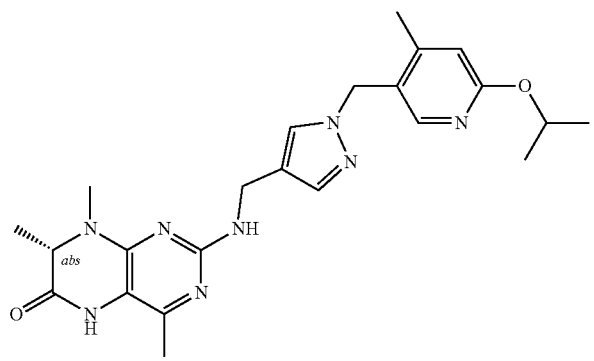 [SMILES: Cc1cc(OC(C)C)ncc1Cn1cc(CNc2nc(C)c3c(n2)N(C)[C@@H](C)C(=O)N3)cn1]
I-168

TABLE A-continued
Exemplary Compounds
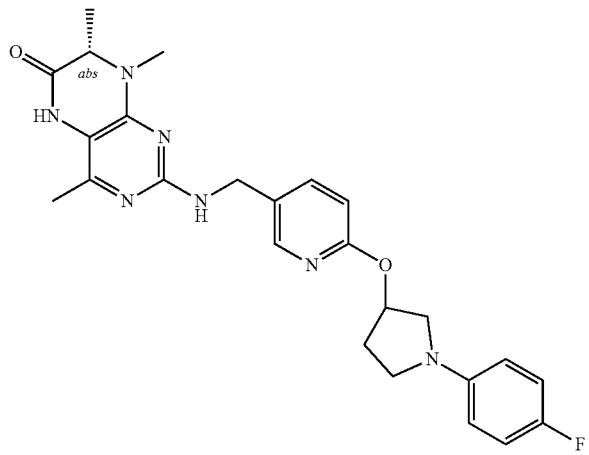 [SMILES: Cc1nc(NCc2ccc(OC3CCN(c4ccc(F)cc4)C3)nc2)nc2c1NC(=O)[C@H](C)N2C]
I-169
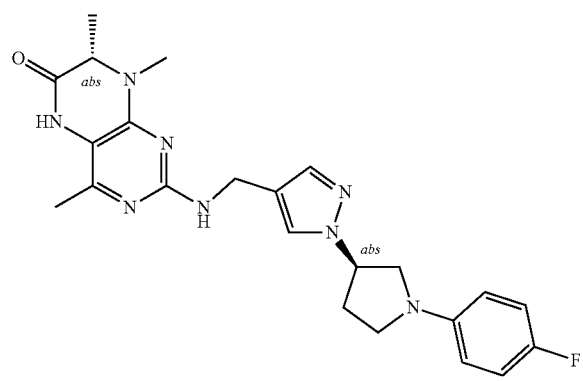 [SMILES: Cc1nc(NCc2cnn([C@@H]3CCN(c4ccc(F)cc4)C3)c2)nc2c1NC(=O)[C@H](C)N2C]
I-170
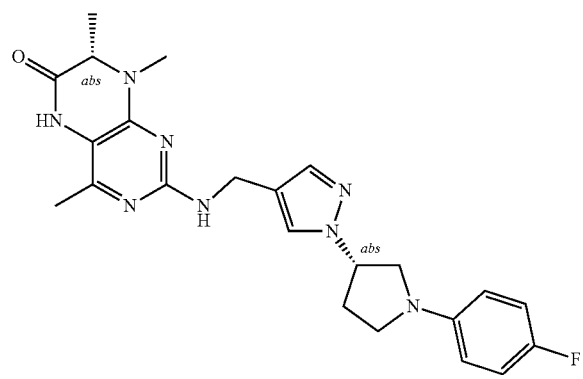 [SMILES: Cc1nc(NCc2cnn([C@H]3CCN(c4ccc(F)cc4)C3)c2)nc2c1NC(=O)[C@H](C)N2C]
I-171
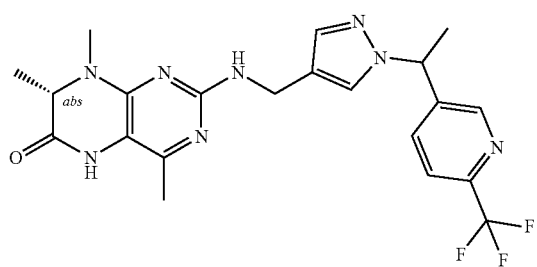 [SMILES: Cc1nc(NCc2cnn(C(C)c3ccc(C(F)(F)F)nc3)c2)nc2c1NC(=O)[C@H](C)N2C]
I-172

TABLE A-continued
Exemplary Compounds
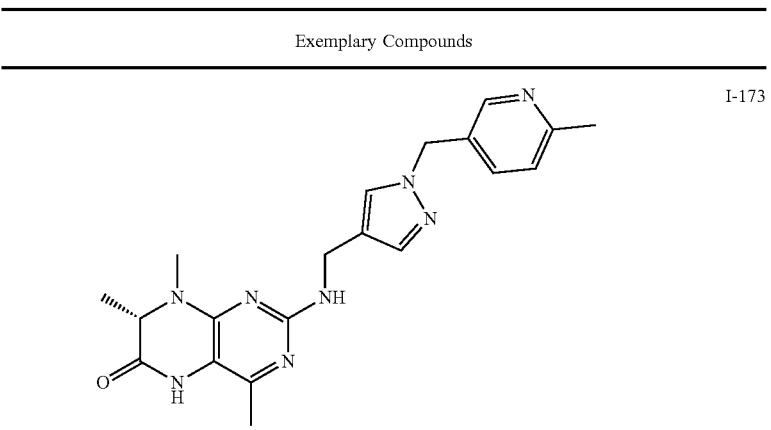
I-173
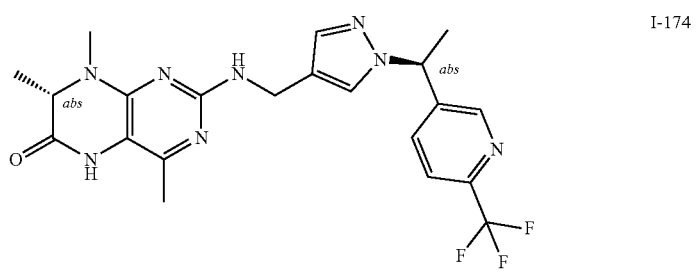
I-174
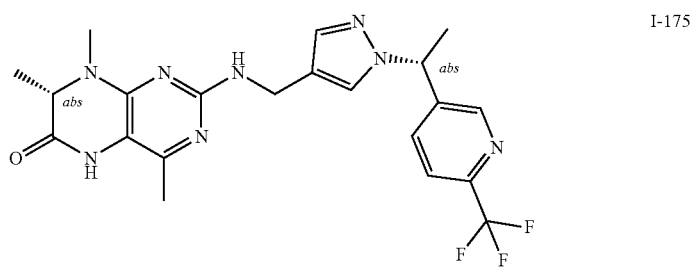
I-175
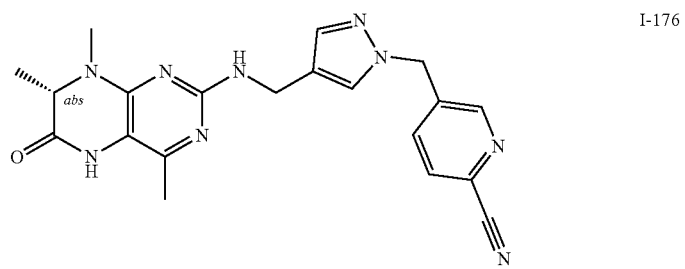
I-176
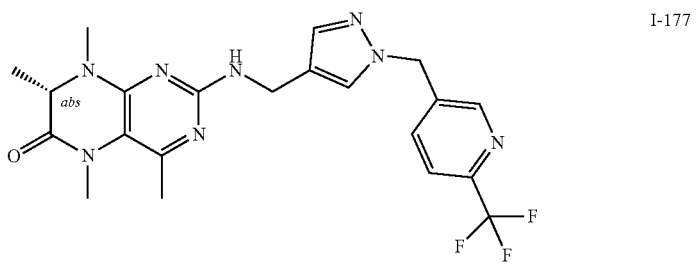
I-177

TABLE A-continued
Exemplary Compounds
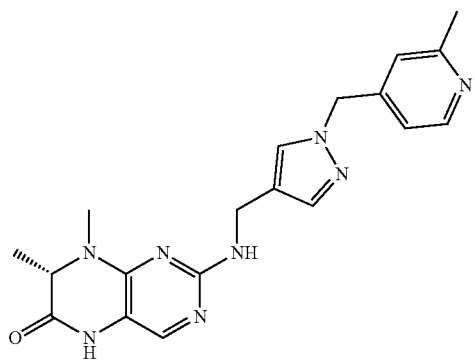 [SMILES: Cc1cc(Cn2cc(CNc3ncc4c(n3)N(C)[C@@H](C)C(=O)N4)cn2)ccn1]
I-178
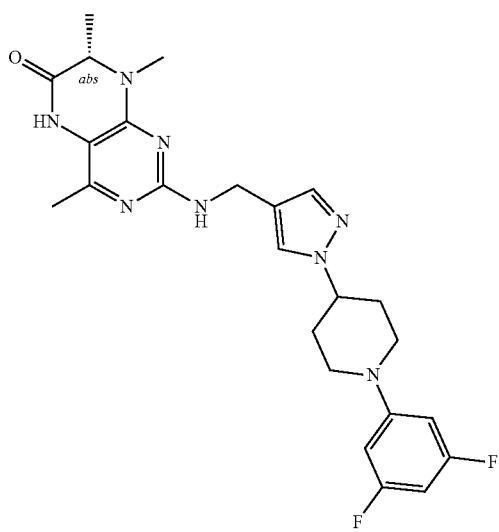 [SMILES: Cc1nc(NCc2cnn(C3CCN(c4cc(F)cc(F)c4)CC3)c2)nc2c1NC(=O)[C@H](C)N2C]
I-179
I-180
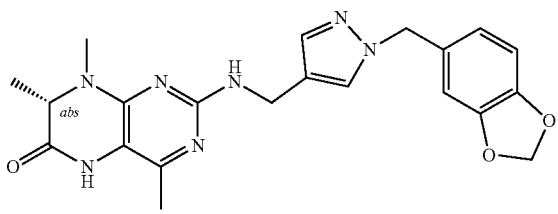 [SMILES: Cc1nc(NCc2cnn(Cc3ccc4c(c3)OCO4)c2)nc2c1NC(=O)[C@H](C)N2C]
I-181
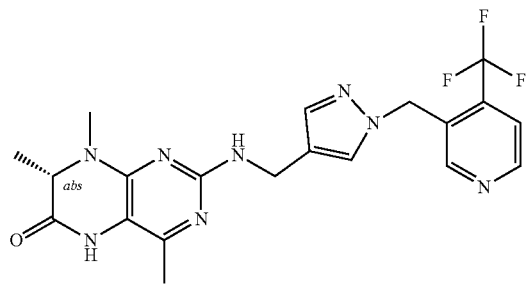 [SMILES: Cc1nc(NCc2cnn(Cc3cnccc3C(F)(F)F)c2)nc2c1NC(=O)[C@H](C)N2C]
I-182

TABLE A-continued
Exemplary Compounds
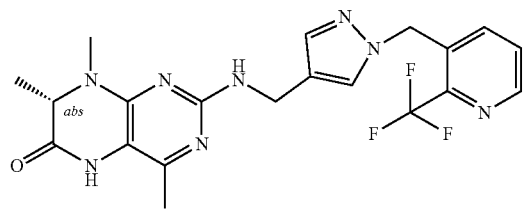 [SMILES: Cc1nc(NCc2cnn(Cc3cccnc3C(F)(F)F)c2)nc2c1NC(=O)[C@H](C)N2C]
I-183
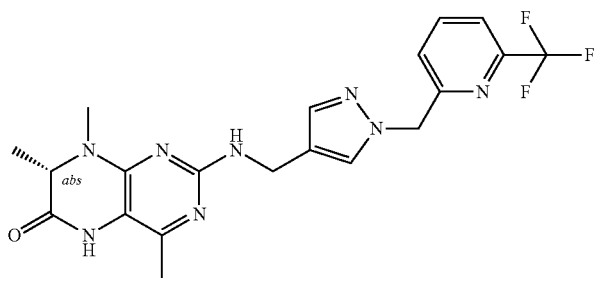 [SMILES: Cc1nc(NCc2cnn(Cc3cccc(C(F)(F)F)n3)c2)nc2c1NC(=O)[C@H](C)N2C]
I-184
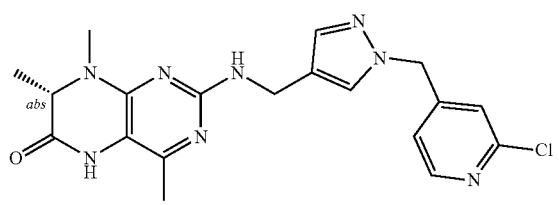 [SMILES: Cc1nc(NCc2cnn(Cc3ccnc(Cl)c3)c2)nc2c1NC(=O)[C@H](C)N2C]
I-185
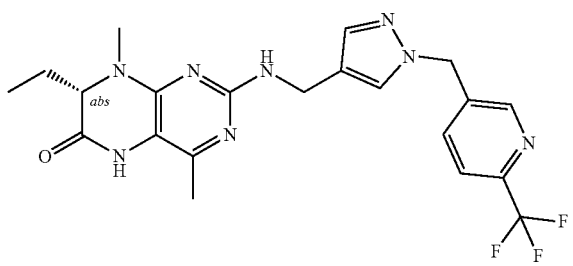 [SMILES: CC[C@H]1C(=O)Nc2c(C)nc(NCc3cnn(Cc4ccc(C(F)(F)F)nc4)c3)nc2N1C]
I-186
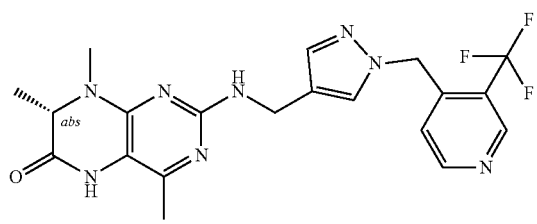 [SMILES: Cc1nc(NCc2cnn(Cc3ccncc3C(F)(F)F)c2)nc2c1NC(=O)[C@H](C)N2C]
I-187
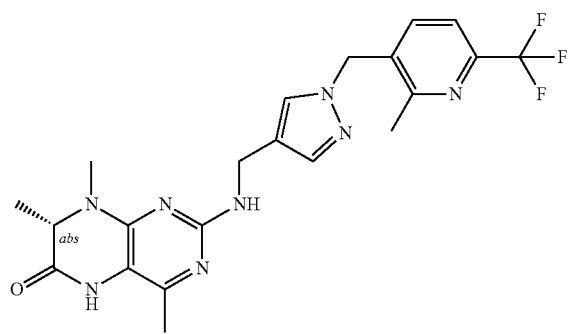 [SMILES: Cc1nc(C(F)(F)F)ccc1Cn1cc(CNc2nc(C)c3c(n2)N(C)[C@@H](C)C(=O)N3)cn1]
I-188

TABLE A-continued
Exemplary Compounds
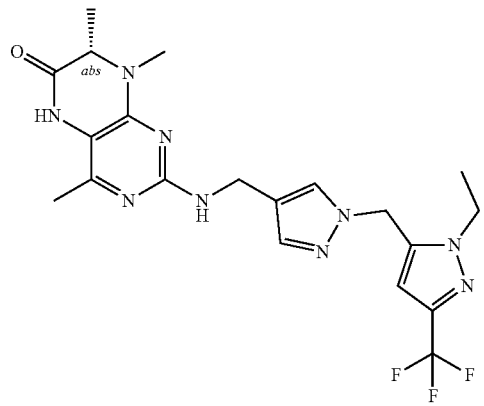 [SMILES: CCn1nc(C(F)(F)F)cc1Cn1cc(CNc2nc(C)c3c(n2)N(C)[C@@H](C)C(=O)N3)cn1]
I-189
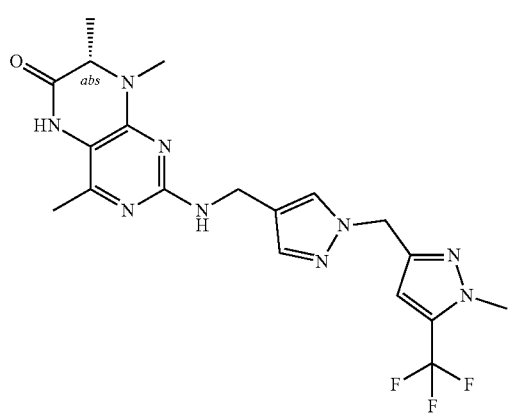 [SMILES: Cc1nc(NCc2cnn(Cc3cc(C(F)(F)F)n(C)n3)c2)nc2c1NC(=O)[C@H](C)N2C]
I-190
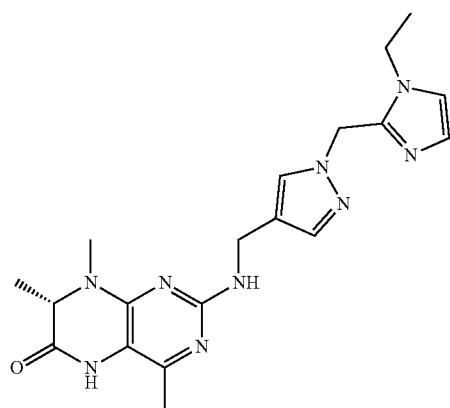 [SMILES: CCn1ccnc1Cn1cc(CNc2nc(C)c3c(n2)N(C)[C@@H](C)C(=O)N3)cn1]
I-191
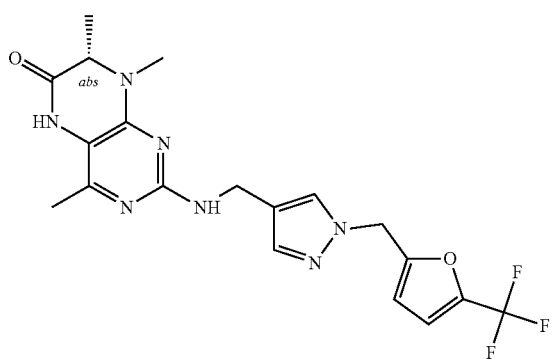 [SMILES: Cc1nc(NCc2cnn(Cc3ccc(C(F)(F)F)o3)c2)nc2c1NC(=O)[C@H](C)N2C]
I-192

TABLE A-continued
Exemplary Compounds
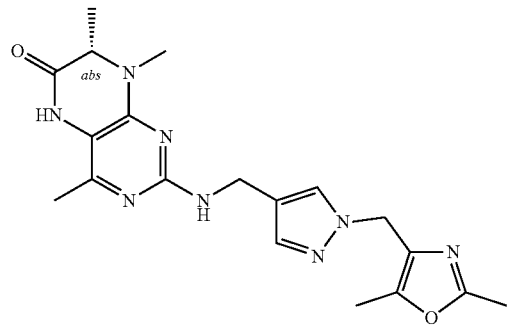 [SMILES: Cc1nc(Cn2cc(CNc3nc(C)c4c(n3)N(C)[C@@H](C)C(=O)N4)cn2)c(C)o1]
I-193
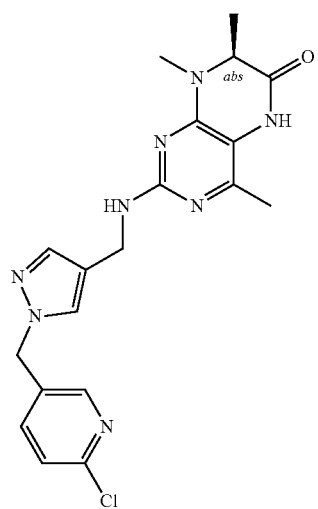 [SMILES: Cc1nc(NCc2cnn(Cc3ccc(Cl)nc3)c2)nc2c1NC(=O)[C@H](C)N2C]
I-194
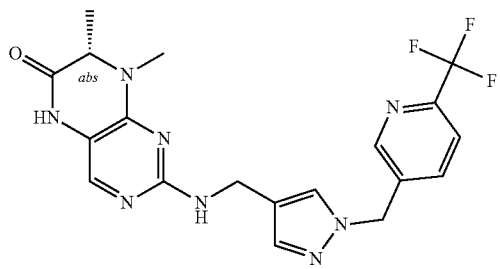 [SMILES: C[C@H]1C(=O)Nc2cnc(NCc3cnn(Cc4ccc(C(F)(F)F)nc4)c3)nc2N1C]
I-195
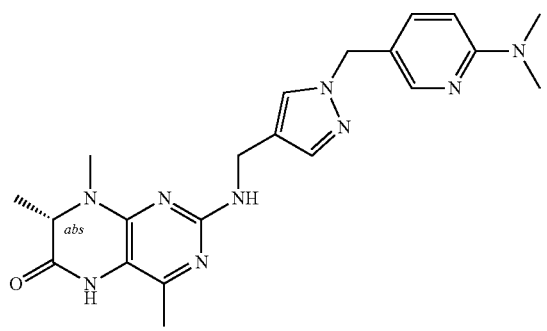 [SMILES: Cc1nc(NCc2cnn(Cc3ccc(N(C)C)nc3)c2)nc2c1NC(=O)[C@H](C)N2C]
I-196

TABLE A-continued
Exemplary Compounds
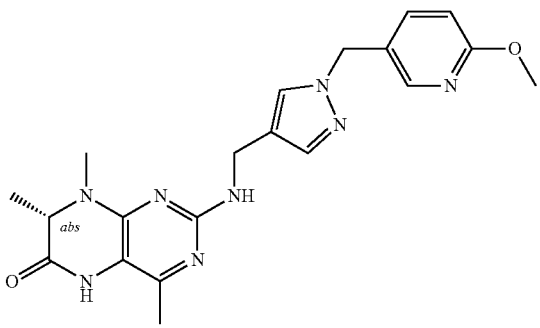 [SMILES: COc1ccc(Cn2cc(CNc3nc(C)c4c(n3)N(C)[C@@H](C)C(=O)N4)cn2)cn1]
I-197
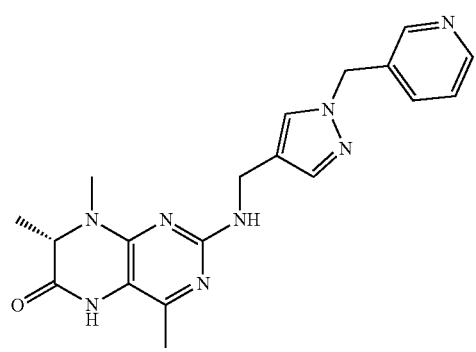 [SMILES: Cc1nc(NCc2cnn(Cc3cccnc3)c2)nc2c1NC(=O)[C@H](C)N2C]
I-198
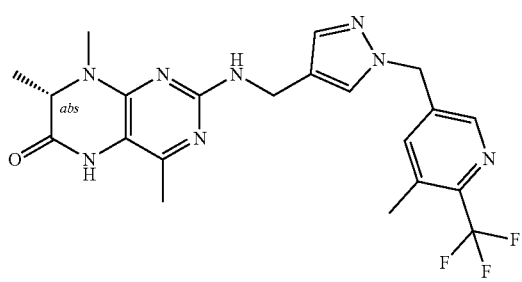 [SMILES: Cc1cc(Cn2cc(CNc3nc(C)c4c(n3)N(C)[C@@H](C)C(=O)N4)cn2)cnc1C(F)(F)F]
I-199
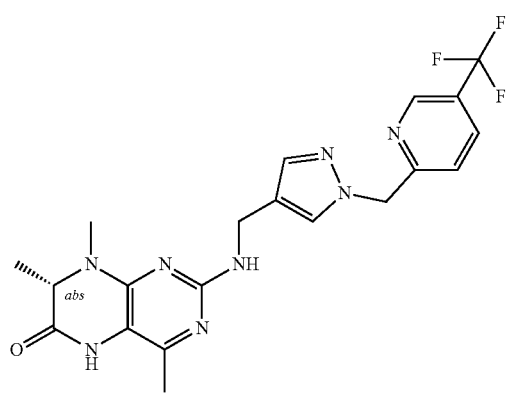 [SMILES: Cc1nc(NCc2cnn(Cc3ccc(C(F)(F)F)cn3)c2)nc2c1NC(=O)[C@H](C)N2C]
I-200

TABLE A-continued
Exemplary Compounds
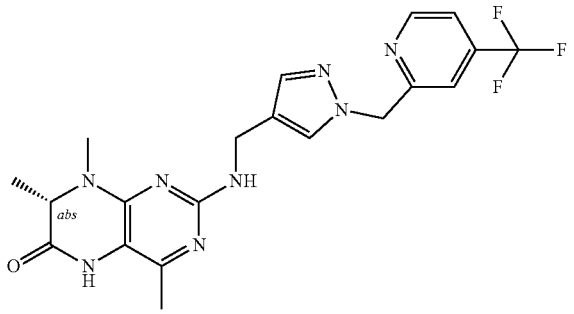 [SMILES: Cc1nc(NCc2cnn(Cc3cc(C(F)(F)F)ccn3)c2)nc2c1NC(=O)[C@H](C)N2C] I-201
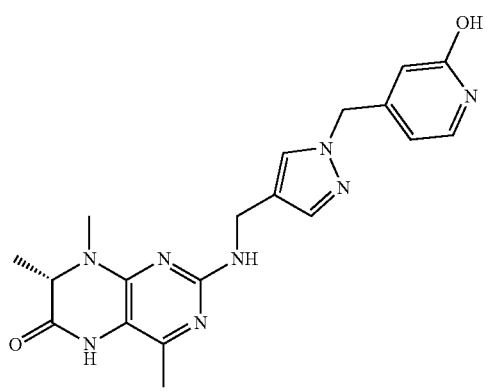 [SMILES: Cc1nc(NCc2cnn(Cc3ccnc(O)c3)c2)nc2c1NC(=O)[C@H](C)N2C] I-202
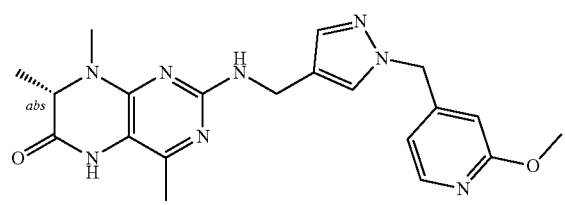 [SMILES: COc1cc(Cn2cc(CNc3nc(C)c4c(n3)N(C)[C@@H](C)C(=O)N4)cn2)ccn1] I-203
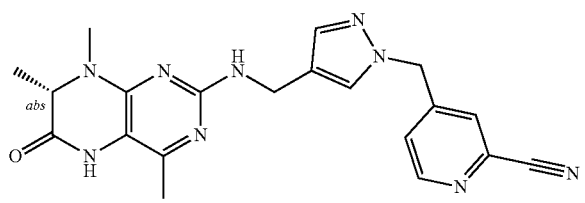 [SMILES: Cc1nc(NCc2cnn(Cc3ccnc(C#N)c3)c2)nc2c1NC(=O)[C@H](C)N2C] I-204
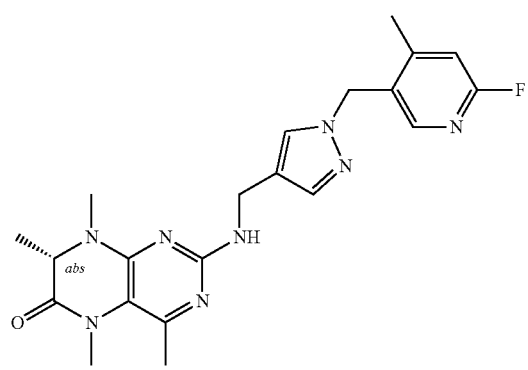 [SMILES: Cc1cc(F)ncc1Cn1cc(CNc2nc(C)c3c(n2)N(C)[C@@H](C)C(=O)N3C)cn1] I-205

TABLE A-continued
Exemplary Compounds
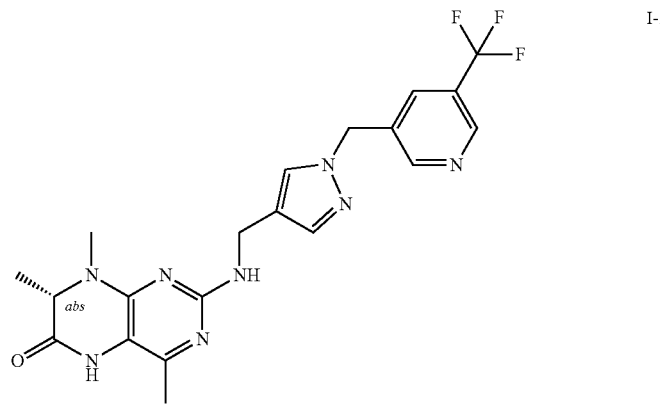
I-206
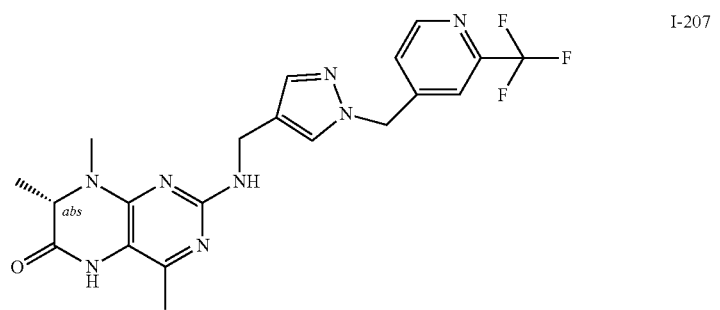
I-207
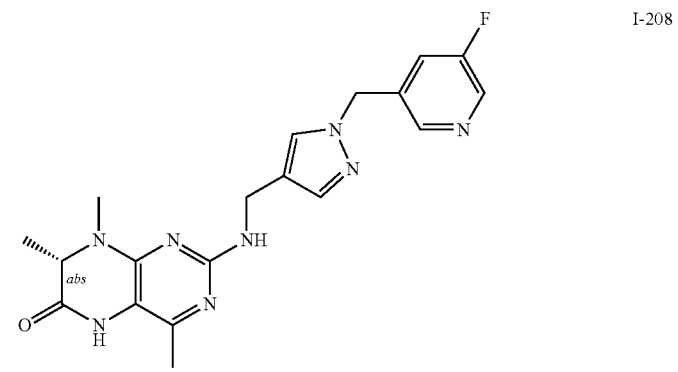
I-208
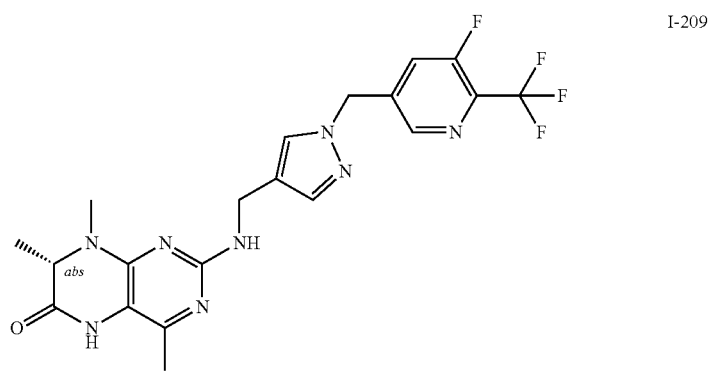
I-209

TABLE A-continued
Exemplary Compounds
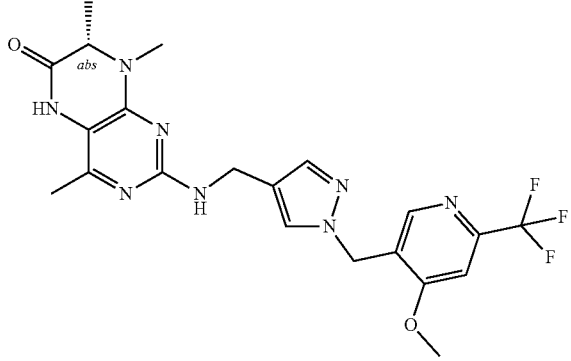 [SMILES: COc1cc(C(F)(F)F)ncc1Cn1cc(CNc2nc(C)c3c(n2)N(C)[C@@H](C)C(=O)N3)cn1]
I-210
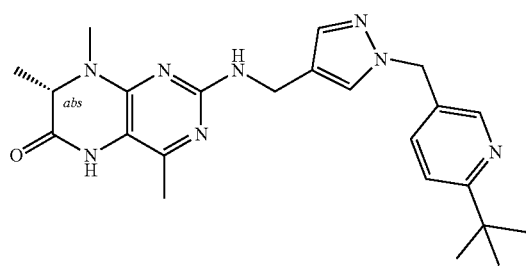 [SMILES: Cc1nc(NCc2cnn(Cc3ccc(C(C)(C)C)nc3)c2)nc2c1NC(=O)[C@H](C)N2C]
I-211
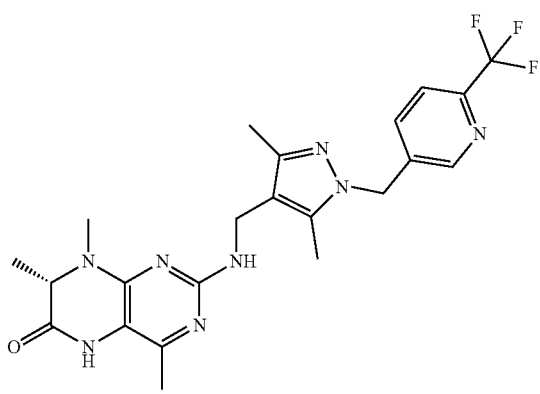 [SMILES: Cc1nn(Cc2ccc(C(F)(F)F)nc2)c(C)c1CNc1nc(C)c2c(n1)N(C)[C@@H](C)C(=O)N2]
I-212
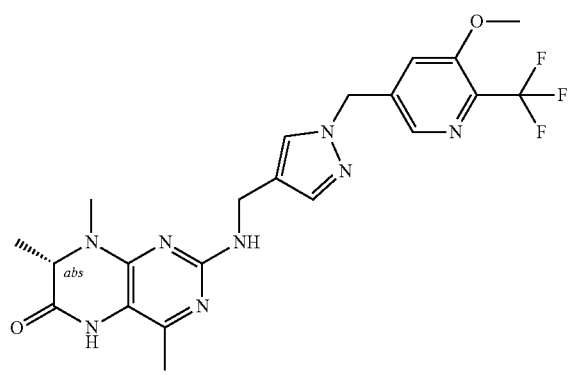 [SMILES: COc1cc(Cn2cc(CNc3nc(C)c4c(n3)N(C)[C@@H](C)C(=O)N4)cn2)cnc1C(F)(F)F]
I-213

TABLE A-continued
Exemplary Compounds
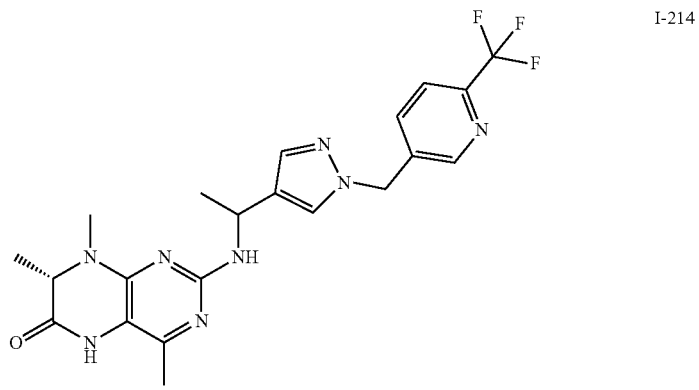
I-214
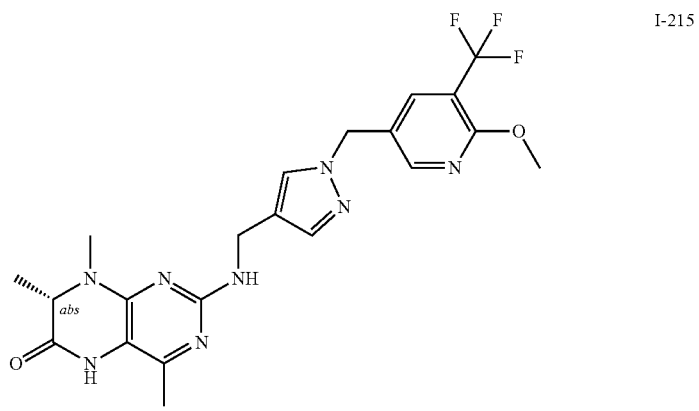
I-215
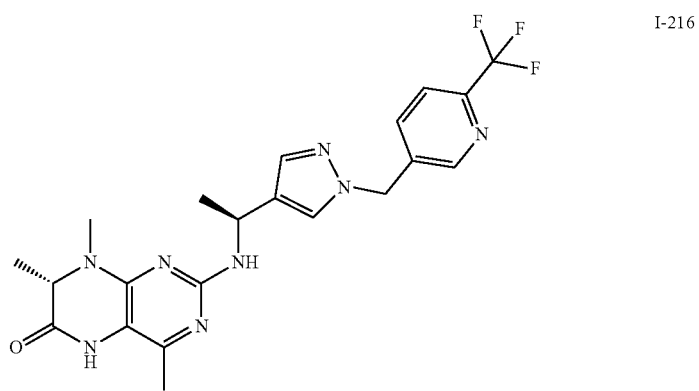
I-216
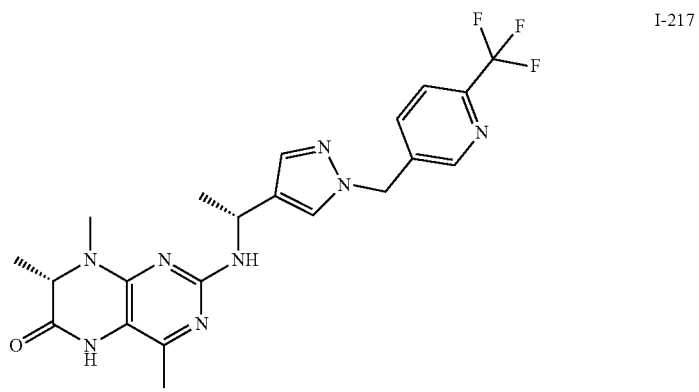
I-217

TABLE A-continued
Exemplary Compounds
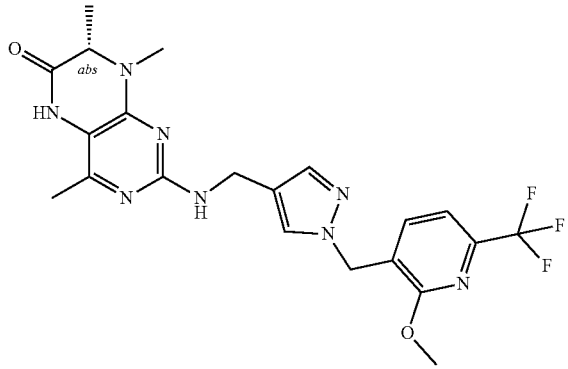 [SMILES: COc1nc(C(F)(F)F)ccc1Cn1cc(CNc2nc(C)c3c(n2)N(C)[C@@H](C)C(=O)N3)cn1]
I-218
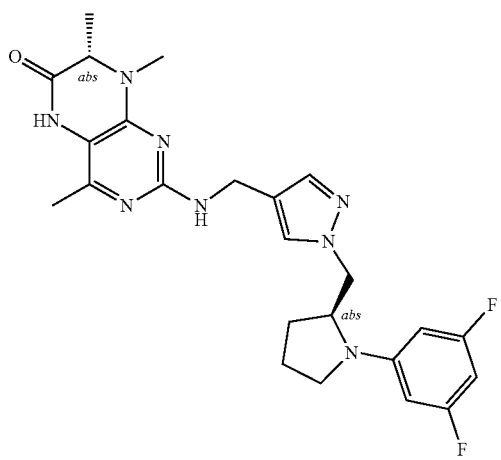 [SMILES: Cc1nc(NCc2cnn(C[C@@H]3CCCN3c3cc(F)cc(F)c3)c2)nc2c1NC(=O)[C@H](C)N2C]
I-219
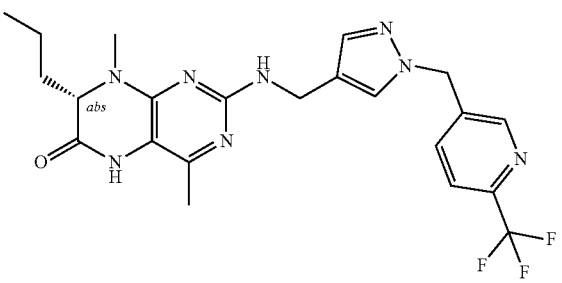 [SMILES: CCC[C@H]1C(=O)Nc2c(C)nc(NCc3cnn(Cc4ccc(C(F)(F)F)nc4)c3)nc2N1C]
I-220
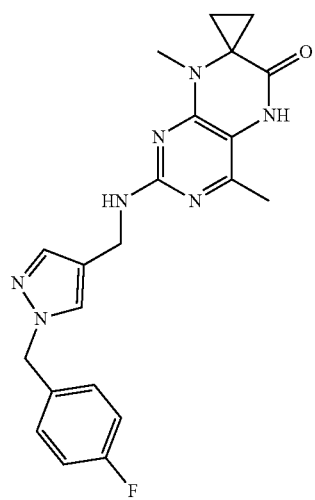 [SMILES: Cc1nc(NCc2cnn(Cc3ccc(F)cc3)c2)nc2c1NC(=O)C1(CC1)N2C]
I-221

TABLE A-continued
Exemplary Compounds
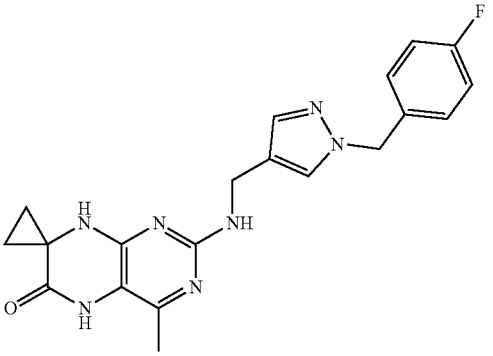 [SMILES: Cc1nc(NCc2cnn(Cc3ccc(F)cc3)c2)nc2c1NC(=O)C1(CC1)N2] I-222
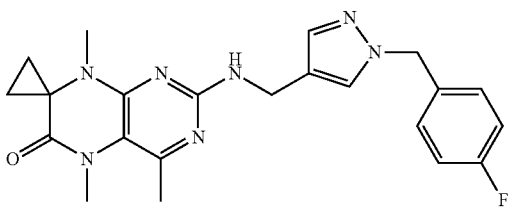 [SMILES: Cc1nc(NCc2cnn(Cc3ccc(F)cc3)c2)nc2c1N(C)C(=O)C1(CC1)N2C] I-223
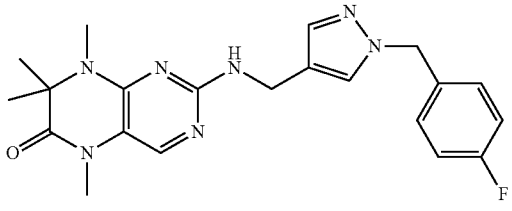 [SMILES: CN1C(=O)C(C)(C)N(C)c2nc(NCc3cnn(Cc4ccc(F)cc4)c3)ncc21] I-224
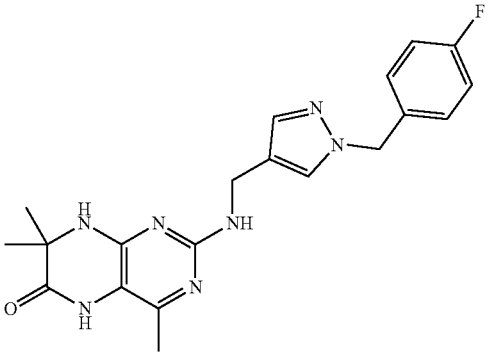 [SMILES: Cc1nc(NCc2cnn(Cc3ccc(F)cc3)c2)nc2c1NC(=O)C(C)(C)N2] I-225
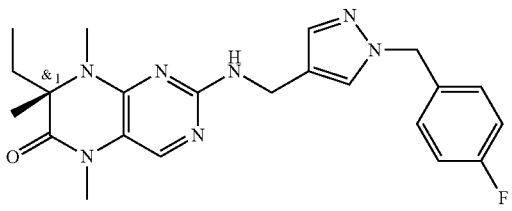 [SMILES: CC[C@@]1(C)C(=O)N(C)c2cnc(NCc3cnn(Cc4ccc(F)cc4)c3)nc2N1C] I-226
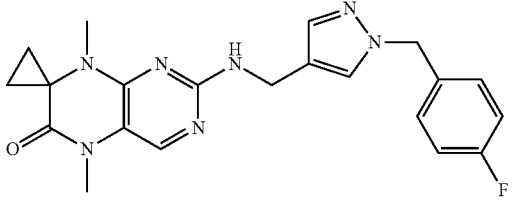 [SMILES: CN1C(=O)C2(CC2)N(C)c2nc(NCc3cnn(Cc4ccc(F)cc4)c3)ncc21] I-227

TABLE A-continued
Exemplary Compounds
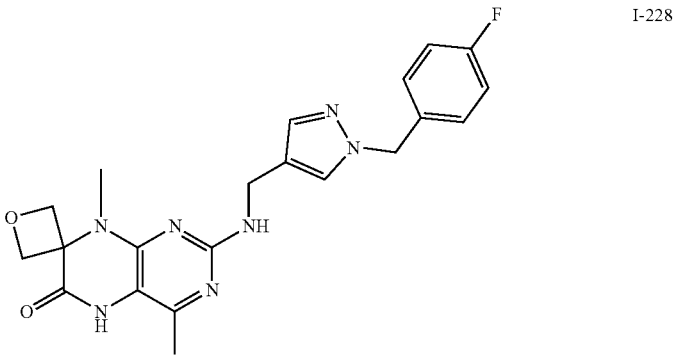 I-228
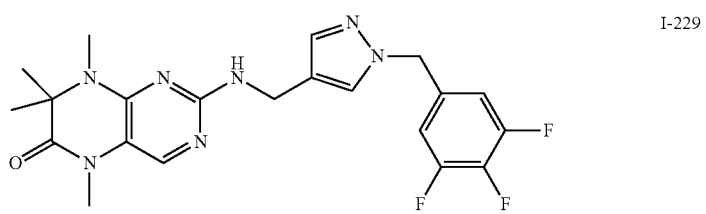 I-229
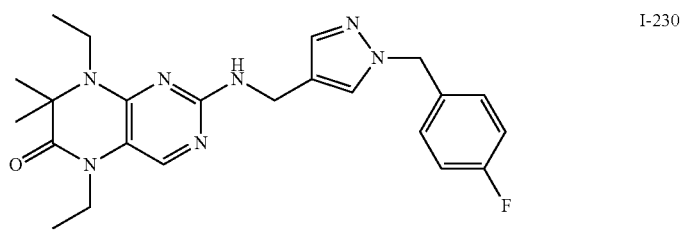 I-230
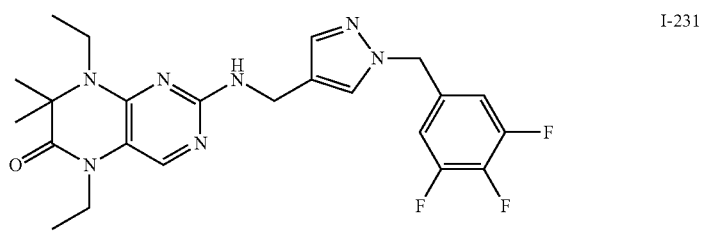 I-231
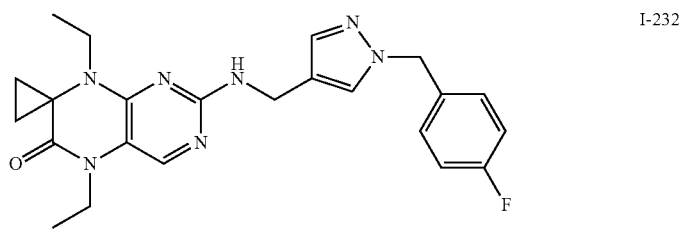 I-232
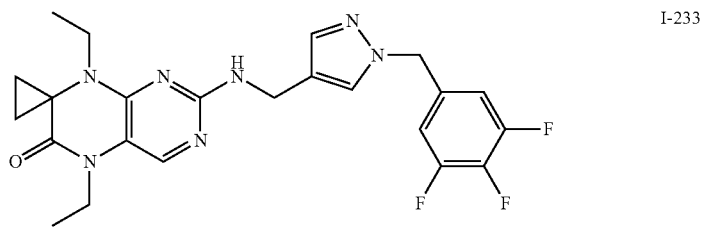 I-233

TABLE A-continued
Exemplary Compounds
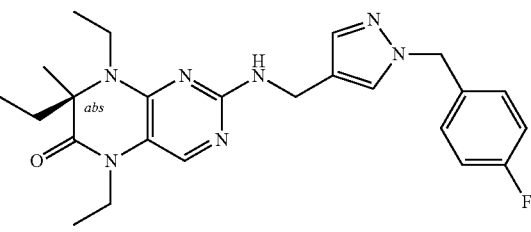 [SMILES: CCN1C(=O)[C@@](C)(CC)N(CC)c2nc(NCc3cnn(Cc4ccc(F)cc4)c3)ncc21]
I-234
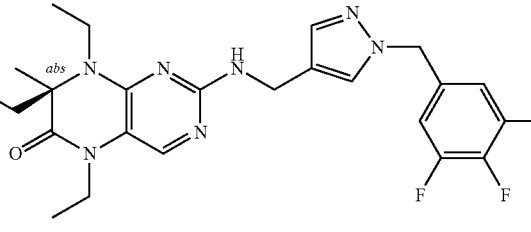
I-235
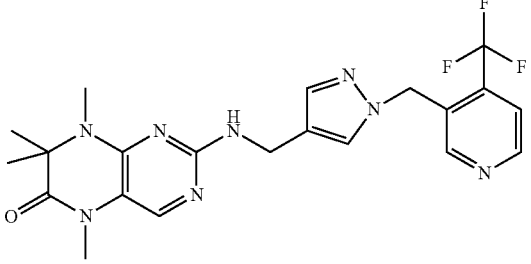
I-236
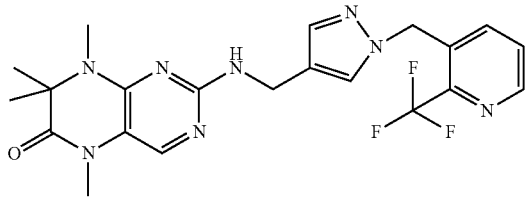 [SMILES: CN1C(=O)C(C)(C)N(C)c2nc(NCc3cnn(Cc4cccnc4C(F)(F)F)c3)ncc21]
I-237
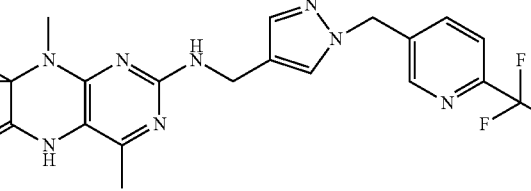
I-238
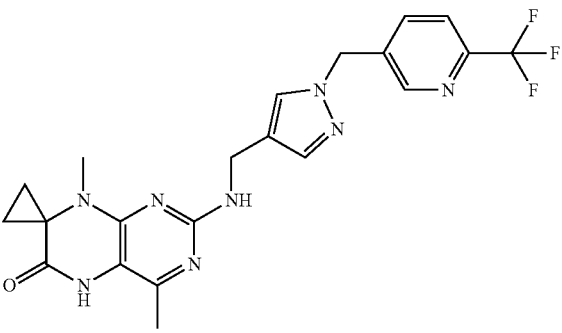 [SMILES: Cc1nc(NCc2cnn(Cc3ccc(C(F)(F)F)nc3)c2)nc2c1NC(=O)C1(CC1)N2C]
I-239

TABLE A-continued
Exemplary Compounds
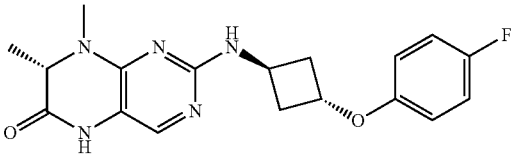 [SMILES: C[C@H]1C(=O)Nc2cnc(N[C@H]3C[C@H](Oc4ccc(F)cc4)C3)nc2N1C]   I-240
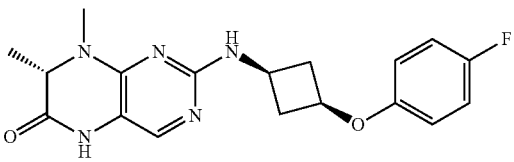 [SMILES: C[C@H]1C(=O)Nc2cnc(N[C@H]3C[C@@H](Oc4ccc(F)cc4)C3)nc2N1C]   I-241
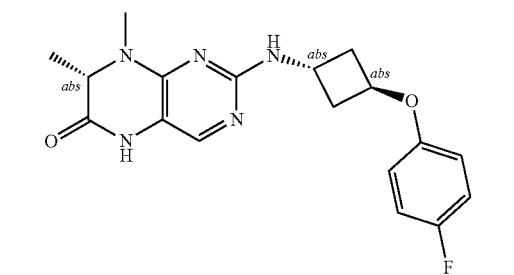 [SMILES: C[C@H]1C(=O)Nc2cnc(N[C@H]3C[C@H](Oc4ccc(F)cc4)C3)nc2N1C]   I-242
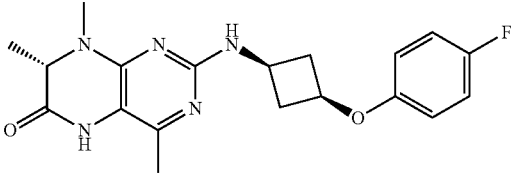 [SMILES: Cc1nc(N[C@H]2C[C@@H](Oc3ccc(F)cc3)C2)nc2c1NC(=O)[C@H](C)N2C]   I-243
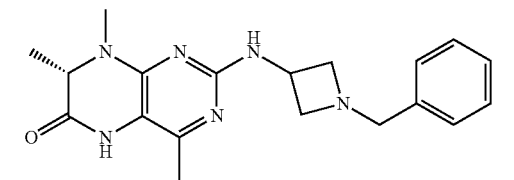 [SMILES: Cc1nc(NC2CN(Cc3ccccc3)C2)nc2c1NC(=O)[C@H](C)N2C]   I-244
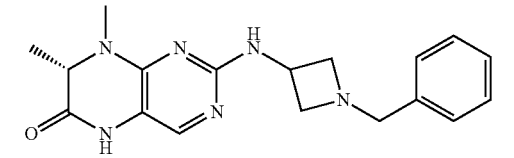 [SMILES: C[C@H]1C(=O)Nc2cnc(NC3CN(Cc4ccccc4)C3)nc2N1C]   I-245
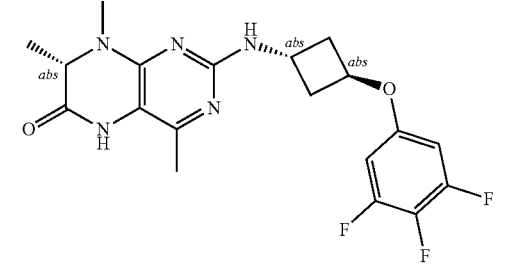 [SMILES: Cc1nc(N[C@H]2C[C@H](Oc3cc(F)c(F)c(F)c3)C2)nc2c1NC(=O)[C@H](C)N2C]   I-246

TABLE A-continued

Exemplary Compounds

| Compound ID |
|---|
| I-247 |
| I-248 |
| I-249 |
| I-250 |
| I-251 |
| I-252 |
| I-253 |

TABLE A-continued
Exemplary Compounds
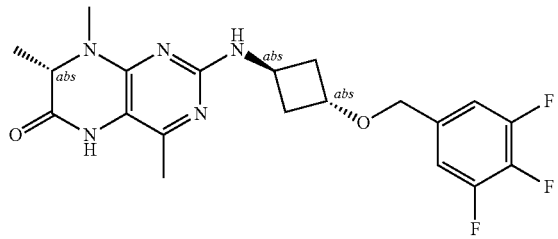 [SMILES: Cc1nc(N[C@H]2C[C@H](OCc3cc(F)c(F)c(F)c3)C2)nc2c1NC(=O)[C@H](C)N2C]
I-254
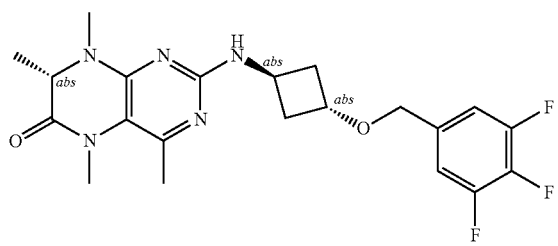 [SMILES: Cc1nc(N[C@H]2C[C@H](OCc3cc(F)c(F)c(F)c3)C2)nc2c1N(C)C(=O)[C@H](C)N2C]
I-255
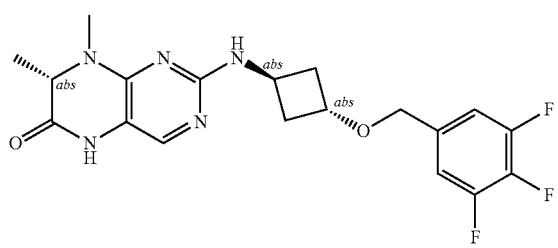 [SMILES: C[C@H]1C(=O)Nc2cnc(N[C@H]3C[C@H](OCc4cc(F)c(F)c(F)c4)C3)nc2N1C]
I-256
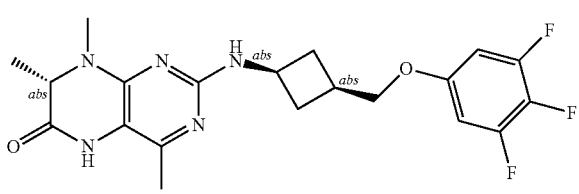 [SMILES: Cc1nc(N[C@H]2C[C@@H](COc3cc(F)c(F)c(F)c3)C2)nc2c1NC(=O)[C@H](C)N2C]
I-257
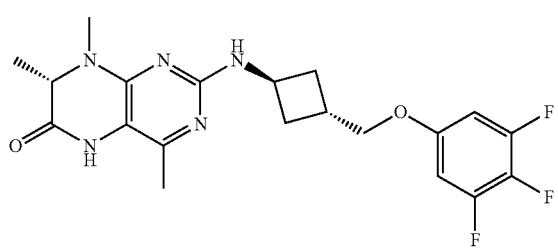 [SMILES: Cc1nc(N[C@H]2C[C@H](COc3cc(F)c(F)c(F)c3)C2)nc2c1NC(=O)[C@H](C)N2C]
I-258

TABLE A-continued
Exemplary Compounds
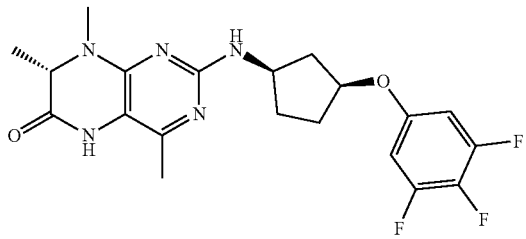
I-259
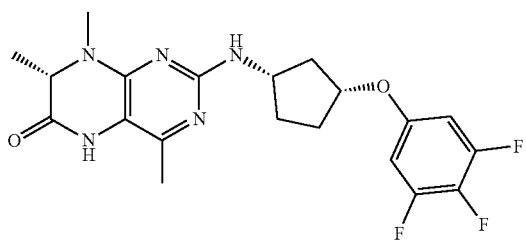
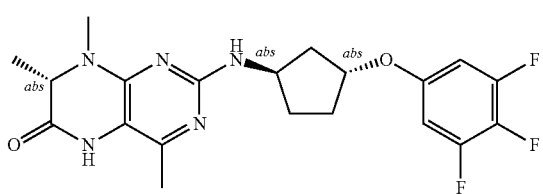
I-260
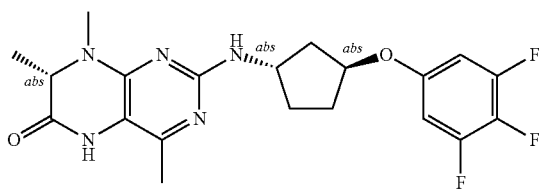
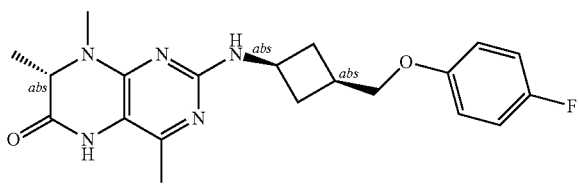 [SMILES: Cc1nc(N[C@H]2C[C@@H](COc3ccc(F)cc3)C2)nc2c1NC(=O)[C@H](C)N2C]
I-261
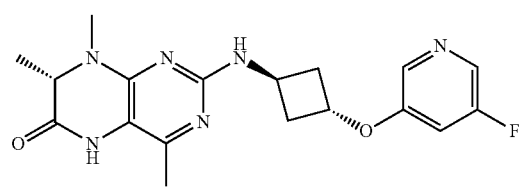 [SMILES: Cc1nc(N[C@H]2C[C@H](Oc3cncc(F)c3)C2)nc2c1NC(=O)[C@H](C)N2C]
I-262
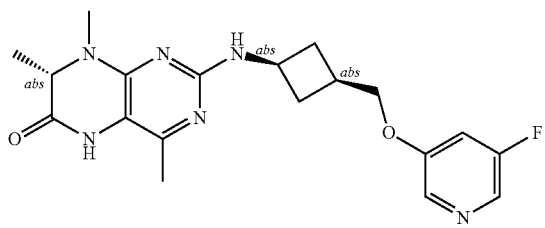 [SMILES: Cc1nc(N[C@H]2C[C@@H](COc3cncc(F)c3)C2)nc2c1NC(=O)[C@H](C)N2C]
I-263

TABLE A-continued
Exemplary Compounds
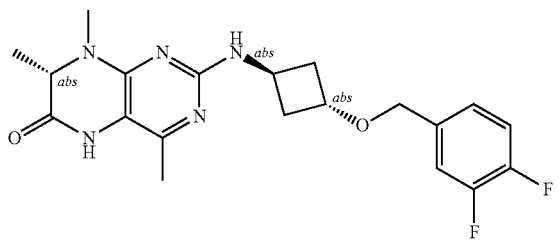 [SMILES: Cc1nc(N[C@H]2C[C@H](OCc3ccc(F)c(F)c3)C2)nc2c1NC(=O)[C@H](C)N2C] I-264
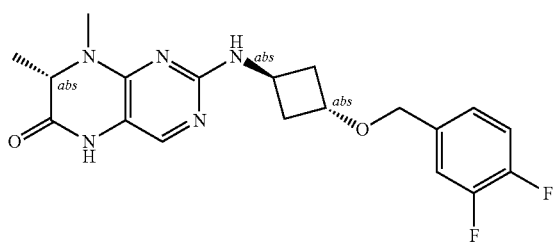 [SMILES: C[C@H]1C(=O)Nc2cnc(N[C@H]3C[C@H](OCc4ccc(F)c(F)c4)C3)nc2N1C] I-265
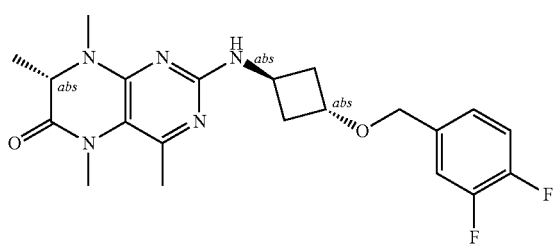 [SMILES: Cc1nc(N[C@H]2C[C@H](OCc3ccc(F)c(F)c3)C2)nc2c1N(C)C(=O)[C@H](C)N2C] I-266
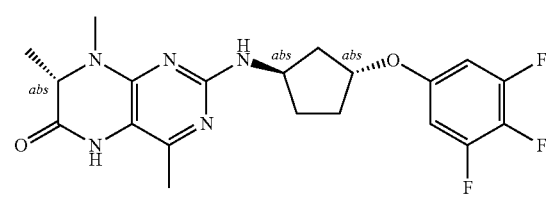 I-267
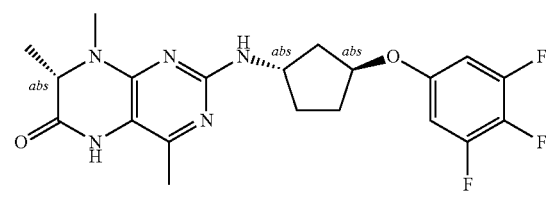 [SMILES: Cc1nc(N[C@H]2CC[C@H](Oc3cc(F)c(F)c(F)c3)C2)nc2c1NC(=O)[C@H](C)N2C] I-268
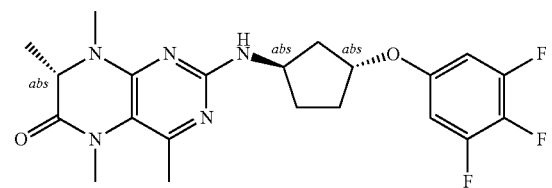 I-269
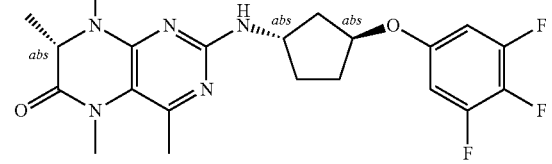

TABLE A-continued
Exemplary Compounds
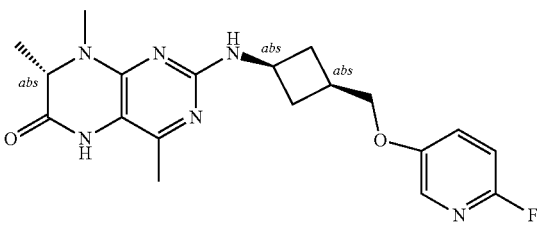 [SMILES: Cc1nc(N[C@H]2C[C@@H](COc3ccc(F)nc3)C2)nc2c1NC(=O)[C@H](C)N2C] I-270
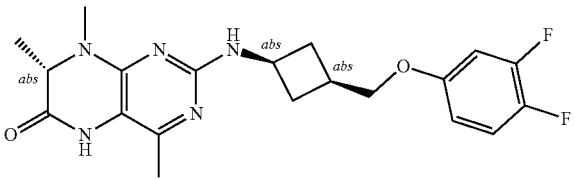 [SMILES: Cc1nc(N[C@H]2C[C@@H](COc3ccc(F)c(F)c3)C2)nc2c1NC(=O)[C@H](C)N2C] I-271
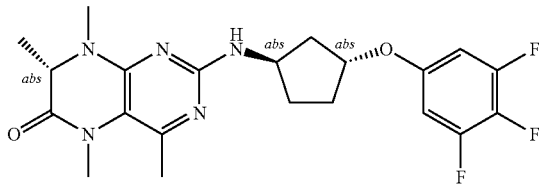 I-272
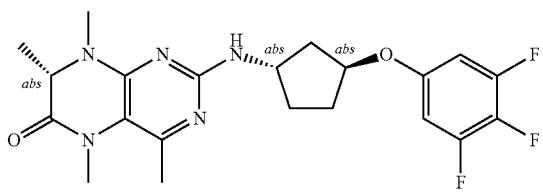 [SMILES: Cc1nc(N[C@H]2CC[C@H](Oc3cc(F)c(F)c(F)c3)C2)nc2c1N(C)C(=O)[C@H](C)N2C] I-273
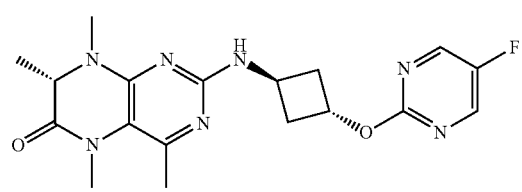 [SMILES: Cc1nc(N[C@H]2C[C@H](Oc3ncc(F)cn3)C2)nc2c1N(C)C(=O)[C@H](C)N2C] I-274
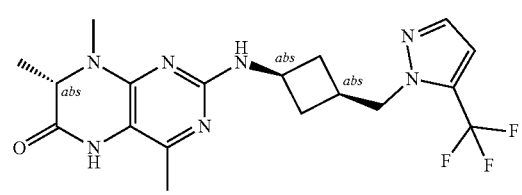 [SMILES: Cc1nc(N[C@H]2C[C@@H](Cn3nccc3C(F)(F)F)C2)nc2c1NC(=O)[C@H](C)N2C] I-275
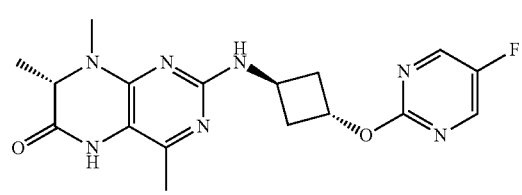 [SMILES: Cc1nc(N[C@H]2C[C@H](Oc3ncc(F)cn3)C2)nc2c1NC(=O)[C@H](C)N2C] I-276
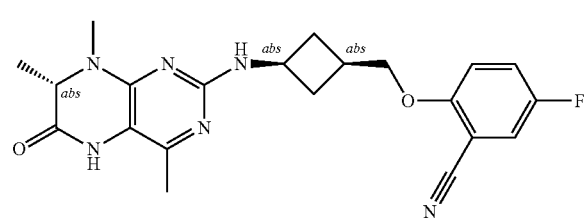 [SMILES: Cc1nc(N[C@H]2C[C@@H](COc3ccc(F)cc3C#N)C2)nc2c1NC(=O)[C@H](C)N2C] I-277

TABLE A-continued
Exemplary Compounds
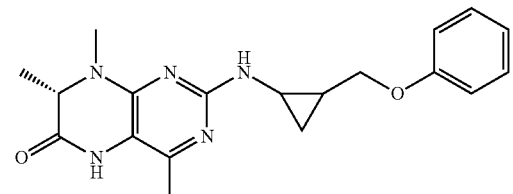 I-278
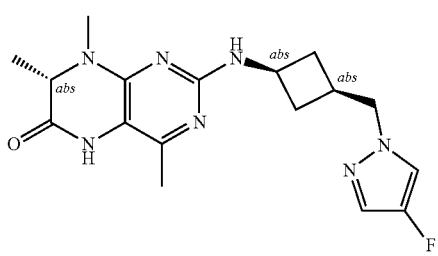 [SMILES: Cc1nc(N[C@H]2C[C@@H](Cn3cc(F)cn3)C2)nc2c1NC(=O)[C@H](C)N2C] I-279
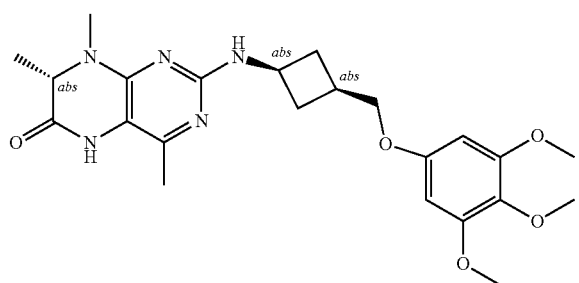 I-280
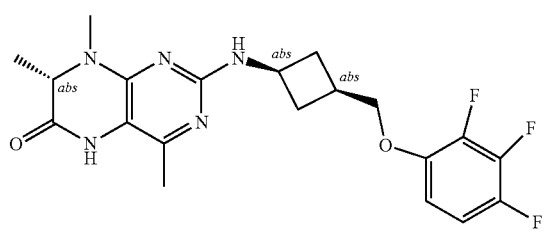 [SMILES: Cc1nc(N[C@H]2C[C@@H](COc3ccc(F)c(F)c3F)C2)nc2c1NC(=O)[C@H](C)N2C] I-281
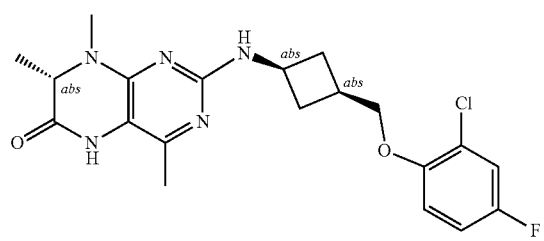 I-282
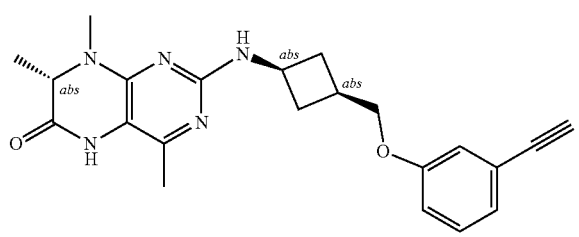 I-283

TABLE A-continued
Exemplary Compounds
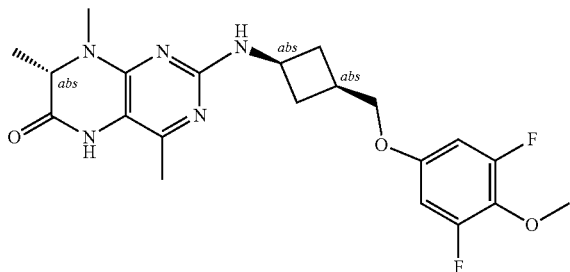 I-284
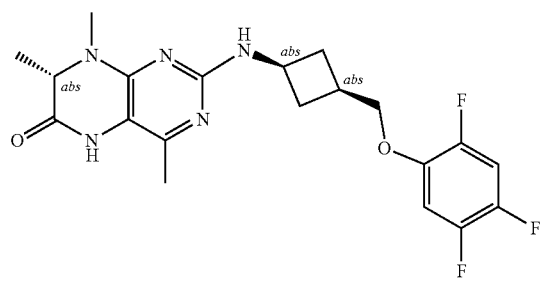 I-285
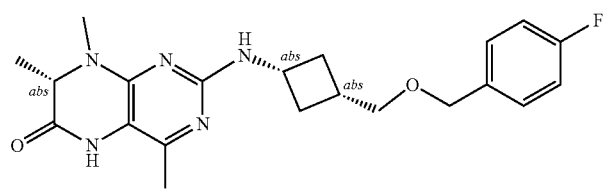 I-286
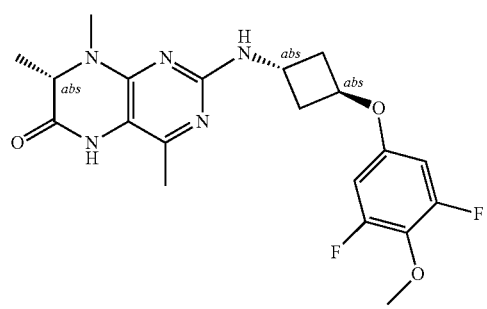 I-287
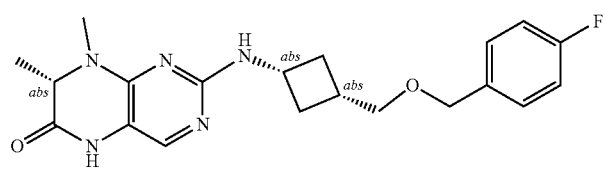 I-288
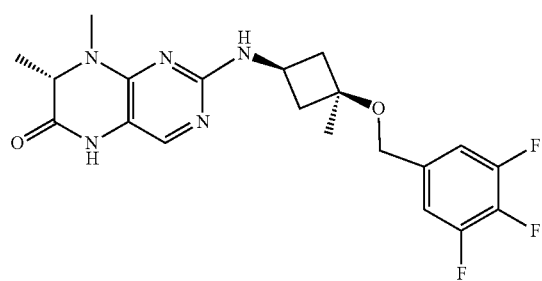 I-289

TABLE A-continued
Exemplary Compounds
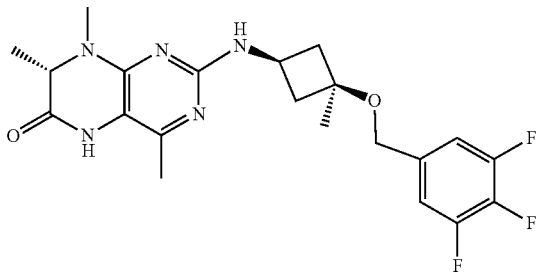 I-290
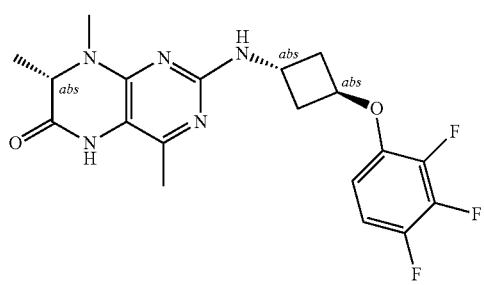 I-291
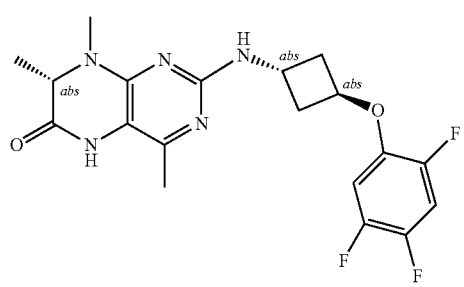 I-292
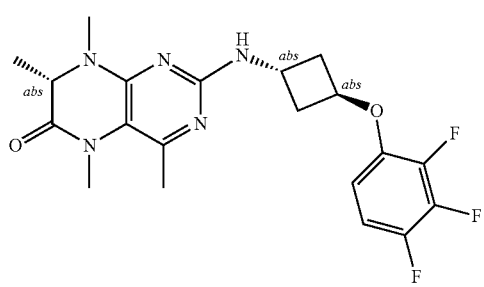 I-293
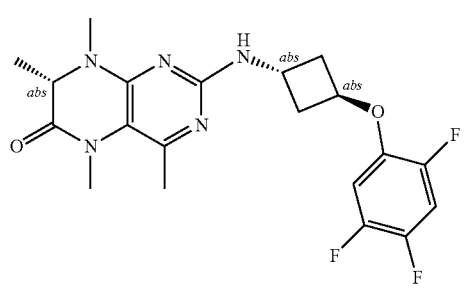 I-294

TABLE A-continued
Exemplary Compounds
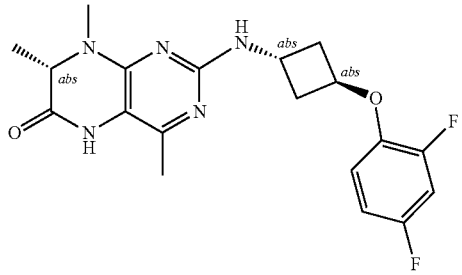
I-295
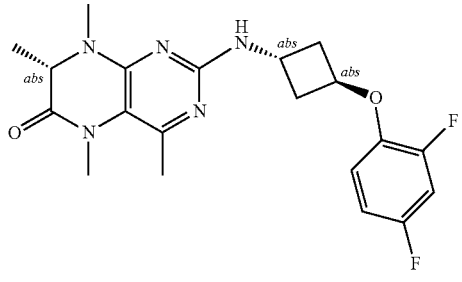
I-296
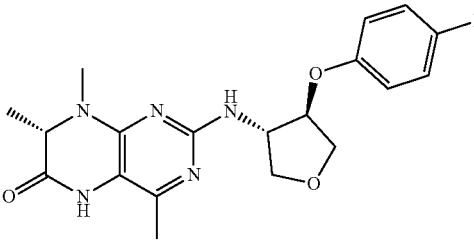
I-297
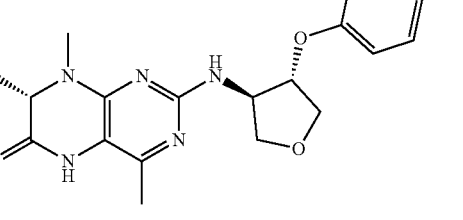
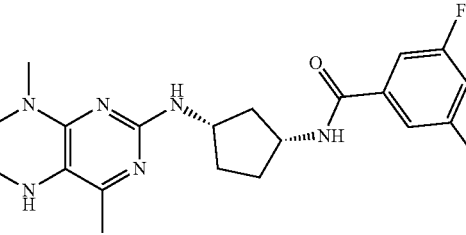
I-298

TABLE A-continued
Exemplary Compounds
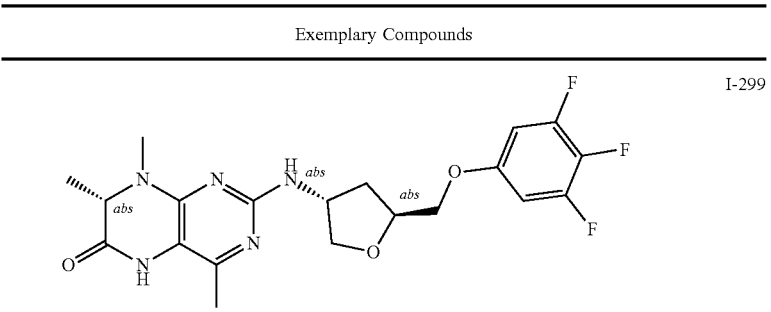
I-299
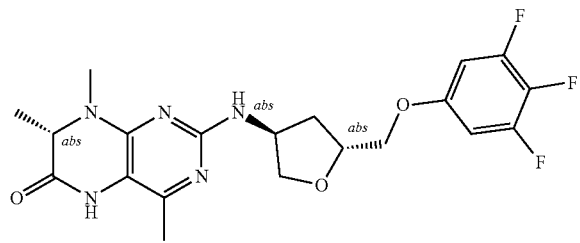
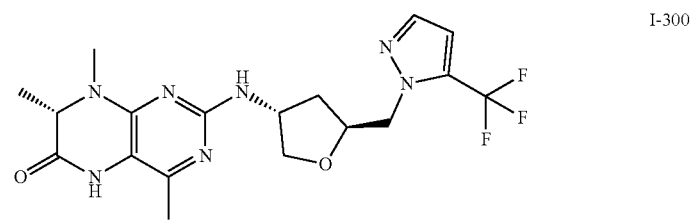
I-300
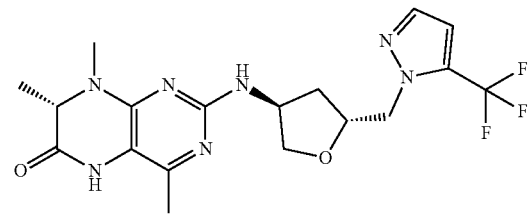
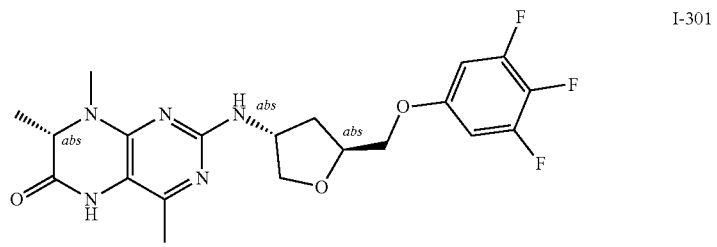
I-301
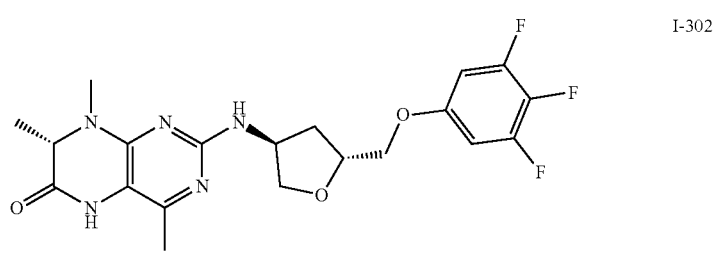
I-302

TABLE A-continued

Exemplary Compounds

I-303

I-304

I-305

I-306

I-307

TABLE A-continued
Exemplary Compounds
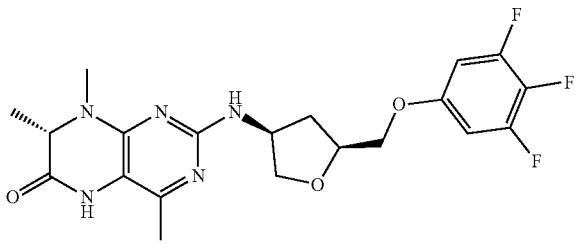 [SMILES: Cc1nc(N[C@@H]2CO[C@H](COc3cc(F)c(F)c(F)c3)C2)nc2c1NC(=O)[C@H](C)N2C]
I-308
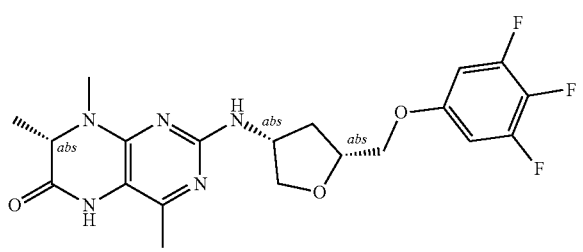 [SMILES: Cc1nc(N[C@H]2CO[C@@H](COc3cc(F)c(F)c(F)c3)C2)nc2c1NC(=O)[C@H](C)N2C]
I-309
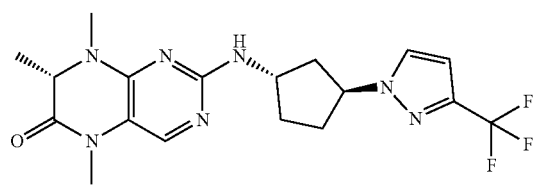 [SMILES: C[C@H]1C(=O)N(C)c2cnc(N[C@H]3CC[C@H](n4ccc(C(F)(F)F)n4)C3)nc2N1C]
I-310
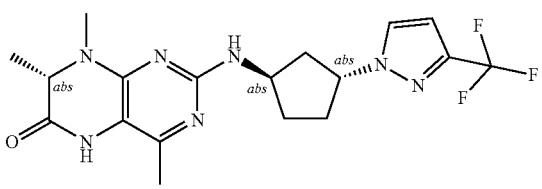 [SMILES: Cc1nc(N[C@@H]2CC[C@@H](n3ccc(C(F)(F)F)n3)C2)nc2c1NC(=O)[C@H](C)N2C]
I-311
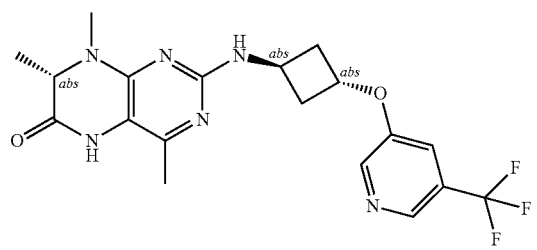 [SMILES: Cc1nc(N[C@H]2C[C@H](Oc3cncc(C(F)(F)F)c3)C2)nc2c1NC(=O)[C@H](C)N2C]
I-312
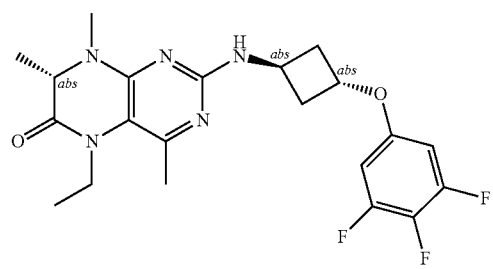 [SMILES: CCN1C(=O)[C@H](C)N(C)c2nc(N[C@H]3C[C@H](Oc4cc(F)c(F)c(F)c4)C3)nc(C)c21]
I-313

TABLE A-continued
Exemplary Compounds
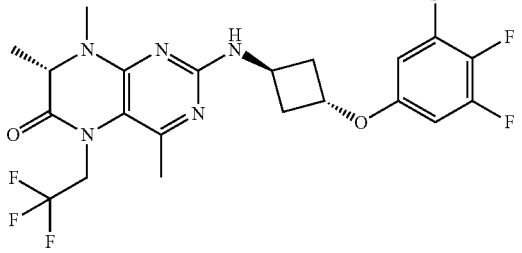
I-314
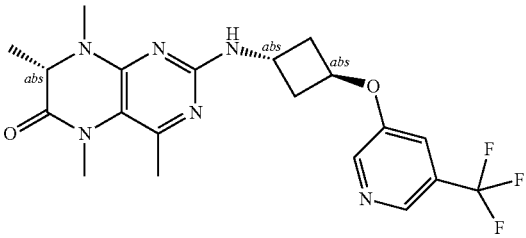 [SMILES: Cc1nc(N[C@H]2C[C@H](Oc3cncc(C(F)(F)F)c3)C2)nc2c1N(C)C(=O)[C@H](C)N2C]
I-315
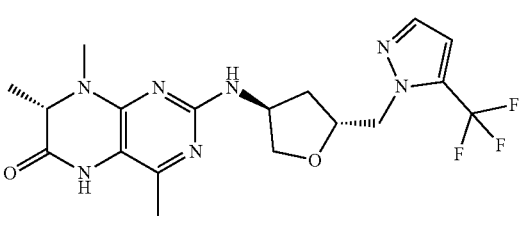
I-316
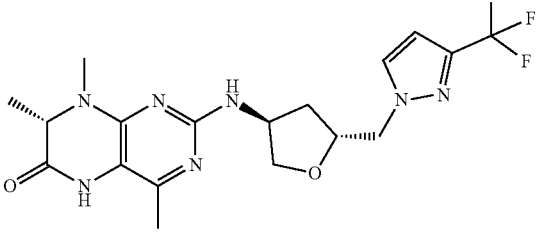
I-317
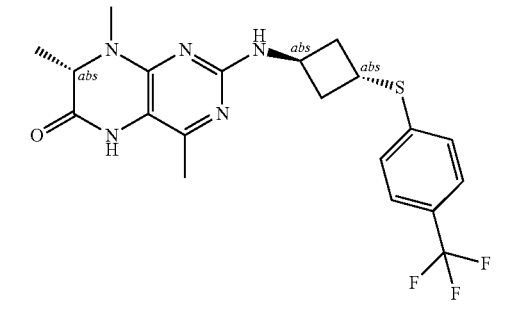 [SMILES: Cc1nc(N[C@H]2C[C@H](Sc3ccc(C(F)(F)F)cc3)C2)nc2c1NC(=O)[C@H](C)N2C]
I-318

TABLE A-continued
Exemplary Compounds
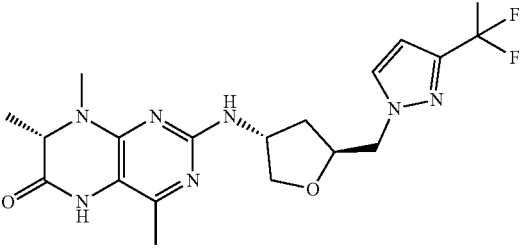 I-319
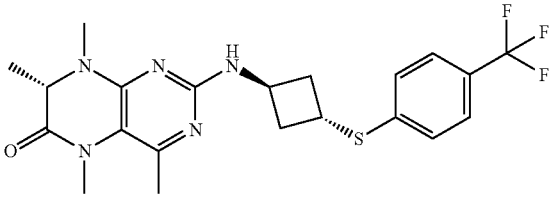 [SMILES: Cc1nc(N[C@H]2C[C@H](Sc3ccc(C(F)(F)F)cc3)C2)nc2c1N(C)C(=O)[C@H](C)N2C] I-320
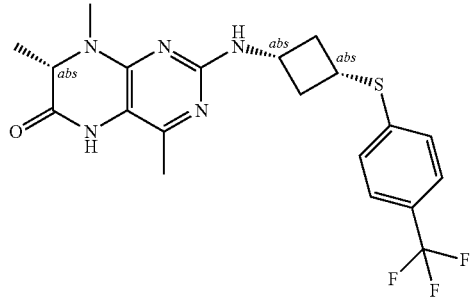 [SMILES: Cc1nc(N[C@H]2C[C@@H](Sc3ccc(C(F)(F)F)cc3)C2)nc2c1NC(=O)[C@H](C)N2C] I-321
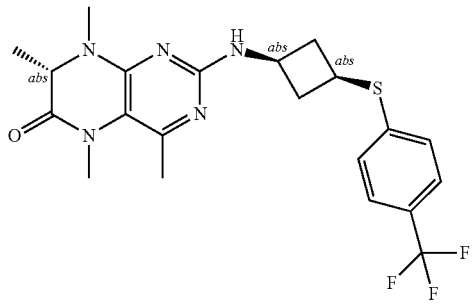 [SMILES: Cc1nc(N[C@H]2C[C@@H](Sc3ccc(C(F)(F)F)cc3)C2)nc2c1N(C)C(=O)[C@H](C)N2C] I-322
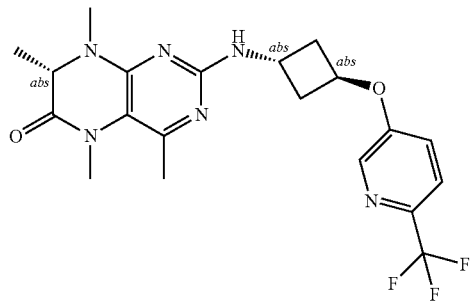 [SMILES: Cc1nc(N[C@H]2C[C@H](Oc3ccc(C(F)(F)F)nc3)C2)nc2c1N(C)C(=O)[C@H](C)N2C] I-323

TABLE A-continued
Exemplary Compounds
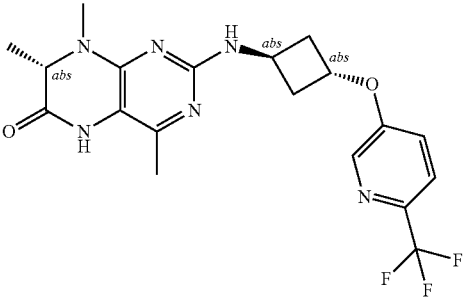 [SMILES: Cc1nc(N[C@H]2C[C@H](Oc3ccc(C(F)(F)F)nc3)C2)nc2c1NC(=O)[C@H](C)N2C] I-324
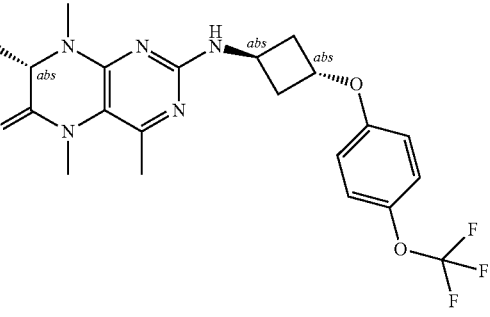 I-325
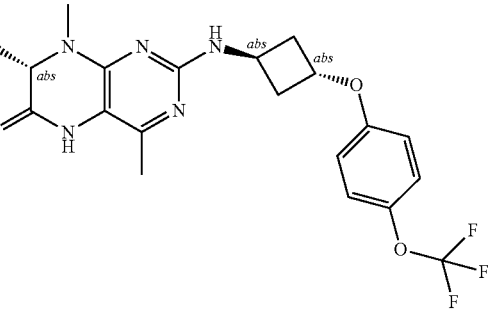 I-326
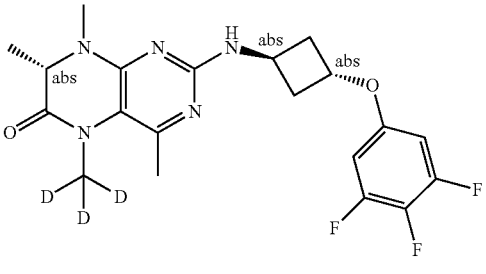 [SMILES: [2H]C([2H])([2H])N1C(=O)[C@H](C)N(C)c2nc(N[C@H]3C[C@H](Oc4cc(F)c(F)c(F)c4)C3)nc(C)c21] I-327
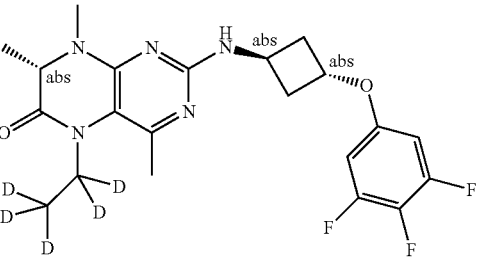 [SMILES: [2H]C([2H])([2H])C([2H])([2H])N1C(=O)[C@H](C)N(C)c2nc(N[C@H]3C[C@H](Oc4cc(F)c(F)c(F)c4)C3)nc(C)c21] I-328

TABLE A-continued
Exemplary Compounds
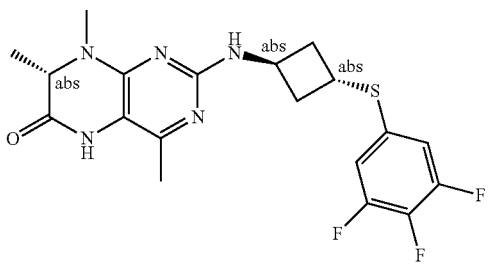 [SMILES: Cc1nc(N[C@H]2C[C@H](Sc3cc(F)c(F)c(F)c3)C2)nc2c1NC(=O)[C@H](C)N2C]
I-329
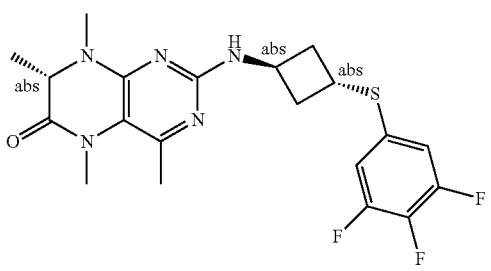 [SMILES: Cc1nc(N[C@H]2C[C@H](Sc3cc(F)c(F)c(F)c3)C2)nc2c1N(C)C(=O)[C@H](C)N2C]
I-330
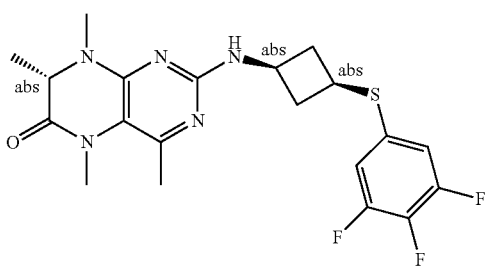
I-331
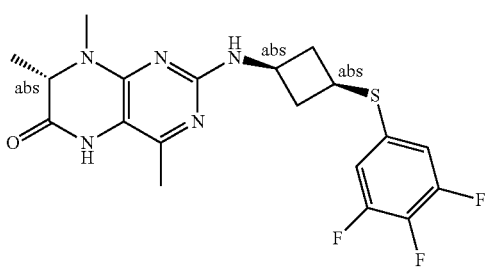 [SMILES: Cc1nc(N[C@H]2C[C@@H](Sc3cc(F)c(F)c(F)c3)C2)nc2c1N(C)C(=O)[C@H](C)N2C]
I-332
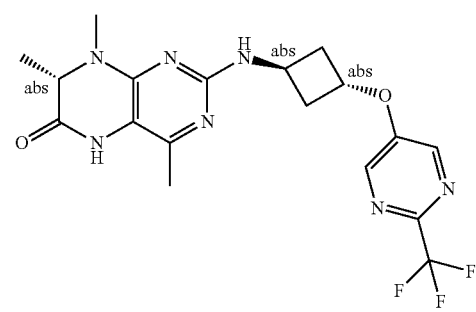 [SMILES: Cc1nc(N[C@H]2C[C@H](Oc3cnc(C(F)(F)F)nc3)C2)nc2c1NC(=O)[C@H](C)N2C]
I-333

TABLE A-continued
Exemplary Compounds
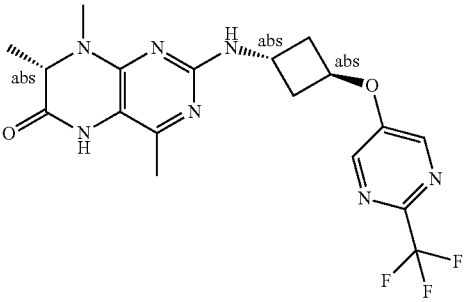 [SMILES: Cc1nc(N[C@H]2C[C@H](Oc3cnc(C(F)(F)F)nc3)C2)nc2c1NC(=O)[C@H](C)N2C]  I-334
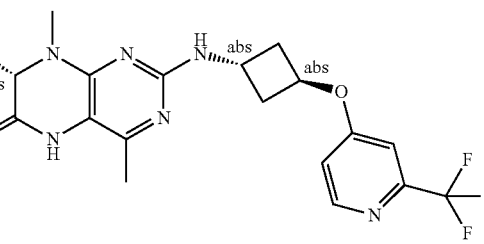  I-335
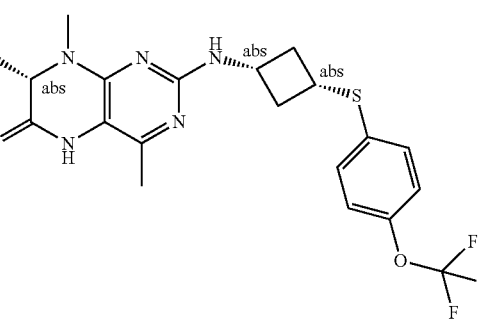  I-336
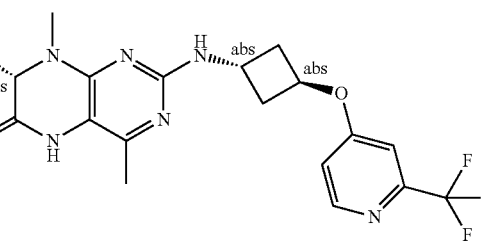  I-337
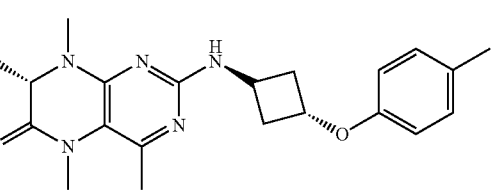  I-338
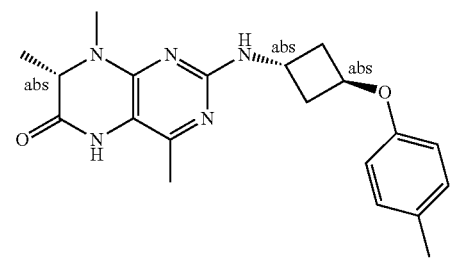 [SMILES: Cc1ccc(O[C@H]2C[C@H](Nc3nc(C)c4c(n3)N(C)[C@@H](C)C(=O)N4)C2)cc1]  I-339

TABLE A-continued
Exemplary Compounds
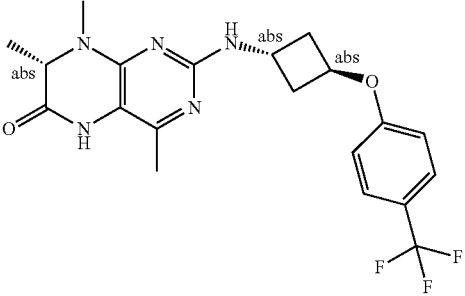 [SMILES: Cc1nc(N[C@H]2C[C@H](Oc3ccc(C(F)(F)F)cc3)C2)nc2c1NC(=O)[C@H](C)N2C]  I-340
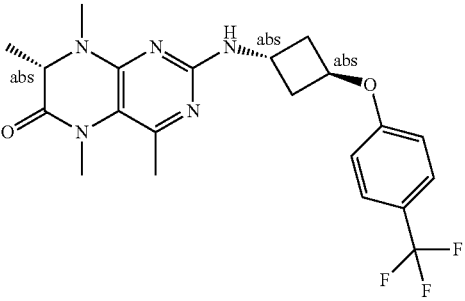 [SMILES: Cc1nc(N[C@H]2C[C@H](Oc3ccc(C(F)(F)F)cc3)C2)nc2c1N(C)C(=O)[C@H](C)N2C]  I-341
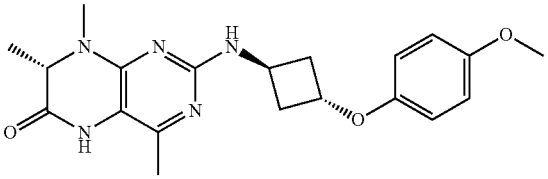  I-342
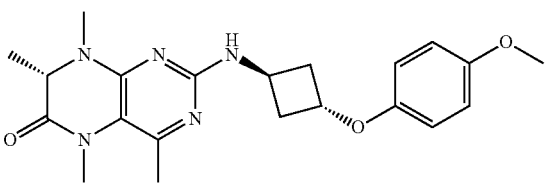  I-343
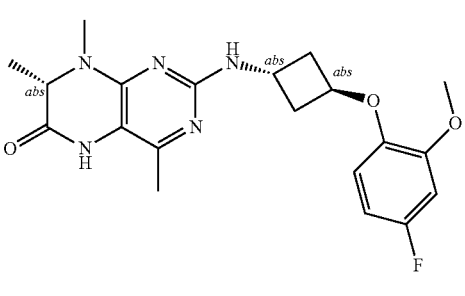 [SMILES: COc1cc(F)ccc1O[C@H]1C[C@H](Nc2nc(C)c3c(n2)N(C)[C@@H](C)C(=O)N3)C1]  I-344
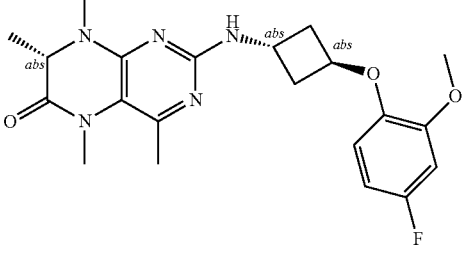  I-345

TABLE A-continued
Exemplary Compounds
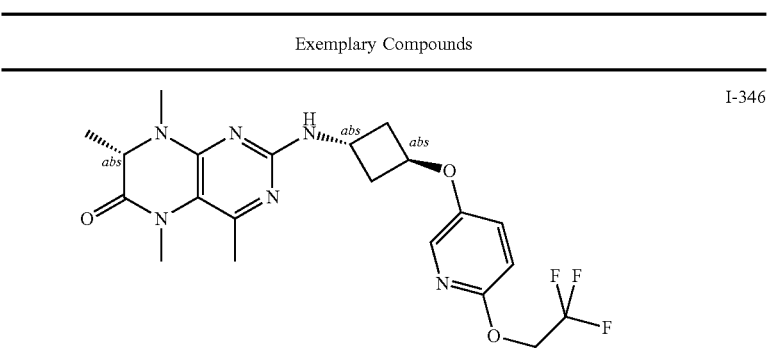
I-346
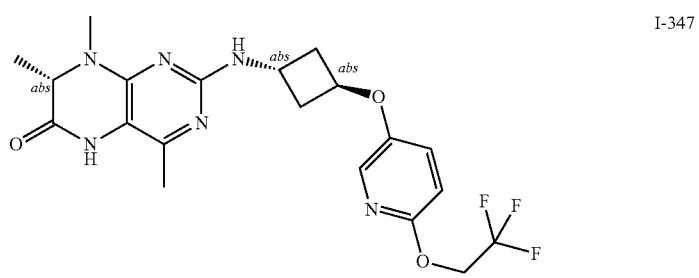
I-347
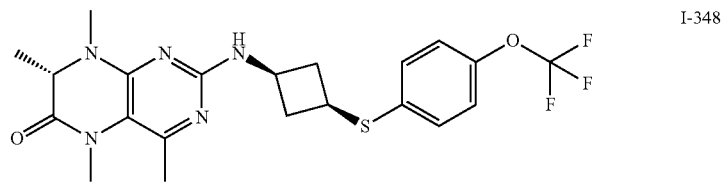
I-348
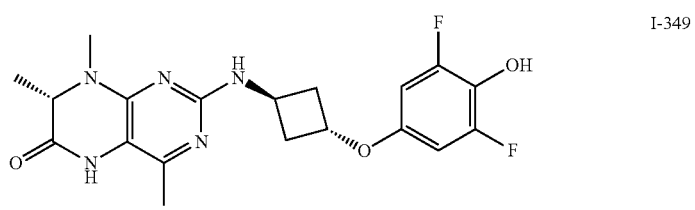
I-349
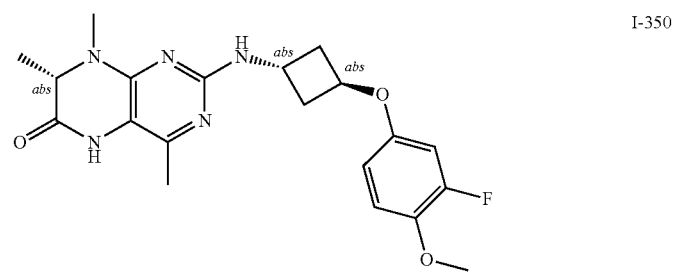
I-350
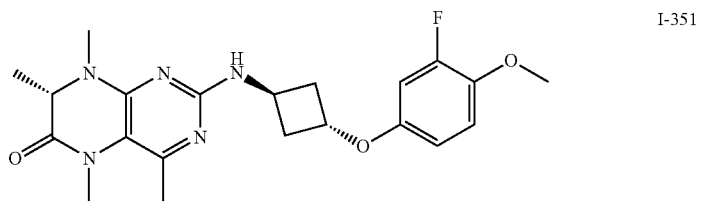
I-351

TABLE A-continued
Exemplary Compounds
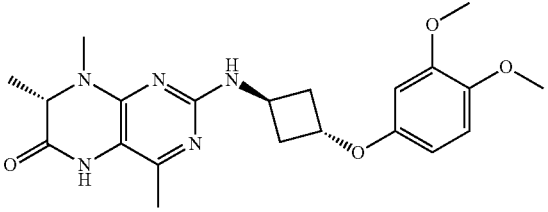 [SMILES: COc1ccc(O[C@H]2C[C@H](Nc3nc(C)c4c(n3)N(C)[C@@H](C)C(=O)N4)C2)cc1OC]
I-352
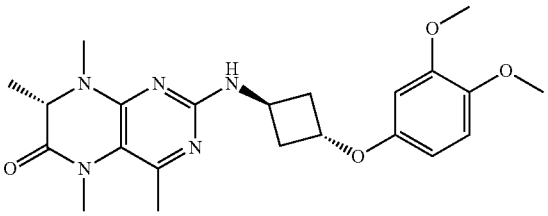
I-353
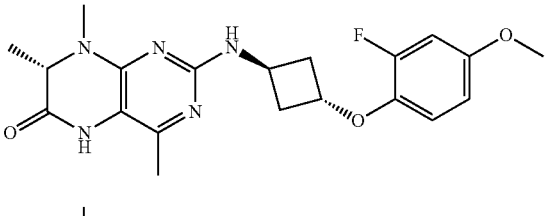
I-354
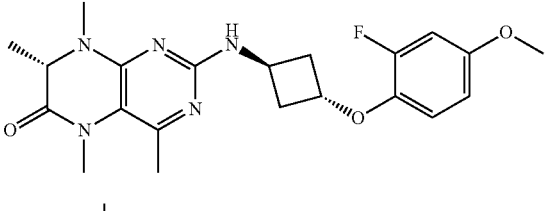
I-355
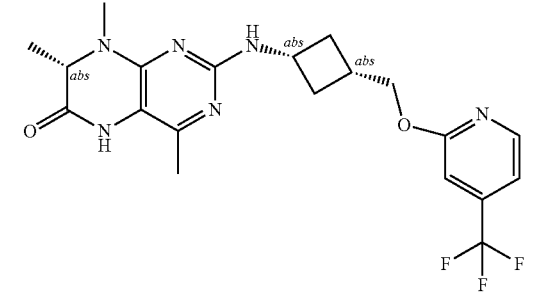 [SMILES: Cc1nc(N[C@H]2C[C@@H](COc3cc(C(F)(F)F)ccn3)C2)nc2c1NC(=O)[C@H](C)N2C]
I-356
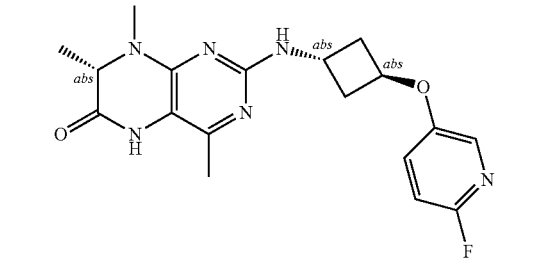 [SMILES: Cc1nc(N[C@H]2C[C@H](Oc3ccc(F)nc3)C2)nc2c1NC(=O)[C@H](C)N2C]
I-357
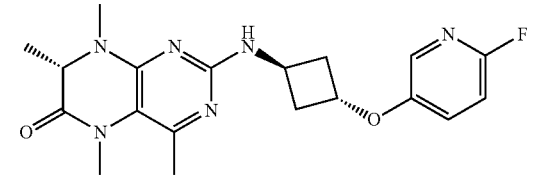 [SMILES: Cc1nc(N[C@H]2C[C@H](Oc3ccc(F)nc3)C2)nc2c1N(C)C(=O)[C@H](C)N2C]
I-358

TABLE A-continued
Exemplary Compounds
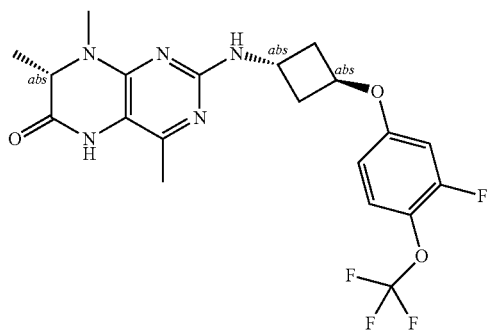 [SMILES: Cc1nc(N[C@H]2C[C@H](Oc3ccc(OC(F)(F)F)c(F)c3)C2)nc2c1NC(=O)[C@H](C)N2C]
I-359
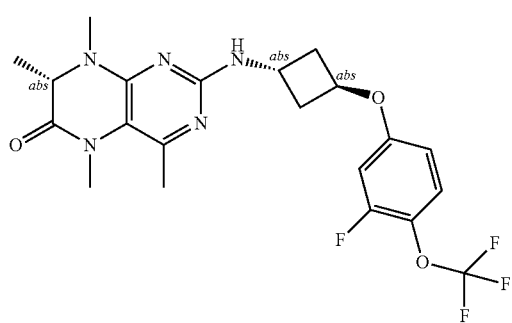 [SMILES: Cc1nc(N[C@H]2C[C@H](Oc3ccc(OC(F)(F)F)c(F)c3)C2)nc2c1N(C)C(=O)[C@H](C)N2C]
I-360
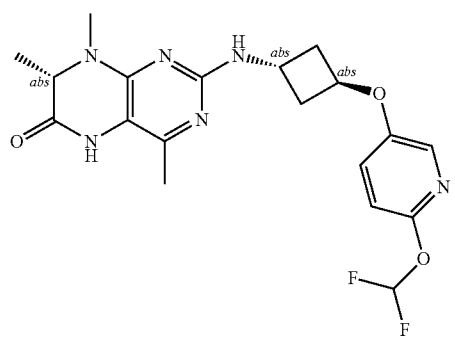 [SMILES: Cc1nc(N[C@H]2C[C@H](Oc3ccc(OC(F)F)nc3)C2)nc2c1NC(=O)[C@H](C)N2C]
I-361
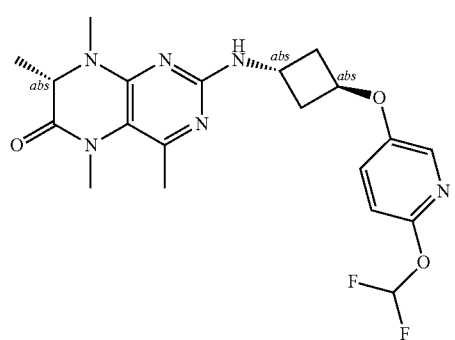 [SMILES: Cc1nc(N[C@H]2C[C@H](Oc3ccc(OC(F)F)nc3)C2)nc2c1N(C)C(=O)[C@H](C)N2C]
I-362
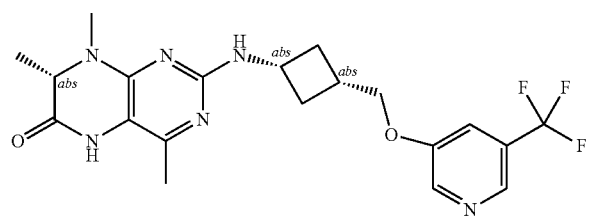 [SMILES: Cc1nc(N[C@H]2C[C@@H](COc3cncc(C(F)(F)F)c3)C2)nc2c1NC(=O)[C@H](C)N2C]
I-363

TABLE A-continued
Exemplary Compounds
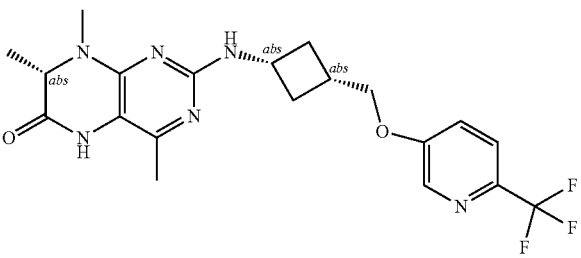 [SMILES: Cc1nc(N[C@H]2C[C@@H](COc3ccc(C(F)(F)F)nc3)C2)nc2c1NC(=O)[C@H](C)N2C] I-364
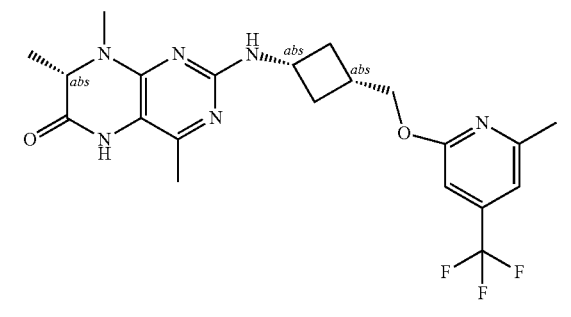 I-365
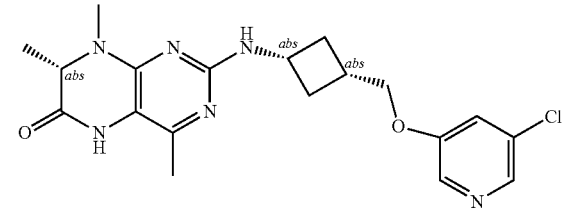 [SMILES: Cc1nc(N[C@H]2C[C@@H](COc3cncc(Cl)c3)C2)nc2c1NC(=O)[C@H](C)N2C] I-366
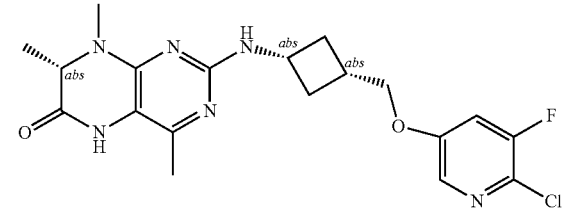 [SMILES: Cc1nc(N[C@H]2C[C@@H](COc3cnc(Cl)c(F)c3)C2)nc2c1NC(=O)[C@H](C)N2C] I-367
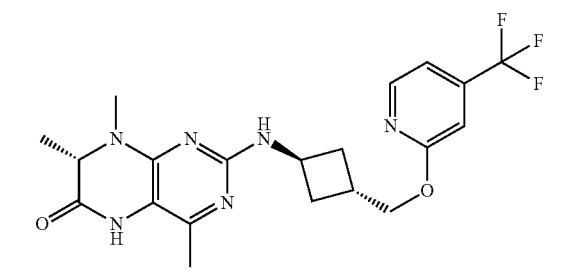 [SMILES: Cc1nc(N[C@H]2C[C@H](COc3cc(C(F)(F)F)ccn3)C2)nc2c1NC(=O)[C@H](C)N2C] I-369
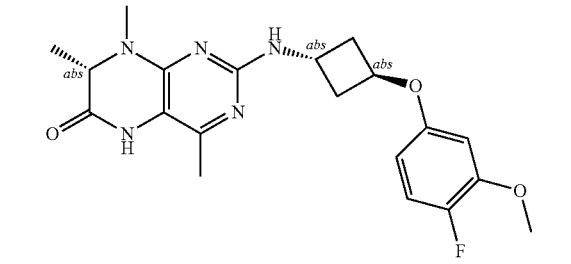 I-370

TABLE A-continued
Exemplary Compounds
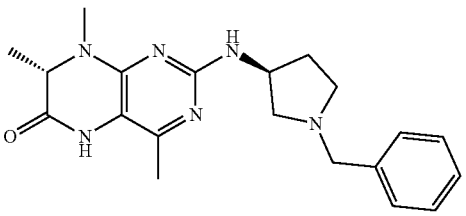 [SMILES: Cc1nc(N[C@H]2CCN(Cc3ccccc3)C2)nc2c1NC(=O)[C@H](C)N2C]
I-371
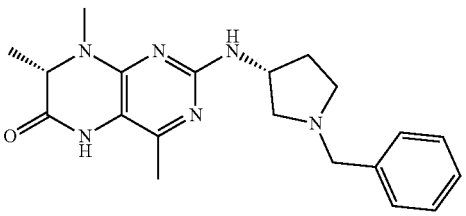 [SMILES: Cc1nc(N[C@@H]2CCN(Cc3ccccc3)C2)nc2c1NC(=O)[C@H](C)N2C]
I-372
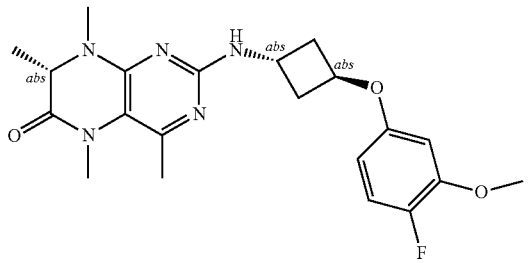 [SMILES: COc1cc(O[C@H]2C[C@H](Nc3nc(C)c4c(n3)N(C)[C@@H](C)C(=O)N4C)C2)ccc1F]
I-373
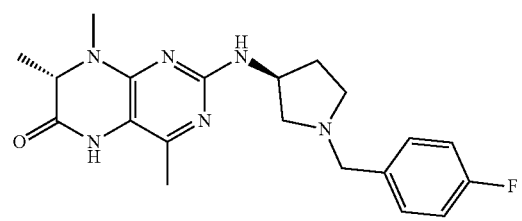 [SMILES: Cc1nc(N[C@H]2CCN(Cc3ccc(F)cc3)C2)nc2c1NC(=O)[C@H](C)N2C]
I-374
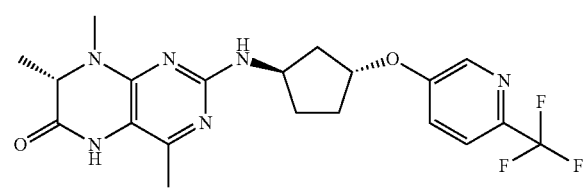 [SMILES: Cc1nc(N[C@@H]2CC[C@@H](Oc3ccc(C(F)(F)F)nc3)C2)nc2c1NC(=O)[C@H](C)N2C]
I-375
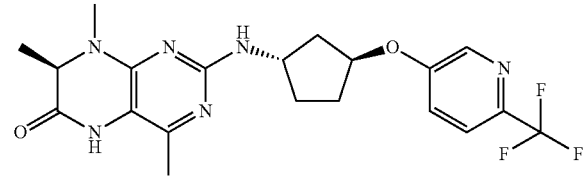 [SMILES: Cc1nc(N[C@H]2CC[C@H](Oc3ccc(C(F)(F)F)nc3)C2)nc2c1NC(=O)[C@H](C)N2C]
I-376

TABLE A-continued
Exemplary Compounds
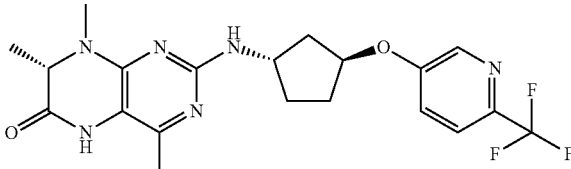  I-377
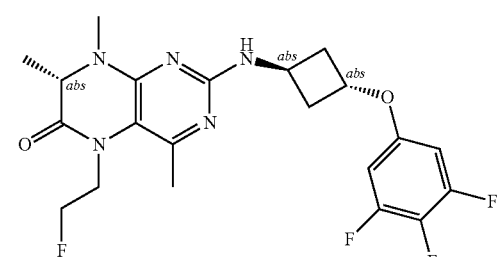  I-381
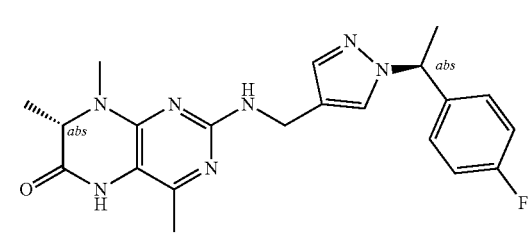  I-382
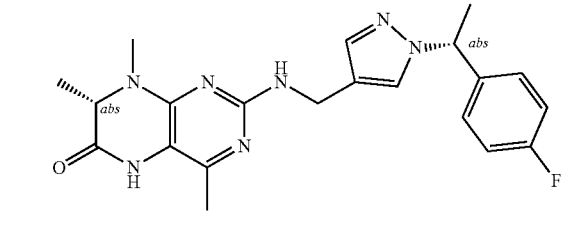  I-383
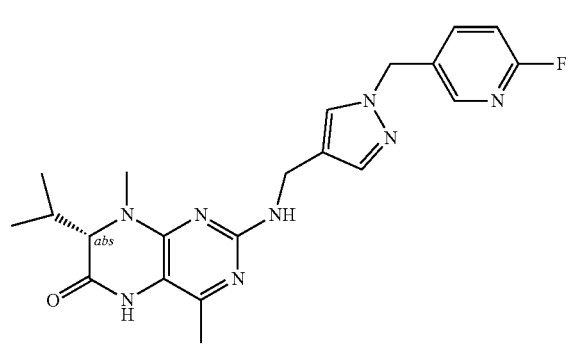 [SMILES: Cc1nc(NCc2cnn(Cc3ccc(F)nc3)c2)nc2c1NC(=O)[C@H](C(C)C)N2C]  I-384

TABLE A-continued
Exemplary Compounds
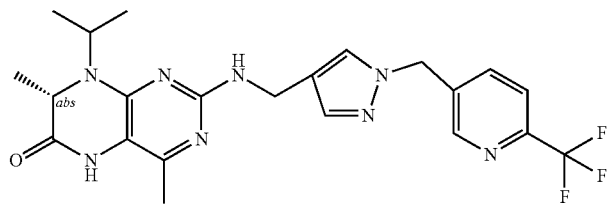 [SMILES: Cc1nc(NCc2cnn(Cc3ccc(C(F)(F)F)nc3)c2)nc2c1NC(=O)[C@H](C)N2C(C)C]
I-385
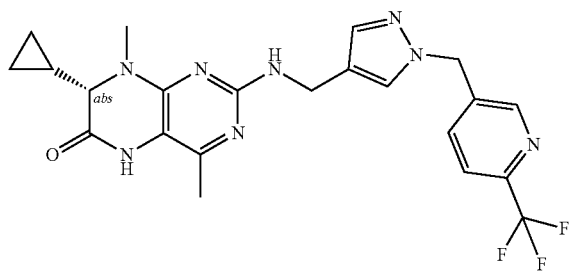 [SMILES: Cc1nc(NCc2cnn(Cc3ccc(C(F)(F)F)nc3)c2)nc2c1NC(=O)[C@H](C1CC1)N2C]
I-386
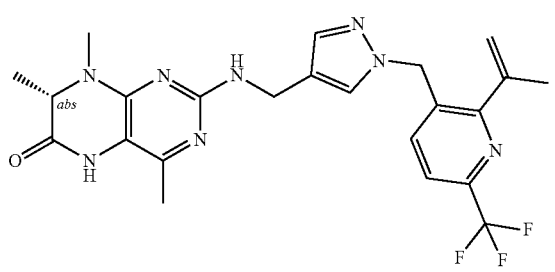 [SMILES: C=C(C)c1nc(C(F)(F)F)ccc1Cn1cc(CNc2nc(C)c3c(n2)N(C)[C@@H](C)C(=O)N3)cn1]
I-387
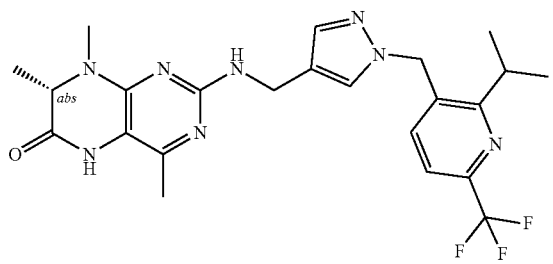 [SMILES: Cc1nc(NCc2cnn(Cc3ccc(C(F)(F)F)nc3C(C)C)c2)nc2c1NC(=O)[C@H](C)N2C]
I-388
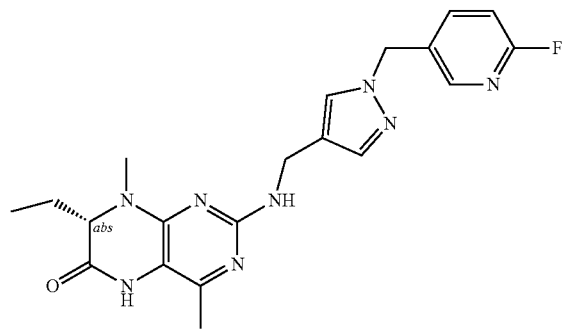 [SMILES: CC[C@H]1C(=O)Nc2c(C)nc(NCc3cnn(Cc4ccc(F)nc4)c3)nc2N1C]
I-389

TABLE A-continued
Exemplary Compounds
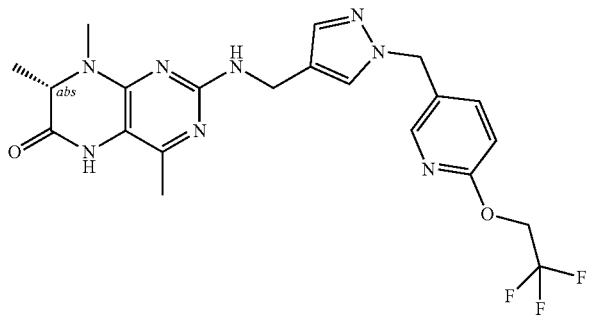 [SMILES: Cc1nc(NCc2cnn(Cc3ccc(OCC(F)(F)F)nc3)c2)nc2c1NC(=O)[C@H](C)N2C]
I-390
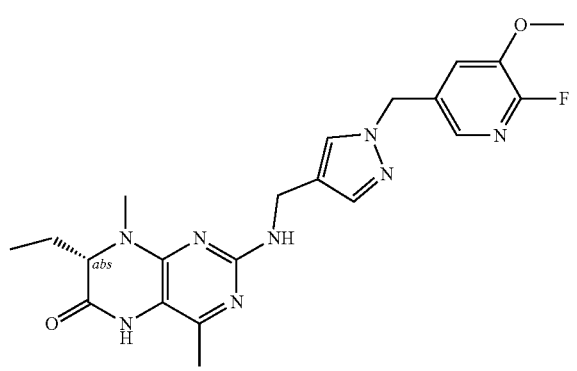 [SMILES: CC[C@H]1C(=O)Nc2c(C)nc(NCc3cnn(Cc4cnc(F)c(OC)c4)c3)nc2N1C]
I-394
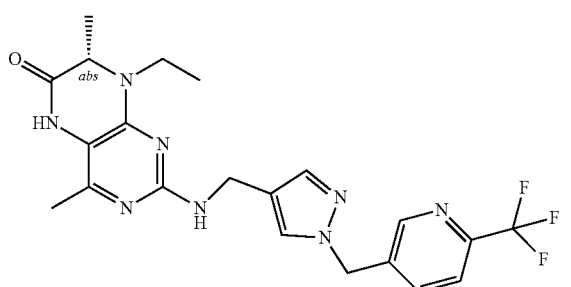
I-395
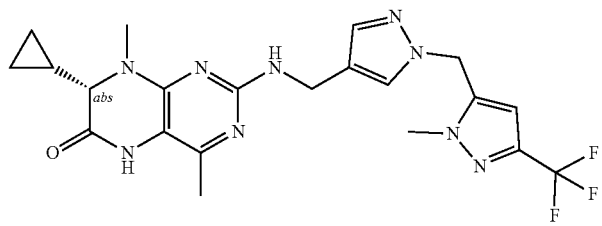 [SMILES: Cc1nc(NCc2cnn(Cc3cc(C(F)(F)F)nn3C)c2)nc2c1NC(=O)[C@H](C1CC1)N2C]
I-396
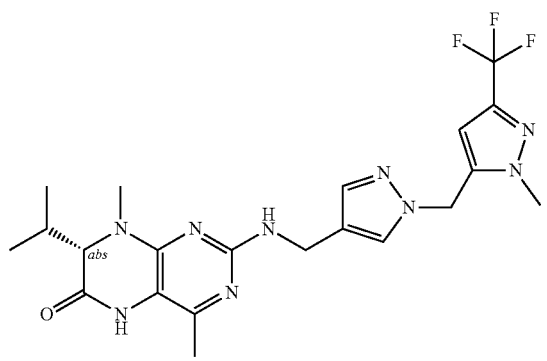 [SMILES: Cc1nc(NCc2cnn(Cc3cc(C(F)(F)F)nn3C)c2)nc2c1NC(=O)[C@H](C(C)C)N2C]
I-397

TABLE A-continued
Exemplary Compounds
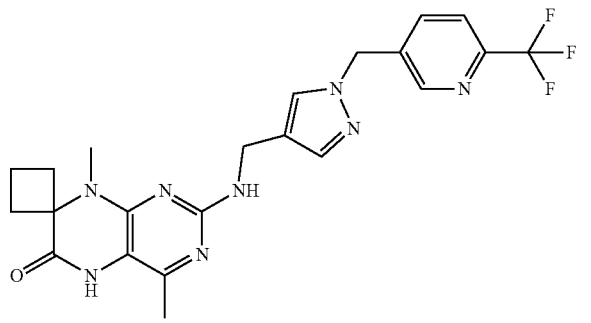 [SMILES: Cc1nc(NCc2cnn(Cc3ccc(C(F)(F)F)nc3)c2)nc2c1NC(=O)C1(CCC1)N2C]
I-398
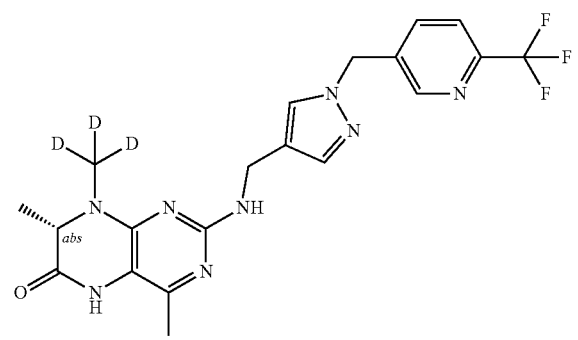 [SMILES: [2H]C([2H])([2H])N1c2nc(NCc3cnn(Cc4ccc(C(F)(F)F)nc4)c3)nc(C)c2NC(=O)[C@@H]1C]
I-400
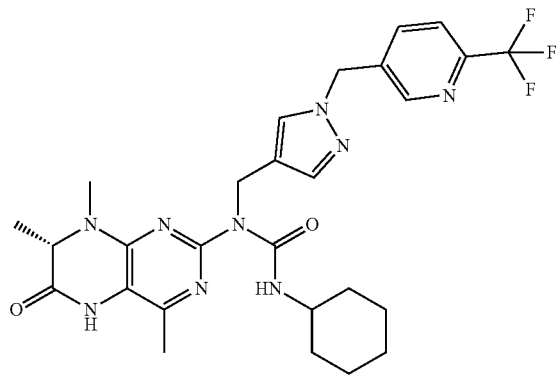 [SMILES: Cc1nc(N(Cc2cnn(Cc3ccc(C(F)(F)F)nc3)c2)C(=O)NC2CCCCC2)nc2c1NC(=O)[C@H](C)N2C]
I-401
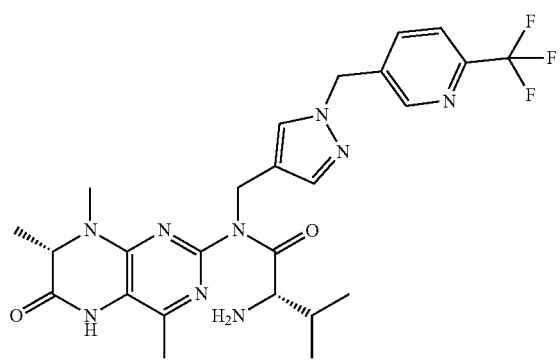 [SMILES: Cc1nc(N(Cc2cnn(Cc3ccc(C(F)(F)F)nc3)c2)C(=O)[C@@H](N)C(C)C)nc2c1NC(=O)[C@H](C)N2C]
I-402

TABLE A-continued
Exemplary Compounds
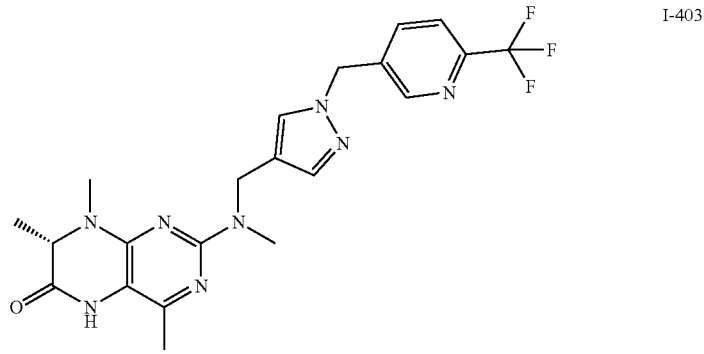
I-403
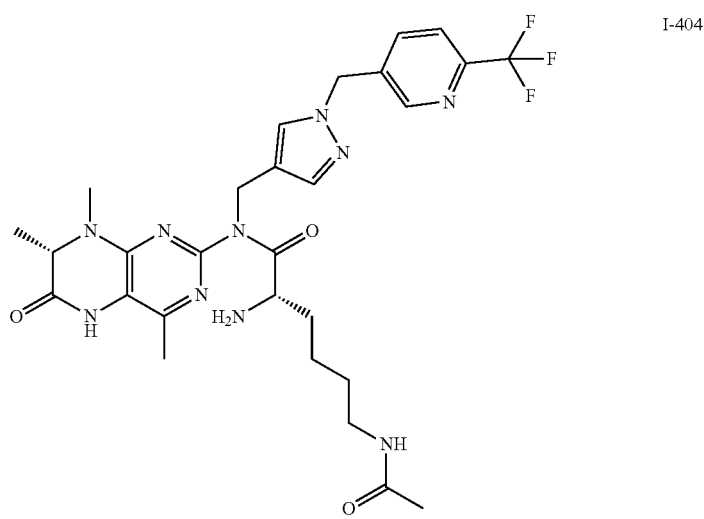
I-404
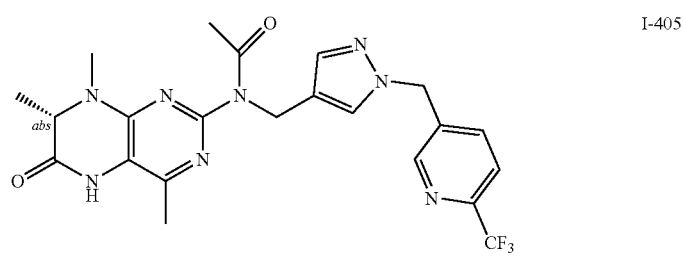
I-405
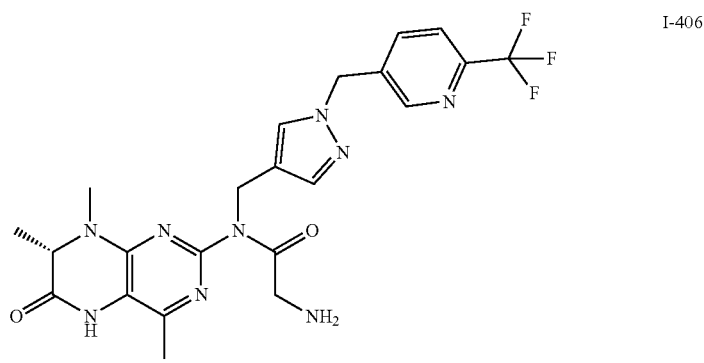
I-406

TABLE A-continued
Exemplary Compounds
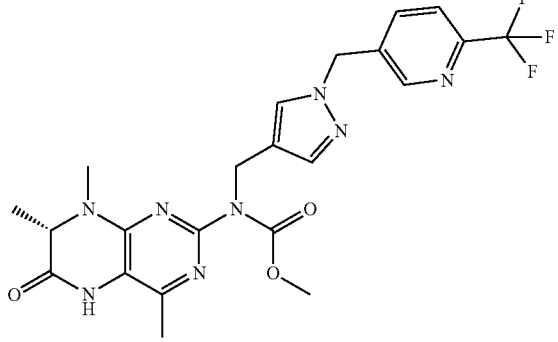
I-407
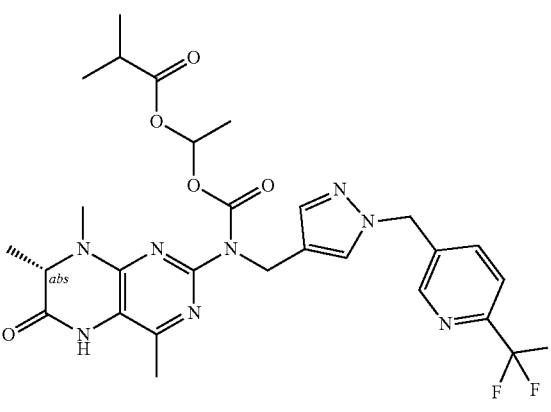
I-408
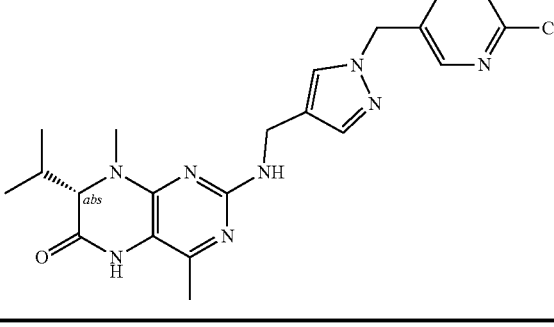
I-409
TABLE B
Exemplary Compounds
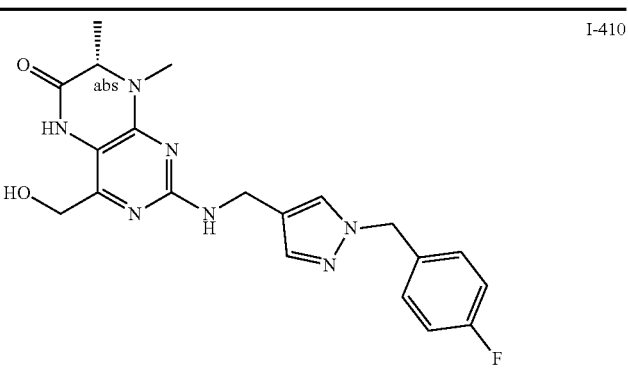
I-410

TABLE B-continued
Exemplary Compounds
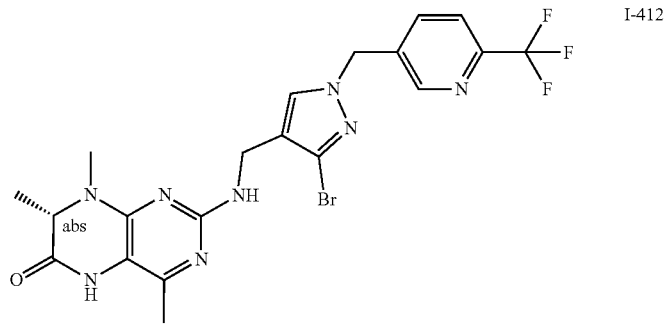
I-412
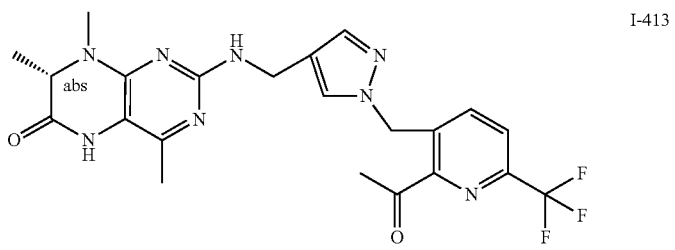
I-413
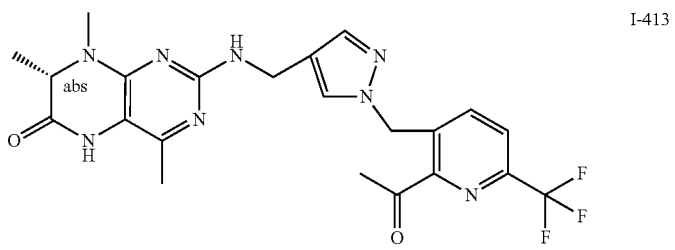
I-413
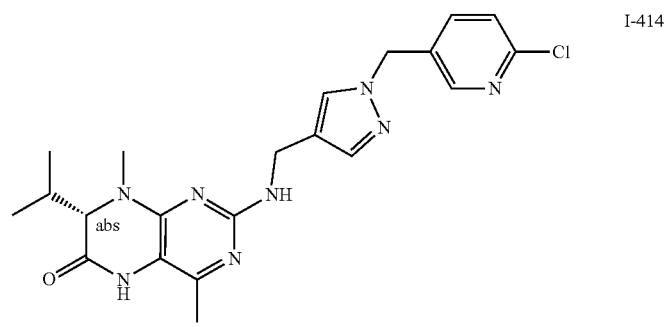
I-414
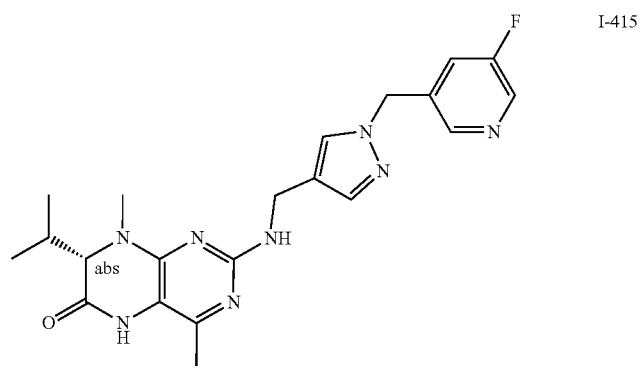
I-415

TABLE B-continued
Exemplary Compounds
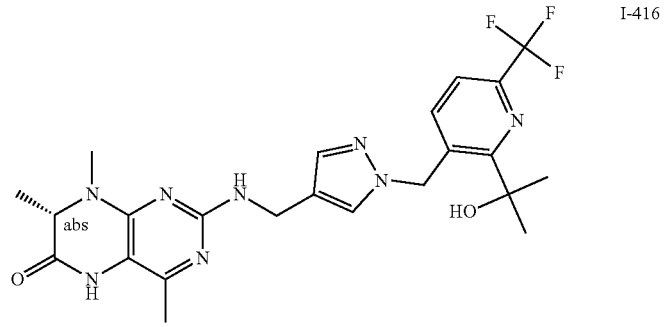
I-416
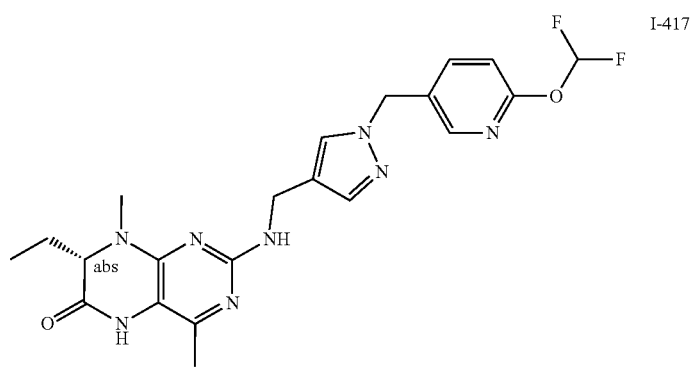
I-417
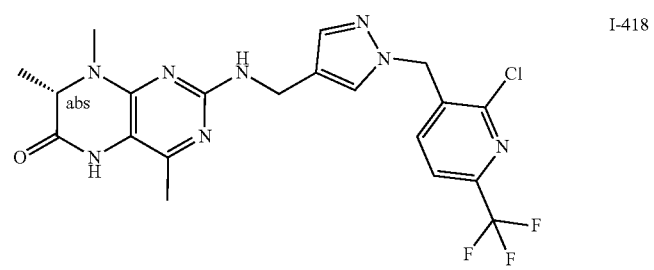
I-418
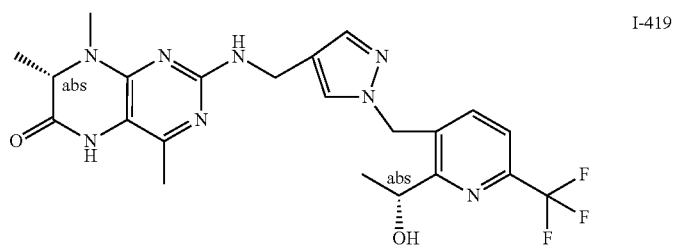
I-419
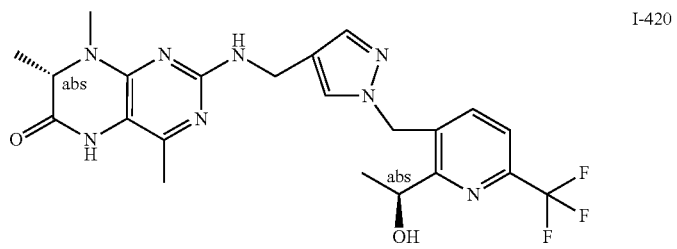
I-420

TABLE B-continued
Exemplary Compounds
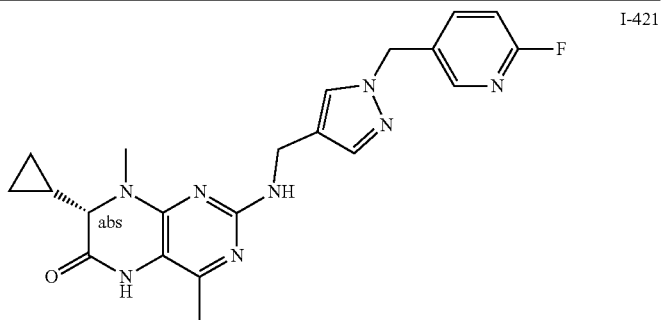
I-421
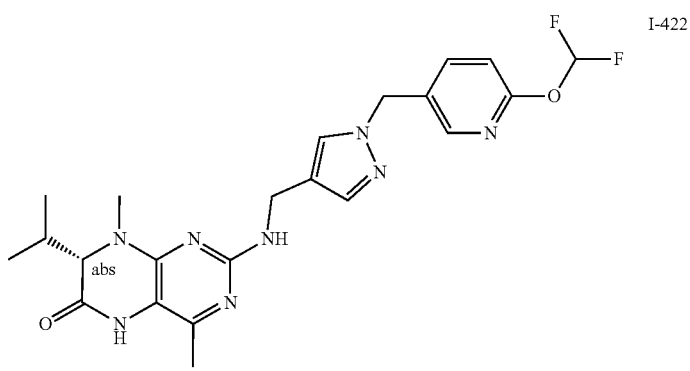
I-422
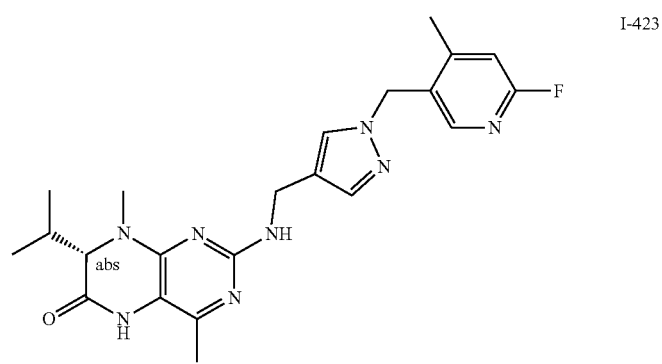
I-423
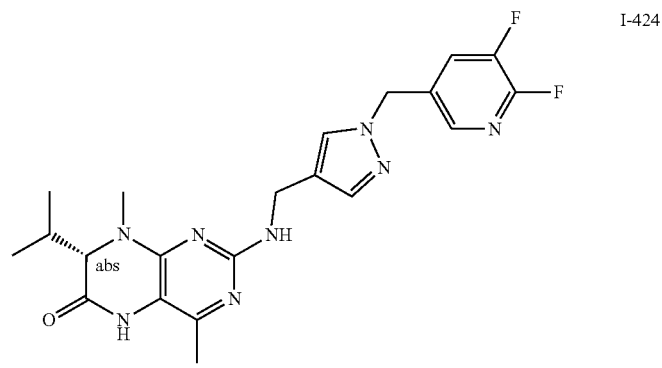
I-424
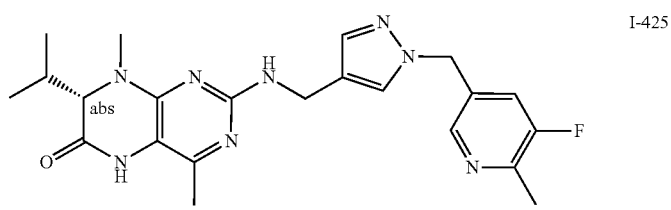
I-425

TABLE B-continued
Exemplary Compounds
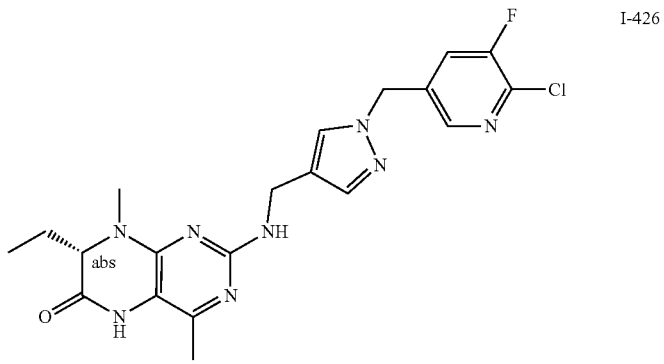
I-426
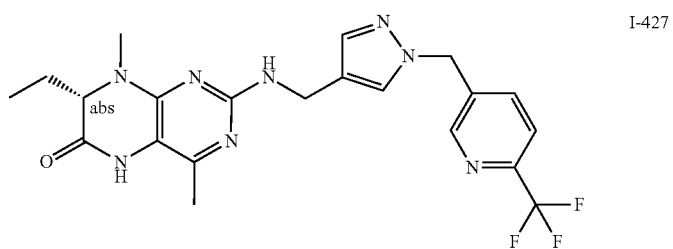
I-427
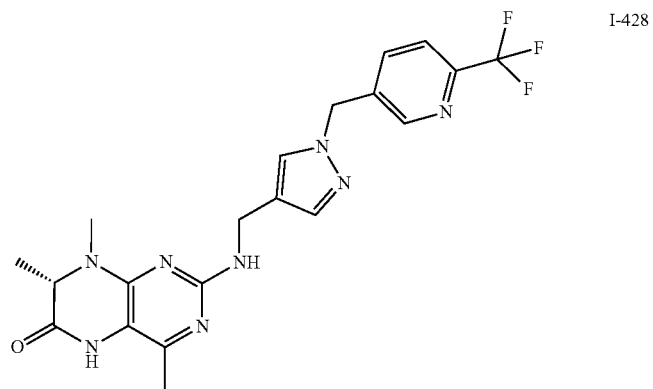
I-428
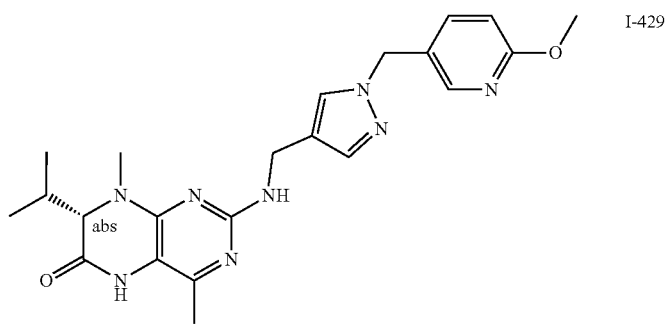
I-429
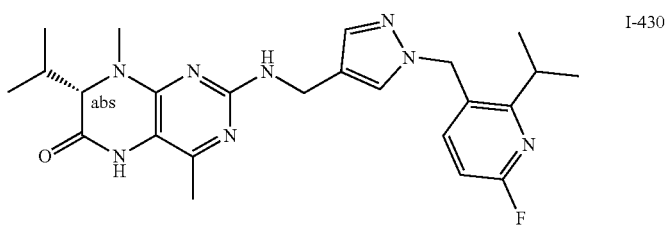
I-430

TABLE B-continued
Exemplary Compounds
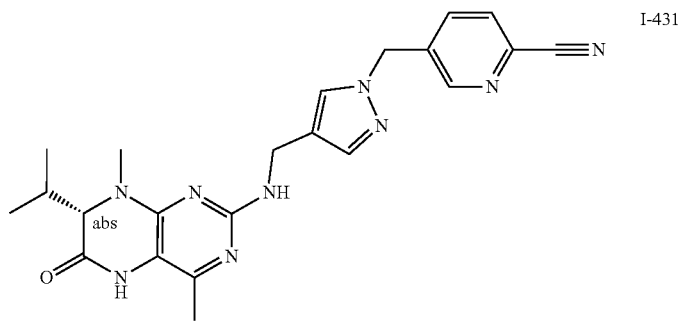
I-431
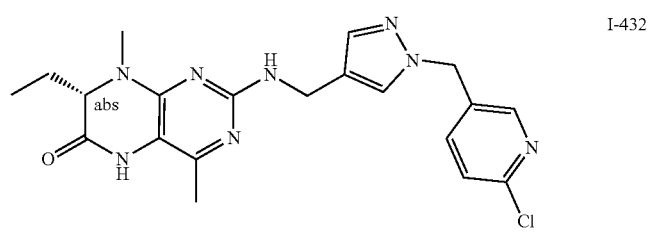
I-432
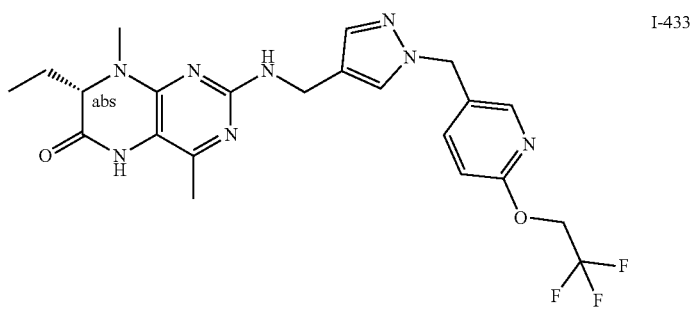
I-433
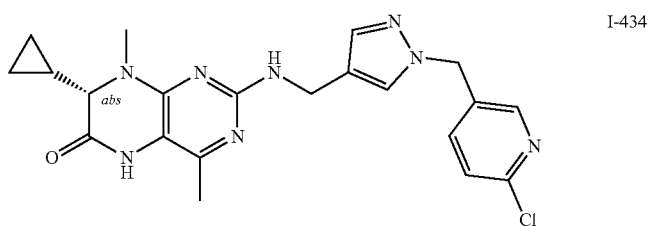
I-434
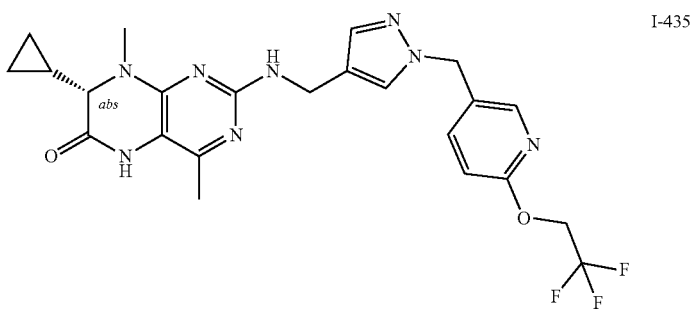
I-435

TABLE B-continued
Exemplary Compounds
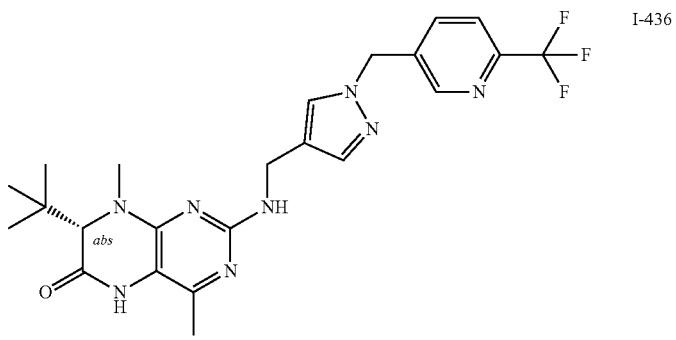
I-436
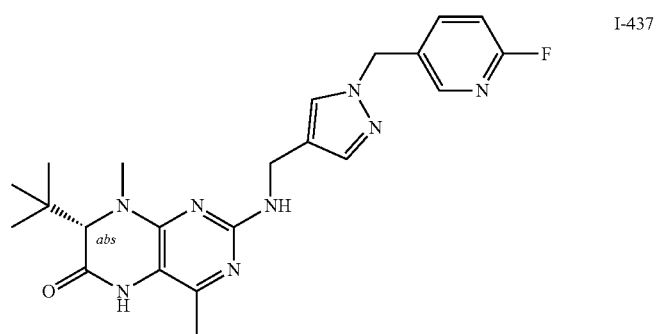
I-437
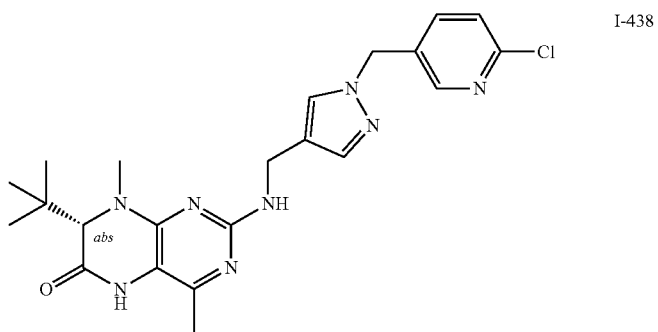
I-438
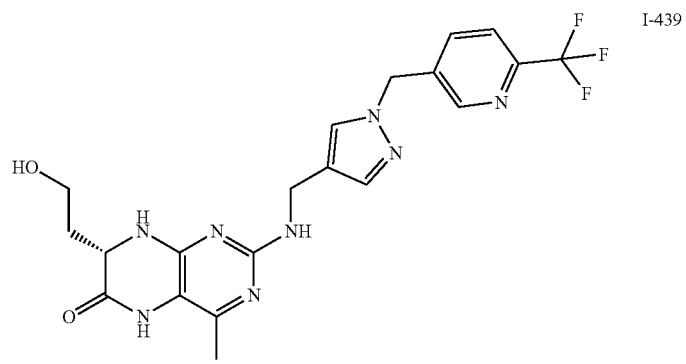
I-439

TABLE B-continued
Exemplary Compounds
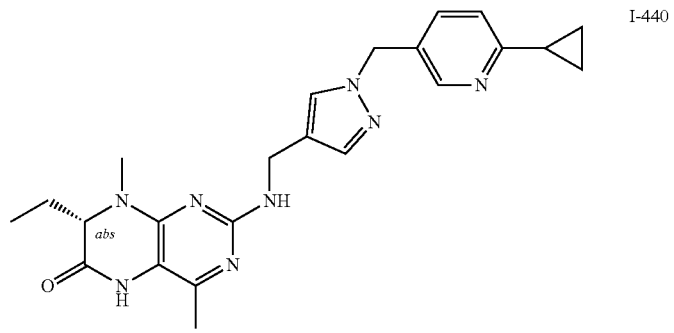
I-440
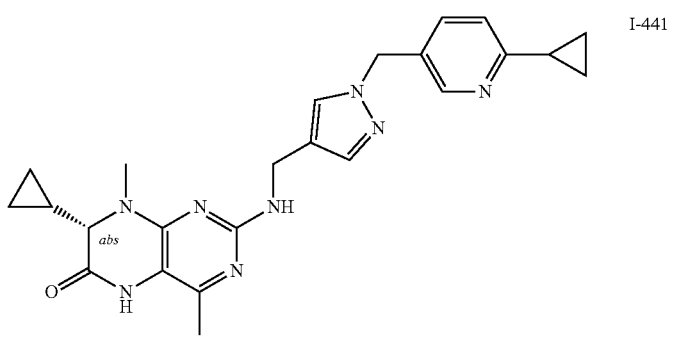
I-441
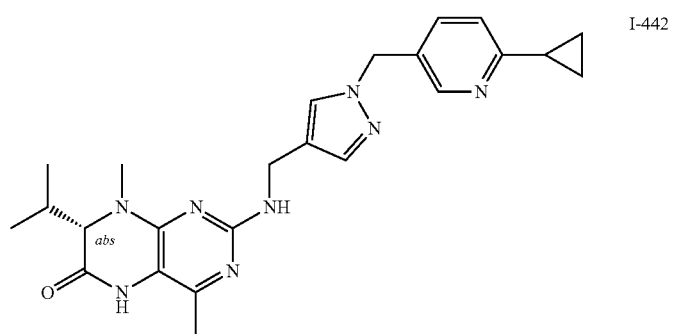
I-442
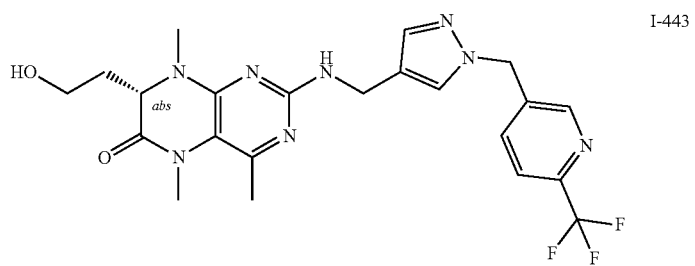
I-443
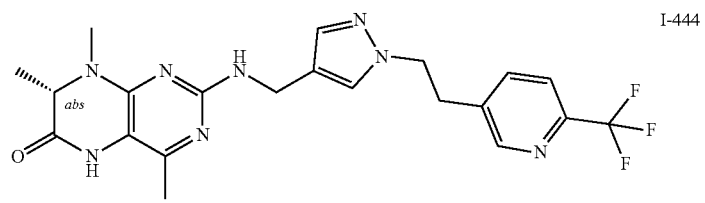
I-444

TABLE B-continued
Exemplary Compounds
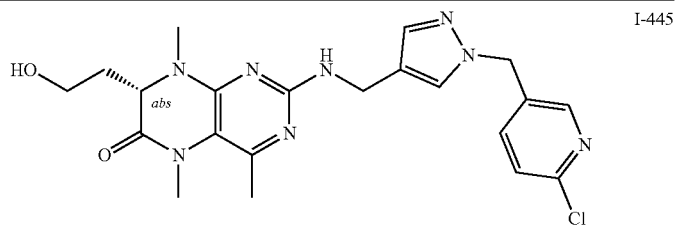
I-445
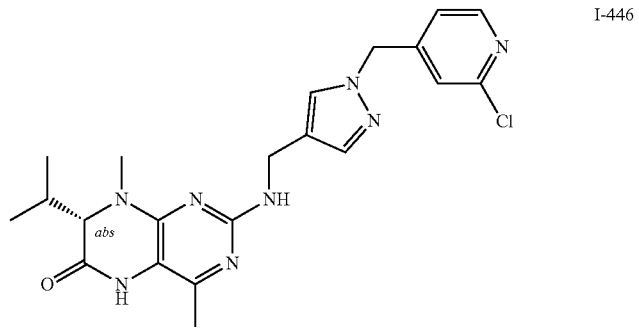
I-446
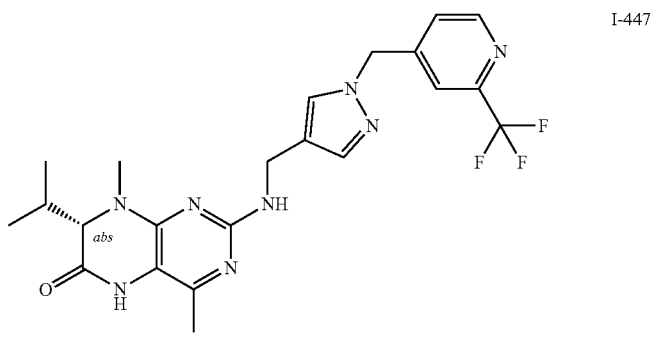
I-447
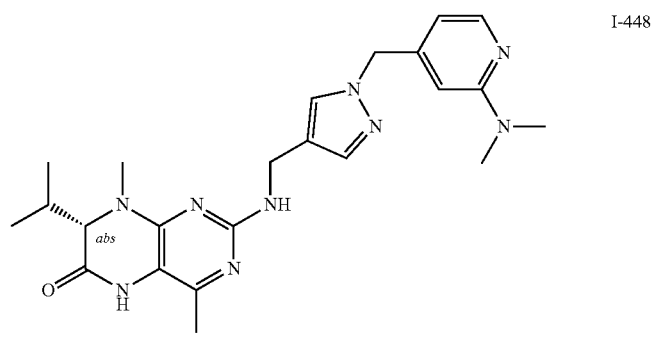
I-448
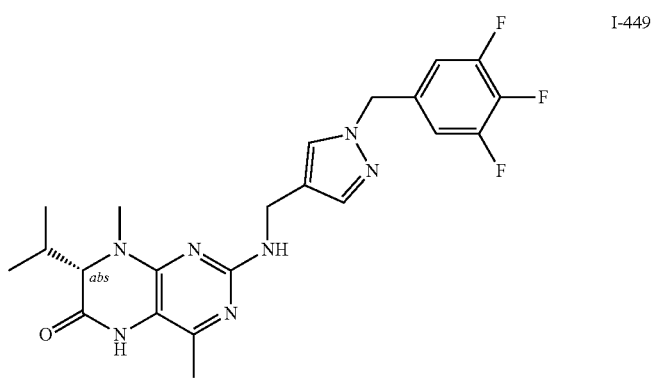
I-449

TABLE B-continued
Exemplary Compounds
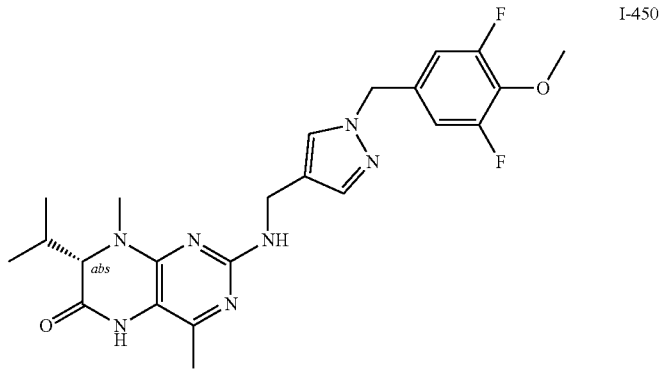
I-450
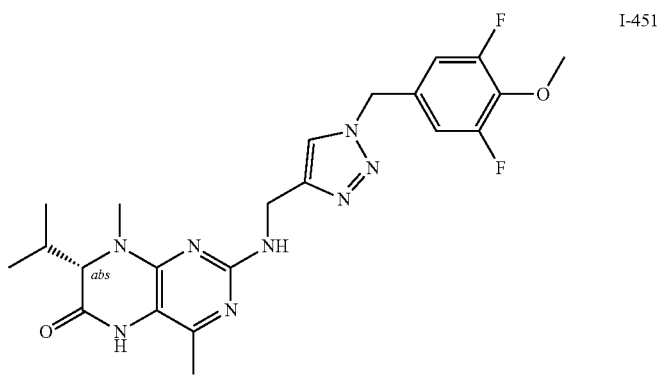
I-451
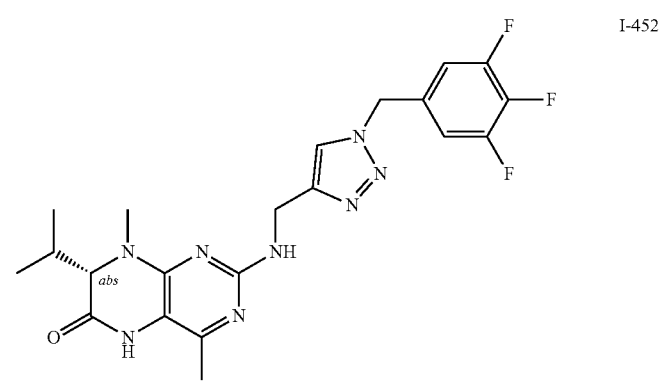
I-452
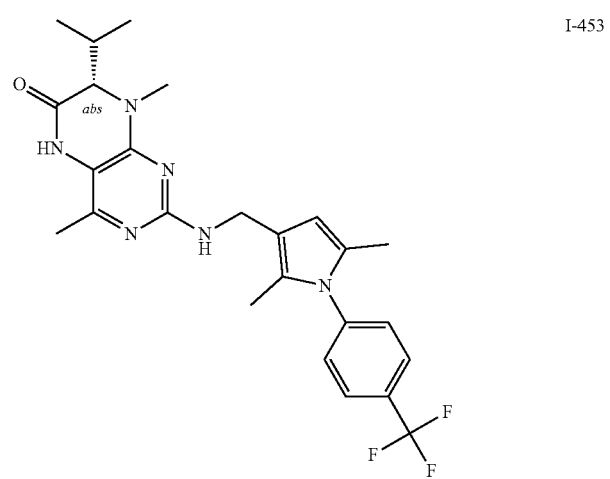
I-453

TABLE B-continued
Exemplary Compounds
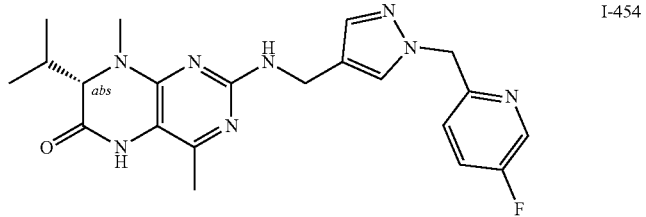
I-454
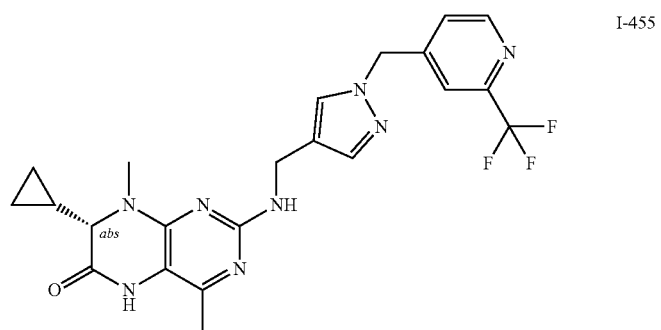
I-455
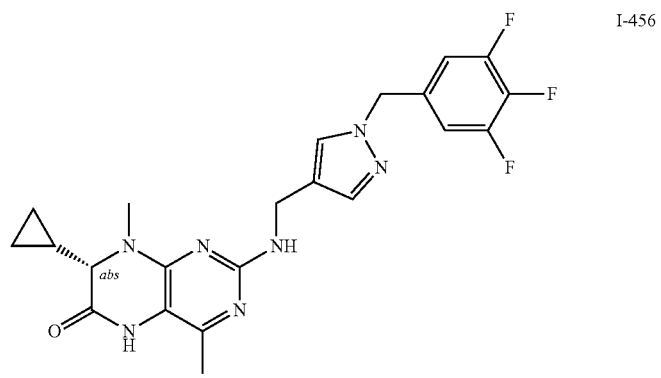
I-456
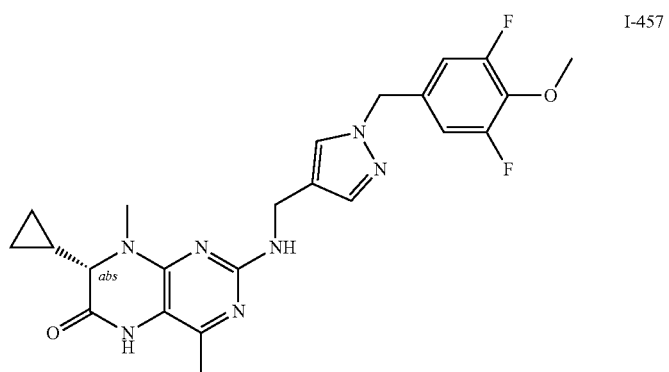
I-457
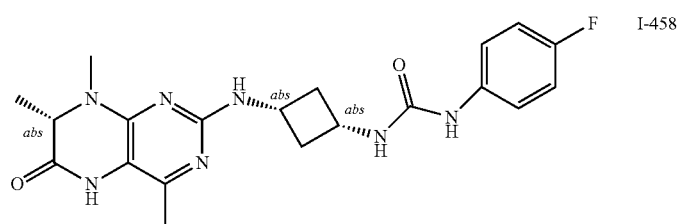
I-458

US 11,572,364 B2
233
TABLE B-continued
Exemplary Compounds
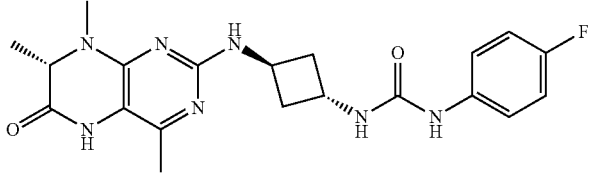 [SMILES: Cc1nc(N[C@H]2C[C@H](NC(=O)Nc3ccc(F)cc3)C2)nc2c1NC(=O)[C@H](C)N2C] I-459
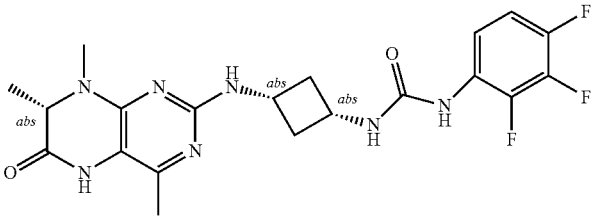 [SMILES: Cc1nc(N[C@H]2C[C@@H](NC(=O)Nc3ccc(F)c(F)c3F)C2)nc2c1NC(=O)[C@H](C)N2C] I-460
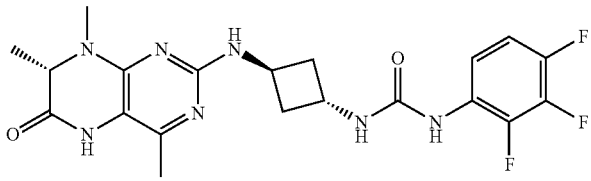 [SMILES: Cc1nc(N[C@H]2C[C@H](NC(=O)Nc3ccc(F)c(F)c3F)C2)nc2c1NC(=O)[C@H](C)N2C] I-461
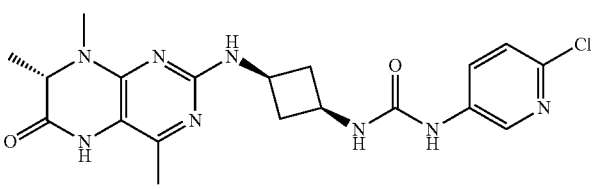 [SMILES: Cc1nc(N[C@H]2C[C@@H](NC(=O)Nc3ccc(Cl)nc3)C2)nc2c1NC(=O)[C@H](C)N2C] I-462
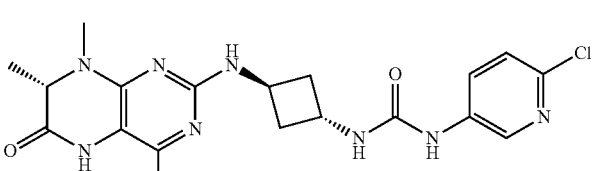 I-463
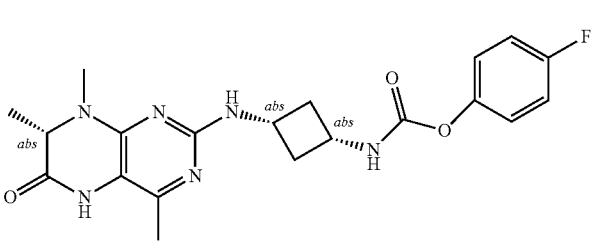 [SMILES: Cc1nc(N[C@H]2C[C@@H](NC(=O)Oc3ccc(F)cc3)C2)nc2c1NC(=O)[C@H](C)N2C] I-464
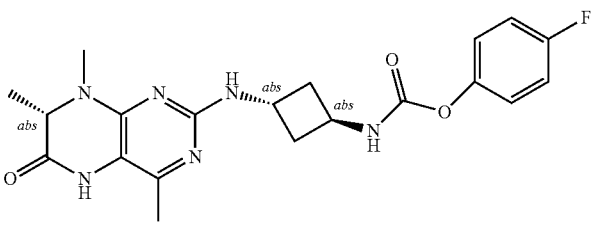 [SMILES: Cc1nc(N[C@H]2C[C@H](NC(=O)Oc3ccc(F)cc3)C2)nc2c1NC(=O)[C@H](C)N2C] I-465

TABLE B-continued
Exemplary Compounds
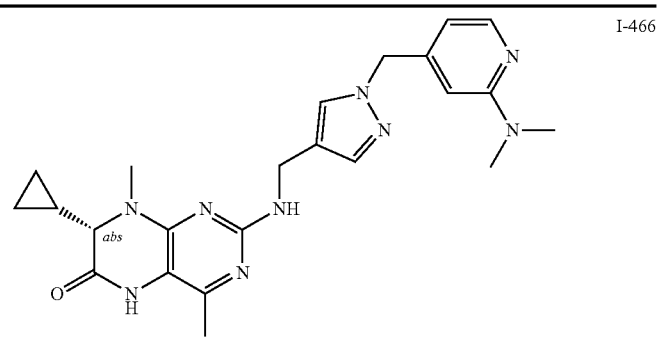
I-466
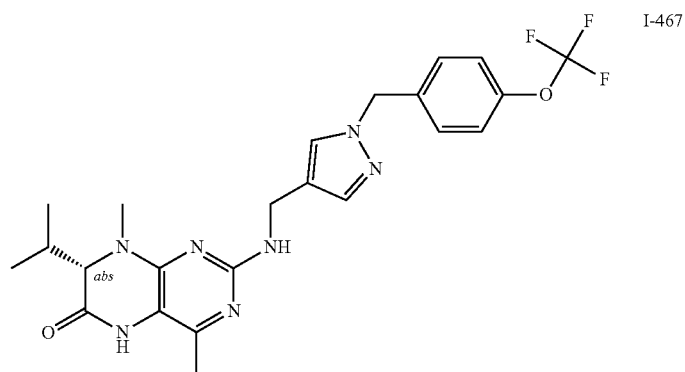
I-467
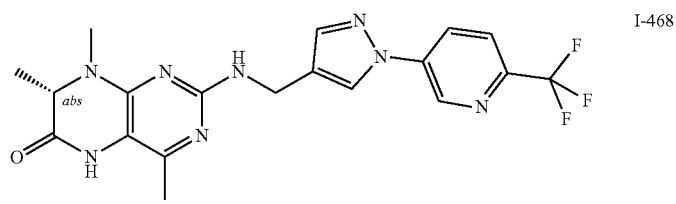
I-468
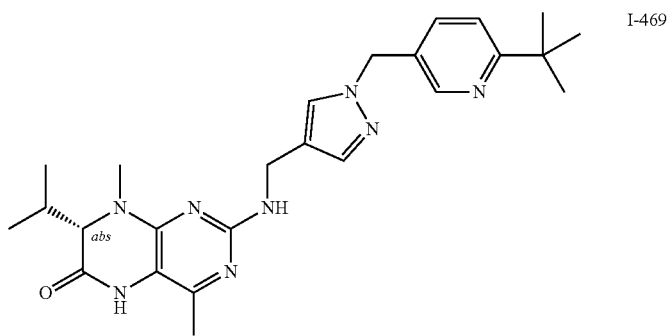
I-469
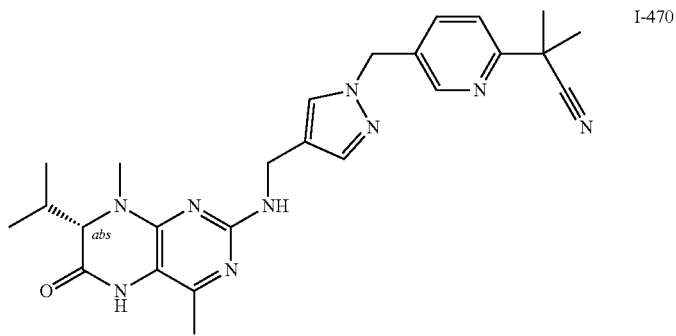
I-470

237
TABLE B-continued
Exemplary Compounds
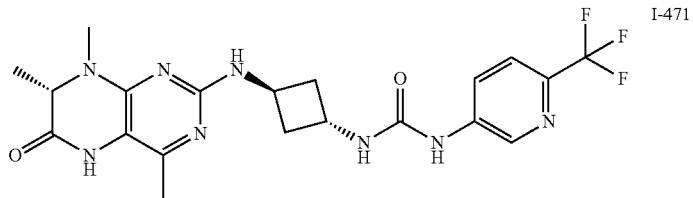
I-471
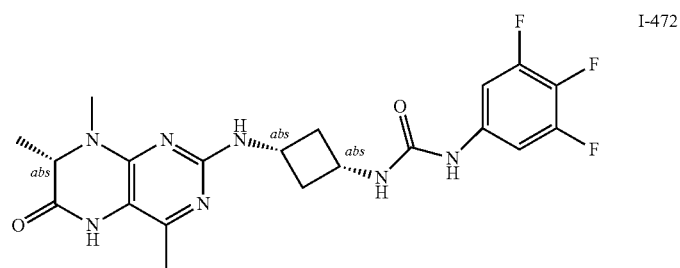
I-472
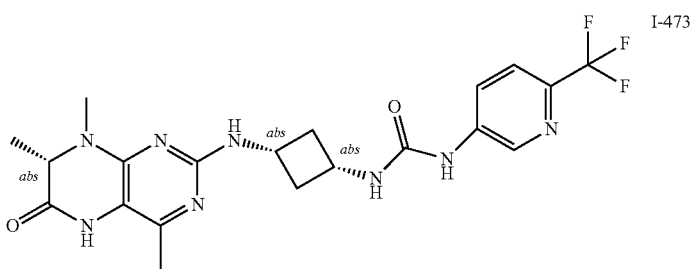
I-473
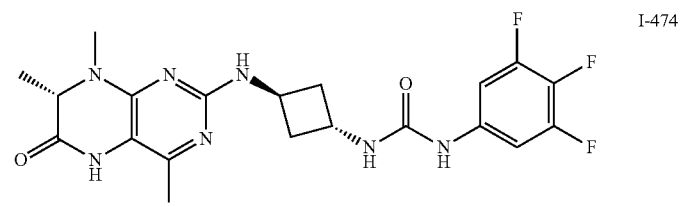
I-474
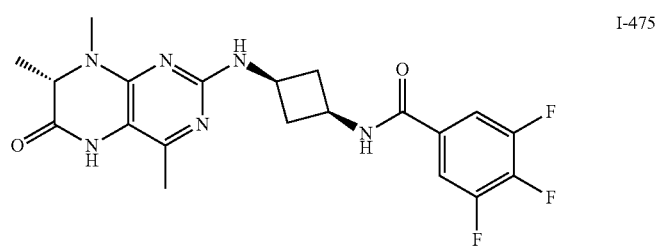
I-475
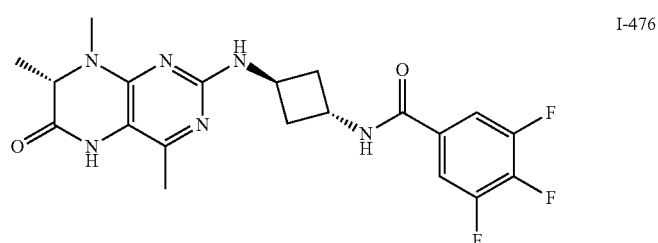
I-476

TABLE B-continued
Exemplary Compounds
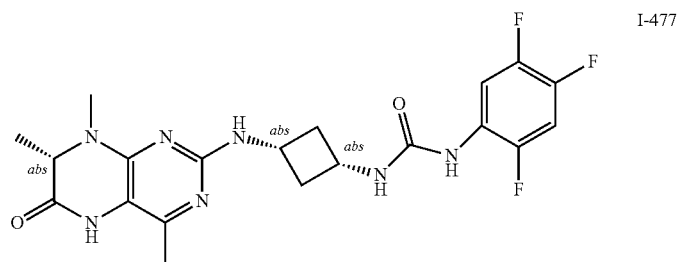
I-477
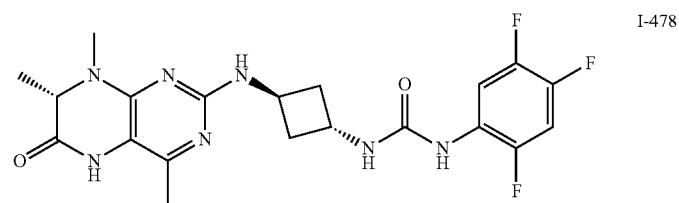
I-478
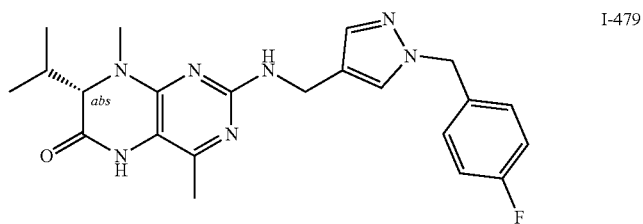
I-479
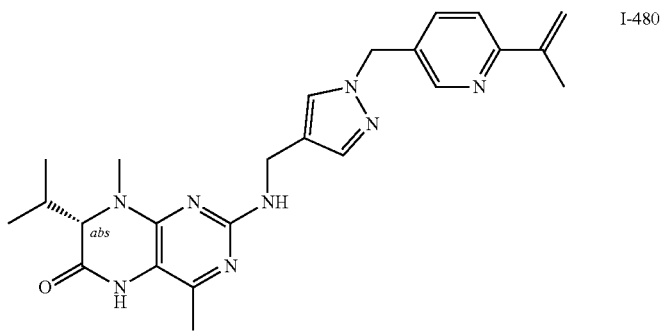
I-480
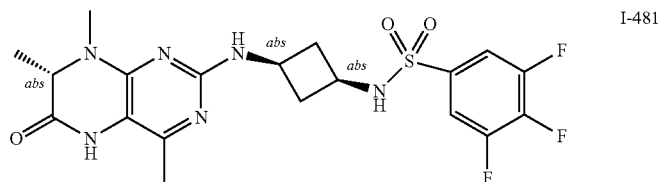
I-481
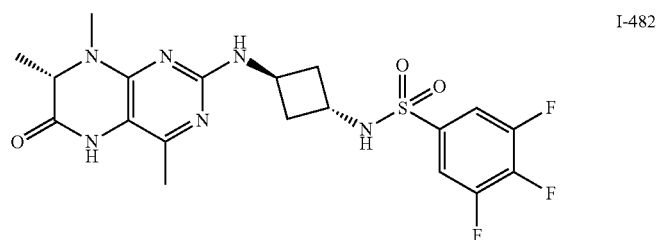
I-482

TABLE B-continued
Exemplary Compounds
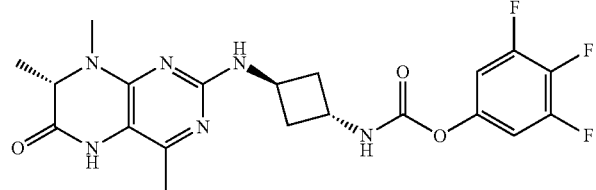 [SMILES: Cc1nc(N[C@H]2C[C@H](NC(=O)Oc3cc(F)c(F)c(F)c3)C2)nc2c1NC(=O)[C@H](C)N2C]
I-483
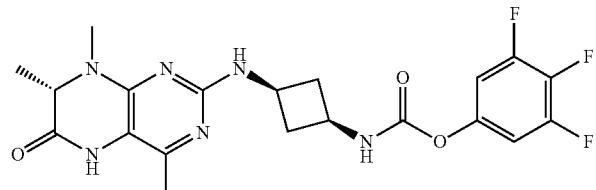
I-484
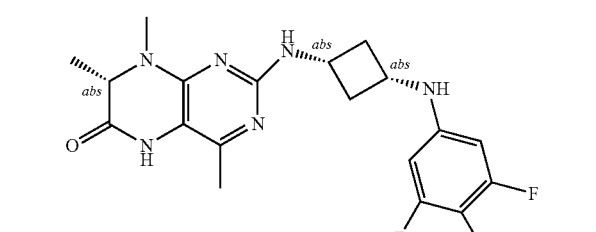
I-485
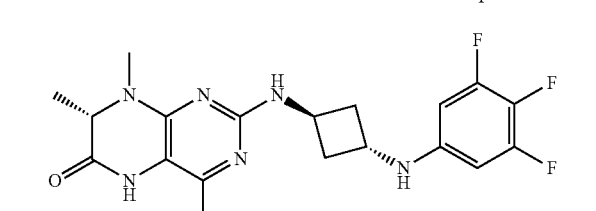
I-486
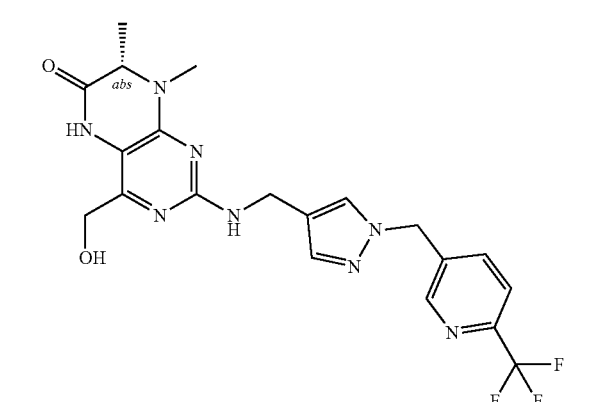
I-487
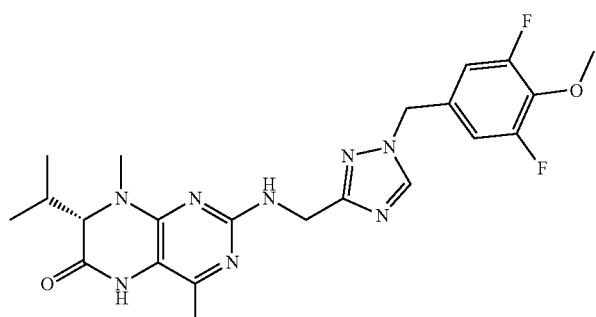
I-488

TABLE B-continued
Exemplary Compounds
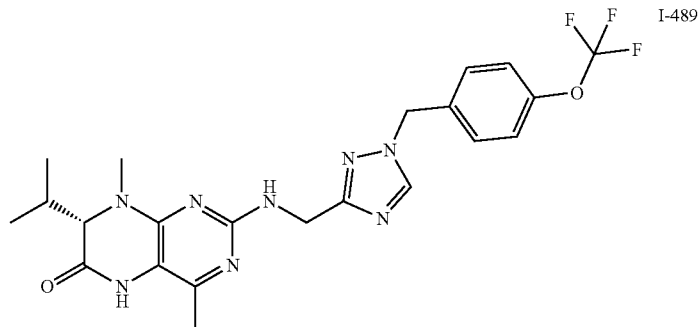
I-489
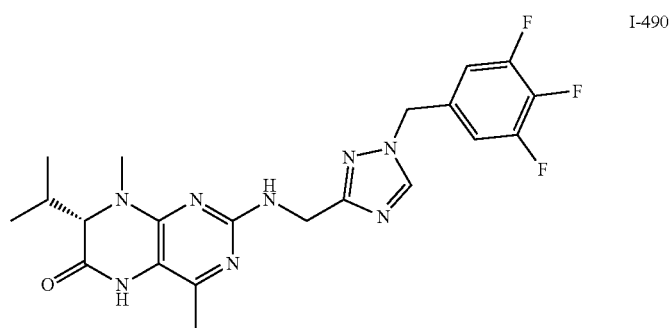
I-490
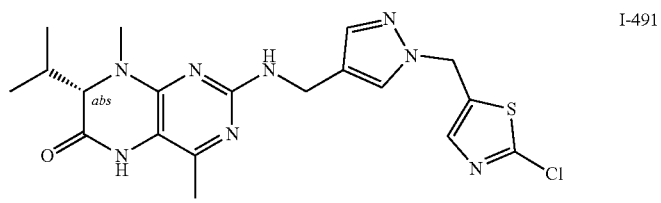
I-491
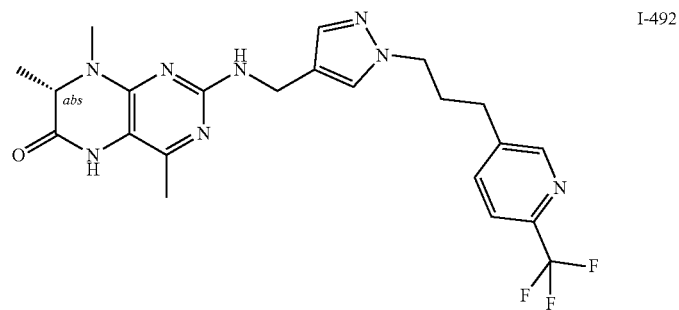
I-492
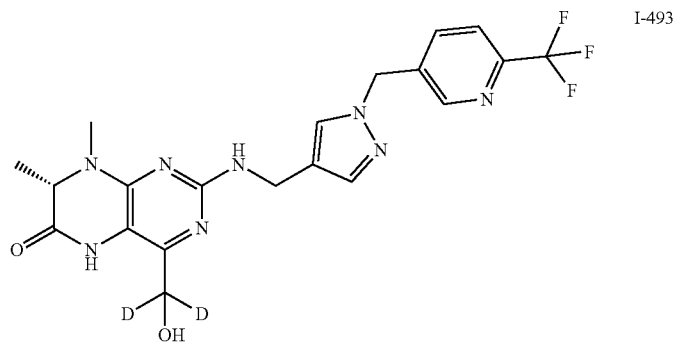
I-493

TABLE B-continued
Exemplary Compounds
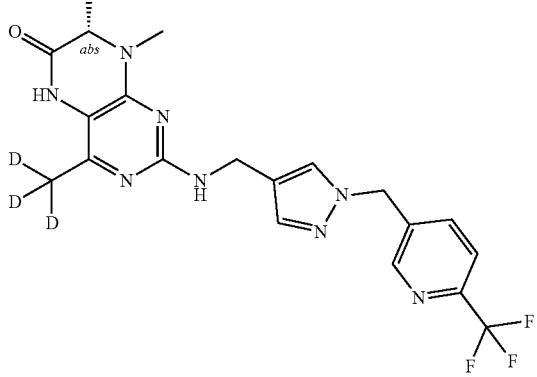
I-494
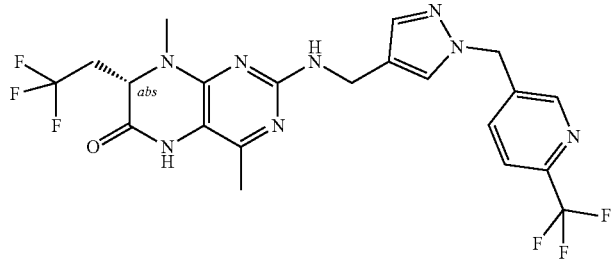 [SMILES: Cc1nc(NCc2cnn(Cc3ccc(C(F)(F)F)nc3)c2)nc2c1NC(=O)[C@H](CC(F)(F)F)N2C]
I-495
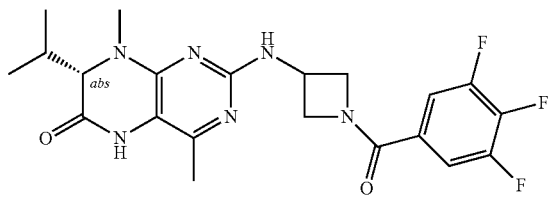 [SMILES: Cc1nc(NC2CN(C(=O)c3cc(F)c(F)c(F)c3)C2)nc2c1NC(=O)[C@H](C(C)C)N2C]
I-496
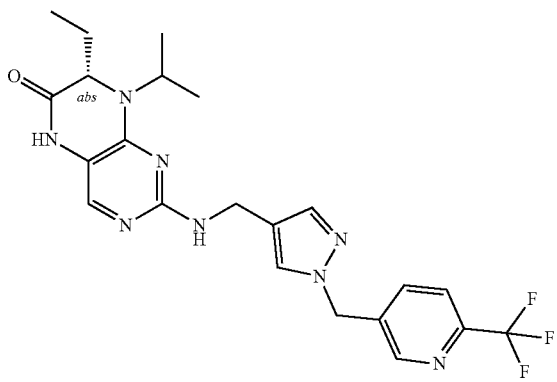 [SMILES: CC[C@H]1C(=O)Nc2cnc(NCc3cnn(Cc4ccc(C(F)(F)F)nc4)c3)nc2N1C(C)C]
I-497
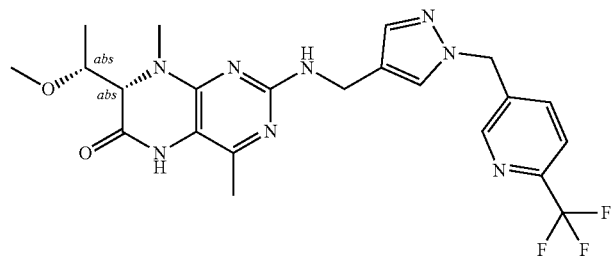 [SMILES: CO[C@H](C)[C@H]1C(=O)Nc2c(C)nc(NCc3cnn(Cc4ccc(C(F)(F)F)nc4)c3)nc2N1C]
I-498

TABLE B-continued

Exemplary Compounds

I-499, I-500, I-501, I-502, I-503, I-504 (chemical structures)

TABLE B-continued
Exemplary Compounds
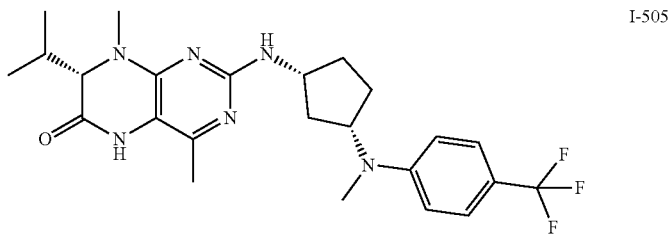
I-505
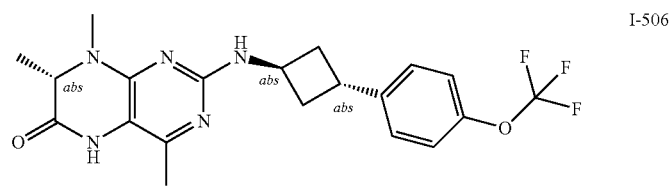
I-506
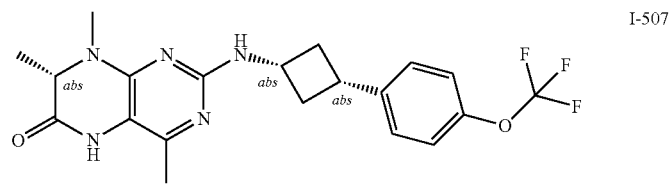
I-507
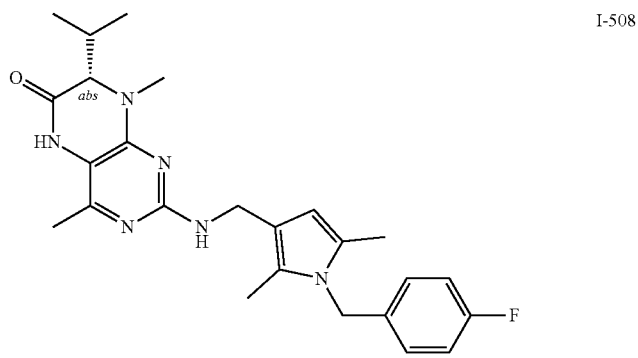
I-508
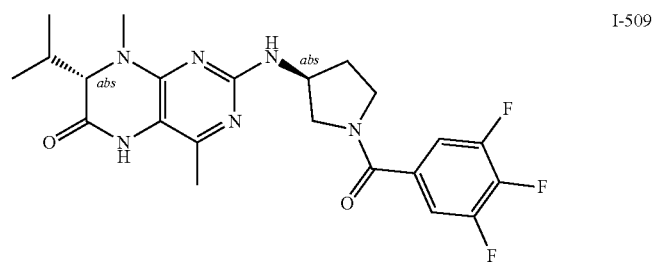
I-509

251
TABLE B-continued
Exemplary Compounds
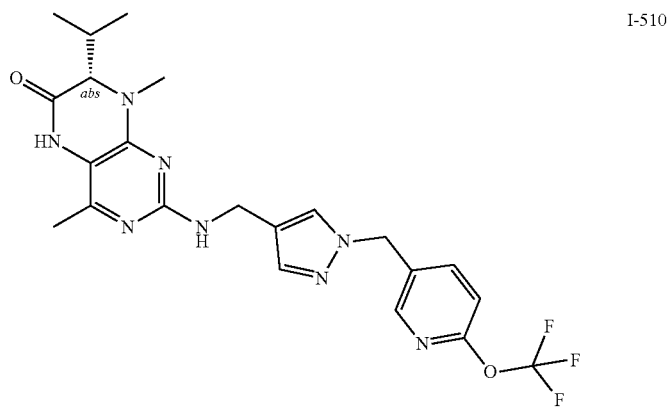
I-510
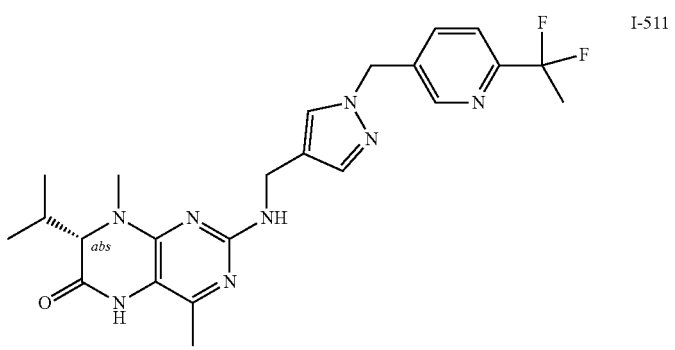
I-511
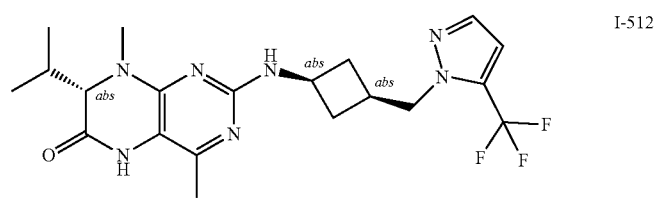
I-512
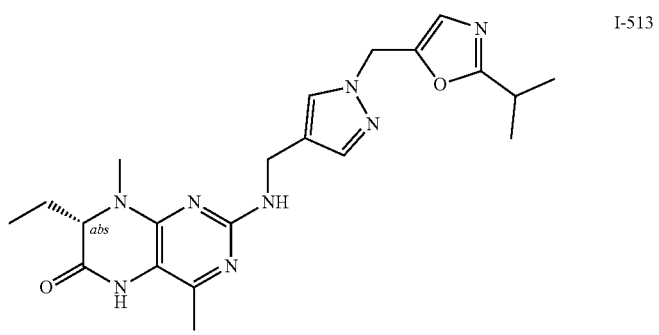
I-513
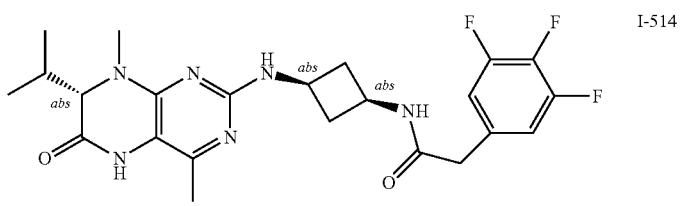
I-514

TABLE B-continued
Exemplary Compounds
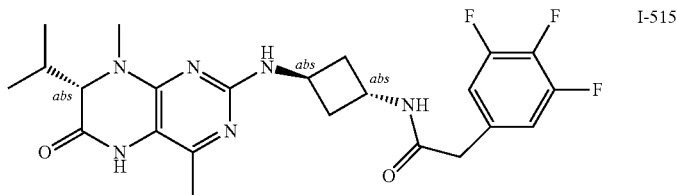
I-515
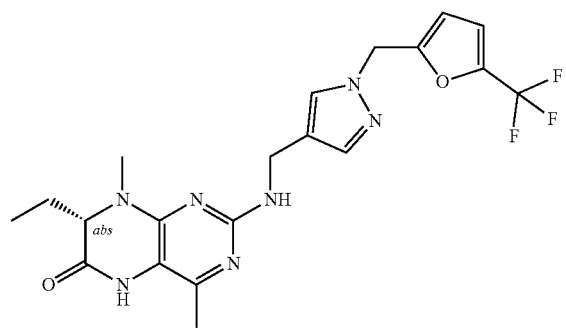 [SMILES: CC[C@H]1C(=O)Nc2c(C)nc(NCc3cnn(Cc4ccc(C(F)(F)F)o4)c3)nc2N1C]
I-516
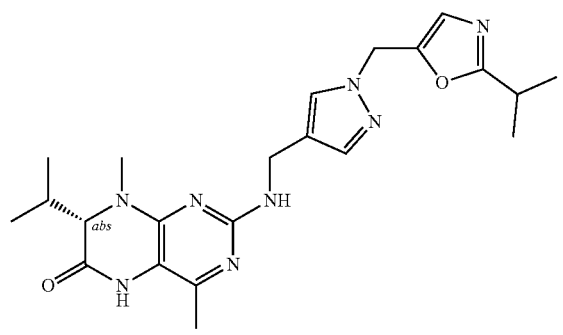 [SMILES: Cc1nc(NCc2cnn(Cc3cnc(C(C)C)o3)c2)nc2c1NC(=O)[C@H](C(C)C)N2C]
I-517
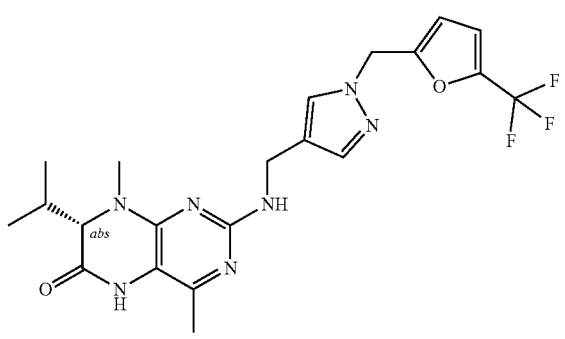 [SMILES: Cc1nc(NCc2cnn(Cc3ccc(C(F)(F)F)o3)c2)nc2c1NC(=O)[C@H](C(C)C)N2C]
I-518

TABLE B-continued
Exemplary Compounds
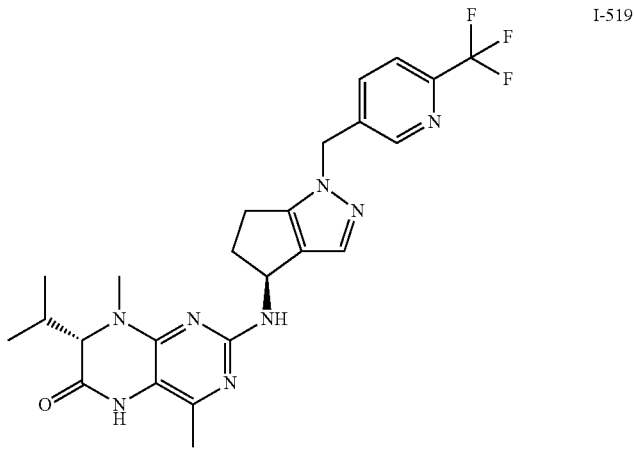
I-519
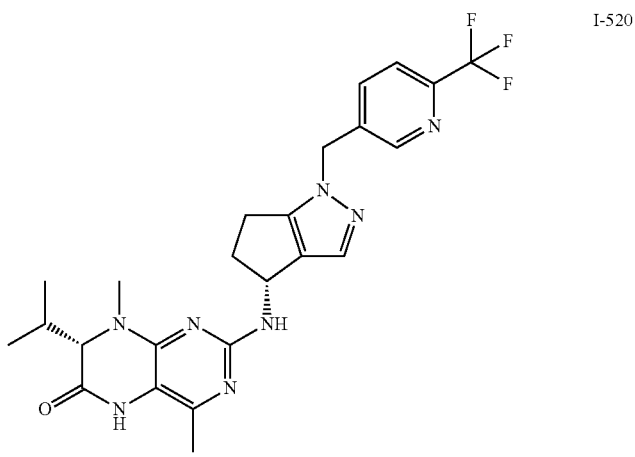
I-520
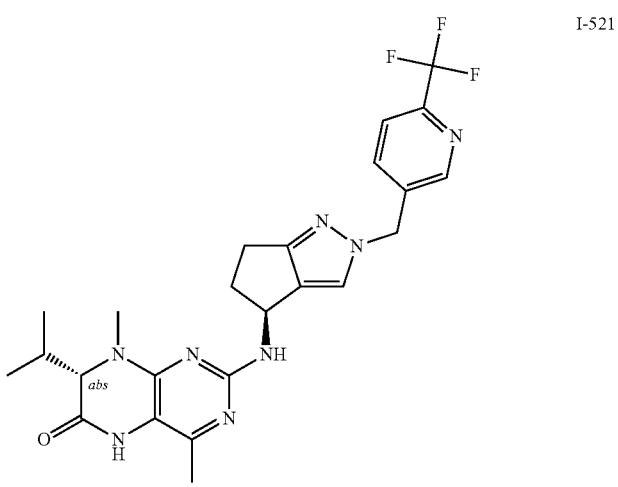
I-521

TABLE B-continued
Exemplary Compounds
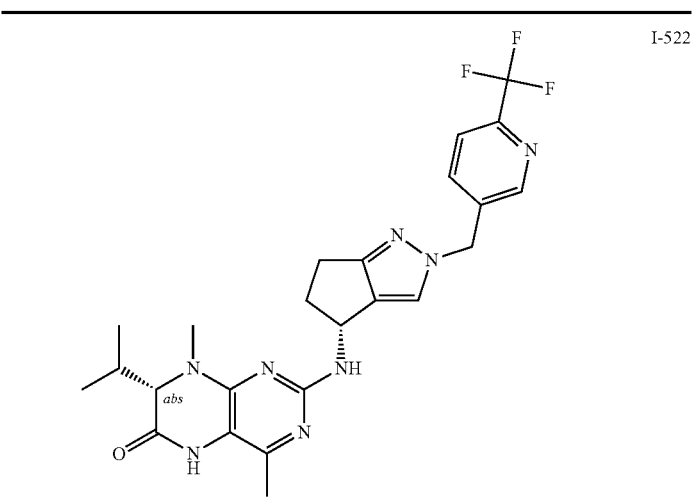 I-522
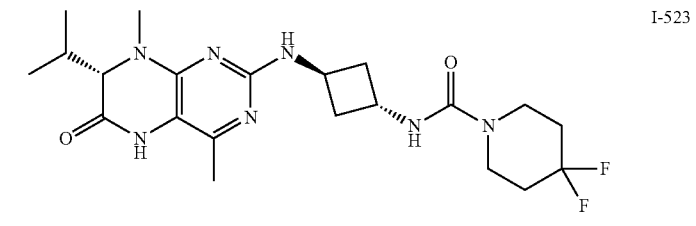 I-523
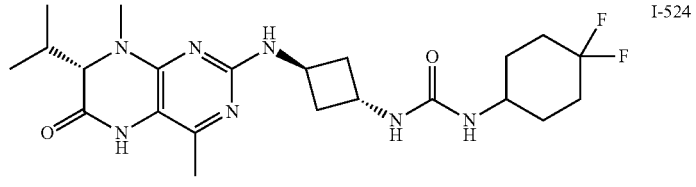 I-524
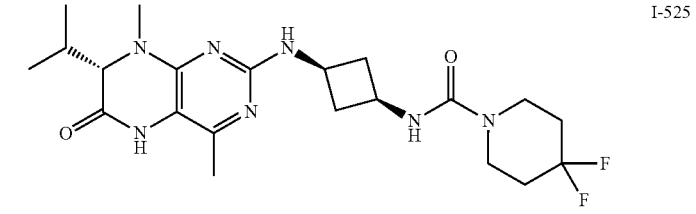 I-525
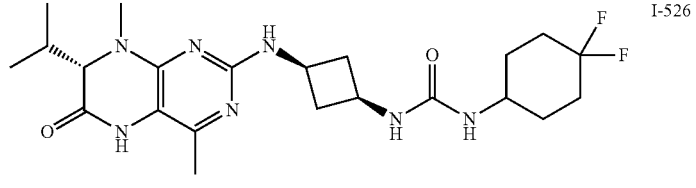 I-526
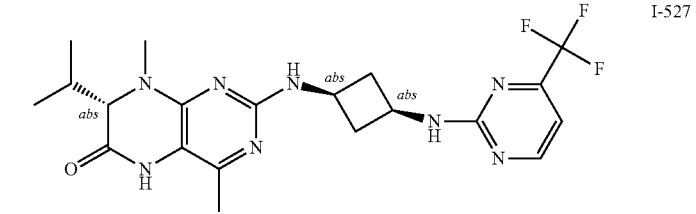 I-527

US 11,572,364 B2
TABLE B-continued
Exemplary Compounds
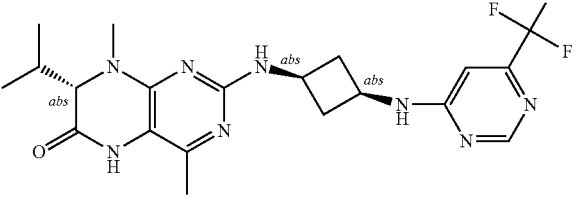 I-528
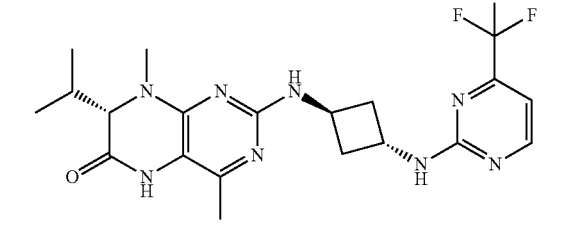 I-529
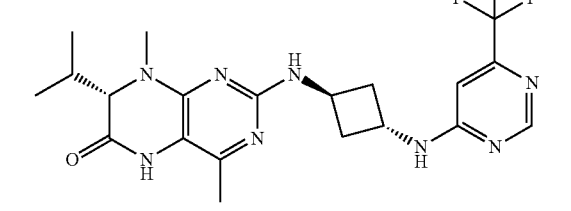 I-530
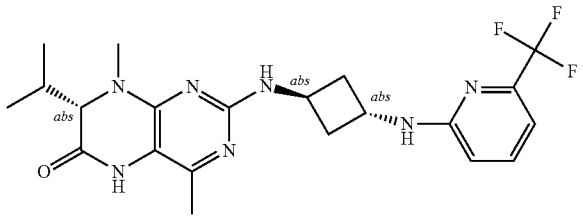 [SMILES: Cc1nc(N[C@H]2C[C@H](Nc3cccc(C(F)(F)F)n3)C2)nc2c1NC(=O)[C@H](C(C)C)N2C] I-531
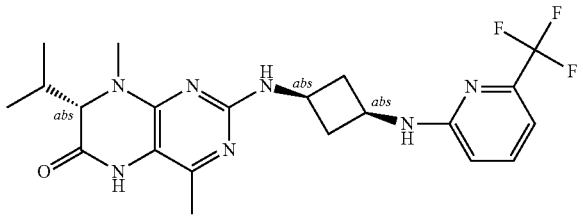 [SMILES: Cc1nc(N[C@H]2C[C@@H](Nc3cccc(C(F)(F)F)n3)C2)nc2c1NC(=O)[C@H](C(C)C)N2C] I-532
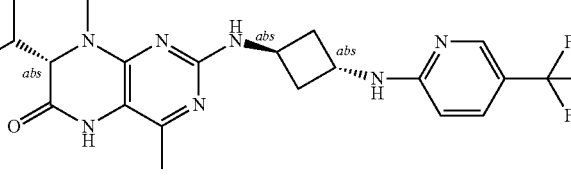 I-533
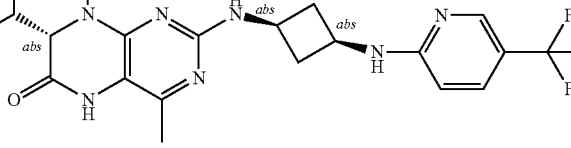 I-534

US 11,572,364 B2
261
TABLE B-continued
Exemplary Compounds
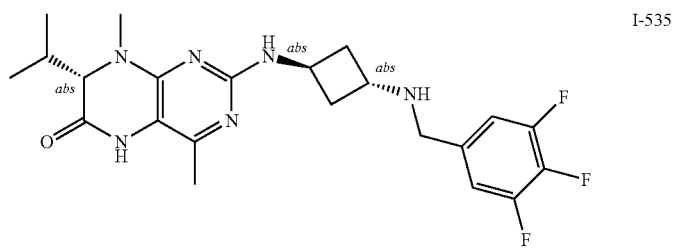 I-535
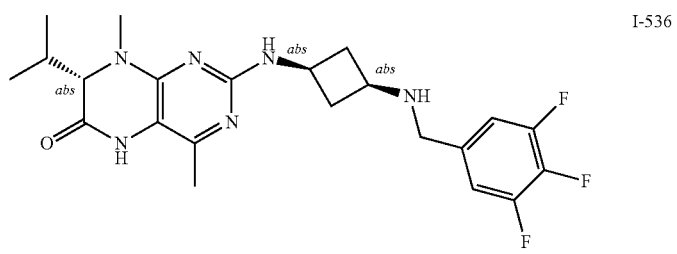 I-536
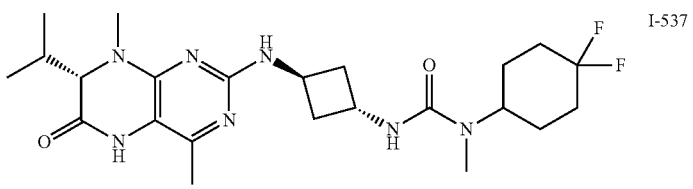 I-537
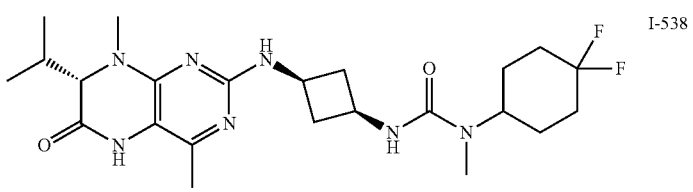 I-538
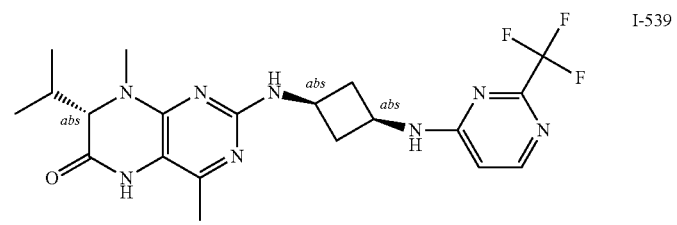 I-539
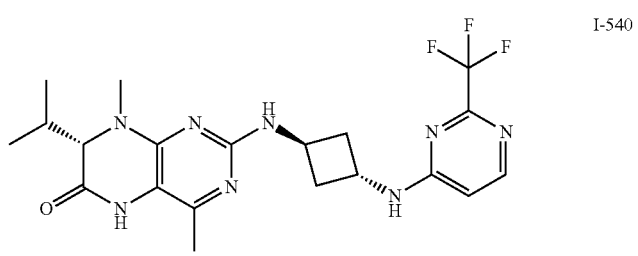 I-540

TABLE B-continued
Exemplary Compounds
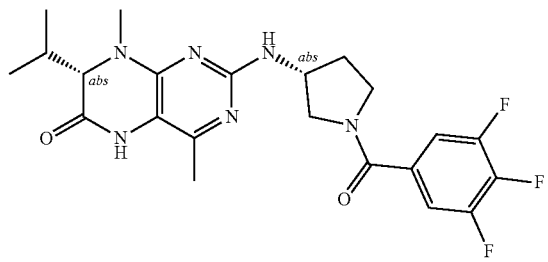 [SMILES: Cc1nc(N[C@@H]2CCN(C(=O)c3cc(F)c(F)c(F)c3)C2)nc2c1NC(=O)[C@H](C(C)C)N2C]
I-541
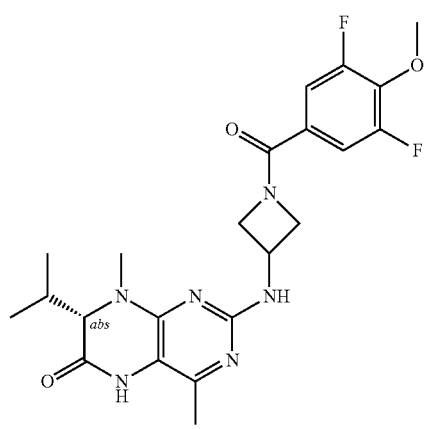 [SMILES: COc1c(F)cc(C(=O)N2CC(Nc3nc(C)c4c(n3)N(C)[C@@H](C(C)C)C(=O)N4)C2)cc1F]
I-542
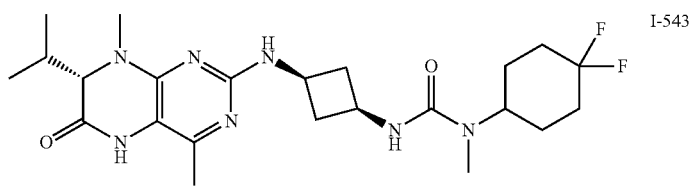
I-543
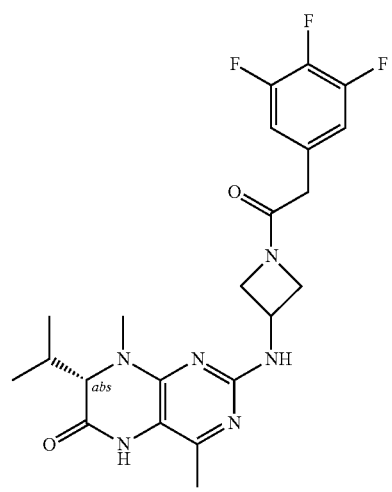 [SMILES: Cc1nc(NC2CN(C(=O)Cc3cc(F)c(F)c(F)c3)C2)nc2c1NC(=O)[C@H](C(C)C)N2C]
I-544

TABLE B-continued
Exemplary Compounds
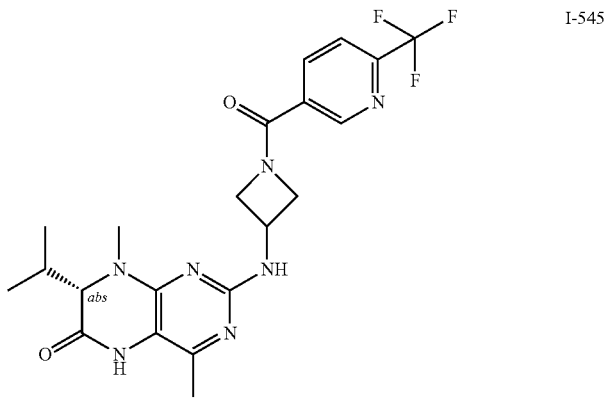
I-545
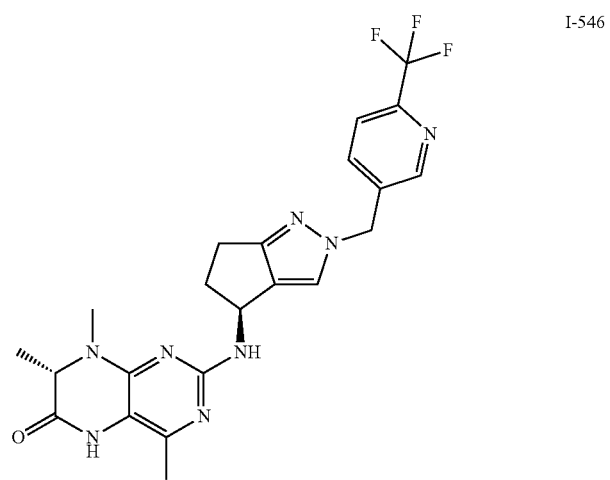
I-546
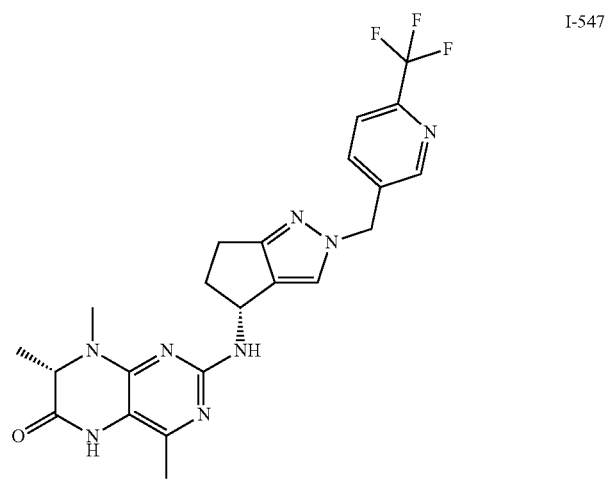
I-547

TABLE B-continued
Exemplary Compounds
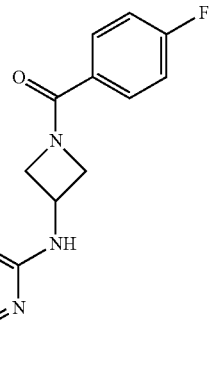
I-548
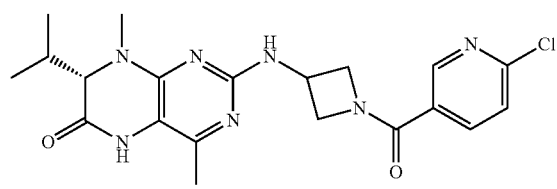 [SMILES: Cc1nc(NC2CN(C(=O)c3ccc(Cl)nc3)C2)nc2c1NC(=O)[C@H](C(C)C)N2C]
I-549
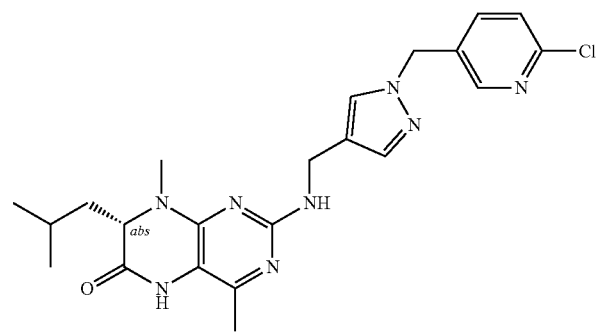 [SMILES: Cc1nc(NCc2cnn(Cc3ccc(Cl)nc3)c2)nc2c1NC(=O)[C@H](CC(C)C)N2C]
I-550
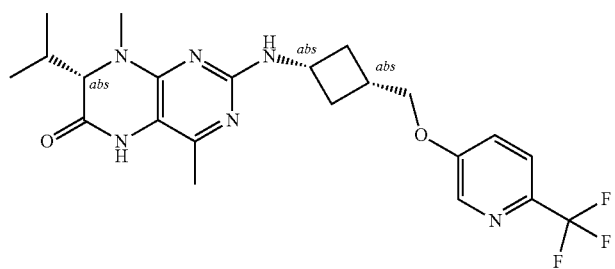 [SMILES: Cc1nc(N[C@H]2C[C@@H](COc3ccc(C(F)(F)F)nc3)C2)nc2c1NC(=O)[C@H](C(C)C)N2C]
I-551
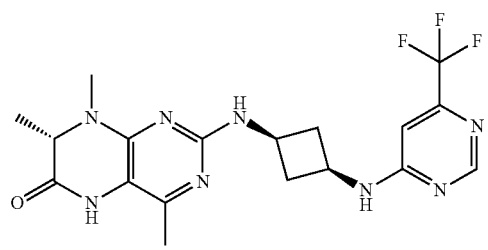 [SMILES: Cc1nc(N[C@H]2C[C@@H](Nc3cc(C(F)(F)F)ncn3)C2)nc2c1NC(=O)[C@H](C)N2C]
I-552

TABLE B-continued
Exemplary Compounds
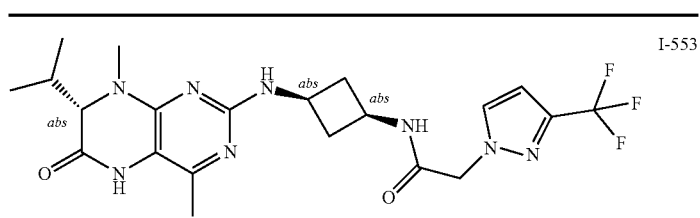
I-553
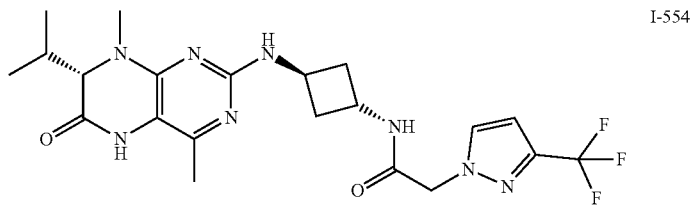
I-554
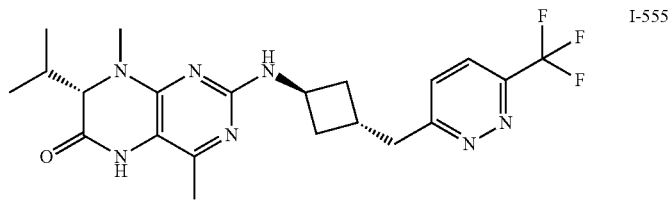
I-555
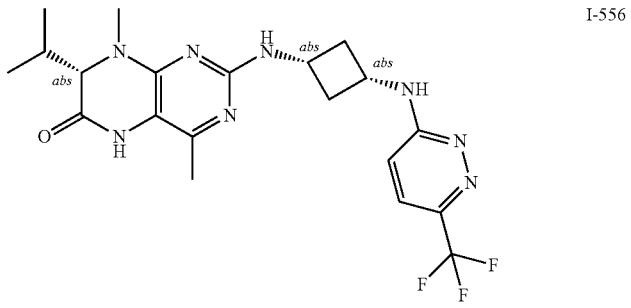
I-556
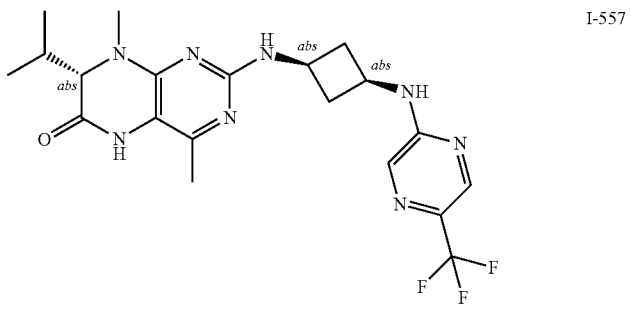
I-557
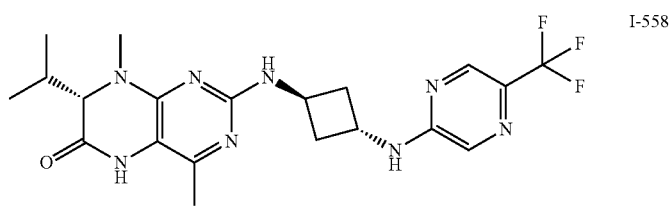
I-558

271
272
TABLE B-continued
Exemplary Compounds
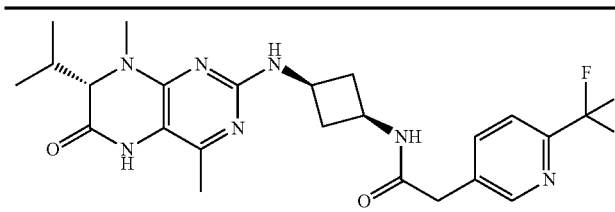
I-559
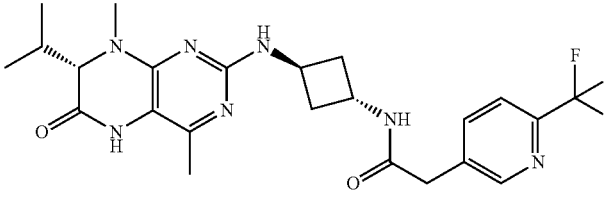
I-560
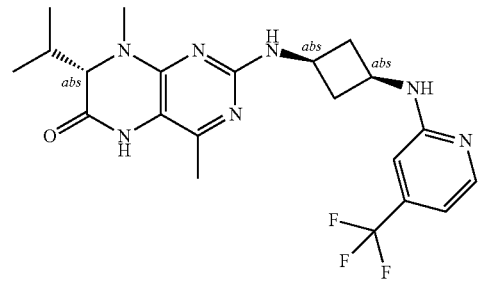 [SMILES: Cc1nc(N[C@H]2C[C@@H](Nc3cc(C(F)(F)F)ccn3)C2)nc2c1NC(=O)[C@H](C(C)C)N2C]
I-561
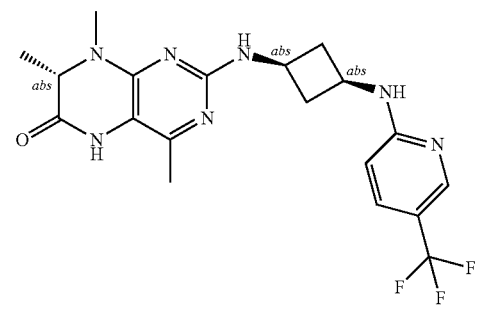 [SMILES: Cc1nc(N[C@H]2C[C@@H](Nc3ccc(C(F)(F)F)cn3)C2)nc2c1NC(=O)[C@H](C)N2C]
I-562
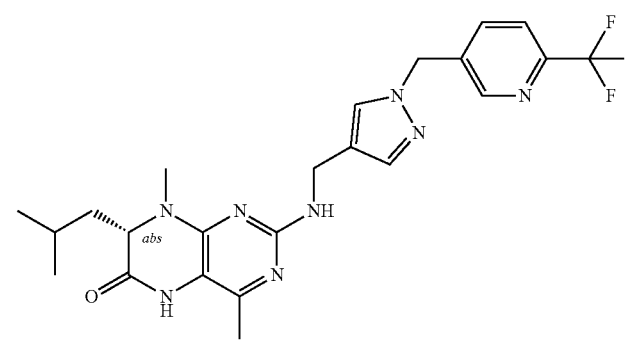
I-563
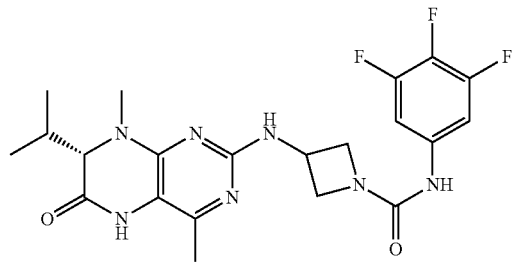 [SMILES: Cc1nc(NC2CN(C(=O)Nc3cc(F)c(F)c(F)c3)C2)nc2c1NC(=O)[C@H](C(C)C)N2C]
I-564

TABLE B-continued
Exemplary Compounds
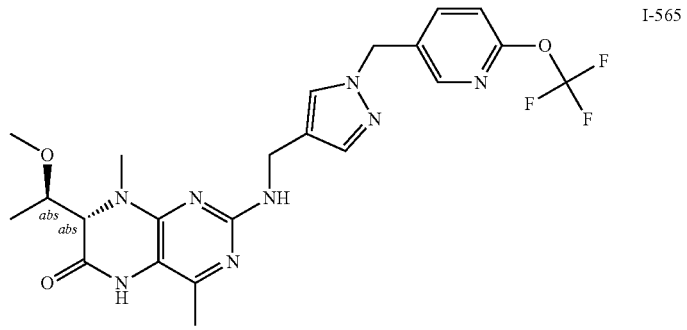
I-565
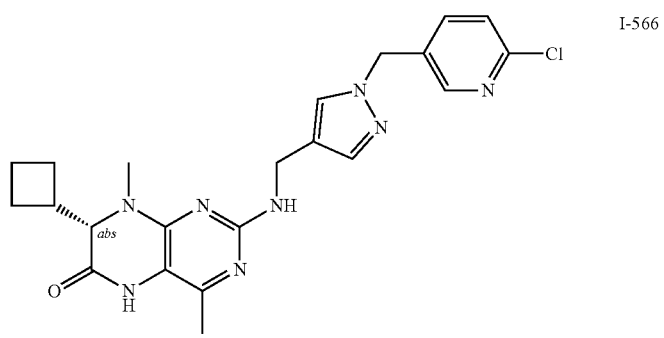
I-566
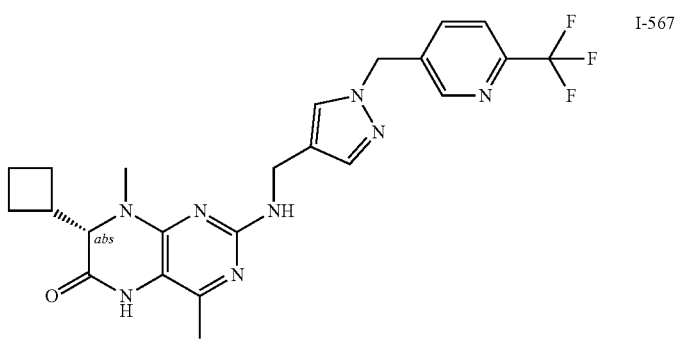
I-567
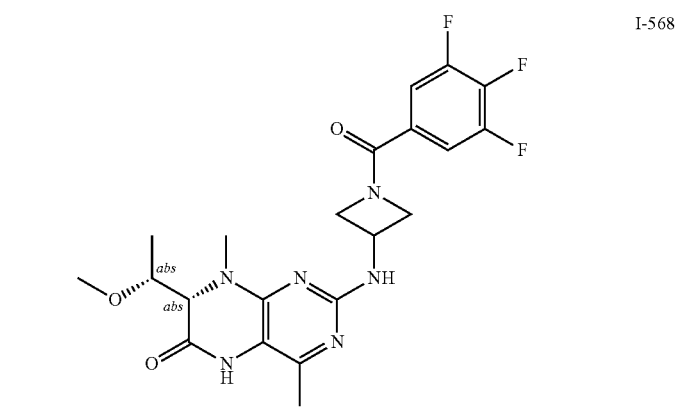
I-568
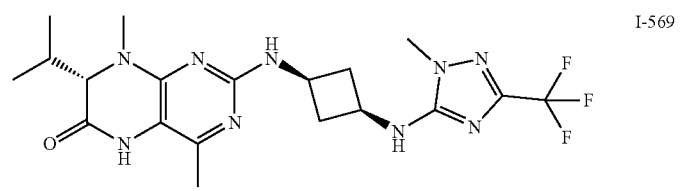
I-569

TABLE B-continued
Exemplary Compounds
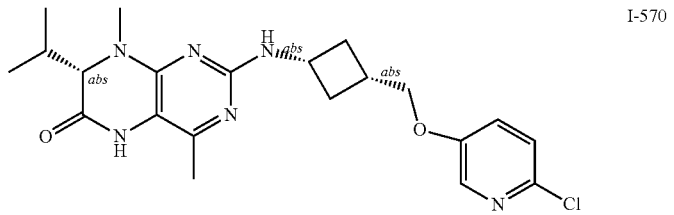
I-570
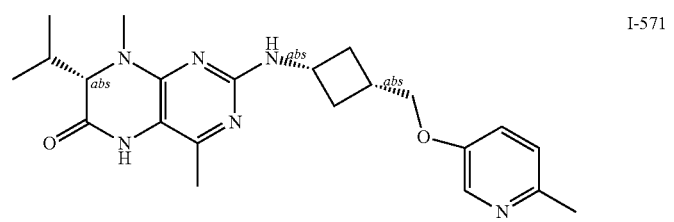
I-571
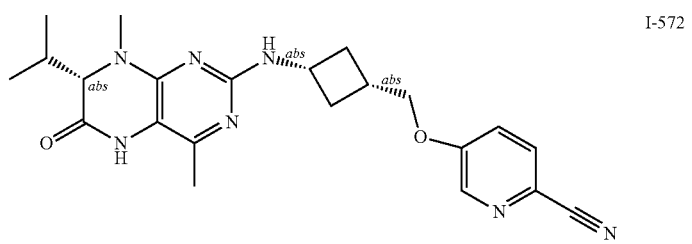
I-572
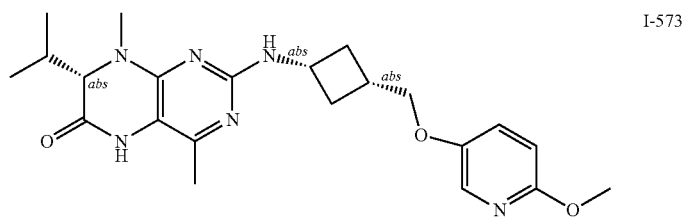
I-573
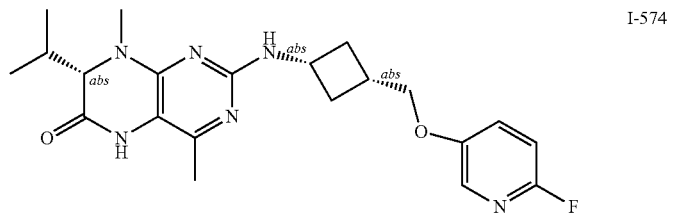
I-574
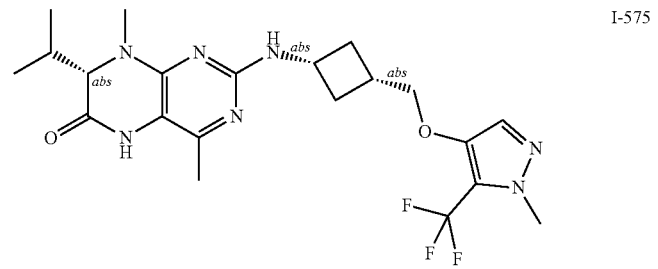
I-575

US 11,572,364 B2
TABLE B-continued
Exemplary Compounds
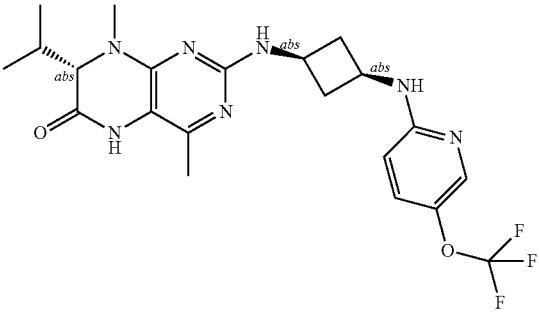 [SMILES: Cc1nc(N[C@H]2C[C@@H](Nc3ccc(OC(F)(F)F)cn3)C2)nc2c1NC(=O)[C@H](C(C)C)N2C] I-576
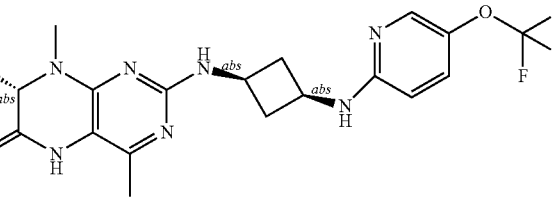 I-577
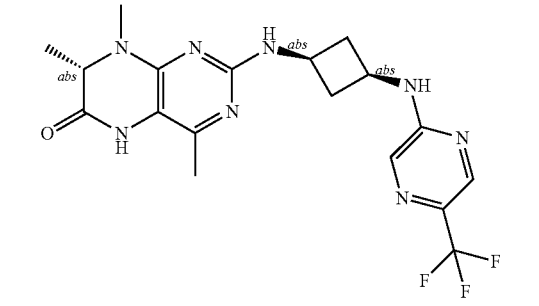 [SMILES: Cc1nc(N[C@H]2C[C@@H](Nc3cnc(C(F)(F)F)cn3)C2)nc2c1NC(=O)[C@H](C)N2C] I-578
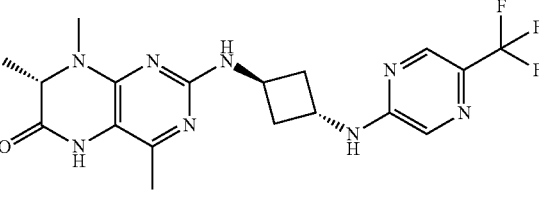 I-579
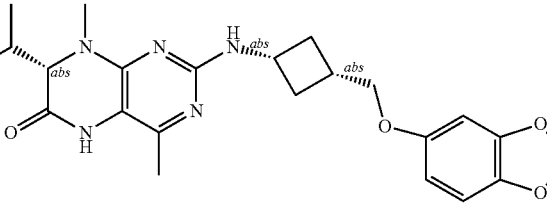 I-580
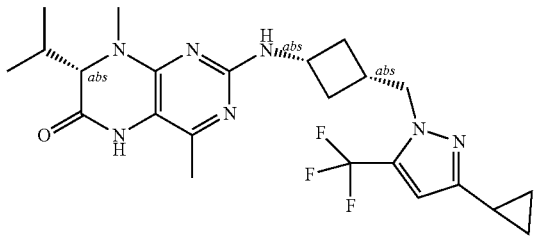 [SMILES: Cc1nc(N[C@H]2C[C@@H](Cn3nc(C4CC4)cc3C(F)(F)F)C2)nc2c1NC(=O)[C@H](C(C)C)N2C] I-581

TABLE B-continued
Exemplary Compounds
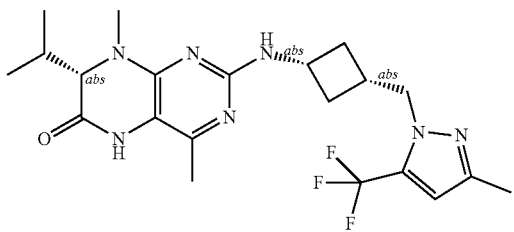 [SMILES: Cc1cc(C(F)(F)F)n(C[C@H]2C[C@@H](Nc3nc(C)c4c(n3)N(C)[C@@H](C(C)C)C(=O)N4)C2)n1]
I-582
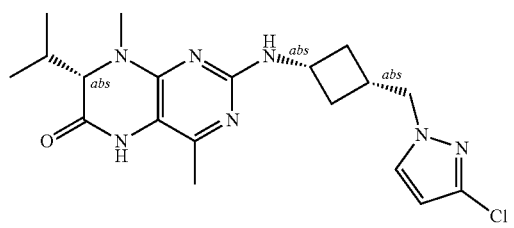 [SMILES: Cc1nc(N[C@H]2C[C@@H](Cn3ccc(Cl)n3)C2)nc2c1NC(=O)[C@H](C(C)C)N2C]
I-583
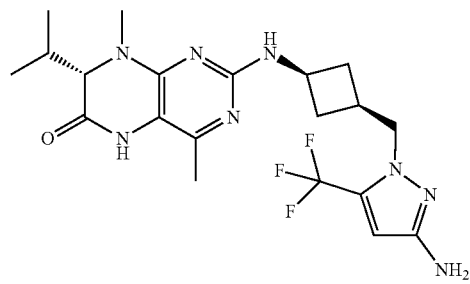 [SMILES: Cc1nc(N[C@H]2C[C@@H](Cn3nc(N)cc3C(F)(F)F)C2)nc2c1NC(=O)[C@H](C(C)C)N2C]
I-584
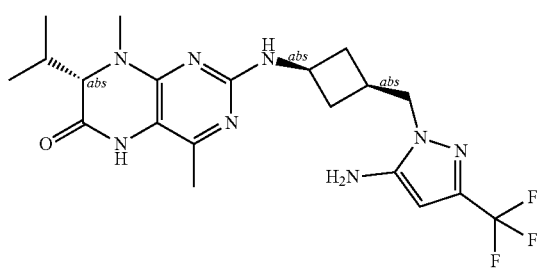 [SMILES: Cc1nc(N[C@H]2C[C@@H](Cn3nc(C(F)(F)F)cc3N)C2)nc2c1NC(=O)[C@H](C(C)C)N2C]
I-585
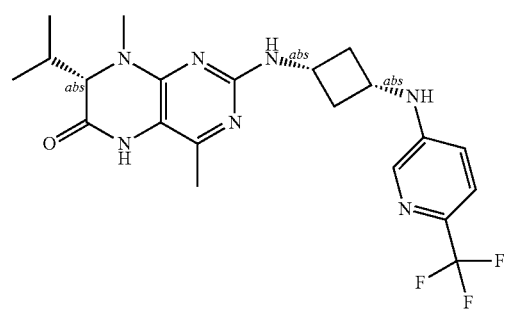 [SMILES: Cc1nc(N[C@H]2C[C@@H](Nc3ccc(C(F)(F)F)nc3)C2)nc2c1NC(=O)[C@H](C(C)C)N2C]
I-586

TABLE B-continued
Exemplary Compounds
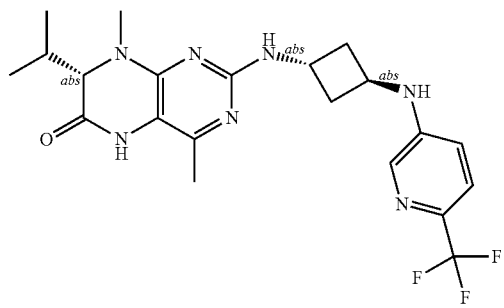 [SMILES: Cc1nc(N[C@H]2C[C@H](Nc3ccc(C(F)(F)F)nc3)C2)nc2c1NC(=O)[C@H](C(C)C)N2C]
I-587
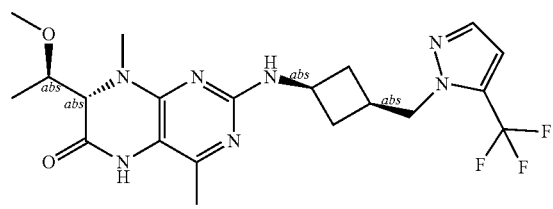 [SMILES: CO[C@H](C)[C@H]1C(=O)Nc2c(C)nc(N[C@H]3C[C@@H](Cn4nccc4C(F)(F)F)C3)nc2N1C]
I-588
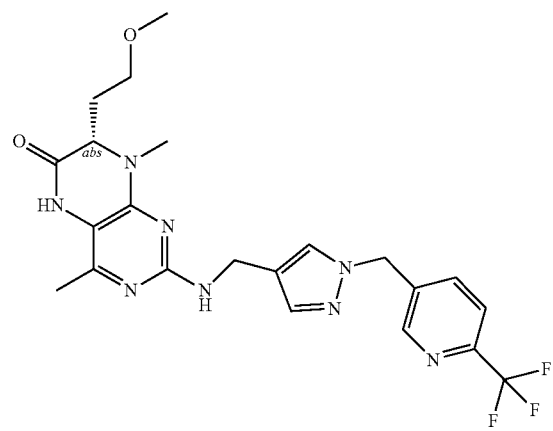 [SMILES: COCC[C@H]1C(=O)Nc2c(C)nc(NCc3cnn(Cc4ccc(C(F)(F)F)nc4)c3)nc2N1C]
I-589
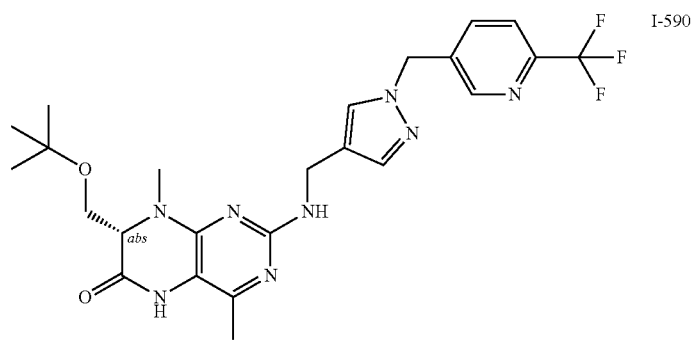
I-590

TABLE B-continued
Exemplary Compounds
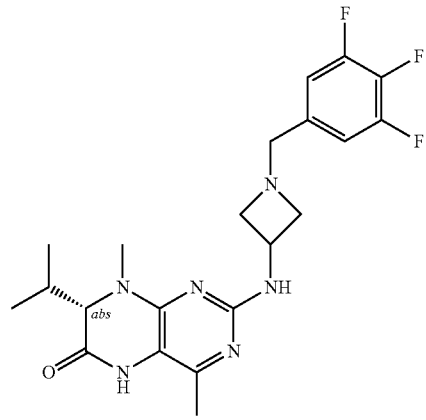 [SMILES: Cc1nc(NC2CN(Cc3cc(F)c(F)c(F)c3)C2)nc2c1NC(=O)[C@H](C(C)C)N2C]
I-591
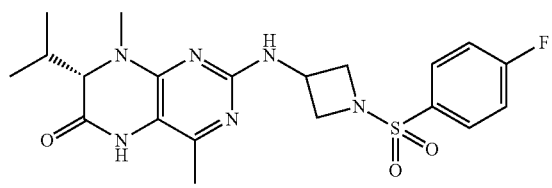 [SMILES: Cc1nc(NC2CN(S(=O)(=O)c3ccc(F)cc3)C2)nc2c1NC(=O)[C@H](C(C)C)N2C]
I-592
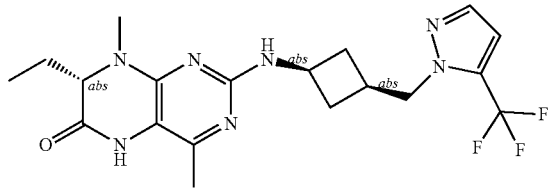 [SMILES: CC[C@H]1C(=O)Nc2c(C)nc(N[C@H]3C[C@@H](Cn4nccc4C(F)(F)F)C3)nc2N1C]
I-593
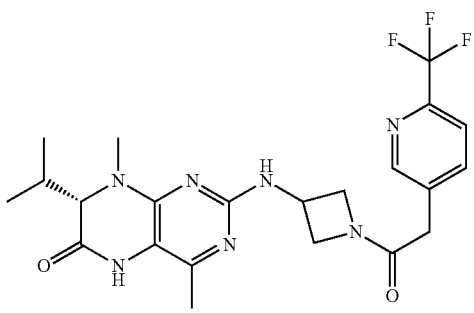 [SMILES: Cc1nc(NC2CN(C(=O)Cc3ccc(C(F)(F)F)nc3)C2)nc2c1NC(=O)[C@H](C(C)C)N2C]
I-594
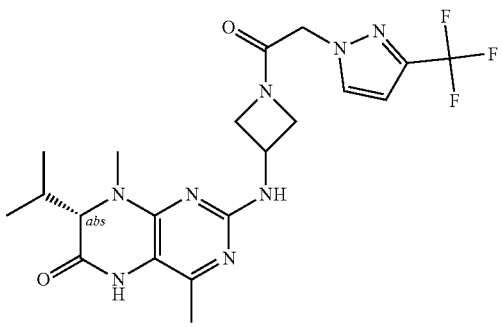 [SMILES: Cc1nc(NC2CN(C(=O)Cn3ccc(C(F)(F)F)n3)C2)nc2c1NC(=O)[C@H](C(C)C)N2C]
I-595

TABLE B-continued
Exemplary Compounds
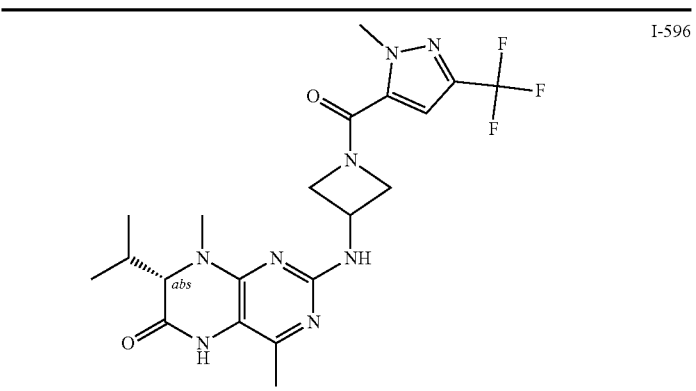
I-596
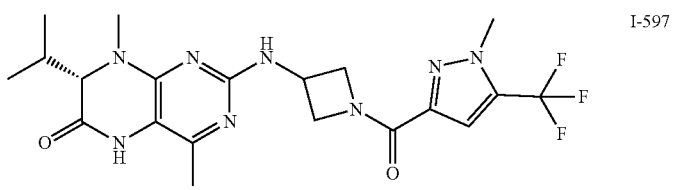
I-597
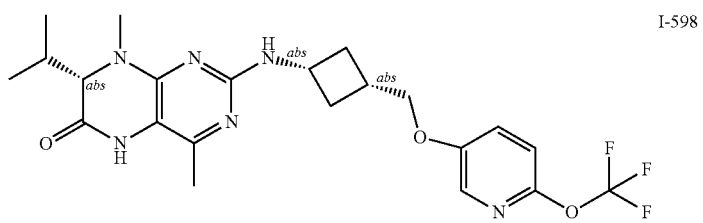
I-598
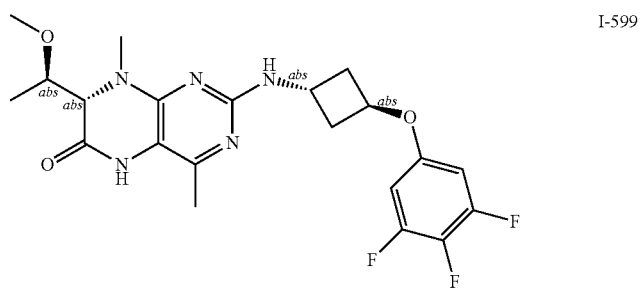
I-599
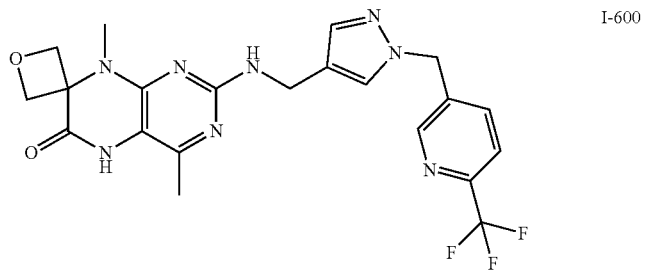
I-600
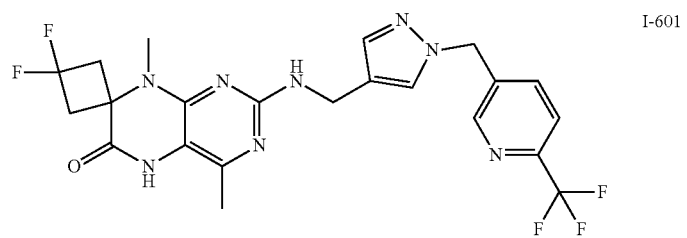
I-601

TABLE B-continued
Exemplary Compounds
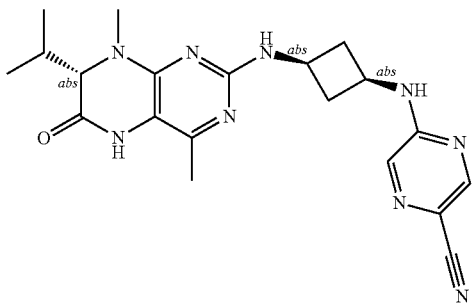 [SMILES: Cc1nc(N[C@H]2C[C@@H](Nc3cnc(C#N)cn3)C2)nc2c1NC(=O)[C@H](C(C)C)N2C]
I-602
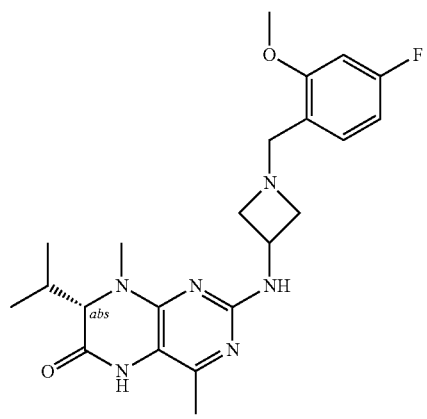 [SMILES: COc1cc(F)ccc1CN1CC(Nc2nc(C)c3c(n2)N(C)[C@@H](C(C)C)C(=O)N3)C1]
I-603
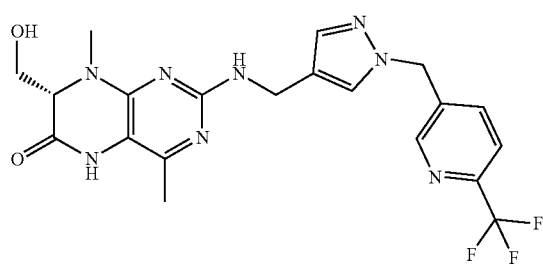 [SMILES: Cc1nc(NCc2cnn(Cc3ccc(C(F)(F)F)nc3)c2)nc2c1NC(=O)[C@H](CO)N2C]
I-604
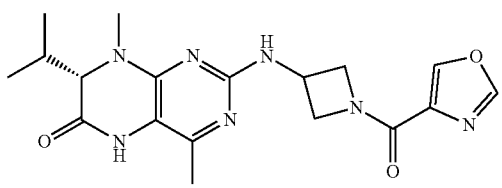 [SMILES: Cc1nc(NC2CN(C(=O)c3cocn3)C2)nc2c1NC(=O)[C@H](C(C)C)N2C]
I-605

TABLE B-continued
Exemplary Compounds
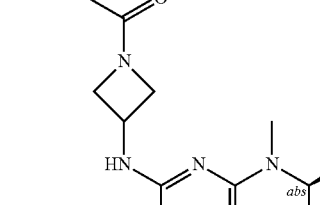
I-606
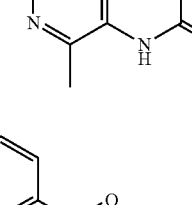
I-607
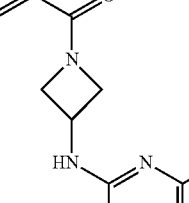
I-608
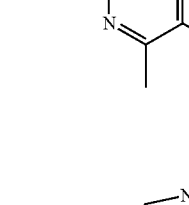
I-609
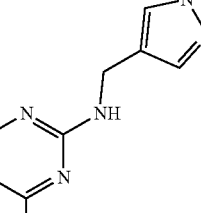
I-610

TABLE B-continued
Exemplary Compounds
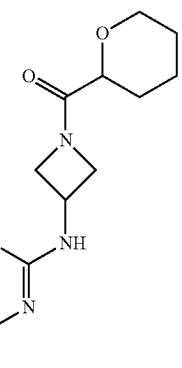
I-611
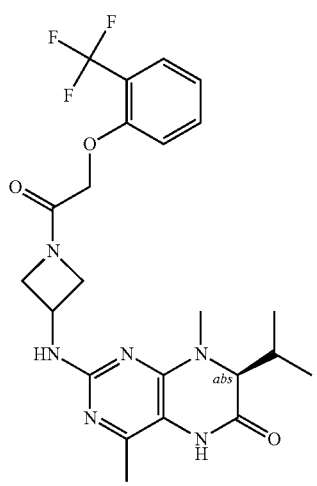 [SMILES: Cc1nc(NC2CN(C(=O)COc3ccccc3C(F)(F)F)C2)nc2c1NC(=O)[C@H](C(C)C)N2C]
I-612
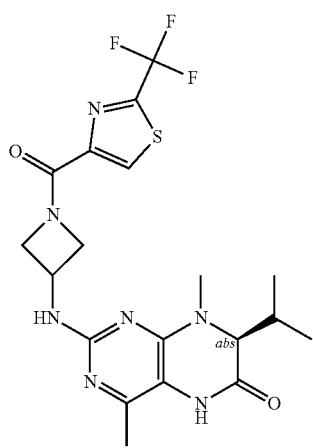 [SMILES: Cc1nc(NC2CN(C(=O)c3csc(C(F)(F)F)n3)C2)nc2c1NC(=O)[C@H](C(C)C)N2C]
I-613

TABLE B-continued
Exemplary Compounds
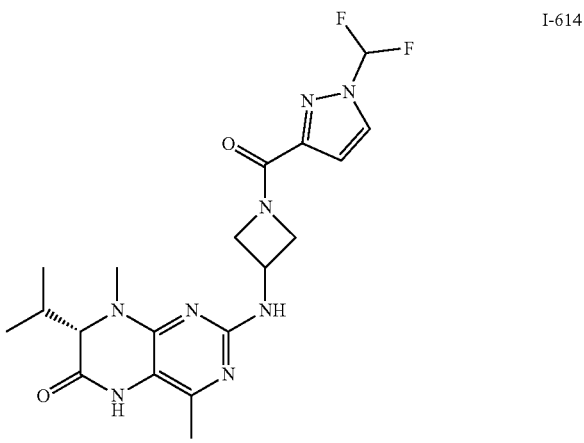
I-614
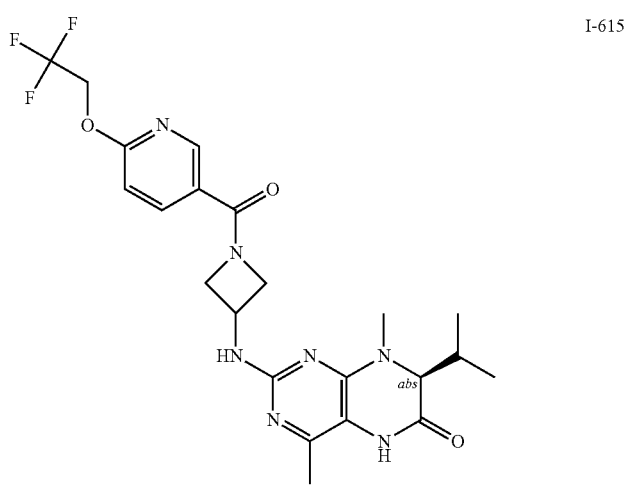
I-615
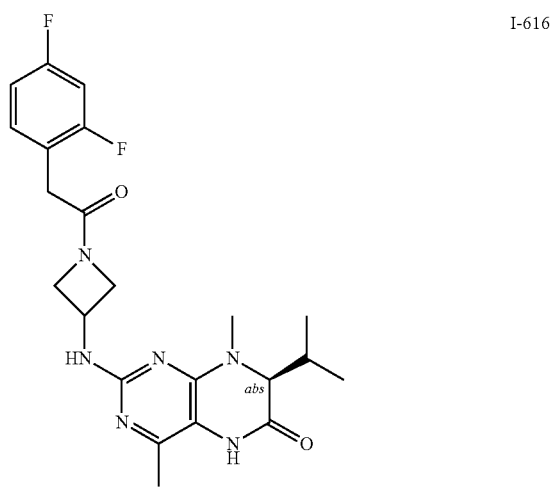
I-616

TABLE B-continued
Exemplary Compounds
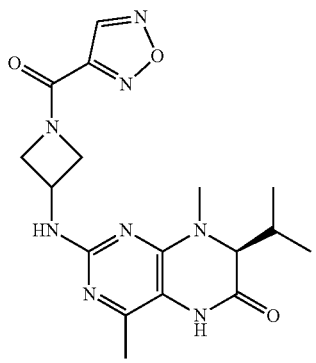 [SMILES: Cc1nc(NC2CN(C(=O)c3cnon3)C2)nc2c1NC(=O)[C@H](C(C)C)N2C]
I-617
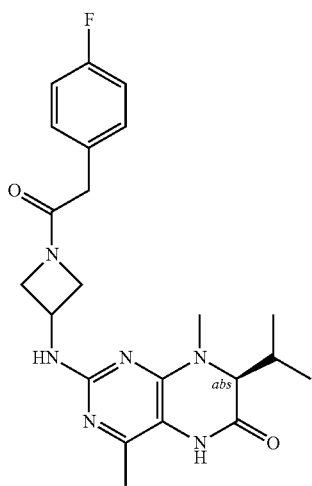 [SMILES: Cc1nc(NC2CN(C(=O)Cc3ccc(F)cc3)C2)nc2c1NC(=O)[C@H](C(C)C)N2C]
I-618
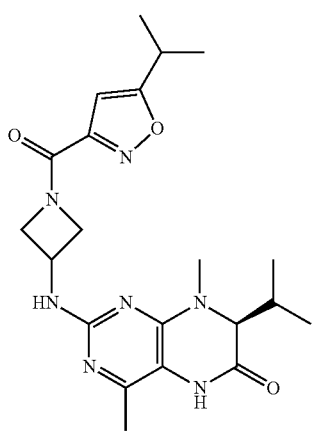 [SMILES: Cc1nc(NC2CN(C(=O)c3cc(C(C)C)on3)C2)nc2c1NC(=O)[C@H](C(C)C)N2C]
I-619

TABLE B-continued
Exemplary Compounds
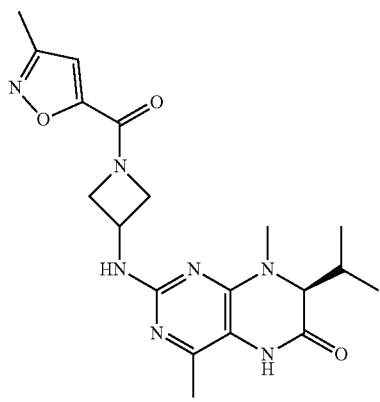 [SMILES: Cc1cc(C(=O)N2CC(Nc3nc(C)c4c(n3)N(C)[C@@H](C(C)C)C(=O)N4)C2)on1]
I-620
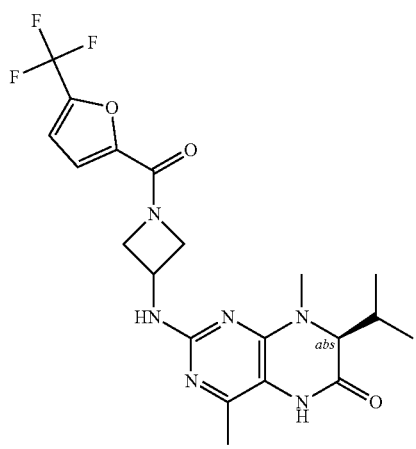 [SMILES: Cc1nc(NC2CN(C(=O)c3ccc(C(F)(F)F)o3)C2)nc2c1NC(=O)[C@H](C(C)C)N2C]
I-621
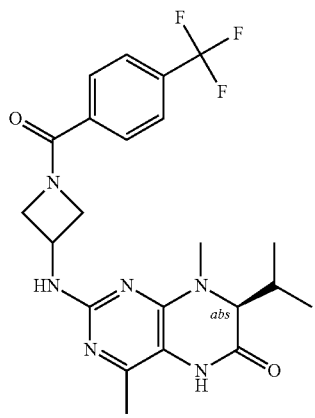 [SMILES: Cc1nc(NC2CN(C(=O)c3ccc(C(F)(F)F)cc3)C2)nc2c1NC(=O)[C@H](C(C)C)N2C]
I-622

TABLE B-continued
Exemplary Compounds
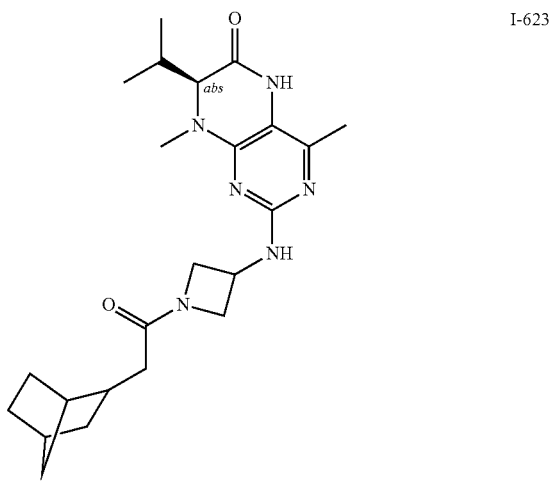
I-623
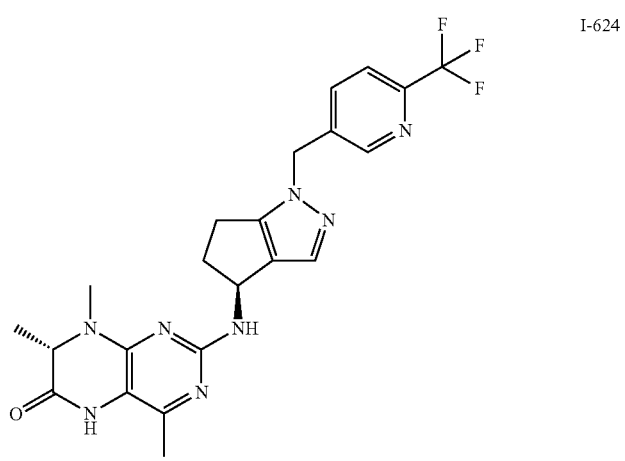
I-624
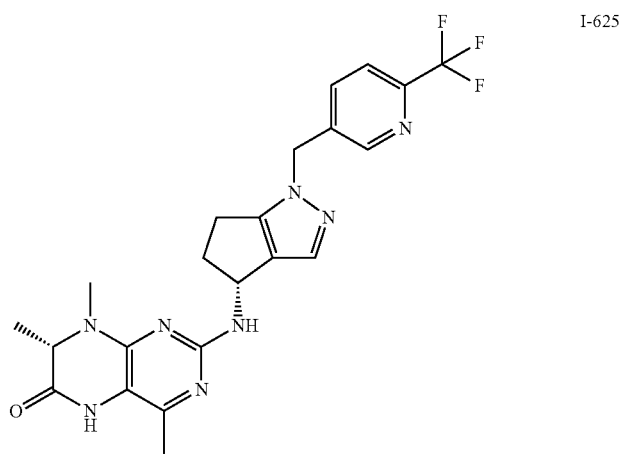
I-625

TABLE B-continued
Exemplary Compounds
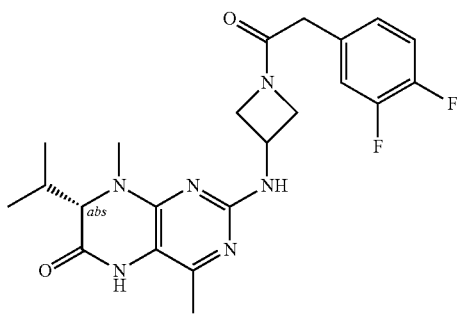 [SMILES: Cc1nc(NC2CN(C(=O)Cc3ccc(F)c(F)c3)C2)nc2c1NC(=O)[C@H](C(C)C)N2C]
I-626
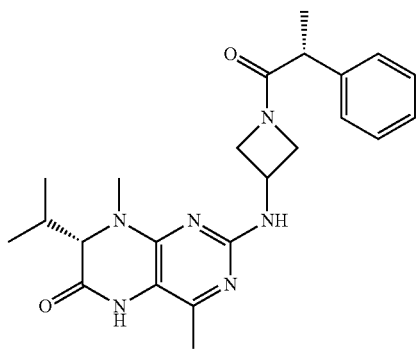 [SMILES: Cc1nc(NC2CN(C(=O)[C@H](C)c3ccccc3)C2)nc2c1NC(=O)[C@H](C(C)C)N2C]
I-627
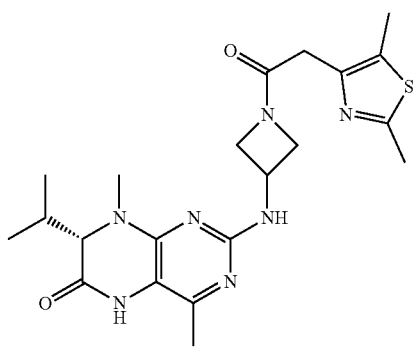 [SMILES: Cc1nc(CC(=O)N2CC(Nc3nc(C)c4c(n3)N(C)[C@@H](C(C)C)C(=O)N4)C2)c(C)s1]
I-628
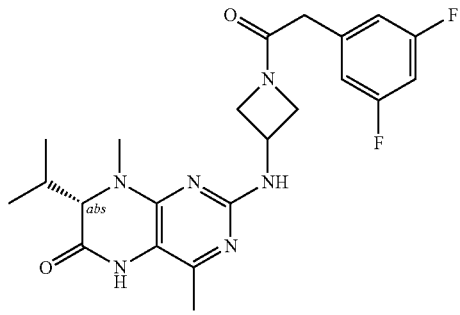 [SMILES: Cc1nc(NC2CN(C(=O)Cc3cc(F)cc(F)c3)C2)nc2c1NC(=O)[C@H](C(C)C)N2C]
I-629

303
TABLE B-continued
Exemplary Compounds
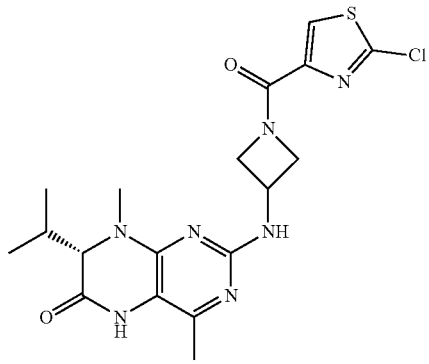 [SMILES: Cc1nc(NC2CN(C(=O)c3csc(Cl)n3)C2)nc2c1NC(=O)[C@H](C(C)C)N2C]
I-630
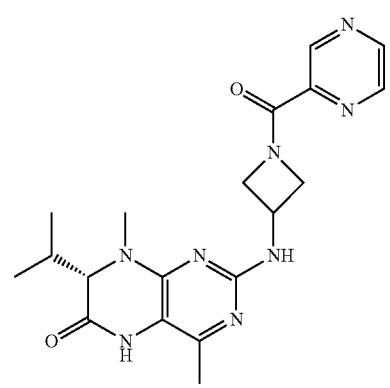 [SMILES: Cc1nc(NC2CN(C(=O)c3cnccn3)C2)nc2c1NC(=O)[C@H](C(C)C)N2C]
I-631
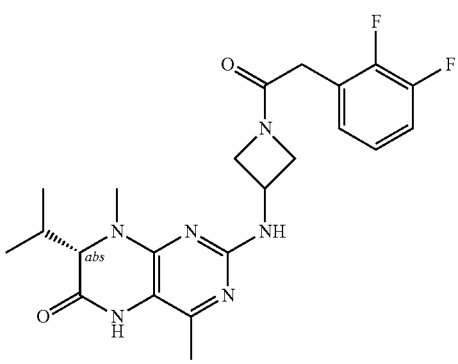 [SMILES: Cc1nc(NC2CN(C(=O)Cc3cccc(F)c3F)C2)nc2c1NC(=O)[C@H](C(C)C)N2C]
I-632
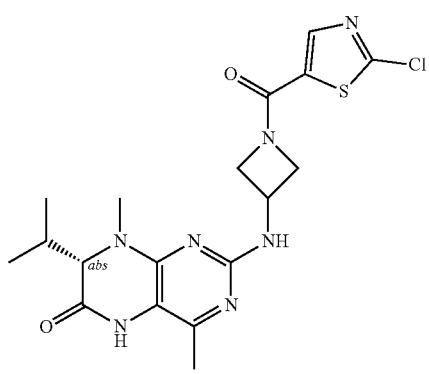 [SMILES: Cc1nc(NC2CN(C(=O)c3cnc(Cl)s3)C2)nc2c1NC(=O)[C@H](C(C)C)N2C]
I-633

TABLE B-continued
Exemplary Compounds
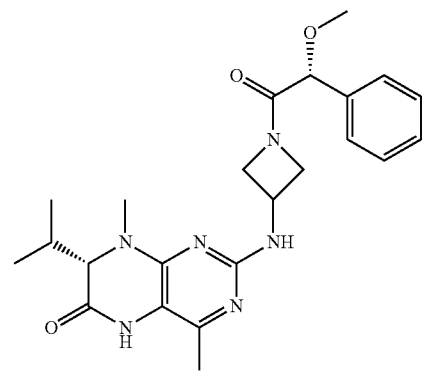 [SMILES: CO[C@@H](C(=O)N1CC(Nc2nc(C)c3c(n2)N(C)[C@@H](C(C)C)C(=O)N3)C1)c1ccccc1]
I-634
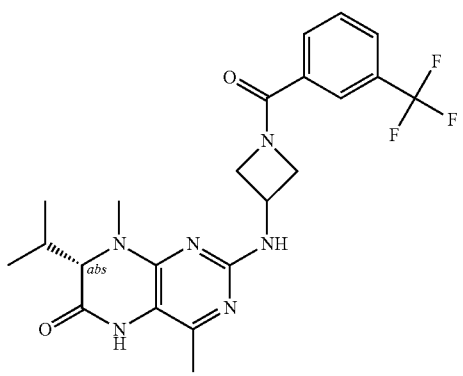 [SMILES: Cc1nc(NC2CN(C(=O)c3cccc(C(F)(F)F)c3)C2)nc2c1NC(=O)[C@H](C(C)C)N2C]
I-635
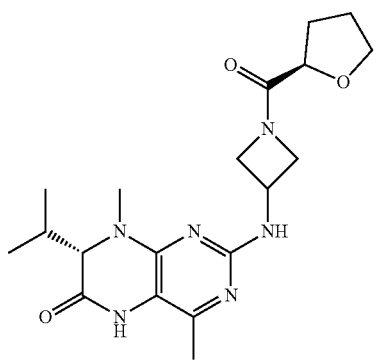 [SMILES: Cc1nc(NC2CN(C(=O)[C@H]3CCCO3)C2)nc2c1NC(=O)[C@H](C(C)C)N2C]
I-636
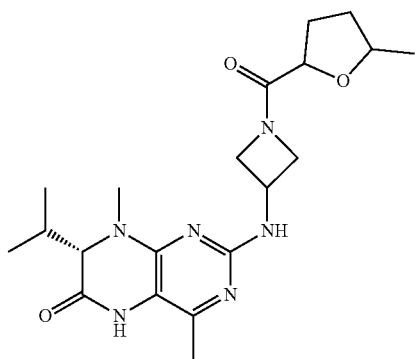 [SMILES: Cc1nc(NC2CN(C(=O)C3CCC(C)O3)C2)nc2c1NC(=O)[C@H](C(C)C)N2C]
I-637

TABLE B-continued
Exemplary Compounds
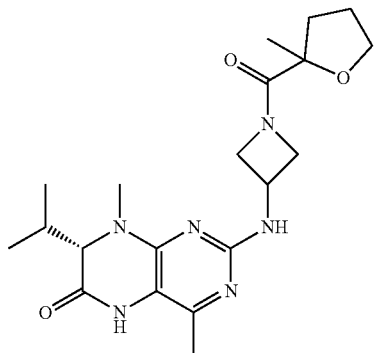 [SMILES: Cc1nc(NC2CN(C(=O)C3(C)CCCO3)C2)nc2c1NC(=O)[C@H](C(C)C)N2C]
I-638
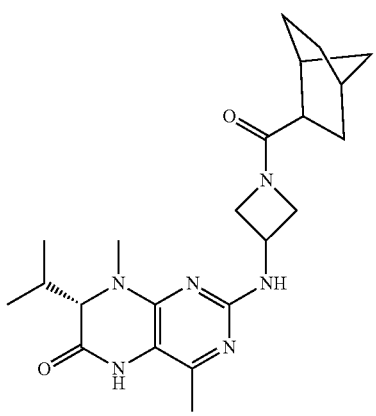 [SMILES: Cc1nc(NC2CN(C(=O)C3CC4CCC3C4)C2)nc2c1NC(=O)[C@H](C(C)C)N2C]
I-639
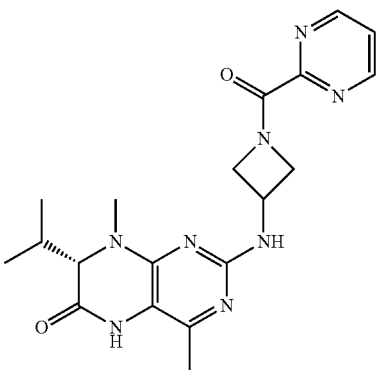 [SMILES: Cc1nc(NC2CN(C(=O)c3ncccn3)C2)nc2c1NC(=O)[C@H](C(C)C)N2C]
I-640
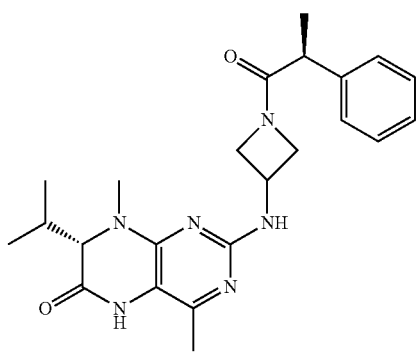
I-641

TABLE B-continued
Exemplary Compounds
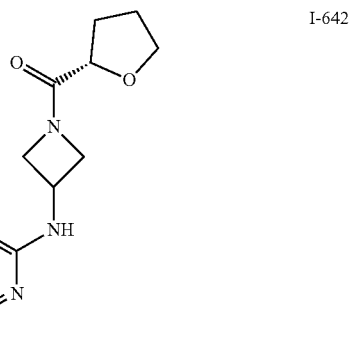
I-642
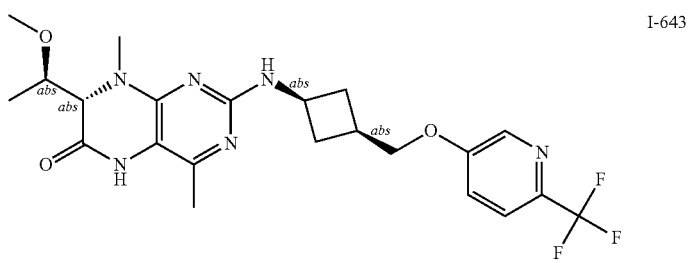
I-643
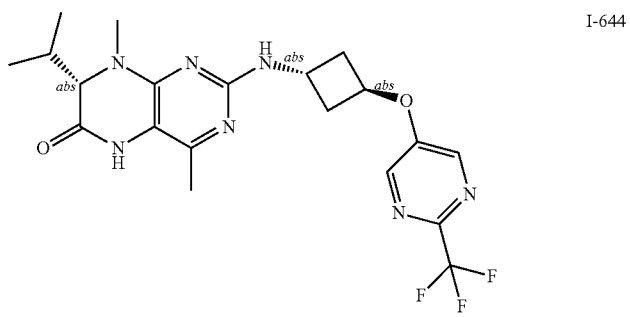
I-644
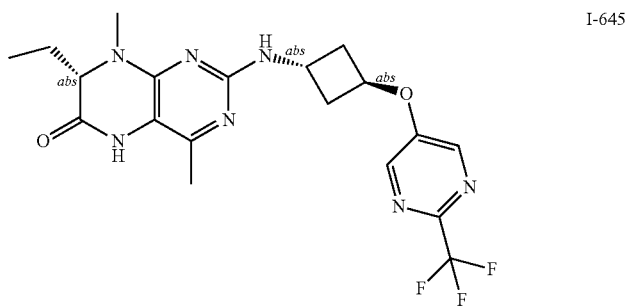
I-645
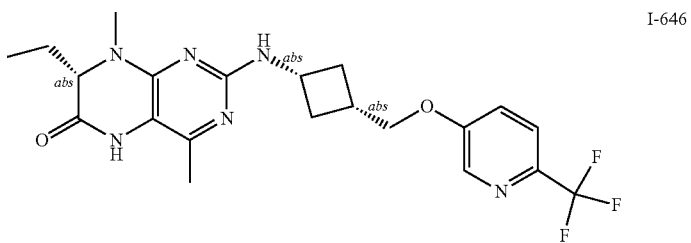
I-646

TABLE B-continued
Exemplary Compounds
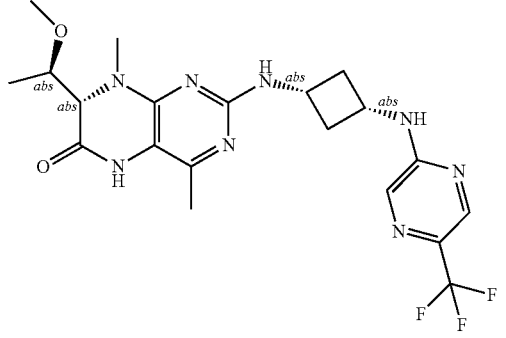 [SMILES: CO[C@H](C)[C@H]1C(=O)Nc2c(C)nc(N[C@H]3C[C@@H](Nc4cnc(C(F)(F)F)cn4)C3)nc2N1C]
I-647
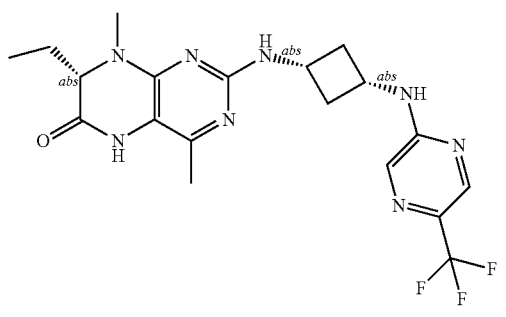 [SMILES: CC[C@H]1C(=O)Nc2c(C)nc(N[C@H]3C[C@@H](Nc4cnc(C(F)(F)F)cn4)C3)nc2N1C]
I-648
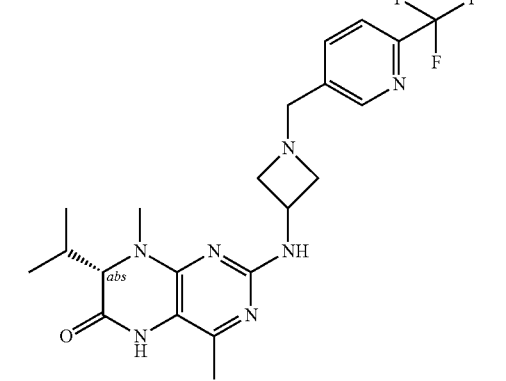
I-649
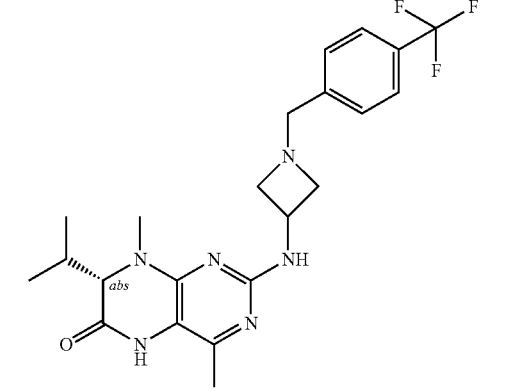 [SMILES: Cc1nc(NC2CN(Cc3ccc(C(F)(F)F)cc3)C2)nc2c1NC(=O)[C@H](C(C)C)N2C]
I-650

TABLE B-continued
Exemplary Compounds
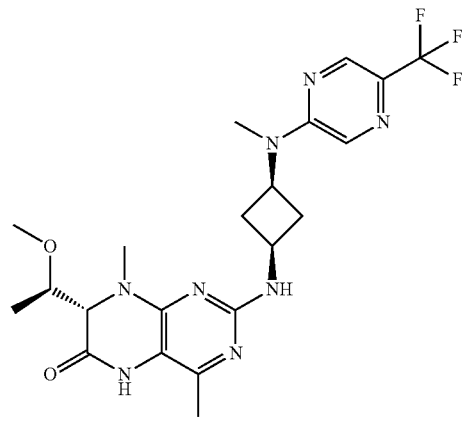 [SMILES: CO[C@H](C)[C@H]1C(=O)Nc2c(C)nc(N[C@H]3C[C@@H](N(C)c4cnc(C(F)(F)F)cn4)C3)nc2N1C]
I-651
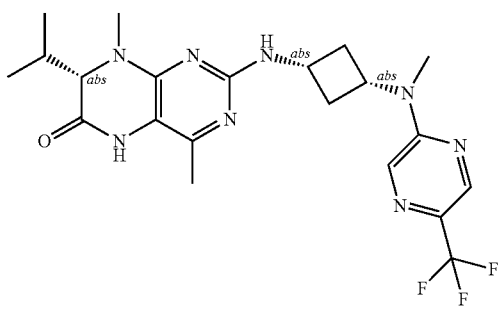 [SMILES: Cc1nc(N[C@H]2C[C@@H](N(C)c3cnc(C(F)(F)F)cn3)C2)nc2c1NC(=O)[C@H](C(C)C)N2C]
I-652
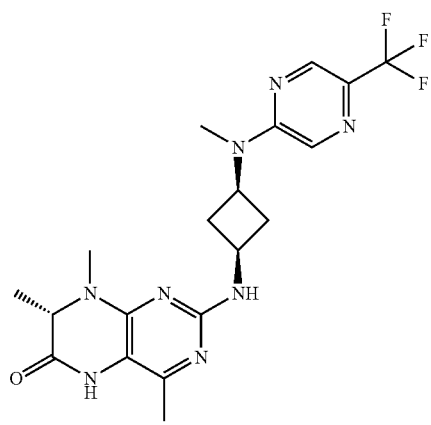 [SMILES: Cc1nc(N[C@H]2C[C@@H](N(C)c3cnc(C(F)(F)F)cn3)C2)nc2c1NC(=O)[C@H](C)N2C]
I-653
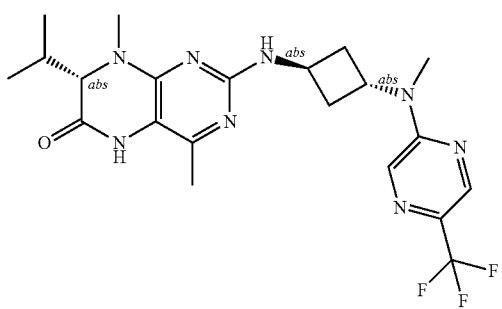 [SMILES: Cc1nc(N[C@H]2C[C@H](N(C)c3cnc(C(F)(F)F)cn3)C2)nc2c1NC(=O)[C@H](C(C)C)N2C]
I-655

TABLE B-continued
Exemplary Compounds
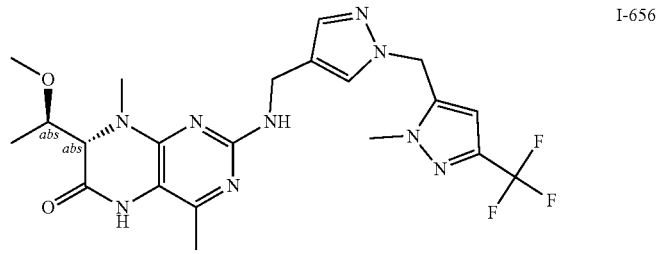
I-656
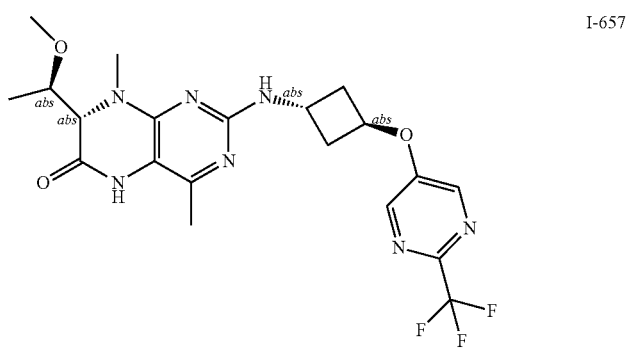
I-657
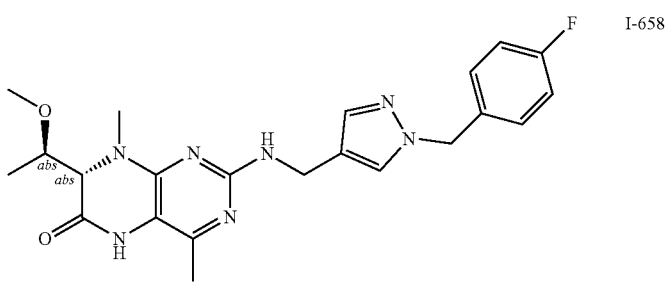
I-658
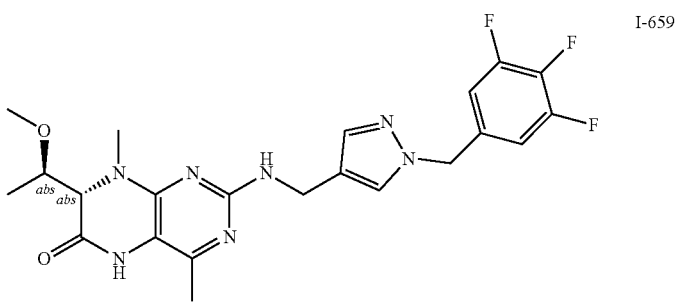
I-659
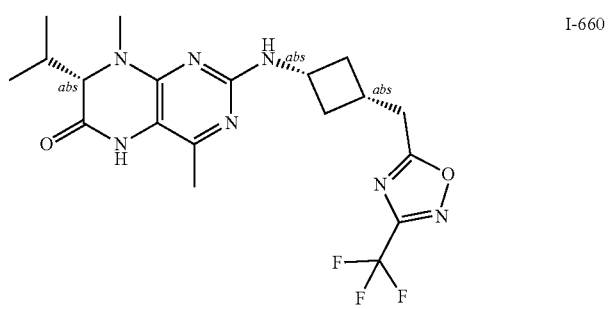
I-660

TABLE B-continued
Exemplary Compounds
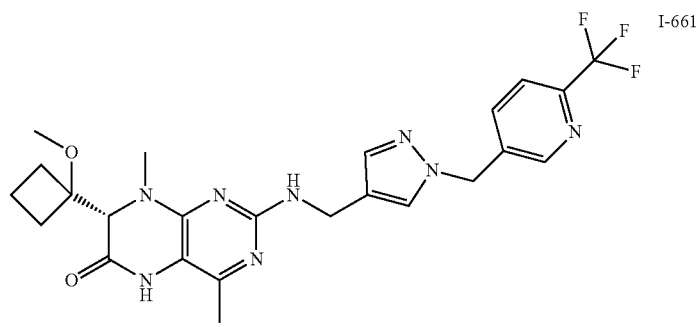
I-661
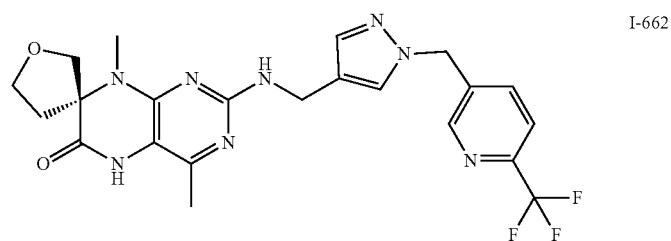
I-662
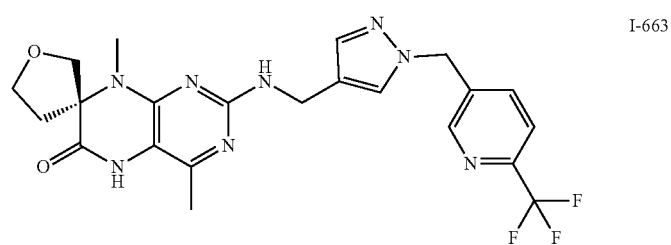
I-663
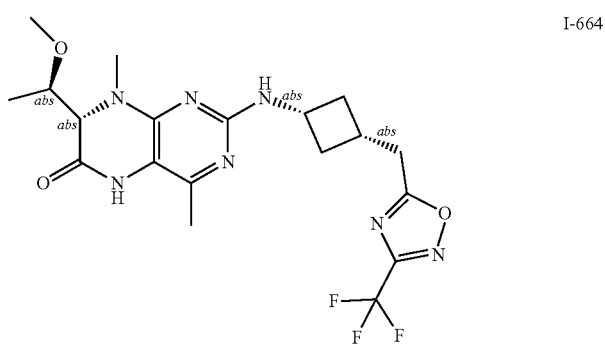
I-664
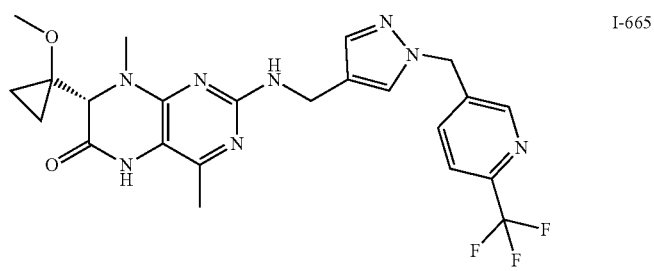
I-665

319
TABLE B-continued
Exemplary Compounds
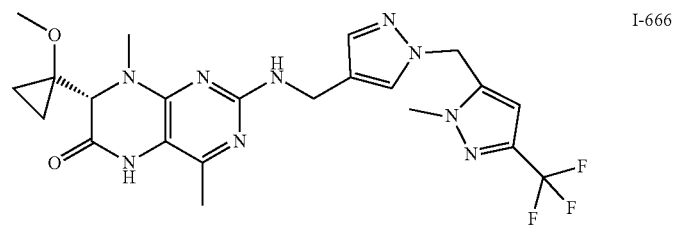 I-666
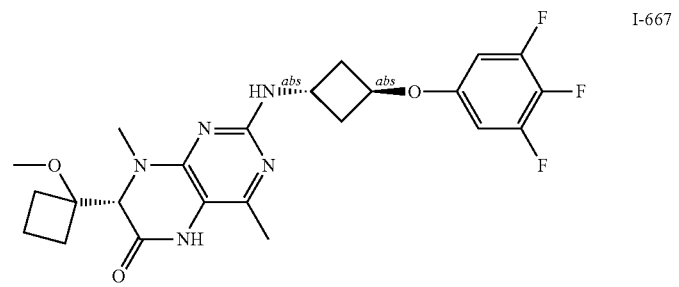 I-667
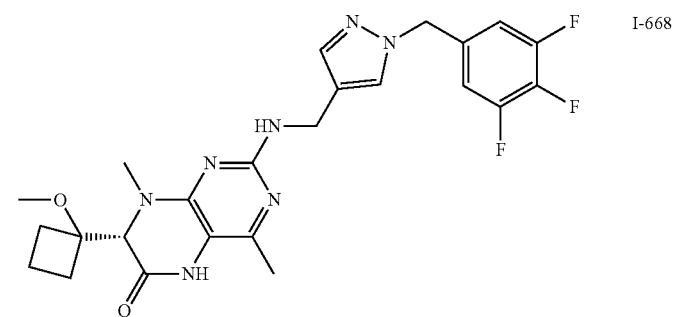 I-668
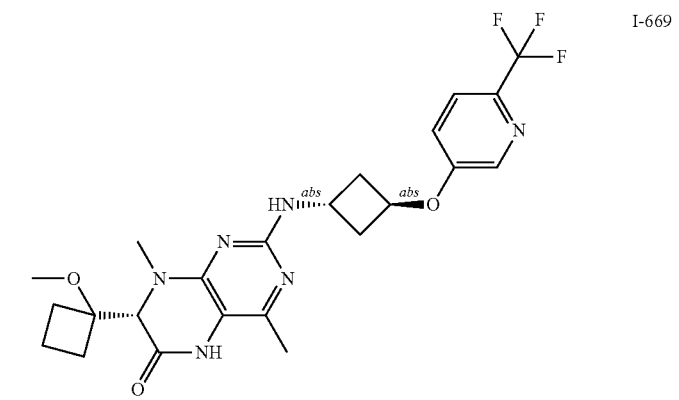 I-669
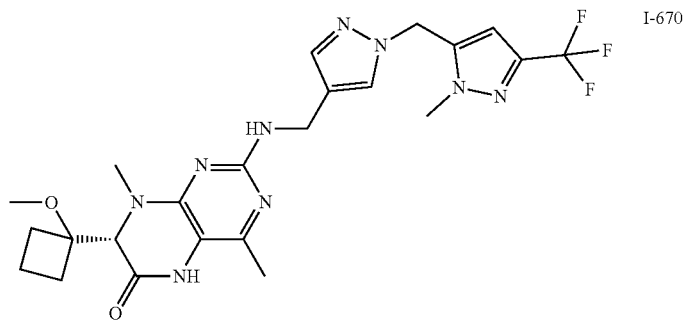 I-670

TABLE B-continued
Exemplary Compounds
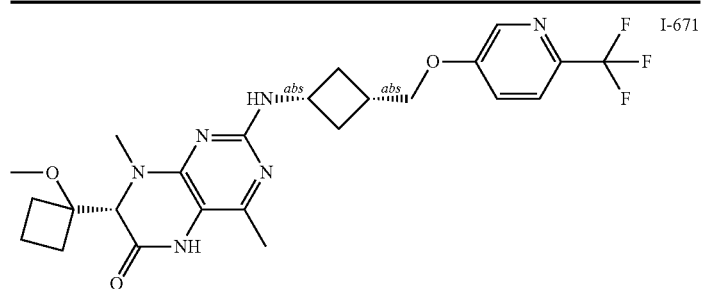
I-671
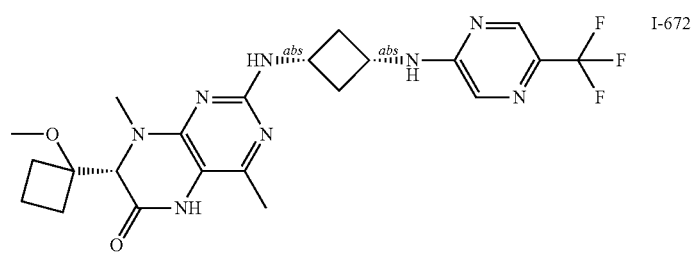
I-672
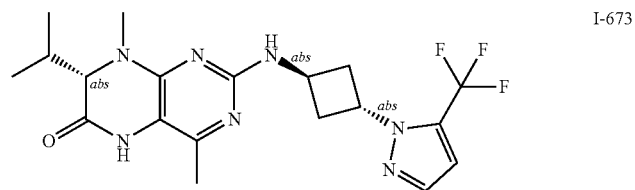
I-673
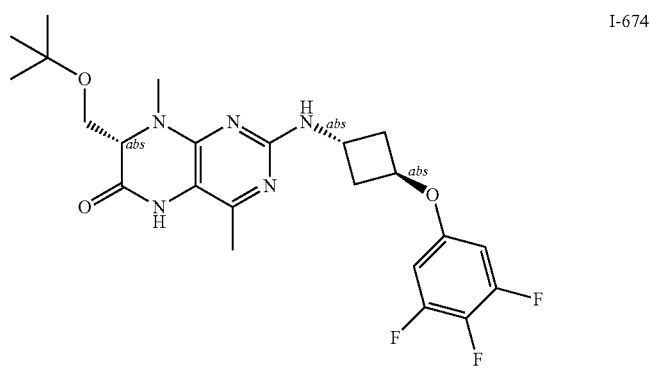
I-674
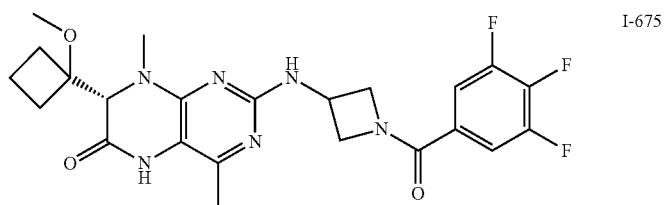
I-675
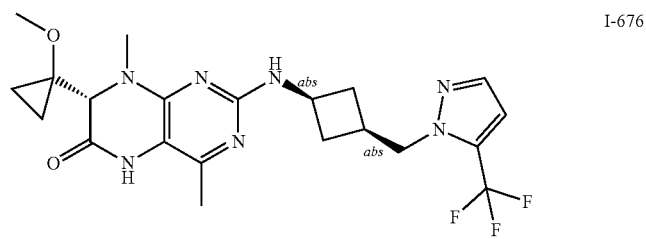
I-676

TABLE B-continued
Exemplary Compounds
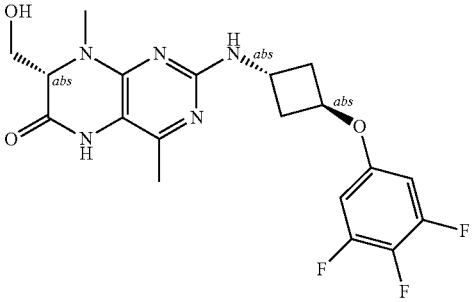 [SMILES: Cc1nc(N[C@H]2C[C@H](Oc3cc(F)c(F)c(F)c3)C2)nc2c1NC(=O)[C@H](CO)N2C]
I-677
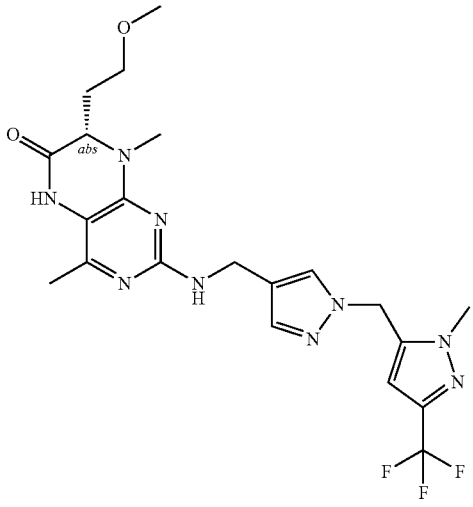 [SMILES: COCC[C@H]1C(=O)Nc2c(C)nc(NCc3cnn(Cc4cc(C(F)(F)F)nn4C)c3)nc2N1C]
I-678
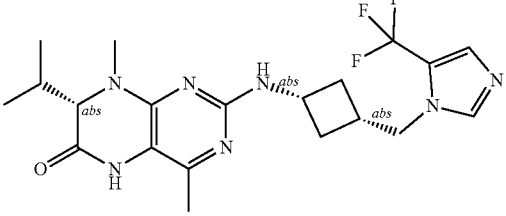
I-679
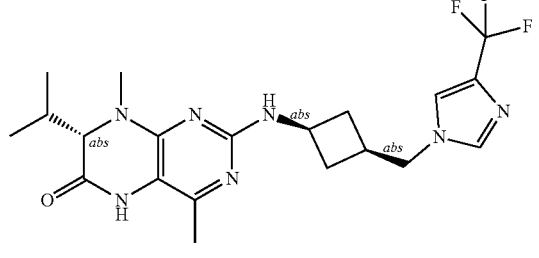
I-680

TABLE B-continued
Exemplary Compounds
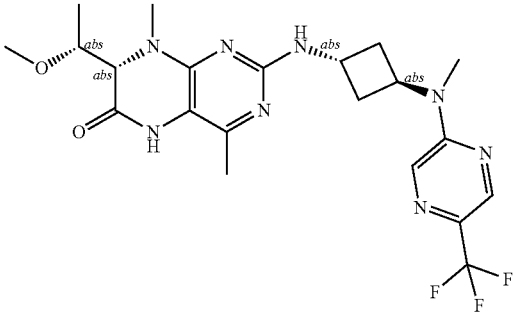 [SMILES: CO[C@H](C)[C@H]1C(=O)Nc2c(C)nc(N[C@H]3C[C@H](N(C)c4cnc(C(F)(F)F)cn4)C3)nc2N1C]
I-681
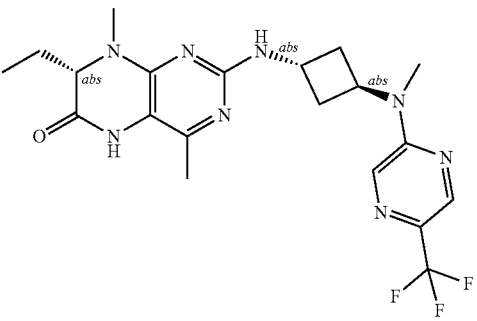 [SMILES: CC[C@H]1C(=O)Nc2c(C)nc(N[C@H]3C[C@H](N(C)c4cnc(C(F)(F)F)cn4)C3)nc2N1C]
I-682
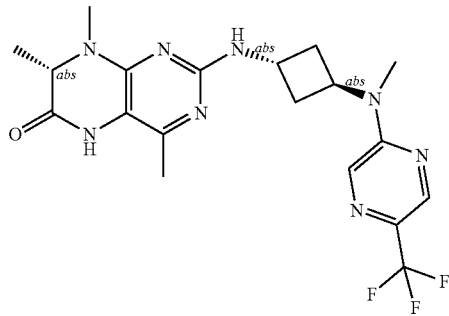 [SMILES: Cc1nc(N[C@H]2C[C@H](N(C)c3cnc(C(F)(F)F)cn3)C2)nc2c1NC(=O)[C@H](C)N2C]
I-683
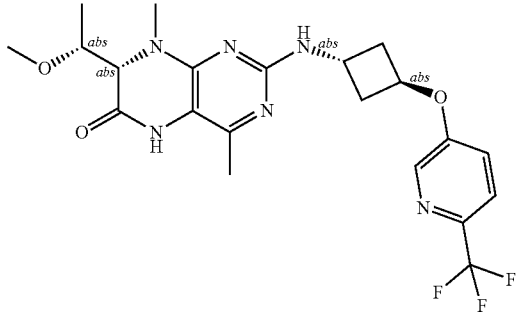 [SMILES: CO[C@H](C)[C@H]1C(=O)Nc2c(C)nc(N[C@H]3C[C@H](Oc4ccc(C(F)(F)F)nc4)C3)nc2N1C]
I-684
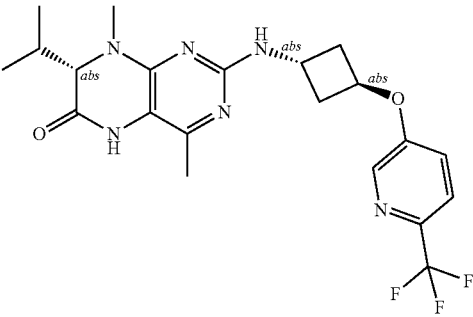 [SMILES: Cc1nc(N[C@H]2C[C@H](Oc3ccc(C(F)(F)F)nc3)C2)nc2c1NC(=O)[C@H](C(C)C)N2C]
I-685

TABLE B-continued
Exemplary Compounds
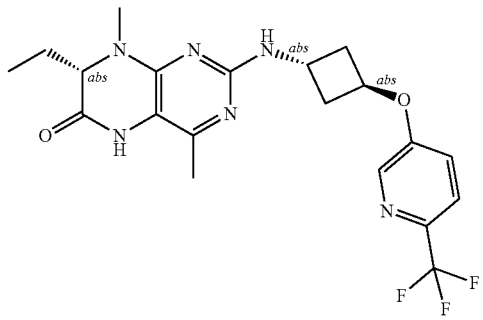 [SMILES: CC[C@H]1C(=O)Nc2c(C)nc(N[C@H]3C[C@H](Oc4ccc(C(F)(F)F)nc4)C3)nc2N1C] I-686
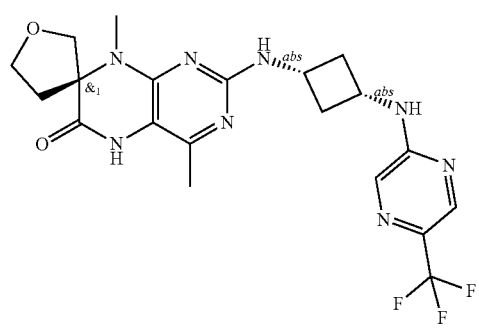 [SMILES: Cc1nc(N[C@H]2C[C@@H](Nc3cnc(C(F)(F)F)cn3)C2)nc2c1NC(=O)[C@@]1(CCOC1)N2C] I-687
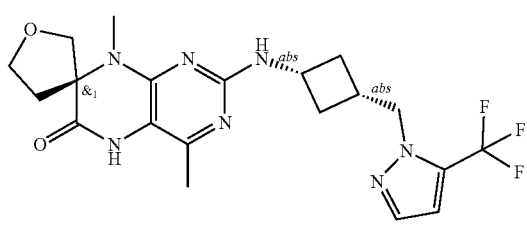 [SMILES: Cc1nc(N[C@H]2C[C@@H](Cn3nccc3C(F)(F)F)C2)nc2c1NC(=O)[C@@]1(CCOC1)N2C] I-688
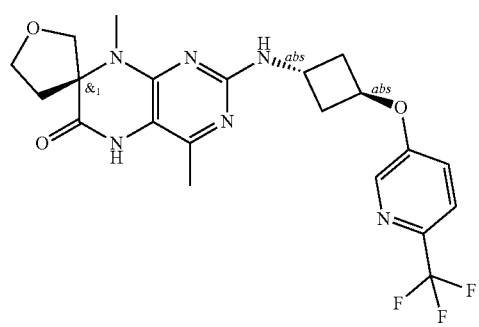 [SMILES: Cc1nc(N[C@H]2C[C@H](Oc3ccc(C(F)(F)F)nc3)C2)nc2c1NC(=O)[C@@]1(CCOC1)N2C] I-689
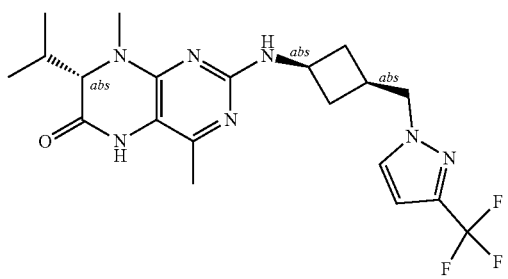 [SMILES: Cc1nc(N[C@H]2C[C@@H](Cn3ccc(C(F)(F)F)n3)C2)nc2c1NC(=O)[C@H](C(C)C)N2C] I-690

TABLE B-continued
Exemplary Compounds
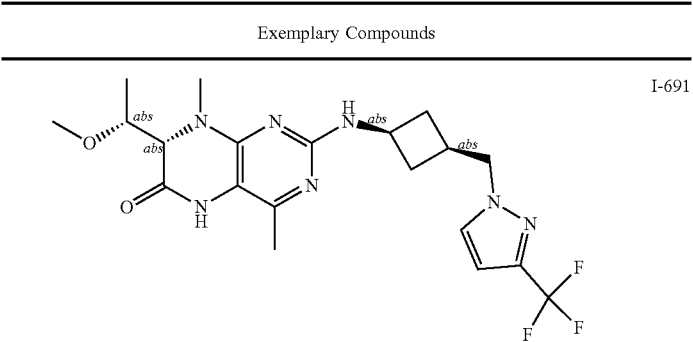
I-691
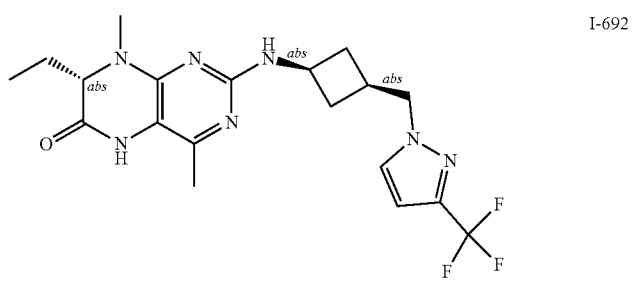
I-692
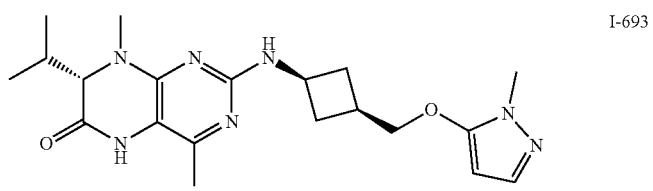
I-693
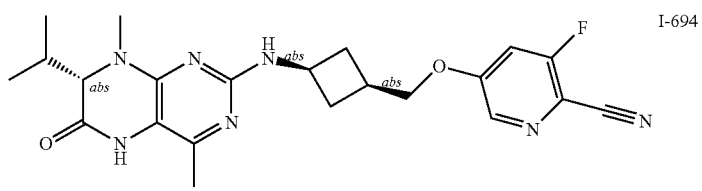
I-694
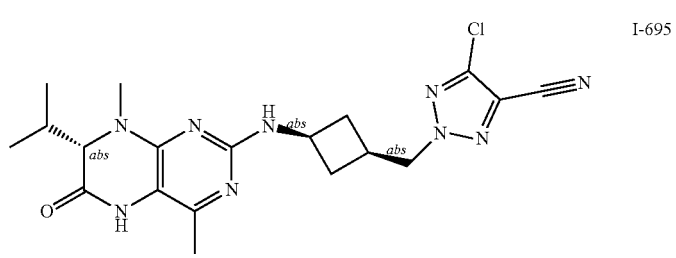
I-695
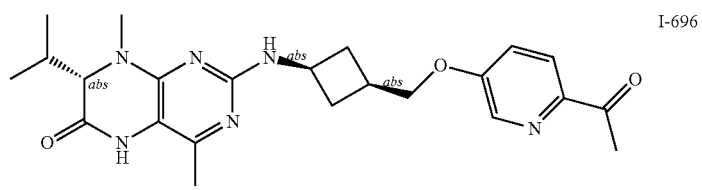
I-696

TABLE B-continued
Exemplary Compounds
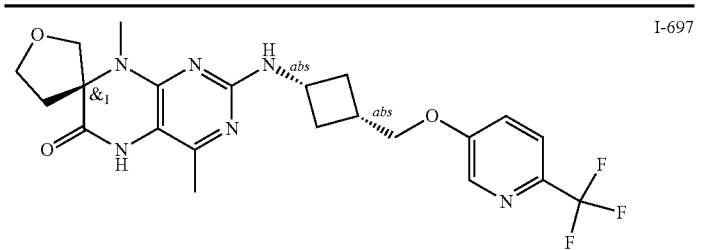
I-697
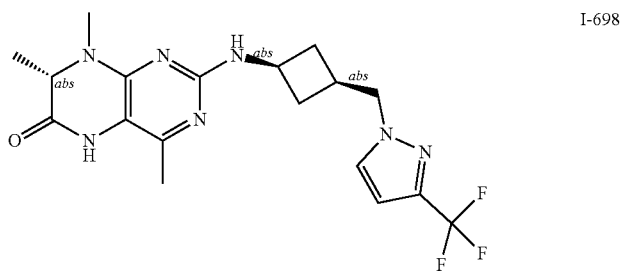
I-698
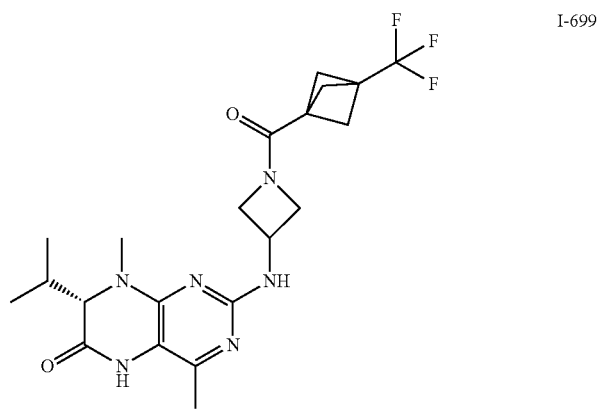
I-699
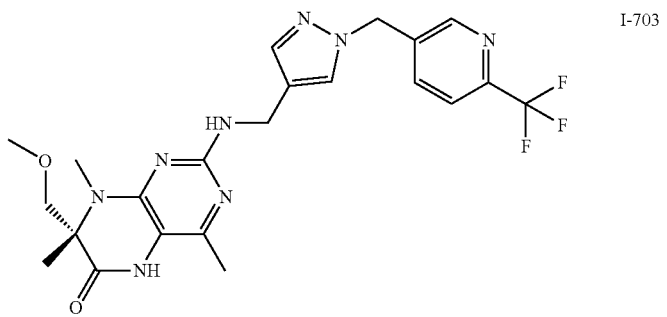
I-703
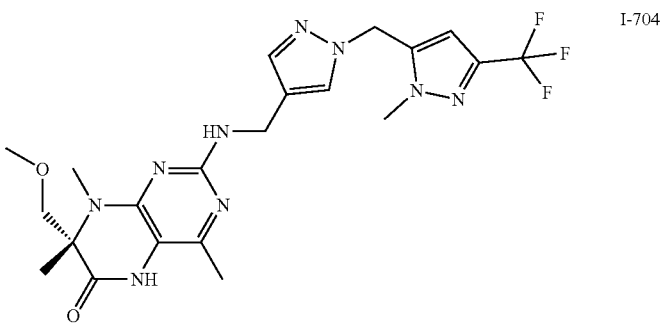
I-704

TABLE B-continued
Exemplary Compounds
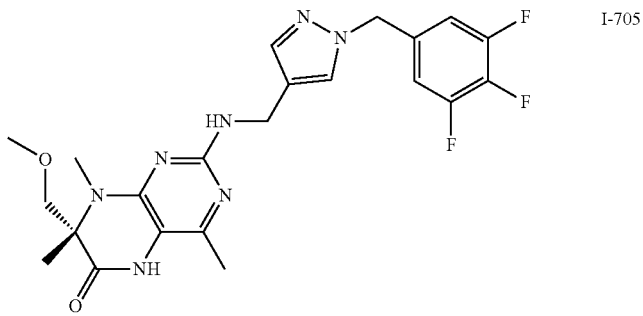 I-705
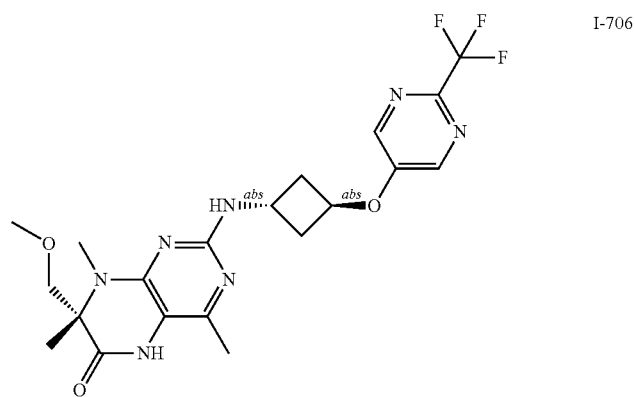 I-706
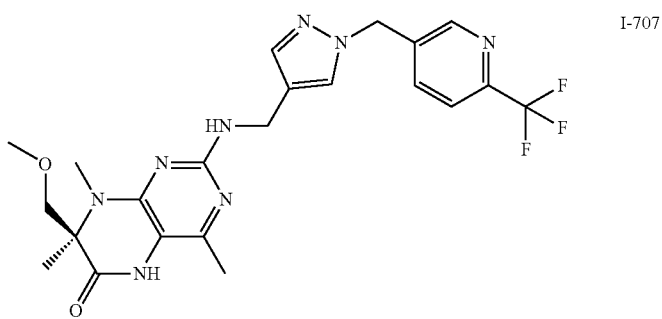 I-707
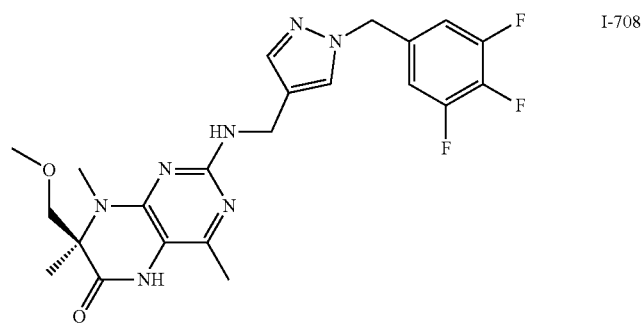 I-708

TABLE B-continued
Exemplary Compounds
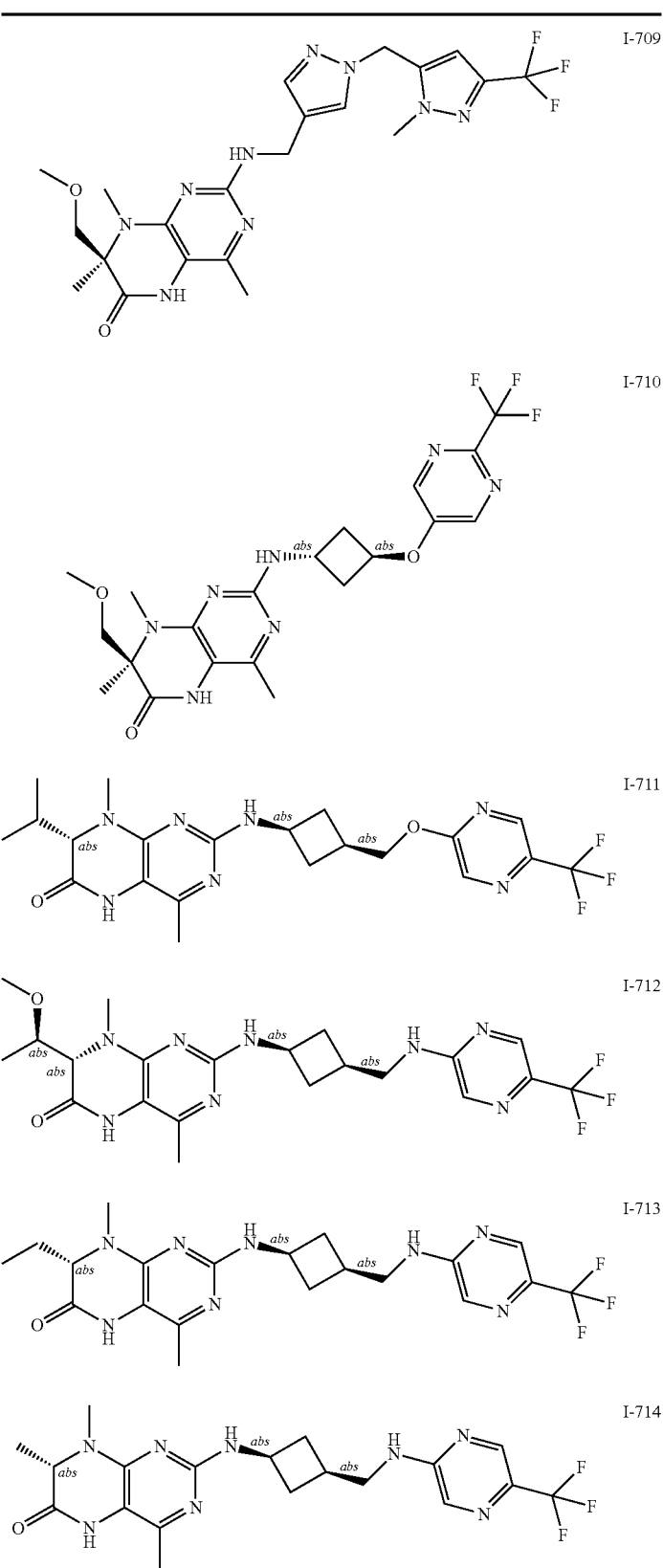

TABLE B-continued
Exemplary Compounds
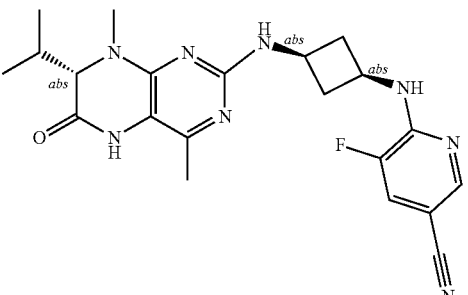  I-715
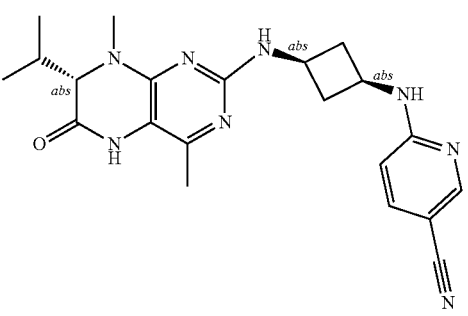 [SMILES: Cc1nc(N[C@H]2C[C@@H](Nc3ccc(C#N)cn3)C2)nc2c1NC(=O)[C@H](C(C)C)N2C]  I-716
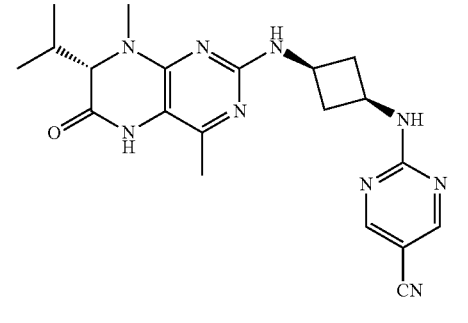 [SMILES: Cc1nc(N[C@H]2C[C@@H](Nc3ncc(C#N)cn3)C2)nc2c1NC(=O)[C@H](C(C)C)N2C]  I-717
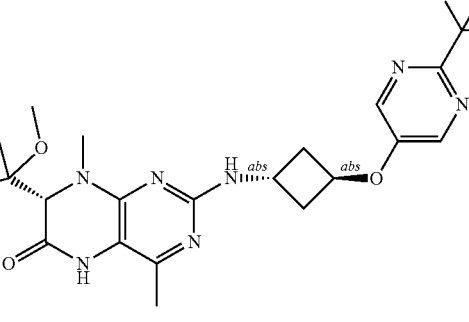  I-718
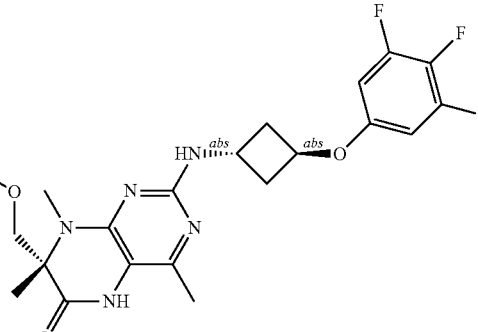  I-719

TABLE B-continued
Exemplary Compounds
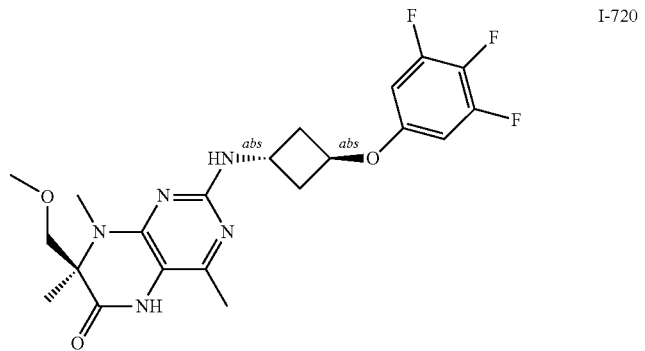
I-720
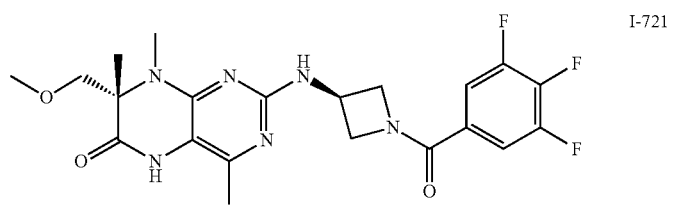
I-721
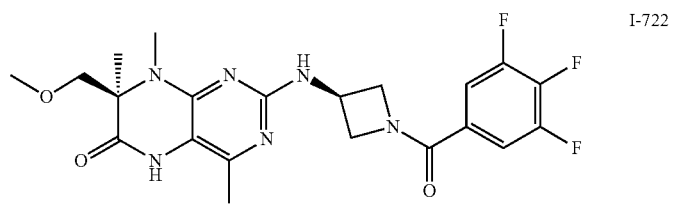
I-722
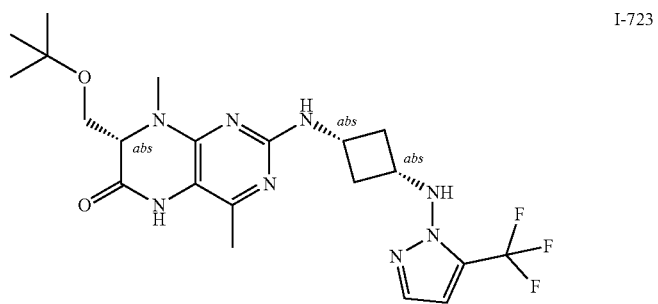
I-723
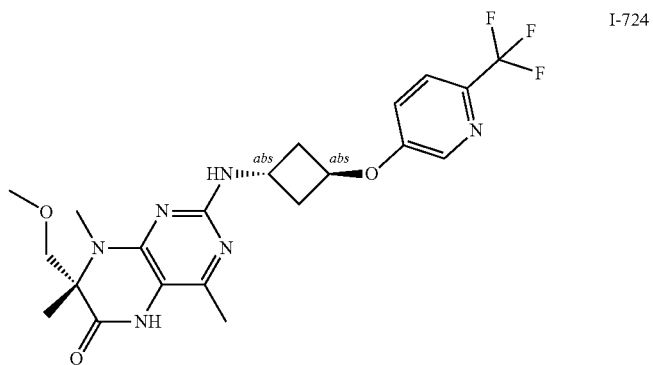
I-724

341
TABLE B-continued
Exemplary Compounds
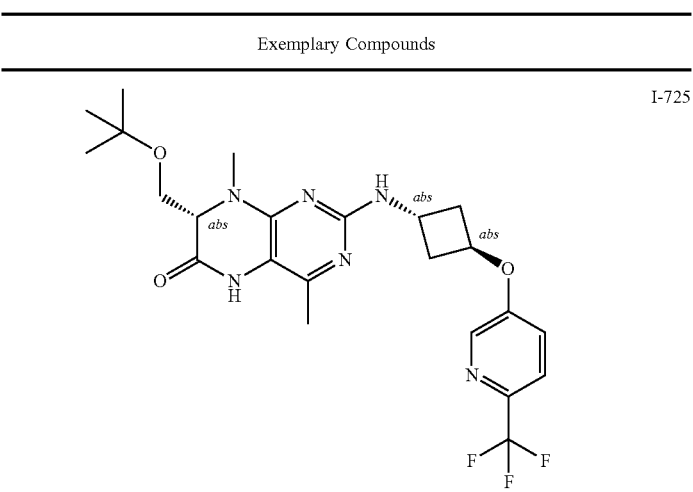
I-725
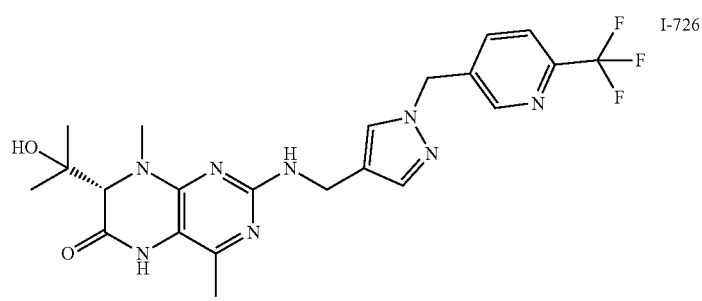
I-726
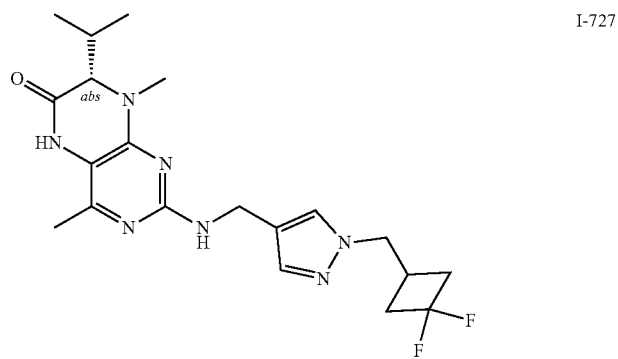
I-727
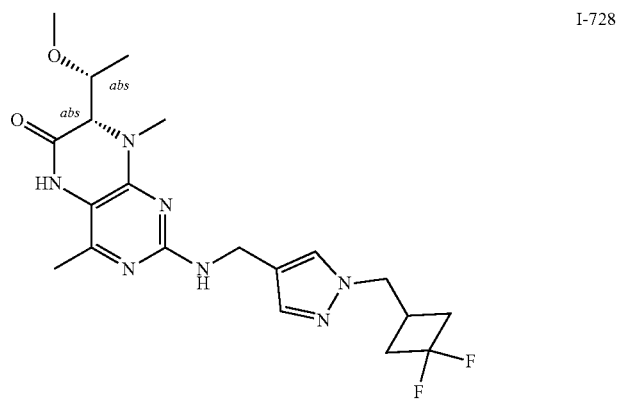
I-728
342

TABLE B-continued
Exemplary Compounds
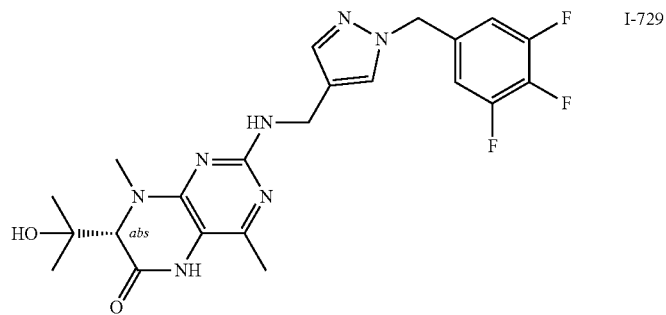
I-729
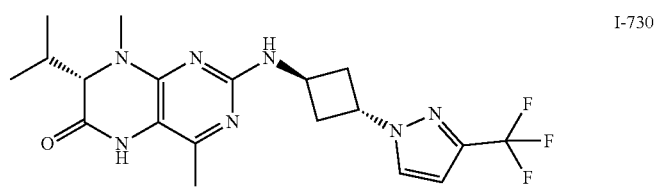
I-730
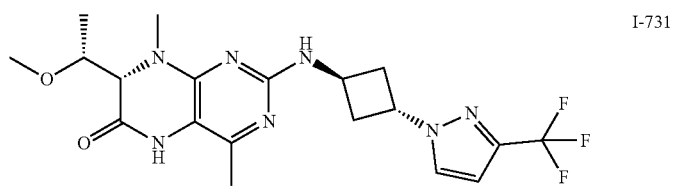
I-731
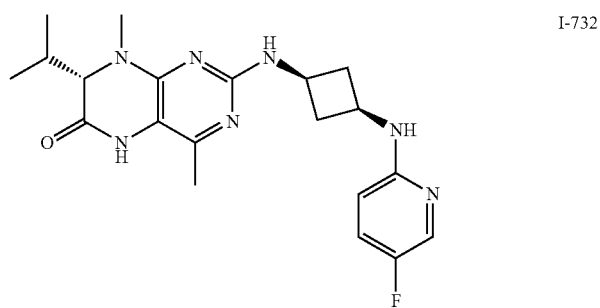
I-732
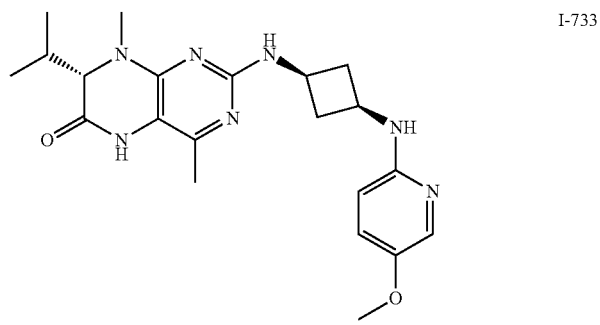
I-733

TABLE B-continued
Exemplary Compounds
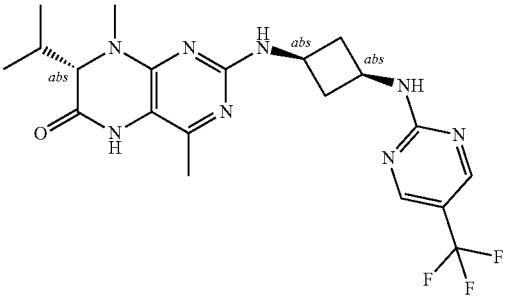 [SMILES: Cc1nc(N[C@H]2C[C@@H](Nc3ncc(C(F)(F)F)cn3)C2)nc2c1NC(=O)[C@H](C(C)C)N2C] I-734
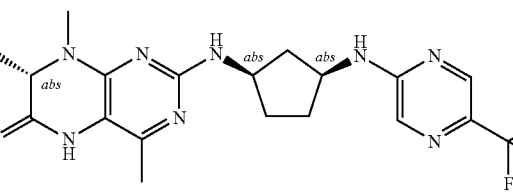 I-735
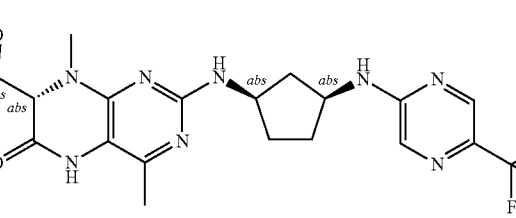 I-736
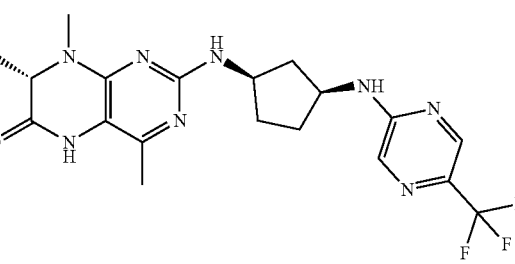 I-737
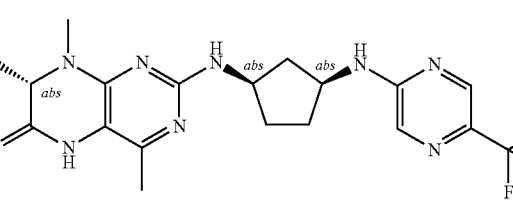 I-738
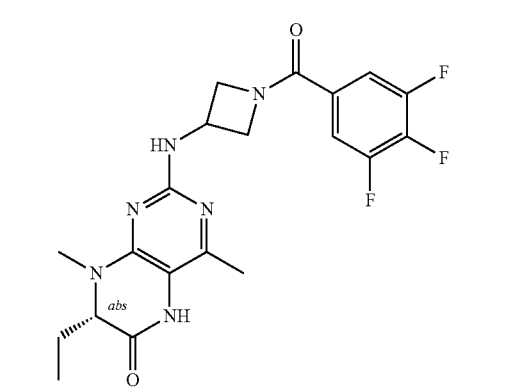 [SMILES: CC[C@H]1C(=O)Nc2c(C)nc(NC3CN(C(=O)c4cc(F)c(F)c(F)c4)C3)nc2N1C] I-739

TABLE B-continued
Exemplary Compounds
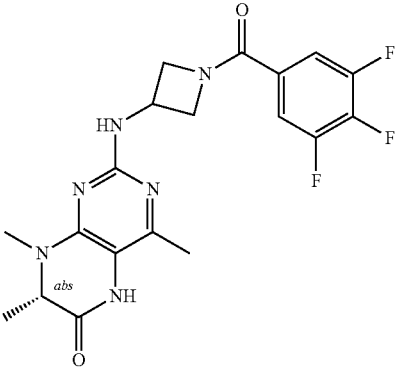 [SMILES: Cc1nc(NC2CN(C(=O)c3cc(F)c(F)c(F)c3)C2)nc2c1NC(=O)[C@H](C)N2C]
I-740
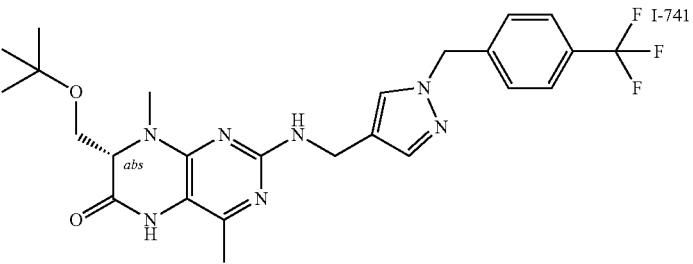
I-741
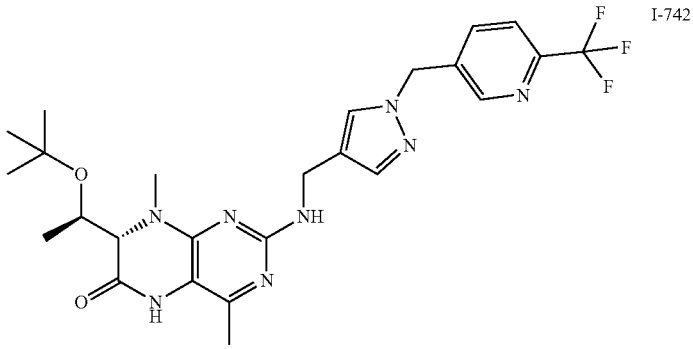
I-742
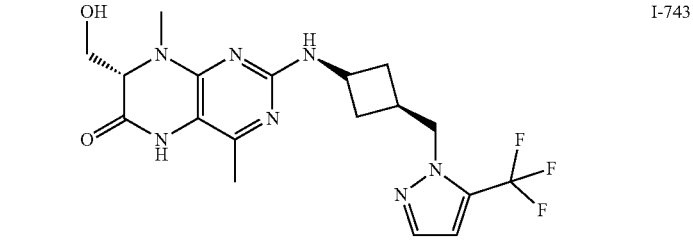
I-743
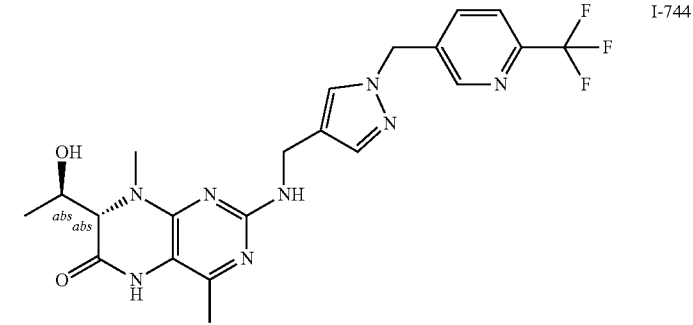
I-744

TABLE B-continued
Exemplary Compounds
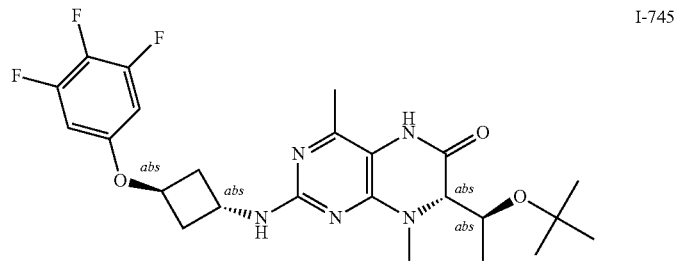
I-745
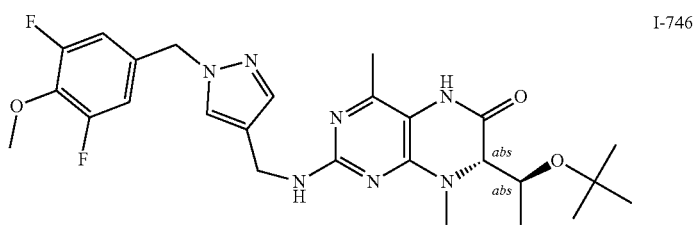
I-746
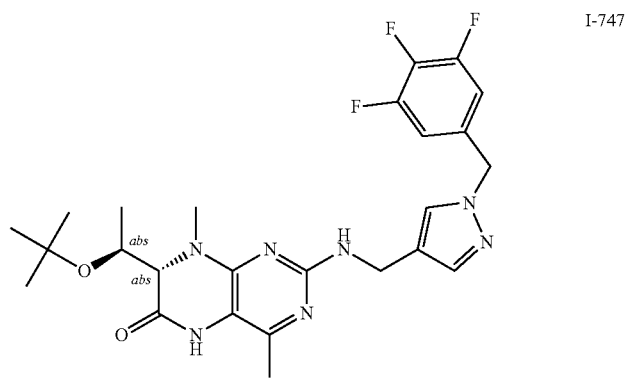
I-747
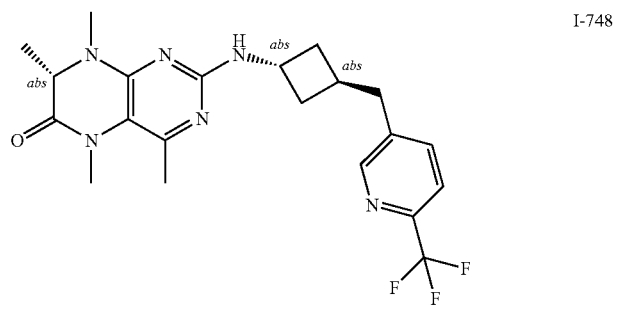
I-748
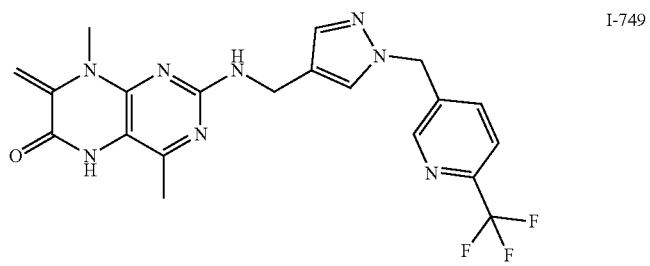
I-749

TABLE B-continued
Exemplary Compounds
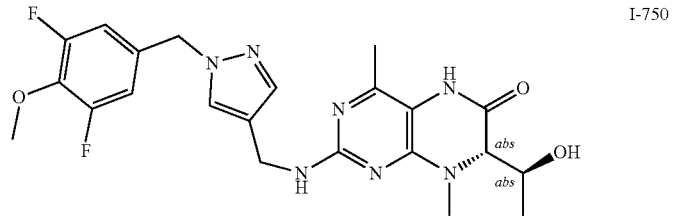
I-750
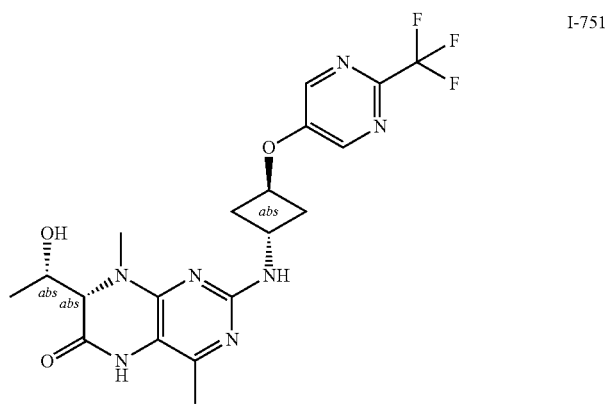
I-751
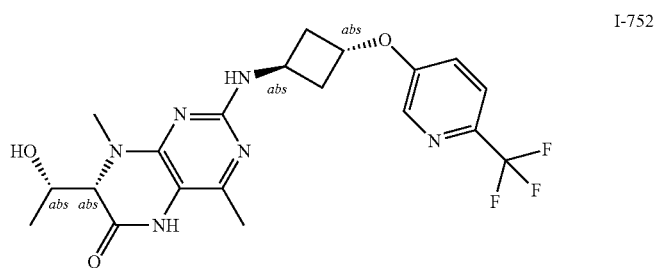
I-752
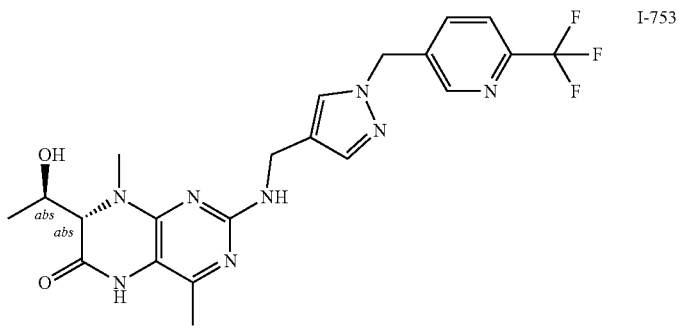
I-753

TABLE B-continued
Exemplary Compounds
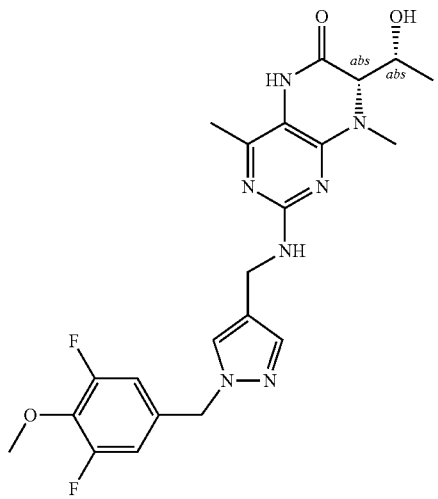 [SMILES: COc1c(F)cc(Cn2cc(CNc3nc(C)c4c(n3)N(C)[C@@H]([C@@H](C)O)C(=O)N4)cn2)cc1F]
I-754
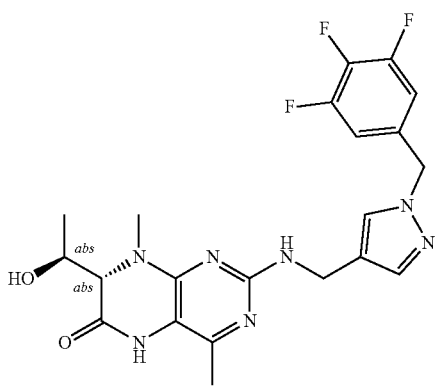 [SMILES: Cc1nc(NCc2cnn(Cc3cc(F)c(F)c(F)c3)c2)nc2c1NC(=O)[C@H]([C@H](C)O)N2C]
I-755
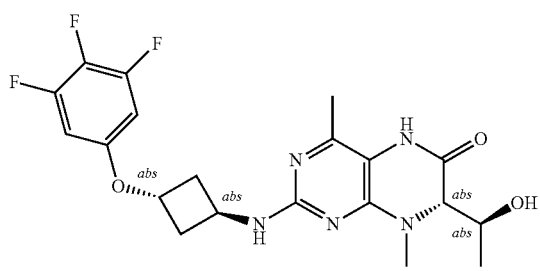 [SMILES: Cc1nc(N[C@H]2C[C@H](Oc3cc(F)c(F)c(F)c3)C2)nc2c1NC(=O)[C@H]([C@H](C)O)N2C]
I-756
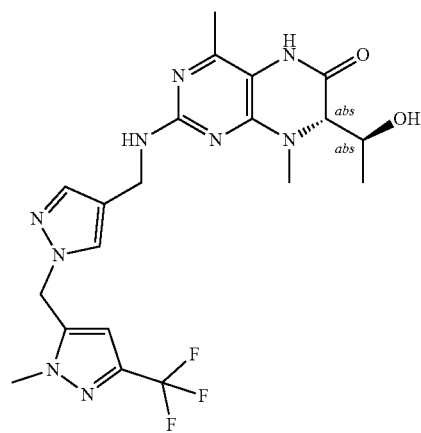 [SMILES: Cc1nc(NCc2cnn(Cc3cc(C(F)(F)F)nn3C)c2)nc2c1NC(=O)[C@H]([C@H](C)O)N2C]
I-757

TABLE B-continued
Exemplary Compounds
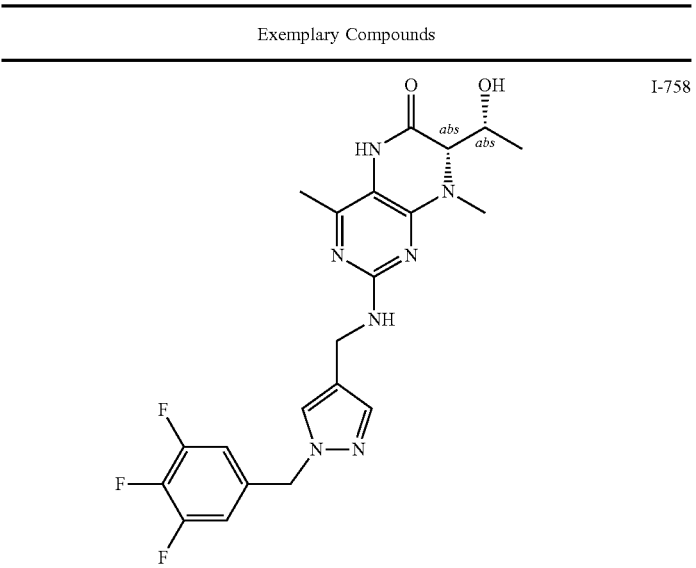
I-758
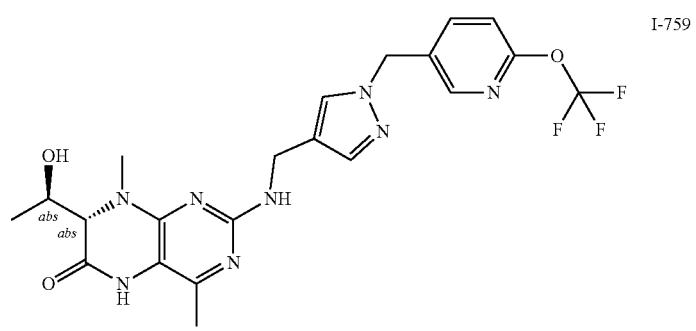
I-759
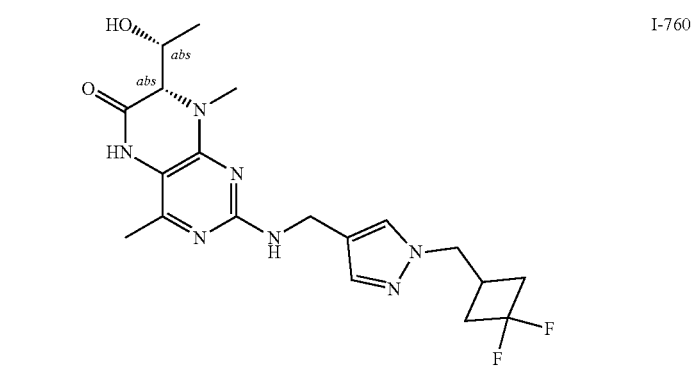
I-760
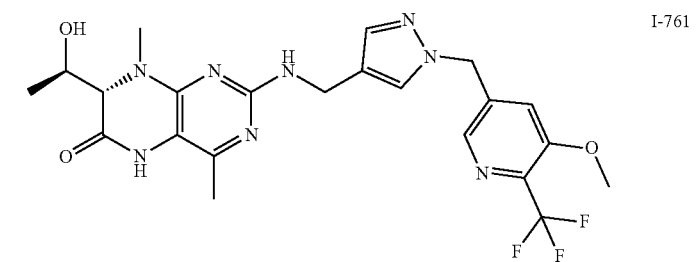
I-761

TABLE B-continued
Exemplary Compounds
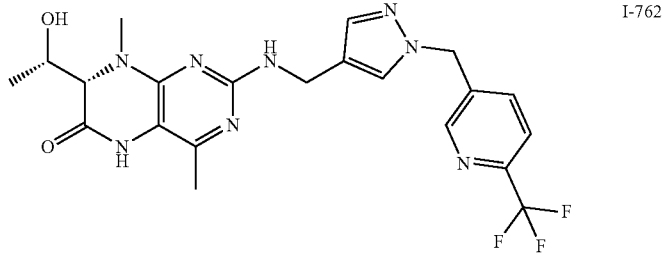
I-762
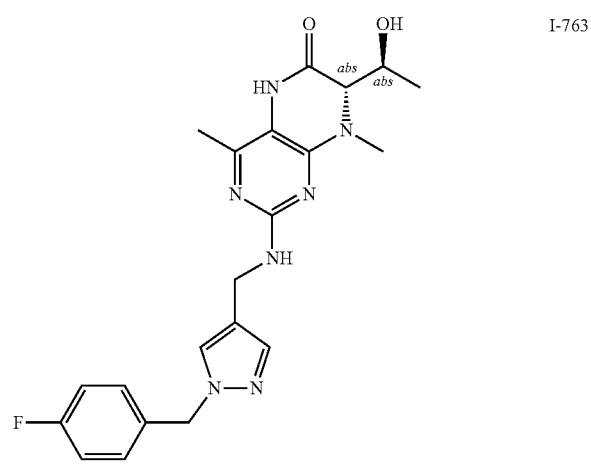
I-763
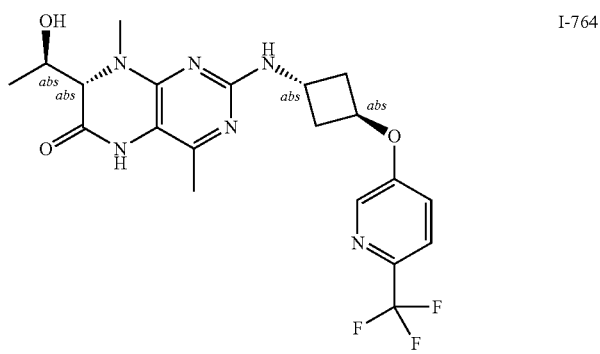
I-764
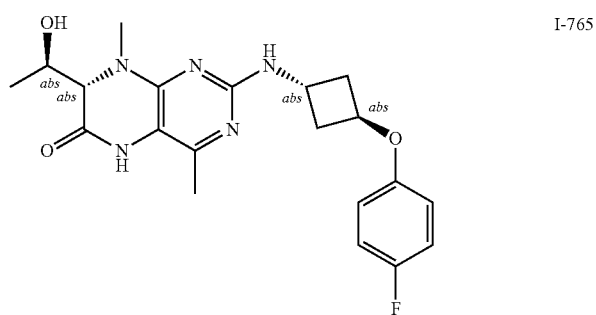
I-765

TABLE B-continued
Exemplary Compounds
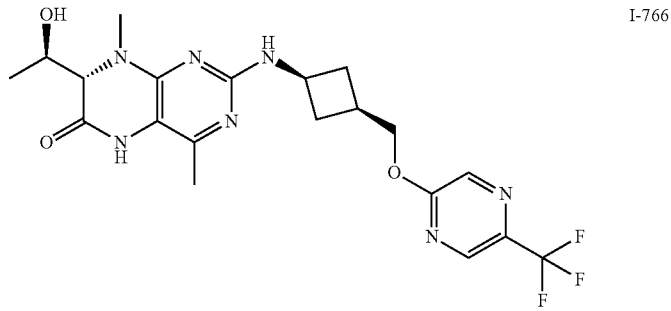
I-766
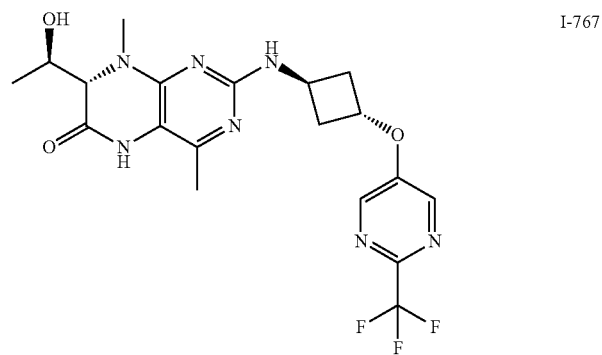
I-767
TABLE C
Exemplary Compounds
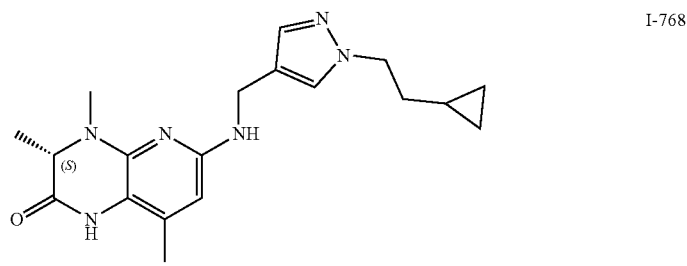
I-768
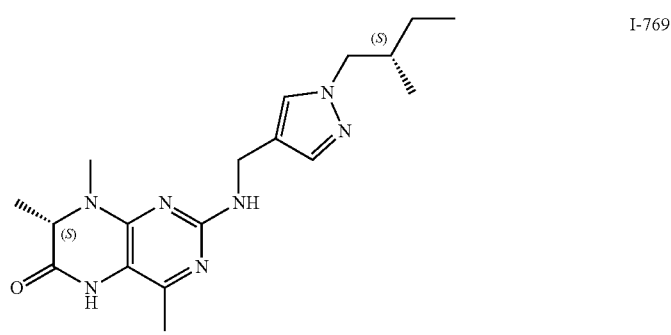
I-769

362
TABLE C-continued
Exemplary Compounds
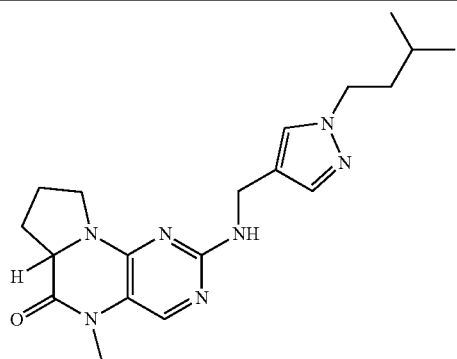
I-770
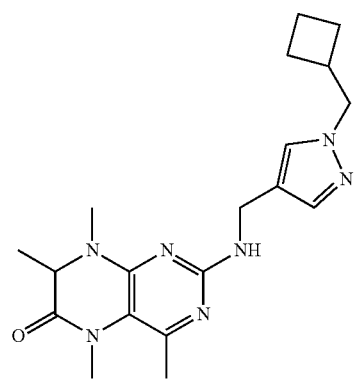 [SMILES: Cc1nc(NCc2cnn(CC3CCC3)c2)nc2c1N(C)C(=O)C(C)N2C]
I-771
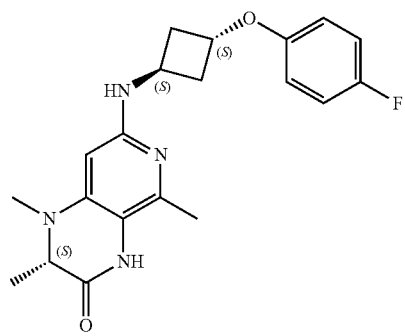
I-772
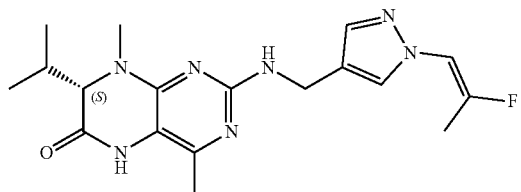
I-773
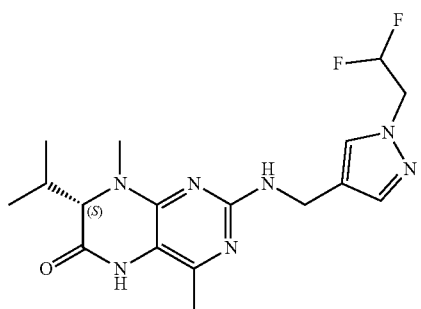
I-774

TABLE C-continued
Exemplary Compounds
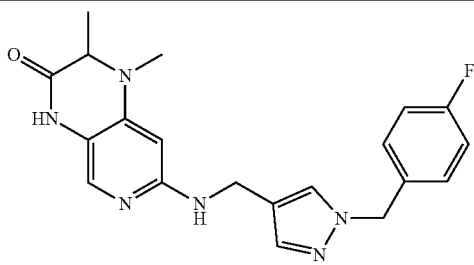
I-775
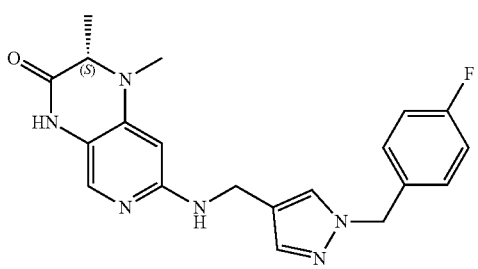
I-776
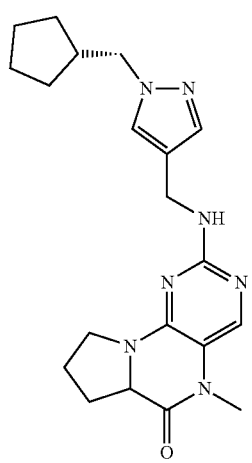
I-777
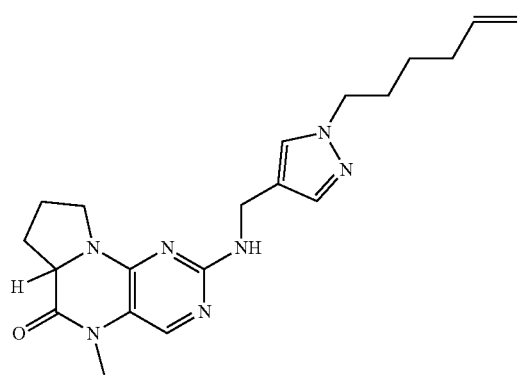 [SMILES: C=CCCCCn1cc(CNc2ncc3c(n2)N2CCCC2C(=O)N3C)cn1]
I-778
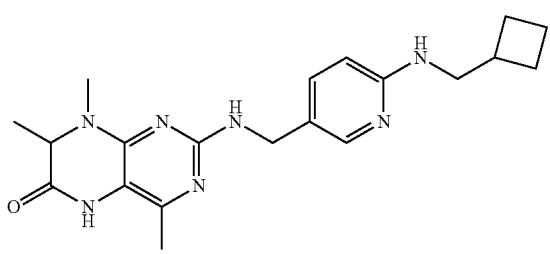 [SMILES: Cc1nc(NCc2ccc(NCC3CCC3)nc2)nc2c1NC(=O)C(C)N2C]
I-779

TABLE C-continued
Exemplary Compounds
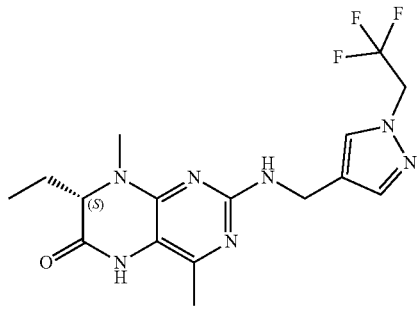
I-780
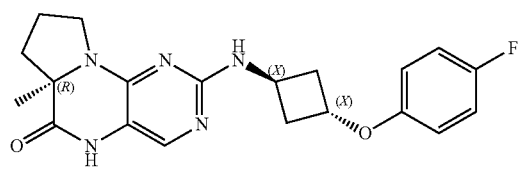
I-781
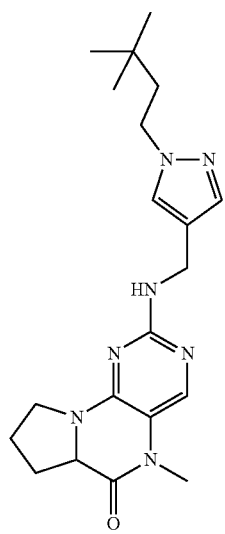 [SMILES: CN1C(=O)C2CCCN2c2nc(NCc3cnn(CCC(C)(C)C)c3)ncc21]
I-782
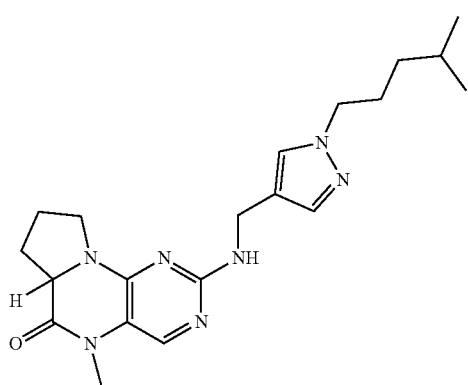 [SMILES: CC(C)CCCn1cc(CNc2ncc3c(n2)N2CCCC2C(=O)N3C)cn1]
I-783

TABLE C-continued
Exemplary Compounds
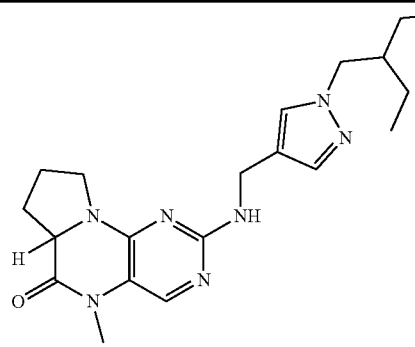
I-784
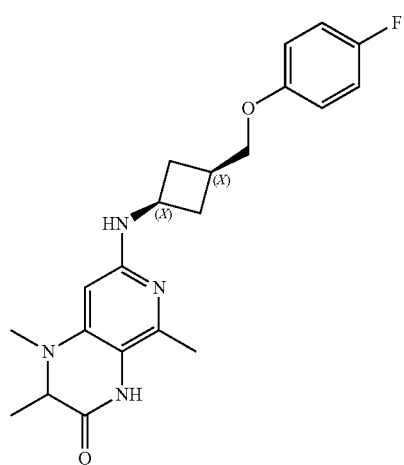
I-785
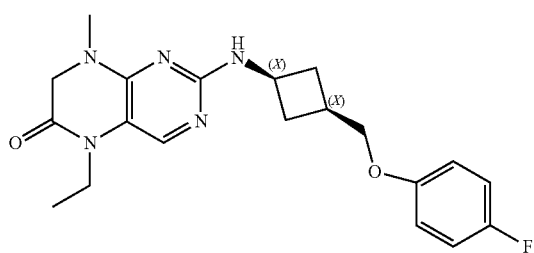
I-786
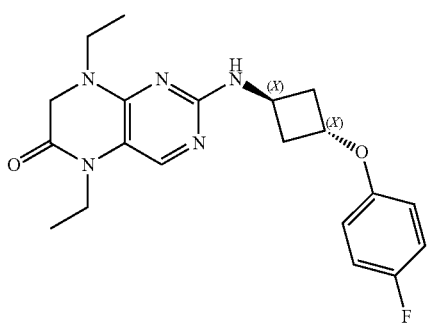
I-787
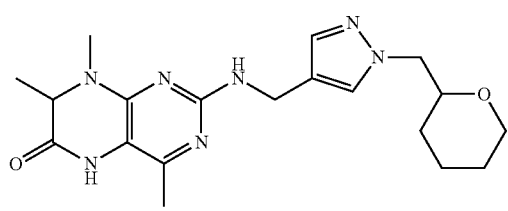 [SMILES: Cc1nc(NCc2cnn(CC3CCCCO3)c2)nc2c1NC(=O)C(C)N2C]
I-788

TABLE C-continued
Exemplary Compounds
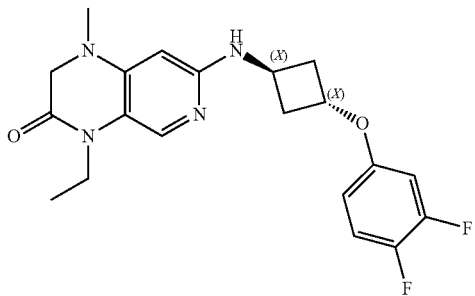
I-789
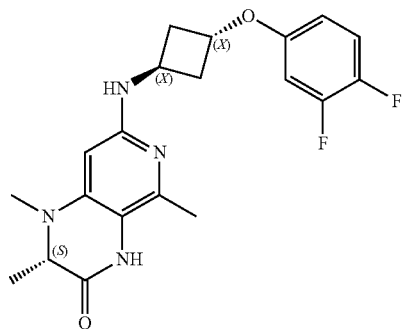
I-790
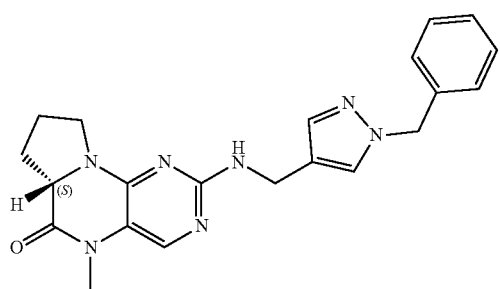
I-791
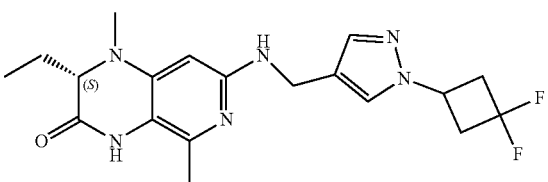
I-792
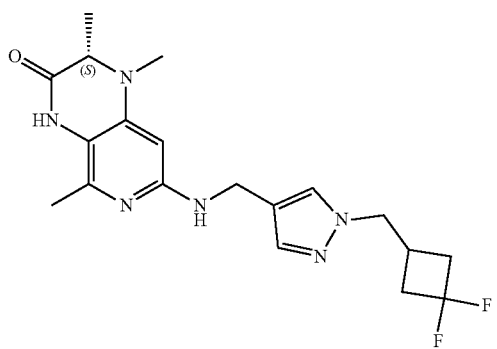
I-793

TABLE C-continued

Exemplary Compounds

I-794

I-795

I-796

I-797

I-798

I-799

TABLE C-continued
Exemplary Compounds
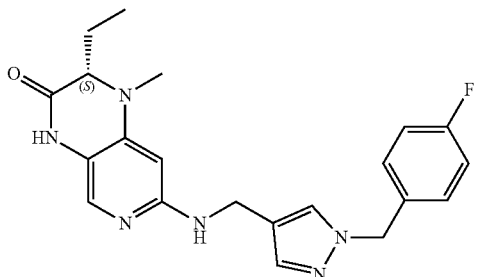
I-800
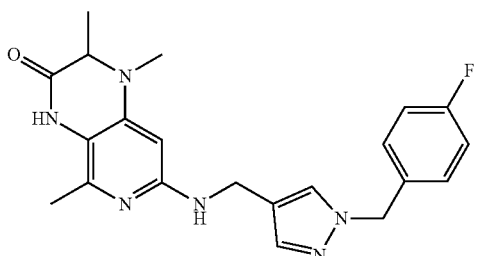
I-801
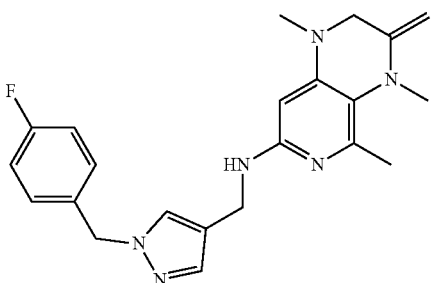
I-802
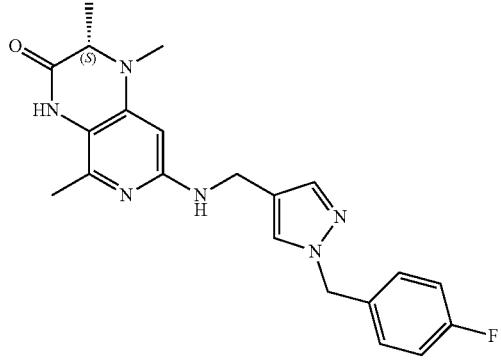
I-803
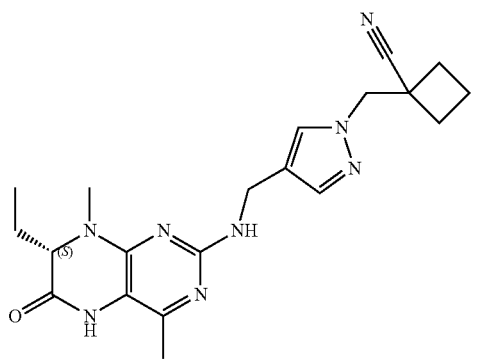
I-804

TABLE C-continued
Exemplary Compounds
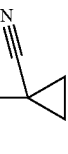
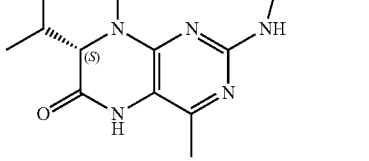
I-805
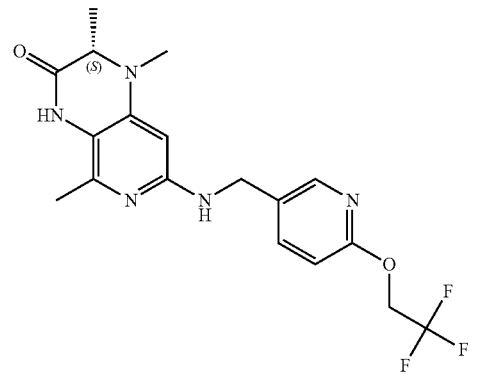
I-806
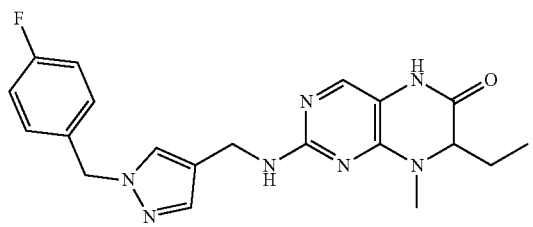 [SMILES: CCC1C(=O)Nc2cnc(NCc3cnn(Cc4ccc(F)cc4)c3)nc2N1C]
I-807
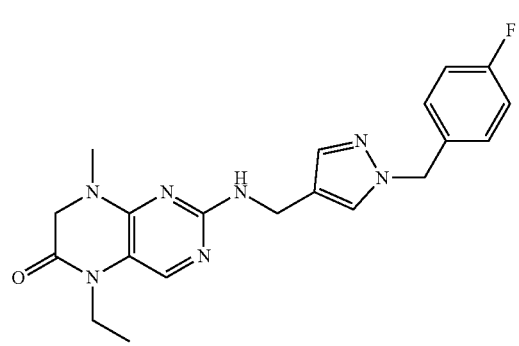 [SMILES: CCN1C(=O)CN(C)c2nc(NCc3cnn(Cc4ccc(F)cc4)c3)ncc21]
I-808
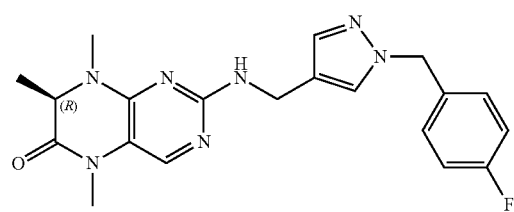
I-809

TABLE C-continued
Exemplary Compounds
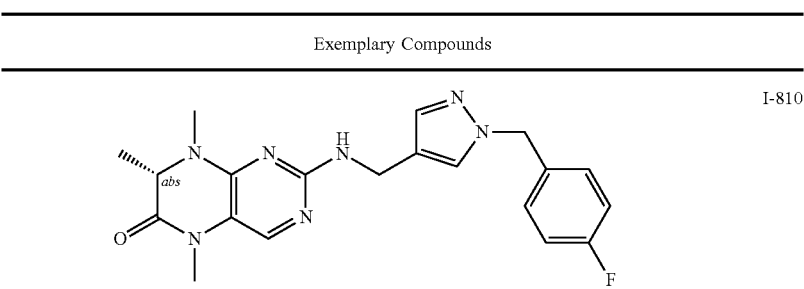
I-810
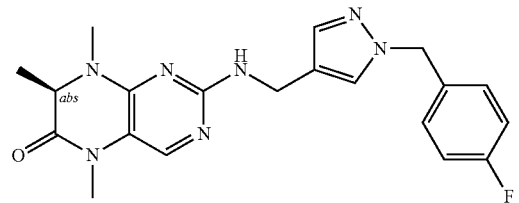
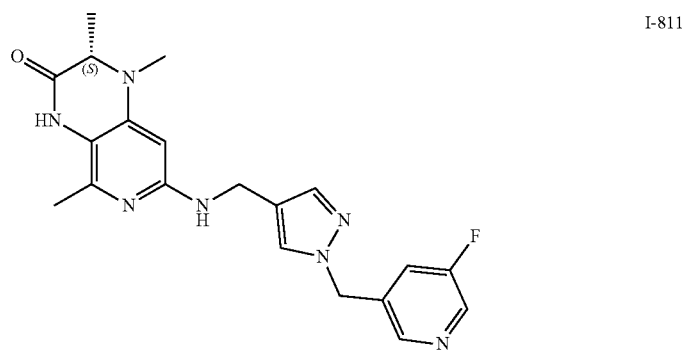
I-811
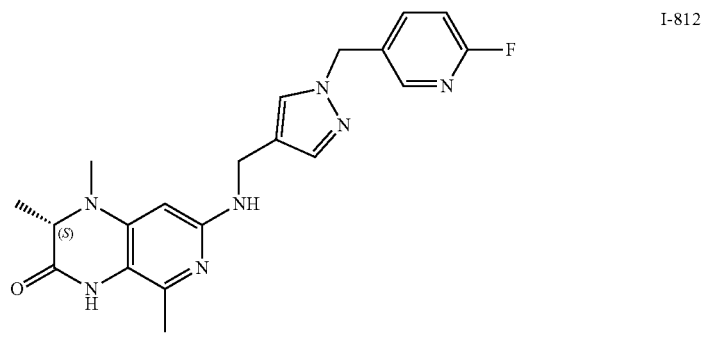
I-812
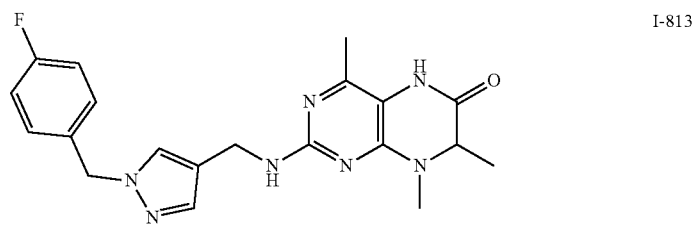
I-813

TABLE C-continued
Exemplary Compounds
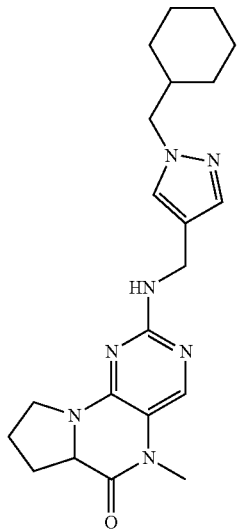 [SMILES: CN1C(=O)C2CCCN2c2nc(NCc3cnn(CC4CCCCC4)c3)ncc21]
I-814
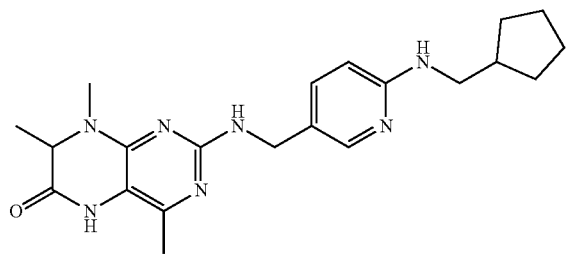 [SMILES: Cc1nc(NCc2ccc(NCC3CCCC3)nc2)nc2c1NC(=O)C(C)N2C]
I-815
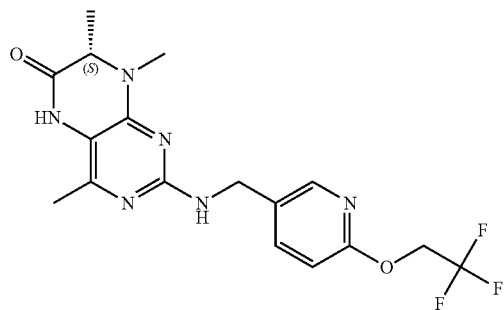
I-816
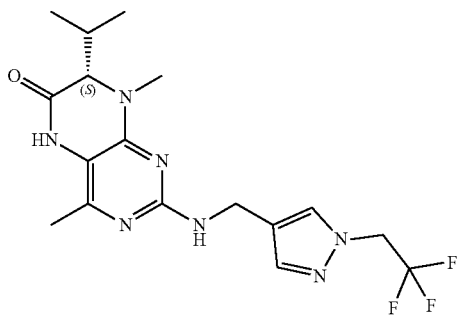
I-817

TABLE C-continued
Exemplary Compounds
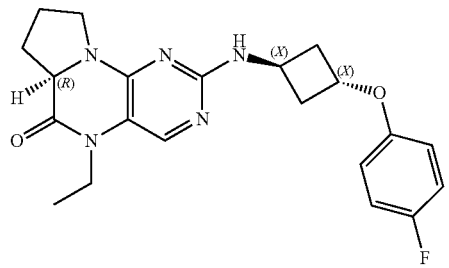
I-818
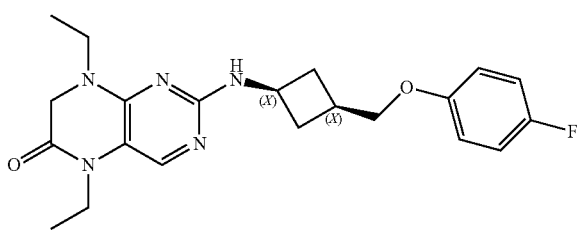
I-819
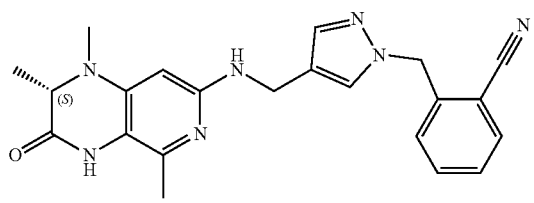
I-820
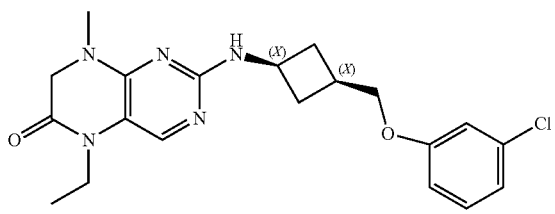
I-821
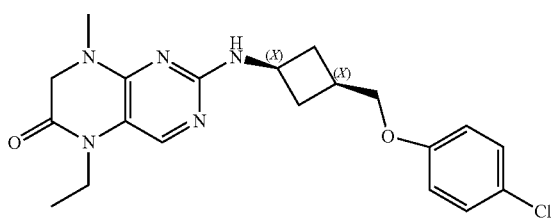
I-822
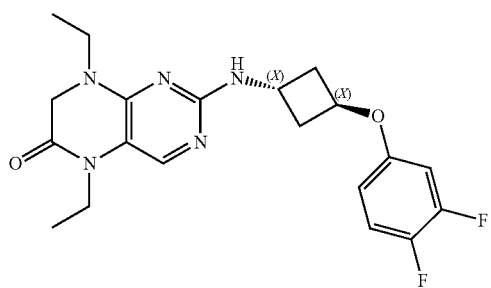
I-823

TABLE C-continued
Exemplary Compounds
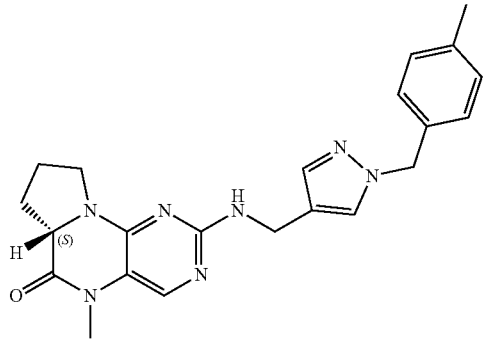
I-824
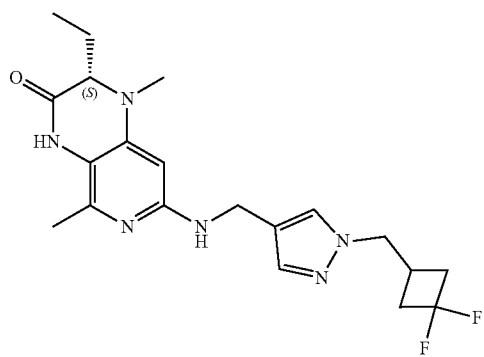
I-825
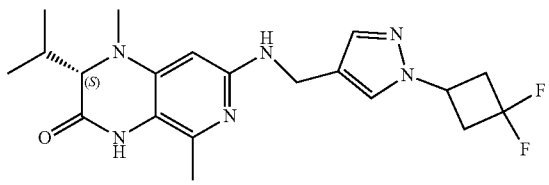
I-826
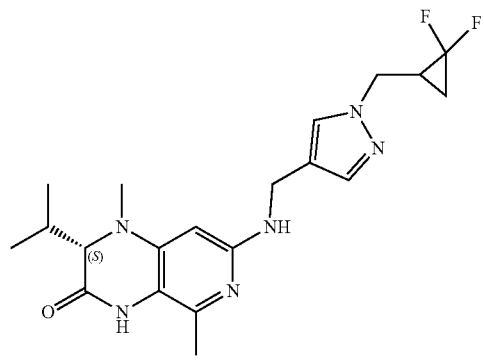
I-827
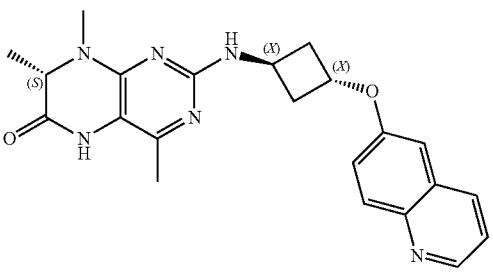
I-828

385 386
TABLE C-continued
Exemplary Compounds
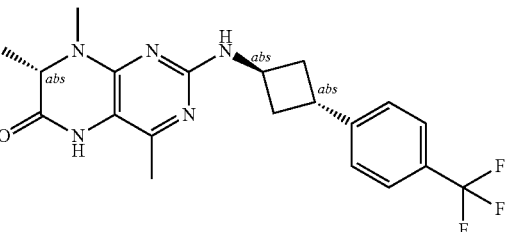 I-829
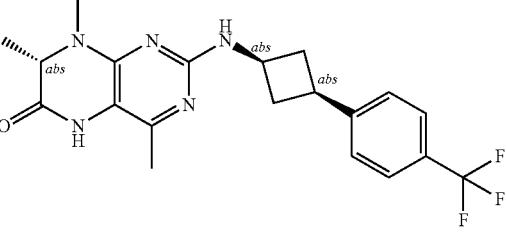 I-830
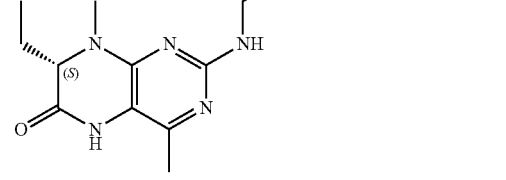 I-831
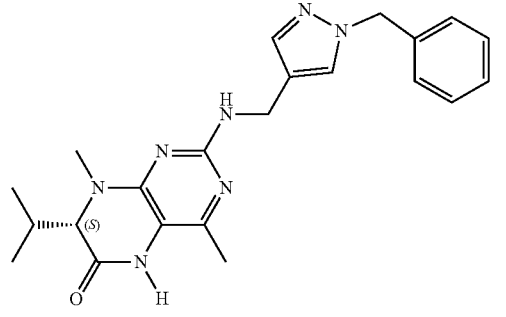 I-832
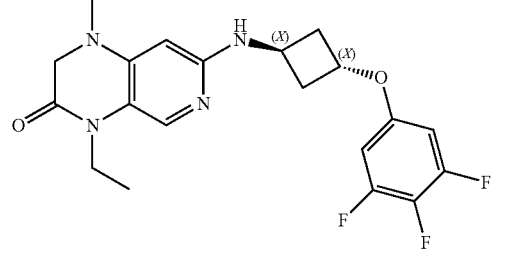 I-833

TABLE C-continued
Exemplary Compounds
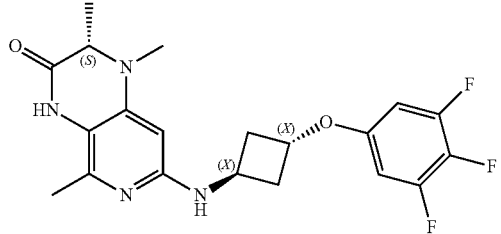
I-834
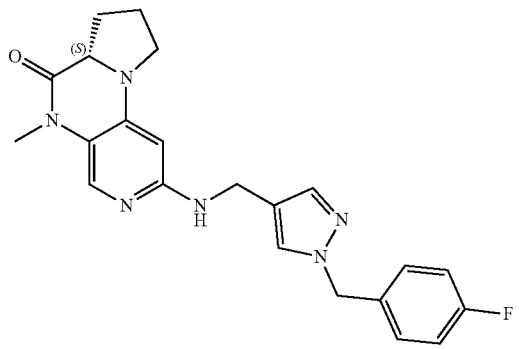
I-835
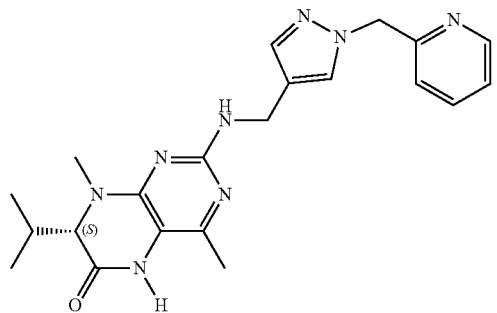
I-836
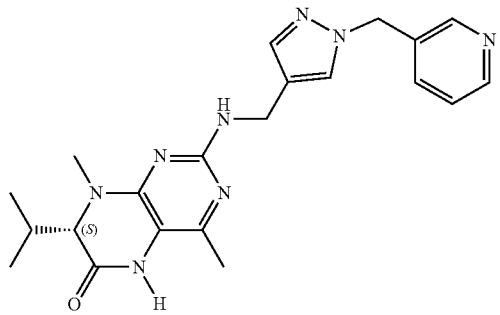
I-837
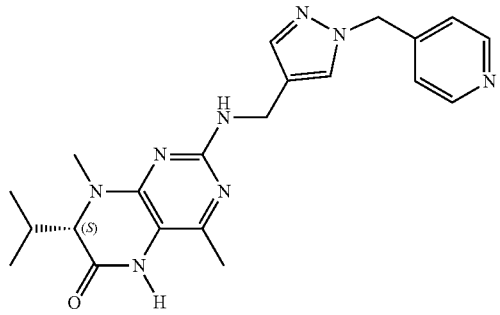
I-838

TABLE C-continued
Exemplary Compounds
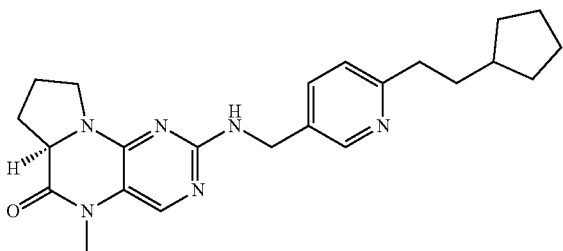 [SMILES: CN1C(=O)[C@H]2CCCN2c2nc(NCc3ccc(CCC4CCCC4)nc3)ncc21]
I-839
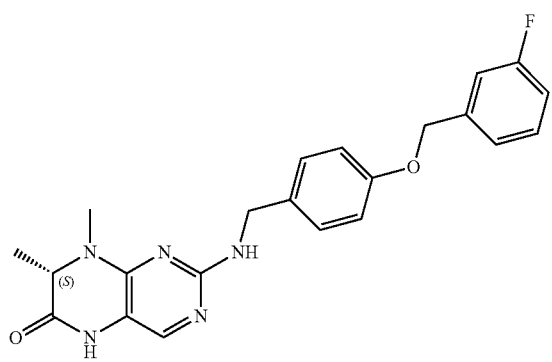
I-840
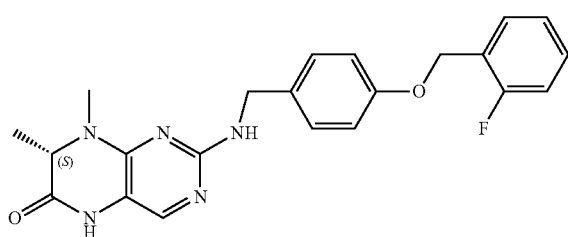
I-841
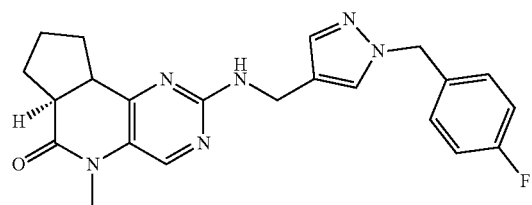 [SMILES: CN1C(=O)[C@H]2CCCC2c2nc(NCc3cnn(Cc4ccc(F)cc4)c3)ncc21]
I-842
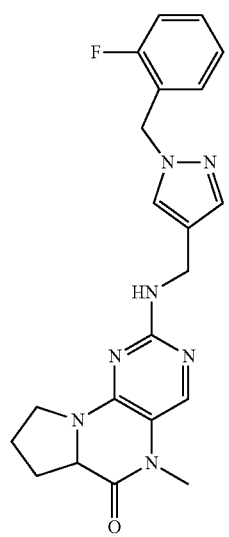 [SMILES: CN1C(=O)C2CCCN2c2nc(NCc3cnn(Cc4ccccc4F)c3)ncc21]
I-843

TABLE C-continued
Exemplary Compounds
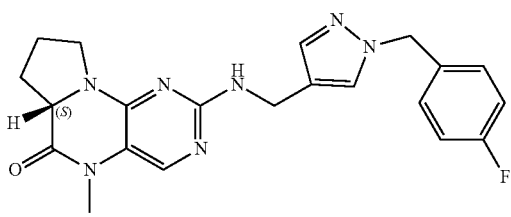
I-844
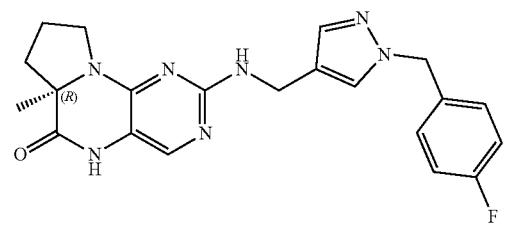
I-845
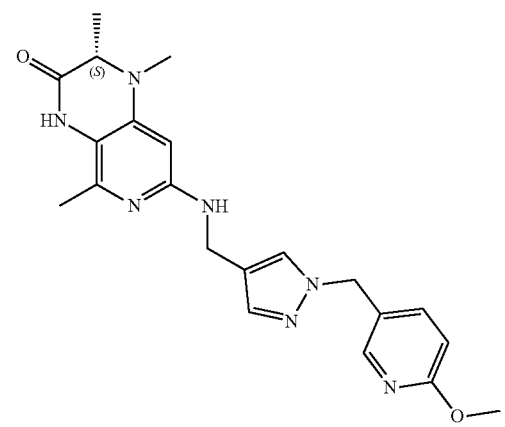
I-846
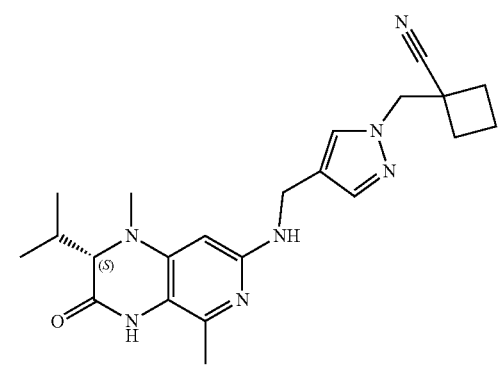
I-847
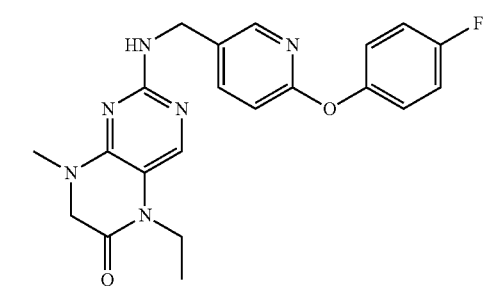 [SMILES: CCN1C(=O)CN(C)c2nc(NCc3ccc(Oc4ccc(F)cc4)nc3)ncc21]
I-848

TABLE C-continued
Exemplary Compounds
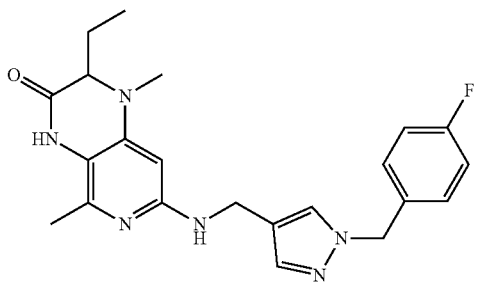 [SMILES: CCC1C(=O)Nc2c(cc(NCc3cnn(Cc4ccc(F)cc4)c3)nc2C)N1C]
I-849
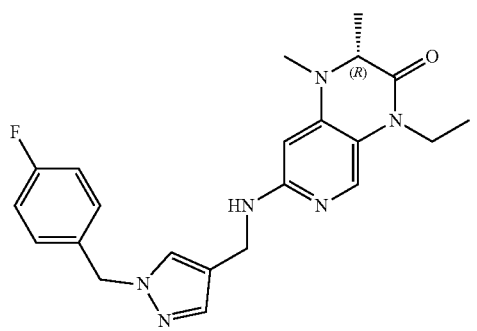
I-850
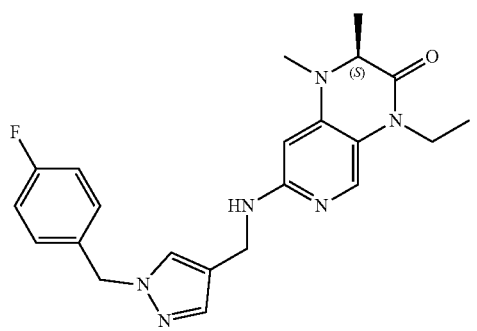
I-851
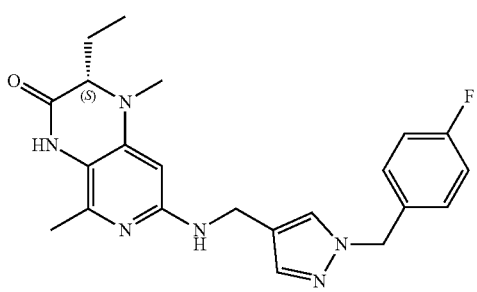
I-852
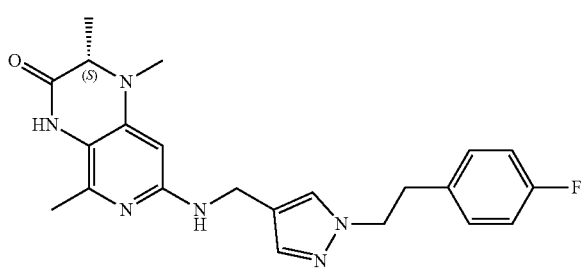
I-853

TABLE C-continued
Exemplary Compounds
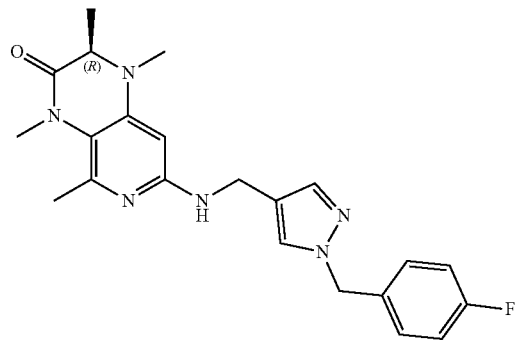
I-854
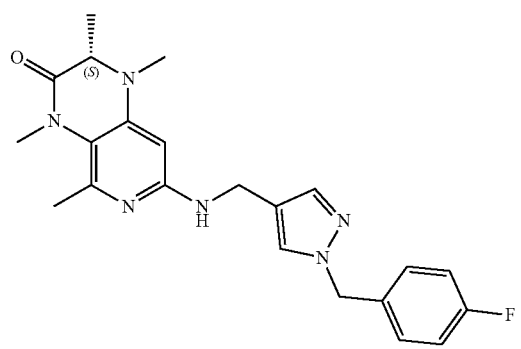
I-855
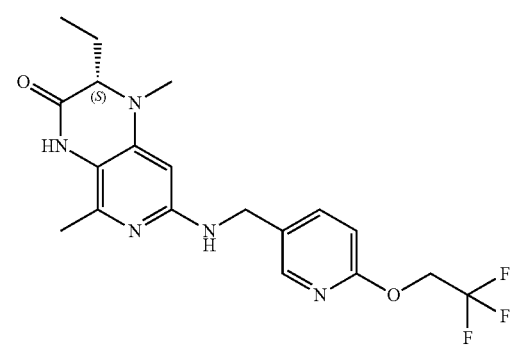
I-856
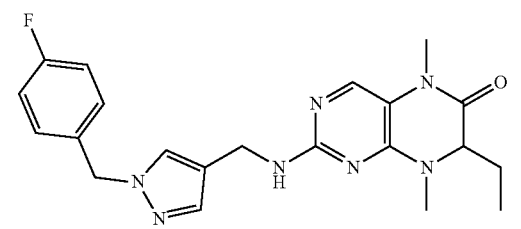 [SMILES: CCC1C(=O)N(C)c2cnc(NCc3cnn(Cc4ccc(F)cc4)c3)nc2N1C]
I-857
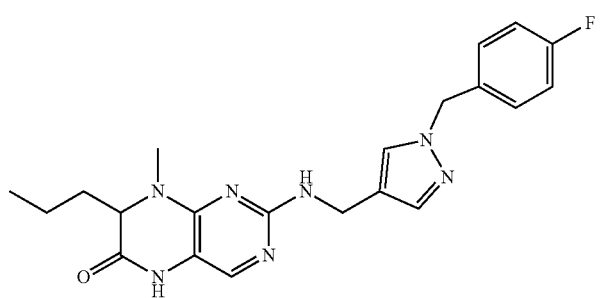 [SMILES: CCCC1C(=O)Nc2cnc(NCc3cnn(Cc4ccc(F)cc4)c3)nc2N1C]
I-858

TABLE C-continued
Exemplary Compounds
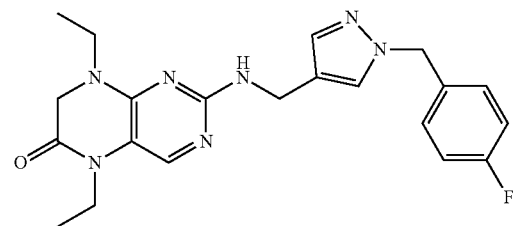 [SMILES: CCN1CC(=O)N(CC)c2cnc(NCc3cnn(Cc4ccc(F)cc4)c3)nc21] I-859
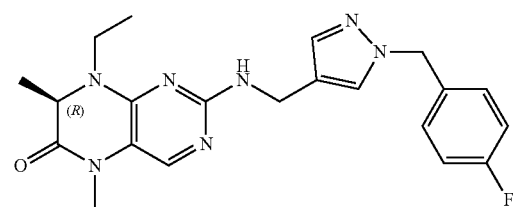 I-860
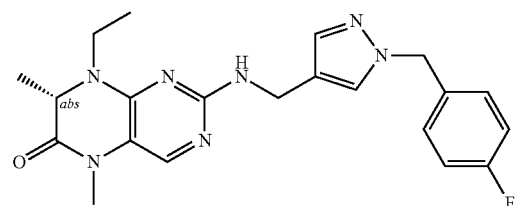 I-861
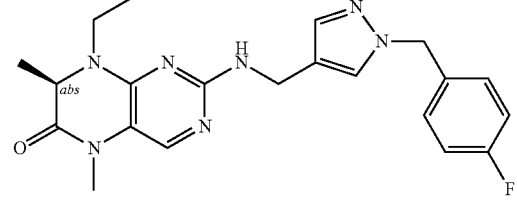
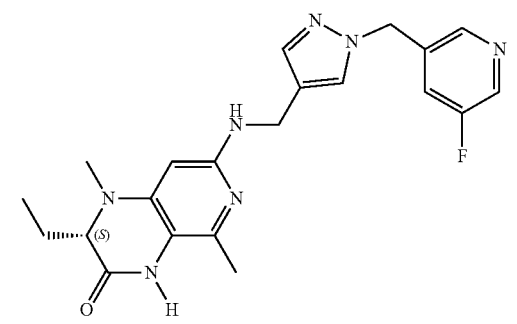 I-862
I-863

TABLE C-continued
Exemplary Compounds
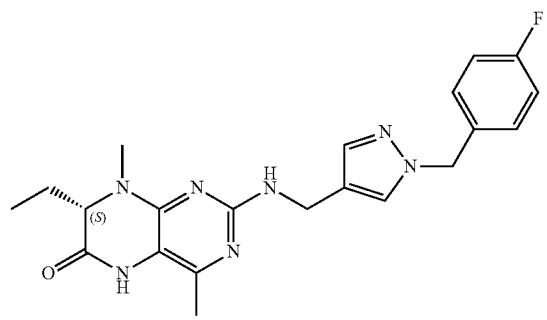
I-864
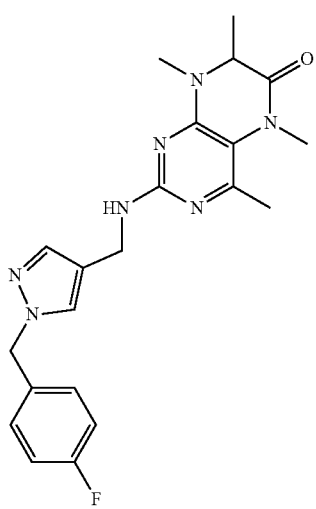 [SMILES: Cc1nc(NCc2cnn(Cc3ccc(F)cc3)c2)nc2c1N(C)C(=O)C(C)N2C]
I-865
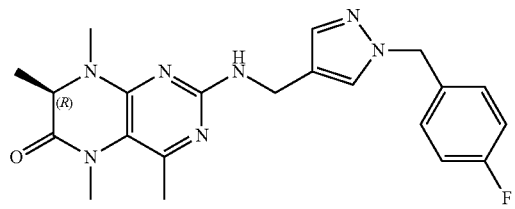
I-866
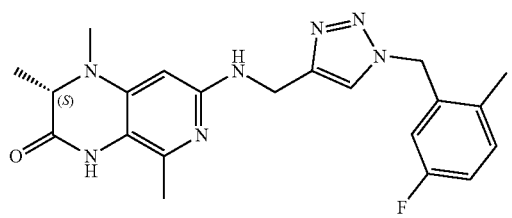
I-867
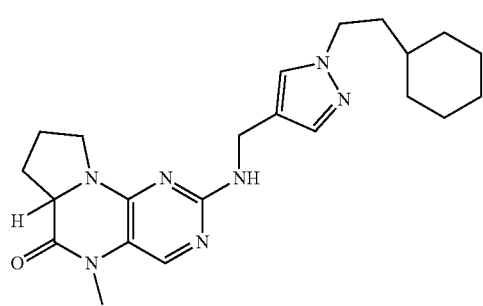 [SMILES: CN1C(=O)C2CCCN2c2nc(NCc3cnn(CCC4CCCCC4)c3)ncc21]
I-868

TABLE C-continued
Exemplary Compounds
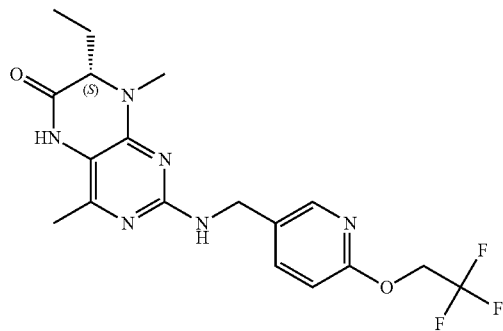
I-869
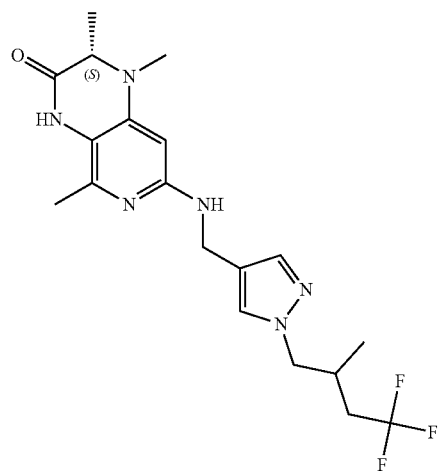
I-870
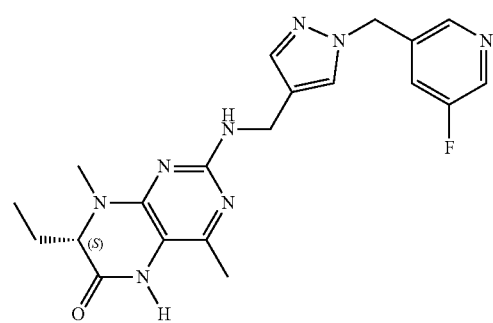
I-871
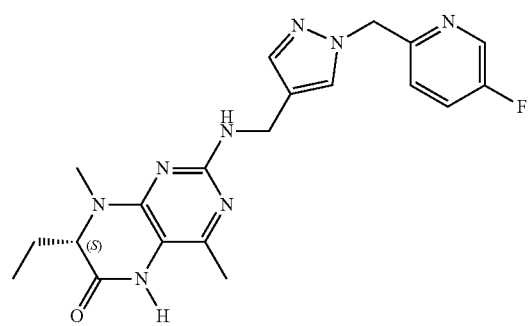
I-872

TABLE C-continued
Exemplary Compounds
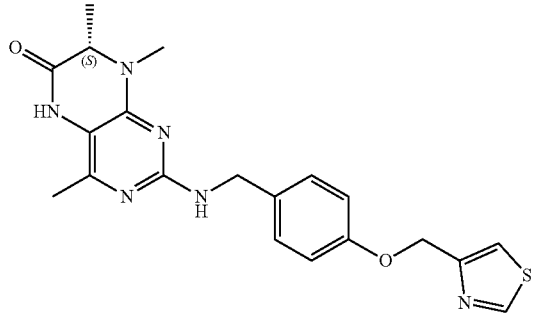
I-873
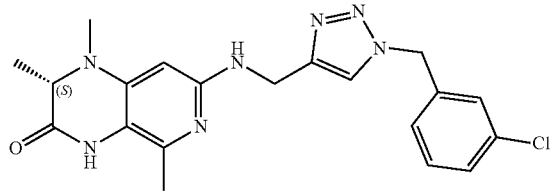
I-874
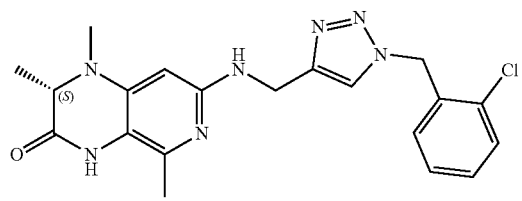
I-875
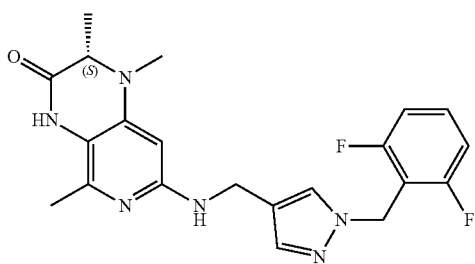
I-876
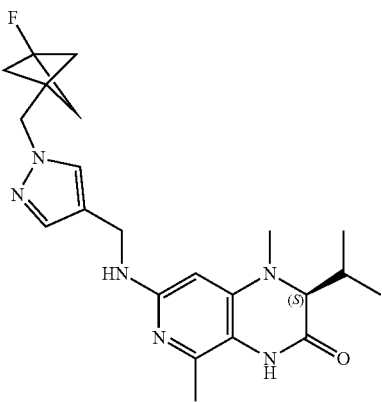
I-877

TABLE C-continued
Exemplary Compounds
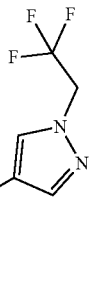 I-878
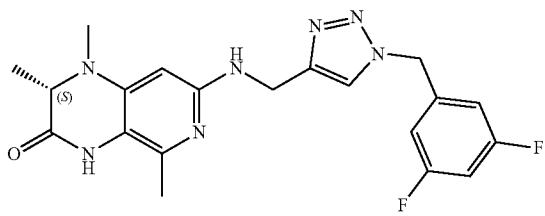 I-879
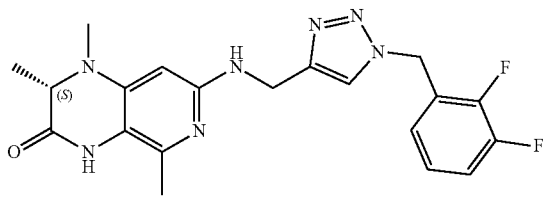 I-880
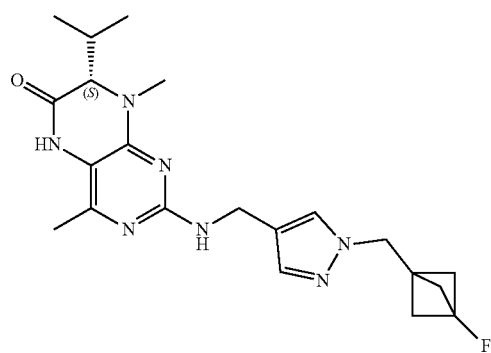 I-881
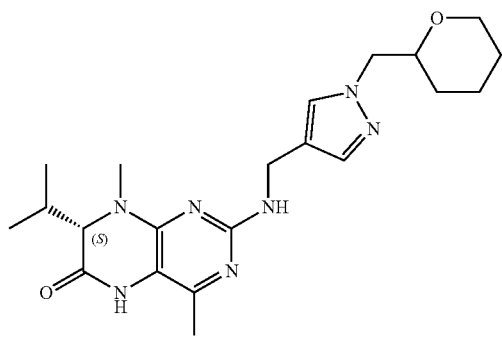 I-882

TABLE C-continued
Exemplary Compounds
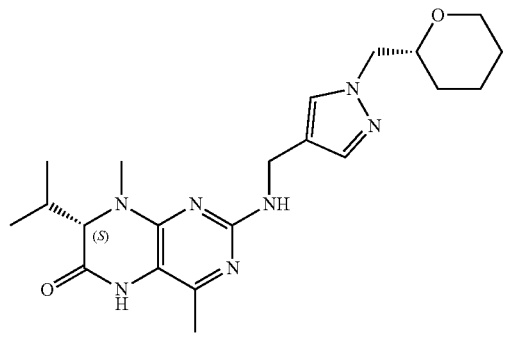
I-883
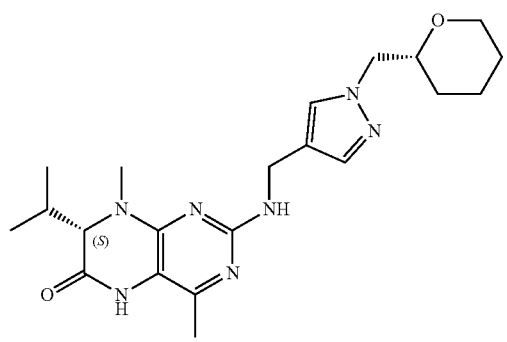
I-884
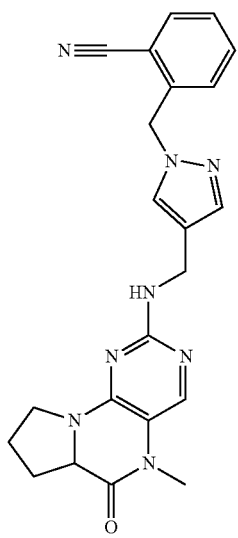 [SMILES: CN1C(=O)C2CCCN2c2nc(NCc3cnn(Cc4ccccc4C#N)c3)ncc21]
I-885
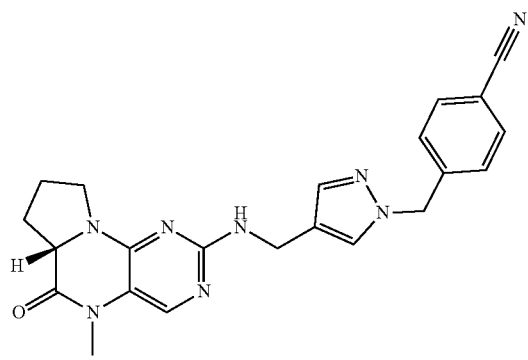 [SMILES: CN1C(=O)[C@@H]2CCCN2c2nc(NCc3cnn(Cc4ccc(C#N)cc4)c3)ncc21]
I-886

TABLE C-continued
Exemplary Compounds
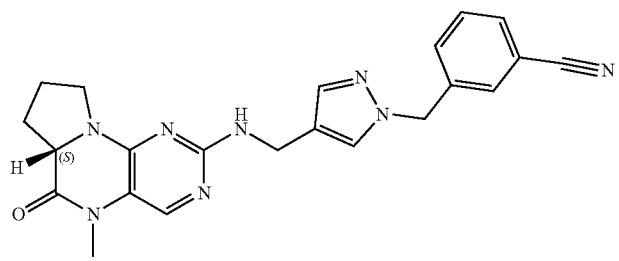
I-887
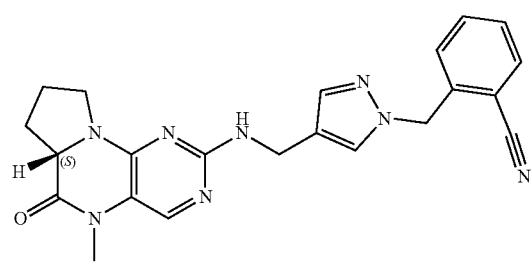
I-888
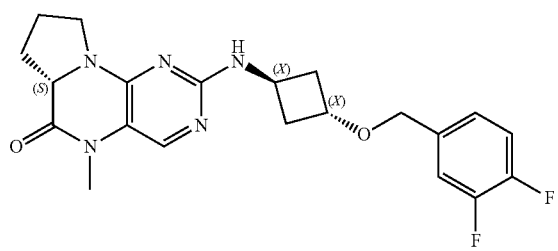
I-889
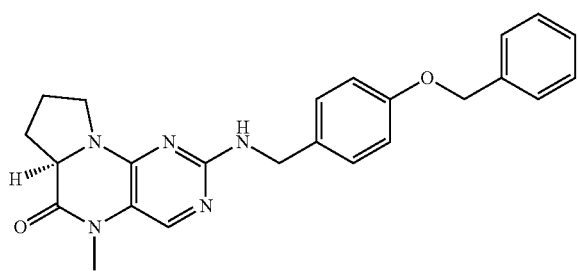 [SMILES: CN1C(=O)[C@H]2CCCN2c2nc(NCc3ccc(OCc4ccccc4)cc3)ncc21]
I-890
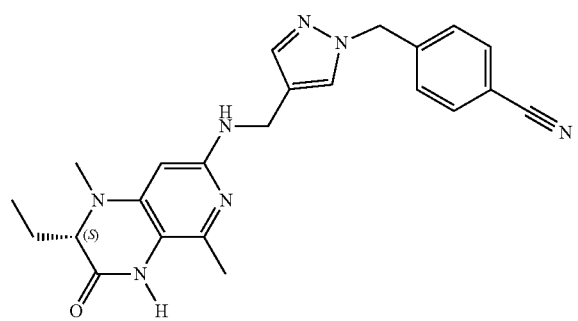
I-891

TABLE C-continued
Exemplary Compounds
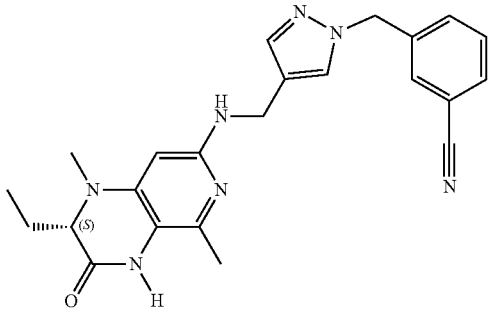
I-892
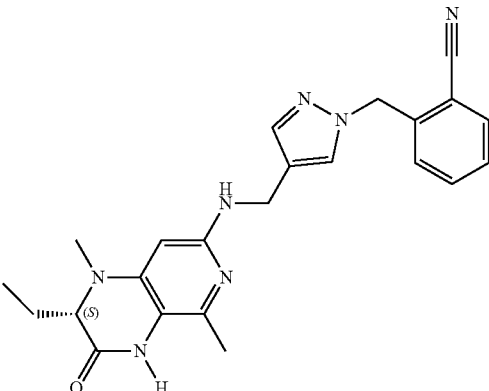
I-893
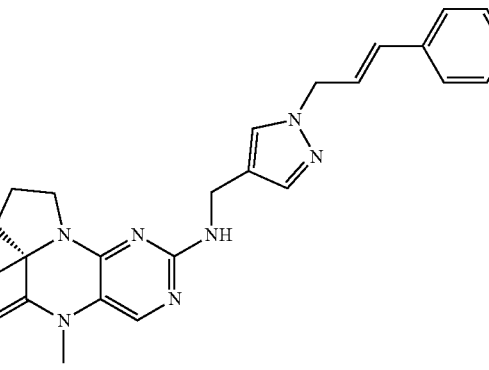
I-894
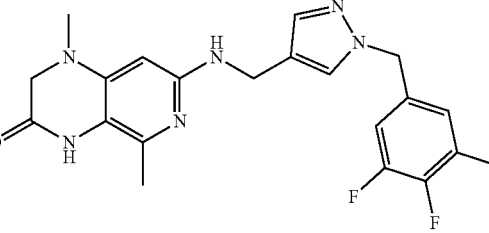
I-895
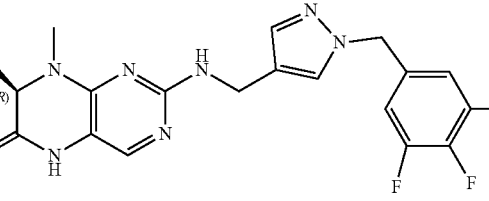
I-896

TABLE C-continued
Exemplary Compounds
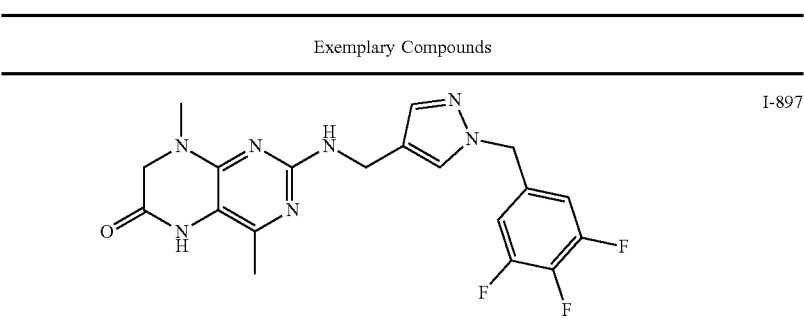 I-897
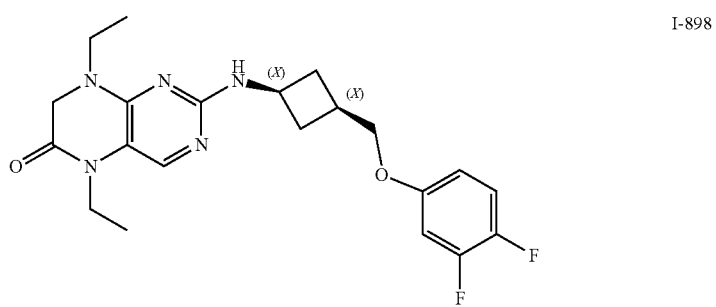 I-898
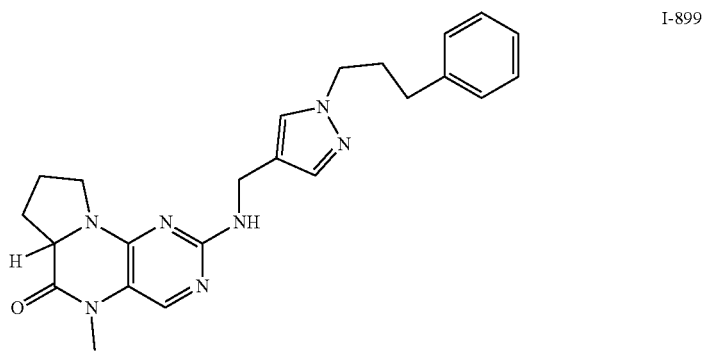 I-899
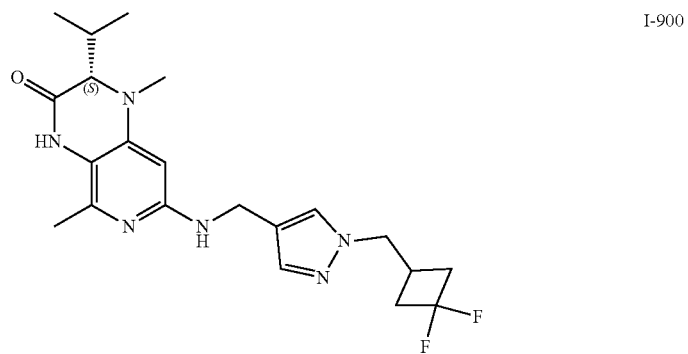 I-900
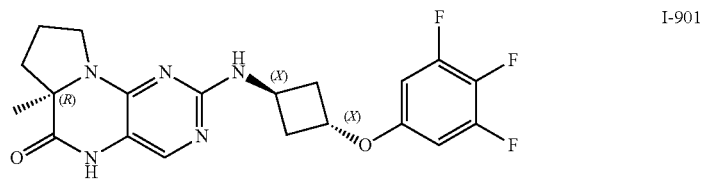 I-901

TABLE C-continued
Exemplary Compounds
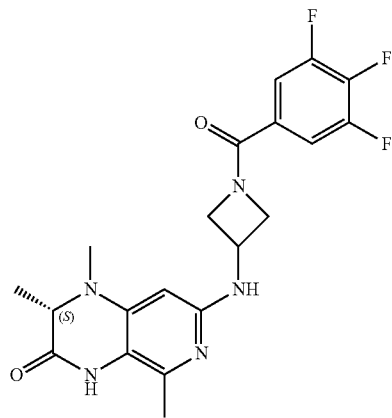
I-902
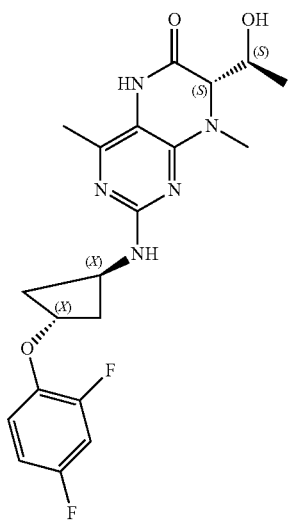
I-903
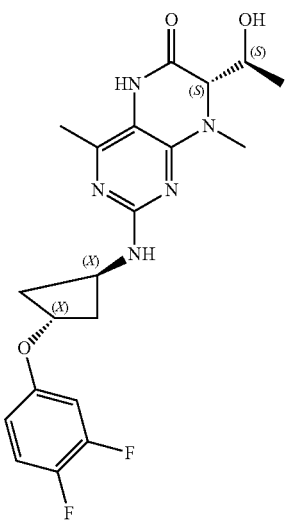
I-904

TABLE C-continued
Exemplary Compounds
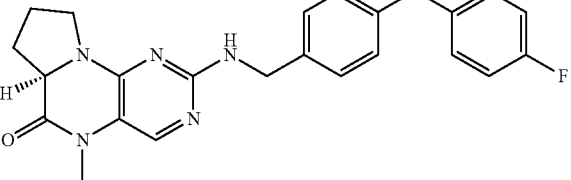
I-905
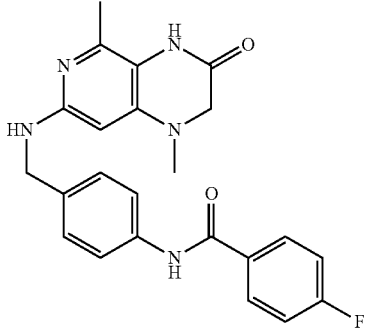 [SMILES: Cc1nc(NCc2ccc(NC(=O)c3ccc(F)cc3)cc2)cc2c1NC(=O)CN2C]
I-906
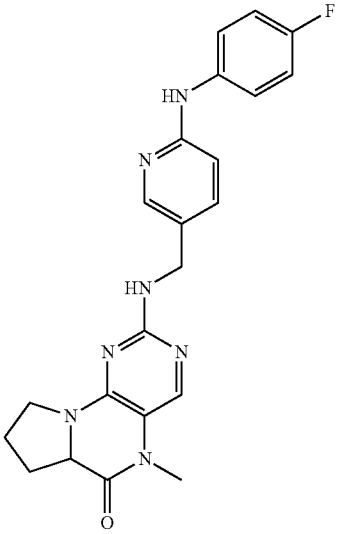 [SMILES: CN1C(=O)C2CCCN2c2nc(NCc3ccc(Nc4ccc(F)cc4)nc3)ncc21]
I-907
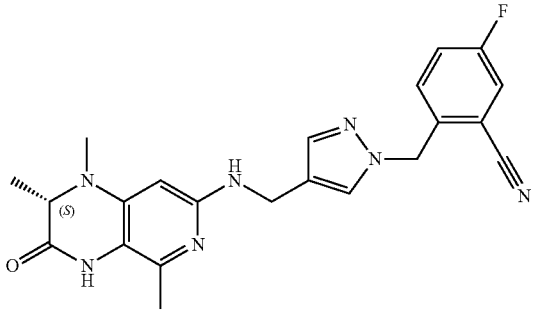
I-908
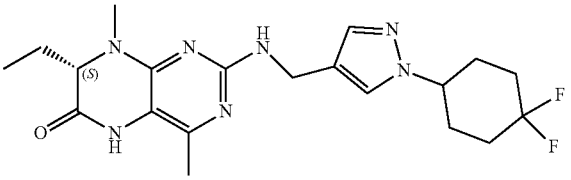
I-909

TABLE C-continued
Exemplary Compounds
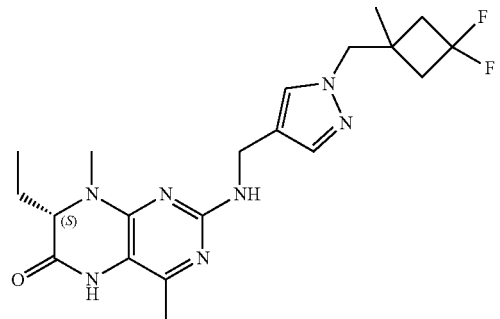
I-910
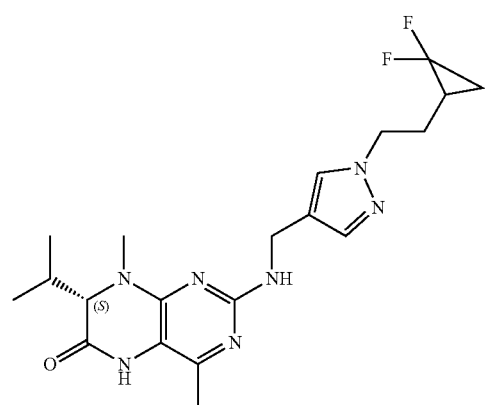
I-911
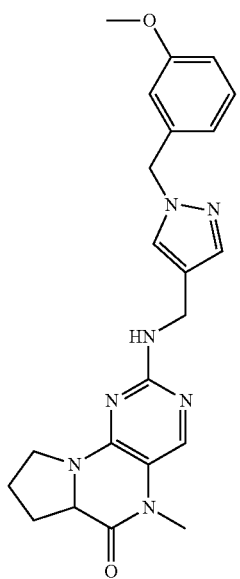 [SMILES: COc1cccc(Cn2cc(CNc3ncc4c(n3)N3CCCC3C(=O)N4C)cn2)c1]
I-912
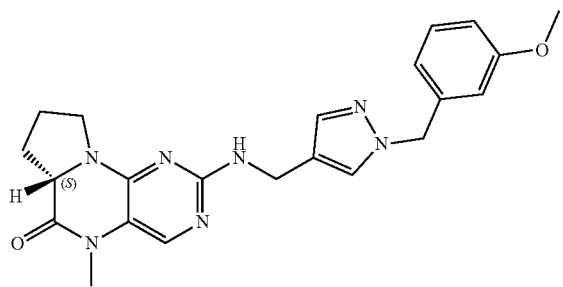
I-913

TABLE C-continued
Exemplary Compounds
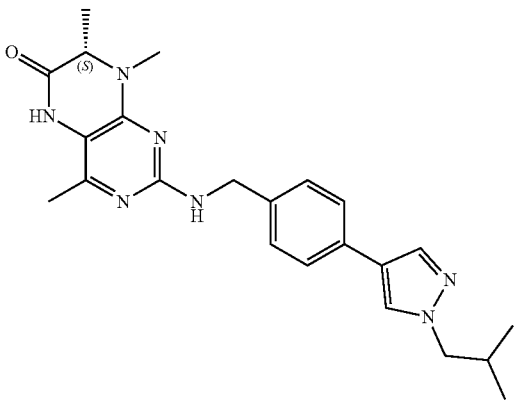
I-914
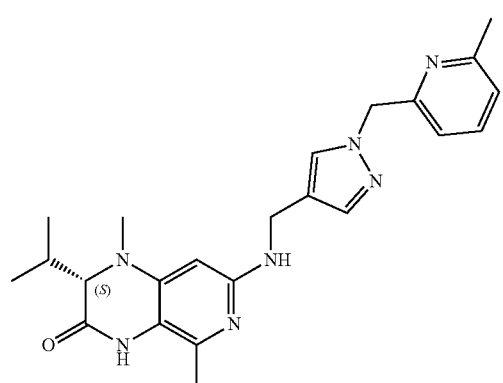
I-915
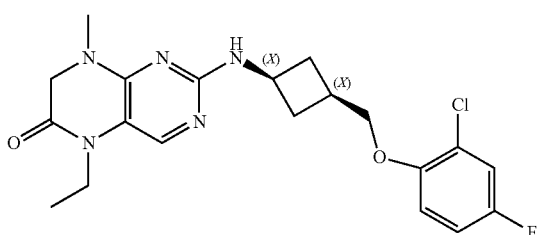
I-916
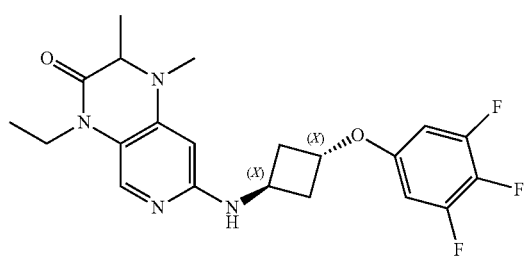
I-917
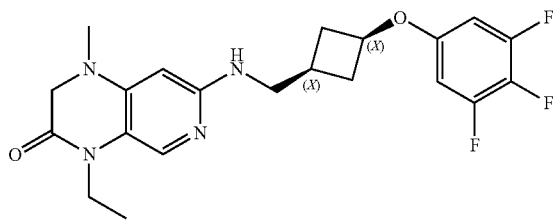
I-918

TABLE C-continued
Exemplary Compounds
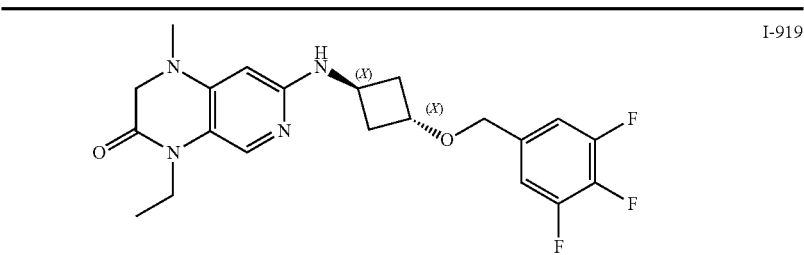 I-919
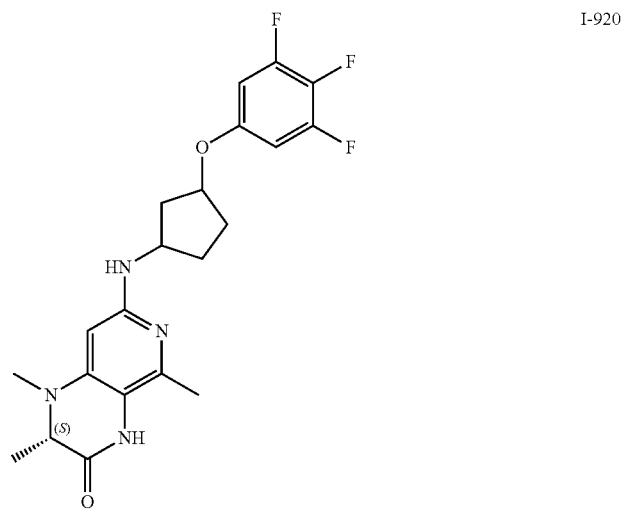 I-920
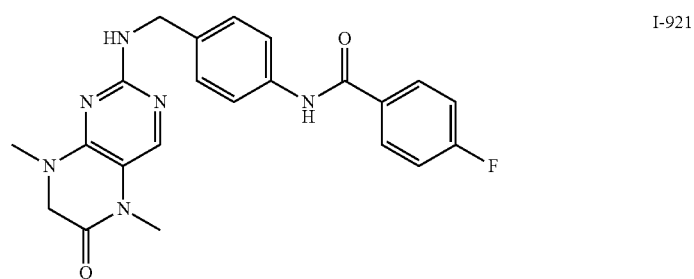 I-921
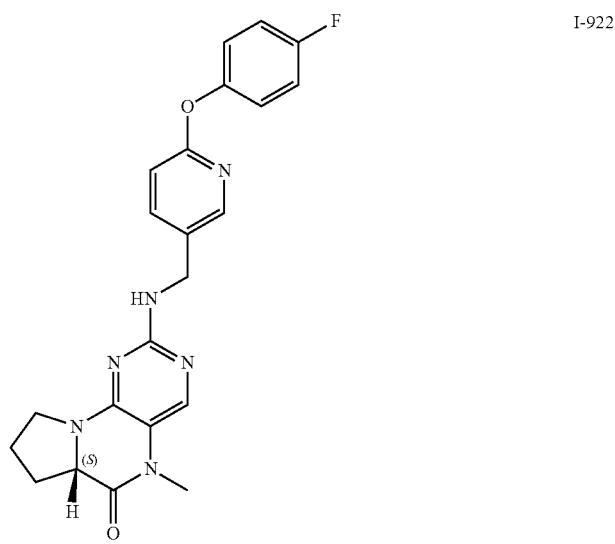 I-922

TABLE C-continued
Exemplary Compounds
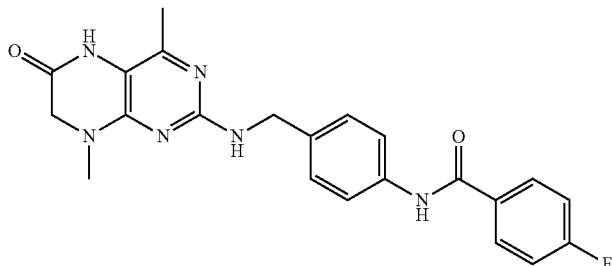 I-923
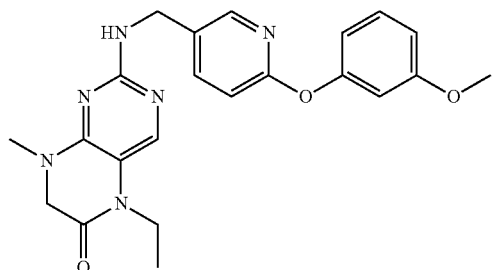 I-924
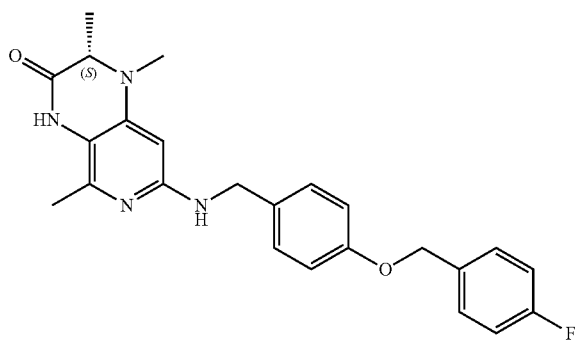 I-925
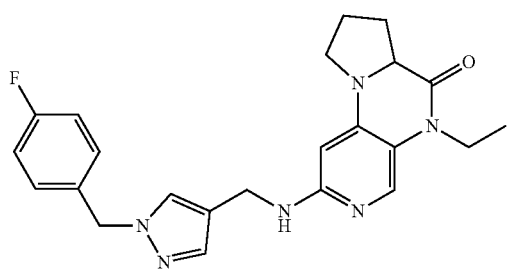 [SMILES: CCN1C(=O)C2CCCN2c2cc(NCc3cnn(Cc4ccc(F)cc4)c3)ncc21] I-926
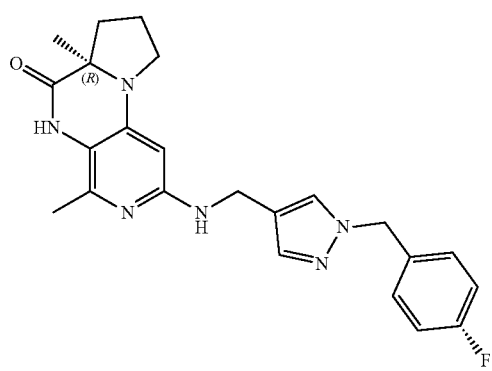 I-927

TABLE C-continued
Exemplary Compounds
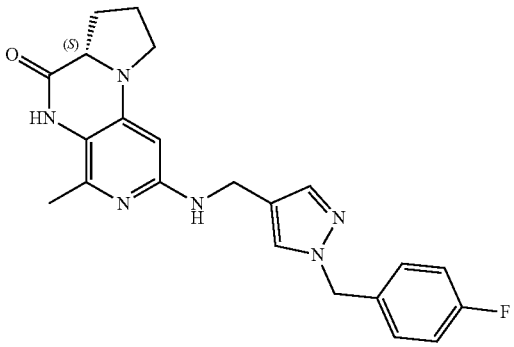
I-928
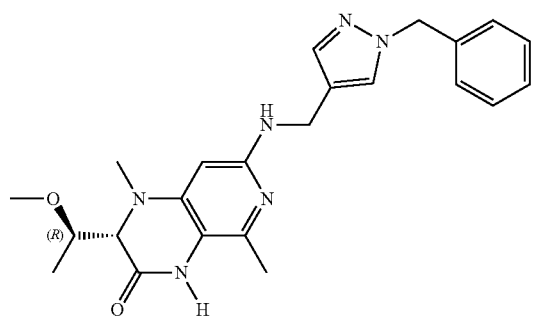
I-929
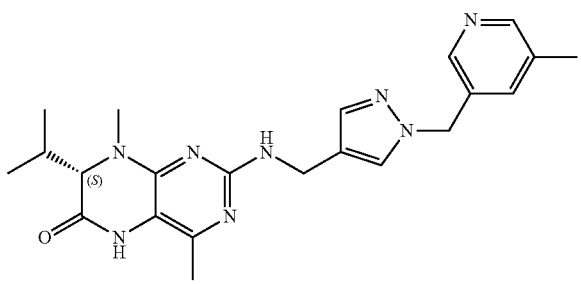
I-930
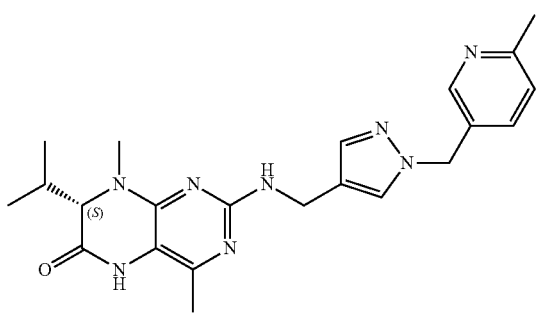
I-931

TABLE C-continued
Exemplary Compounds
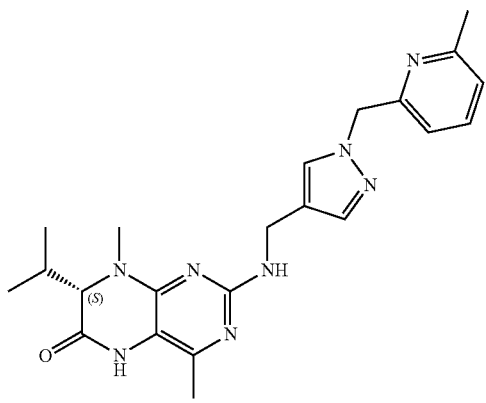
I-932
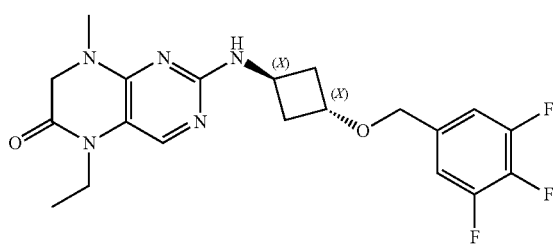
I-933
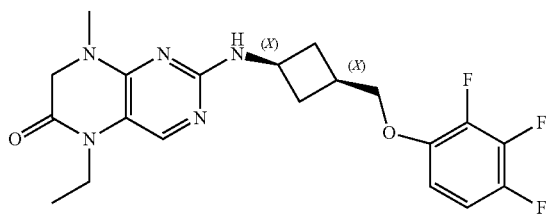
I-934
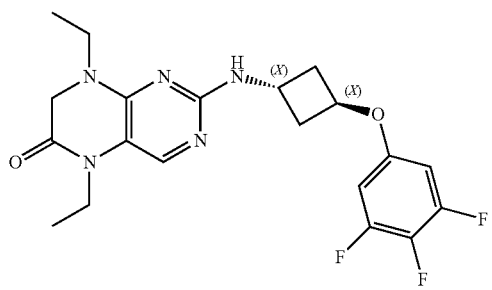
I-935
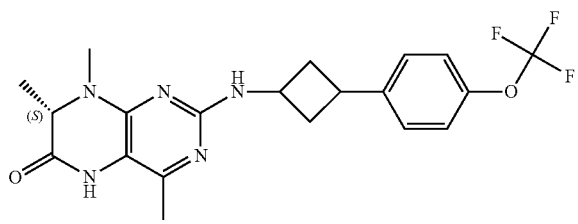
I-936

TABLE C-continued
Exemplary Compounds
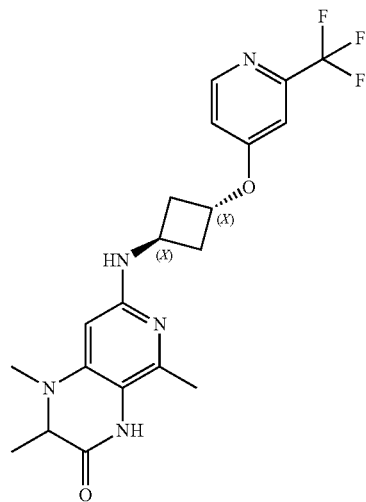
I-937
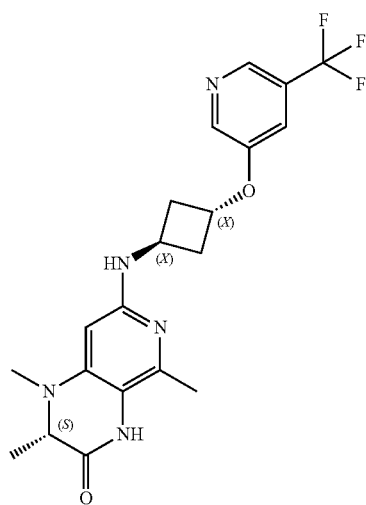
I-938
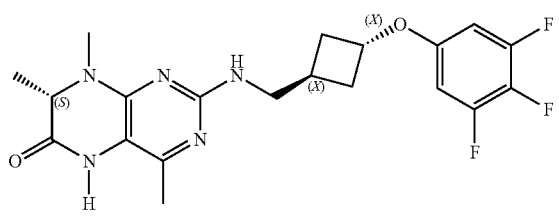
I-939
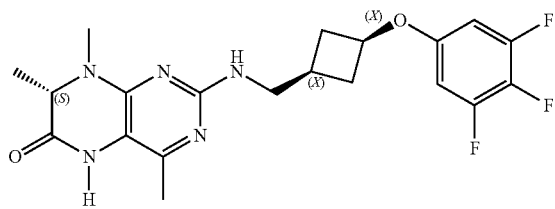
I-940

TABLE C-continued

Exemplary Compounds

I-941

I-942

I-943

I-944

I-945

I-946

TABLE C-continued
Exemplary Compounds
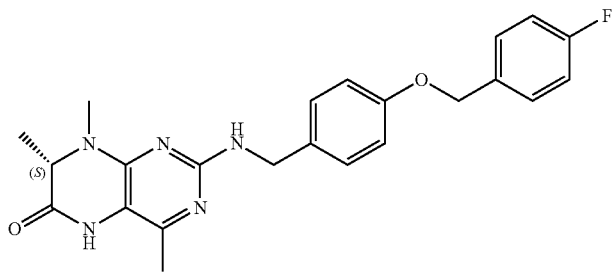 I-947
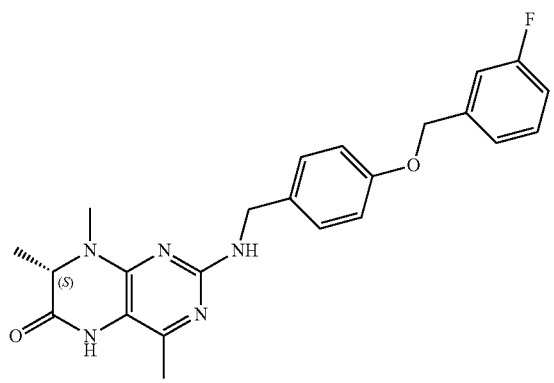 I-948
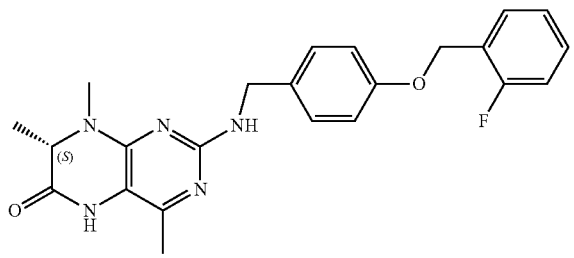 I-949
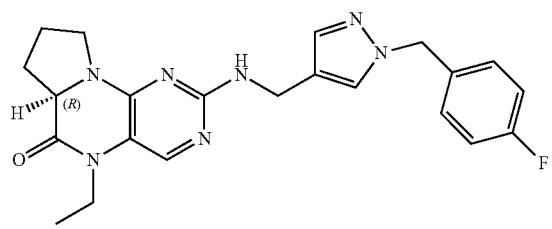 I-950
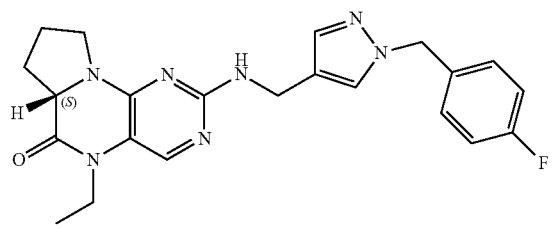 I-951

TABLE C-continued

Exemplary Compounds

I-952

I-953

I-954

I-955

I-956

I-957

TABLE C-continued
Exemplary Compounds
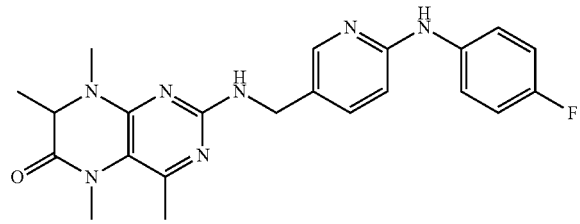 [SMILES: Cc1nc(NCc2ccc(Nc3ccc(F)cc3)nc2)nc2c1N(C)C(=O)C(C)N2C] I-958
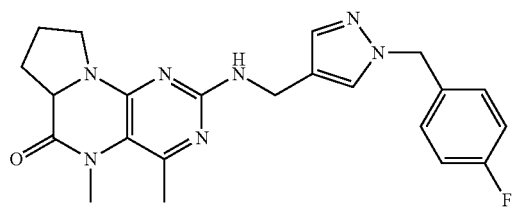 [SMILES: Cc1nc(NCc2cnn(Cc3ccc(F)cc3)c2)nc2c1N(C)C(=O)C1CCCN21] I-959
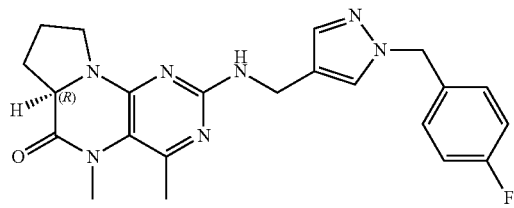 I-960
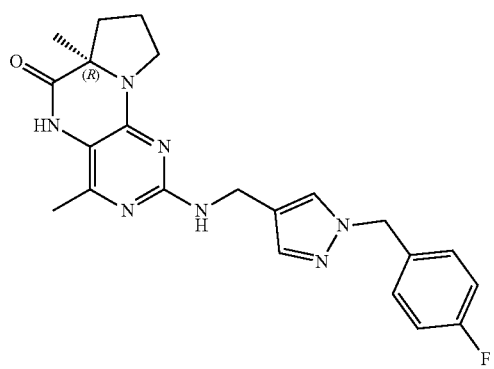 I-961
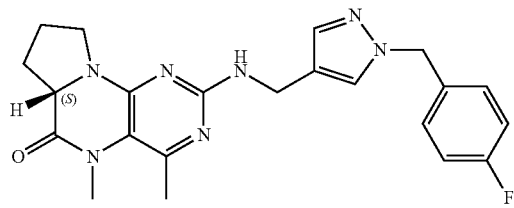 I-962
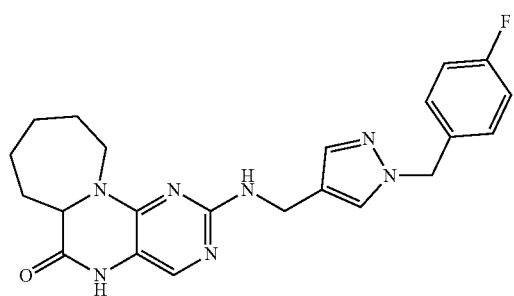 [SMILES: O=C1Nc2cnc(NCc3cnn(Cc4ccc(F)cc4)c3)nc2N2CCCCCC12] I-963

TABLE C-continued
Exemplary Compounds
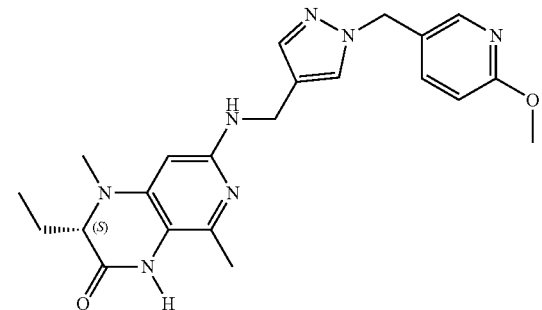
I-964
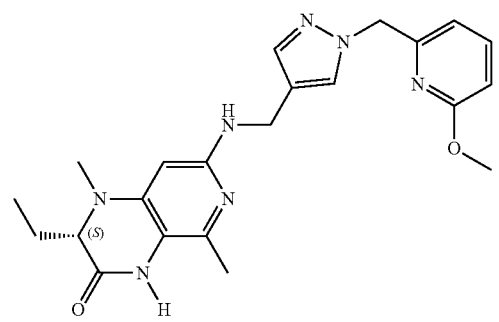
I-965
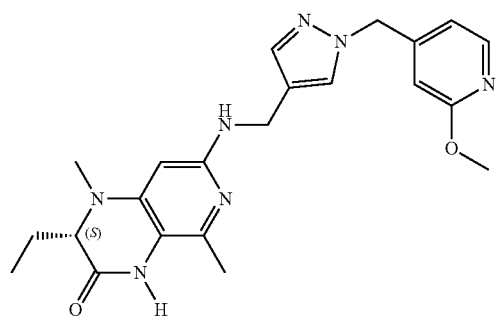
I-966
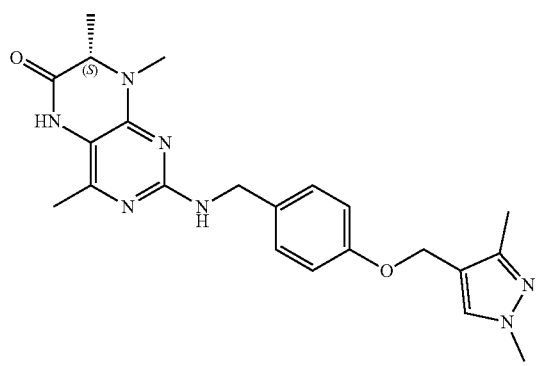
I-967

TABLE C-continued
Exemplary Compounds
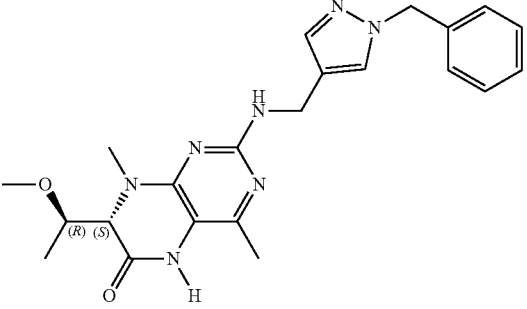
I-968
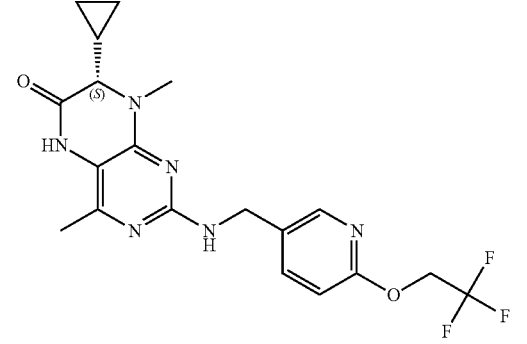
I-969
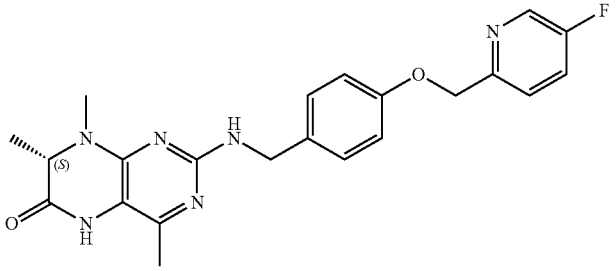
I-970
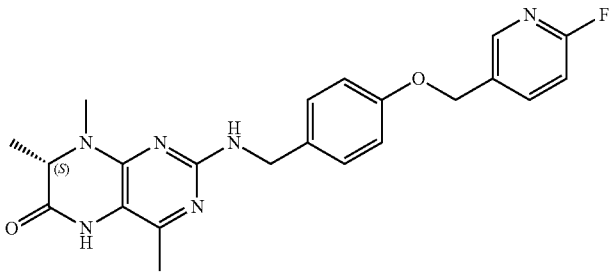
I-971
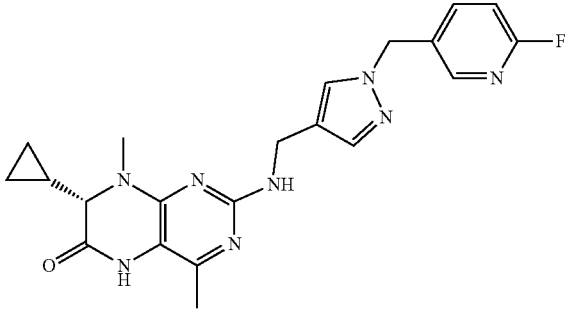 [SMILES: Cc1nc(NCc2cnn(Cc3ccc(F)nc3)c2)nc2c1NC(=O)[C@H](C1CC1)N2C]
I-972

TABLE C-continued
Exemplary Compounds
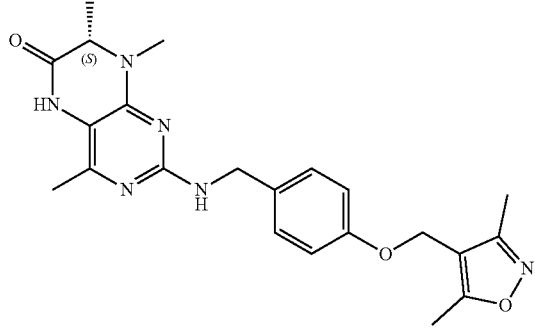
I-973
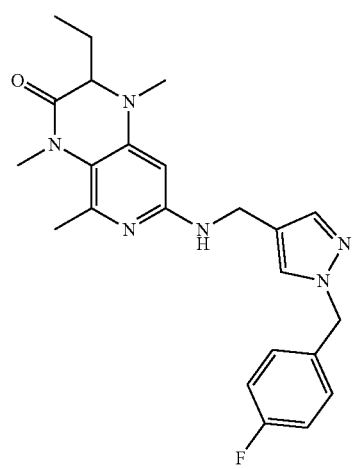 [SMILES: CCC1C(=O)N(C)c2c(cc(NCc3cnn(Cc4ccc(F)cc4)c3)nc2C)N1C]
I-974
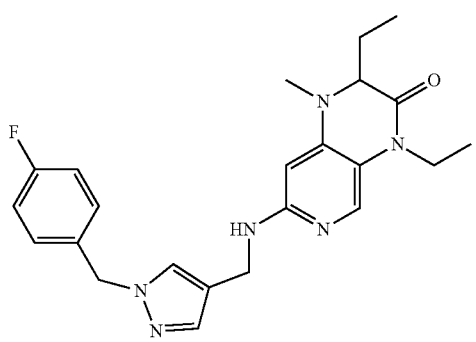 [SMILES: CCC1C(=O)N(CC)c2cnc(NCc3cnn(Cc4ccc(F)cc4)c3)cc2N1C]
I-975
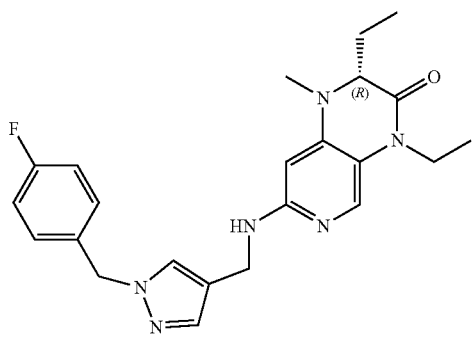
I-976

TABLE C-continued
Exemplary Compounds
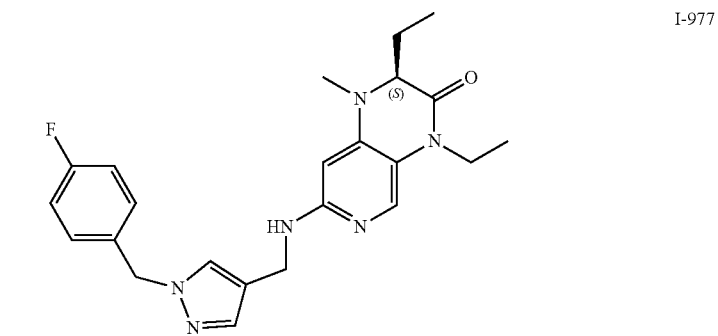
I-977
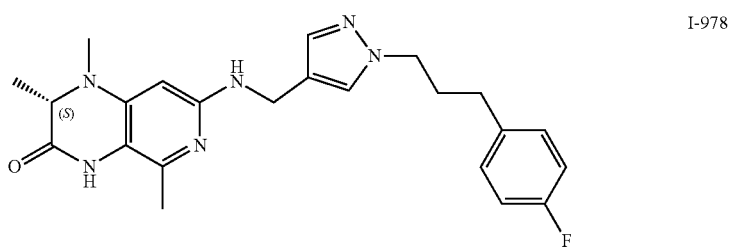
I-978
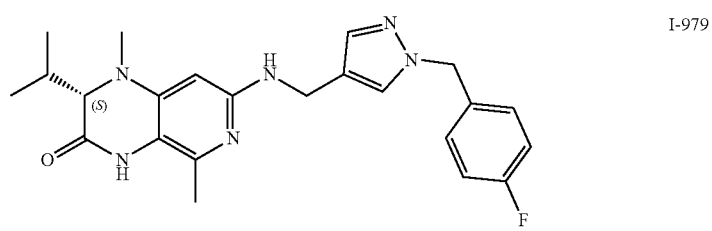
I-979
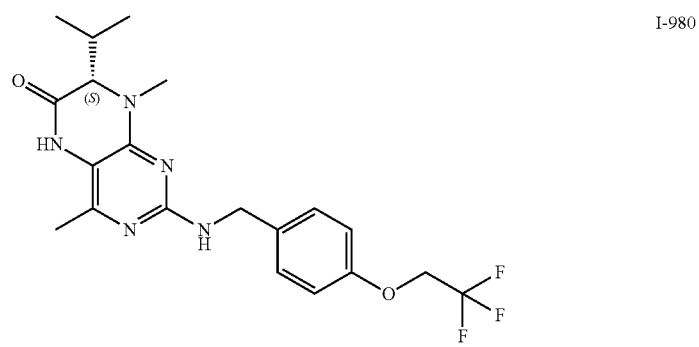
I-980
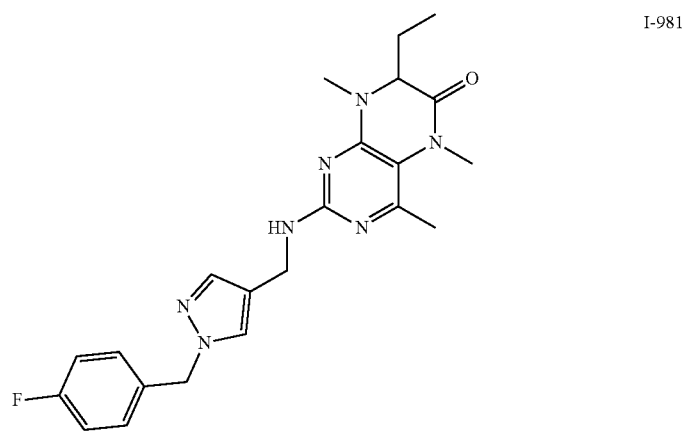
I-981

TABLE C-continued
Exemplary Compounds
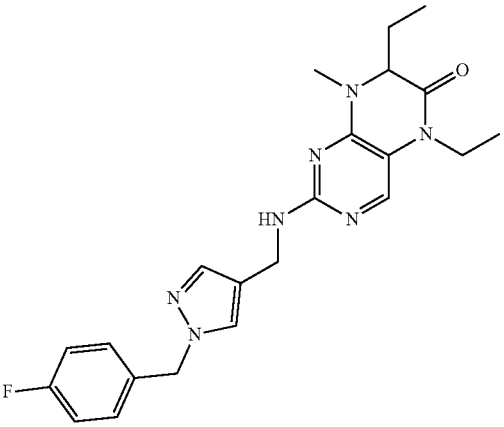 [SMILES: CCC1C(=O)N(CC)c2cnc(NCc3cnn(Cc4ccc(F)cc4)c3)nc2N1C]
I-982
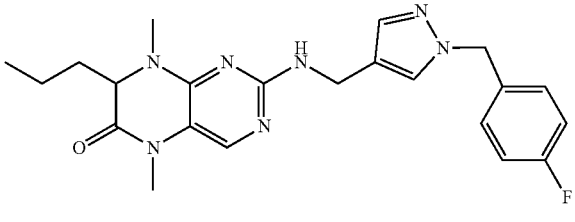 [SMILES: CCCC1C(=O)N(C)c2cnc(NCc3cnn(Cc4ccc(F)cc4)c3)nc2N1C]
I-983
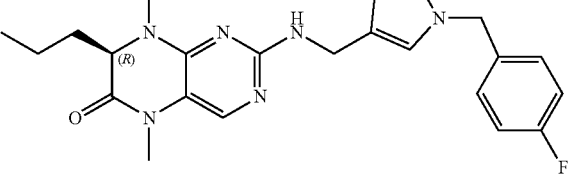
I-984
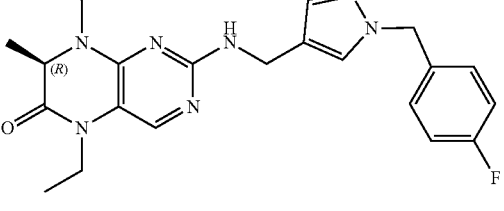
I-985
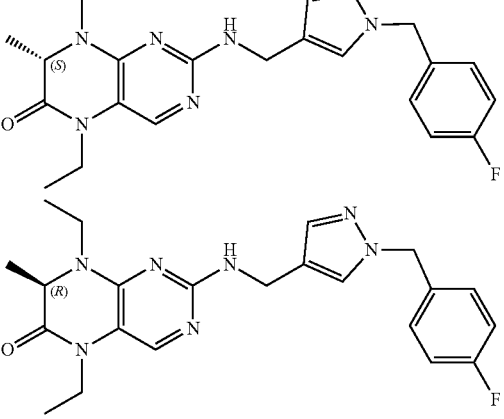
I-986

TABLE C-continued
Exemplary Compounds
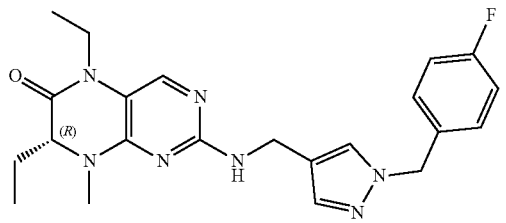
I-987
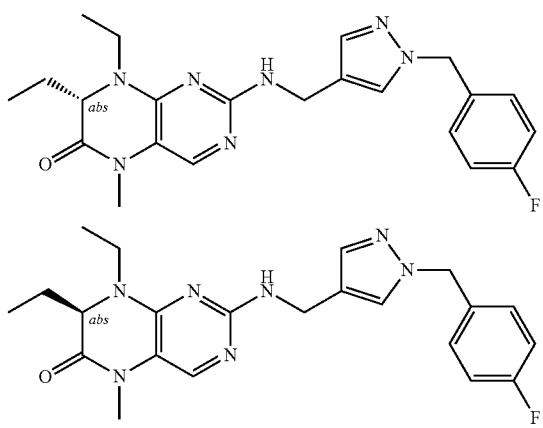
I-988
I-988
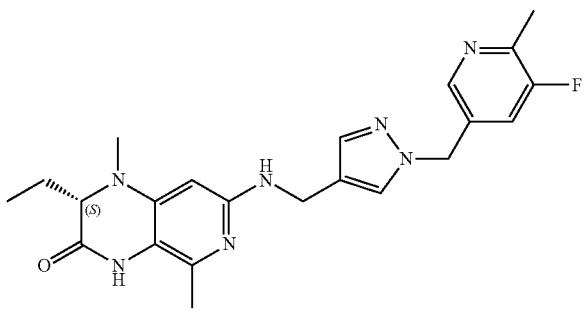
I-989
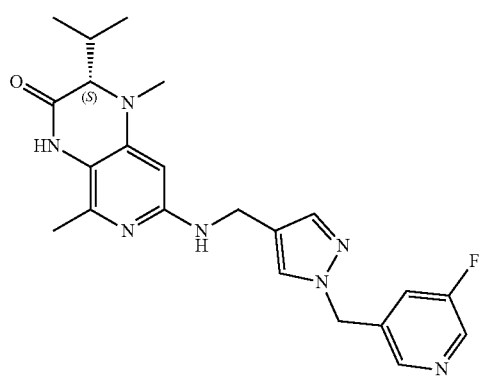
I-990

TABLE C-continued
Exemplary Compounds
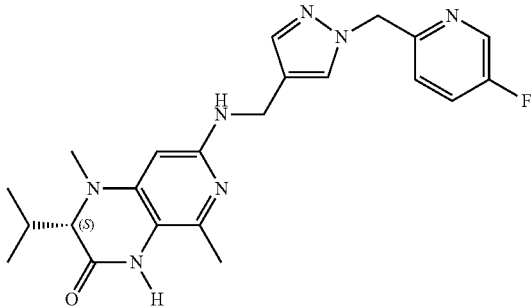
I-991
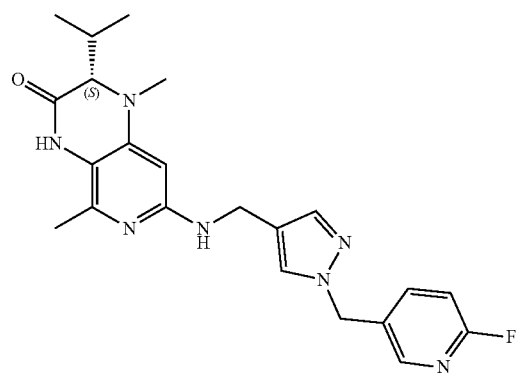
I-992
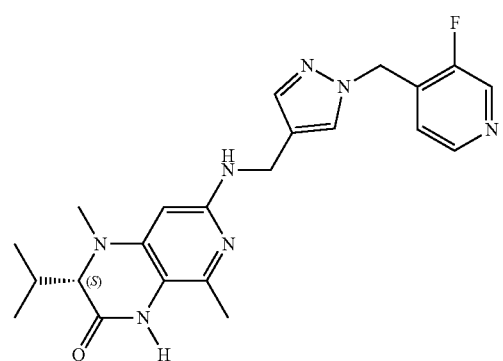
I-993
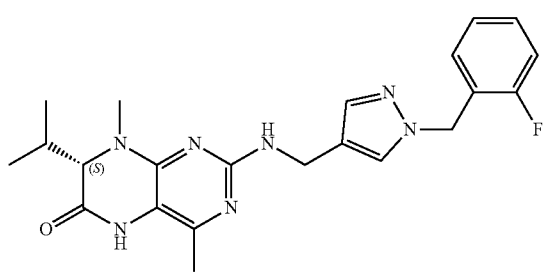
I-994

455
456
TABLE C-continued
Exemplary Compounds
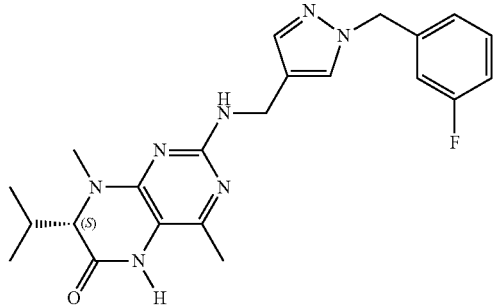
I-995
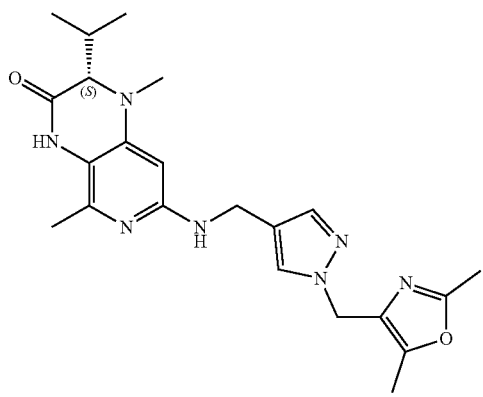
I-996
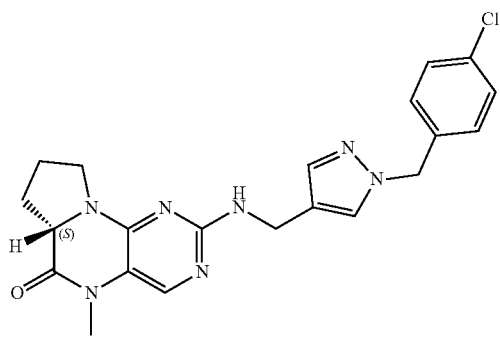
I-997
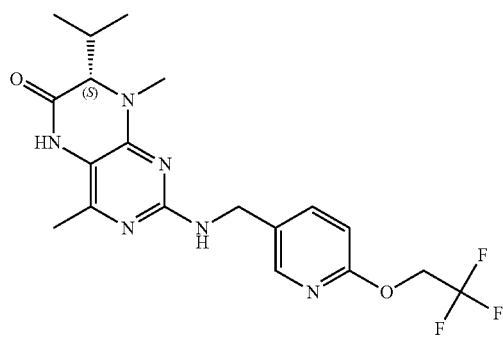
I-998

TABLE C-continued
Exemplary Compounds
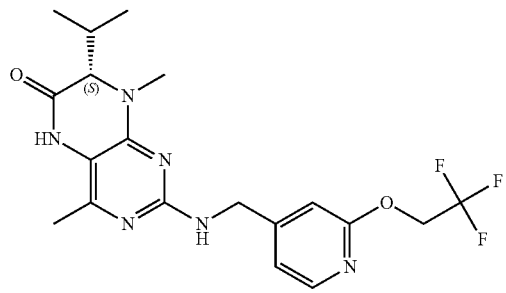
I-999
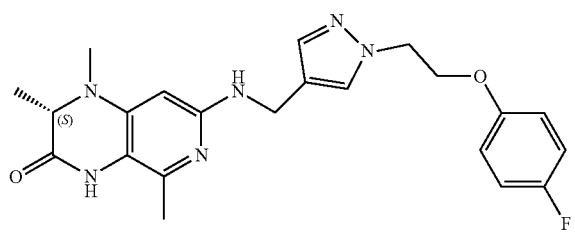
I-1000
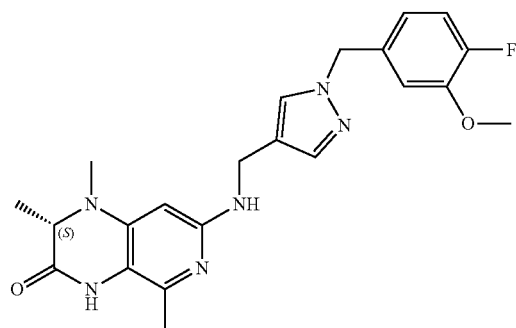
I-1001
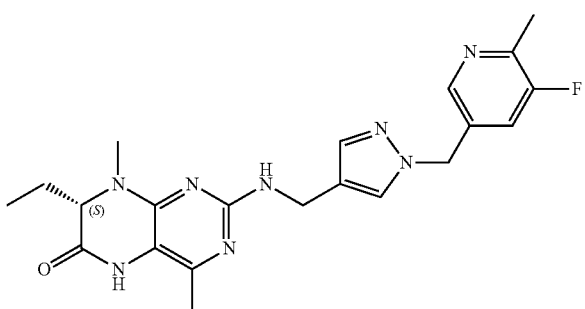
I-1002
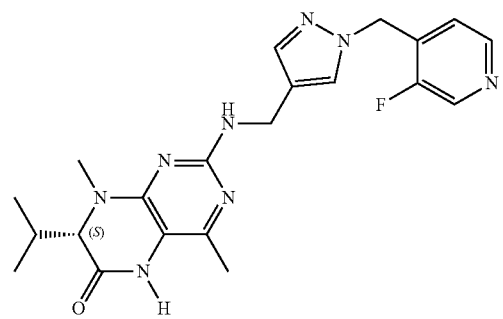
I-1003

TABLE C-continued
Exemplary Compounds
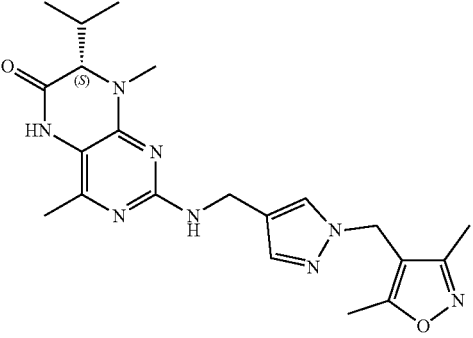
I-1004
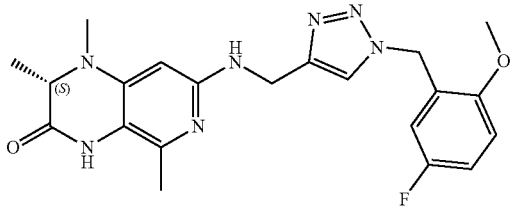
I-1005
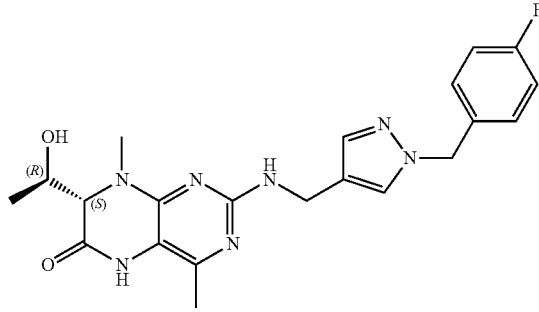
I-1006
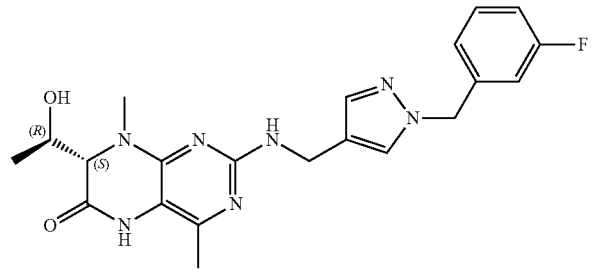
I-1007
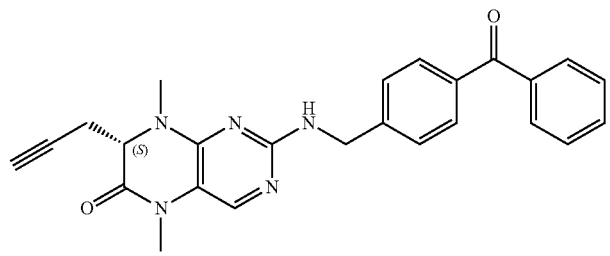
I-1008

TABLE C-continued
Exemplary Compounds
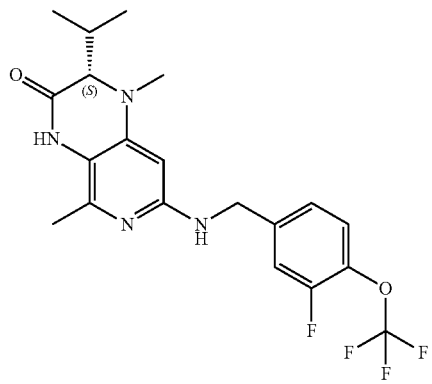
I-1009
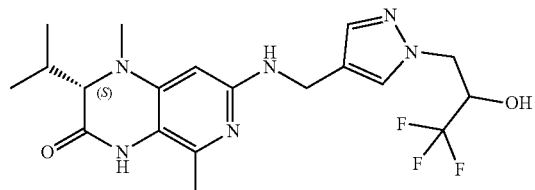
I-1010
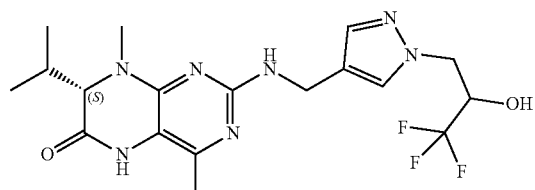
I-1011
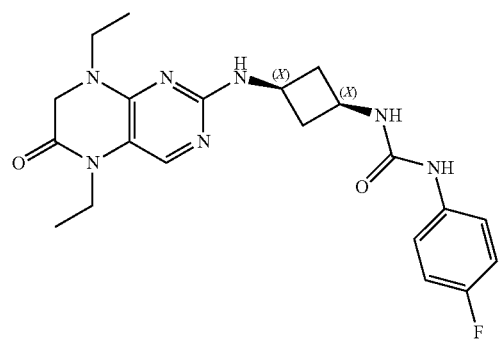
I-1012
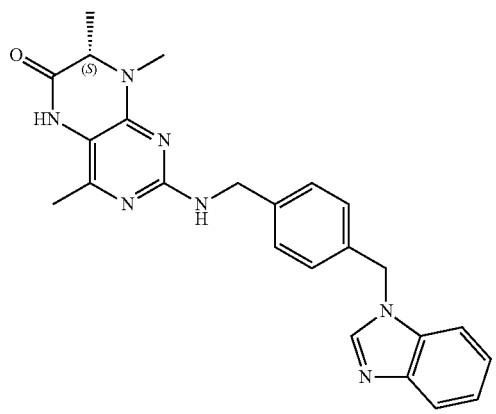
I-1013

TABLE C-continued
Exemplary Compounds
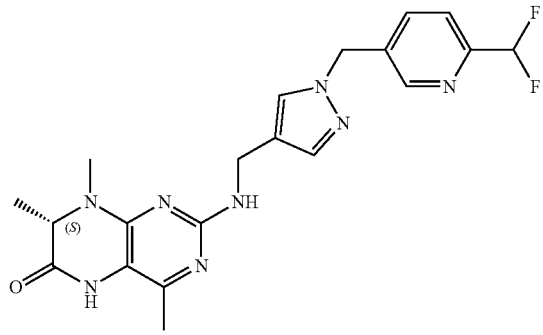
I-1014
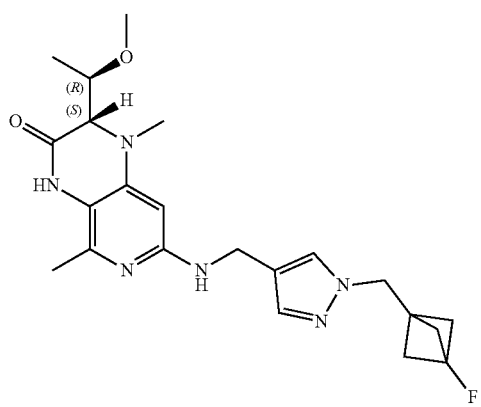
I-1015
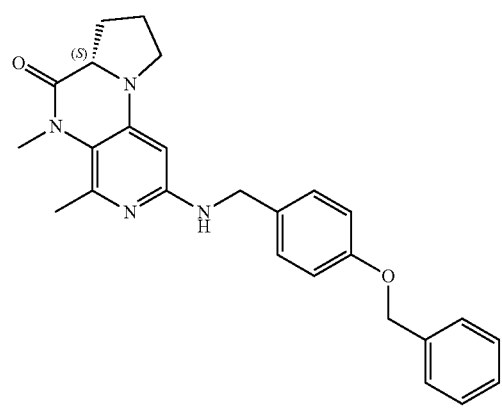
I-1016
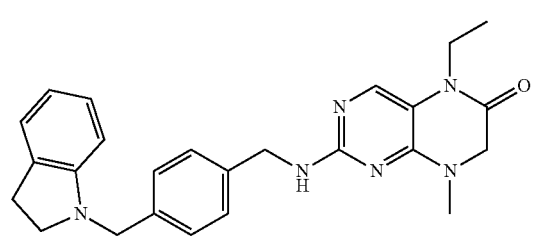 [SMILES: CCN1C(=O)CN(C)c2nc(NCc3ccc(CN4CCc5ccccc54)cc3)ncc21]
I-1017

TABLE C-continued
Exemplary Compounds
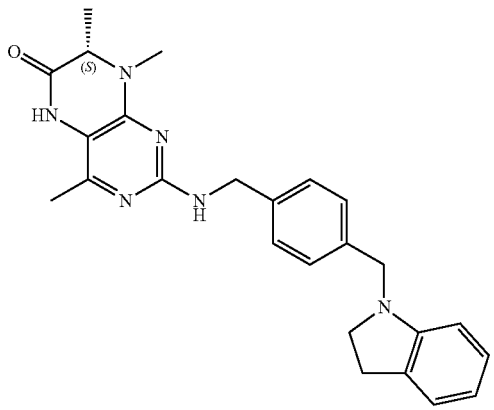
I-1018
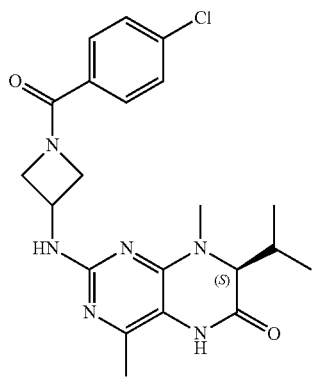
I-1019
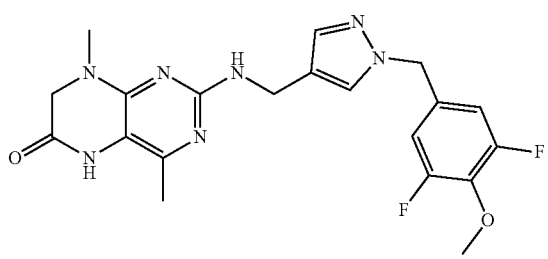 [SMILES: COc1c(F)cc(Cn2cc(CNc3nc(C)c4c(n3)N(C)CC(=O)N4)cn2)cc1F]
I-1020
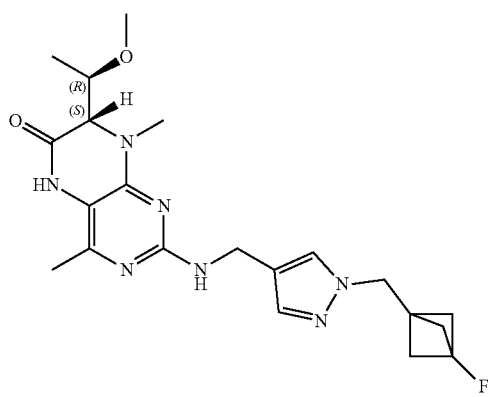
I-1021

TABLE C-continued
Exemplary Compounds
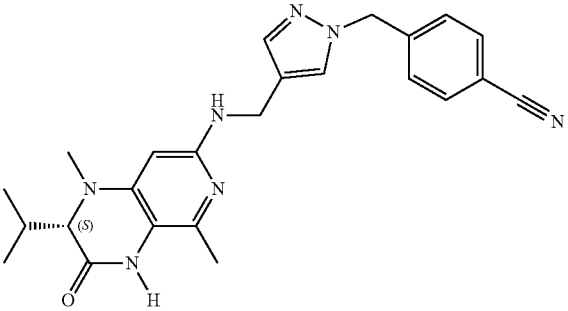 I-1022
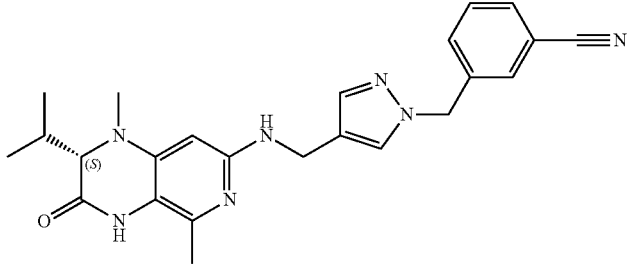 I-1023
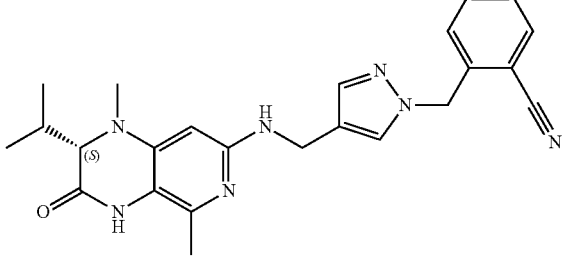 I-1024
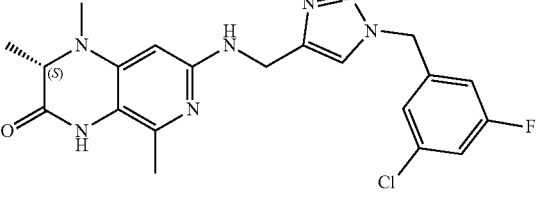 I-1025
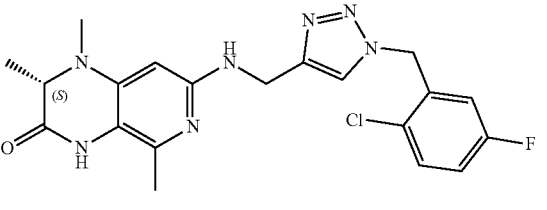 I-1026
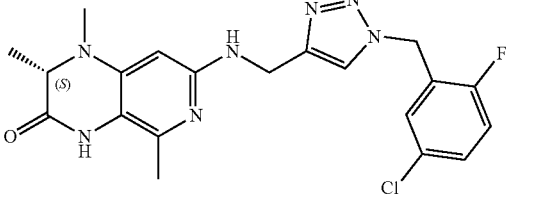 I-1027

TABLE C-continued
Exemplary Compounds
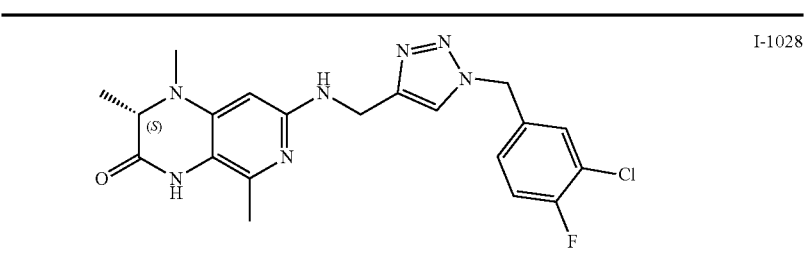 I-1028
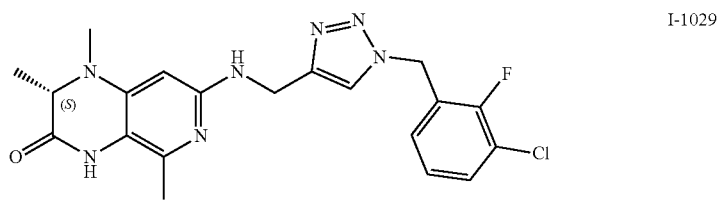 I-1029
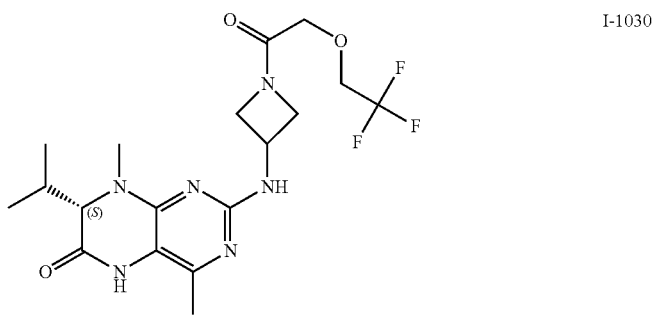 I-1030
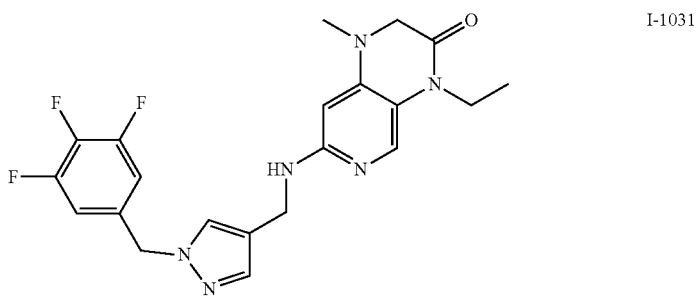 I-1031
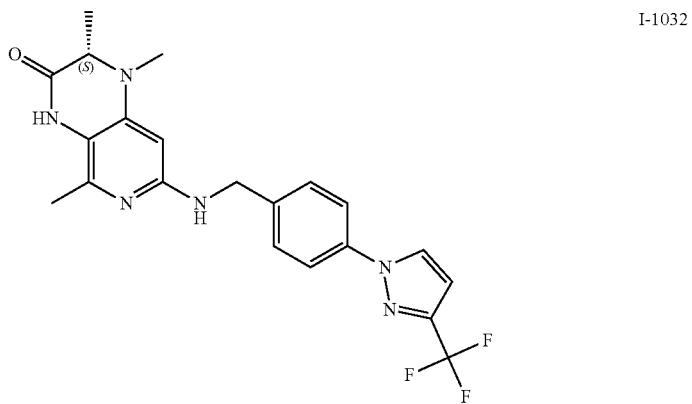 I-1032

TABLE C-continued
Exemplary Compounds
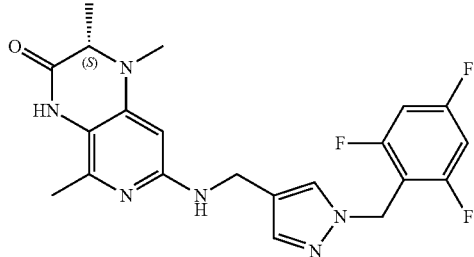
I-1033
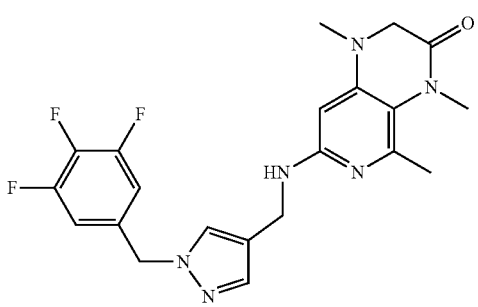 [SMILES: Cc1nc(NCc2cnn(Cc3cc(F)c(F)c(F)c3)c2)cc2c1N(C)C(=O)CN2C]
I-1034
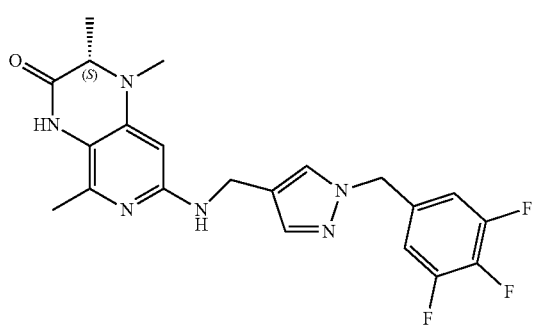
I-1035
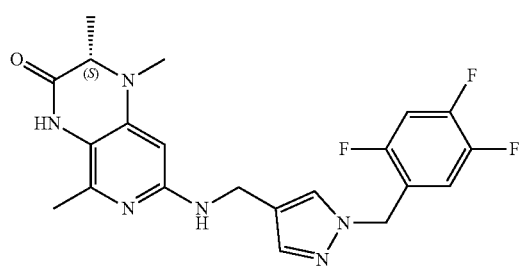
I-1036
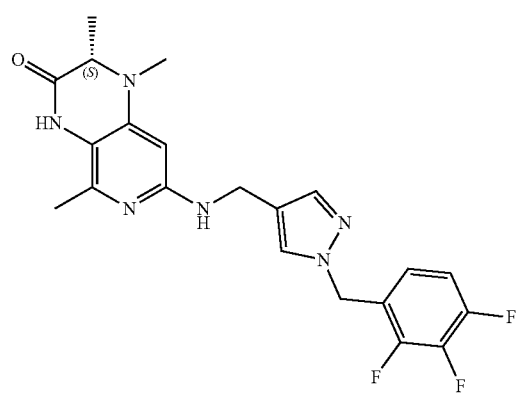
I-1037

TABLE C-continued
Exemplary Compounds
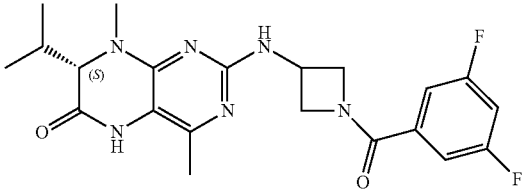 I-1038
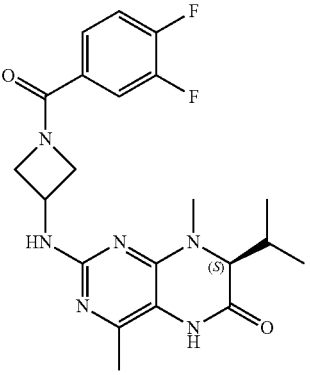 I-1039
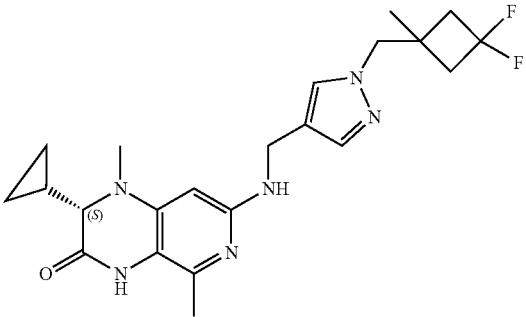 I-1040
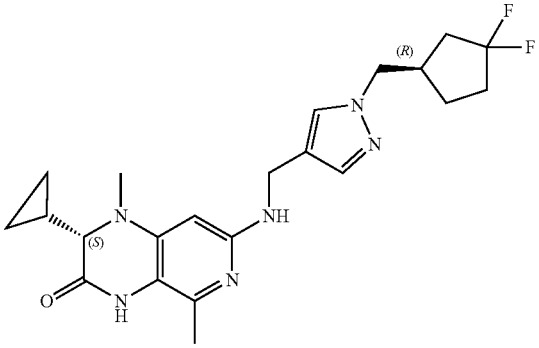 I-1041
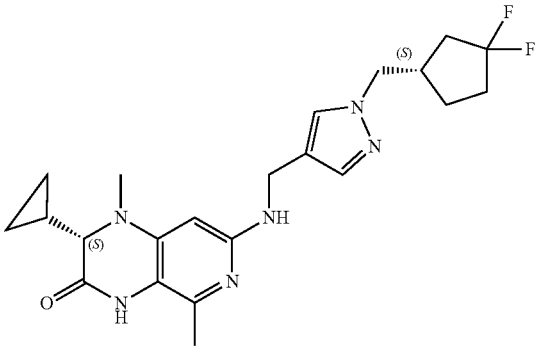 I-1042

TABLE C-continued
Exemplary Compounds
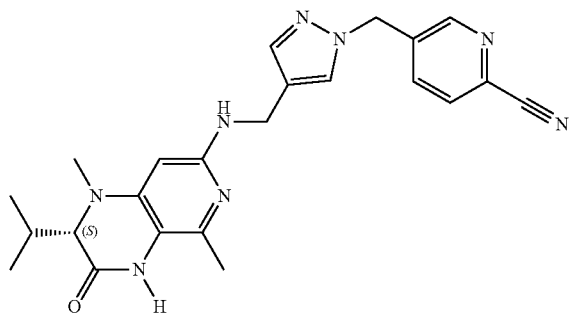
I-1043
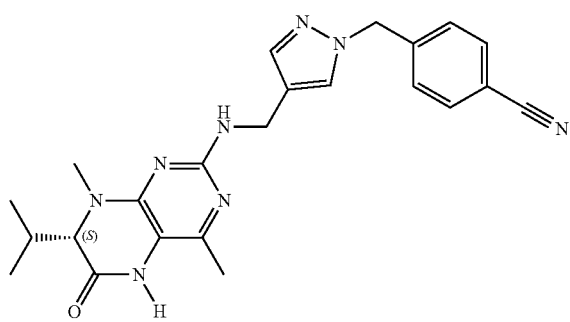
I-1044
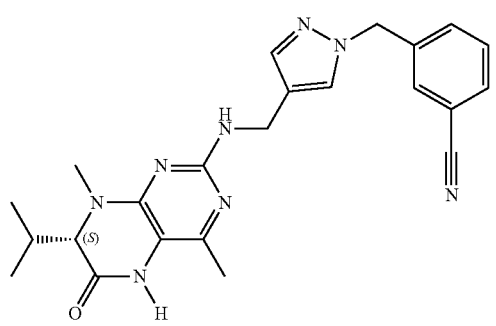
I-1045
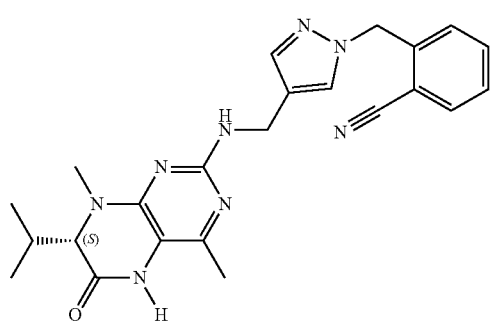
I-1046

TABLE C-continued
Exemplary Compounds
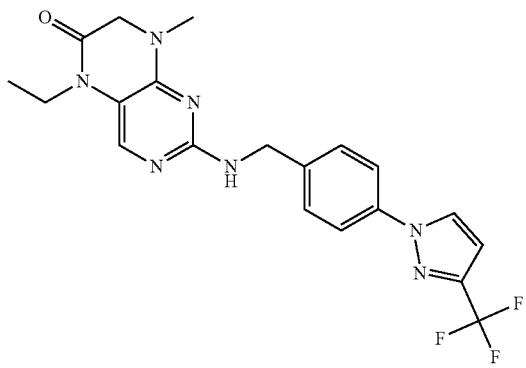 [SMILES: CCN1C(=O)CN(C)c2nc(NCc3ccc(-n4ccc(C(F)(F)F)n4)cc3)ncc21]
I-1047
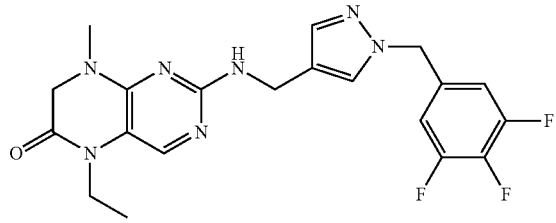 [SMILES: CCN1C(=O)CN(C)c2nc(NCc3cnn(Cc4cc(F)c(F)c(F)c4)c3)ncc21]
I-1048
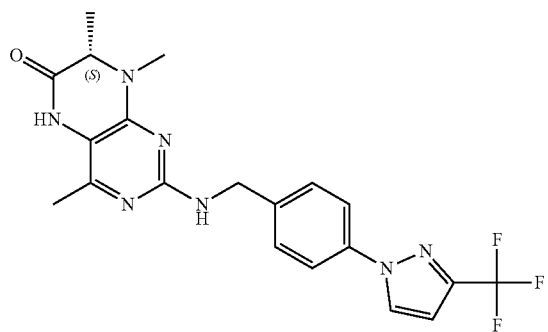
I-1049
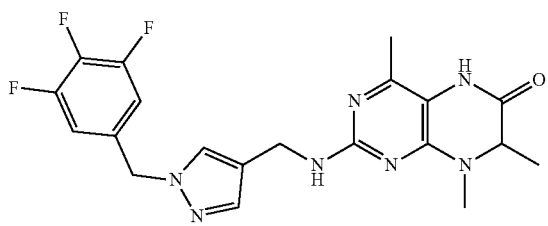 [SMILES: Cc1nc(NCc2cnn(Cc3cc(F)c(F)c(F)c3)c2)nc2c1NC(=O)C(C)N2C]
I-1050
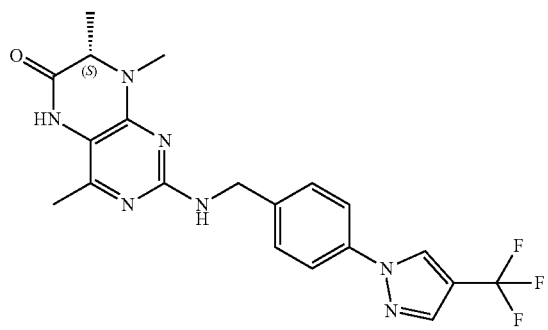
I-1051

TABLE C-continued
Exemplary Compounds
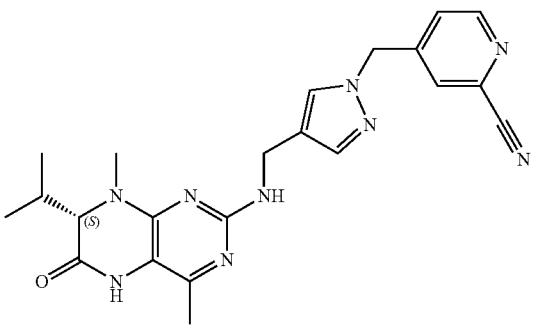
I-1052
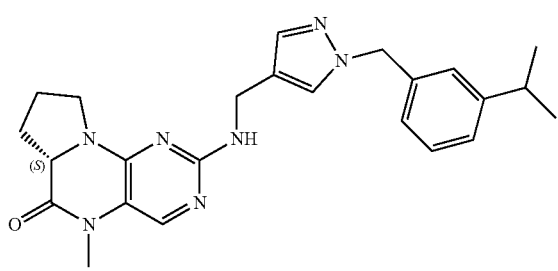
I-1053
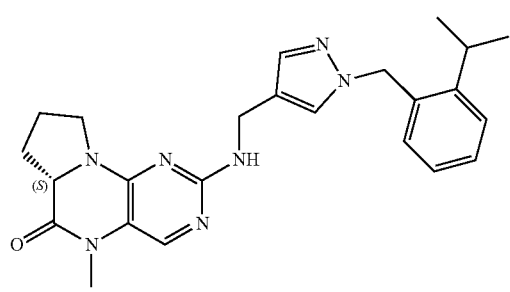
I-1054
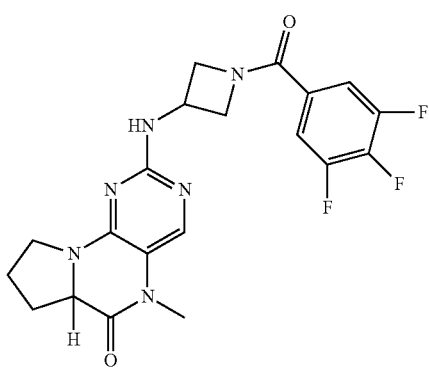 [SMILES: CN1C(=O)C2CCCN2c2nc(NC3CN(C(=O)c4cc(F)c(F)c(F)c4)C3)ncc21]
I-1055
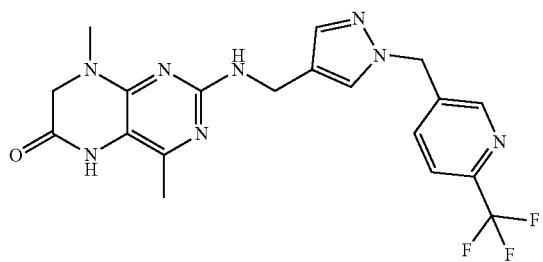 [SMILES: Cc1nc(NCc2cnn(Cc3ccc(C(F)(F)F)nc3)c2)nc2c1NC(=O)CN2C]
I-1056

TABLE C-continued
Exemplary Compounds
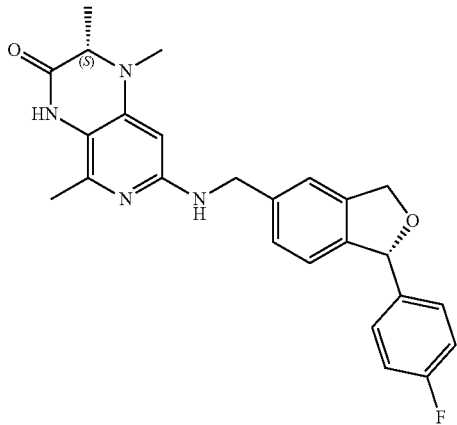
I-1057
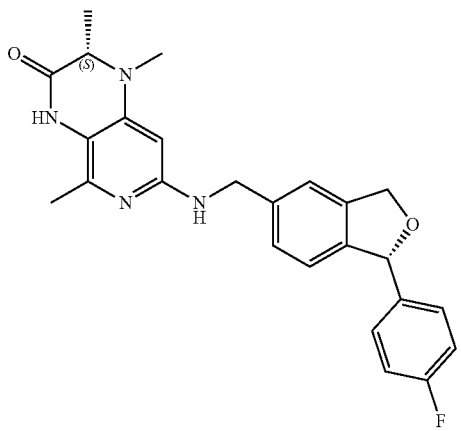
I-1058
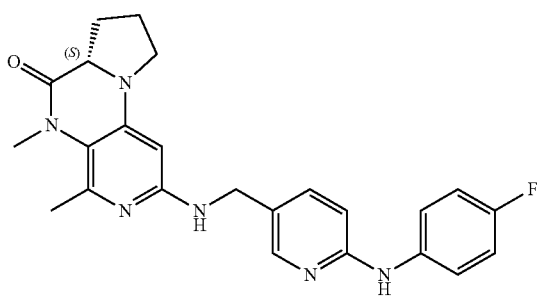
I-1059
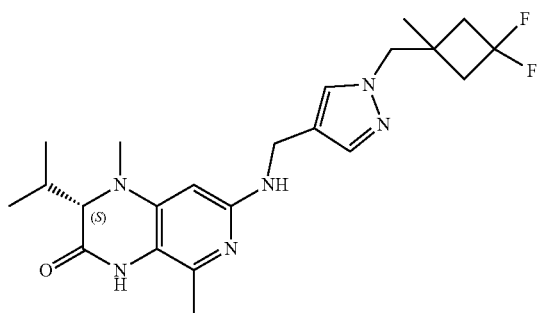
I-1060

TABLE C-continued

Exemplary Compounds

I-1061

I-1062

I-1063

I-1064

I-1065

TABLE C-continued
Exemplary Compounds
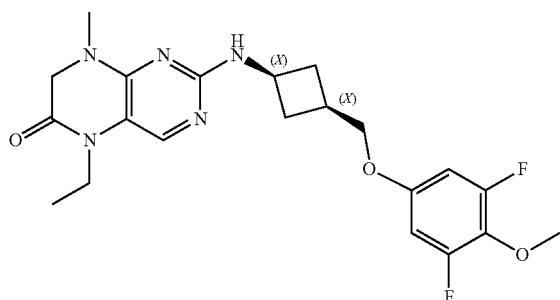
I-1066
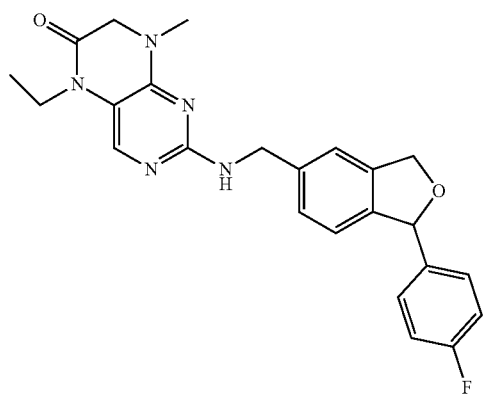 [SMILES: CCN1C(=O)CN(C)c2nc(NCc3ccc4c(c3)COC4c3ccc(F)cc3)ncc21]
I-1067
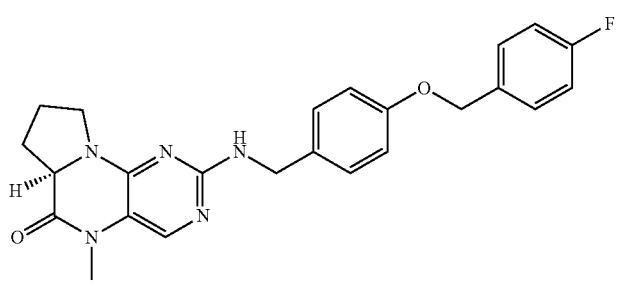 [SMILES: CN1C(=O)[C@H]2CCCN2c2nc(NCc3ccc(OCc4ccc(F)cc4)cc3)ncc21]
I-068
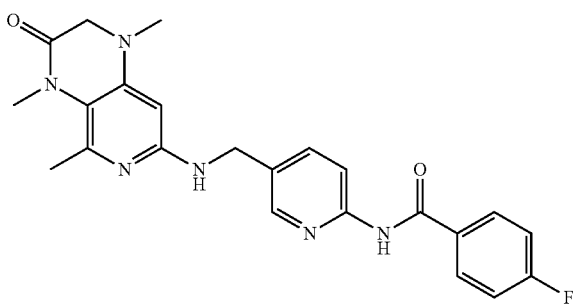 [SMILES: Cc1nc(NCc2ccc(NC(=O)c3ccc(F)cc3)nc2)cc2c1N(C)C(=O)CN2C]
I-069
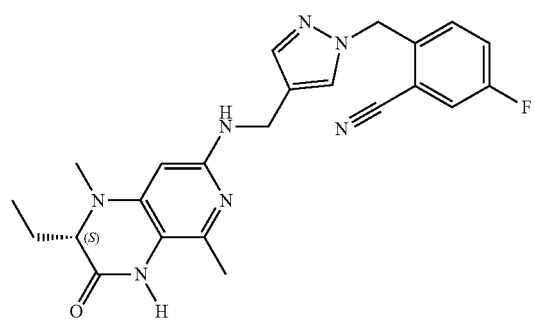
I-070

TABLE C-continued
Exemplary Compounds
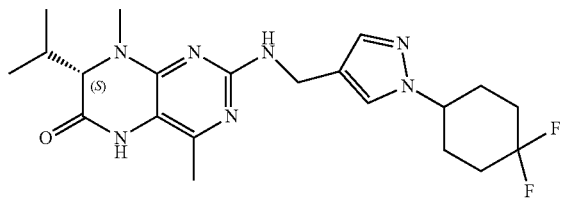 I-1071
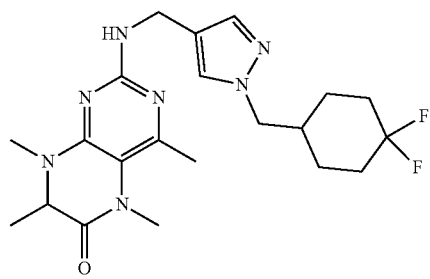 [SMILES: Cc1nc(NCc2cnn(CC3CCC(F)(F)CC3)c2)nc2c1N(C)C(=O)C(C)N2C] I-1072
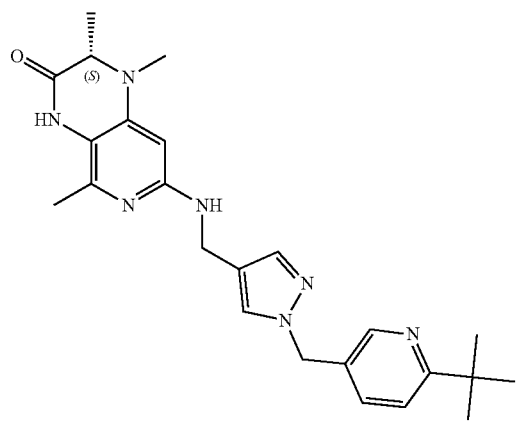 I-1073
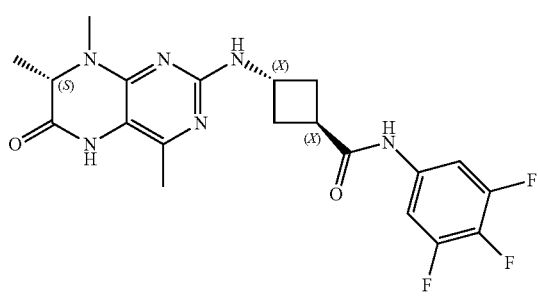 I-1074
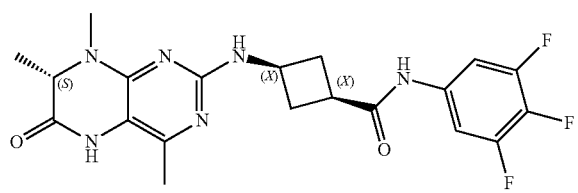 I-1075

TABLE C-continued
Exemplary Compounds
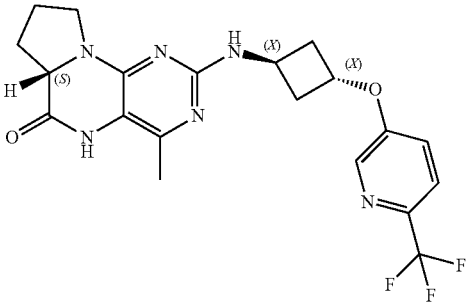 I-1076
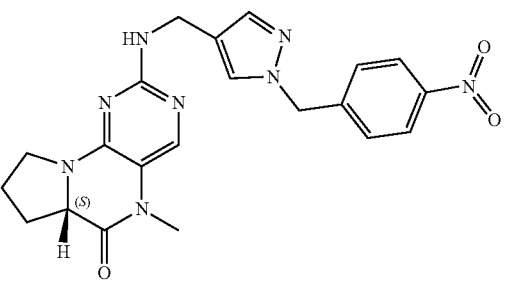 I-1077
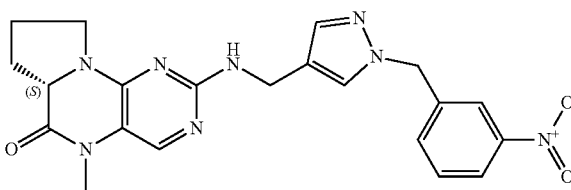 I-1078
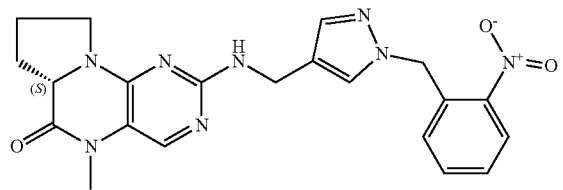 I-1079
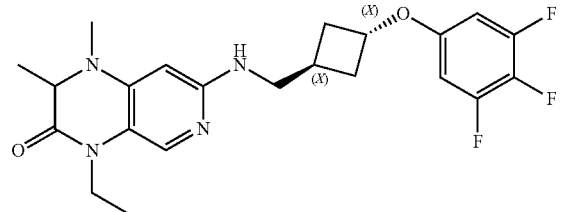 I-1080
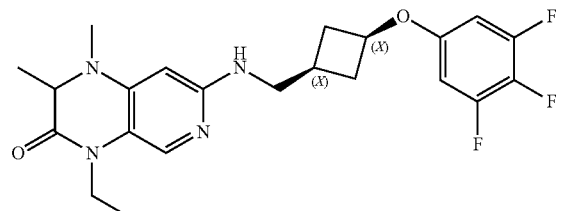 I-1081

TABLE C-continued

Exemplary Compounds

| | |
|---|---|
| (structure) | I-1082 |
| (structure) | I-1083 |
| (structure) | I-1084 |
| (structure) | I-1085 |
| (structure) | I-1086 |
| (structure) | I-1087 |

TABLE C-continued
Exemplary Compounds
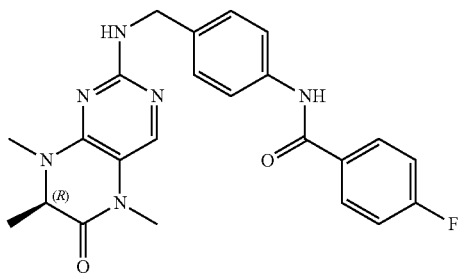 I-1088
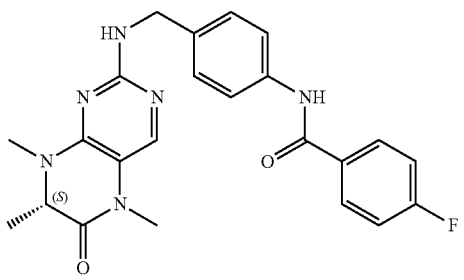 I-1089
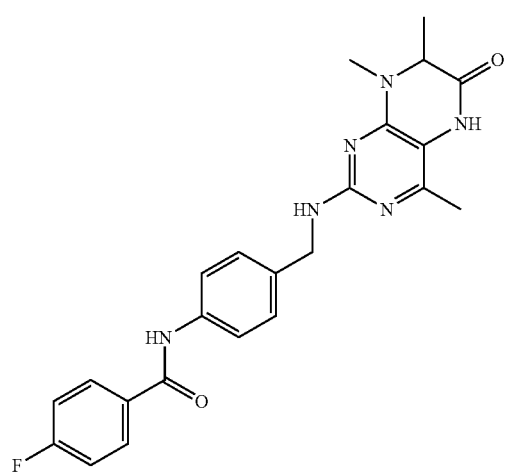 I-1090
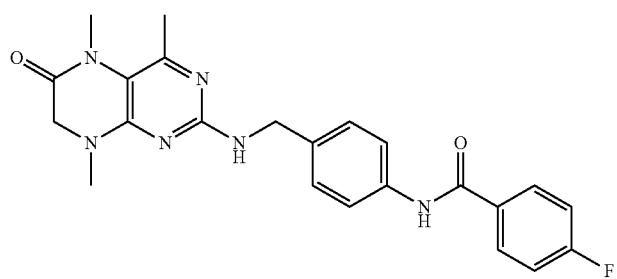 [SMILES: Cc1nc(NCc2ccc(NC(=O)c3ccc(F)cc3)cc2)nc2c1N(C)C(=O)CN2C] I-1091

495
496
TABLE C-continued
Exemplary Compounds
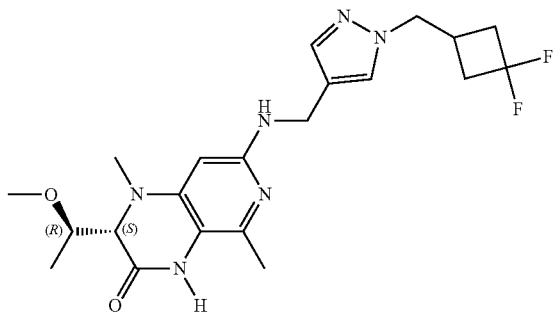
I-1092
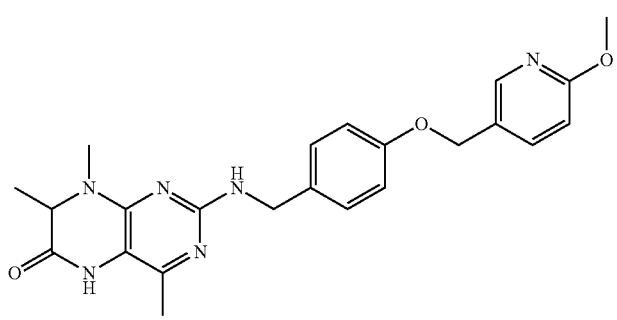
I-1093
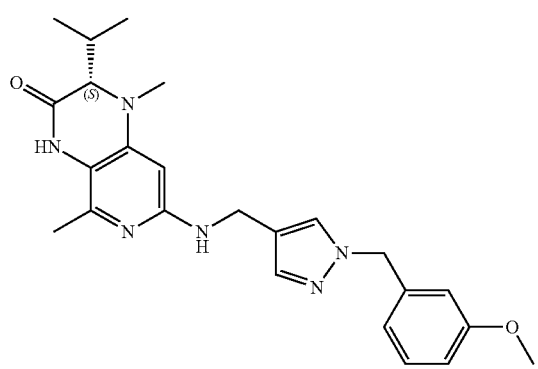
I-1094
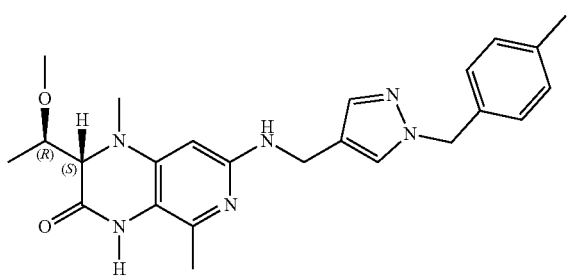
I-1095

TABLE C-continued
Exemplary Compounds
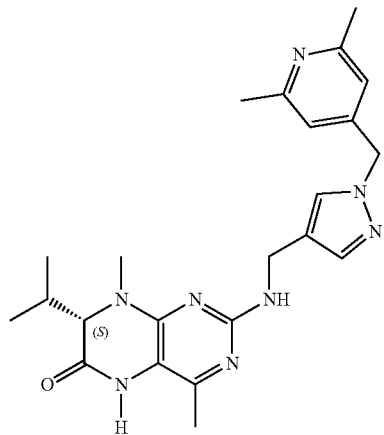
I-1096
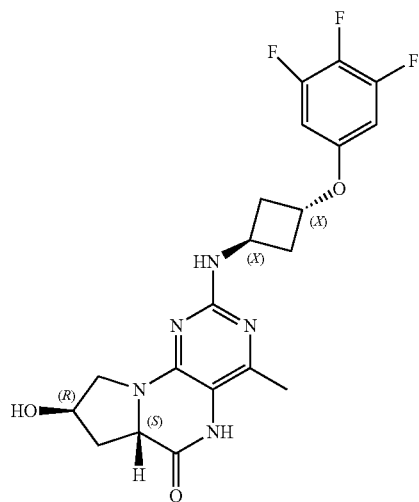
I-1097
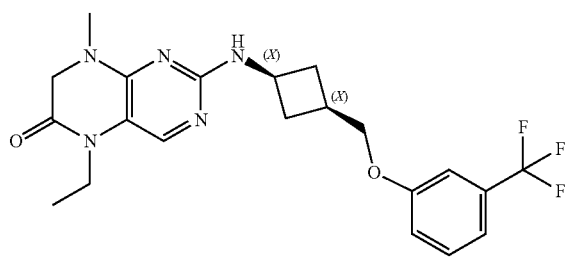
I-1098
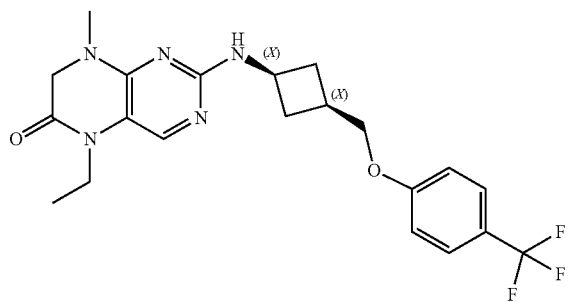
I-1099

TABLE C-continued

Exemplary Compounds

| | |
|---|---|
| (structure) | I-1100 |
| (structure) | I-1101 |
| (structure) | I-1102 |
| (structure) | I-1103 |
| (structure) | I-1104 |

TABLE C-continued

Exemplary Compounds

| Structure | ID |
|---|---|
| (chemical structure) | I-1105 |
| (chemical structure) | I-1106 |
| (chemical structure) | I-1107 |
| (chemical structure) | I-1108 |
| (chemical structure) | I-1109 |
| (chemical structure) | I-1110 |

TABLE C-continued
Exemplary Compounds
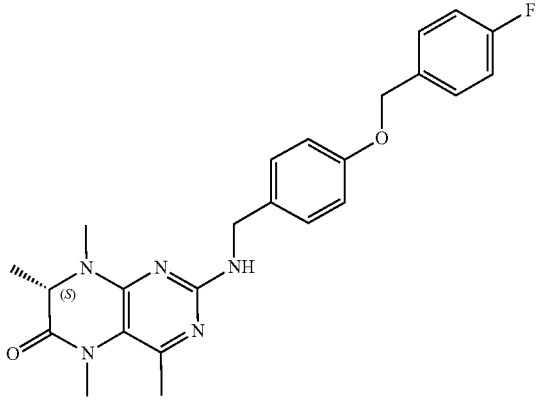 I-1111
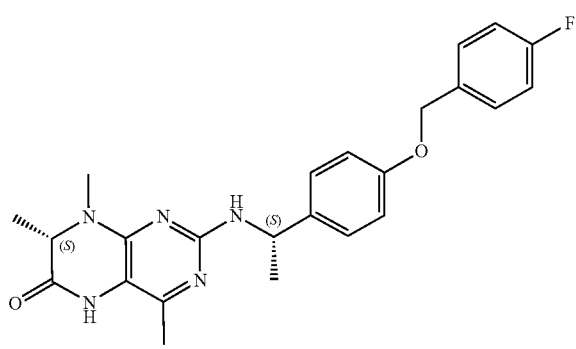 I-1112
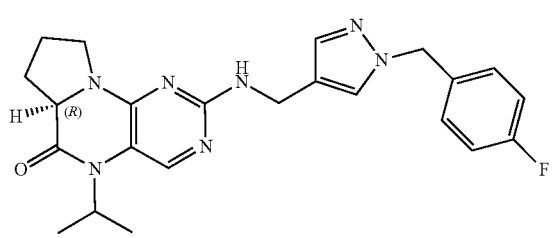 I-1113
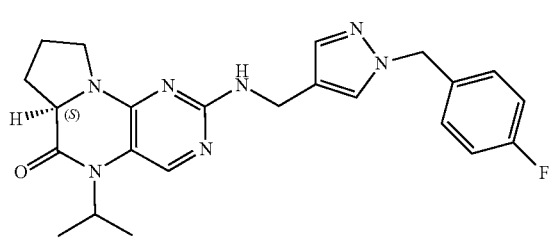 I-1114

TABLE C-continued
Exemplary Compounds
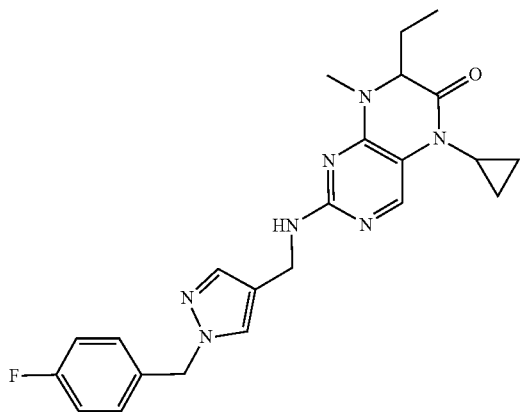 [SMILES: CCC1C(=O)N(C2CC2)c2cnc(NCc3cnn(Cc4ccc(F)cc4)c3)nc2N1C]
I-1115
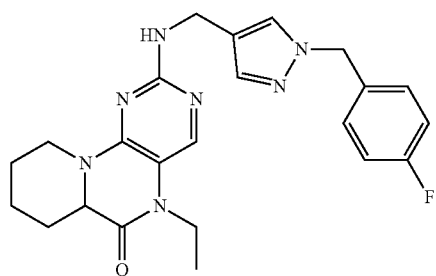 [SMILES: CCN1C(=O)C2CCCCN2c2nc(NCc3cnn(Cc4ccc(F)cc4)c3)ncc21]
I-1116
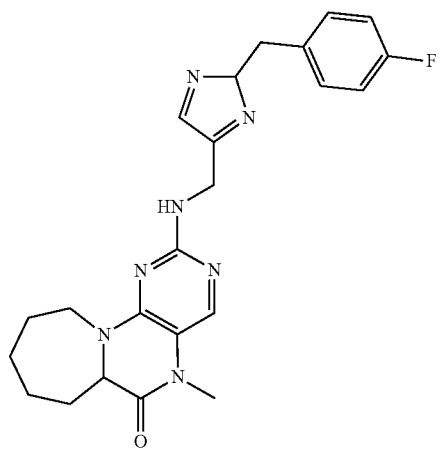 [SMILES: CN1C(=O)C2CCCCCN2c2nc(NCC3=NC(Cc4ccc(F)cc4)N=C3)ncc21]
I-1117
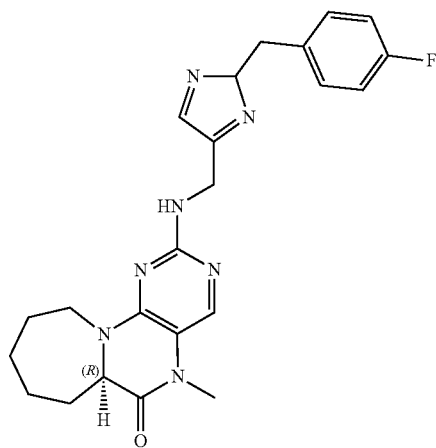
I-1118

TABLE C-continued
Exemplary Compounds
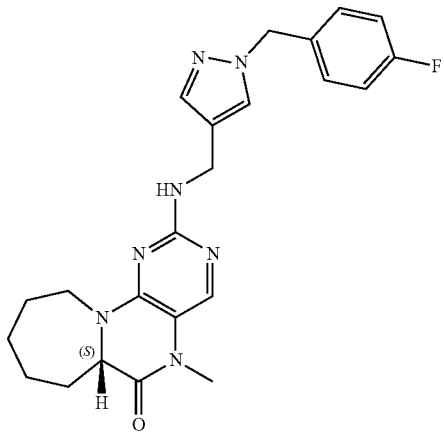
I-1119
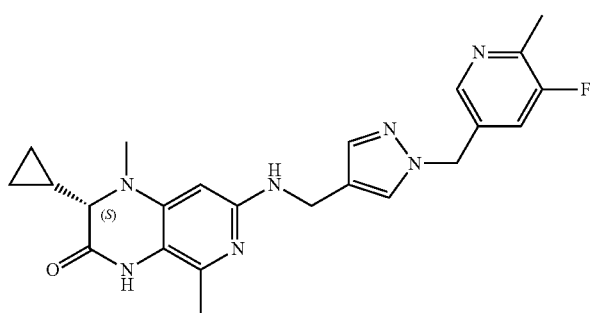
I-1120
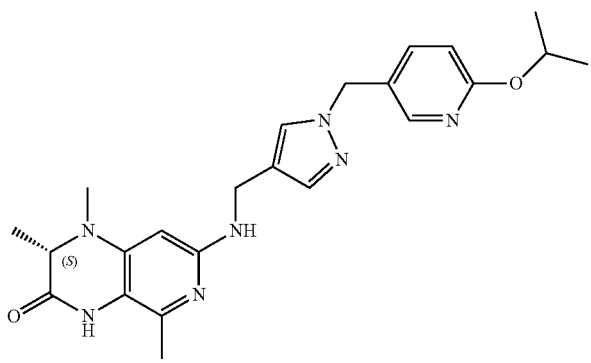
I-1121
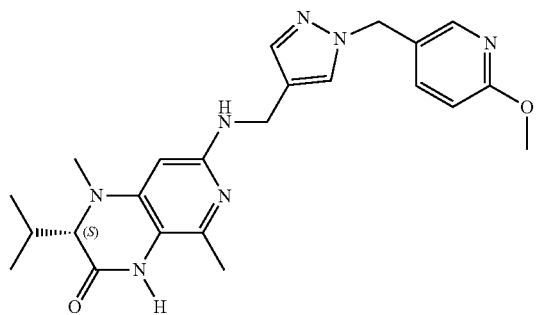
I-1122

TABLE C-continued
Exemplary Compounds
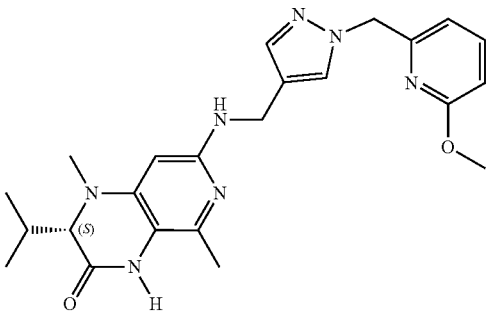
I-1123
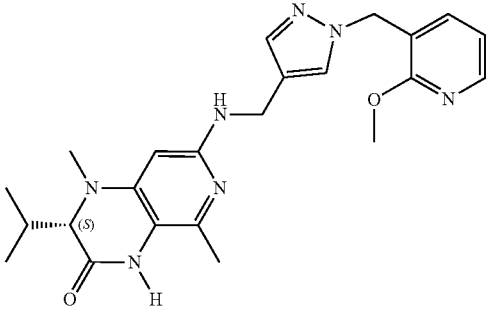
I-1124
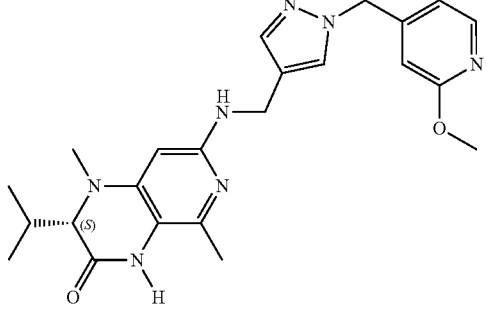
I-1125
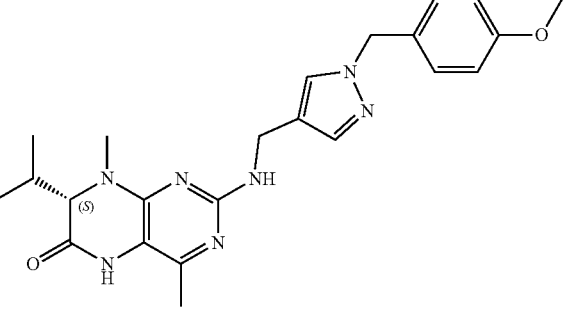
I-1126
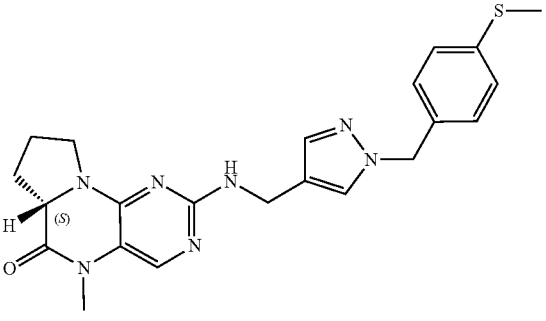
I-1127

TABLE C-continued
Exemplary Compounds
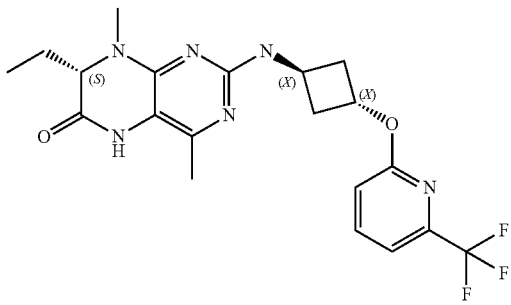
I-1128
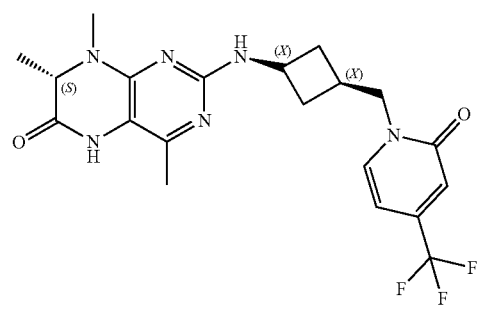
I-1129
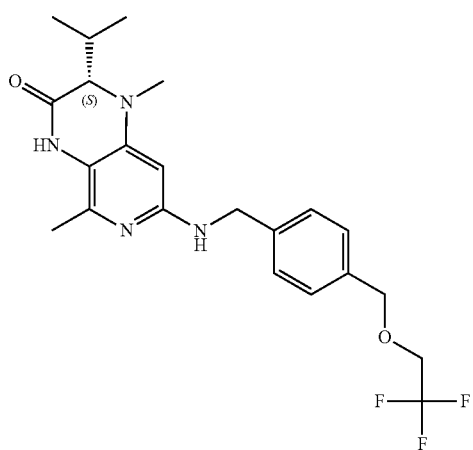
I-1130
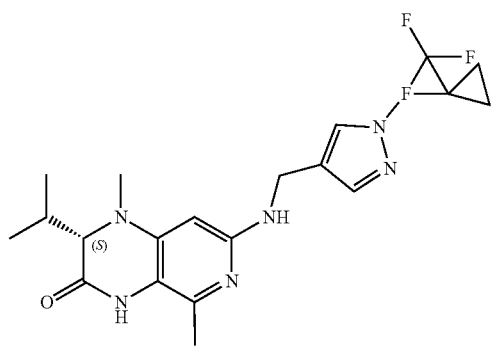
I-1131

TABLE C-continued
Exemplary Compounds
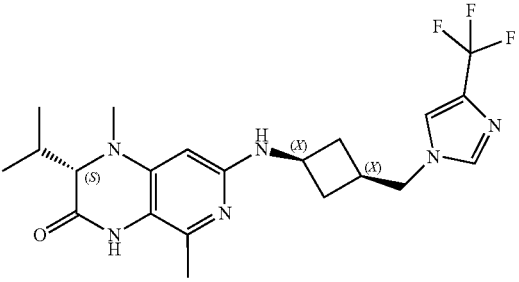
I-1132
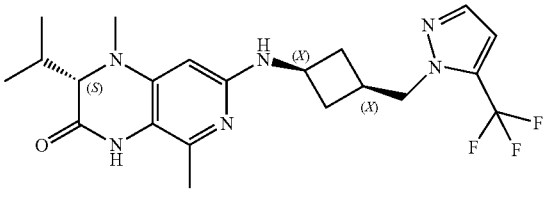
I-1133
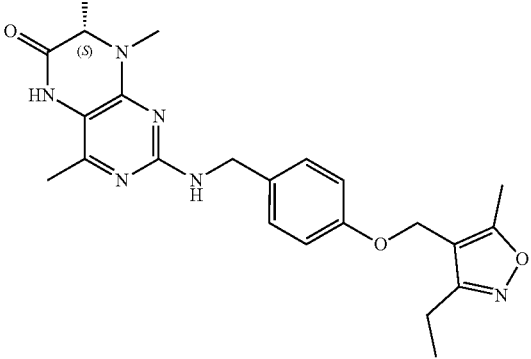
I-1134
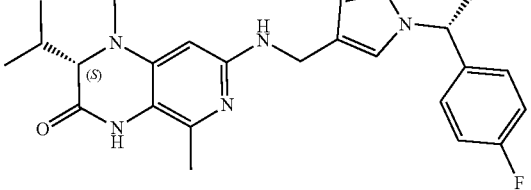
I-1135
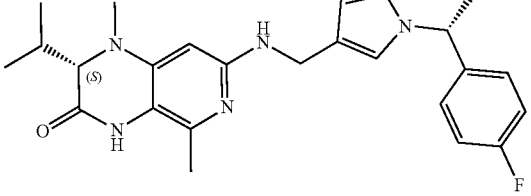
I-1136
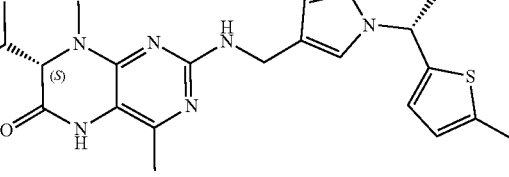
I-1137

TABLE C-continued
Exemplary Compounds
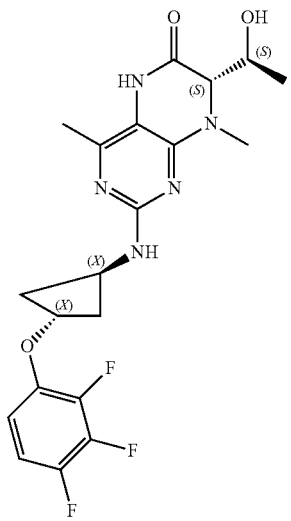
I-1138
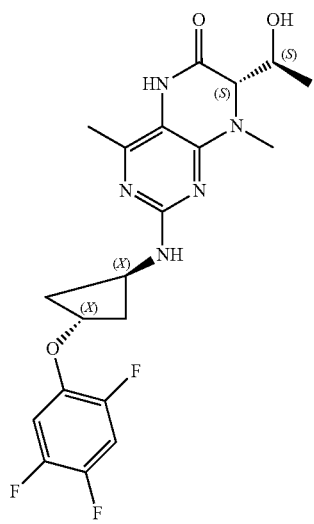
I-1139
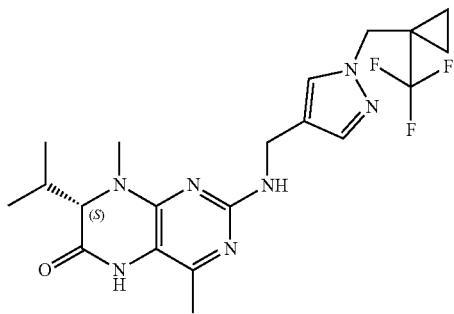
I-1140

TABLE C-continued
Exemplary Compounds
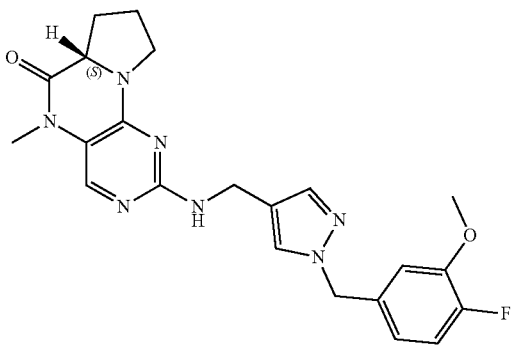 I-1141
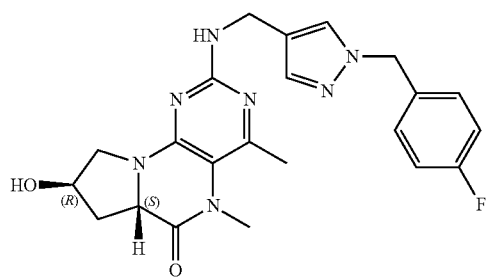 I-1142
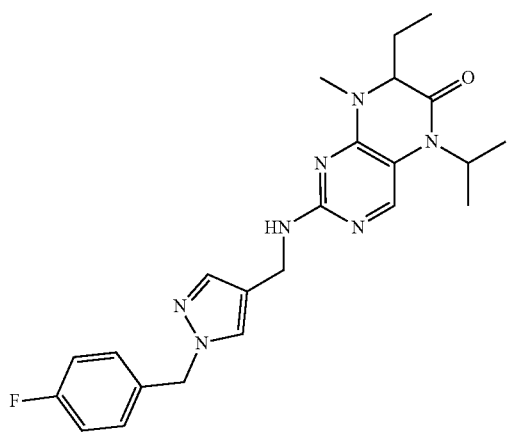 [SMILES: CCC1C(=O)N(C(C)C)c2cnc(NCc3cnn(Cc4ccc(F)cc4)c3)nc2N1C] I-1143
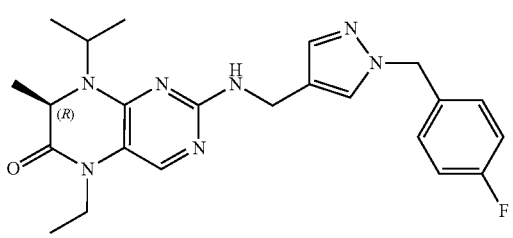 I-1144

TABLE C-continued
Exemplary Compounds
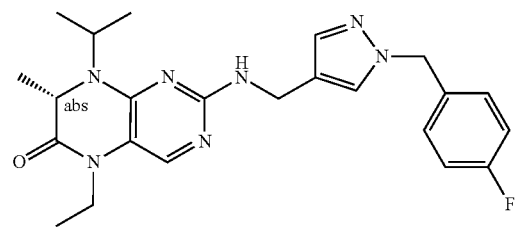
I-1145
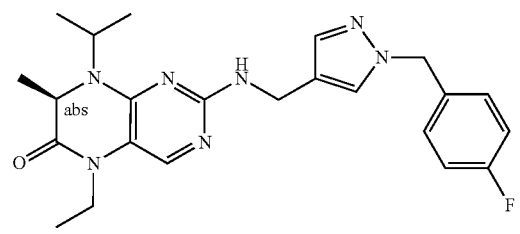
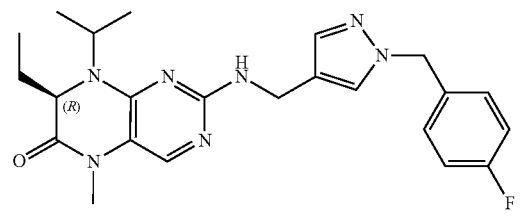
I-1146
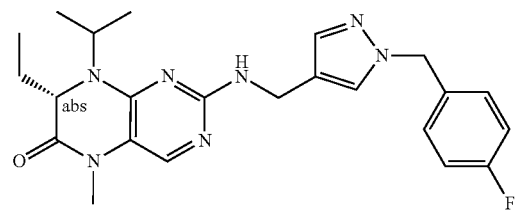
I-1147
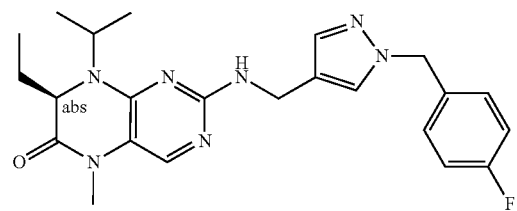
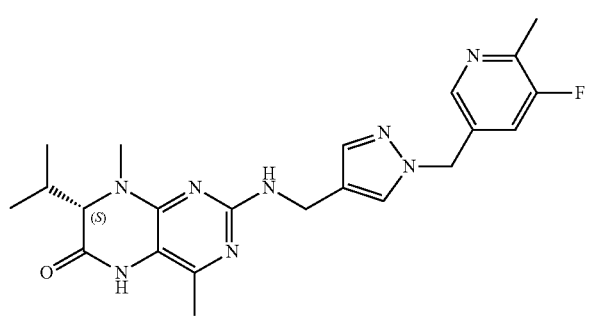
I-1148

TABLE C-continued
Exemplary Compounds
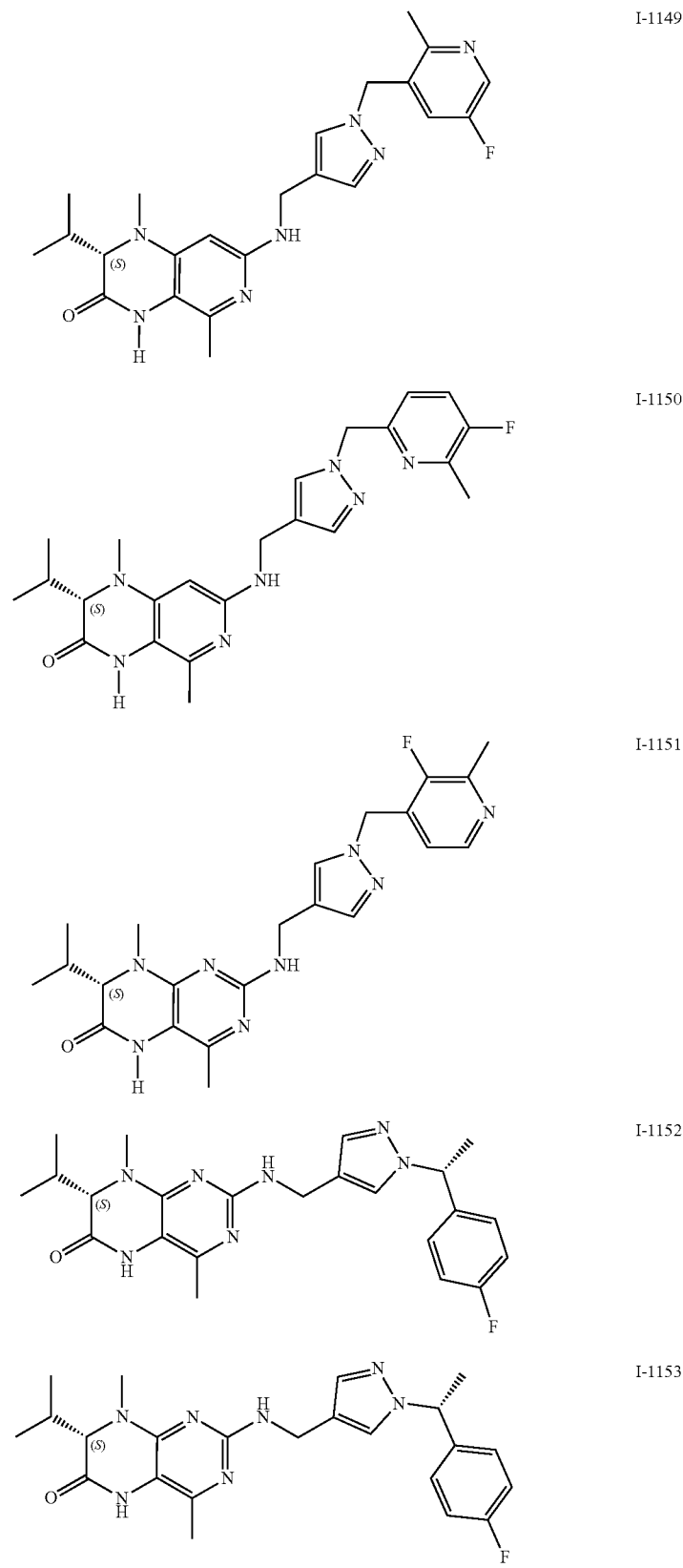
I-1149
I-1150
I-1151
I-1152
I-1153

TABLE C-continued
Exemplary Compounds
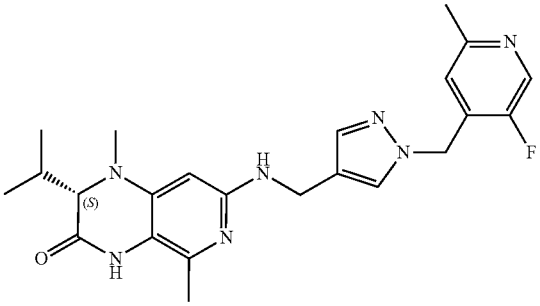
I-1154
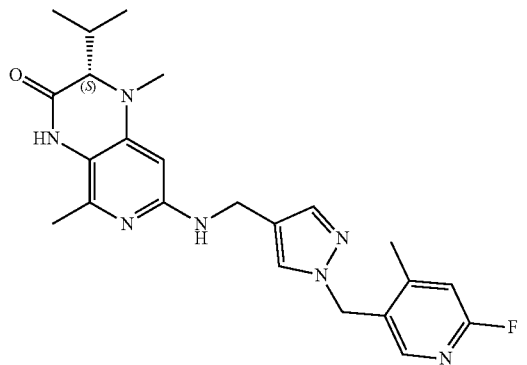
I-1155
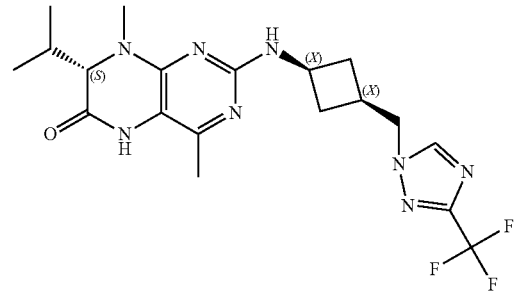
I-1156
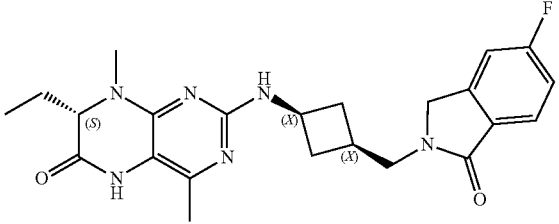
I-1157
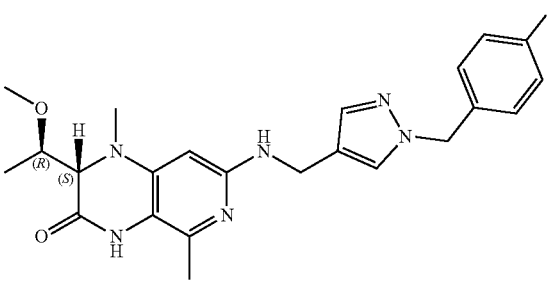
I-1158

TABLE C-continued
Exemplary Compounds
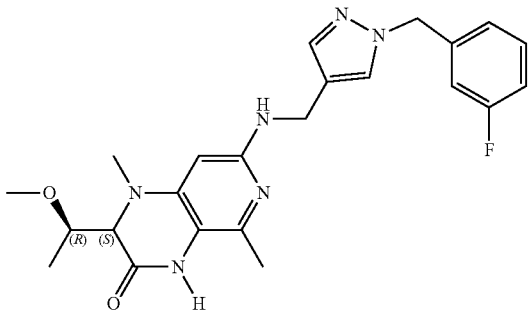
I-1159
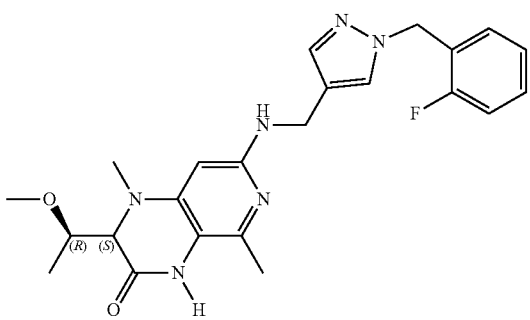
I-1160
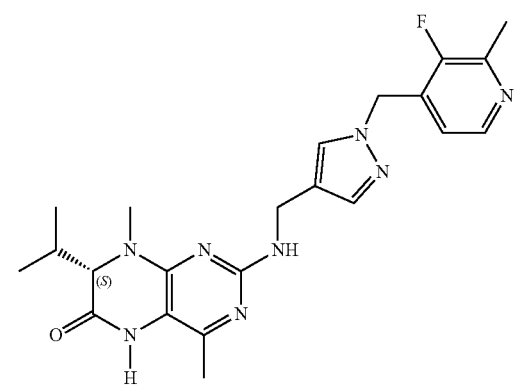
I-1161
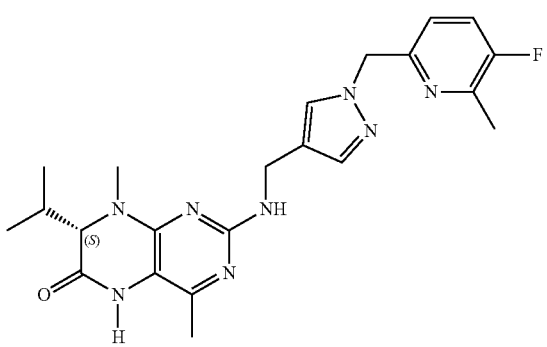
I-1162

TABLE C-continued
Exemplary Compounds
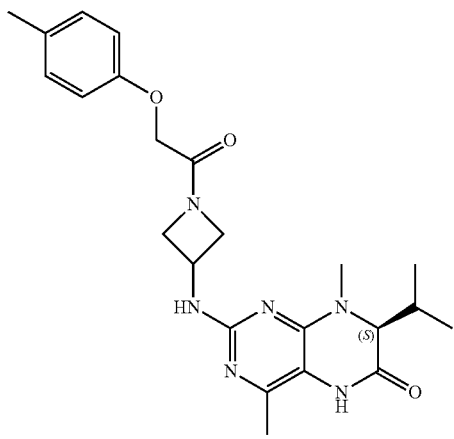
I-1163
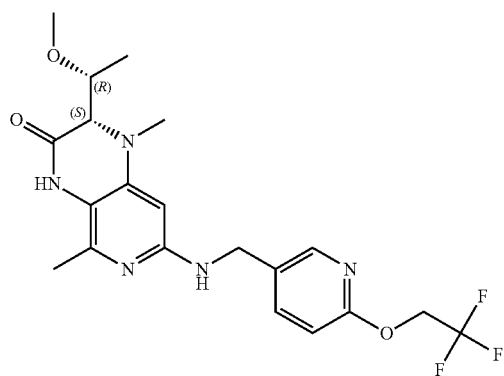
I-1164
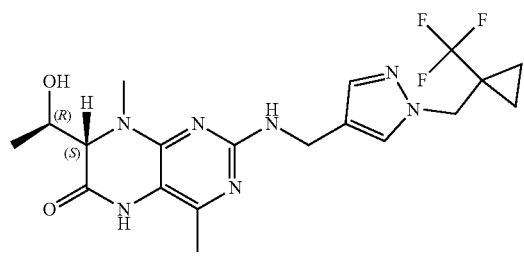
I-1165
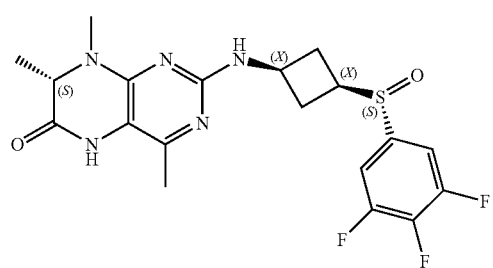
I-1166

TABLE C-continued
Exemplary Compounds
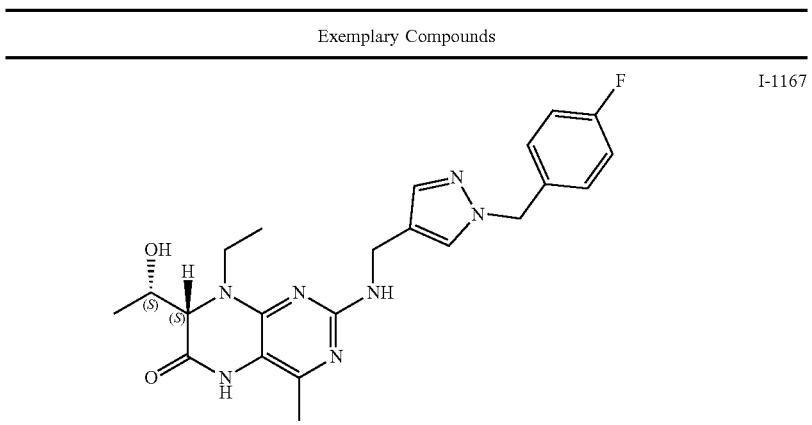
I-1167
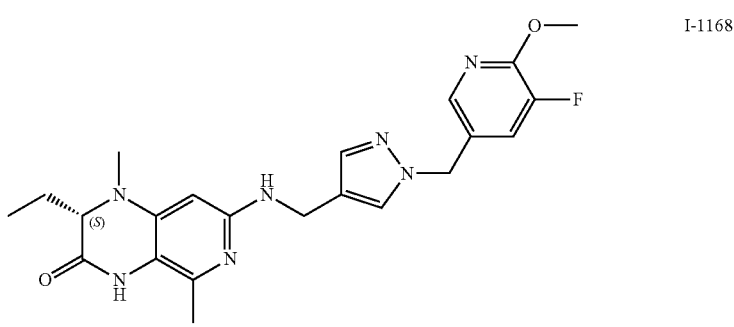
I-1168
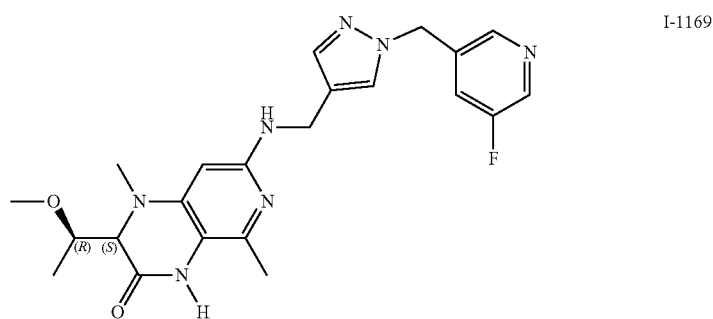
I-1169
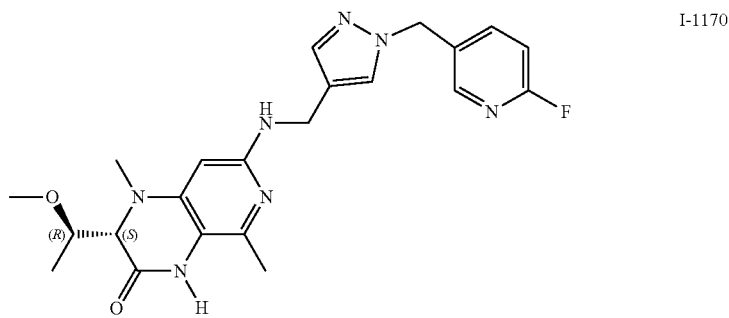
I-1170
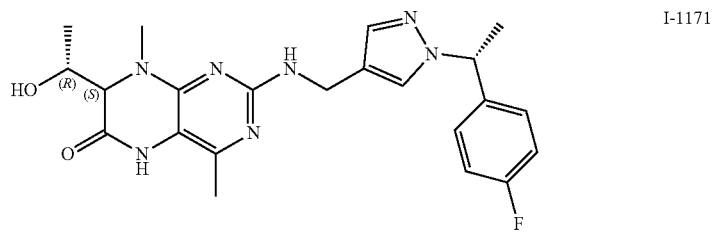
I-1171

US 11,572,364 B2
531
532
TABLE C-continued
Exemplary Compounds
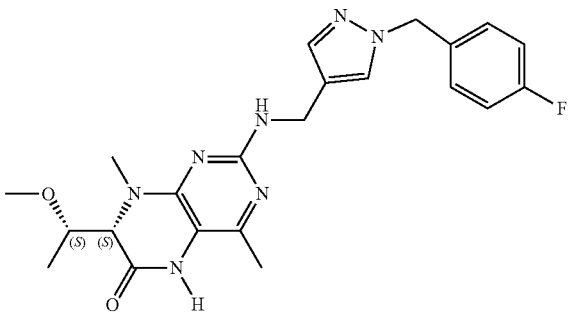
I-1172
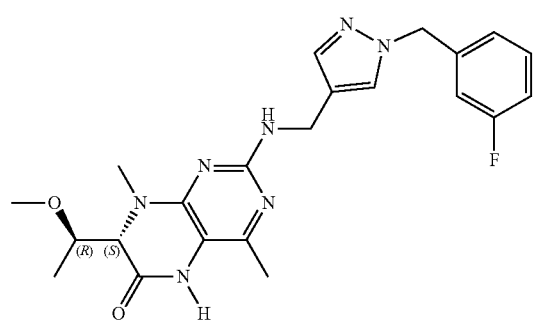
I-1173
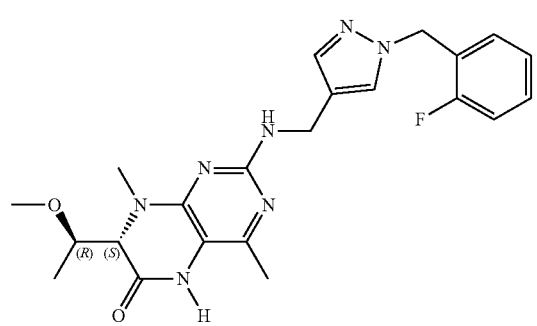
I-1174
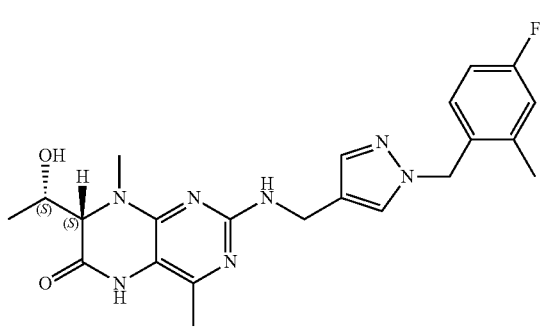
I-1175

TABLE C-continued
Exemplary Compounds
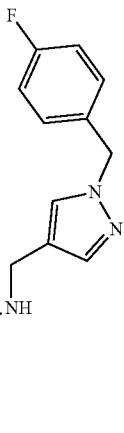
I-1176
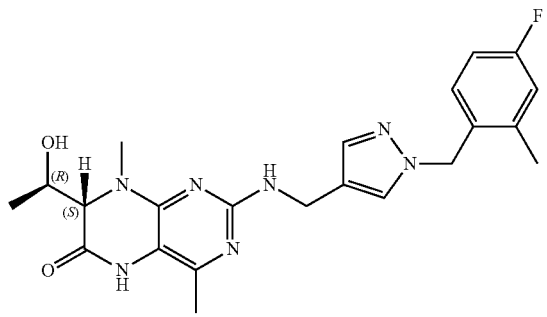
I-1177
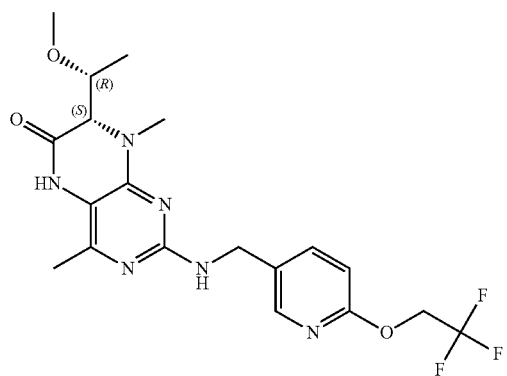
I-1178
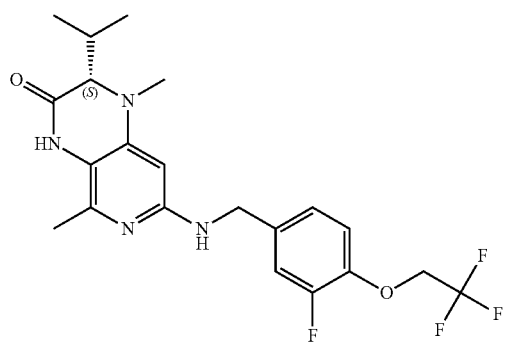
I-1179

TABLE C-continued
Exemplary Compounds
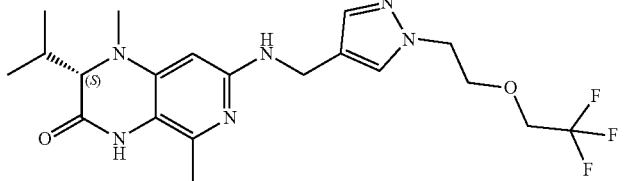
I-1180
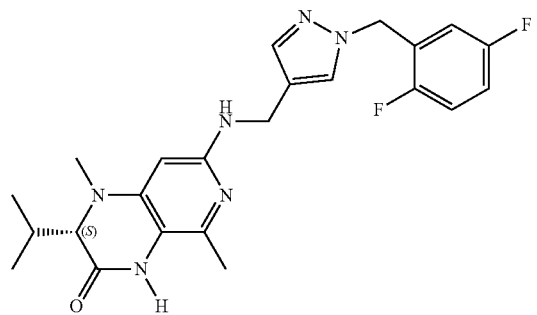
I-1181
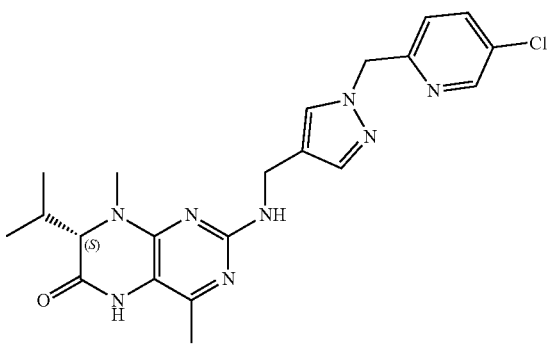
I-1182
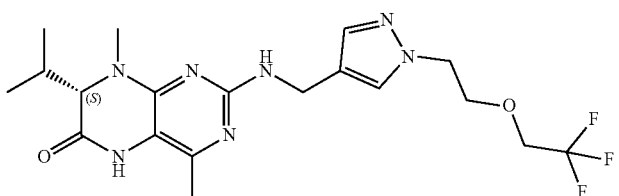
I-1183
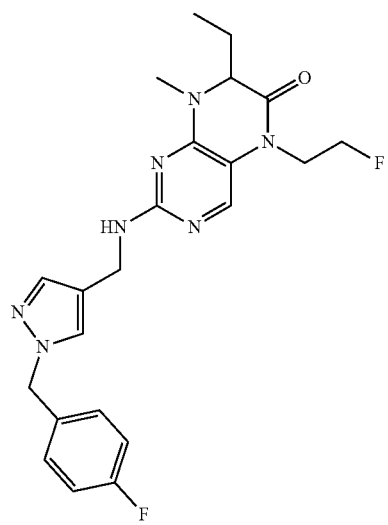 [SMILES: CCC1C(=O)N(CCF)c2cnc(NCc3cnn(Cc4ccc(F)cc4)c3)nc2N1C]
I-1184

TABLE C-continued
Exemplary Compounds
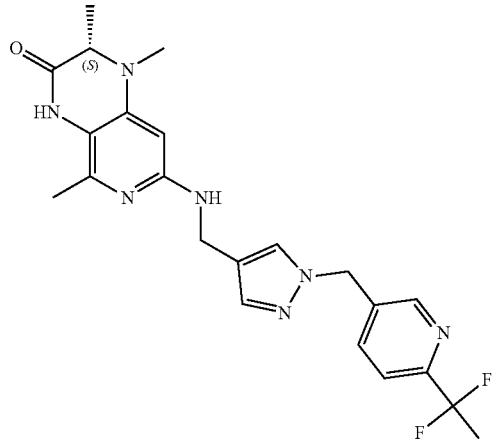
I-1185
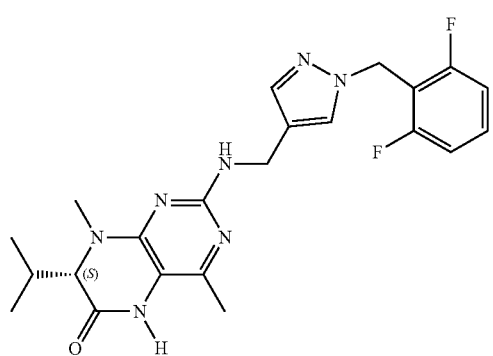
I-1186
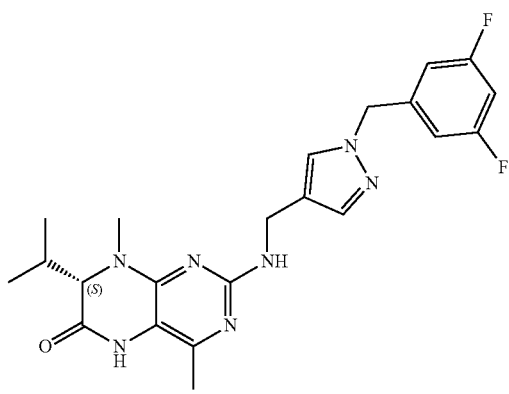
I-1187
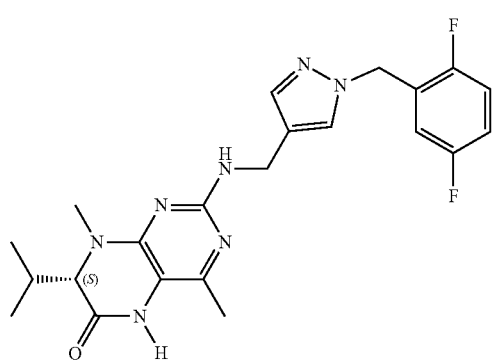
I-1188

TABLE C-continued
Exemplary Compounds
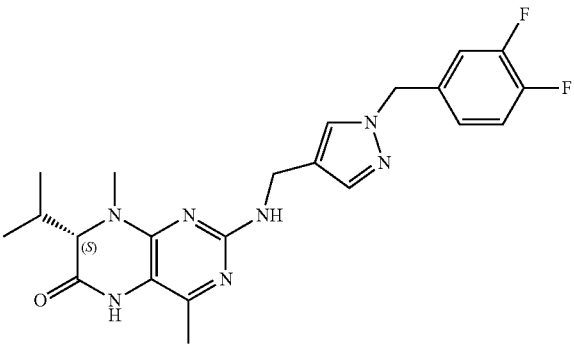
I-1189
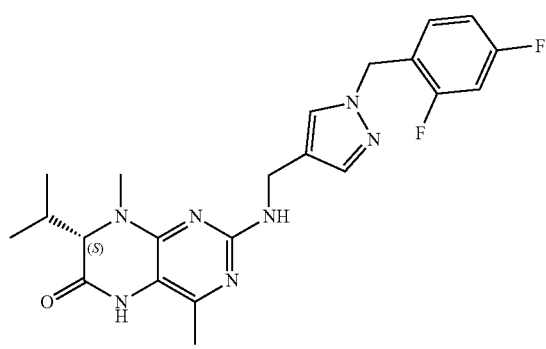
I-1190
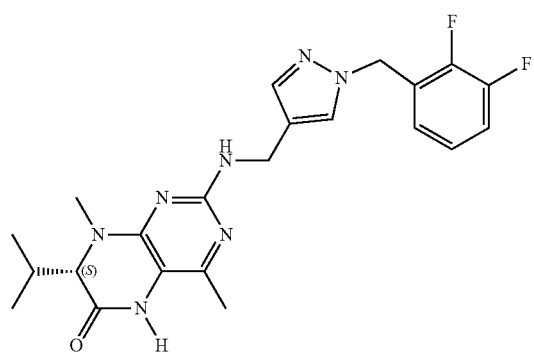
I-1191
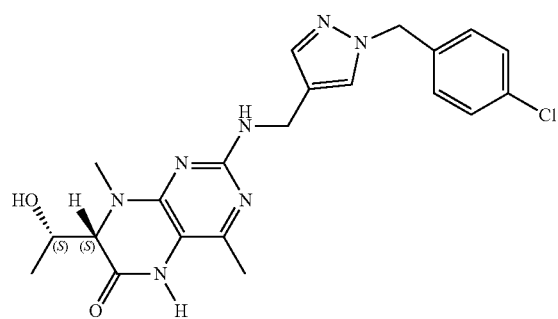
I-1192

TABLE C-continued
Exemplary Compounds
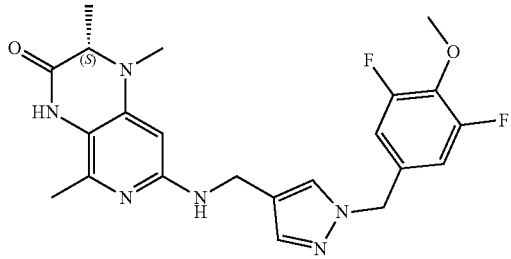
I-1193
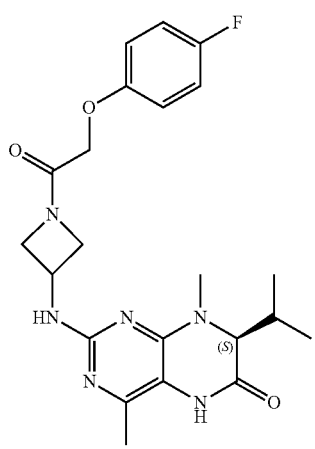
I-1194
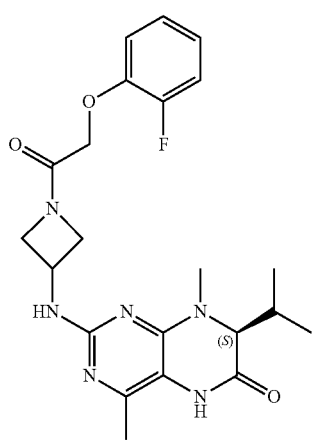
I-1195
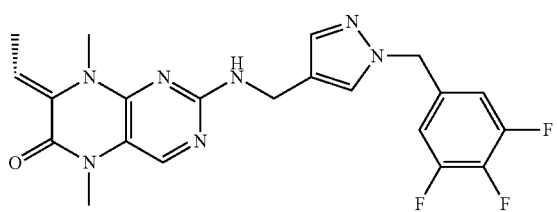
I-1196

TABLE C-continued
Exemplary Compounds
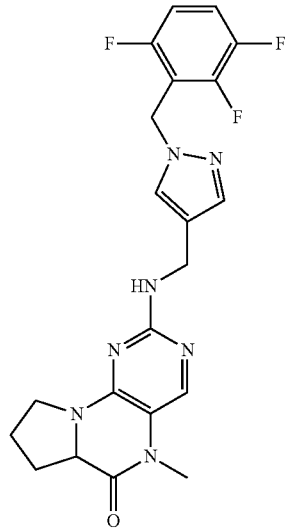 [SMILES: CN1C(=O)C2CCCN2c2nc(NCc3cnn(Cc4c(F)ccc(F)c4F)c3)ncc21]
I-1197
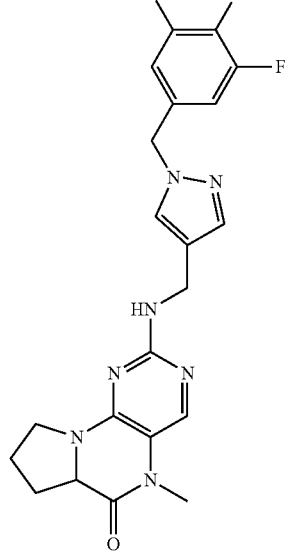
I-1198

I-1199
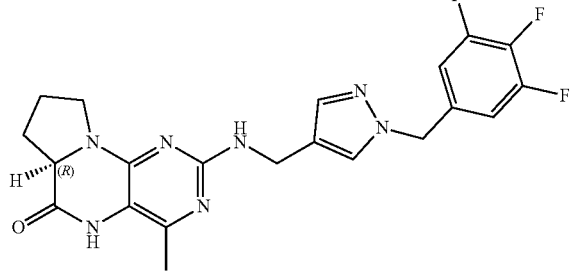
I-1200

TABLE C-continued
Exemplary Compounds
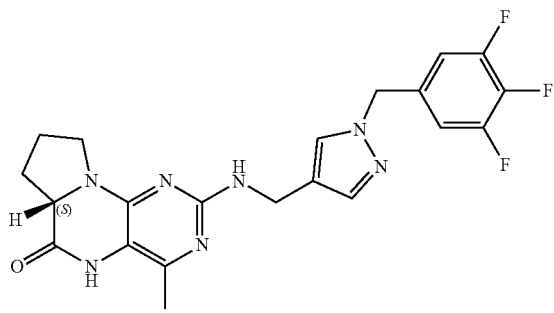 I-1201
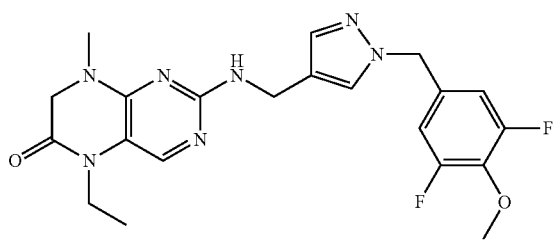 [SMILES: CCN1C(=O)CN(C)c2nc(NCc3cnn(Cc4cc(F)c(OC)c(F)c4)c3)ncc21] I-1202
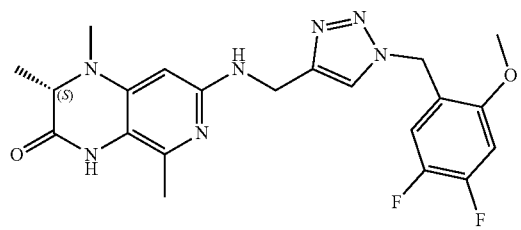 I-1203
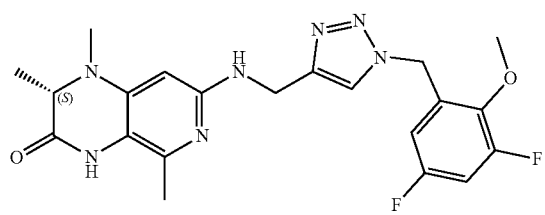 I-1204
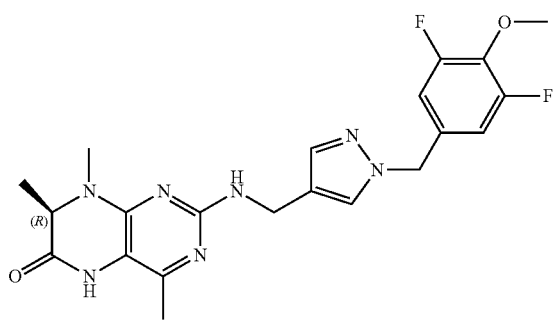 I-1205

TABLE C-continued
Exemplary Compounds
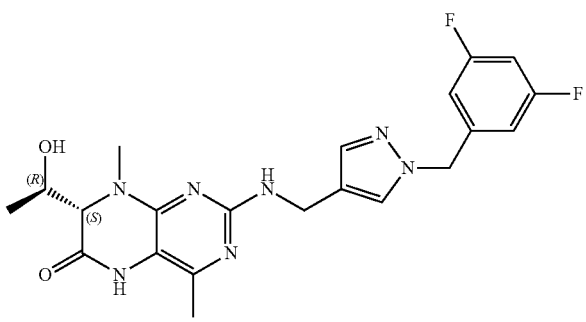
I-1206
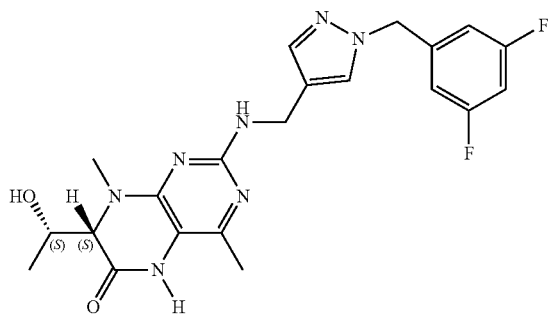
I-1207
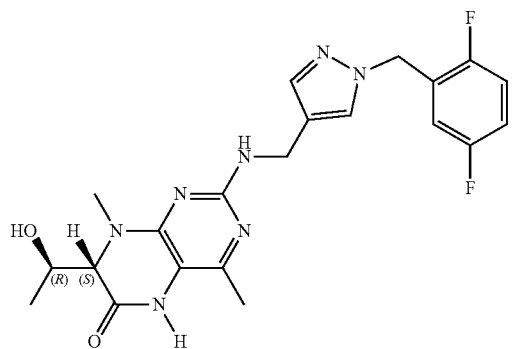
I-1208
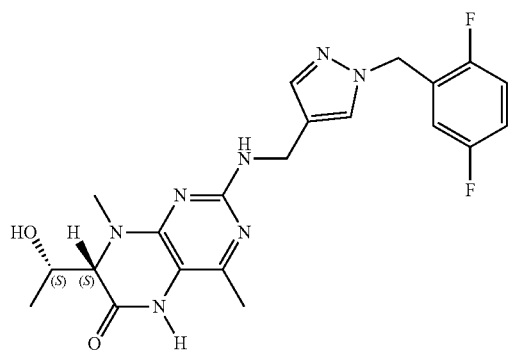
I-1209

TABLE C-continued
Exemplary Compounds
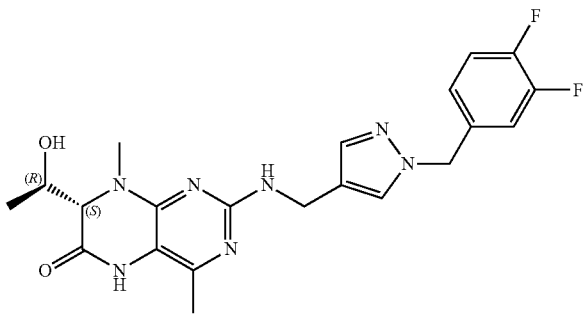
I-1210
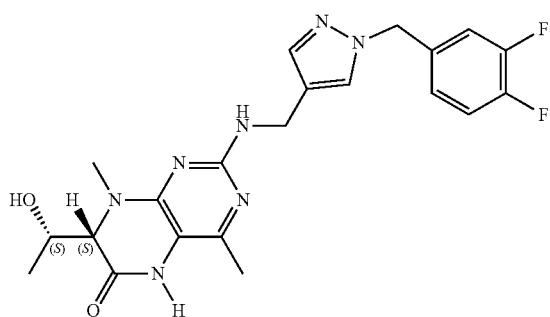
I-1211
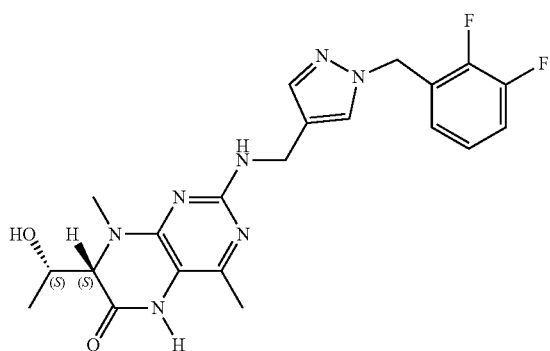
I-1212
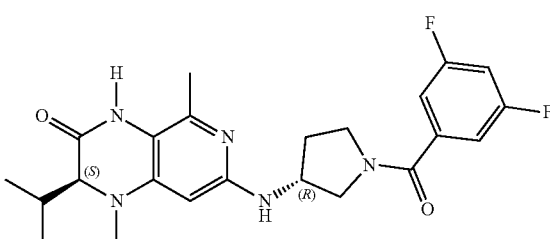
I-1213
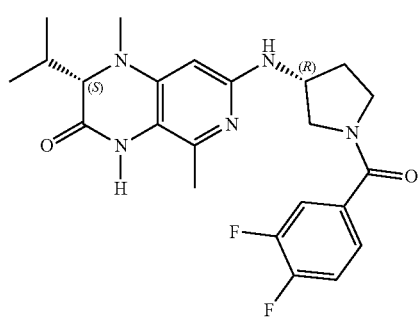
I-1214

TABLE C-continued
Exemplary Compounds
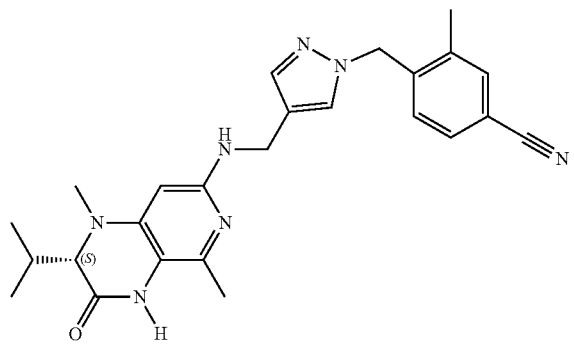
I-1215
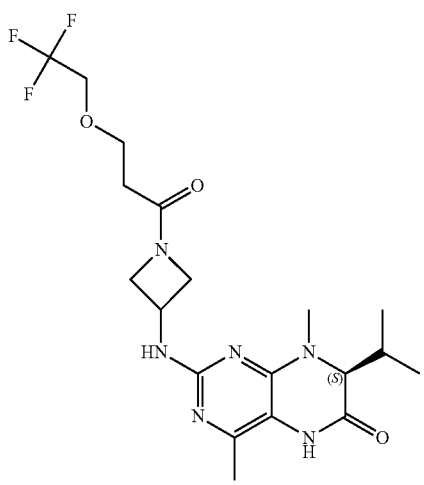
I-1216
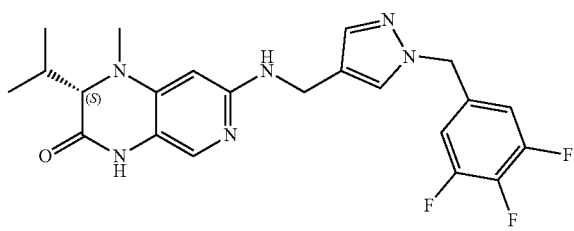
I-1217
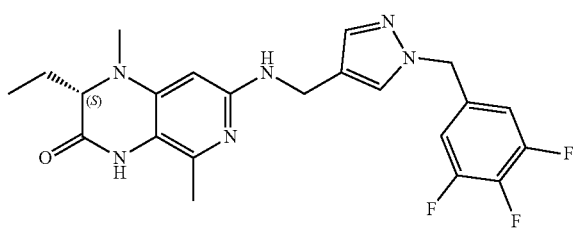
I-1218
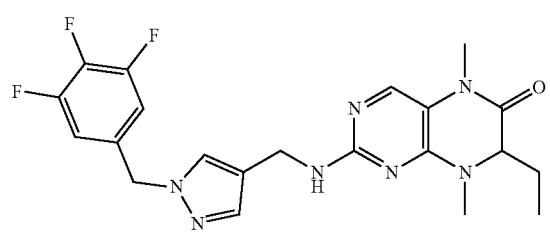 [SMILES: CCC1C(=O)N(C)c2cnc(NCc3cnn(Cc4cc(F)c(F)c(F)c4)c3)nc2N1C]
I-1219

TABLE C-continued
Exemplary Compounds
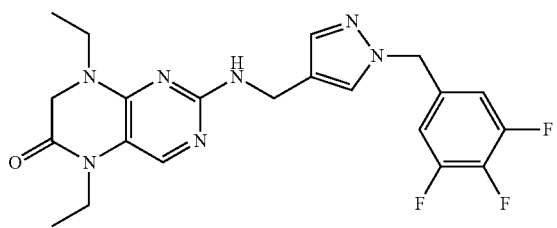 [SMILES: CCN1CC(=O)N(CC)c2cnc(NCc3cnn(Cc4cc(F)c(F)c(F)c4)c3)nc21] I-1220
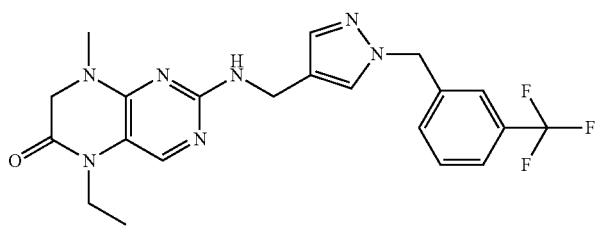 [SMILES: CCN1C(=O)CN(C)c2nc(NCc3cnn(Cc4cccc(C(F)(F)F)c4)c3)ncc21] I-1221
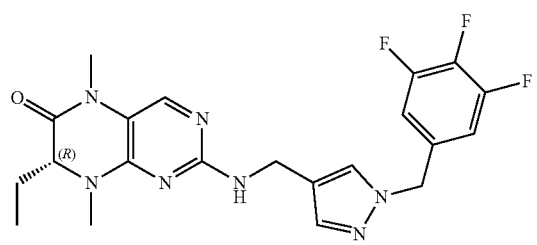 I-1222
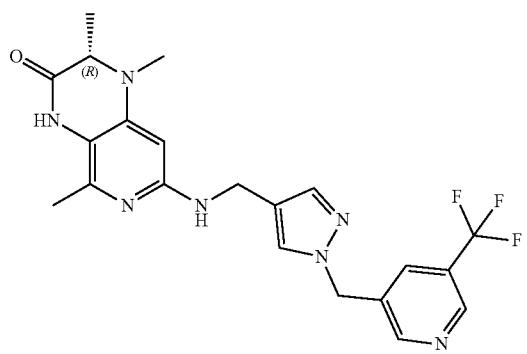 I-1223
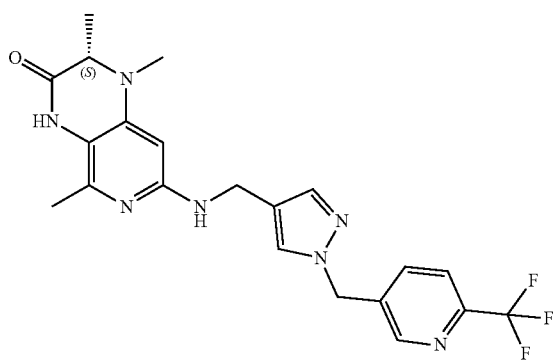 I-1224

TABLE C-continued
Exemplary Compounds
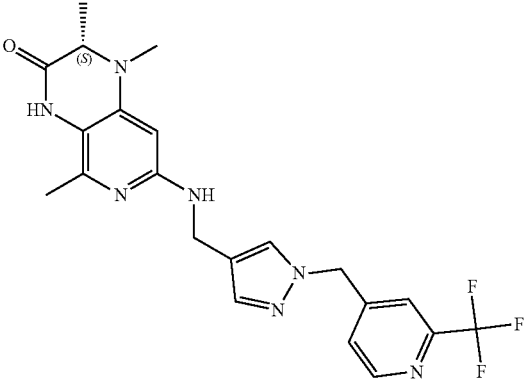
I-1225
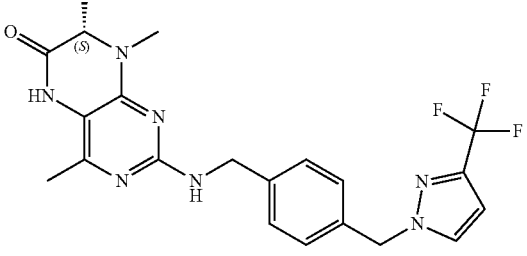
I-1226
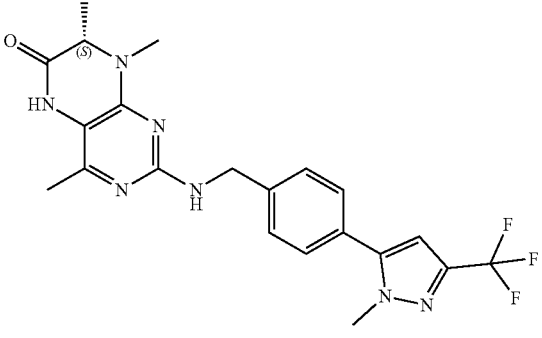
I-1227
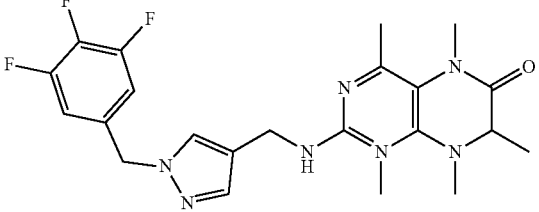
I-1228
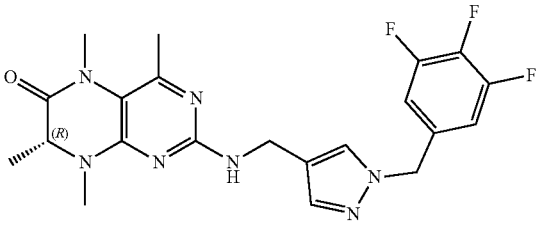
I-1229

TABLE C-continued
Exemplary Compounds
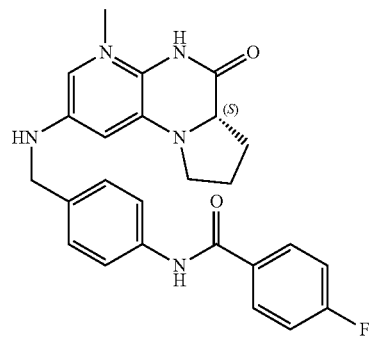
I-1230
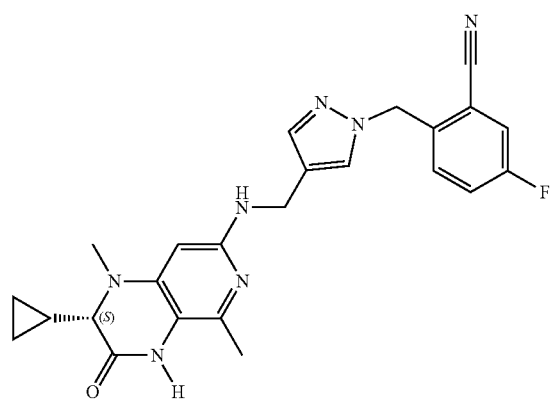
I-1231
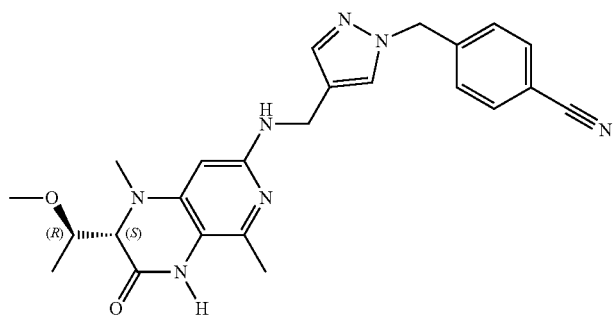
I-1232
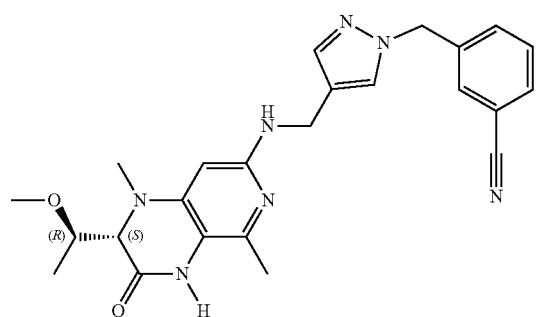
I-1233

TABLE C-continued
Exemplary Compounds
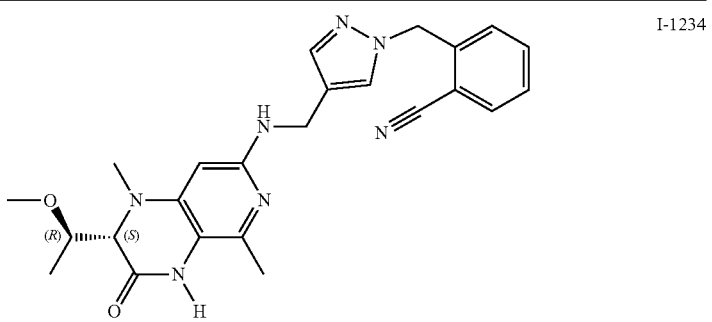
I-1234
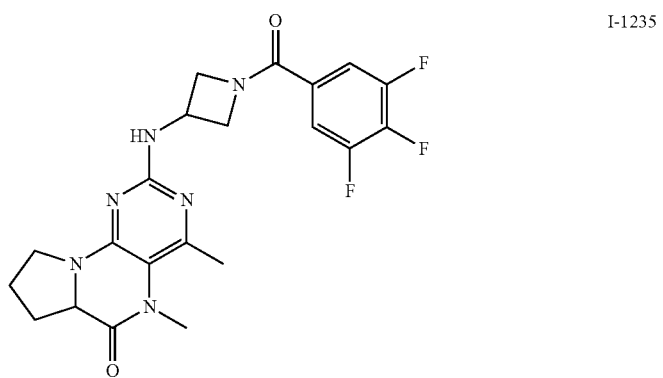
I-1235
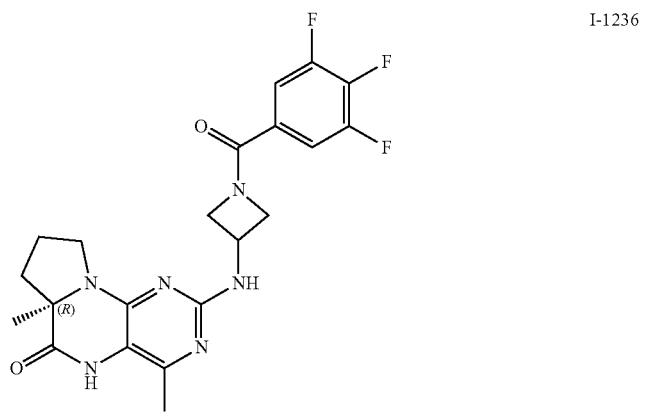
I-1236
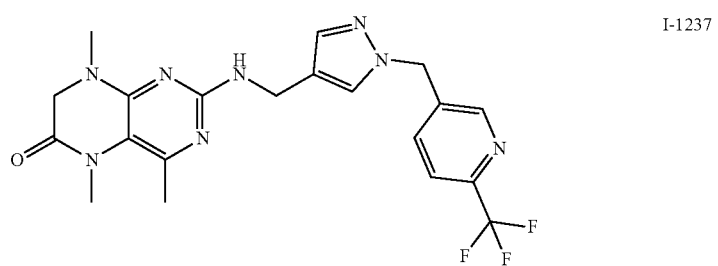
I-1237

TABLE C-continued
Exemplary Compounds
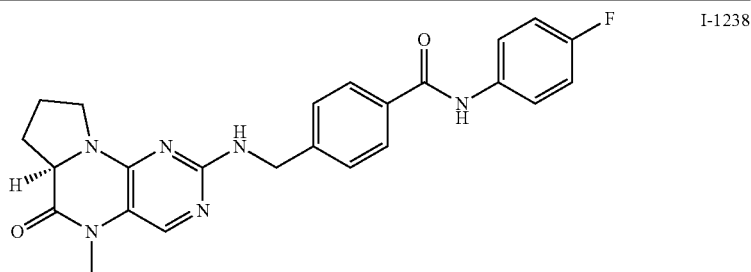
I-1238
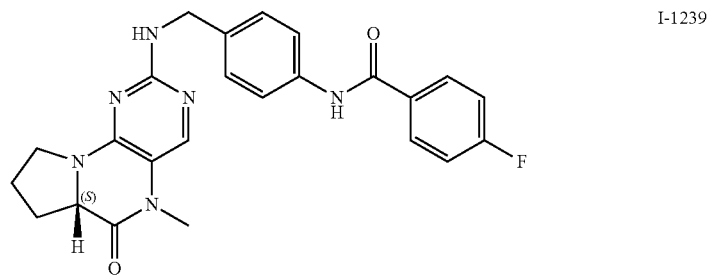
I-1239
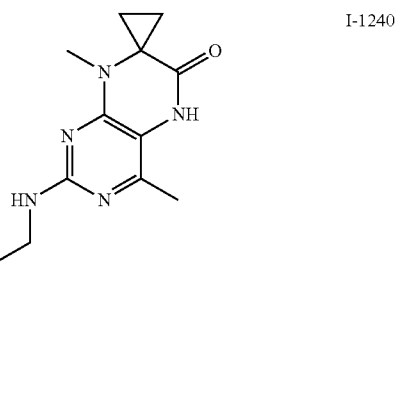
I-1240
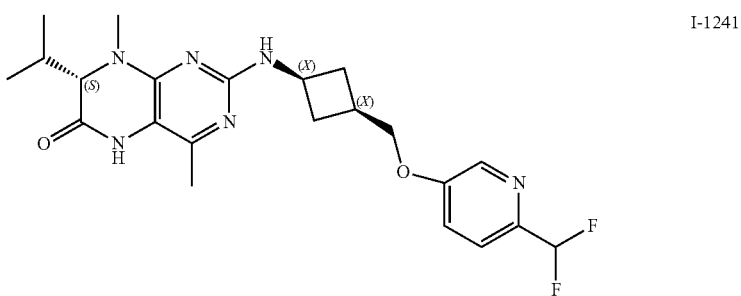
I-1241
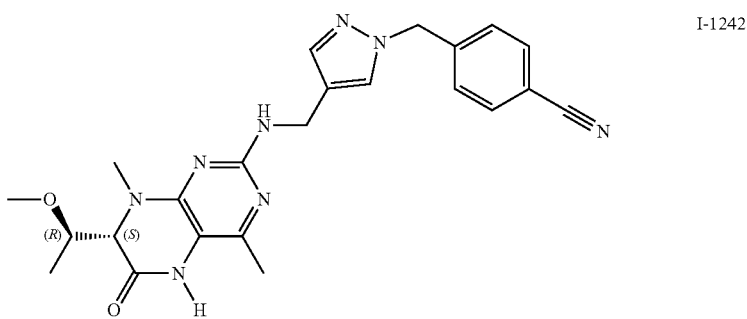
I-1242

TABLE C-continued
Exemplary Compounds
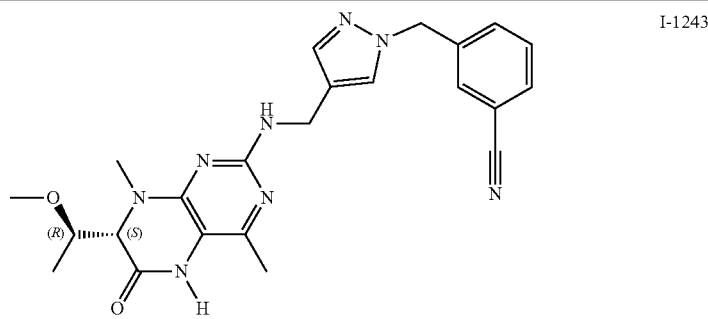
I-1243
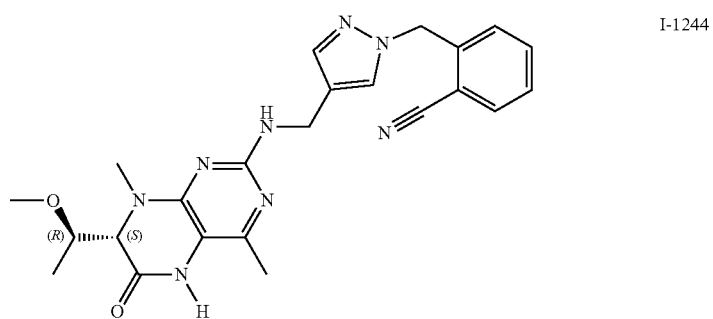
I-1244
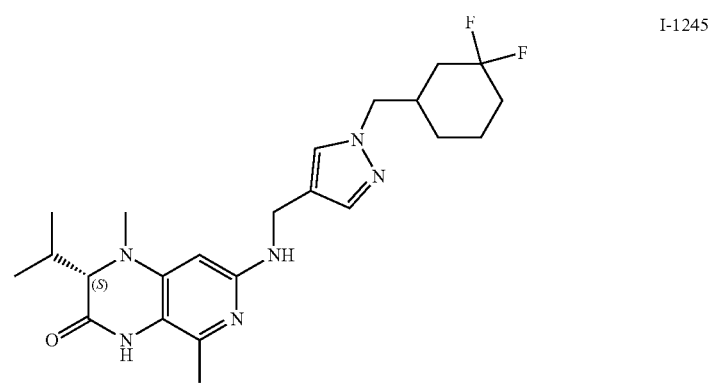
I-1245
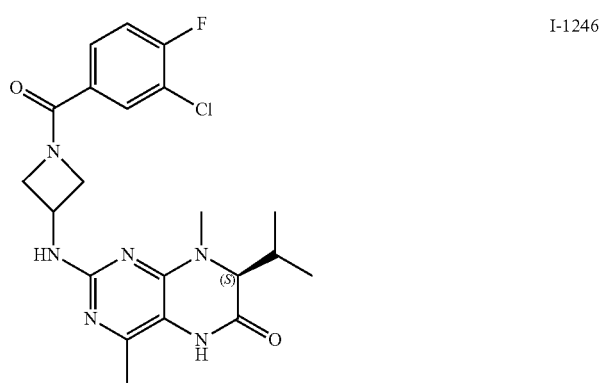
I-1246

TABLE C-continued
Exemplary Compounds
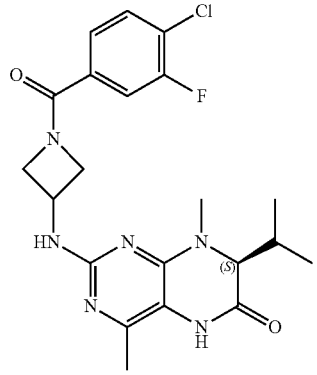
I-1247
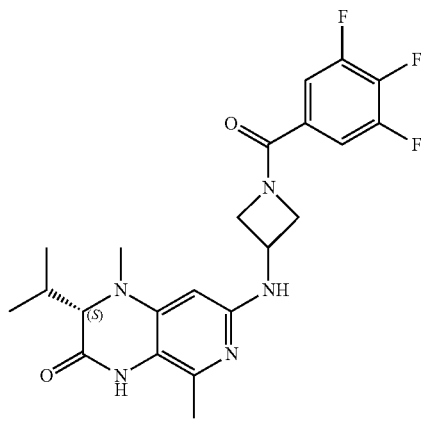
I-1248
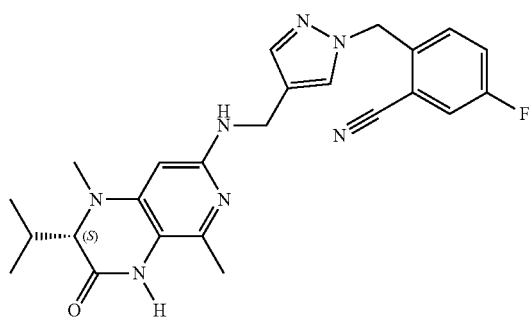
I-1249
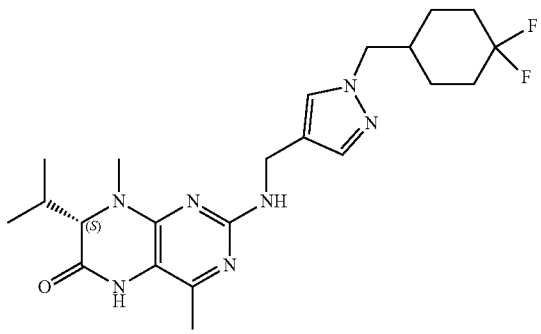
I-1250

TABLE C-continued
Exemplary Compounds
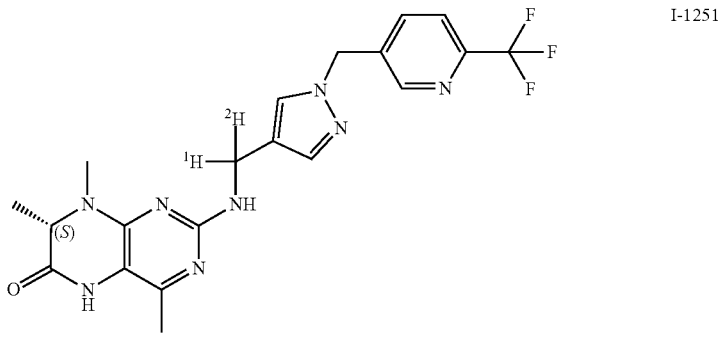
I-1251
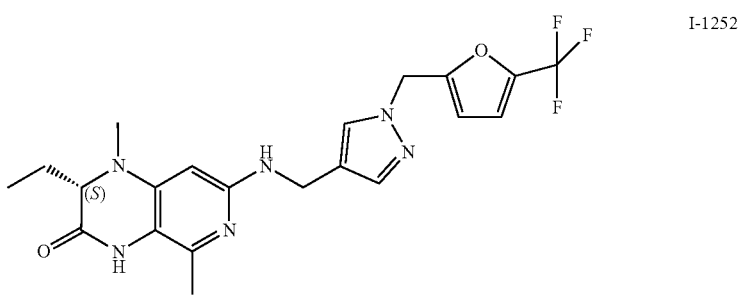
I-1252
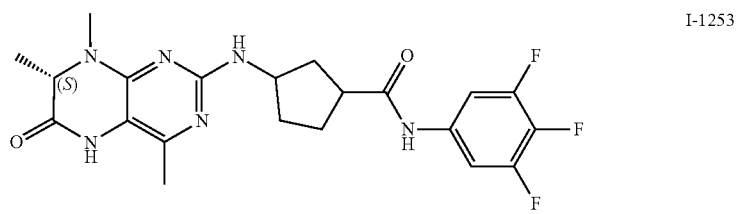
I-1253
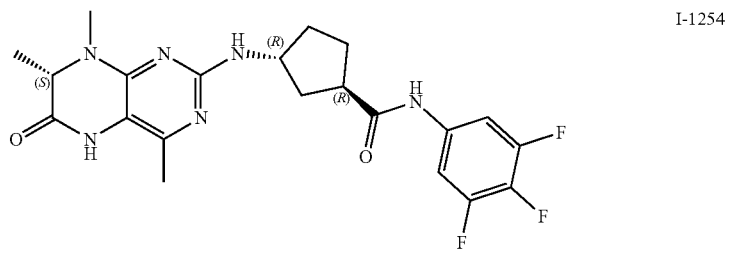
I-1254
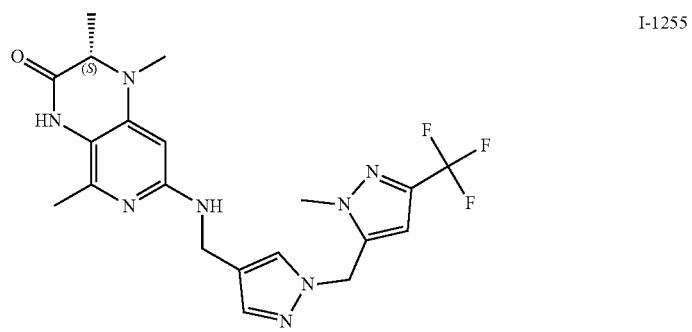
I-1255

TABLE C-continued

Exemplary Compounds

I-1256

I-1257

I-1258

I-1259

I-1260

TABLE C-continued
Exemplary Compounds
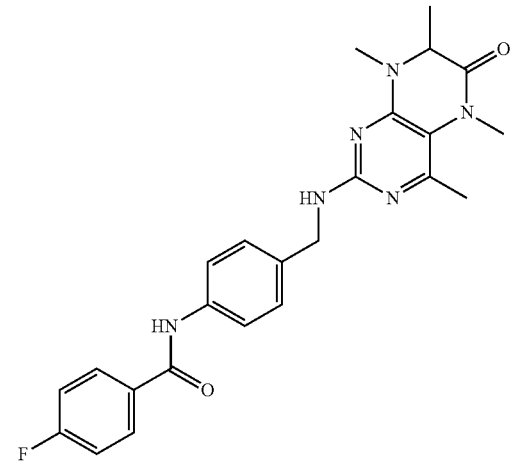 [SMILES: Cc1nc(NCc2ccc(NC(=O)c3ccc(F)cc3)cc2)nc2c1N(C)C(=O)C(C)N2C]
I-1261
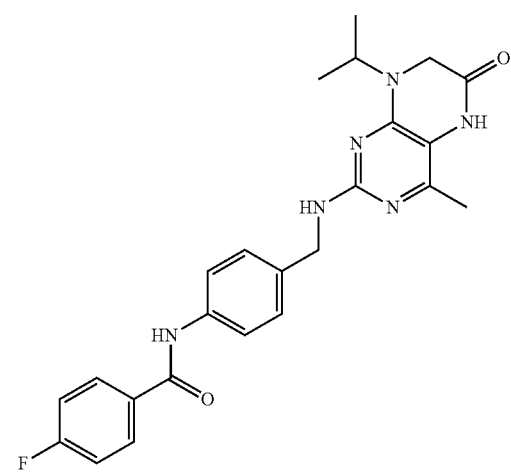 [SMILES: Cc1nc(NCc2ccc(NC(=O)c3ccc(F)cc3)cc2)nc2c1NC(=O)CN2C(C)C]
I-1262
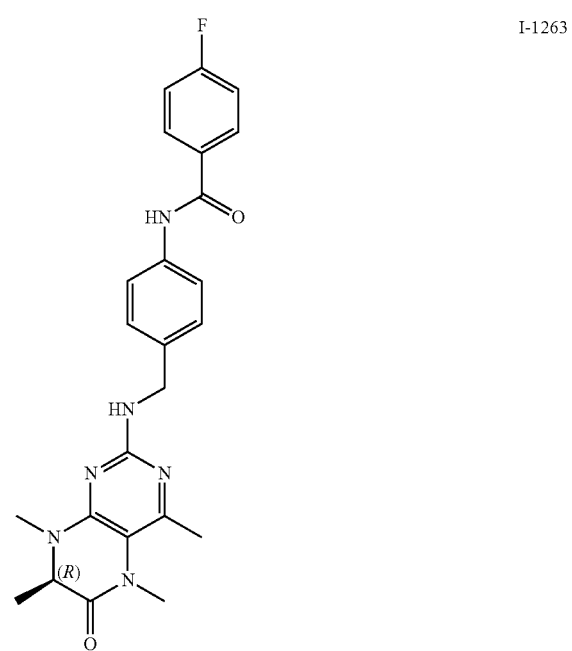
I-1263

TABLE C-continued
Exemplary Compounds
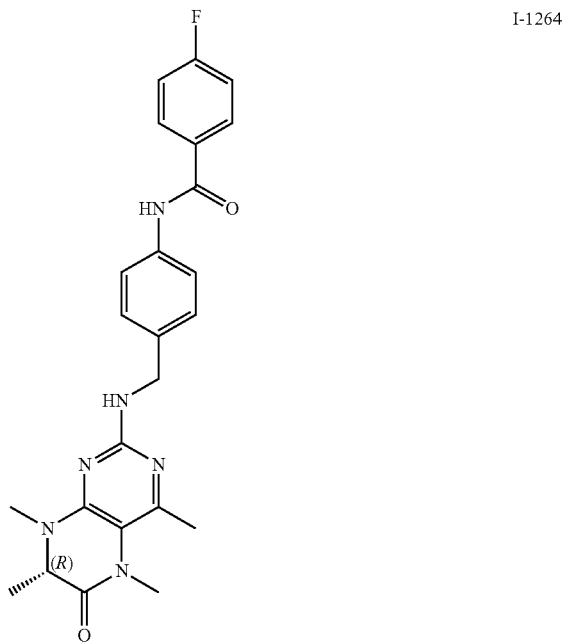
I-1264
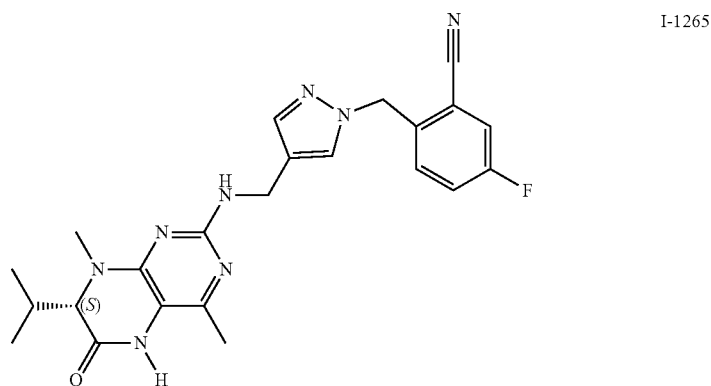
I-1265
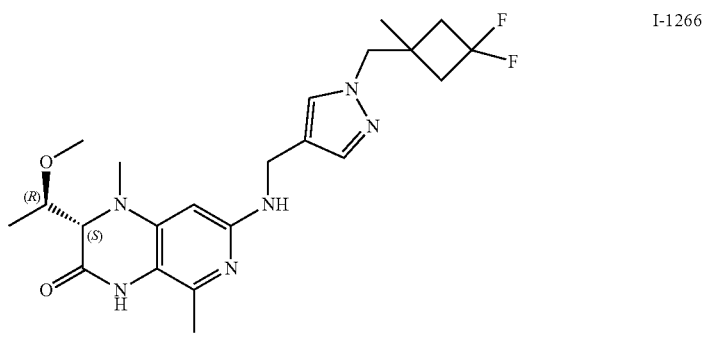
I-1266

TABLE C-continued
Exemplary Compounds
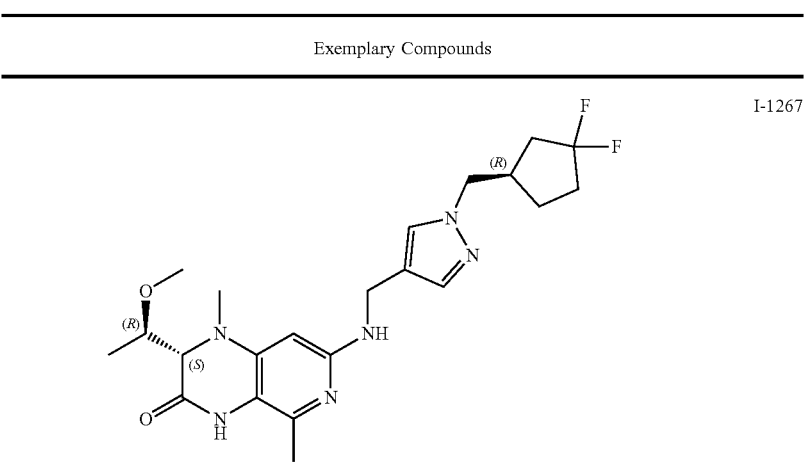 I-1267
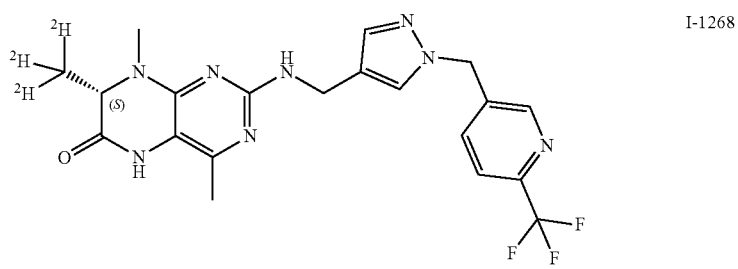 I-1268
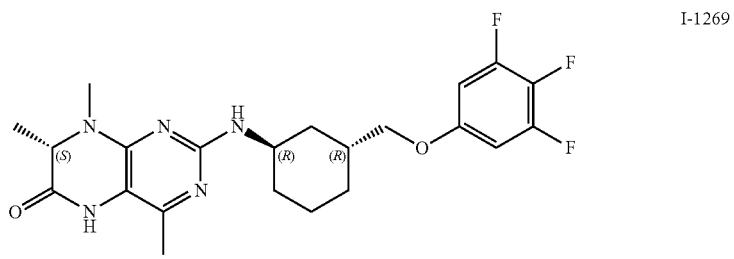 I-1269
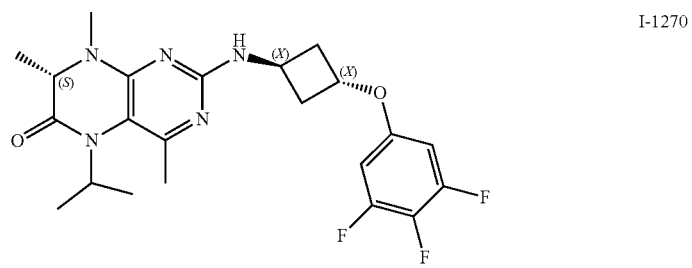 I-1270
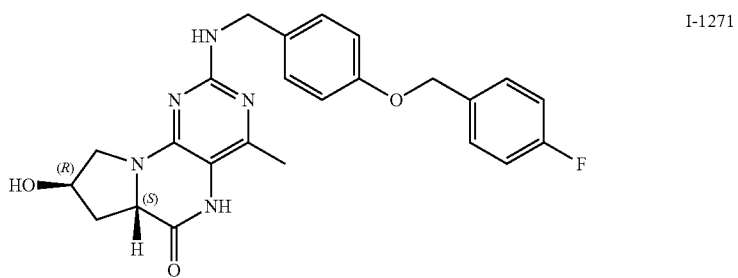 I-1271

TABLE C-continued
Exemplary Compounds
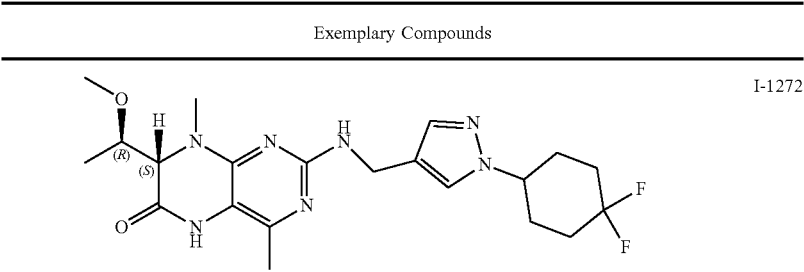
I-1272
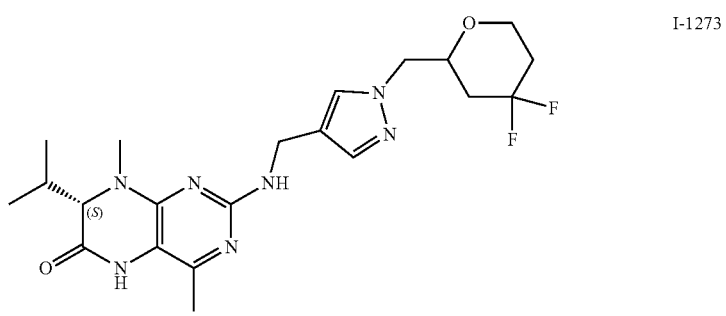
I-1273
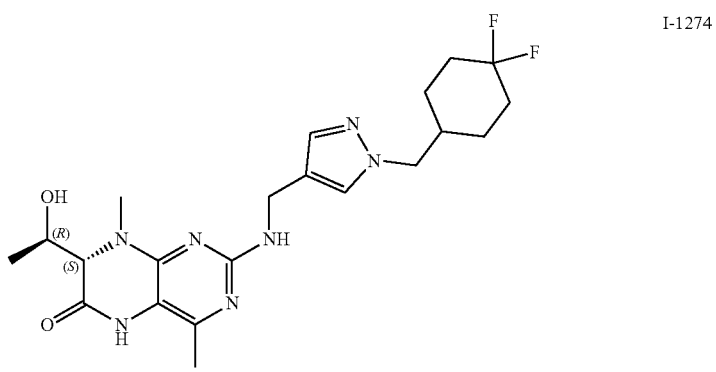
I-1274
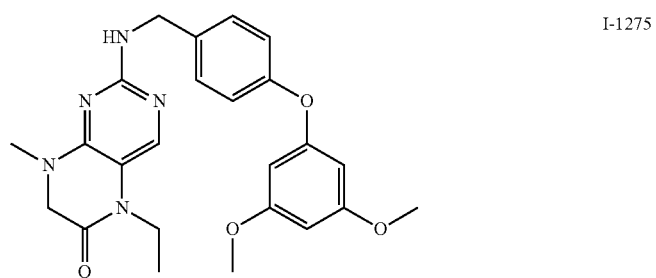
I-1275
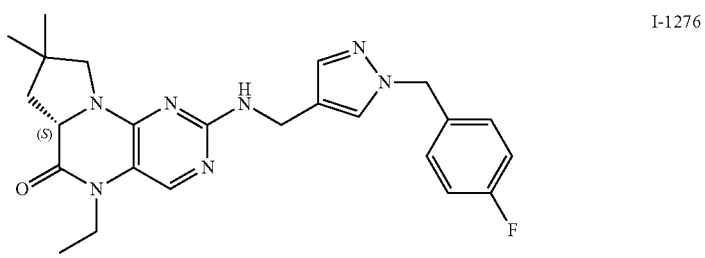
I-1276

TABLE C-continued
Exemplary Compounds
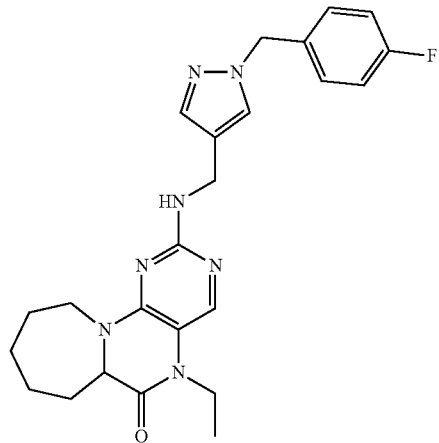 [SMILES: CCN1C(=O)C2CCCCCN2c2nc(NCc3cnn(Cc4ccc(F)cc4)c3)ncc21]
I-1277
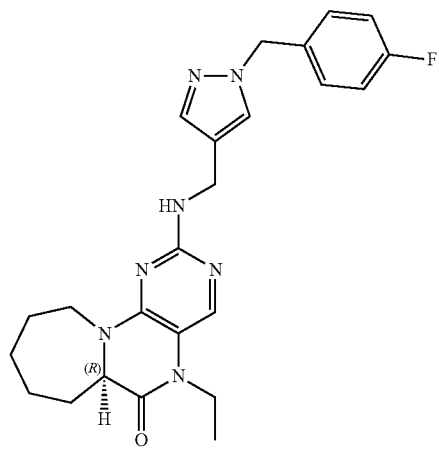
I-1278
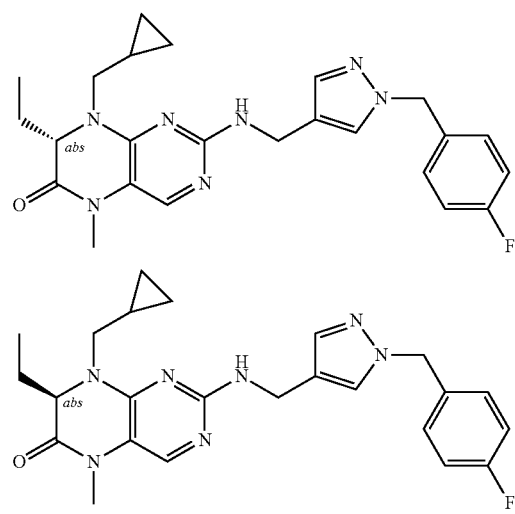
I-1279

TABLE C-continued
Exemplary Compounds
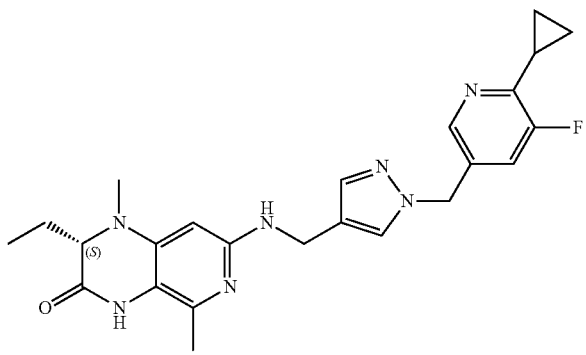
I-1280
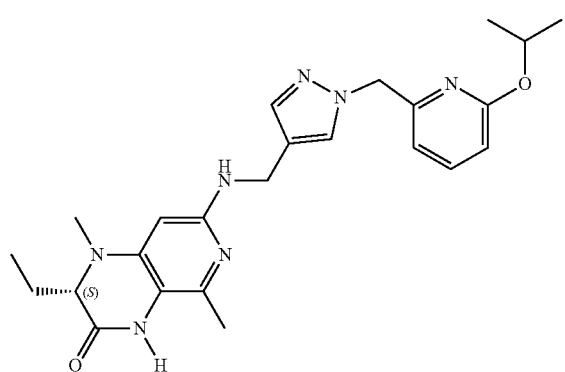
I-1281
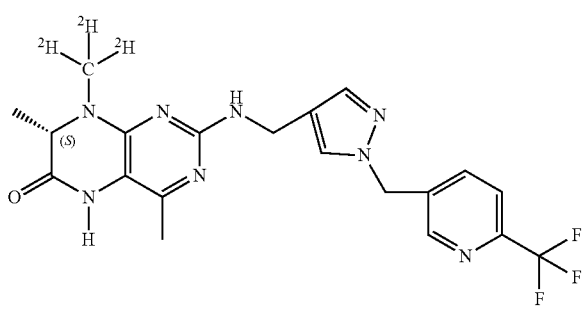
I-1282
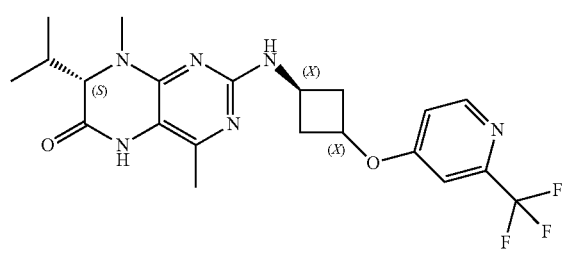
I-1283
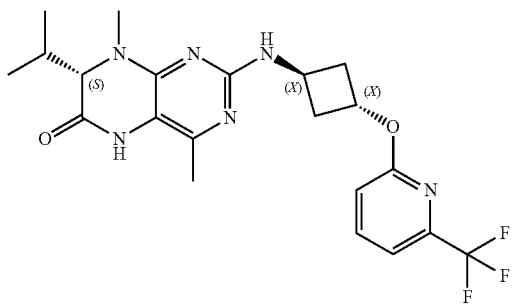
I-1284

TABLE C-continued

Exemplary Compounds

I-1285
I-1286
I-1287
I-1288
I-1289
I-1290

TABLE C-continued
Exemplary Compounds
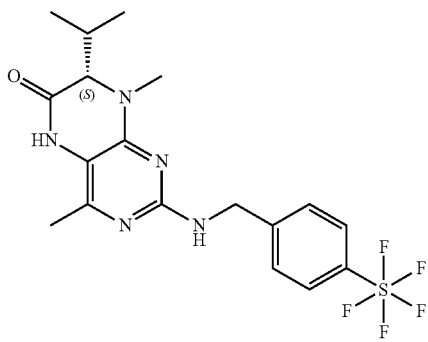
I-1291
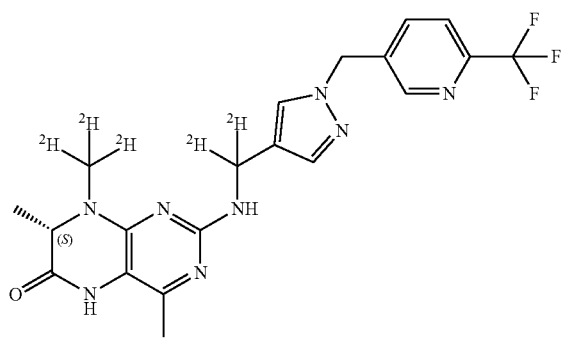
I-1292
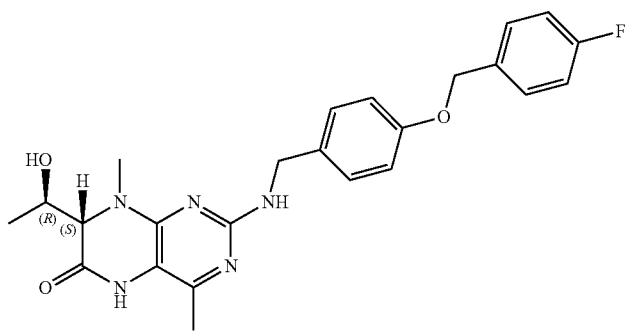
I-1293
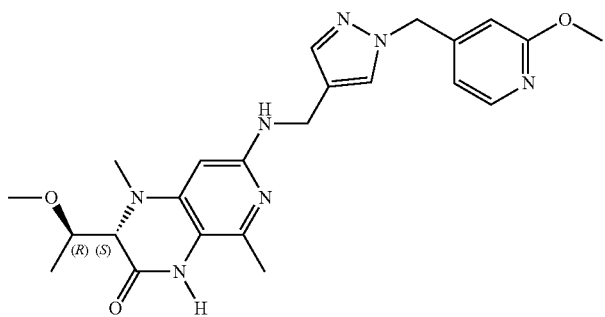
I-1294

TABLE C-continued
Exemplary Compounds
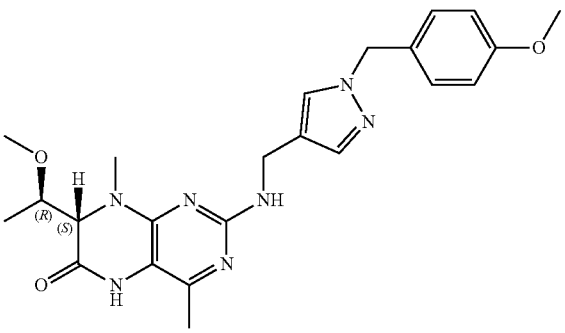
I-1295
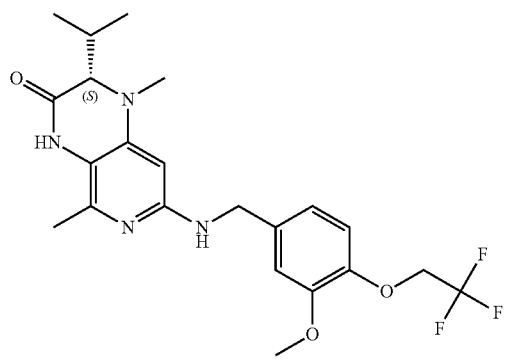
I-1296
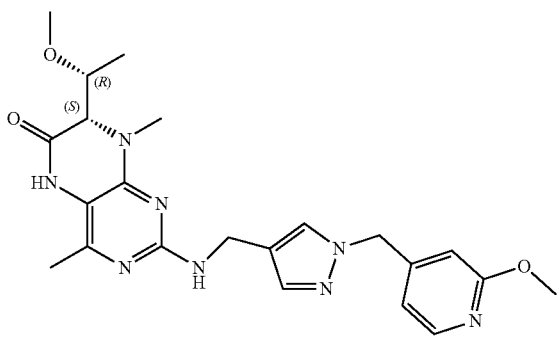
I-1297
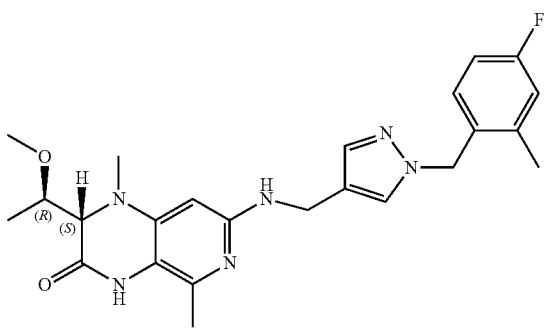
I-1298

TABLE C-continued
Exemplary Compounds
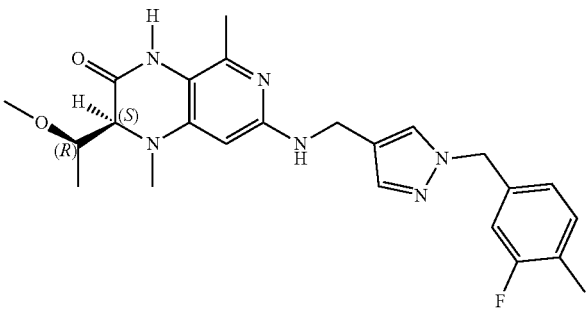
I-1299
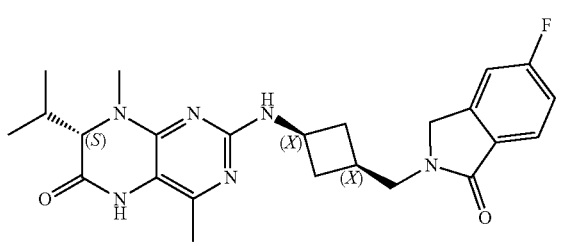
I-1300
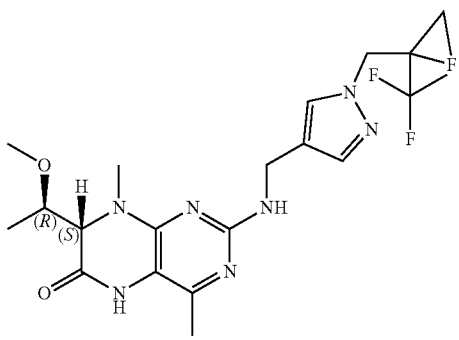
I-1301
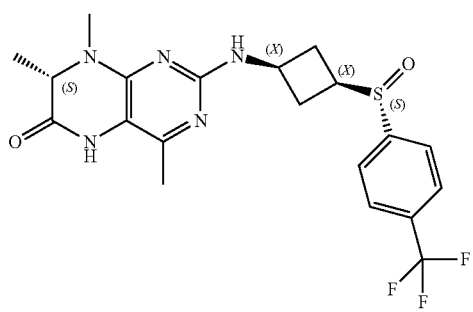
I-1302
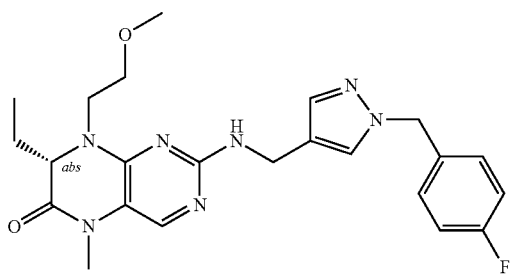
I-1303

TABLE C-continued
Exemplary Compounds
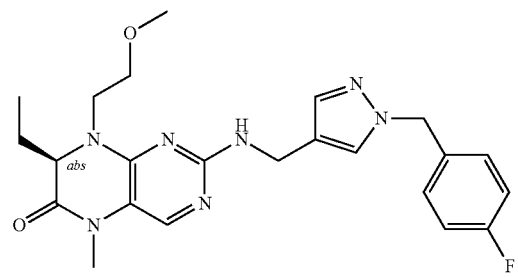
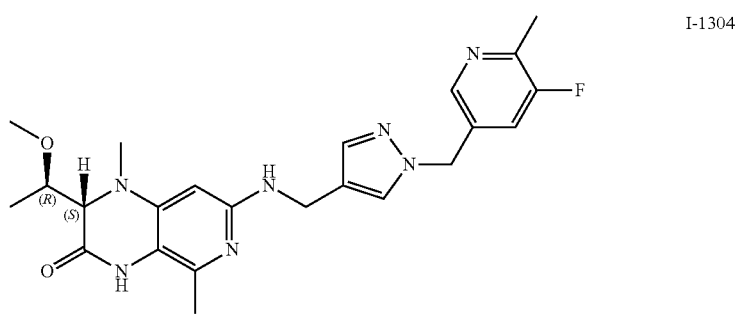
I-1304
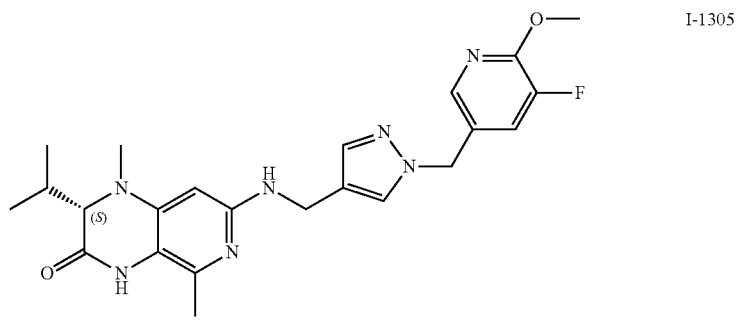
I-1305
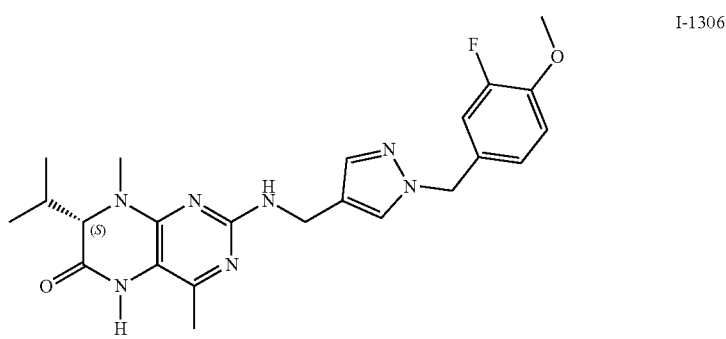
I-1306

TABLE C-continued
Exemplary Compounds
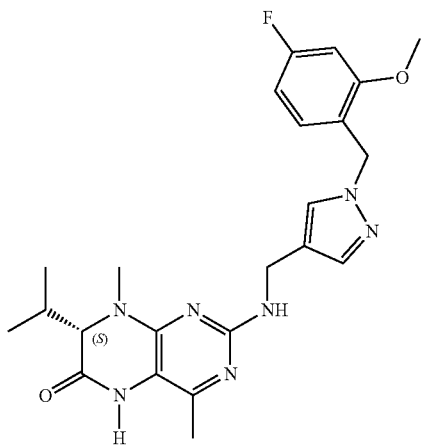
I-1307
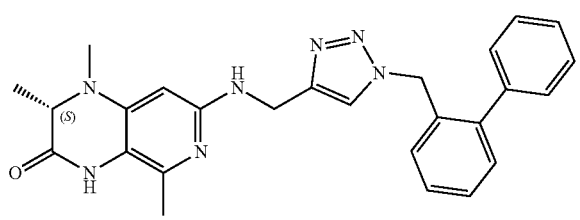
I-1308
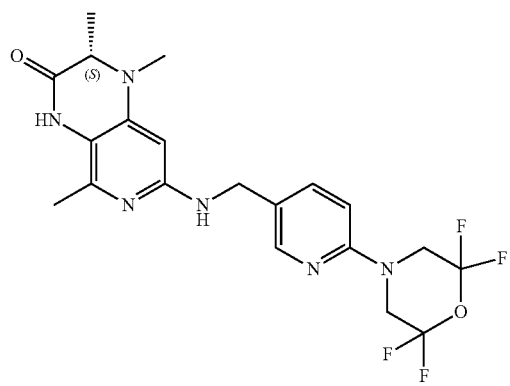
I-1309
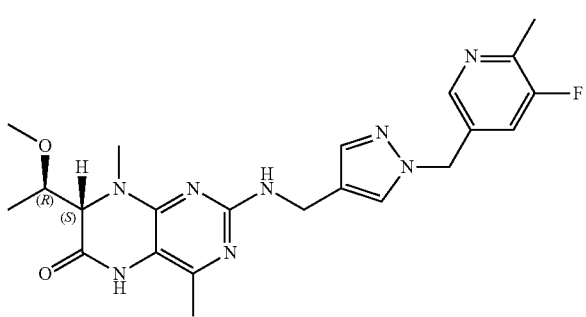
I-1310

TABLE C-continued
Exemplary Compounds
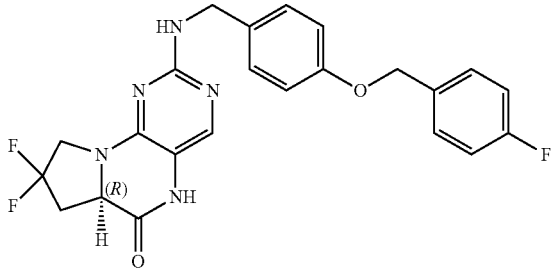
I-1311
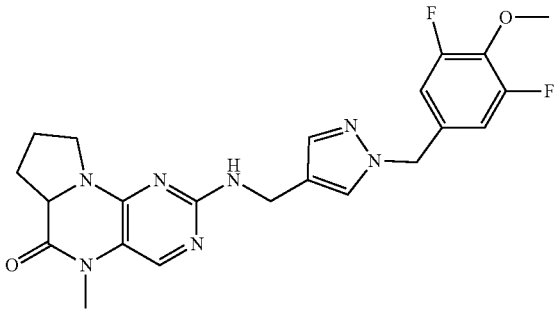 [SMILES: COc1c(F)cc(Cn2cc(CNc3ncc4c(n3)N3CCCC3C(=O)N4C)cn2)cc1F]
I-1312
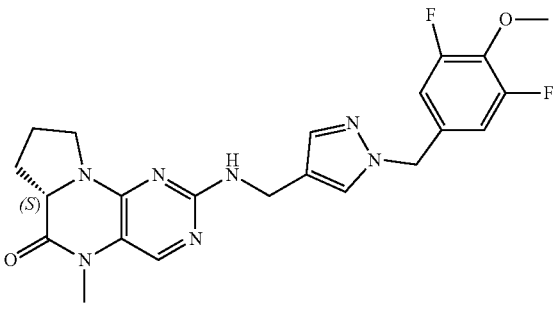
I-1313
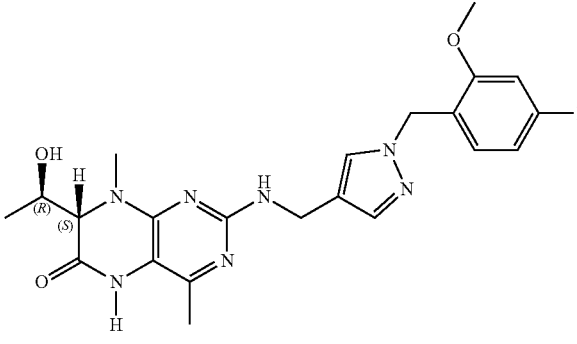
I-1314
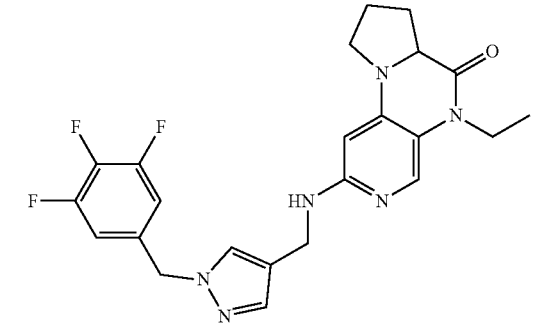 [SMILES: CCN1C(=O)C2CCCN2c2cc(NCc3cnn(Cc4cc(F)c(F)c(F)c4)c3)ncc21]
I-1315

TABLE C-continued
Exemplary Compounds
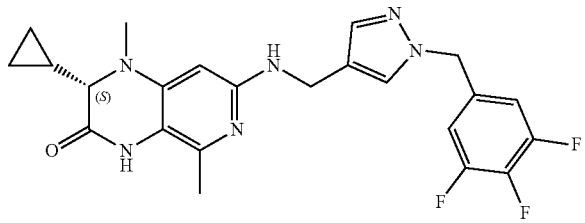
I-1316
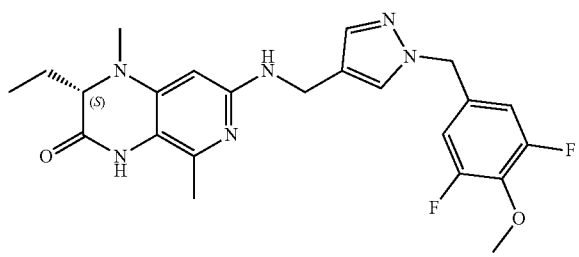
I-1317
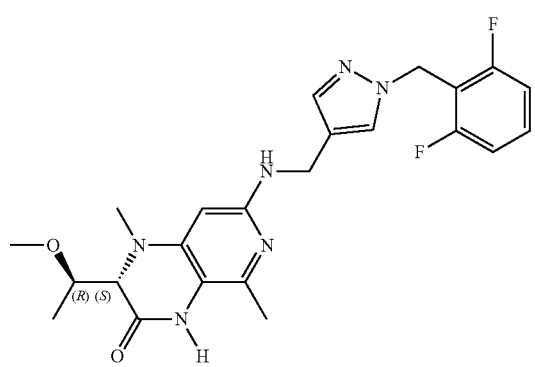
I-1318
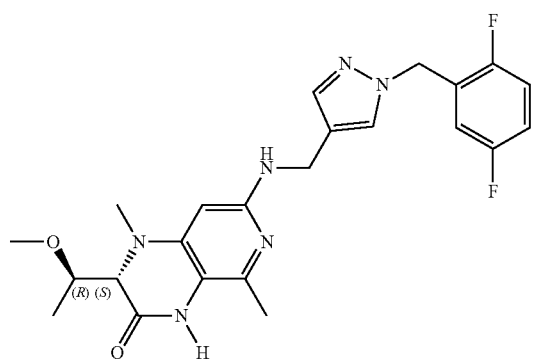
I-1319
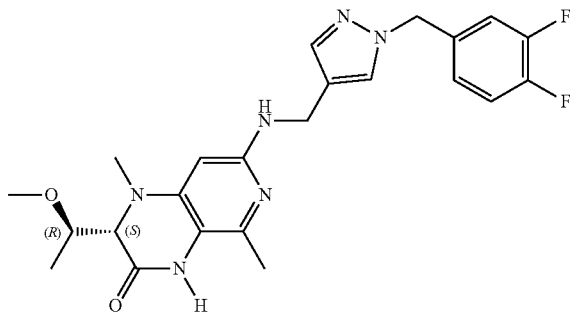
I-1320

TABLE C-continued
Exemplary Compounds
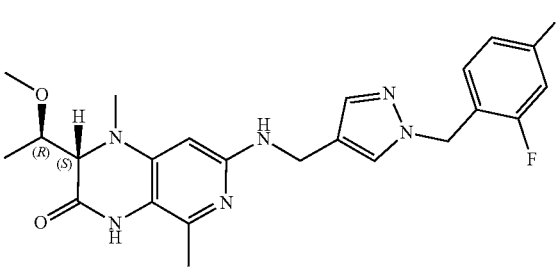
I-1321
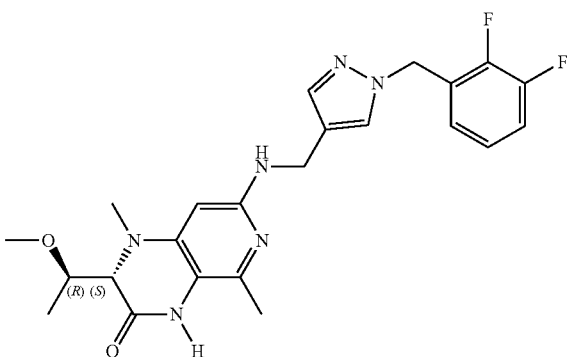
I-1322
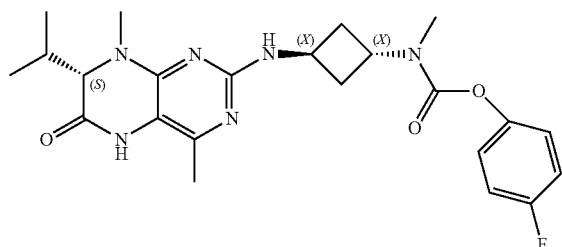
I-1323
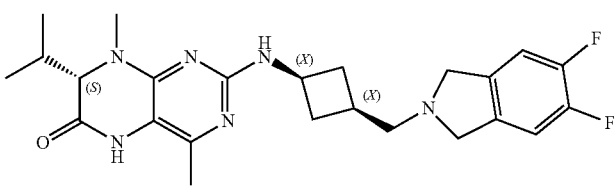
I-1324
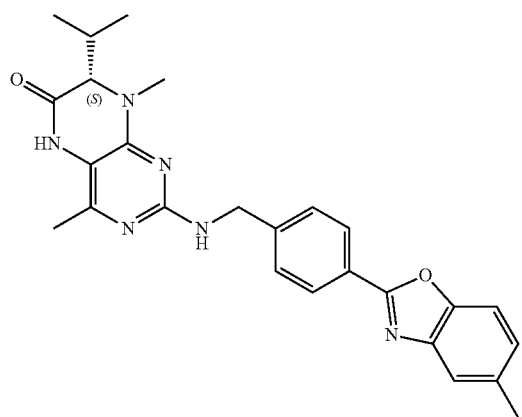
I-1325

TABLE C-continued
Exemplary Compounds
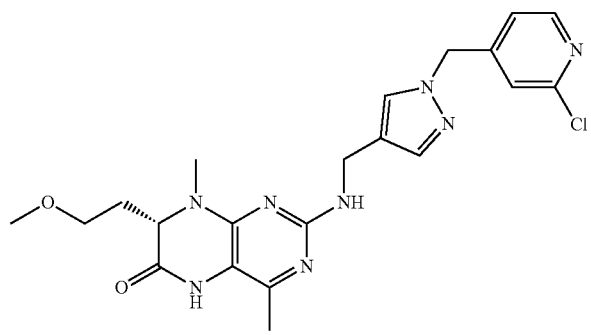 [SMILES: COCC[C@H]1C(=O)Nc2c(C)nc(NCc3cnn(Cc4ccnc(Cl)c4)c3)nc2N1C]
I-1326
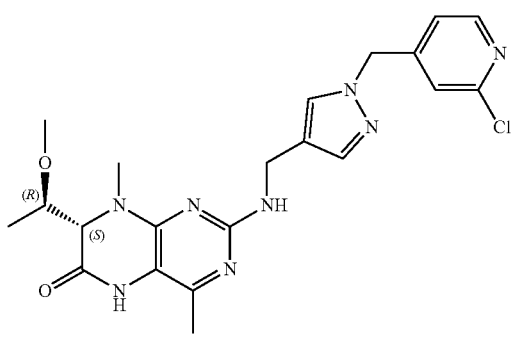
I-1327
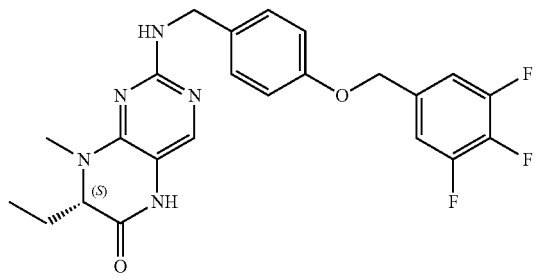
I-1328
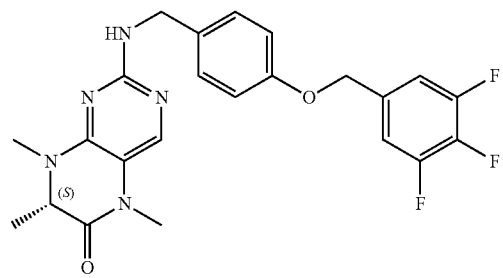
I-1329
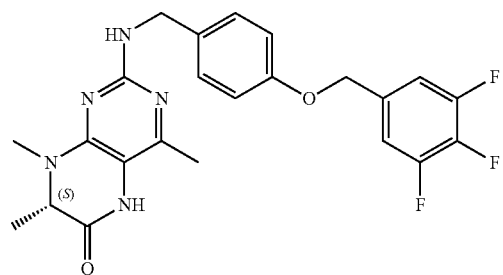
I-1330

TABLE C-continued
Exemplary Compounds
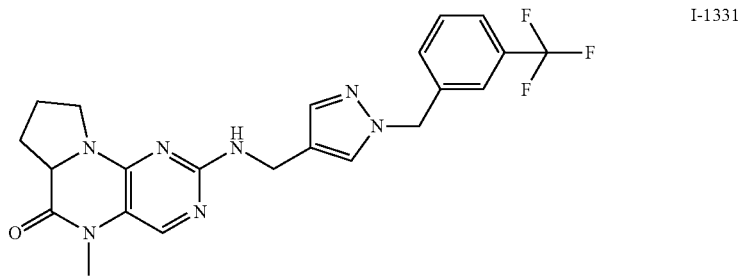 I-1331
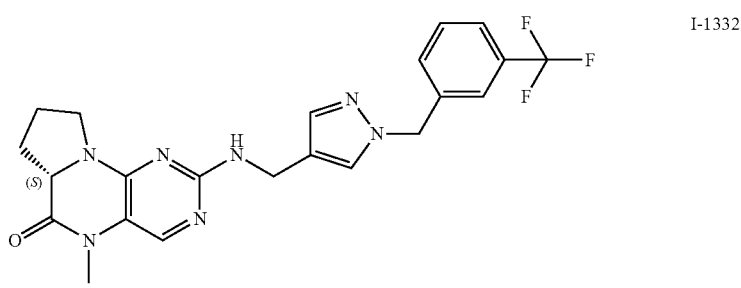 I-1332
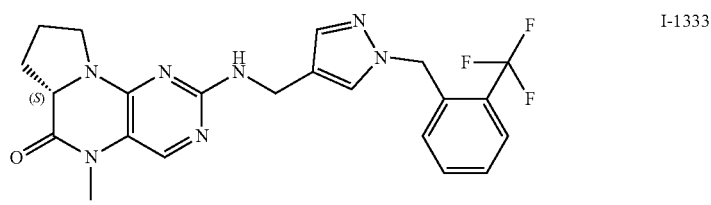 I-1333
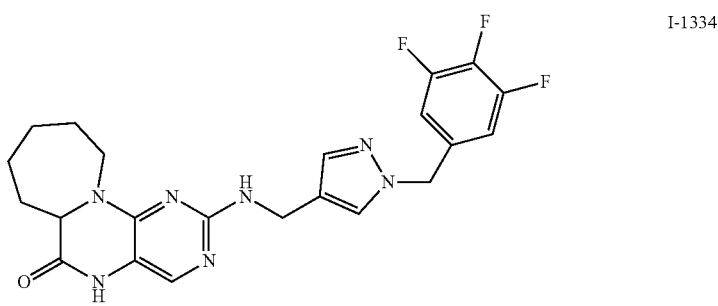 I-1334
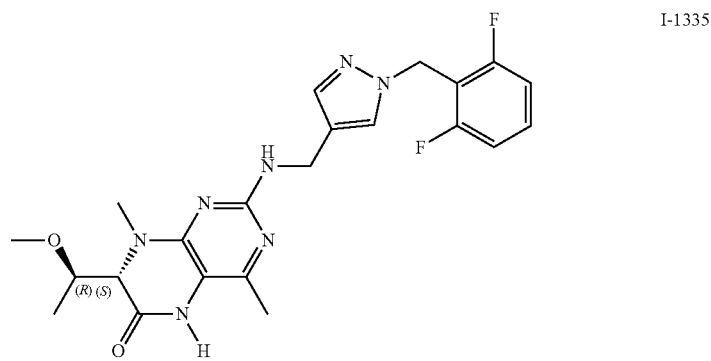 I-1335

TABLE C-continued
Exemplary Compounds
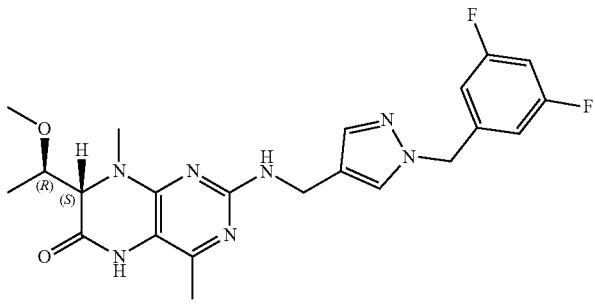
I-1336
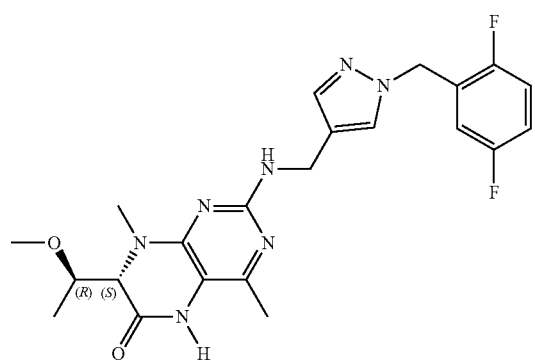
I-1337
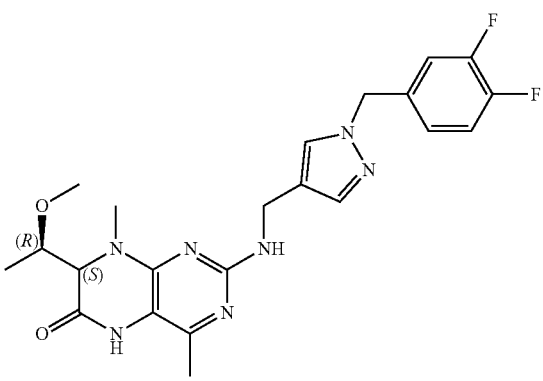
I-1338
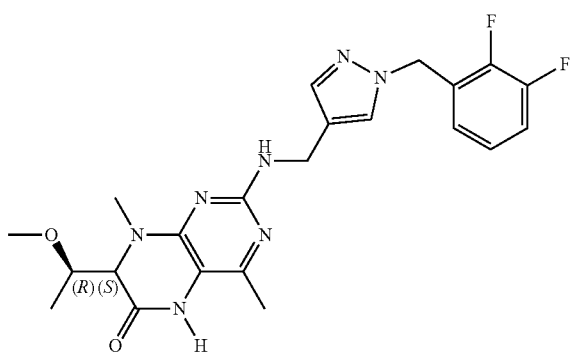
I-1339

TABLE C-continued
Exemplary Compounds
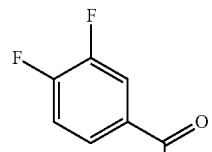
I-1340
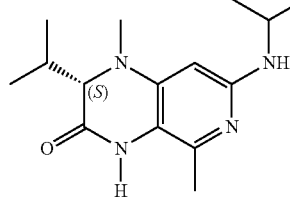
I-1341
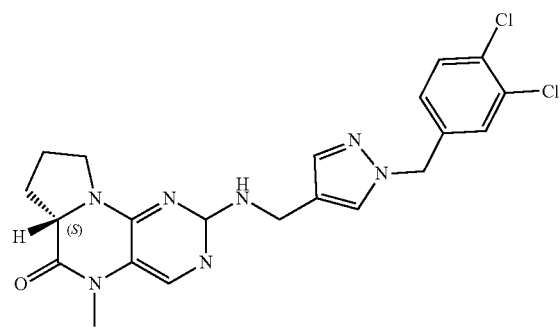
I-1342
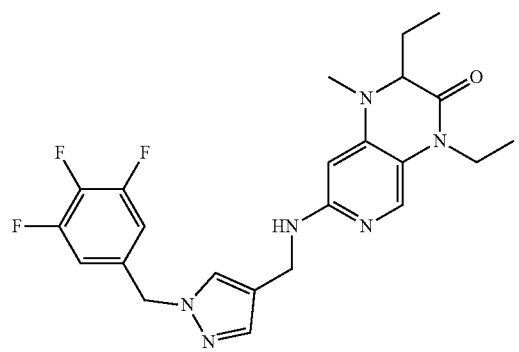 [SMILES: CCC1C(=O)N(CC)c2cnc(NCc3cnn(Cc4cc(F)c(F)c(F)c4)c3)cc2N1C]
I-1343
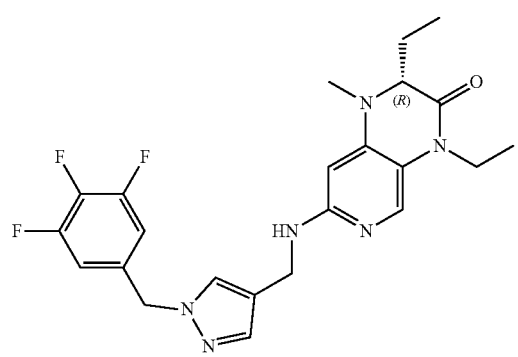

TABLE C-continued
Exemplary Compounds
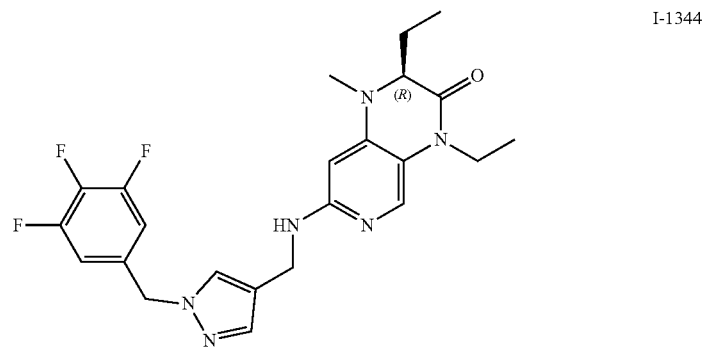
I-1344
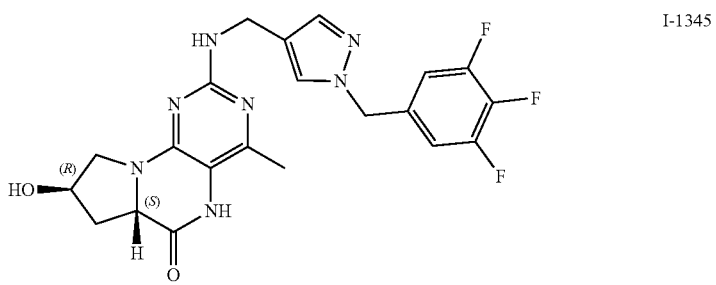
I-1345
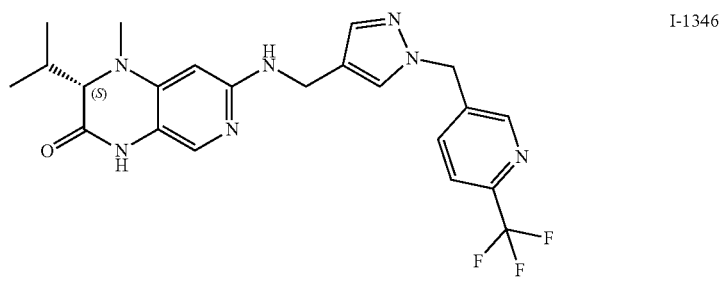
I-1346
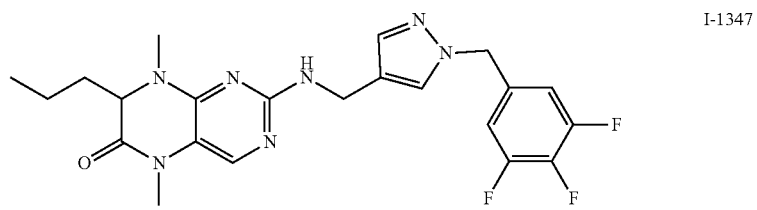
I-1347
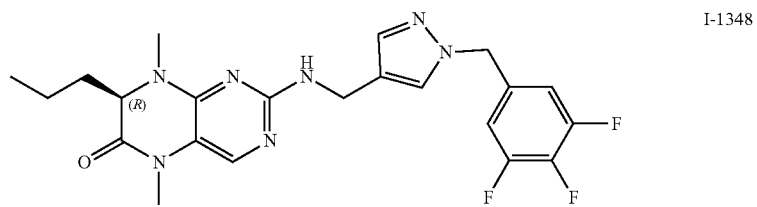
I-1348
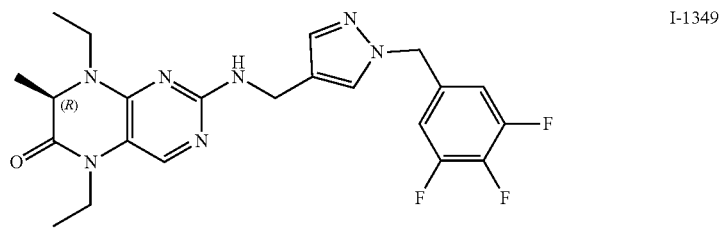
I-1349

TABLE C-continued
Exemplary Compounds
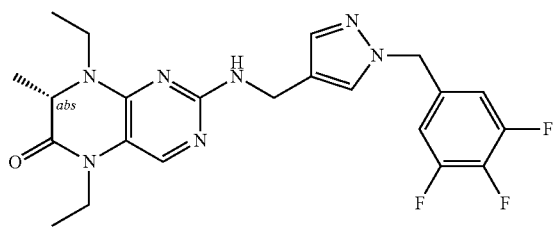
I-1350
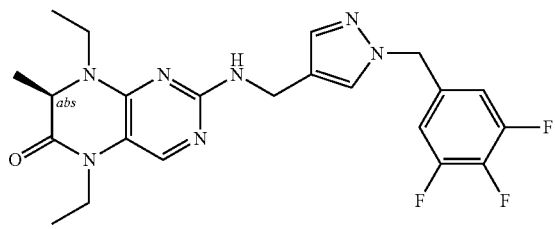
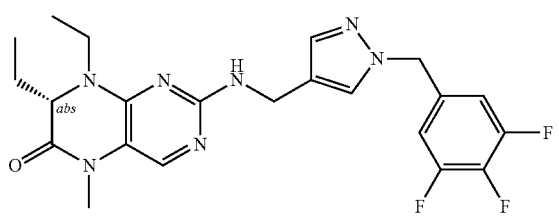
I-1351
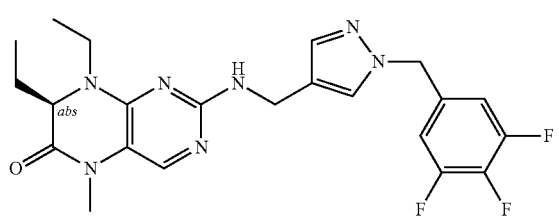
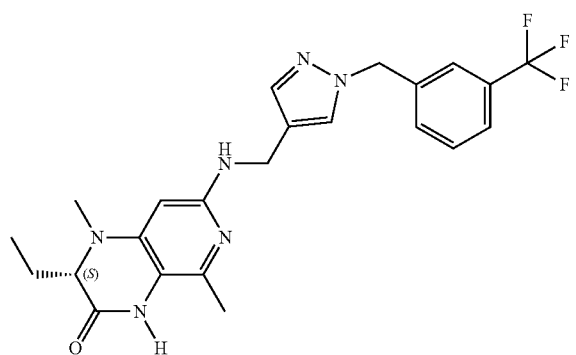
I-1352

TABLE C-continued

Exemplary Compounds

I-1353

I-1354

I-1355

I-1356

I-1357

TABLE C-continued
Exemplary Compounds
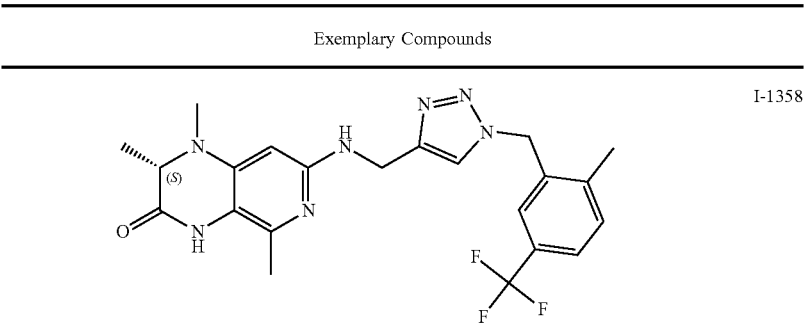
I-1358
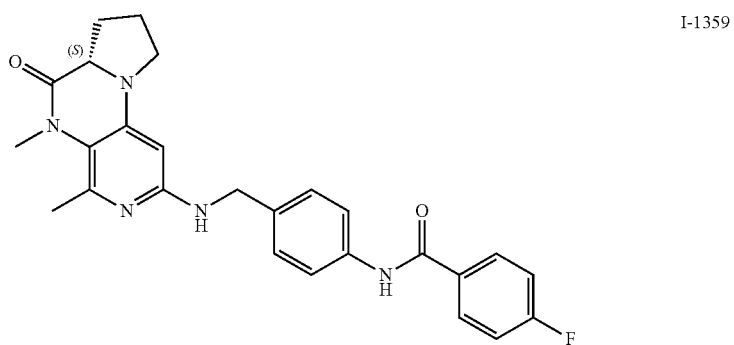
I-1359
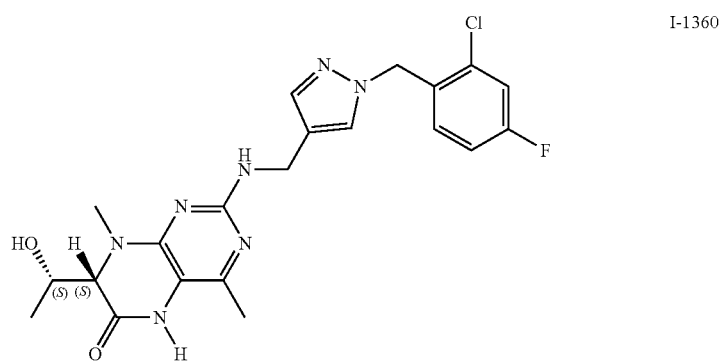
I-1360
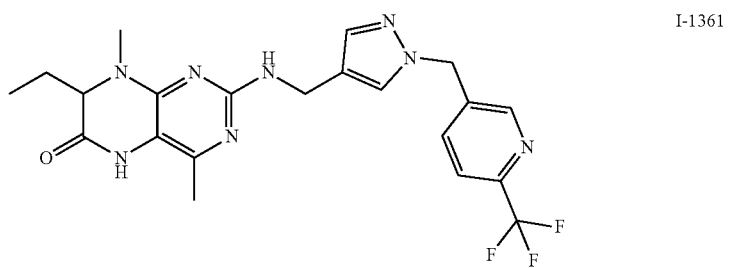
I-1361

TABLE C-continued
Exemplary Compounds
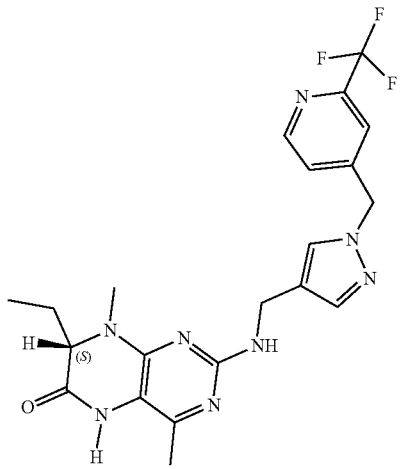
I-1362
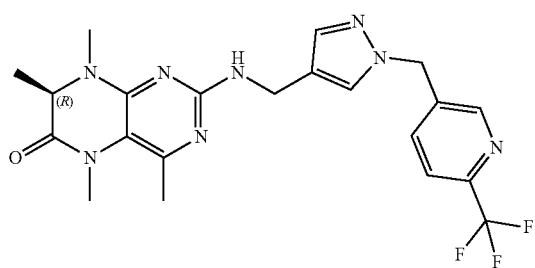
I-1363
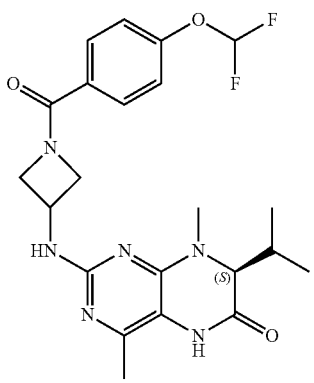
I-1364
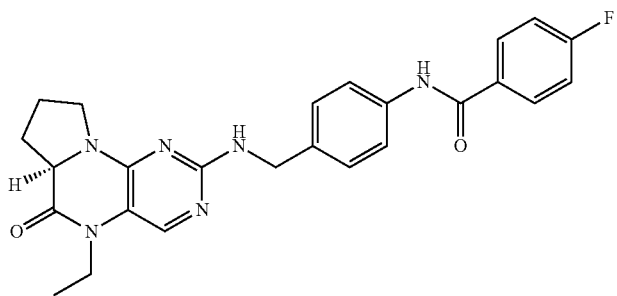 [SMILES: CCN1C(=O)[C@H]2CCCN2c2nc(NCc3ccc(NC(=O)c4ccc(F)cc4)cc3)ncc21]
I-1365

TABLE C-continued
Exemplary Compounds
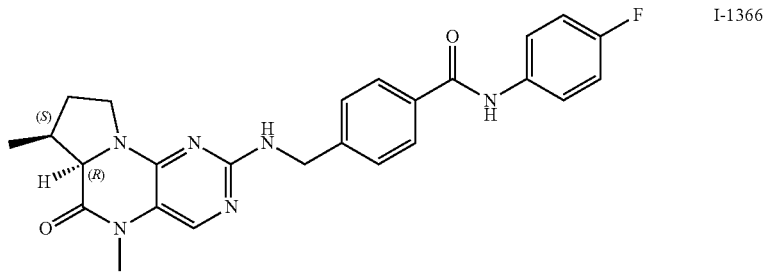
I-1366
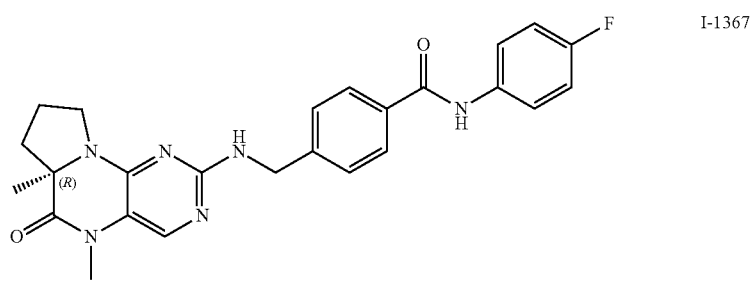
I-1367
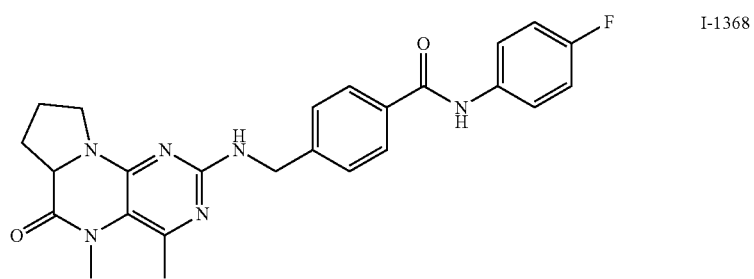
I-1368
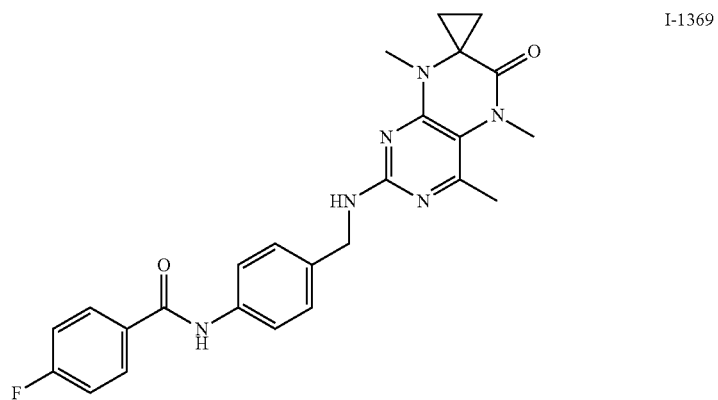
I-1369
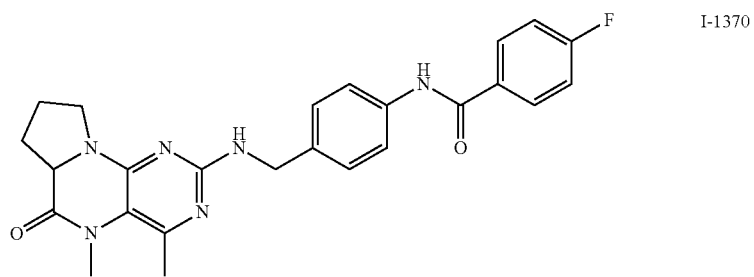
I-1370

US 11,572,364 B2
621                                                                                                622
TABLE C-continued
Exemplary Compounds
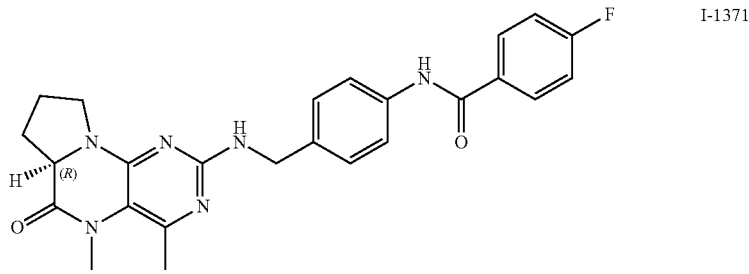 I-1371
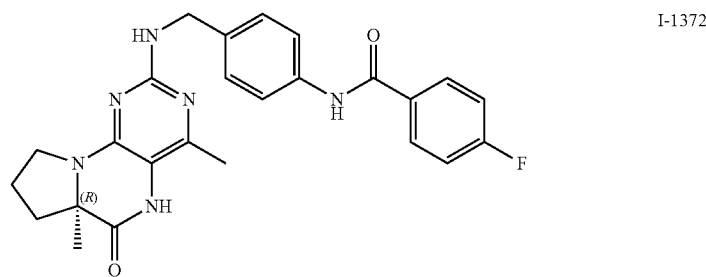 I-1372
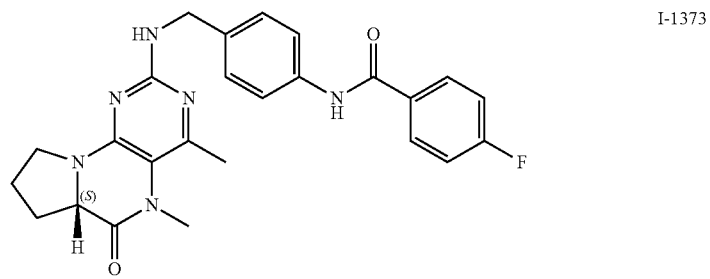 I-1373
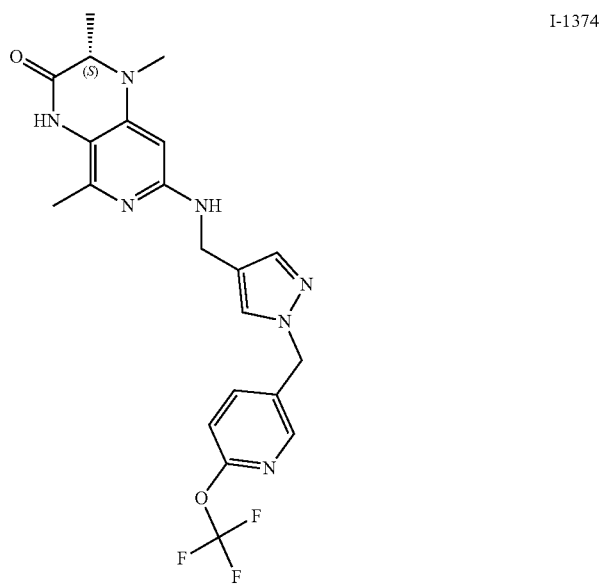 I-1374

TABLE C-continued
Exemplary Compounds
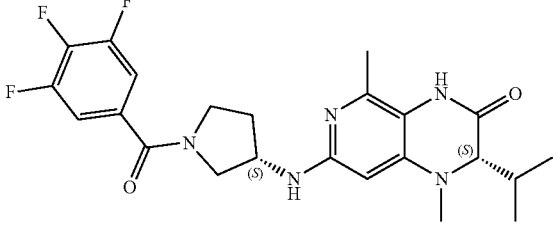
I-1375
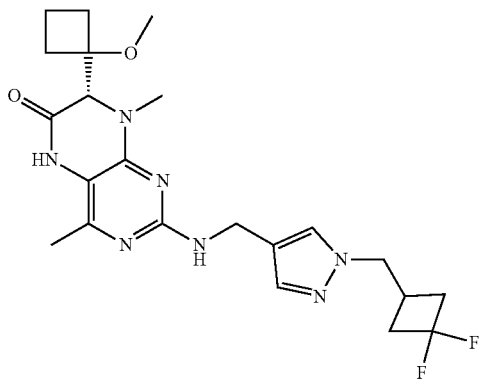 [SMILES: COC1([C@H]2C(=O)Nc3c(C)nc(NCc4cnn(CC5CC(F)(F)C5)c4)nc3N2C)CCC1]
I-1376
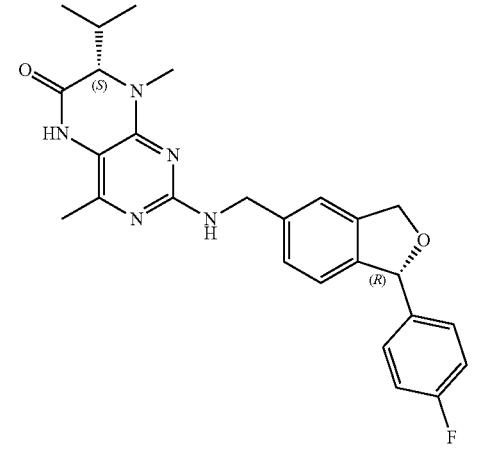
I-1377
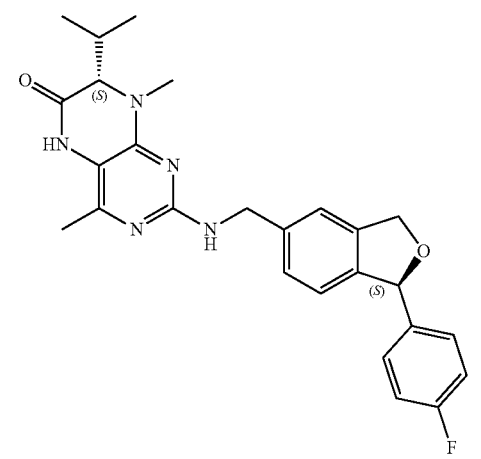
I-1378

TABLE C-continued
Exemplary Compounds
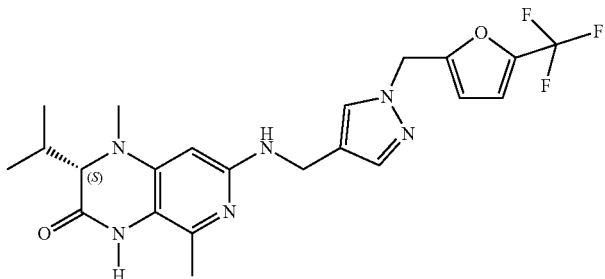
I-1379
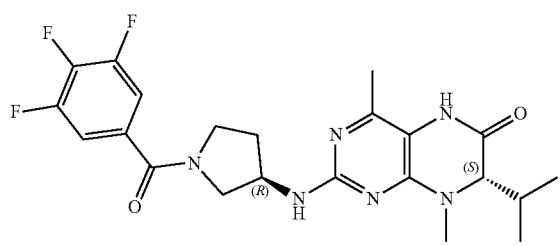
I-1380
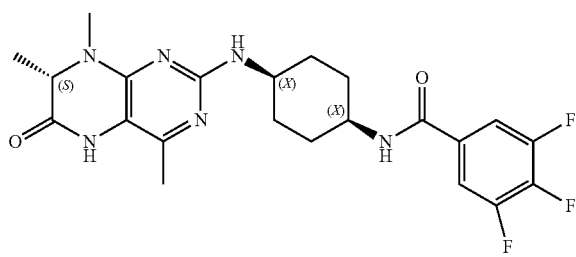
I-1381
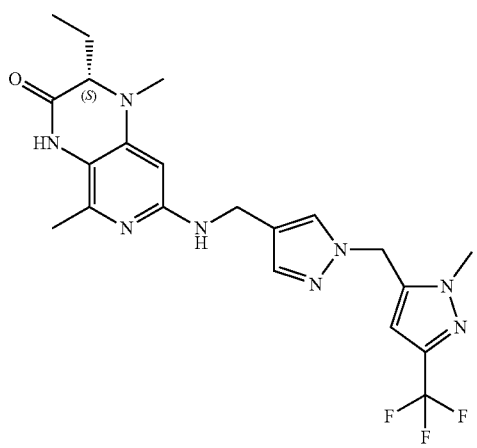
I-1382
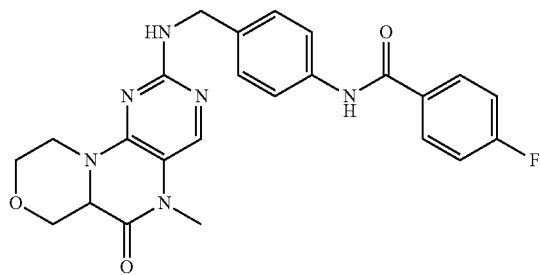 [SMILES: CN1C(=O)C2COCCN2c2nc(NCc3ccc(NC(=O)c4ccc(F)cc4)cc3)ncc21]
I-1383

TABLE C-continued
Exemplary Compounds
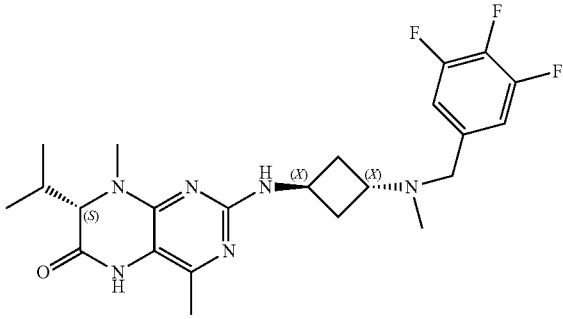
I-1384
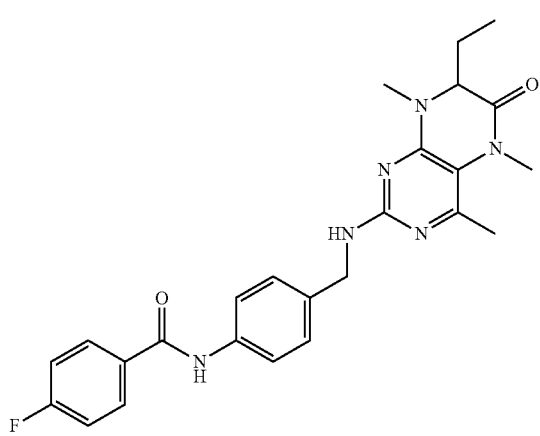 [SMILES: CCC1C(=O)N(C)c2c(C)nc(NCc3ccc(NC(=O)c4ccc(F)cc4)cc3)nc2N1C]
I-1385
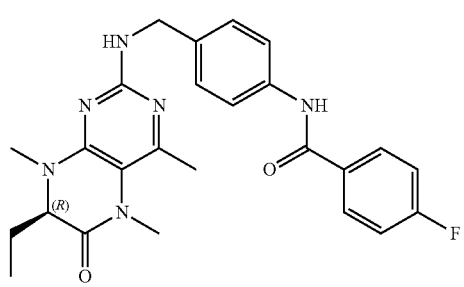
I-1386
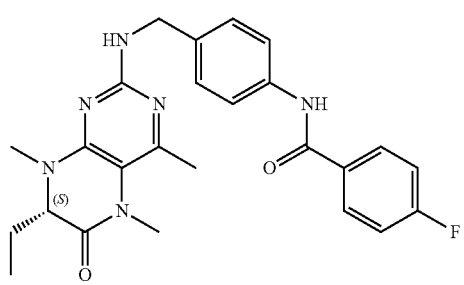
I-1387

TABLE C-continued
Exemplary Compounds
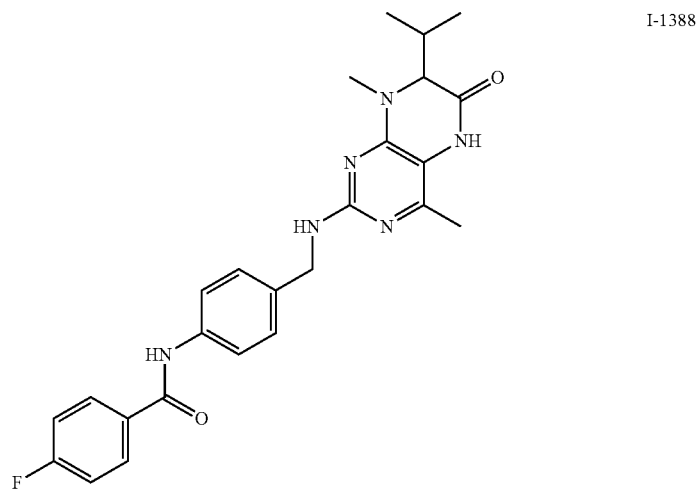
I-1388
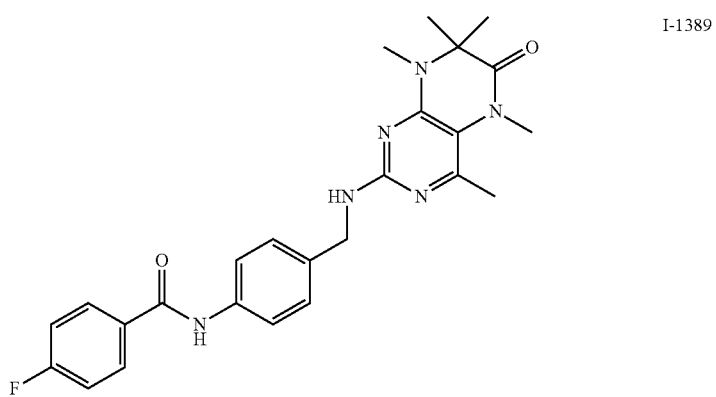
I-1389
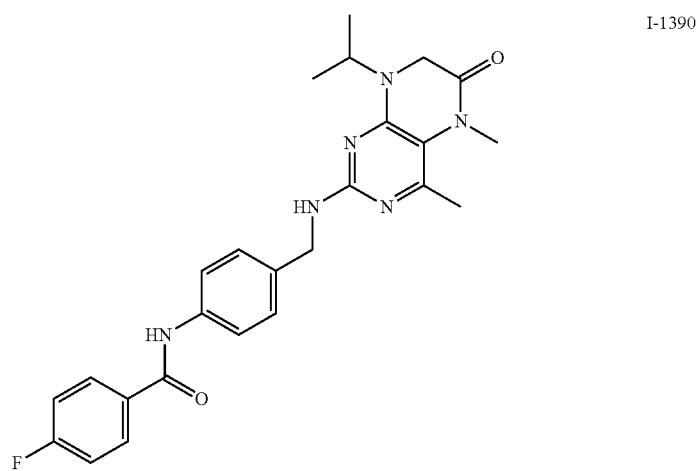
I-1390

TABLE C-continued
Exemplary Compounds
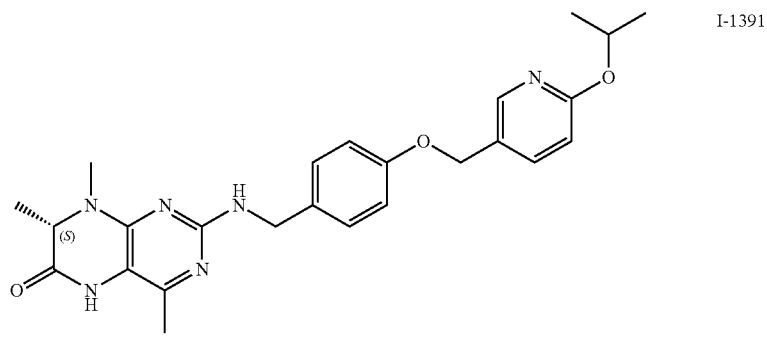
I-1391
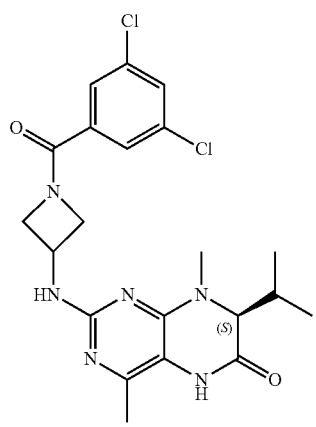
I-1392
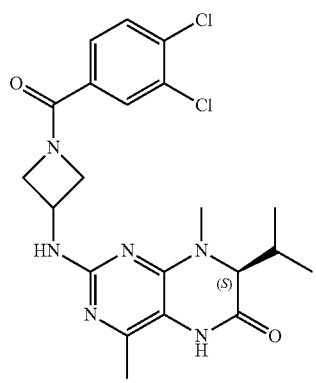
I-1393
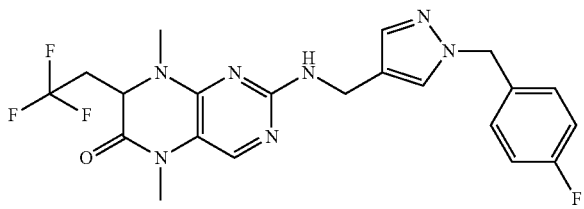 [SMILES: CN1C(=O)C(CC(F)(F)F)N(C)c2nc(NCc3cnn(Cc4ccc(F)cc4)c3)ncc21]
I-1394
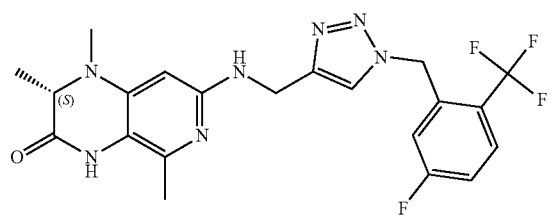
I-1395

TABLE C-continued
Exemplary Compounds
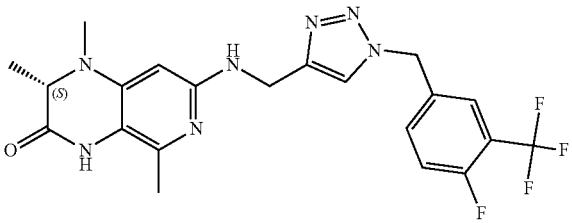 I-1396
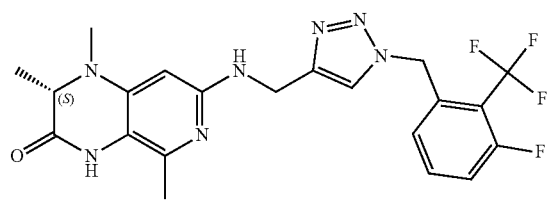 I-1397
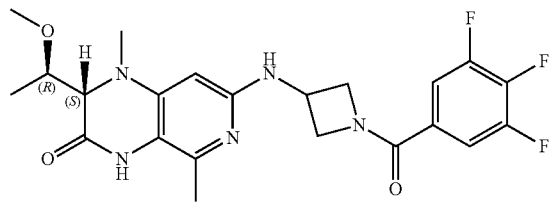 I-1398
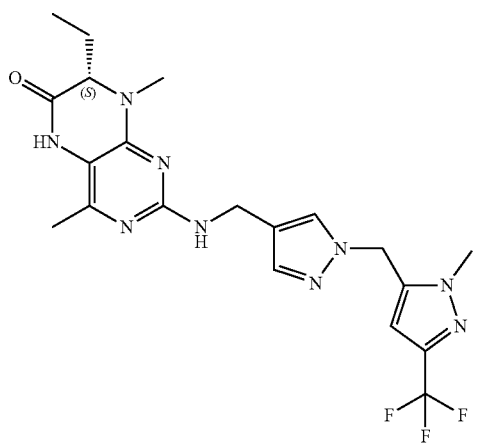 I-1399
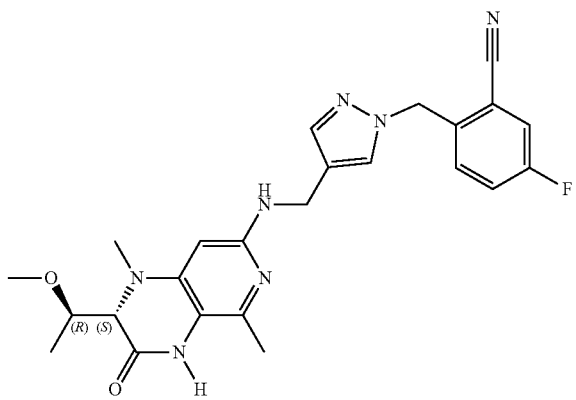 I-1400

TABLE C-continued
Exemplary Compounds
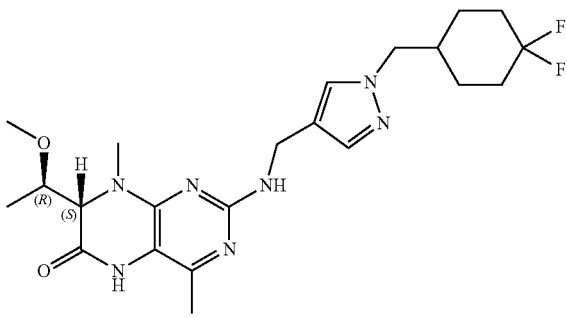
I-1401
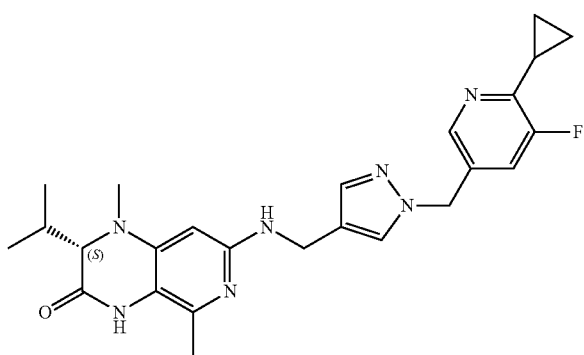
I-1402
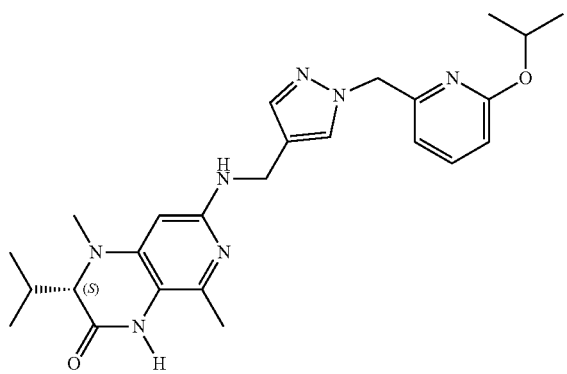
I-1403
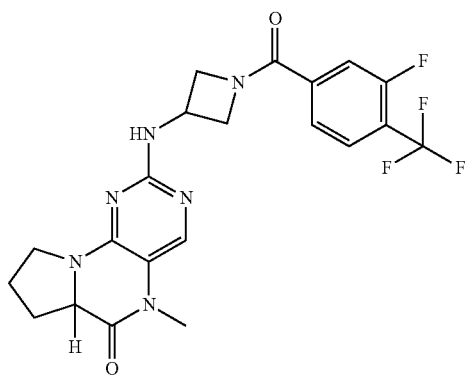 [SMILES: CN1C(=O)C2CCCN2c2nc(NC3CN(C(=O)c4ccc(C(F)(F)F)c(F)c4)C3)ncc21]
I-1404

TABLE C-continued

Exemplary Compounds

I-1405

I-1406

I-1407

I-1408

I-1409

TABLE C-continued
Exemplary Compounds
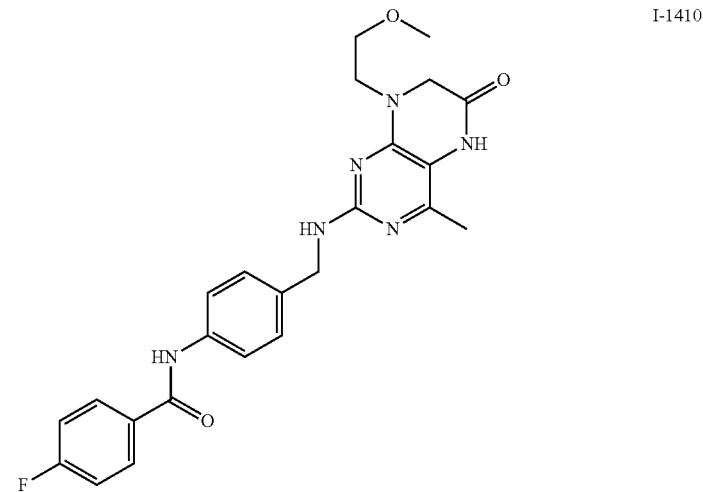
I-1410
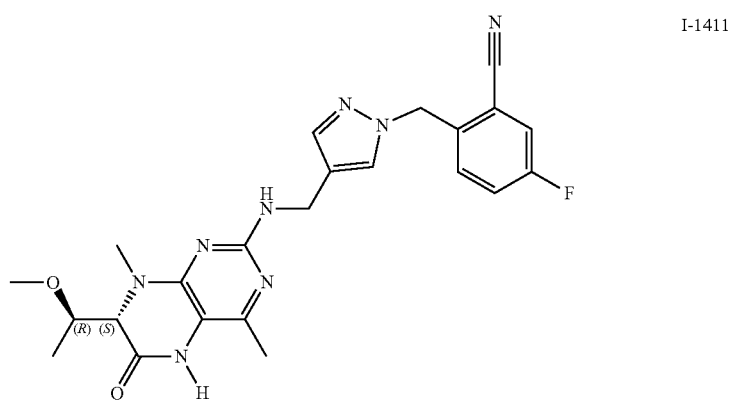
I-1411
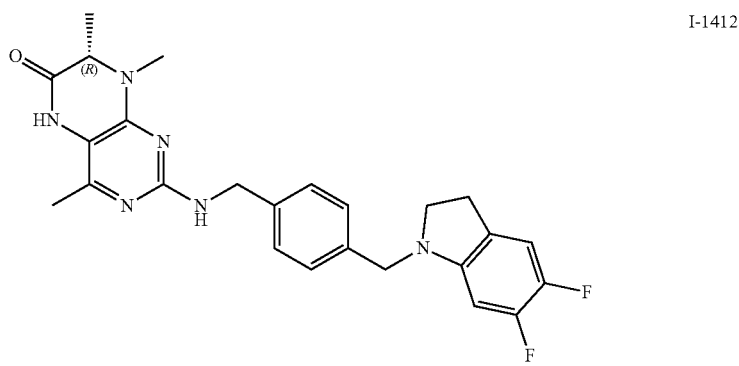
I-1412

TABLE C-continued
Exemplary Compounds
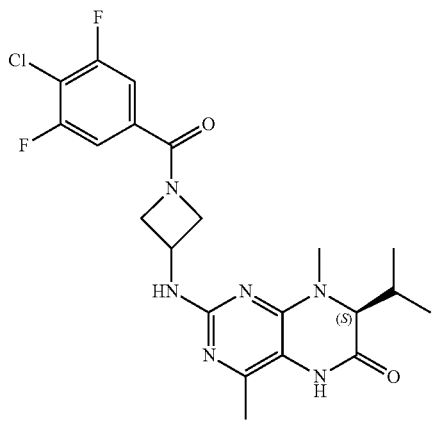
I-1413
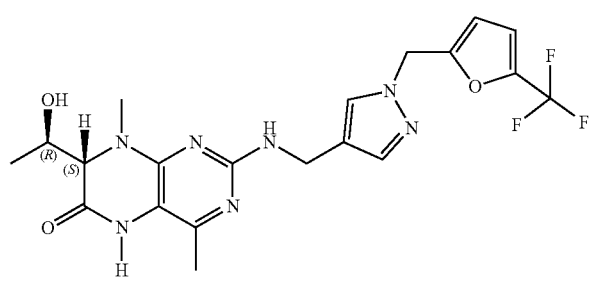
I-1414
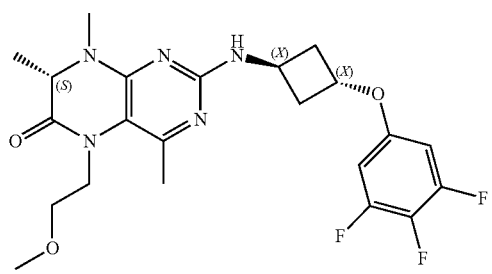
I-1415
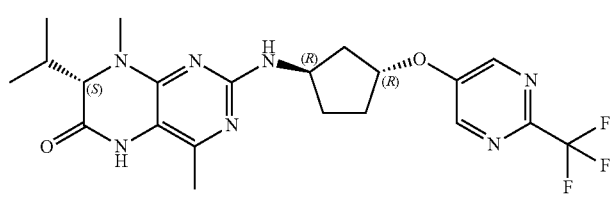
I-1416
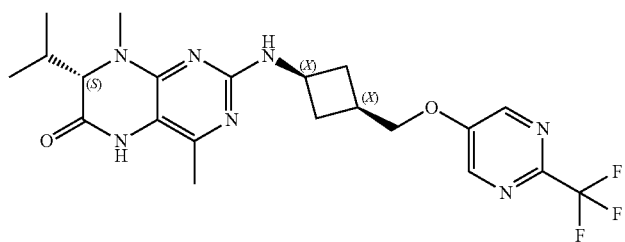
I-1417

TABLE C-continued
Exemplary Compounds
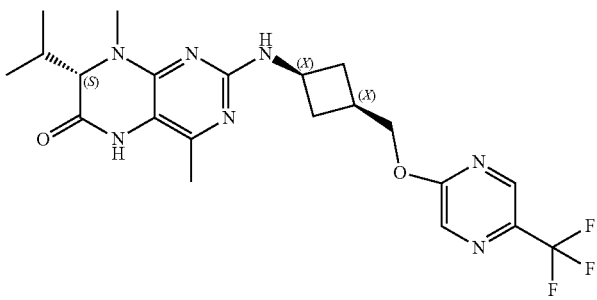
I-1418
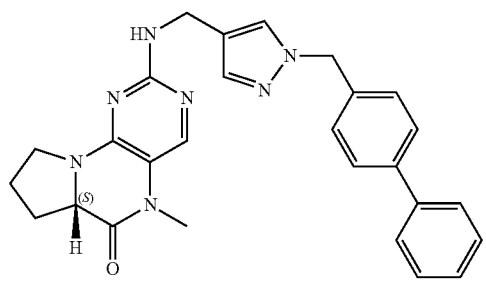
I-1419
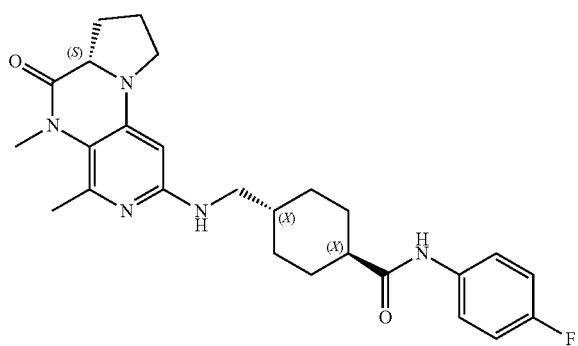
I-1420
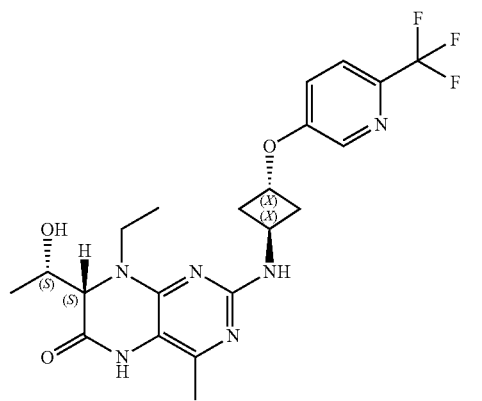
I-1421

TABLE C-continued

Exemplary Compounds

| | |
|---|---|
| (structure) | I-1422 |
| (structure) | I-1423 |
| (structure) | I-1424 |
| (structure) | I-1425 |
| (structure) | I-1426 |

TABLE C-continued
Exemplary Compounds
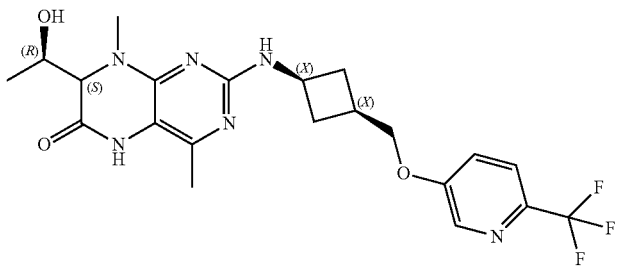
I-1427
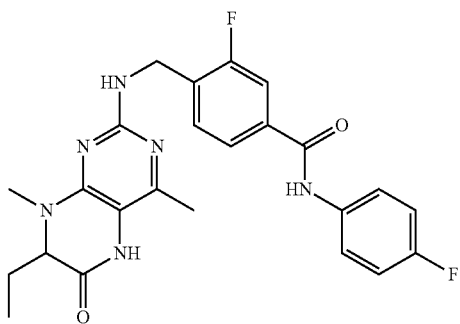 [SMILES: CCC1C(=O)Nc2c(C)nc(NCc3ccc(C(=O)Nc4ccc(F)cc4)cc3F)nc2N1C]
I-1428
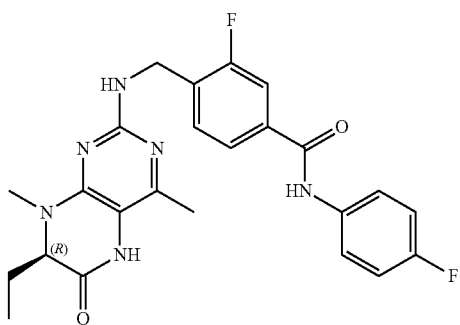
I-1429
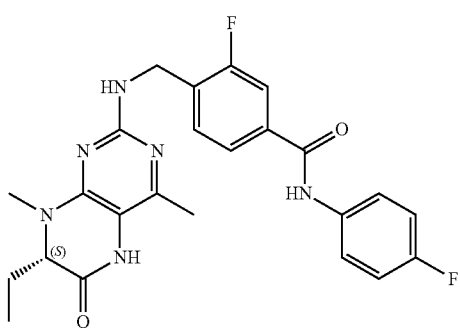
I-1430

TABLE C-continued
Exemplary Compounds
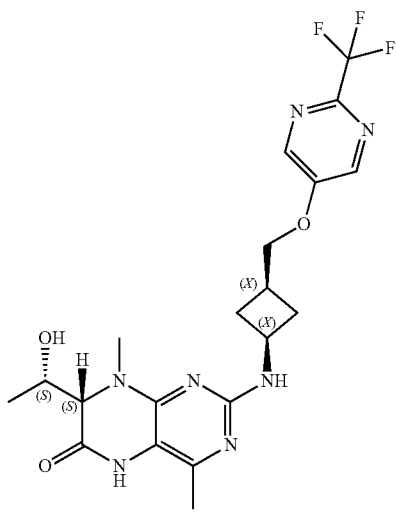
I-1431
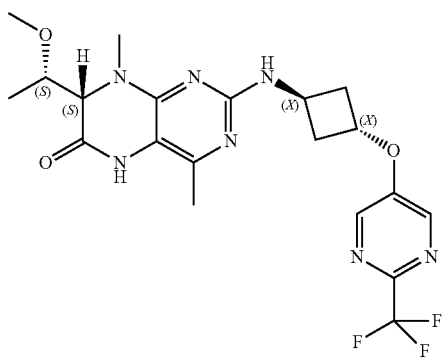
I-1432
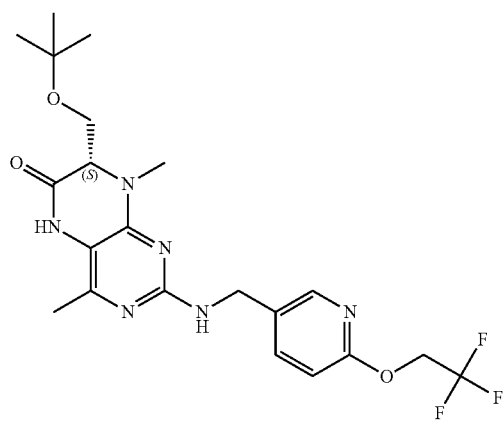
I-1433

TABLE C-continued
Exemplary Compounds
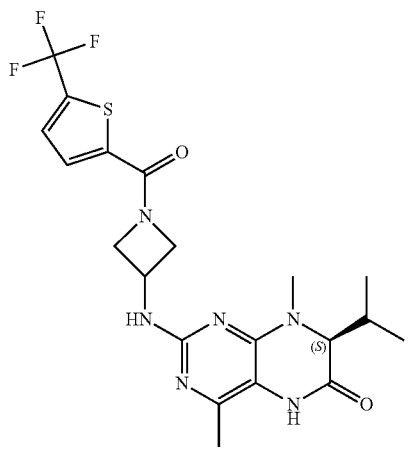
I-1434
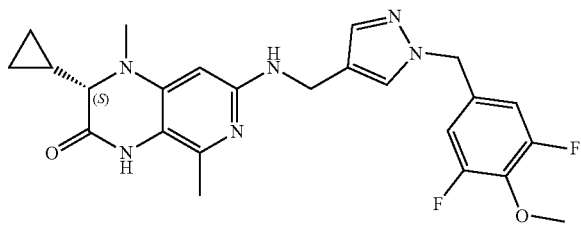
I-1435
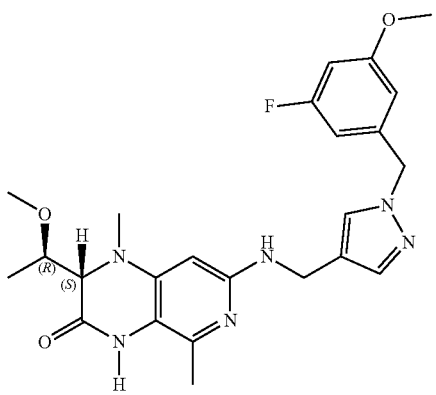
I-1436
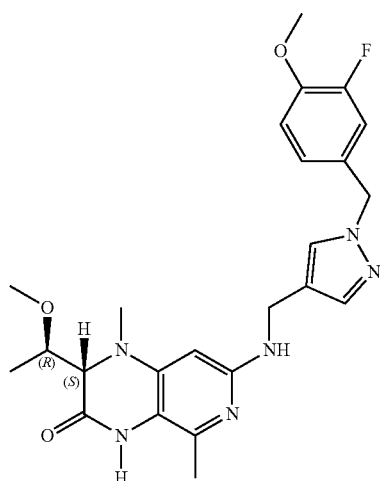
I-1437

TABLE C-continued
Exemplary Compounds
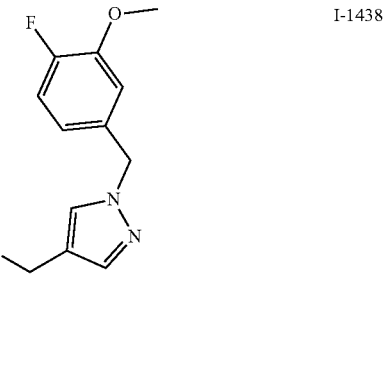
I-1438
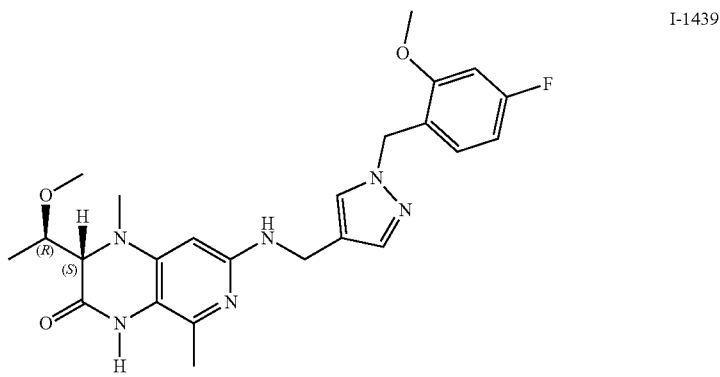
I-1439
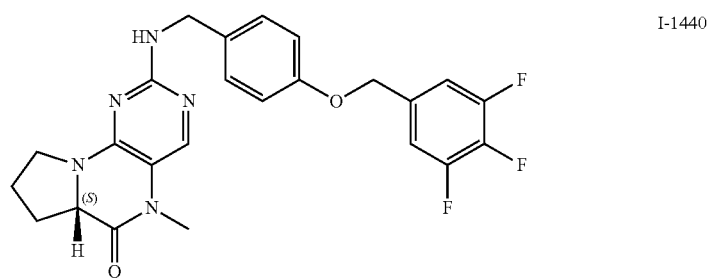
I-1440
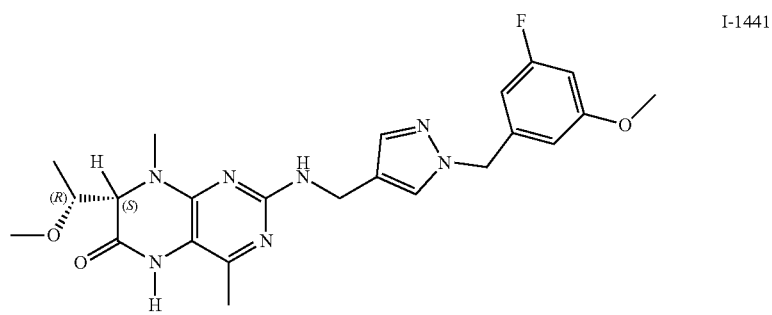
I-1441

TABLE C-continued
Exemplary Compounds
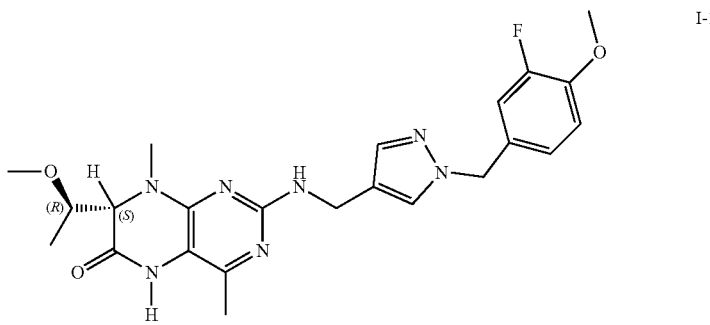
I-1442
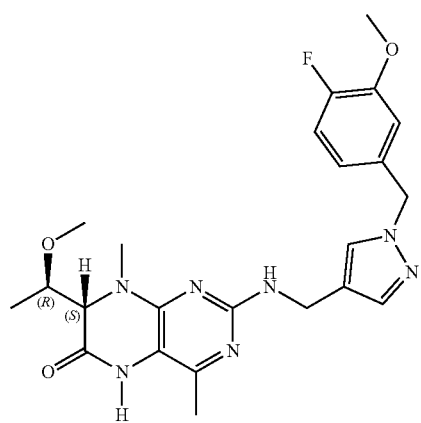
I-1443
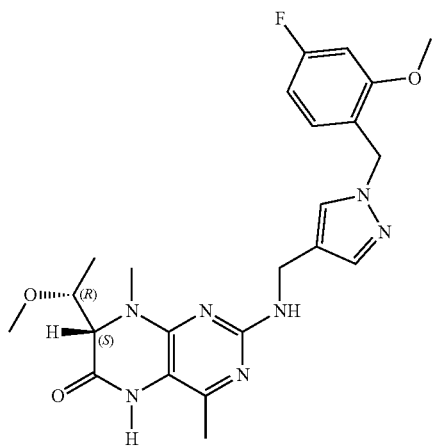
I-1444
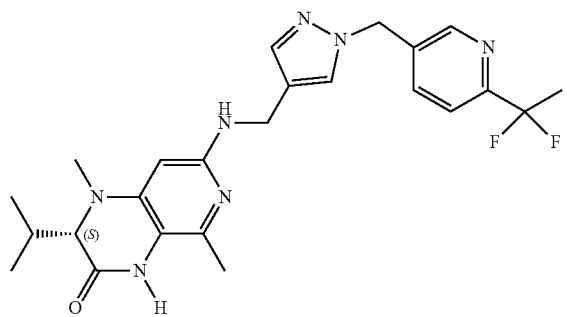
I-1445

TABLE C-continued
Exemplary Compounds
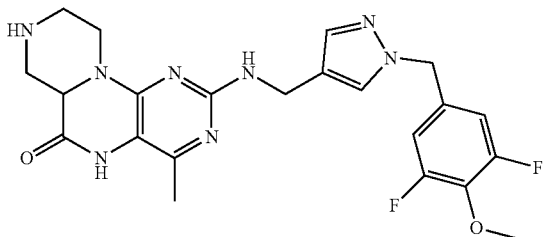
I-1446
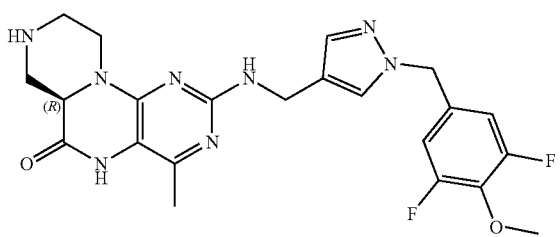
I-1447
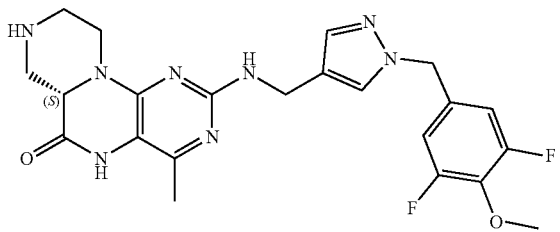
I-1448
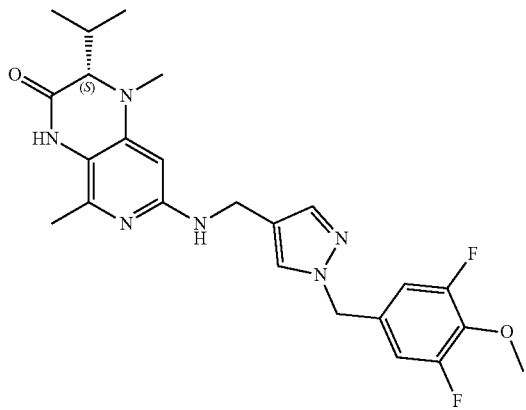
I-1449
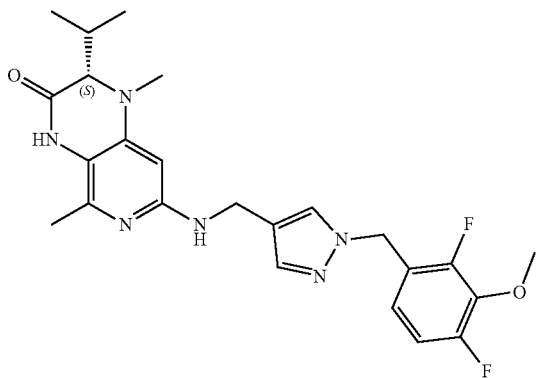
I-1450

TABLE C-continued
Exemplary Compounds
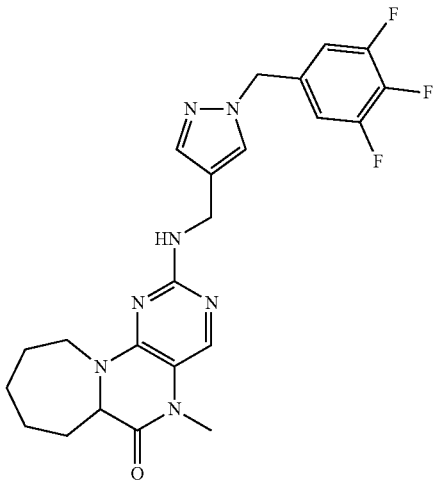 [SMILES: CN1C(=O)C2CCCCCN2c2nc(NCc3cnn(Cc4cc(F)c(F)c(F)c4)c3)ncc21]
I-1451
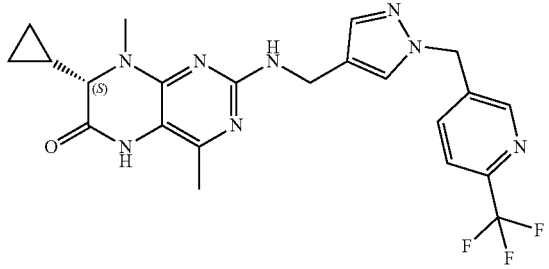
I-1452
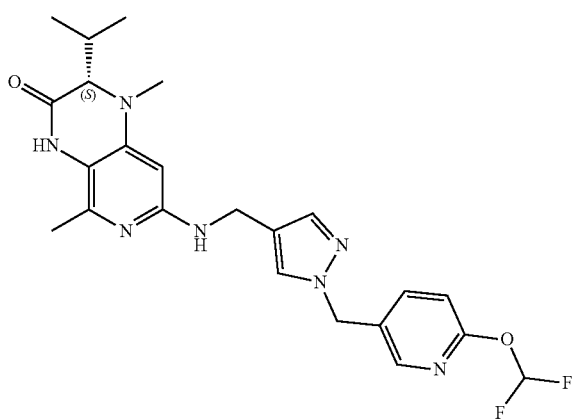
I-1453
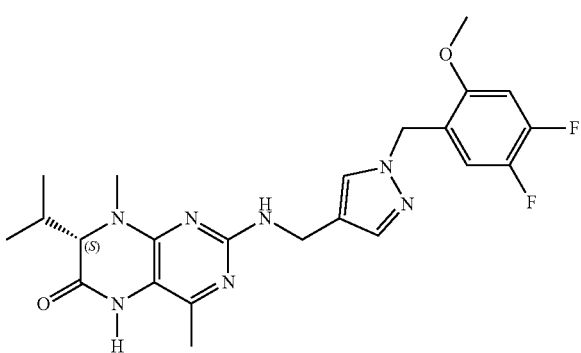
I-1454

TABLE C-continued
Exemplary Compounds
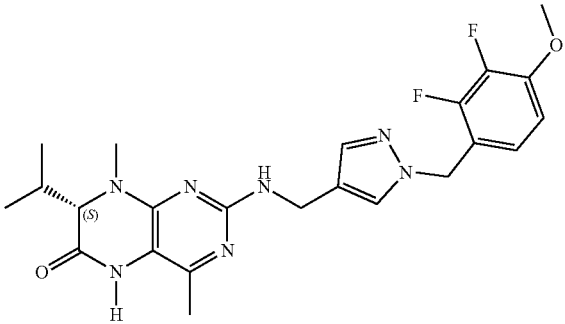
I-1455
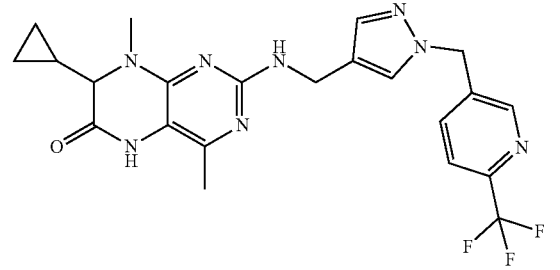 [SMILES: Cc1nc(NCc2cnn(Cc3ccc(C(F)(F)F)nc3)c2)nc2c1NC(=O)C(C1CC1)N2C]
I-1456
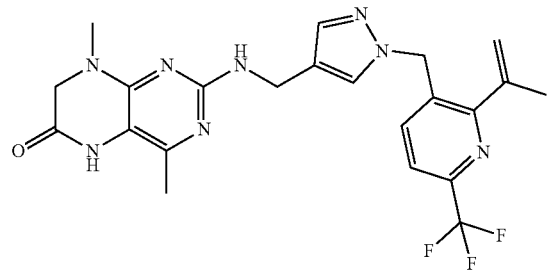 [SMILES: C=C(C)c1nc(C(F)(F)F)ccc1Cn1cc(CNc2nc(C)c3c(n2)N(C)CC(=O)N3)cn1]
I-1457
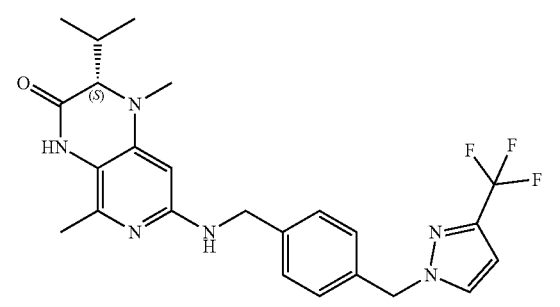
I-1458
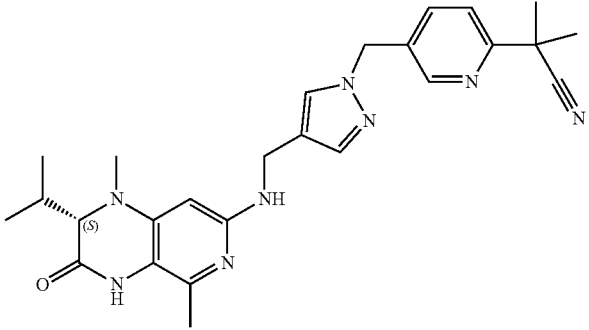
I-1459

TABLE C-continued
Exemplary Compounds
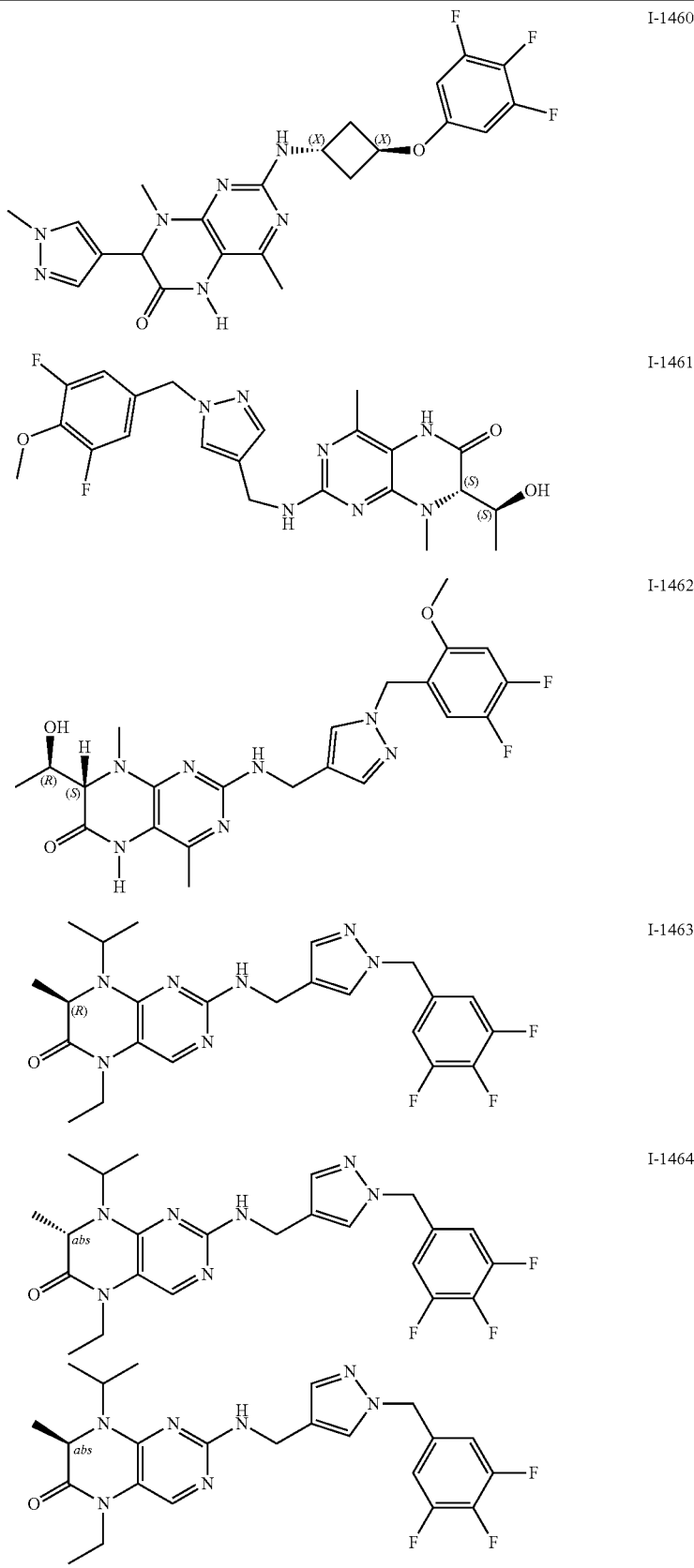
I-1460
I-1461
I-1462
I-1463
I-1464

TABLE C-continued
Exemplary Compounds
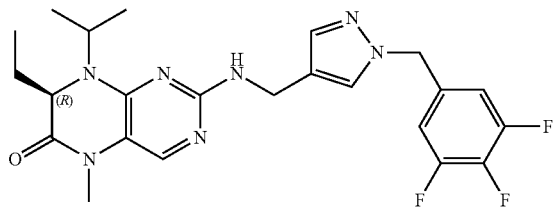
I-1465
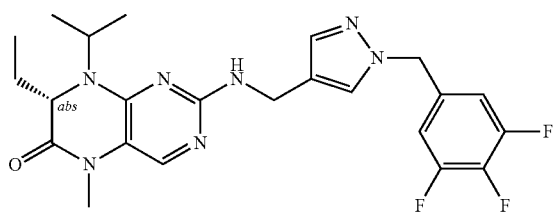
I-1466
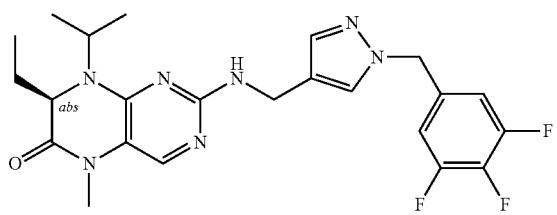
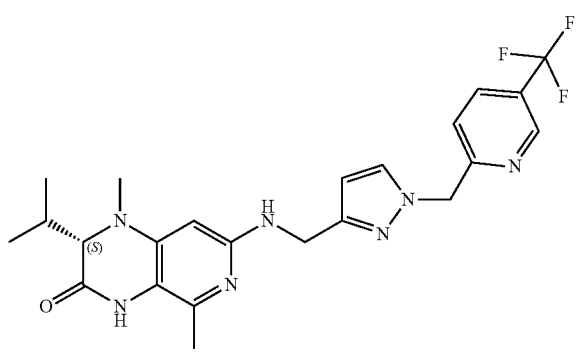
I-1467
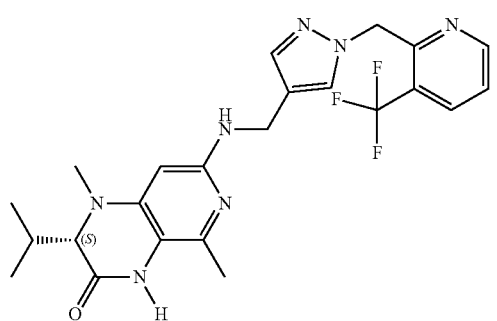
I-1468

TABLE C-continued
Exemplary Compounds
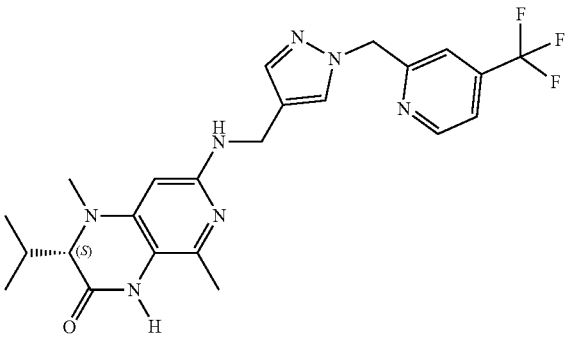
I-1469
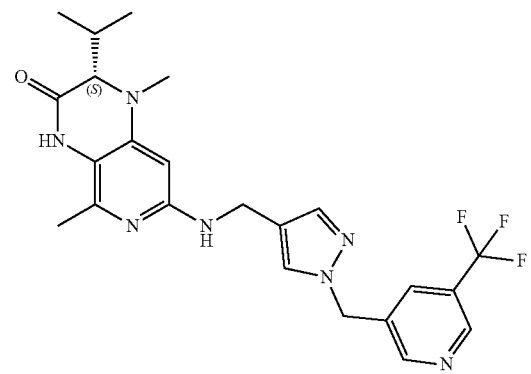
I-1470
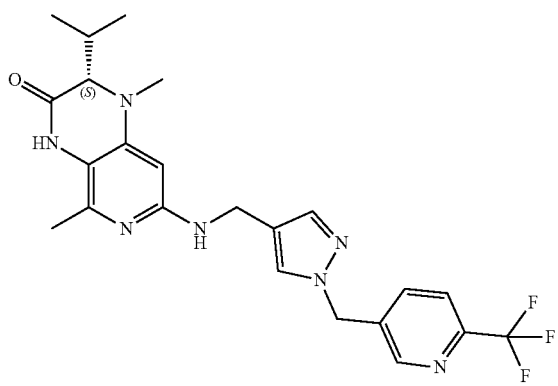
I-1471
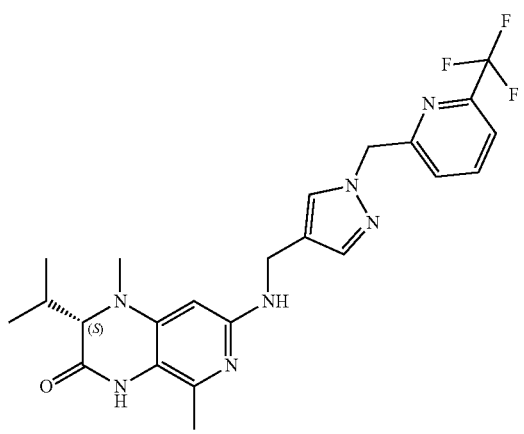
I-1472

TABLE C-continued
Exemplary Compounds
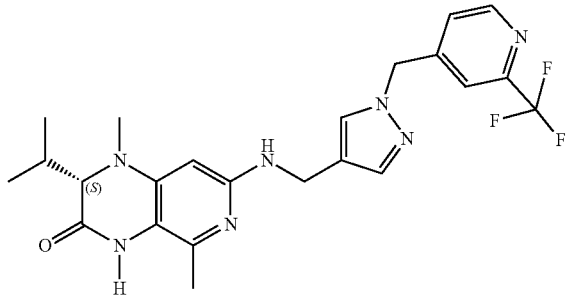 I-1473
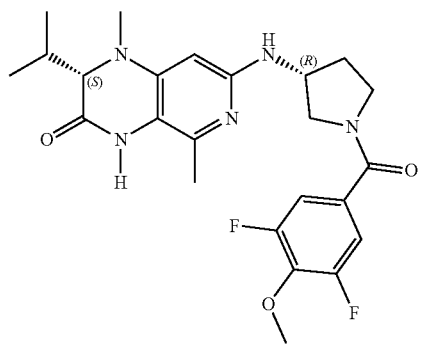 I-1474
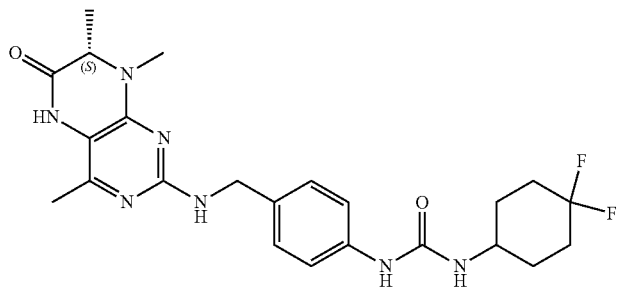 I-1475
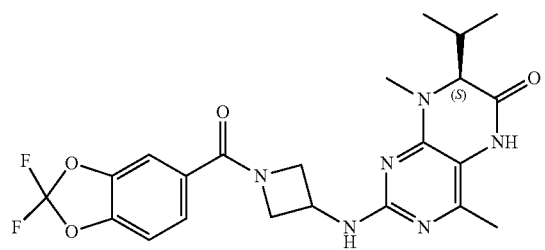 I-1476

TABLE C-continued
Exemplary Compounds
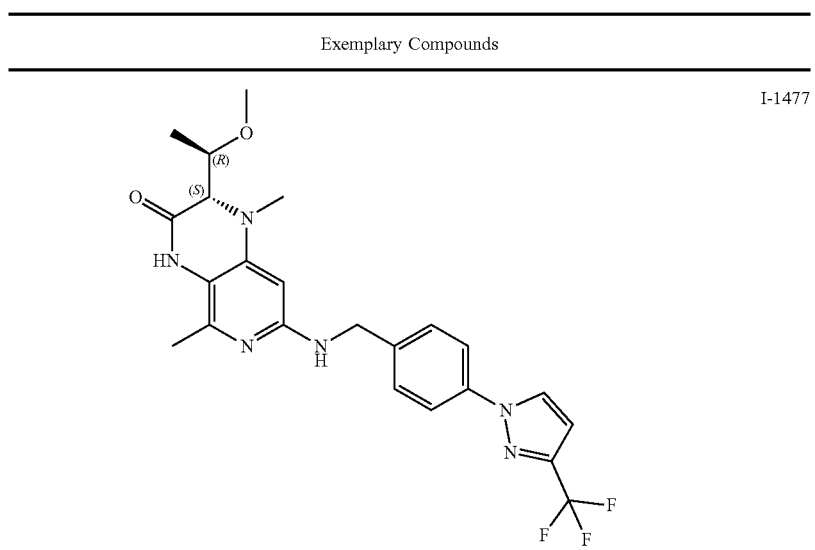
I-1477
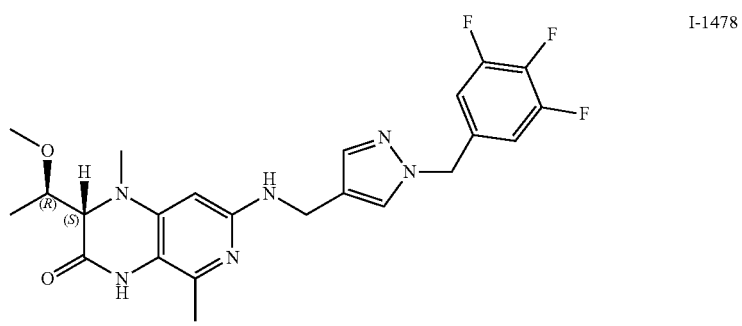
I-1478
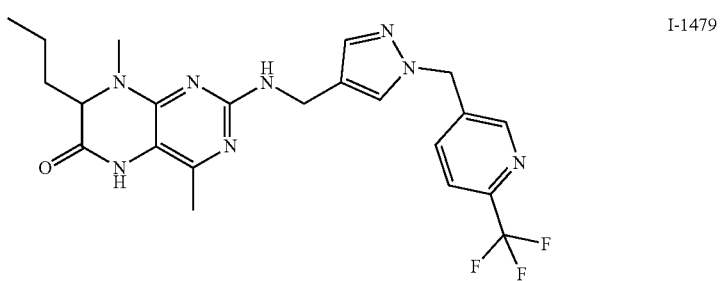
I-1479
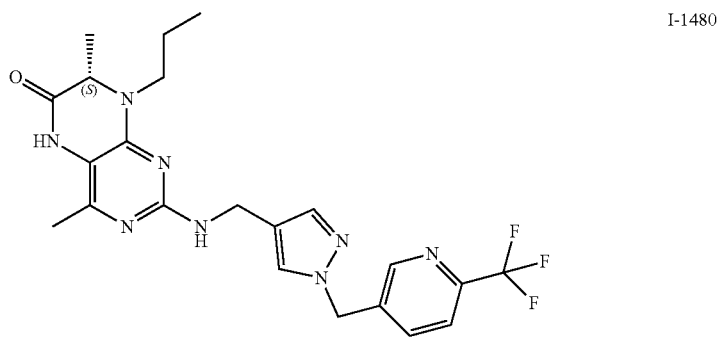
I-1480

TABLE C-continued
Exemplary Compounds
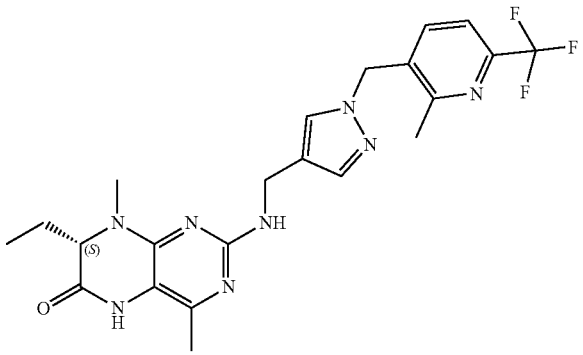
I-1481
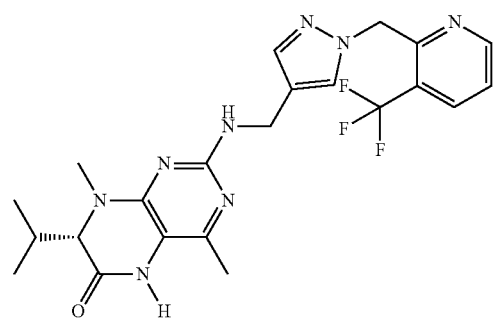 [SMILES: Cc1nc(NCc2cnn(Cc3ncccc3C(F)(F)F)c2)nc2c1NC(=O)[C@H](C(C)C)N2C]
I-1482
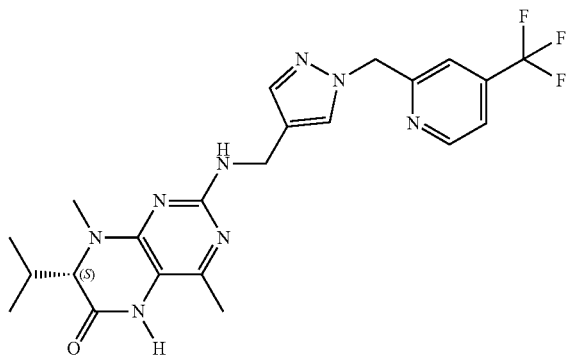
I-1483
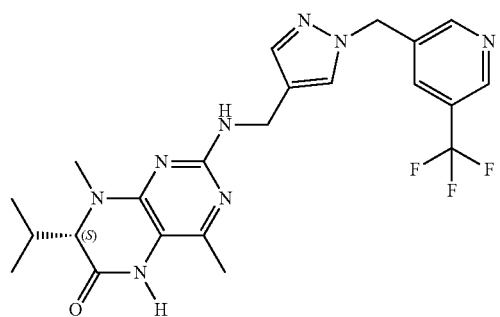
I-1484

TABLE C-continued
Exemplary Compounds
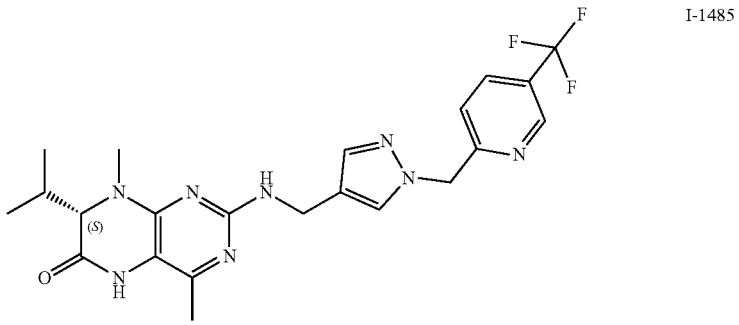
I-1485
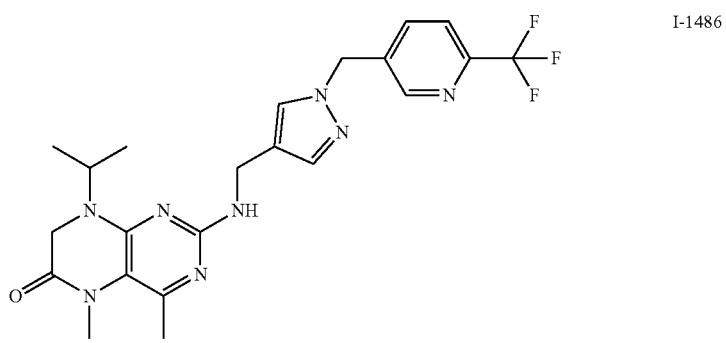
I-1486
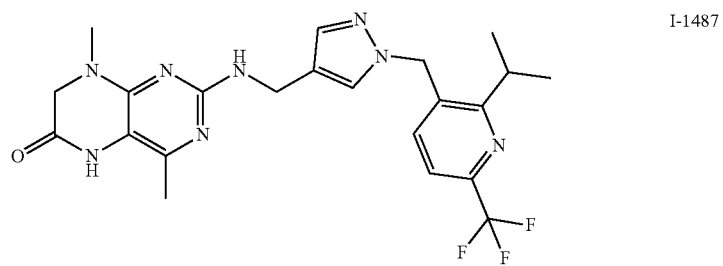
I-1487
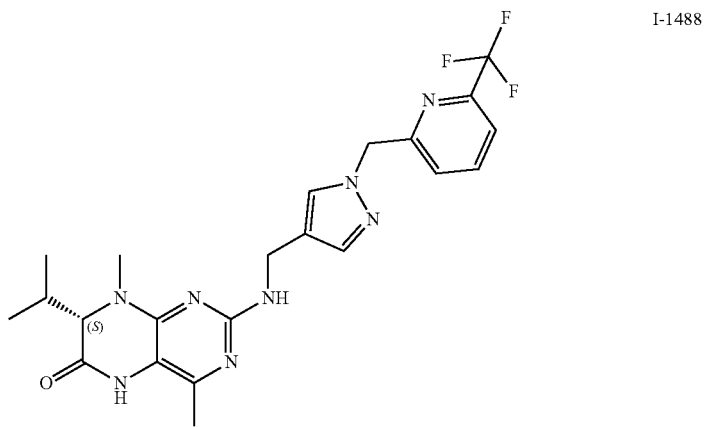
I-1488

TABLE C-continued
Exemplary Compounds
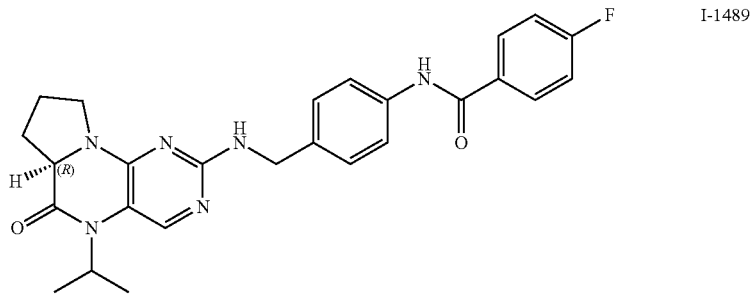
I-1489
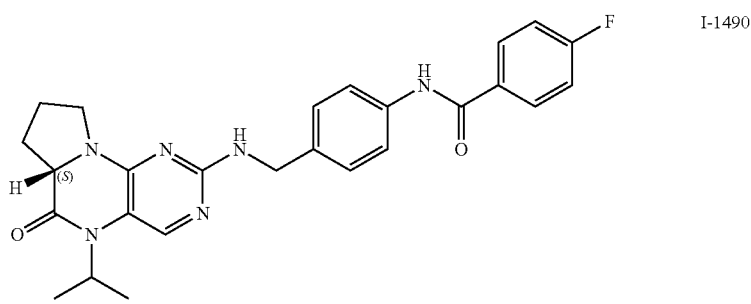
I-1490
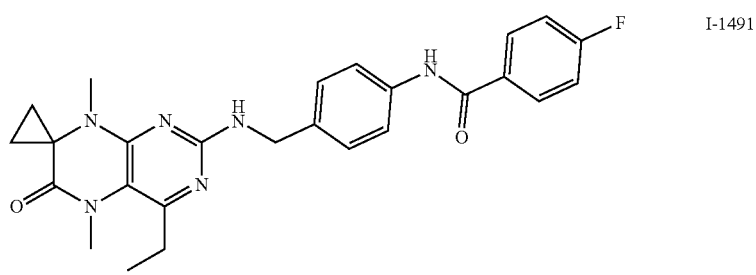
I-1491
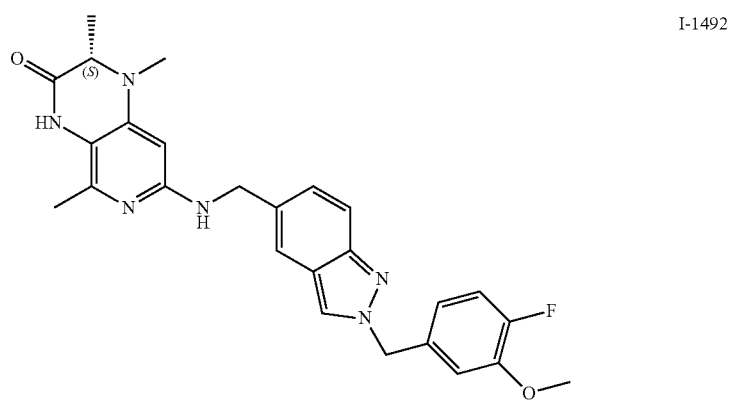
I-1492

TABLE C-continued
Exemplary Compounds
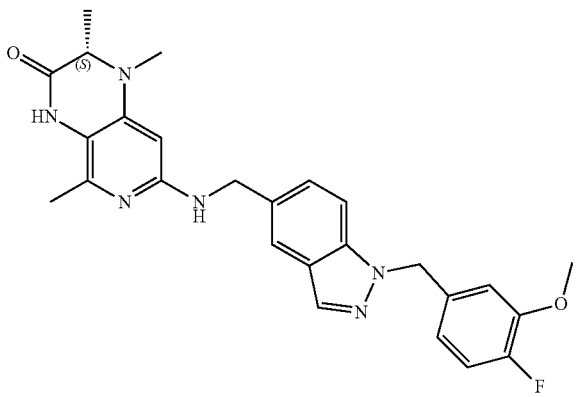
I-1493
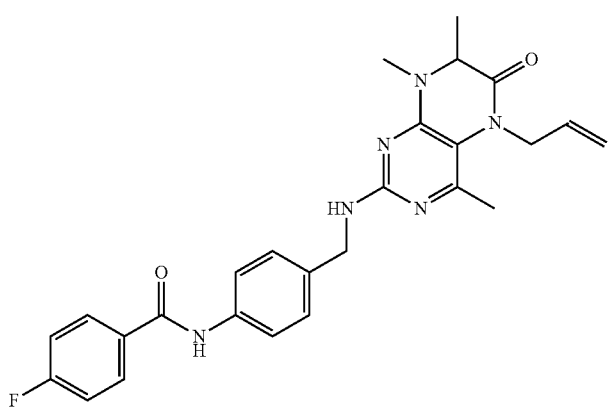 [SMILES: C=CCN1C(=O)C(C)N(C)c2nc(NCc3ccc(NC(=O)c4ccc(F)cc4)cc3)nc(C)c21]
I-1494
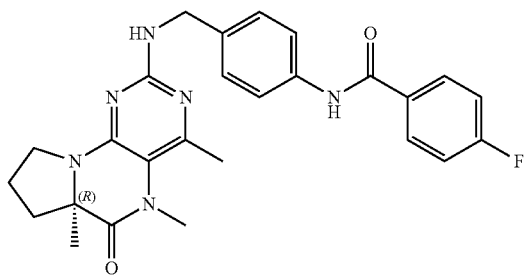
I-1495
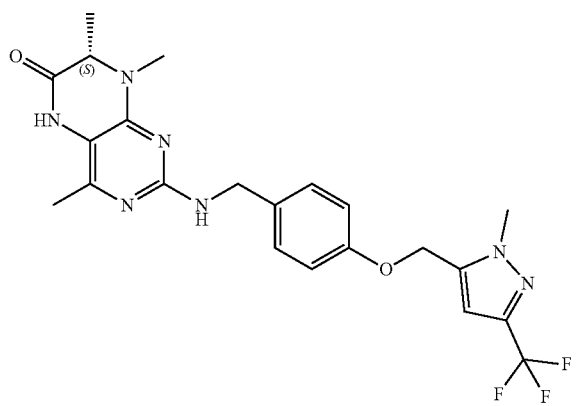
I-1496

TABLE C-continued
Exemplary Compounds
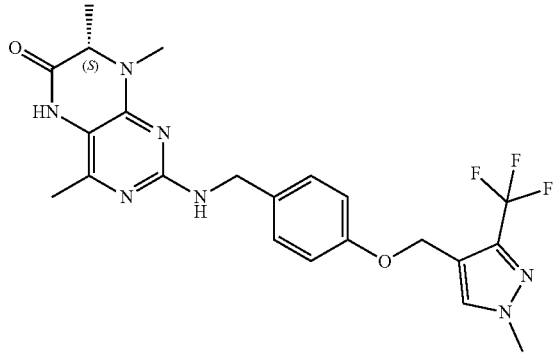
I-1497
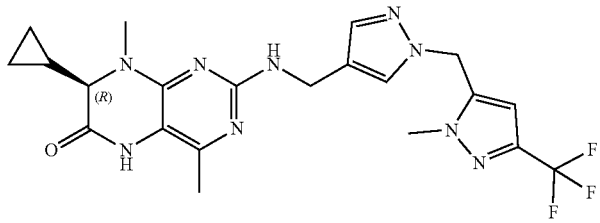
I-1498
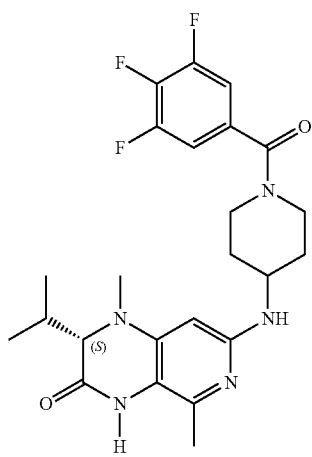
I-1499
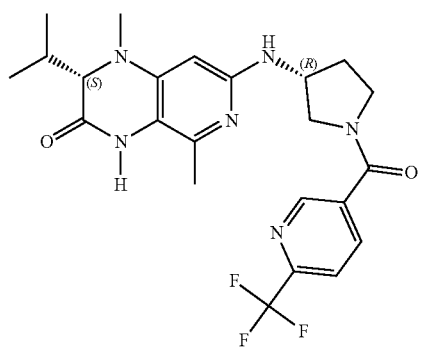
I-1500

TABLE C-continued
Exemplary Compounds
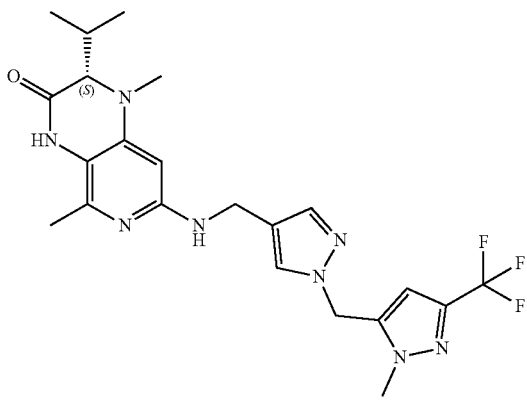
I-1501
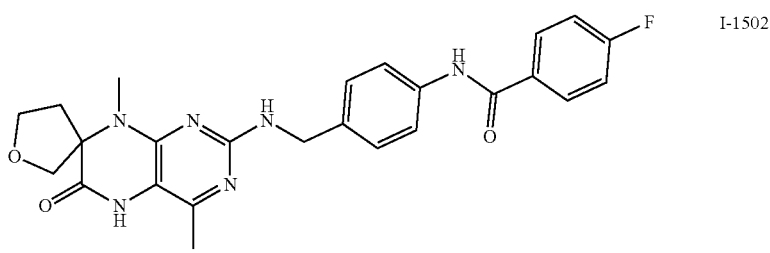
I-1502
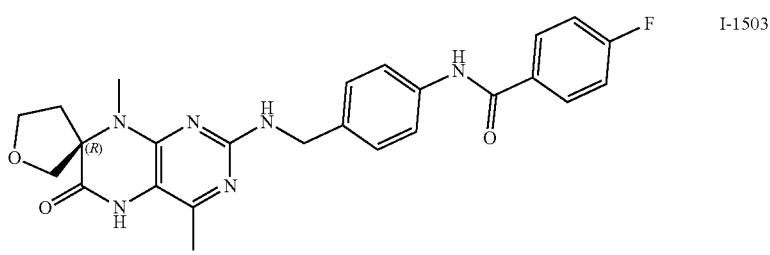
I-1503
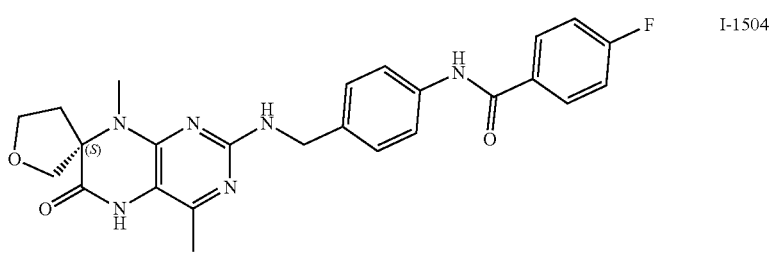
I-1504
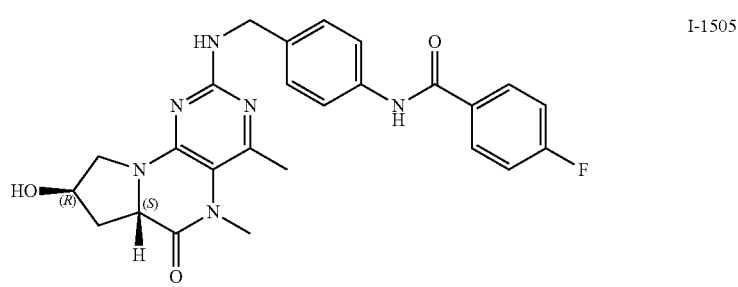
I-1505

TABLE C-continued
Exemplary Compounds
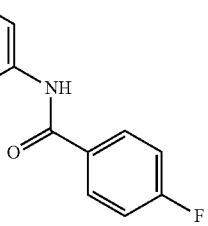
I-1506
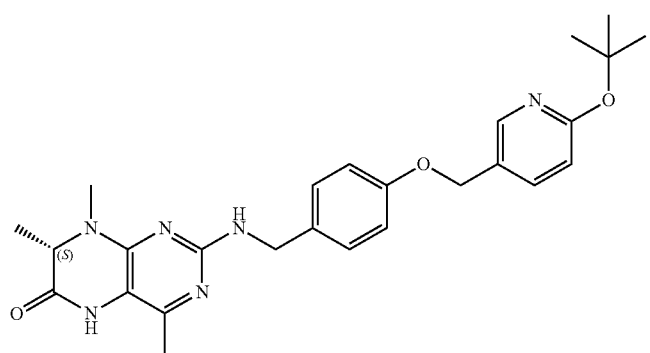
I-1507
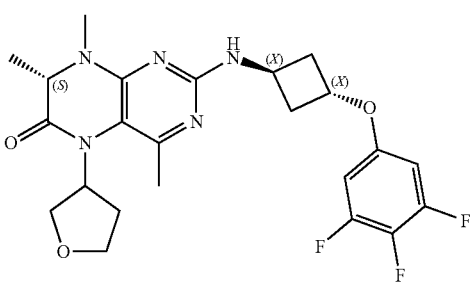
I-1508
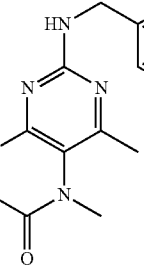
I-1509
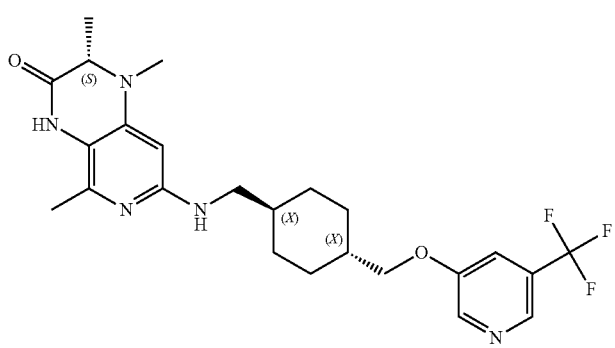
I-1510

TABLE C-continued
Exemplary Compounds
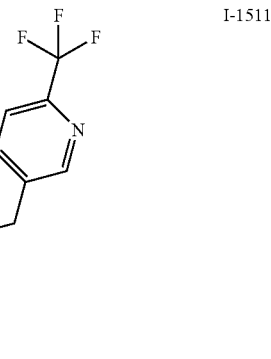
I-1511
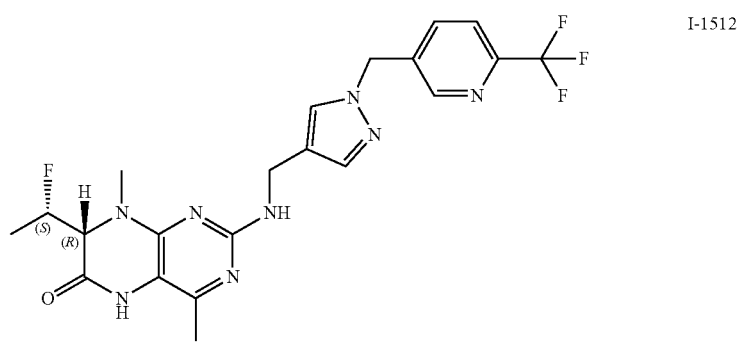
I-1512
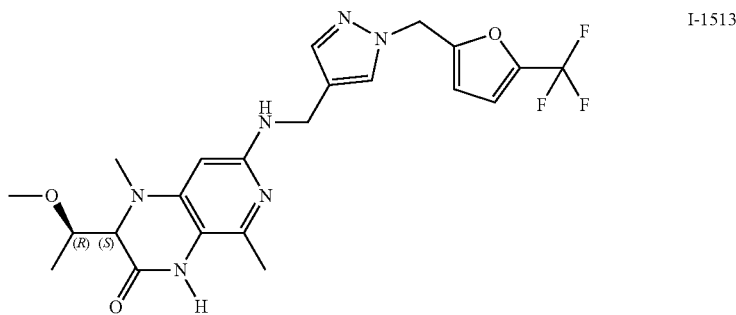
I-1513
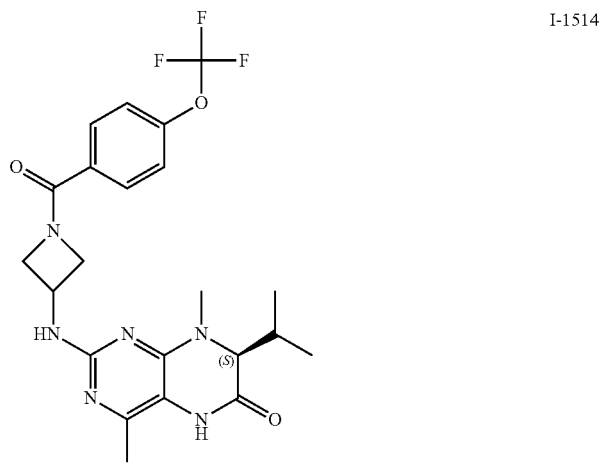
I-1514

TABLE C-continued
Exemplary Compounds
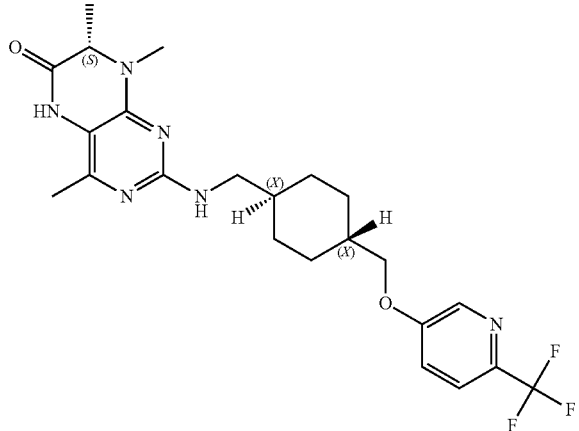
I-1515
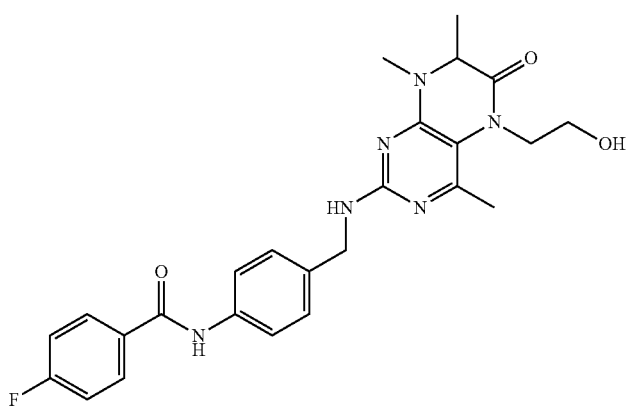 [SMILES: Cc1nc(NCc2ccc(NC(=O)c3ccc(F)cc3)cc2)nc2c1N(CCO)C(=O)C(C)N2C]
I-1516
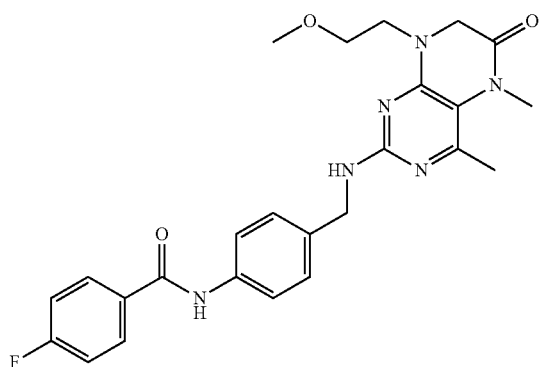 [SMILES: COCCN1CC(=O)N(C)c2c(C)nc(NCc3ccc(NC(=O)c4ccc(F)cc4)cc3)nc21]
I-1517
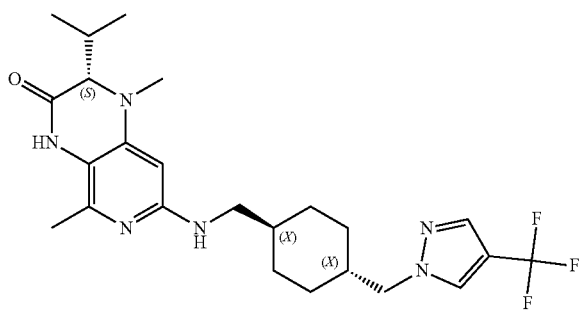
I-1518

TABLE C-continued
Exemplary Compounds
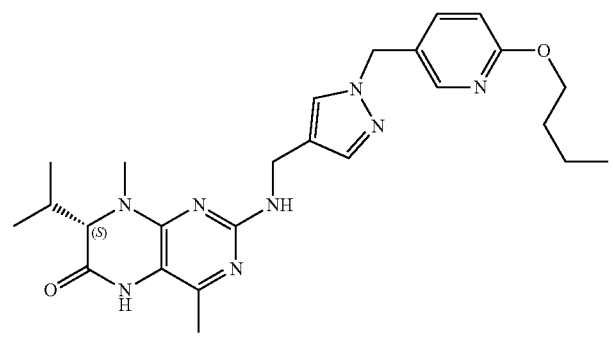
I-1519
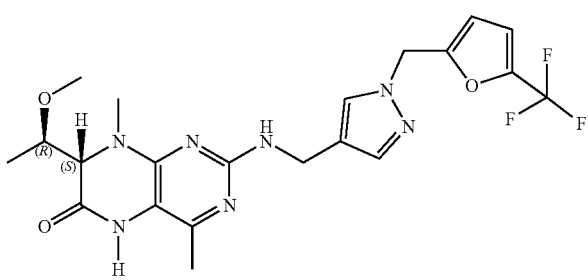
I-1520
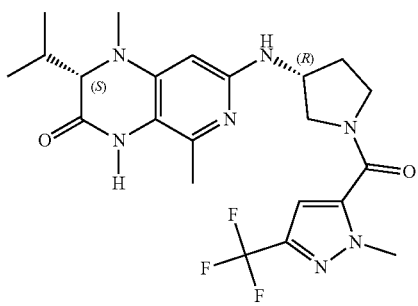
I-1521
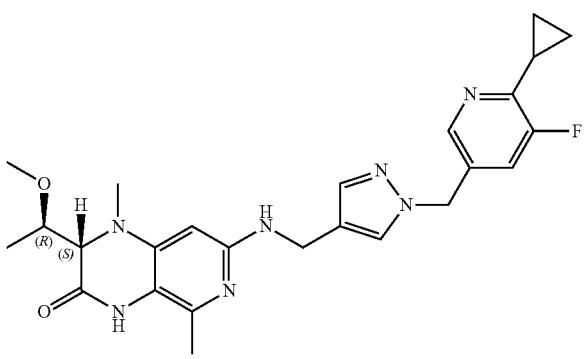
I-1522
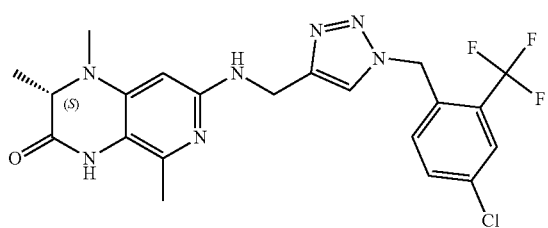
I-1523

TABLE C-continued
Exemplary Compounds
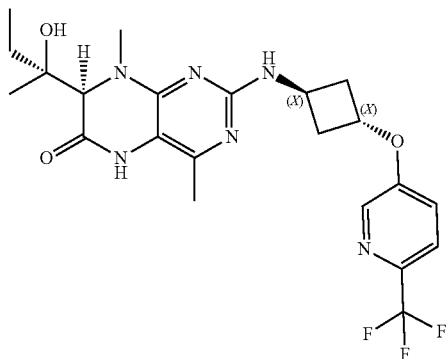
I-1524
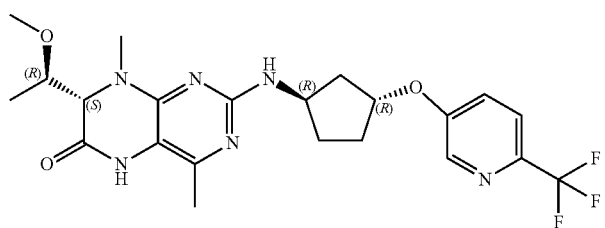
I-1525
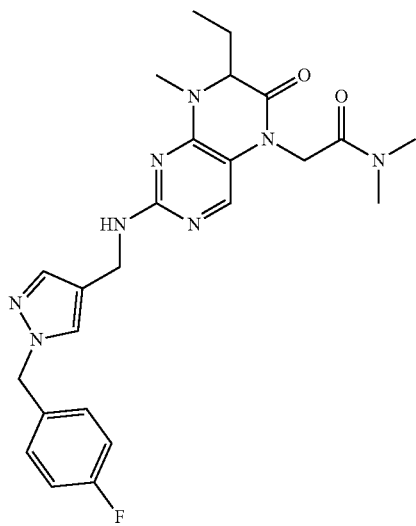 [SMILES: CCC1C(=O)N(CC(=O)N(C)C)c2cnc(NCc3cnn(Cc4ccc(F)cc4)c3)nc2N1C]
I-1526
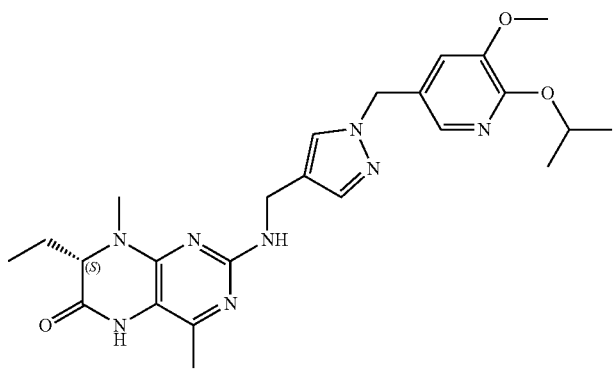
I-1527

TABLE C-continued
Exemplary Compounds
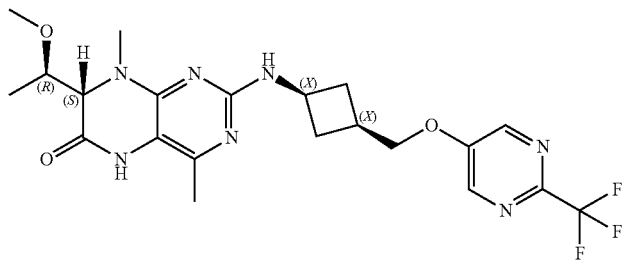
I-1528
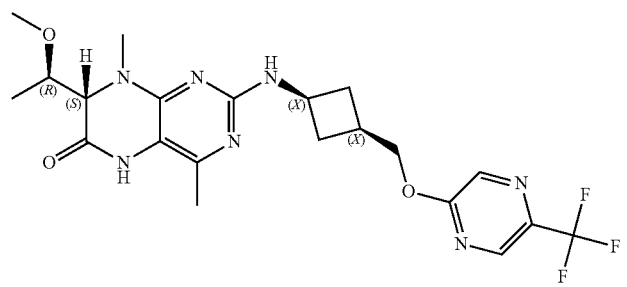
I-1529
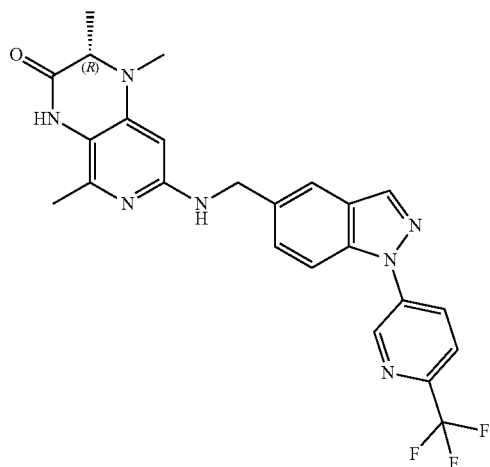
I-1530
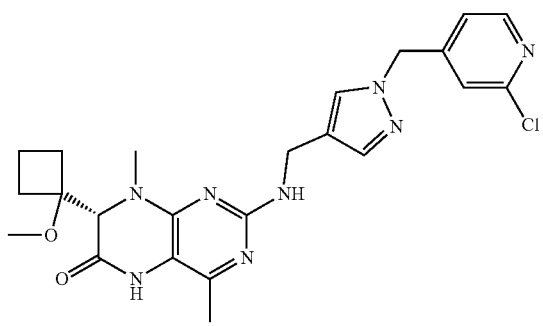 [SMILES: COC1([C@H]2C(=O)Nc3c(C)nc(NCc4cnn(Cc5ccnc(Cl)c5)c4)nc3N2C)CCC1]
I-1531
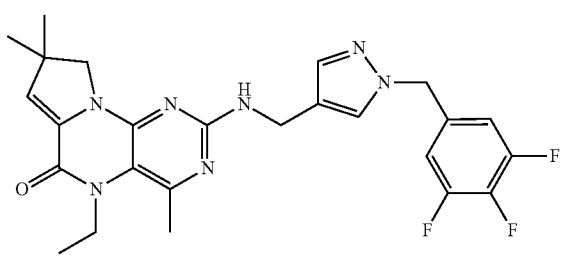 [SMILES: CCN1C(=O)C2=CC(C)(C)CN2c2nc(NCc3cnn(Cc4cc(F)c(F)c(F)c4)c3)nc(C)c21]
I-1532

TABLE C-continued
Exemplary Compounds
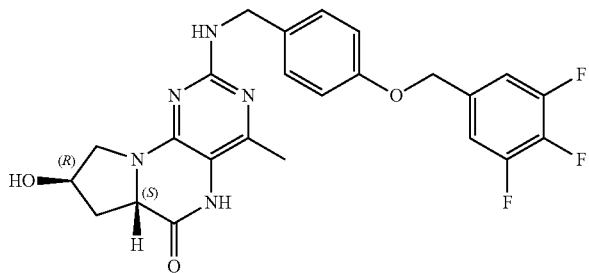
I-1533
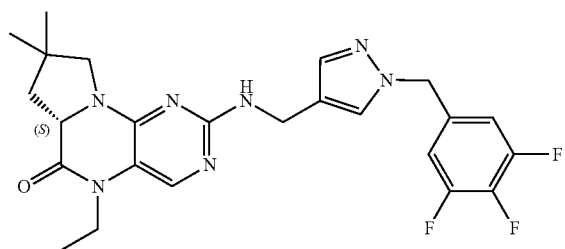
I-1534
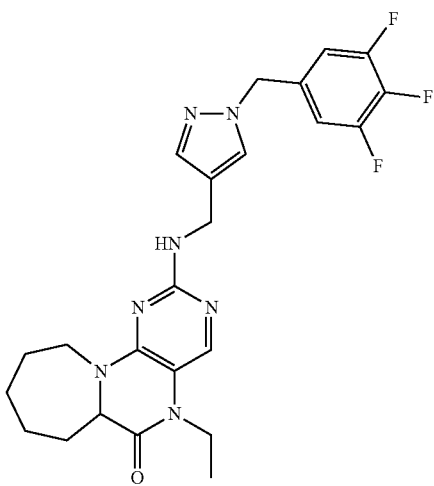
I-1535
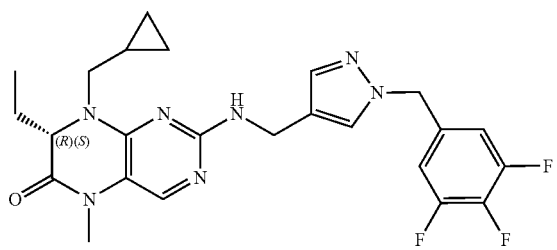
I-1536
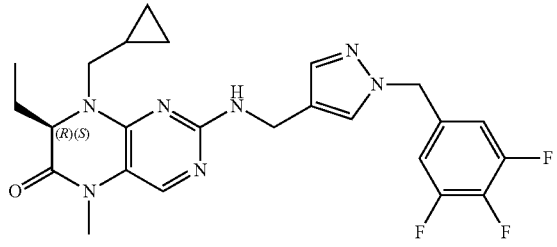

TABLE C-continued
Exemplary Compounds
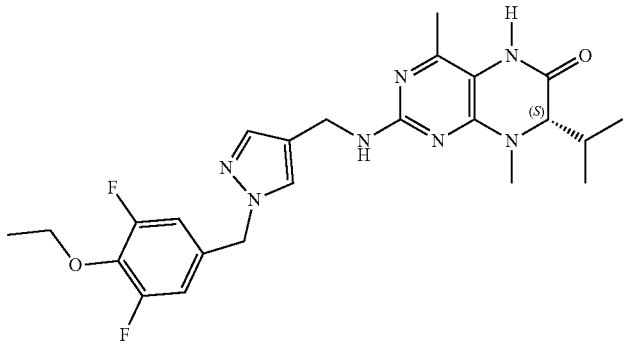
I-1537
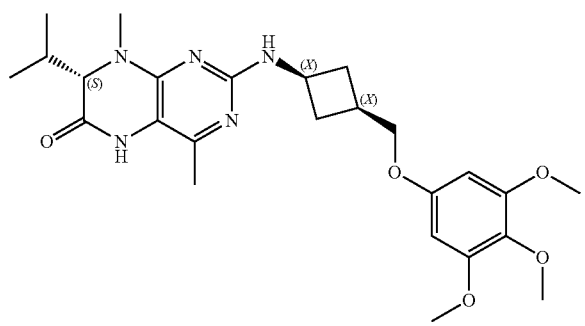
I-1538
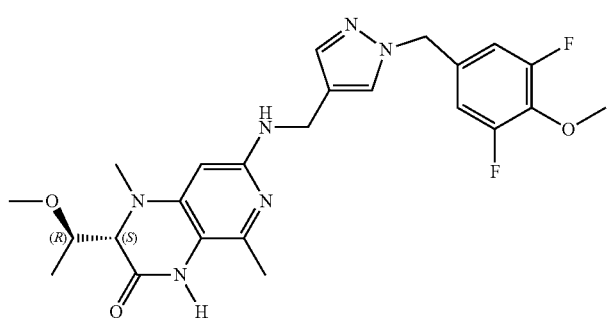
I-1539
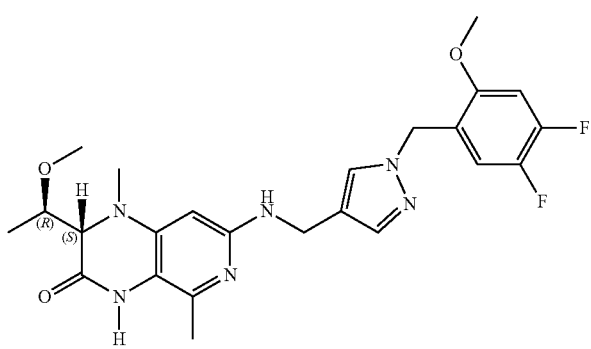
I-1540

TABLE C-continued
Exemplary Compounds
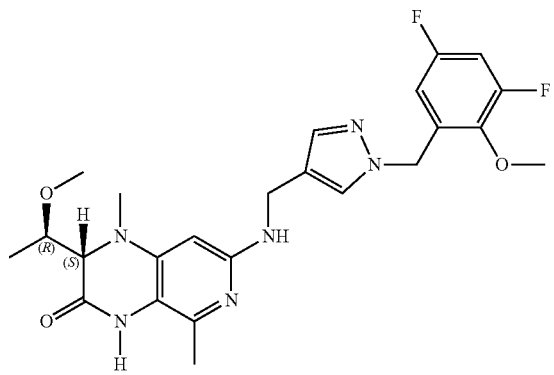
I-1541
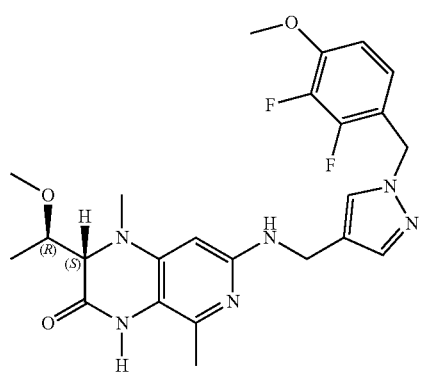
I-1542
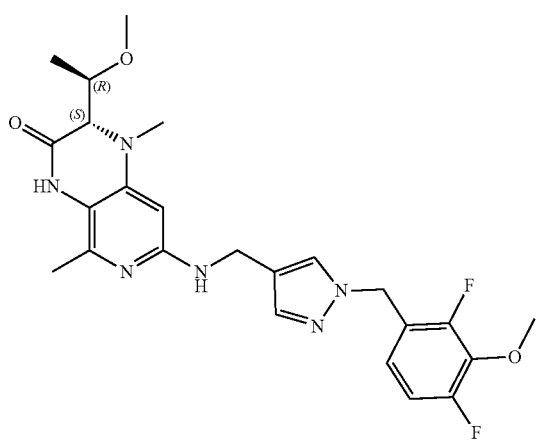
I-1543

TABLE C-continued
Exemplary Compounds
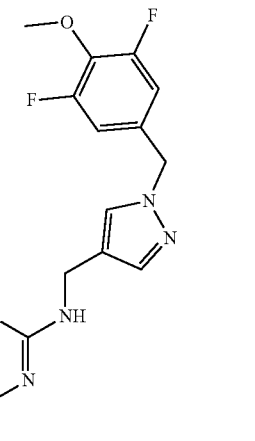
I-1544
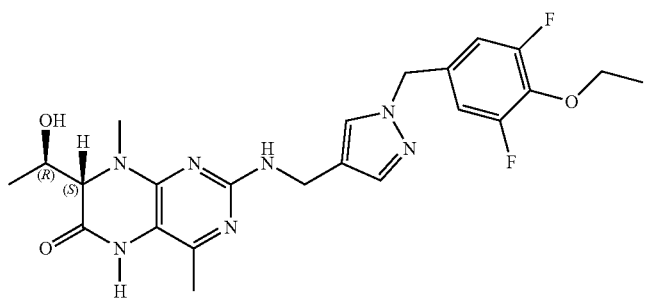
I-1545
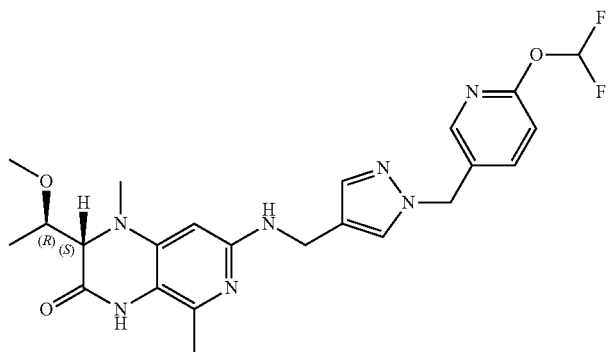
I-1546
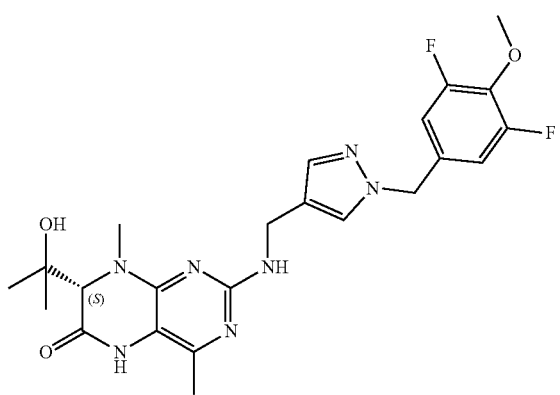
I-1547

TABLE C-continued
Exemplary Compounds
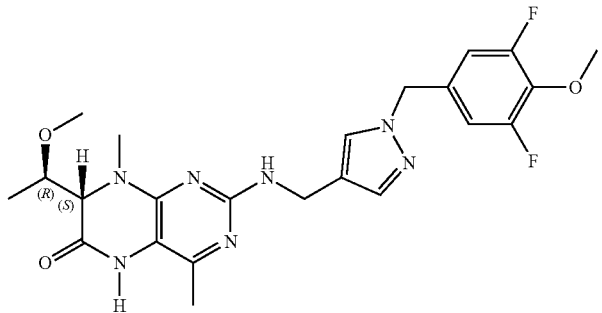
I-1548
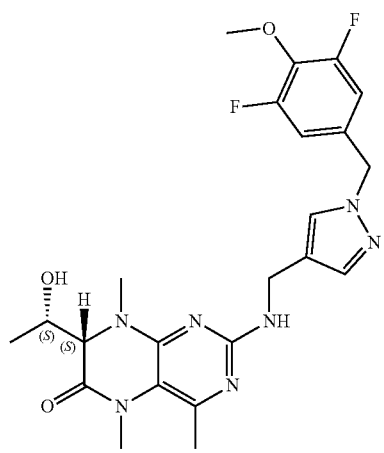
I-1549
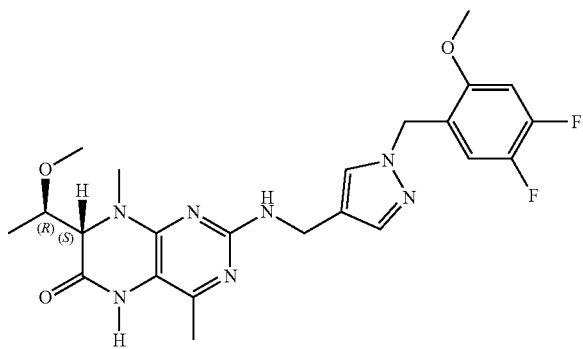
I-1550

TABLE C-continued
Exemplary Compounds
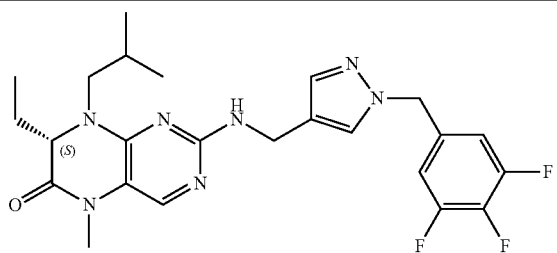
I-1551
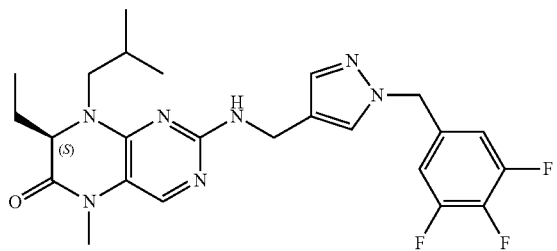
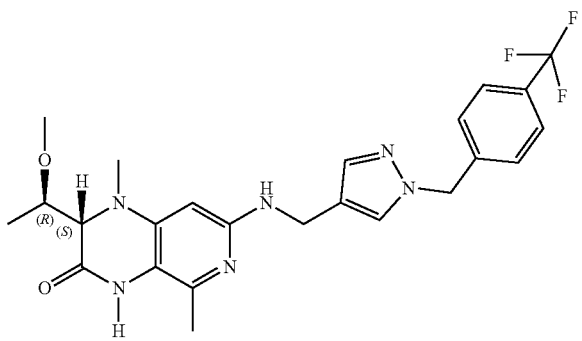
I-1552
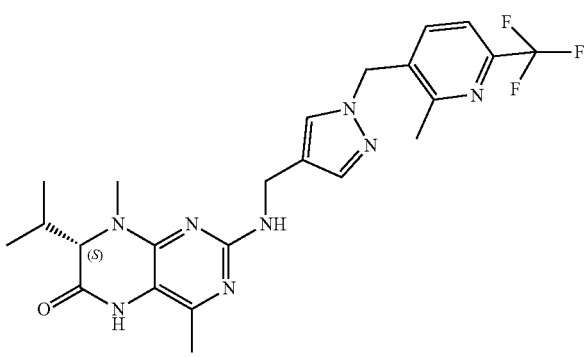
I-1553
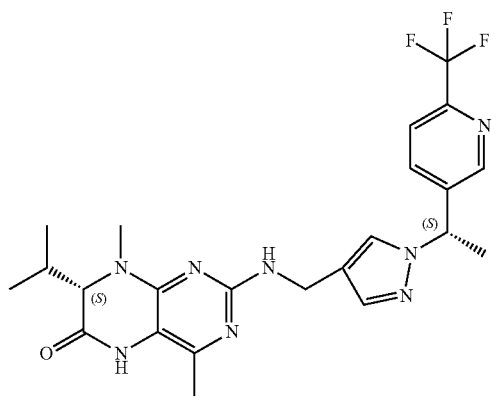
I-1554

TABLE C-continued
Exemplary Compounds
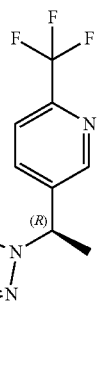
I-1555
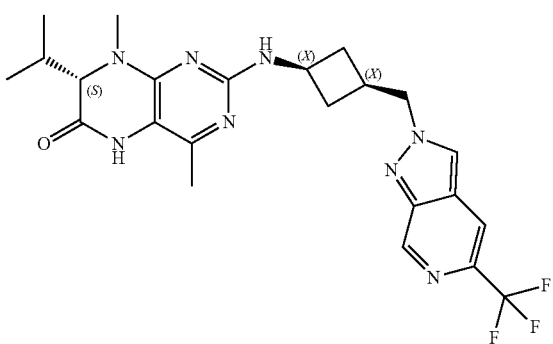
I-1556
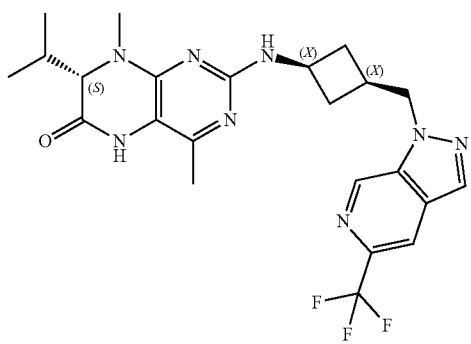
I-1557

TABLE C-continued
Exemplary Compounds
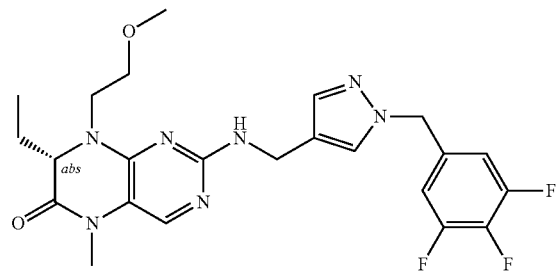
I-1558
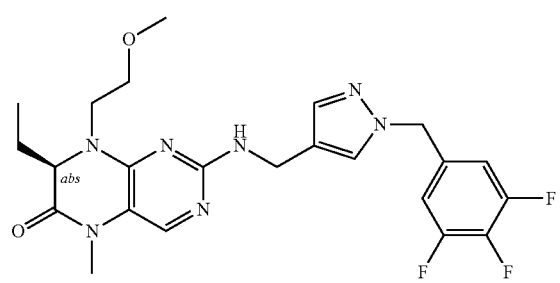
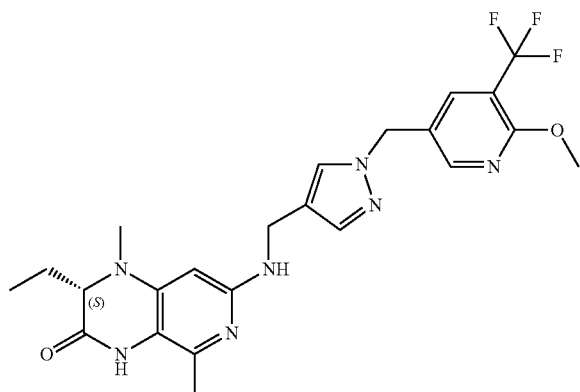
I-1559
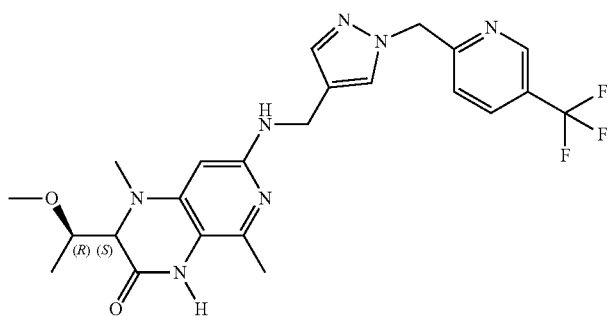
I-1560
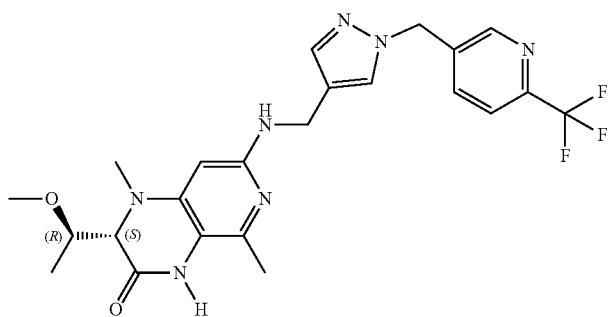
I-1561

TABLE C-continued
Exemplary Compounds
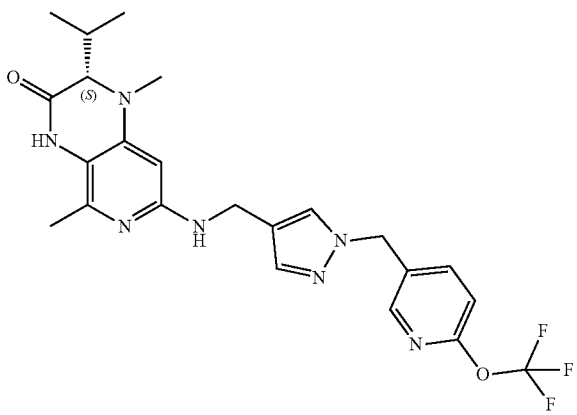
I-1562
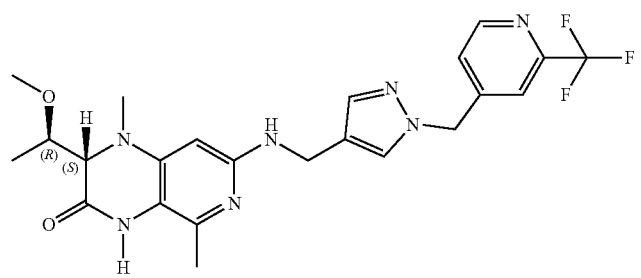
I-1563
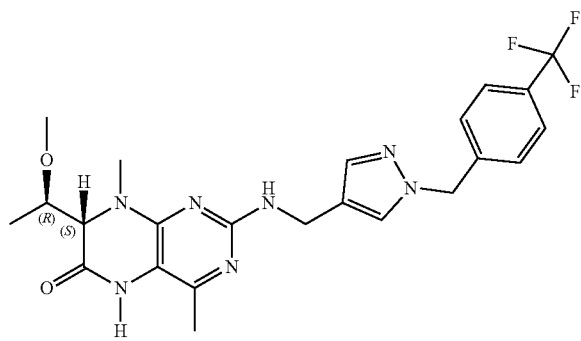
I-1564
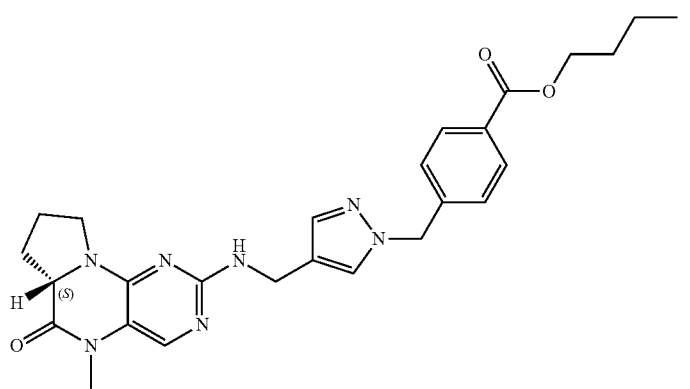
I-1565

TABLE C-continued
Exemplary Compounds
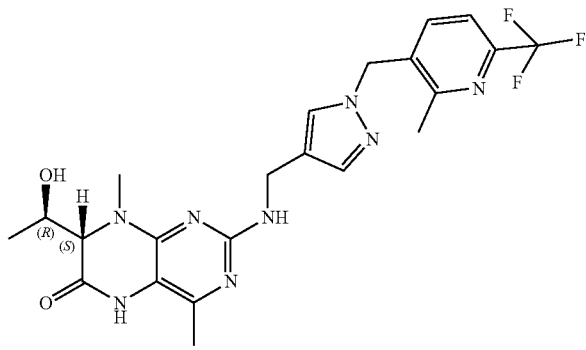
I-1566
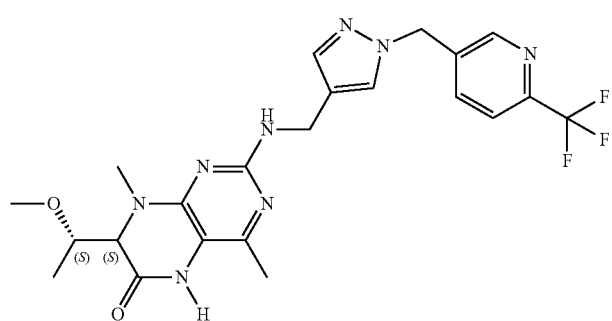
I-1567
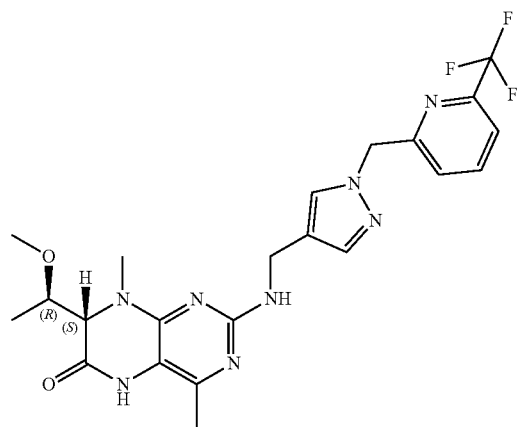
I-1568
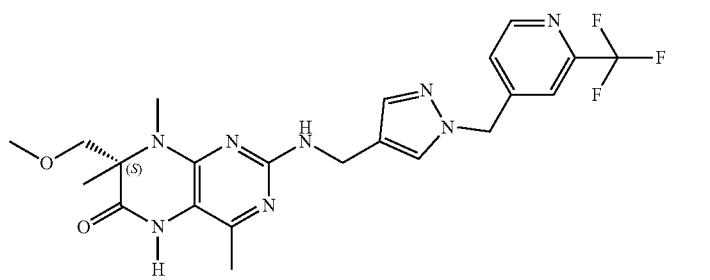
I-1569

TABLE C-continued
Exemplary Compounds
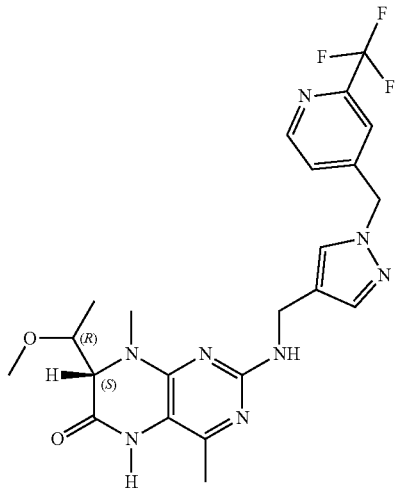
I-1570
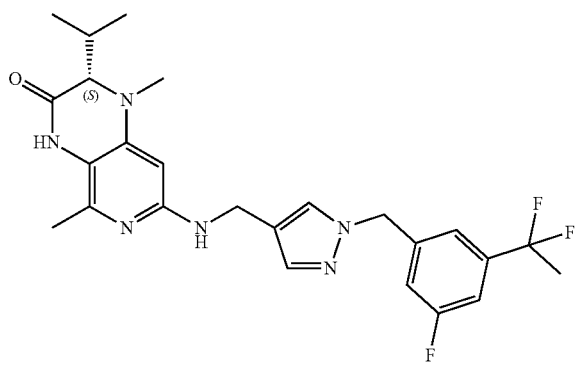
I-1571
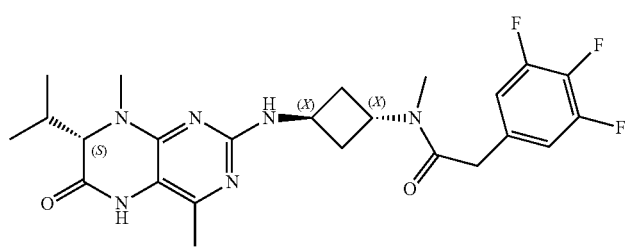
I-1572
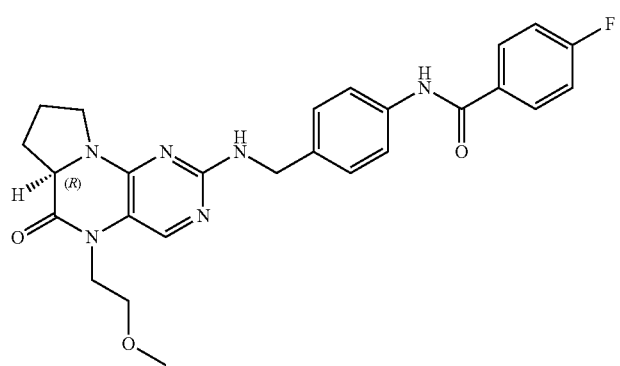
I-1573

TABLE C-continued
Exemplary Compounds
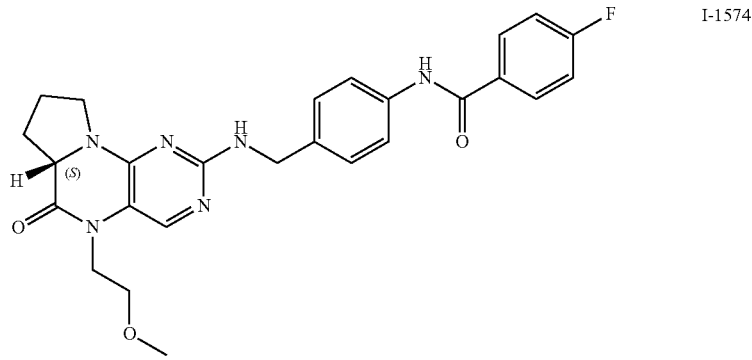
I-1574
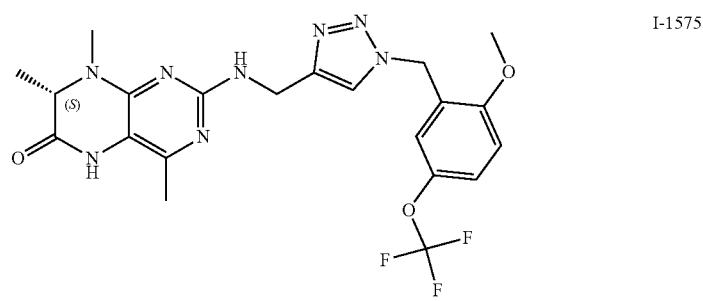
I-1575
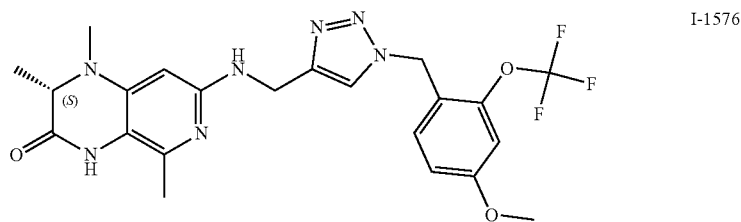
I-1576
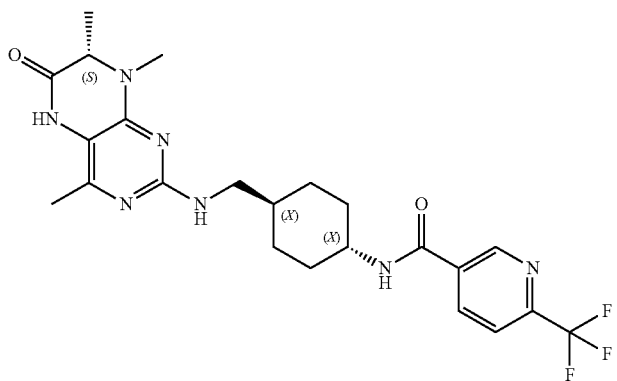
I-1577

TABLE C-continued
Exemplary Compounds
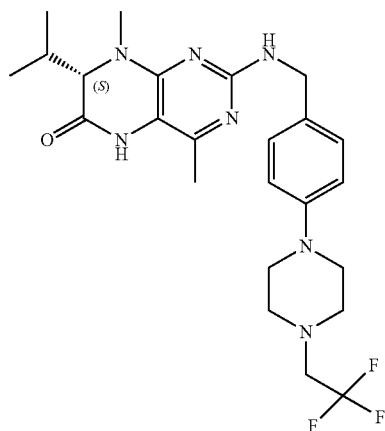
I-1578
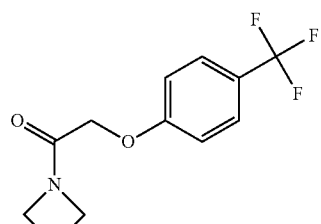
I-1579
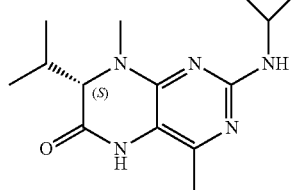
I-1580
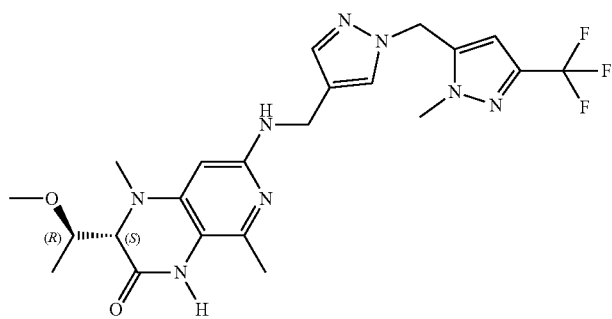
I-1581
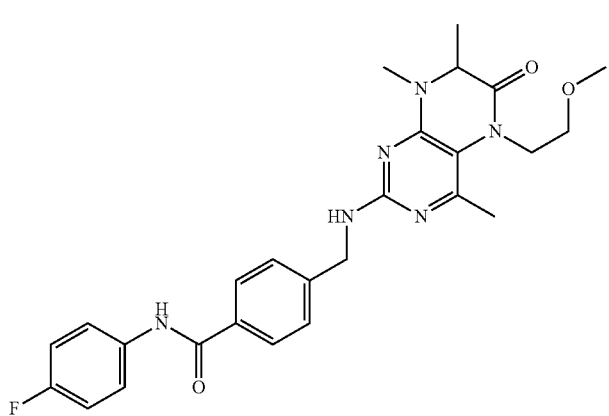 [SMILES: COCCN1C(=O)C(C)N(C)c2nc(NCc3ccc(C(=O)Nc4ccc(F)cc4)cc3)nc(C)c21]

TABLE C-continued
Exemplary Compounds
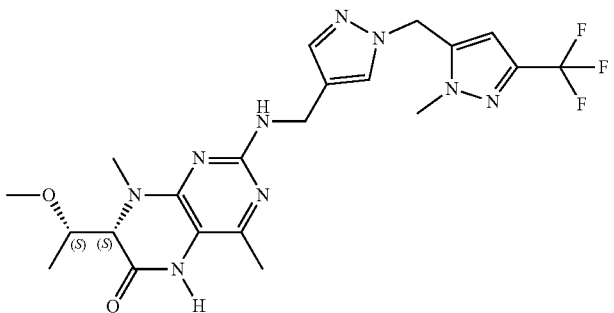 I-1582
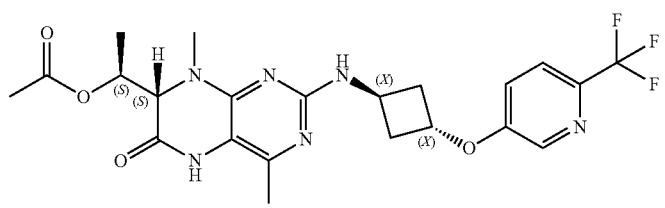 I-1583
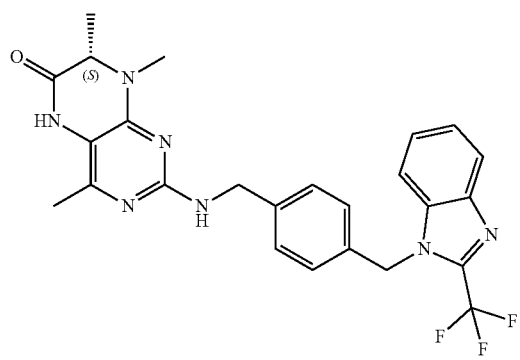 I-1584
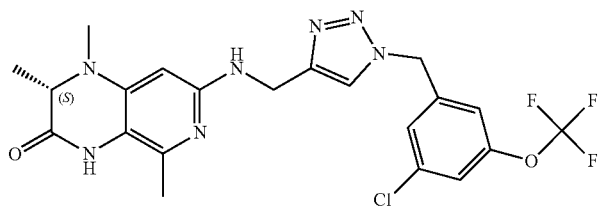 I-1585
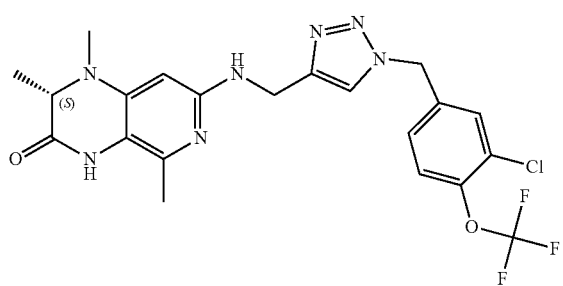 I-1586

TABLE C-continued
Exemplary Compounds
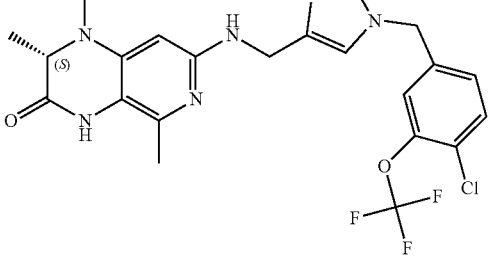
I-1587
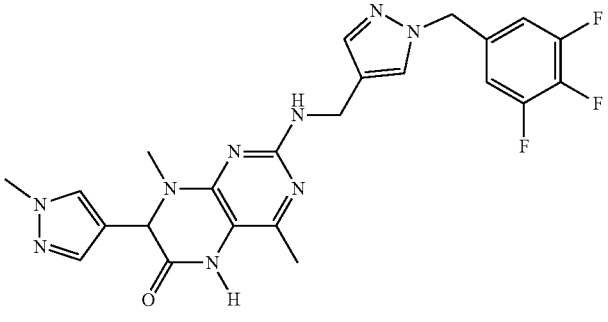 [SMILES: Cc1nc(NCc2cnn(Cc3cc(F)c(F)c(F)c3)c2)nc2c1NC(=O)C(c1cnn(C)c1)N2C]
I-1588
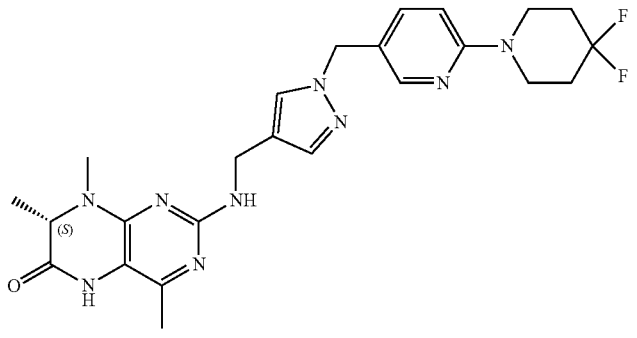
I-1589
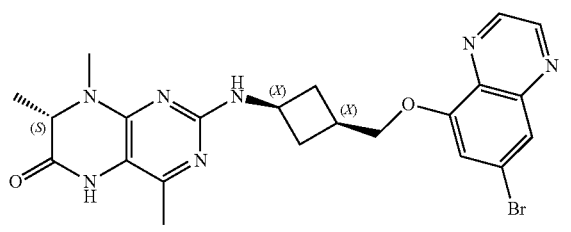
I-1590
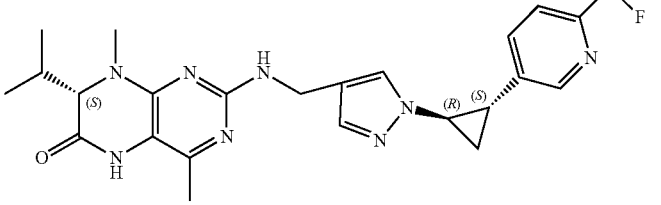
I-1591

TABLE C-continued
Exemplary Compounds
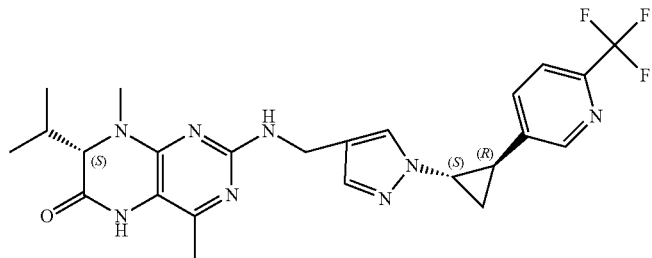
I-1592
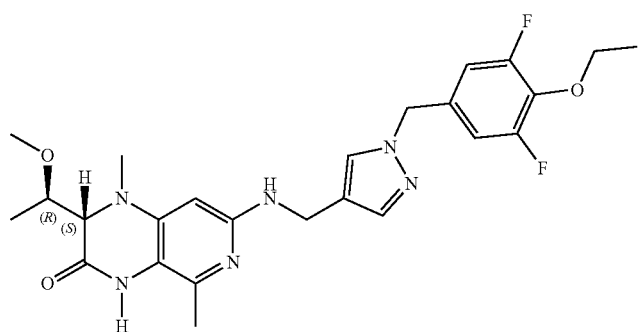
I-1593
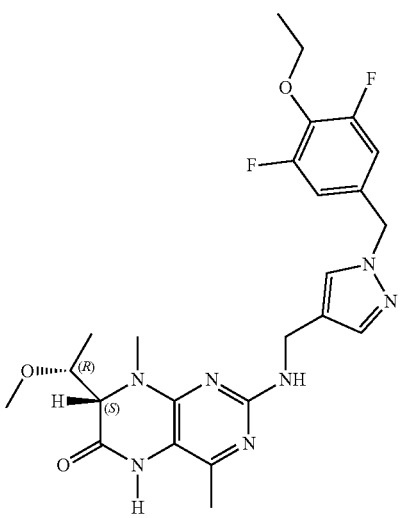
I-1594
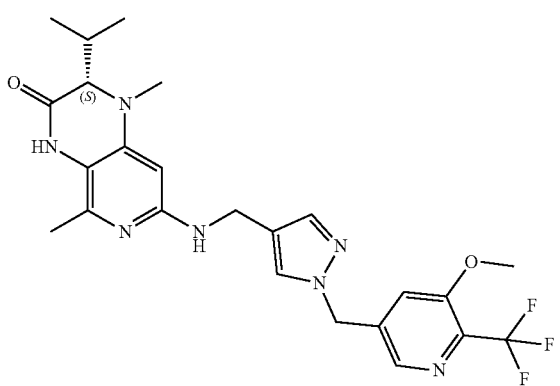
I-1595

TABLE C-continued
Exemplary Compounds
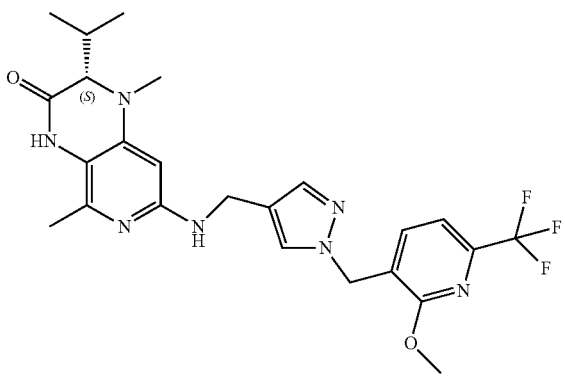
I-1596
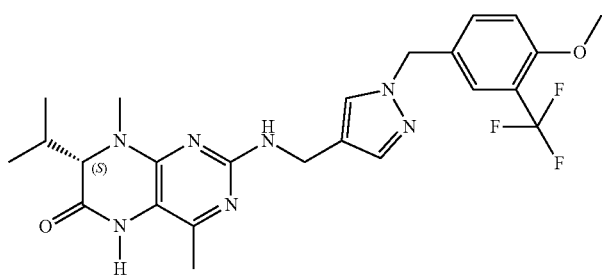
I-1597
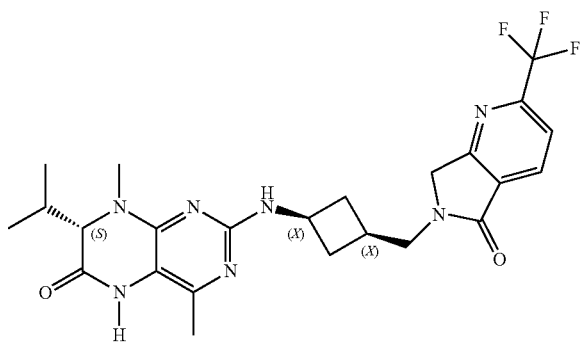
I-1598
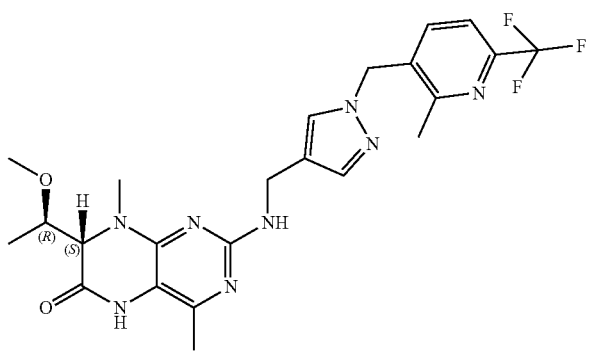
I-1599

TABLE C-continued
Exemplary Compounds
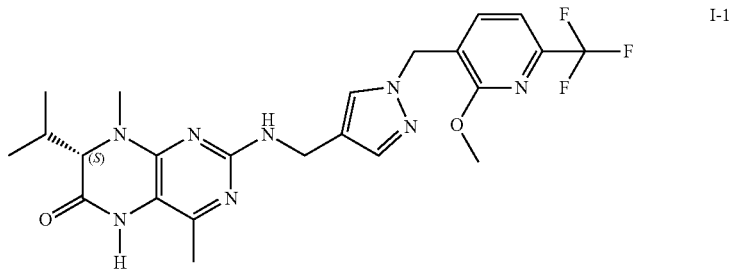
I-1600
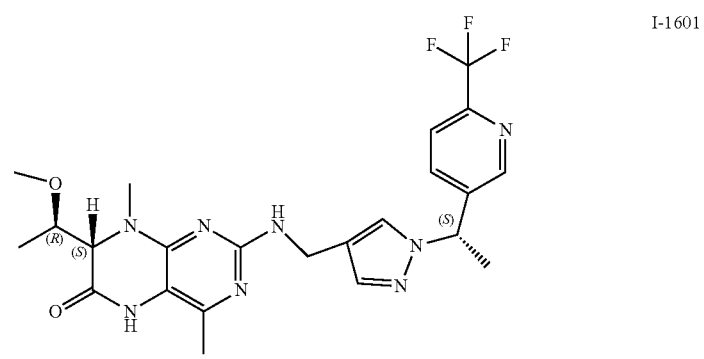
I-1601
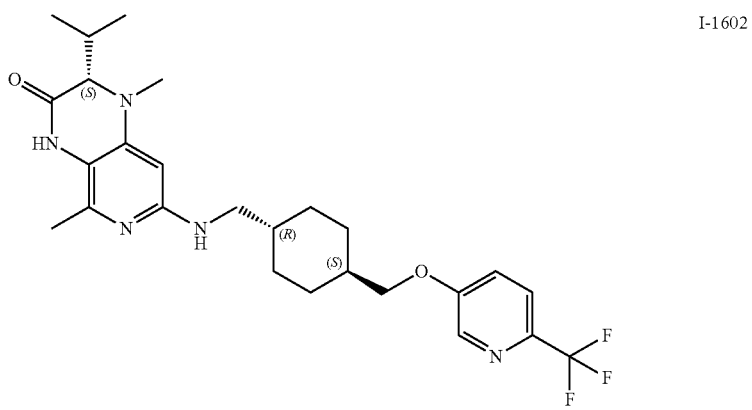
I-1602
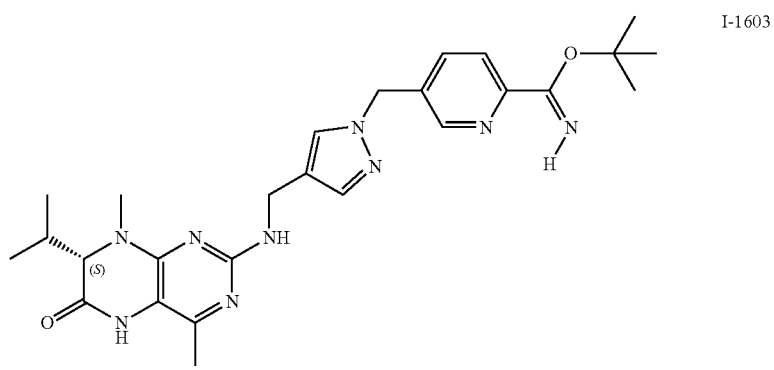
I-1603

TABLE C-continued
Exemplary Compounds
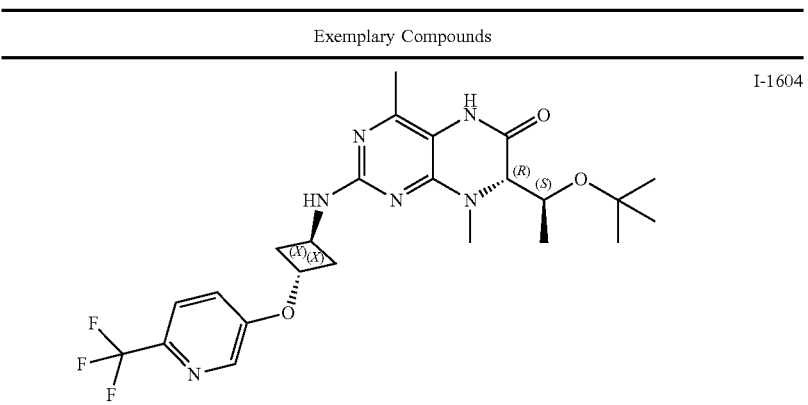
I-1604
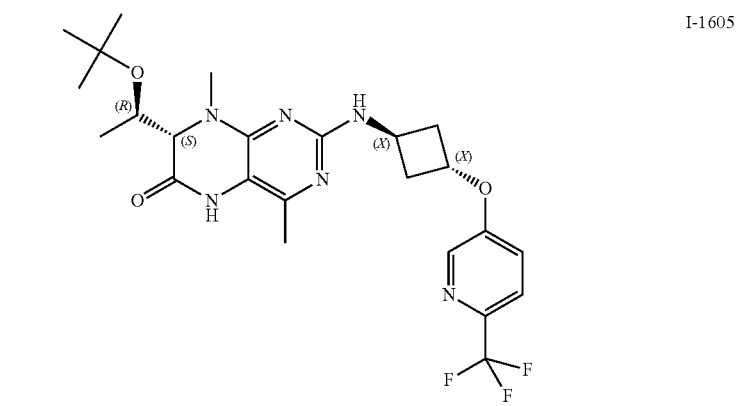
I-1605
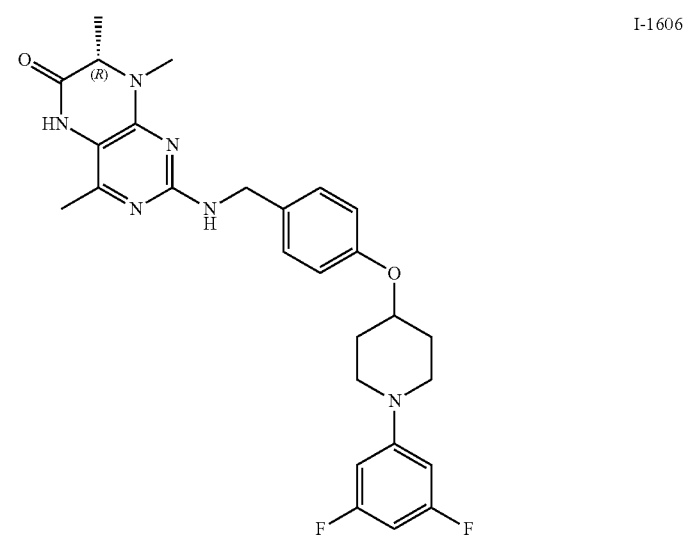
I-1606

TABLE C-continued
Exemplary Compounds
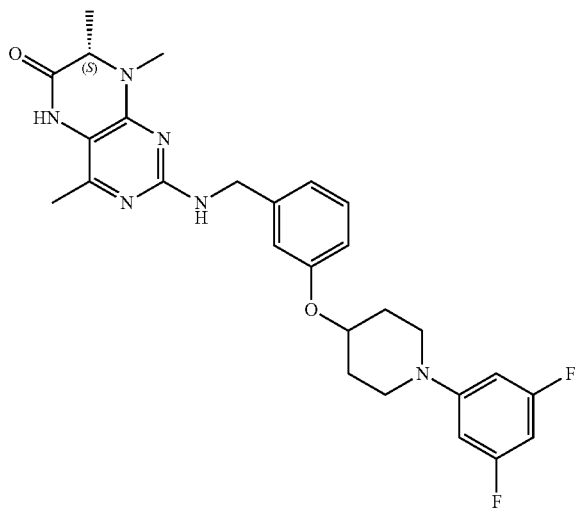
I-1607
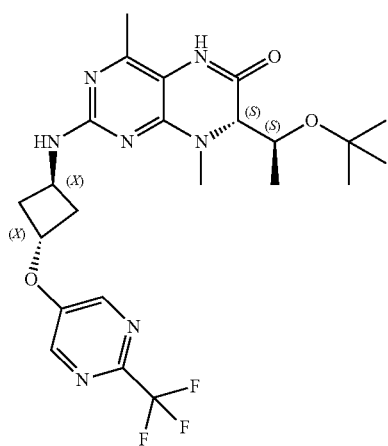
I-1608
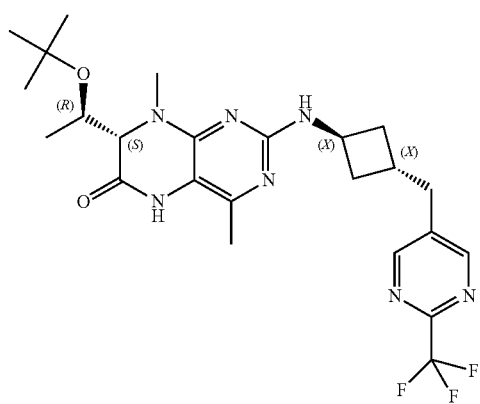
I-1609

TABLE C-continued
Exemplary Compounds
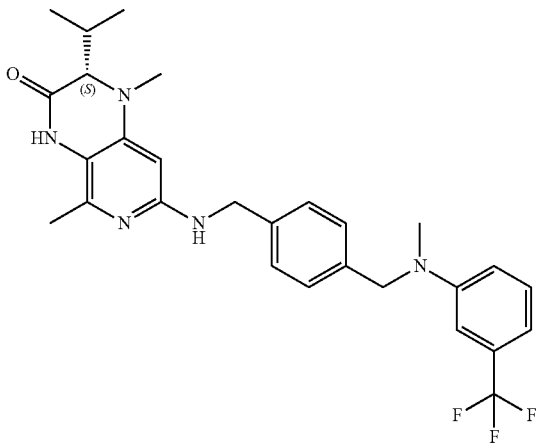
I-1610
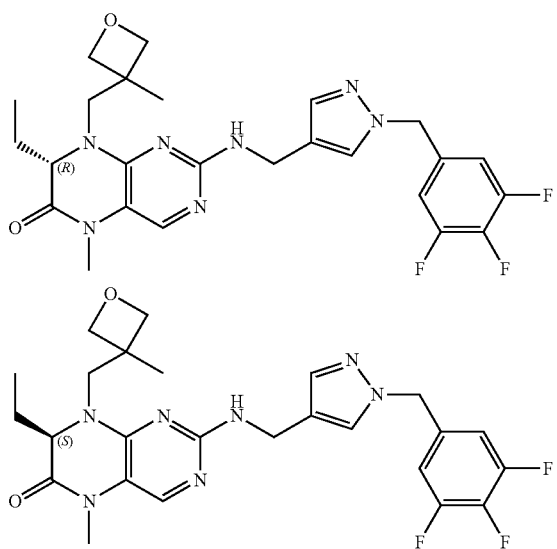
I-1611
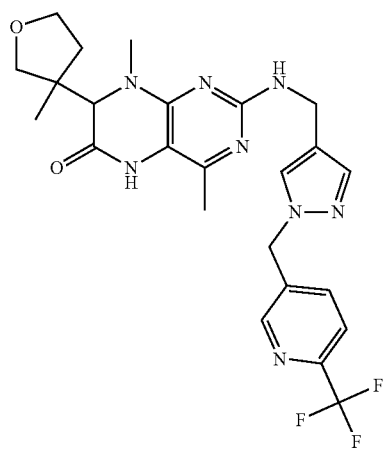 [SMILES: Cc1nc(NCc2cnn(Cc3ccc(C(F)(F)F)nc3)c2)nc2c1NC(=O)C(C1(C)CCOC1)N2C]
I-1612

TABLE C-continued
Exemplary Compounds
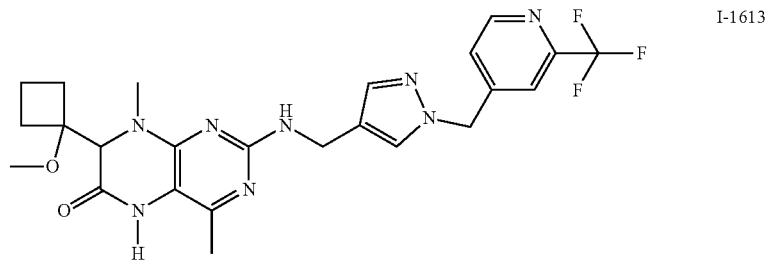
I-1613
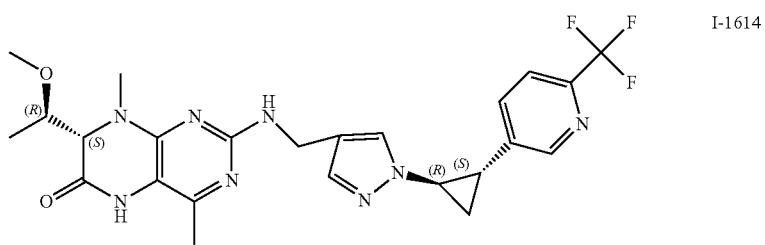
I-1614
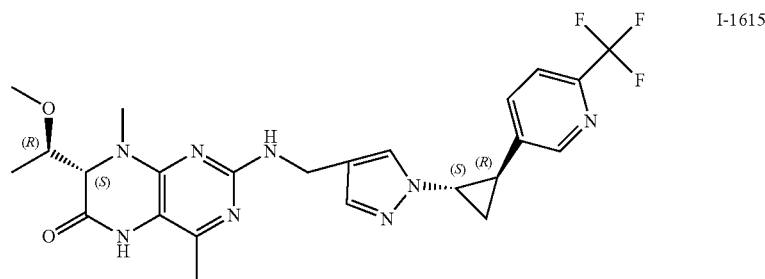
I-1615
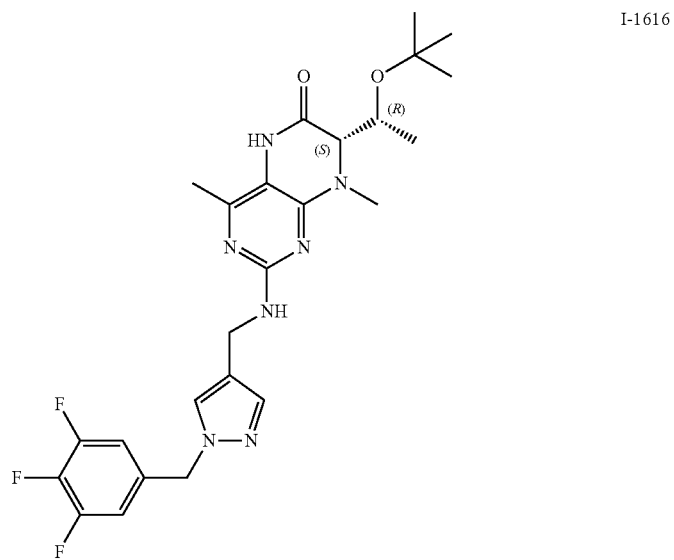
I-1616

TABLE C-continued
Exemplary Compounds
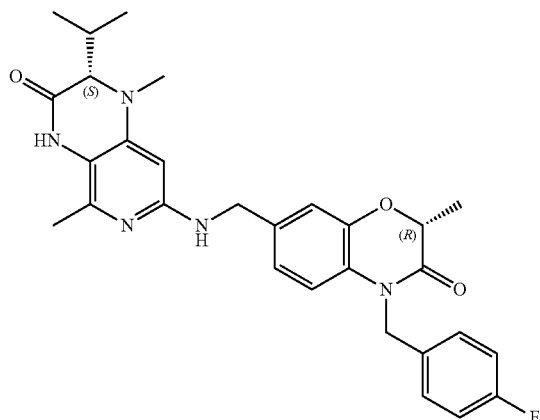
I-1617
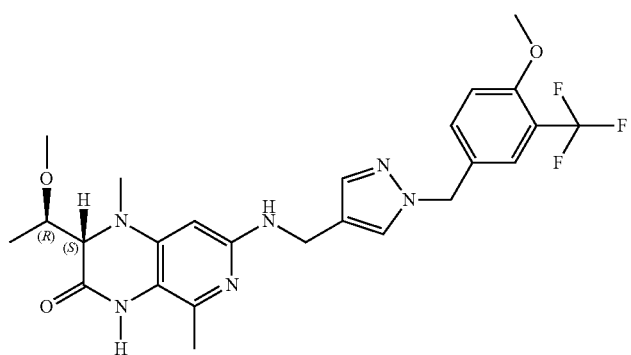
I-1618
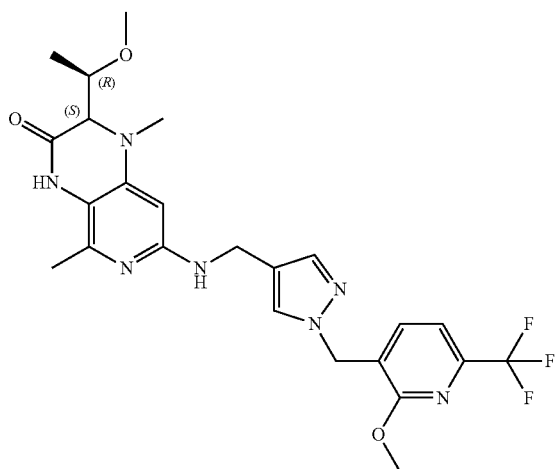
I-1619
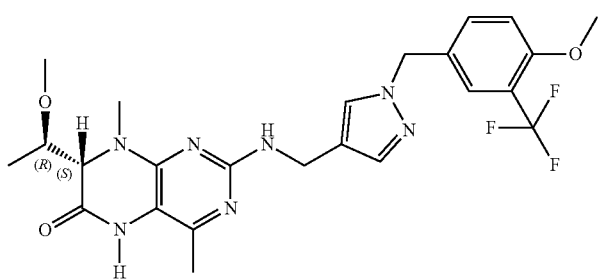
I-1620

TABLE C-continued
Exemplary Compounds
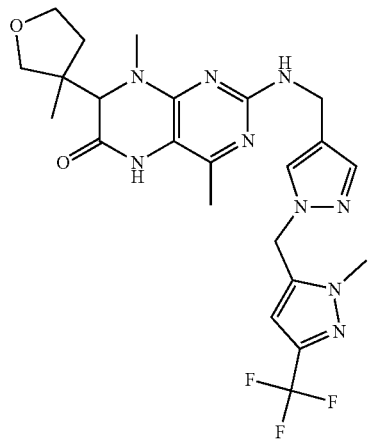 [SMILES: Cc1nc(NCc2cnn(Cc3cc(C(F)(F)F)nn3C)c2)nc2c1NC(=O)C(C1(C)CCOC1)N2C]
I-1621
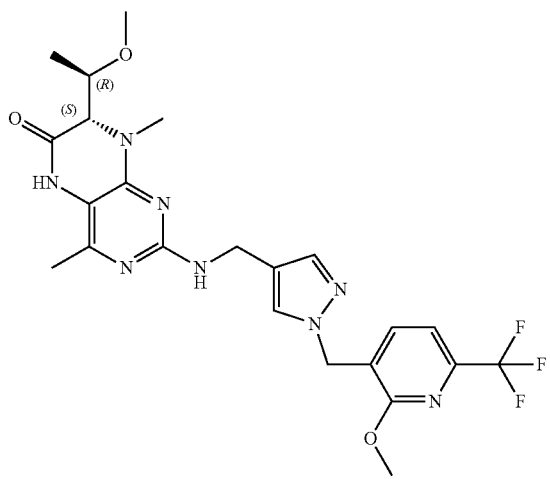
I-1622
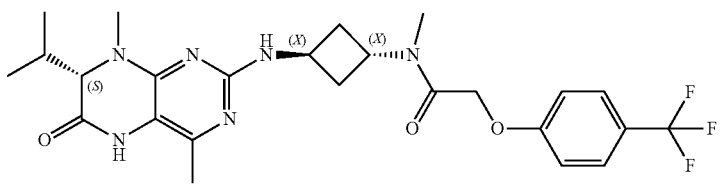
I-1623
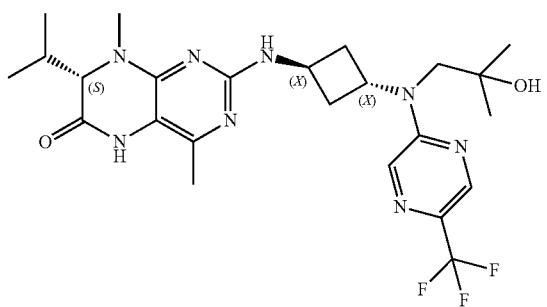
I-1624

TABLE C-continued
Exemplary Compounds
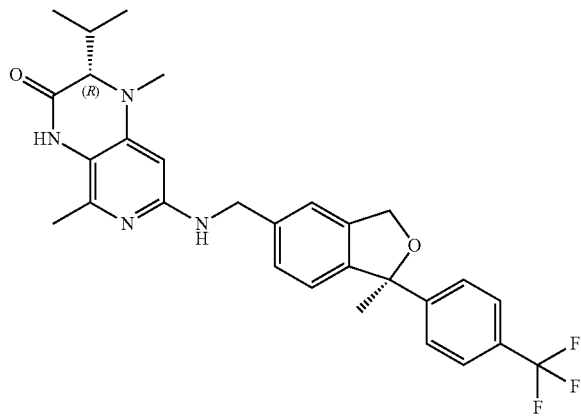
I-1625
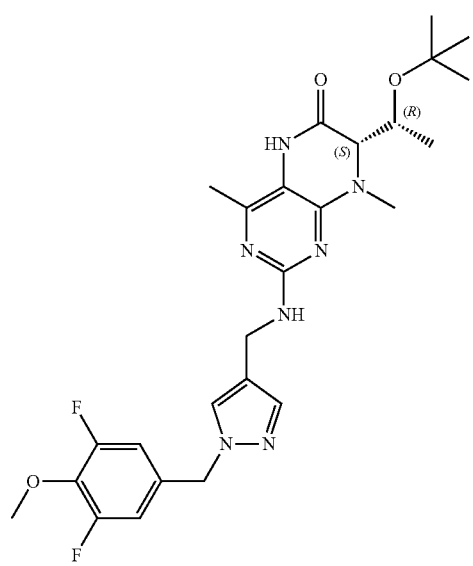
I-1626
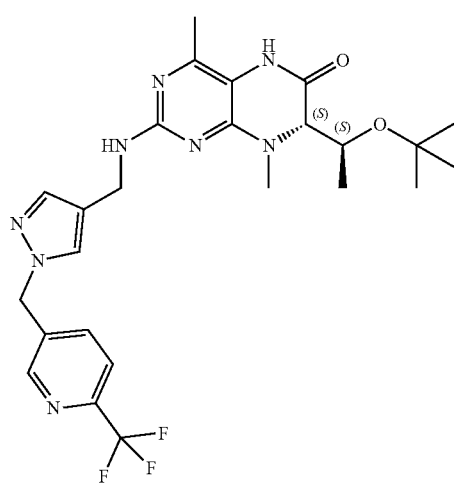
I-1627

TABLE C-continued
Exemplary Compounds
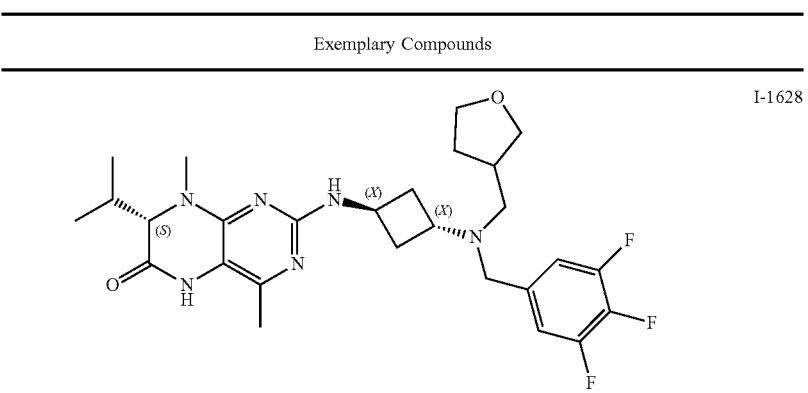
I-1628
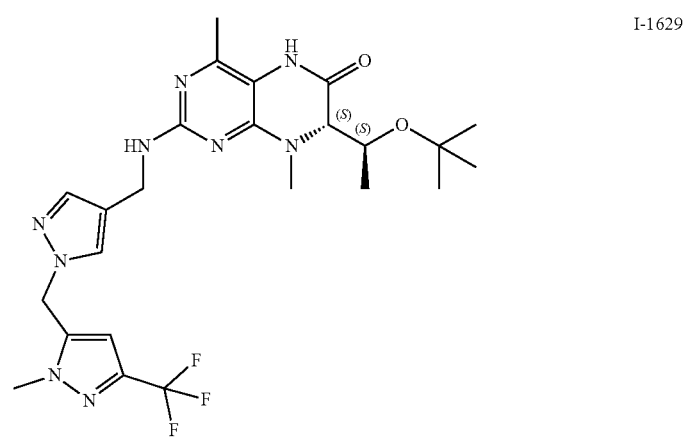
I-1629
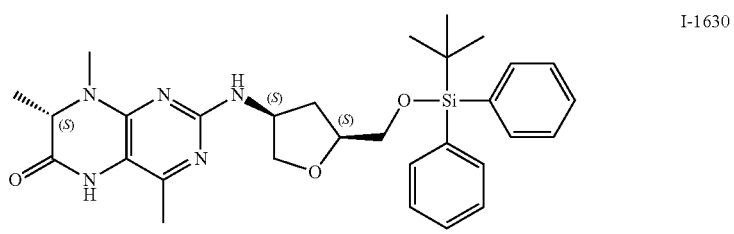
I-1630
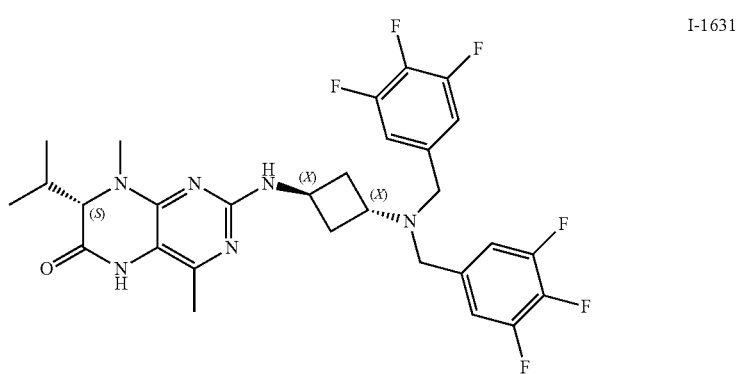
I-1631

TABLE C-continued
Exemplary Compounds
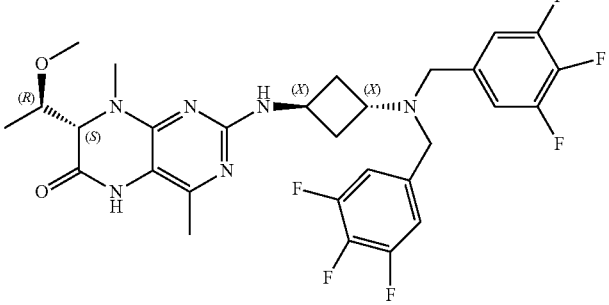 I-1632
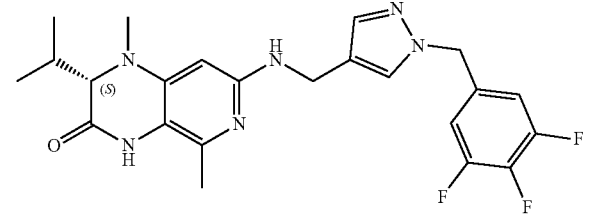 I-1633
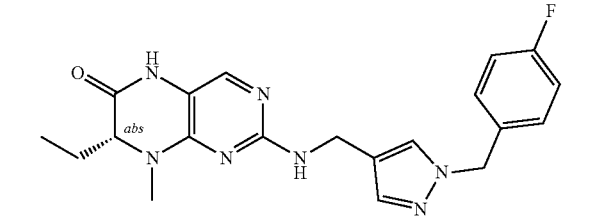 [SMILES: CC[C@@H]1C(=O)Nc2cnc(NCc3cnn(Cc4ccc(F)cc4)c3)nc2N1C] I-1634
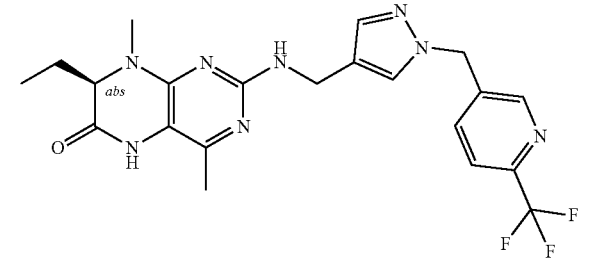 [SMILES: CC[C@@H]1C(=O)Nc2c(C)nc(NCc3cnn(Cc4ccc(C(F)(F)F)nc4)c3)nc2N1C] I-1635
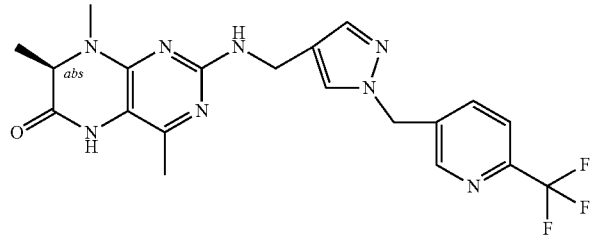 [SMILES: Cc1nc(NCc2cnn(Cc3ccc(C(F)(F)F)nc3)c2)nc2c1NC(=O)[C@@H](C)N2C] I-1636
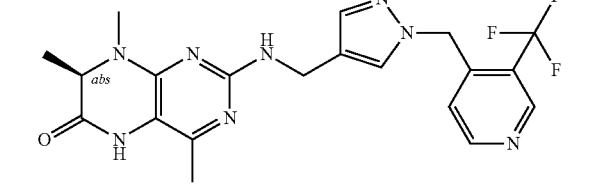 I-1637

TABLE C-continued
Exemplary Compounds
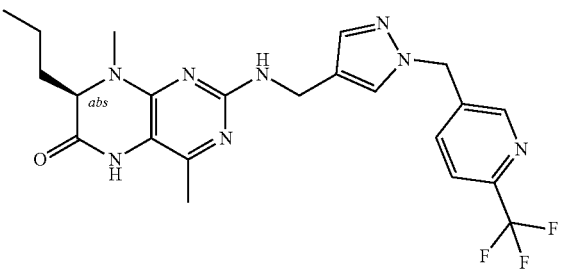 [SMILES: CCC[C@@H]1C(=O)Nc2c(C)nc(NCc3cnn(Cc4ccc(C(F)(F)F)nc4)c3)nc2N1C]
I-1638
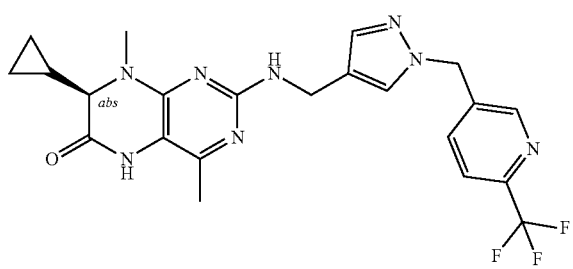 [SMILES: Cc1nc(NCc2cnn(Cc3ccc(C(F)(F)F)nc3)c2)nc2c1NC(=O)[C@@H](C1CC1)N2C]
I-1639
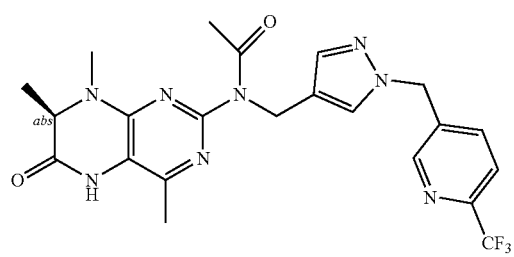 [SMILES: CC(=O)N(Cc1cnn(Cc2ccc(C(F)(F)F)nc2)c1)c1nc(C)c2c(n1)N(C)[C@H](C)C(=O)N2]
I-1640
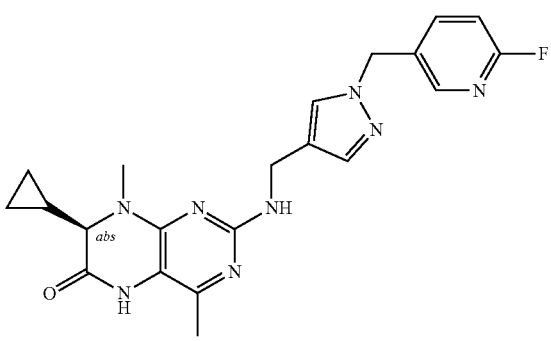 [SMILES: Cc1nc(NCc2cnn(Cc3ccc(F)nc3)c2)nc2c1NC(=O)[C@@H](C1CC1)N2C]
I-1641
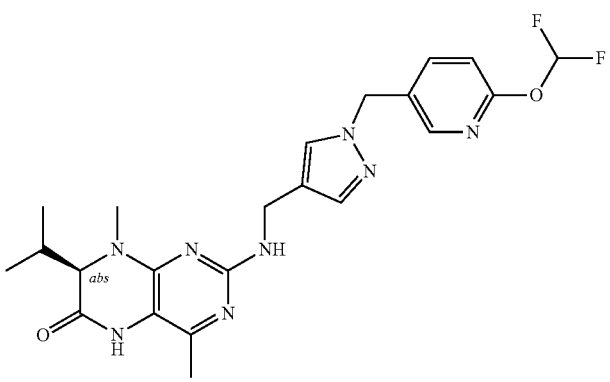 [SMILES: Cc1nc(NCc2cnn(Cc3ccc(OC(F)F)nc3)c2)nc2c1NC(=O)[C@@H](C(C)C)N2C]
I-1642

TABLE C-continued
Exemplary Compounds
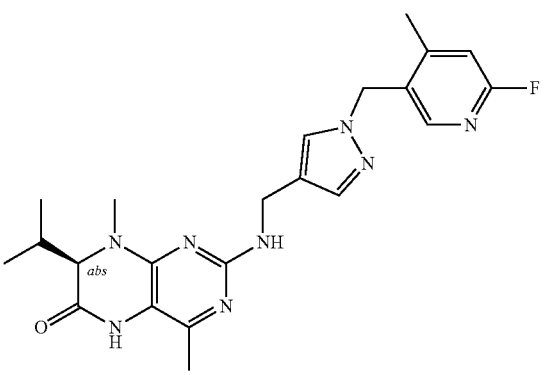 [SMILES: Cc1cc(F)ncc1Cn1cc(CNc2nc(C)c3c(n2)N(C)[C@H](C(C)C)C(=O)N3)cn1]
I-1643
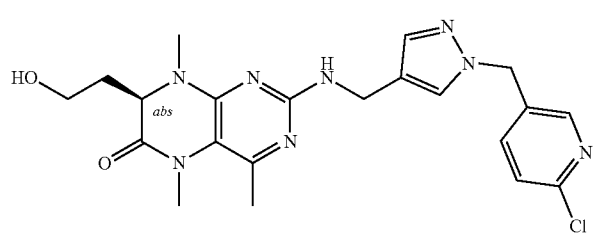 [SMILES: Cc1nc(NCc2cnn(Cc3ccc(Cl)nc3)c2)nc2c1N(C)C(=O)[C@@H](CCO)N2C]
I-1644
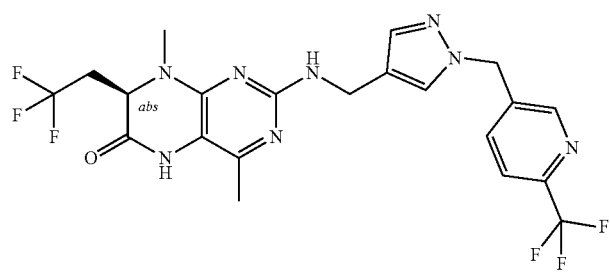 [SMILES: Cc1nc(NCc2cnn(Cc3ccc(C(F)(F)F)nc3)c2)nc2c1NC(=O)[C@@H](CC(F)(F)F)N2C]
I-1645
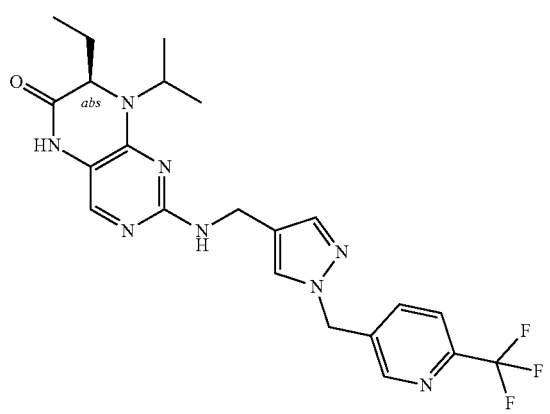 [SMILES: CC[C@@H]1C(=O)Nc2cnc(NCc3cnn(Cc4ccc(C(F)(F)F)nc4)c3)nc2N1C(C)C]
I-1646

TABLE C-continued

Exemplary Compounds

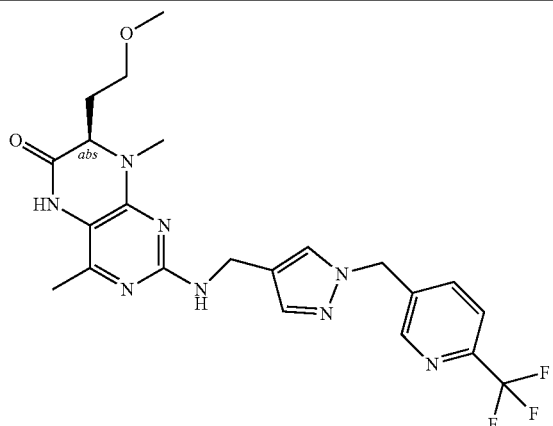

I-1647

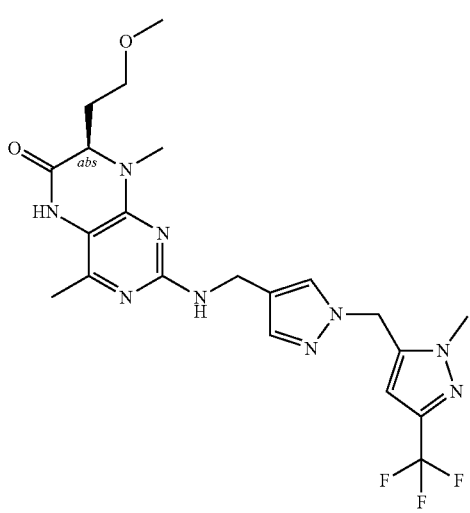 [SMILES: COCC[C@@H]1C(=O)Nc2c(C)nc(NCc3cnn(Cc4cc(C(F)(F)F)nn4C)c3)nc2N1C]

I-1648

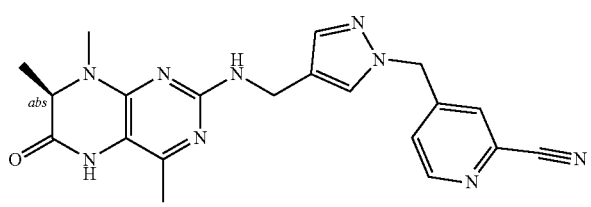 [SMILES: Cc1nc(NCc2cnn(Cc3ccnc(C#N)c3)c2)nc2c1NC(=O)[C@@H](C)N2C]

I-1649

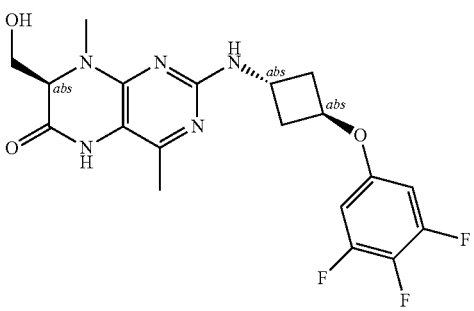 [SMILES: Cc1nc(N[C@H]2C[C@H](Oc3cc(F)c(F)c(F)c3)C2)nc2c1NC(=O)[C@@H](CO)N2C]

I-1650

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3rd edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3rd edition, John Wiley & Sons, 1999, and Philip Kocienski, in "Protecting Groups", Georg Thieme Verlag Stuttgart, New York, 1994, the entireties of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl) ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3rd edition, John Wiley & Sons, 1999, and Philip Kocienski, in "Protecting Groups", Georg Thieme Verlag Stuttgart, New York, 1994, the entireties of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See, for example, "March's Advanced Organic Chemistry", 5th Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below.

In one aspect, the present invention provides a method for synthesizing a compound of Formula I, or subformulae thereof, or a salt thereof, comprising reacting a compound of formula:

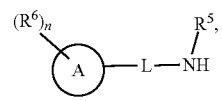

or a salt thereof, and a compound of formula:

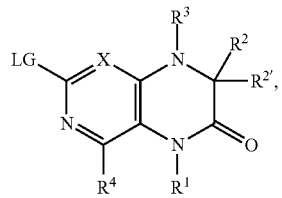

or a salt thereof, wherein LG is a leaving group, and each of Ring A, L, $R^1$, $R^2$, $R^{2'}$, $R^3$, $R^4$, $R^5$, $R^6$, and n is as defined above and described in embodiments herein, both singly and in combination.

In some embodiments, the present invention provides a compound of formula:

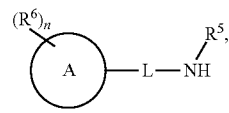

or a salt thereof, wherein each of Ring A, L, $R^5$, $R^6$, and n is as defined above and described in embodiments herein, both singly and in combination.

In some embodiments, the present invention provides a compound of formula:

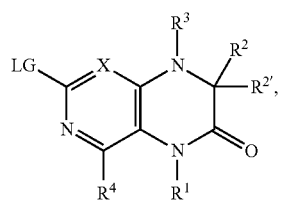

or a salt thereof, wherein LG is a leaving group, and each of $R^1$, $R^2$, $R^{2'}$, $R^3$, and $R^4$ is as defined above and described in embodiments herein, both singly and in combination In some embodiments, the present invention provides a method for synthesizing a compound of Formula VI-a, or a salt thereof, comprising reacting a compound of formula:

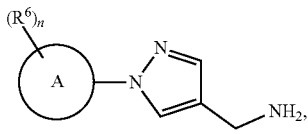

or a salt thereof, and a compound of formula:

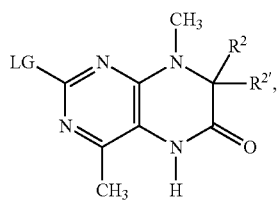

or a salt thereof, wherein LG is a leaving group, and each of Ring A, $R^2$, $R^{2'}$, $R^6$, and n is as defined above and described in embodiments herein, both singly and in combination.

In some embodiments, the present invention provides a method for synthesizing a compound of Formula VI-b, or a salt thereof, comprising reacting a compound of formula:

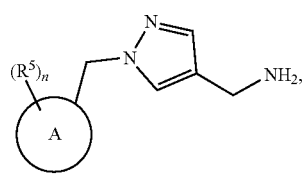

or a salt thereof, and a compound of formula:

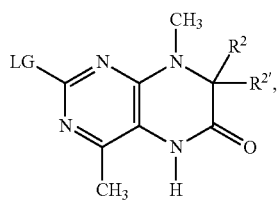

or a salt thereof, wherein LG is a leaving group, and each of Ring A, $R^2$, $R^{2'}$, $R^6$, and n is as defined above and described in embodiments herein, both singly and in combination.

In some embodiments, the present invention provides a method for synthesizing a compound of Formula VI-c, or a salt thereof, comprising reacting a compound of formula:

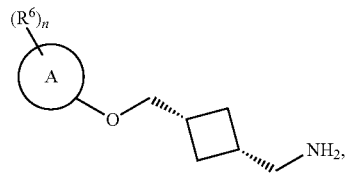

or a salt thereof, and a compound of formula:

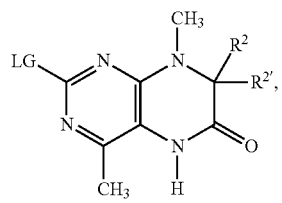

or salt thereof, wherein LG is a leaving group, and each of Ring A, $R^2$, $R^{2'}$, $R^6$, and n is as defined above and described in embodiments herein, both singly and in combination.

In some embodiments, the present invention provides a compound of formula:

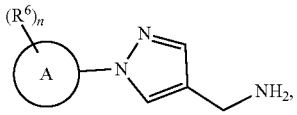

or a salt thereof, wherein each of Ring A, $R^6$, and n is as defined above and described in embodiments herein, both singly and in combination.

In some embodiments, the present invention provides a compound of formula:

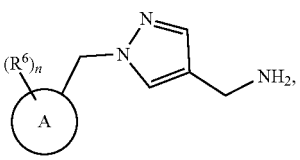

or a salt thereof, wherein each of Ring A, $R^6$, and n is as defined above and described in embodiments herein, both singly and in combination.

In some embodiments, the present invention provides a compound of formula:

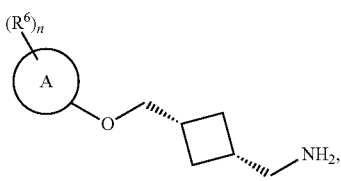

or a salt thereof, wherein each of Ring A, $R^6$, and n is as defined above and described in embodiments herein, both singly and in combination.

In some embodiments, the present invention provides a compound of formula:

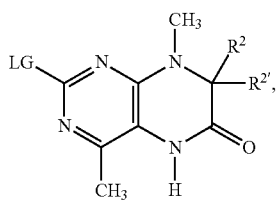

or a salt thereof, wherein LG is a leaving group, and each of $R^2$ and $R^{2'}$ is as defined above and described in embodiments herein, both singly and in combination.

5. Uses, Formulation and Administration

The present invention provides methods of treating a subject with cancer. The methods comprise administering a pharmaceutically effective amount of a chemical entity of the invention described herein (e.g., a chemical entity that is a compound of the invention described herein, or a pharmaceutically acceptable salt thereof, or a composition thereof) to the subject.

The present invention also provides methods of inhibiting cancer cell growth, including processes of cellular proliferation, invasiveness, and metastasis in a biological system. In some embodiments, the methods are employed to inhibit or reduce cancer cell growth, invasiveness, metastasis, or tumor incidence in a subject with cancer.

The present invention also provides use of a chemical entity of the invention described herein for treating a subject with cancer and use of such compounds in the manufacture of an medicament for treating a subject with cancer.

The present invention also provides methods of treating a subject with cancer, comprising administering a wolframin-dependent modulator of endoplasmic reticulum (ER) stress and/or unfold protein response (UPR) or a wolframin-dependent modulator of calcium flux at or in the ER to the subject. In some embodiments, a method of treating a subject with cancer, comprises administering a wolframin-dependent modulator of endoplasmic reticulum (ER) stress and/or unfold protein response (UPR) to the subject.

In some embodiments, the present invention provides an in vitro method comprising administering a wolframin modulator in a cancer cell or tumor of a subject with cancer.

The present invention also provides methods of treating a subject with cancer, comprising:
measuring an expression level of wolfram syndrome 1 gene (WFS1) or the protein encoded by WFS1 in a cancer cell or tumor of the subject; and
administering a wolframin-dependent modulator of endoplasmic reticulum (ER) stress and/or unfold protein response (UPR) or a wolframin-dependent modulator of calcium flux at or in the ER to the subject if said expression level of WFS1 or the protein encoded by WFS1 is greater than a reference value from a subject with the same cancer.

The present invention also provides a method of sensitizing a cancer cell or tumor of a subject with cancer to an anticancer treatment, comprising increasing the expression of wolframin in a cancer cell or tumor of a subject with cancer; and wherein the anticancer treatment comprises administering a chemical entity of the invention described herein to the cancer cell or tumor.

The present invention also provides a method of treating a subject with cancer comprising increasing the expression of wolframin in a cancer cell or tumor of a subject with cancer, and administering a chemical entity of the invention described herein to the subject.

The present invention also provides a method of treating a subject with cancer, comprising measuring an expression level of wolfram syndrome 1 gene (WFS1) or the protein encoded by WFS1 in a cancer cell or tumor of the subject, and administering a wolframin-dependent modulator of endoplasmic reticulum (ER) stress and/or unfolded protein response (UPR) or a wolframin-dependent modulator of calcium flux at or in the ER to the subject if said expression level of WFS1 or the protein encoded by WFS1 is greater than a reference value from a subject with the same cancer.

The present invention also provides a method of measuring a binding constant of a candidate molecule to a wolframin complex, comprising measuring the displacement of a radiolabeled probe that binds to a wolframin complex by a candidate molecule which may bind to the wolframin complex, wherein the radiolabeled probe is a radiolabeled wolframin-dependent modulator, such as a or a radiolabeled wolframin-dependent modulator of calcium flux at or in the ER or radiolabeled wolframin-dependent modulator of endoplasmic reticulum (ER) stress and/or unfolded protein response (UPR). In some embodiments, a wolframin complex is a complex of wolframin and wolframi-binding or wolframin-associated protein(s).

The present invention also provides a method of measuring a binding constant of a candidate molecule to wolframin, comprising measuring the displacement of a radiolabeled probe that binds to wolframin by a candidate molecule which may bind to the wolframin, wherein the radiolabeled probe is a radiolabeled wolframin-dependent modulator, such as a or a radiolabeled wolframin-dependent modulator of calcium flux at or in the ER or radiolabeled wolframin-dependent modulator of endoplasmic reticulum (ER) stress and/or unfolded protein response (UPR).

The present invention also provides a method of screening candidate molecules to determine whether they are wolframin-dependent modulator of endoplasmic reticulum (ER) stress and/or unfolded protein response (UPR), comprising introducing a candidate molecule into a cancer cell(s) that comprises a wolframin complex and has been treated with another molecule which binds to the wolframin complex and modulates ER and/or UPR or its binding to the wolframin complex modulates ER and/or UPR.

The present invention also provides a method of screening candidate molecules to determine whether they are wolframin-dependent modulator of calcium flux at or in the endoplasmic reticulum (ER), comprising introducing a candidate molecule into a cancer cell(s) that comprises a wolframin complex and has been treated with another molecule which binds to the wolframin complex and modulates calcium flux at or in the ER or its binding to the wolframin complex modulates calcium flux at or in the ER.

The present invention also provides a method of screening candidate molecules to determine whether they are wolframin-dependent modulator (e.g., wolframin-dependent modulator of endoplasmic reticulum (ER) stress and/or unfolded protein response (UPR) or a wolframin-dependent modulator calcium flux at or in the endoplasmic reticulum (ER)), said method comprising monitoring a sensitive cell for induction of calcium flux, ER Stress, or the UPR; and comparing the degree to which the same effect occurs in a genetically matched cell that has been engineered to not express wolfrmin or to express a different level of wolframin, or which through a spontaneous mutation is similar in all regards to the sensitive cell except for the level of wolframin that is expressed.

The present invention also provides a method of sensitizing a cancer cell or tumor of a subject with cancer to an anticancer treatment, comprising increasing the expression of wolframin in a cancer cell or tumor of a subject with cancer; and wherein the anticancer treatment comprises administering a chemical entity described herein to the cancer cell or tumor.

The present invention also provides a method of sensitizing a cancer cell or tumor of a subject to an anticancer treatment, comprising: increasing the expression of wolframin in a cancer cell or tumor of a subject with cancer; and wherein the anticancer treatment comprises administering a wolframin-dependent modulator, such as a wolframin-dependent modulator of endoplasmic reticulum (ER) stress and/or unfolded protein response (UPR) or a wolframin-dependent modulator of calcium flux at or in the ER, to the cancer cell or tumor.

The present invention also provides a method of treating a subject with cancer, comprising: increasing the expression of wolframin in a cancer cell or tumor of a subject with cancer; and administering a chemical entity of the invention described herein to the subject.

The present invention also provides a method of treating a subject with cancer, comprising: increasing the expression of wolframin in a cancer cell or tumor of a subject with cancer; and administering a wolframin-dependent modulator described herein, such as a wolframin-dependent modulator of endoplasmic reticulum (ER) stress and/or unfolded protein response (UPR) or a wolframin-dependent modulator of calcium flux at or in the ER, to the subject.

In some embodiments, a method of treating a subject with cancer comprises increasing the expression of wolframin in a cancer cell or tumor of a subject with cancer; and administering a chemical entity of the invention as described herein to the subject.

In some embodiments, a method of treating a subject with cancer comprises increasing the expression of wolframin in a cancer cell or tumor of a subject with cancer; and administering a wolframin-dependent modulator of endoplasmic reticulum (ER) stress and/or unfold protein response (UPR) or a wolframin-dependent modulator of calcium flux (collectively, a "wolframin-dependent modulator") to the subject. In embodiments, such a wolframin-dependent modulator (e.g., a wolframin-dependent modulator of endoplasmic reticulum (ER) stress and/or unfold protein response (UPR) or a wolframin-dependent modulator of calcium flux) is a small molecule (e.g., a chemical entity of the invention described herein), a polypeptide, a nucleic acid molecule, or an antibody or fragment thereof.

In some embodiments, a method of treating a subject with cancer comprises measuring an expression level of wolfram syndrome 1 gene (WFS1) or the protein encoded by WFS1 (wolframin) in a cancer cell or tumor of a subject with cancer; and administering a wolframin-dependent modulator (e.g, wolframin-dependent modulator of endoplasmic reticulum (ER) stress and/or unfold protein response (UPR) or wolframin-dependent modulator of calcium flux) to the subject if said expression level of WFS1 or the protein encoded by WFS1 is greater than a reference value from a subject with the same cancer. In some embodiments, a wolframin-dependent modulator (e.g, wolframin-dependent endoplasmic reticulum (ER) stress and/or unfold protein response (UPR) or wolframin-dependent modulator of calcium flux) is a small molecule (e.g., a chemical entity of the invention described herein), a polypeptide, a nucleic acid molecule, or an antibody or fragment thereof.

In some embodiments, a method of sensitizing a cancer cell or tumor of a subject with cancer to an anticancer treatment comprises increasing the expression of wolframin in a cancer cell or tumor of the subject; and wherein the anticancer treatment comprises administering any of the wolframin-modulators of the invention (e.g., a wolframin-dependent modulator of endoplasmic reticulum (ER) stress and/or unfolded protein response (UPR) or a wolframin-dependent modulator of calcium flux) to the cancer cell or tumor. In some embodiments, the wolframin-modulators are small molecules (e.g, a chemical entity of the invention as described herein. In some embodiments, the wolframin-modulators are polypeptides, nucleic acid molecules, or antibodies or fragments thereof.

In some embodiments, a chemical entity of the invention described herein is a compound of the invention as described herein. In some embodiments, a chemical entity of the invention described herein is a pharmaceutically acceptable salt of a compound of the invention as described herein. In some embodiments, a chemical entity of the invention described herein is a composition of the invention as described herein.

Also provided herein is a kit for predicting the likelihood of response of a subject with cancer to an anticancer treatment: a) reagents to measure an expression level of wolfram syndrome 1 gene (WFS1) or the protein encoded by WFS1 in a cancer cell or tumor of the subject; and b) a guideline comprising instructions about whether or not a patient with cancer to be under an anticancer treatment would respond to an anticancer treatment with a chemical entity of the invention described herein, wherein an expression level of WFS1 or the protein encoded by WFS1 greater than a reference value from a subject with the same cancer indicates that the subject to be under an anticancer treatment is likely to respond to the anticancer treatment with a chemical entity of the invention described herein.

In some embodiments of the kits and methods provided herein, a wolframin-dependent moleculator is a wolframin-dependent modulator of endoplasmic reticulum (ER) stress and/or unfolded protein response (UPR) or a wolframin-dependent modulator of calcium flux at or in the ER. In some embodiments, each of the wolframin-dependent moleculators is a small molecule. In embodiments, said small molecule is a chemical entity of the invention described herein.

In some embodiments of the kits and methods provided herein, a wolframin-dependent moleculator is a wolframin-dependent moleculator of endoplasmic reticulum (ER) stress and/or unfolded protein response (UPR) or a wolframin-dependent modulator of calcium flux at or in the ER. In some embodiments, each of the wolframin-dependent moleculators is a polypeptide, nucleic acid molecule, or an antibody or a fragment thereof.

In some embodiments, a wolframin-dependent modulator is a polypeptide.

In some embodiments, a wolframin-dependent modulator is a nucleic acid molecule. In some embodiments, a nucleic acid molecule modulates activity or function of a wolframin complex to cause ER stress and/or UPR. In some embodiments, this can be monitored using conventional methods well known in the art, for example by screening using real time PCR as described in the examples.

In embodiments, a wolframin-dependent modulator is an antibody or fragment thereof (e.g., an antibody that can open a wolframin $Ca^{2+}$ channel, or a fragment thereof).

The present invention also provides a method of predicting the likelihood of response of a subject with cancer to an anticancer treatment with a compound or composition of the invention described herein. In one embodiment, the method comprises measuring a level of endoplasmic reticulum (ER) stress or unfold protein response (UPR) in a tumor of the subject.

The present invention also provides a method of treating a subject with cancer, comprising: a) measuring an expression level of wolfram syndrome 1 gene (WFS1) or the protein encoded by WFS1 in a cancer cell or tumor of a subject with cancer; and b) administering a pharmaceutically effective amount of a chemical entity of the invention described herein to the subject if said expression level of WFS1 or the protein encoded by WFS1 is greater than a reference value from a subject with the same cancer.

In some embodiments, the present invention provides a method of treating a subject with cancer, comprising administering a pharmaceutically effective amount of a chemical entity of the invention described herein, wherein an expression level of wolfram syndrome 1 gene (WFS1) or the protein encoded by WFS1 in a tumor of the subject is greater than a reference value from a subject with the same cancer.

In some embodiments, the present invention provides an in vitro method for predicting the likelihood of response of a subject with cancer to an anticancer treatment with a chemical entity of the invention described herein, comprising measuring an expression level of endoplasmic reticulum (ER) stress or unfold protein (UPR) response in a tumor sample obtained from the subject.

Pharmaceutically Acceptable Compositions

According to another embodiment, the invention provides a composition comprising a compound of this invention, or a pharmaceutically acceptable derivative thereof, and a pharmaceutically acceptable carrier, adjuvant, or vehicle. In certain embodiments, the amount of compound in compositions of this invention is such that is effective to cause cancer cell death in a biological sample or in a patient. In certain embodiments, the amount of compound in compositions of this invention is such that is effective to induce UPR in cancer cells in a biological sample or in a patient. In certain embodiments, the amount of compound in compositions of this invention is such that is effective to induce ER stress in cancer cells in a biological sample or in a patient. In certain embodiments, the amount of compound in compositions of this invention is such that is effective to induce calcium release from the ER via WFS1 in cancer cells in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

As used herein, the term "active metabolite or residue thereof" means that a metabolite or residue thereof also results in cell death.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for treatment of cellular proliferative disorders. As provided above, the compounds described herein have been found capable of causing calcium release from the endoplasmic reticulum (ER) via a putative $Ca^{2+}$ channel known as Wolframin (WFS1), inducing ER stress and the "unfolded protein response" (UPR), and resulting cell death.

In some embodiments, the present invention provides a method for treating a cellular proliferative disorder in a patient comprising administering to said patient a compound of the present invention, or a composition comprising said compound. In some embodiments, the present invention provides a compound of the present invention, or a composition comprising said compound, for use in the treatment of a cellular proliferative disorder. Such disorders are described in detail herein. In some embodiments, a cellular proliferative disorder is a cancer characterized by Wolframin (WFS1) overexpression in the cancer cells. In some embodiments, a cancer characterized by Wolframin (WFS1) overexpression is selected from non-small cell lung cancer (NSCLC), myeloma, multiple myeloma, hepatocellular carcinoma (HCC), breast cancer, bladder cancer, kidney cancer, and melanoma. In some embodiments, a method for treating a cellular proliferative disorder as described herein further comprises determining the Wolframin (WFS1) expression level. In some embodiments, the Wolframin (WFS1) expression level is determined by immunohistochemistry and/or microarray probe intensity.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the present invention provides a method for inducing ER stress in a patient in need thereof, comprising administering a compound of the present invention, or a composition comprising said compound. In some embodiments, the present invention provides a method for inducing the "unfolded protein response" (UPR) in a patient in need thereof, comprising administering a compound of the present invention, or a composition comprising said compound. In some embodiments, the present invention provides a method for causing calcium release from the endoplasmic reticulum (ER) via a putative $Ca^{2+}$ channel known as Wolframin (WFS1) in a patient in need thereof, comprising administering a compound of the present invention, or a composition comprising said compound.

In some embodiments, the present invention provides a compound of any one of Formulas I-VIII, or a composition comprising said compound, for use in causing calcium release from the endoplasmic reticulum (ER) via a putative $Ca^{2+}$ channel known as Wolframin (WFS1) in a subject in need thereof. In some embodiments, the present invention provides a compound of any one of Formulas I-VIII, or a composition comprising said compound, for use in inducing ER stress in a subject in need thereof. In some embodiments, the present invention provides a compound of any one of Formulas I-VIII, or a composition comprising said compound, for use in inducing the "unfolded protein response" (UPR) in a subject in need thereof.

The activity of a compound utilized in this invention as an inhibitor of cell proliferation may be assayed in vitro or in vivo. Detailed conditions for assaying a compound in this invention are set forth in the Examples below.

Cellular Proliferative Disorders

The present invention features methods and compositions for the diagnosis and prognosis of cellular proliferative disorders (e.g., cancer) and the treatment of these disorders. Cellular proliferative disorders described herein include, e.g., cancer, obesity, and proliferation-dependent diseases. Such disorders may be diagnosed using methods known in the art.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the present invention provides a method for treating a cancer that presents as a solid tumor, such as a sarcoma, carcinoma, or lymphoma, comprising the step of administering a disclosed compound, or a pharmaceutically acceptable salt thereof, to a patient in need thereof. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

The present invention further features methods and compositions for the diagnosis, prognosis and treatment of viral-associated cancers, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, the present invention provides a method for treating a cancer in a patient in need thereof, comprising administering to the patient any of the compounds, salts or pharmaceutical compositions described herein. In some embodiments, a cancer is any of the cancers described herein. In some embodiments, a cancer is melanoma cancer. In some embodiments, a cancer is breast cancer. In some embodiments, a cancer is lung cancer. In some embodiments, a cancer is small cell lung cancer (SCLC). In some embodiments, a cancer is non-small cell lung cancer (NSCLC). In some embodiments, a cancer is myeloma. In some embodiments, a cancer is multiple myeloma. In some embodiments, a cancer is hepatocellular carcinoma (HCC). In some embodiments, a cancer is bladder cancer. In some embodiments, a cancer is kidney cancer. In some embodiments, a cancer is melanoma.

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

The compounds and compositions, according to the method of the present invention, may be administered using any amount and any route of administration effective for treating or lessening the severity of a cellular proliferative disorder. The exact amount required will vary from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiment, the invention relates to a method of inducing ER stress in a biological sample comprising the step of contacting said biological sample with a compound of this invention, or a composition comprising said compound.

In some embodiment, the invention relates to a method of inducing the "unfolded protein response" (UPR) in a biological sample comprising the step of contacting said biological sample with a compound of this invention, or a composition comprising said compound.

In certain embodiments, the invention relates to a method of causing calcium release from the endoplasmic reticulum (ER) via a putative $Ca^{2+}$ channel known as Wolframin (WFS1) in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Co-Administration of Additional Therapeutic Agents

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

In some embodiments, the additional therapeutic agent is selected from an immunostimulatory therapeutic compound. In some embodiments, the immunostimulatory therapeutic compound is selected from elotuzumab, mifamurtide, an agonist or activator of a toll-like receptor, or an activator of RORγt.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, an immunostimulatory therapeutic compound, and an immune checkpoint inhibitor.

Other checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck & Co.), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Other checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Other checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Other checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck & Co.), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Other checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck & Co.), an agonistic anti-ICOS antibody, in Phase 1 (NCT02723955); JTX-2011 (Jounce Therapeutics), an agonistic anti-ICOS antibody, in Phase 1 (NCT02904226).

Other checkpoint inhibitors that may be used in the present invention include killer IgG-like receptor (KTR) inhibitors. KTR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Other checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, *Trillium* Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Other checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Other checkpoint inhibitors that may be used in the present invention include agonists of stimulator of interferon genes protein (STING, also known as transmembrane protein 173, or TMEM173). Agonists of STING that are being studied in clinical trials include MK-1454 (Merck & Co.), an agonistic synthetic cyclic dinucleotide, in lymphoma (NCT03010176); and ADU-5100 (MIW815, Aduro Biotech/Novartis), an agonistic synthetic cyclic dinucleotide, in Phase 1 (NCT02675439 and NCT03172936).

Other checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Other checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

In another aspect, the present invention provides a method of treating cancer in a patient in need thereof, wherein said method comprises administering to said patient a compound disclosed herein or a pharmaceutically acceptable salt thereof in combination with one or more additional therapeutic agents selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor.

In some embodiments, the IDO inhibitor is selected from epacadostat, indoximod, capmanitib, GDC-0919, PF-06840003, BMS:F001287, Phy906/KD108, or an enzyme that breaks down kynurenine.

In some embodiments, the PARP inhibitor is selected from olaparib, rucaparib, niraparib, iniparib, talazoparib, or veliparib.

In some embodiments, the HDAC inhibitor is selected from vorinostat, romidepsin, panobinostat, belinostat, entinostat, or chidamide.

In some embodiments, the CDK 4/6 inhibitor is selected from palbociclib, ribociclib, abemaciclib or trilaciclib.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, a second therapeutic agent selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor, and a third therapeutic agent selected from an immune checkpoint inhibitor. In some embodiments, the immune checkpoint inhibitor is selected from nivolumab, pembrolizumab, ipilimumab, avelumab, durvalumab, atezolizumab, or pidilizumab.

Another immunostimulatory therapeutic that may be used in the present invention is recombinant human interleukin 15 (rhIL-15). rhIL-15 has been tested in the clinic as a therapy for melanoma and renal cell carcinoma (NCT01021059 and NCT01369888) and leukemias (NCT02689453). Another immunostimulatory therapeutic that may be used in the present invention is recombinant human interleukin 12 (rhIL-12). Another suitable IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). Recombinant human interleukin 12 (rhIL-12) has been tested in the clinic for many oncological indications, for example, as a therapy for lymphoma (NM-IL-12, Neumedicines, Inc.), (NCT02544724 and NCT02542124).

In some embodiments, the PI3K inhibitor is selected from idelalisib, alpelisib, taselisib, pictilisib, copanlisib, duvelisib, PQR309, or TGR1202.

In another aspect, the present invention provides a method of treating cancer in a patient in need thereof, wherein said method comprises administering to said patient a compound disclosed herein or a pharmaceutically acceptable salt thereof in combination with one or more additional therapeutic agents selected from a platinum-based therapeutic, a taxane, a nucleoside inhibitor, or a therapeutic agent that interferes with normal DNA synthesis, protein synthesis, cell replication, or will otherwise inhibit rapidly proliferating cells.

In some embodiments, the platinum-based therapeutic is selected from cisplatin, carboplatin, oxaliplatin, nedaplatin, picoplatin, or satraplatin.

In some embodiments, the taxane is selected from paclitaxel, docetaxel, albumin-bound paclitaxel, cabazitaxel, or SID530.

In some embodiments, the therapeutic agent that interferes with normal DNA synthesis, protein synthesis, cell replication, or will otherwise interfere with the replication of rapidly proliferating cells is selected from trabectedin, mechlorethamine, vincristine, temozolomide, cytarabine, lomustine, azacitidine, omacetaxine mepesuccinate, asparaginase Erwinia chrysanthemi, eribulin mesylate, capecetrine, bendamustine, ixabepilone, nelarabine, clorafabine, trifluridine, or tipiracil.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, a second therapeutic agent selected from a platinum-based therapeutic, a taxane, a nucleoside inhibitor, or a therapeutic agent that interferes with normal DNA synthesis, protein synthesis, cell replication, or will otherwise inhibit rapidly proliferating cells, and a third therapeutic agent selected from an immune checkpoint inhibitor.

In some embodiments, the immune checkpoint inhibitor is selected from nivolumab, pembrolizumab, ipilimumab, avelumab, durvalumab, atezolizumab, or pidilizumab.

In some embodiments, any one of the foregoing methods further comprises the step of obtaining a biological sample from the patient and measuring the amount of a disease-related biomarker.

In some embodiments, the biological sample is a blood sample.

In some embodiments, the disease-related biomarker is selected from circulating CD8+ T cells or the ratio of CD8+ T cells:Treg cells.

In one aspect, the present invention provides a method of treating an advanced cancer, comprising administering a compound disclosed herein or a pharmaceutically acceptable salt thereof or pharmaceutical composition thereof, either as a single agent (monotherapy), or in combination with a chemotherapeutic, a targeted therapeutic, such as a kinase inhibitor, and/or an immunomodulatory therapy, such as an immune checkpoint inhibitor. In some embodiments, the immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the additional therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaecuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In some embodiments, the additional therapeutic agent is an mTOR inhibitor, which inhibits cell proliferation, angiogenesis and glucose uptake. Approved mTOR inhibitors useful in the present invention include everolimus (Afinitor®, Novartis); temsirolimus (Torisel®, Pfizer); and sirolimus (Rapamune®, Pfizer).

In some embodiments, the additional therapeutic agent is a Poly ADP ribose polymerase (PARP) inhibitor. Approved PARP inhibitors useful in the present invention include olaparib (Lynparza®, AstraZeneca); rucaparib (Rubraca®, Clovis Oncology); and niraparib (Zejula®, Tesaro). Other PARP inhibitors being studied which may be used in the present invention include talazoparib (MDV3800/BMN 673/LT00673, Medivation/Pfizer/Biomarin); veliparib (ABT-888, AbbVie); and BGB-290 (BeiGene, Inc.).

In some embodiments, the additional therapeutic agent is a phosphatidylinositol 3 kinase (PI3K) inhibitor. Approved PI3K inhibitors useful in the present invention include idelalisib (Zydelig®, Gilead). Other PI3K inhibitors being studied which may be used in the present invention include alpelisib (BYL719, Novartis); taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, the additional therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, the additional therapeutic agent is a histone deacetylase (HDAC) inhibitor. Approved HDAC inhibitors useful in the present invention include vorinostat (Zolinza®, Merck & Co.); romidepsin (Istodax®, Celgene); panobinostat (Farydak®, Novartis); and belinostat (Beleodaq®, Spectrum Pharmaceuticals). Other HDAC inhibitors being studied which may be used in the present invention include entinostat (SNDX-275, Syndax Pharmaceuticals) (NCT00866333); and chidamide (Epidaza®, HBI-8000, Chipscreen Biosciences, China).

In some embodiments, the additional therapeutic agent is a CDK inhibitor, such as a CDK 4/6 inhibitor. Approved CDK 4/6 inhibitors useful in the present invention include palbociclib (Ibrance®, Pfizer); and ribociclib (Kisqali®, Novartis). Other CDK 4/6 inhibitors being studied which may be used in the present invention include abemaciclib (Ly2835219, Eli Lilly); and trilaciclib (G1T28, G1 Therapeutics).

In some embodiments, the additional therapeutic agent is an indoleamine (2,3)-dioxygenase (IDO) inhibitor. IDO inhibitors being studied which may be used in the present invention include epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); and an enzyme that breaks down kynurenine (Kynase, Kyn Therapeutics).

In some embodiments, the additional therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, the additional therapeutic agent is an aromatase inhibitor. Approved aromatase inhibitors which may be used in the present invention include exemestane (Aromasin®, Pfizer); anastazole (Arimidex®, AstraZeneca) and letrozole (Femara®, Novartis).

In some embodiments, the additional therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, the additional therapeutic agent is a folic acid inhibitor. Approved folic acid inhibitors useful in the present invention include pemetrexed (Alimta®, Eli Lilly).

In some embodiments, the additional therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, the additional therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, the additional therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, the additional therapeutic agent is a glutaminase inhibitor. Glutaminase inhibitors being studied which may be used in the present invention include CB-839 (Calithera Biosciences).

In some embodiments, the additional therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, the additional therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, the additional therapeutic agent is a nucleoside inhibitor, or other therapeutic that interfere with normal DNA synthesis, protein synthesis, cell replication, or will otherwise inhibit rapidly proliferating cells. Such nucleoside inhibitors or other therapeutics include trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck & Co.); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, the additional therapeutic agent is a platinum-based therapeutic, also referred to as platins. Platins cause cross-linking of DNA, such that they inhibit DNA repair and/or DNA synthesis, mostly in rapidly reproducing cells, such as cancer cells. Approved platinum-based therapeutics which may be used in the present invention include cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); and nedaplatin (Aqupla®, Shionogi). Other platinum-based therapeutics which have undergone clinical testing and may be used in the present invention include picoplatin (Poniard Pharmaceuticals); and satraplatin (JM-216, Agennix).

In some embodiments, the additional therapeutic agent is a taxane compound, which causes disruption of microtubules, which are essential for cell division. Approved taxane compounds which may be used in the present invention include paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), and cabazitaxel (Jevtana®, Sanofi-Aventis). Other taxane compounds which have undergone clinical testing and may be used in the present invention include SID530 (SK Chemicals, Co.) (NCT00931008).

In some embodiments, the additional therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, the present invention provides a method of treating prostate cancer comprising administering to a patient in need thereof an effective amount of a compound disclosed herein or a pharmaceutically acceptable salt thereof or pharmaceutical composition thereof in combination with an additional therapeutic agent that interferes with the synthesis or activity of androgens. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, the additional therapeutic agent is a selective estrogen receptor modulator (SERM), which interferes with the synthesis or activity of estrogens. Approved SERMs useful in the present invention include raloxifene (Evista®, Eli Lilly).

In some embodiments, the additional therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, the additional therapeutic agent is an inhibitor of interaction between the two primary p53 suppression proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, the additional therapeutic agent is an inhibitor of transforming growth factor-beta (TGF-beta or TGFß). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978.

Additional Co-Administered Therapeutic Agents—Targeted Therapeutics and Immunomodulatory Drugs In some embodiments, the additional therapeutic agent is selected from a targeted therapeutic or immunomodulatory drug. Adjuvant therapies with targeted therapeutics or immunomodulatory drugs have shown promising effectiveness when administered alone but are limited by the development of tumor immunity over time or evasion of the immune response.

In some embodiments, the present invention provides a method of treating cancer, such as a cancer described herein, comprising administering to a patient in need thereof an effective amount of a compound disclosed herein or a pharmaceutically acceptable salt thereof or pharmaceutical composition thereof in combination with an additional therapeutic agent such as a targeted therapeutic or an immunomodulatory drug. In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In other embodiments, the immunomodulatory therapeutic is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, the additional therapeutic agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAdl), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, the additional therapeutic agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, the present invention comprises administering to said patient a compound disclosed herein or a pharmaceutically acceptable salt thereof in combination with a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

Additional Co-Administered Therapeutic Agents—Immunostimulatory Drugs

In some embodiments, the additional therapeutic agent is an immunostimulatory drug. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the present invention provides a method of treating cancer, such as a cancer described herein, comprising administering to a patient in need thereof an effective amount of a compound disclosed herein or a pharmaceutically acceptable salt thereof or pharmaceutical composition thereof in combination with an additional therapeutic agent such as a immunostimulatory drug, such as an immune checkpoint inhibitor. In some embodiments, the compound and the checkpoint inhibitor are administered simultaneously or sequentially. In some embodiments, a compound disclosed herein is administered prior to the initial dosing with the immune checkpoint inhibitor. In certain embodiments, the immune checkpoint inhibitor is administered prior to the initial dosing with the compound disclosed herein.

In certain embodiments, the immune checkpoint inhibitor is selected from a PD-1 antagonist, a PD-L1 antagonist, or a CTLA-4 antagonist. In some embodiments, a compound disclosed herein or a pharmaceutically acceptable salt thereof is administered in combination with nivolumab (anti-PD-1 antibody, Opdivo®, Bristol-Myers Squibb); pembrolizumab (anti-PD-1 antibody, Keytruda®, Merck & Co.); ipilimumab (anti-CTLA-4 antibody, Yervoy®, Bristol-Myers Squibb); durvalumab (anti-PD-L1 antibody, Imfinzi®, AstraZeneca); or atezolizumab (anti-PD-L1 antibody, Tecentriq®, Genentech).

Other immune checkpoint inhibitors suitable for use in the present invention include REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; and PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

Another paradigm for immune-stimulation is the use of oncolytic viruses. In some embodiments, the present invention provides a method for treating a patient by administering a compound disclosed herein or a pharmaceutically acceptable salt thereof or pharmaceutical composition thereof in combination with an immunostimulatory therapy such as oncolytic viruses. Approved immunostimulatory oncolytic viruses which may be used in the present invention include talimogene laherparepvec (live, attenuated herpes simplex virus, Imlygic®, Amgen).

In some embodiments, the additional therapeutic agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. An activator of RORγt, that is being studied which may be used in the present invention is LYC-55716 (Lycera), which is currently being evaluated in clinical trials for the treatment of solid tumors (NCT02929862).

In some embodiments, the additional therapeutic agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other checkpoint inhibitors that may be used in the present invention include inhibitors of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

Other checkpoint inhibitors that may be used in the present invention include inhibitors of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

Checkpoint inhibitors that may be used in the present invention also include inhibitors of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Other immune-oncology agents that may be used in the present invention in combination with a compound disclosed herein include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

Other additional therapeutic agents that may be used in the present invention include glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

A compound of the current invention may also be used to advantage in combination with other antiproliferative compounds. Such antiproliferative compounds include, but are not limited to checkpoint inhibitors; aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd$_6$244 from AstraZeneca, PD181461 from Pfizer and leucovorin.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signalling processes should proceed.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, T6, and memory CD8+ (ap) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFRi ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α-γ- or δ-tocopherol or α-γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MM1270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuranosylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; $Zd_6474$; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Biomarkers

The invention also provides methods of predicting the likelihood of response of a patient to an anticancer treatment with a compound of the invention described herein or a pharmaceutically acceptable salt thereof. In some embodiments, the methods comprise measuring a level of endoplasmic reticulum (ER) stress or unfold protein response (UPR) in a tumor of the patient. Without being bound to a particular theory, ER stress may generate UPR. ER stress or UPR can be caused by, for example, disruption of intracellular calcium homeostasis, disruption of glycosylation, and/or disruption of nutrient availability. In some embodiments, measuring a level of ER stress or unfold protein response is performed prior to the anticancer treatment. In some embodiments, the level of ER stress or unfolded protein response is a level of Wolfram syndrome 1 (WFS1) or the protein encoded by WFS1.

WFS1 is a gene expressing the wolframin protein. In some embodiments, the protein encoded by WFS1 is wolframin. WFS1 (gene ID 7466, accession number AF084481) encodes the protein wolframin (accession number AAC64943) which is a transmembrane protein that resides in the ER and plays a role in regulating calcium homeostasis.

In some embodiments, methods of predicting the likelihood of response of a patient to an anticancer treatment with a compound of the invention described herein or a pharmaceutically acceptable salt thereof further comprise determining whether to treat the patient with a compound of the invention described herein or a pharmaceutically acceptable salt thereof, wherein the patient will be treated with the compound if the level of WFS1 or the protein encoded by WFS1 is greater than a reference value from a patient with the same cancer. The "reference value from a patient with the same cancer" is a cut-off value (cut-off point or standard value) for WFS1 or protein encoded by WFS1 expression levels or scores thereof (e.g., mRNA copies or immunohistochemistry staining density, or a combination thereof).

The invention also provides methods of treating a patient with cancer, comprising: measuring an expression level of WFS1 or the protein encoded by WFS1 in a tumor of the patient; and administering a pharmaceutically effective amount of a compound of the invention to the patient if said expression level of WFS1 or the protein encoded by WFS1 is greater than a reference value from a patient with the same cancer. In some embodiments, the methods further comprise administering a pharmaceutically effective amount of a compound of the invention, wherein an expression level of WFS1 or the protein encoded by WFS1 in a tumor of the patient is greater than a reference value from a patient with the same cancer.

The invention also provides in vitro methods for predicting the likelihood of response of a patient to an anticancer treatment with a compound of the invention. The methods comprise a) measuring an expression level of ER stress or unfold protein response in a tumor sample obtained form the patient. In some embodiments, the expression level of ER stress or unfolded protein response is a level of WFS1 or the protein encoded by WFS1. In some embodiments, the methods further comprise b) applying the expression levels of ER stress or unfold protein response in a tumor sample obtained form the patient to a mathematical equation in order to calculate a patient expression score; and c) comparing the patient expression score to a reference level; and identifying the patient as more likely to respond to the anticancer treatment with a compound of the invention is above the reference level. In some embodiments, a patient signature score above the reference level indicates a patient's high likelihood to respond to treatment with a compound of the invention, whereas a patient signature score below the reference level indicates that said patient is less likely to respond to that treatment. The tumor samples can be any suitable samples taken from a patient. Examples include blood, plasma, and biopsy samples.

The expression level of ER stress or unfold protein response, such as the expression level of WFS1 or the protein encoded by WFS1, can be measured by any method known in the art, such as RT-PCR, northern hybridization, ELISA, immunohistochemistry, and/or immunoblotting. In some embodiments, the expression level of WFS1 is an mRNA expression level. RNA sequencing or microarray measurements (e.g., GeneChip Human Genome U133 Plus 2.0 Array) can also be employed for measuring mRNA expression levels.

In some embodiments, the patient expression score can be calculated from the sum of log 2-transformed mRNA expression levels measured prior to treatment. In some embodiments, the patient expression score is calculated based on mRNA expression levels obtained by RT PCR measurements. The patient expression score calculated using RT PCR may be different from the value calculated based on the microarray technology. However, the patient expression score based on RT PCR can be converted into the value obtained when using microarray technology by established correlation between these methods, as well known to the person of skill in the art.

The invention also provides kits and devices for predicting the likelihood of response of a patient to an anticancer treatment with a compound of the invention. The kits or devices comprise a) reagents to measure an expression level of WFS1 or the protein encoded by WFS1 in a tumor of the patient; and b) a guideline comprising instructions about whether or not a patient would respond to an anticancer treatment with a compound of the invention, wherein an expression level of WFS1 or the protein encoded by WFS1 greater than a reference value from a patient with the same cancer indicates that the patient is likely to respond to the anticancer treatment. The guideline can be a comparator module which comprises a reference value or a set of reference values to which the level of WFS1 in the sample is compared. The comparator module can be in any suitable form. In some embodiments, it is in the form a display device, for example, a strip of colour or numerically coded material which is designed to be placed next to the readout of the sample measurement to indicate the response levels. In some embodiments, the expression level of WFS1 or the protein encoded by WFS1 in the tumor of a patient with cancer is used to predict the likelihood of response of that patient to the compounds of the invention described herein.

EXEMPLIFICATION

General Synthetic Methods

The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Example 1: Preparation of Intermediates

List of Abbreviations

The following abbreviations are used in the examples below:
Ac acetyl
AcOH acetic acid
$Ac_2O$ acetic anhydride
aq aqueous
ATP adenosine triphosphate
$BF_3.OEt_2$ boron trifluoride diethyl ether
Bn benzyl
$Br_2$ Bromine
ACN, $CH_3CN$ acetonitrile
$CD_3OD$ methanol-$d_4$
$CDCl_3$ chloroform-d
COD 1,5-cyclooctadiene
Conc. concentrate
$Cs_2CO_3$ cesium carbonate
CuI copper(I) iodide
$CuSO_4$ copper(II) sulfate
CV column volume
CA commercially available
° C. degree Celcius
DBU 1,8-diazabicyclo[5.4.0]undec-7-ene
DCM methylene chloride or dichloromethane
DIPEA N,N-diisopropylethylamine
DMAP 4-dimethylaminopyridine
DMF dimethylformamide
DMSO dimethylsulfoxide
DMSO-d6 deutered dimethylsulfoxide
EA ethylacetate
Equiv equivalent
EtOAc ethyl acetate
g gram(s)
HATU O-(7-azabenzotriazol-1-yl),N,N,N'',N''-tetramethyl-uroniumhexafluorophosphate
h hour(s)
HCl hydrochloric acid
Hex hexanes
HPLC high pressure liquid chromatography
LCMS liquid chromatography mass spectrometry
M molar
MHz megahertz
mg milligram(s)
mL milliliter(s)
mM millimolar
MeOH methanol
MeONa sodium methoxide
min minute(s)
MS mass spectrometer
MTBE methyl tert-butyl ether
µM micromolar
N normal (molar) concentration
$^1HNMR$ proton nuclear magnetic resonance
NMO N-methylmorpholine-N-oxide
ON overnight
$Pd_2(dba)_3$ Tris(dibenzylideneacetone)dipalladium(0)
Pd/C palladium on carbon
$Pd(OH)_2$ dihydroxy palladium t-butyl X-phos 2-Di-tert-butylphosphino-2',4',6'-triisopropylbiphenyl psi pound per square inch Py pyridine r.b.f. (rbf) round bottom flask RT (rt or r. t.) room temperature S-Phos 2-Dicyclohexylphosphino-2',6'-dimethoxybiphenyl TBAF tetrabutylammonium fluoride TBDMSOTf tert-butyldimethylsilyl trifluoromethanesulfonate TBS tert-butyldimethylsilyl TEA triethylamine Tf trifluoromethanesulfonyl TFA trifluoroacetic acid THF tetrahydrofuran TLC thin layer chromatography TMS trimethylsilyl TMSI trimethylsilyl iodide TMSN$_3$ trimethylsilyl azide TMSOTf trimethylsilyl trifluoromethanesulfonate TPAP Tetrapropylammonium perruthenate UPLC ultra performance liquid chromatography A. Dihydropteridin-One Intermediates Preparation

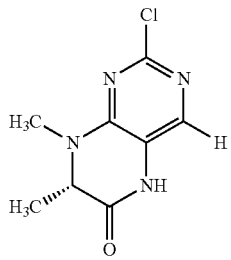

(A-1)

A-1. (7S)-2-Chloro-7,8-dimethyl-7,8-dihydropteridin-6(5H)-one 2,4-Dichloropyrimidin-5-amine (30 g, 159.4 mmol), (2S)-2-(methylamino)propanoic acid (29.59 g, 286.9 mmol), and sodium bicarbonate (48.20 g, 573.8 mmol) were taken into EtOH (285 mL) and water (15.00 mL) and heated to 80° C. for 3 hours. The reaction was cooled to room temperature then cooled in an ice bath. The precipitate was collected by vacuum filtration and washed with water. The filter cake was suspended in water and stirred for 1 hour at room temperature. The solids were collected, washed with water, and dried overnight in a vacuum oven at 50° C. to provide 26 g (75% yield) of the desired product. $^1$H NMR (300 MHz, DMSO-d6) δ 10.76 (s, 1H), 7.50 (s, 1H), 4.19 (q, J=6.9 Hz, 1H), 2.99 (s, 3H), 1.33 (d, J=6.9 Hz, 3H); ESMS (M+H)=212.95; Chiral HPLC—99% ee (AD-H column; 30% (1:1 EtOH/MeOH) in heptane): Rt=6.052 mins. (99.3% ee); [α]$_D$=±16.21 (c=1.03, MeOH).

A-2. (7S)-2-Chloro-4,7,8-trimethyl-7,8-dihydropteridin-6(5H)-one

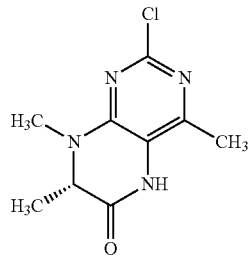

(A-2)

2,4-Dichloro-6-methyl-pyrimidin-5-amine (200 g, 1.123 mol), (2S)-2-(methylamino)propanoic acid (208.4 g, 2.021 mol), and sodium bicarbonate (339.6 g, 4.043 mol) were taken into EtOH (1.900 L) and water (100.0 mL), and heated to reflux overnight. The mixture was cooled to room temperature. The resulting precipitate was filtered and washed three times with water. The filter cake was taken into water (2 L), and stirred for 0.5 h. The solid was collected by vacuum filtration, washed with EtOH (2×300 ml), and dried under vacuum at 50° C. overnight to provide the product as an off-white solid, 196.7 g, 77% yield. Chiral HPLC: (Chiralpak AD-H column, 20% EtOH/hex, 20 min run, 98% ee. $^1$H NMR (300 MHz, DMSO-d6) δ 10.39 (s, 1H), 4.21 (q, J=6.8 Hz, 1H), 3.00 (s, 3H), 2.25 (s, 3H), 1.30 (d, J=6.9 Hz, 3H). ESMS (M+H)=227.04; [α]$_D$=+40.42° (c=1, MeOH/DCM 1/4). The R-isomer of A-2: [α]$_D$=−42.42° (c=1, DMSO).

A-3. (7S)-2-Chloro-4,5,7,8-tetramethyl-7H-pteridin-6-one

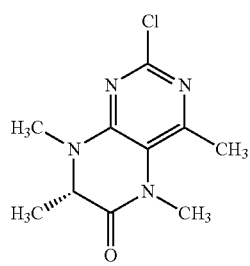

(A-3)

(7S)-2-Chloro-4,7,8-trimethyl-5,7-dihydropteridin-6-one (118 g, 521 mmol) and potassium carbonate (107.9 g, 791 mmol) were taken into 1.5 L of DMF and cooled to 0° C. Iodomethane 32.4 ml, 520.6 mmol) was added to the reaction mixture and the reaction was warmed to room temperature.

The reaction was poured into 4.5 L of water and extracted with ethyl acetate (2×1.5 L). The extracts were combined and dried over anhydrous sodium sulfate, filtered, and evaporated in vacuo to afford the crude product. The crude product was purified by column chromatography (1.5 kg SiO$_2$) and eluted with a gradient of 5-80% ethyl acetate in hexanes. The desired fractions were combined and evaporated in vacuo to provide the desired product, wt. 99 g. Chiral HPLC (IC column, 40% ethanol/hexane, 20 mins run.)Rt=3.983 mins. (99% ee); ¹H NMR (300 MHz, CDCl₃) δ 4.11 (q, J=6.9 Hz, 1H), 3.35 (s, 3H), 3.11 (s, 3H), 2.50 (s, 3H), 1.25 (d, J=6.9 Hz, 3H); ESMS(M+1)=241.18; [α]$_D$=−73.5° (c=1, methanol).

A-4. (7S)-2-Chloro-8-isopropyl-4,7-dimethyl-5,7-dihydropteridin-6-one

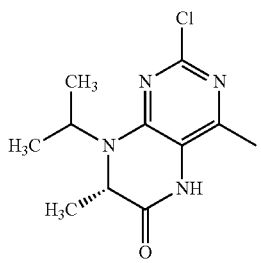

(A-4)

Step 1: Methyl (2S)-2-(isopropylamino)propanoate

To a mixture of methyl (2S)-2-aminopropanoate (Hydrochloric Acid (2.8 g, 20.06 mmol) in MeOH (60 mL) and acetone (10 mL, 136.2 mmol) was added 10% Pd/C (642.0 mg, 0.6033 mmol), followed by 3 drops of N-methylmorpholine. The mixture was hydrogenated under hydrogen at 50 psi overnight. The reaction was filtered through celite and the filtrate evaporated in vacuo. The residue was taken into 100 mL of ethyl acetate and stirred for 10 minutes. The white solid was collected by vacuum to provide the title product, wt. 2.8 g (77% yield). [α]$_D$=3.3° (c=1, methanol). ¹H NMR (300 MHz, DMSO-d6) δ 9.60 (s, 1H), 9.11 (s, 1H), 4.19 (d, J=6.8 Hz, 1H), 3.77 (s, 3H), 3.35 (t, J=6.2 Hz, 1H), 1.48 (d, J=7.1 Hz, 3H), 1.26 (t, J=6.3 Hz, 6H). ESMS(M+1)=146.15.

Step 2: (7S)-2-Chloro-8-isopropyl-4,7-dimethyl-5,7-dihydropteridin-6-one

Methyl (2S)-2-(isopropylamino)propanoate hydrochloride (1.41 g, 7.762 mmol) was suspended in 10 mL of cyclohexane and neutralized with 2M NaOH (4.4 ml, 8.800 mmol). The organic layer was separated and added to a solution of 2,4-dichloro-6-methyl-5-nitro-pyrimidine (1.6 g, 7.7 mmol) and NaHCO₃ (2.6 g, 30.9 mmol) in 40 mL of cyclohexane. The mixture was heated to reflux equipped with a Dean-Stark trap to remove water. After 4 hours, the mixture was hot-filtered through celite and washed with dichloromethane. The filtrate was evaporated in vacuo. The residue was dissolved in THF (20 mL). Platinum (Strem 78-1614, 3% wt, 506 mg, 0.078 mmol) and bis[(E)-1-methyl-3-oxo-but-1-enoxy]-oxo-vanadium (103 mg, 0.388 mmol) was added to the mixture and hydrogenated with hydrogen at 50 psi for 18 hours. The reaction was filtered through Celite, the filtrate evaporated in vacuo. The crude product was purified by column chromatography(SiO₂) eluting with a gradient of 0-80% ethyl acetate in dichloromethane to provide the title compound as a white solid, wt. 600 mg (30.5% yield). ¹H NMR (300 MHz, DMSO-d6) δ 10.38 (s, 1H), 4.58-4.41 (m, 1H), 4.25 (q, J=6.7 Hz, 1H), 2.27 (s, 3H), 1.37-1.15 (m, 9H). ESMS(M+1)=255.07.

A-5. 2-Chloro-4,8-dimethyl-7,8-dihydropteridin-6(5H)-one

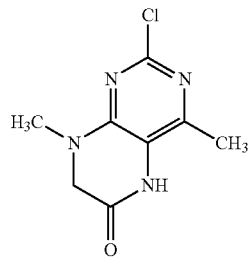

(A-5)

2,4-dichloro-6-methyl-pyrimidin-5-amine (5 g, 28.09 mmol), 2-methylaminoacetic acid (2.503 g, 28.09 mmol), and NaHCO₃ (8.493 g, 101.1 mmol) were taken into 20 ml of 95% ethanol. The reaction was refluxed for 4 days then cooled and poured onto ice and stirred. The precipitate was collected and washed well with water. The filter cake was placed in a flask and stirred in 100 ml of water, filtered, washed well with water and ethanol then dried under vacuum at 55° C. for 24 hours to provide the desired product, wt. 5.2 g. ¹H NMR (300 MHz, DMSO-d6) δ 10.35 (s, 1H), 4.11 (s, 2H), 2.96 (s, 3H), 2.23 (s, 3H);

A-6. (7S)-2-Chloro-7-cyclopropyl-4,8-dimethyl-7,8-dihydropteridin-6(5H)-one

Step 1: Methyl (S)-2-((tert-butoxycarbonyl)(methyl)amino)-2-cyclopropylacetate To a solution of (S)-2-(tert-butoxycarbonylamino)-2-cyclopropyl-acetic acid (408 g, 1.896 mol) and silver(I) oxide (879 g, 3.792 mol) in DMF (5 L) at 10° C. was added iodomethane (550 ml, 8.835 mol)) dropwise over 2 hours. The mixture was allowed to warm to room temperature then heated at 45° C. for 18 hours. The reaction mixture was cooled to room temperature and filtered over Celite. The Celite pad was washed with 1 L of methyl t-butyl ether (MTBE). The filtrate was diluted with 8 L of MTBE and washed with 4 L of 0.5 M sodium thiosulfate. The organic layer was washed brine, dried over anhydrous magnesium sulfate, and concentrated in vacuo to provide the title product as a colorless oil, wt. 431.99 g (93.6% yield). 1H NMR (300 MHz, CDCl₃) δ 3.94 (d, J=23.5 Hz, 0.5H), 3.74 (s, 3H), 3.52 (d, J=14.5 Hz, 0.5H), 2.98 (d, J=7.9 Hz, 3H), 1.45 (s, 9H), 1.20 (s, 1H), 0.82-0.68 (m, 1H), 0.57 (s, 2H), 0.42-0.28 (m, 1H)

Step 2: Methyl (S)-2-amino-2-cyclopropylacetate hydrochloride

To a cooled (10° C.) solution of methyl (S)-2-((tert-butoxycarbonyl)(methyl)amino)-2-cyclopropyl acetate (431.9 g, 1.775 mol)) in dichloromethane (750 mL) was added a 4 M HCl (3 L, 12 mol). The reaction was allowed to warm to room temperature and stirred overnight (~18 hours). The reaction was concentrated in vacuo and the resulting residue triturated with MTBE. The resulting white solid was collected under vacuum and dried to provide the title product, wt. 286.85 g (89.95% yield). 1H NMR (300 MHz, DMSO-d6) δ 9.83 (s, 2H), 3.76 (s, 3H), 3.48 (dd, J=14.1, 7.4 Hz, 1H), 2.59 (s, 3H), 1.23-1.07 (m, 1H), 0.80-0.60 (m, 3H), 0.55-0.41 (m, 1H).

Step 3: Methyl 2-((2-chloro-6-methyl-5-nitropyrimidin-4-yl)(methyl)amino)-2-cyclopropylacetate In a 3-neck 12 L flask equipped with a Dean Stark trap was added a mixture of methyl (S)-2-amino-2-cylopropylacetate hydrochloride (286.85 g, 1.597 mol), 2,4-dichloro-6-methyl-5-nitro-pyrimidine (316.3 g, 1.521 mol), and sodium bicarbonate (636.3 g, 7.574 mol) in cyclohexane (3.8 L). The mixture was refluxed for 3 hours. The mixture was allowed to cool to 70° C. and filtered through a pad of Celite then washed with 2 L oc hot cyclohexane. The filtrate was concentrated in vacuo to provide a viscous oil that contained a ppt. The oil was redissolved in cyclohexane and filtered through Celite. The filtrate was concentrated in vacuo to provide the product as a clear yellow viscous oil, wt. 498.56 g. Some cyclohexane solvent still present. Product yield was assumed to be quantitative. 1H NMR (300 MHz, CDCl$_3$) δ 4.35 (d, J=9.9 Hz, 1H), 3.80 (s, 3H), 3.04 (s, 3H), 2.47 (s, 3H), 1.36-1.23 (m, 1H), 0.89 (tdd, J=13.3, 6.4, 5.0 Hz, 1H), 0.78-0.65 (m, 2H), 0.50-0.35 (m, 1H). ESMS (M+1)=+315.0.

Step 4: (7S)-2-Chloro-7-cyclopropyl-4,8-dimethyl-7,8-dihydropteridin-6(5H)-one A suspension of Methyl 2-((2-chloro-6-methyl-5-nitropyrimidin-4-yl)(methyl)amino)-2-cyclopropylacetate (478.7 g, 1.521 mol) and Pt/C (50 g, 7.69 mmol) was shaken on a Parr apparatus under 40 psi of hydrogen for 6 hours. VO(acac)$_2$ (40 g, 150.9 mmol) was added to the reaction and the reaction shaken overnight under 35 psi of hydrogen. The reaction was filtered through a pad of Celite on top of Florisil. The filter pad was washed with a 1:1 mixture of dichloromethane/methanol (2 L) then 1.5 L of methanol. The filtrate was concentrated to ~ 1 L and a tan precipitate formed. The precipitate was collected by vacuum filtration and washed well with heptane to provide an off-white solid. The solid was dried under vacuum to provide the title product, wt. 278.69 g, 72.5% yield. 1H NMR (300 MHz, DMSO-d6) δ 10.43 (s, 1H), 3.54 (d, J=9.1 Hz, 1H), 3.09 (s, 3H), 2.27 (s, 3H), 0.95 (tdd, J=9.0, 6.7, 3.5 Hz, 1H), 0.57 (tdd, J=7.4, 5.9, 1.3 Hz, 2H), 0.52-0.33 (m, 2H); ESMS (M+1)=253.23. [α]$^{22.9}_D$=-51.23 (c=1, DMSO).

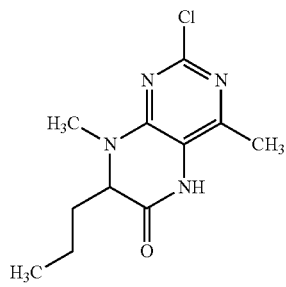

A-7. 2-Chloro-4,8-dimethyl-7-propyl-7,8-dihydropteridin-6(5H)-one 2,4-dichloro-6-methyl-pyrimidin-5-amine (2 g, 11.23 mmol), 2-(methylamino)pentanoic acid (1.915 g, 14.60 mmol), and sodium bicarbonate (3.396 g, 40.43 mmol) were taken into 20 ml of 95% ethanol. The reaction was refluxed for 4 days then cooled and poured onto ice and stirred. The solid was collected and washed well with water. The filter cake was placed in a flask and stirred in the present of 300 ml of water. This was washed well with water and ethanol then dried under vacuum at 55° C. for 24 hours to provide the title product wt. 2.05 g (71.7% yield); 1H NMR (300 MHz, DMSO-d6) δ 10.40 (s, 1H), 4.21 (dd, J=6.2, 4.2 Hz, 1H), 3.01 (s, 3H), 2.24 (s, 3H), 1.89-1.64 (m, 2H), 1.17 (q, J=7.5 Hz, 2H), 0.85 (t, J=7.2 Hz, 3H). ESMS(M+1)=255.14.

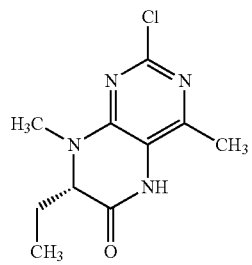

A-8. (7S)-2-Chloro-7-ethyl-4,8-dimethyl-7,8-dihydropteridin-6(5H)-one (2S)-2-(methylamino)butanoic acid trifluoroacetate salt (7.939 g, 23 mmol), 2,4-dichloro-6-methyl-pyrimidin-5-amine (3 g, 16.85 mmol) and sodium bicarbonate (7.078 g, 84.25 mmol) were taken into 95% EtOH (95 mL) and heated to reflux for 20 hours. The reaction was cooled to room temperature and 1N HCl was used to neutralize the solution to pH 6. The aqueous mixture was extracted with dichloromethane (3×30 ml). The combined organic extracts were washed with water, dried over anhydrous sodium sulfate, filtered and evaporated to provide an off white solid that was purified by column chromatography (SiO$_2$) eluting with a gradient of 0-20% methanol/dichloromethane to provide the title product as a white solid. 1H NMR (300 MHz, CDCl$_3$) δ 8.35 (s, 1H), 4.16 (dd, J=6.3, 3.6 Hz, 1H), 3.13 (s, 3H), 2.33 (s, 3H), 2.02 (td, J=7.3, 3.6 Hz, 1H), 1.94-1.76 (dq, 1H), 0.91 (t, J=7.5 Hz, 3H); [α]$_D$=+46.6° (chloroform; c=1)

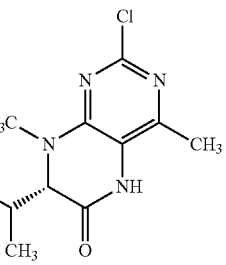

A-9. (7S)-2-Chloro-7-isopropyl-4,8-dimethyl-7,8-dihydropteridin-6(5H)-one

The compound was prepared following the procedure used for Intermediate A-6 (step 3 & 4) by reaction of dichloro-6-methyl-5-nitro-pyrimidine (25 g, 120 mmol) and methyl methyl-L-valinate (24.02 g, 132.2 mmol) followed by reduction and cyclization to provide the title product, wt. 22.81 g (72% overall yield). 1H NMR (300 MHz, CDCl$_3$) δ 9.46 (s, 1H), 3.98 (d, J=4.1 Hz, 1H), 3.19 (s, 3H), 2.38 (s, 3H), 2.34-2.18 (m, 1H), 1.10 (d, J=7.0 Hz, 3H), 0.94 (d, J=6.9 Hz, 3H); ESMS(M+1)=255.12; [α]$_D$=+66.24° (chloroform; c=1).

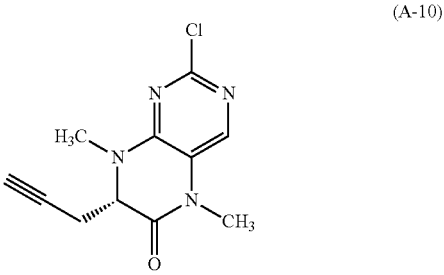 [SMILES: C#CC[C@H]1C(=O)N(C)c2cnc(Cl)nc2N1C]

(A-10)

A-10. (7S)-2-Chloro-5,8-dimethyl-7-(prop-2-yn-1-yl)-7,8-dihydropteridin-6(5H)-one Step 1: (7S)-2-Chloro-7-(prop-2-yn-1-yl)-7,8-dihydropteridin-6(5H)-one 2,4-Dichloro-5-amino-pyrimidine (1 g, 6.1 mmol), (2S)-2-aminopent-4-ynoic acid (1.035 g, 9.15 mmol), and diisopropylethylamine (3.2 mL, 18.29 mmol) were taken into ethanol (10 mL) and heated to 120° C. for 22 hours. The reaction was cooled to room temperature and a precipitate formed that was collected by vacuum filtration and washed well with ethanol to provide the desired product, wt. 780 mg (57% yield); ESMS(M+1)=233.08

Step 2: (7S)-2-Chloro-5,8-dimethyl-7-(prop-2-yn-1-yl)-7,8-dihydropteridin-6(5H)-one Iodomethane (335 μl, 5.39 mmol) was added to a mixture of (7S)-2-Chloro-7-(prop-2-yn-1-yl)-7,8-dihydropteridin-6 (5H)-one (500 mg, 2.25 mmol) and cesium carbonate (2.2 g, 6.74 mmol) in DMF (5 ml) and stirred at room temperature for 20 hours. The reaction was poured into water (50 ml) and extracted with ethyl acetate (3×100 ml). The combined extracts were washed with water (2×25 ml) and brine (25 ml), dried over anhydrous sodium sulfate, filtered, and evaporated in vacuo to provide the title product. Wt. 400 mg (71% yield); ESMS (M+1)=251.09.

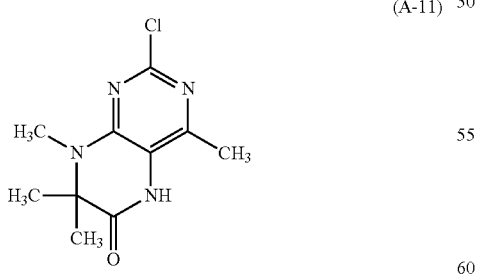

(A-11)

A-11. 2-Chloro-4,7,7-tetramethyl-7,8-dihydropteridin-6(5H)-one

2-Methyl-2-(methylamino)propanoic acid (2 g, 17.07 mmol), 2,4-dichloro-6-methyl-pyrimidin-5-amine (2 g, 11.23 mmol), and sodium carbonate (1.190 g, 11.23 mmol) were taken into n-butanol (15 mL) and heated in a microwave to 165° C. for 75 minutes. The reaction was cooled to room temperature and the solvent was evaporated in vacuo. Water was added to the residue and a precipitate formed. This was collected by vacuum filtration and washed well with water to provide 650 mg of the desired product. The aqueous filtrate was extracted with ethyl acetate (3×100 ml). The extracts were combined, dried over sodium sulfate, filtered, and evaporated in vacuo to provide 1.3 g of additional product. Total product obtained 1.95 g; 1H NMR (300 MHz, CDCl$_3$) δ 7.64 (s, 1H), 3.30 (s, 3H), 3.11 (s, 3H), 1.53 (s, 6H). ESMS(M+1)=241.14.

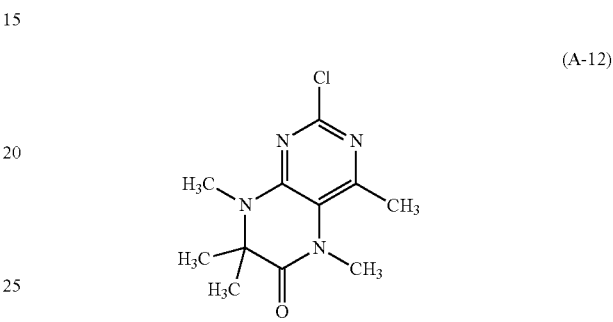

(A-12)

A-12. 2-Chloro-4,5,7,7,8-pentamethyl-7,8-dihydropteridin-6(5H)-one

Sodium hydride (60% oil dispersion; 9 mg, 0.22 mmol) was added portionwise to a cooled (0° C.) solution of A-11. 2-Chloro-4,7,7,8-tetramethyl-7,8-dihydropteridin-6(5H)-one (45 mg, 0.187 mmol) and iodomethane (14 μL, 0.22 mmol) in DMF (2 ml). The mixture was stirred for 1 hour then warmed to room temperature overnight. The reaction was quenched with the addition of water and extracted with ethyl acetate (10 mL). The extract was dried over sodium sulfate, filtered, and evaporated in vacuo to give the desired product. 1H NMR (300 MHz, CDCl$_3$) δ 3.27 (d, J=1.3 Hz, 3H), 3.05 (d, J=1.2 Hz, 3H), 2.42 (d, J=2.0 Hz, 3H), 1.34 (d, J=1.2 Hz, 6H).

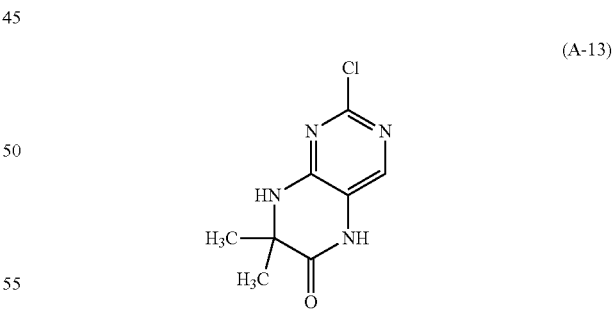

(A-13)

A-13. 2-Chloro-7,7-dimethyl-7,8-dihydropteridin-6 (5H)-one

Step 1: Methyl 2-[(2-chloro-5-nitro-pyrimidin-4-yl) amino]-2-methyl-propanoate

A solution of 2,4-dichloro-5-nitro-pyrimidine (4.61 g, 23.8 mmol) in THF (50 mL) was cooled to −78° C. Methyl 2-amino-2-methyl-propanoate hydrochloride (3.650 g, 23.8 mmol) was added to the cooled solution followed by the addition of diisopropylethylamine (8.3 mL, 47.5 mmol). The reaction was stirred for 30 minutes then allowed to warm to room temperature. Water (100 ml) was added to the reaction and extracted with ethyl acetate (3×50 ml), The combined extracts were dried over anhydrous sodium sulfate, filtered, and evaporated in vacuo to afford the crude product. The crude product was purified by column chromatography (SiO$_2$) eluting with ethyl acetate/hexanes to afford the title product, wt. 4.96 g that was used in step 2.

Step 2: 2-Chloro-7,7-dimethyl-7,8-dihydropteridin-6 (5H)-one

Iron powder (4 g, 14.4 mmol) was added to a solution of methyl 2-[(2-chloro-5-nitro-pyrimidin-4-yl)amino]-2-methyl-propanoate (4.03 g, 14.4 mmol) in acetic acid (50 mL) and heated to 100 C for 1.5 hours. The solvent was evaporated in vacuo and the residue taken into 100 ml of saturated sodium bicarbonate and extracted with dichloromethane (2×100 mL). The combined extracts were dried over anhydrous sodium sulfate, filtered, and evaporated in vacuo to afford a residue that was washed with diethyl ether to provide the title product, wt. 567 mg.

A second extraction was performed with dichloromethane (10% methanol), dried with sodium sulfate, filtered, and evaporated in vacuo to provide an additional 1.08 g of product. 1H NMR (400 MHz, DMSO-d6) δ 10.68 (s, 1H), 8.50 (s, 1H), 7.48 (s, 1H), 1.34 (s, 3H), 0.95 (s, 3H); ESMS (M+1)=212.82

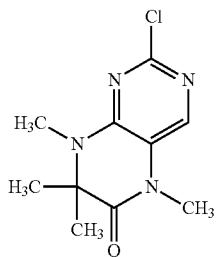

A-14. 2-Chloro-5,7,7,8-tetramethyl-7,8-dihydropteridin-6(5H)-one

Sodium hydride (60% oil dispersion; 103 mg, 4.29 mmol) was added portionwise to a cooled (0° C.) solution of 2-chloro-7,7-dimethyl-7,8-dihydropteridin-6(5H)-one, A-13 (320 mg, 1.43 mmol) and iodomethane (350 µL, 5.72 mmol) in DMF (5 ml). The reaction was warmed to room temperature and stirred for 2 hours. The reaction was poured onto 25 ml of water and extracted with ethyl acetate (3×50 ml). The combined extracts were washed with water (25 ml) and brine (50 ml), dried over sodium sulfate, filtered, and evaporated in vacuo. The crude product was purified by column chromatography (SiO$_2$) eluting with a gradient of 0-80% ethyl acetate in hexanes to afford the desired product., wt. 158 mg; 1H NMR (400 MHz, DMSO-d6) δ 7.86 (d, J=5.0 Hz, 1H), 3.23 (d, J=10.2 Hz, 3H), 3.04 (s, 3H), 1.49 (s, 6H); ESMS (M+1)=269.14.

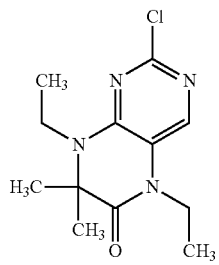

A-15. 2-Chloro-5,8-diethyl-7,7-dimethyl-7,8-dihydropteridin-6(5H)-one

Iodoethane (158 µl, 1.98 mmol) was added to a mixture of (A-13) 2-Chloro-7,7-dimethyl-7,8-dihydropteridin-6(5H)-one (308 mg, 0.7 mmol) and cesium carbonate (690 mg, 2.12 mmol) in DMF (2 ml) and stirred at room temperature for 12 hours. The reaction was poured into water (25 ml) and extracted with ethyl acetate (3×25 ml). The combined extracts were washed with brine, dried over sodium sulfate, filtered and evaporated in vacuo. The crude product was purified by column chromatography (SiO$_2$) eluting with a gradient of 0-80% ethyl acetate in hexanes to afford the desired product, wt. 158 mg; ESMS(M+1)=269.14.

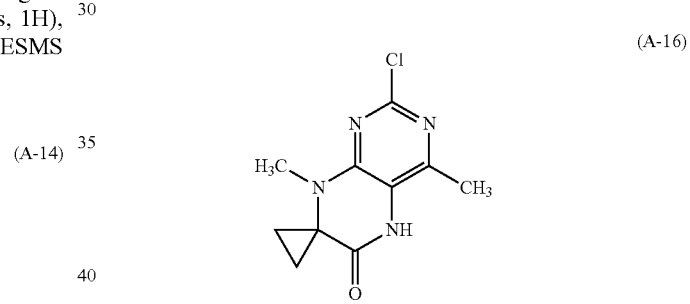

A-16. 2'—Chloro-4',8'-dimethyl-5',8'-dihydro-6'H-spiro[cyclopropane-1,7'-pteridin]-6'-one Step 1: Ethyl 1-(methylamino)cyclopropane-1-carboxylate A 2 M solution of sodium carbonate (15 mL of 2 M, 29.89 mmol) was added to a mixture of ethyl 1-aminocyclopropanecarboxylate hydrochloride (1.65 g, 9.963 mmol) in THF followed by the addition of di-tert-butyl dicarbonate (3.3 g, 14.94 mmol). The reaction was stirred for 16 hours at room temperature. Diethyl ether (50 mL) was added to the reaction and the aqueous layer separated. The organic layer was washed with 1N HCl (10 mL), water (10 mL) and brine, dried over MgSO$_4$, filtered, and evaporated in vacuo to afford a clear oil. The clear oil was dissolved in THF and cooled to 0° C. Sodium hydride (1.2 g, 49.82 mmol) was added in portions wise. After 30 minutes, iodomethane (1.9 mL, 30 mmol) was added and the reaction was warmed to room temperature. A solution of saturated ammonium chloride (20 mL) was added and the reaction extracted with diethyl ether (3×20 mL). The combined organic extracts were washed with brine, dried over MgSO$_4$, and concentrated to give ethyl 1-((tert-butoxycarbonyl)(methyl)amino)

cyclopropane-1-carboxylate as a clear liquid, wt. 3.7 g. 1H NMR (400 MHz, CDCl₃) δ 4.21-4.13 (m, 2H), 2.90-2.84 (m, 3H), 1.53-1.48 (m, 9H), 1.46 (d, J=8.0 Hz, 5H), 1.26 (d, J=7.0 Hz, 2H).

To ethyl 1-(tert-butoxycarbonyl(methyl)amino)cyclopropanecarboxylate (3.7 g, 15.21 mmol) in dichloromethane (10 mL) was added TFA (8 mL, 99.63 mmol). After 1h, the reaction was concentrated to give the desired product which was neutralized to provide the title compound as a light yellow oil, wt. 900 mg (63% yield). 1H NMR (300 MHz, CDCl₃) δ 4.16 (q, J=7.1 Hz, 2H), 2.46 (s, 3H), 1.97 (s, 1H), 1.32-1.22 (m, 5H), 0.99 (dq, J=7.5, 3.9 Hz, 2H). ESMS(M+1)=144.22.

Step 2: Ethyl 1-((2-chloro-6-methyl-5-nitropyrimidin-4-yl)(methyl)amino)cyclopropane-1-carboxylate A solution of ethyl 1-(methylamino)cyclopropane-1-carboxylate (0.87 g, 6.1 mmol) in THF was added to a cooled (0° C.) mixture of 2,4-dichloro-6-methyl-5-nitro-pyrimidine (1.264 g, 6.1 mmol) and N,N-diisopropylethylamine (1.3 mL, 7.291 mmol) in tetrahydrofuran (12 mL) and stirred for 1 hour. The reaction was quenched with aq. NH₄Cl (5 mL) and extracted with ethyl acetate. The organic layer was dried over anhydrous sodium sulfate, filtered, and evaporated in vacuo afford the crude product as a red liquid. The crude was purified by column chromatography (SiO₂)eluting with a gradient of 0-30% ethyl acetate in hexane in to give the desired product, wt 468 mg (24.5% yield); ESMS(M+1)=315.43.

Step 3: 2'—Chloro-4',8'-dimethyl-5',8'-dihydro-6'H-spiro[cyclopropane-1,7'-pteridin]-6'-one A mixture of ethyl 1-((2-chloro-6-methyl-5-nitropyrimidin-4-yl)(methyl)amino)cyclopropane-1-carboxylate (570 mg, 1.8 mmol) and Fe (607.0 mg, 10.87 mmol) in acetic acid (5.700 mL) were refluxed for 1 hour. The solvent was removed in vacuo and 1N HCl (10 ML) was added. The yellow precipitate was filtered off and the filtrate neutralized with potassium carbonate to pH 10, then extracted with ethyl acetate (3×10 mL) and dichloromethane/methanol(20/1 ratio, 3×10 mL). The combined organic layers were dried over MgSO₄, filtered, and concentrated to give the title product as a white solid (310 mg); 1H NMR (300 MHz, Methanol-d4) δ 3.03 (s, 3H), 2.37 (s, 3H), 1.77-1.41 (m, 4H). ESMS(M+1)=239.46.

(A-17)

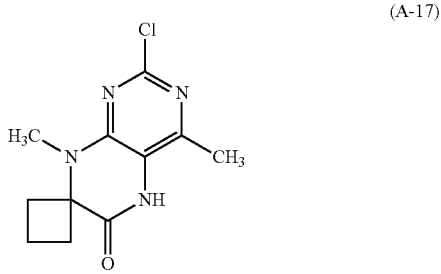 [SMILES: Cc1nc(Cl)nc2c1NC(=O)C1(CCC1)N2C]

A-17. 2'—Chloro-4',8'-dimethyl-5',8'-dihydro-6'H-spiro[cyclobutane-1,7'-pteridin]-6'-one Step 1: 1-[tert-Butoxycarbonyl(methyl)amino]cyclobutane carboxylic Acid Sodium hydride (60% w/w oil dispersion, 1.200 g, 30.00 mmol) was added to a cooled (0° C.) solution of 1-(tert-butoxycarbonylamino)cyclobutane-1-carboxylic acid (2.153 g, 10.00 mmol) in THF (100 mL). After 15 min stirring, iodomethane (7.296 g, 3.200 mL, 51.40 mmol) was added. The mixture was allowed to reach room temperature and stirred overnight. Ethyl acetate (100 mL) and water (100 mL) were added. After 10 min stirring, solvents were evaporated under reduced pressure and replaced with diethyl ether which was washed with saturated sodium bicarbonate (3×50 ml). The combined aqueous layer was adjusted to pH 3 with 1 N potassium hydrogen sulfate and extracted with ethyl acetate. The organic layer was washed with brine, dried over sodium sulfate and evaporated in vacuo to provide the title product as a yellow solid (1.4 g, quantitative yield). ¹H NMR (300 MHz, Methanol-d4) δ 7.52-7.21 (m, 5H), 5.12 (d, J=4.1 Hz, 2H), 4.67 (dq, J=24.5, 7.4 Hz, 1H), 1.41 (d, J=7.3 Hz, 3H).

Step 2: Methyl 1-(tert-butoxycarbonyl(methyl)amino)cyclobutanecarboxylate

1-[tert-butoxycarbonyl(methyl)amino]cyclobutanecarboxylic acid (2.293 g, 10 mmol) in benzene (15 mL) and MeOH (5 mL) (3:1 ratio) were added dropwise to a solution of (trimethylsilyl)diazomethane (6.000 mL of 2 M, 12.00 mmol) in diethyl ether. After 1 hour, the reaction was evaporated in vacuo to provide methyl 1-[tert-butoxycarbonyl(methyl)amino]cyclobutanecarboxylate (quantitative yield) as a light yellow liquid. ¹H NMR (300 MHz, CDCl₃) δ 3.65 (s, 3H), 2.74 (d, J=10.6 Hz, 3H), 2.38 (t, J=10.2 Hz, 2H), 2.34-2.20 (m, 2H), 2.00 (p, J=9.2 Hz, 1H), 1.71 (tq, J=10.0, 6.8, 5.0 Hz, 1H), 1.30 (s, 9H).

Step 3: Methyl 1-(methylamino)cyclobutane carboxylate hydrochloride

Methyl 1-[tert-butoxycarbonyl(methyl)amino]cyclobutanecarboxylate (2.433 g, 10 mmol) in dioxane was added HCl (20 mL of 4 M, 80.00 mmol) in dioxane. After stirring for 2h, no more SM showed in LCMS and the solution was concentrated to dryness. The residue was triturated with diethyl ether (2×10 mL) to provide the desired product as yellow sticky gum, which was used in the next step. ESMS (M+1)=144.06.

Step 4: Methyl 1-[(2-chloro-6-methyl-5-nitro-pyrimidin-4-yl)-methylamino]cyclobutanecarboxylate At 0° C., a cooled solution of K₂CO₃ (1.32 g, 9.205 mmol) in ice water (10 mL) was added to 2,4-dichloro-6-methyl-5-nitro-pyrimidine and methyl 1-(methylamino)cyclobutanecarboxylate hydrochloride (661.5 mg, 3.682 mmol) in acetone (20 mL) and stirred for 1 hour at 0° C. The reaction was quenched with saturated NH₄Cl (5 mL) and extracted with diethyl ether. extracts were evaporated in vacuo to provide the desired product as a red liquid. Purification by silica gel chromatography (0-30% EtOAc/Hexane for 30 minutes) provided desired product, methyl 1-[(2-chloro-6-methyl-5-nitro-pyrimidin-4-yl)-methylamino]cyclobutanecarboxylate, as yellow sticky liquid (206 mg, 17.5% yield. major isomer with lower R_f). ¹H NMR (300 MHz, CDCl₃) δ 3.71 (s, 3H), 2.81 (s, 3H), 2.65 (ddd, J=13.5, 5.8, 3.7 Hz, 2H), 2.41 (s, 3H), 2.39-2.24 (m, 2H), 2.24-2.06 (m, 1H), 1.92-1.71 (m, 1H). ESMS(M+1)=315.12.

Step 5: 2-Chloro-4,8-dimethyl-spiro[5H-pteridine-7,1'-cyclobutane]-6-one

Methyl 1-[(2-chloro-6-methyl-5-nitro-pyrimidin-4-yl)-methylamino]cyclobutanecarboxylate (200 mg, 0.6355 mmol), Zn (210.2 mg, 3.214 mmol) and NH₄Cl (354 mg, 6.618 mmol) in anhydrous methanol was heated to reflux. After 1h, not much product formed. The reflux was kept overnight. The reaction went to completion and cooled down to RT. Dichloromethane (20 mL) was added. The cloudy solution was filtered and concentrated. The crude product was purified by column chromatography (SiO₂) eluting with 0-10% MeOH in dichloromethane to give the desired product, 2-chloro-4,8-dimethyl-spiro[5H-pteridine-7,1'-cyclobutane]-6-one (62 mg, 0.2442 mmol, 38% yield) as a yellow solid. $^1$H NMR (300 MHz, CDCl₃) δ 3.27 (d, J=1.8 Hz, 3H), 2.82-2.46 (m, 4H), 2.31 (d, J=1.8 Hz, 3H), 2.06 (dddd, J=17.5, 9.3, 3.3, 1.6 Hz, 1H), 1.91 (dqd, J=10.3, 5.2, 2.6 Hz, 1H). ESMS(M+1)=253.14

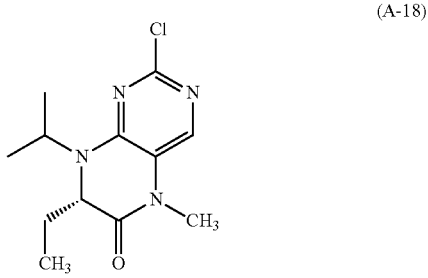 [SMILES: CC[C@H]1C(=O)N(C)c2cnc(Cl)nc2N1C(C)C]

(A-18)

A-18 (7S)-2-Chloro-7-ethyl-8-isopropyl-5-methyl-7,8-dihydropteridin-6(5H)-one

Step 1: (7S)-2-Chloro-7-ethyl-7,8-dihydropteridin-6(5H)-one 2,4-Dichloropyrimidin-5-amine (5.4 g, 32.92 mmol), (R)-2-aminobutanoic acid (4.07 g, 39.5 mmol), and diisopropylethylamine (23 ml, 131.7 mmol) was taken into n-butanol (80 ml) and water (40 ml) and heated to 128 C for 24 hours. The solvent was evaporated in vacuo. To the residue was added 100 ml of water and extracted with ethyl acetate (3×80 ml). The extracts were combined, dried over sodium sulfate, filtered, and evaporated in vacuo to afford the product that was triturated with isopropanol to provide a solid that was collected by vacuum filtration and dried to provide 2.46 g of the product. The filtrate was evaporated in vacuo to give additional crude product. This was purified by column chromatography (SiO₂) eluting a gradient of 0-100% ethyl acetate in hexanes to provide 1.46 g of additional product. Total product obtained. 3.92 g. 1H NMR (400 MHz, DMSO-d6) δ 10.66 (s, 1H), 8.46 (s, 1H), 7.51 (s, 1H), 4.21 (td, J=4.8, 1.7 Hz, 1H), 1.77 (dddd, J=44.2, 13.9, 7.2, 5.1 Hz, 2H), 0.86 (t, J=7.4 Hz, 3H); ESMS (M+1)-213.12.

Step 2: (7S)-2-Chloro-7-ethyl-5-methyl-7,8-dihydropteridin-6(5H)-one

To a mixture of (7S)-2-chloro-7-ethyl-7,8-dihydropteridin-6(5H)-one (1.46 g, 6.65 mmol) and potassium carbonate (2.02 g, 14.6 mmol) in 20 ml of acetone was added iodomethane (0.5 ml, 8 mmol). The reaction was stirred at room temperature for 2 days. The solvent was evaporated in vacuo and the residue was taken into water and stirred. The precipitate was collected by vacuum filtration, washed well with water, and dried under vacuum to provide the title product, wt. 1.41 g (92% yield). 1H NMR (400 MHz, DMSO-d6) δ 8.62 (s, 1H), 7.80 (s, 1H), 4.28 (t, J=4.8 Hz, 1H), 3.21 (s, 3H), 2.07-1.49 (m, 2H), 0.84 (t, J=7.4 Hz, 3H); ESMS (M+1)=227.09.

Step 3: (7S)-2-Chloro-7-ethyl-8-isopropyl-5-methyl-7,8-dihydropteridin-6(5H)-one (7S)-2-Chloro-7-ethyl-5-methyl-7,8-dihydropteridin-6(5H)-one (205 mg, 0.9 mmol) was taken into 2 ml of DMF. Sodium hydride (60% oil dispersion; 72 mg, 1.8 mmol) was added to the solution followed by the addition of 2-iodopropane (180 µl, 1.8 mmol). After 1 hour, 0.2 ml of methanol was added to the reaction then evaporated in vacuo. The crude was purified by column chromatography (SiO₂) eluting with 0-100% ethyl acetate in hexanes to afford 157 mg of the desired product. 1H NMR (400 MHz, DMSO-d6) δ 7.87 (s, 1H), 4.49-4.26 (m, 2H), 3.24 (s, 3H), 1.92-1.59 (m, 2H), 1.33 (d, J=6.8 Hz, 6H), 0.74 (t, J=7.5 Hz, 3H); ESMS (M+1)=269.46.

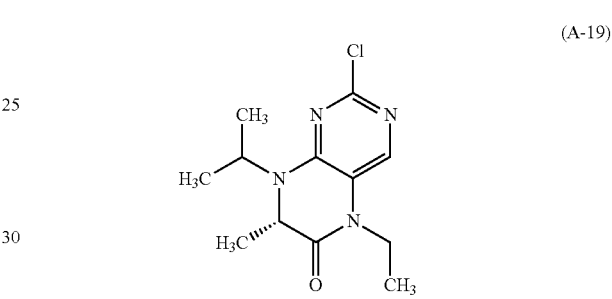

(A-19)

A-19 (7S)-2-Chloro-5-ethyl-8-isopropyl-7-methyl-7,8-dihydropteridin-6(5H)-one

Step 1: (7S)-2-Chloro-7-methyl-7,8-dihydropteridine-6(5H)-one

The compound was prepared by reaction of 2,4-Dichloropyrimidin-5-amine (11 g, 67 mmol) and (2S)-2-aminopropanoic acid (7.17 g, 80.5 mmol) via the procedure reported for A-18, Step 1 to provide the desired product, wt. 9.7 g (72% yield); ESMS(M+1)=199.03

Step 2: (7S)-2-Chloro-5-ethyl-7-methyl-7,8-dihydropteridin-6(5H)-one

The compound was prepared by reaction of (7S)-2-chloro-7-methyl-7,8-dihydropteridine-6(5H)-one and iodoethane via procedure reported for A-18, Step 2 to provide the desired product, wt. 3.31 g (74% yield) 1H NMR (400 MHz, DMSO-d6) δ 8.57 (s, 1H), 7.89 (s, 1H), 4.30 (q, J=6.8 Hz, 1H), 3.84 (ddd, J=14.1, 7.0, 2.2 Hz, 2H), 3.32 (s, 1H), 1.36 (d, J=6.8 Hz, 3H), 1.09 (t, J=7.1 Hz, 3H); ESMS(M+1)=227.13.

Step 3: (7S)-2-Chloro-5-ethyl-8-isopropyl-7-methyl-7,8-dihydropteridin-6(5H)-one The compound was prepared via the same procedure found for A-18, Step 3 to provide the desired product, wt. 515 mg (52% yield); 1H NMR (400 MHz, DMSO-d6) δ 8.57 (s, 1H), 7.89 (s, 1H), 4.30 (q, J=6.8 Hz, 1H), 3.84 (ddd, J=14.1, 7.0, 2.2 Hz, 2H), 3.32 (s, 1H), 1.36 (d, J=6.8 Hz, 3H), 1.09 (t, J=7.1 Hz, 3H); ESMS(M+1)=269.14.

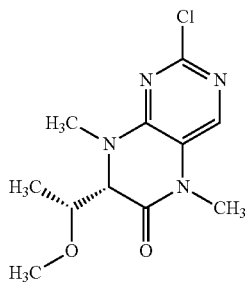

(A-20)

A-20. (S)-2-Chloro-7-((R)-1-methoxyethyl)-5,8-dimethyl-7,8-dihydropteridin-6(5H)-one Step 1: (7S)-2-Chloro-7-((R)-1-methoxyethyl)-7,8-dihydropteridin-6(5H)-one (2S,3R)-2-Amino-3-methoxy-butanoic acid (1 g, 7.5 mmol), 2,4-dichloropyrimidin-5-amine (1000 mg, 6.1 mmol), and N,N-diisopropylethylamine (3.2 mL, 18.23 mmol) was taken into ethanol (15 mL) and heated at 100° C. for 16 hours. The reaction was cooled to room temperature. A precipitate formed upon cooling. The precipitate was collected by vacuum filtration, washed with hexanes, and dried to provide the desired product (800 mg, 54%); ESMS (M+1)=243.12.

Step 2: (7S)-2-Chloro-7-((R)-1-methoxyethyl)-5,8-dimethyl-7,8-dihydropteridin-6(5H)-one (7S)-2-Chloro-7-((R)-1-methoxyethyl)-7,8-dihydropteridin-6(5H)-one (0.75 g, 3.09 mmol) and cesium carbonate (3.02 g, 9.27 mmol), and iodomethane (470 µl, 7.42 mmol) was taken into DMF (5 ml) and stirred for 2 hours. Water was added to the reaction mixture and extracted with ethyl acetate (3×50 ml). The combined extracts were washed with water and brine, dried over anhydrous sodium sulfate, filtered, and evaporated in vacuo to afford the desired product. 1H NMR (400 MHz, DMSO-d6) δ 7.82 (d, J=21.5 Hz, 1H), 4.39 (dd, J=14.6, 2.7 Hz, 1H), 3.81-3.61 (m, 1H), 3.34 (s, 3H), 3.23 (d, J=7.9 Hz, 3H), 3.12 (dd, J=13.8, 10.2 Hz, 6H), 1.12 (dd, J=22.7, 6.5 Hz, 3H); ESMS (M+1)=271.12

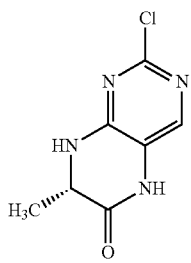

(A-21)

A-21. (7S)-2-Chloro-7-methyl-7,8-dihydropteridin-6(5H)-one 2,4-Dichloropyrimidin-5-amine (11 g, 67.08 mmol), (2S)-2-aminopropanoic acid (7.172 g, 80.5 mmol) and N,N-diisopropylethylamine (46 mL, 268 mmol) in ethanol (100 mL) was heated at 128° C. for 14 h. The reaction was evaporated in vacuo to half volume. Water (100 ml) was added to the mixture at room temperature and stirred for 1 hour. The resulting precipitate was collected by vacuum filtration, washed well with water and dried to provide the desired product wt. 9.56 g; Analytical SFC (column: cellulose 2 (40% ethanol, 60% CO$_2$, isocratic): Rt 0.983 mins.) showed a S:R mixture 2:1; ESMS(M+1)=199.03.

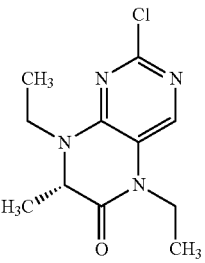

(A-22)

A-22. (7S)-2-Chloro-5,8-diethyl-7-methyl-7,8-dihydropteridin-6(5H)-one

Iodoethane (650 µL, 8.04 mmol) was added to a mixture of (7S)-2-chloro-7-methyl-7,8-dihydro-5H-pteridin-6-one (577 mg, 2.87 mmol) and cesium carbonate (2.81 g, 8.6 mmol) in DMF (5 ml) and stirred at room temperature for 12 hours. The reaction was evaporated in vacuo to give a solid residue. Water (50 ml) was added to the residue and extracted with ethyl acetate (3×50 ml). The combined extracts were washed with brine, dried over sodium sulfate, filtered, and evaporated in vacuo to afford the crude product. The crude was purified by column chromatography (SiO$_2$) eluting with a gradient of 10% ethyl acetate in hexanes too 100% ethyl acetate. Evaporation of the desired fractions afforded the desired product, wt. 581 mg; ESMS(M+1)= 255.14.

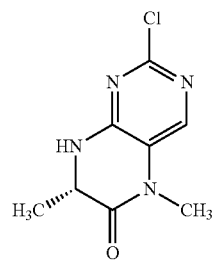

(A-23)

A-23. (7S)-2-Chloro-5,7-dimethyl-7,8-dihydropteridin-6(5H)-one

To a (7S)-2-chloro-7-methyl-7,8-dihydropteridin-6(5H)-one (4.37 g, 21.76 mmol) in acetone (63.97 mL) was added potassium carbonate (6.616 g, 47.87 mmol) and iodomethane (1.625 mL, 26.1 mmol) and the reaction was stirred at room temperature for 2 days. The reaction was evaporated in vacuo to provide a solid residue. Water (6 ml) was added to the solid, filtered, and washed with water (2×) and dried to provide the desired product: wt. 4.0519 g; The analytical SFC (column: cellulose 2 (40% ethanol, 60% $CO_2$, isocratic): Rt 0.927 mins.) shows the S:R ratio remains 2:1; 1H NMR (300 MHz, DMSO-d6) δ 8.63 (s, 1H), 7.81 (s, 1H), 4.32 (q, J=6.7 Hz, 1H), 3.20 (s, 3H), 1.37 (d, J=6.8 Hz, 3H); ESMS (M+1)=203.13.

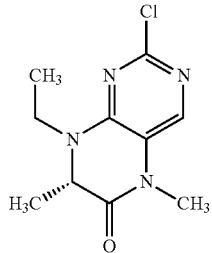

(A-24)

A-24. (7S)-2-Chloro-8-ethyl-5,7-dimethyl-7,8-dihydropteridin-6(5H)-one

Iodoethane (400 μL, 4.911 mmol) was added to a mixture of (7S)-2-Chloro-5,7-dimethyl-7,8-dihydropteridin-6(5H)-one and cesium carbonate (2.1 g; 6.55 mmol) in 5 ml of DMF (6 mL) and stirred 50° C. for 1 hour. The reaction was evaporated in vacuo to afford a solid residue. Water (30 ml) was added and the solution was extracted with ethyl acetate (3×30 ml). The combined extracts were washed with brine, dried over sodium, sulfate, filtered, and evaporated to afford gum that was triturated with ether/hexane to provide the desired product as a solid, wt. 0.7 g. The analytical SFC (column: cellulose 2 (40% ethanol, 60% $CO_2$, isocratic): Rt 0.74 mins.) demonstrates the S:R ratio is 3:2; ESMS (M+1)= 241.09.

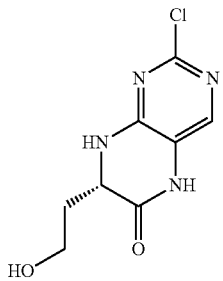

(A-25)

A-25. (7S)-2-chloro-7-(2-hydroxyethyl)-7,8-dihydropteridin-6(5H)-one 2,4-Dichloropyrimidin-5-amine (5 g, 30.5 mmol), (2S)-2-amino-4-hydroxy-butanoic acid (5 g, 42 mmol) and diisopropylethylamine (16 mL, 91.5 mmol) were taken into ethanol (10 mL) and heated to 120° C. for 22 hours. The reaction was cooled to room temperature and a precipitate formed. The precipitate was collected by vacuum filtration, washed with ethanol, and dried to provide the desired product, wt. 4.76 g (68.% yield); ESMS(M+1)=229.07; Chiral HPLC (ChiralPAK IC column; 50%/MeOH/50% Ethanol): Rt 6.625 mins., 81% ee.

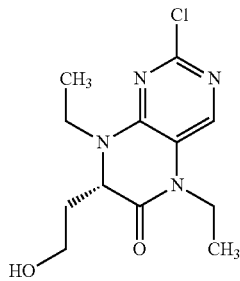

(A-26)

A-26. (7S)-2-Chloro-5,8-diethyl-7-(2-hydroxyethyl)-7,8-dihydropteridin-6(5H)-one Iodoethane (1.5 ml, 19.25 mmol) was added to a mixture of (7S)-2-chloro-7-(2-hydroxyethyl)-7,8-dihydropteridin-6 (5H)-one (2 g, 8.75 mmol) and cesium carbonate (8.55 g, 26.24 mmol) in DMF (25 mL). The reaction was stirred for 20 hours at room temperature. Water (10 ml) was added to the reaction followed by extraction with ethyl acetate (3×25 mL). The combined extracts were washed with brine (1×20 mL) and water (2×20 mL), dried over sodium sulfate, filtered, and concentrated to dryness to afford the desired product, ESMS(M+1)=285.13.

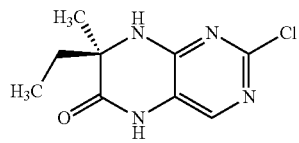

(A-27)

A-27. (7R)-2-Chloro-7-ethyl-7-methyl-7,8-dihydropteridin-6(5H)-one 2,4-Dichloropyrimidin-5-amine (8.677 g, 52.9 mmol), (2R)-2-amino-2-methylbutanoic acid (6.198 g, 52.9 mmol) and N,N-diisopropylethylamine (36.86 mL, 212 mmol) were taken into ethanol (100 mL) and heated at 128° C. for 14 hours. The reaction mixture was evaporated in vacuo to half volume followed by the addition of 100 ml of water and stirred at room temperature for 1 hour. The resulting precipitate was collected by vacuum filtration and washed with water. The crude was stirred in isopropanol and filtered to remove the insoluble starting material. The filtrates were concentrated in vacuo, stirred in dichloromethane, and filtered to provide the desired product, wt. 1.71 g; 1H NMR (400 MHz, DMSO-d6) δ 10.68 (s, 1H), 8.47 (s, 1H), 7.51 (s, 1H), 1.88 (dd, J=13.8, 7.3 Hz, 1H), 1.53 (dd, J=13.9, 7.3 Hz, 1H), 1.38 (s, 3H), 0.82 (t, J=7.3 Hz, 3H); ESMS(M+1)= 227.13.

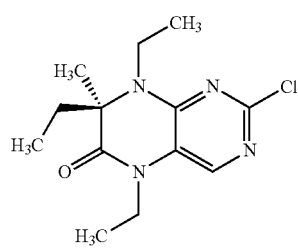

A-28. (7R)-2-Chloro-5,7,8-triethyl-7-methyl-7,8-dihydropteridin-6(5H)-one

Iodoethane (363 uL, 4.54 mmol) was added to a mixture of (7R)-2-chloro-7-ethyl-7-methyl-5,8-dihydropteridin-6-one (368 mg, 1.6 mmol) and cesium carbonate (1.59 g, 4.87 mmol) in DMF (2.7 mL) and stirred at room temperature for 12 hours. The reaction was evaporated in vacuo to provide a residue. Water (50 ml) was added and extracted with ethyl acetate (3×50 ml). The combined ethyl acetate extracts were washed with brine, dried over sodium sulfate, filtered, and evaporated in vacuo to provide the crude product. The crude product was purified by column chromatography eluting with a gradient of 10-100% ethyl acetate in hexanes to provide the desired product, wt. 386 mg; ESMS (M+1)= 283.55.

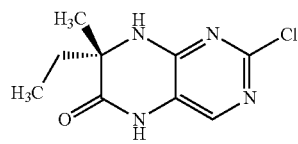

A-29. (7S)-2-Chloro-7-ethyl-7-methyl-7,8-dihydropteridin-6(5H)-one

The compound was prepared by reaction of 2,4-dichloropyrimidin-5-amine and (2S)-2-amino-2-methylbutanoic acid via the procedure reported for A-27 to provide 5.43 g of the desired product; 1H NMR (400 MHz, DMSO-d6) δ 10.68 (s, 1H), 8.47 (s, 1H), 7.51 (s, 1H), 1.88 (dd, J=13.8, 7.3 Hz, 1H), 1.53 (dq, J=14.6, 7.3 Hz, 1H), 1.38 (s, 3H), 0.83 (t, J=7.3 Hz, 3H); ESMS(M+1)=227.09.

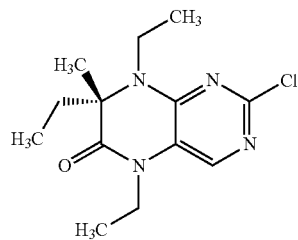

A-30. (7S)-2-Chloro-5,7,8-triethyl-7-methyl-7,8-dihydropteridin-6(5H)-one

The compound was prepared by reaction of intermediate A-29 and iodoethane via the procedure reported for A-28 to provide 643 mg of the desired product; 1H NMR (400 MHz, DMSO-d6) δ 7.87 (s, 1H), 3.98 (dd, J=14.1, 7.1 Hz, 1H), 3.80 (dd, J=14.1, 7.0 Hz, 1H), 3.68 (dd, J=14.1, 7.0 Hz, 1H), 3.41 (dt, J=14.1, 6.9 Hz, 1H), 1.89 (dq, J=14.5, 7.2 Hz, 2H), 1.59 (s, 3H), 1.14 (dt, J=27.7, 7.0 Hz, 6H), 0.68 (t, J=7.4 Hz, 3H); ESMS(M+1)=283.19.

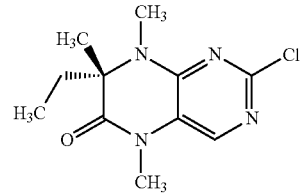

A-31. (7S)-2-Chloro-7-ethyl-5,7,8-trimethyl-7,8-dihydropteridin-6(5H)-one

The compound was prepared by reaction of compound A-29 and iodomethane via the procedure reported for A-28 to provide the desired product, 246 mg (66% yield); ESMS (M+1)=255.14.

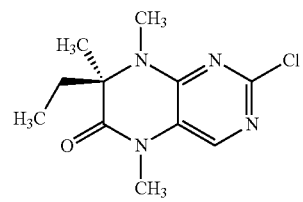

A-32. (7R)-2-Chloro-7-ethyl-5,7,8-trimethyl-7,8-dihydropteridin-6(5H)-one

The compound was prepared by reaction of compound A-27 and iodomethane via the procedure reported for A-28 to provide the desired product, 263 mg (70% yield); ESMS (M+1)=255.14.

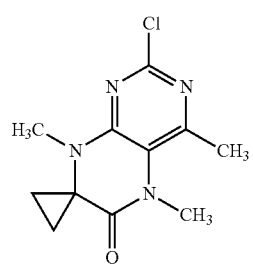

A-33. 2'—Chloro-4',5',8'-trimethyl-5',8'-dihydro-6'H-spiro[cyclopropane-1,7'-pteridin]-6'-one Sodium hydride (40.00 mg, 1.000 mmol) was added to a cooled (0° C.) solution of 2-chloro-4,8-dimethyl-spiro[5H-pteridine-7,1'-cyclopropane]-6-one, A-16 (120 mg, 0.5 mmol) and iodomethane (50 μL, 0.7500 mmol) in DMF (10 ml) The mixture was stirred for 1 hour, then warmed to room temperature and stirred for 16 hours. The reaction was quenched with saturated NH4Cl, then poured into a saturated NaHCO$_3$ solution, and extracted with ethyl acetate. The extract was dried over MgSO$_4$, filtered, and evaporated to give desired product, wt. 54 mg (40% yield). 1H NMR (300 MHz, CDCl$_3$) δ 3.27 (s, 3H), 2.87 (s, 3H), 2.43 (s, 3H), 1.39-1.30 (m, 2H), 1.16-1.09 (m, 2H). ESMS(M+1)=253.46.

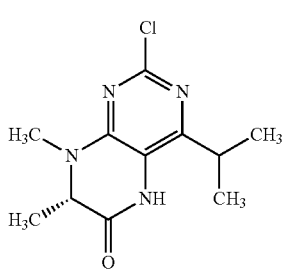

(A-34)

A-34. (7S)-2-Chloro-4-isopropyl-7,8-dimethyl-7,8-dihydropteridin-6(5H)-one (2S)-2-(Methylamino)propanoic acid (500.3 mg, 4.852 mmol), 2,4-dichloro-6-isopropylpyrimidin-5-amine (500 mg, 2.426 mmol), and sodium bicarbonate (713.3 mg, 8.491 mmol) were taken into 95% ethanol and heated to 90° C. for 16 hours. Water was added to the reaction mixture followed by extraction with ethyl acetate (3×150 ml). The combined extracts were washed with water and brine, dried over anhydrous sodium sulfate, filtered, and evaporated in vacuo to provide the crude product. The crude product was purified by prep C18 column (10-100% acetonitrile in water (0.1% TFA)). The desired fractions were combined and evaporated in vacuo to provide the title product, wt. 500 mg (81% yield). 1H NMR (300 MHz, CDCl$_3$) δ 8.49 (s, 1H), 4.20 (q, J=6.9 Hz, 1H), 3.15 (s, 3H), 2.97 (p, J=6.7 Hz, 1H), 1.49 (d, J=6.9 Hz, 3H), 1.29 (dd, J=11.1, 6.7 Hz, 6H); ESMS (M+1) 253.07.

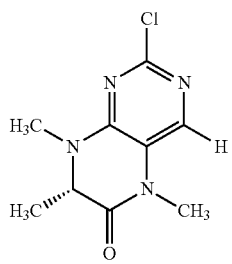

(A-35)

A-35. (7S)-2-Chloro-5,7,8-trimethyl-7,8-dihydropteridin-6(5H)-one (7S)-2-Chloro-7,8-dimethyl-7,8-dihydropteridin-6(5H)-one, (Compound A-1; 9.1 g, 40.15 mmol) and potassium carbonate (8.32 g, 60.22 mmol) were taken into DMF (100 ml) and cooled to 0° C. Iodomethane (3 ml, 48.18 mmol) was added to the cooled solution and stirred overnight. The reaction was poured into water (200 ml) and extracted with ethyl acetate (3×150 ml). The combined extracts were washed with 150 ml of water and brine (200 ml) then dried over anhydrous sodium sulfate, filtered, and evaporated in vacuo to afford the crude product. The crude was purified by column chromatography (SiO$_2$) eluting with 5-80% ethyl acetate/hexanes. The desired fractions were evaporated to afford the desired product as a white solid (6 g; 62% yield). $^1$H NMR (300 MHz, CDCl$_3$) δ 7.60 (s, 1H), 4.17 (q, J=6.9 Hz, 1H), 3.26 (s, 3H), 3.07 (s, 3H), 1.38 (d, J=6.9 Hz, 3H). [α]$_D$=24.1° (chloroform; c=1).

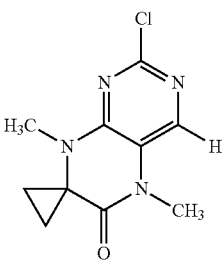

(A-36)

A-36. 2'—Chloro-5',8'-dimethyl-5',8'-dihydro-6'H-spiro[cyclopropane-1,7'-pteridin]-6'-one The compound was prepared by the same method as described in A-16 and A-33 to provide the title product. 1H 1H NMR (300 MHz, CDCl$_3$) δ 7.53 (s, 1H), 3.22 (s, 3H), 2.82 (s, 3H), 1.46 (dd, J=8.1, 5.4 Hz, 2H), 1.24 (dt, J=9.5, 4.5 Hz, 2H). ESMS(M+1)=239.11.

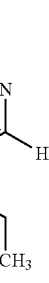

(A-37)

A-37. 2'—Chloro-5',8'-diethyl-5',8'-dihydro-6'H-spiro[cyclopropane-1,7'-pteridin]-6'-one Step 1: Ethyl 1-((2-chloro-5-nitropyrimidin-4-yl)amino)cyclopropane-1-carboxylate The compound was prepared in a similar manner as intermediate A-16 by the reaction of 2,4-dichloromethane-5-nitropyrimidine and ethyl 1-aminocyclopropane-1-carboxylate to provide the title compound as a yellow solid; wt. 1.23 g (99% yield); ESMS(M+1)=286.97.

Step 2: 2'—Chloro-5',8'-dihydro-6'H-spiro[cyclopropane-1,7'-pteridin]-6'-one (A-53)

The compound was prepared in a similar fashion as Intermediate A-13, Step 2 to provide the title compound, wt. 1.72 g. 1H NMR (400 MHz, DMSO-d6) δ 10.68 (s, 1H), 8.50 (s, 1H), 7.48 (s, 1H), 1.34 (s, 2H), 0.95 (s, 2H).

Step 3: 2'—Chloro-5',8'-diethyl-5',8'-dihydro-6'H-spiro[cyclopropane-1,7'-pteridin]-6'-one Iodoethane (600 μl, 7.3 mmol) was added to a mixture of 2'-chloro-5',8'-dihydro-6'H-spiro[cyclopropane-1,7'-pteridin]-6'-one (575 mg, 2.61 mmol) and cesium carbonate (2.55 g, 7.84 mmol) in DMF (4 ml) and heated to 50° C. for 2 hours. Water (50 ml) was added to the reaction and extracted with ethyl acetate (3×50 ml). The combined extracts were washed with brine, dried over sodium sulfate, filtered, and evaporated in vacuo to afford the crude product. The crude product was purified by column chromatography (SiO$_2$) eluting with a gradient of 0-30% ethyl acetate in hexane. The desired fractions were evaporated in vacuo to afford the title compound, 192 mg (27% yield). 1H NMR (300 MHz, CDCl$_3$) δ 7.58 (s, 1H), 3.85 (q, J=7.1 Hz, 2H), 3.30 (q, J=7.0 Hz, 2H), 1.53 (dd, J=7.8, 5.6 Hz, 2H), 1.26-1.06 (m, 8H); ESMS(M+1)=267.48.

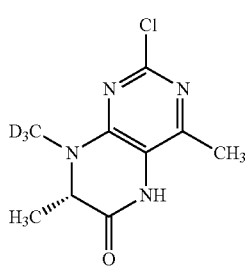

(A-38)

A-38. (7S)-2-chloro-4,7-dimethyl-8-(methyl-d3)-7,8-dihydropteridin-6(5H)-one

Step 1: N-((benzyloxy)carbonyl)-N-(methyl-d3)-L-alanine

At 0° C., NaH (537.5 mg, 13.44 mmol) was added to a solution of (2S)-2-(benzyloxycarbonylamino)propanoic acid (1 g, 4.480 mmol) in THF (100 mL). After stirring for 15 minutes, trideuterio(iodo)methane (3.6 g, 24.83 mmol) was added and mixture was warmed to room temperature and stirred overnight. Ethyl acetate (100 mL) and water (100 mL) were added. After 10 min stirring, solvents were evaporated under reduced pressure and replaced with diethyl ether. The solution was washed with saturated NaHCO$_3$ several times. The combined aqueous layer was adjusted to pH=3 with aqueous 1N KHSO$_4$ solution and extracted with ethyl acetate. The organic layer was washed with brine and dried over Na$_2$SO$_4$. Evaporation of the solvent gave product 1, (2S)-2-[benzyloxycarbonyl(trideuteriomethyl)amino]-propanoic acid as yellow oil (1.1 g, quantitative yield). 1H NMR (300 MHz, Methanol-d4) δ 7.52-7.21 (m, 5H), 5.12 (d, J=4.1 Hz, 2H), 4.67 (dq, J=24.5, 7.4 Hz, 1H), 1.41 (d, J=7.3 Hz, 3H).

Step 2

(methyl-d3)-L-alanine(2S)-2-[benzyloxycarbonyl(trideuteriomethyl)amino]propanoic acid 1 (1.1 g, 4.578 mmol) in methanol was added to 10% Pd/C (487.2 mg, 0.4578 mmol). The mixture was hydrogenated under hydrogen (50 Psi) for 20 hours. The reaction mixture was filtered through MeOH-washed Florisil. The filtrate was evaporated in vacuo and dried to give the title product as a white solid (477 mg, 98% yield), 1H NMR (400 MHz, DMSO-d6) δ 3.09 (q, J=6.9 Hz, 1H), 1.22 (d, J=7.1 Hz, 3H).

Step 3: (S)-2-chloro-4,7-dimethyl-8-(methyl-d3)-7,8-dihydropteridin-6(5H)-one (2S)-2-(trideuteriomethylamino)propanoic acid 2 (477 mg, 4.494 mmol), 2,4-dichloro-6-methyl-pyrimidin-5-amine (640.0 mg, 3.595 mmol) and sodium bicarbonate (1.087 g, 12.94 mmol) were taken into EtOH (9.5 mL) and water (0.5 mL) and refluxed overnight. The reaction was neutralized with 6N HCl neutralize the solution to pH 6 then extracted with dichloromethane (30 mL). The aqueous layer was separated and extracted with dichloromethane twice (2×10 mL). The combined organic extracts were washed with water and concentrated to give pink solid. Dichloromethane (10 mL) was added to the solid and centrifuged to separate solid. The step was repeated once more and the resulting white solid was clean product. The combined dichloromethane layers was purified by column chromatography (SiO$_2$; 40 g) eluting with a gradient of 10-40% methanol in dichloromethane to give more product 3, (7S)-2-chloro-4,7-dimethyl-8-(trideuteriomethyl)-5,7-dihydropteridin-6-one, as white solid (402 mg, 48.7% yield). 1H NMR (300 MHz, CD$_3$OD) δ 4.15 (d, J=4.0 Hz, 1H), 2.33 (s, 3H), 1.46 (d, J=6.9 Hz, 3H).

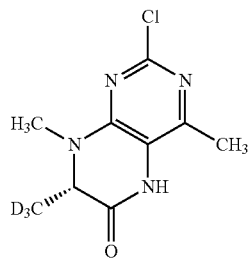

(A-39)

A-39. (7S)-2-chloro-4,8-dimethyl-7-(methyl-d3)-7,8-dihydropteridin-6(5H)-one

The compound was prepared by the procedure described in A-2 via reaction of methyl N-methyl-L-alanine-3,3,3-d3 and 2,4-dichloro-6-methylpyrimidin-5-amine to provide the title product. 83% yield; ESMS(M+1)=231.07

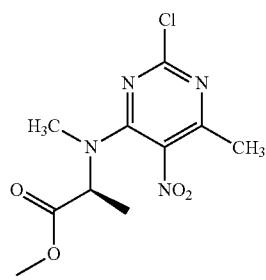

(A-40)

A-40. Methyl N-(2-chloro-6-methyl-5-nitropyrimidin-4-yl)-N-methyl-L-alaninate

A solution of 2,4-Dichloro-6-methyl-5-nitro-pyrimidine (1.86 g, 8.96 mmol) in 20 ml of acetone was added dropwise to a mixture of methyl (2S)-2-(methylamino)propanoate (1 g, 8.54 mmol) and potassium carbonate (1.77 g, 12.8 mmol) in acetone and water. The reaction was stirred at room temperature for 16 hours. The mixture was evaporated in vacuo and the residue was taken into a water and extracted with ethyl acetate (3×75 ml). The combined extracts were combined, washed with brine, dried over sodium sulfate, filtered, and evaporated in vacuo to afford the title product as a viscous yellow oil, wt. 1.54 g (62.5% yield). 1H NMR (300 MHz, CDCl$_3$) δ 5.34 (q, J=7.3 Hz, 1H), 3.78 (s, 3H), 2.88 (s, 3H), 2.48 (s, 3H), 1.57 (d, J=7.3 Hz, 3H).

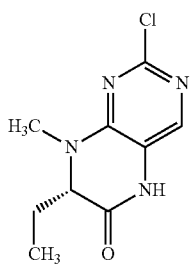

(A-41)

A-41. (7S)-2-Chloro-7-ethyl-8-methyl-7,8-dihydropteridin-6(5H)-one

The compound was prepared by reaction of (2S)-2-(methylamino)butanoic acid trifluoroacetate salt and 2,4-dichloro-6-methyl-pyrimidin-5-amine following the procedure reported for intermediate A-8 to provide the title product as a white solid, 89% yield. 1H NMR (300 MHz, Methanol-d4) δ 7.55 (s, 1H), 4.34 (dd, J=5.5, 3.5 Hz, 1H), 3.16 (s, 3H), 2.04 (dtdd, J=12.3, 9.0, 6.5, 2.7 Hz, 2H), 0.89 (t, J=7.5 Hz, 3H).

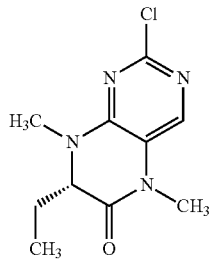

(A-42)

A-42. (7S)-2-Chloro-7-ethyl-5,8-dimethyl-7,8-dihydropteridin-6(5H)-one

The compound was prepared by reaction of Intermediate A-41 and iodomethane following the same procedure reported for intermediate A-35 to provide the title product as yellow crystalline solid. 1H NMR (300 MHz, CDCl$_3$) δ 7.65 (s, 1H), 4.26 (dd, J=5.9, 3.5 Hz, 1H), 3.35 (s, 3H), 3.16 (s, 3H), 2.16-1.77 (m, 2H), 0.84 (t, J=7.5 Hz, 3H).

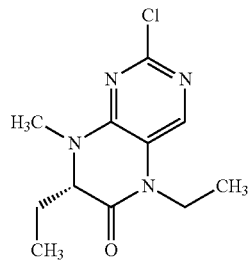

(A-43)

A-43. (7S)-2-Chloro-5,7-diethyl-8-methyl-7,8-dihydropteridin-6(5H)-one

The compound was prepared by reaction of Intermediate A-41 and iodoethane following the same procedure reported for intermediate A-35 to provide the title product. 1H NMR (300 MHz, CDCl$_3$) δ 7.66 (s, 1H), 4.23 (dd, J=5.9, 3.5 Hz, 1H), 4.06 (dq, J=14.3, 7.2 Hz, 1H), 3.85 (dq, J=14.2, 7.1 Hz, 1H), 3.49 (q, J=7.0 Hz, 0H), 3.15 (s, 3H), 2.04 (dtd, J=15.0, 7.5, 3.6 Hz, 1H), 1.89 (dtd, J=14.5, 7.4, 5.8 Hz, 1H), 1.26 (q, J=7.3 Hz, 4H), 0.83 (t, J=7.5 Hz, 3H).

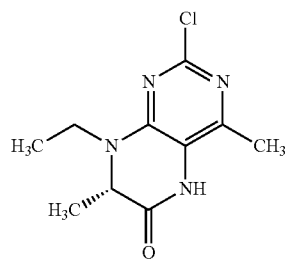

(A-44)

A44. (7S)-2-Chloro-8-ethyl-4,7-dimethyl-7,8-dihydropteridin-6(5H)-one

Step 1. Methyl N-(2-chloro-6-methyl-5-nitropyrimidin-4-yl)-N-ethyl-L-alaninate

The compound was prepared by reaction of 2,4-dichloro-6-methyl-5-nitro-pyrimidine and methyl (2S)-2-(ethylamino)propanoate in the same manner as A-40 to provide the title product, wt. 1.24 g (61% yield). ESMS(M+1)= 303.38.

Step 2. (7S)-2-Chloro-8-ethyl-4,7-dimethyl-7,8-dihydropteridin-6(5H)-one

The compound was prepared by reduction of methyl N-(2-chloro-6-methyl-5-nitropyrimidin-4-yl)-N-ethyl-L-alaninate. The starting material was dissolved in 40 ml of THF and hydrogenated (50 psi) overnight in the presence of platinum (351 mg, 0.054 mmol) and bis[(E)-1-methyl-3-oxo-but-1-enoxy]-oxo-vanadium (70.11 mg, 0.26 mmol). The reaction was filtered and evaporated to provide the title product that was used without further purification. ESMS (M+1)=241.42.

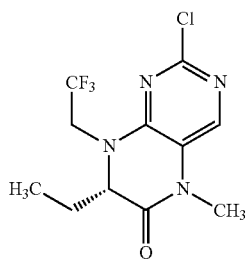

(A-45)

A-45. (7S)-2-Chloro-7-ethyl-5-methyl-8-(2,2,2-trifluoroethyl)-7,8-dihydropteridin-6(5H)-one The compound was prepared by reaction of (7S)-2-chloro-7-ethyl-5-methyl-7,8-dihydropteridin-6-one (Intermediate A-47) and 1,1,1-trifluoro-2-iodo-ethane following the procedure reported for A-24 to afford the title product. 1H NMR (300 MHz, CDCl3) δ 7.74 (s, 1H), 5.27-5.04 (m, 1H), 4.29 (dt, J=17.2, 8.6 Hz, 1H), 3.55-3.33 (m, 1H), 3.31 (d, J=4.2 Hz, 3H), 2.04-1.82 (m, 1H), 1.73 (ddd, J=23.1, 15.2, 7.9 Hz, 1H), 0.86-0.73 (m, 3H); ESMS (M+1)=309.08.

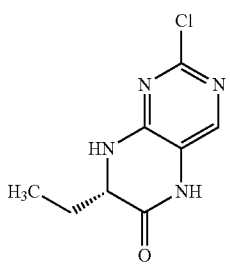

(A-46)

A-46. (7S)-2-Chloro-7-ethyl-7,8-dihydropteridin-6(5H)-one 2,4-Dichloropyrimidin-5-amine (15 g, 91.47 mmol), (2S)-2-aminobutanoic acid (11.32 g, 109.8 mmol) and diisopropylethylamine (64 mL, 366 mmol)) were taken into ethanol (120 mL) and and heated at 128° C. for 14 hours. The reaction was evaporated to half volume and water (100 ml) was added to the mixture. A precipitate formed that was collected by vacuum filtration yielding 6.85 g of the product as a mixture of the S and R enantiomers. The filtrate was concentrated to remove water and a precipitate began to from, The precipitate was collected by vacuum filtration, washed well with water to afford 9.16 g of the product as the S enantiomer. SFC chromatography (SW column; 40 nm×16 nm; 25% methanol in CO₂, isocratic; 2 ml/min). Rt 0.474 mins. (93.5% ee). 1H NMR (400 MHz, DMSO-d6) δ 10.66 (s, 1H), 8.46 (s, 1H), 7.51 (s, 1H), 4.21 (td, J=4.8, 1.7 Hz, 1H), 1.77 (dddd, J=44.2, 13.9, 7.2, 5.1 Hz, 2H), 0.86 (t, J=7.4 Hz, 3H); ESMS (M+1)=213.12.

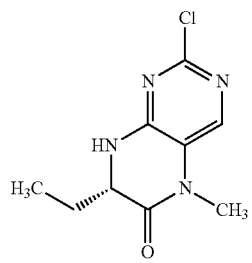

(A-47)

A-47. (7S)-2-Chloro-7-ethyl-5-methyl-7,8-dihydropteridin-6(5H)-one

To a solution of (7S)-2-Chloro-7-ethyl-7,8-dihydropteridin-6(5H)-one (1.46 g, 6.65 mmol) in acetone (21 ml) was added potassium carbonate (2.02 g, 14.6 mmol) and iodomethane (500 ul, 8 mmol) and the mixture was stirred at room temperature for 2 days. The reaction was evaporated in vacuo to provide a solid residue. Water (10 ml) was added and stirred at room temperature for 30 minutes. The precipitate was collected by vacuum filtration and washed well with water. The solid was dried under vacuum at 50° C. to afford the title product, wt. 1.41 g (92% yield). 1H NMR (400 MHz, DMSO-d6) δ 8.62 (s, 1H), 7.80 (s, 1H), 4.28 (t, J=4.8 Hz, 1H), 3.21 (s, 3H), 2.07-1.49 (m, 2H), 0.84 (t, J=7.4 Hz, 3H). ESMS (M+1)=227.09. SFC chromatography (SW column; 40 nm×16 nm; 25% methanol in CO2, isocratic; 2 ml/min): Rt 0.671 mins. (95% ee).

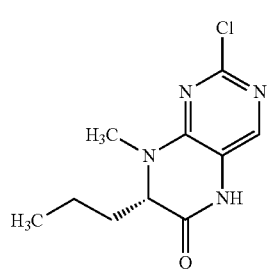

(A-49)

A-49. (7S)-2-chloro-8-methyl-7-propyl-7,8-dihydropteridin-6(5H)-one (S)-2-(methylamino)pentanoic acid hydrochloride (613 mg, 3.66 mmol) and 2,4-dichloropyrimidin-5-amine (500 mg, 3.05 mmol were taken into ethanol (20 ml) and diisopropylethylamine (2.7 ml, 15.24 mmol) and heated to 120° C. for 24 hours. The reaction was cooled room temperature and a precipitate formed. The precipitate was collected by vacuum filtration and washed with ethanol. The solid was dried under vacuum at 50° C. to provide the title product, wt. 420 mg (57% yield); 1H NMR (300 MHz, DMSO-d6) δ 7.45 (s, 1H), 4.18 (d, J=3.5 Hz, 1H), 2.99 (s, 3H), 1.91-1.66 (m, 2H), 1.13 (dt, J=14.9, 7.6 Hz, 2H), 0.83 (t, J=7.3 Hz, 3H); ESMS (M+1)=241.09.

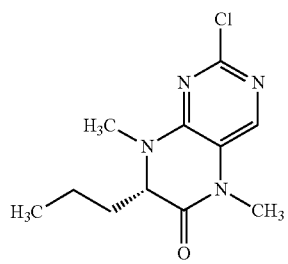

(A-50)

A-50. (7S)-2-chloro-5,8-dimethyl-7-propyl-7,8-dihydropteridin-6(5H)-one (7S)-2-chloro-8-methyl-7-propyl-7,8-dihydropteridin-6(5H)-one, A-49 (200 mg, 0.83 mmol), iodomethane (62 ul, 1 mmol), and potassium carbonate (345 mg, 2.5 mmol) were taken into acetone and stirred at room temperature for 16 hours. The reaction was evaporated in vacuo to provide a solid that was taken into water and extracted with ethyl acetate. The organic layer was dried over anhydrous sodium sulfate, filtered, and evaporated in vacuo to afford the title product, wt. 200 mg (96% yield). 1H NMR (300 MHz, CDCl$_3$) δ 7.65 (s, 1H), 4.25 (dd, J=6.1, 3.8 Hz, 1H), 3.34 (s, 3H), 3.15 (s, 3H), 2.04-1.70 (m, 2H), 1.34-1.13 (m, 2H), 0.91 (t, J=7.3 Hz, 3H); ESMS (M+1)=255.14.

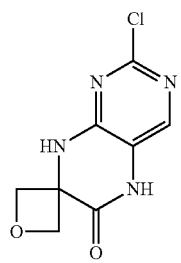

(A-51)

A-51. 2'—Chloro-5',8'-dihydro-6'H-spiro[oxetane-3,7'-pteridin]-6'-one 2,4-Dichloropyrimidin-5-amine (235 mg, 1.433 mmol), (2R)-2-aminobutanoic acid (155.6 mg, 1.509 mmol) and DIPEA (779.9 mg, 1.051 mL, 6.034 mmol) was taken into n-BuOH (20 mL) and water (10 mL) and heated at 128° C. for 24 hours. The solvent was evaporated in vacuo. To the residue was added water (30 ml) that was extracted with ethyl acetate (2×) and dichloromethane (2×). The combined organic layers were dried over MgSO$_4$, filtered and evaporated. The crude product was purified by column chromatography (SiO$_2$) eluting with 10-100% ethyl acetate in hexanes to provide the title product (28.1 mg). ESMS (M+1)=227.04.

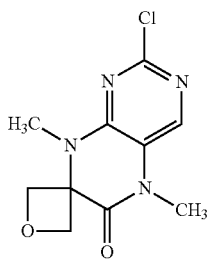

(A-52)

A-52. 2'—Chloro-5',8'-dimethyl-5',8'-dihydro-6'H-spiro[oxetane-3,7'-pteridin]-6'-one To 2-chlorospiro[5,8-dihydropteridine-7,3'-oxetane]-6-one (148 mg, 0.6481 mmol) in DMF (2.4 mL) at 0° C. was added MeI (552.0 mg, 242.1 µL, 3.889 mmol), followed by the addition of NaH (155.5 mg, 3.889 mmol). The reaction temperature was raised to room temperature and stirred for 2 hours. The solvent was evaporated and water (20 ml) was added to the residue followed by extraction with dichloromethane (3×). The extracts were combined and dried over sodium sulfate, filtered, and evaporated to afford the crude product. The crude was purified by column chromatography (SiO$_2$) eluting with a gradient of 10-100% ethyl acetate in hexanes to provide the title product as a white solid: 1H NMR (300 MHz, CDCl$_3$) δ 7.60 (s, 1H), 5.25 (d, 2H), 4.80 (d, 2H), 3.51 (s, 3H), 3.31 (s, 3H). ESMS 255.09 (M+1).

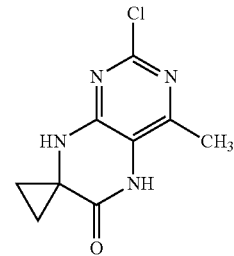

(A-53)

A-53: 2'-chloro-4'-methyl-5',8'-dihydro-6'H-spiro[cyclopropane-1,7'-pteridin]-6'-one

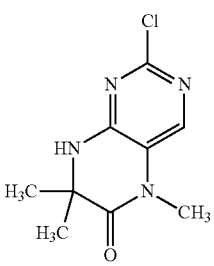

(A-54)

A-54: 2-Chloro-5,7,7-trimethyl-7,8-dihydropteridin-6(5H)-one

The compound was prepared in the same manner as intermediate A-47. ESMS (M+1)=227.71.

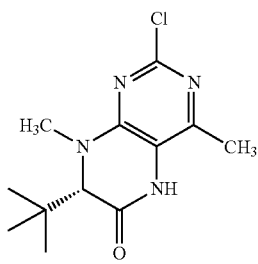

A-55

A-55. (7S)-7-(tert-butyl)-2-chloro-4,8-dimethyl-7,8-dihydropteridin-6(5H)-one

Step 1: Methyl (S)-2-((2-chloro-6-methyl-5-nitropyrimidin-4-yl)(methyl)amino)-3,3-dimethylbutanoate The compound was prepared by reaction of methyl (S)-3,3-dimethyl-2-(methylamino)butanoate hydrochloride and 2,4-dichloro-5-nitro-6-methylpyrimidine (965 mg, 4.64 mmol) following the procedure description in A-4 to provide the title product. 1H NMR (300 MHz, CDCl$_3$) δ 8.64 (s, 1H), 3.79 (d, J=0.9 Hz, 1H), 3.30 (s, 3H), 2.36 (s, 3H), 1.03 (s, 8H). ESI-MS m/z calc. 268.1091, found 269.22 (M+1))$^+$+. Chiral HPLC: >95% ee, Acq. Method. 20% MeOH-30% EtOH-50% Hex in 20 mins on Chiral PAK IC column [α]$^{22.9}_D$=68.9° (c=1, CHCl$_3$).

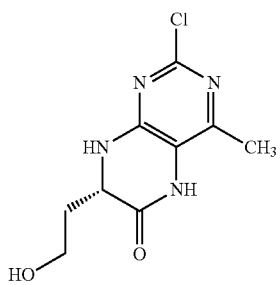

A-56

A-56. (7S)-2-chloro-7-(2-hydroxyethyl)-4-methyl-7,8-dihydropteridin-6(5H)-one

The compound was prepared in a similar manner as A-2 by reaction of 2,4-dichloro-6-methyl-pyrimidin-5-amine (2 g, 11.23 mmol) and (2S)-2-amino-4-hydroxy-butanoic acid (1.338 g, 11.23 mmol) to provide the title product (1.2 g, 42% yield). 1H NMR (300 MHz, DMSO-d6) δ 10.19 (s, 1H), 8.18 (s, 1H), 4.54 (t, J=5.0 Hz, 1H), 4.18 (td, J=5.8, 1.9 Hz, 1H), 3.53 (tdd, J=6.5, 4.8, 1.8 Hz, 2H), 2.22 (s, 3H), 1.87 (qd, J=6.5, 2.9 Hz, 2H). ESI-MS m/z calc. 242.05705, found 243.1 (M+1)$^+$.

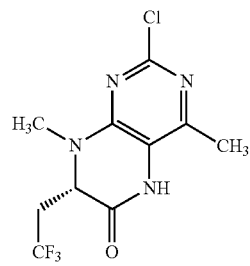

A-57

A-57. (S)-2-chloro-4,8-dimethyl-7-(2,2,2-trifluoroethyl)-7,8-dihydropteridin-6(5H)-one The compound was prepared by reaction of methyl 3,3,3-trifluoro-2-(methylamino)propanoate and 2,4-dichloro-5-nitro-6-methylpyrimidine following the procedure description in A-6 to provide the title product; ESI-MS m/z 269.16 (M+1)$^+$. The product was used without further characterization.

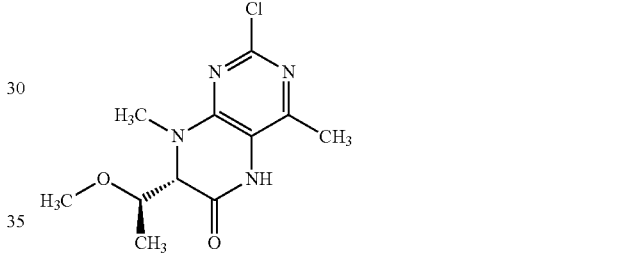

A-59

A-59. (7S)-2-chloro-7-((R)-1-methoxyethyl)-4,8-dimethyl-7,8-dihydropteridin-6(5H)-one The compound was prepared by reaction of methyl (2S,3R)-3-methoxy-2-(methylamino)butanoate hydrochloride (14.07 g, 71.2 mmol) and 2,4-dichloro-5-nitro-6-methylpyrimidine (14.1 g, 67.8 mmol) following the procedure description in A-6 to provide the title product (7S)-2-chloro-7-[(1R)-1-methoxyethyl]-4,8-dimethyl-5,7-dihydropteridin-6-one (10.5 g, 57%) 1H NMR (300 MHz, CDCl$_3$) δ 8.77 (s, 1H), 4.03 (d, J=5.0 Hz, 1H), 3.74-3.59 (m, 1H), 3.28 (d, J=5.9 Hz, 6H), 2.37 (s, 3H), 1.28 (d, J=6.4 Hz, 3H). ESI-MS m/z calc. 270.08835, found 271.16 (M+1)$^+$; 269.16 (M−1)+. [α]$_D$=+32.14° (c=1.0, CHCl$_3$), temp 23.2° C.

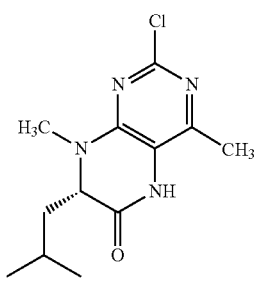

A-60

A-60. (7S)-2-chloro-7-isobutyl-4,8-dimethyl-7,8-dihydropteridin-6(5H)-one

The compound was prepared by reaction of (2S)-4-methyl-2-(methylamino)pentanoic acid (1.15 g, 7.920 mmol) and 2,4-dichloro-6-methyl-pyrimidin-5-amine (1 g, 5.617 mmol) following the procedure description in A-2 to provide the title product (7S)-2-chloro-7-isobutyl-4,8-dimethyl-5,7-dihydropteridin-6-one (570 mg, 29%) 1H NMR (300 MHz, CDCl$_3$) δ 8.63 (s, 1H), 4.12 (d, J=6.6 Hz, 1H), 3.16 (s, 3H), 2.47 (s, 3H), 1.79 (dp, J=12.9, 6.5 Hz, 1H), 1.67 (d, J=6.5 Hz, 1H), 0.99 (s, 2H), 0.95 (d, J=6.5 Hz, 3H). ESI-MS m/z calc. 268.1091, found 269.13 (M+1)$^+$.

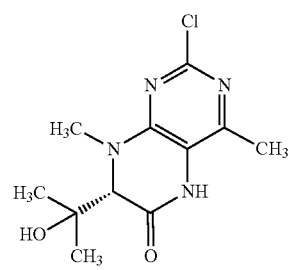

A-61

A-61. (S)-2-chloro-7-(2-hydroxypropan-2-yl)-4,8-dimethyl-7,8-dihydropteridin-6(5H)-one Step 1. Methyl (S)-2-((2-chloro-6-methyl-5-nitropyrimidin-4-yl)(methyl)amino)-3-hydroxy-3-methylbutanoate 2,4-Dichloro-6-methyl-5-nitro-pyrimidine (377 mg, 1.758 mmol), methyl (2S)-3-hydroxy-3-methyl-2-(methylamino)butanoate (Trifluoroacetate salt) (388 mg, 1.410 mmol), and NaHCO$_3$ (762 mg, 9.071 mmol) were taken into cyclohexane (7 mL). The reaction flask was equipped with a Dean-Stark trap and the reaction was heated to 110° C. for 4 hours. Water and dichloromethane were added to the reaction. The phases were separated on a phase separator. The organic layer evaporated in vacuo and the residue purified by column chromatography (SiO$_2$) eluting with a gradient of heptanes to 80% ethyl acetate. ESI-MS m/z 333.12.

Step 2. (7S)-2-Chloro-7-(2-hydroxypropan-2-yl)-4,8-dimethyl-7,8-dihydropteridin-6(5H)-one Methyl (S)-2-((2-chloro-6-methyl-5-nitropyrimidin-4-yl)(methyl)amino)-3-hydroxy-3-methylbutanoate (148 mg, 0.44 mmol) and platinum (58 mg, 0.008919 mmol) were placed in a Parr bottle with THF (5 ml) and placed under 50 psi hydrogen for 3 days. To the reaction bis[(Z)-1-methyl-3-oxo-but-1-enoxy]-oxo-vanadium (3 mg, 0.01131 mmol) was added to the reaction and placed on the Parr at 50 psi for 16 hours. The reaction was filtered and washed with MeOH and DCM. The volatiles were removed in vacuo and purified by column chromatography (SiO$_2$) eluting with a gradient of heptanes to 80% ethyl acetate. 1H NMR (400 MHz, DMSO-d6) δ 10.39 (s, 1H), 4.81 (s, 1H), 3.94 (s, 1H), 3.21-3.09 (m, 4H), 2.22 (s, 3H), 1.20 (s, 3H), 1.01 (s, 3H); ESI-MS m/z 271.14.

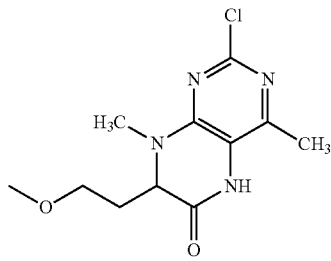

A-62

A-62. 2-chloro-7-(2-methoxyethyl)-4,8-dimethyl-7,8-dihydropteridin-6(5H)-one $^1$H NMR (400 MHz, DMSO-d6) δ 10.34 (s, 1H), 4.28 (dd, J=6.6, 3.8 Hz, 1H), 3.31-3.26 (m, 1H), 3.22-3.16 (m, 1H), 3.00 (s, 6H), 2.24 (s, 3H), 2.08-2.00 (m, 1H), 1.99-1.93 (m, 1H). ESI-MS m/z 271.2 (M+1)$^+$.

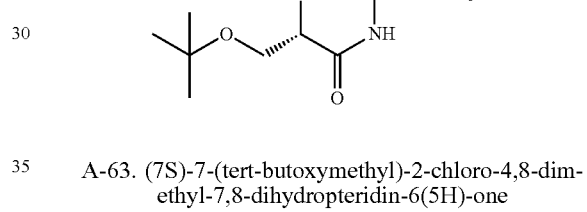

A-63

A-63. (7S)-7-(tert-butoxymethyl)-2-chloro-4,8-dimethyl-7,8-dihydropteridin-6(5H)-one The compound was prepared by reaction of methyl (2S)-3-tert-butoxy-2-(methylamino)propanoate (2.56 g, 13.5 mmol) and 2,4-dichloro-5-nitro-6-methylpyrimidine (2.8 g, 13.46 mmol) following the procedure description in A-6 to provide the title product (1.4 g, 86% yield). 1H NMR (300 MHz, CDCl$_3$) δ 8.34 (s, 1H), 4.16 (t, J=2.6 Hz, 1H), 3.75 (d, J=2.6 Hz, 2H), 3.15 (s, 3H), 2.32 (s, 3H), 1.04 (s, 8H). ESI-MS m/z calc. 298.11966, found 299.18 (M+1)$^+$; [α]$_D$=+32.14° (c=1.0, CHCl$_3$), at 23.2° C. Chiral HPLC (ChiralPAK IC column; 20% methanol/30% ethanol/50% hexanes; 20 mins) Rt 4.56 mins (95% ee).

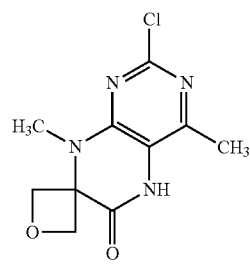

A-64

A-64. 2'-chloro-4',8'-dimethyl-5',8'-dihydro-6'H-spiro[oxetane-3,7'-pteridin]-6'-one The compound was prepared by reaction of methyl 3-(methylamino)oxetane-3-carboxylate and 2,4-dichloro-5- nitro-6-methylpyrimidine following the procedure description in A-6 to provide the title product (41% yield). 1H NMR (400 MHz, DMSO-d6) δ 2.23 (s, 3H), 3.36 (s, 3H), 4.81 (d, J=7.6 Hz, 2H), 5.01 (d, J=7.2 Hz, 2H), 10.55 (s, 1H). ESI-MS m/z calc. 255.2 (M+1)⁺

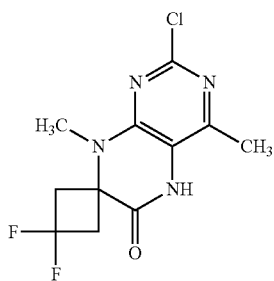

A-65

A-65. 2'-chloro-3,3-difluoro-4',8'-dimethyl-5',8'-dihydro-6'H-spiro[cyclobutane-1,7'-pteridin]-6'-one The compound was prepared by reaction of methyl 3,3-difluoro-1-(methylamino)cyclobutane-1-carboxylate and 2,4-dichloro-5-nitro-6-methylpyrimidine following the procedure description in A-6 to provide the title product. 1H NMR (400 MHz, DMSO-d6) δ 10.72 (s, 1H), 3.43-3.35 (m, 2H), 3.35-3.28 (m, 2H), 3.16 (s, 3H), 2.28 (s, 3H). ESI-MS m/z calc. 289.2 (M+1)⁺

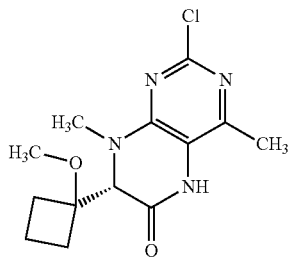

A-66

A-66. (7S)-2-chloro-7-(1-methoxycyclobutyl)-4,8-dimethyl-7,8-dihydropteridin-6(5H)-one The compound was prepared by reaction methyl 2-(1-methoxycyclobutyl)-2-(methylamino)acetate (5.5 g, 24.6 mmol) and 2,4-dichloro-5-nitro-6-methylpyrimidine 5.56 g, 25.9 mmol) following the procedure description in A-6 to provide the title product as a pair of enantiomers. The enantiomers were separated by SFC (Cellulose-2, 20×250 mm; 40% Ethanol (5 mM Ammonia)/60% CO₂, isocratic; 80 ml/min) to afford the title product (3.86 g). 1H NMR (300 MHz, CDCl₃) δ 8.66 (s, 1H), 4.28-4.15 (m, 1H), 3.25 (s, 3H), 2.51-2.13 (m, 6H), 2.00-1.65 (m, 3H). ESI-MS m/z calc. 296.104, found 297.04 (M+1)⁺; [α]_D=17.08°, temp=25.1° C. Chiral HPLC: SFC Cellulose-2 column, 4.6 mm×100 mm, 40% EtOH (5 mM ammonia)/60% CO₂ isocratic gradient, 1 ml/min; 6 min run) Rt 1.04 mins. (97% ee).

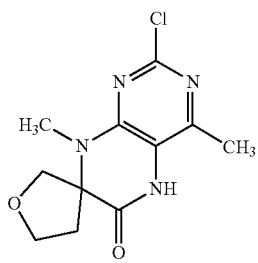

A-67

A-67. 2'-chloro-4',8'-dimethyl-4,5,5',8'-tetrahydro-2H,6'H-spiro[furan-3,7'-pteridin]-6'-one The compound was prepared by reaction methyl 3-(methylamino)tetrahydrofuran-3-carboxylate and 2,4-dichloro-5-nitro-6-methylpyrimidine following the procedure description in A-6 to provide the title product as a racemic mixture. 1H NMR (400 MHz, DMSO-d6) δ 2.22-2.30 (m, 4H), 2.47 (t, J=4.0 Hz, 1H), 3.01 (s, 3H), 3.70 (q, J=7.6 Hz, 1H), 4.02 (d, J=10.0 Hz, 1H), 4.08-4.16 (m, 2H), 10.59 (s, 1H); ESI-MS m/z 269.1 (M+1)⁺.

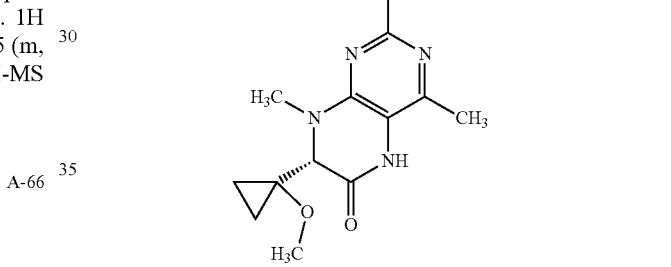

A-68

A-68. (7S)-2-chloro-7-(1-methoxycyclopropyl)-4,8-dimethyl-7,8-dihydropteridin-6(5H)-one The compound was prepared by reaction of methyl (2S)-2-(1-methoxycyclopropyl)-2-(methylamino)acetate hydrochloride (840 mg, 4.006 mmol) and 2,4-dichloro-5-nitro-6-methylpyrimidine (820 mg, 3.942 mmol) following the procedure description in A-6 to provide the title product 1H NMR (300 MHz, CDCl₃) δ 8.23 (s, 1H), 3.68 (s, 1H), 3.28 (s, 3H), 3.13 (s, 3H), 2.36 (s, 3H), 1.17-1.07 (m, 1H), 1.06-0.94 (m, 2H), 0.89-0.73 (m, 1H). ESI-MS m/z calc. 282.08835, found 283.1 (M+1)⁺. [α]_D=+10.5° (c=1.0; CHCl₃) at 24° C.

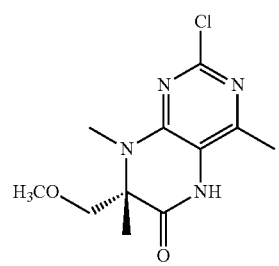

A-69

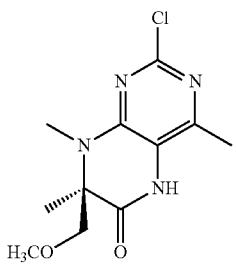

A-70

A-69 & A-70. (7R)-2-chloro-7-(methoxymethyl)-4,7,8-trimethyl-7,8-dihydropteridin-6(5H)-one and (7S)-2-chloro-7-(methoxymethyl)-4,7,8-trimethyl-7,8-dihydropteridin-6(5H)-one The compound was prepared by reaction of methyl 3-methoxy-2-methyl-2-(methylamino)propanoate (6 g, 30.3 mmol) and 2,4-dichloro-5-nitro-6-methylpyrimidine (6 g, 28.85 mmol) following the procedure description in A-4 to provide the title product as a mixture of enantiomers. The enantiomers were separated by SFC (Cellulose-2, 20×250 mm; 40% Ethanol (5 mM Ammonia)/60% $CO_2$, isocratic; 80 ml/min) 1H NMR (300 MHz, $CDCl_3$) δ 8.22 (s, 1H), 3.81 (d, J=9.9 Hz, 1H), 3.58 (d, J=9.9 Hz, 1H), 3.32 (s, 3H), 3.14 (s, 3H), 2.33 (s, 3H), 1.56 (s, 3H). ESI-MS m/z calc. 270.08835, found 271.1 $(M+1)^+$.

Enantiomer A: $[\alpha]D=+34.32°$, temp=22.8° C. (c=1, MeOH). Chiral SFC (Cellulose-2, 4.6×100 mm; 40% Ethanol (5 mM Ammonia)/60% $CO_2$; Isocratic, 1 ml/min) Rt 0.826 mins. (99.8% ee).

Enantiomer B: $[\alpha]D=-23.7°$, temp=23.7° C. (c=1, MeOH). Chiral SFC (Cellulose-2, 4.6×100 mm; 40% Ethanol (5 mM Ammonia)/60% $CO_2$; Isocratic, 1 ml/min) Rt 0.996 mins. (94.6% ee).

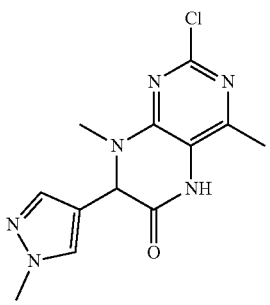

A-71

A-71. 2-chloro-4,8-dimethyl-7-(1-methyl-1H-pyrazol-4-yl)-7,8-dihydropteridin-6(5H)-one The compound was prepared following the procedure reported for A-6 via reaction of 2,4-dichloro-6-methyl-5-nitro-pyrimidine (1.04 g, 4.850 mmol) and methyl 2-(methylamino)-2-(1-methylpyrazol-4-yl)acetate hydrochloride (853 mg, 3.883 mmol) to provide the title product. 1H NMR (400 MHz, DMSO-d6) δ 10.46 (s, 1H), 7.55 (s, 1H), 7.21 (t, J=5.3 Hz, 1H), 5.11 (s, 1H), 3.69 (s, 3H), 2.87 (d, J=17.1 Hz, 3H), 2.24 (s, 3H). ESI-$^M$S m/z calc. 292.08392

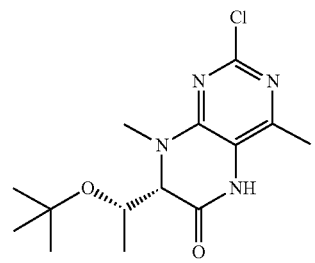

A-72

A-72. (S)-7-((S)-1-(tert-butoxy)ethyl)-2-chloro-4,8-dimethyl-7,8-dihydropteridin-6(5H)-one

Step 1: Methyl O-(tert-butyl)-N-(2-chloro-6-methyl-5-nitropyrimidin-4-yl)-N-methyl-L-allothreoninate Methyl (2S,3R)-3-tert-butoxy-2-(methylamino)butanoate (2.65 g, 13 mmol), 2,4-dichloro-6-methyl-5-nitro-pyrimidine (4.85 g, 23.32 mmol), and $NaHCO_3$ (3.3 g, 39.28 mmol) and stirred at room temperature for 16 hours. After filtration to remove the solid, the solution was concentrated and the crude product was purified by column chromatography ($SiO_2$, 40 g) eluting with a gradient of 0-30% EtOAc in Hexanes to give the title product as a sticky oil (2 g, 23% yield). 1H NMR (400 MHz, $CDCl_3$) δ 5.49 (d, J=4.0 Hz, 1H), 4.53 (qd, J=6.3, 3.9 Hz, 1H), 3.78 (s, 3H), 3.13 (s, 3H), 2.48 (s, 3H), 1.24 (d, J=6.3 Hz, 3H), 1.18 (s, 9H). ESI-MS m/z calc. 374.1357, found 375.52 $(M+1)^+$

Step 2: (S)-7-((S)-1-(tert-butoxy)ethyl)-2-chloro-4,8-dimethyl-7,8-dihydropteridin-6(5H)-one Methyl O-(tert-butyl)-N-(2-chloro-6-methyl-5-nitropyrimidin-4-yl)-N-methyl-L-allothreoninate (2 g) was dissolved followed by the addition of Platinum (165 mg, 0.025 mmol) on wood and hydrogenated for 4 days. The reaction was filtered through Celite to remove the catalyst. The filtrate was evaporated in vacuo to provide the title product as a white solid (1.7 g). 1H NMR (300 MHz, $CDCl_3$) δ 8.35 (s, 1H), 4.15-3.99 (m, 1H), 3.93 (d, J=4.1 Hz, 1H), 3.31 (d, J=1.8 Hz, 3H), 2.35 (d, J=2.0 Hz, 3H), 1.60 (d, J=2.0 Hz, 5H), 1.32 (dd, J=6.4, 2.0 Hz, 3H), 1.13-0.98 (m, 9H). ESI-MS m/z calc. 312.1353, found 313.28 (M+1) 7. Chiral HPLC: (Chiralpak IC column, 20% EtOH/30% EtOH/50% hex, 20 min run, 95% ee; $[\alpha]_D=+60.44°$ (chloroform; c=0.5 @ 24.5° C.).

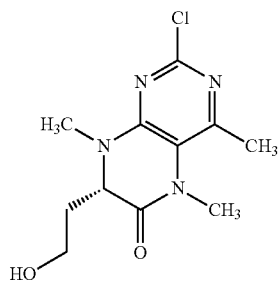

A-73

A-73. (7S)-2-chloro-7-(2-hydroxyethyl)-4,8-dimethyl-7,8-dihydropteridin-6(5H)-one Iodomethane (1.1 ml, 17.5 mmol) was added to a mixture of (7S)-2-chloro-7-(2-hydroxyethyl)-4-methyl-7,8-dihydropteridin-6(5H)-one (2 g, 8 mmol) and cesium carbonate (7.78 g, 23.9 mmol) in DMF (25 ml) and stirred for 16 hours. Water was added to the reaction mixture and extracted with ethyl acetate (3×10 ml). The combined extracts were washed with brine (20 ml), and water (2×20 ml). The organic extract was dried over anhydrous sodium sulfate, filtered, and evaporated in vacuo to afford the title product. 1H NMR (300 MHz, DMSO-d6) δ 4.60 (t, J=4.8 Hz, 1H), 4.27 (dd, J=7.0, 5.8 Hz, 1H), 3.34 (m, 2H), 3.24 (s, 3H), 3.05 (s, 3H), 2.40 (s, 3H), 1.68 (m, 2H). ESI-MS m/z calc. 268.1091, found 269.22 (M+1)$^+$.

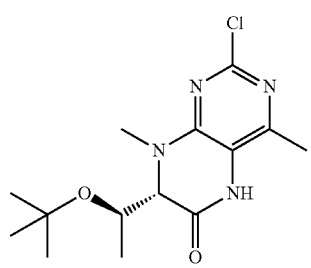

A-74

A-74. (S)-7-((R)-1-(tert-butoxy)ethyl)-2-chloro-4,8-dimethyl-7,8-dihydropteridin-6(5H)-one The compound was prepared in a similar manner as A-72. 1H NMR (300 MHz, CDCl$_3$) δ 8.35 (s, 1H), 4.15-3.99 (m, 1H), 3.93 (d, J=4.1 Hz, 1H), 3.31 (d, J=1.8 Hz, 3H), 2.35 (d, J=2.0 Hz, 3H), 1.60 (d, J=2.0 Hz, 5H), 1.32 (dd, J=6.4, 2.0 Hz, 3H), 1.13-0.98 (m, 9H). ESI-MS m/z 313.28 (M+1)$^+$; [α]=60.44° (c=0.5, CHCl$_3$) at 24.2° C. Chiral HPLC: Chiralpak IC column (20% methanol/30% ethanol/50% hexanes) >95% ee.

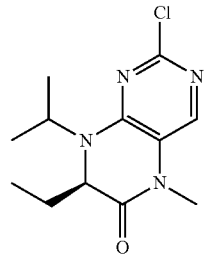

A-75

A-75. (7R)-2-Chloro-7-ethyl-8-isopropyl-5-methyl-7,8-dihydropteridin-6(5H)-one The compound was prepared in the same manner as intermediate A-3 to provide the title product. (7R)-2-chloro-7-ethyl-8-isopropyl-5,7-dihydropteridin-6-one (10.8 g, 77%) 1H NMR (300 MHz, CDCl$_3$) δ 9.12 (s, 1H), 7.67 (s, 1H), 4.61 (p, J=6.8 Hz, 1H), 4.29 (dd, J=7.4, 3.3 Hz, 1H), 2.13-1.92 (m, 1H), 1.81 (dt, J=14.5, 7.4 Hz, 1H), 1.40 (dd, J=11.4, 6.8 Hz, 6H), 0.96 (t, J=7.5 Hz, 3H). ESI-MS m/z calc. 254.09344, found 255.16 (M+1)$^+$; 253.16 (M−1)+.

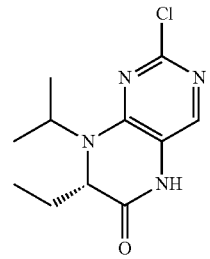

A-76

A-76. (S)-2-Chloro-7-ethyl-8-isopropyl-7,8-dihydropteridin-6(5H)-one

The compound was prepared in the same manner as intermediate A-4 to provide the title product. 1H NMR (300 MHz, CDCl$_3$) δ 9.24 (s, 1H), 7.68 (s, 1H), 4.61 (p, J=6.8 Hz, 1H), 4.29 (dd, J=7.5, 3.3 Hz, 1H), 2.00 (ddt, J=15.1, 7.6, 3.8 Hz, 1H), 1.81 (dt, J=14.5, 7.4 Hz, 1H), 1.40 (dd, J=11.3, 6.8 Hz, 6H), 0.96 (t, J=7.5 Hz, 3H). ESI-MS m/z calc. 254.09344, found 255.16 (M+1)$^+$; 253.16 (M−1)+; [α]$_D$=+207.58° (c=1.0, CHCl$_3$).

A. Preparation of Side Chain Amine Intermediates

The following side chain amines were prepared by the following reaction schemes. A representative procedure follows for each scheme.

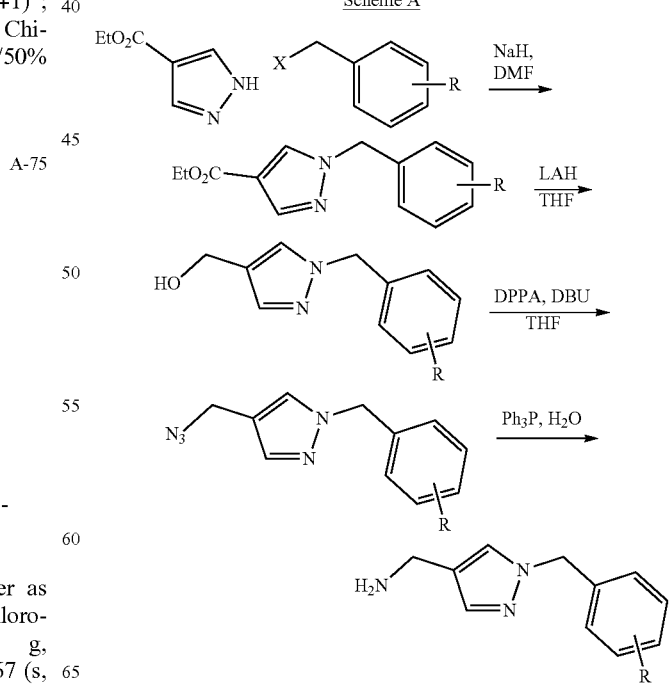

Scheme A

Method A: Synthesis of (1-(4-Fluorobenzyl)-1H-pyrazol-4-yl)methanamine hydrochloride (B-2) via Scheme A

Step 1: Ethyl 1-(4-fluorobenzyl)-1H-pyrazole-4-carboxylate

Sodium hydride (60% oil dispersion; (2.869 g, 71.7 mmol)) was added portion wise to a cold (0° C.) solution of ethyl 1H-pyrazole-4-carboxylate (6.7 g, 47.81 mmol) in DMF (70 mL). The mixture was stirred for 1 hour at 0° C. followed by the addition of 1-(bromomethyl)-4-fluoro-benzene (10.85 g, 57.38 mmol). The reaction was warmed to room temperature and stirred for 18 hours. The reaction mixture was poured into water and the resulting precipitate was collected by vacuum filtration, washed with water, and dried under vacuum at 50° C. for 20 hours to afford the title compound, wt. 8.3 g (70% yield); 1H NMR (400 MHz, DMSO-d6) δ 8.47 (d, J=0.7 Hz, 1H), 7.87 (d, J=0.7 Hz, 1H), 7.34 (dd, J=8.6, 5.6 Hz, 2H), 7.18 (t, J=8.9 Hz, 2H), 5.35 (s, 2H), 4.20 (q, J=7.1 Hz, 2H), 1.25 (t, J=7.1 Hz, 3H).

Step 2: (1-(4-Fluorobenzyl)-1H-pyrazol-4-yl)methanol

A solution of ethyl 1-[(4-fluorophenyl)methyl]pyrazole-4-carboxylate (10 g, 40.28 mmol) in THF (50 mL) was added dropwise to a cooled (0° C.) solution of Lithium aluminum hydride (60 mL of 1 M, 60 mmol) in THF. After stirring for 1 hour at 0° C., the reaction was warmed to room temperature for 30 minutes, then quenched with 1N HCl until a clear solution was obtained. The clear solution was extracted with ethyl acetate (3×50 ml). The combined extracts were washed with water and brine, dried over sodium sulfate, filtered, and evaporated in vacuo to afford the crude product, wt. 7.5 g (90% yield); 1H NMR (400 MHz, Methanol-d4) δ 7.64 (s, 1H), 7.49 (s, 1H), 7.25 (dd, J=8.8, 5.3 Hz, 2H), 7.05 (t, J=8.8 Hz, 2H), 5.28 (s, 2H), 4.49 (s, 2H); ESMS(M+11)=207.0.

Step 3: 4-(Azidomethyl)-1-(4-fluorobenzyl)-1H-pyrazole

A mixture of (1-(4-Fluorobenzyl)-1H-pyrazol-4-yl)methanol (8 g, 38.8 mmol) and (azido(phenoxy)phosphoryl)oxybenzene (16.0 g, 12.5 mL, 58.2 mmol) was dissolved in dry THF (100 ml) and cooled to 0° C. under Nitrogen. DBU (8.7 mL, 58.2 mmol) was added to the reaction and stirred for 2 h at 0° C. and then warmed to room temperature for 16 hours. The reaction mixture was diluted with ethyl acetate and washed with water (2×50 mL) and 5% HCl (10 mL). The organic layer was concentrated in vacuo and purified by column chromatography eluting with a gradient of 10-35% ethyl acetate in hexanes to provide the title compound, wt. 7.2 g (90% yield); 1H NMR (400 MHz, CDCl₃) δ 7.56 (s, 1H), 7.41 (s, 1H), 7.25-7.16 (m, 2H), 7.12-6.96 (m, 2H), 5.28 (s, 2H), 4.23 (s, 2H).

Step 4: (1-(4-Fluorobenzyl)-1H-pyrazol-4-yl)methanamine

Triphenylphosphine (13.6 g, 51.9 mmol) and water (8 ml) were added to a solution of 4-(azidomethyl)-1-[(4-fluorophenyl)methyl]pyrazole (8 g, 34.60 mmol) in dichloromethane (100 mL) and stirred at room temperature for 16 hours; 30 mL of 1N HCl was added to the reaction mixture. The organic layer was separated and discarded. The aqueous layer was washed with dichloromethane and separated. The aqueous layer was evaporated in vacuo resulting in a white solid. The HCl salt of the product was dissolved in methanol and precipitated out of solution by diethyl ether (5 times the methanol volume). The precipitate was collected by vacuum filtration and dried over vacuum at 50° C. to provide the desired product, wt. 6.4 g (76% yield); 1H NMR (400 MHz, DMSO-d6) δ 8.15 (brs, 3H), 7.88 (s, 1H), 7.56 (s, 1H), 7.32 (dt, J=8.0, 3.3 Hz, 2H), 7.18 (td, J=8.9, 1.2 Hz, 2H), 5.32 (s, 2H), 3.87 (q, J=5.7 Hz, 2H).

Scheme B

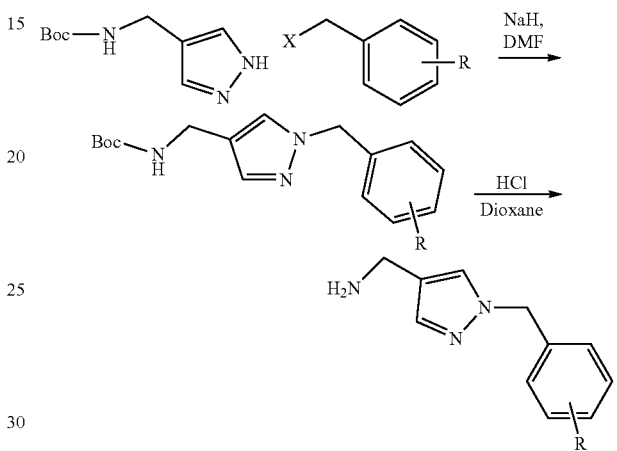

Method B: Synthesis of (1-(3,4,5-Trifluorobenzyl)-1H-pyrazol-4-yl)methanamine hydrochloride (B-23) via Scheme B

Step 1: tert-Butyl ((1-(3,4,5-trifluorobenzyl)-1H-pyrazol-4-yl)methyl)carbamate tert-Butyl N-(1H-pyrazol-4-ylmethyl)carbamate (6.07 g, 29.85 mmol) was dissolved in 60 ml of anhydrous DMF (60 ml) to give a clear pale solution, The solution was cooled to 2° C. and sodium hydride (1.253 g, 31.34 mmol) was added to the mixture portion wise and stirred for 30 mins. 5-(Bromomethyl)-1,2,3-trifluoro-benzene (7.540 g, 32.84 mmol) was added dropwise over 10 minutes. The reaction was stirred at 2° C. for 2 hours then warmed to room temperature over 2 hours. The reaction was poured onto 180 ml of cold water and extracted with ethyl acetate (2×200 ml). The combined ethyl acetate extracts was washed with brine, dried over sodium sulfate, filtered, and evaporated in vacuo to provide the crude product. The reaction was purified by column chromatography (SiO₂; 220 g column) eluting with a gradient of 0-90% ethyl acetate in hexanes. The desired fractions were evaporated in vacuo to provide the desired product as a viscous oil that crystallizes upon standing. Wt. 9.1 g; 1H NMR (300 MHz, CDCl₃) δ 7.49 (s, 1H), 7.38 (s, 1H), 6.87-6.73 (m, 2H), 5.19 (s, 2H), 4.72 (s, 1H), 4.17 (d, J=5.8 Hz, 2H), 1.45 (s, 9H).

Step 2: (1-(3,4,5-Trifluorobenzyl)-1H-pyrazol-4-yl)methanamine tert-Butyl ((1-(3,4,5-trifluorobenzyl)-1H-pyrazol-4-yl)methyl)carbamate (9.1 g, 26.66 mmol) was dissolved in dioxane (64 mL). A solution of 4 N HCl (67 ml, 267 mmol)

was added to the solution and heated at 55° C. for 3 hours. A white precipitate formed. Approximately 2/3 of the dioxane was evaporated in vacuo followed by the addition of ditheyl ether and stirred for 30 minutes. The white precipitate was collected by vacuum filtration and dried under vacuum at 50° C. for 20 hours to afford 7.4 g of the product as the hydrochloride salt. (100% yield); 1H NMR (300 MHz, DMSO-d6) δ 8.27 (s, 3H), 7.96 (s, 1H), 7.62 (s, 1H), 7.19 (dd, J=8.7, 6.9 Hz, 2H), 5.36 (s, 2H), 3.88 (q, J=5.6 Hz, 2H).

Scheme C

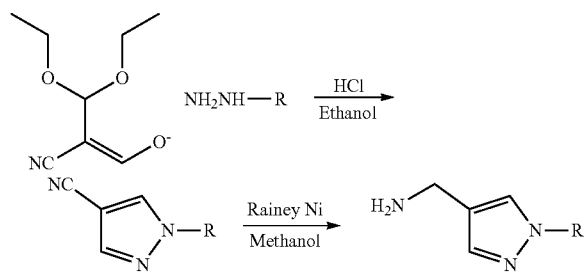

Method C: Synthesis of (1-(2,3-Dihydro-1H-inden-2-yl)-1H-pyrazol-4-yl)methanamine (B-44) via Scheme C Step 1: 1-(2,3-Dihydro-1H-inden-2-yl)-1H-pyrazole-4-carbonitrile A mixture of sodium (Z)-2-cyano-3,3-diethoxyprop-1-en-1-olate (298 mg, 1.54 mmol) and (2,3-dihydro-1H-inden-2-yl)hydrazine methane sulfonic acid salt (343 mg, 1.40 mmol) was taken into 6 ml of ethanol. Concentrated HCl (270 ul, 2.83 mmol) was added to the mixture and heated to 80° C. for 2 hours. Solvent was removed to ½ volume, water added to the mixture, and the resulting solid collected and dried to afford the title compound, wt. 246 mg (87% yield). 1H NMR (300 MHz, CDCl$_3$) δ 7.81 (s, 1H), 7.74 (s, 1H), 7.34-7.20 (m, 4H), 5.24 (tt, J=7.5, 5.0 Hz, 1H), 3.56 (dd, J=16.3, 7.5 Hz, 2H), 3.36 (dd, J=16.3, 5.0 Hz, 2H); ESMS (M+1)=210.12.

Step 2: (1-(2,3-Dihydro-1H-inden-2-yl)-1H-pyrazol-4-yl)methanamine 1-(2,3-Dihydro-1H-inden-2-yl)-1H-pyrazole-4-carbonitrile (240 mg, 1.15 mmol) was taken into methanol (30 ml). Rainey nickel (40 mg, 0.68 mmol) was added and the reaction hydrogenated under hydrogen (50 psi) for 3 hours. The reaction was filtered and the filtrate evaporated in vacuo to afford the title product, 237 mg (97% yield). 1H NMR (400 MHz, CDCl$_3$) δ 7.35 (s, 1H), 7.17 (dd, J=11.4, 7.2 Hz, 5H), 5.17-4.96 (m, 1H), 3.75 (s, 1H), 3.40 (dd, J=16.1, 7.6 Hz, 2H), 3.31-3.09 (m, 2H); ESMS(M+1)=214.22.

Scheme D

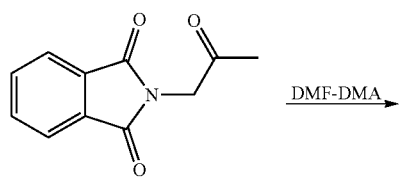

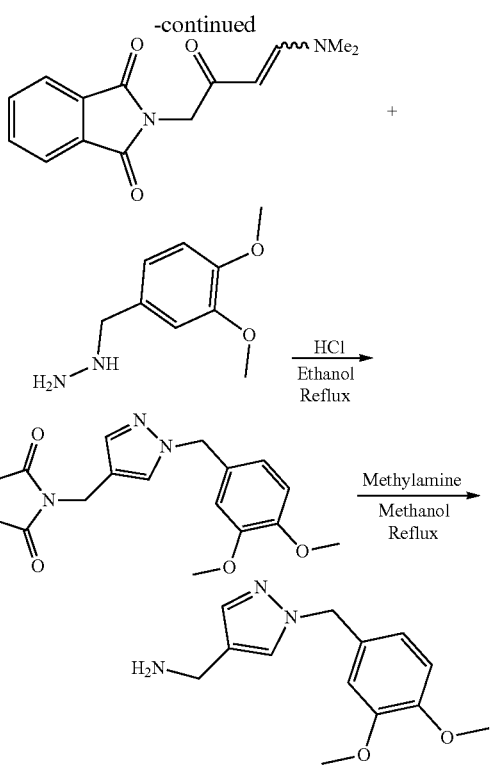

Method D: (1-(3,4-dimethoxybenzyl)-1H-pyrazol-3-yl)methanamine hydrochloride

Step 1: (E&Z)-2-(4-(Dimethylamino)-2-oxobut-3-en-1-yl)isoindoline-1,3-dione

A mixture of 2-(2-oxopropyl)isoindoline-1,3-dione (2.03 g, 10 mmol) and 1,1-dimethoxy-N,N-dimethyl-methanamine (1.3 ml, 10 mmol) was irradiated by microwave at 180° C. for 20 minutes. The resulting solid was recrystallized from ethanol to provide the title product as a mixture of cis-& trans-isomers 2.34 g (91% yield). ESMS(M+1)= 259.10.

Step 2: 2-((1-(3,4-Dimethoxybenzyl)-1H-pyrazol-3-yl)methyl)isoindoline-1,3-dione (E & Z)-2-(4-(Dimethylamino)-2-oxobut-3-en-1-yl)isoindoline-1,3-dione (1 g, and (3,4-dimethoxybenzyl)hydrazine (1 g, mmol) was taken into ethanol (10 ml) and conc HCl (1 ml) and heated to reflux for 3 hours. The reaction was evaporated in vacuo and the residue purified by column chromatography (SiO$_2$) eluting with a gradient of 0-10% methanol in dichloromethane to give the desired product as a yellow solid, wt. 1.1 g. 1H NMR (400 MHz, CDCl$_3$) δ 7.78-7.71 (m, 2H), 7.71-7.64 (m, 2H), 7.52 (d, J=1.8 Hz, 1H), 6.57 (d, J=8.1 Hz, 1H), 6.54-6.49 (m, 1H), 6.50-6.42 (m, 2H), 5.49 (s, 2H), 4.85 (s, 2H), 3.78 (d, J=0.8 Hz, 3H), 3.73 (d, J=0.8 Hz, 3H).

Step 3: (1-(3,4-dimethoxybenzyl)-1H-pyrazol-3-yl)methanamine hydrochloride

A mixture of 2-((1-(3,4-dimethoxybenzyl)-1H-pyrazol-3-yl)methyl)isoindoline-1,3-dione (1.1 g, 2.92 mmol) and methylamine (2M solution in methanol; 7.3 ml, 14.6 mmol)

in methanol was refluxed for 2 hours. The solvent was removed in vacuo. The compound was taken into 2M HCl in methanol and precipitated with the addition of diethyl ether to provide the title product, wt. 638 mg (89% yield). 1H NMR (400 MHz, Methanol-d4) δ 7.61 (d, J=2.0 Hz, 1H), 6.91 (d, J=8.2 Hz, 1H), 6.79 (d, J=2.1 Hz, 1H), 6.72-6.64 (m, 1H), 6.59-6.49 (m, 1H), 5.40 (s, 2H), 4.20 (s, 2H), 3.80 (s, 3H), 3.77 (s, 3H).

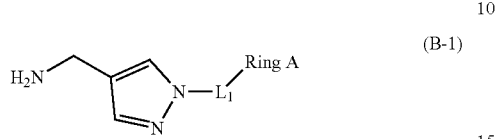

(B-1)

B-1. (1-(4-Fluoro-2-methoxybenzyl)-1H-pyrazol-4-yl)methanamine hydrochloride Prepared by Method B. 1H NMR (300 MHz, DMSO-d6) δ 8.14 (s, 3H), 7.76 (s, 1H), 7.53 (s, 1H), 7.05 (dd, J=8.3, 6.9 Hz, 1H), 6.96 (dd, J=11.3, 2.4 Hz, 1H), 6.74 (td, J=8.5, 2.5 Hz, 1H), 5.22 (s, 2H), 3.86 (dd, J=10.1, 4.3 Hz, 2H), 3.84 (d, J=4.4 Hz, 3H); ESMS(M+1)=236.10.

B-2. (1-(4-Fluorobenzyl)-1H-pyrazol-4-yl)methanamine hydrochloride

Prepared by Method A. 1H NMR (400 MHz, DMSO-d6) δ 8.20 (s, 3H), 7.89 (s, 1H), 7.57 (s, 1H), 7.32 (dd, J=8.6, 5.6 Hz, 2H), 7.18 (t, J=8.9 Hz, 2H), 5.32 (s, 2H), 3.86 (q, J=5.8 Hz, 2H); ESMS(M+1)=206.36.

B-3. (1-(3-Fluorobenzyl)-1H-pyrazol-4-yl)methanamine hydrochloride

Prepared by Method B. 1H NMR (400 MHz, Methanol-d4) δ 7.96 (s, 1H), 7.73 (s, 1H), 7.32 (dt, 1H), 7.05 (m, J=3H), 5.41 (s, 2H), 4.06 (s, 2H); ESMS(M+1)=206.19.

B-4. (1-(1-(4-Fluorophenyl)ethyl)-1H-pyrazol-4-yl)methanamine

Prepared by Method A. 1H NMR (400 MHz, DMSO-d6) δ 8.17 (s, 3H), 7.90 (s, 1H), 7.58 (s, 1H), 7.38-7.27 (m, 2H), 7.16 (td, J=8.7, 1.4 Hz, 2H), 5.65 (q, J=7.1 Hz, 1H), 3.86 (q, J=5.7 Hz, 2H), 1.76 (dd, J=7.1, 1.3 Hz, 3H).

B-5. (1-(4-(Trifluoromethyl)benzyl)-1H-pyrazol-4-yl)methanamine hydrochloride Prepared by Method B. ESMS(M+1)=256.19

B-6. (1-(3-(Trifluoromethyl)benzyl)-1H-pyrazol-4-yl)methanamine hydrochloride Prepared by Method B. ESMS(M+1)=256.26

B-7. (1-(2-(Trifluoromethyl)benzyl)-1H-pyrazol-4-yl)methanamine hydrochloride Prepared by Method B. 1H NMR (300 MHz, Methanol-d4) δ 7.90 (s, 1H), 7.81-7.72 (m, 2H), 7.64-7.45 (m, 2H), 7.04 (d, J=7.6 Hz, 1H), 5.62 (s, 2H), 4.08 (s, 2H); ESMS(M+1)=256.17

B-8. 4-((4-(Aminomethyl)-1H-pyrazol-1-yl)methyl)benzonitrile hydrochloride

Prepared by Method B. 1H NMR (300 MHz, Methanol-d4) δ 7.85 (d, J=0.8 Hz, 1H), 7.67 (d, J=8.3 Hz, 2H), 7.61 (d, J=0.8 Hz, 1H), 7.39-7.28 (m, 2H), 5.42 (s, 2H), 4.01 (s, 2H); ESMS(M+1)=213.12

B-9. (1-(2-Isopropylbenzyl)-1H-pyrazol-4-yl)methanamine hydrochloride

Prepared by Method B. ESMS(M+1)=230.43

B-10. (1-(3-Isopropylbenzyl)-1H-pyrazol-4-yl)methanamine hydrochloride

Prepared by Method B. ESMS(M+1)=230.39

B-11. (1-(3,4-Difluorobenzyl)-1H-pyrazol-4-yl)methanamine hydrochloride

Prepared by Method B. ESMS(M+1)=224.11

B-12. (1-(2,4-Difluorobenzyl)-1H-pyrazol-4-yl)methanamine hydrochloride

Prepared by Method B. ESMS(M+1)=224.07

B-13. (1-(2-Chloro-4-fluorobenzyl)-1H-pyrazol-4-yl)methanamine hydrochloride Prepared by Method B. 1H NMR (300 MHz, Methanol-d4) δ 7.91 (s, 1H), 7.71 (s, 1H), 7.36-7.18 (m, 2H), 7.17-7.04 (m, 1H), 5.48 (s, 2H), 4.06 (s, 2H); ESMS(M+1)=240.1

B-14. (1-(4-Fluoro-2-methylbenzyl)-1H-pyrazol-4-yl)methanamine hydrochloride Prepared by Method B. 1H NMR (300 MHz, Methanol-d4) δ 7.83 (d, J=14.2 Hz, 2H), 7.15 (dd, J=8.5, 5.8 Hz, 1H), 7.05-6.86 (m, 2H), 5.42 (s, 2H), 4.06 (s, 2H), 2.31 (s, 3H); ESMS(M+1)=220.2.

B-15. (1-(4-Fluoro-2-(trifluoromethyl)benzyl)-1H-pyrazol-4-yl)methanamine hydrochloride Prepared by Method B. 1H NMR (300 MHz, Methanol-d4) δ 7.88 (s, 1H), 7.71 (s, 1H), 7.55 (dd, J=9.0, 2.7 Hz, 1H), 7.36 (td, J=8.3, 2.7 Hz, 1H), 7.13 (dd, J=8.8, 5.3 Hz, 1H), 5.57 (s, 2H), 4.07 (s, 2H); ESMS(M+1)=274.23.

B-16. (1-(4-Fluoro-3-methoxybenzyl)-1H-pyrazol-4-yl)methanamine hydrochloride Prepared by Method B. 1H NMR (400 MHz, Methanol-d4) δ 7.93 (s, 1H), 7.71 (s, 1H), 7.14-6.93 (m, 2H), 6.84 (ddd, J=8.3, 4.1, 2.0 Hz, 1H), 5.34 (s, 2H), 4.05 (s, 2H), 3.85 (d, J=1.2 Hz, 3H); ESMS(M+1)=236.09

B-17. (1-(3-Fluoro-4-methoxybenzyl)-1H-pyrazol-4-yl)methanamine hydrochloride Prepared by Method B. ESMS(M+1)=236.0

B-18. 2-((4-(Aminomethyl)-1H-pyrazol-1-yl)methyl)-5-fluorobenzonitrile hydrochloride Prepared by Method B. ESMS(M+1)=231.18

B-19. (1-(Benzo[d][1,3]dioxol-5-ylmethyl)-1H-pyrazol-4-yl)methanamine hydrochloride Prepared by Method B. ESMS(M+1)=232.18

B-20. (1-(3,5-Difluoro-4-methoxybenzyl)-1H-pyrazol-4-yl)methanamine hydrochloride Prepared by Method B. 1H NMR (300 MHz, DMSO-d6) δ 11.81 (s, 1H), 8.33 (s, 3H), 7.95 (s, 1H), 7.61 (s, 1H), 7.11-6.92 (m, 2H), 5.31 (s, 2H), 3.96 (s, 3H), 3.78 (m, 2H); ESMS(M+1)=254.24.

B-21. (1-(2,4-Difluoro-3-methoxybenzyl)-1H-pyrazol-4-yl)methanamine hydrochloride Prepared by Method B. 1H NMR (300 MHz, Methanol-d4) δ 6.60 (s, 1H), 6.36 (s, 1H), 5.78-5.62 (m, 2H), 4.09 (s, 2H), 2.76 (s, 2H), 2.66 (s, 3H); ESMS(M+1)=254.15.

B-22. (1-(2,3,4-Trifluorobenzyl)-1H-pyrazol-4-yl)methanamine hydrochloride

Prepared by Method B. 1H NMR (300 MHz, DMSO-d6) δ 8.18 (br.s, 3H), 7.92 (s, 1H), 7.58 (s, 1H), 7.41-7.26 (m, 1H), 7.23-7.08 (m, 1H), 5.43 (s, 2H), 3.93 (br.s, 1H), 3.87 (q, J=5.7 Hz, 2H); 1H NMR (300 MHz, Methanol-d4) δ 7.66 (s, 1H), 7.50 (s, 1H), 7.15-6.94 (m, 2H), 5.36 (s, 2H), 3.69 (s, 2H); ESMS(M+1)=242.14.

B-23. (1-(3,4,5-Trifluorobenzyl)-1H-pyrazol-4-yl)methanamine hydrochloride

Prepared by Method B. 1H NMR (300 MHz, DMSO-d6) δ 8.22 (s, 3H), 7.95 (s, 1H), 7.61 (s, 1H), 7.18 (dd, J=8.8, 6.7 Hz, 2H), 5.36 (s, 2H), 3.88 (q, J=5.6 Hz, 2H); ESMS(M+1)=242.13.

B-24. (1-(2,4,5-Trifluorobenzyl)-1H-pyrazol-4-yl)methanamine hydrochloride

Prepared by Method B. 1H NMR (400 MHz, DMSO-d6) δ 8.14 (s, 3H), 7.90 (s, 1H), 7.65-7.58 (m, 1H), 7.58 (s, 1H), 7.37 (ddd, J=10.9, 9.0, 6.8 Hz, 1H), 5.36 (s, 2H), 3.88 (q, J=5.7 Hz, 2H); ESMS(M+1)=242.13.

B-25. (1-(4-Fluorophenethyl)-1H-pyrazol-4-yl)methanamine hydrochloride

Prepared by Method B. ESMS(M+1)=220.11

B-26. (1-(3,4-Difluorophenethyl)-1H-pyrazol-4-yl)methanamine hydrochloride

Prepared by Method B. ESMS(M+1)=238.12

B-27. (1-(2,4-Difluorophenethyl)-1H-pyrazol-4-yl)methanamine hydrochloride

Prepared by Method B. ESMS(M+1)=238.12

B-28. (1-(3,4,5-Trifluorophenethyl)-1H-pyrazol-4-yl)methanamine hydrochloride Prepared by Method B. ESMS(M+1)=256.00.

B-29. (1-(2,4,6-Trifluorophenethyl)-1H-pyrazol-4-yl)methanamine hydrochloride Prepared by Method B. ESMS(M+1)=256.00.

B-30. (1-(3,5-Difluorophenethyl)-1H-pyrazol-4-yl)methanamine hydrochloride

Prepared by Method B. ESMS(M+1)=238.26.

B-31. (1-(4-Ethoxyphenethyl)-1H-pyrazol-4-yl)methanamine hydrochloride

Prepared by Method B. ESMS(M+1)=246.18

B-32. (1-(3-(4-Fluorophenyl)propyl)-1H-pyrazol-4-yl)methanamine hydrochloride Prepared by Method B. ESMS(M+1)=234.12.

B-33. (1-(2-(4-Fluorophenoxy)ethyl)-1H-pyrazol-4-yl)methanamine hydrochloride Prepared by Method B. ESMS(M+1)=236.14.

B-34. (1-((trans)-3-(4-Fluorophenyl)cyclobutyl)-1H-pyrazol-4-yl)methanamine hydrochloride Prepared by Method B. 1H NMR (400 MHz, CDCl₃) δ 7.52 (s, 1H), 7.44 (s, 1H), 7.30-7.17 (m, 2H), 7.02 (t, J=8.7 Hz, 2H), 4.94-4.78 (m, 1H), 3.79 (s, 2H), 3.75 (m, 1H), 3.05-2.90 (m, 2H), 2.73-2.57 (m, 2H), 1.79 (s, 2H). ESMS (M+1)=245.9

B-35. (1-(2-Cyclohexylethyl)-1H-pyrazol-4-yl)methanamine hydrochloride

Prepared by Method B. 1H NMR (400 MHz, Methanol-d4) δ 8.11 (s, 1H), 7.96 (s, 1H), 4.41-4.25 (m, 2H), 4.11 (s, 2H), 1.88-1.53 (m, 7H), 1.25 (dd, J=15.2, 8.2 Hz, 4H), 1.01 (t, J=11.1 Hz, 2H).

B-36. (1-(2-(Tetrahydro-2H-pyran-4-yl)ethyl)-1H-pyrazol-4-yl)methanamine hydrochloride Prepared by Method B. 1H NMR (400 MHz, Methanol-d4) δ 8.08 (s, 1H), 7.93 (s, 1H), 4.21 (t, J=6.8 Hz, 2H), 3.92 (s, 2H), 3.68 (dd, J=11.4, 3.8 Hz, 3H), 3.19-2.99 (m, 2H), 1.65 (q, J=6.4 Hz, 2H), 1.38 (dd, J=35.5, 11.9 Hz, 4H), 1.23-0.89 (m, 3H).

B-37. (1-(2-(4,4-Difluorocyclohexyl)methyl)-1H-pyrazol-4-yl)methanamine hydrochloride Prepared by Method B. 1H NMR (300 MHz, Methanol-d4) δ 7.86 (s, 1H), 7.69 (s, 1H), 4.10 (d, J=7.2 Hz, 2H), 4.05 (s, 2H), 2.14-1.90 (m, 4H), 1.89-1.71 (m, 1H), 1.65 (dd, J=14.0, 3.6 Hz, 2H), 1.43-1.22 (m, 2H).

B-38. (1-(Cyclobutylmethyl)-1H-pyrazol-4-yl)methanamine hydrochloride

Prepared by Method B. ESMS(M+1)=166.14.

B-39. (1-((3,3-Difluorocyclobutyl)methyl)-1H-pyrazol-4-yl)methanamine hydrochloride Prepared by Method B. 1H NMR (400 MHz, DMSO-d6) δ 8.12 (br s, 3H), 7.83 (s, 1H), 7.55 (d, J=0.8 Hz, 1H), 4.24 (d, J=6.3 Hz, 2H), 3.87 (q, J=5.8 Hz, 2H), 2.65-2.35 (m, 5H); ESMS(M+1)=202.10.

B-40. (1-(2-Cyclopentylethyl)-1H-pyrazol-4-yl)methanamine hydrochloride

Prepared by Method B. ESMS(M+1)=194.18.

B-41. (1-(2-Cyclopropylethyl)-1H-pyrazol-4-yl)methanamine hydrochloride

Prepared by Method B. ESMS(M+1)=166.14

B-42. (S)-(1-(2-Methylbutyl)-1H-pyrazol-4-yl)methanamine hydrochloride

Prepared by Method B. 1H NMR (400 MHz, Methanol-d4) δ 8.02 (s, 1H), 7.89 (s, 1H), 4.12 (dd, J=13.9, 6.7 Hz, 1H), 4.01 (d, J=2.2 Hz, 2H), 4.00-3.92 (m, 1H), 1.98-1.76 (m, 1H), 1.38-1.18 (m, 1H), 1.18-0.95 (m, 1H), 0.83 (t, J=7.4 Hz, 3H), 0.77 (d, J=6.7 Hz, 3H); ESMS(M+1)=168.07.

B-43. (1-(Bicyclo[2.2.1]heptan-2-ylmethyl)-1H-pyrazol-4-yl)methanamine hydrochloride Prepared Method B. ESMS(M+1)=206.25.

B-44. (1-(2,3-Dihydro-1H-inden-2-yl)-1H-pyrazol-4-yl)methanamine hydrochloride Prepared by Method C. 1H NMR (400 MHz, CDCl3) δ 7.35 (s, 1H), 7.17 (dd, J=11.4, 7.2 Hz, 5H), 5.17-4.96 (m, 1H), 3.75 (s, 1H), 3.40 (dd, J=16.1, 7.6 Hz, 2H), 3.31-3.09 (m, 2H); ESMS(M+1)=214.22

B-45. 2-(4-(Aminomethyl)-1H-pyrazol-1-yl)-1-(4-fluorophenyl)ethan-1-one hydrochloride Prepared by Method B. ESMS(M+1)=234.07

B-46. (1-(6-Fluoro-2,3-dihydro-1H-inden-1-yl)-1H-pyrazol-4-yl)methanamine hydrochloride Prepared by Method B. ESMS(M+1)=232.13

B-47. (1-(3-(Trifluoromethyl)phenyl)-1H-pyrazol-4-yl)methanamine hydrochloride Prepared by Method C. ESMS(M+1)=242.36.

B-48. (1-(2,4-Difluorophenyl)-1H-pyrazol-4-yl)methanamine hydrochloride

Prepared by Method C ESMS(M+1)=210.36

B-49. (1-(3,4-Dimethoxybenzyl)-1H-pyrazol-4-yl)methanamine hydrochloride

Prepared by Method D.

B-50. (1-(2-(4-Fluorophenyl)-2-methylpropyl)-1H-pyrazol-4-yl)methanamine

Prepared by Method A. 40% yield. ESMS(M+1)=248.16.

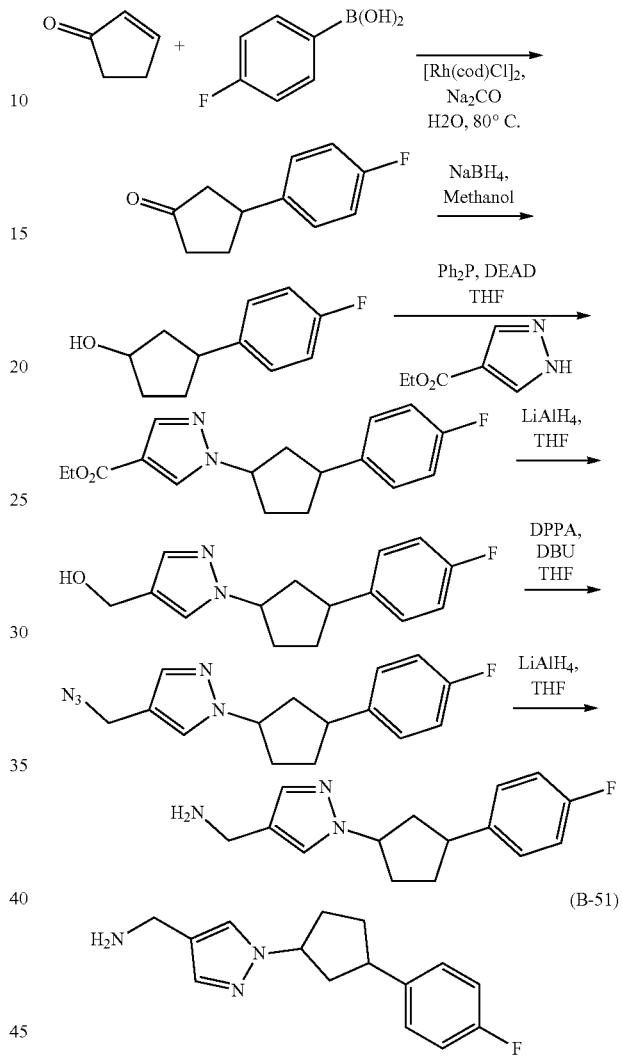

(B-51)

B-51. Preparation of (1-(3-(4-Fluorophenyl)cyclopentyl)-1H-pyrazol-4-yl)methanamine Step 1: 3-(4-Fluorophenyl)cyclopentan-1-one A vial charged with [Rh(cod)Cl]₂ (180.2 mg, 0.3654 mmol) and (4-fluorophenyl)boronic acid (4.261 g, 30.45 mmol) was flushed with nitrogen. To the reaction vial was added sequentially, water (60 mL) (degassed for >1 hr with nitrogen) followed by sodium carbonate (2.582 g, 24.36 mmol). The mixture was stirred under a nitrogen atmosphere until the sodium carbonate was fully dissolved (~3 min). Cyclopent-2-en-1-one (1.0 g, 12.18 mmol) was added to the mixture. The heterogeneous mixture was heated to 80° C. under a nitrogen atmosphere.

After 1 hr, the reaction was cooled to room temperature. The aqueous mixture was extracted with ethyl acetate (2×) and again with dichloromethane (2×). The combined organic layers were dried over anhydrous sodium sulfate, filtered through a short plug of silica gel (~8 gram) and concentrated to provide the desired product wt. 2.09 g, 96%. yield. 1H NMR (400 MHz, CDCl$_3$) δ 7.23-7.14 (m, 1H), 7.01 (dd, J=12.0, 5.3 Hz, 1H), 3.39 (ddd, J=18.1, 11.1, 6.9 Hz, 1H), 2.66 (dd, J=18.0, 7.6 Hz, 1H), 2.54-2.36 (m, 1H), 2.29 (dt, J=11.1, 9.9 Hz, 1H), 2.03-1.84 (m, 1H).

Step 2: 3-(4-Fluorophenyl)cyclopentan-1-ol

Sodium borohydride (424.5 mg, 11.2 mmol) was added to a solution of 3-(4-fluorophenyl)cyclopentan-1-one (2.0 g, 11.22 mmol) in anhydrous methanol (40.00 mL) at 0 C. The solution was kept at 0° C. for 2 hours. After 3 hrs, the mixture was evaporated in vacuo and the crude material was partitioned between dichloromethane and 2N HCl. The aqueous layer was extracted with dichloromethane. and the combined organic extracts were dried over Na$_2$SO$_4$, concentrated, and filtered through a short silica plug to give a pale orange oil. (1.94 g) NMR indicated this material was a mixture of 41:59 of trans:cis Step 3: Ethyl 1-(3-(4-fluorophenyl)cyclopentyl)-1H-pyrazole-4-carboxylate A stirred solution of 3-(4-fluorophenyl)cyclopentanol (1.87 g, 10.38 mmol) and ethyl 1H-pyrazole-4-carboxylate (1.631 g, 11.64 mmol) in THE (46 mL) was dried over 3A molecular sieves for ~3 hours to remove traces of water. The solution was transferred to a dry vial charged with triphenylphosphine (4.03 g, 15.4 mmol) and the solution was stirred at room temperature.

Diethyl azodicarboxylate (6.4 mL of 40% w/v, 14.7 mmol) was added dropwise over 20 minutes. The yellow solution was stirred at room temperature for 30 minutes, then heated to 60° C. for 2 hours. The reaction was cooled to room temperature and stirred overnight. The reaction was evaporated in vacuo. The crude product was purified by flash chromatography (SiO$_2$, gradient elution 30-100% EtOAc in hexanes) to provide 2.09 g of the title product as a mixture of cis and trans isomers (45:55 cis:trans). ESMS(M+1)= 303.08.

Step 4: (1-(3-(4-Fluorophenyl)cyclopentyl)-1H-pyrazol-4-yl)methanol

A 1 M solution of lithium aluminum hydride (14.00 mL, 14.00 mmol) was added dropwise to a cooled (0° C.) solution of ethyl 1-(3-(4-fluorophenyl)cyclopentyl)-1H-pyrazole-4-carboxylate (2.09 g, 6.9 mmol) in THF (27 mL). After addition, the mixture was slowly warmed to room temperature. After 6 hours, the reaction was quenched with the addition of water (0.5 mL), 15% NaOH (0.5 mL) and water (0.5 mL). Diethyl ether was added to the reaction and the mixture was stirred for ~30 minutes. The mixture was filtered through a silica plug to remove the aluminum salts. The filtrate was evaporated in vacuo to provide the product as a colorless viscous oil (1.72 g). 1H NMR (400 MHz, CDCl$_3$) δ 7.47 (s, 1H), 7.42 (s, 1H), 7.15 (ddd, J=14.0, 8.5, 4.3 Hz, 2H), 6.92 (t, J=8.7 Hz, 2H), 4.86-4.64 (m, 1H), 3.40 (tt, J=9.9, 7.5 Hz, 0.6H), 3.10 (tt, J=11.5, 7.1 Hz, 0.4H), 2.62-1.54 (m, 6H).

Step 5: 4-(Azidomethyl)-1-(3-(4-fluorophenyl)cyclopentyl)-1H-pyrazole

To a cooled (0° C.) solution of (1-(3-(4-fluorophenyl) cyclopentyl)-1H-pyrazol-4-yl)methanol (1.72 g, 6.608 mmol) in dry THF (35 mL) was added DBU (1.257 g, 1.235 mL, 8.260 mmol) followed by dropwise addition of DPPA (2.18 g, 1.7 mL, 7.93 mmol). The mixture was kept at 0° C. for 2 hours and allowed to warm to room temperature overnight. The reaction was partitioned between dichloromethane and saturated sodium bicarbonate. The aqueous layer was extracted with dichloromethane. The combined organic extracts were dried over anhydrous sodium sulfate, filtered, and concentrated in vacuo. The crude product was purified by flash chromatography (SiO$_2$) eluting with a gradient of 0-100% ethyl acetate in hexanes). The desired fractions were combined and evaporated to provide the product as a mixture of diastereomers. NMR showed a clean mixture of diastereomers with a ratio of trans:cis=~60:40.

Step 6: (1-(3-(4-fluorophenyl)cyclopentyl)-1H-pyrazol-4-yl)methanamine

A solution of 4-(azidomethyl)-1-(3-(4-fluorophenyl)cyclopentyl)pyrazole (1.44 g, 5.047 mmol) in dry tetrahydrofuran (7 mL) was added dropwise to a solution of lithium aluminum hydride (10.17 mL of 1 M, 10.17 mmol) in tetrahydrofuran at room temperature over 5 minutes (reaction turned yellow during addition).

After 3 hours, the reaction was quenched with the addition of 0.1 mL of water, 0.1 mL of 15% NaOH, and 0.3 mL of water. The mixture was diluted with diethyl ether (15 mL) and stirred at room temperature. The reaction was filtered, to remove the aluminum salts, and rinsed with several portions of diethyl ether. The filtrate was evaporated in vacuo to provide the desired product, Wt. 586 mg. 1H NMR confirmed product as a mixture of diastereomers. 1H NMR (300 MHz, CDCl$_3$) δ 7.49 (s, 1H), 7.44 (s, 1H), 7.27-7.17 (m, 2H), 7.00 (t, J=8.7 Hz, 2H), 4.94-4.68 (m, 1H), 3.81 (d, 2H), 3.48 (m, 0.6H), 3.18 (m, 0.4H), 2.72-1.91 (m, 6H). (trans: cis=~ 60:40).

B-52. (1-((6-(Trifluoromethyl)pyridin-3-yl)methyl)-1H-pyrazol-4-yl)methanamine hydrochloride Prepared by Method B in 2 steps Step 1: tert-butyl ((1-((6-(trifluoromethyl)pyridin-3-yl)methyl)-1H-pyrazol-4-yl)methyl)carbamate tert-Butyl N-(1H-pyrazol-4-ylmethyl)carbamate (18.9 g, 95.83 mmol) and 5-(chloromethyl)-2-(trifluoromethyl)pyridine (19.67 g, 100.6 mmol) was taken into 190 ml of DMF and cooled to 0° C. Sodium hydride (60% w/w oil dispersion; 4.22 g, 105.4 mmol) was added to the mixture portionwise keeping the temperature below 10° C. The mixture was stirred overnight allowing the temperature to warm to room temperature. Water (1 L) was added to the reaction mixture and a white precipitate formed. The mixture was stirred for 30 mins then filtered and the filter cake washed with water and heptane and dried under vacuum at 50° C. for 18 hours to provide the title compound, wt. 33.5 g (98% yield). 1H NMR (300 MHz, CDCl$_3$) δ 8.62 (s, 1H), 7.74-7.61 (m, 2H), 7.52 (s, 1H), 7.44 (s, 1H), 5.38 (s, 2H), 4.74 (s, 1H), 4.19 (d, J=5.8 Hz, 2H), 1.46 (s, 9H).

Step 2: (1-((6-(Trifluoromethyl)pyridin-3-yl) methyl)-1H-pyrazol-4-yl)methanamine hydrochloride tert-Butyl ((1-((6-(trifluoromethyl)pyridin-3-yl)methyl)-1H-pyrazol-4-yl)methyl)carbamate (33.5 g, 94 mmol) was dissolved into 200 ml of dioxane and 4M HCl in dioxane (235 ml) was added to the solution. The solution was stirred at room temperature for 3 hours followed by heating at 50° C. for 2 hours. The dioxane was evaporated in vacuo to afford a viscous gum. Dichloromethane (300 ml) was added to the gum and stirred at room temperature for 30 mins resulting in formation of a solid. The solid was collected by vacuum filtration, washed with dichloromethane and dried under vacuum at 50° C. for 18 hours to afford the title product, wt. 31.2 g (90.8% yield). $^1$H NMR (300 MHz, DMSO-d6) δ 8.66 (s, 1H), 8.07 (s, 3H), 7.96 (s, 1H), 7.92 (s, 2H), 7.59 (s, 1H), 5.54 (s, 2H), 3.91 (d, J=4.0 Hz, 2H); F19 NMR (282.4 MHz, DMSO-d6) −66.38, −73.62 ppm; ESMS(M+1)=257.14.

B-53. (1-((6-Fluoropyridin-3-yl)methyl)-1H-pyrazol-4-yl)methanamine hydrochloride Prepared by Method B. 1H NMR (300 MHz, Methanol-d4) δ 8.16 (d, J=2.4 Hz, 1H), 7.96-7.82 (m, 2H), 7.65 (s, 1H), 7.08 (dd, J=8.5, 2.6 Hz, 1H), 5.42 (s, 2H), 4.05 (s, 2H).

B-54. (1-((6-Fluoro-4-methylpyridin-3-yl)methyl)-1H-pyrazol-4-yl)methanamine hydrochloride Prepared by Method B. 1H NMR (300 MHz, DMSO-d6) δ 7.97 (bs, 4H), 7.83 (d, J=0.8 Hz, 1H), 7.55 (d, J=0.8 Hz, 1H), 7.11-7.04 (m, 1H), 5.39 (s, 2H), 3.90 (q, J=5.7 Hz, 2H), 2.34 (d, J=0.8 Hz, 3H). ESMS(M+1)=221.18.

B-55. (1-((6-Methylpyridin-3-yl)methyl)-1H-pyrazol-4-yl)methanamine hydrochloride Prepared by Method B. ESMS(M+1)=203.25.

B-56. 5-((4-(Aminomethyl)-1H-pyrazol-1-yl)methyl)picolinonitrile hydrochloride Prepared by Method B. 1H NMR (300 MHz, DMSO-d6) δ 8.63 (dd, J=2.1, 0.9 Hz, 1H), 8.05 (dd, J=8.0, 0.9 Hz, 1H), 8.00 (br, 3H), 7.96 (d, J=0.8 Hz, 1H), 7.85 (dd, J=8.0, 2.2 Hz, 1H), 7.59 (d, J=0.8 Hz, 1H), 5.54 (s, 2H), 3.91 (q, J=5.7 Hz, 2H). ESMS(M+1)=214.16.

B-57. (1-((6-(trifluoromethyl)pyridin-3-yl)methyl)-1H-pyrazol-4-yl)methan-d2-amine

Step 1. 1-((6-(trifluoromethyl)pyridin-3-yl)methyl)-1H-pyrazole-4-carbonitrile 4-cyanopyrazole (570 mg, 6.123 mmol) and 5-(chloromethyl)-2-trifluoromethyl pyridine (1.257 g, 6.429 mmol) were taken into DMF (10 mL). The mixture was stirred until reactants were dissolved. The solution was cooled to 0° C. followed by the addition of sodium hydride (270 mg, 6.7 mmol) portion wise. The solution was stirred at room temperature for 2 hours. The reaction was quenched with saturated NH$_4$Cl (10 mL). Dichloromethane (20 mL) and water (20 mL) were added to the reaction and the organic layer separated. The aqueous layer was extracted twice with dichloromethane (10 mL). The combined organic layers were washed with water (10 mL) and brine (2×10 mL), dried over sodium sulfate, filtered, and concentrated to give the crude product. The crude product was purified by column chromatography eluting with a gradient of 0-30% ethyl acetate in hexane. The desired fractions were evaporated to provide the desired product as a white solid (1.4 g, 90.7% yield). 1H NMR (300 MHz, CDCl$_3$) δ 8.74-8.63 (m, 1H), 7.94 (d, J=0.6 Hz, 1H), 7.89 (s, 1H), 7.75 (qd, J=8.0, 1.4 Hz, 2H), 5.46 (s, 2H).

Step 2. (1-((6-(trifluoromethyl)pyridin-3-yl)methyl)-1H-pyrazol-4-yl)methan-d2-amine 1-((6-(trifluoromethyl)pyridin-3-yl)methyl)-1H-pyrazole-4-carbonitrile (261.1 mg, 1.031 mmol), dichlorocobalt hexahydrate (54 mg, 0.2270 mmol) and di-tert-butyl dicarbonate (270.0 mg, 1.24 mmol) were taken into trideuteriomethanol (10 ml) and cooled to 0° C. Sodium borodeuteride (130 mg, 3.1 mmol) was added to the solution in portions. The reaction, which turned black, was stirred for 2 hours. The solvent was evaporated in vacuo to give a black residue. To the residue was added dichloromethane (10 ml) and water (5 ml). The organic layer was collected and filtered to remove solid suspension. The organic layer was washed with brine, dried over MgSO4, filtered, and evaporated in vacuo to provide the desired product as white solid (255 mg, 69% yield which was used without further purification. 1H NMR (300 MHz, CDCl$_3$) δ 8.62 (s, 1H), 7.68 (t, J=1.5 Hz, 2H), 7.52 (s, 1H), 7.45 (s, 1H), 6.24 (s, 2H), 5.38 (s, 3H), 4.74 (s, 1H), 1.54 (s, 9H). 19F NMR (282 MHz, CDCl$_3$) δ −67.97.

B-58. (1-((2-Fluoropyridin-4-yl)methyl)-1H-pyrazol-4-yl)methanamine hydrochloride Prepared by Method B. ESMS(M+1)=207.15.

B-59. (1-((4-(Trifluoromethyl)pyridin-3-yl)methyl)-1H-pyrazol-4-yl)methanamine hydrochloride Prepared by Method B. ESMS(M+1)=257.17.

B-60. (1-((2-(Trifluoromethyl)pyridin-3-yl)methyl)-1H-pyrazol-4-yl)methanamine hydrochloride Prepared by Method B. ESMS(M+1)=257.12.

B-61. (1-((6-(Trifluoromethyl)pyridin-2-yl)methyl)-1H-pyrazol-4-yl)methanamine hydrochloride Prepared by Method B. 1H NMR-1H NMR (400 MHz, Methanol-d4) δ 8.00 (t, J=7.9 Hz, 1H), 7.94 (s, 1H), 7.74 (d, J=7.8 Hz, 1H), 7.65 (s, 1H), 7.39 (d, J=7.9 Hz, 1H), 5.54 (s, 2H), 4.06 (s, 2H). ESMS(M+1)=257.12.

B-62. (1-((3-(Trifluoromethyl)pyridin-4-yl)methyl)-1H-pyrazol-4-yl)methanamine hydrochloride Prepared by Method B. 1H NMR-1H NMR (400 MHz, Methanol-d4) δ 8.91 (s, 1H), 8.70 (d, J=5.2 Hz, 1H), 7.93 (s, 1H), 7.72 (s, 1H), 6.81 (d, J=5.1 Hz, 1H), 5.67 (s, 2H), 4.09 (s, 2H). ESMS(M+1)=257.21.

B-63. (1-((2-Methyl-6-(trifluoromethyl)pyridin-3-yl)methyl)-1H-pyrazol-4-yl)methanamine hydrochloride Prepared by Method B. ESMS(M+1)=271.22.

B-64. (1-((6-Methoxypyridin-3-yl)methyl)-1H-pyrazol-4-yl)methanamine hydrochloride Prepared by Method B. 1H NMR (300 MHz, Methanol-d4) δ 8.18-8.00 (m, 1H), 7.83 (d, J=2.3 Hz, 1H), 7.61 (q, J=4.7, 2.9 Hz, 2H), 6.84-6.66 (m, 1H), 5.30 (d, J=2.7 Hz, 2H), 4.13-3.96 (m, 2H), 3.89 (d, J=2.8 Hz, 3H). ESMS(M+1)=219.25.

B-65. (1-(Tetrahydro-2H-pyran-4-yl)-1H-pyrazol-4-yl)methanamine

Prepared by Method C. 1H NMR (300 MHz, Methanol-d4) δ 7.60 (s, 1H), 7.50 (s, 1H), 4.45-4.30 (m, 1H), 4.10 (d, J=12 Hz, 2H), 3.80 (s, 2H), 3.65-3.50 (m, 2H), 2.10-1.90 (m, 4H). ESMS(M+1)=182.61.

B-66. (1-((5-Methyl-6-(trifluoromethyl)pyridin-3-yl)methyl)-1H-pyrazol-4-yl)methanamine hydrochloride Prepared by Method B. 1H NMR (300 MHz, DMSO-d6) δ 8.42 (d, J=2.0 Hz, 1H), 8.01-7.91 (m, 4H), 7.82-7.74 (m, 1H), 7.58 (d, J=0.8 Hz, 1H), 5.48 (s, 2H), 3.91 (q, J=5.6 Hz, 2H), 2.89 (s, 3H). ESMS(M+1)=271.18.

B-67. (1-((6-Chloropyridin-3-yl)methyl)-1H-pyrazol-4-yl)methanamine hydrochloride Prepared by Method B. 1H NMR (300 MHz, Methanol-d4) δ 8.37 (d, J=3.1 Hz, 1H), 8.02 (s, 1H), 7.90-7.77 (m, 1H), 7.77-7.64 (m, 1H), 7.52 (dt, J=8.4, 2.2 Hz, 1H), 5.48 (t, J=3.2 Hz, 2H), 4.07 (d, J=3.3 Hz, 2H). ESMS(M+1)=223.16.

B-68. (1-((5-(Trifluoromethyl)pyridin-2-yl)methyl)-1H-pyrazol-4-yl)methanamine hydrochloride Prepared by Method B. 1H NMR (400 MHz, Methanol-d4) δ 8.83 (s, 1H), 8.10 (dd, J=8.2, 2.3 Hz, 1H), 7.94 (s, 1H), 7.65 (s, 1H), 7.35 (d, J=8.3 Hz, 1H), 5.56 (s, 2H), 4.06 (s, 2H). ESMS(M+1)=257.21.

B-69. (1-((4-(Trifluoromethyl)pyridin-2-yl)methyl)-1H-pyrazol-4-yl)methanamine hydrochloride Prepared by Method B. 1H NMR-1H NMR (400 MHz, Methanol-d4) δ 8.77 (d, J=5.1 Hz, 1H), 7.94 (s, 1H), 7.66 (s, 1H), 7.63 (d, J=5.1 Hz, 1H), 7.46 (s, 1H), 5.57 (s, 2H), 4.06 (s, 2H). ESMS(M+1)=257.21.

B-70. (1-((5-(Trifluoromethyl)pyridin-3-yl)methyl)-1H-pyrazol-4-yl)methanamine hydrochloride Prepared by Method B. 1H NMR (300 MHz, Methanol-d4) δ 8.95 (s, 1H), 8.80 (d, J=2.5 Hz, 1H), 8.18 (s, 1H), 7.98 (s, 1H), 7.68 (d, J=2.0 Hz, 1H), 5.57 (s, 2H), 4.06 (s, 2H). ESMS(M+1)=257.13.

B-71. (1-((2-(Trifluoromethyl)pyridin-4-yl)methyl)-1H-pyrazol-4-yl)methanamine hydrochloride Prepared by Method B. 1H NMR (400 MHz, DMSO-d6) 1H NMR (400 MHz, DMSO-d6) δ 3.88-3.92 (m, 2H), 5.57 (s, 2H), 3.90 (s, 2H), 7.43 (d, J=4.4 Hz, 1H), 7.68 (s, 1H), 7.72 (s, 1H), 8.04 (s, 1H), 8.39 (bs, 3H), 8.74 (d, J=4.8 Hz, 1H). ESMS(M+1)=256.92.

B-72. (1-((4-Methoxy-6-(trifluoromethyl)pyridin-3-yl)methyl)-1H-pyrazol-4-yl)methanamine hydrochloride Prepared by Method B. 1H NMR (300 MHz, Methanol-d4) δ 8.21 (s, 1H), 7.89 (s, 1H), 7.63 (s, 1H), 7.51 (s, 1H), 5.44 (s, 2H), 5.44 (s, 2H), 4.04 (s, 5H). ESMS(M+1)=287.45.

B-73. (1-((6-(tert-Butyl)pyridin-3-yl)methyl)-1H-pyrazol-4-yl)methanamine hydrochloride Prepared by Method B. 1H NMR (300 MHz, DMSO-d6) δ 8.53-8.45 (m, 1H), 7.95 (br, 3H), 7.90 (d, J=0.8 Hz, 1H), 7.77-7.63 (m, 1H), 7.55 (d, J=0.8 Hz, 1H), 7.50 (dd, J=8.3, 0.9 Hz, 1H), 5.38 (s, 2H), 3.90 (q, J=5.7 Hz, 2H), 1.30 (s, 9H). ESMS(M+1)=245.24.

B-74. (1-((5-Fluoro-6-(trifluoromethyl)pyridin-3-yl)methyl)-1H-pyrazol-4-yl)methanamine hydrochloride Prepared by Method B. ESMS(M+1)=275.19.

B-75. (1-((2-Methoxy-6-(trifluoromethyl)pyridin-3-yl)methyl)-1H-pyrazol-4-yl)methanamine hydrochloride Prepared by Method B. 1H NMR (300 MHz, Methanol-d4) δ 7.91 (s, 1H), 7.67 (s, 1H), 7.53 (d, J=7.4 Hz, 1H), 7.35 (d, J=7.6 Hz, 1H), 5.42 (s, 2H), 4.20-3.81 (m, 5H). ESMS(M+1)=287.36.

B-76. (1-((6-Methoxy-5-(trifluoromethyl)pyridin-3-yl)methyl)-1H-pyrazol-4-yl)methanamine hydrochloride Prepared by Method B. 1H NMR (300 MHz, Methanol-d4) δ 8.34 (s, 1H), 7.92 (s, 1H), 7.87 (d, J=2.6 Hz, 1H), 7.62 (d, J=2.7 Hz, 1H), 5.36 (d, J=2.7 Hz, 2H), 4.13-3.80 (m, 5H). ESMS(M+1)=287.21.

B-77. (1-((5-Methoxy-6-(trifluoromethyl)pyridin-3-yl)methyl)-1H-pyrazol-4-yl)methanamine hydrochloride Prepared by Method B. 1H NMR (300 MHz, Methanol-d4) δ 8.10 (s, 1H), 7.99 (s, 1H), 7.72 (d, J=11.2 Hz, 2H), 5.65-5.43 (m, 2H), 4.12 (s, 2H), 4.02 (d, J=1.6 Hz, 2H). ESMS(M+1)=287.11.

B-78. (1-((5-Fluoropyridin-3-yl)methyl)-1H-pyrazol-4-yl)methanamine hydrochloride Prepared by Method B. ESMS(M+1)=207.13.

B-79. (1-((6-Fluoro-4-methylpyridin-3-yl)methyl)-1H-pyrazol-4-yl)methanamine hydrochloride Prepared by Method B. 1H NMR (300 MHz, Methanol-d4) δ 7.87 (s, 1H), 7.78-7.72 (m, 1H), 7.63-7.53 (m, 1H), 6.93 (d, J=1.4 Hz, 1H), 5.38 (s, 2H), 3.99 (s, 2H), 2.32 (d, J=0.8 Hz, 3H). ESMS(M+1)=221.18

B-80. (1-(2,4,6-trifluorobenzyl)-1H-pyrazol-4-yl)methanamine hydrochloride

Prepared by Method B. 1H NMR (300 MHz, Methanol-d4) δ 7.83 (s, 1H), 7.56 (d, J=0.7 Hz, 1H), 6.95 (dd, J=9.0, 7.7 Hz, 2H), 5.40 (d, J=1.2 Hz, 2H), 4.01 (s, 2H); ESMS(M+1)=242.13.

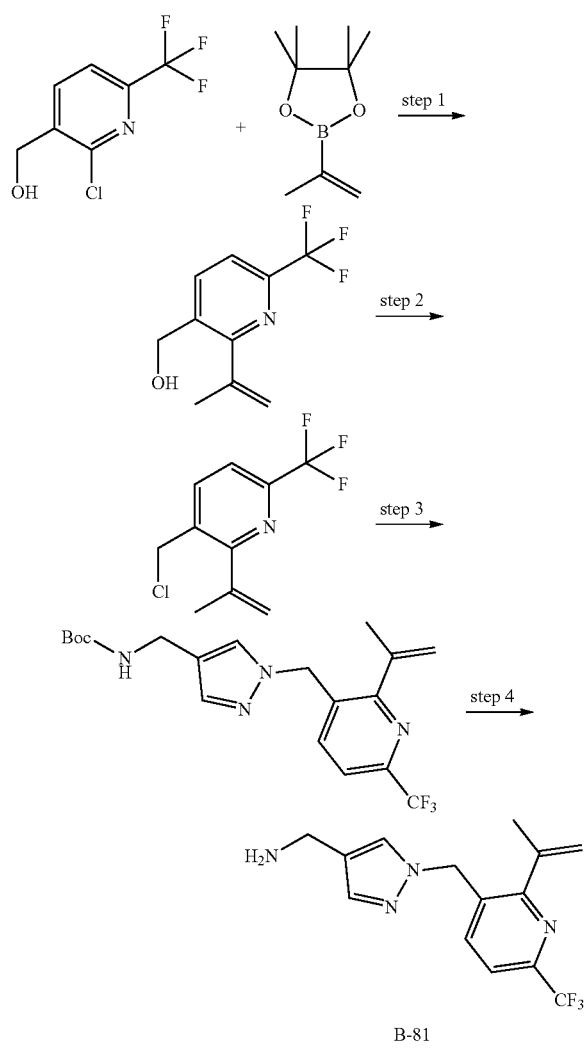

B-81. (1-((2-(prop-1-en-2-yl)-6-(trifluoromethyl) pyridin-3-yl)methyl)-1H-pyrazol-4-yl)methanamine hydrochloride Step 1: (2-(Prop-1-en-2-yl)-6-(trifluoromethyl)pyridin-3-yl)methanol A mixture of (2-bromo-6-(trifluoromethyl)pyridin-3-yl)methanol (3.06 g, 11.95 mmol), 2-isopropenyl-4,4,5,5-tetramethyl-1,3,2-dioxaborolane (3.4 mL,), and NaHCO₃ (2.01 g, 23.93 mmol) was taken into DME (60 mL) and water (20 mL) and purged with nitrogen for 10 minutes. Pd(dppf)Cl₂ (490 mg, 0.6000 mmol) was added to the mixture then heated to reflux for 2 hours. The solvent was removed in vacuo, 100 ml of ethyl acetate was added and washed with saturated sodium bicarbonate. The organic layer was dried over anhydrous sodium sulfate, filtered, and evaporated to afford the crude product that was purified by column chromatography (SiO₂, 80 g) eluting with a gradient of heptane to 60% ethyl acetate/heptane. The desired fractions were combined and evaporated in vacuo to afford the product as a clear colorless oil (2.2 g, 85% yield). 1H NMR (300 MHz, CDCl₃) δ 8.09 (d, J=8.0 Hz, 1H), 7.62 (d, J=8.0 Hz, 1H), 5.54-5.42 (m, 1H), 5.09 (s, 1H), 4.86 (d, J=5.4 Hz, 2H), 2.20 (d, J=1.0 Hz, 3H), 1.93 (t, J=5.6 Hz, 1H). ESI-MS m/z calc. 217.07144, found 218.13 (M+1).

Step 2: 3-(Chloromethyl)-2-isopropenyl-6-(trifluoromethyl)pyridine

Thionyl chloride (1.5 ml, 20.6 mmol) was added to a solution of (2-(Prop-1-en-2-yl)-6-(trifluoromethyl)pyridin-3-yl)methanol (2.2 g, 10.13 mmol) in dichloromethane (18 mL) and stirred at room temperature for 3 h. The reaction was evaporated in vacuo to afford a yellow oil. The oil was taken into 80 ml of dichloromethane and washed with 40 ml of saturated sodium bicarbonate. The organic layer was dried over anhydrous sodium sulfate, filtered, and evaporated in vacuo to afford the title product as a light yellow oil (2.3 g, 96% yield) that was used directly in Step 3. 1H NMR (300 MHz, CDCl₃) δ 8.02 (d, J=8.0 Hz, 1H), 7.61 (d, J=8.1 Hz, 1H), 5.59-5.47 (m, 1H), 5.28-5.16 (m, 1H), 4.74 (s, 2H), 2.30-2.13 (m, 3H). ESI-MS m/z calc. 235.03757, found 236.13 (M+1)+.

Step 3: tert-Butyl ((1-((2-(prop-1-en-2-yl)-6-(trifluoromethyl)pyridin-3-yl)methyl)-1H-pyrazol-4-yl) methyl)carbamate tert-Butyl ((1H-pyrazol-4-yl)methyl)carbamate (1.85 g, 9.380 mmol) and 3-(chloromethyl)-2-isopropenyl-6-(trifluoromethyl)pyridine (2.30 g, 9.761 mmol) was taken into anhydrous DMF (20 mL) and cooled to 0° C. Sodium hydride (434 mg, 10.85 mmol) was added to the mixture portionwise and stirred overnight at room temperature. The reaction was quenched with the addition of water (80 mL) and an oil crashed out. The mixture was extracted with ethyl acetate (2×50 ml). The organic extracts were combined, dried over anhydrous sodium sulfate, filtered, and evaporated in vacuo to afford the crude product. The crude product was purified by column chromatography (SiO2, 80 g) eluting with a gradient of heptane to 100% ethyl acetate. The desired fractions were combined and evaporated to afford the desired product as a viscous oil that solidified to a white solid (3.7 g, 100% yield). 1H NMR (300 MHz, CDCl₃) δ 7.57-7.48 (m, 2H), 7.45 (d, J=8.1 Hz, 1H), 7.38 (s, 1H), 5.59-5.50 (m, 1H), 5.43 (s, 2H), 5.08 (d, J=0.9 Hz, 1H), 4.74 (s, 1H), 4.19 (d, J=6.0 Hz, 2H), 2.23-2.13 (m, 3H), 1.46 (s, 9H). ESI-MS m/z calc. 396.1773, found 397.24 (M+1)+;

Step 4: (1-((2-(prop-1-en-2-yl)-6-(trifluoromethyl) pyridin-3-yl)methyl)-1H-pyrazol-4-yl)methanamine tert-Butyl ((1-((2-(prop-1-en-2-yl)-6-(trifluoromethyl) pyridin-3-yl)methyl)-1H-pyrazol-4-yl)methyl)carbamate 2 g, 5.04 mmol) was taken into dichloromethane (20 ml) and TFA (4 ml, 3.9 mmol) and stirred at room temperature for 4 hours. The solvent was removed in vacuo and the residue was washed with hexanes, filtered, and dried to afford the title product (1.4 g, 90% yield). 1H NMR (300 MHz, DMSO-d6) δ 8.17 (br, 3H), 7.92 (s, 1H), 7.80 (d, J=8.1 Hz, 1H), 7.61 (s, 1H), 7.57 (d, J=8.1 Hz, 1H), 5.55 (s, 2H), 5.54 (s, 1H), 5.19 (s, 1H), 3.90 (q, J=5.7 Hz, 2H), 2.09 (s, 3H). ESI-MS m/z calc. 296.12488, found 297.2 (M+1)+

B-82. (3,5-dimethyl-1-((6-(trifluoromethyl)pyridin-3-yl)methyl)-1H-pyrazol-4-yl)methanamine hydrochloride Prepared by Method B. ESMS(M+1)=285.21.

B-83. (1-((6-(2,2,2-Trifluoroethoxy)pyridin-3-yl)methyl)-1H-pyrazol-4-yl)methanamine trifluoroacetic Acid Prepared by Method B. 1H NMR (300 MHz, DMSO-d6) δ 8.17 (d, J=2.4 Hz, 1H), 7.93 (t, J=6.3 Hz, 3H), 7.88 (s, 1H), 7.72 (dd, J=8.5, 2.4 Hz, 1H), 7.54 (s, 1H), 6.99 (d, J=8.5 Hz, 1H), 5.33 (s, 2H), 4.98 (q, J=9.1 Hz, 2H), 3.89 (q, J=5.7 Hz, 2H); ESMS(M+1)=287.24

B-84. (1-((6-Fluoro-5-methoxypyridin-3-yl)methyl)-1H-pyrazol-4-yl)methanamine hydrochloride Prepared by Method B. 1H NMR (300 MHz, Methanol-d4) δ 7.92 (d, J=2.4 Hz, 1H), 7.77-7.60 (m, 2H), 7.62-7.49 (m, 1H), 5.42 (d, J=2.4 Hz, 2H), 4.09 (s, 2H), 3.94 (t, J=2.4 Hz, 3H). ESMS(M+1)=237.50.

B-85. (1-((3,5-Dimethylisoxazol-4-yl)methyl)-1H-pyrazol-4-yl)methanamine hydrochloride Prepared by Method B. 1H NMR (400 MHz, Methanol-d4) δ 7.79 (s, 1H), 7.59 (s, 1H), 5.17 (s, 2H), 4.02 (s, 2H), 3.66 (s, 1H), 2.42 (s, 3H), 2.16 (s, 3H);

B-86. (1-((1,3-Dimethyl-1H-pyrazol-4-yl)methyl)-1H-pyrazol-4-yl)methanamine hydrochloride Prepared by Method B. 1H NMR (300 MHz, Methanol-d4) δ 7.99 (s, 1H), 7.87 (s, 1H), 7.61 (s, 1H), 5.28 (s, 2H), 4.03 (s, 2H), 3.98 (s, 3H), 2.34 (s, 3H).

B-87. (1-((3-Ethyl-5-methylisoxazol-4-yl)methyl)-1H-pyrazol-4-yl)methanamine hydrochloride Prepared by Method B. 1H NMR (300 MHz, CDCl₃) δ 7.42 (s, 1H), 7.22 (s, 1H), 5.01 (s, 2H), 4.66 (s, 1H), 4.12 (d, J=5.5 Hz, 2H), 2.94 (s, 1H), 2.87 (d, J=0.5 Hz, 1H), 2.55 (q, J=7.5 Hz, 2H), 2.39 (s, 3H), 1.43 (s, 9H), 1.18 (t, J=7.6 Hz, 3H).

B-88. (1-((1-Methyl-3-(trifluoromethyl)-1H-pyrazol-4-yl)methyl)-1H-pyrazol-4-yl)methanamine hydrochloride Prepared by Method B. 1H NMR (400 MHz, Methanol-d4) δ 7.76 (s, 1H), 7.73 (s, 1H), 7.61 (s, 1H), 5.31 (s, 2H), 4.02 (s, 2H), 3.92 (s, 3H). ESMS(M+1)=261.07.

B-89. (1-((1-Methyl-3-(trifluoromethyl)-1H-pyrazol-5-yl)methyl)-1H-pyrazol-4-yl)methanamine hydrochloride Prepared by Method B. 1H NMR (400 MHz, Methanol-d4) δ 7.87 (s, 1H), 7.63 (s, 1H), 6.56 (s, 1H), 5.52 (s, 2H), 4.04 (s, 2H), 3.92 (s, 3H); ESMS(M+1)=261.15.

B-90. (1-((1-Ethyl-3-(trifluoromethyl)-1H-pyrazol-5-yl)methyl)-1H-pyrazol-4-yl)methanamine hydrochloride Prepared by Method B. 1H NMR (400 MHz, Methanol-d4) δ 7.84 (s, 1H), 7.61 (s, 1H), 6.63 (s, 1H), 5.35 (s, 2H), 4.26 (q, J=7.2 Hz, 2H), 4.03 (s, 2H), 1.43 (t, J=7.2 Hz, 3H).

B-91. (1-((1-Methyl-5-(trifluoromethyl)-1H-pyrazol-3-yl)methyl)-1H-pyrazol-4-yl)methanamine hydrochloride Prepared by Method B. 1H NMR (400 MHz, Methanol-d4) δ 7.87 (s, 1H), 7.64 (s, 1H), 6.67 (s, 1H), 5.35 (s, 2H), 4.04 (s, 2H), 3.95 (d, J=0.6 Hz, 3H).

B-92. (1-((1-Ethyl-1H-imidazol-2-yl)methyl)-1H-pyrazol-4-yl)methanamine hydrochloride Prepared by Method B. 1H NMR (400 MHz, Methanol-d4) δ 8.10 (s, 1H), 7.72 (d, J=2.1 Hz, 1H), 7.67 (s, 1H), 7.61 (d, J=2.1 Hz, 1H), 5.83 (s, 2H), 4.33 (q, J=7.3 Hz, 2H), 4.07 (s, 2H), 1.39 (t, J=7.3 Hz, 3H); ESMS(M+1)=206.14.

B-93. (1-((5-(Trifluoromethyl)furan-2-yl)methyl)-1H-pyrazol-4-yl)methanamine hydrochloride Prepared by Method B. 1H NMR (400 MHz, Methanol-d4) δ 7.90 (s, 1H), 7.64 (s, 1H), 6.95 (dd, J=3.4, 1.1 Hz, 1H), 6.66-6.54 (m, 1H), 5.44 (s, 2H), 4.04 (s, 2H). ESMS(M+1)=246.04.

B-94. (1-((2,5-Dimethyloxazol-4-yl)methyl)-1H-pyrazol-4-yl)methanamine hydrochloride Prepared by Method B. 1H NMR (400 MHz, Methanol-d4) δ 7.89 (s, 1H), 7.65 (s, 1H), 5.29 (s, 2H), 4.04 (s, 2H), 2.53 (s, 3H), 2.39 (s, 3H).

B-95 (1-(2-phenylpropyl)-1H-pyrazol-4-yl)methanamine hydrochloride

Prepared by Method A. ESMS(M+1)=216.20.

B-96. (1-(2-(4-fluorophenyl)propyl)-1H-pyrazol-4-yl)methanamine hydrochloride Prepared by Method A. ESMS(M+1)=233.13.

B-97. (1-(1-phenylpropan-2-yl)-1H-pyrazol-4-yl)methanamine hydrochloride

Prepared by Method A. ESMS(M+1)=216.24.

Scheme E

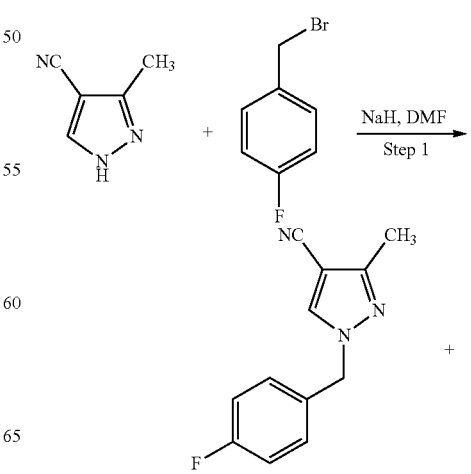

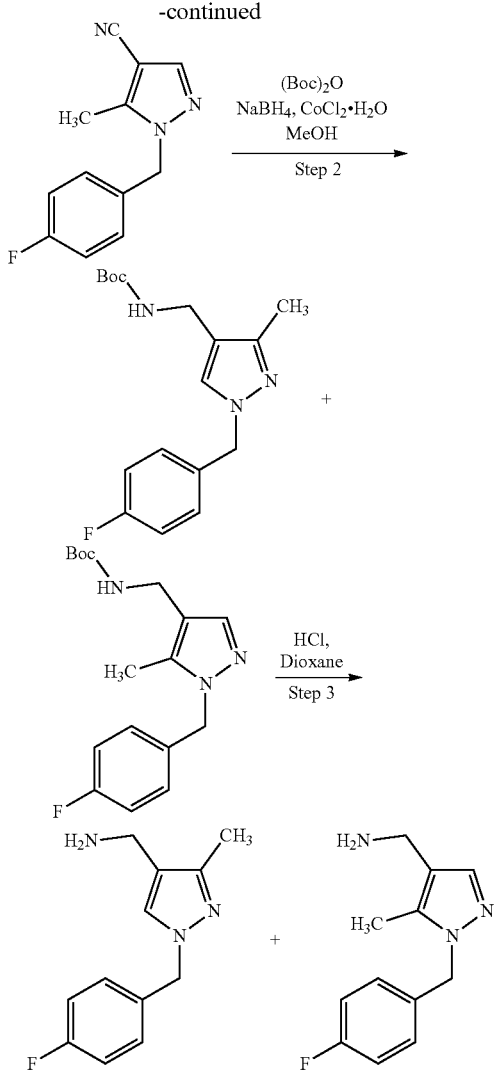

B-98. (1-(4-fluorobenzyl)-3-methyl-1H-pyrazol-4-yl)methanamine hydrochloride and (1-(4-fluorobenzyl)-5-methyl-1H-pyrazol-4-yl)methanamine hydrochloride Step 1: 1-(4-fluorobenzyl)-3-methyl-1H-pyrazole-4-carbonitrile and 1-(4-fluorobenzyl)-5-methyl-1H-pyrazole-4-carbonitrile 3-Cyano-2-methylpyrazole and 1-(bromomethyl)-4-fluorobenzene (964.0 mg, 5.100 mmol) was taken into DMF (5 ml) and cooled to 0° C. Sodium hydride (240.0 mg, 6.000 mmol) was added to the reaction portionwise. The reaction was warmed to room temperature and stirred for 12 hrs. (Observed two regioisomers by LC/MS). The reaction was quenched with saturated NH₄Cl (10 mL) and extracted with ethyl acetate (3×20 mL). The combined extracts were washed with brine, dried over MgSO₄ and concentrated to give crude mixture which was purified by column chromatography (SiO₂) eluting with a gradient of 0-50% ethyl acetate in hexane to provide inseparable regioisomers. ESMS(M+1)=216.14.

Step 2: tert-butyl ((1-(4-fluorobenzyl)-3-methyl-1H-pyrazol-4-yl)methyl)carbamate and tert-butyl ((1-(4-fluorobenzyl)-5-methyl-1H-pyrazol-4-yl)methyl) carbamate The mixture of regioisomers from Step 1 (1-(4-fluorobenzyl)-3-methyl-1H-pyrazole-4-carbonitrile and 1-(4-fluorobenzyl)-5-methyl-1H-pyrazole-4-carbonitrile (430.5 mg, 2.000 mmol), Boc₂O (525 mg, 2.400 mmol), and dichlorocobalt hexahydrate (235.6 mg, 0.99 mmol) were taken into MeOH (5 mL) and cooled to 0° C. Sodium borohydride (940 mg, 1 mL, 24.8 mmol) was added to the mixture portion wise (the reaction turned black) and stirred for 1 hour. The reaction was evaporated in vacuo to afford a black solid. This was suspended in ethyl acetate (30 mL) and H₂O (15 mL). The organic layer was collected and filtered to remove remaining solids. The filtrate was washed with brine and dried over MgSO₄ to provide the crude product that was purified by column chromatography (SiO₂) eluting with a gradient of 0-50% ethyl acetate in hexane to give two peaks. The top spot was minor and the bottom spot was major. By HNMR and TLC, both spot were not separated cleanly so combined for next step (ratio: 1:2.3).

Top spot (ratio 1:1.3): ¹H NMR (400 MHz, CDCl₃) δ 7.30 (d, J=69.7 Hz, 1H), 7.18-7.00 (m, 2H), 29.9 Hz, 2H), 6.96 (td, J=8.7, 6.6 Hz, 2H), 5.14 (d, J=4.53 (m, 1H), 4.92-(d, J=23.8 Hz, 3H), 4.07 (t, J=4.9 Hz, 2H), 2.16 (d, J=23.8 Hz, 3H), 1.41 (d, J=3.1 Hz, 9H).

Bottom Spot (ratio 1:3): NMR (400 MHz, CDCl₃) δ 7.23 (s, 1H), 7.17 (ddd, J=8.1, 5.2, 2.5 Hz, 2H), 7.05-6.94 (m, 2H), 5.26-5.06 (m, 2H), 4.65 (s, 1H), 4.10 (d, J=5.1 Hz, 2H), 2.28-2.09 (m, 3H), 1.44 (q, J=2.5, 2.1 Hz, 10H). ESMS(M+1)=320.09.

Step 3: (1-(4-fluorobenzyl)-3-methyl-1H-pyrazol-4-yl)methanamine hydrochloride and (1-(4-fluorobenzyl)-5-methyl-1H-pyrazol-4-yl)methanamine hydrochloride The mixture of regioisomers from Step 2 (1 g, 3.26 mmol) were taken into 1,4-dioxane (2 mL). A solution of 4 M HCl (4 mL, 16 mmol) in dioxane was added to the solution and stirred at room temperature for 3 hours. Diethyl ether (10 mL) was added to the solution and a yellow precipitate formed. This was collected and dried to provide a mixture of regioisomers that were not separable. ¹H NMR (400 MHz, Methanol-d4) δ 8.77 (s, 1H), 8.60-8.28 (m, 1H), 8.11 (td, J=5.9, 2.8 Hz, 1H), 7.95 (dddt, J=13.5, 8.7, 6.5, 2.6 Hz, 2H), 6.05 (dt, J=27.0, 2.4 Hz, 2H), 4.63 (dq, J=5.2, 2.7 Hz, 2H), 4.06-3.86 (m, 2H), 3.00 (dt, J=22.3, 1.8 Hz, 3H). ESMS (M+1)=220.11.

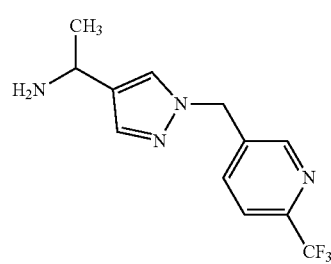

(B-99)

B-99. 1-(1-((6-(trifluoromethyl)pyridin-3-yl)methyl)-1H-pyrazol-4-yl)ethan-1-amine

Step 1. 1-(1-((6-(trifluoromethyl)pyridin-3-yl)methyl)-1H-pyrazol-4-yl)ethan-1-one Sodium hydride (60% oil dispersion; 800 mg, 20 mmol) was added to a cooled (0° C.) solution of 1-(1H-pyrazol-4-yl)ethanone (2 g, 18.2 mmol) in DMF (20 ml) and stirred for 1 hour at 0° C. 5-(Chloromethyl)-2-(trifluoromethyl)pyridine (3.91 g, 20 mmol) was added to the reaction and allowed to warm to room temperature overnight. The reaction mixture was poured into ice water and extracted with ethyl acetate (3×75 ml). The combined organic extracts were dried over magnesium sulfate, filtered, and evaporated in vacuo. The crude product was purified by column chromatography (SiO$_2$) eluting with a gradient of 0-5% methanol in dichloromethane. The desired fractions were evaporated to afford the title product as a yellow solid. ESMS(M+1)= 270.14.

Step 2. 1-(1-((6-(trifluoromethyl)pyridin-3-yl)methyl)-1H-pyrazol-4-yl)ethan-1-ol Sodium borohydride (565 mg, 14.9 mmol) was added to a solution of 1-(1-((6-(trifluoromethyl)pyridin-3-yl)methyl)-1H-pyrazol-4-yl)ethan-1-one (4 g, 14.86 mmol) in methanol (100 ml) and stirred for 30 minutes at room temperature. The reaction was quenched by the addition of water and 1 N HCl. The organics were evaporated in vacuo, water (50 ml) added to the solution and extracted with ethyl acetate (3×75 ml). The combined organic extracts were dried over magnesium sulfate, filtered, and evaporated in vacuo to afford the crude product that was purified by column chromatography (SiO$_2$) eluting with a gradient of 0-20% methanol in dichloromethane. The desired fractions were combined to provide the title product as a yellow oil. 1H NMR (300 MHz, DMSO-d6) δ 8.73-8.60 (m, 1H), 7.98-7.83 (m, 2H), 7.75 (t, J=0.7 Hz, 1H), 7.41 (d, J=0.6 Hz, 1H), 5.45 (s, 2H), 4.92 (d, J=4.8 Hz, 1H), 4.68 (qd, J=6.4, 4.7 Hz, 1H), 1.32 (d, J=6.4 Hz, 3H). ESMS (M+1)=272.17.

Step 3. 5-((4-(1-Azidoethyl)-1H-pyrazol-1-yl)methyl)-2-(trifluoromethyl)pyridine A mixture of 1-(1-((6-(trifluoromethyl)pyridin-3-yl)methyl)-1H-pyrazol-4-yl)ethan-1-ol (3.9 g, 14.4 mmol) and diphenylphosphorylazide (5.94 g, 4.65 mmol) was taken into anhydrous THF (55 ml) under nitrogen and cooled to 0° C. DBU (3.2 ml, 21.6 mmol) was added to the mixture and stirred at 0° C. for 2 hours, then warmed to room temperature for 20 hours. The reaction was diluted with ethyl acetate (200 ml) and washed with water (2×50 ml) and 5% HCl (10 ml). The organic layer was dried over magnesium sulfate, filtered, and evaporated in vacuo. The crude was purified by column chromatography (SiO$_2$) eluting with a gradient of 10-30% ethyl acetate in hexanes. The desired fractions were combined and evaporated in vacuo to afford the title product (wt. 2.2 g, 51.6% yield) as a yellow oil that was used in the next step without further purification. ESMS (M+1)=297.17.

Step 4. 1-(1-((6-(trifluoromethyl)pyridin-3-yl)methyl)-1H-pyrazol-4-yl)ethan-1-amine hydrochloride To a solution of 5-[[4-(1-azidoethyl)pyrazol-1-yl]methyl]-2-(trifluoromethyl)pyridine (2.2 g, 7.426 mmol) in dichloromethane (20 mL) was added triphenylphosphine (2.9 g, 11.14 mmol) and water (7 mL) and the mixture was stirred at room temperature overnight. The reaction was not complete, so it was heated at 50° C. for 5 hours. The mixture was diluted with dichloromethane and washed with 1 N HCl (50 ml). The aqueous layer was collected and washed with dichloromethane. The aqueous layer was frozen and lyophilized to provide the title product, wt. 1.7 g (66.7% yield). 1H NMR (300 MHz, DMSO-d6) δ 8.66 (s, 1H), 8.30 (s, 3H), 8.02 (s, 1H), 7.92 (s, 2H), 7.65 (s, 1H), 5.53 (s, 2H), 4.58-4.24 (m, 1H), 1.49 (d, J=6.8 Hz, 3H). ESMS (M+1)= 271.18.

Scheme F

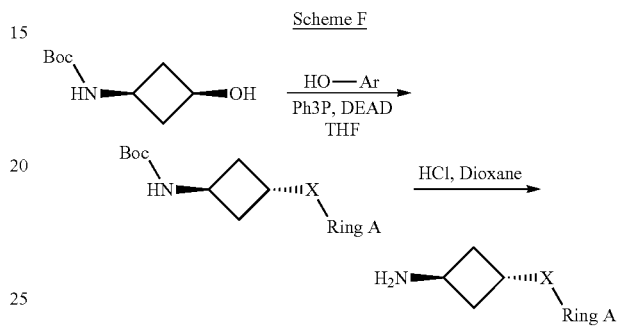

General Procedure for the Synthesis of the Intermediates in Table 1 (Prepared as in Scheme F)

B-101. trans-3-(3,4,5-Trifluorophenoxy)cyclobutan-1-amine hydrochloride

Step 1: tert-Butyl trans-3-(3,4,5-trifluorophenoxy)cyclobutyl)carbamate cis-tert-Butyl N-(3-hydroxycyclobutyl)carbamate (8.06 g, 43 mmol) and triphenylphosphine (12.42 g, 11 mL, 47.4 mmol) were taken into THF (120 mL) and cooled to 0° C. Diethylazodicarboxylate (DEAD) (20.62 g, 21.6 mL of 40% w/w, 47.4 mmol) was added to the solution followed by the addition of 3,4,5-trifluorophenol (7.01 g, 47.4 mmol). The reaction was stirred at room temperature for 1 hour then heated at 50° C. for 1 h. The solvent was removed and the reaction was dissolved in 100 ml of dichloromethane and washed twice with 2N sodium hydroxide. The organic layer was evaporated and the crude product purified by column chromatography (SiO$_2$) eluting with a gradient of 10-50% ethyl acetate in hexanes to provide 12.1 g (89% yield) of the desired product. 1H NMR (300 MHz, CDCl$_3$) δ 6.46-6.31 (m, 2H), 4.74 (d, J=10.4 Hz, 1H), 4.68 (td, J=6.9, 3.5 Hz, 1H), 4.30 (s, 1H), 2.55 (ddd, J=11.9, 8.2, 3.6 Hz, 2H), 2.41 (dd, J=12.7, 6.3 Hz, 2H), 1.47 (s, 9H).

Step 2: trans-3-(3,4,5-Trifluorophenoxy)cyclobutan-1-amine hydrochloride tert-Butyl trans-3-(3,4,5-trifluorophenoxy)cyclobutyl)carbamate (12.18 g, 38.39 mmol) was taken into 50 ml of methanol and 75 ml of a solution of 2M HCl in diethyl ether. The solution was heated at 50° C. for 40 mins. The solvent was evaporated in vacuo and the residue triturated with hexanes to give the product as a white solid, wt. 9.6 g (99% yield). 1H NMR (300 MHz, Methanol-d4) δ 6.72-6.53 (m, 2H), 4.97-4.89 (m, 1H), 4.06-3.88 (m, 1H), 2.77-2.49 (m, 4H). ESMS(M+1)=218.17.

All compounds in Table 1 were made via the same reaction procedure described above for B-101:

TABLE 1

| Intermediate | X-Ring A | NMR | ESMS(M + 1) |
| --- | --- | --- | --- |
| B-100 | 4-fluorophenoxy | 1H NMR (300 MHz, CD$_3$OD) δ 7.01 (t, J = 8.4 Hz, 2H), 6.81 (dd, J = 8.4, 4.0 Hz, 2H), 4.94 (s, 1H), 3.99 (s, 1H), 2.83-2.48 (m, 4H). | 181.6 |
| B-101 | 3,4,5-trifluorophenoxy | 1H NMR (300 MHz, CD$_3$OD) δ 6.72-6.53 (m, 2H), 4.97-4.89 (m, 1H), 4.06-3.88 (m, 1H), 2.77-2.49 (m, 4H). | 216.37 |
| B-102 | 3,4-difluorophenoxy | 1H NMR (300 MHz, CD$_3$OD) δ 7.17 (dd, J = 19.5, 9.2 Hz, 1H), 6.76 (ddd, J = 12.2, 6.6, 3.0 Hz, 1H), 6.66-6.54 (m, 1H), 4.93 (dd, J = 6.8, 4.2 Hz, 1H), 3.98 (tt, J = 8.3, 6.0 Hz, 1H), 2.78-2.45 (m, 4H). | 200.29 |
| B-103 | 5-fluoropyridin-3-yloxy | 1H NMR (300 MHz, CD$_3$OD) δ 8.65 (d, J = 1.8 Hz, 1H), 8.52 (d, J = 2.1 Hz, 1H), 8.15-8.05 (m, 1H), 5.33-5.21 (m, 1H), 4.17-3.96 (m, 1H), 2.86 (dt, J = 12.9, 6.5 Hz, 2H), 2.80-2.63 (m, 2H). | 183.13 |
| B-104 | 2,6-difluoro-4-methoxyphenoxy | 1H NMR (300 MHz, CD$_3$OD) δ 6.59-6.42 (m, 2H), 3.99 (dd, J = 14.1, 6.3 Hz, 1H), 3.85 (s, 3H), 3.30 (d, J = 1.6 Hz, 1H), 2.73-2.53 (m, 4H). | |
| B-105 | 5-fluoropyrimidin-2-yloxy | 1H NMR (300 MHz, CD$_3$OD) □ 8.54 (d, J = 0.7 Hz, 1H), 8.33 (d, J = 0.6 Hz, 1H), 5.25 (dtd, J = 86.9, 6.7, 4.0 Hz, 1H), 4.08-3.91 (m, 1H), 2.79-2.56 (m, 4H). | 183.18 |
| B-106 | 2,3,4-trifluorophenoxy | 1H NMR (300 MHz, CDCl$_3$) δ 8.29 (s, 3H), 7.34-7.16 (m, 1H), 6.80 (tdd, J = 9.5, 4.7, 2.6 Hz, 1H), 5.07 (s, 1H), 3.85 (s, 1H), 2.61 (dd, J = 12.7, 6.1 Hz, 2H), 2.45 (dd, J = 9.0, 5.0 Hz, 2H). | 218.33 |
| B-107 | 2,4,5-trifluorophenoxy | 1H NMR (300 MHz, DMSO-d6) δ 8.40 (s, 3H), 7.62 (td, J = 10.9, 7.8 Hz, 1H), 7.15 (dt, J = 12.1, 7.9 Hz, 1H), 5.12-4.95 (m, 1H), 3.84 (s, 1H), 2.75-2.57 (m, 2H), 2.49-2.34 (m, 2H). | 218.33 |

TABLE 1-continued

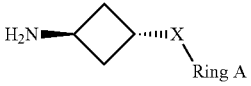

| Intermediate | Ring A X | NMR | ESMS(M + 1) |
|---|---|---|---|
| B-108 | 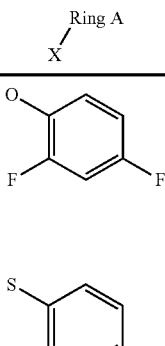 | 1H NMR (300 MHz, DMSO-d6) δ 8.31 (s, 3H), 7.31 (ddd, J = 11.8, 8.9, 2.8 Hz, 1H), 7.11-6.89 (m, 2H), 5.01 (t, J = 7.8 Hz, 1H), 3.93-3.76 (m, 1H), 2.71-2.54 (m, 2H), 2.48-2.33 (m, 2H). | 200.06 |
| B-109 | 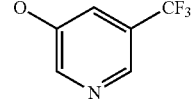 | 1H NMR (400 MHz CD3OD) δ 7.41-7.28 (m, 2H), 7.14-7.01 (m, 2H), 4.16-3.86 (m, 2H), 2.77-2.62 (m, 2H), 2.38 (ddd, J = 14.3, 8.0, 4.3 Hz, 2H). | 198.05 |
| B-110 | 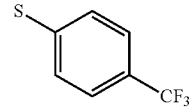 | 1H NMR (400 MHz, CD3OD) δ 8.76 (d, J = 39.6 Hz, 1H), 8.70 (s, 1H), 8.11 (s, 1H), 5.26 (s, 1H), 4.14-3.97 (m, 1H), 2.88-2.56 (m, 4H). | 233.03 |
| B-111 | 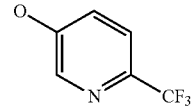 | 1H NMR (400 MHz, CD3OD) δ 7.58 (d, J = 8.2 Hz, 2H), 7.37 (d, J = 8.2 Hz, 2H), 4.23 (tt, J = 8.3, 4.1 Hz, 1H), 4.05 (p, J = 7.5 Hz, 1H), 2.84 (ddd, J = 12.3, 8.6, 4.3 Hz, 2H), 2.44 (ddd, J = 14.5, 7.9, 3.9 Hz, 2H). | 247.97 |
| B-112 | 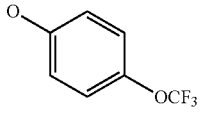 | 1H NMR (400 MHz, CD3OD) δ 8.30 (d, J = 2.5 Hz, 1H), 7.76 (d, J = 8.7 Hz, 1H), 7.42 (dd, J = 19.3, 12.4 Hz, 1H), 5.14 (s, 1H), 4.11-3.98 (m, 1H), 2.71 (tdd, J = 14.1, 11.0, 4.8 Hz, 4H). | 233.03 |
| B-113 | 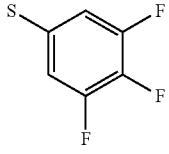 | 1H NMR (400 MHz, CD3OD) δ 7.20 (d, J = 9.0 Hz, 2H), 6.92-6.86 (m, 2H), 5.02-4.91 (m, 1H), 4.06-3.90 (m, 1H), 2.78-2.55 (m, 4H). | 248.02 |
| B-114 | 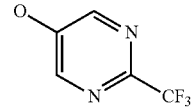 | 1H NMR (400 MHz, CD3OD) δ 7.11-6.95 (m, 2H), 4.82 (s, 5H), 4.15-4.04 (m, 1H), 4.00 (dd, J = 15.0, 7.4 Hz, 1H), 2.83-2.66 (m, 2H), 2.45-2.32 (m, 2H). | 234.1 |
| B-115 | 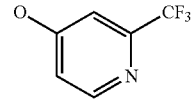 | 1H NMR (300 MHz, CD3OD) δ 8.54 (s, 2H), 5.16 (d, J = 25.9 Hz, 1H), 4.05 (s, 1H), 2.74 (s, 4H). | 234.12 |
| B-116 |  | 1H NMR (400 MHz, CD3OD) δ 8.70 (d, J = 5.4 Hz, 1H), 8.51 (s, 1H), 7.54 (s, 1H), 7.38 (d, J = 4.3 Hz, 1H), 5.38 (s, 1H), 4.12 (s, 1H), 3.02-2.84 (m, 2H), 2.84-2.66 (m, 2H) | 233.13 |

TABLE 1-continued
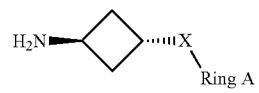
| Intermediate | Ring A<br>X | NMR | ESMS(M + 1) |
|---|---|---|---|
| B-117 | 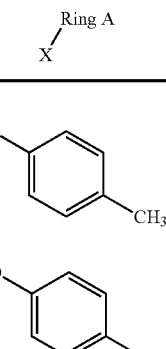 | | 178.16 |
| B-118 | 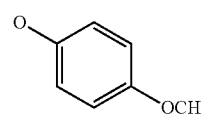 | | 232.13 |
| B-119 | 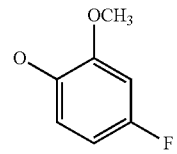 | | 194.04 |
| B-120 | 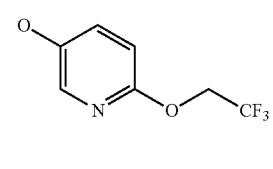 [SMILES: Oc1ccc(OCC(F)(F)F)nc1] | 1H NMR (400 MHz, CD$_3$OD) δ 6.86-6.72 (m, 2H), 6.58 (td, J = 8.5, 2.9 Hz, 1H), 4.99-4.89 (m, 1H), 4.07-3.93 (m, 1H), 3.83 (s, 3H), 3.03-2.24 (m, 4H). | 212.1 |
| B-121 | 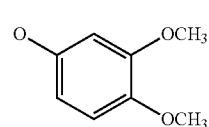 | 1H NMR (400 MHz, CD$_3$OD) δ 7.70 (d, J = 3.0 Hz, 1H), 7.33 (dd, J = 9.0, 3.0 Hz, 1H), 6.87 (dd, J = 9.0, 0.5 Hz, 1H), 5.02-4.90 (m, 1H), 4.77 (t, J = 8.8 Hz, 2H), 4.08-3.88 (m, 1H), 2.69-2.52 (m, 4H) | 263.11 |
| B-122 | 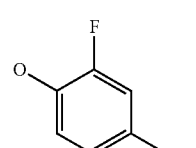 | | 224.17 |
| B-123 | 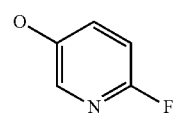 | | 212.15 |
| B-124 | 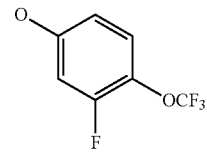 [SMILES: Oc1ccc(OC(F)(F)F)c(F)c1] | | 183.11 |
| B-125 |  | | 266.12 |

TABLE 1-continued

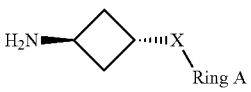

| Intermediate | Ring A X | NMR | ESMS(M + 1) |
|---|---|---|---|
| B-126 | 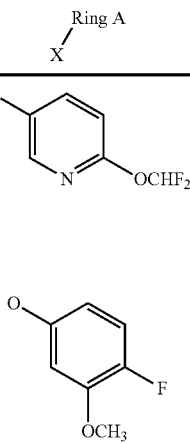 | 1H NMR (400 MHz, CD$_3$OD) δ 7.83 (d, J = 2.9 Hz, 1H), 7.49 (dd, J = 8.9, 2.9 Hz, 1H), 7.31 (t, J = 73.2 Hz, 1H), 7.02 (d, J = 8.9 Hz, 1H), 5.12-5.06 (m, 1H), 4.08-3.93 (m, 1H), 2.85-2.69 (m, 2H), 2.69-2.55 (m, 2H). | 231.14 |
| B-127 | 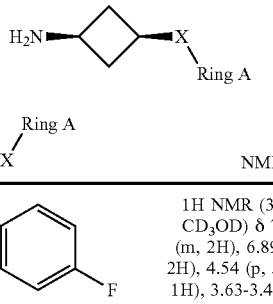 | Commercially available from ChemTek | |

Scheme G

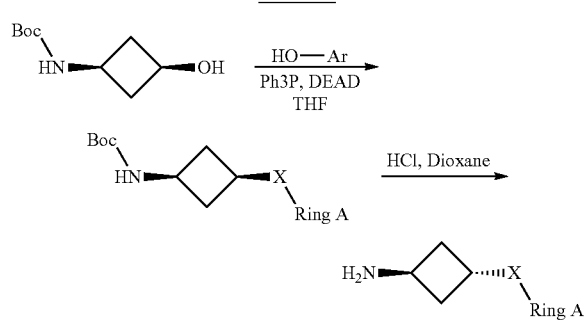

General Procedure for the Synthesis of the Intermediates in Table 2 (Scheme G)

The compounds were prepared in 2 steps by (1) reaction of trans-tert-Butyl N-(3-hydroxycyclobutyl)carbamate and aphenylthiol, phenol, or pyrazole derivative, followed by (2) deprotection to provide the intermediate using the procedures described for scheme F (see procedure for B-101).

TABLE 2

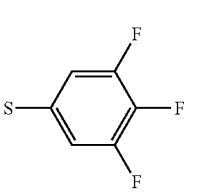

| Intermediate | Ring A X | NMR | ESMS (M +1) |
|---|---|---|---|
| B-128 | 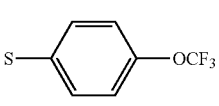 | 1H NMR (300 MHz, CD$_3$OD) δ 7.06-6.95 (m, 2H), 6.89-6.78 (m, 2H), 4.54 (p, J = 6.9 Hz, 1H), 3.63-3.47 (m, 1H), 3.04-2.86 (m, 2H), 2.25 (dddd, J = 10.1, 8.6, 6.1, 2.5 Hz, 2H). | 182.12 |
| B-129 | 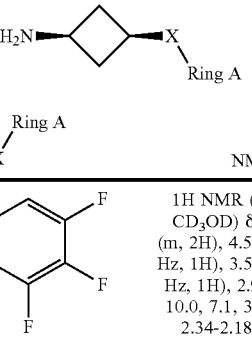 | 1H NMR (300 MHz, CD$_3$OD) δ 6.73-6.59 (m, 2H), 4.57 (p, J = 6.9 Hz, 1H), 3.56 (p, J = 8.0 Hz, 1H), 2.99 (dtd, J = 10.0, 7.1, 3.0 Hz, 2H), 2.34-2.18 (m, 2H). | 218.17 |
| B-130 | 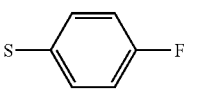 | 1H NMR (300 MHz, CD$_3$OD) δ 7.48-7.32 (m, 2H), 7.14-7.01 (m, 2H), 3.85-3.49 (m, 2H), 2.93-2.74 (m, 2H), 2.31-2.08 (m, 2H). | 198.1 |
| B-131 | 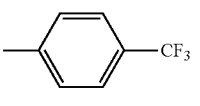 | 1H NMR (400 MHz, CD$_3$OD) δ 7.58 (d, J = 8.3 Hz, 2H), 7.41 (d, J = 8.3 Hz, 2H), 3.86 (ddq, J = 25.0, 8.7, 7.6 Hz, 2H), 3.05-2.89 (m, 2H), 2.33-2.14 (m, 2H). | 248.02 |
| B-132 | 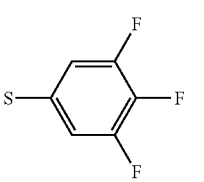 | 1H NMR (400 MHz, DMSO-d6) δ 8.34 (s, 3H), 7.32-7.18 (m, 2H), 3.79 (tt, J = 9.4, 7.4 Hz, 1H), 3.68-3.51 (m, 1H), 2.78 (dtd, J = 10.3, 7.4, 2.9 Hz, 2H), 2.24-2.10 (m, 2H). | 234.12 |
| B-133 | 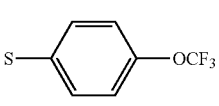 | 1H NMR (400 MHz, CD$_3$OD) δ 7.42-7.33 (m, 2H), 7.23 (dd, J = 8.8, 0.8 Hz, 2H), 3.89-3.67 (m, 2H), 2.99-2.82 (m, 2H), 2.27-2.09 (m, 2H). | 264.1 |

The following intermediates in Table 3 were prepared in 2 steps by (1) reaction of cis-tert-butyl (N-(3-(hydroxymethyl)cyclobutyl)carbamate and a phenol, thiophenol, or pyrazole derivative followed by (2) deprotection to provide the desired intermediate using the procedures described for intermediate B-101.

TABLE 3

| Intermediate | L-Ring A | NMR | ESMS (M +1) |
|---|---|---|---|
| B-134 | (3,5-difluorophenoxy) | 1H NMR (300 MHz, CD₃OD) δ 6.81-6.63 (m, 2H), 3.96 (d, J = 5.4 Hz, 2H), 3.83-3.65 (m, 1H), 2.72-2.57 (m, 1H), 2.56-2.42 (m, 2H), 2.25-2.03 (m, 2H). | 232.17 |
| B-135 | (4-fluorophenoxy) | 1H NMR (300 MHz, CD₃OD) δ 7.08-6.85 (m, 4H), 3.95 (d, J = 5.4 Hz, 2H), 3.73 (p, J = 8.2 Hz, 1H), 2.72-2.58 (m, 1H), 2.57-2.40 (m, 2H), 2.19-1.99 (m, 2H). | 196.19 |
| B-136 | (5-fluoropyridin-3-yloxy) | 1H NMR (300 MHz, CD₃OD) δ 8.63 (s, 2H), 8.24 (d, J = 9.9 Hz, 1H), 4.31 (d, J = 4.9 Hz, 1H), 4.14 (dt, J = 6.9, 4.1 Hz, 1H), 3.86-3.77 (m, 1H), 2.75 (s, 1H), 2.64-2.47 (m, 2H), 2.34-2.17 (m, 2H). | 197.18 |
| B-137 | (6-fluoropyridin-3-yloxy) | 1H NMR (300 MHz, CD₃OD) δ 7.86 (d, J = 1.4 Hz, 1H), 7.59 (ddd, J = 9.4, 6.6, 3.4 Hz, 1H), 7.08-6.93 (m, 1H), 4.28-4.10 (m, 1H), 4.01 (dd, J = 23.5, 6.5 Hz, 2H), 3.84-3.65 (m, 1H), 2.74-2.33 (m, 3H), 2.24-2.04 (m, 2H). | 197.18 |
| B-138 | (3,4-difluorophenoxy) | 1H NMR (300 MHz, CD₃OD) δ 7.25-7.07 (m, 1H), 6.88 (ddd, J = 12.4, 6.7, 3.0 Hz, 1H), 6.73 (ddd, J = 9.0, 4.0, 2.5 Hz, 1H), 3.95 (d, J = 5.4 Hz, 2H), 3.82-3.64 (m, 1H), 2.72-2.43 (m, 3H), 2.09 (ddd, J =18.8, 9.3, 2.6 Hz, 2H). | |
| B-139 | (5-(trifluoromethyl)-1H-pyrazol-1-yl) | 1H NMR (300 MHz, CD₃OD) δ 7.77 (s, 1H), 6.59 (s, 1H), 4.29 (d, J = 7.1 Hz, 2H), 3.68 (p, J = 8.2 Hz, 1H), 2.79-2.55 (m, 1H), 2.53-2.37 (m, 2H), 1.99 (ddd, J = 19.0, 9.5, 2.7 Hz, 2H). | 220.2 |
| B-140 | (2-cyano-4-fluorophenoxy) | 1H NMR (300 MHz, CD₃OD) δ 7.43 (ddd, J = 19.1, 8.0, 3.1 Hz, 2H), 7.20 (dd, J = 9.2, 4.1 Hz, 1H), 4.12 (d, J = 5.8 Hz, 2H), 3.74 (td, J = 16.4, 8.2 Hz, 1H), 2.80-2.63 (m, 1H), 2.55 (dtd, J = 10.5, 7.6, 2.7 Hz, 2H), 2.11 (ddd, J = 18.8, 9.3, 2.6 Hz, 2H). | 221.19 |

Scheme H (B-141)

B-141. trans-3-(3,4,5-Trifluorophenoxy)cyclopentan-1-amine

Step 1: tert-Butyl ((trans)-3-(3,4,5-trifluorophenoxy)cyclopentyl)carbamate

A mixture of tert-butyl (cis-3-hydroxycyclopentyl)carbamate (63.5 g, 315.5 mmol), triphenylphosphine (107.6 g, 410.2 mmol) and 3,4,5-trifluorophenol (60.74 g, 410.2 mmol) in THF (750 mL) was cooled down to 0° C. Diisopropyl azodicarboxylate (82 mL, 410.2 mmol) was added dropwise, maintaining the reaction temperature below 10° C. The reaction was slowly warmed to room temperature and stirred overnight. The solvent was evaporated in vacuo, the residue was dissolved in 2 L of dichloromethane and washed with 1 N NaOH (2×1 L); the organic layer was dried over Na₂SO₄, filtered, and evaporated. The residue was dissolved in dichloromethane and eluted through a 1.5 L plug of silica gel. The filtrate was evaporated in vacuo and purified through a 1 L plug of silica gel eluting with dichloromethane. The first 2 L of the filtrate was concentrated to provide the product (90 g, 86% yield) as white solid. 1H NMR (300 MHz, CDCl₃) δ 6.49-6.38 (m, 2H), 4.69 (ddd, J=8.4, 5.8, 2.5 Hz, 1H), 4.49 (s, 1H), 4.18 (d, J=6.9 Hz, 1H), 2.37-2.06 (m, 3H), 1.82 (dddd, J=20.4, 14.1, 9.1, 7.6 Hz, 2H), 1.47 (d, J=6.1 Hz, 9H).

Step 2: trans-3-(3,4,5-Trifluorophenoxy)cyclopentan-1-amine hydrochloride

A 4M solution of HCl in dioxane (100 ml, 400 mmol) was added to a solution of tert-Butyl ((trans)-3-(3,4,5-trifluorophenoxy)cyclopentyl)carbamate (13.5 g, 40.7 mmol) in dioxane (80 ml). The reaction was stirred at room temperature for 18 hours. Diethyl ether was add to the residue and stirred at room temperature. The white solid was collected by vacuum filtration, washed with diethyl ether, and dried in an oven to provide the title product, 10.3 g (95% yield). 1H NMR (300 MHz, DMSO-d6) δ 8.27 (s, 3H), 7.08-6.83 (m, 2H), 5.06-4.86 (m, 1H), 3.74-3.58 (m, 1H), 2.35-1.90 (m, 4H), 1.85-1.53 (m, 2H).

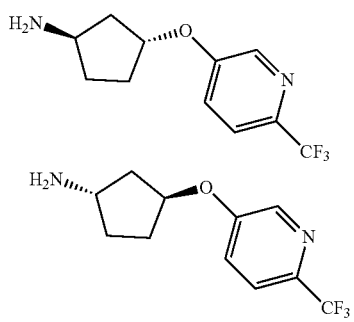

(B-142)

B-142. trans-3-((6-(Trifluoromethyl)pyridin-3-yl)oxy)cyclopentan-1-amine

The compound was prepared in the same manner as intermediate B-141 to provide the title compound as a diastereomeric pair of trans isomers. ESMS(M+1)=247.13.

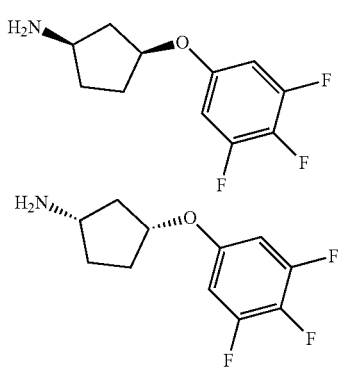

(B-143)

B-143. cis-3-(3,4,5-Trifluorophenoxy)cyclopentan-1-amine hydrochloride

The compound was prepared in the same manner as the procedure reported for intermediate B-142 to provide the title compound (82% yield) as a mixture of cis-diastereomers. 1H NMR (300 MHz, CDCl₃) δ 6.53-6.41 (m, 2H), 4.77 (s, 1H), 4.66 (ddd, J=8.1, 5.3, 2.5 Hz, 1H), 4.14 (s, 1H), 2.41-2.24 (m, 1H), 2.17-2.02 (m, 1H), 2.02-1.90 (m, 2H), 1.85-1.64 (m, 2H), 1.46 (s, 9H);

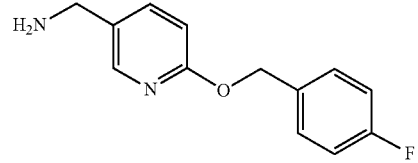

(B-144)

B-144. (6-((4-fluorobenzyl)oxy)pyridin-3-yl)methanamine hydrochloride

Step 1: 6-((4-fluorobenzyl)oxy)nicotinonitrile

Sodium hydride (60% oil dispersion; 640 mg, 16 mmol) was added to a cooled solution (0° C.) of (4-fluorophenyl)methanol (1.9 g, 15 mmol) in DMF (20 ml). After stirring for 30 minutes, 6-chloronicotinonitrile (2.6 g, 19 mmol) was added to the mixture and the reaction was warmed to room temperature and stirred for 14 hours. The mixture was poured into a saturated ammonium chloride solution and a grey precipitate formed. The precipitate was collected by vacuum filtration and washed well with water. The collected filter cake was dried in a vacuum oven at 50° C. for 16 hours to provide the title product, wt. 1.6 g. 1H NMR (400 MHz, CDCl₃) δ 8.37 (dd, J=2.3, 0.8 Hz, 1H), 7.66 (dt, J=8.7, 1.6 Hz, 1H), 7.34-7.23 (m, 2H), 6.94 (t, J=8.7 Hz, 2H), 6.73 (dd, J=8.6, 0.8 Hz, 1H), 5.26 (s, 2H); ESMS(M+1)=228.8.

Step 2: tert-Butyl ((6-((4-fluorobenzyl)oxy)pyridin-3-yl)methyl)carbamate 6-((4-fluorobenzyl)oxy)nicotinonitrile (1.23 g, 5.23 mmol), Boc₂0 (1.37 g, 6.27 mmol), and dichlorocobalt hexahydrate (249 mg, 1.046 mmol) were taken into methanol (20 ml) and cooled to 0° C. Sodium borohydride (980 mg, 1.047 mmol) was added to the mixture portion wise and stirred for 1 hour. The solvent was evaporated in vacuo to afford a black residue. This was taken into ethyl acetate and water. The organic layer was collected and filtered to remove the fine solid, then washed with brine and dried over anhydrous sodium sulfate, filtered, and evaporated in vacuo to provide the title product, wt. 1.6 g (82.9% yield). 1H NMR (400 MHz, CDCl₃) δ 8.08 (d, J=2.4 Hz, 1H), 7.57 (dd, J=8.5, 2.4 Hz, 1H), 7.44 (dd, J=8.5, 5.4 Hz, 2H), 7.07 (t, J=8.7 Hz, 2H), 6.78 (d, J=8.5 Hz, 1H), 5.34 (s, 2H), 4.82 (s, 1H), 4.26 (d, J=6.0 Hz, 2H), 1.47 (s, 9H); ESMS(M+1)= 333.15.

Step 3: (6-((4-fluorobenzyl)oxy)pyridin-3-yl)methanamine hydrochloride tert-Butyl ((6-((4-fluorobenzyl)oxy)pyridin-3-yl)methyl)carbamate (1.6 g, 4.81 mmol) was dissolved in 10 ml of dioxane. A 4M solution of HCl in dioxane (6 ml, 24 mmol) was added to the solution and stirred at room temperature for 1 hour (a precipitate formed 10 minutes after addition). The solvent was evaporated to provide a residue that was triturated with diethyl ether and stirred for 1 hour resulting in a white precipitate. The solid was collected by vacuum filtration, washed with diethyl ether, and dried under vacuum to provide the title product, wt. 1.28 g (quantitative yield). 1H NMR (400 MHz, Methanol-d4) δ 8.33 (d, J=24.6 Hz, 1H), 8.09 (s, 1H), 7.59-7.40 (m, 2H), 7.20 (d, J=8.5 Hz, 1H), 7.16-6.98 (m, 2H), 5.42 (d, J=15.3 Hz, 2H), 4.15 (d, J=16.2 Hz, 2H); ESMS(M+1)=233.03.

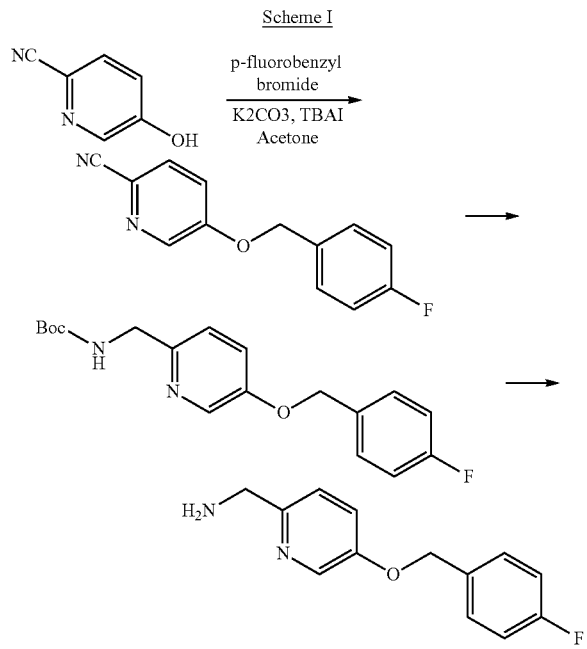

B-145. (6-((1-(4-Fluorophenyl)pyrrolidin-3-yl)oxy)pyridin-3-yl)methanamine Step 1: 1-(4-fluorophenyl)pyrrolidin-3-ol Sodium borohydride (535 mg, 14.1 mmol) was added to a cooled solution (0° C.) of 1-(4-fluorophenyl)pyrrolidin-3-one (1.94 g, 10.83 mmol) in MeOH (12 mL) and stirred for 3 hours. After warming to room temperature, the reaction was quenched by the addition of water and saturated sodium bicarbonate followed by extraction with ethyl acetate (3×75 ml). The combined organic extracts were washed with brine, dried over sodium sulfate, filtered, and evaporated in vacuo. The resulting residue was triturated with diethyl ether to obtain the product as a solid, wt. 1.86 g (81% yield). ESMS(M+1)=181.92.

Step 2: 6-((1-(4-fluorophenyl)pyrrolidin-3-yl)oxy)nicotinonitrile

Sodium hydride (97 mg, 2.21 mmol) was added to a solution of 1-(4-fluorophenyl)pyrrolidin-3-ol (400 mg, 2.43 mmol) in DMF (4 ml) and stirred at room temperature. 6-Fluoronicotinonitrile (295 mg, 2.43 mmol) was added to the reaction and stirred at room temperature overnight. Water (75 ml) was added to the reaction and extracted with ethyl acetate (3×75 ml). The combined extracts were washed with brine, dried over anhydrous sodium sulfate, filtered, and evaporated in vacuo. The crude product was purified by column chromatography (SiO$_2$) eluting with a gradient of 0-10% methanol(0.1% ammonia) in dichloromethane. Evaporation of the desired fractions afforded 410 mg (62% yield) of the title compound. ESMS(M+1)=284.55.

Step 3: (6-((1-(4-fluorophenyl)pyrrolidin-3-yl)oxy)pyridin-3-yl)methanamine

A mixture of 6-((1-(4-fluorophenyl)pyrrolidin-3-yl)oxy)nicotinonitrile (410 mg, 1.45 mmol) and nickel were taken into 7 N ammonia in methanol(20 ml) and hydrogenated at 3 bar overnight. The reaction was filtered and evaporated in vacuo to afford the title compound, 405 mg (82.8% yield); ESMS(M+1)=285.16.

B-146. (6-(4-(trifluoromethyl)-1H-pyrazol-1-yl)pyridin-3-yl)methanamine

Step 1: 6-(4-(trifluoromethyl)-1H-pyrazol-1-yl)nicotinonitrile

Sodium hydride (310 mg, 7.77 mmol) was added to a solution of 4-(trifluoromethyl)-1H-pyrazole (877 mg, 6.45 mmol) in anhydrous DMF (5 mL). After 10 minutes, 4-(trifluoromethyl)-1H-pyrazole (877 mg, 6.45 mmol) was added to the mixture and heated to 80° C. for 1 hour. The reaction was cooled to room temperature and poured into water (125 ml) resulting in the formation of a precipitate. The precipitate was filtered, washed with water, and dried under vacuum to provide the title product, wt. 1.44 g (88% yield). ESMS(M+1)=239.3.

Step 2: (6-(4-(trifluoromethyl)-1H-pyrazol-1-yl)pyridin-3-yl)methanamine

A mixture of 6-(4-(trifluoromethyl)-1H-pyrazol-1-yl)nicotinonitrile (1.26 g, 5.27 mmol) and nickel (~300 mg) in 7N ammonia in methanol (25 ml) was hydrogenated at 3 bar overnight. The mixture was filtered and the filtrate concentrated to afford the title product, wt. 1.26 g (83% yield). The product was used without further purification. ESMS (M+1)=243.35.

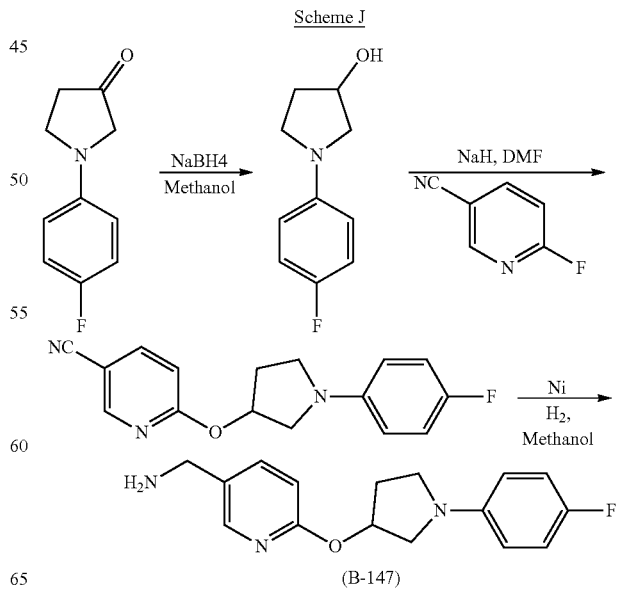

(B-147)

B-147. (6-((1-(4-Fluorophenyl)pyrrolidin-3-yl)oxy)pyridin-3-yl)methanamine

Step 1: 1-(4-fluorophenyl)pyrrolidin-3-ol

Sodium borohydride (535 mg, 14.1 mmol) was added to a cooled solution (0° C.) of 1-(4-fluorophenyl)pyrrolidin-3-one (1.94 g, 10.83 mmol) in MeOH (12 mL) and stirred for 3 hours. After warming to room temperature, the reaction was quenched by the addition of water and saturated sodium bicarbonate and extracted with ethyl acetate (3×75 ml). The organic extracts were combined, washed with brine, dried over sodium sulfate, filtered, and evaporated in vacuo. The residue was triturated with diethyl ether to obtain the product as a solid, wt. 1.86 g (81% yield). ESMS(M+1)=181.92.

Step 2: 6-((1-(4-fluorophenyl)pyrrolidin-3-yl)oxy)nicotinonitrile

Sodium hydride (97 mg, 2.21 mmol) was added to a solution of 1-(4-fluorophenyl)pyrrolidin-3-ol (400 mg, 2.43 mmol) in DMF (4 ml) and stirred at room temperature. 6-Fluoronicotinonitrile (295 mg, 2.43 mmol) was added to the reaction and stirred at room temperature overnight. Water (75 ml) was added to the reaction followed by extraction with ethyl acetate (3×75 ml). The combined extracts were washed with brine, dried over anhydrous sodium sulfate, filtered, and evaporated in vacuo. The crude product was purified by column chromatography (SiO2) eluting with a gradient of 0-10% methanol(0.1% ammonia) in dichloromethane. Evaporation of the desired fractions afforded 410 mg (62% yield) of the title compound. ESMS (M+1)=284.55.

Step 3: (6-((1-(4-fluorophenyl)pyrrolidin-3-yl)oxy)pyridin-3-yl)methanamine A mixture of 6-((1-(4-fluorophenyl)pyrrolidin-3-yl)oxy)nicotinonitrile (410 mg, 1.45 mmol) and nickel were taken into 7 N ammonia in methanol(20 ml) and hydrogenated at 3 bar overnight. The reaction was filtered and evaporated in vacuo to afford the title compound, 405 mg (82.8% yield); ESMS(M+1)=285.16.

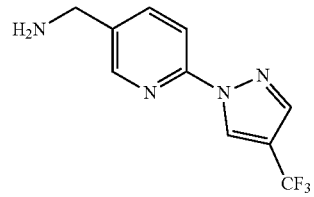

(B-148)

B-148. (6-(4-(Trifluoromethyl)-1H-pyrazol-1-yl)pyridin-3-yl)methanamine

Step 1. 6-(4-(trifluoromethyl)-1H-pyrazol-1-yl)nicotinonitrile

Sodium hydride (310 mg, 7.8 mmol) was added to a solution of 4-(trifluoromethyl)-1H-pyrazole (877 mg, 6.45 mmol) in DMF (5 mL) and stirred at room temperature for 10 minutes. 6-Fluoropyridine-3-carbonitrile (730 mg, 6 mmol) was added to the mixture then at 80° C. for 1 hour. The reaction was cooled to room temperature then poured into water (125 ml). The precipitate was collected by vacuum filtration and washed well with water to provide the title product, wt. 1.4 g. ESMS(M+1)=239.3.

Step 2. (6-(4-(Trifluoromethyl)-1H-pyrazol-1-yl)pyridin-3-yl)methanamine

Approximately, 300 mg of nickel (washed with methanol) was added to a solution of 6-(4-(trifluoromethyl)-1H-pyrazol-1-yl)nicotinonitrile in 25 ml of 7 N NH3 in methanol. And hydrogenated (3 bar) overnight. The reaction was filtered through Celite and concentrated in vacuo to afford the title product. ESMS(M+1)=243.35.

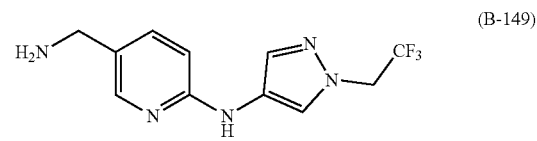 [SMILES: NCc1ccc(Nc2cnn(CC(F)(F)F)c2)nc1]

(B-149)

B-149. 5-(Aminomethyl)-N-(1-(2,2,2-trifluoroethyl)-1H-pyrazol-4-yl)pyridin-2-amine

Step 1. 6-((1-(2,2,2-trifluoroethyl)-1H-pyrazol-4-yl)amino)nicotinonitrile

A mixture of 6-fluoropyridine-3-carbonitrile (680 mg, 5.569 mmol), 1-(2,2,2-trifluoroethyl)pyrazol-4-amine (895 mg, 5.420 mmol), and potassium carbonate (1.74 g, 12.6 mmol) were taken into 10 ml of DMF and microwaved for 30 minutes at 160 C. The reaction was poured into water and extracted with ethyl acetate (3×50 mL). The combined organic extracts were washed with water (2×20 mL) and brine (1×20 mL), and dried over anhydrous sodium sulfate and concentrated in vacuo to provide the title product, wt. 1.4 g; ESMS (M+1)=268.01.

Step 2. 5-(Aminomethyl)-N-(1-(2,2,2-trifluoroethyl)-1H-pyrazol-4-yl)pyridin-2-amine To a mixture of methanol washed Nickel (about 0.3 g) in methanol (50 mL) was added 6-((1-(2,2,2-trifluoroethyl)-1H-pyrazol-4-yl)amino)nicotinonitrile (1,600 mg, 5.988 mmol) and 7N NH3 in M methanol (20 ml). The mixture was hydrogenated at 3 bar for 18 hours. The nickel was magnetically retrieved and the reaction filtered through Celite. The filtrate was evaporated in vacuo to afford the title product that was used without further purification, wt. 1.2 g; ESMS (M+1)=272.15.

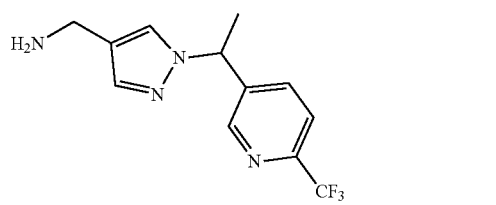

(B-150)

B-150. (1-(1-(6-(Trifluoromethyl)pyridin-3-yl)ethyl)-1H-pyrazol-4-yl)methanamine Prepared by Method A. ESMS (M+1)=271.13.

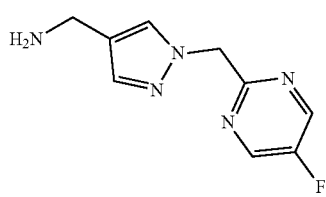

B-151. (1-((5-Fluoropyrimidin-2-yl)methyl)-1H-pyrazol-4-yl)methanamine hydrochloride Prepared by Method B. 1H NMR (400 MHz, Methanol-d4) δ 8.70 (d, J=0.8 Hz, 2H), 8.08-8.03 (m, 1H), 7.78-7.73 (m, 1H), 5.65 (d, J=1.1 Hz, 2H), 4.10 (s, 2H). ESMS(M+1)=208.18.

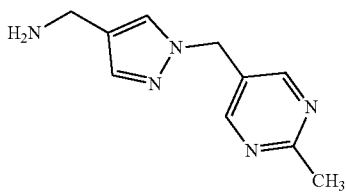

B-152. (1-((2-Methylpyrimidin-5-yl)methyl)-1H-pyrazol-4-yl)methanamine hydrochloride Prepared by Method B. ESMS(M+1)=208.18.

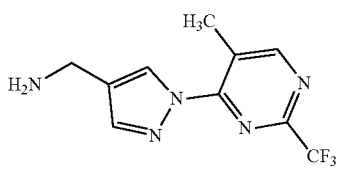

B-153. (1-(5-methyl-2-(trifluoromethyl)pyrimidin-4-yl)-1H-pyrazol-4-yl)methanamine hydrochloride

Step A: tert-Butyl ((1-(5-methyl-2-(trifluoromethyl)pyrimidin-4-yl)-1H-pyrazol-4-yl)methyl)carbamate tert-Butyl ((1H-pyrazol-4-yl)methyl)carbamate (320 mg, 1.62 mmol) and 5-(chloromethyl)-2-(trifluoromethyl)pyrimidine (318 mg, 1.62 mmol) were taken into 6 ml of anhydrous DMF and cooled to 0° C. Sodium hydride (60% oil dispersion w/w; 85 mg, 2.12 mmol) was added to the solution. The reaction was warmed to room temperature and stirred for 16 hours. Water was added to the reaction and a precipitate formed. The precipitate was collected by vacuum filtration and washed well with water. The crude product was purified column chromatography (SiO₂) eluting with 0-100% ethyl acetate in heptane. The desired fractions were combined and evaporated to afford the title product, wt. 150 mg (24% yield). 1H NMR (300 MHz, CDCl₃) δ 8.73 (s, 1H), 8.62 (s, 1H), 7.80 (s, 1H), 4.85 (s, 1H), 4.30 (d, J=5.9 Hz, 2H), 2.79 (s, 3H), 1.50 (s, 9H); ESMS (M+1)=358.23.

Step B: (1-(5-methyl-2-(trifluoromethyl)pyrimidin-4-yl)-1H-pyrazol-4-yl)methanamine hydrochloride tert-Butyl ((1-(5-methyl-2-(trifluoromethyl)pyrimidin-4-yl)-1H-pyrazol-4-yl)methyl)carbamate (142 mg, 0.397 mmol) was taken into 5 ml of 4M HCl in dioxane (20 mmol) and stirred at room temperature for 2 hours. The resulting precipitate was collected by vacuum filtration, washed well with diethyl ether, and dried under vacuum to provide the title product, wt. 130 mg (99% yield). 1H NMR (400 MHz, Methanol-d4) δ 8.91 (s, 1H), 8.87 (s, 1H), 7.98 (s, 1H), 4.17 (s, 2H), 2.77 (s, 3H).

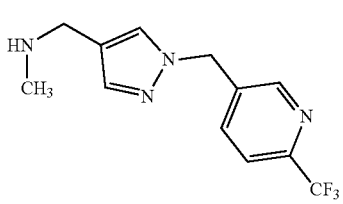 [SMILES: CNCc1cnn(Cc2ccc(C(F)(F)F)nc2)c1]

B-154. N-methyl-1-(1-((6-(trifluoromethyl)pyridin-3-yl)methyl)-1H-pyrazol-4-yl)methanamine trifluoroacetic Acid Salt

Step 1: tert-butyl methyl((1-((6-(trifluoromethyl)pyridin-3-yl)methyl)-1H-pyrazol-4-yl)methyl)carbamate Sodium hydride (60% oil dispersion w/w; 675 mg, 16.84 mmol) was added to a cooled (0° C.) solution of tert-butyl ((1-((6-(trifluoromethyl)pyridin-3-yl)methyl)-1H-pyrazol-4-yl)methyl)carbamate (4 g, 11.23 mmol) in DMF (100 ml) and stirred under nitrogen for 30 minutes. Iodomethane (0.91 ml, 14.6 mmol) was added to the mixture. The reaction was warmed to room temperature and stirred for 2 hours. The solution was poured onto ice water (100 ml) and extracted with ethyl acetate (2×100 ml). The combined extracts were washed with saturated sodium bicarbonate and brine, dried over anhydrous sodium sulfate, filtered, and evaporated in vacuo to afford the crude product. The product was purified by column chromatography (SiO₂, 80 g) eluting with a gradient of 0-20% methanol in dichloromethane. The desired fractions were collected and evaporated in vacuo to afford the title product, wt 3 g (72.1% yield). 1H NMR (300 MHz, DMSO-d6) δ 8.65 (s, 1H), 7.94-7.83 (m, 2H), 7.81 (s, 1H), 7.42 (s, 1H), 5.49 (s, 2H), 4.18 (s, 2H), 2.89 (s, 3H), 1.39 (s, 9H). ESMS (M+1)=371.17.

Step 2: N-methyl-1-(1-((6-(trifluoromethyl)pyridin-3-yl)methyl)-1H-pyrazol-4-yl)methanamine trifluoro acetic Acid Salt Trifluoroacetic acid (4.2 ml, 54 mmol) was to a solution of tert-Butyl methyl((1-((6-(trifluoromethyl)pyridin-3-yl)methyl)-1H-pyrazol-4-yl)methyl)carbamate (2 g, 5.4 mmol) in 15 ml of dichloromethane and stirred at room temperature for 2 hours. The solvent was removed in vacuo to afford a residue that was dried under vacuum at 50° C. for 18 hours to afford the title product, wt. 2.4 g (89.2% yield). 1H NMR (300 MHz, DMSO-d6) δ 8.66 (br, 3H), 8.00 (d, J=0.8 Hz, 1H), 7.91 (d, J=1.5 Hz, 2H), 7.61 (d, J=0.8 Hz, 1H), 5.55 (s, 2H), 4.01 (t, J=5.6 Hz, 2H), 2.54 (t, J=5.4 Hz, 3H). ESMS (M+1)=271.18.

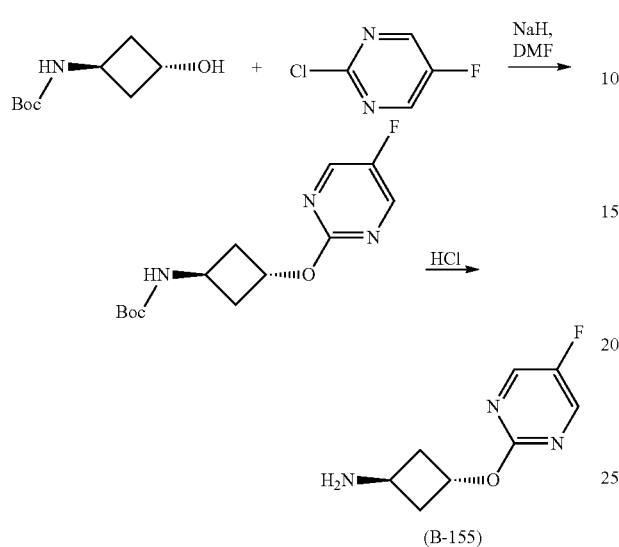

B-155. trans-3-((5-fluoropyrimidin-2-yl)oxy)cyclobutan-1-amine hydrochloride

Step 1: tert-butyl (trans-3-((5-fluoropyrimidin-2-yl)oxy)cyclobutyl)carbamate Sodium hydride (480 mg, 12 mmol) was added to a solution of tert-butyl (trans-3-hydroxycyclobutyl)carbamate (2.04 g, 10.9 mmol) and 2-chloro-5-fluoropyrimidine (1.45 g, 10.9 mmol) in 10 ml of anhydrous DMF at room temperature for 18 hours. Reaction was not complete, so the reaction was heated at 90° C. for 24 hours. The reaction was cooled to room temperature then poured into water (100 ml) and extracted with ethyl acetate (3×100 ml). The combined extracts were washed with water (2×50 ml) and brine (50 ml), dried over anhydrous sodium sulfate, filtered, and evaporated in vacuo. The crude product was purified by column chromatography (SiO$_2$) eluting with a gradient of 0-100% ethyl acetate in hexanes. The desired fractions were evaporated in vacuo to afford the title product, wt. 1.71 g (55% yield). 1H NMR (300 MHz, CDCl$_3$) δ 8.37 (s, 1H), 8.18 (d, J=1.0 Hz, 1H), 5.26 (dt, J=7.3, 2.9 Hz, 1H), 4.86 (dt, J=6.8, 3.2 Hz, 1H), 4.38-4.27 (m, 1H), 2.67-2.39 (m, 4H), 1.46 (s, 9H).

Step 2: trans-3-((5-fluoropyrimidin-2-yl)oxy)cyclobutan-1-amine hydrochloride 4M HCl (50 ml, 200 mmol) in dioxane was added to a solution of tert-butyl (trans-3-((5-fluoropyrimidin-2-yl)oxy)cyclobutyl)carbamate in 50 ml of dioxane and stirred at room temperature for 2 hours. A precipitate formed that was collected by vacuum filtration and washed with diethyl ether and hexanes to afford the title product, wt. 1.3 g (98% yield). 1H NMR (300 MHz, Methanol-d4) δ 8.54 (d, J=0.7 Hz, 1H), 8.33 (d, J=0.6 Hz, 1H), 5.25 (dtd, J=86.9, 6.7, 4.0 Hz, 1H), 4.08-3.91 (m, 1H), 2.79-2.56 (m, 4H).

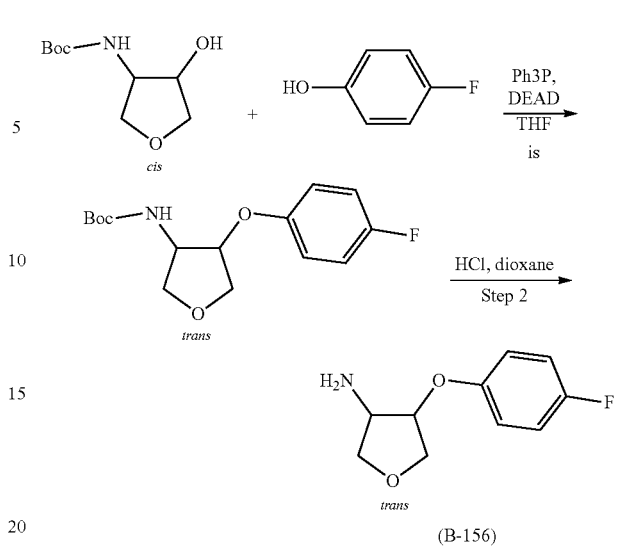

B-156: trans-4-(4-fluorophenoxy)tetrahydrofuran-3-amine

Step 1: tert-butyl (trans-4-(4-fluorophenoxy)tetrahydrofuran-3-yl)carbamate tert-butyl (cis-4-hydroxytetrahydrofuran-3-yl)carbamate (600 mg, 2.95 mmol), 4-fluorophenol (496 mg, 4.43 mmol), and triphenylphosphine (1.16 g, 4.43 mmol) were dissolved into 5 ml of anhydrous THF and cooled to 0° C. diisopropyl azodicarboxylate (0.9 ml, 4.43 mmol) was added to the mixture dropwise. The reaction was warmed to room temperature and stirred for 18 hours. The solvent was removed in vacuo to afford the crude product that was purified by column chromatography (SiO$_2$) eluting with a gradient of 0-100% ethyl acetate in heptane to afford the title product, wt. 375 mg (43% yield). ESMS (M+1)=298.39.

Step 2: trans-4-(4-fluorophenoxy)tetrahydrofuran-3-amine

Trifluoro acetic acid (1 ml, 12. 8 mmol) was added to a solution of tert-butyl (trans-4-(4-fluorophenoxy)tetrahydrofuran-3-yl)carbamate (375 mg, 1.26 mmol) in 2 ml of dichloromethane and stirred at room temperature for 16 hours. The reaction was evaporated in vacuo and the residue dissolved in saturated sodium bicarbonate (10 ml) and extracted with dichloromethane (2×10 ml). The combined extracts were dried over anhydrous sodium sulfate, filtered, and evaporated in vacuo to afford the title product as a clear yellow oil, wt. 234 mg (94% yield); ESMS (M+1)=198.07.

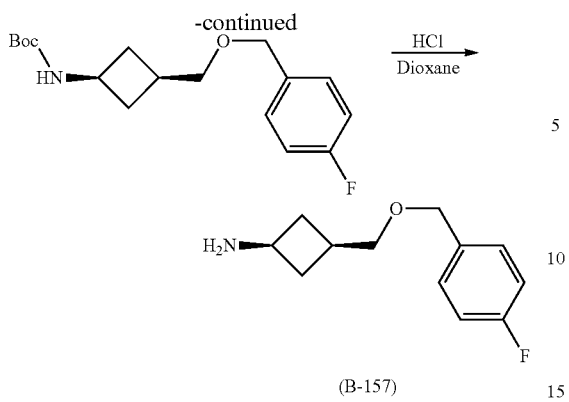

(B-157)

B-157: cis-3-(((4-fluorobenzyl)oxy)methyl)cyclobutan-1-amine hydrochloride

Step 1: tert-butyl (cis-3-(((4-fluorobenzyl)oxy)methyl)cyclobutyl)carbamate Sodium hydride (220 mg, 5.47 mmol) was added to a solution of tert-butyl ((cis-3-(hydroxymethyl)cyclobutyl)carbamate (1 g, 4.97 mmol) and 4-fluorobenzyl bromide (940 mg, 5.47 mmol) in THF (10 ml) at 0° C. The reaction was warmed to room temperature and stirred for 16 hours. Water (50 ml) was added to the reaction followed by extraction with ethyl acetate (3×100 ml). The combined extracts were washed with water (2×50 ml) and brine (50 ml), dried over anhydrous sodium sulfate, filtered, and evaporated in vacuo to afford the title product, 1.3 g (98% yield). ESMS (M+1)=310.14.

Step 2: cis-3-(((4-fluorobenzyl)oxy)methyl)cyclobutan-1-amine hydrochloride tert-butyl (cis-3-(((4-fluorobenzyl)oxy)methyl)cyclobutyl)carbamate (1.3 g, 4.2 mmol) was taken into 4M HCl in dioxane (50 ml) and stirred at room temperature for 2 hours. The reaction was evaporated in vacuo to afford the crude product that purified by reverse MPLC (C18 column) eluting with 10-100% Acetonitrile in water (0.1% TFA). The desired fractions were evaporated in vacuo to afford the desired product that was dissolved in dichloromethane and precipitated by the addition of diethyl ether. The precipitate was collected by vacuum filtration, washed with diethyl ether and hexanes, and dried under vacuum at 50° C. to afford the title product, wt. 600 mg(58% yield). ESMS (M+1)=210.47.

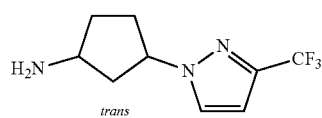

(B-158)

B-158: trans-3-(3-(trifluoromethyl)-1H-pyrazol-1-yl)cyclopentan-1-amine hydrochloride The compound was prepared in a similar manner as reported for procedure B-141 via reaction of cis-tert-butyl (3-(3-(trifluoromethyl)-1H-pyrazol-1-yl)cyclopentyl)carbamate and 3-(trifluoromethyl)-1H-pyrazole followed by deprotection to afford the title product. ESMS (M+1)=220.11.

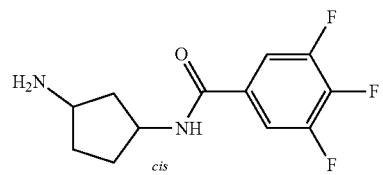

B-159: cis-N-(3-aminocyclopentyl)-3,4,5-trifluorobenzamide

Step 1: tert-butyl cis-(3-(3,4,5-trifluorobenzamido)cyclopentyl)carbamate 3,4,5-Trifluorobenzoyl chloride (70 µl, 0.38 mmol) was added to a mixture of tert-butyl cis-N-(3-aminocyclopentyl)carbamate (70 mg, 0.345 mmol) in dichloromethane (1.5 ml) and triethylamine (60 µl, 0.41 mmol). The mixture was stirred at room temperature for 16 hours. The reaction was quenched with saturated sodium bicarbonate and extracted with dichloromethane. The organic layer was evaporated in vacuo to afford the crude product. The product was purified by column chromatography eluting with a gradient of 0-100% ethyl acetate in heptane to afford the title product, wt. 92 mg (74% yield). ESMS (M+1)=359.13.

Step 2: cis-N-(3-aminocyclopentyl)-3,4,5-trifluorobenzamide tert-butyl cis-(3-(3,4,5-trifluorobenzamido)cyclopentyl)carbamate (92 mg, 0.26 mmol) was dissolved in dichloromethane (1 ml) and TFA (0.2 ml, 2.6 mmol) and stirred at room temperature for 16 hours. The reaction was evaporated in vacuo to afford the title product as a TFA salt, wt. 95 mg. ESMS (M+1)=259.10.

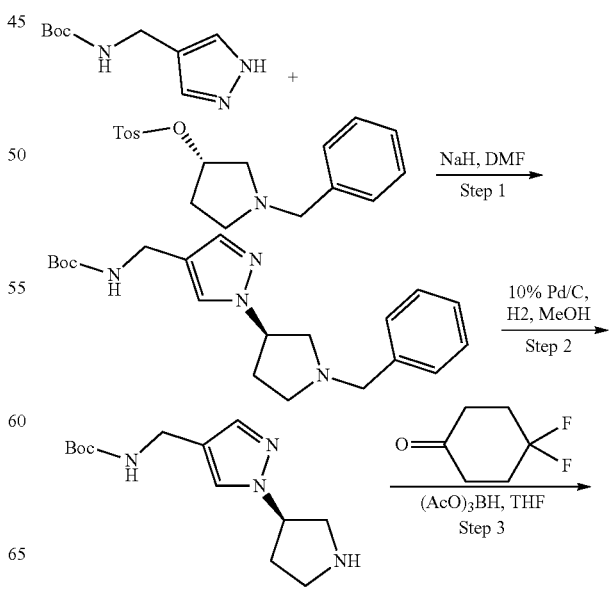

-continued

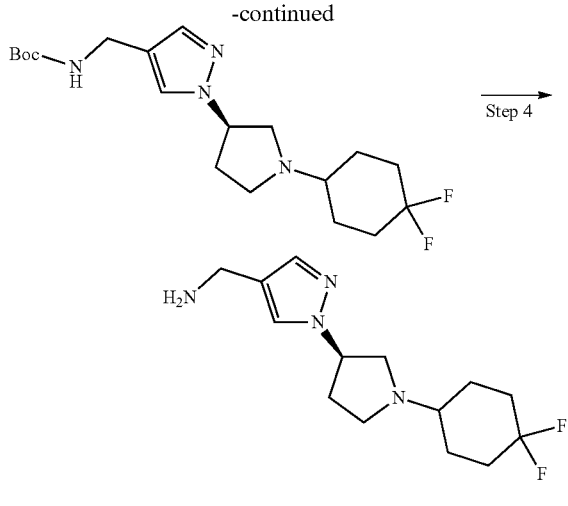

B-160 (R)-(1-(1-(4,4-difluorocyclohexyl)pyrrolidin-3-yl)-1H-pyrazol-4-yl)methanamine dihydrochloride Step 1: Benzyl (R)-3-(4-(((tert-butoxycarbonyl)amino)methyl)-1H-pyrazol-1-yl)pyrrolidine-1-carboxylate Sodium hydride (125 mg, 3.125 mmol) was added to a solution of tert-butyl N-(1H-pyrazol-4-ylmethyl)carbamate (454 mg, 2.302 mmol) in DMF (5 mL) and stirred for 10 minutes. Benzyl (3S)-3-(p-tolylsulfonyloxy)pyrrolidine-1-carboxylate (1.04 g, 2.76 mmol) was added to the mixture and stirred for 18 hours. The reaction was diluted with EtOAc (100 ml) and washed with water (50 ml), saturated NaHCO$_3$ (50 ml), and brine(50 ml). The organic layer was dried over sodium sulfate, filtered, and evaporated in vacuo. The crude product was purified by column chromatography (SiO$_2$) eluting with 10% methanol in dichloromethane to provide 2.76 g (55% yield) of the title compound. $^1$H NMR (300 MHz, CD$_3$OD) δ 7.60-7.17 (m, 7H), 6.86 (s, 1H), 5.45 (s, 1H), 5.09 (s, 2H) 4.97-4.76 (m, 2H), 4.06 (d, J=4.1 Hz, 2H), 3.90-3.40 (m, 4H), 2.43-2.20 (m, 2H), 1.41 (s, 9H).

Step 2: tert-Butyl (R)-((1-(pyrrolidin-3-yl)-1H-pyrazol-4-yl)methyl)carbamate

To a slurry of 10% Pd/C (50 mg) in methanol (25 mL) was added benzyl (3R)-3-(4-(((tert-butoxycarbonyl)amino)methyl)pyrazol-1-yl)pyrrolidine-1-carboxylate (483 mg, 1.21 mmol) and the resulting slurry stirred under a hydrogen balloon for 14 hours. The mixture was filtered, washed with methanol, and concentrated in vacuo to provide 261 mg (81% yield) of the crude product. ESMS(M+1)=267.38 (M+1).

Step 3. tert-butyl (R)-((1-(1-(4,4-difluorocyclohexyl)pyrrolidin-3-yl)-1H-pyrazol-4-yl)methyl)carbamate To a solution of tert-Butyl (R)-((1-(pyrrolidin-3-yl)-1H-pyrazol-4-yl)methyl)carbamate (360 mg, 1.35 mmol) in THF was added 4,4-difluorocyclohexanone (290 mg, 2.16 mmol) and sodium triacetoxyborohydride (460 mg, 2.16 mmol) and the reaction stirred for 16 hours. Saturated NaHCO$_3$ (75 mL) was added to the reaction mixture followed by extraction with EtOAc (3×75 mL). The combined organic fractions were washed with water (40 mL) and brine (40 mL). The organic layer was dried over sodium sulfate, filtered and concentrated in vacuo. The crude was purified by column chromatography (SiO$_2$) eluting with a gradient of 0-10% methanol in dichloromethane to provide 520 mg (100% yield) of product that was used in the next step without further purification. ESMS(M+1)=385.69.

Step 4: (R)-(1-(1-(4,4-difluorocyclohexyl)pyrrolidin-3-yl)-1H-pyrazol-4-yl)methanamine dihydrochloride To a solution of tert-butyl (R)-((1-(1-(4,4-difluorocyclohexyl)pyrrolidin-3-yl)-1H-pyrazol-4-yl)methyl)carbamate (515 mg, 1.340 mmol) in dichloromethane (8 mL) was added 4 M HCl in methanol (4 ml, 16.00 mmol) and the mixture stirred for 3 hours. The reaction was concentrated to dryness under vacuum to provide 550 mg (100% yield) of the product. ESMS(M+1)=285.34.

B-161. (S)-(1-(1-(4,4-difluorocyclohexyl)pyrrolidin-3-yl)-1H-pyrazol-4-yl)methanamine dihydrochloride The compound was prepared in a similar manner as reported for B-160 to provide the title product, 510 mg (90% yield). ESI-MS(M+1)=285.38.

B-162. (S)-(1-(1-(4-fluorophenyl)pyrrolidin-3-yl)-1H-pyrazol-4-yl)methanamine hydrochloride Step 1: Benzyl (S)-3-(4-(((tert-butoxycarbonyl)amino)methyl)-1H-pyrazol-1-yl)pyrrolidine-1-carboxylate Sodium hydride (540 mg, 13.5 mmol) was added to a mixture of tert-butyl N-(1H-pyrazol-4-ylmethyl)carbamate (1.78 g, 9.0 mmol) in DMF (12 mL) at 10° C. The mixture was stirred for 30 minutes then warmed to room temperature. Benzyl (3R)-3-(p-tolylsulfonyloxy)pyrrolidine-1-carboxylate (4.4 g, 11.7 mmol) was added to the mixture and stirred overnight. The reaction was diluted with ethyl acetate (300 ml) and washed with 0.5N HCl (75 ml), saturated sodium bicarbonate (75 ml), and brine(100 ml). The organic layer was dried over sodium sulfate, filtered, and concentrated in vacuo. The crude product was purified by column chromatography (SiO$_2$) eluting with a gradient of 0-100% ethyl acetate in dichloromethane to provide 1.99 g (55% yield) of title compound. ESMS(M+1)=399.42.

Step 2: tert-Butyl (S)-((1-(pyrrolidin-3-yl)-1H-pyrazol-4-yl)methyl)carbamate

To a slurry of 10% Pd/C (100 mg) in methanol (20 ml) was added benzyl (S)-3-(4-(((tert-butoxycarbonyl)-amino)methyl)-1H-pyrazol-1-yl)pyrrolidine-1-carboxylate (1.59 mg, 3.97 mmol) in methanol (20 ml). A hydrogen atmosphere via balloon was added and the reaction was stirred overnight. The mixture was filtered and concentrated to dryness under vacuum provided to provide 0.99 g (94% yield) of crude product. ESMS(M+1)=267.38.

Step 3. tert-butyl (S)-((1-(1-(4-fluorophenyl)pyrrolidin-3-yl)-1H-pyrazol-4-yl)methyl)carbamate To a mixture of tert-Butyl (S)-((1-(pyrrolidin-3-yl)-1H-pyrazol-4-yl)methyl)carbamate (370 mg, 1.389 mmol), (4-fluorophenyl)boronic acid (310.9 mg, 2.2 mmol), anhydrous copper acetate (379 mg) and 4A molecular sieves (700 mg) in dichloromethane (10 mL) was added pyridine (170 µL, 2.1 mmol). The resulting mixture was stirred at room temperature under a drierite tube for 70 hours. The mixture was filtered over a pad of silica gel eluting with 10% methanol in dichloromethane and concentrated to dryness under vacuum. The crude product was purified by column chromatography (SiO₂) eluting with a gradient of 0-100% ethyl acetate in dichloromethane to provide the title compound, 140 mg (28% yield). ESMS(M+1)=361.3.

Step 4: (S)-(1-(1-(4-fluorophenyl)pyrrolidin-3-yl)-1H-pyrazol-4-yl)methanamine hydrochloride To a solution of tert-butyl (S)-((1-(1-(4-fluorophenyl)pyrrolidin-3-yl)-1H-pyrazol-4-yl)methyl)carbamate (236 mg, 0.65 mmol) in dichloromethane (3 mL) was added 2 M hydrogen chloride (2.5 ml of 2 M, 5.000 mmol) in diethyl ether. The resulting mixture was stirred for 3 hours. The reaction was concentrated to dryness to provide 133 mg (68% yield) of title product. ESMS(M+1)=261.4.

B-163. (R)-(1-(1-(4-fluorophenyl)pyrrolidin-3-yl)-1H-pyrazol-4-yl)methanamine hydrochloride The compound was prepared in a similar manner as reported for B-162 to provide the title product, 510 mg (90% yield). ESI-MS(M+1)=261.38.

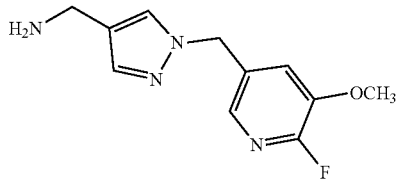 [SMILES: COc1cc(Cn2cc(CN)cn2)cnc1F]

B-164. (1-((6-Fluoro-5-methoxypyridin-3-yl)methyl)-1H-pyrazol-4-yl)methanamine trifluoroacetic Acid The compound was prepared by Method B. 1H NMR (300 MHz, Methanol-d4) δ 7.92 (d, J=2.4 Hz, 1H), 7.77-7.60 (m, 2H), 7.62-7.49 (m, 1H), 5.42 (d, J=2.4 Hz, 2H), 4.09 (s, 2H), 3.94 (t, J=2.4 Hz, 3H). ESMS(M+1)=237.5.

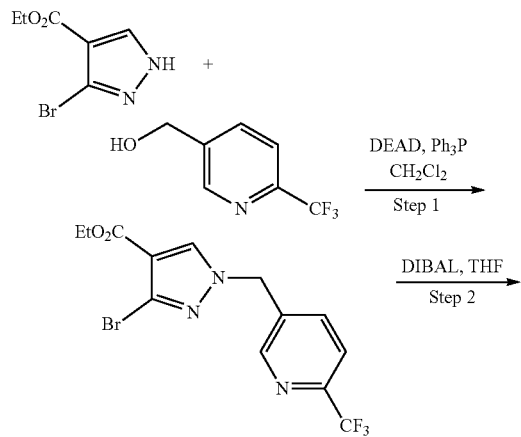

Scheme for B-165:

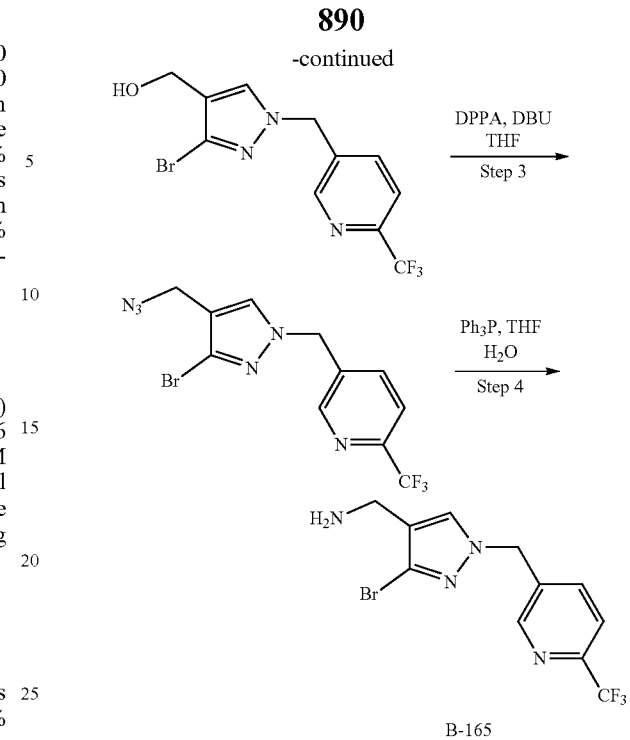

B-165. (3-bromo-1-((6-(trifluoromethyl)pyridin-3-yl)methyl)-1H-pyrazol-4-yl)methanamine Step 1: Ethyl 3-bromo-1-((6-(trifluoromethyl)pyridin-3-yl)methyl)-1H-pyrazole-4-carboxylate Di-(tert-Butyl)-azodicarboxylate (1.98 g, 8.6 mmol) was added dropwise to a cooled (0° C.) solution of ethyl 3-bromo-1H-pyrazole-4-carboxylate (1.57 g, 7.17 mmol), [6-(trifluoromethyl)-3-pyridyl]methanol (1.3 g, 7.34 mmol), and triphenylphosphine (2.26 g, 8.6 mmol) in dichloromethane (40 mL) and stirred for 30 min. The reaction was allowed to warm to room and stirred overnight. The solution was then poured onto ice water (20 ml) and extracted with dichloromethane. The reaction was evaporated in vacuo to give a viscous oil. The residue was purified by column chromatography (SiO₂, 4 g) eluting with a gradient of hexanes to 50% ethyl acetate. The desired fractions were combined and evaporated to provide the title product as clear oil (1.3 g, 48% yield). 1H NMR (300 MHz, CDCl₃) δ 8.78-8.56 (m, 1H), 7.92 (s, 1H), 7.85-7.73 (m, 1H), 7.70 (dd, J=8.1, 0.8 Hz, 1H), 5.37 (s, 2H), 4.30 (q, J=7.1 Hz, 2H), 1.34 (t, J=7.1 Hz, 3H). ESI-MS m/z calc. 376.9987, found 378.08 (M+1)⁺;

Step 2: (3-bromo-1-((6-(trifluoromethyl)pyridin-3-yl)methyl)-1H-pyrazol-4-yl)methanol A 1M solution of DIBAL(9.9 ml, 9.9 mmol) in toluene was added to a cooled (−78° C.) solution of ethyl 3-bromo-1-((6-(trifluoromethyl)pyridin-3-yl)methyl)-1H-pyrazole-4-carboxylate (1.25 g, 3.306 mmol) in THF (10 mL). The reaction was warmed to 0° C. and stirred for 2 hours. The reaction was quenched by the addition of EtOAc (30 mL). After stirring for 15 mins, Rochelle salt solution (30 mL) was added. Ethyl acetate (25 ml) was added and the organic layer was separated. The aqueous layer was extracted with ethyl acetate (2×20 mL). The combined organic layers was Step 3: 5-((4-(Azidomethyl)-3-bromo-1H-pyrazol-1-yl)methyl)-2-(trifluoromethyl)pyridine DBU (600 uL, 3.95 mmol) was added dropwise to a cooled solution (0° C.) of (3-bromo-1-((6-(trifluoromethyl)pyridin-3-yl)methyl)-1H-pyrazol-4-yl)methanol (1.1 g, 3.27 mmol) and diphenylphosphoryl azide (900 uL, 4.1 mmol) in anhydrous THF (20 ml). After 10 mins, the reaction turned cloudy. The reaction was warmed to room temperature and stirred overnight. The reaction turned to a clear tan color solution. The reaction was diluted with ethyl acetate (30 ml) and washed with aqueous ammonium chloride (10 ml) and brine (10 ml). The organic layer was dried over MgSO₄, filtered and evaporated in vacuo to afford a tan oil that was purified by column chromatography (SiO₂) eluting with a gradient of hexanes to 30% ethyl acetate. The desired fractions were combined and evaporated to afford the title product as a white solid (1.18 g, 66% yield). 1H NMR (300 MHz, CDCl₃) δ 8.70-8.58 (m, 1H), 7.71 (qd, J=8.2, 1.5 Hz, 2H), 7.44 (s, 1H), 5.36 (s, 2H), 4.21 (s, 2H).

Step 4: (3-bromo-1-((6-(trifluoromethyl)pyridin-3-yl)methyl)-1H-pyrazol-4-yl)methanamine Triphenylphosphine (860 mg, 3.24 mmol) was added to a solution of 5-((4-(Azidomethyl)-3-bromo-1H-pyrazol-1-yl)methyl)-2-(trifluoromethyl)pyridine (782 mg, 2.16 mmol) in THF (18 mL) and water (2 mL) and stirred overnight at room temperature. The reaction was concentrated to remove most of the solvent. Aqueous 2 N HCl (20 mL) and dichloromethane (20 mL) was added to the residue. The organic layer was separated and the aqueous layer was washed with dichloromethane (10 mL×2). The aqueous layer was concentrated to give a white solid that was dried under vacuum at 60° C. for 16 hours to afford the title product (745 mg, 93% yield). 1H NMR (400 MHz, Methanol-d4) δ 8.65-8.58 (m, 1H), 7.98 (d, J=1.0 Hz, 1H), 7.92 (dd, J=8.2, 2.1 Hz, 1H), 7.77 (dd, J=8.2, 0.8 Hz, 1H), 5.47 (s, 2H), 3.95 (s, 2H). ESI-MS m/z calc. 334.0041, found 335.03 (M+1)⁺.

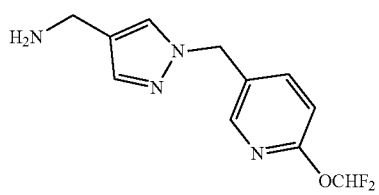

(B-166)

B-166. (1-((6-(Difluoromethoxy)pyridin-3-yl)methyl)-1H-pyrazol-4-yl)methanamine trifluoroacetic Acid The compound was prepared by method B. 1H NMR (300 MHz, Methanol-d4) δ 8.22-8.10 (m, 1H), 7.86 (d, J=0.8 Hz, 1H), 7.81-7.70 (m, 1H), 7.62 (d, J=0.8 Hz, 1H), 7.76-7.27 (t, J=73.0 Hz, 1H), 6.95 (dd, J=8.5, 0.7 Hz, 1H), 5.36 (s, 2H), 4.03 (s, 2H). ESMS(M+1)=255.21.

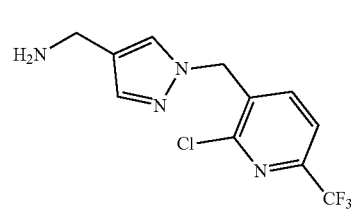

(B-167)

B-167. (1-((2-Chloro-6-(trifluoromethyl)pyridin-3-yl)methyl)-1H-pyrazol-4-yl)methanamine trifluoroacetic Acid The compound was prepared by Method B. ESMS (M+1)=290.16.

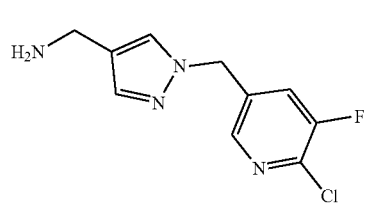

(B-168)

B-168. (1-((6-Chloro-5-fluoropyridin-3-yl)methyl)-1H-pyrazol-4-yl)methanamine trifluoroacetic Acid The compound was prepared by Method B. 1H NMR (300 MHz, Methanol-d4) δ 8.18-8.04 (m, 1H), 7.95-7.82 (m, 1H), 7.63 (s, 1H), 7.59 (dd, J=8.9, 2.0 Hz, 1H), 5.42 (s, 2H), 4.02 (s, 2H). ESMS(M+1)=241.07.

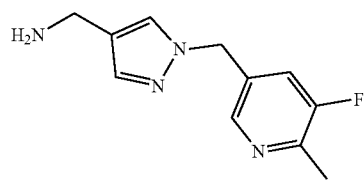 [SMILES: Cc1ncc(Cn2cc(CN)cn2)cc1F]

B-169. (1-((5-Fluoro-6-methylpyridin-3-yl)methyl)-1H-pyrazol-4-yl)methanamine trifluoroacetic Acid The compound was prepared by Method B. 1H NMR (300 MHz, Methanol-d4) δ 8.18 (s, 1H), 7.88 (s, 1H), 7.62 (d, J=0.8 Hz, 1H), 7.42 (dd, J=10.0, 1.7 Hz, 1H), 5.39 (s, 2H), 4.02 (s, 2H), 2.46 (d, J=2.9 Hz, 3H). ESMS(M+1)=221.11.

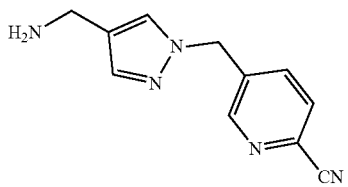 [SMILES: N#Cc1ccc(Cn2cc(CN)cn2)cn1]

B-170. 5-((4-(Aminomethyl)-1H-pyrazol-1-yl)methyl)picolinonitrile

The compound was prepared by Method B. 1H NMR (300 MHz, Methanol-d4) δ 8.64-8.54 (m, 1H), 7.97 (s, 1H), 7.87-7.79 (m, 2H), 7.68 (d, J=3.8 Hz, 1H), 5.51 (d, J=11.5 Hz, 2H), 4.09 (s, 3H). ESMS(M+1)=214.13.

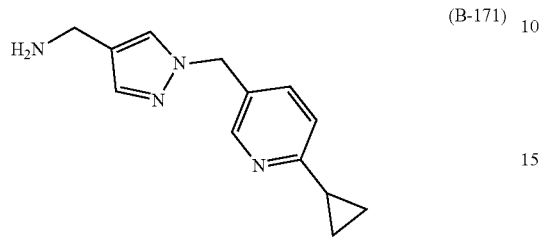

(B-171)

B-171. (1-((6-Cyclopropylpyridin-3-yl)methyl)-1H-pyrazol-4-yl)methanamine trifluoroacetic Acid The compound was prepared by Method B. 1H NMR (300 MHz, Methanol-d4) δ 8.50 (d, J=2.0 Hz, 1H), 8.21-8.09 (m, 1H), 7.96 (s, 1H), 7.66 (s, 1H), 7.55 (d, J=8.5 Hz, 1H), 5.51 (s, 2H), 4.05 (s, 2H), 2.32 (tt, J=8.7, 4.9 Hz, 1H), 1.53-1.30 (m, 3H), 1.28-1.06 (m, 2H). ESMS(M+1)=229.22.

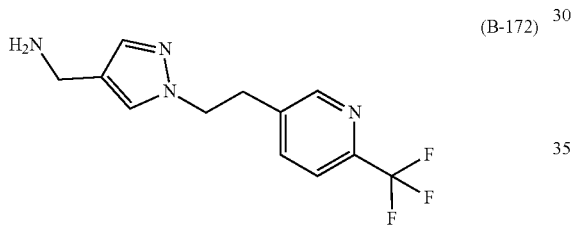

(B-172)

B-172. (1-(2-(6-(Trifluoromethyl)pyridin-3-yl)ethyl)-1H-pyrazol-4-yl)methanamine The compound was prepared by Method B. 1H NMR (300 MHz, DMSO-d6) δ 8.52 (s, 1H), 7.93 (s, 6H), 7.82 (d, J=1.1 Hz, 1H), 7.71 (s, 1H), 7.52 (s, 1H), 4.44 (t, J=6.9 Hz, 2H), 3.85 (dd, J=7.1, 4.4 Hz, 3H), 3.23 (t, J=6.9 Hz, 2H). ESMS(M+1)=271.25.

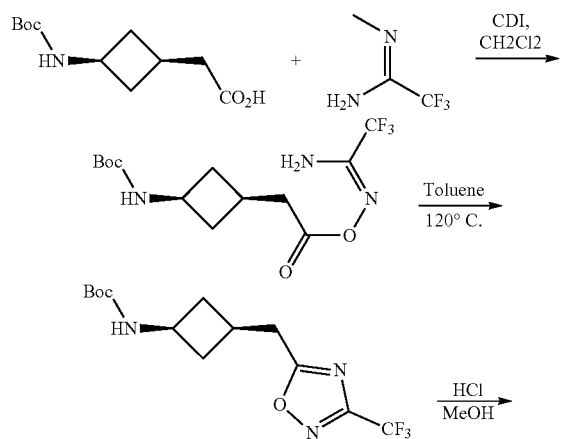

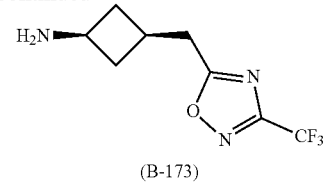

(B-173)

B-173. cis-3-((3-(trifluoromethyl)-1,2,4-oxadiazol-5-yl)methyl)cyclobutan-1-amine hydrochloride Step 1: tert-butyl (cis-3-(2-((((Z)-1-amino-2,2,2-trifluoroethylidene)amino)oxy)-2-oxoethyl)cyclobutyl)carbamate Carbonyl diimidazole(450 mg, 2.8 mmol) was added to a solution of cis-2-[3-(tert-Butoxycarbonylamino)cyclobutyl] acetic acid 527 mg, 2.3 mmol) in dichloromethane (8 ml) and stirred at room temperature. After 5 minutes, 2,2,2-trifluoro-N'-hydroxy-acetamidine (300 mg, 2.3 mmol) was added and the reaction was stirred at RT for 2 hours. The reaction was evaporated in vacuo to dryness and carried on to Step 2.

Step 2: tert-butyl (cis-3-((3-(trifluoromethyl)-1,2,4-oxadiazol-5-yl)methyl)cyclobutyl)carbamate The crude product from Step 1 was dissolved in 10 ml of toluene and refluxed for 12 hours. The reaction mixture was evaporated in vacuo and the crude purified by column chromatography (SiO₂) eluting with a gradient of heptanes to 100% ethyl acetate. The relevant fractions were combined and evaporated in vacuo to afford the title product (249 mg, 34% yield). 1H NMR (400 MHz, CDCl₃) δ 7.29 (s, 1H), 4.66 (s, 1H), 4.03 (s, 1H), 3.10 (d, J=7.3 Hz, 2H), 2.72-2.56 (m, 2H), 2.57-2.43 (m, 1H), 1.79-1.66 (m, 2H), 1.46 (s, 9H). ESI-MS m/z calc. 321.13004, found 325.3 (M+1)⁺

Step 3: cis-3-((3-(trifluoromethyl)-1,2,4-oxadiazol-5-yl)methyl)cyclobutan-1-amine hydrochloride tert-Butyl (cis-3-((3-(trifluoromethyl)-1,2,4-oxadiazol-5-yl)methyl)cyclobutyl)carbamate (239 mg, 0.74 mmol) was dissolved in methanol (8 ml) and a 4M solution of HCl in dioxane was added and the mixture heated at 50° C. for 20 mins. The reaction was evaporated in vacuo to afford a solid. This was washed with diethyl ether and hexanes, filtered and dried to afford the title product as a white solid (171 mg, 89% yield). 1H NMR (400 MHz, Methanol-d4) δ 3.71 (p, J=8.3 Hz, 1H), 3.23 (d, J=7.1 Hz, 2H), 2.76-2.55 (m, 3H), 2.00 (qd, J=9.5, 8.9, 2.5 Hz, 2H). ESI-MS m/z calc. 221.07759, found 222.1 (M+1)⁺

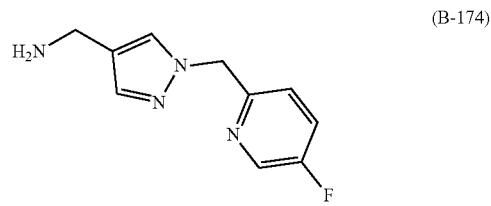 [SMILES: NCc1cnn(Cc2ccc(F)cn2)c1]

(B-174)

B-174. (1-((5-fluoropyridin-2-yl)methyl)-1H-pyrazol-4-yl)methanamine

The compound was prepared by Method B. ESMS (M+1)=207.28.

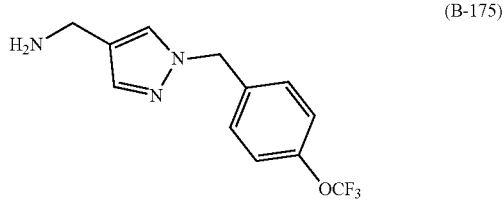 [SMILES: NCc1cnn(Cc2ccc(OC(F)(F)F)cc2)c1]

(B-175)

B-175. (1-(4-(Trifluoromethoxy)benzyl)-1H-pyrazol-4-yl)methanamine hydrochloride The compound was prepared by Method B. ESMS (M+1)=272.17.

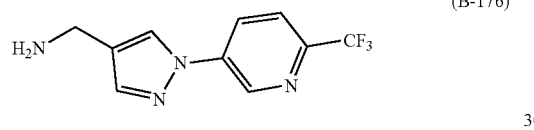

(B-176)

B-176. (1-(6-(Trifluoromethyl)pyridin-3-yl)-1H-pyrazol-4-yl)methanamine

Step A. tert-butyl ((1-(6-(trifluoromethyl)pyridin-3-yl)-1H-pyrazol-4-yl)methyl)carbamate A 2M solution of sodium t-butoxide (3.8 ml, 7.6 mmol) in THF was added to a suspension of (tert-Butyl ((1H-pyrazol-4-yl)methyl)carbamate (500 mg, 2.54 mmol) and 5-bromo-2-(trifluoromethyl)pyridine (573 mg, 2.54 mmol) in tert-butanol (12.5 ml) in a sealed tube. The mixture was sonicated for 10 mins. until mixed well. The mixture was degassed with nitrogen followed by the addition of t-BuX-Phos palladacycle Gen 2 (0.06 equiv.). The reaction was sealed and heated at 60 C for 1 hour. The crude product was purified by column chromatography (SiO$_2$) eluting a gradient of dichloromethane to 20% methanol in dichloromethane. The desired fraction were collected, treated with Biotage MP-TMT resin, filtered, and evaporated to provide the title product that was used without for further purification.

1H NMR (300 MHz, DMSO-d6) δ 9.26 (d, J=2.5 Hz, 1H), 8.57 (s, 1H), 8.45 (dd, J=8.4, 2.6 Hz, 1H), 8.04 (d, J=8.6 Hz, 1H), 7.78 (s, 1H), 7.27 (s, 1H), 4.08 (d, J=5.9 Hz, 2H), 1.40 (s, 9H). ESMS (M+1)=343.32.

Step B. (1-(6-(trifluoromethyl)pyridin-3-yl)-1H-pyrazol-4-yl)methanamine trifluoroacetate tert-Butyl ((1-(6-(trifluoromethyl)pyridin-3-yl)-1H-pyrazol-4-yl)methyl)carbamate (105 mg, 0.03 mmol) was dissolved in dichloromethane and TFA (25 uL, 0.03 mmol) was added and the reaction stirred at room temperature for 3 hours. The reaction was evaporated in vacuo to afford 109 mg of the desired product. 1H NMR (300 MHz, DMSO-d6) δ 9.28 (d, J=2.6 Hz, 1H), 8.77 (s, 1H), 8.48 (dd, J=8.7, 2.6 Hz, 1H), 8.28-8.03 (m, 4H), 7.99 (s, 1H), 4.03 (q, J=5.7 Hz, 2H). ESMS (M+1)=243.23.

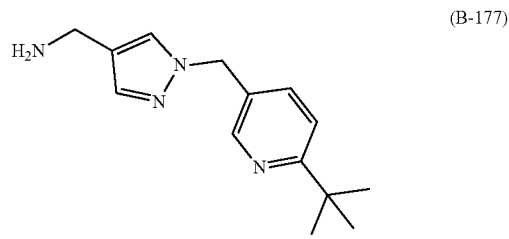 [SMILES: CC(C)(C)c1ccc(Cn2cc(CN)cn2)cn1]

(B-177)

B-177. (1-((6-(tert-Butyl)pyridin-3-yl)methyl)-1H-pyrazol-4-yl)methanamine

The compound was prepared by Method B. 1H NMR (300 MHz, CDCl$_3$) δ 8.50-8.42 (m, 1H), 7.54-7.44 (m, 2H), 7.41-7.30 (m, 2H), 5.25 (s, 2H), 4.70 (s, 1H), 4.16 (d, J=5.8 Hz, 2H), 1.45 (s, 9H), 1.36 (s, 9H). ESMS (M+1)=345.34.

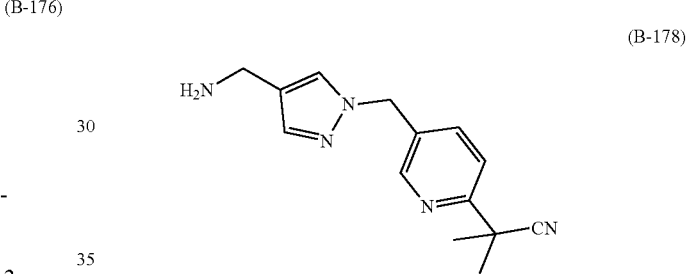

(B-178)

B-178. 2-(5-((4-(aminomethyl)-1H-pyrazol-1-yl)methyl)pyridin-2-yl)-2-methylpropanenitrile The compound was prepared by Method B. 1H NMR (300 MHz, Methanol-d4) δ 8.49 (d, J=2.3 Hz, 1H), 7.90 (s, 1H), 7.75 (dd, J=8.2, 2.4 Hz, 1H), 7.68-7.52 (m, 2H), 5.42 (s, 2H), 4.04 (s, 2H), 1.72 (s, 6H). ESMS (M+1)=256.21.

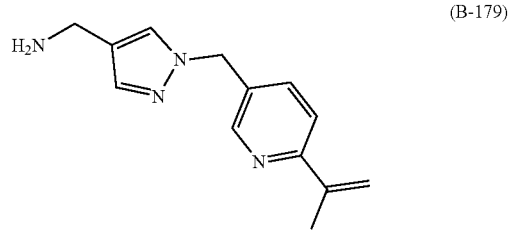 [SMILES: C=C(C)c1ccc(Cn2cc(CN)cn2)cn1]

(B-179)

B-179. (1-((6-(prop-1-en-2-yl)pyridin-3-yl)methyl)-1H-pyrazol-4-yl)methanamine

Step A. tert-Butyl ((1-((6-(prop-1-en-2-yl)pyridin-3-yl)methyl)-1H-pyrazol-4-yl)methyl)carbamate tert-Butyl ((1-((6-chloropyridin-3-yl)methyl)-1H-pyrazol-4-yl)methyl)carbamate (970 mg, 3 mmol) and isopropenylboronic acid (515 mg, 6 mmol) was taken into 15 ml of anhydrous dioxane and degassed by with nitrogen. Pd(dppf)Cl2 was added to the mixture and the reaction heated at 80 C for 7 days. The solvent was evaporated in vacuo. The resulting residue was taken into ethyl acetate (20 ml) and washed with water (2×10 ml) and brine. The organic layer was collected and dried over anhydrous sodium sulfate, filtered, and evaporated to provide the crude product that was purified by column chromatography (SiO$_2$) eluting with a gradient of hexanes to 50% ethyl acetate. The desired fractions were combined an devaporated to provide the desired product as a light brown solid (530 mg, 49.9% yield). 1H NMR (300 MHz, CDCl$_3$) δ 8.54-8.38 (m, 1H), 7.58-7.42 (m, 3H), 7.37 (s, 1H), 5.85 (dd, J=1.6, 0.9 Hz, 1H), 5.40-5.19 (m, 3H), 4.76 (s, 1H), 4.14 (dd, J=8.3, 6.3 Hz, 3H), 2.20 (dd, J=1.5, 0.8 Hz, 3H), 1.44 (s, 9H). ESMS (M+1)=329.17.

Step B. (1-((6-(prop-1-en-2-yl)pyridin-3-yl)methyl)-1H-pyrazol-4-yl)methanamine trifluoro acetic acetate The compound was prepared by deprotection of the Boc protecting by treating with TFA to afford the desired product. 1H NMR (300 MHz, Methanol-d4) δ 8.52 (s, 1H), 8.01 (dd, J=17.4, 8.0 Hz, 2H), 7.93 (d, J=3.4 Hz, 1H), 7.66 (d, J=5.0 Hz, 1H), 5.90 (d, J=2.3 Hz, 1H), 5.57 (d, J=8.0 Hz, 2H), 5.50 (s, 2H), 2.23 (dq, J=1.5, 0.7 Hz, 3H). ESMS (M+1)=229.18.

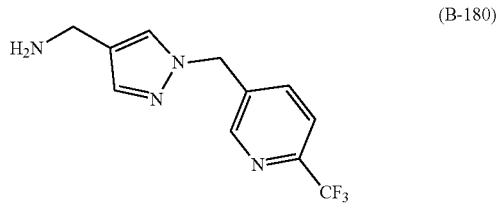 [SMILES: NCc1cnn(Cc2ccc(C(F)(F)F)nc2)c1]

(B-180)

B-180. (1-((6-(trifluoromethyl)pyridin-3-yl)methyl)-1H-imidazol-4-yl)methanamine Step A. 1-((6-(trifluoromethyl)pyridin-3-yl)methyl)-1H-imidazole-4-carbonitrile 1H-imidazole-4-carbonitrile (300 mg, 3.22 mmol) and 5-(chloromethyl)-2-(trifluoromethyl)pyridine (662 mg, 3.385 mmol) were taken into anhydrous DMF (5 ml) and cooled to 0° C. Sodium hydride (150 mg, 3.7 mmol) was added to the solution portionwise and stirred at room temperature for 2 hours. The reaction was quenched with saturated ammonium chloride (10 ml) followed by evaporation of the solvent in vacuo. The residue was suspended in dichloromethane (20 ml) and water (20 ml). The aqueous layer was extracted further with dichloromethane (20 ml). The organic layers were combined, washed with water and brine, dried over anhydrous sodium sulfate, filtered, and evaporated in vacuo to provide the crude product which was purified by column chromatography (SiO$_2$) eluting with a gradient of heptanes to 100% ethyl acetate to provide the title product as a white solid (79 mg, 9.7% yield). 1H NMR (300 MHz, CDCl$_3$) S H NMR (300 MHz, (m, 1H), 8.79-8.57 (m, 1H), 8.50-8.23 (m, 1H), 8.02-7.83 (m, 2H), 7.84-7.72 (m, 1H), 5.56 (s, 2H).

Step B. tert-butyl ((1-((6-(trifluoromethyl)pyridin-3-yl)methyl)-1H-imidazol-4-yl)methyl)carbamate 1-((6-(trifluoromethyl)pyridin-3-yl)methyl)-1H-imidazole-4-carbonitrile (80 mg, 0.32 mmol), dichlorocobalt hexahydrate (15 mg, 0.063 mmol) and di-tert-butyl dicarbonate (83.5 mg, 0.3826 mmol) were taken into methanol and cooled to 0° C. followed by the addition of sodium borohydride (36.5 mg, 0.96 mmol) portionwise. The reaction was stirred for 2 hours. After evaporation of the reaction, dichloromethane and water was added and the organic layer was collected and filtered to remove the solid suspension. The organic layer was washed with brine, dried over anhydrous magnesium sulfate, and evaporated in vacuo to provide the crude product which was purified by column chromatography (SiO$_2$, 4 g) eluting with a gradient of dichloromethane to 10% methanol to afford the title product as a white solid (67 mg, 57% yield). 1H NMR (300 MHz, CDCl$_3$) δ 8.48-8.29 (m, 1H), 7.57 (d, J=8.1 Hz, 1H), 7.49-7.33 (m, 2H), 7.05-6.83 (m, 1H), 5.28 (s, 2H), 5.17 (t, J=6.9 Hz, 1H), 4.18 (d, J=6.1 Hz, 2H), 1.25 (s, 9H); 19 F NMR (282 MH z, CDCl$_3$) δ−67.91.

Step C. (1-((6-(trifluoromethyl)pyridin-3-yl)methyl)-1H-imidazol-4-yl)methanamine tert-Butyl ((1-((6-(trifluoromethyl)pyridin-3-yl)methyl)-1H-imidazol-4-yl)methyl)carbamate (68 mg, 0.1822 mmol) was taken into dichloromethane and TFA (207.8 mg, 140.4 µL, 1.822 mmol) and stirred at room temperature for 1 hour. The reaction was evaporated in vacuo to provide a residue that was triturated with diethyl ether to afford the product as a white solid (67 mg (100% yield) that was used without further purification.

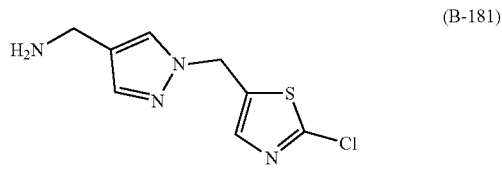 [SMILES: NCc1cnn(Cc2cnc(Cl)s2)c1]

(B-181)

B-181. (1-((2-chlorothiazol-5-yl)methyl)-1H-pyrazol-4-yl)methanamine

The compound was prepared by Method B. 1H NMR (300 MHz, DMSO-d6) δ 7.66 (m, 2H), 7.36 (d, J=0.8 Hz, 1H), 7.16 (t, J=5.7 Hz, 1H), 5.52 (s, 2H), 3.93 (d, J=6.0 Hz, 2H), 1.37 (s, 9H). ESMS (M+1)=329.08.

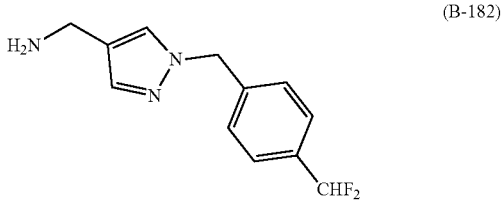 [SMILES: NCc1cnn(Cc2ccc(C(F)F)cc2)c1]

(B-182)

B-182. (1-((6-(difluoromethyl)pyridin-3-yl)methyl)-1H-pyrazol-4-yl)methanamine

The compound was prepared by Method B. ESMS (M+1)=239.13.

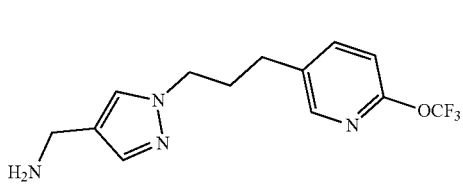

(B-183)

B-183. (1-(3-(6-(trifluoromethyl)pyridin-3-yl)propyl)-1H-pyrazol-4-yl)methanamine trifluoro acetic Acid The compound was prepared by Method B. 1H NMR (300 MHz, DMSO-d6) δ 8.62 (d, J=2.1 Hz, 1H), 7.99 (s, 3H), 7.93 (dd, J=8.2, 2.1 Hz, 1H), 7.87-7.78 (m, 2H), 7.53 (s, 1H), 4.14 (t, J=6.9 Hz, 2H), 3.90 (q, J=5.7 Hz, 2H), 2.67 (t, J=7.6 Hz, 2H), 2.20-2.01 (m, 2H). ESMS (M+1)=285.21

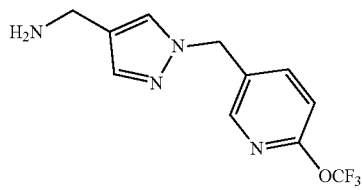

(B-184)

B-184. (1-((6-(trifluoromethoxy)pyridin-3-yl)methyl)-1H-pyrazol-4-yl)methanamine trifluoro acetic Acid The compound was prepared by Method B. 1H NMR (300 MHz, Methanol-d4) δ 8.27 (d, J=2.5 Hz, 1H), 7.95-7.91 (m, 1H), 7.91-7.82 (m, 1H), 7.67 (s, 1H), 7.17 (d, J=8.5 Hz, 1H), 5.46 (s, 2H), 4.07 (s, 2H). ESMS (M+1)=273.23.

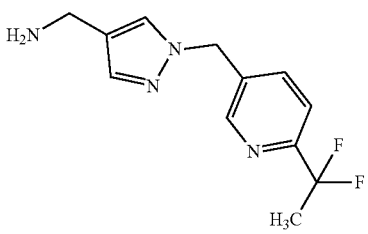

(B-185)

B-185. (1-((6-(1,1-difluoroethyl)pyridin-3-yl)methyl)-1H-pyrazol-4-yl)methanamine hydrochloride The compound was prepared by Method B. 1H NMR (300 MHz, Methanol-d4) δ 8.65-8.54 (m, 1H), 8.04-7.93 (m, 2H), 7.80 (dd, J=8.2, 0.8 Hz, 1H), 7.67 (s, 1H), 5.52 (s, 2H), 4.05 (s, 2H), 1.99 (td, J=18.7, 0.6 Hz, 3H). ESMS (M+1)=253.14.

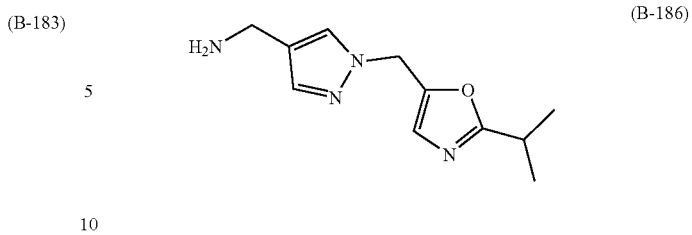

(B-186)

B-186. (1-((2-isopropyloxazol-5-yl)methyl)-1H-pyrazol-4-yl)methanamine trifluoroacetic Acid The compound was prepared by Method B. 1H NMR (300 MHz, CD$_3$OD) δ 7.94-7.71 (m, 2H), 7.59 (s, 1H), 5.22 (s, 2H), 4.02 (s, 2H), 3.17-2.94 (m, 1H), 1.41-1.15 (m, 6H).

(B-187)

B-187. (1-(3,5-difluoro-4-methoxybenzyl)-1H-1,2,4-triazol-3-yl)methanamine

Step 1: 1-(3,5-difluoro-4-methoxybenzyl)-1H-1,2,4-triazole-3-carbonitrile 1H-1,2,4-triazole-3-carbonitrile (2 g, 21.26 mmol), 5-(bromomethyl)-1,3-difluoro-2-methoxy-benzene (5.55 g, 23.4 mmol), and potassium carbonate were taken into acetonitrile (20 ml) and stirred at room temperature for 3 days. The reaction was diluted with 20 ml of water and extracted with ethyl acetate (3×20 ml). The combined extracts was washed with brine, dried over anhydrous sodium sulfate, filtered, and evaporated in vacuo to afford the crude product. as a white solid that was purified by column chromatography elutine with a gradient of heptanes to 100% ethyl acetate to provide the title product as a white solid (2.33 g, 43% yield). 1H NMR (300 MHz, Methanol-d4) δ 9.01 (s, 1H), 7.21 (m, 2H), 5.5 (s, 2H), 3.92 (s, 3H).

Step 2: (1-(3,5-difluoro-4-methoxybenzyl)-1H-1,2,4-triazol-3-yl)methanamine 1-(3,5-difluoro-4-methoxybenzyl)-1H-1,2,4-triazole-3-carbonitrile (1 g, 4 mmol) was added to a slurry of raney nickel in methanol and ammonia and placed on the Paar shaker under 50 psi of hydrogen. The reaction mixture was filtered through Celite and the filtrate evaporated in vacuo. The crude product was purified by column chromatography (SiO$_2$) eluting with a gradient of dichloromethane to 70% ethyl acetate to afford the title product as a white solid (796 mg, 78% yield); ESMS(M+1)=255.11.

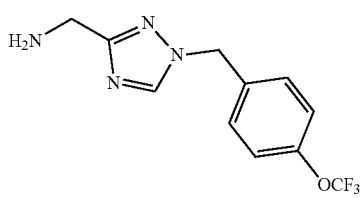

B-188. (1-(4-(trifluoromethoxy)benzyl)-1H-1,2,4-triazol-3-yl)methanamine

The compound was prepared in 2 steps by the procedure reported for B-187. ESMS(M+1)=273.12.

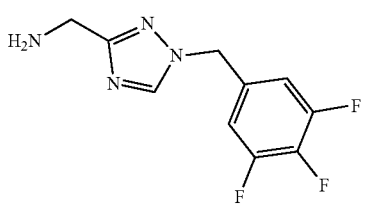

B-189. (1-(3,4,5-trifluorobenzyl)-1H-1,2,4-triazol-3-yl)methanamine

The compound was prepared in 2 steps by the procedure reported for B-187; ESMS(M+1)=243.09.

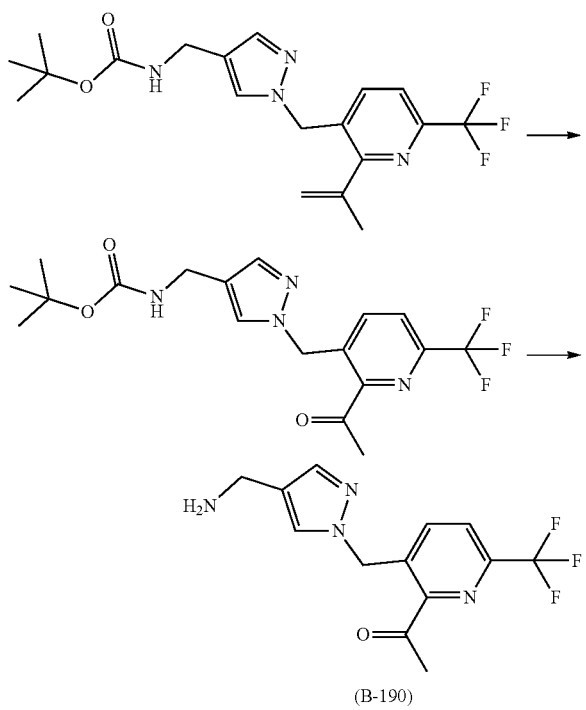

(B-190)

B-190. 1-[3-[[4-(aminomethyl)pyrazol-1-yl]methyl]-6-(trifluoromethyl)-2-pyridyl]ethanone hydrochloride Step 1: tert-Butyl ((1-((2-acetyl-6-(trifluoromethyl)pyridin-3-yl)methyl)-1H-pyrazol-4-yl)methyl)carbamate Sodium periodate (4.32 g, 20.20 mmol) was added to a solution of tert-butyl ((1-((2-(prop-1-en-2-yl)-6-(trifluoromethyl)pyridin-3-yl)methyl)-1H-pyrazol-4-yl)methyl)carbamate, B-81 (2 g, 5.045 mmol) in THF (10.00 mL), acetone (10.00 mL), and water (10.00 mL) and cooled in an ice bath. Trichlororuthenium monohydrate (46 mg, 0.204 mmol) was added to the mixture and stirred for 2 hours. The reaction was filtered through Celite and the filtrate evaporated in vacuo. The resulting residue was dissolved in dichloromethane and washed with brine. The organic layer was dried over anhydrous sodium sulfate, filtered, and evaporated in vacuo. The crude oil was purified by column chromatography (SiO₂) eluting with a gradient of heptane to 60% ethyl acetate. Evaporation of the desired fractions afforded the product (1.6 g) that was used immediately in the next step.

Step 2: 1-(3-((4-(aminomethyl)-1H-pyrazol-1-yl)methyl)-6-(trifluoromethyl)pyridin-2-yl)ethan-1-one hydrochloride tert-Butyl ((1-((2-acetyl-6-(trifluoromethyl)pyridin-3-yl)methyl)-1H-pyrazol-4-yl)methyl)carbamate (1.6 g) was taken into dichloromethane (10 ml) and 2.1 ml of TFA and stirred for 2 hours. The reaction was evaporated in vacuo and the resulting oil was dissolved in dichloromethane and washed with 10% sodium carbonate. The organic layer was dried over anhydrous sodium sulfate, filtered and evaporated. The resulting oil was dissolved in diethyl ether and 5 ml of 1N HCl in diethyl ether was added resulting in a white solid that was collected and dried to afford the title product (1.03 g, 61% yield). 1H NMR (300 MHz, DMSO-d6) δ 8.27 (s, 3H), 8.09 (d, J=8.2 Hz, 1H), 7.97 (s, 1H), 7.67 (s, 1H), 7.38 (d, J=8.2 Hz, 1H), 5.76 (d, J=2.7 Hz, 2H), 3.91 (q, J=5.6 Hz, 2H), 2.68 (s, 3H). ESI-MS m/z calc. 298.10416, found 299.13 (M+1)+.

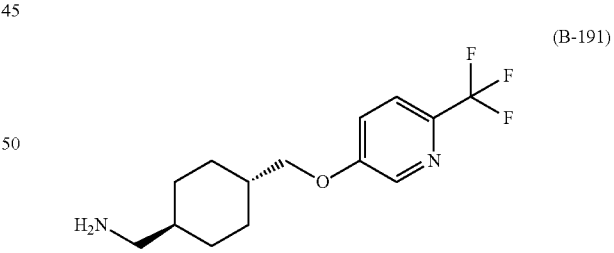

B-191. (trans-4-(((6-(trifluoromethyl)pyridin-3-yl)oxy)methyl)cyclohexyl)methanamine Step 1: tert-Butyl ((trans-4-(((6-(trifluoromethyl)pyridin-3-yl)oxy)methyl)cyclohexyl)methyl)carbamate Diisopropyl azodicarboxylate (500 uL, 2.59 mmol) was added dropwise to a solution of tert-butyl ((trans-4-(hydroxymethyl)cyclohexyl)methyl)carbamate (525 mg, 2.16 mmol), 6-(trifluoromethyl)pyridin-3-ol (410 mg, 2.514 mmol), and triphenylphosphine (854 mg, 3.26 mmol) in THF (15 ml) and the reaction stirred overnight. Water (25 ml) was added to the reaction mixture followed by extraction with ethyl acetate (3×25 ml). The combined organic extracts were washed with brin, dried over anhydrous sodium sulfate, filtered, and evaporated in vacuo to afford the crude product. This was purified by column chromatography (SiO$_2$) eluting with a gradient of 0-100% dichloromethane-ethyl acetate. The desired fractions were combined and evaporated to afford the title product (670 mg, 13% yield). 1H NMR (300 MHz, CD$_3$CN) δ 8.38 (d, J=2.8 Hz, 1H), 7.72 (d, J=8.7 Hz, 1H), 7.44 (dd, J=8.6, 2.6 Hz, 1H), 5.30 (s, 1H), 3.95 (d, J=6.4 Hz, 2H), 2.91 (t, J=6.4 Hz, 2H), 2.12 (d, J=10.0 Hz, 2H), 1.91-1.69 (m, 4H), 1.40 (d, J=16.5 Hz, 10H), 1.28-0.85 (m, 5H).

Step 2: (trans-4-(((6-(trifluoromethyl)pyridin-3-yl)oxy)methyl)cyclohexyl)methanamine dihydrochloride tert-Butyl ((trans-4-(((6-(trifluoromethyl)pyridin-3-yl)oxy)methyl)cyclohexyl)methyl)carbamate (670 mg) was taken into 10 ml of dichloromethane. A solution of 4M HCl (2 ml, 8 mmol) in dioxane was added to the solution and stirred for 1 hour. The reaction was evaporated in vacuo to afford a solid that was washed with diethyl ether and hexanes, filtered and evaporated to afford the title product (411 mg). 1H NMR (300 MHz, DMSO-d6) δ 8.44 (d, J=2.8 Hz, 1H), 7.83 (d, J=8.7 Hz, 4H), 7.59 (dd, J=8.7, 2.6 Hz, 1H), 3.98 (d, J=6.3 Hz, 2H), 2.66 (s, 2H), 1.83 (dd, J=30.4, 16.5 Hz, 5H), 1.55 (s, 1H), 1.21-0.80 (m, 4H). ESI-MS m/z calc. 288.14496, found 289.57 (M+1)$^+$.

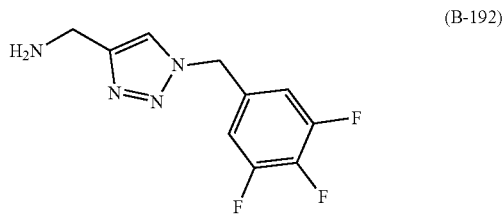 [SMILES: NCc1cn(Cc2cc(F)c(F)c(F)c2)nn1]

(B-192)

B-192. (1-(3,4,5-Trifluorobenzyl)-1H-1,2,3-triazol-4-yl)methanamine 5-(bromomethyl)-1,2,3-trifluoro-benzene (1 g, 4.44 mmol) was added dropwise to a solution of sodium azide (315 mg, 4.85 mmol) in DMSO (30 ml) and stirred at room temperature for 15 mins. Propargylamine (245 mg, 4.44 mmol) was added to the solution followed by the addition of triethylamine (100 uL, 0.66 mmol) and CuBr (637 mg, 4.44 mmol). The reaction was stirred at room temperature for 30 mins. The reaction was poured into ice water(200 ml) and the resulting precipitate was filtered and washed with dilute ammonium hydroxide and water. The crude solid was purified by preparative reverse phase chromatography (C18 column) eluting with 0 to 100% acetonitrile/water (TFA modifier). The desired fractions were combined and evaporated in vacuo to provide the product as a yellow oil (930 mg, 86% yield). ESMS (M+1)=243.15

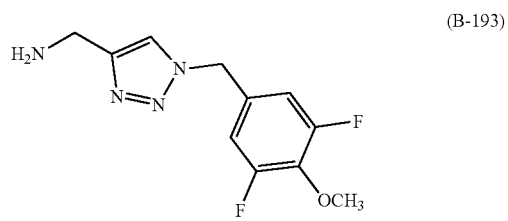 [SMILES: COc1c(F)cc(Cn2cc(CN)nn2)cc1F]

(B-193)

B-193. (1-(3,5-Difluoro-4-methoxybenzyl)-1H-1,2,3-triazol-4-yl)methanamine

The compound was prepared by the same procedure as B-192 to provide the desired product. ESMS (M+1)=255.17.

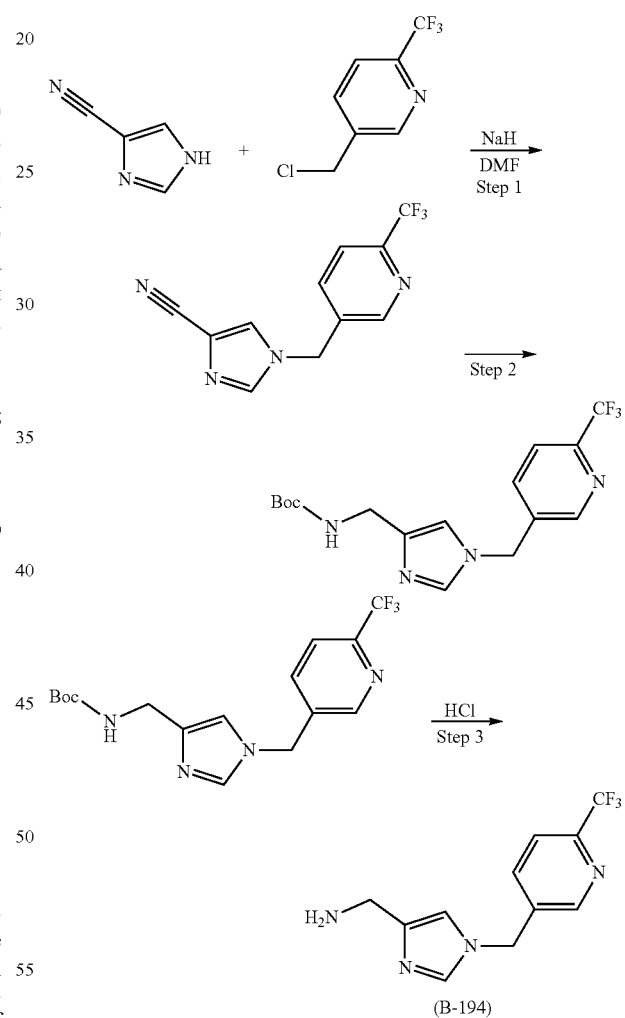

(B-194)

B-194. (1-((6-(trifluoromethyl)pyridin-3-yl)methyl)-1H-imidazol-4-yl)methanamine Step 1: 1-((6-(trifluoromethyl)pyridin-3-yl)methyl)-1H-imidazole-4-carbonitrile 1H-imidazole-4-carbonitrile (300 mg, 3.22 mmol) and chloromethyl)-2-(trifluoromethyl)pyridine (662 mg, 3.385 mmol) were taken into anhydrous DMF(5 ml) and cooled to 0° C. Sodium hydride (150 mg, 3.72 mmol) was added to the mixture portionwise then warmed to room temperature. After stirring for 2 hours, the reaction was quenched with saturated ammonium chloride (10 ml). The mixture was diluted with dichloromethane (25 ml) and water (20 ml) and the layers separated. The aqueous was extracted with dichloromethane (2×10 ml). The combined organic extracts was washed with water (10 ml) and brine (2×10 ml), dried over anhydrous sodium sulfate, filtered, and evaporated in vacuo. The crude product was purified by column chromatography (SiO$_2$) eluting with to provide a white solid (79 mg, 9.7% yield). 1H NMR (300 MHz, CDCl$_3$) δ H NMR (300 MHz, (m, 1H), 8.79-8.57 (m, 1H), 8.50-8.23 (m, 1H), 8.02-7.83 (m, 2H), 7.84-7.72 (m, 1H), 5.56 (s, 2H).

Step 2: tert-Butyl ((1-((6-(trifluoromethyl)pyridin-3-yl)methyl)-1H-imidazol-4-yl)methyl)carbamate 1-((6-(trifluoromethyl)pyridin-3-yl)methyl)-1H-imidazole-4-carbonitrile (79 mg, 0.32 mmol), dichlorocobalt hexahydrate (15 mg, 0.063 mmol) and Boc$_2$O(83 mg, 0.383) were taken into methanol and cooled to 0° C. Sodium borohydride (36.5 mg, 0.96 mmol) was added to the solution portionwise and stirred for 2 hours. The reaction was evaporated in vacuo. The black residue was suspended in dichloromethane and water. The organic layer was collected and filtered to remove solid suspension. The organic layer was washed with brine, dried over anhydrous magnesium sulfate filtered, and evaporated in vacuo. The resulting residue was purified by column chromatography (SiO$_2$, 4 g) eluting with a gradient of 0-10% methanol in dichloromethane, The desired fractions were combined and evaporated in vacuo to afford the title product as a white solid (67 mg, 57% yield). 1H NMR (300 MHz, CDCl$_3$) δ 8.48-8.29 (m, 1H), 7.57 (d, J=8.1 Hz, 1H), 7.49-7.33 (m, 2H), 7.05-6.83 (m, 1H), 5.28 (s, 2H), 5.17 (t, J=6.9 Hz, 1H), 4.18 (d, J=6.1 Hz, 2H), 1.25 (s, 9H). ESMS (M+1)=357.19.

Step 3: (1-((6-(trifluoromethyl)pyridin-3-yl)methyl)-1H-imidazol-4-yl)methanamine tert-Butyl ((1-((6-(trifluoromethyl)pyridin-3-yl)methyl)-1H-imidazol-4-yl)methyl)carbamate (68 mg, 0.182 mmol) was dissolved in dichloromethane (2 ml) and TFA (140 uL, 1.82 mmol) and stirred at room temperature for 1 hour. The reaction was evaporated in vacuo. The resulting residue was triturated with diethyl ether to afford a white solid (68 mg, quantitative yield). The compound was used without further characterization.

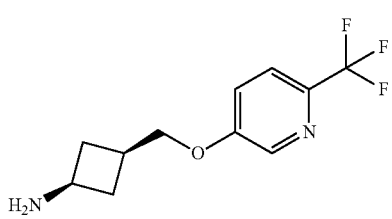

(B-195)

B-195. cis-3-(((6-(trifluoromethyl)pyridin-3-yl)oxy)methyl)cyclobutan-1-amine

Step 1: tert-butyl (cis-3-(((6-(trifluoromethyl)pyridin-3-yl)oxy)methyl)-cyclobutyl)carbamate Diethyl azodicarobxylate (13 mL of 40% w/w, 28 mmol) was added dropwise to a solution of tert-butyl (cis-3-(hydroxymethyl)-cyclobutyl)carbamate (4.699 g, 23.35 mmol), 6-(trifluoromethyl)pyridin-3-ol (4.2 g, 25.7 mmol) and triphenylphosphine (7.349 g, 6.492 mL, 28.02 mmol) in THF (80 mL) at room temperature and stirred for 1 hour. The solvent was evaporated. The residue was dissolved in dichloromethane (100 ml) and washed with 2N sodium hydroxide (2×). The solvent was evaporated in vacuo to give an oil that was purified by column chromatography (SiO$_2$) eluting with a gradient hexanes to 100% ethyl acetate. The desired fractions were evaporated to afford the title product (3.11 g, 38% yield). 1H NMR (400 MHz, CDCl$_3$) δ 8.39 (d, J=2.8 Hz, 1H), 7.63 (d, J=8.7 Hz, 1H), 7.29-7.20 (m, 1H), 4.73 (s, 1H), 4.17-4.08 (m, 1H), 4.02 (d, J=5.4 Hz, 2H), 2.68-2.37 (m, 3H), 1.91-1.75 (m, 2H), 1.47 (s, 9H). ESI-MS m/z calc. 346.15042, found 347.27 (M+1)$^+$;

Step 2: cis-3-(((6-(trifluoromethyl)pyridin-3-yl)oxy)methyl)cyclobutan-1-amine tert-Butyl (cis-3-(((6-(trifluoromethyl)pyridin-3-yl)oxy)methyl)-cyclobutyl)carbamate (3.11 g, 9 mmol) was taken into a 4M solution of hydrogen chloride (25 mL of 4 M, 100.0 mmol) in dioxane. After stirring for 2 hours, diethyl ether was added ot the mixture and the white solid was collected and dried to afford a white solid: 2.42 g 1H NMR (400 MHz, DMSO-d6) δ 8.46 (d, J=2.8 Hz, 1H), 8.16 (s, 3H), 7.85 (d, J=8.7 Hz, 1H), 7.61 (dd, J=8.7, 2.9 Hz, 1H), 4.14 (d, J=6.2 Hz, 2H), 3.63 (s, 1H), 2.57 (dt, J=7.9, 1.7 Hz, 0H), 2.36 (tdd, J=9.4, 6.1, 2.2 Hz, 2H), 2.04 (d, J=10.2 Hz, 2H). ESI-MS m/z calc. 246.09799, found 247.13 (M+1)$^+$.

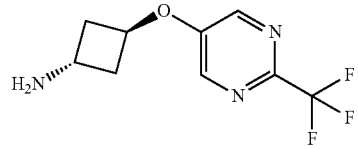 [SMILES: N[C@H]1C[C@H](Oc2cnc(C(F)(F)F)nc2)C1]

B-196. trans-3-((2-(trifluoromethyl)pyrimidin-5-yl)oxy)cyclobutan-1-amine

Step 1: tert-butyl (trans-3-((2-(trifluoromethyl)pyrimidin-5-yl)oxy)cyclobutyl)-carbamate Diethyl azodicarboxylate (3.375 g, 3.530 mL of 40% w/w, 7.752 mmol) was added to a solution of tert-butyl (cis-3-hydroxycyclobutyl)carbamatecarbamate (1.33 g, 7.11 mmol), 2-(trifluoromethyl)pyrimidin-5-ol (1.06 g, 6.46 mmol) and triphenylphosphine (2.033 g, 1.796 mL, 7.752 mmol) in THF (20 mL) was added a dropwise at room temperature. The reaction was heated to 50° C. for 1 hour. The reaction was evaporated in vacuo and the residue purified by column chromatography (SiO2) eluting with a gradient of heptane to 100% ethyl acetate. The desired fractions were combined and evaporated in vacuo to afford 1.79 g of the title product. 1H NMR (400 MHz, CDCl$_3$) δ 8.40 (s, 2H), 5.02-4.86 (m, 1H), 4.80 (s, 1H), 4.35 (s, 1H), 2.63 (ddd, J=11.7, 8.2, 3.4 Hz, 2H), 2.55 (d, J=5.7 Hz, 2H), 1.47 (s, 9H).

Step 2: trans-3-((2-(trifluoromethyl)pyrimidin-5-yl)oxy)cyclobutan-1-amine

To tert-butyl (trans-3-((2-(trifluoromethyl)pyrimidin-5-yl)oxy)cyclobutyl)-carbamate (1.77 g, 5.289 mmol) was added a solution of hydrogen chloride (27.58 mL of 4 M, 110.3 mmol) in dioxane and the mixture stirred at room temperature for 16 hours. A precipitate had formed. Diethyl ether was added to the mixture and stirred. The white solid was collected, washed with diethyl ether, and dried under vacuum at 50° C. to afford the title product as a white solid 1.28 g. 1H NMR (300 MHz, CD$_3$OD) δ 8.54 (s, 2H), 5.16 (d, J=25.9 Hz, 1H), 4.05 (s, 1H), 2.74 (s, 4H).

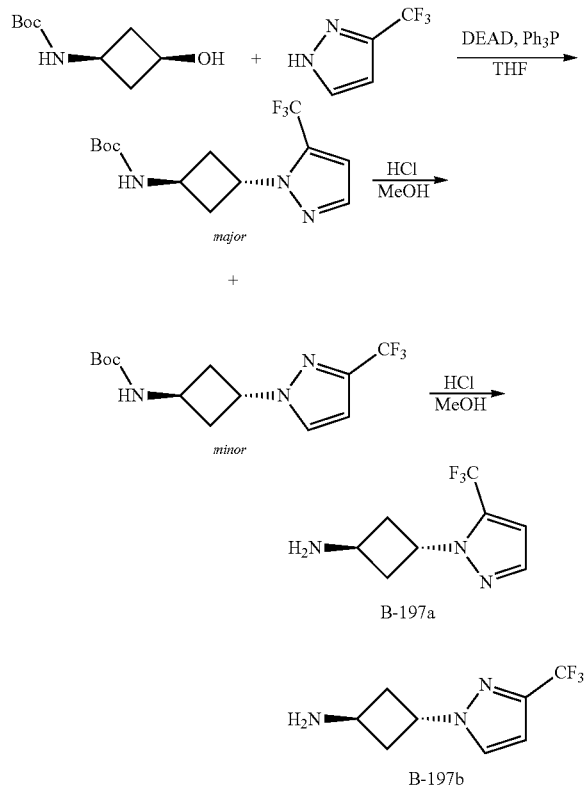

B-197a. trans-3-(5-(trifluoromethyl)-1H-pyrazol-1-yl)cyclobutan-1-amine hydrochloride B-197b. trans-3-(3-(trifluoromethyl)-1H-pyrazol-1-yl)cyclobutan-1-amine hydrochloride Step 1: tert-butyl (trans-3-(3-(trifluoromethyl)-1H-pyrazol-1-yl)cyclobutyl)carbamate and tert-butyl (trans-3-(5-(trifluoromethyl)-1H-pyrazol-1-yl)cyclobutyl)carbamate Diethyl azodicarboxylate (27 mL of 40% w/w, 59.29 mmol) was added to a cooled (0° C.) mixture of tert-butyl (cis-3-hydroxycyclobutyl)carbamate (10.09 g, 53.89 mmol) and triphenylphosphine (15.78 g, 60.16 mmol) in THF (150 mL) followed by the addition of 3-(trifluoromethyl)-4H-pyrazole (8.18 g, 60.11 mmol). The reaction was heated at 50° C. for 12 hours. The solvent was removed and the residue was purified by column chromatography (SiO$_2$) eluting with a gradient of heptanes to ethyl acetate isolating two regioisomers.

Peak 1 (minor product) as tert-butyl (trans-3-(3-(trifluoromethyl)-1H-pyrazol-1-yl)cyclobutyl)carbamate (4.09 g, 24% yield) 1H NMR (400 MHz, CDCl$_3$) δ 7.57 (d, J=1.9 Hz, 1H), 6.62 (d, J=1.9 Hz, 1H), 5.06 (t, J=7.2 Hz, 1H), 4.81 (s, 1H), 4.39 (s, 1H), 3.02 (ddd, J=13.7, 8.2, 5.7 Hz, 1H), 2.56 (d, J=21.7 Hz, 2H), 1.49 (d, J=2.1 Hz, 9H). ESI-M S m/z 319.4.

Peak 2 (major product) as tert-butyl (trans-3-(5-(trifluoromethyl)-1H-pyrazol-1-yl)cyclobutyl)carbamate. (10.82 g, 64%) 1H NMR (400 MHz, CDCl$_3$) δ 7.54-7.42 (m, 1H), 6.54 (d, J=2.4 Hz, 1H), 5.00-4.87 (m, 1H), 4.81 (s, 1H), 4.37 (s, 1H), 3.00-2.84 (m, 2H), 2.59 (s, 2H), 1.48 (s, 9H). ESI-M S m/z 319.4.

Step 2

B-197a. trans-3-(3-(trifluoromethyl)-1H-pyrazol-1-yl)cyclobutan-1-amine hydrochloride tert-Butyl (trans-3-(3-(trifluoromethyl)-1H-pyrazol-1-yl)cyclobutyl)carbamate (4.22 g, 13.36 mmol) was dissolved in methanol (35 mL). A solution of 2 M HCl in diethyl ether (31 mL, 62.00 mmol) was added and stirred at 50° C. for 1 hour. The reaction was evaporated in vacuo and the resulting solid was washed with diethyl ether and hexanes to provide the title product as a white solid (3.1 g, 96% yield). 1H NMR (400 MHz, Methanol-d4) δ 7.67 (d, J=1.9 Hz, 1H), 6.77 (d, J=1.9 Hz, 1H), 5.34-5.27 (m, 1H), 4.19-4.11 (m, 1H), 3.09-2.99 (m, 2H), 2.84-2.77 (m, 2H). ESI-MS m/z 206.08 (M+1)$^+$.

B-197b. trans-3-(5-(trifluoromethyl)-1H-pyrazol-1-yl)cyclobutan-1-amine hydrochloride tert-Butyl (trans-3-(5-(trifluoromethyl)-1H-pyrazol-1-yl)cyclobutyl)carbamate (10.82 g, 35.44 mmol) was dissolved in methanol (100 mL). A solution of 2M HCl in diethyl ether (80 mL, 160 mmol) was added to the solution and stirred at 50° C. for 1 hour. The reaction was evaporated in vacuo and the resulting solid was washed with diethyl ether and hexanes to provide the title product as a white solid (8.37 g, 98% yield). 1H NMR (400 MHz, Methanol-d4) δ 7.82 (dd, J=2.4, 1.1 Hz, 1H), 6.60 (d, J=2.4 Hz, 1H), 5.17 (ddd, J=13.9, 9.0, 5.1 Hz, 1H), 4.17 (ttd, J=8.5, 5.8, 0.9 Hz, 1H), 2.95 (dddt, J=14.0, 8.5, 5.5, 1.8 Hz, 2H), 2.87-2.69 (m, 2H). ESI-MS m/z calc. 205.08269, found 219.85 (M+1)$^+$.

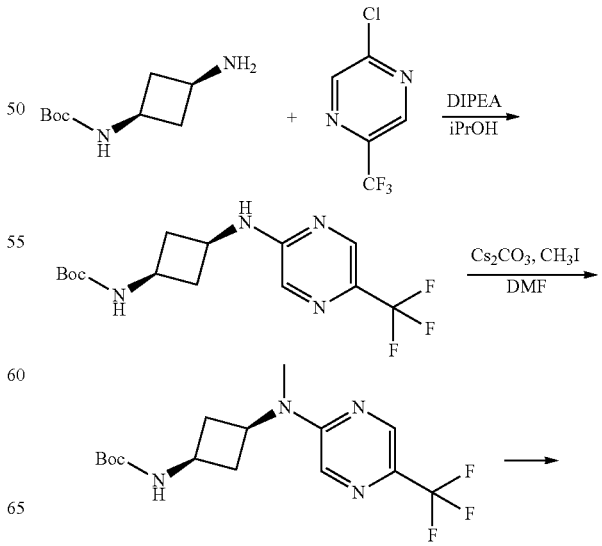

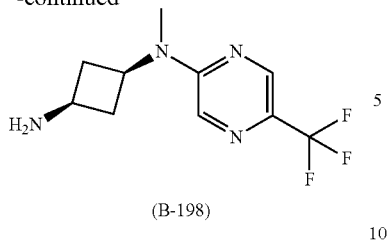

(B-198)

B-198. cis-N1-methyl-N1-(5-(trifluoromethyl)pyrazin-2-yl)cyclobutane-1,3-diamine

Step 1: tert-butyl (cis-3-((5-(trifluoromethyl)pyrazin-2-yl)amino)cyclobutyl)carbamate A mixture of tert-butyl (cis-3-aminocyclobutyl)carbamate (2.0355 g, 10.93 mmol), 2-chloro-5-(trifluoromethyl)pyrazine (2.2 g, 12.05 mmol) and Diisopropylethylamine (2.86 mL, 16.42 mmol) were taken into isopropanol (2 mL) was heated in a microwave tube for 1 hour at 150° C. The reaction was diluted with 100 ml of ethyl acetate and washed with brine. The organic layer was dried over anhydrous sodium sulfate, filtered, and evaporated in vacuo to afford a solid that was triturated with diethyl ether. The white solid was collected by vacuum filtration to provide the title product as a white solid (3.32 g, 89% yield). 1H NMR (300 MHz, CDCl$_3$) δ 8.34 (s, 1H), 7.87 (d, J=1.5 Hz, 1H), 5.18 (s, 1H), 4.71 (s, 1H), 3.92 (d, J=8.2 Hz, 1H), 3.51 (s, 1H), 2.95 (dtd, J=10.0, 7.3, 2.9 Hz, 2H), 1.90 (d, J=9.4 Hz, 2H), 1.47 (s, 9H). ESI-MS m/z 333.18 (M+1).

Step 2: tert-butyl (cis-3-(methyl(5-(trifluoromethyl)pyrazin-2-yl)amino)cyclobutyl)carbamate A mixture of tert-butyl (cis-3-((5-(trifluoromethyl)pyrazin-2-yl)amino)cyclobutyl)carbamate (510 mg, 1.496 mmol), cesium carbonate (975 mg, 2.992 mmol) and iodomethane (140 μL, 2.249 mmol) in DMF (8 mL) was stirred at room temperature for 24 hours. The reaction mixture was evaporated in vacuo and the resulting residue was treated with equal amounts of water and ethyl acetate (25 ml). The organic layer was washed with brine, dried over anhydrous sodium sulfate, filtered, and evaporate in vacuo to provide the product (518 mg, 99% yield). 1H NMR (400 MHz, CDCl$_3$) δ 8.39 (s, 1H), 8.03 (d, J=1.4 Hz, 1H), 4.70 (s, 1H), 4.46 (t, J=8.4 Hz, 1H), 3.90 (s, 1H), 3.13 (s, 3H), 2.85-2.72 (m, 2H), 2.10 (t, J=10.8 Hz, 2H), 1.48 (s, 9H). ESI-MS m/z 347.23 (M+1)$^+$

Step 3: cis-N1-methyl-N1-(5-(trifluoromethyl)pyrazin-2-yl)cyclobutane-1,3-diamine tert-Butyl (cis-3-(methyl(5-(trifluoromethyl)pyrazin-2-yl)amino)cyclobutyl)carbamate (410 mg, 1.168 mmol) was taken into methanol (6 mL). A solution of HCl (6 mL of 4 M, 24.00 mmol) in dioxane was added and the reaction was heated at 50° C. The reaction was evaporated in vacuo and the resulting residue triturated with heptanes then filtered to provide a white solid (430 mg, quantitative yield) as the title product. 1H NMR (400 MHz, Methanol-d4) δ 8.45-8.33 (m, 1H), 8.30-8.12 (m, 1H), 4.77 (tt, J=9.6, 7.4 Hz, 1H), 3.61-3.54 (m, 1H), 3.19 (s, 3H), 2.83-2.70 (m, 2H), 2.43 (dt, J=12.3, 8.9 Hz, 2H). ESI-MS 246.95 (M+1)$^+$.

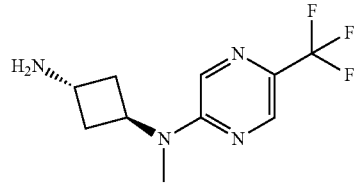

(B-199)

B-199. trans-N1-methyl-N1-(5-(trifluoromethyl)pyrazin-2-yl)cyclobutane-1,3-diamine The compound was prepared in a similar manner as B-198. 1H NMR (400 MHz, Methanol-d4) δ 8.39 (s, 1H), 8.24 (dt, J=4.3, 2.1 Hz, 1H), 5.40 (p, J=8.4 Hz, 1H), 3.99-3.83 (m, 1H), 3.22 (d, J=1.5 Hz, 3H), 2.93-2.78 (m, 2H), 2.55 (ddt, J=11.8, 5.1, 2.9 Hz, 2H). ESI-MS m/z 247.13 (M+1)$^+$.

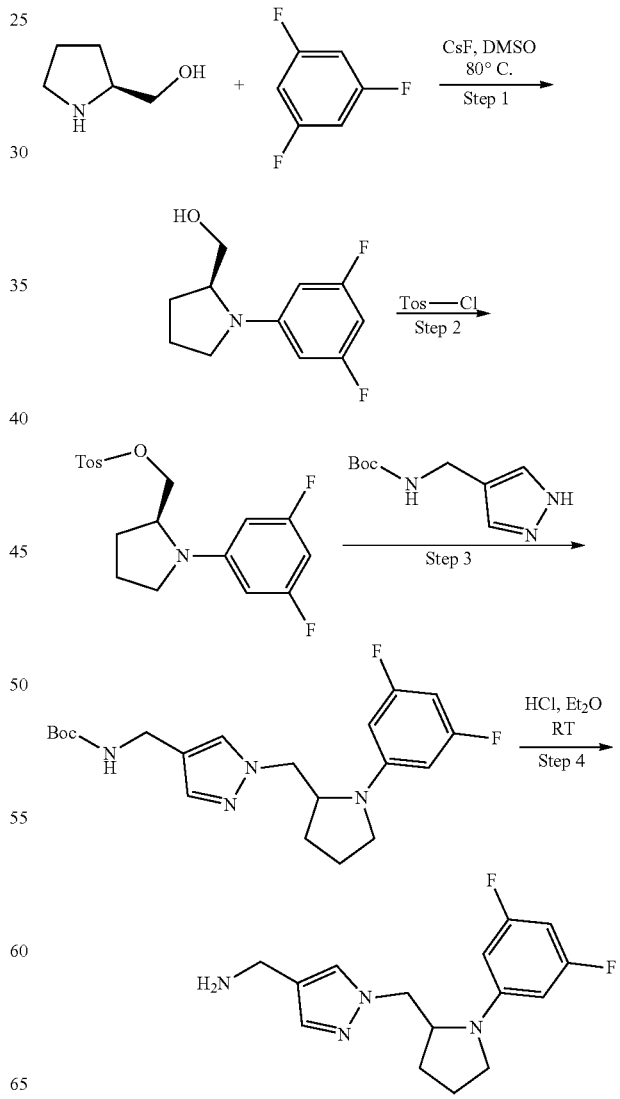

B-200. (S)-(1-((1-(3,5-difluorophenyl)pyrrolidin-2-yl)methyl)-1H-pyrazol-4-yl)methanamine Hydrochloride

Step 1. (S)-(1-(3,5-difluorophenyl)pyrrolidin-2-yl)methanol

To a mixture of [(2S)-pyrrolidin-2-yl]methanol (600 mg, 5.9 mmol) and 1,3,5-trifluorobenzene (1.02 g, 7.7 mmol) in DMSO (0.5 mL) was added cesium fluoride (1.17 g, 7.7 mmol). The reaction was heated to 80° C. and stirred for 48 hours. Water (75 mL) was added to the reaction mixture followed by extraction with ethyl acetate (3×75 mL). The combined organic extracts were washed with water (2×40 mL) and brine (1×40 mL), dried over sodium sulfate, filtered, and evaporated in vacuo to provide 1.3 g (100% yield) of title compound that was used in steps. ESMS(M+1)=214.01.

Step 2. (S)-(1-(3,5-difluorophenyl)pyrrolidin-2-yl)methyl 4-methylbenzenesulfonate To a solution of (S)-(1-(3,5-difluorophenyl)pyrrolidin-2-yl)methanol (1.1 g, 5.16 mmol) and triethylamine (1.1 g, 10.87 mmol) in dichloromethane (15 mL) was added 4-methylbenzenesulfonyl chloride (1.1 g, 5.77 mmol) and the reaction was stirred for 16 hours. Diethyl ether (100 ml) was added to the mixture and stirred. A precipitate formed that was filtered off and rinsed with diethyl ether (50 ml). The filtrate was washed with saturated aqueous sodium bicarbonate (50 ml) and brine (50 ml). The organic layer was dried over sodium sulfate, filtered, and evaporated in vacuo to provide 1.8 g (100% yield) of the title product that was used without further purification in Step 3. ESMS(M+1)=368.32.

Step 3. tert-Butyl (S)-((1-((1-(3,5-difluorophenyl)pyrrolidin-2-yl)methyl)-1H-pyrazol-4-yl)methyl)carbamate Sodium hydride (92 mg, 2.29 mmol) was added to a solution of tert-butyl N-(1H-pyrazol-4-ylmethyl)carbamate (376 mg, 1.91 mmol) in DMF (4 mL) and stirred for 1 hour. (S)-(1-(3,5-difluorophenyl)pyrrolidin-2-yl)methyl 4-methylbenzenesulfonate (771 mg, 2.1 mmol) in 2 ml of DMF was added dropwise and the reaction was stirred for 16 hours at room temperature. Water (75 mL) was added to the reaction mixture followed by extraction with ethyl acetate (3×75 mL). The combined extracts were washed with water (2×40 mL) and brine (40 mL), dried over sodium sulfate, filtered, and evaporated in vacuo. The crude product was purified by column chromatography (SiO₂) eluting with a gradient of 0-100% ethyl acetate in dichloromethane to provide the title product, wt. 555 mg (74% yield). ESMS(M+1)=393.43.

Step 4. (S)-(1-((1-(3,5-difluorophenyl)pyrrolidin-2-yl)methyl)-1H-pyrazol-4-yl)methanamine Hydrochloride To a mixture of tert-Butyl (S)-((1-((1-(3,5-difluorophenyl)pyrrolidin-2-yl)methyl)-1H-pyrazol-4-yl)methyl)carbamate (555 mg, 1.414 mmol) in dichloromethane (3 ml) was added a 1M solution of HCl (10 ml, 10 mmol) in diethyl ether. The reaction was stirred for 2 hours and additional 5 ml of 4M HCL (20 mmol) in dioxane was added. The reaction stirred overnight and then evaporated in vacuo to provide the title compound, 104 mg (22% yield). ESMS(M+1)=293.44.

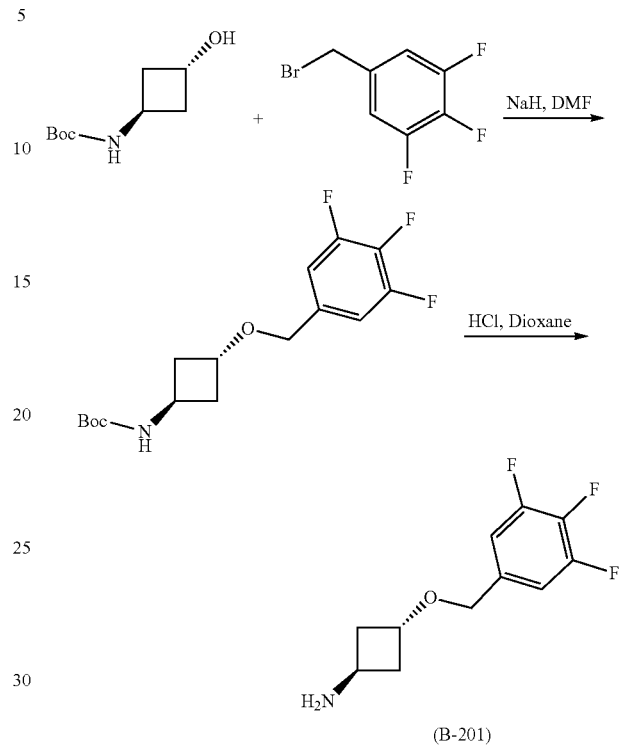

(B-201)

B-201: trans-3-((3,4-difluorobenzyl)oxy)cyclobutan-1-amine hydrochloride

Step 1. tert-butyl (trans-3-((3,4-difluorobenzyl)oxy)cyclobutyl)carbamate

Sodium hydride (329 mg, 8.23 mmol) was added to a cooled solution (0° C.) of tert-butyl (trans-3-hydroxycyclobutyl)carbamate 1.4 g, 7.48 mmol) and 3,4-difluorobenzyl bromide (1.01 g, 7.48 mmol) in DMF (10 ml) and stirred at room temperature. Water was added to the reaction and the resulting white precipitate was collected by vacuum filtration, washed well with water, and dried under vacuum to provide the title product, 2.01 g (89^% yield). ESMS(M+1)=314.21

Step 2. trans-3-((3,4-difluorobenzyl)oxy)cyclobutan-1-amine hydrochloride

The compound was prepared by deprotection of tert-butyl (trans-3-((3,4-difluorobenzyl)oxy)cyclobutyl)carbamate (2.01 g, 6.415 mmol) by dissolving in 20 mL of 4M HCl (80.00 mmol) in dioxane. The reaction was stirred for 2 hours, then evaporated in vacuo to provide the title product as the hydrochloride salt, wt. 1.45 g(90.51% yield). ESMS (M+1)=214.16. B-202 and B-203 were prepared in a similar manner as the procedure described for B-201:

B-202 trans-3-((3,4,5-trifluorobenzyl)oxy)cyclobutan-1-amine hydrochloride

ESMS(M+1)=232.22.

B-203 cis-3-methyl-3-((3,4,5-trifluorobenzyl)oxy)cyclobutan-1-amine hydrochloride

ESMS(M+1)=246.18.

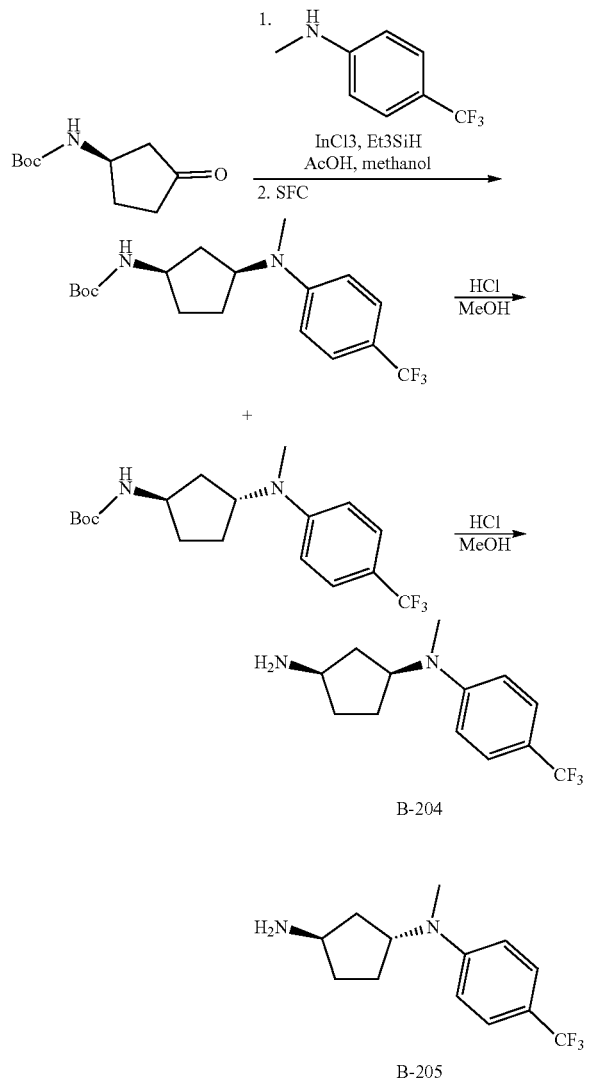

B-204. (1R,3R)-N1-methyl-N1-(4-(trifluoromethyl)phenyl)cyclopentane-1,3-diamine hydrochloride and B-205. (1S,3R)-N1-methyl-N1-(4-(trifluoromethyl)phenyl)cyclopentane-1,3-diamine hydrochloride Step 1: tert-butyl ((1R,3R)-3-(methyl(4-(trifluoromethyl)phenyl)amino)-cyclopentyl)carbamate and tert-butyl ((1R,3S)-3-(methyl(4-(trifluoromethyl)phenyl)amino)cyclopentyl)-carbamate Acetic acid (8 ml) was added to a mixture of tert-butyl (R)-(3-oxocyclopentyl)carbamate (773 mg, 3.880 mmol) and N-methyl-4-(trifluoromethyl)aniline (710 mg, 4.06 mmol) in methanol (8 mL) and stirred at room temperature for 20 mins. Triethylsilane (1.25 ml, 7.83 mmol) was added to the mixture followed by the addition of Indium(III) chloride (260 mg, 1.17 mmol) and stirred at room temperature for 12 hours. The reaction was neutralized with saturated sodium bicarbonate and extracted with ethyl acetate. The organic layer was separated, dried over magnesium sulfate, filtered, and evaporated to afford the crude product. The crude product was purified by column chromatography (SiO$_2$) eluting with a gradient of 0-100% ethyl acetate in heptanes to afford a mixture of the product as diastereomers (726 mg, 52% yield). The diasteromers were separated by SFC (OJ-H column, 20×250 mm; 10% methanol (5 mM ammonia)/90% CO$_2$, Isocratic, 80 ml/min) to provide:

tert-butyl ((1R,3R)-3-(methyl(4-(trifluoromethyl)phenyl)amino)cyclopentyl)-carbamate (296 mg): SFC Rt 0.646 mins. 1H NMR (400 MHz, CDCl$_3$) δ 7.46 (d, J=8.6 Hz, 2H), 6.79 (d, J=8.8 Hz, 2H), 4.55 (s, 1H), 4.44 (dt, J=16.3, 8.3 Hz, 1H), 4.11 (s, 1H), 2.85 (s, 3H), 2.26-2.16 (m, 1H), 2.13-2.00 (m, 2H), 1.87-1.74 (m, 1H), 1.73-1.62 (m, 1H), 1.48 (s, 9H). ESI-MS m/z calc. 358.1868, found 359.25 (M+1)$^+$; [α]=43.3° (c=1.0, methanol).

tert-butyl ((1R,3S)-3-(methyl(4-(trifluoromethyl)phenyl)amino)cyclopentyl)-carbamate (312 mg): SFC Rt 0.79 mins. 1H NMR (400 MHz, CDCl$_3$) δ 7.46 (d, J=8.6 Hz, 2H), 6.79 (d, J=8.8 Hz, 2H), 4.58 (s, 1H), 4.28 (dq, J=15.9, 8.0 Hz, 1H), 3.97 (s, 1H), 2.87 (s, 3H), 2.47-2.31 (m, 1H), 2.18-2.05 (m, 1H), 1.96 (dt, J=14.5, 8.1 Hz, 1H), 1.85-1.72 (m, 1H), 1.56 (ddd, J=18.3, 9.3, 6.2 Hz, 1H), 1.47 (s, 9H). ESI-MS m/z calc. 358.1868, found 359.25 (M+1)$^+$; [α]=−46° (c=1.0, methanol).

Step 2: B-204. (1R,3R)-N1-methyl-N1-(4-(trifluoromethyl)phenyl)cyclopentane-1,3-diamine hydrochloride The compound was prepared by deprotection of tert-butyl ((1R,3R)-3-(methyl(4-(trifluoromethyl)phenyl)amino)cyclopentyl)-carbamate (296 mg) in methanol (6 ml) and 4 M HCl in dioxane (6 ml). Evaporation of the reaction afforded the title product as a hydrochloride salt (290 mg). 1H NMR (400 MHz, CD$_3$OD) δ 4.68 (s, 1H), 3.95 (s, 1H), 3.66 (s, 3H), 2.36 (d, J=46.8 Hz, 2H), 2.11 (t, J=39.1 Hz, 3H), 1.81 (s, 1H); ESI-MS m/z calc. 258.13437, found 259.2 (M+1)$^+$.

B-205. (1S,3R)-N1-methyl-N1-(4-(trifluoromethyl)phenyl)cyclopentane-1,3-diamine hydrochloride The compound was prepared by the same procedure to provide product as the HCl salt (320 mg). 1H NMR (400 MHz, CD$_3$OD) δ 8.15 (d, J=8.1 Hz, 2H), 7.97 (d, J=8.3 Hz, 2H), 4.64-4.42 (m, 1H), 3.87-3.71 (m, 1H), 3.66-3.56 (m, 1H), 3.38 (s, 3H), 2.52 (s, 1H), 2.16 (ddd, J=60.7, 30.2, 11.4 Hz, 5H). ESI-MS m/z calc. 258.13437, found 259.2 (M+1)$^+$;

B-206. (1R,3S)-N1-methyl-N1-(4-(trifluoromethyl)phenyl)cyclopentane-1,3-diamine hydrochloride The compound prepared in the same manner as B-204 & B-205 to provide the product. 1H NMR (400 MHz, CD$_3$OD) δ 8.19 (d, J=7.7 Hz, 2H), 7.98 (d, J=7.6 Hz, 2H), 4.53 (d, J=43.6 Hz, 1H), 3.86-3.72 (m, 1H), 3.38 (d, J=17.7 Hz, 3H), 2.53 (s, 1H), 2.33-2.01 (m, 5H). ESI-MS m/z calc. 258.13437, found 259.2 (M+1)$^+$;

B-207. (1S,3S)-N1-methyl-N1-(4-(trifluoromethyl)phenyl)cyclopentane-1,3-diamine hydrochloride The compound was prepared in the same manner as B-204 and B-205 to provide the product. 1H NMR (400 MHz, CD$_3$OD) δ 8.13 (d, J=8.5 Hz, 2H), 7.97 (d, J=8.5 Hz, 2H), 4.77-4.65 (m, 1H), 4.02-3.86 (m, 1H), 3.36 (d, J=8.3 Hz, 3H), 2.65-2.35 (m, 2H), 2.24 (dd, J=62.9, 22.4 Hz, 3H), 1.83 (ddt, J=13.3, 11.1, 7.8 Hz, 1H). ESI-MS m/z calc. 258.13437, found 259.2 (M+1)$^+$.

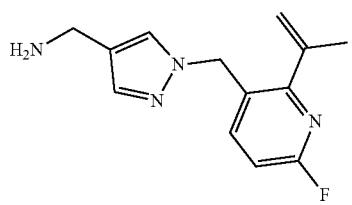 [SMILES: C=C(C)c1nc(F)ccc1Cn1cc(CN)cn1]

B-208. (1-((6-Fluoro-2-(prop-1-en-2-yl)pyridin-3-yl)methyl)-1H-pyrazol-4-yl)methanamine trifluoroacetate acid salt The compound was prepared in the same manner as reported for intermediate B-81. ESI-MS m/z 247.13 (M+1)$^+$.

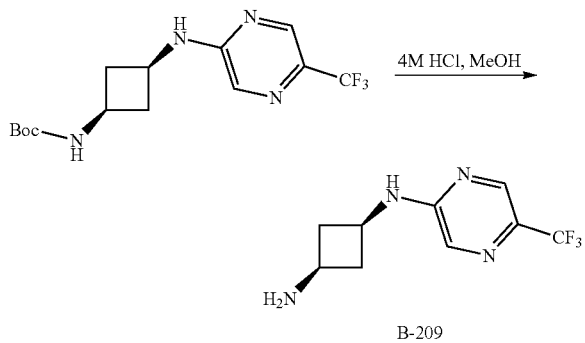

B-209. cis-N1-(5-(trifluoromethyl)pyrazin-2-yl)cyclobutane-1,3-diamine

A 4 M solution of HCl (22 ml, 88 mmol) in dioxane was added to a solution of tert-butyl (cis-3-((5-(trifluoromethyl)pyrazin-2-yl)amino)cyclobutyl)carbamate (see product for B-198, Step 1; 2 g, 5.89 mmol) in methanol (25 ml) and stirred at room temperature for 2 hours. The reaction was evaporated in vacuo and the resulting solid was triturated with diethyl ether, filtered, and dried in vacuum oven at 50° C. to provide the title product (1.98 g, 90% yield). 1H NMR (400 MHz, Methanol-d4) δ 8.36 (d, J=1.2 Hz, 1H), 8.26 (s, 1H), 4.43-4.19 (m, 1H), 3.83-3.69 (m, 1H), 2.97 (dtd, J=10.1, 7.3, 2.9 Hz, 2H), 2.39 (qt, J=8.9, 2.5 Hz, 2H). ESI-MS m/z calc. 232.09358, found 233.13 (M+1)$^+$.

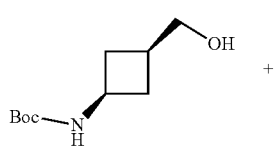

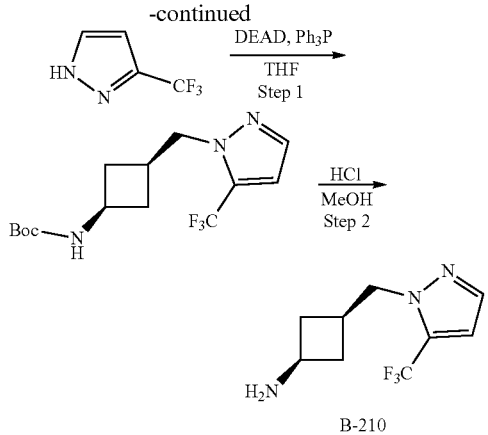

B-210. cis-3-((5-(trifluoromethyl)-1H-pyrazol-1-yl)methyl)cyclobutan-1-amine hydrochloride The compound was prepared 2 steps in the same manner as B-197 to provide the title product. 1H NMR (300 MHz, CD$_3$OD) δ 7.77 (s, 1H), 6.59 (s, 1H), 4.29 (d, J=7.1 Hz, 2H), 3.68 (p, J=8.2 Hz, 1H), 2.79-2.55 (m, 1H), 2.53-2.37 (m, 2H), 1.99 (ddd, J=19.0, 9.5, 2.7 Hz, 2H). ESI-MS m/z found 220.2 (M+1)$^+$.

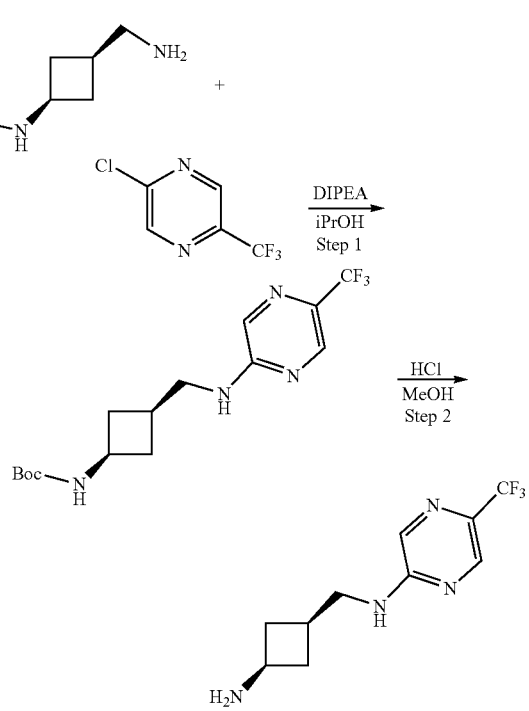

B-211. N-((cis-3-aminocyclobutyl)methyl)-5-(trifluoromethyl)pyrazin-2-amine dihydrochloride The compound was in two steps in the same manner as B-197 to provide the title product. $^1$H NMR (400 MHz, Methanol-d4) δ 8.25 (d, J=1.3 Hz, 1H), 8.03 (s, 0H), 3.66 (s, 2H), 3.55-3.47 (m, 2H), 2.50 (d, J=6.5 Hz, 3H), 1.94 (d, J=7.2 Hz, 2H). ESI-MS m/z calc. 246.10924, found 247.18 (M+1)$^+$.

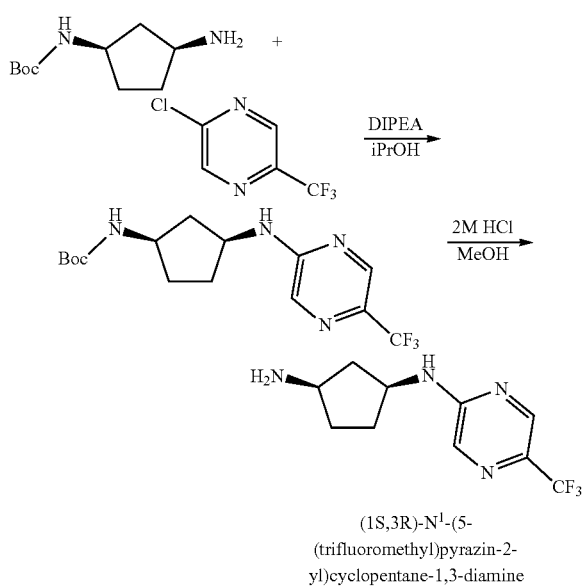

(1S,3R)-N¹-(5-(trifluoromethyl)pyrazin-2-yl)cyclopentane-1,3-diamine

B-212

B-212. (1S,3R)-N1-(5-(trifluoromethyl)pyrazin-2-yl)cyclopentane-1,3-diamine hydrochloride The compound was prepared in a similar manner as B-197 to provide the title product. ¹H NMR (400 MHz, Methanol-d4) δ 8.26 (p, J=1.4 Hz, 2H), 4.32 (q, J=6.9 Hz, 1H), 3.78-3.66 (m, 1H), 2.71 (dt, J=14.3, 7.5 Hz, 1H), 2.20 (dddt, J=11.2, 9.2, 5.7, 3.3 Hz, 2H), 1.93 (tdd, J=10.5, 8.0, 5.1 Hz, 2H), 1.75 (dt, J=13.5, 7.8 Hz, 1H).

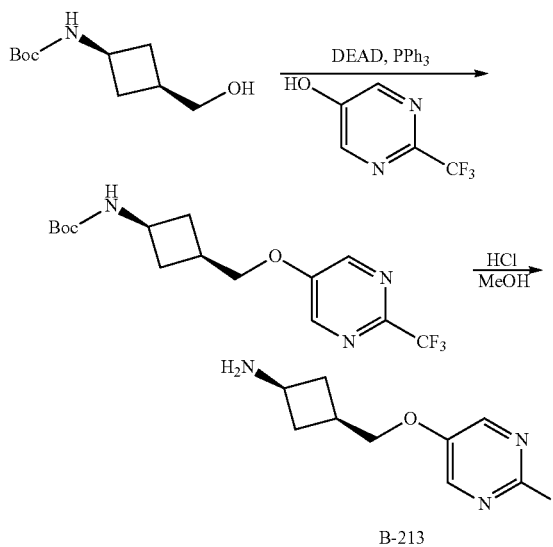

B-213

B-213. (1S,3S)-3-(((2-(trifluoromethyl)pyrimidin-5-yl)oxy)methyl)cyclobutan-1-amine Step 1: tert-butyl ((1s,3s)-3-(((2-(trifluoromethyl)pyrimidin-5-yl)oxy)methyl)-cyclobutyl)carbamate To cis-tert-butyl N-[3-(hydroxymethyl)cyclobutyl]carbamate (5.8 g, 28.8 mmol) and triphenylphosphane (9.1 g, 34.7 mmol) in THF (80 mL) at room temp was added diethylazodicarboxylate (15.8 mL of 40% w/w, 34.69 mmol), followed by 2-(trifluoromethyl)pyrimidin-5-ol (5.0 g, 30.5 mmol). The reaction mixture was stirred at room temperature for 1 hour. THF was removed, added 100 mL dichloromethane, washed with 2 N NaOH twice. The organic phase was concentrated in vacuo. The resulting residue was purified by silica gel chromatography using EtOAc/heptanes to afford 8.17 grams of desired product: ¹H NMR (400 MHz, Chloroform-d) δ 8.51 (s, 2H), 4.72 (s, 1H), 4.11 (d, J=5.5 Hz, 2H), 2.67-2.41 (m, 3H), 1.84-1.74 (m, 1H).

Step 2: (1S,3S)-3-(((2-(trifluoromethyl)pyrimidin-5-yl)oxy)methyl)cyclobutan-1-amine To tert-butyl N-[3-[[2-(trifluoromethyl)pyrimidin-5-yl]oxymethyl]cyclobutyl]carbamate, 3, (8.17 g, 23.51 mmol) in Methanol (20 mL) was added hydrogen chloride (27 mL of 4 M solution, 108 mmol) in dioxane at room temperature. Stir at 50° C. for 30 minutes. The organics were evaporated and the resulting residue was washed with ether-heptane to afford 6.5 g of desired product as HCl salt: ¹H NMR (300 MHz, Methanol-d4) δ 8.61 (s, 2H), 4.20 (d, J=5.5 Hz, 2H), 3.73 (tt, J=8.7, 7.6 Hz, 1H), 2.77-2.60 (m, 1H), 2.57-2.40 (m, 2H), 2.24-1.94 (m, 2H); ESI-MS m/z calc. 247.09, found 248.17 (M+1)⁺; Retention time: 0.58 minutes.

Example 2. Preparation of Compounds of the Invention

2A. Preparation of Compounds of Table 4

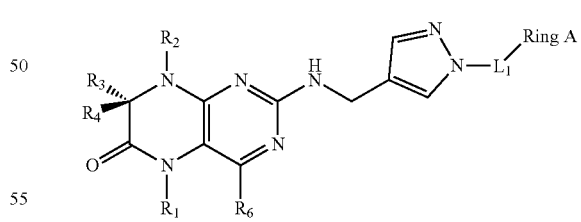

TABLE 4

| Comp # | L₁-Ring A | R₁ | R₂ | R₃ | R₄ | R₆ |
|---|---|---|---|---|---|---|
| Comp 53 | ~CH₂-phenyl | H | Me | Me | H | Me |

TABLE 4-continued
| Comp # | L₁-Ring A | R₁ | R₂ | R₃ | R₄ | R₆ |
|---|---|---|---|---|---|---|
| Comp 1 | 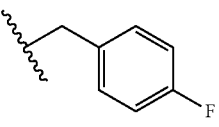 [SMILES: *Cc1ccc(F)cc1] | Me | Me | Me | H | Me |
| Comp 27 | 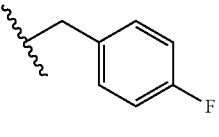 [SMILES: *Cc1ccc(F)cc1] | Me | Me | Me | H | H |
| Comp 4 | 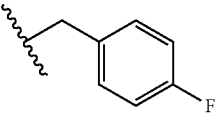 | H | Me | Me | H | Me |
| Comp 41 | 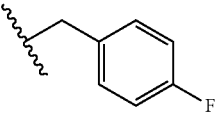 [SMILES: *Cc1ccc(F)cc1] | H | Me | Me | H | H |
| Comp 22 | 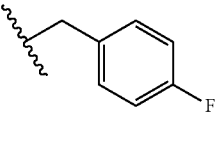 [SMILES: *Cc1ccc(F)cc1] | Me | Et | Me | H | H |
| Comp 19 | 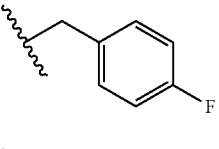 [SMILES: *Cc1ccc(F)cc1] | Et | Me | Et | H | H |
| Comp 32 | 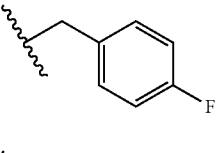 | Me | i-Pr | Et | H | H |
| Comp 52 | 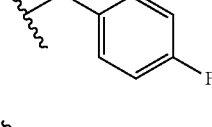 | Et | i-Pr | Me | H | H |
| Comp 24 | 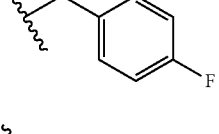 | Me | Me | n-Pr | H | H |
| Comp 26 | 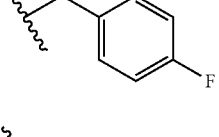 | Me | Me | 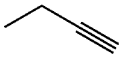 | H | H |
| Comp 20 | 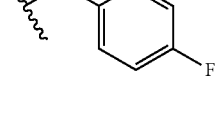 | Me | Me | 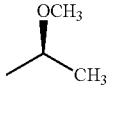 | H | H |

TABLE 4-continued
| Comp # | L₁-Ring A | R₁ | R₂ | R₃ | R₄ | R₆ |
|---|---|---|---|---|---|---|
| Comp 30 | 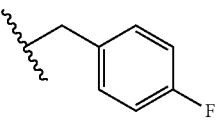 | Et | Et | Me | H | H |
| Comp 11 | 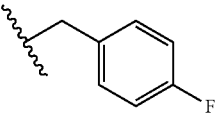 | H | H | —(CH₂)₂—OH | H | H |
| Comp 38 | 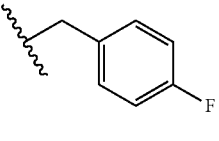 [SMILES: *Cc1ccc(F)cc1] | Et | Et | —(CH₂)₂—OH | H | H |
| Comp 34 | 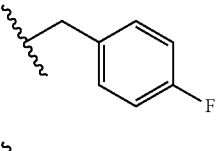 | Et | Et | Et | Me | H |
| Comp 221 | 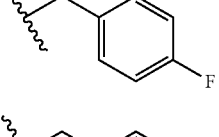 | H | Me | Spiro-c-Pr | Me | |
| Comp 222 | 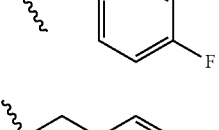 | H | H | Spiro-c-Pr | Me | |
| Comp 223 | 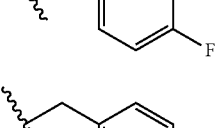 | Me | Me | Spiro-c-Pr | Me | |
| Comp 227 | 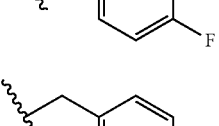 | Me | Me | Spiro-c-Pr | H | |
| Comp 232 | 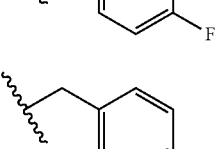 | Et | Et | Spiro-c-Pr | H | |
| Comp 228 | 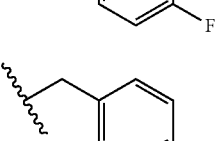 | Me | Me | 3-Spiro-oxetane | H | |
| Comp 224 | 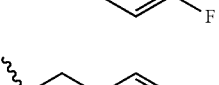 | Me | Me | Me | Me | H |
| Comp 225 | 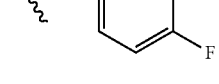 | Me | H | Me | Me | H |

TABLE 4-continued
| Comp # | L₁-Ring A | R₁ | R₂ | R₃ | R₄ | R₆ |
|---|---|---|---|---|---|---|
| Comp 230 | 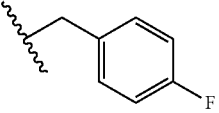 [SMILES: *Cc1ccc(F)cc1] | Et | Et | Me | Me | H |
| Comp 9 | 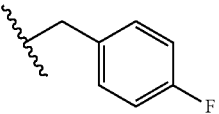 [SMILES: *Cc1ccc(F)cc1] | H | Me | Et | H | H |
| Comp 2 | 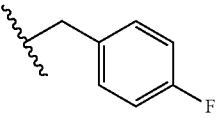 | Me | Me | Me | Et | H |
| Comp 3 | 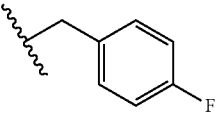 | Me | Me | Et | Me | H |
| Comp 234 | 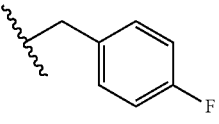 | Et | Et | Me | Et | H |
| Comp 69 | 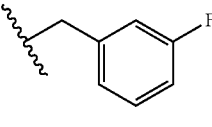 | H | Me | Me | H | Me |
| Comp 55 | 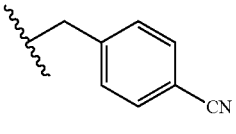 [SMILES: *Cc1ccc(C#N)cc1] | H | Me | Me | H | Me |
| Comp 71 | 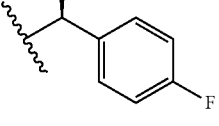 | H | Me | Me | H | Me |
| Comp 72 | 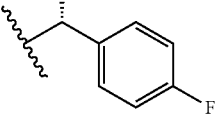 | H | Me | Me | H | Me |
| Comp 149 | 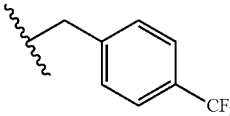 | H | Me | Me | H | Me |
| Comp 147 | 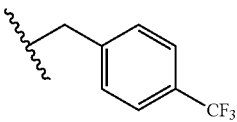 | H | Me | Me | H | H |

TABLE 4-continued

| Comp # | L₁-Ring A | R₁ | R₂ | R₃ | R₄ | R₆ |
|---|---|---|---|---|---|---|
| Comp 45 | 3-CF₃-benzyl | H | Me | Me | H | H |
| Comp 49 | 3-CF₃-benzyl | Et | Et | CH₂CH₂OH | H | H |
| Comp 47 | 3-CF₃-benzyl | H | Me | Me | H | Me |
| Comp 68 | 2-CF₃-benzyl | H | Me | Me | H | Me |
| Comp 78 | 2-iPr-benzyl | H | Me | Me | H | Me |
| Comp 79 | 2-iPr-benzyl | H | Me | Me | H | H |
| Comp 80 | 3-iPr-benzyl | H | Me | Me | H | Me |
| Comp 81 | 3-iPr-benzyl | H | Me | Me | H | H |
| Comp 14 | 3,4,5-triF-benzyl | Me | Me | Me | H | Me |
| Comp 122 | 3,4,5-triF-benzyl | H | Me | Me | H | Me |

TABLE 4-continued

| Comp # | L₁-Ring A | R₁ | R₂ | R₃ | R₄ | R₆ |
|---|---|---|---|---|---|---|
| Comp 42 | 3,4,5-trifluorobenzyl | H | Me | Me | H | H |
| Comp 229 | 3,4,5-trifluorobenzyl | Me | Me | Me | Me | H |
| Comp 15 | 3,4,5-trifluorobenzyl | Me | Me | Et | H | H |
| Comp 36 | 3,4,5-trifluorobenzyl | Me | i-Pr | Et | H | H |
| Comp 33 | 3,4,5-trifluorobenzyl | Me | CH₂CF₃ | Et | H | H |
| Comp 51 | 3,4,5-trifluorobenzyl | Et | i-Pr | Me | H | H |
| Comp 31 | 3,4,5-trifluorobenzyl | Et | Et | Me | H | H |
| Comp 231 | 3,4,5-trifluorobenzyl | Et | Et | Me | Me | H |
| Comp 35 | 3,4,5-trifluorobenzyl | Et | Et | Et | Me | H |

TABLE 4-continued

| Comp # | L₁-Ring A | R₁ | R₂ | R₃ | R₄ | R₆ |
|---|---|---|---|---|---|---|
| Comp 235 | 3,4,5-trifluorobenzyl | Et | Et | Me | Et | H |
| Comp 39 | 3,4,5-trifluorobenzyl | H | H | CH₂CH₂OH | H | H |
| Comp 37 | 3,4,5-trifluorobenzyl | Et | Et | CH₂CH₂OH | H | H |
| Comp 233 | 3,4,5-trifluorobenzyl | Et | Et | Spiro-c-Pr | | H |
| Comp 23 | 3,4,5-trifluorobenzyl | Me | Me | n-Pr | H | H |
| Comp 25 | 3,4,5-trifluorobenzyl | Me | Me | CH₂CH₂C≡CH | H | H |
| Comp 21 | 3,4,5-trifluorobenzyl | Me | Me | CH(OCH₃)CH₃ | H | H |
| Comp 140 | 3,4-difluorobenzyl | H | Me | Me | H | Me |
| Comp 28 | 3,4-difluorobenzyl | Me | Me | Me | H | Me |
| Comp 141 | 3,4-difluorobenzyl | H | Me | Me | H | H |

TABLE 4-continued

| Comp # | L₁-Ring A | R₁ | R₂ | R₃ | R₄ | R₆ |
|---|---|---|---|---|---|---|
| Comp 29 | 2,4-difluorobenzyl | Me | Me | Me | H | Me |
| Comp 65 | 2-chloro-4-fluorobenzyl | H | Me | Me | H | Me |
| Comp 66 | 2-trifluoromethyl-4-fluorobenzyl | H | Me | Me | H | Me |
| Comp 67 | 2-trifluoromethyl-4-fluorobenzyl | H | Me | Me | H | Me |
| Comp 17 | 2,3,4-trifluorobenzyl | Me | Me | Me | H | Me |
| Comp 16 | 2,4,5-trifluorobenzyl | Me | Me | Me | H | Me |
| Comp 18 | 2,4,6-trifluorobenzyl | Me | Me | Me | H | Me |
| Comp 146 | 3-fluoro-4-methoxybenzyl | H | Me | Me | H | Me |
| Comp 75 | 3-methoxy-4-fluorobenzyl | H | Me | Me | H | Me |
| Comp 148 | 3-methoxy-4-fluorobenzyl | H | Me | Me | H | H |
| Comp 181 | benzo[d][1,3]dioxol-5-ylmethyl | H | Me | Me | H | Me |

TABLE 4-continued

| Comp # | L₁-Ring A | R₁ | R₂ | R₃ | R₄ | R₆ |
|---|---|---|---|---|---|---|
| Comp 83 | 4-F, 2-OCH₃ benzyl | H | Me | Me | H | Me |
| Comp 84 | 4-F, 2-OCH₃ benzyl | Me | Me | Me | H | Me |
| Comp 87 | 4-F, 2-OH benzyl | H | Me | Me | H | Me |
| Comp 46 | 3,5-diF, 4-OCH₃ benzyl | H | Me | Me | H | Me |
| Comp 44 | 3,5-diF, 4-OCH₃ benzyl | H | Me | Me | H | H |
| Comp 48 | 3,5-diF, 4-OCH₃ benzyl | Et | Et | —(CH₂)₂—OH | H | H |
| Comp 88 | 2,4-diF, 3-OCH₃ benzyl | H | Me | Me | H | Me |
| Comp 63 | 4-F, 2-CN benzyl | Me | Me | Me | H | Me |
| Comp 64 | 4-F, 2-CN benzyl | H | Me | Me | H | Me |
| Comp 8 | 4-F phenethyl | Me | Me | Me | H | Me |

TABLE 4-continued
| Comp # | L₁-Ring A | R₁ | R₂ | R₃ | R₄ | R₆ |
| --- | --- | --- | --- | --- | --- | --- |
| Comp 6 | 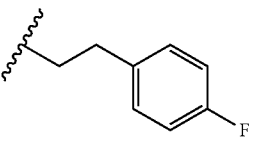 [SMILES: *CCc1ccc(F)cc1] | H | Me | Me | H | Me |
| Comp 13 | 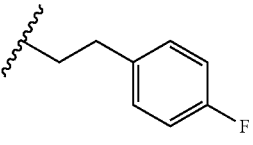 [SMILES: *CCc1ccc(F)cc1] | H | H | —(CH₂)₂—OH | H | H |
| Comp 123 | 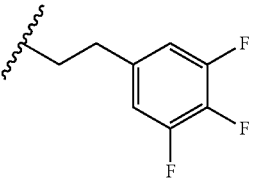 [SMILES: *CCc1cc(F)c(F)c(F)c1] | H | Me | Me | H | Me |
| Comp 103 | 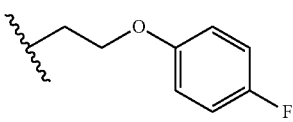 [SMILES: *CCOc1ccc(F)cc1] | H | Me | Me | H | Me |
| Comp 109 | 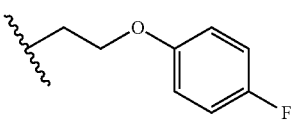 [SMILES: *CCOc1ccc(F)cc1] | H | Me | Me | H | H |
| Comp 104 | 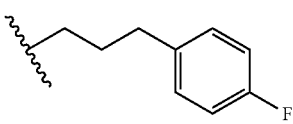 [SMILES: *CCCc1ccc(F)cc1] | H | Me | Me | H | Me |
| Comp 110 | 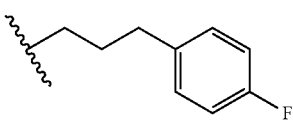 | H | Me | Me | H | H |
| Comp 105 | 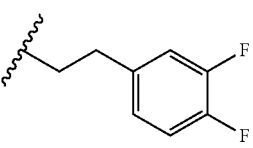 | H | Me | Me | H | Me |
| Comp 111 | 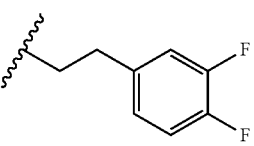 [SMILES: *CCc1ccc(F)c(F)c1] | H | Me | Me | H | H |
| Comp 119 | 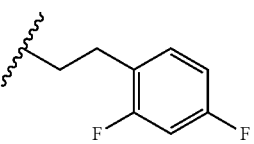 [SMILES: *CCc1ccc(F)cc1F] | H | Me | Me | H | H |

TABLE 4-continued

| Comp # | L₁-Ring A | R₁ | R₂ | R₃ | R₄ | R₆ |
|---|---|---|---|---|---|---|
| Comp 106 | 2,4-difluorophenylpropyl | H | Me | Me | H | Me |
| Comp 121 | 4-ethoxyphenylpropyl | H | Me | Me | H | H |
| Comp 108 | 4-ethoxyphenylpropyl | H | Me | Me | H | Me |
| Comp 120 | 3,5-difluorophenylpropyl | H | Me | Me | H | H |
| Comp 107 | 3,5-difluorophenylpropyl | H | Me | Me | H | Me |
| Comp 112 | trans-3-(4-fluorophenyl)cyclobutyl | H | Me | Me | H | Me |
| Comp 137 | trans-3-(4-fluorophenyl)cyclopentyl | H | Me | Me | H | Me |
| Comp 113 | cyclohexylpropyl | H | Me | Me | H | Me |
| Comp 115 | (tetrahydropyran-4-yl)propyl | H | Me | Me | H | Me |

TABLE 4-continued

| Comp # | L₁-Ring A | R₁ | R₂ | R₃ | R₄ | R₆ |
|---|---|---|---|---|---|---|
| Comp 58 | 4,4-difluorocyclohexylmethyl | H | Me | Me | H | Me |
| Comp 5 | cyclobutylmethyl | H | Me | Me | H | Me |
| Comp 7 | cyclobutylmethyl | Me | Me | Me | H | Me |
| Comp 61 | 3,3-difluorocyclobutylmethyl | H | Me | Me | H | Me |
| Comp 133 | 2-cyclopentylethyl | H | Me | Me | H | Me |
| Comp 134 | norbornylmethyl | H | Me | Me | H | Me |
| Comp 118 | tetrahydropyran-4-yl | H | Me | Me | H | Me |
| Comp 91 | 3-(4-fluorophenyl)-3-oxopropyl | H | Me | Me | H | Me |
| Comp 116 | indan-2-yl | H | Me | Me | H | Me |
| Comp 117 | 6-fluoroindan-1-yl | H | Me | Me | H | Me |
| Comp 97 | 3-(trifluoromethyl)phenyl | H | Me | Me | H | Me |
| Comp 98 | 2,4-difluorophenyl | H | Me | Me | H | Me |

TABLE 4-continued

| Comp # | L₁-Ring A | R₁ | R₂ | R₃ | R₄ | R₆ |
|---|---|---|---|---|---|---|
| Comp 76 | 3,4-dimethoxybenzyl | H | Me | Me | H | Me |
| Comp 154 | trans-2-(4-fluorophenyl)cyclopropyl | H | Me | Me | H | Me |
| Comp 155 | trans-2-(4-fluorophenyl)cyclopropyl | H | Me | Me | H | Me |
| Comp 153 | trans-2-(4-fluorophenyl)cyclopropyl | Me | Me | Me | H | Me |
| Comp 152 | trans-2-(4-fluorophenyl)cyclopropyl | Me | Me | Me | H | Me |
| Comp 89 | (S)-2-phenylpropyl | H | Me | Me | H | Me |
| Comp 90 | (R)-2-phenylpropyl | H | Me | Me | H | Me |
| Comp 95 | (S)-2-(4-fluorophenyl)propyl | H | Me | Me | H | Me |
| Comp 96 | (R)-2-(4-fluorophenyl)propyl | H | Me | Me | H | Me |
| Comp 92 | 2-(4-fluorophenyl)-2-methylpropyl | H | Me | Me | H | Me |

TABLE 4-continued

| Comp # | L₁-Ring A | R₁ | R₂ | R₃ | R₄ | R₆ |
|---|---|---|---|---|---|---|
| Comp 101 | 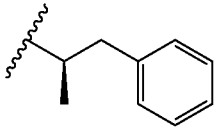 [SMILES: *[C@H](C)Cc1ccccc1] | H | Me | Me | H | Me |
| Comp 102 | 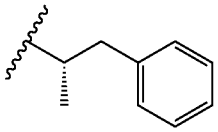 [SMILES: *[C@@H](C)Cc1ccccc1] | H | Me | Me | H | Me |
| Comp 99 | 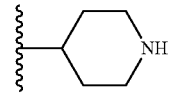 | H | Me | Me | H | Me |
| Comp 124 | 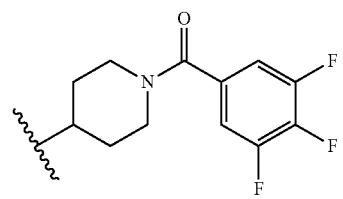 [SMILES: *C1CCN(C(=O)c2cc(F)c(F)c(F)c2)CC1] | H | Me | Me | H | Me |
| Comp 125 | 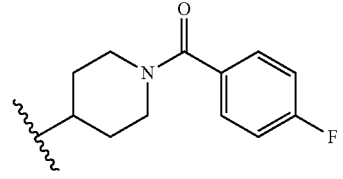 [SMILES: *C1CCN(C(=O)c2ccc(F)cc2)CC1] | H | Me | Me | H | Me |
| Comp 130 | 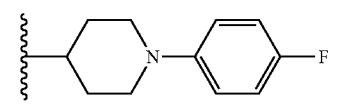 | H | Me | Me | H | Me |
| Comp 179 | 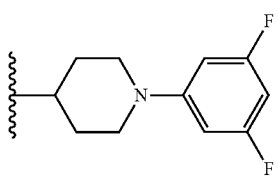 [SMILES: *C1CCN(c2cc(F)cc(F)c2)CC1] | H | Me | Me | H | Me |

A. General procedure for Method A

Compound 46: (7S)-2-(((1-(3,5-difluoro-4-methoxybenzyl)-1H-pyrazol-4-yl)methyl)amino)-4,7,8-trimethyl-7,8-dihydropteridin-6(5H)-one (7S)-2-chloro-4,7,8-trimethyl-7,8-dihydropteridin-6(5H)-one (9.4 g, 41.5 mmol) and (1-(3,5-difluoro-4-methoxy-5-methylbenzyl)-1H-pyrazol-4-yl)methanamine hydrochloride (13.8 g, 42.3 mmol) were taken into 170 ml of t-butanol and degassed with nitrogen. Sodium t-butoxide (13.94 g, 145 mmol) was added to the mixture followed by the addition of t-BuXPhos palladium(II) phenethylamine chloride (also know as tBuXPhos Pd Gen 1) (570 mg, 0.83 mmol). The reaction was purged with nitrogen for 5 minutes, then heated to 50° C. for 2 hours. The solvent was evaporated in vacuo and water (200 ml) was added to the residue and extracted with dichloromethane (2×200 ml). The combined organic extracts were washed with brine, dried over anhydrous sodium sulfate, filtered, and evaporated to afford the crude product. The crude product was purified by column chromatography (330 g SiO) eluting with a gradient of 0-20% methanol in dichloromethane. The desired fractions were combined and evaporated in vacuo to afford a green solid. The green solid was dissolved in dichloromethane (100 ml) and 4.5 g of Biotage MP-TMT resin was stirred at room temperature for 16 hours (to remove Pd). The solvent was filtered through Florosil and Celite to obtain a clear colorless solution. The filtrate was evaporated in vacuo to afford a white foam. Heptane was added to the residue and stirred for 1 hour. The resulting material was collected by vacuum filtration and dried in a vacuum oven at 50° C. for 20 hours to provide the title product, wt. 15 g (80.7% yield). 1H NMR (300 MHz, DMSO-d6) δ 9.82 (s, 1H), 7.68 (s, 1H), 7.40 (d, J=0.5 Hz, 1H), 7.06-6.87 (m, 2H), 6.60 (t, J=5.9 Hz, 1H), 5.21 (s, 2H), 4.22 (d, J=6.0 Hz, 2H), 4.00 (q, J=6.8 Hz, 1H), 3.88 (t, J=0.9 Hz, 3H), 2.94 (s, 3H), 2.13 (s, 3H), 1.18 (d, J=6.8 Hz, 3H); F19 NMR δ −128.50, −128.53 ppm;

ESMS(M+1)=444.28. mp=136-138° C. Chiral HPLC (AD-H column; 40% isopropanol/60% hexane/0.1% diethylamine) Rt=8.906 mins. (98% ee); $[\alpha]_D$=44.020 (c=1, methanol).

B. General procedure for Method B

Compound 1: (7S)-2-(((1-(4-fluorobenzyl)-1H-pyrazol-4-yl)methyl)amino)-4,5,7,8-tetramethyl-7,8-dihydropteridin-6(5H)-one (7S)-2-Chloro-4,5,7,8-tetramethyl-7H-pteridin-6-one (90 g, 373.9 mmol) and (1-(4-fluorobenzyl)-1H-pyrazol-4-yl) methanamine hydrochloride (108.4 g, 448.7 mmol) was taken into n-butanol (1.35 L) and heated at reflux for 20 hours under nitrogen. The solvent was removed in vacuo. The resulting residue was taken into saturated sodium bicarbonate (1 L) and extracted with ethyl acetate (1.5 L). The aqueous was extracted further with ethyl acetate (1 L). The extracts were combined, washed with brine, dried over anhydrous sodium sulfate, filtered, and evaporated in vacuo to afford the crude product. The crude was purified by column chromatography ($SiO_2$) eluting with a gradient of 0-100% acetone in hexanes. The desired fractions were combined and evaporated in vacuo. tert-Butyl methyl ether (500 ml) and heptane (200 ml) was added to the evaporated material. The title product was obtained by subsequent vacuum filtration followed by washing with t-Butyl methyl ether, then drying in a vacuum oven at 50° C. overnight, wt. 59 g (38.1% yield). 1H NMR (300 MHz, $CD_3OD$) δ 7.60 (s, 1H), 7.48 (s, 1H), 7.22 (dd, J=8.5, 5.4 Hz, 2H), 7.03 (t, J=8.8 Hz, 2H), 5.25 (s, 2H), 4.39 (s, 2H), 4.03 (q, J=6.9 Hz, 1H), 3.27 (s, 3H), 3.00 (s, 3H), 2.32 (s, 3H), 1.15 (d, J=6.9 Hz, 3H); F19 NMR δ 118.04 ppm; ESMS(M+1)=410.36 mins. Chiral HPLC (IA column; 40% ethanol/60% hexane, isocratic), Rt=12.775 mins.; [α]D=20.2° (c=1, methanol).

Compound 53. (7S)-2-(((1-benzyl-1H-pyrazol-4-yl)methyl)amino)-4,7,8-trimethyl-7,8-dihydropteridin-6(5H)-one The compound was prepared by general procedure Method B via reaction of intermediate A-2 and (1-benzyl-1H-pyrazol-4-yl)methanamine hydrochloride to provide the title compound; Yield 41%; 1H NMR (300 MHz, Methanol-d4) δ 7.85 (s, 1H), 7.68 (s, 1H), 7.28-7.18 (m, 3H), 7.18-7.10 (m, 2H), 5.29 (s, 2H), 4.43 (s, 2H), 4.18 (q, J=6.8 Hz, 1H), 3.08 (s, 3H), 2.19 (s, 3H), 1.40 (d, J=6.9 Hz, 3H); ESMS (M+H)=378.34.

Compound 27: (7S)-2-(((1-(4-fluorobenzyl)-1H-pyrazol-4-yl)methyl)amino)-5,7,8-trimethyl-7,8-dihydropteridin-6(5H)-one The compound was prepared by general procedure Method B via reaction of intermediates A-35 and B-2 to provide the title compound; Yield 78%: 1H NMR (300 MHz, CDCl3) δ 7.44 (s, 2H), 7.28 (s, 1H), 7.11 (dd, J=8.5, 5.4 Hz, 2H), 6.94 (t, J=8.6 Hz, 2H), 5.13 (d, J=10.9 Hz, 2H), 4.96 (d, J=27.5 Hz, 1H), 4.32 (t, J=7.4 Hz, 2H), 4.05 (q, J=6.8 Hz, 1H), 3.18 (s, 3H), 2.94 (s, 3H), 1.29 (d, J=6.8 Hz, 3H); ESMS (M+H)=396.14.

Compound 4: (7S)-2-(((1-(4-fluorobenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-2 to provide the title compound; Yield 68.8%; 1H NMR (300 MHz, $CDCl_3$) δ 8.07 (s, 1H), 7.53 (s, 1H), 7.34 (s, 1H), 7.20 (dd, J=8.7, 5.3 Hz, 2H), 7.04 (t, J=8.7 Hz, 2H), 5.24 (s, 2H), 4.81 (t, J=5.5 Hz, 1H), 4.42 (d, J=5.7 Hz, 2H), 4.08 (q, J=6.8 Hz, 1H), 3.04 (s, 3H), 2.22 (s, 3H), 1.40 (d, J=6.9 Hz, 3H); ESMS (M+H)=396.32; Chiral HPLC (AD-H column; 40% isopropanol/60% hexanes(0.1% diethylamine, isocratic): Rt 7.018 mins. (98% ee); $[\alpha]_D^{20}$+44.80 (c=1, methanol).

Compound 41: (7S)-2-(((1-(4-fluorobenzyl)-1H-pyrazol-4-yl)methyl)amino)-7,8-dimethyl-7,8-dihydropteridin-6(5H)-one The compound was prepared by general procedure Method B via reaction of intermediates A-1 and B-2 to provide the title compound; Yield 62% 1H NMR (300 MHz, $CDCl_3$) δ 7.63-7.48 (m, 3H), 7.29-7.17 (m, 2H), 7.09-6.97 (m, 2H), 5.26 (s, 2H), 4.48 (d, J=5.4 Hz, 2H), 4.23 (q, J=6.9 Hz, 1H), 3.21 (s, 3H), 1.58 (d, J=6.9 Hz, 3H); ESMS (M+H)=382.31.

Compound 22: (7S)-8-ethyl-2-(((1-(4-fluorobenzyl)-1H-pyrazol-4-yl)methyl)amino)-5,7-dimethyl-7,8-dihydropteridin-6(5H)-one The compound was prepared by general procedure Method A via reaction of intermediates A-24 and B-2 to provide the title compound; Yield 62% 1H NMR (300 MHz, $CDCl_3$) δ 7.45 (d, J=4.9 Hz, 2H), 7.27 (s, 1H), 7.16-7.09 (m, 2H), 7.02-6.89 (m, 2H), 5.15 (s, 2H), 4.93 (t, J=5.1 Hz, 1H), 4.32 (t, J=7.3 Hz, 2H), 4.09 (dd, J=14.4, 7.6 Hz, 1H), 3.93 (dq, J=14.4, 7.2 Hz, 1H), 3.18 (s, 3H), 3.01 (tt, J=12.2, 6.1 Hz, 1H), 1.28 (d, J=6.8 Hz, 3H), 1.16-1.06 (m, 3H); ESMS (M+H)=410.23.

Compound 19: (7S)-5,7-Diethyl-2-(((1-(4-fluorobenzyl)-1H-pyrazol-4-yl)methyl)amino)-8-methyl-7,8-dihydropteridin-6(5H)-one The compound was prepared by general procedure Method B via reaction of intermediates A-43 and B-2 to provide the title compound; $^1H$ NMR (300 MHz, $CDCl_3$) δ δ 7.51 (s, 2H), 7.34 (d, J=0.8 Hz, 1H), 7.23-7.11 (m, 2H), 7.00 (t, J=8.7 Hz, 1H), 5.21 (s, 2H), 4.90 (t, J=5.7 Hz, 1H), 4.40 (d, J=5.7 Hz, 2H), 4.08 (dd, J=6.0, 3.7 Hz, 1H), 3.97 (dq, J=14.3, 7.2 Hz, 1H), 3.77 (dq, J=14.2, 7.1 Hz, 1H), 3.01 (s, 3H), 1.95 (dtt, J=15.0, 7.5, 3.7 Hz, 1H), 1.79 (dqd, J=14.7, 7.4, 5.9 Hz, 1H), 1.22 (t, J=7.2 Hz, 3H), 0.79 (t, J=7.5 Hz, 3H); ESMS(M+1)=424.23.

Compound 32: (7S)-7-ethyl-2-(((1-(4-fluorobenzyl)-1H-pyrazol-4-yl)methyl)amino)-8-isopropyl-5-methyl-7,8-dihydropteridin-6(5H)-one The compound was prepared by general procedure Method A via reaction of intermediates A-18 and B-2 to provide the title compound; 46% yield. 1H NMR (300 MHz, $CDCl_3$) δ 7.44 (s, 2H), 7.27 (s, 1H), 7.17-7.09 (m, 2H), 7.00-6.89 (m, 2H), 5.15 (s, 2H), 4.96 (s, 1H), 4.44 (dt, J=13.7, 6.8 Hz, 1H), 4.34 (d, J=5.6 Hz, 2H), 4.13 (dd, J=7.6, 3.4 Hz, 1H), 3.20 (s, 3H), 1.81 (dtt, J=15.1, 7.5, 3.8 Hz, 1H), 1.69-1.57 (m, 1H), 1.25 (t, J=6.5 Hz, 6H), 0.78 (t, J=7.5 Hz, 3H); ESMS(M+1)=438.32.

Compound 52: (7S)-7-ethyl-2-(((1-(4-fluorobenzyl)-1H-pyrazol-4-yl)methyl)amino)-8-isopropyl-5-methyl-7,8-dihydropteridin-6(5H)-one The compound was prepared by general procedure Method A via reaction of intermediates A-19 and B-2 to provide the title compound; 47% yield. 1H NMR (300 MHz, CDCl$_3$) δ 7.52 (s, 1H), 7.44 (s, 1H), 7.27 (s, 1H), 7.15-7.06 (m, 2H), 6.98-6.88 (m, 2H), 5.15 (s, 2H), 5.01 (t, J=5.1 Hz, 1H), 4.54 (hept, J=6.8 Hz, 1H), 4.33 (d, J=5.6 Hz, 2H), 4.24-4.08 (m, 1H), 3.93-3.76 (m, 1H), 3.68 (dq, J=14.2, 7.1 Hz, 1H), 2.62 (s, 1H), 1.29-1.07 (m, 12H); ESMS(M+1)=438.32

Compound 24: (7S)-2-(((1-(4-fluorobenzyl)-1H-pyrazol-4-yl)methyl)amino)-5,8-dimethyl-7-propyl-7,8-dihydropteridin-6(5H)-one The compound was prepared by general procedure Method A via reaction of intermediates A-50 and B-2 to provide the title compound; 1H NMR (300 MHz, Methanol-d4) δ 7.61 (d, J=0.8 Hz, 1H), 7.53-7.44 (m, 2H), 7.28-7.17 (m, 2H), 7.10-6.97 (m, 2H), 5.25 (s, 2H), 4.37 (s, 2H), 4.19 (dd, J=5.7, 4.2 Hz, 1H), 3.26 (s, 3H), 3.05 (s, 3H), 1.90-1.70 (m, 2H), 1.18 (dtt, J=9.1, 7.3, 6.0 Hz, 2H), 0.87 (t, J=7.3 Hz, 3H); ESMS(M+1)=424.23

Compound 26: (7S)-2-(((1-(4-fluorobenzyl)-1H-pyrazol-4-yl)methyl)amino)-5,8-dimethyl-7-(prop-2-yn-1-yl)-7,8-dihydropteridin-6(5H)-one The compound was prepared by general procedure Method B via reaction of intermediates A-10 and B-2 to provide the title compound; 5% yield. 1H NMR (300 MHz, Methanol-d4) δ 7.76 (d, J=0.8 Hz, 1H), 7.57 (d, J=0.8 Hz, 1H), 7.42 (s, 1H), 7.33-7.22 (m, 2H), 7.12-7.00 (m, 2H), 5.29 (s, 2H), 4.62-4.49 (m, 3H), 3.28 (d, J=7.8 Hz, 6H), 3.05 (ddd, J=17.7, 4.8, 2.7 Hz, 1H), 2.90 (dt, J=17.7, 2.8 Hz, 1H); ESMS(M+1)=420.22

Compound 20: (7S)-2-(((1-(4-fluorobenzyl)-1H-pyrazol-4-yl)methyl)amino)-7-((R)-1-methoxyethyl)-5,8-dimethyl-7,8-dihydropteridin-6(5H)-one The compound was prepared by general procedure Method B via reaction of intermediates A-20 and B-2 to provide the title compound; 1H NMR (300 MHz, Methanol-d4) δ 7.78-7.66 (m, 2H), 7.58-7.50 (m, 1H), 7.42-7.21 (m, 2H), 7.05 (t, J=8.7 Hz, 2H), 5.28 (s, 2H), 4.51 (s, 2H), 4.44-4.22 (m, 1H), 3.90-3.66 (m, 1H), 3.29-3.14 (m, 9H), 1.32-1.13 (m, 3H); ESMS(M+1)=440.21.

Compound 30: (7S)-5,8-diethyl-2-(((1-(4-fluorobenzyl)-1H-pyrazol-4-yl)methyl)amino)-7-methyl-7,8-dihydropteridin-6(5H)-one The compound was prepared by general procedure Method A via reaction of intermediates A-22 and B-2 to provide the title compound; 44% yield. 1H NMR (300 MHz, CDCl$_3$) δ 7.48 (s, 1H), 7.45 (d, J=4.0 Hz, 1H), 7.27 (s, 1H), 7.15-7.06 (m, 2H), 6.99-6.88 (m, 2H), 5.15 (s, 2H), 4.95 (dd, J=17.0, 3.5 Hz, 1H), 4.32 (t, J=7.3 Hz, 2H), 4.19-3.60 (m, 4H), 3.14-2.92 (m, 1H), 1.25 (t, J=6.9 Hz, 3H), 1.14 (dt, J=14.2, 5.4 Hz, 6H); ESMS (M+H)=424.27.

Compound 11: (7S)-2-(((1-(4-Fluorobenzyl)-1H-pyrazol-4-yl)methyl)amino)-7-(2-hydroxyethyl)-7,8-dihydropteridin-6(5H)-one The compound was prepared by procedure Method B via reaction of intermediates A-25 and B-2 to provide the title product. 1H NMR (300 MHz, Methanol-d4) δ 7.77 (d, J=4.4 Hz, 1H), 7.60 (d, J=2.6 Hz, 1H), 7.32-7.13 (m, 3H), 7.06 (t, J=8.7 Hz, 2H), 5.30 (s, 2H), 4.63-4.41 (m, 3H), 3.81-3.68 (m, 2H), 2.45-2.01 (m, 2H); ESMS(M+1)=398.24.

Compound 38: (7S)-5,8-diethyl-2-(((1-(4-fluorobenzyl)-1H-pyrazol-4-yl)methyl)amino)-7-(2-hydroxyethyl)-7,8-dihydropteridin-6(5H)-one The compound was prepared by general procedure Method B via reaction of intermediates A-26 and B-2 to provide the title compound; 14% yield. 1H NMR (300 MHz, Methanol-d4) δ 7.84 (s, 1H), 7.70 (t, J=1.0 Hz, 1H), 7.56-7.48 (m, 1H), 7.32-7.21 (m, 2H), 7.11-6.99 (m, 2H), 5.28 (s, 2H), 4.66-4.34 (m, 5H), 4.22-3.77 (m, 4H), 2.52-2.26 (m, 2H), 1.32-1.12 (m, 6H); ESMS (M+H)=454.43.

Compound 34: (7S)-5,7,8-triethyl-2-(((1-(4-fluorobenzyl)-1H-pyrazol-4-yl)methyl)amino)-7-methyl-7,8-dihydropteridin-6(5H)-one The compound was prepared by general procedure Method A via reaction of intermediates A-30 and B-2 to provide the title compound; 43% yield. 1H NMR (300 MHz, Methanol-d4) δ 8.31 (s, 1H), 8.16 (s, 1H), 7.54 (s, 1H), 7.43 (dd, J=8.6, 5.2 Hz, 2H), 7.21-7.08 (m, 2H), 5.56 (s, 2H), 4.63 (d, J=2.8 Hz, 2H), 3.99 (dt, J=14.0, 7.0 Hz, 1H), 3.82 (tq, J=14.0, 6.9 Hz, 2H), 3.52 (dq, J=13.9, 6.9 Hz, 1H), 3.31 (dt, J=3.3, 1.6 Hz, 1H), 2.16-1.92 (m, 2H), 1.70 (s, 3H), 1.20 (m, 6H), 0.76 (t, J=7.4 Hz, 3H); ESMS (M+H)=452.27.

Compound 221: 2'-(((1-(4-fluorobenzyl)-1H-pyrazol-4-yl)methyl)amino)-4',8'-dimethyl-5',8'-dihydro-6'H-spiro[cyclopropane-1,7'-pteridin]-6'-one The compound was prepared by general procedure Method B via reaction of intermediates A-16 and B-2 to provide the title compound; 17% yield. 1H NMR (300 MHz, Methanol-d4) δ 7.67 (s, 1H), 7.49 (s, 1H), 7.23 (dd, J=8.5, 5.5 Hz, 2H), 7.03 (t, J=8.7 Hz, 2H), 5.25 (s, 2H), 4.46 (s, 2H), 2.94 (s, 3H), 2.24 (s, 3H), 1.61 δ 1.37 (m, 4H); ESMS(M+H)=408.42.

Compound 222: 2'-(((1-(4-fluorobenzyl)-1H-pyrazol-4-yl)methyl)amino)-4'-methyl-5',8'-dihydro-6'H-spiro[cyclopropane-1,7'-pteridin]-6'-one The compound was prepared by the general procedure Method B via reaction of intermediates A-53 and B-2 to provide the title compound; 23% yield. 1H NMR (300 MHz, Methanol-d4) δ 8.02 (s, 1H), 7.82 (d, J=6.0 Hz, 1H), 7.20 (dt, J=8.7, 5.9 Hz, 2H), 7.06-6.92 (m, 2H), 5.34 (s, 2H), 4.33 (s, 2H), 2.13 (s, 3H), 1.45 (dd, J=8.0, 4.9 Hz, 2H), 1.03 (dd, J=8.0, 5.0 Hz, 2H); ESMS (M+1)=394.38.

Compound 223: 2'-(((1-(4-fluorobenzyl)-1H-pyrazol-4-yl)methyl)amino)-4',5',8'-trimethyl-5',8'-dihydro-6'H-spiro[cyclopropane-1,7'-pteridin]-6'-one The compound was prepared by general procedure Method B via reaction of intermediates A-33 and B-2 to provide the title compound; 32% yield. 1H NMR (300 MHz, DMSO-d6) δ 12.78 (br.s, 1H), 7.97 (br.s, 1H), 7.78 (s, 1H), 7.45 (s, 1H), 7.32-7.24 (m, 2H), 7.21-7.12 (m, 2H), 5.27 (s, 2H), 4.40 (d, J=5.7 Hz, 2H), 3.40 (s, 1H), 3.23 (s, 3H), 2.98 (s, 3H), 2.40 (s, 3H), 1.52-1.43 (m, 2H), 1.34-1.26 (m, 2H); ESMS (M+H)=422.18.

Compound 227: 2'-(((1-(4-fluorobenzyl)-1H-pyrazol-4-yl)methyl)amino)-5',8'-dimethyl-5',8'-dihydro-6'H-spiro[cyclopropane-1,7'-pteridin]-6'-one The compound was prepared by general procedure Method A via reaction of intermediates A-36 and B-2 to provide the title compound; 25% yield. 1H NMR (300 MHz, Methanol-d4) δ 8.13 (d, J=13.9 Hz, 1H), 7.94 (s, 1H), 7.47-7.30 (m, 3H), 7.21-6.99 (m, 2H), 5.46 (s, 2H), 4.56 (s, 2H), 3.23 (s, 3H), 2.96 (d, J=10.3 Hz, 3H), 1.63-1.54 (m, 4H); ESMS (M+H)=408.2.

Compound 232: 5',8'-diethyl-2'-(((1-(4-fluorobenzyl)-1H-pyrazol-4-yl)methyl)amino)-5',8'-dihydro-6'H-spiro[cyclopropane-1,7'-pteridin]-6'-one The compound was prepared by general procedure Method A via reaction of intermediates A-37 and B-2 to provide the title compound; 79% yield. 1H NMR (300 MHz, Methanol-d4) δ 8.26 (s, 1H), 8.10 (s, 1H), 7.47 (s, 1H), 7.45-7.35 (m, 2H), 7.19-7.08 (m, 2H), 5.54 (s, 2H), 4.60 (s, 2H), 3.85 (q, J=7.1 Hz, 2H), 3.39 (q, J=6.9 Hz, 2H), 1.65-1.44 (m, 4H), 1.20 (q, J=7.5 Hz, 3H), 1.10 (t, J=7.0 Hz, 3H); ESMS (M+H)=436.25.

Compound 228: 2'-(((1-(4-fluorobenzyl)-1H-pyrazol-4-yl)methyl)amino)-5',8'-dimethyl-5',8'-dihydro-6'H-spiro[oxetane-3,7'-pteridin]-6'-one The compound was prepared by general procedure Method A via reaction of intermediates A-52 and B-2 to provide the title compound, 40% yield). 1H NMR (300 MHz, CDCl₃) δ 7.44 (d, J=3.5 Hz, 2H), 7.28 (s, 1H), 7.17-7.07 (m, 2H), 7.03-6.88 (m, 2H), 5.21 (t, J=7.2 Hz, 2H), 5.14 (s, 2H), 4.76 (t, J=8.3 Hz, 2H), 4.35 (d, J=5.7 Hz, 2H), 3.40 (s, 3H), 3.23 (s, 3H); ESMS (M+1)=424.23.

Compound 224: 2-(((1-(4-fluorobenzyl)-1H-pyrazol-4-yl)methyl)amino)-5,7,7,8-tetramethyl-7,8-dihydropteridin-6(5H)-one The compound was prepared by general procedure Method B via reaction of intermediates A-14 and B-2 to provide the title compound; 27% yield. 1H NMR (300 MHz, Methanol-d4) δ 8.09 (s, 1H), 7.93 (s, 1H), 7.44 (s, 1H), 7.36 (s, 2H), 7.11 (t, J=8.1 Hz, 2H), 5.46 (s, 2H), 4.58 (s, 2H), 3.26 (s, 3H), 3.24 (s, 3H), 1.68 (d, J=14.7 Hz, 6H); ESMS (M+H)=409.89.

Compound 225: 2-(((1-(4-Fluorobenzyl)-1H-pyrazol-4-yl)methyl)amino)-5,7,7-trimethyl-7,8-dihydropteridin-6(5H)-one The compound was prepared by general procedure Method B via reaction of intermediates A-54 and B-2 to provide the title compound; 55% yield. 1H NMR (300 MHz, Methanol-d4) δ 7.99 (s, 1H), 7.81 (s, 1H), 7.43 (s, 1H), 7.31 (dd, J=8.5, 5.3 Hz, 2H), 7.08 (td, J=8.7, 4.7 Hz, 2H), 5.39 (s, 2H), 4.49 (s, 2H), 3.26 (d, J=6.4 Hz, 3H), 1.56 (s, 6H); ESMS (M+1)=395.89.

Compound 230: 5,8-diethyl-2-(((1-(4-fluorobenzyl)-1H-pyrazol-4-yl)methyl)amino)-7,7-dimethyl-7,8-dihydropteridin-6(5H)-one The compound was prepared by general procedure Method A via reaction of intermediates A-15 and B-2 to provide the title compound; 61% yield. 1H NMR (300 MHz, Methanol-d4) δ 8.43 (s, 1H), 8.28 (s, 1H), 7.56 (s, 1H), 7.47 (dd, J=8.6, 5.3 Hz, 2H), 7.15 (t, J=8.7 Hz, 2H), 5.63 (s, 2H), 4.65 (s, 2H), 3.88 (q, J=7.1 Hz, 2H), 3.73 (q, J=6.9 Hz, 2H), 1.64 (s, 6H), 1.18 (dt, J=9.4, 7.1 Hz, 6H); ESMS (M+H)=438.27.

Compound 9: (7S)-7-ethyl-2-(((1-(4-fluorobenzyl)-1H-pyrazol-4-yl)methyl)amino)-8-methyl-7,8-dihydropteridin-6(5H)-one The compound was prepared by general procedure Method B via reaction of intermediates A-41 and B-2 to provide the title compound; 61% yield. ¹H NMR (300 MHz, CDCl₃) δ 7.65 (s, 1H), 7.48 (d, J=0.7 Hz, 1H), 7.25-7.15 (m, 2H), 7.13 (s, 1H), 6.99 (t, J=8.8 Hz, 2H), 5.22 (s, 2H), 4.43 (s, 2H), 4.30 (dd, J=5.3, 3.4 Hz, 1H), 3.16 (s, 3H), 2.10-1.85 (m, 2H), 0.78 (t, J=7.5 Hz, 3H); ESMS (M+H)=396.18. Analytical SFC (AD-H column; 45% Methanol (0.2% diethylamine)/55% CO2; isocratic): Rt 6.12 mins. (99% ee); $[\alpha]_D$=26.7° (c=1, DMSO).

Compound 2: (7S)-7-ethyl-2-(((1-(4-fluorobenzyl)-1H-pyrazol-4-yl)methyl)amino)-5,7,8-trimethyl-7,8-dihydropteridin-6(5H)-one The compound was prepared by general procedure Method B via reaction of intermediates A-32 and B-2 to provide the title product; 44%. 1H NMR (300 MHz, CDCl₃) δ 7.48 (d, J=7.2 Hz, 1H), 7.45 (s, 1H), 7.34 (s, 1H), 7.17 (dd, J=8.4, 5.4 Hz, 2H), 6.99 (t, J=8.6 Hz, 2H), 5.20 (s, 2H), 5.09 (s, 1H), 4.39 (d, J=5.5 Hz, 2H), 3.27 (s, 3H), 2.98 (s, 3H), 2.16 (dq, J=14.7, 7.4 Hz, 1H), 1.72 (tt, J=12.4, 6.2 Hz, 1H), 0.76 (t, J=7.3 Hz, 3H); ESMS (M+H)=424.27.

Compound 3: (7R)-7-ethyl-2-(((1-(4-fluorobenzyl)-1H-pyrazol-4-yl)methyl)amino)-5,7,8-trimethyl-7,8-dihydropteridin-6(5H)-one The compound was prepared by general procedure Method B via reaction of intermediates A-31 and B-2 to provide the title product; 45%. 1H NMR (300 MHz, CDCl₃) δ 7.53 (s, 1H), 7.47 (s, 1H), 7.36 (s, 1H), 7.20 (dd, J=8.4, 5.4 Hz, 2H), 7.02 (t, J=8.6 Hz, 2H), 5.23 (s, 2H), 4.96 (d, J=22.6 Hz, 1H), 4.41 (d, J=5.6 Hz, 2H), 3.28 (s, 3H), 3.01 (d, J=7.4 Hz, 3H), 2.19 (td, J=14.7, 7.4 Hz, 1H), 1.76 (dq, J=14.5, 7.3 Hz, 1H), 0.80 (t, J=7.3 Hz, 3H); ESMS (M+H)=424.32.

Compound 234: (7R)-5,7,8-triethyl-2-(((1-(4-fluorobenzyl)-1H-pyrazol-4-yl)methyl)amino)-7-methyl-7,8-dihydropteridin-6(5H)-one The compound This compound was made in a similar manner as described above using intermediates A-28 and B-2. 1H NMR (300 MHz, CDCl₃) δ 7.44 (d, J=3.5 Hz, 2H), 7.28 (s, 1H), 7.17-7.07 (m, 2H), 7.03-6.88 (m, 2H), 5.21 (t, J=7.2 Hz, 2H), 5.14 (s, 2H), 4.76 (t, J=8.3 Hz, 2H), 4.35 (d, J=5.7 Hz, 2H), 3.40 (s, 3H), 3.23 (s, 3H); ESMS (M+1)=424.23.

Compound 69: (7S)-2-(((1-(3-fluorobenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-3 to provide the title product; 76% yield. 1H NMR (300 MHz, CDCl₃) δ 8.16 (s, 1H), 7.55 (d, J=0.8 Hz, 1H), 7.41-7.24 (m, 3H), 7.07-6.93 (m, 2H), 6.92-6.82 (m, 1H), 5.27 (s, 2H), 4.85 (t, J=5.7 Hz, 1H), 4.43 (d, J=5.7 Hz, 2H), 4.08 (q, J=6.8 Hz, 1H), 3.04 (s, 3H), 2.23 (s, 3H), 1.40 (d, J=6.8 Hz, 3H); ESMS (M+H)=396.23; $[\alpha]_D^{20}$ +45.0° (c=1, methanol).

Compound 55: (7S)-4-((4-(((4,7,8-trimethyl-6-oxo-5,6,7,8-tetrahydropteridin-2-yl)amino)methyl)-1H-pyrazol-1-yl)methyl)benzonitrile The compound was prepared by general procedure Method A via reaction of intermediates A-2 and B-8 to provide the title product; 49% yield. 1H NMR (300 MHz, CDCl₃) δ 7.77 (s, 1H), 7.73-7.64 (m, 2H), 7.57 (s, 1H), 7.34 (d, J=8.0 Hz, 2H), 5.41 (s, 2H), 4.52 (s, 2H), 4.30 (q, J=6.9 Hz, 1H), 3.23 (s, 3H), 2.28 (s, 4H), 1.52 (d, J=6.9 Hz, 3H); ESMS (M+H)=403.18. $[\alpha]_D$=14.2° (c=1, DMSO).

Compound 382: (7S)-2-(((1-(1-(4-fluorophenyl)ethyl)-1H-pyrazol-4-yl)methyl)amino)-4,7,8-trimethyl-7,8-dihydropteridin-6(5H)-one The compound was prepared by general procedure Method B via reaction of intermediates A-2 and B-4 to afford the title product as a mixture of diastereomers. The diastereomers were separated by SFC chromatography (Whelk-02, 10×250 mm column; 40% MeOH(0.2% Et₂N), 60% CO₂, isocratic; 15 ml/min) and assigned as diastereomer A (Rt 5.337 mins) and B (Rt 7.164 mins)

Compound 71: (7S)-2-(((1-((S)-1-(4-fluorophenyl)ethyl)-1H-pyrazol-4-yl)methyl)amino)-4,7,8-trimethyl-7,8-dihydropteridin-6(5H)-one 1H NMR (300 MHz, Methanol-d4) δ 7.76 (s, 1H), 7.58 (s, 1H), 7.29 (dd, J=8.6, 5.4 Hz, 2H), 7.08 (t, J=8.7 Hz, 2H), 5.62-5.50 (m, 1H), 4.53 (s, 2H), 4.33 (dd, J=13.9, 6.9 Hz, 1H), 3.25 (s, 3H), 2.31 (s, 3H), 1.88 (d, J=7.1 Hz, 3H), 1.55 (d, J=6.9 Hz, 3H); ESMS (M+H)=410.27. Analytical SFC chromatography (Whelk-02 column, 4.6×100 mm; 40% MeOH(0.2% Et₂N), 60% CO₂, isocratic; 5 ml/min): Rt 5.053 mins. (97.4% de).

Compound 72: (7S)-2-(((1-((R)-1-(4-fluorophenyl)ethyl)-1H-pyrazol-4-yl)methyl)amino)-4,7,8-trimethyl-7,8-dihydropteridin-6(5H)-one 1H NMR (300 MHz, Methanol-d4) δ 7.76 (s, 1H), 7.58 (s, 1H), 7.29 (dd, J=8.6, 5.4 Hz, 2H), 7.08 (t, J=8.7 Hz, 2H), 5.62-5.50 (m, 1H), 4.53 (s, 2H), 4.33 (dd, J=13.9, 6.9 Hz, 1H), 3.25 (s, 3H), 2.31 (s, 3H), 1.88 (d, J=7.1 Hz, 3H), 1.55 (d, J=6.9 Hz, 3H); ESMS(M+1)=410.31. Analytical SFC chromatography (Whelk-02 column, 4.6×100 mm; 40% MeOH(0.2% Et₂N), 60% CO₂, isocratic; 5 ml/min): Rt 6.505 mins. (99.2% de).

Compound 149: (7S)-4,7,8-trimethyl-2-(((1-(4-(trifluoromethyl)benzyl)-1H-pyrazol-4-yl)methyl)amino)-7,8-dihydropteridin-6(5H)-one The compound was prepared by general procedure Method A via reaction of intermediates A-2 and B-5 to provide the title product; 48% yield. 1H NMR (300 MHz, CDCl₃) δ 8.14 (s, 1H), 7.66-7.52 (m, 3H), 7.40 (d, J=0.8 Hz, 1H), 7.35-7.28 (m, 2H), 5.33 (s, 2H), 4.96 (s, 1H), 4.44 (d, J=5.7 Hz, 2H), 4.08 (q, J=6.8 Hz, 1H), 3.05 (s, 3H), 2.24 (s, 3H), 1.41 (d, J=6.9 Hz, 3H); ESMS (M+H)=446.17.

Compound 147: (7S)-7,8-dimethyl-2-(((1-(4-(trifluoromethyl)benzyl)-1H-pyrazol-4-yl)methyl)amino)-7,8-dihydropteridin-6(5H)-one The compound was prepared by general procedure Method A via reaction of intermediates A-1 and B-5 to provide the title product; 48% yield. 1H NMR (300 MHz, CDCl₃) δ 7.55-7.46 (m, 3H), 7.40-7.33 (m, 1H), 7.26-7.16 (m, 3H), 5.24 (s, 2H), 4.38 (d, J=5.7 Hz, 2H), 3.96 (q, J=6.8 Hz, 1H), 2.98 (s, 3H), 1.35 (d, J=6.9 Hz, 3H); ESMS (M+H)=432.35.

Compound 45: (7S)-7,8-dimethyl-2-(((1-(3-(trifluoromethyl)benzyl)-1H-pyrazol-4-yl)methyl)amino)-7,8-dihydropteridin-6(5H)-one The compound was prepared by general procedure Method B via reaction of intermediates A-1 and B-6 to provide the title product; 48% yield. 1H NMR (300 MHz, CDCl₃) δ 7.63-7.35 (m, 7H), 5.33 (s, 2H), 4.48 (d, J=5.6 Hz, 2H), 4.17 (q, J=6.9 Hz, 1H), 3.16 (s, 3H), 1.54 (d, J=7.0 Hz, 3H); ESMS (M+H)=432.27.

Compound 49: (7S)-5,8-diethyl-7-(2-hydroxyethyl)-2-(((1-(3-(trifluoromethyl)benzyl)-1H-pyrazol-4-yl)methyl)amino)-7,8-dihydropteridin-6(5H)-one The compound was prepared by general procedure Method B via reaction of intermediates A-26 and B-6 to provide the title product; 14% yield. 1H NMR (300 MHz, CDCl₃) δ 7.66-7.35 (m, 7H), 5.34 (s, 2H), 4.46 (d, J=5.8 Hz, 2H), 4.32 (dd, J=9.0, 4.1 Hz, 1H), 4.07 (ddt, J=39.0, 14.3, 7.1 Hz, 2H), 3.84-3.61 (m, 3H), 3.11 (dt, J=14.1, 7.1 Hz, 1H), 2.13 (dt, J=8.3, 4.5 Hz, 1H), 1.82 (tt, J=9.2, 4.7 Hz, 1H), 1.24 (td, J=7.1, 6.0 Hz, 6H); ESMS (M+H)=504.28.

Compound 47: (7S)-4,7,8-trimethyl-2-(((1-(3-(trifluoromethyl)benzyl)-1H-pyrazol-4-yl)methyl)amino)-7,8-dihydropteridin-6(5H)-one The compound was prepared by general procedure Method A via reaction of intermediates A-2 and B-6 to provide the title product; 65% yield. 1H NMR (300 MHz, CDCl₃) δ 7.61-7.32 (m, 6H), 5.33 (s, 2H), 4.83 (s, 1H), 4.45 (s, 2H), 4.45-3.70 (m, 1H), 3.04 (s, 3H), 2.20 (s, 3H), 1.41 (d, J=6.8 Hz, 3H); ESMS (M+H)=446.28; $[\alpha]_D^{20}$ +49.20 (c=1, methanol).

Compound 68: (7S)-4,7,8-trimethyl-2-(((1-(2-(trifluoromethyl)benzyl)-1H-pyrazol-4-yl)methyl)amino)-7,8-dihydropteridin-6(5H)-one The compound was prepared by general procedure Method A via reaction of intermediates A-2 and B-7 to provide the title product; 48% yield. 1H NMR (300 MHz, CDCl₃) δ 7.69 (d, J=7.7 Hz, 1H), 7.58 (s, 1H), 7.52-7.37 (m, 3H), 6.98 (d, J=7.6 Hz, 1H), 5.50 (s, 2H), 4.44 (d, J=5.7 Hz, 2H), 4.08 (q, J=6.8 Hz, 1H), 3.05 (s, 3H), 2.23 (s, 3H), 1.41 (d, J=6.8 Hz, 3H); ESMS (M+H)=446.24.

Compound 78: (7S)-2-(((1-(2-isopropylbenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-9 to provide the title product; 45% yield. 1H NMR (300 MHz, CDCl$_3$) δ 7.53 (d, J=0.8 Hz, 1H), 7.39-7.31 (m, 2H), 7.25-7.13 (m, 2H), 7.13-7.03 (m, 1H), 5.35 (s, 2H), 4.79 (s, 1H), 4.38 (d, J=5.7 Hz, 2H), 4.07 (q, J=6.8 Hz, 1H), 3.16 (p, J=6.8 Hz, 1H), 3.02 (s, 3H), 2.19 (s, 3H), 1.40 (d, J=6.9 Hz, 3H), 1.19-1.10 (m, 6H); ESMS (M+H)=420.33.

Compound 79: (7S)-2-(((1-(2-isopropylbenzyl)-1H-pyrazol-4-yl)methyl)amino)-7,8-dimethyl-7,8-dihydropteridin-6(5H)-one The compound was prepared by general procedure Method A via reaction of intermediates A-1 and B-9 to provide the title product; 48% yield. 1H NMR (300 MHz, CDCl$_3$) δ 7.58-7.51 (m, 1H), 7.41-7.30 (m, 3H), 7.27-7.03 (m, 3H), 5.34 (s, 2H), 4.40 (d, J=5.8 Hz, 2H), 4.06 (q, J=6.8 Hz, 1H), 3.16 (p, J=6.8 Hz, 1H), 3.03 (s, 3H), 1.44 (d, J=6.9 Hz, 3H), 1.14 (d, J=6.8 Hz, 6H); ESMS (M+H)=406.23.

Compound 80: (7S)-2-(((1-(3-isopropylbenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-10 to provide the title product; 62% yield. 1H NMR (300 MHz, CDCl$_3$) δ 7.57 (d, J=18.7 Hz, 2H), 7.38-7.15 (m, 2H), 7.10 (s, 1H), 7.02 (d, J=7.5 Hz, 1H), 5.26 (s, 2H), 4.81 (d, J=6.4 Hz, 1H), 4.42 (d, J=5.7 Hz, 2H), 4.08 (q, J=6.8 Hz, 1H), 3.05 (s, 3H), 2.90 (p, J=6.9 Hz, 1H), 2.21 (s, 3H), 1.41 (d, J=6.8 Hz, 3H), 1.25 (d, J=6.9 Hz, 6H); ESMS (M+H)=420.28.

Compound 81: (7S)-2-(((1-(3-isopropylbenzyl)-1H-pyrazol-4-yl)methyl)amino)-7,8-dimethyl-7,8-dihydropteridin-6(5H)-one The compound was prepared by general procedure Method A via reaction of intermediates A-1 and B-10 to provide the title product; 60% yield. 1H NMR (300 MHz, CDCl$_3$) δ 7.55 (d, J=0.8 Hz, 1H), 7.44-7.34 (m, 2H), 7.33-6.98 (m, 4H), 5.26 (s, 2H), 4.44 (d, J=5.8 Hz, 2H), 4.08 (q, J=6.8 Hz, 1H), 3.06 (s, 3H), 2.89 (p, J=6.9 Hz, 1H), 1.45 (d, J=6.9 Hz, 3H), 1.24 (d, J=6.9 Hz, 6H); ESMS (M+H)=406.32.

Compound 14: (7S)-4,5,7,8-tetramethyl-2-(((1-(3,4,5-trifluorobenzyl)-1H-pyrazol-4-yl)methyl)amino)-7,8-dihydropteridin-6(5H)-one The compound was prepared by general procedure Method B via reaction of intermediates A-3 and B-23 to provide the title product; 31% yield. 1H NMR (300 MHz, DMSO-d6) δ 7.73 (s, 1H), 7.43 (s, 1H), 7.13 (dd, J=8.7, 6.8 Hz, 2H), 6.86 (t, J=5.6 Hz, 1H), 5.27 (s, 2H), 4.34-4.16 (m, 2H), 4.02 (q, J=6.8 Hz, 1H), 3.18 (s, 3H), 2.92 (s, 3H), 2.27 (s, 3H), 1.05 (d, J=6.8 Hz, 3H); ESMS (M+H)=446.31; [α]$_D^{20}$+23.4° (c=1, methanol).

Compound 122: (7S)-4,7,8-trimethyl-2-(((1-(3,4,5-trifluorobenzyl)-1H-pyrazol-4-yl)methyl)amino)-7,8-dihydropteridin-6(5H)-one The compound was prepared by general procedure Method A via reaction of intermediates A-2 and B-23 to provide the title product; 44% yield. 1H NMR (300 MHz, CDCl$_3$) δ 8.72 (s, 1H), 7.55 (s, 1H), 7.39 (s, 1H), 6.79 (t, J=7.0 Hz, 2H), 5.20 (s, 2H), 4.90 (t, J=5.9 Hz, 1H), 4.44 (d, J=5.8 Hz, 2H), 4.07 (q, J=6.8 Hz, 1H), 3.05 (s, 3H), 2.25 (s, 3H), 1.40 (d, J=6.9 Hz, 3H); ESMS (M+H)=432.15.

Compound 42: (7S)-7,8-dimethyl-2-(((1-(3,4,5-trifluorobenzyl)-1H-pyrazol-4-yl)methyl)amino)-7,8-dihydropteridin-6(5H)-one The compound was prepared by general procedure Method A via reaction of intermediates A-1 and B-23 to provide the title product; 65% yield. 1H NMR (400 MHz, Methanol-d4) δ 7.66 (s, 1H), 7.52 (s, 1H), 7.37 (s, 1H), 6.92 (dd, J=8.5, 6.6 Hz, 2H), 5.26 (s, 2H), 4.38 (s, 2H), 4.11 (q, J=6.9 Hz, 1H), 3.05 (s, 3H), 1.38 (d, J=6.9 Hz, 3H); ESMS (M+H)=418.29; [α]$_D^{20}$+39.2° (c=1.04, DMSO).

Compound 229: 5,7,7,8-tetramethyl-2-(((1-(3,4,5-trifluorobenzyl)-1H-pyrazol-4-yl)methyl)amino)-7,8-dihydropteridin-6(5H)-one The compound was prepared by general procedure Method A via reaction of intermediates A-14 and B-23 to provide the title product; 91% yield. 1H NMR (300 MHz, DMSO-d6) δ 12.77 (s, 1H), 8.40 (s, 1H), 7.87 (s, 1H), 7.59 (s, 1H), 7.52 (s, 1H), 7.16 (dd, J=8.8, 6.8 Hz, 2H), 5.31 (s, 2H), 4.44 (d, J=5.7 Hz, 2H), 3.19 (d, J=4.2 Hz, 3H), 3.17 (s, 3H), 1.57 (s, 6H); ESMS (M+H)=446.4.

Compound 15: (7S)-7-Ethyl-5,8-dimethyl-2-(((1-(3,4,5-trifluorobenzyl)-1H-pyrazol-4-yl)methyl)amino)-7,8-dihydropteridin-6(5H)-one The compound was prepared by reaction by general procedure Method B via reaction of intermediates A-42 and B-23 to provide the title product. $^1$H NMR (300 MHz, CDCl$_3$) δ 1H) δ 7.65 (s, 1H), 7.44 (s, 1H) 7.28 (s, 1H), 6.92-6.68 (m, 2H), 5.15 (s, 2H), 4.39 (s, 2H), 4.29 (dd, J=5.4, 3.4 Hz, 1H), 3.12 (s, 4H), 3.11 (s, 4H), 1.91 (pd, J=7.3, 4.4 Hz, 2H), 0.64 (t, J=7.4 Hz, 3H); ESMS(M+1)= 446.19.

Compound 36: (7S)-7-ethyl-8-isopropyl-5-methyl-2-(((1-(3,4,5-trifluorobenzyl)-1H-pyrazol-4-yl)methyl)amino)-7,8-dihydropteridin-6(5H)-one The compound was prepared by general procedure Method A via reaction of intermediates A-18 and B-23 to provide the title product; 388% yield. 1H NMR (300 MHz, CDCl$_3$) δ 7.46 (d, J=4.2 Hz, 1H), 7.45 (s, 1H), 7.32 (s, 1H), 6.76-6.67 (m, 2H), 5.12 (s, 2H), 5.01 (s, 1H), 4.45 (dt, J=13.1, 6.5 Hz, 1H), 4.37 (d, J=5.7 Hz, 2H), 4.14 (dd, J=7.6, 3.4 Hz, 1H), 3.20 (s, 3H), 1.90-1.74 (m, 1H), 1.73-1.54 (m, 1H), 1.31-1.21 (m, 6H), 0.78 (t, J=7.5 Hz, 3H); ESMS (M+H)=474.28.

Compound 33: (7S)-7-ethyl-5-methyl-2-(((1-(3,4,5-trifluorobenzyl)-1H-pyrazol-4-yl)methyl)amino)-8-(2,2,2-trifluoroethyl)-7,8-dihydropteridin-6(5H)-one The compound was prepared by general procedure Method B via reaction of intermediates A-45 and B-23 to provide the title product; 30.4% yield. 1H NMR (300 MHz, Methanol-d4) δ 7.98 (d, J=9.7 Hz, 1H), 7.81 (s, 1H), 7.68 (s, 1H), 7.04 (td, J=7.9, 5.0 Hz, 2H), 5.38 (d, J=11.1 Hz, 2H), 5.16-5.02 (m, 1H), 4.71-4.50 (m, 2H), 4.17 (dt, J=17.4, 8.6 Hz, 1H), 3.31 (d, J=1.1 Hz, 5H), 2.10-1.90 (m, 3H), 0.86 (t, J=7.4 Hz, 3H); ESMS (M+1)=514.12.

Compound 51: (7S)-5-ethyl-8-isopropyl-7-methyl-2-(((1-(3,4,5-trifluorobenzyl)-1H-pyrazol-4-yl)methyl)amino)-7,8-dihydropteridin-6(5H)-one The compound was prepared by general procedure Method A via reaction of intermediates A-19 and B-23 to provide the title product; 80% yield. 1H NMR (300 MHz, CDCl$_3$) δ 7.54 (s, 1H), 7.45 (d, J=10.6 Hz, 1H), 7.33 (s, 1H), 6.76-6.67 (m, 2H), 5.12 (s, 2H), 5.00 (t, J=5.5 Hz, 1H), 4.54 (dq, J=13.2, 6.6 Hz, 1H), 4.35 (t, J=5.8 Hz, 2H), 4.18 (q, J=6.7 Hz, 1H), 3.87 (dq, J=14.3, 7.1 Hz, 1H), 3.77-3.58 (m, 1H), 1.19 (m, 12H); ESMS (M+H)=474.37.

Compound 31: (7S)-5,8-diethyl-7-methyl-2-(((1-(3,4,5-trifluorobenzyl)-1H-pyrazol-4-yl)methyl)amino)-7,8-dihydropteridin-6(5H)-one The compound was prepared by general procedure Method A via reaction of intermediates A-22 and B-23 to provide the title product; 75% yield. 1H NMR (300 MHz, CDCl$_3$) δ 7.49 (d, J=5.9 Hz, 1H), 7.45 (d, J=10.3 Hz, 1H), 7.33 (s, 1H), 6.77-6.67 (m, 2H), 5.12 (s, 2H), 4.97 (d, J=5.2 Hz, 1H), 4.36 (d, J=5.6 Hz, 2H), 4.10 (q, J=6.8 Hz, 1H), 4.00-3.62 (m, 3H), 3.04 (dq, J=14.1, 7.1 Hz, 1H), 1.26 (t, J=7.7 Hz, 3H), 1.14 (dd, J=13.5, 7.1 Hz, 6H); ESMS (M+H)=460.28.

Compound 231: 5,8-diethyl-7,7-dimethyl-2-(((1-(3,4,5-trifluorobenzyl)-1H-pyrazol-4-yl)methyl)amino)-7,8-dihydropteridin-6(5H)-one The compound was prepared by general procedure Method A via reaction of intermediates A-15 and B-23 to provide the title product; 42% yield. 1H NMR (300 MHz, Methanol-d4) δ 6.69 (d, J=10.6 Hz, 1H), 6.47 (d, J=8.9 Hz, 1H), 5.82 (dd, J=8.2, 6.8 Hz, 2H), 4.16 (s, 2H), 3.37 (s, 2H), 2.63 (dq, J=27.4, 6.7 Hz, 4H), 0.44 (d, J=4.4 Hz, 6H), 0.02 (dt, J=13.6, 6.8 Hz, 6H); ESMS (M+H)=474.24.

Compound 35: (7S)-5,7,8-triethyl-7-methyl-2-(((1-(3,4,5-trifluorobenzyl)-1H-pyrazol-4-yl)methyl)amino)-7,8-dihydropteridin-6(5H)-one The compound was prepared by general procedure Method A via reaction of intermediates A-30 and B-23 to provide the title product; 62% yield. 1H NMR (300 MHz, Methanol-d4) δ 8.31 (s, 1H), 8.08 (d, J=8.5 Hz, 1H), 7.56 (s, 1H), 7.20 (dd, J=13.3, 5.9 Hz, 2H), 5.57 (s, 2H), 4.65 (d, J=2.6 Hz, 2H), 4.02 (dt, J=14.3, 7.1 Hz, 1H), 3.96-3.77 (m, 2H), 3.56 (dq, J=13.4, 6.6 Hz, 1H), 2.15-1.90 (m, 2H), 1.70 (s, 3H), 1.21 (t, J=7.0 Hz, 6H), 0.76 (d, J=7.4 Hz, 3H); ESMS (M+H)=488.28.

Compound 235: (7R)-5,7,8-triethyl-7-methyl-2-(((1-(3,4,5-trifluorobenzyl)-1H-pyrazol-4-yl)methyl)amino)-7,8-dihydropteridin-6(5H)-one This compound was made in a similar manner as described above using intermediates A-28 and B-28. 1H NMR (300 MHz, Methanol-d4) δ 6.73 (s, 1H), 6.58 (s, 1H), 5.86 (s, 1H), 5.78 (dd, J=8.5, 5.3 Hz, 2H), 5.45 (t, J=8.7 Hz, 2H), 3.93 (s, 2H), 2.96 (d, J=3.2 Hz, 2H), 2.41-2.24 (m, 1H), 2.20-2.01 (m, 2H), 1.82 (dq, J=13.8, 6.9 Hz, 1H), 1.61 (dd, J=3.2, 1.6 Hz, 1H), 1.04 (s, 1H), 0.61 (s, 2H), 0.47-0.16 (m, 2H); ESMS (M+1)=452.31.

Compound 39: (7S)-7-(2-Hydroxyethyl)-2-(((1-(3,4,5-trifluorobenzyl)-1H-pyrazol-4-yl)methyl)amino)-7,8-dihydropteridin-6(5H)-one The compound was prepared by general procedure Method B via reaction of intermediates A-25 and B-23 to provide the title product. 1H NMR (300 MHz, Methanol-d4) δ 7.79 (s, 1H), 7.59 (d, J=0.8 Hz, 1H), 7.19 (s, 1H), 6.95 (dd, J=8.4, 6.6 Hz, 2H), 5.29 (s, 2H), 4.64-4.43 (m, 3H), 3.74 (dd, J=6.8, 5.5 Hz, 2H), 2.31-2.00 (m, 2H); ESMS(M+1)=434.14.

Compound 37: (7S)-5,8-diethyl-7-(2-hydroxyethyl)-2-(((1-(3,4,5-trifluorobenzyl)-1H-pyrazol-4-yl)methyl)amino)-7,8-dihydropteridin-6(5H)-one The compound was prepared by general procedure Method B via reaction of intermediates A-26 and B-23 to provide the title product; 4% yield. 1H NMR (300 MHz, Methanol-d4) δ 7.76 (s, 1H), 7.54 (d, J=14.2 Hz, 1.5H), 7.42 (s, 0.5H), 7.03-6.91 (m, 2H), 5.29 (s, 2H), 4.67-4.39 (m, 4H), 4.24-3.77 (m, 4H), 3.75-3.36 (m, 2H), 2.53-2.21 (m, 2H), 1.32-1.12 (m, 6H; ESMS (M+H)=490.26.

Compound 233: 5',8'-diethyl-2'-(((1-(3,4,5-trifluorobenzyl)-1H-pyrazol-4-yl)methyl)amino)-5',8'-dihydro-6'H-spiro[cyclopropane-1,7'-pteridin]-6'-one The compound was prepared by general procedure Method A via reaction of intermediates A-37 and B-23 to provide the title product; 46% yield. 1H NMR (300 MHz, Methanol-d4) δ 8.13 (s, 1H), 7.92 (s, 1H), 7.47 (d, J=3.3 Hz, 1H), 7.14-7.06 (m, 2H), 5.47 (s, 2H), 4.58 (s, 2H), 3.85 (q, J=7.1 Hz, 2H), 3.48-3.36 (77 m, 2H), 1.65-1.52 (m, 2H), 1.53-1.42 (m, 2H), 1.24-1.16 (m, 3H), 1.16-1.06 (m, 3H); ESMS (M+H)=472.21.

Compound 23: (7S)-5,8-dimethyl-7-propyl-2-(((1-(3,4,5-trifluorobenzyl)-1H-pyrazol-4-yl)methyl)amino)-7,8-dihydropteridin-6(5H)-one The compound was prepared by general procedure Method B via reaction of intermediates A-50 and B-23 to provide the title product; 45% yield. 1H NMR (300 MHz, Methanol-d4) δ 7.71-7.64 (m, 1H), 77.52 (d, J=3.1 Hz, 2H), 6.92 (dd, J=8.5, 6.6 Hz, 2H), 5.30-5.23 (m, 2H), 4.40 (s, 2H), 4.19 (dd, J=5.8, 4.2 Hz, 1H), 3.26 (s, 3H), 3.06 (s, 3H), 1.90-1.70 (m, 2H), 1.30-1.09 (m, 2H), 0.87 (t, J=7.3 Hz, 3H); ESMS (M+H)=460.19.

Compound 25: (7S)-5,8-dimethyl-7-(prop-2-yn-1-yl)-2-(((1-(3,4,5-trifluorobenzyl)-1H-pyrazol-4-yl)methyl)amino)-7,8-dihydropteridin-6(5H)-one The compound was prepared by general procedure Method B via reaction of intermediates A-10 and B-23 to provide the title product; 5% yield. 1H NMR (300 MHz, Methanol-d4) δ 7.81 (d, J=0.8 Hz, 1H), 7.63-7.56 (m, 1H), 7.42 (s, 1H), 6.98 (dd, J=8.4, 6.6 Hz, 2H), 5.30 (d, J=1.1 Hz, 2H), 4.62-4.49 (m, 3H), 3.29 (d, J=1.5 Hz, 6H), 3.06 (ddd, J=17.6, 4.8, 2.7 Hz, 1H), 2.90 (dt, J=18.0, 2.9 Hz, 1H); ESMS (M+H)=456.19.

Compound 21: (7S)-7-((R)-1-methoxyethyl)-5,8-dimethyl-2-(((1-(3,4,5-trifluorobenzyl)-1H-pyrazol-4-yl)methyl)amino)-7,8-dihydropteridin-6(5H)-one The compound was prepared by general procedure Method B via reaction of intermediates A-20 and B-23 to provide the title product; 6% yield. 1H NMR (300 MHz, Methanol-d4) δ 7.78 (s, 1H), 7.59 (dd, J=1.9, 0.8 Hz, 1H), 7.38 (d, J=13.5 Hz, 1H), 7.03-6.91 (m, 2H), 5.30 (s, 2H), 4.54 (s, 2H), 4.39 (dd, J=11.5, 2.7 Hz, 1H), 3.93-3.75 (m, 1H), 3.35 (s, 3H), 3.28-3.22 (m, 6H), 1.24 (dd, J=23.0, 6.5 Hz, 3H); ESMS (M+H)=476.17.

Compound 140: (7S)-2-(((1-(3,4-difluorobenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-11 to provide the title product; 72% yield. 1H NMR (300 MHz, CDCl$_3$) δ 8.41 (s, 1H), 7.54 (s, 1H), 7.37 (s, 1H), 7.21-6.88 (m, 3H), 5.22 (s, 2H), 4.85 (t, J=5.7 Hz, 1H), 4.43 (d, J=5.7 Hz, 2H), 4.08 (q, J=6.8 Hz, 1H), 3.05 (s, 3H), 2.24 (s, 3H), 1.41 (d, J=6.8 Hz, 3H); ESMS (M+H)=414.12.

Compound 28: (7S)-2-(((1-(3,4-difluorobenzyl)-1H-pyrazol-4-yl)methyl)amino)-4,5,7,8-tetramethyl-7,8-dihydropteridin-6(5H)-one The compound was prepared by general procedure Method B via reaction of intermediates A-3 and B-11 to provide the title product; 4% yield. 1H NMR (300 MHz, Methanol-d4) δ 7.80 (s, 1H), 7.60 (s, 1H), 7.31-7.01 (m, 3H), 5.31 (s, 2H), 4.54 (s, 2H), 4.31 (q, J=6.9 Hz, 1H), 3.32 (s, 3H), 3.24 (s, 3H), 2.46 (s, 3H), 1.37 (d, J=7.0 Hz, 3H); ESMS (M+H)=428.23.

Compound 141: (7S)-2-(((1-(3,4-difluorobenzyl)-1H-pyrazol-4-yl)methyl)amino)-7,8-dimethyl-7,8-dihydropteridin-6(5H)-one The compound was prepared by general procedure Method A via reaction of intermediates A-1 and B-11 to provide the title product; 45% yield. 1H NMR (300 MHz, CDCl$_3$) δ 7.57 (s, 1H), 7.41 (d, J=19.3 Hz, 2H), 7.20-6.90 (m, 4H), 5.22 (s, 2H), 4.46 (d, J=5.6 Hz, 2H), 4.06 (q, J=6.8 Hz, 1H), 3.08 (s, 3H), 1.44 (d, J=6.8 Hz, 3H); ESMS (M+H)=400.12.

Compound 29: (7S)-2-(((1-(2,4-difluorobenzyl)-1H-pyrazol-4-yl)methyl)amino)-4,5,7,8-tetramethyl-7,8-dihydropteridin-6(5H)-one The compound was prepared by general procedure Method B via reaction of intermediates A-3 and B-12 to provide the title product; 4% yield. 1H NMR (300 MHz, Methanol-d4) δ 7.76 (s, 1H), 7.58 (s, 1H), 7.29 (td, J=8.5, 6.3 Hz, 1H), 7.07-6.89 (m, 3H), 5.35 (s, 2H), 4.52 (s, 2H), 4.38-4.22 (m, 1H), 3.32 (s, 3H), 3.24 (s, 3H), 2.45 (s, 3H), 1.37 (d, J=7.0 Hz, 3H); ESMS (M+H)=428.23.

Compound 65: (7S)-2-(((1-(2-chloro-4-fluorobenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-13 to provide the title product; 6% yield. 1H NMR (300 MHz, CDCl$_3$) δ 7.55 (s, 1H), 7.43 (s, 1H), 7.16 (dd, J=8.3, 2.5 Hz, 1H), 7.09-6.89 (m, 2H), 5.35 (s, 2H), 4.80 (t, J=5.8 Hz, 1H), 4.43 (d, J=5.7 Hz, 2H), 4.09 (q, J=6.8 Hz, 1H), 3.06 (s, 3H), 2.20 (s, 3H), 1.41 (d, J=6.9 Hz, 3H); ESMS (M+H)=430.21.

Compound 66: (7S)-2-(((1-(4-fluoro-2-methylbenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-14 to provide the title product; 55% yield. 1H NMR (300 MHz, CDCl$_3$) δ 7.75 (s, 1H), 7.53 (d, J=0.8 Hz, 1H), 7.22 (d, J=0.8 Hz, 1H), 7.09-6.82 (m, 3H), 5.24 (s, 2H), 4.78 (t, J=5.6 Hz, 1H), 4.40 (d, J=5.6 Hz, 2H), 4.08 (q, J=6.8 Hz, 1H), 3.04 (s, 3H), 2.23 (d, J=16.9 Hz, 6H), 1.40 (d, J=6.9 Hz, 3H); ESMS (M+H)=410.23.

Compound 67: (7S)-2-(((1-(4-fluoro-2-(trifluoromethyl)benzyl)-1H-pyrazol-4-yl)methyl)amino)-4,7,8-trimethyl-7,8-dihydropteridin-6(5H)-one The compound was prepared by general procedure Method A via reaction of intermediates A-2 and B-15 to provide the title product; 76% yield. 1H NMR (300 MHz, CDCl$_3$) δ 7.57 (s, 1H), 7.45-7.35 (m, 2H), 7.18 (td, J=8.2, 2.7 Hz, 1H), 7.02 (dd, J=8.5, 5.5 Hz, 1H), 5.45 (s, 2H), 4.44 (d, J=5.7 Hz, 2H), 4.08 (q, J=6.8 Hz, 1H), 3.06 (s, 3H), 2.63 (s, 1H), 2.24 (s, 3H), 1.41 (d, J=6.8 Hz, 3H); ESMS (M+H)=464.2.

Compound 17: (7S)-4,5,7,8-tetramethyl-2-(((1-(2,3,4-trifluorobenzyl)-1H-pyrazol-4-yl)methyl)amino)-7,8-dihydropteridin-6(5H)-one The compound was prepared by general procedure Method B via reaction of intermediates A-3 and B-22 to provide the title product; 53% yield. 1H NMR (300 MHz, DMSO-d6) δ 13.14 (s, 1H), 8.10 (s, 1H), 7.84 (s, 1H), 7.48 (d, J=0.8 Hz, 1H), 7.32 (dddd, J=10.2, 9.3, 7.3, 2.1 Hz, 1H), 7.20-6.98 (m, 1H), 5.44 (s, 2H), 5.39 (s, 2H), 4.42 (d, J=5.7 Hz, 2H), 4.36 (q, J=7.0 Hz, 1H), 3.22 (s, 3H), 3.17 (s, 3H), 2.42 (s, 3H), 1.27 (d, J=6.9 Hz, 3H); ESMS (M+H)=446.3.

Compound 16: (7S)-4,5,7,8-tetramethyl-2-(((1-(2,4,5-trifluorobenzyl)-1H-pyrazol-4-yl)methyl)amino)-7,8-dihydropteridin-6(5H)-one The compound was prepared by general procedure Method B via reaction of intermediates A-3 and B-24 to provide the title product; 53% yield 1H NMR (300 MHz, CDCl$_3$) δ 7.53 (s, 1H), 7.44 (s, 1H), 7.03-6.86 (m, 2H), 5.25 (s, 2H), 5.21 (s, 1H), 4.44 (d, J=5.8 Hz, 2H), 4.01 (q, J=6.9 Hz, 1H), 3.29 (s, 3H), 3.02 (s, 3H), 2.36 (s, 3H), 1.21 (d, J=6.9 Hz, 3H); ESMS (M+H)=446.3. Chiralpak IB column (25% ethanol/75% hexane): Rt 10.838 mins.; 96.2% ee. $[\alpha]_D^{20}$+15.2° (c=1, methanol).

Compound 18: (7S)-4,5,7,8-tetramethyl-2-(((1-(2,4,6-trifluorobenzyl)-1H-pyrazol-4-yl)methyl)amino)-7,8-dihydropteridin-6(5H)-one The compound was prepared by general procedure Method B via reaction of intermediates A-3 and B-80 to provide the title product; 35% yield 1H NMR (300 MHz, Methanol-d4) δ 7.72 (s, 1H), 7.50 (d, J=0.7 Hz, 1H), 6.95 (ddd, J=9.0, 7.8, 4.7 Hz, 2H), 5.36 (d, J=1.2 Hz, 2H), 4.50 (d, J=1.8 Hz, 2H), 4.38-4.19 (m, 1H), 3.25 (s, 3H), 2.45 (s, 3H), 1.99 (s, 3H), 1.37 (d, J=7.0 Hz, 3H); ESMS (M+H)=446.15.

Compound 146: (7S)-2-(((1-(3-fluoro-4-methoxybenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-17 to provide the title product; 52% yield 1H NMR (300 MHz, CDCl₃) δ 8.02 (s, 1H), 7.53 (d, J=0.8 Hz, 1H), 7.38-7.31 (m, 1H), 7.02-6.87 (m, 3H), 5.19 (s, 2H), 4.91 (s, 1H), 4.42 (d, J=5.7 Hz, 2H), 4.08 (q, J=6.8 Hz, 1H), 3.89 (s, 3H), 3.05 (s, 3H), 2.23 (s, 3H), 1.41 (d, J=6.9 Hz, 3H); ESMS (M+H)=426.32

Compound 75: (7S)-2-(((1-(4-fluoro-3-methoxybenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-16 to provide the title product; 84% yield 1H NMR (400 MHz, CDCl₃) δ 7.88 (s, 1H), 7.45 (d, J=0.8 Hz, 1H), 7.27 (d, J=0.8 Hz, 1H), 6.96 (ddd, J=11.0, 8.2, 0.8 Hz, 1H), 6.75 (dd, J=8.0, 2.1 Hz, 1H), 6.67 (ddd, J=8.4, 4.2, 2.1 Hz, 1H), 5.13 (s, 2H), 4.79 (s, 1H), 4.34 (dd, J=5.5, 1.3 Hz, 2H), 4.06-3.94 (m, 1H), 3.77 (d, J=0.8 Hz, 3H), 2.96 (d, J=0.9 Hz, 3H), 2.14 (s, 3H), 1.32 (dd, J=6.8, 0.9 Hz, 3H); ESMS (M+H)=426.18.

Compound 148: (7S)-2-(((1-(3-fluoro-4-methoxybenzyl)-1H-pyrazol-4-yl)methyl)amino)-7,8-dimethyl-7,8-dihydropteridin-6(5H)-one The compound was prepared by general procedure Method A via reaction of intermediates A-1 and B-17 to provide the title product; 34% yield 1H NMR (300 MHz, CDCl₃) δ 7.54 (d, J=0.8 Hz, 1H), 7.45-7.37 (m, 2H), 7.03-6.86 (m, 3H), 5.19 (s, 2H), 4.44 (d, J=5.7 Hz, 2H), 4.09 (q, J=6.8 Hz, 1H), 3.88 (s, 3H), 3.08 (s, 3H), 1.46 (d, J=6.9 Hz, 3H); ESMS (M+H)=411.98.

Compound 181: (7S)-2-(((1-(benzo[d][1,3]dioxol-5-ylmethyl)-1H-pyrazol-4-yl)methyl)amino)-4,7,8-trimethyl-7,8-dihydropteridin-6(5H)-one The compound was prepared by general procedure Method A via reaction of intermediates A-2 and B-19 to provide the title product; 31% yield. 1H NMR (300 MHz, CDCl₃) δ 7.50 (d, J=0.8 Hz, 1H), 7.39 (d, J=0.8 Hz, 1H), 6.84-6.67 (m, 3H), 5.96 (s, 2H), 5.16 (s, 2H), 4.44 (d, J=5.7 Hz, 2H), 4.15 (q, J=6.8 Hz, 1H), 3.14 (s, 3H), 2.32 (s, 3H), 1.50 (d, J=6.9 Hz, 3H); ESMS (M+H)=422.18.

Compound 83: (7S)-2-(((1-(4-fluoro-2-methoxybenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-1 to provide the title product; 84% yield. 1H NMR (400 MHz, DMSO-d6) δ 9.79 (s, 1H), 7.53 (s, 1H), 7.34 (s, 1H), 6.98-6.92 (m, 1H), 6.93-6.87 (m, 1H), 6.70 (td, J=8.5, 2.5 Hz, 1H), 6.52 (t, J=6.0 Hz, 1H), 5.15 (s, 2H), 4.18 (dd, J=8.4, 6.5 Hz, 1H), 3.99 (q, J=6.7 Hz, 1H), 3.80 (s, 3H), 3.08 (s, 1H), 2.93 (s, 3H), 2.12 (s, 3H), 1.18 (d, J=6.8 Hz, 3H); ESMS (M+H)=426.3.

Compound 84: (7S)-2-(((1-(4-fluoro-2-methoxybenzyl)-1H-pyrazol-4-yl)methyl)amino)-4,5,7,8-tetramethyl-7,8-dihydropteridin-6(5H)-one The compound was prepared by general procedure Method B via reaction of intermediates A-3 and B-1 to provide the title product; 30% yield. 1H NMR (400 MHz, Methanol-d4) δ 8.36 (s, 2H), 7.48 (dt, J=22.5, 11.3 Hz, 1H), 6.88 (ddd, J=9.7, 7.4, 2.4 Hz, 1H), 6.80-6.69 (m, 1H), 5.59 (s, 2H), 4.62 (d, J=15.7 Hz, 2H), 4.32 (q, J=6.9 Hz, 1H), 3.86 (s, 3H), 3.35-3.31 (m, 4H), 3.21 (s, 3H), 2.51 (s, 3H), 1.37 (d, J=7.0 Hz, 3H); ESMS (M+H)=440.26.

Compound 87: (7S)-2-(((1-(4-fluoro-2-hydroxybenzyl)-1H-pyrazol-4-yl)methyl)amino)-4,7,8-trimethyl-7,8-dihydropteridin-6(5H)-one (7S)-2-(((1-(4-Fluoro-2-methoxybenzyl)-1H-pyrazol-4-yl)methyl)amino)-4,7,8-trimethyl-7,8-dihydropteridin-6(5H)-one (Compound 83; 350 mg, 0.765 mmol) was dissolved in 20 ml of dichloromethane. A 1M solution of boron tribromide (4.6 ml, 4.6 mmol) was added to the solution and stirred at room temperature for 18 hours. The reaction was quenched by the addition of methanol followed by evaporation of the reaction mixture in vacuo. The resulting crude product was purified by preparative HPLC (C18 column; 10-100% Acetonitrile/water (0.1% TFA)). The desired fractions were evaporated in vacuo to afford the title product. wt. 249 mg (71% yield). 1H NMR (300 MHz, Methanol-d4) δ 8.35 (d, J=3.7 Hz, 2H), 7.46 (dd, J=8.4, 6.6 Hz, 1H), 6.76-6.56 (m, 2H), 4.62 (s, 2H), 4.33 (q, J=6.9 Hz, 1H), 3.19 (s, 3H), 2.34 (s, 3H), 1.52 (d, J=6.9 Hz, 3H); ESMS (M+H)=412.21.

Compound 44: (7S)-2-(((1-(3,5-difluoro-4-methoxybenzyl)-1H-pyrazol-4-yl)methyl)amino)-7,8-dimethyl-7,8-dihydropteridin-6(5H)-one The compound was prepared by general procedure Method A via reaction of intermediates A-1 and B-20 to provide the title product; 27% yield 1H NMR (400 MHz, DMSO-d6) δ 10.74 (s, 1H), 8.34 (s, 1H), 7.83 (s, 1H), 7.49 (s, 1H), 7.27 (s, 1H), 6.98 (d, J=8.9 Hz, 2H), 5.25 (s, 2H), 4.39 (d, J=5.6 Hz, 2H), 4.31 (q, J=6.9 Hz, 1H), 3.89 (d, J=1.0 Hz, 3H), 3.15 (s, 3H), 1.44 (d, J=6.9 Hz, 3H); ESMS (M+H)=430.24.

Compound 48: (7S)-2-(((1-(3,5-difluoro-4-methoxybenzyl)-1H-pyrazol-4-yl)methyl)amino)-5,8-diethyl-7-(2-hydroxyethyl)-7,8-dihydropteridin-6(5H)-one The compound was prepared by general procedure Method B via reaction of intermediates A-26 and B-20 to provide the title product; 18% yield. 1H NMR (300 MHz, CDCl₃) δ 7.53 (d, J=0.8 Hz, 1H), 7.49-7.42 (m, 1H), 7.37 (s, 1H), 6.75 (dq, J=8.2, 0.6 Hz, 2H), 5.18 (s, 2H), 4.52-4.32 (m, 3H), 4.27-3.95 (m, 4H), 3.87-3.61 (m, 2H), 3.18 (ddt, J=14.1, 11.3, 7.1 Hz, 1H), 2.30-2.10 (m, 1H), 1.88 (ddt, J=14.2, 9.5, 4.7 Hz, 1H), 1.34-1.18 (m, 8H); ESMS (M+H)=502.3.

Compound 88: (7S)-2-(((1-(2,4-difluoro-3-methoxybenzyl)-1H-pyrazol-4-yl)methyl)amino)-4,7,8-trimethyl-7,8-dihydropteridin-6(5H)-one The compound was prepared by general procedure Method A via reaction of intermediates A-2 and B-21 to provide the title product; 75% yield. 1H NMR (300 MHz, CDCl$_3$) δ 9.33 (bs, 1H), 7.50 (d, J=1.4 Hz, 1H), 7.41 (s, 1H), 6.92-6.70 (m, 2H), 5.25 (s, 2H), 4.97 (d, J=7.1 Hz, 1H), 4.47-4.34 (m, 2H), 4.12-4.00 (m, 1H), 3.99 (q, J=1.2 Hz, 3H), 3.10-2.95 (m, 3H), 2.25 (s, 3H), 1.46-1.30 (m, 3H); ESMS (M+H)=444.28.

Compound 63: (7S)-5-fluoro-2-((4-(((4,5,7,8-tetramethyl-6-oxo-5,6,7,8-tetrahydropteridin-2-yl)amino)methyl)-1H-pyrazol-1-yl)methyl)benzonitrile The compound was prepared by general procedure Method B via reaction of intermediates A-3 and B-18 to provide the title product; 27% yield. 1H NMR (300 MHz, CDCl$_3$) δ 7.55 (d, J=4.0 Hz, 2H), 7.44-7.26 (m, 3H), 5.45 (d, J=1.7 Hz, 2H), 4.88 (t, J=5.9 Hz, 1H), 4.45 (dd, J=5.8, 1.7 Hz, 2H), 4.08-3.94 (m, 1H), 3.31 (d, J=1.5 Hz, 3H), 3.02 (d, J=1.5 Hz, 3H), 2.36 (d, J=1.5 Hz, 3H), 1.21 (dd, J=6.9, 1.6 Hz, 3H); ESMS (M+H)=435.37.

Compound 64: (7S)-5-fluoro-2-((4-(((4,7,8-trimethyl-6-oxo-5,6,7,8-tetrahydropteridin-2-yl)amino)methyl)-1H-pyrazol-1-yl)methyl)benzonitrile The compound was prepared by general procedure Method B via reaction of intermediates A-2 and B-18 to provide the title product; 27% yield. 1H NMR (300 MHz, CDCl$_3$) δ 7.59-7.50 (m, 3H), 7.39 (dt, J=7.7, 1.6 Hz, 1H), 7.34-7.24 (m, 2H), 5.44 (d, J=0.8 Hz, 2H), 4.83 (t, J=5.8 Hz, 1H), 4.44 (d, J=5.8 Hz, 2H), 4.09 (q, J=6.8 Hz, 1H), 3.06 (s, 3H), 2.21 (s, 3H), 1.41 (d, J=6.9 Hz, 3H); ESMS (M+H)=421.3.

Compound 8: (7S)-2-(((1-(4-fluorophenethyl)-1H-pyrazol-4-yl)methyl)amino)-4,5,7,8-tetramethyl-7,8-dihydropteridin-6(5H)-one The compound was prepared by general procedure Method B via reaction of intermediates A-3 and B-25 to provide the title product; 13% yield. 1H NMR (300 MHz, Methanol-d4) δ 7.53 (s, 1H), 7.34 (s, 1H), 7.07-6.96 (m, 2H), 6.95-6.82 (m, 2H), 4.43 (d, J=2.4 Hz, 2H), 4.32 (tdd, J=6.9, 4.4, 3.1 Hz, 3H), 3.34 (s, 3H), 3.21 (s, 3H), 3.08 (t, J=6.8 Hz, 2H), 2.46 (s, 3H), 1.38 (d, J=7.0 Hz, 3H); ESMS (M+H)=424.3.

Compound 6: (7S)-2-(((1-(4-fluorophenethyl)-1H-pyrazol-4-yl)methyl)amino)-4,7,8-trimethyl-7,8-dihydropteridin-6(5H)-one The compound was prepared by general procedure Method B via reaction of intermediates A-2 and B-25 to provide the title product; 13% yield. 1H NMR (300 MHz, Methanol-d4) δ 7.52 (s, 1H), 7.36-7.29 (m, 1H), 7.06-6.95 (m, 2H), 6.94-6.81 (m, 2H), 4.41 (d, J=2.0 Hz, 2H), 4.39-4.24 (m, 3H), 3.24 (d, J=19.9 Hz, 3H), 3.08 (t, J=6.7 Hz, 2H), 2.30 (d, J=2.7 Hz, 3H), 1.55 (dd, J=8.1, 7.0 Hz, 3H); ESMS (M+H)=410.3.

Compound 13: (7S)-2-(((1-(4-fluorophenethyl)-1H-pyrazol-4-yl)methyl)amino)-7-(2-hydroxyethyl)-7,8-dihydropteridin-6(5H)-one The compound was prepared by procedure Method B via reaction of intermediates A-25 and B-25 to provide the title product. ESMS(M+1)=412.24.

Compound 123: (7S)-4,7,8-trimethyl-2-(((1-(3,4,5-trifluorophenethyl)-1H-pyrazol-4-yl)methyl)amino)-7,8-dihydropteridin-6(5H)-one The compound was prepared by general procedure Method A via reaction of intermediates A-2 and B-28 to provide the title product; 6% yield. 1H NMR (300 MHz, CDCl$_3$) δ 7.89 (s, 1H), 7.44 (d, J=0.8 Hz, 1H), 7.06 (d, J=0.8 Hz, 1H), 6.55 (dd, J=8.3, 6.5 Hz, 2H), 4.70 (t, J=5.8 Hz, 1H), 4.30 (dd, J=5.8, 2.7 Hz, 2H), 4.17 (t, J=6.9 Hz, 2H), 4.00 (q, J=6.8 Hz, 1H), 2.99 (d, J=16.7 Hz, 5H), 2.14 (s, 3H), 1.33 (d, J=6.8 Hz, 3H); ESMS (M+H)=446.2.

Compound 103: (7S)-2-(((1-(2-(4-fluorophenoxy)ethyl)-1H-pyrazol-4-yl)methyl)amino)-4,7,8-trimethyl-7,8-dihydropteridin-6(5H)-one The compound was prepared by general procedure Method A via reaction of intermediates A-2 and B-33 to provide the title product; 57% yield. 1H NMR (300 MHz, CDCl$_3$): ppm 2.05-2.16 (m, 1H), 2.19 (s, 3H), 2.26-2.38 (m, 1H), 2.77 (d, J=6.7 Hz, 2H), 3.04-3.22 (m, 1H), 3.29-3.80 (m, 4H), 4.43 (d, J=5.7 Hz, 2H), 4.81-5.03 (m, 1H), 5.21 (s, 2H), 5.57 (s, 1H), 6.97-7.06 (m, 2H), 7.13-7.20 (m, 2H), 7.34 (s, 1H), 7.51 (s, 1H); ESMS (M+H)=396.2.

Compound 109: (7S)-2-(((1-(2-(4-fluorophenoxy)ethyl)-1H-pyrazol-4-yl)methyl)amino)-7,8-dimethyl-7,8-dihydropteridin-6(5H)-one The compound was prepared by general procedure Method A via reaction of intermediates A-1 and B-33 to provide the title product; 34% yield. 1H NMR (300 MHz, CDCl$_3$) δ 7.58-7.50 (m, 2H), 7.41 (s, 1H), 7.01-6.88 (m, 2H), 6.83-6.72 (m, 2H), 4.45 (ddd, J=5.8, 4.6, 1.4 Hz, 4H), 4.29 (dd, J=5.6, 4.9 Hz, 2H), 4.07 (q, J=6.8 Hz, 1H), 3.08 (s, 3H), 1.45 (d, J=6.9 Hz, 3H); ESMS (M+H)=412.26.

Compound 104: (7S)-2-(((1-(3-(4-fluorophenyl)propyl)-1H-pyrazol-4-yl)methyl)amino)-4,7,8-trimethyl-7,8-dihydropteridin-6(5H)-one The compound was prepared by general procedure Method A via reaction of intermediates A-2 and B-32 to provide the title product; 50% yield. 1H NMR (300 MHz, CDCl$_3$) δ 7.51 (d, J=0.8 Hz, 1H), 7.34 (d, J=0.8 Hz, 1H), 7.18-7.07 (m, 2H), 7.05-6.92 (m, 2H), 4.88-4.79 (m, 1H), 4.48-4.39 (m, 2H), 4.08 (td, J=7.0, 2.4 Hz, 3H), 3.07 (s, 3H), 2.58 (dd, J=8.5, 6.7 Hz, 2H), 2.27-2.09 (m, 5H), 1.41 (d, J=6.8 Hz, 3H); ESMS (M+H)=424.2.

Compound 110: (7S)-2-(((1-(3-(4-fluorophenyl)propyl)-1H-pyrazol-4-yl)methyl)amino)-7,8-dimethyl-7,8-dihydropteridin-6(5H)-one The compound was prepared by general procedure Method A via reaction of intermediates A-1 and B-32 to provide the title product; 49% yield. 1H NMR (300 MHz, CDCl$_3$) δ 7.53 (d, J=0.8 Hz, 1H), 7.44-7.35 (m, 2H), 7.18-7.07 (m, 2H), 7.03-6.91 (m, 2H), 4.46 (dd, J=5.7, 2.7 Hz, 2H), 4.07 (td, J=6.9, 4.5 Hz, 3H), 3.09 (s, 3H), 2.58 (dd, J=8.5, 6.7 Hz, 2H), 2.25-2.08 (m, 2H), 1.44 (d, J=6.9 Hz, 3H); ESMS (M+H)=410.27.

Compound 105: (7S)-2-(((1-(3,4-difluorophenethyl)-1H-pyrazol-4-yl)methyl)amino)-4,7,8-trimethyl-7,8-dihydropteridin-6(5H)-one The compound was prepared by general procedure Method A via reaction of intermediates A-2 and B-26 to provide the title product; 52% yield. 1H NMR (300 MHz, CDCl$_3$) δ 7.77 (s, 1H), 7.53 (d, J=0.8 Hz, 1H), 7.17-6.95 (m, 2H), 6.90-6.67 (m, 2H), 4.81 (t, J=5.7 Hz, 1H), 4.38 (dd, J=5.8, 2.4 Hz, 2H), 4.27 (t, J=7.0 Hz, 2H), 4.16-4.02 (m, 1H), 3.09 (d, J=18.5 Hz, 5H), 2.22 (s, 3H), 1.42 (d, J=6.9 Hz, 3H); ESMS (M+H)=428.24.

Compound 111: (7S)-2-(((1-(3,4-difluorophenethyl)-1H-pyrazol-4-yl)methyl)amino)-7,8-dimethyl-7,8-dihydropteridin-6(5H)-one The compound was prepared by general procedure Method A via reaction of intermediates A-1 and B-26 to provide the title product; 55% yield. 1H NMR (300 MHz, CDCl$_3$) δ 7.54 (d, J=0.7 Hz, 1H), 7.43 (s, 1H), 7.17 (s, 1H), 7.02 (dt, J=10.3, 8.3 Hz, 1H), 6.90-6.72 (m, 2H), 4.40 (dd, J=5.8, 3.5 Hz, 2H), 4.27 (t, J=7.0 Hz, 2H), 4.11 (q, J=6.8 Hz, 1H), 3.10 (d, J=11.6 Hz, 4H), 1.46 (d, J=6.9 Hz, 3H); ESMS (M+H)=414.24.

Compound 119: (7S)-2-(((1-(2,4-difluorophenethyl)-1H-pyrazol-4-yl)methyl)amino)-7,8-dimethyl-7,8-dihydropteridin-6(5H)-one The compound was prepared by general procedure Method A via reaction of intermediates A-1 and B-27 to provide the title product; 26% yield. 1H NMR (300 MHz, CDCl$_3$) δ 7.53 (s, 1H), 7.42 (s, 1H), 7.21 (s, 1H), 6.96-6.64 (m, 3H), 4.40 (dd, J=5.9, 3.4 Hz, 2H), 4.27 (t, J=7.1 Hz, 2H), 4.10 (q, J=6.9 Hz, 1H), 3.12 (d, J=18.1 Hz, 5H), 1.47 (d, J=6.8 Hz, 3H); ESMS (M+H)=414.19.

Compound 106: (7S)-2-(((1-(2,4-difluorophenethyl)-1H-pyrazol-4-yl)methyl)amino)-4,7,8-trimethyl-7,8-dihydropteridin-6(5H)-one The compound was prepared by general procedure Method A via reaction of intermediates A-2 and B-27 to provide the title product; 38% yield. 1H NMR (300 MHz, CDCl$_3$) δ 7.51 (d, J=0.8 Hz, 2H), 7.16 (d, J=0.8 Hz, 1H), 6.96-6.65 (m, 4H), 4.75 (t, J=5.8 Hz, 1H), 4.42-4.23 (m, 4H), 4.16-4.03 (m, 2H), 3.21-3.10 (m, 2H), 3.06 (s, 3H), 2.21 (s, 3H), 1.42 (d, J=6.9 Hz, 3H); ESMS (M+H)=428.24.

Compound 121: (7S)-2-(((1-(4-ethoxyphenethyl)-1H-pyrazol-4-yl)methyl)amino)-7,8-dimethyl-7,8-dihydropteridin-6(5H)-one The compound was prepared by general procedure Method A via reaction of intermediates A-1 and B-31 to provide the title product; 37% yield. 1H NMR (300 MHz, CDCl$_3$) δ 7.54 (d, J=0.8 Hz, 1H), 7.41 (s, 1H), 7.22 (d, J=0.8 Hz, 1H), 6.99 (d, J=8.6 Hz, 2H), 6.80 (d, J=8.6 Hz, 2H), 4.41 (dd, J=5.7, 1.8 Hz, 2H), 4.31-4.19 (m, 2H), 4.05 (dq, J=27.2, 6.9 Hz, 3H), 3.09 (s, 5H), 1.51-1.35 (m, 6H); ESMS (M+H)=422.25.

Comp 108: (7S)-2-(((1-(4-ethoxyphenethyl)-1H-pyrazol-4-yl)methyl)amino)-4,7,8-trimethyl-7,8-dihydropteridin-6(5H)-one The compound was prepared by general procedure Method A via reaction of intermediates A-2 and B-31 to provide the title product; 55% yield. 1H NMR (300 MHz, CDCl$_3$) δ 7.76 (s, 1H), 7.52 (s, 1H), 7.16 (s, 1H), 7.03-6.93 (m, 2H), 6.85-6.76 (m, 2H), 4.79 (t, J=5.6 Hz, 1H), 4.38 (d, J=5.6 Hz, 2H), 4.26 (t, J=7.3 Hz, 2H), 4.05 (dq, J=21.0, 6.9 Hz, 3H), 3.07 (d, J=6.5 Hz, 5H), 2.23 (s, 3H), 1.48-1.36 (m, 6H); ESMS (M+H)=436.29.

Compound 120: (7S)-2-(((1-(3,5-difluorophenethyl)-1H-pyrazol-4-yl)methyl)amino)-7,8-dimethyl-7,8-dihydropteridin-6(5H)-one The compound was prepared by general procedure Method A via reaction of intermediates A-1 and B-30 to provide the title product; 8% yield. 1H NMR (300 MHz, CDCl$_3$) δ 7.54 (d, J=0.8 Hz, 1H), 7.42 (s, 1H), 7.25-7.18 (m, 1H), 6.72-6.53 (m, 3H), 4.46-4.36 (m, 2H), 4.29 (t, J=7.1 Hz, 2H), 4.10 (q, J=6.8 Hz, 1H), 3.20-3.05 (m, 5H), 1.46 (d, J=6.8 Hz, 3H); ESMS (M+H)=414.19.

Compound 107: (7S)-2-(((1-(3,5-difluorophenethyl)-1H-pyrazol-4-yl)methyl)amino)-4,7,8-trimethyl-7,8-dihydropteridin-6(5H)-one The compound was prepared by general procedure Method A via reaction of intermediates A-2 and B-30 to provide the title product; 6.4% yield. 1H NMR (300 MHz, CDCl$_3$) δ 7.53 (d, J=0.7 Hz, 1H), 7.41 (s, 1H), 7.17 (d, J=0.8 Hz, 1H), 6.74-6.53 (m, 3H), 4.81 (s, 1H), 4.44-4.23 (m, 4H), 4.10 (q, J=6.9 Hz, 1H), 3.15 (t, J=7.1 Hz, 2H), 3.06 (s, 3H), 2.21 (s, 3H), 1.42 (d, J=6.8 Hz, 3H); ESMS (M+H)=428.24.

Compound 112: (7S)-2-(((trans-1-(3-(4-fluorophenyl)cyclobutyl)-1H-pyrazol-4-yl)methyl)amino)-4,7,8-trimethyl-7,8-dihydropteridin-6(5H)-one The compound was prepared by general procedure Method A via reaction of intermediates A-2 and B-34 to provide the title product; 80% yield. 1H NMR (300 MHz, Methanol-d4) δ 7.71 (s, 1H), 7.53 (s, 1H), 7.40-7.29 (m, 2H), 7.11-6.99 (m, 2H), 5.01-4.89 (m, 1H), 4.40 (s, 2H), 4.08 (q, J=6.8 Hz, 1H), 3.81-3.63 (m, 1H), 3.08 (s, 3H), 2.93 (ddd, J=13.0, 6.5, 3.0 Hz, 2H), 2.71-2.56 (m, 2H), 2.18 (s, 3H), 1.33 (d, J=6.8 Hz, 4H); ESMS (M+H)=436.25.

Compound 137: (7S)-2-(((1-(3-(4-fluorophenyl)cyclopentyl)-1H-pyrazol-4-yl)methyl)amino)-4,7,8-trimethyl-7,8-dihydropteridin-6(5H)-one The compound was prepared by general procedure Method A via reaction of intermediates A-2 and B-51 to provide the title product, 82% yield. ESMS (M+1)=450.17.

Compound 113: (7S)-2-(((1-(2-cyclohexylethyl)-1H-pyrazol-4-yl)methyl)amino)-4,7,8-trimethyl-7,8-dihydropteridin-6(5H)-one The compound was prepared by general procedure Method A via reaction of intermediates A-2 and B-35 to provide the title product; 94% yield. 1H NMR (300 MHz, CDCl$_3$) δ 7.84 (s, 0H), 7.48 (d, J=0.8 Hz, 1H), 7.35 (d, J=0.8 Hz, 1H), 4.83 (s, 1H), 4.47-4.36 (m, 2H), 4.17-4.04 (m, 3H), 3.07 (s, 3H), 2.24 (d, J=1.0 Hz, 3H), 1.79-1.59 (m, 7H), 1.42 (d, J=6.9 Hz, 3H), 1.23 (ddd, J=22.4, 7.7, 3.9 Hz, 3H), 1.06-0.82 (m, 3H); ESMS (M+H)=398.26.

Compound 115: (7S)-4,7,8-trimethyl-2-(((1-(2-(tetrahydro-2H-pyran-4-yl)ethyl)-1H-pyrazol-4-yl)methyl)amino)-7,8-dihydropteridin-6(5H)-one The compound was prepared by general procedure Method A via reaction of intermediates A-2 and B-36 to provide the title product; 21% yield. 1H NMR (300 MHz, CDCl$_3$) δ 8.61 (s, 1H), 7.40 (s, 1H), 7.27 (s, 1H), 4.89 (d, J=6.4 Hz, 1H), 4.35 (d, J=5.6 Hz, 2H), 4.03 (dt, J=8.8, 7.0 Hz, 3H), 3.93-3.72 (m, 2H), 3.28 (td, J=11.6, 2.0 Hz, 2H), 2.99 (s, 3H), 2.18 (s, 3H), 1.73 (q, J=7.0 Hz, 2H), 1.60-1.47 (m, 2H), 1.33 Compound 58 (d, J=6.9 Hz, 3H), 1.20 (t, J=5.3 Hz, 3H); ESMS (M+H)=400.15.

Compound 58: (7S)-2-(((1-((4,4-difluorocyclohexyl) methyl)-1H-pyrazol-4-yl)methyl)amino)-4,7,8-trimethyl-7,8-dihydropteridin-6(5H)-one The compound was prepared by general procedure Method A via reaction of intermediates A-2 and B-37 to provide the title product; 15% yield. 1H NMR (400 MHz, CDCl$_3$) δ 7.39 (d, J=4.7 Hz, 2H), 4.41 (dd, J=12.9, 6.5 Hz, 2H), 4.08 (q, J=6.4 Hz, 1H), 3.39 (d, J=4.0 Hz, 2H), 3.08 (d, J=4.4 Hz, 3H), 2.22 (d, J=4.4 Hz, 3H), 2.16-2.04 (m, 3H), 1.98 (t, J=9.4 Hz, 1H), 1.84-1.57 (m, 4H), 1.48-1.36 (m, 3H); ESMS (M+H)=420.33.

Compound 5: (7S)-2-(((1-(cyclobutylmethyl)-1H-pyrazol-4-yl)methyl)amino)-4,7,8-trimethyl-7,8-dihydropteridin-6(5H)-one The compound was prepared by general procedure Method B via reaction of intermediates A-2 and B-38 to provide the title product; 29% yield. 1H NMR (300 MHz, Methanol-d4) δ 7.69 (s, 1H), 7.56 (s, 1H), 4.51 (s, 2H), 4.31 (q, J=6.9 Hz, 1H), 4.14 (d, J=7.3 Hz, 2H), 3.26 (s, 3H), 2.79 (p, J=7.6 Hz, 1H), 2.29 (s, 3H), 2.11-1.72 (m, 6H), 1.58-1.49 (m, 3H); ESMS (M+H)=356.3.

Compound 7: (7S)-2-(((1-(cyclobutylmethyl)-1H-pyrazol-4-yl)methyl)amino)-4,5,7,8-tetramethyl-7,8-dihydropteridin-6(5H)-one The compound was prepared by general procedure Method B via reaction of intermediates A-3 and B-38 to provide the title product; 25% yield. 1H NMR (300 MHz, Methanol-d4) δ 7.66 (s, 1H), 7.51 (s, 1H), 4.52 (s, 2H), 4.32 (q, J=7.0 Hz, 1H), 4.12 (d, J=7.3 Hz, 2H), 3.33 (s, 3H), 3.27 (s, 3H), 2.86-2.70 (m, 1H), 2.46 (s, 3H), 2.11-1.71 (m, 6H), 1.38 (d, J=7.0 Hz, 3H); ESMS (M+H)=370.34.

Compound 61: (7S)-2-(((1-((3,3-difluorocyclobutyl) methyl)-1H-pyrazol-4-yl)methyl)amino)-4,7,8-trimethyl-7,8-dihydropteridin-6(5H)-one The compound was prepared by general procedure Method AB via reaction of intermediates A-2 and B-39 to provide the title product; 13% yield. 1H NMR (400 MHz, DMSO-d6) δ 9.80 (s, 1H), 7.60 (s, 1H), 7.36 (s, 1H), 6.50 (t, J=6.0 Hz, 1H), 4.21 (dd, J=6.0, 2.1 Hz, 2H), 4.15 (d, J=6.3 Hz, 2H), 4.00 (q, J=6.8 Hz, 1H), 2.95 (s, 3H), 2.58 (dddd, J=17.9, 9.3, 4.8, 1.8 Hz, 2H), 2.46-2.26 (m, 2H), 2.13 (s, 3H), 1.19 (d, J=6.8 Hz, 3H); ESMS (M+H)=392.25.

Compound 133: (7S)-2-(((1-(2-cyclopentylethyl)-1H-pyrazol-4-yl)methyl)amino)-4,7,8-trimethyl-7,8-dihydropteridin-6(5H)-one The compound was prepared by general procedure Method A via reaction of intermediates A-2 and B-40 to provide the title product; 42% yield. 1H NMR (300 MHz, Methanol-d4) δ 7.55 (s, 1H), 7.43 (s, 1H), 4.37 (s, 2H), 4.13-4.02 (m, 3H), 3.07 (s, 3H), 2.18 (s, 3H), 1.88-1.43 (m, 9H), 1.33 (d, J=6.8 Hz, 3H), 1.20-1.02 (m, 2H); ESMS (M+H)=384.25.

Compound 134: (7S)-2-(((1-(bicyclo[2.2.1]heptan-2-ylmethyl)-1H-pyrazol-4-yl)methyl)amino)-4,7,8-trimethyl-7,8-dihydropteridin-6(5H)-one The compound was prepared by general procedure Method A via reaction of intermediates A-2 and B-43 to provide the title product as a mixture of diastereomers; 22% yield. 1H NMR (300 MHz, Methanol-d4) δ 7.56 (s, 1H), 7.42 (s, 1H), 4.38 (s, 2H), 4.18-4.02 (m, 2H), 3.86 (qd, J=13.7, 7.9 Hz, 1H), 3.09 (s, 3H), 2.47-2.31 (m, 1H), 2.19 (s, 4H), 1.95 (d, J=16.3 Hz, 1H), 1.80-1.46 (m, 3H), 1.36 (t, J=8.4 Hz, 6H), 1.20 (ddd, J=23.4, 14.1, 4.7 Hz, 2H), 0.78 (ddd, J=12.3, 5.4, 2.1 Hz, 1H); ESMS (M+H)=396.27.

The diastereomers were initially separated by SFC (column: Chiralpak AD-H, 10×250 mm[30% MeOH (0.2% diethylamine)/70% CO$_2$, isocratic; 10 ml/min). to afford peak C and D and a mixture of peaks A and B. Stereochemistry was arbitrarly assigned.

Compound 150

Peak C: Retention time: 1.193 min (99% de); wt. 17 mg $^1$H NMR (300 MHz, Methanol-d4) δ 7.55 (s, 1H), 7.42 (s, 1H), 4.37 (s, 2H), 4.07 (dd, J=7.5, 4.7 Hz, 3H), 3.07 (s, 3H), 2.48-2.29 (m, 1H), 2.18 (s, 4H), 1.97 (s, 1H), 1.80-1.47 (m, 3H), 1.46-1.15 (m, 8H), 0.78 (ddd, J=12.3, 5.4, 2.2 Hz, 1H). ESMS(M+1)=396.21

Compound 151

Peak D: Retention time: 1.375 min (99.2% de) 23 mg $^1$H NMR (300 MHz, Methanol-d4) δ 7.55 (s, 1H), 7.41 (s, 1H), 4.37 (s, 2H), 4.07 (dd, J=7.5, 3.0 Hz, 3H), 3.07 (s, 3H), 2.47-2.29 (m, 1H), 2.19 (d, J=6.3 Hz, 4H), 1.97 (s, 1H), 1.63 (dtdd, J=23.1, 15.7, 7.7, 3.5 Hz, 3H), 1.44-1.09 (m, 8H), 0.78 (ddd, J=12.3, 5.5, 2.1 Hz, 1H). ESMS(M+1)=396.32

Compounds 156 and 157

(Peaks A & B) were separated by chiral HPLC (column: Chiralpak OJ-H; 20% 1:1 MeOH:EtOH/80% Hexanes (0.2% DEA), isocratic, 20 ml/min).

Compound 156

Peak A: Retention time: 11.38 minutes (100% de) 9.3 mg; ESMS(M+1)=396.36.

Compound 157

Peak B: Retention time: 13.89 min (96.4% de) 8.0 mg ESMS(M+1)=396.32

Compound 114: (7S)-4,7,8-trimethyl-2-(((1-((S)-2-methylbutyl)-1H-pyrazol-4-yl)methyl)amino)-7,8-dihydropteridin-6(5H)-one The compound was prepared by general procedure Method A via reaction of intermediates A-2 and B-42 to provide the title product; 18% yield. 1H NMR (300 MHz, CDCl$_3$) δ 7.96 (s, 1H), 7.49 (d, J=0.7 Hz, 1H), 7.33 (d, J=0.8 Hz, 1H), 4.85 (s, 1H), 4.43 (d, J=5.6 Hz, 2H), 4.09 (q, J=6.9 Hz, 1H), 4.00 (dd, J=13.6, 6.6 Hz, 1H), 3.83 (dd, J=13.6, 7.8

Hz, 1H), 3.07 (s, 3H), 2.24 (s, 3H), 2.07-1.87 (m, 1H), 1.42 (d, J=6.9 Hz, 3H), 1.41-1.03 (m, 2H), 0.99-0.88 (m, 3H), 0.86 (d, J=6.7 Hz, 3H); ESMS (M+H)=358.23.

Compound 118: (7S)-4,7,8-trimethyl-2-(((1-(tetrahydro-2H-pyran-4-yl)-1H-pyrazol-4-yl)methyl) amino)-7,8-dihydropteridin-6(5H)-one The compound was prepared by general procedure Method A via reaction of intermediates A-2 and B-65 to provide the title product; 56% yield. 1H NMR (300 MHz, Methanol-d4) δ 7.64 (s, 1H), 7.46 (s, 1H), 4.45-4.25 (m, 3H), 4.14-3.93 (m, 3H), 3.62-3.44 (m, 2H), 3.07 (s, 3H), 2.18 (s, 3H), 2.02 (ddd, J=12.2, 10.6, 3.9 Hz, 4H), 1.33 (d, J=6.8 Hz, 3H); ESMS (M+H)=372.23.

Compound 126: (7S)-4,7,8-trimethyl-2-(((6-((1-(2,2,2-trifluoroethyl)-1H-pyrazol-4-yl)amino)pyridin-3-yl)methyl)amino)-7,8-dihydropteridin-6(5H)-one The compound was prepared by general procedure Method A via reaction of intermediates A-2 and B-149 to provide the title product; 8% yield. 1H NMR (300 MHz, Methanol-d4) δ 8.07 (d, J=5.9 Hz, 2H), 7.95 (s, 1H), 7.62-7.45 (m, 2H), 6.63 (d, J=8.5 Hz, 2H), 6.33 (s, 1H), 5.49 (s, 1H), 4.57 (s, 1H), 4.39 (s, 2H), 4.06 (d, J=6.8 Hz, 1H), 3.88 (d, J=1.0 Hz, 2H), 3.57 (s, 1H), 3.05 (d, J=7.6 Hz, 3H), 2.17 (s, 3H), 1.32 (d, J=6.8 Hz, 3H); ESMS (M+H)=462.24.

Compound 91: (7S)-2-(((1-(2-(4-fluorophenyl)-2-oxoethyl)-1H-pyrazol-4-yl)methyl)amino)-4,7,8-trimethyl-7,8-dihydropteridin-6(5H)-one The compound was prepared by general procedure Method B via reaction of intermediates A-2 and B-45 to provide the title product; 18% yield. 1H NMR (300 MHz, DMSO-d6) δ 9.85 (s, 1H), 8.09 (dd, J=8.9, 5.5 Hz, 2H), 7.58 (d, J=0.8 Hz, 1H), 7.49-7.33 (m, 3H), 6.65 (d, J=6.4 Hz, 1H), 5.75 (s, 2H), 4.25 (dd, J=6.1, 3.4 Hz, 2H), 4.00 (q, J=6.8 Hz, 1H), 3.33 (s, 2H), 2.14 (s, 3H), 1.19 (d, J=6.8 Hz, 3H); ESMS (M+H)=424.24. Chiral HPLC 95.5% ee.

Compound 116: (7S)-2-(((1-(2,3-dihydro-1H-inden-2-yl)-1H-pyrazol-4-yl)methyl)amino)-4,7,8-trimethyl-7,8-dihydropteridin-6(5H)-one The compound was prepared by general procedure Method A via reaction of intermediates A-2 and B-44 to provide the title product; 53% yield. 1H NMR (400 MHz, Methanol-d4) δ 8.31 (s, 1H), 8.19 (d, J=9.9 Hz, 1H), 7.29 (t, J=8.9 Hz, 2H), 7.23 (dd, J=6.3, 2.3 Hz, 2H), 5.52 (dd, J=9.6, 5.4 Hz, 1H), 4.56 (s, 2H), 4.34-4.24 (m, 1H), 3.65 (dd, J=16.7, 7.3 Hz, 2H), 3.46-3.34 (m, 2H), 3.13 (d, J=0.8 Hz, 3H), 2.30 (dd, J=7.9, 3.7 Hz, 3H), 1.51 (d, J=6.2 Hz, 3H); ESMS(M+1)=404.2.

Compound 117: (7S)-2-(((1-(6-fluoro-2,3-dihydro-1H-inden-1-yl)-1H-pyrazol-4-yl)methyl)amino)-4,7,8-trimethyl-7,8-dihydropteridin-6(5H)-one The compound was prepared by general procedure Method A via reaction of intermediates A-2 and B-46 to provide the title product; 61% yield. 1H NMR (400 MHz, Methanol-d4) δ 7.61 (dd, J=12.0, 6.1 Hz, 1H), 7.61-7.52 (m, 1H), 7.37-7.21 (m, 1H), 7.03-6.89 (m, 1H), 6.77-6.61 (m, 1H), 5.84 (d, J=5.2 Hz, 1H), 4.49 (s, 2H), 4.25 (dt, J=15.2, 7.4 Hz, 1H), 3.37-3.26 (m, 1H), 3.24-3.15 (m, 3H), 3.17- 3.01 (m, 1H), 2.92 (dd, J=14.0, 6.3 Hz, 1H), 2.67 (ddd, J=16.7, 10.5, 5.9 Hz, 1H), 2.39 (dt, J=21.8, 7.9 Hz, 1H), 2.31-2.25 (m, 3H), 1.55-1.45 (m, 3H); ESMS(M+1)=422.2.

Compound 97: (7S)-4,7,8-trimethyl-2-(((1-(3-(trifluoromethyl)phenyl)-1H-pyrazol-4-yl)methyl) amino)-7,8-dihydropteridin-6(5H)-one The compound was prepared by general procedure Method A via reaction of intermediates A-2 and B-47 to provide the title product; 61% yield. 1H NMR (300 MHz, Methanol-d4) δ 8.27 (s, 1H), 8.13-7.91 (m, 2H), 7.82-7.50 (m, 3H), 4.49 (s, 2H), 4.08 (q, J=6.8 Hz, 1H), 3.09 (s, 3H), 2.23 (d, J=19.0 Hz, 3H), 1.34 (d, J=6.8 Hz, 3H); ESMS(M+1)=432.17. 95% ee.

Compound 98: (7S)-2-(((1-(2,4-difluorophenyl)-1H-pyrazol-4-yl)methyl)amino)-4,7,8-trimethyl-7,8-dihydropteridin-6(5H)-one The compound was prepared by general procedure Method A via reaction of intermediates A-2 and B-48 to provide the title product; 61% yield. 1H NMR (300 MHz, Methanol-d4) δ 7.97 (d, J=2.7 Hz, 1H), 7.84-7.61 (m, 2H), 7.33-6.90 (m, 2H), 4.47 (s, 2H), 4.08 (q, J=6.8 Hz, 1H), 3.09 (s, 3H), 2.19 (s, 3H), 1.33 (d, J=6.8 Hz, 3H); ESMS(M+1)= 400.32. 95% ee.

Compound 76: (7S)-2-(((1-(3,4-dimethoxybenzyl)-1H-pyrazol-3-yl)methyl)amino)-4,7,8-trimethyl-7,8-dihydropteridin-6(5H)-one The compound was prepared by general procedure Method A via reaction of intermediates A-2 and B-49 to provide the title product; 20% yield. 1H NMR (400 MHz, CDCl3) δ 9.20 (s, 1H), 7.45 (d, J=1.8 Hz, 1H), 6.77 (d, J=8.2 Hz, 1H), 6.73-6.63 (m, 2H), 6.22 (d, J=1.8 Hz, 1H), 5.34 (s, 2H), 5.01-4.86 (m, 1H), 4.55 (dd, J=5.9, 2.4 Hz, 2H), 4.04 (q, J=6.8 Hz, 1H), 3.84 (d, J=2.1 Hz, 3H), 3.77 (s, 3H), 2.95 (s, 3H), 2.24 (s, 3H), 1.37 (d, J=6.8 Hz, 3H); ESMS(M+1)= 438.25.

Compound 154 and compound 155: (7S)-2-(((1-((1R,2R)-2-(4-fluorophenyl)cyclopropyl)-1H-pyrazol-4-yl)methyl)amino)-4,7,8-trimethyl-7,8-dihydropteridin-6(5H)-one and (7S)-2-(((1-((1S,2S)-2-(4-fluorophenyl)cyclopropyl)-1H-pyrazol-4-yl) methyl)amino)-4,7,8-trimethyl-7,8-dihydropteridin-6 (5H)-one The compounds were prepared by general procedure Method A via reaction of intermediate A-2 and (1-((cis)-2-(4-fluorophenyl)cyclopropyl)-1H-pyrazol-4-yl)methanamine to provide the title products as a diastereomeric mixture (Compound 144). The diastereomers were separated by SFC (Column: AD-H column, 20×250 mm; 35% IPA (0.2% diethylamine), 65% $CO_2$, isocratic) to provide diastereomer A & B:

Diastereomer A: Retention time: 1.023 mins.; 97.4% ee; 121 mg; 1H NMR (400 MHz, CDCl3) δ 9.07 (s, 1H), 7.39 (d, J=4.3 Hz, 2H), 7.09-6.98 (m, 2H), 6.91 (t, J=8.6 Hz, 2H), 4.89 (t, J=5.1 Hz, 1H), 4.40-4.27 (m, 2H), 3.97 (q, J=6.7 Hz, 1H), 3.58 (dt, J=7.6, 3.9 Hz, 1H), 2.96 (s, 3H), 2.48 (ddd, J=9.7, 6.6, 3.2 Hz, 1H), 2.18 (s, 3H), 1.77-1.64 (m, 1H), 1.31 (d, J=6.8 Hz, 3H); ESMS(M+1)=422.29.

Diastereomer B: Retention time: 1.214 mins.; 96.2% ee; 126 mg; 1H NMR (400 MHz, CDCl3) δ 9.41 (s, 1H), 7.39

(s, 2H), 7.03 (dd, J=8.0, 5.5 Hz, 2H), 6.89 (t, J=8.5 Hz, 2H), 5.16 (s, 1H), 4.39-4.25 (m, 2H), 3.97 (q, J=6.7 Hz, 1H), 3.56 (dt, J=7.6, 3.6 Hz, 1H), 2.97 (s, 3H), 2.47 (ddd, J=9.7, 6.6, 3.3 Hz, 1H), 2.19 (s, 3H), 1.70 (dt, J=10.0, 5.2 Hz, 1H), 1.31 (d, J=6.7 Hz, 3H); ESMS(M+1)=422.29.

Compound 152 and compound 153: (7S)-2-(((1-((1R,2R)-2-(4-fluorophenyl)cyclopropyl)-1H-pyrazol-4-yl)methyl)amino)-4,5,7,8-tetramethyl-7,8-dihydropteridin-6(5H)-one and (7S)-2-(((1-((1S,2S)-2-(4-fluorophenyl)cyclopropyl)-1H-pyrazol-4-yl)methyl)amino)-4,5,7,8-tetramethyl-7,8-dihydropteridin-6(5H)-one The compound was prepared by general procedure Method A via reaction of intermediate A-3 and (1-((cis)-2-(4-fluorophenyl)cyclopropyl)-1H-pyrazol-4-yl)methanamine to provide the title products as a diastereomeric mixture (Compound 145). The diastereomers were separated by SFC (column: AD-H column, 10×250 mm; 40% MeOH (0.2% diethylamine), 60% CO$_2$, isocratic) to provide diastereomer A & B:

Diastereomer A: Retention time: 0.919 mins.; 99% ee; 51 mg; 1H NMR (400 MHz, CDCl$_3$) δ 7.41 (s, 2H), 7.06 (dd, J=10.3, 3.4 Hz, 2H), 6.92 (dd, J=12.2, 5.0 Hz, 2H), 4.89 (s, 1H), 4.33 (dd, J=14.9, 5.9 Hz, 2H), 3.92 (q, J=6.8 Hz, 1H), 3.58 (dt, J=7.6, 3.8 Hz, 1H), 3.22 (s, 3H), 2.94 (s, 3H), 2.56-2.45 (m, 1H), 2.28 (s, 3H), 1.72 (dt, J=10.1, 5.2 Hz, 1H), 1.39-1.29 (m, 1H), 1.12 (d, J=6.9 Hz, 3H); ESMS(M+1)=436.29.

Diastereomer B: Retention time: 11.118 mins.; 99% ee; 52 mg; 1H NMR (400 MHz, CDCl$_3$) δ 7.41 (s, 2H), 7.10-6.97 (m, 2H), 6.92 (t, J=8.6 Hz, 2H), 4.88 (s, 1H), 4.42-4.29 (m, 2H), 3.92 (q, J=6.8 Hz, 1H), 3.58 (dt, J=7.6, 3.9 Hz, 1H), 3.22 (s, 3H), 2.94 (s, 3H), 2.49 (tt, J=15.5, 7.7 Hz, 1H), 2.28 (s, 3H), 2.09 (d, J=25.6 Hz, 1H), 1.72 (dt, J=6.0, 5.2 Hz, 1H), 1.40-1.29 (m, 1H), 1.12 (d, J=6.9 Hz, 3H); ESMS(M+1)=436.29.

Compound 89 and compound 90: (7S)-4,7,8-trimethyl-2-(((1-((S)-2-phenylpropyl)-1H-pyrazol-4-yl)methyl)amino)-7,8-dihydropteridin-6(5H)-one and (7S)-4,7,8-trimethyl-2-(((1-((R)-2-phenylpropyl)-1H-pyrazol-4-yl)methyl)amino)-7,8-dihydropteridin-6(5H)-one The compounds were prepared by general procedure Method A via reaction of intermediate A-2 and B-95 to provide the title products as a mixture of diastereomers (Compound 85). The diastereomers were separated by chiral HPLC (Chiralpak AD-H column; 30% 1:1 MeOH:EtOH/Hexanes 0.2% DEA).

Diastereomer A: Retention time: 13.37 min; wt. 55.5 mg; 1H NMR (300 MHz, Methanol-d4) δ 7.42 (s, 1H), 7.28-7.04 (m, 6H), 4.28 (s, 2H), 4.19 (d, J=7.6 Hz, 2H), 4.08 (q, J=6.8 Hz, 1H), 3.04 (s, 3H), 2.17 (s, 3H), 1.33 (d, J=6.8 Hz, 3H), 1.21 (d, J=7.0 Hz, 3H), 1.15 (d, J=6.1 Hz, 1H); ESMS(M+1)=406.22

Diastereomer B: Retention time: 18.23 min.; Wt. 52.6 mg; 1H NMR (300 MHz, Methanol-d4) δ 7.42 (s, 1H), 7.28-7.05 (m, 6H), 4.28 (d, J=6.1 Hz, 2H), 4.19 (dd, J=7.6, 2.2 Hz, 2H), 4.08 (q, J=6.8 Hz, 1H), 3.03 (s, 3H), 2.17 (s, 3H), 1.33 (d, J=6.8 Hz, 3H), 1.21 (d, J=7.0 Hz, 3H). ESMS(M+1)=406.22.

Compound 95 and compound 96: (7S)-2-(((1-((S)-2-(4-fluorophenyl)propyl)-1H-pyrazol-4-yl)methyl)amino)-4,7,8-trimethyl-7,8-dihydropteridin-6(5H)-one and (7S)-2-(((1-((R)-2-(4-fluorophenyl)propyl)-1H-pyrazol-4-yl)methyl)amino)-4,7,8-trimethyl-7,8-dihydropteridin-6(5H)-one The compounds were prepared by general procedure Method A via reaction of intermediate A-2 and B-96 to provide the title products as a mixture of diastereomers (Compound 86). The diastereomers were separated by chiral HPLC (Chiralpak AD-H 30% 1:1 MeOH:EtOH/Hexanes 0.2% DEA) to provide:

Diastereomer A: Retention time: 14.96 min.; 99% ee; wt. 20 mg; 1H NMR (300 MHz, Methanol-d4) δ 7.97 (s, 1H), 7.73 (s, 1H), 7.25-7.08 (m, 2H), 6.93 (dd, J=12.1, 5.3 Hz, 2H), 4.56-4.24 (m, 5H), 3.19 (s, 3H), 2.32 (s, 3H), 1.54 (dd, J=6.9, 2.2 Hz, 3H), 1.30 (d, J=6.9 Hz, 3H). ESMS(M+1)=424.23.

Diastereomer B: Retention time: 18.04 min.; 99% ee; wt. 20 mg; 1H NMR (300 MHz, Methanol-d4) δ 7.97 (s, 1H), 7.73 (s, 1H), 7.25-7.08 (m, 2H), 6.93 (dd, J=12.1, 5.3 Hz, 2H), 4.56-4.24 (m, 5H), 3.19 (s, 3H), 2.32 (s, 3H), 1.54 (dd, J=6.9, 2.2 Hz, 3H), 1.30 (d, J=6.9 Hz, 3H). ESMS(M+1)=424.23.

Compound 92: (7S)-2-(((1-(2-(4-fluorophenyl)-2-methylpropyl)-1H-pyrazol-4-yl)methyl)amino)-4,7,8-trimethyl-7,8-dihydropteridin-6(5H)-one The compound was prepared by general procedure Method A via reaction of intermediates A-2 and B-50 to provide the title product; 92% yield. 1H NMR (300 MHz, Methanol-d4) δ 7.42 (s, 1H), 7.27 (dd, J=9.0, 5.3 Hz, 2H), 6.94 (t, J=8.9 Hz, 2H), 6.86 (s, 1H), 4.42-4.26 (m, 3H), 4.23 (s, 2H), 3.19 (s, 3H), 2.29 (s, 3H), 1.54 (d, J=6.9 Hz, 3H), 1.34 (d, J=4.4 Hz, 6H); ESMS(M+1)=438.23.

Compound 101 and compound 102: (7S)-4,7,8-trimethyl-2-(((1-((R)-1-phenylpropan-2-yl)-1H-pyrazol-4-yl)methyl)amino)-7,8-dihydropteridin-6(5H)-one and (7S)-4,7,8-trimethyl-2-(((1-((S)-1-phenylpropan-2-yl)-1H-pyrazol-4-yl)methyl)amino)-7,8-dihydropteridin-6(5H)-one The compounds were prepared by general procedure Method A via reaction of intermediate A-2 and B-97 to provide the title products as a mixture of the diastereomers (Compound 93). The diastereomers were separated by chiral HPLC (Chiralpak OJ-H; 30% 1:1 MeOH:EtOH(0.2% DEA)/70% Hexanes to provide:

Diastereomer A: RT=7.55 min; wt. 164.9 mg; 1H NMR (300 MHz, Methanol-d4) δ 7.86 (s, 1H), 7.20-7.07 (m, 2H), 6.97 (d, J=6.9 Hz, 1H), 4.46 (d, J=4.3 Hz, 1H), 4.31 (q, J=6.9 Hz, 1H), 3.14 (dd, J=11.8, 5.5 Hz, 3H), 2.31 (s, 2H), 1.62 (d, J=5.8 Hz, 2H), 1.52 (d, J=6.9 Hz, 2H). ESMS(M+1)=406.22.

Diastereomer B: RT=13.30 min.; wt. 141.7 mg; 1H NMR (300 MHz, Methanol-d4) δ 8.11 (s, 1H), 8.05 (s, 1H), 7.25-7.07 (m, 3H), 7.01 (dd, J=7.7, 1.6 Hz, 2H), 4.51 (s, 2H), 4.32 (q, J=6.9 Hz, 1H), 3.26-3.04 (m, 5H), 2.32 (s, 3H), 1.65 (d, J=6.8 Hz, 3H), 1.54 (d, J=6.9 Hz, 3H). ESMS(M+1)=406.22.

Compound 99: (7S)-4,7,8-Trimethyl-2-(((1-(piperidin-4-yl)-1H-pyrazol-4-yl)methyl)amino)-7,8-dihydropteridin-6(5H)-one. To a solution of isopropyl (7S)-4-(4-(((4,7,8-trimethyl-6-oxo-5,6,7,8-tetrahydropteridin-2-yl)amino)

methyl)-1H-pyrazol-1-yl)piperidine-1-carboxylate (88 mg, 0.193 mmol) in dichloromethane (2 mL) at 0 C was added 1M solution of BBr$_3$ (1 mL, 0.964 mmol) in dichloromethane. The reaction mixture was stirred for 30 minutes at 0 C, then warmed to room temperature and stirred for 16 hours. The reaction was quenched with methanol (2 mL) and the solvent evaporated in vacuo. The residue was purified by column chromatography (125 g C-18 column; gradient 5-95% ACN/water 0.1% TFA) to afford the title product (52 mg, 58%). $^1$H NMR (300 MHz, Methanol-d4) δ 7.73 (s, 1H), 7.56 (s, 1H), 4.57-4.43 (m, 3H), 4.30 (q, J=6.9 Hz, 1H), 3.55 (dd, J=13.3, 3.2 Hz, 2H), 3.27 (s, 3H), 3.19 (td, J=13.0, 4.6 Hz, 2H), 2.34-2.16 (m, 7H), 1.53 (d, J=6.9 Hz, 3H); ESMS (M+1)=371.24. The following compounds (Compounds 124 and 125) were prepared by the general procedure provided.

To a suspension of (7S)-4,7,8-trimethyl-2-(((1-(piperidin-4-yl)-1H-pyrazol-4-yl)methyl)amino)-7,8-dihydropteridin-6(5H)-one (Compound 99; 60 mg, 0.162 mmol) and DIPEA (85 uL, 0.486 mmol) in dichloromethane (1 ml) was added the appropriate acid chloride (0.162 mmol). The resulting solution was stirred for 16 hours at room temperature then quenched with water (2 ml). The organic layer was separated and the solvent evaporated under a stream of nitrogen. The residue was purified by reverse phase chromatography (C18 column; gradient 5-95% ACN/water 0.1% TFA). The desired fraction were evaporated and the purified material dissolved in 1 ml of methanol and passed through a PL-HCO3 resin cartridge to provide the desired product.

Compound 124: (7S)-4,7,8-Trimethyl-2-(((1-(1-(3,4,5-trifluorobenzoyl)piperidin-4-yl)-1H-pyrazol-4-yl)methyl)amino)-7,8-dihydropteridin-6(5H)-one Obtained from the reaction of (7S)-4,7,8-trimethyl-2-(((1-(piperidin-4-yl)-1H-pyrazol-4-yl)methyl)amino)-7,8-dihydropteridin-6(5H)-one and 3,4,5-trifluorobenzoyl chloride to provide 15 mg of the title product. $^1$H NMR (300 MHz, Methanol-d4) δ 7.65 (s, 1H), 7.48 (s, 1H), 7.30 (dd, J=7.7, 6.6 Hz, 2H), 5.48 (s, 2H), 4.68 (bs, 1H), 4.51-4.33 (m, 3H), 4.07 (q, J=6.8 Hz, 1H), 3.77 (bs, 1H), 3.07 (s, 3H), 2.18 (s, 3H), 2.13-1.92 (m, 4H); ESMS(M+1)=529.16.

Compound 125: (7S)-2-(((1-(1-(4-Fluorobenzoyl)piperidin-4-yl)-1H-pyrazol-4-yl)methyl)amino)-4,7,8-trimethyl-7,8-dihydropteridin-6(5H)-one Obtained from the reaction of (7S)-4,7,8-trimethyl-2-(((1-(piperidin-4-yl)-1H-pyrazol-4-yl)methyl)amino)-7,8-dihydropteridin-6(5H)-one and 4-fluorobenzoyl chloride to provide 6.6 mg of the title product. $^1$H NMR (300 MHz, Methanol-d4) δ 7.66 (s, 1H), 7.55-7.44 (m, 3H), 7.20 (t, J=8.8 Hz, 2H), 4.53-4.33 (m, 4H), 4.07 (q, J=6.9 Hz, 1H), 3.85 (bs, 1H), 3.07 (s, 3H), 2.18 (s, 3H), 2.01 (s, 4H), 1.33 (d, J=6.8 Hz, 3H); ESMS(M+1)=493.24.

Compound 130: (7S)-2-(((1-(1-(4-fluorophenyl)piperidin-4-yl)-1H-pyrazol-4-yl)methyl)amino)-4,7,8-trimethyl-7,8-dihydropteridin-6(5H)-one To a suspension of (7S)-4,7,8-trimethyl-2-(((1-(piperidin-4-yl)-1H-pyrazol-4-yl)methyl)amino)-7,8-dihydropteridin-6(5H)-one (Compound 99; 100 mg, 0.270 mg) and 1-bromo-4-fluorobenzene (57.0 mg, 0.324 mmol) in t-butanol (3 mL) at RT was added NaOtBu (540 mL, 2M in THF, 1.08 mmol). The solution was degassed for 10 min with N$_2$ and t-BuX-Phos Palladacycle (19 mg, 0.027 mmol) was added. The reaction mixture was warmed to 50° C. and stirred for 16 hours. The cooled solution was diluted with DMSO (1 mL) and filtered through Florisil and purified by column chromatography (C-18 column; gradient 5-95% ACN/water 0.1% TFA). The desired fraction were evaporated in vacu, dissolved in methanol and free based through a PL-HCO$_3$ MP resin cartridge, and evaporated to afford the desired product (2.1 mg, 1.6%) as a clear glass. $^1$H NMR (300 MHz, Methanol-d4) δ 7.48 (s, 1H), 7.35 (s, 1H), 7.16 (dd, J=9.1, 5.1 Hz, 2H), 7.03 (t, J=8.8 Hz, 2H), 4.99 (s, 2H), 4.18 (m, 1H), 4.07 (dd, J=13.8, 6.9 Hz, 1H), 3.20-3.03 (m, 3H), 2.96 (s, 3H), 2.76-2.62 (m, 2H), 2.17 (s, 3H), 2.01 (d, J=12.5 Hz, 2H), 1.90-1.72 (m, 3H), 1.33 (d, J=6.8 Hz, 3H); ESMS(M+1)=465.24.

Compound 179: (7S)-2-(((1-(1-(3,5-difluorophenyl)piperidin-4-yl)-1H-pyrazol-4-yl)methyl)amino)-4,7,8-trimethyl-7,8-dihydropteridin-6(5H)-one In a sealed tube was placed 1,3,5-Trifluorobenzene (Compound 99; 325 mg, 2.45 mmol) was added to a solution of (7S)-4,7,8-trimethyl-2-(((1-(piperidin-4-yl)-1H-pyrazol-4-yl)methyl)amino)-7,8-dihydropteridin-6(5H)-one (140 mg, 0.3779 mmol) in DMSO (1 mL) and triethylamine (0.5 ml) and heated at 70° C. for 20 hours. Reaction incomplete so heated at 170° C. for 2 hours. The reaction was cooled to room temperature and poured into 75 ml of water and extracted with ethyl acetate (3×75 ml). The combined extracts were washed with brine, dried over anhydrous sodium sulfate, filtered, and evaporated in vacuo. The crude product was purified by column chromatography (SiO$_2$) eluting with a gradient of 0-10% methanol (0.1% ammonia) in dichloromethane to afford the title product, wt. 68 mg (35% yield). $^1$H NMR (400 MHz, Methanol-d4) δ 7.65 (s, 1H), 7.47 (s, 1H), 6.53 (d, J=9.1 Hz, 2H), 6.27 (t, J=9.1 Hz, 1H), 4.45-4.19 (m, 3H), 4.09 (q, J=6.9 Hz, 1H), 3.87 (d, J=13.1 Hz, 2H), 3.09 (s, 3H), 2.95 (dd, J=17.9, 7.0 Hz, 2H), 2.65 (d, J=1.0 Hz, 5H), 2.26-1.96 (m, 6H), 1.35 (d, J=6.8 Hz, 3H); ESMS(M+1)=483.44. Chiral HPLC(Chiral PAK IC column, 4.6×250 mm; 50% hexane/30% ethanol/20% methanol/0.1% diethylamine): Rt=9.473 minutes; 97% ee.

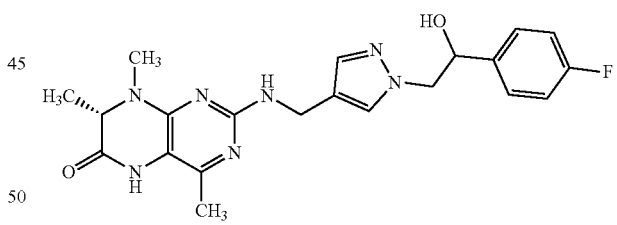

Compound 131 and 132: (7S)-2-[[1-[(2S)-2-(4-fluorophenyl)-2-hydroxy-ethyl]pyrazol-4-yl]methyl-amino]-4,7,8-trimethyl-5,7-dihydropteridin-6-one and (7S)-2-[[1-[(2R)-2-(4-fluorophenyl)-2-hydroxy-ethyl]pyrazol-4-yl]methylamino]-4,7,8-trimethyl-5,7-dihydropteridin-6-one Sodium borohydride (36 mg, 0.9446 mmol) was added to a solution of (7S)-2-[[1-[2-(4-fluorophenyl)-2-oxo-ethyl]pyrazol-4-yl]methylamino]-4,7,8-trimethyl-5,7-dihydropteridin-6-one (200 mg, 0.4723 mmol) in methanol (10 mL) at room temperature. The reaction was stirred for 2 hours followed by the addition of 2 ml of acetone to quench the reaction. The solvent was removed in vacuo and the resulting curde was taken into 5 ml of water and extracted with ethyl acetate (2×25 ml). The combined extracts were dried over anhydrous sodium sulfate, filtered, and evaporated in vacuo to afford the crude product that was purified by column chromatography eluting with a gradient of 0-20% methanol in dichloromethane. The desired fractions were evaporated in vacuo to afford 135 mg (62% yield) of the title products as a mixture of diastereomers (Compound 100). 1H NMR (300 MHz, DMSO-d6) δ 9.83 (s, 1H), 7.47 (d, J=0.6 Hz, 1H), 7.33 (d, J=0.7 Hz, 1H), 7.32-7.25 (m, 2H), 7.09 (td, J=9.0, 0.9 Hz, 2H), 6.53 (t, J=5.9 Hz, 1H), 5.64 (d, J=4.7 Hz, 1H), 4.89 (q, J=5.8 Hz, 1H), 4.25-4.07 (m, 4H), 4.05-3.91 (m, 1H), 2.95 (s, 3H), 2.13 (s, 3H), 1.19 (d, J=6.8 Hz, 3H). ESMS(M+1)=426.36.

The diastereomers were separated by chiral HPLC (OJ-H column, 20×250 mm; 70% Hexanes/15% methanol/15% ethanol/0.2% diethylamine, isocratic; 20 ml/min flow rate) to provide 18 mg of each diastereomer:

Diastereomer A: Rt 8.897 mins.; 90.8% ee

Diastereomer B: Rt 11.245 mins.; 86% ee.

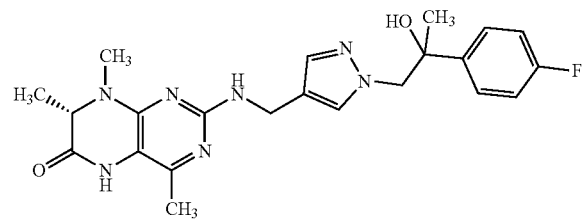 [SMILES: Cc1nc(NCc2cnn(CC(C)(O)c3ccc(F)cc3)c2)nc2c1NC(=O)[C@H](C)N2C]

Compound 128: (7S)-2-(((1-(2-(4-fluorophenyl)-2-hydroxypropyl)-1H-pyrazol-4-yl)methyl)amino)-4,7,8-trimethyl-7,8-dihydropteridin-6(5H)-one To a solution of (7S)-2-[[1-[2-(4-fluorophenyl)-2-oxo-ethyl]pyrazol-4-yl]methylamino]-4,7,8-trimethyl-5,7-dihydropteridin-6-one (125 mg, 0.29 mmol) in dry THE was added MeMgBr (405.5 mg, 393.7 μL of 3 M, 1.18 mmol) at −78° C. The reaction was stirred at −78° C. for 2 hours. The reaction was warmed to room temperature and stirred for 24 hours. The reaction was quenched with a saturated ammonium chloride and extracted with dichloromethane. The extracts were evaporated in vacuo to afford the crude product. The product and unreacted starting material were not separable so the crude was taken up into methanol and 0.3 ml of hydrazine was added to the solution and stirred for 2 hours. The mixture was evaporated in vacuo and the crude product purified by column chromatography eluting with a gradient of dichloromethane to 0-20% methanol in dichloromethane. The desired fractions were evaporated to provide the desired product, wt. 6.9 mg (5% yield). 1H NMR (300 MHz, DMSO-d6) δ 10.48 (s, 1H), 7.79 (brs, 1H), 7.45 (s, 1H), 7.39 (dd, J=8.7, 5.6 Hz, 2H), 7.32 (s, 1H), 7.04 (t, J=8.9 Hz, 2H), 5.48 (brs, 1H), 4.39-4.30 (m, 2H), 4.24 (s, 2H), 3.15 (s, 3H), 2.26 (s, 3H), 1.42 (d, J=6.9 Hz, 3H), 1.36 (d, J=1.1 Hz, 3H); ESMS(M+1)=440.32.

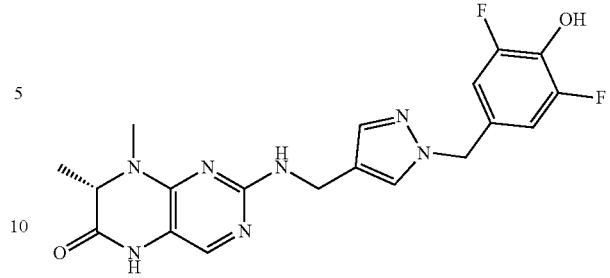

Compound 50: (7S)-2-(((1-(3,5-difluoro-4-hydroxybenzyl)-1H-pyrazol-4-yl)methyl)amino)-7,8-dimethyl-7,8-dihydropteridin-6(5H)-one (7S)-2-(((1-(3,5-difluoro-4-methoxybenzyl)-1H-pyrazol-4-yl)methyl)amino)-7,8-dimethyl-7,8-dihydropteridin-6(5H)-one (34 mg, 0.07781 mmol) was taken into 10 ml of dichloromethane. A 1 M solution of boron tribromide (400 ul; 0.4 mmol) in dichloromethane was added to the solution and stirred at room temperature for 18 hours. Methanol was added to the mixture to quench the reaction. The solvent was evaporated in vacuo to provide a residue that was dissolved in DMSO, filtered, and purified by reverse phase preparative HPLC (Acetontirle/water/TFA). The desired fractions were neutralized by passing through a PL-HCO3 MPSPE cartridge. Evaporation of the solvent afforded 14 mg of the desired product. 1H NMR (300 MHz, Methanol-d4) δ 7.64 (d, J=0.8 Hz, 1H), 7.52 (d, J=0.8 Hz, 1H), 7.40 (s, 1H), 6.83-6.74 (m, 2H), 5.20 (s, 2H), 4.40 (s, 2H), 4.14 (q, J=6.9 Hz, 1H), 3.08 (s, 3H), 1.42 (d, J=6.9 Hz, 3H); ESMS (M+H)=416.26.

Compound 73 and 74: (7S)-2-(((1-(4-fluorobenzyl)-3-methyl-1H-pyrazol-4-yl)methyl)amino)-4,7,8-trimethyl-7,8-dihydropteridin-6(5H)-one and (7S)-2-(((1-(4-fluorobenzyl)-5-methyl-1H-pyrazol-4-yl)methyl)amino)-4,7,8-trimethyl-7,8-dihydropteridin-6(5H)-one The compounds were prepared by general procedure Method A via reaction of intermediate A-2 and B-98 to provide the title products as a mixture of the regioisomers. The mixture was inseparable by column chromatography. The regioisomers were separated by SFC(column: AD-H, 110×250 mm; 40% methanol(0.2% diethylamine/60% CO₂) to provide each individual regioisomer.

Peak A: Rt 0.783 minutes. Major, (93 mg, 46% yield) 1H NMR (300 MHz, CDCl₃) δ 8.91-8.32 (m, 1H), 7.27 (d, J=5.4 Hz, 1H), 7.23-7.11 (m, 2H), 7.02 (dd, J=9.6, 7.6 Hz, 2H), 5.17 (s, 2H), 4.69 (t, J=5.3 Hz, 1H), 4.35 (d, J=5.4 Hz, 2H), 4.06 (q, J=6.8 Hz, 1H), 3.03 (s, 3H), 2.27 (s, 3H), 2.24 (s, 3H), 1.40 (d, J=6.9 Hz, 3H). ESMS(M+1)=410.16.

Peak B: Rt 1.595 minutes. Minor, (53 mg, 26% yield) 1H NMR (400 MHz, CDCl₃) δ 8.97 (s, 1H), 7.49 (s, 1H), 7.14-6.91 (m, 4H), 5.23 (s, 2H), 4.81-4.61 (m, 1H), 4.34 (d, J=5.3 Hz, 2H), 4.06 (q, J=6.8 Hz, 1H), 3.05 (s, 3H), 2.25 (s, 3H), 2.19 (s, 3H), 1.39 (d, J=6.8 Hz, 3H). ESMS(M+1)=449.32.

TABLE 5

2B. Preparation of Compound of Table 5

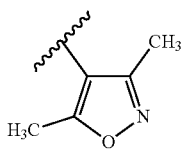

| Compound No. | Ring A | Method |
|---|---|---|
| Compound 138 | 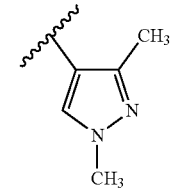 | A |
| Compound 139 | 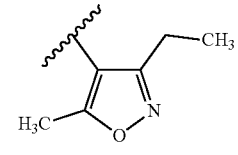 | A |
| Compound 158 | 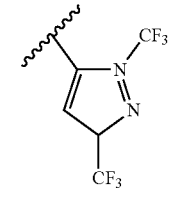 | A |
| Compound 159 | 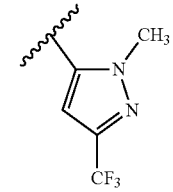 [SMILES: *c1cc(C(F)(F)F)nn1C] | A |
| Compound 160 | 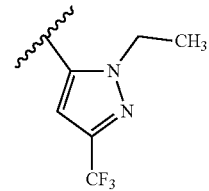 | A |
| Compound 189 | 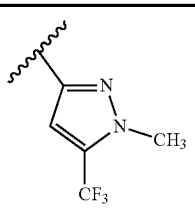 | A |

TABLE 5-continued

2B. Preparation of Compound of Table 5

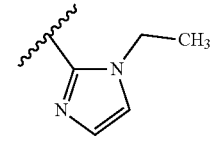 [SMILES: *c1nccn1CC]

| Compound No. | Ring A | Method |
|---|---|---|
| Compound 190 | 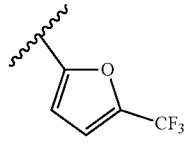 [SMILES: *c1ccc(C(F)(F)F)o1] | A |
| Compound 191 | 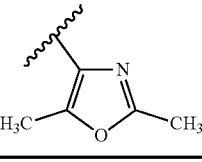 | A |
| Compound 192 | | A |
| Compound 193 | | A |

Compound 138: (7S)-2-(((1-((3,5-dimethylisoxazol-4-yl)methyl)-1H-pyrazol-4-yl)methyl)amino)-4,7,8-trimethyl-7,8-dihydropteridin-6(5H)-one The compound was prepared by procedure Method A via reaction of intermediates A-2 and B-85 to provide the title product, 48% yield. 1H NMR (300 MHz, Methanol-d4) δ 7.58 (s, 1H), 7.47 (s, 1H), 5.11 (s, 2H), 4.36 (s, 2H), 4.07 (q, J=6.9 Hz, 1H), 3.04 (s, 3H), 2.36 (s, 3H), 2.17 (s, 3H), 2.06 (s, 3H), 1.32 (d, J=6.8 Hz, 3H); ESMS (M+H)=397.15. Chiral TlPLC(ChiralPAiK IC column; 20% methanol/30% ethanol/50% hexanes, isocratic) Rt 13.781 mins.; 9800 ee.

Compound 139: (7S)-2-(((1-((1,3-dimethyl-1H-pyrazol-4-yl)methyl)-1H-pyrazol-4-yl)methyl)amino)-4,7,8-trimethyl-7,8-dihydropteridin-6(5H)-one The compound was prepared by procedure Method A via reaction of intermediates A-2 and B-86 to provide the title product. 1H NMR (400 MHz, Methanol-d4) δ 7.49 (s, 1H), 7.48 (s, 1H), 7.43 (s, 1H), 5.09 (s, 1H), 4.35 (s, 2H), 4.06 (q, J=6.8 Hz, 1H), 3.77 (s, 3H), 3.03 (s, 3H), 2.16 (s, 3H), 2.08 (s, 3H), 1.32 (d, J=6.8 Hz, 3H); ESMS (M+H)=396.16. Chiral HPLC(ChiralPAK IC column; 20% methanol/30% ethanol/50% hexanes, isocratic) Rt 15.157 mins.; 97% ee.

Compound 158: (7S)-2-(((1-((3-ethyl-5-methyl-isoxazol-4-yl)methyl)-1H-pyrazol-4-yl)methyl)amino)-4,7,8-trimethyl-7,8-dihydropteridin-6(5H)-one The compound was prepared by procedure Method A via reaction of intermediates A-2 and B-87 to provide the title product. 1H NMR (400 MHz, Methanol-d4) δ 7.54 (s, 1H), 7.46 (s, 1H), 5.10 (s, 2H), 4.36 (s, 2H), 4.07 (q, J=6.8 Hz, 1H), 3.04 (s, 3H), 2.47 (q, J=7.6 Hz, 2H), 2.36 (s, 3H), 2.17 (s, 3H), 1.33 (d, J=6.8 Hz, 3H), 1.05 (t, J=7.6 Hz, 3H); ESMS (M+H)=411.29.

Compound 159: (7S)-4,7,8-trimethyl-2-(((1-((1-methyl-3-(trifluoromethyl)-1H-pyrazol-4-yl)methyl)-1H-pyrazol-4-yl)methyl)amino)-7,8-dihydropteridin-6(5H)-one The compound was prepared by procedure Method A via reaction of intermediates A-2 and B-88 to provide the title product. 1H NMR (400 MHz, Methanol-d4) δ 7.69 (s, 1H), 7.60 (s, 1H), 7.51 (s, 1H), 5.25 (s, 2H), 4.54-4.41 (m, 2H), 4.30 (q, J=6.9 Hz, 1H), 3.90 (s, 3H), 3.23 (s, 3H), 2.28 (s, 3H), 1.52 (d, J=6.9 Hz, 3H). ESMS (M+H)=450.22.

Compound 160: (7S)-4,7,8-trimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one The compound was prepared by procedure Method A via reaction of intermediates A-2 and B-89 to provide the title product. 1H NMR (300 MHz, DMSO-d6) δ 9.81 (s, 1H), 7.67 (s, 1H), 7.40 (s, 1H), 6.68-6.51 (m, 2H), 5.44 (s, 2H), 4.30-4.12 (m, 2H), 3.99 (q, J=6.8 Hz, 1H), 3.88 (s, 3H), 2.93 (s, 3H), 2.12 (s, 3H), 1.18 (d, J=6.8 Hz, 3H); ESMS (M+H)=450.17; Chiral HPLC(ChiralPAK IC column; 20% methanol/30% ethanol/50% hexanes, isocratic) Rt 7.083 mins.; 97% ee. [α]$_D^{20}$+48.2° (c=0.71, 1:1 methanol/dichloromethane).

Compound 189: (7S)-2-(((1-((1-ethyl-3-(trifluoromethyl)-1H-pyrazol-5-yl)methyl)-1H-pyrazol-4-yl)methyl)amino)-4,7,8-trimethyl-7,8-dihydropteridin-6(5H)-one The compound was prepared by procedure Method A via reaction of intermediates A-2 and B-90 to provide the title product. 1H NMR (400 MHz, CDCl₃) δ 8.11 (s, 1H), 7.50 (s, 1H), 7.44-7.39 (m, 1H), 6.46 (s, 1H), 5.51 (s, 1H), 5.23 (s, 2H), 4.46-4.36 (m, 2H), 4.23 (q, J=7.2 Hz, 2H), 4.08 (q, J=6.9 Hz, 1H), 3.06 (s, 3H), 2.24 (s, 3H), 1.46 (t, J=7.2 Hz, 3H), 1.42 (d, J=6.9 Hz, 3H); ESMS (M+H)=464.26. Chiral HPLC(ChiralPAK IC column; 20% methanol/30% ethanol/50% hexanes, isocratic) Rt 6.691 mins.; 92% ee.

Compound 190: (7S)-4,7,8-trimethyl-2-(((1-((1-methyl-5-(trifluoromethyl)-1H-pyrazol-3-yl)methyl)-1H-pyrazol-4-yl)methyl)amino)-7,8-dihydropteridin-6(5H)-one The compound was prepared by procedure Method A via reaction of intermediates A-2 and B-91 to provide the title product. 1H NMR (400 MHz, CDCl₃) δ 8.05 (s, 1H), 7.52 (s, 1H), 7.45 (s, 1H), 6.54 (s, 1H), 5.25 (s, 2H), 4.45 (d, J=5.8 Hz, 2H), 4.13 (q, J=6.9 Hz, 1H), 3.98 (s, 3H), 3.12 (s, 3H), 2.28 (s, 3H), 1.48 (d, J=6.8 Hz, 3H). ESMS (M+H)=450.26. Chiral HPLC(ChiralPAK IC column; 20% methanol/30% ethanol/50% hexanes, isocratic) Rt 8.817 mins.; 95.6% ee.

Compound 191: (7S)-2-(((1-((1-ethyl-1H-imidazol-2-yl)methyl)-1H-pyrazol-4-yl)methyl)amino)-4,7,8-trimethyl-7,8-dihydropteridin-6(5H)-one The compound was prepared by procedure Method A via reaction of intermediates A-2 and B-92 to provide the title product. 1H NMR (400 MHz, CDCl₃) δ 8.38 (s, 1H), 7.44 (s, 1H), 7.38 (s, 1H), 6.98 (d, J=5.7 Hz, 1H), 6.89 (d, J=1.2 Hz, 1H), 5.35 (s, 2H), 4.34 (t, J=7.4 Hz, 2H), 4.04 (q, J=6.9 Hz, 1H), 3.97 (q, J=7.3 Hz, 2H), 3.01 (s, 3H), 2.21 (s, 3H), 1.38 (d, J=6.9 Hz, 3H), 1.19 (t, J=7.3 Hz, 3H); ESMS (M+H)=396.3. Chiral HPLC(ChiralPAK IC column; 20% methanol/30% ethanol/50% hexanes, isocratic) Rt 17.014 mins.; 99% ee.

Compound 192: (7S)-4,7,8-trimethyl-2-(((1-((5-(trifluoromethyl)furan-2-yl)methyl)-1H-pyrazol-4-yl)methyl)amino)-7,8-dihydropteridin-6(5H)-one The compound was prepared by procedure Method A via reaction of intermediates A-2 and B-93 to provide the title product. 1H NMR (400 MHz, Methanol-d4) δ 7.64 (s, 1H), 7.49 (s, 1H), 6.95-6.86 (m, 1H), 6.49 (d, J=3.4 Hz, 1H), 5.35 (s, 2H), 4.39 (s, 2H), 4.07 (q, J=6.8 Hz, 1H), 3.05 (s, 3H), 2.17 (s, 3H), 1.33 (d, J=6.9 Hz, 3H); ESMS (M+H)=436.29. Chiral HPLC(ChiralPAK IC column; 20% methanol/30% ethanol/50% hexanes, isocratic) Rt 6.85 mins.; 91.6% ee.

Compound 193: (7S)-2-(((1-((2,5-dimethyloxazol-4-yl)methyl)-1H-pyrazol-4-yl)methyl)amino)-4,7,8-trimethyl-7,8-dihydropteridin-6(5H)-one The compound was prepared by procedure Method A via reaction of intermediates A-2 and B-94 to provide the title product. 1H NMR (400 MHz, Methanol-d4) δ 7.58 (s, 1H), 7.44 (s, 1H), 5.08 (s, 2H), 4.37 (s, 2H), 4.06 (q, J=6.8 Hz, 1H), 3.05 (s, 3H), 2.35 (s, 3H), 2.23 (s, 3H), 2.17 (s, 3H), 1.32 (d, J=6.8 Hz, 3H); ESMS (M+H)=397.31. Chiral HPLC (ChiralPAK IC column; 20% methanol/30% ethanol/50% hexanes, isocratic) Rt 11.821 mins.; 92% ee.

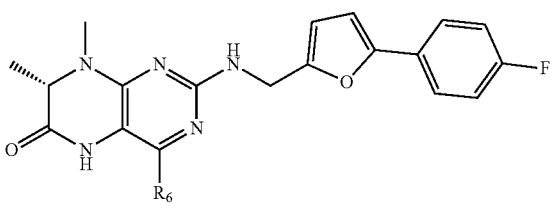

Compound 40 R₆=CH3: (7S)-2-(((5-(4-Fluorophenyl)furan-2-yl)methyl)amino)-4,7,8-trimethyl-7,8-dihydropteridin-6(5H)-one The compound was prepared by procedure Method A via reaction of intermediate A-2 and (5-(4-fluorophenyl)furan-2-yl)methanamine to provide the title product. 1H NMR (300 MHz, Methanol-d4) δ 7.71-7.59 (m, 2H), 7.16-7.03 (m, 2H), 6.63 (d, J=3.3 Hz, 1H), 6.33 (dt, J=3.3, 0.8 Hz, 1H), 4.63-4.56 (m, 2H), 4.14 (q, J=6.9 Hz, 1H), 3.13 (s, 3H), 2.22 (s, 3H), 1.39 (d, J=6.9 Hz, 3H); ESMS(M+1)=382.31.

Compound 43 R₆=H: (7S)-2-(((5-(4-fluorophenyl)furan-2-yl)methyl)amino)-7,8-dimethyl-7,8-dihydropteridin-6(5H)-one The compound was prepared by procedure Method A via reaction of intermediate A-1 and (5-(4-fluorophenyl)furan-2-yl)methanamine to provide the title product. 1H NMR (300 MHz, CDCl₃) δ 7.68-7.56 (m, 2H), 7.40 (s, 1H), 7.13-7.00 (m, 2H), 6.51 (d, J=3.3 Hz, 1H), 6.36-6.28 (m, 1H), 4.69-4.60 (m, 2H), 4.14 (q, J=6.9 Hz, 1H), 3.13 (s, 3H), 1.50 (d, J=6.9 Hz, 3H); ESMS(M+1)=368.26.

Compound 59: (7S)-4,7,8-trimethyl-2-(((4-phenylthiazol-2-yl)methyl)amino)-7,8-dihydropteridin-6(5H)-one The compound was prepared by procedure Method B via reaction of intermediate A-2 and (4-phenylthiazol-2-yl)methanamine to provide the title product. ESMS(M+1)=381.33.

Compound 60: (S)-4,7,8-trimethyl-2-(((2-(piperidin-1-yl)pyridin-4-yl)methyl)amino)-7,8-dihydropteridin-6(5H)-one The compound was prepared by procedure Method B via reaction of intermediate A-2 and (2-(piperidin-1-yl)pyridin-4-yl)methanamine to provide the title product. 1H NMR (400 MHz, Methanol-d4) δ 7.85 (d, J=6.6 Hz, 1H), 7.34 (s, 1H), 6.94 (d, J=6.5 Hz, 1H), 4.71 (s, 2H), 4.28 (q, J=6.9 Hz, 1H), 3.71 (d, J=5.5 Hz, 4H), 3.14 (s, 3H), 2.34 (s, 3H), 1.76 (s, 6H), 1.51 (d, J=6.9 Hz, 3H); ESMS(M+1)=382.32.

Compound 62: (S)-4,7,8-trimethyl-2-(((2-morpholinopyridin-4-yl)methyl)amino)-7,8-dihydropteridin-6(5H)-one The compound was prepared by procedure Method B via reaction of intermediate A-2 and (2-morpholinopyridin-4-yl)methanamine to provide the title product. ESMS(M+1)=384.39.

TABLE 6

2C. Preparation of Compounds of Table 6.

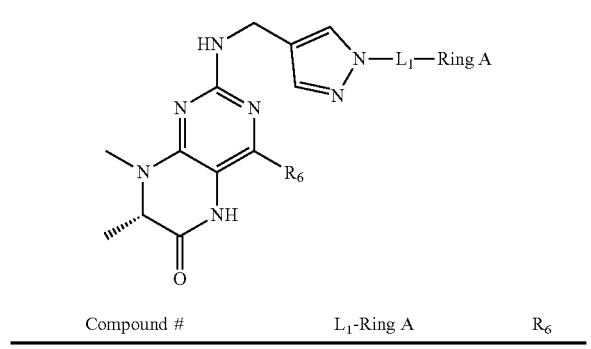

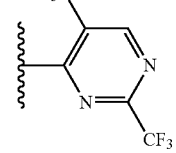

| Compound # | L₁-Ring A | R₆ |
|---|---|---|
| Compound 161 | 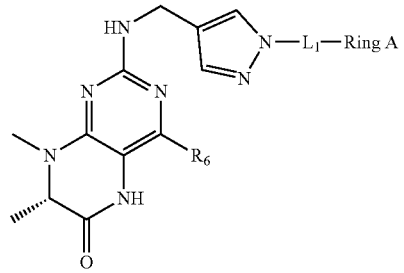 | Me |
| Compound 162 | | Me |
| Compound 163 | | Me |
| Compound 164 | | H |
| Compound 165 | | H |
| Compound 166 | | H |

Compound 161: (7S)-4,7,8-trimethyl-2-(((1-(5-methyl-2-(trifluoromethyl)pyrimidin-4-yl)-1H-pyrazol-4-yl)methyl)amino)-7,8-dihydropteridin-6(5H)-one The compound was prepared by procedure Method B via reaction of intermediates A-2 and B-153 to provide the title product. 1H NMR (300 MHz, CDCl₃) δ 8.77-8.67 (m, 2H), 7.85 (d, J=0.8 Hz, 1H), 4.57 (dd, J=6.0, 2.5 Hz, 2H), 4.20 (q, J=6.8 Hz, 1H), 3.24 (s, 3H), 2.79 (t, J=0.8 Hz, 3H), 2.36 (s, 3H), 1.55 (d, J=6.9 Hz, 3H); ESMS(M+1)=448.19.

Compound 162: (7S)-2-(((1-((5-fluoropyrimidin-2-yl)methyl)-1H-pyrazol-4-yl)methyl)amino)-4,7,8-trimethyl-7,8-dihydropteridin-6(5H)-one The compound was prepared by procedure Method B via reaction of intermediates A-2 and B-151 to provide the title product. 1H NMR (300 MHz, CDCl₃) δ 8.60 (d, J=0.5 Hz, 2H), 7.57 (dd, J=5.6, 0.8 Hz, 2H), 5.53 (d, J=1.0 Hz, 2H), 4.48 (d, J=5.7 Hz, 2H), 4.11 (q, J=6.9 Hz, 1H), 3.10 (s, 3H), 2.27 (s, 3H), 1.45 (d, J=6.9 Hz, 3H); ESMS(M+1)=398.26.

Compound 163: (7S)-4,7,8-trimethyl-2-(((1-((2-methylpyrimidin-5-yl)methyl)-1H-pyrazol-4-yl)methyl)amino)-7,8-dihydropteridin-6(5H)-one The compound was prepared by procedure Method B via reaction of intermediates A-2 and B-152 to provide the title product. 1H NMR (300 MHz, CDCl₃) δ 8.54 (s, 2H), 7.55-7.46 (m, 2H), 5.24 (s, 2H), 4.43 (s, 2H), 4.11 (q, J=6.9 Hz, 1H), 3.11 (s, 3H), 2.72 (s, 3H), 2.27 (s, 3H), 1.46 (d, J=6.9 Hz, 3H); ESMS(M+1)=393.89.

Compound 164: (7S)-7,8-dimethyl-2-(((1-(5-methyl-2-(trifluoromethyl)pyrimidin-4-yl)-1H-pyrazol-4-yl)methyl)amino)-7,8-dihydropteridin-6(5H)-one The compound was prepared by procedure Method B via reaction of intermediates A-1 and B-153 to provide the title product. 1H NMR (300 MHz, CDCl₃) δ 8.75-8.65 (m, 2H), 7.84 (d, J=0.9 Hz, 1H), 7.36 (s, 1H), 4.56-4.49 (m, 2H), 4.14 (q, J=6.9 Hz, 1H), 3.18 (s, 3H), 2.77 (t, J=0.8 Hz, 3H), 1.50 (d, J=6.9 Hz, 3H); ESMS(M+1)=434.27.

Compound 165: (7S)-2-(((1-((5-fluoropyrimidin-2-yl)methyl)-1H-pyrazol-4-yl)methyl)amino)-7,8-dimethyl-7,8-dihydropteridin-6(5H)-one The compound was prepared by procedure Method B via reaction of intermediates A-1 and B-151 to provide the title product. 1H NMR (300 MHz, CDCl₃) δ 8.63-8.56 (m, 2H), 7.66-7.53 (m, 3H), 5.54 (d, J=1.0 Hz, 2H), 4.50 (d, J=5.6 Hz, 2H), 4.19 (q, J=6.9 Hz, 1H), 3.16 (s, 3H), 1.52 (d, J=7.0 Hz, 3H); ESMS(M+1)=384.21.

Compound 166: (7S)-7,8-dimethyl-2-(((1-((2-methylpyrimidin-5-yl)methyl)-1H-pyrazol-4-yl)methyl)amino)-7,8-dihydropteridin-6(5H)-one The compound was prepared by procedure Method B via reaction of intermediates A-1 and B-152 to provide the title product. 1H NMR (300 MHz, CDCl₃) δ 8.57 (s, 2H), 7.69 (s, 1H), 7.62-7.50 (m, 2H), 5.28 (d, J=2.4 Hz, 2H), 4.47 (d, J=5.6 Hz, 2H), 4.20 (q, J=6.8 Hz, 1H), 3.17 (s, 3H), 2.73 (s, 3H), 1.54 (d, J=7.0 Hz, 3H); ESMS(M+1)=380.25.

2D. Preparation of Compounds of Table 7 General Scheme

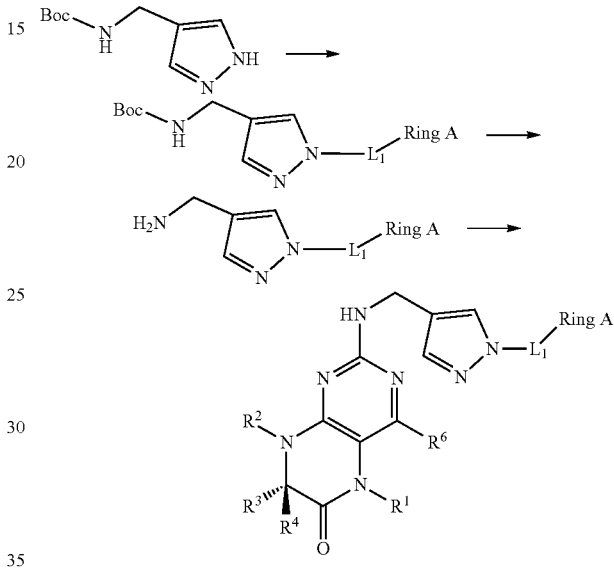

TABLE 7

| Comp # | Ring A–L₁ | R¹ | R² | R³ | R⁴ | R⁶ | Prep Method |
|---|---|---|---|---|---|---|---|
| Comp 136 | 5-(CF₃)pyridin-3-yl-CH₂ | H | Me | Me | H | Me | A |
| Comp 177 | 5-(CF₃)pyridin-3-yl-CH₂ | Me | Me | Me | H | Me | B |
| Comp 77 | 6-F-pyridin-3-yl-CH₂ | H | Me | Me | H | Me | A |
| Comp 82 | 6-F-pyridin-3-yl-CH₂ | Me | Me | Me | H | Me | B |

TABLE 7-continued

| Comp # | L₁–Ring A | R¹ | R² | R³ | R⁴ | R⁶ | Prep Method |
|---|---|---|---|---|---|---|---|
| Comp 94 | 4-methyl-6-fluoropyridin-3-yl-CH₂- | H | Me | Me | H | Me | A |
| Comp 129 | 6-isopropoxypyridin-3-yl-CH₂- | Me | Me | Me | H | Me | C |
| Comp 135 | 6-isopropoxypyridin-3-yl-CH₂- | H | Me | Me | H | Me | C |
| Comp 167 | 6-tert-butoxypyridin-3-yl-CH₂- | H | Me | Me | H | Me | C |
| Comp 168 | 4-methyl-6-isopropoxypyridin-3-yl-CH₂- | H | Me | Me | H | Me | C |
| Comp 10 | 6-(methylamino)pyridin-3-yl-CH₂- | H | Me | Me | H | Me | D |
| Comp 173 | 6-methylpyridin-3-yl-CH₂- | H | Me | Me | H | Me | A |
| Comp 174 | (R)-1-(6-(trifluoromethyl)pyridin-3-yl)ethyl- | H | Me | Me | H | Me | A |
| Comp 175 | (S)-1-(6-(trifluoromethyl)pyridin-3-yl)ethyl- | H | Me | Me | H | Me | A |

TABLE 7-continued

| Comp # | Ring A–L₁ | R¹ | R² | R³ | R⁴ | R⁶ | Prep Method |
|---|---|---|---|---|---|---|---|
| Comp 176 | 5-(2-cyanopyridyl)methyl | H | Me | Me | H | Me | A |
| Comp 178 | 5-(2-methylpyridyl)methyl | H | Me | Me | H | Me | B |
| Comp 180 | 4-(2-fluoropyridyl)methyl | H | Me | Me | H | Me | A |
| Comp 182 | 3-(4-trifluoromethylpyridyl)methyl | H | Me | Me | H | Me | A |
| Comp 183 | 3-(2-trifluoromethylpyridyl)methyl | H | Me | Me | H | Me | A |
| Comp 184 | 2,6-bis(trifluoromethyl)... pyridyl methyl | H | Me | Me | H | Me | B |
| Comp 187 | 4-(3-trifluoromethylpyridyl)methyl | H | Me | Me | H | Me | B |
| Comp 188 | 3-(2-methyl-6-trifluoromethylpyridyl)methyl | H | Me | Me | H | Me | A |
| Comp 194 | 5-(2-chloropyridyl)methyl | H | Me | Me | H | Me | See procedure |
| Comp 195 | 5-(6-trifluoromethylpyridazinyl)methyl | H | Me | Me | H | H | B |
| Comp 196 | 5-(2-dimethylaminopyridyl)methyl | H | Me | Me | H | Me | D |

TABLE 7-continued

| Comp # | Ring A / L₁ | R¹ | R² | R³ | R⁴ | R⁶ | Prep Method |
|---|---|---|---|---|---|---|---|
| Comp 197 | 5-(2-methoxypyridin-5-yl)methyl | H | Me | Me | H | Me | A |
| Comp 198 | (pyridin-3-yl)methyl | H | Me | Me | H | Me | See procedure |
| Comp 199 | (3-methyl-2-trifluoromethylpyridin-5-yl)methyl | H | Me | Me | H | Me | A |
| Comp 185 | (2-chloropyridin-4-yl)methyl | H | Me | Me | H | Me | B |
| Comp 200 | (5-trifluoromethylpyridin-2-yl)methyl | H | Me | Me | H | Me | B |
| Comp 201 | (4-trifluoromethylpyridin-2-yl)methyl | H | Me | Me | H | Me | B |
| Comp 12 | (2-dimethylaminopyridin-4-yl)methyl | H | Me | Me | H | Me | B |
| Comp 202 | (2-hydroxypyridin-5-yl)methyl | H | Me | Me | H | Me | B |
| Comp 203 | (2-methoxypyridin-4-yl)methyl | H | Me | Me | H | Me | B |
| Comp 204 | (2-cyanopyridin-4-yl)methyl | H | Me | Me | H | Me | B |
| Comp 206 | (3-trifluoromethylpyridin-5-yl)methyl | H | Me | Me | H | Me | A |
| Comp 207 | (2-trifluoromethylpyridin-4-yl)methyl | H | Me | Me | H | Me | B |

TABLE 7-continued

| Comp # | Ring A / L₁ | R¹ | R² | R³ | R⁴ | R⁶ | Prep Method |
|---|---|---|---|---|---|---|---|
| Comp 210 | 5-(4-methoxy-2-trifluoromethylpyridyl)methyl | H | Me | Me | H | Me | A |
| Comp 211 | 5-(2-tert-butylpyridyl)methyl | H | Me | Me | H | Me | A |
| Comp 209 | 5-(3-fluoro-2-trifluoromethylpyridyl)methyl | H | Me | Me | H | Me | A |
| Comp 218 | 5-(2-methoxy-6-trifluoromethylpyridyl)methyl | H | Me | Me | H | Me | A |
| Comp 215 | 5-(3-trifluoromethyl-2-methoxypyridyl)methyl | H | Me | Me | H | Me | A |
| Comp 213 | 5-(3-methoxy-2-trifluoromethylpyridyl)methyl | H | Me | Me | H | Me | A |
| Comp 208 | 5-(5-fluoropyridyl)methyl | H | Me | Me | H | Me | B |
| Comp 205 | 5-(4-methyl-2-fluoropyridyl)methyl | Me | Me | Me | H | Me | B |
| Comp 385 | 5-(2-trifluoromethylpyridyl)methyl | H | i-Pr | Me | H | Me | A |
| Comp 220 | 5-(2-trifluoromethylpyridyl)methyl | H | Me | n-Pr | H | Me | A |

TABLE 7-continued

| Comp # | Ring A–L₁ | R¹ | R² | R³ | R⁴ | R⁶ | Prep Method |
|---|---|---|---|---|---|---|---|
| Comp 383 | 5-(2-CF₃-pyridyl)methyl | H | Me | i-Pr | H | Me | A |
| Comp 384 | 5-(2-F-pyridyl)methyl | H | Me | i-Pr | H | Me | A |
| Comp 400 | 5-(2-CF₃-pyridyl)methyl | H | CD3 | Me | H | Me | A |
| Comp 386 | 5-(2-CF₃-pyridyl)methyl | H | Me | c-Pr | H | Me | A |
| Comp 387 | 3-(6-CF₃-2-isopropenyl-pyridyl)methyl | H | Me | Me | H | Me | A |
| Comp 388 | 3-(2-i-Pr-6-CF₃-pyridyl)methyl | H | Me | Me | H | Me | A |
| Comp 238 | 5-(2-CF₃-pyridyl)methyl | H | Me | Me | Me | Me | A |
| Comp 237 | 3-(2-CF₃-pyridyl)methyl | Me | Me | Me | Me | H | A |
| Comp 236 | 3-(4-CF₃-pyridyl)methyl | Me | Me | Me | Me | H | A |
| Comp 186 | 5-(2-CF₃-pyridyl)methyl | H | Me | Et | H | Me | A |
| Comp 390 | 5-(2-(2,2,2-trifluoroethoxy)-pyridyl)methyl | H | Me | Me | H | Me | A |

TABLE 7-continued

| Comp # | Ring A–L₁ | R¹ | R² | R³ | R⁴ | R⁶ | Prep Method |
|---|---|---|---|---|---|---|---|
| Comp 394 | 5-(methylene)-3-methoxy-2-fluoropyridine | H | Me | Et | H | Me | A |
| Comp 389 | 5-(methylene)-2-fluoropyridine | H | Me | Et | H | Me | A |
| Comp 395 | 5-(methylene)-2-(trifluoromethyl)pyridine | H | Et | Me | H | Me | A |
| Comp 396 | 5-(methylene)-1-methyl-3-(trifluoromethyl)-1H-pyrazole | H | Me | c-Pr | H | Me | A |
| Comp 397 | 5-(methylene)-1-methyl-3-(trifluoromethyl)-1H-pyrazole | H | Me | i-Pr | Me | | A |
| Comp 398 | 5-(methylene)-2-(trifluoromethyl)pyridine | H | Me | Spiro-c-Bu | Me | | A |
| Comp 239 | 5-(methylene)-2-(trifluoromethyl)pyridine | H | Me | Spiro-c-Pr | Me | | A |

Compound 136: (7S)-4,7,8-trimethyl-2-(((1-((6-(trifluoromethyl)pyridin-3-yl)methyl)-1H-pyrazol-4-yl)methyl)amino)-7,8-dihydropteridin-6(5H)-one A mixture of (7S)-2-Chloro-4,7,8-trimethyl-7,8-dihydropteridin-6(5H)-one (A-2; 40 g, 176.5 mmol), (1-((6-(Trifluoromethyl)pyridin-3-yl)methyl)-1H-pyrazol-4-yl)methanamine hydrochloride (B-52; 78.4 g, 212 mmol), and sodium tert-butoxide (59.4 g, 618 mmol) was taken into tert-butanol (640 ml) and purged with nitrogen. tfluXPhos Pd Gen 1 (2.42 g, 3.53 mmol) was added to the mixture and an exotherm was observed (temperature rose to 48° C.). The reaction temperature was maintained at 50° C. for 30 minutes. The solvent was removed under vacuum and the resulting residue was taken into water (1 liter) and extracted with dichloromethane (2×600 ml). The extracts were washed with brine, dried over anhydrous sodium sulfate, and filtered. Celite (110 g) was added to the filtrate and the solvent evaporated in vacuo. The solid residue was dry loaded onto 1.5 kg of silica gel and eluted with a gradient of 0-20% methanol in dichloromethane. The desired fractions were evaporated in vacuo to afford a green foam. The foam product was dissolved in 600 ml of dichloromethane and 35 g f Biotage Mp-TMT resin was added and stirred overnight. The solvent was filtered through a pad of Florisil and washed with ethyl acetate. The filtrate was evaporated in vacuo. Heptane ((800 ml) was added to the resulting material and stirred for 30 minutes followed by vacuum filtration and subsequent washing with heptane. The material washed with heptane was then dried in a vacuum oven at 55° C. to provide the title product, 64 g (80.4% yield). $^1$H NMR (300 MHz, CDCl$_3$) δ 8.61 (s, 1H), 7.68 (t, J=1.4 Hz, 2H), 7.57 (d, J=0.7 Hz, 1H), 7.44 (d, J=0.8 Hz, 1H), 5.38 (s, 2H), 4.95 (s, 1H), 4.48-4.38 (m, 2H), 4.09 (q, J=6.8 Hz, 1H), 3.06 (s, 3H), 2.22 (s, 3H), 1.42 (d, J=6.9 Hz, 3H). ESMS(M+1)=447.3; Chiral HPLC (ChiralPAK IC column; 20% MeOH/30%

EtOH/50% hexanes (0.1% Diethylamine), isocratic) Rt 7.548 (98.6% ee). [α]$_D$=45.5° (c=1, methanol); mp=175-176° C.

Compound 177: (7S)-4,5,7,8-tetramethyl-2-(((1-((6-(trifluoromethyl)pyridin-3-yl)methyl)-1H-pyrazol-4-yl)methyl)amino)-7,8-dihydropteridin-6(5H)-one The compound was prepared by general procedure Method B via reaction of intermediates A-3 and B-52 to provide the title compound. Yield, 20%. 1H NMR (300 MHz, DMSO-d6) δ 8.66-8.60 (m, 1H), 7.97-7.81 (m, 2H), 7.77 (s, 1H), 7.44 (s, 1H), 6.83 (t, J=6.0 Hz, 1H), 5.45 (s, 2H), 4.25 (dd, J=6.0, 2.3 Hz, 2H), 4.01 (q, J=6.7 Hz, 1H), 3.18 (s, 3H), 2.92 (s, 3H), 2.27 (s, 3H), 1.05 (d, J=6.8 Hz, 3H); ESMS(M+1)=461.43; Chiral HPLC (ChiralPAK IC column; 20% MeOH/30% EtOH/50% hexanes (0.1% Diethylamine), isocratic) Rt 10.137 mins. (99% ee).

Compound 77: (7S)-2-(((1-((6-fluoropyridin-3-yl)methyl)-1H-pyrazol-4-yl)methyl)amino)-4,5,7-trimethyl-7,8-dihydropteridin-6(5H)-one The compound was prepared by general procedure Method A via reaction of intermediates A-2 and B-53 to provide the title compound; 88 mg, yield 38.31%; 1H NMR (400 MHz, CDCl$_3$) δ 8.90 (s, 1H), 8.05 (dd, J=2.4, 1.1 Hz, 1H), 7.58 (ddd, J=8.7, 7.6, 2.6 Hz, 1H), 7.45 (s, 1H), 7.31 (s, 1H), 6.83 (dd, J=8.5, 2.9 Hz, 1H), 5.18 (s, 2H), 5.06-4.89 (m, 1H), 4.34 (dd, J=5.8, 2.2 Hz, 2H), 3.99 (q, J=6.8 Hz, 1H), 2.96 (d, J=0.7 Hz, 3H), 2.17 (d, J=0.8 Hz, 3H), 1.32 (d, J=6.9 Hz, 3H). ESMS(M+1)=397.11. Chiral HPLC (ChiralPAK IC column; 20% MeOH/30% EtOH/50% hexanes (0.1% Diethylamine), isocratic) Rt 3.751 mins. (98% ee). [α]$_D$=47.0° (c=0.97, methanol).

Compound 82: (7S)-2-(((1-((6-fluoropyridin-3-yl)methyl)-1H-pyrazol-4-yl)methyl)amino)-4,5,7,8-tetramethyl-7,8-dihydropteridin-6(5H)-one The compound was prepared by general procedure Method B via reaction of intermediates A-3 and B-53 to provide the title compound; Yield, 58.05%; $^1$H NMR (300 MHz, CDCl$_3$) δ 8.23-8.07 (m, 1H), 7.67 (td, J=7.9, 2.6 Hz, 1H), 7.55 (s, 1H), 7.41 (s, 1H), 6.92 (dd, J=8.4, 3.0 Hz, 1H), 5.29 (d, J=11.6 Hz, 2H), 5.20 (s, 1H), 4.44 (d, J=5.8 Hz, 2H), 4.02 (q, J=6.8 Hz, 1H), 3.30 (s, 3H), 3.02 (s, 3H), 2.37 (s, 3H), 1.21 (d, J=6.9 Hz, 3H). ESMS(M+1)=411.27; Chiral HPLC (ChiralPAK IC column; 20% MeOH/30% EtOH/50% hexanes (0.1% Diethylamine), isocratic) Rt 16.201 mins (65% ee).

Compound 94: (7S)-2-(((1-((6-fluoro-4-methylpyridin-3-yl)methyl)-1H-pyrazol-4-yl)methyl)amino)-4,7,8-trimethyl-7,8-dihydropteridin-6(5H)-one The compound was prepared by general procedure A via reaction of A-2 and B-54 to provide the title compound; Yield 32%; 1H NMR (300 MHz, CDCl$_3$) δ 7.84 (s, 1H), 7.45 (s, 1H), 7.25 (s, 1H), 6.76 (s, 1H), 5.21 (s, 2H), 4.33 (s, 2H), 3.99 (q, J=6.7 Hz, 1H), 2.98 (s, 3H), 2.24 (s, 3H), 2.13 (s, 3H), 1.32 (d, J=6.8 Hz, 3H); ESMS(M+1)=411.32.

Compound 129: (7S)-2-(((1-((6-isopropoxypyridin-3-yl)methyl)-1H-pyrazol-4-yl)methyl)amino)-4,5,7,8-tetramethyl-7,8-dihydropteridin-6(5H)-one Sodium hydride (12.48 mg, 0.5200 mmol) was added to a solution of (S)-2-(((1-((6-fluoropyridin-3-yl)methyl)-1H-pyrazol-4-yl)methyl)amino)-4,7,8-trimethyl-7,8-dihydropteridin-6(5H)-one (44 mg, 0.1040 mmol) in isopropanol (1.5 mL). The mixture was heated at 60° C. for 3 hours. The reaction was quenched with saturated NH4Cl solution and extracted with ethyl acetate (2×15 mL). The combined organic extracts was washed with brine, dried over MgSO4 and concentrated in vacuo to afford the crude product, which was purified by column chromatography (SiO$_2$) (eluting with a gradient of 0-6% methanol in dichloromethane to provide the desired product. Yield, 87.2%. $^1$H NMR (300 MHz, CDCl$_3$) δ 7.97 (dd, J=2.5, 0.8 Hz, 1H), 7.46-7.39 (m, 1H), 7.36 (dd, J=8.6, 2.6 Hz, 1H), 7.26 (d, J=0.8 Hz, 1H), 6.56 (dd, J=8.5, 0.7 Hz, 1H), 5.20 (dt, J=12.4, 6.1 Hz, 1H), 5.08 (s, 2H), 4.92 (t, J=5.7 Hz, 1H), 4.33 (d, J=5.7 Hz, 2H), 3.91 (q, J=6.9 Hz, 1H), 3.21 (s, 3H), 2.91 (s, 3H), 2.26 (s, 3H), 1.25 (d, J=6.2 Hz, 6H), 1.11 (d, J=6.9 Hz, 3H). ESMS(M+1)=451.35.

The following three compounds, Compound 135, 167, and 168, were prepared by the general procedure as reported for Compound 129.

Compound 135: (7S)-2-(((1-((6-isopropoxypyridin-3-yl)methyl)-1H-pyrazol-4-yl)methyl)amino)-4,7,8-trimethyl-7,8-dihydropteridin-6(5H)-one The compound was prepared by the procedure reported for Compound 129 via reaction of (7S)-2-(((1-((6-fluoropyridin-3-yl)methyl)-1H-pyrazol-4-yl)methyl)amino)-4,7,8-trimethyl-7,8-dihydropteridin-6(5H)-one and isopropanol to provide the title compound; Yield, 93%; 1H NMR (300 MHz, CDCl$_3$) δ 9.01 (s, 1H), 8.09-7.97 (m, 1H), 7.50 (d, J=0.8 Hz, 1H), 7.43 (dd, J=8.5, 2.6 Hz, 1H), 7.33 (d, J=0.8 Hz, 1H), 6.64 (dd, J=8.5, 0.7 Hz, 1H), 5.28 (p, J=6.2 Hz, 1H), 5.16 (s, 2H), 4.92 (t, J=5.7 Hz, 1H), 4.40 (d, J=5.7 Hz, 2H), 4.05 (q, J=6.9 Hz, 1H), 3.02 (s, 3H), 2.24 (s, 3H), 1.39 (d, J=6.9 Hz, 3H), 1.33 (d, J=6.2 Hz, 6H). ESMS(M+1)=437.25.

Compound 167: (7S)-2-(((1-((6-(tert-butoxy)-4-methylpyridin-3-yl)methyl)-1H-pyrazol-4-yl)methyl)amino)-4,7,8-trimethyl-7,8-dihydropteridin-6(5H)-one The compound was prepared by procedure reported for Compound 129 via reaction of t-butanol and (S)-2-(((1-((6-fluoro-4-methylpyridin-3-yl)methyl)-1H-pyrazol-4-yl)methyl)amino)-4,7,8-trimethyl-7,8-dihydropteridin-6(5H)-one to provide the title compound; Yield, 0.7%. 1H NMR (300 MHz, CDCl$_3$) δ 7.88 (s, 1H), 7.49 (d, J=0.8 Hz, 1H), 7.31-7.25 (m, 1H), 6.53-6.44 (m, 1H), 5.17 (s, 2H), 4.40 (d, J=5.6 Hz, 2H), 4.12 (q, J=6.9 Hz, 1H), 3.11 (s, 3H), 2.32 (s, 3H), 2.13 (d, J=0.8 Hz, 3H), 1.57 (s, 9H), 1.48 (d, J=6.9 Hz, 3H); ESMS(M+1)=465.44.

Compound 168: (7S)-2-(((1-((6-isopropoxy-4-methylpyridin-3-yl)methyl)-1H-pyrazol-4-yl)methyl)amino)-4,7,8-trimethyl-7,8-dihydropteridin-6(5H)-one The compound was prepared by procedure reported for Compound 129 via reaction of isopropanol and (7S)-2-(((1-((6-fluoro-4-methylpyridin-3-yl)methyl)-1H-pyrazol-4-yl)methyl)amino)-4,7,8-trimethyl-7,8-dihydropteridin-6(5H)-one (Compound 94) to provide the title compound. Yield, 1.4%. 1H NMR (300 MHz, CDCl$_3$) δ 8.92 (s, 1H), 7.88 (s, 1H), 7.46 (d, J=0.8 Hz, 1H), 7.32-7.22 (m, 1H), 6.54-6.42 (m, 1H), 5.26-5.18 (m, 1H), 5.16 (s, 2H), 4.38 (d, J=5.6 Hz, 2H), 4.12 (q, J=6.9 Hz, 1H), 3.12 (s, 3H), 2.32 (s, 3H), 2.13 (d, J=0.8 Hz, 3H), 1.49 (d, J=6.9 Hz, 3H), 1.30 (d, J=6.2 Hz, 5H). ESMS(M+1)=451.44.

Compound 10: (7S)-4,7,8-trimethyl-2-(((1-((6-(methylamino)pyridin-3-yl)methyl)-1H-pyrazol-4-yl)methyl)amino)-7,8-dihydropteridin-6(5H)-one (Method D)

To a solution of (7S)-2-[[1-[(6-fluoro-3-pyridyl)methyl]pyrazol-4-yl]methylamino]-4,7,8-trimethyl-5,7-dihydropteridin-6-one (100 mg, 0.2486 mmol) in MeOH (2 mL) was added methylamine (68.26 µL of 4.37 M, 0.2983 mmol), the mixture was heated in a sealed vessel over the weekend. LCMS indicted completion of the reaction. After removal of the solvent, the crude material was purified on reverse phase C18 chromatography (ACN/H2O 0-50% in 20 cv) to give desired product. Yield, 60%. 1H NMR (300 MHz, CDCl$_3$) δ 8.03-7.90 (m, 1H), 7.83 (q, J=8.2 Hz, 2H), 7.64 (q, J=6.3 Hz, 1H), 7.03 (h, J=7.3, 6.7 Hz, 1H), 5.38-5.18 (m, 2H), 4.53 (q, J=6.3 Hz, 2H), 4.31 (tt, J=6.8, 3.4 Hz, 1H), 3.03 (q, J=6.9 Hz, 3H), 2.30 (q, J=6.6 Hz, 3H), 1.61-1.40 (m, 3H). ESI-MS m/z calc. 407.44, found 408.35.

Compound 173: (7S)-4,7,8-trimethyl-2-(((1-((6-methylpyridin-3-yl)methyl)-1H-pyrazol-4-yl)methyl)amino)-7,8-dihydropteridin-6(5H)-one The compound was prepared by general procedure Method A via reaction of intermediates A-2 and B-55 to provide the title compound; Yield 82.5%. 1H NMR (300 MHz, DMSO-d6) δ 10.17 (s, 1H), 8.36 (s, 1H), 7.73 (s, 1H), 7.52 (dd, J=7.9, 2.4 Hz, 1H), 7.41 (s, 1H), 7.20 (d, J=8.0 Hz, 1H), 5.26 (s, 2H), 4.30 (d, J=5.8 Hz, 2H), 4.16 (q, J=6.9 Hz, 1H), 3.04 (s, 3H), 2.43 (s, 3H), 2.19 (s, 3H), 1.30 (d, J=6.8 Hz, 3H). ESMS(M+1)=393.31.

Compound 174 and compound 175: (7S)-4,7,8-Trimethyl-2-(((1-((S)-1-(6-(trifluoromethyl)pyridin-3-yl)ethyl)-1H-pyrazol-4-yl)methyl)amino)-7,8-dihydropteridin-6(5H)-one and (7S)-4,7,8-Trimethyl-2-(((1-((R)-1-(6-(trifluoromethyl)pyridin-3-yl)ethyl)-1H-pyrazol-4-yl)methyl)amino)-7,8-dihydropteridin-6(5H)-one The compounds were prepared by general procedure Method A via reaction of intermediates A-2 and B-150 to provide a mixture of diastereomers (Compound 172); 64% yield. The diastereomers were separated by SFC (IC Column, 10×250 mm; 40% ethanol(0.2% diethylamine)/60% CO2, Isocratic; 10 ml/min) to provide the diastereomer A and diastereomer B.

Diastereomer A: Chiral HPLC(Chiral PAK IC column, 4.6×250 mm; 50% hexane/30% ethanol/20% methanol/0.1% diethylamine): Rt=6.81 mins.; 99% ee. 1H NMR (300 MHz, DMSO-d6) δ 9.81 (s, 1H), 8.62 (s, 1H), 7.86 (d, J=1.5 Hz, 2H), 7.79 (d, J=0.8 Hz, 1H), 7.44 (d, J=0.8 Hz, 1H), 6.58 (brs, 1H), 5.77 (q, J=7.1 Hz, 1H), 4.23 (d, J=6.0 Hz, 2H), 4.00 (q, J=6.9 Hz, 1H), 2.94 (s, 3H), 2.13 (s, 3H), 1.82 (d, J=7.1 Hz, 3H), 1.19 (d, J=6.8 Hz, 3H). ESMS(M+1)=461.48.

Diastereomer B: Chiral HPLC(Chiral PAK IC column, 4.6×250 mm; 50% hexane/30% ethanol/20% methanol/0.1% diethylamine): Rt=7.17 mins.; 99% ee. 1H NMR (300 MHz, DMSO-d6) δ 9.87 (s, 1H), 8.62 (s, 1H), 7.86 (d, J=1.5 Hz, 2H), 7.80 (d, J=0.9 Hz, 1H), 7.45 (d, J=0.8 Hz, 1H), 6.68 (brs, 1H), 5.78 (q, J=7.1 Hz, 1H), 4.25 (d, J=5.9 Hz, 2H), 4.02 (q, J=6.8 Hz, 1H), 2.95 (s, 3H), 2.14 (s, 3H), 1.82 (d, J=7.1 Hz, 3H), 1.21 (d, J=6.8 Hz, 3H). ESMS(M+1)=461.48.

Compound 176: (7S)-5-((4-(((4,7,8-trimethyl-6-oxo-5,6,7,8-tetrahydropteridin-2-yl)amino)methyl)-1H-pyrazol-1-yl)methyl)picolinonitrile The compound was prepared by general procedure Method A via reaction of intermediates A-2 and B-56 to provide the title compound; 15% yield. 1H NMR (300 MHz, DMSO-d6) δ 9.79 (s, 1H), 8.59 (d, J=2.1 Hz, 1H), 8.00 (d, J=8.0 Hz, 1H), 7.83-7.70 (m, 2H), 7.42 (s, 1H), 6.56 (t, J=6.0 Hz, 1H), 5.44 (s, 2H), 4.22 (dd, J=6.2, 1.5 Hz, 2H), 3.99 (q, J=6.8 Hz, 1H), 2.93 (s, 3H), 2.13 (s, 3H), 1.18 (d, J=6.8 Hz, 3H). ESMS(M+1)=404.3.

Compound 178: (7S)-4,7,8-trimethyl-2-(((1-((2-methylpyridin-4-yl)methyl)-1H-pyrazol-4-yl)methyl)amino)-7,8-dihydropteridin-6(5H)-one The compound was prepared by general procedure Method A via reaction of intermediate A-2 and (1-((2-methylpyridin-4-yl)methyl)-1H-pyrazol-4-yl)methanamine hydrochloride to provide the title compound; 43% yield. 1H NMR (400 MHz, Methanol-d4) δ 8.62 (d, J=6.2 Hz, 1H), 7.89 (s, 1H), 7.66 (s, 1H), 7.58 (s, 1H), 7.49 (d, J=6.2 Hz, 1H), 5.65 (s, 2H), 4.57 (s, 2H), 4.30 (q, J=6.9 Hz, 1H), 3.27 (s, 3H), 2.75 (s, 3H), 2.31 (s, 3H), 1.53 (d, J=6.9 Hz, 3H); ESMS(M+1)=393.30.

Compound 180: (7S)-2-(((1-((2-fluoropyridin-4-yl)methyl)-1H-pyrazol-4-yl)methyl)amino)-4,7,8-trimethyl-7,8-dihydropteridin-6(5H)-one The compound was prepared by general procedure Method A via reaction of intermediates A-2 and B-58 to provide the title compound; 14% yield. 1H NMR (300 MHz, CDCl$_3$) δ 8.16 (d, J=5.2 Hz, 1H), 7.57 (d, J=9.3 Hz, 2H), 7.03-6.92 (m, 1H), 6.64 (s, 1H), 5.33 (s, 2H), 4.49 (s, 2H), 4.15 (q, J=6.9 Hz, 1H), 3.17 (s, 3H), 2.30 (s, 3H), 1.50 (d, J=6.9 Hz, 3H); ESMS(M+1)=397.26.

Compound 182: (7S)-4,7,8-trimethyl-2-(((1-((4-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-2 and B-59 to provide the title compound; 51% yield. 1H NMR (300 MHz, CDCl$_3$) δ 8.79-8.70 (m, 1H), 8.34-8.27 (m, 1H), 7.62-7.52 (m, 2H), 7.49 (s, 1H), 5.52 (s, 2H), 4.48 (d, J=5.8 Hz, 2H), 4.13 (q, J=6.9 Hz, 1H), 3.12 (s, 3H), 2.30 (s, 3H), 1.47 (d, J=6.9 Hz, 3H). ESMS(M+1)=447.18.

Compound 183: (7S))-4,7,8-trimethyl-2-(((1-((2-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-2 and B-60 to provide the title compound; 56% yield. 1H NMR (300 MHz, CDCl$_3$) δ 8.64 (d, J=4.2 Hz, 1H), 7.62-7.44 (m, 3H), 7.38 (d, J=7.7 Hz, 1H), 5.53 (s, 2H), 4.51 (d, J=5.7 Hz, 2H), 4.20 (q, J=6.9 Hz, 1H), 3.20 (s, 3H), 2.38 (s, 3H), 1.56 (d, J=6.9 Hz, 3H); ESMS(M+1)=447.15.

Compound 184: (7S)-4,7,8-trimethyl-2-(((1-((6-(trifluoromethyl)pyridin-2-yl)methyl)-1H-pyrazol-4-yl)methyl)amino)-7,8-dihydropteridin-6(5H)-one The compound was prepared by general procedure Method A via reaction of intermediates A-2 and B-61 to provide the title compound; 41% yield. 1H NMR (400 MHz, Methanol-d4) δ 7.95 (t, J=7.8 Hz, 1H), 7.75 (s, 1H), 7.70 (d, J=7.8 Hz, 1H), 7.54 (s, 1H), 7.20 (d, J=7.9 Hz, 1H), 5.48 (s, 2H), 4.43 (s, 2H), 4.09 (q, J=6.9 Hz, 1H), 3.08 (s, 3H), 2.19 (s, 3H), 1.35 (d, J=6.9 Hz, 3H); ESMS(M+1)=447.28.

Compound 187: (7S)-4,7,8-trimethyl-2-(((1-((3-(trifluoromethyl)pyridin-4-yl)methyl)-1H-pyrazol-4-yl)methyl)amino)-7,8-dihydropteridin-6(5H)-one The compound was prepared by general procedure Method A via reaction of intermediates A-2 and B-62 to provide the title compound; 48% yield. 1H NMR (400 MHz, Methanol-d4) δ 8.86 (s, 1H), 8.65 (d, J=5.3 Hz, 1H), 7.75 (s, 1H), 7.61 (s, 1H), 6.66 (d, J=5.3 Hz, 1H), 5.61 (s, 2H), 4.45 (s, 2H), 4.09 (q, J=6.8 Hz, 1H), 3.08 (s, 3H), 2.19 (s, 3H), 1.34 (d, J=6.9 Hz, 3H); ESMS(M+1)=447.32. Chiral HPLC (Chiralpak AD-H; 50% (1:1 MeOH-EtOH)/50% Heptane (0.2% diethylamine): 70% ee.

Compound 188: (S)-4,7,8-trimethyl-2-(((1-((2-methyl-6-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-2 and B-63 to provide the title compound; 17% yield. 1H NMR (300 MHz, CDCl₃) δ 9.47 (s, 1H), 7.55 (d, J=0.7 Hz, 1H), 7.45 (d, J=7.9 Hz, 1H), 7.39-7.32 (m, 1H), 7.22 (d, J=7.9 Hz, 1H), 5.31 (s, 2H), 5.11 (t, J=5.9 Hz, 1H), 4.57-4.29 (m, 2H), 4.03 (q, J=6.8 Hz, 1H), 3.01 (s, 3H), 2.57 (s, 3H), 2.24 (s, 3H), 1.37 (d, J=6.8 Hz, 3H). ESMS(M+1)=461.43. Chiral HPLC(Chiral PAK IC column, 4.6×250 mm; 50% hexane/30% ethanol/20% methanol/0.1% diethylamine): Rt=7.998 mins., (97% ee).

Compound 194: (7S)-2-(((1-((6-chloropyridin-3-yl)methyl)-1H-pyrazol-4-yl)methyl)amino)-4,7,8-trimethyl-7,8-dihydropteridin-6(5H)-one Step 1: Methyl N-(2-(((1-((6-chloropyridin-3-yl)methyl)-1H-pyrazol-4-yl)methyl)amino)-6-methyl-5-nitropyrimidin-4-yl)-N-methyl-L-alaninate A mixture of intermediates A-40 (Methyl N-(2-chloro-6-methyl-5-nitropyrimidin-4-yl)-N-methyl-L-alaninate; 400 mg, 1.39 mmol) and intermediate B-67 ((1-((6-Chloropyridin-3-yl)methyl)-1H-pyrazol-4-yl)methanamine hydrochloride; 482 mg, 1.45 mmol) were taken into N-methylpyrrolidin-2-one (5 ml) and triethylamine (1 ml, 7 mmol) and heated at 60° C. for 2 hours. The reaction was cooled to room temperature and poured onto ice resulting in a yellow precipitate. The precipitate was collected by vacuum filtration then purified by column chromatography (SiO₂) eluting with a gradient of 0-8% methanol in dichloromethane. The desired fractions were evaporated in vacuo to provide the title product, wt. 312 mg (46.8% yield). 1H NMR (300 MHz, CDCl₃) δ 8.32 (d, J=2.5 Hz, 1H), 7.59-7.45 (m, 2H), 7.38 (s, 1H), 7.32 (d, J=8.2 Hz, 1H), 5.49 (s, 1H), 5.27 (s, 2H), 4.92 (d, J=7.4 Hz, 1H), 4.40 (dt, J=14.2, 8.4 Hz, 2H), 3.65 (s, 3H), 2.87 (s, 3H), 2.42 (s, 3H), 1.53 (d, J=7.4 Hz, 3H); ESMS(M+1)=475.35.

Step 2: (7S)-2-(((1-((6-chloropyridin-3-yl)methyl)-1H-pyrazol-4-yl)methyl)amino)-4,7,8-trimethyl-7,8-dihydropteridin-6(5H)-one Platinum on carbon (30 mg) was added to a solution of methyl N-(2-(((1-((6-chloropyridin-3-yl)methyl)-1H-pyrazol-4-yl)methyl)amino)-6-methyl-5-nitropyrimidin-4-yl)-N-methyl-L-alaninate (150 mg, 0.31 mmol) in tetrahydrofuran (5 ml) and placed under hydrogen at 50 psi for 16 hours. The reaction was filtered through Celite and Florisil and rinsed well with dichloromethane. The solvent was evaporated in vacuo and the crude product purified column chromatography eluting with a gradient of 0-10% methanol in dichloromethane. The desired fractions were evaporated to provide the title product, 47 mg (35% yield). 1H NMR (300 MHz, CDCl₃) δ 9.21 (s, 1H), 8.27 (dd, J=2.5, 0.8 Hz, 1H), 7.52 (d, J=0.7 Hz, 1H), 7.50-7.43 (m, 1H), 7.38 (d, J=0.8 Hz, 1H), 7.31-7.24 (m, 1H), 5.24 (s, 2H), 5.00 (t, J=5.8 Hz, 1H), 4.41 (dd, J=5.8, 1.6 Hz, 2H), 4.05 (q, J=6.8 Hz, 1H), 3.02 (s, 3H), 2.24 (s, 3H), 1.38 (d, J=6.8 Hz, 3H). ESMS(M+1)=413.46. Chiral HPLC (ChiralPAK IC column; 20% methanol/30% ethanol/50% hexane): Rt 15.484 minutes; (95% ee).

Compound 195: (7S)-7,8-dimethyl-2-(((1-((6-(trifluoromethyl)pyridin-3-yl)methyl)-1H-pyrazol-4-yl)methyl)amino)-7,8-dihydropteridin-6(5H)-one The compound was prepared by general procedure Method B via reaction of intermediates A-1 and B-52 to provide the title compound; 15% yield. 1H NMR (400 MHz, Methanol-d4) δ 8.53 (s, 1H), 7.83-7.74 (m, 1H), 7.72 (s, 1H), 7.53 (s, 1H), 7.37 (s, 1H), 5.45 (s, 1H), 4.38 (s, 1H), 4.10 (q, J=6.9 Hz, 1H), 3.05 (s, 1H), 1.38 (d, J=6.9 Hz, 1H). ESMS(M+1)=433.28. Chiral HPLC(Chiral PAK IC column, 4.6×250 mm; 50% hexane/30% ethanol/20% methanol/0.1% diethylamine): Rt 16.928 mins. (97.8% ee).

Compound 196: (7S)-2-(((1-((6-(dimethylamino)pyridin-3-yl)methyl)-1H-pyrazol-4-yl)methyl)amino)-4,7,8-trimethyl-7,8-dihydropteridin-6(5H)-one (7S)-2-(((1-((6-fluoropyridin-3-yl)methyl)-1H-pyrazol-4-yl)methyl)amino)-4,7,8-trimethyl-7,8-dihydropteridin-6(5H)-one (200 mg, 0.4972 mmol) and N,N-dimethylamine (75.55 µL, 0.5966 mmol) were taken into methanol and heated at 70° C. in a sealed tube for 16 hours. The reaction evaporated in vacuo and the crude purified by column chromatography (SiO₂) eluting with gradient of 0-20% methanol in dichloromethane. The desired fractions were combined and evaporated to afford the title compound, wt. 144 mg (67% yield). 1H NMR (300 MHz, DMSO-d6) δ 10.05 (s, 1H), 8.04 (d, J=2.4 Hz, 1H), 7.61 (s, 1H), 7.42 (dd, J=8.7, 2.5 Hz, 1H), 7.35 (s, 1H), 7.05 (brs, 1H), 6.58 (d, J=8.8 Hz, 1H), 5.09 (s, 2H), 4.24 (d, J=5.9 Hz, 2H), 4.09 (q, J=6.9 Hz, 1H), 2.98 (s, 9H), 2.16 (s, 3H), 1.25 (d, J=6.9 Hz, 3H). ESMS(M+1)=422.4.

Compound 197: (7S)-2-(((1-((6-methoxypyridin-3-yl)methyl)-1H-pyrazol-4-yl)methyl)amino)-4,7,8-trimethyl-7,8-dihydropteridin-6(5H)-one The compound was prepared by general procedure Method A via reaction of intermediates A-2 and B-64 to provide the title compound; 40% yield. 1H NMR (300 MHz, CDCl$_3$) δ 8.46 (s, 1H), 8.09 (dd, J=2.5, 0.8 Hz, 1H), 7.51 (d, J=0.8 Hz, 1H), 7.47 (dd, J=8.6, 2.5 Hz, 1H), 7.34 (d, J=0.8 Hz, 1H), 6.73 (dd, J=8.6, 0.7 Hz, 1H), 5.19 (s, 2H), 4.98 (s, 1H), 4.41 (d, J=5.7 Hz, 2H), 3.94 (s, 3H), 3.04 (s, 3H), 2.23 (s, 3H), 1.40 (d, J=6.8 Hz, 3H). ESMS(M+1)=409.34.

Compound 198: (7S)-4,7,8-trimethyl-2-(((1-(pyridin-3-ylmethyl)-1H-pyrazol-4-yl)methyl)amino)-7,8-dihydropteridin-6(5H)-one Methyl N-(2-(((1-((6-chloropyridin-3-yl)methyl)-1H-pyrazol-4-yl)methyl)amino)-6-methyl-5-nitropyrimidin-4-yl)-N-methyl-L-alaninate (See compound 194, step 1; 75 mg, 0.13 mmol) and 10% palladium/carbon (13 mg) was taken in methanol (5 ml) and hydrogenated under hydrogen at 50 psi for 16 hours. The reaction was filtered through Celite and the filtrate evaporated in vacuo. The crude product was purified by reverse phase chromatography (C18) to provide the title product, wt 16 mg (33% yield). 1H NMR (300 MHz, Methanol-d4) δ 8.81-8.67 (m, 1H), 8.65 (s, 1H), 8.30 (d, J=8.2 Hz, 1H), 7.94 (t, J=7.1 Hz, 1H), 7.80 (s, 1H), 7.61-7.44 (m, 1H), 5.49 (d, J=4.3 Hz, 2H), 4.45 (s, 2H), 4.30-4.09 (m, 1H), 3.20-3.05 (m, 3H), 2.30-2.04 (m, 3H), 1.54-1.32 (m, 3H); ESMS(M+1)=379.39.

Compound 199: (7S)-4,7,8-trimethyl-2-(((1-((5-methyl-6-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-2 and B-66 to provide the title compound; 69% yield. 1H NMR (300 MHz, DMSO-d6) δ 9.83 (s, 1H), 8.46-8.36 (m, 1H), 7.74 (s, 1H), 7.73-7.68 (m, 1H), 7.41 (d, J=0.8 Hz, 1H), 6.61 (t, J=6.0 Hz, 1H), 5.39 (s, 2H), 4.22 (dd, J=6.1, 1.9 Hz, 2H), 4.01 (dd, J=11.0, 7.0 Hz, 1H), 2.93 (s, 3H), 2.41 (d, J=2.2 Hz, 3H), 2.13 (s, 3H), 1.18 (d, J=6.8 Hz, 3H). ESMS(M+1)=461.39.

Compound 185: (7S)-2-(((1-((2-chloropyridin-4-yl)methyl)-1H-pyrazol-4-yl)methyl)amino)-4,7,8-trimethyl-7,8-dihydropteridin-6(5H)-one The compound was prepared by general method B via reaction of intermediate A-2 and [1-[(2-chloro-4-pyridyl)methyl]pyrazol-4-yl]methanamine hydrochloride to provide the title compound; 58% yield. 1H NMR (400 MHz, Methanol-d4) δ 8.30 (d, J=5.1 Hz, 1H), 7.78 (d, J=8.4 Hz, 1H), 7.60 (d, J=7.4 Hz, 1H), 7.13 (d, J=5.2 Hz, 1H), 7.11 (s, 1H), 5.40 (s, 2H), 4.54 (s, 2H), 4.29 (t, J=6.9 Hz, 1H), 3.25 (d, J=3.6 Hz, 3H), 2.29 (s, 3H), 1.51 (dd, J=14.4, 7.2 Hz, 3H). ESMS(M+1)=413.25.

Compound 200: (7S)-4,7,8-trimethyl-2-(((1-((5-(trifluoromethyl)pyridin-2-yl)methyl)-1H-pyrazol-4-yl)methyl)amino)-7,8-dihydropteridin-6(5H)-one The compound was prepared by general procedure Method A via reaction of intermediates A-2 and B-68 to provide the title compound; 27% yield. 1H NMR (400 MHz, Methanol-d4) δ 8.82 (s, 1H), 8.05 (dd, J=8.3, 2.1 Hz, 1H), 7.74 (s, 1H), 7.54 (s, 1H), 7.15 (d, J=8.2 Hz, 1H), 5.50 (s, 2H), 4.42 (s, 2H), 4.07 (q, J=6.8 Hz, 1H), 3.06 (s, 3H), 2.18 (s, 3H), 1.32 (d, J=6.8 Hz, 3H). ESMS(M+1)=447.28.

Compound 201: (7S)-4,7,8-trimethyl-2-(((1-((4-(trifluoromethyl)pyridin-2-yl)methyl)-1H-pyrazol-4-yl)methyl)amino)-7,8-dihydropteridin-6(5H)-one The compound was prepared by general procedure Method A via reaction of intermediates A-2 and B-69 to provide the title compound; 11% yield. 1H NMR (400 MHz, Methanol-d4) δ 8.76 (d, J=5.1 Hz, 1H), 7.84 (s, 1H), 7.64-7.55 (m, 2H), 7.32 (s, 1H), 5.52 (s, 2H), 4.54 (s, 2H), 4.30 (q, J=6.9 Hz, 1H), 3.25 (s, 2H), 2.28 (s, 2H), 1.52 (d, J=6.9 Hz, 2H). ESMS(M+1)=447.28.

Compound 12: (7S)-2-(((1-((2-(dimethylamino)pyridin-4-yl)methyl)-1H-pyrazol-4-yl)methyl)amino)-4,7,8-trimethyl-7,8-dihydropteridin-6(5H)-one The compound was prepared by general method B via reaction of A-2 and 4-((4-(aminomethyl)-1H-pyrazol-1-yl)methyl)-N,N-dimethylpyridin-2-amine dihydrochloride to provide the title compound; 46% yield. 1H NMR (400 MHz, Methanol-d4) δ 7.85 (d, J=6.0 Hz, 1H), 7.83 (d, J=6.7 Hz, 1H), 7.63 (s, 1H), 6.92 (s, 1H), 6.61 (dd, J=6.7, 1.4 Hz, 1H), 5.45 (s, 2H), 4.55 (s, 2H), 4.30 (q, J=6.9 Hz, 1H), 3.26 (d, J=6.3 Hz, 3H), 3.25 (s, 6H), 2.30 (s, 3H), 1.53 (d, J=6.9 Hz, 3H). ESMS(M+1)=422.39.

Compound 202: (7S)-2-(((1-((2-hydroxypyridin-4-yl)methyl)-1H-pyrazol-4-yl)methyl)amino)-4,7,8-trimethyl-7,8-dihydropteridin-6(5H)-one The compound was prepared by general method by via reaction of intermediates A-2 and (1-((2-methoxy-4-pyridyl)methyl)-1H-pyrazol-4-yl)methanamine hydrochloride. Under the conditions of the reaction, the methoxy group was lost to provide the title compound; 52% yield. 1H NMR (400 MHz, Methanol-d4) δ 7.79 (s, 1H), 7.59 (d, J=7.2 Hz, 1H), 7.42 (d, J=6.8 Hz, 1H), 6.26 (dd, J=6.8, 1.4 Hz, 1H), 6.07 (s, 1H), 5.25 (d, J=10.6 Hz, 2H), 4.53 (s, 2H), 4.30 (p, J=7.0 Hz, 1H), 3.26-3.22 (m, 3H), 2.29 (s, 3H), 1.58-1.49 (m, 3H); ESMS(M+1)=395.35.

Compound 203: (7S)-2-(((1-((2-methoxypyridin-4-yl)methyl)-1H-pyrazol-4-yl)methyl)amino)-4,7,8-trimethyl-7,8-dihydropteridin-6(5H)-one The compound was prepared by general method A via reaction of A-2 and (1-((2-methoxypyridin-4-yl)methyl)-1H-pyrazol-4-yl)methanamine hydrochloride to provide the title compound; 21% yield. 1H NMR (400 MHz, CDCl$_3$) δ 8.55 (s, 1H), 8.02 (d, J=5.3 Hz, 1H), 7.46 (s, 1H), 7.31 (s, 1H), 6.55 (d, J=5.3 Hz, 1H), 6.36 (s, 1H), 5.14 (s, 2H), 4.83 (t, J=5.4 Hz, 1H), 4.34 (t, J=7.6 Hz, 2H), 3.98 (q, J=6.9 Hz, 1H), 3.83 (s, 3H), 2.96 (s, 3H), 2.16 (s, 3H), 1.31 (t, J=7.1 Hz, 3H). ESMS(M+1)=409.28.

Compound 204: (7S)-4-((4-(((4,7,8-trimethyl-6-oxo-5,6,7,8-tetrahydropteridin-2-yl)amino)methyl)-1H-pyrazol-1-yl)methyl)picolinonitrile The compound was prepared by general method B via reaction of A-2 and 4-((4-(aminomethyl)-1H-pyrazol-1-yl)methyl)picolinonitrile hydrochloride to provide the title compound; 34% yield. 1H NMR (400 MHz, Methanol-d4) δ 8.63 (d, J=5.1 Hz, 1H), 7.82 (s, 1H), 7.62 (s, 1H), 7.48 (s, 1H), 7.40 (d, J=4.8 Hz, 1H), 5.46 (s, 2H), 4.56 (d, J=15.7 Hz, 2H), 4.30 (q, J=6.9 Hz, 1H), 3.25 (s, 3H), 2.29 (s, 3H), 1.53 (d, J=6.9 Hz, 3H). ESMS(M+1)=404.17.

Compound 206: (7S)-4,7,8-trimethyl-2-(((1-((5-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-2 and B-70 to provide the title compound; 21% yield. 1H NMR (300 MHz, CDCl$_3$) δ 8.85 (s, 1H), 8.69 (d, J=2.0 Hz, 1H), 7.85 (s, 1H), 7.76 (t, J=2.2 Hz, 1H), 7.63-7.50 (m, 1H), 7.45 (d, J=0.8 Hz, 1H), 5.37 (s, 2H), 5.03 (s, 1H), 4.45 (dd, J=5.8, 1.8 Hz, 2H), 4.09 (q, J=6.9 Hz, 1H), 3.06 (s, 4H), 2.23 (s, 3H), 1.42 (d, J=6.8 Hz, 3H). ESMS(M+1)=447.43.

Compound 207: (7S)-4,7,8-trimethyl-2-(((1-((2-(trifluoromethyl)pyridin-4-yl)methyl)-1H-pyrazol-4-yl)methyl)amino)-7,8-dihydropteridin-6(5H)-one The compound was prepared by general procedure Method B via reaction of intermediates A-2 and B-71 to provide the title compound; 49% yield. 1H NMR (400 MHz, Methanol-d4) δ 8.62 (d, J=5.0 Hz, 1H), 7.75 (s, 1H), 7.58 (s, 1H), 7.50 (s, 1H), 7.33 (d, J=4.9 Hz, 1H), 5.47 (s, 2H), 4.44 (s, 2H), 4.09 (q, J=6.9 Hz, 1H), 3.07 (s, 3H), 2.19 (s, 3H), 1.34 (d, J=6.9 Hz, 3H). ESMS=447.28. Chiral HPLC (Chiralpak AD-H; 50% (Methanol:ethanol/50% Heptane): 99.3% ee.

Compound 210: (7S)-2-(((1-((4-methoxy-6-(trifluoromethyl)pyridin-3-yl)methyl)-1H-pyrazol-4-yl)methyl)amino)-4,7,8-trimethyl-7,8-dihydropteridin-6(5H)-one The compound was prepared by general procedure Method A via reaction of intermediates A-2 and B-72 to provide the title compound; 22% yield. 1H NMR (300 MHz, Methanol-d4) δ 8.08 (s, 1H), 7.67 (s, 1H), 7.47 (d, J=15.8 Hz, 2H), 5.49 (s, 1H), 5.36 (s, 2H), 4.39 (s, 2H), 4.00 (s, 3H), 3.05 (s, 3H), 2.18 (s, 3H), 1.32 (d, J=6.6 Hz, 3H). ESMS (M+1)=477.42. Chiral HPLC (Chiralpak IC, 4.6×250 mm; 50% hexane/30% ethanol/20% methanol/0.1% diethylamine). Rt=8.40 mins.; 97.5% ee.

Compound 211: (7S)-2-(((1-((6-(tert-butyl)pyridin-3-yl)methyl)-1H-pyrazol-4-yl)methyl)amino)-4,7,8-trimethyl-7,8-dihydropteridin-6(5H)-one The compound was prepared by general procedure Method A via reaction of intermediates A-2 and B-73 to provide the title compound; 89% yield. 1H NMR (300 MHz, DMSO-d6) δ 9.82 (s, 1H), 8.40 (d, J=2.3 Hz, 1H), 7.77-7.65 (s, 1H), 7.54 (dd, J=8.2, 2.4 Hz, 1H), 7.37 (td, J=4.1, 3.6, 0.9 Hz, 2H), 6.58 (t, J=6.0 Hz, 1H), 5.25 (s, 2H), 4.21 (s, 1H), 3.99 (q, J=6.8 Hz, 1H), 2.93 (s, 3H), 2.12 (s, 3H), 1.27 (s, 9H), 1.18 (d, J=6.8 Hz, 3H). ESMS(M+1)=435.45. Chiral HPLC (Chiralpak IC, 4.6×250 mm; 50% hexane/30% ethanol/20% methanol/0.1% diethylamine). Rt=8.59 mins.; 97.9% ee.

Compound 209: (7S)-2-(((1-((5-fluoro-6-(trifluoromethyl)pyridin-3-yl)methyl)-1H-pyrazol-4-yl)methyl)amino)-4,7,8-trimethyl-7,8-dihydropteridin-6(5H)-one The compound was prepared by general procedure Method A via reaction of intermediates A-2 and B-74 to provide the title compound; 29% yield. 1H NMR (300 MHz, CDCl$_3$) δ 9.14 (s, 1H), 8.28 (s, 1H), 7.49 (s, 1H), 7.31-7.04 (m, 1H), 5.26 (d, J=21.4 Hz, 2H), 4.95 (t, J=5.8 Hz, 1H), 4.36 (dd, J=5.6, 2.3 Hz, 2H), 3.98 (q, J=6.8 Hz, 1H), 2.95 (s, 3H), 2.17 (s, 3H), 1.31 (d, J=6.8 Hz, 3H); ESMS(M+1) =465.35. Chiral HPLC (Chiralpak IC, 4.6×250 mm; 50% hexane/30% ethanol/20% methanol/0.1% diethylamine). Rt=5.59 mins.; 95% ee.

Compound 218: (7S)-2-(((1-((2-methoxy-6-(trifluoromethyl)pyridin-3-yl)methyl)-1H-pyrazol-4-yl)methyl)amino)-4,7,8-trimethyl-7,8-dihydropteridin-6(5H)-one The compound was prepared by general procedure Method A via reaction of intermediates A-2 and B-75 to provide the title compound; 18% yield. 1H NMR (300 MHz, Methanol-d4) δ 7.70 (s, 1H), 7.55 (s, 1H), 7.33 (s, 2H), 5.35 (s, 2H), 4.43 (s, 2H), 4.24-3.90 (m, 4H), 3.08 (s, 3H), 2.21 (s, 3H), 1.35 (d, J=6.6 Hz, 3H). ESMS(M+1)=477.33. Chiral HPLC (Chiralpak IC, 4.6×250 mm; 50% hexane/30% ethanol/20% methanol/0.1% diethylamine). Rt=5.59 mins.; 95.9% ee.

Compound 215: (7S)-2-(((1-((6-methoxy-5-(trifluoromethyl)pyridin-3-yl)methyl)-1H-pyrazol-4-yl)methyl)amino)-4,7,8-trimethyl-7,8-dihydropteridin-6(5H)-one The compound was prepared by general procedure Method A via reaction of intermediates A-2 and B-76 to provide the title compound; 78% yield. 1H NMR (300 MHz, CDCl$_3$) δ 8.28-8.18 (m, 1H), 7.81-7.73 (m, 1H), 7.69 (s, 1H), 7.54 (d, J=0.7 Hz, 1H), 7.39 (d, J=0.8 Hz, 1H), 5.24 (s, 2H), 4.89 (s, 1H), 4.48-4.35 (m, 2H), 4.10 (t, J=6.9 Hz, 1H), 4.05 (s, 3H), 3.05 (s, 3H), 2.22 (s, 3H), 1.41 (d, J=6.9 Hz, 3H). ESMS(M+1)=477.37.

Compound 213: (7S)-2-(((1-((5-methoxy-6-(trifluoromethyl)pyridin-3-yl)methyl)-1H-pyrazol-4-yl)methyl)amino)-4,7,8-trimethyl-7,8-dihydropteridin-6(5H)-one The compound was prepared by general procedure Method A via reaction of intermediates A-2 and B-77 to provide the title compound; 44% yield. 1H NMR (300 MHz, Methanol-d4) δ 8.12-7.97 (m, 1H), 7.80 (d, J=2.6 Hz, 1H), 7.62 (d, J=2.6 Hz, 1H), 7.55 (s, 1H), 5.60-5.33 (m, 2H), 4.58-4.31 (m, 2H), 4.15 (tdd, J=6.8, 6.3, 5.6, 2.2 Hz, 1H), 4.06-3.77 (m, 3H), 3.12 (dt, J=3.6, 1.7 Hz, 3H), 2.26 (dd, J=2.5, 1.1 Hz, 3H), 1.51-1.19 (m, 3H); ESMS(M+1)= 477.28. Chiral HPLC (Chiralpak IC, 4.6×250 mm; 50% hexane/30% ethanol/20% methanol/0.1% diethylamine). Rt=5.59 mins.; 92% ee.

Compound 208: (7S)-2-(((1-((5-fluoropyridin-3-yl)methyl)-1H-pyrazol-4-yl)methyl)amino)-4,7,8-trimethyl-7,8-dihydropteridin-6(5H)-one The compound was prepared by general procedure Method B via reaction of intermediates A-2 and B-78 to provide the title compound; 12% yield. 1H NMR (300 MHz, CDCl$_3$) δ 8.35 (d, J=2.7 Hz, 1H), 8.26 (d, J=1.7 Hz, 1H), 7.48 (d, J=0.7 Hz, 1H), 7.33 (d, J=0.8 Hz, 1H), 7.13 (ddt, J=8.9, 2.6, 1.2 Hz, 1H), 5.23 (d, J=0.9 Hz, 3H), 4.84 (t, J=5.8

Hz, 1H), 4.41-4.29 (m, 2H), 3.99 (q, J=6.8 Hz, 1H), 2.96 (s, 3H), 2.15 (s, 3H), 1.32 (d, J=6.9 Hz, 3H); ESMS(M+1)= 397.32.

Compound 205: (7S)-2-(((1-((6-fluoro-4-methylpyridin-3-yl)methyl)-1H-pyrazol-4-yl)methyl) amino)-4,5,7,8-tetramethyl-7,8-dihydropteridin-6 (5H)-one The compound was prepared by general procedure Method B via reaction of intermediates A-3 and B-79 to provide the title compound; 16% yield. 1H NMR (300 MHz, CDCl$_3$) δ 7.96 (s, 1H), 7.53 (d, J=0.7 Hz, 1H), 7.28 (d, J=1.7 Hz, 2H), 6.79 (dt, J=2.3, 0.7 Hz, 1H), 5.27 (s, 2H), 4.90 (t, J=5.8 Hz, 1H), 4.01 (q, J=6.9 Hz, 1H), 3.30 (s, 3H), 3.00 (s, 3H), 2.35 (s, 3H), 2.30 (d, J=0.8 Hz, 3H), 1.92 (s, 1H), 1.20 (d, J=6.9 Hz, 3H); ESMS(M+1)=425.41. Chiral HPLC (Chiralpak IC, 4.6×250 mm; 50% hexane/30% ethanol/20% methanol/0.1% diethylamine). Rt=5.59 mins.; 80% ee.

Compound 385: (7S)-8-isopropyl-4,7-dimethyl-2-(((1-((6-(trifluoromethyl)pyridin-3-yl)methyl)-1H-pyrazol-4-yl)methyl)amino)-7,8-dihydropteridin-6 (5H)-one The compound was prepared by general procedure Method A via reaction of intermediates A-4 and B-52 to provide the title compound; 69% yield. 1H NMR (300 MHz, DMSO-d6) δ 13.06 (s, 1H), 10.49 (s, 1H), 8.64 (s, 1H), 7.99 (s, 1H), 7.94-7.77 (m, 3H), 7.49 (s, 1H), 5.49 (s, 2H), 4.61-4.38 (m, 3H), 4.31 (q, J=6.8 Hz, 1H), 2.29 (s, 3H), 1.46-1.15 (m, 9H); ESMS(M+1)=475.24. Chiral HPLC (Chiralpak IC, 4.6×250 mm; 50% hexane/30% ethanol/20% methanol/0.1% diethylamine). Rt=6.045 mins.; 95.7% ee.

Compound 220: (7S)-4,8-dimethyl-7-propyl-2-(((1-((6-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-7 and B-52 to provide the title product as a mixture of enantiomers that were separated by SFC (Column AD-H, 10×250 mm; 30% Ethanol(0.2% diethylamine)/70% CO2, isocratic) to provide the title product (Peak A: Rt=0.739 mins.; 99.6% ee). 1H NMR (300 MHz, DMSO-d6) δ 9.87 (s, 1H), 8.71-8.54 (m, 1H), 7.87 (td, J=8.1, 1.5 Hz, 2H), 7.76 (s, 1H), 7.42 (s, 1H), 6.59 (t, J=5.9 Hz, 1H), 5.45 (s, 2H), 4.22 (d, J=6.0 Hz, 2H), 4.00 (dd, J=6.8, 4.0 Hz, 1H), 2.96 (s, 3H), 2.11 (s, 3H), 1.81-1.48 (m, 2H), 1.29-1.10 (m, 2H), 0.83 (t, J=7.3 Hz, 3H). ESMS(M+1)=475.3.

Compound 383: (7S)-7-isopropyl-4,8-dimethyl-2-(((1-((6-(trifluoromethyl)pyridin-3-yl)methyl)-1H-pyrazol-4-yl)methyl)amino)-7,8-dihydropteridin-6 (5H)-one The compound was prepared by general procedure Method A via reaction of intermediates A-9 and B-52 to provide the title compound; 66% yield. 1H NMR (300 MHz, CDCl$_3$) δ 8.60 (s, 1H), 8.54 (bs, 1H), 7.57 (s, 1H), 7.50 (s, 1H), 5.38 (s, 2H), 4.49 (d, J=5.6 Hz, 2H), 3.95 (d, J=4.2 Hz, 1H), 3.17 (s, 3H), 2.28 (s, 4H), 1.10 (d, J=7.0 Hz, 3H), 0.93 (d, J=7.0 Hz, 3H). ESMS(M+1)=475.25. Chiral HPLC (Chiralpak IC, 4.6×250 mm; 50% hexane/30% ethanol/20% methanol/0.1% diethylamine). Rt=6.125 mins.; (95% ee).

Compound 384: (7S)-2-(((1-((6-fluoropyridin-3-yl) methyl)-1H-pyrazol-4-yl)methyl)amino)-7-isopropyl-4,8-dimethyl-7,8-dihydropteridin-6(5H)-one The compound was prepared by general procedure Method A via reaction of intermediates A-9 and B-53 to provide the title compound; 16% yield. 1H NMR (300 MHz, Methanol-d4) δ 8.14-8.04 (m, 1H), 7.92-7.77 (m, 2H), 7.62 (d, J=0.7 Hz, 1H), 7.09-6.99 (m, 1H), 5.38 (s, 2H), 4.52 (s, 2H), 4.14 (d, J=3.8 Hz, 1H), 3.24 (s, 3H), 2.36-2.29 (m, 2H), 2.27 (s, 3H), 1.09 (d, J=7.0 Hz, 3H), 0.85 (d, J=6.9 Hz, 3H). ESMS(M+1)=425.32. Chiral HPLC (Chiralpak IC, 4.6×250 mm; 50% hexane/30% ethanol/20% methanol/0.1% diethylamine). Rt=9.887 mins. (98.4% ee); [α]$_D$=89.1° (c=1, methanol).

Compound 400: (7S)-4,7-dimethyl-8-(methyl-d3)-2-(((1-((6-(trifluoromethyl)pyridin-3-yl)methyl)-1H-pyrazol-4-yl)methyl)amino)-7,8-dihydropteridin-6 (5H)-one The compound was prepared by general procedure Method A via reaction of intermediates A-38 and B-52 to provide the title compound; 84% yield. 1H NMR (300 MHz, CDCl$_3$) δ 8.83 (s, 1H), 8.51 (d, J=1.7 Hz, 1H), 7.68-7.53 (m, 2H), 7.53-7.41 (m, 1H), 7.42-7.29 (m, 1H), 5.29 (s, 2H), 4.44-4.24 (m, 2H), 3.99 (q, J=6.9 Hz, 1H), 2.17 (s, 3H), 1.32 (d, J=6.9 Hz, 3H). ESMS(M+1)=450.26. Chiral HPLC (Chiralpak IC, 4.6×250 mm; 20% methanol/30% ethanol/50% hexane(0.1% diethylamine); Rt 7.88 mins. (97% ee).

Compound 386: (7S)-7-Cyclopropyl-4,8-dimethyl-2-(((1-((6-(trifluoromethyl)pyridin-3-yl)methyl)-1H-pyrazol-4-yl)methyl)amino)-7,8-dihydropteridin-6 (5H)-one The compound was prepared by general procedure method A via reaction of A6 and B-52 to provide the title compound; 46% yield. 1H NMR (300 MHz, DMSO-d6) δ 9.86 (s, 1H), 8.63 (d, J=1.3 Hz, 1H), 7.87 (td, J=7.8, 1.5 Hz, 2H), 7.77 (s, 1H), 7.44 (d, J=0.7 Hz, 1H), 6.64 (t, J=6.0 Hz, 1H), 5.45 (s, 2H), 4.24 (dd, J=6.0, 3.1 Hz, 2H), 3.31 (d, J=8.9 Hz, 1H), 3.02 (s, 3H), 2.14 (s, 3H), 0.95-0.72 (m, 1H), 0.60-0.26 (m, 4H); ESMS(M+1)=473.32.

Compound 387: (7S)-4,7,8-Trimethyl-2-(((1-((2-(prop-1-en-2-yl)-6-(trifluoromethyl)pyridin-3-yl) methyl)-1H-pyrazol-4-yl)methyl)amino)-7,8-dihydropteridin-6(5H)-one The compound was prepared by general procedure method A via reaction of A-2 and B-81 to provide the title compound; 71% yield. 1H NMR (300 MHz, DMSO-d6) δ 9.80 (s, 1H), 7.74 (d, J=8.1 Hz, 1H), 7.68 (d, J=0.8 Hz, 1H), 7.49 (d, J=8.1 Hz, 1H), 7.43 (d, J=0.8 Hz, 1H), 6.56 (t, J=6.1 Hz, 1H), 5.48 (d, J=7.6 Hz, 2H), 5.46 (s, 1H), 5.16 (s, 1H), 4.24 (dd, J=6.0, 2.4 Hz, 2H), 3.99 (q, J=6.8 Hz, 1H), 2.94 (s, 3H), 2.13 (s, 3H), 2.05 (t, J=1.2 Hz, 3H), 1.19 (d, J=6.8 Hz, 3H). ESMS(M+1)=487.23.

Compound 388: (7S)-2-(((1-((2-isopropyl-6-(trifluoromethyl)pyridin-3-yl)methyl)-1H-pyrazol-4-yl) methyl)amino)-4,7,8-trimethyl-7,8-dihydropteridin-6 (5H)-one To a solution (7S)-4,7,8-trimethyl-2-(((1-((2-(prop-1-en-2-yl)-6-(trifluoromethyl)pyridin-3-yl)methyl)-1H-pyrazol- 4-yl)methyl)amino)-7,8-dihydropteridin-6(5H)-one (220 mg, 0.44 mmol) in 20 ml of methanol was added 10% Pd/C (100 mg). The reaction was placed under an atmosphere of hydrogen (1 atm) and stirred at room temperature for 18 hours. The reaction was filtered through Celite and the filtrate evaporated in vacuo. The crude product was purified by column chromatography eluting with a gradient of 0-20% methanol in dichloromethane. The desired fractions were evaporated to afford the product, wt. 204 mg (90% yield). 1H NMR (300 MHz, DMSO-d6) δ 9.80 (s, 1H), 7.69 (d, J=0.8 Hz, 1H), 7.65 (s, 1H), 7.49 (d, J=8.0 Hz, 1H), 7.42 (d, J=0.8 Hz, 1H), 6.56 (t, J=6.1 Hz, 1H), 5.49 (s, 2H), 4.23 (dd, J=6.1, 2.6 Hz, 2H), 3.99 (q, J=6.8 Hz, 1H), 3.40 (h, J=6.7 Hz, 1H), 2.92 (s, 3H), 2.12 (s, 3H), 1.18 (d, J=6.8 Hz, 3H), 1.11 (d, J=6.6 Hz, 6H). ESMS(M+1)=489.25.

Compound 238: 4,7,7,8-Tetramethyl-2-(((1-((6-(trifluoromethyl)pyridin-3-yl)methyl)-1H-pyrazol-4-yl)methyl)amino)-7,8-dihydropteridin-6(5H)-one The compound was prepared by general procedure Method B via reaction of intermediates A-11 and B-52 to provide the title compound; 12.6% yield. 1H NMR (300 MHz, CDCl$_3$) δ 8.60 (s, 1H), 7.68 (t, J=1.5 Hz, 2H), 7.60-7.53 (m, 2H), 7.46 (s, 1H), 5.38 (s, 2H), 4.46 (d, J=5.8 Hz, 2H), 3.09 (s, 3H), 2.25 (s, 3H), 1.54 (s, 6H); ESMS(M+1)=461.32.

Compound 237: 5,7,7,8-Tetramethyl-2-(((1-((2-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-14 and B-61 to provide the title compound; 25% yield. 1H NMR (300 MHz, CDCl$_3$) δ 8.79-8.71 (m, 1H), 8.31 (d, J=1.0 Hz, 1H), 7.63-7.48 (m, 3H), 7.37 (s, 1H), 5.52 (s, 2H), 4.50 (d, J=5.8 Hz, 2H), 3.28 (s, 3H), 3.16 (s, 3H), 1.60 (s, 6H). ESMS(M+1)=461.18.

Compound 236: 5,7,7,8-Tetramethyl-2-(((1-((4-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-14 and B-59 to provide the title compound; 35% yield. 1H NMR (300 MHz, CDCl$_3$) δ 8.64 (d, J=4.3 Hz, 1H), 7.62-7.44 (m, 3H), 7.38 (d, J=7.8 Hz, 1H), 7.23 (s, 1H), 5.54 (s, 2H), 4.53 (d, J=5.7 Hz, 2H), 3.25 (d, J=12.2 Hz, 6H), 1.66 (d, J=0.9 Hz, 6H). ESMS(M+1)=461.18.

Compound 186: (7S)-7-ethyl-4,8-dimethyl-2-(((1-((6-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-8 and B-52 to provide the title compound; 80% yield. 1H NMR (300 MHz, DMSO-d6) δ 9.87 (s, 1H), 8.63 (s, 1H), 7.85 (q, J=8.1 Hz, 2H), 7.75 (s, 1H), 7.42 (s, 1H), 6.55 (t, J=6.2 Hz, 1H), 5.45 (s, 2H), 4.22 (d, J=6.0 Hz, 2H), 3.99 (dd, J=6.4, 3.6 Hz, 1H), 2.96 (s, 3H), 2.11 (s, 3H), 1.72 (m, 2H), 0.74 (t, J=7.4 Hz, 3H). ESMS(M+1)=461.48. Chiral HPLC (Chiralpak IC, 4.6×250 mm; 50% hexane/30% ethanol/20% methanol/0.1% diethylamine). Rt=7.095 mins.; 95.1% ee.

Compound 392: (7S)-2-(((1-(4-fluorobenzyl)-1H-pyrazol-4-yl)methyl)amino)-4,5,7,8-tetramethyl-7,8-dihydropteridin-6(5H)-one 1H NMR (300 MHz, Methanol-d4) δ 7.60 (s, 1H), 7.48 (s, 1H), 7.22 (dd, J=8.5, 5.4 Hz, 2H), 7.03 (t, J=8.8 Hz, 2H), 5.25 (s, 2H), 4.39 (s, 2H), 4.03 (q, J=6.9 Hz, 1H), 3.27 (s, 3H), 3.00 (s, 3H), 2.32 (s, 3H), 1.15 (d, J=6.9 Hz, 3H); F19 NMR δ 118.04 ppm; ESMS(M+1)=410.36 mins. Chiral HPLC (IA column; 40% ethanol/60% hexane, isocratic), Rt=12.775 mins. (98% ee) [a]$_D$=20.2° (c=1, methanol).

Compound 390: (7S)-4,7,8-trimethyl-2-(((1-((6-(2,2,2-trifluoroethoxy)pyridin-3-yl)methyl)-1H-pyrazol-4-yl)methyl)amino)-7,8-dihydropteridin-6(5H)-one The compound was prepared by general procedure Method A via reaction of intermediates A-2 and B-83 to provide the title compound; 88% yield. 1H NMR (300 MHz, DMSO-d6) δ 9.84 (s, 1H), 8.13 (d, J=2.3 Hz, 1H), 7.74-7.62 (m, 2H), 7.37 (s, 1H), 6.95 (d, J=8.5 Hz, 1H), 6.60 (t, J=6.0 Hz, 1H), 5.24 (s, 2H), 4.97 (q, J=9.1 Hz, 2H), 4.21 (d, J=6.0 Hz, 2H), 3.99 (q, J=6.7 Hz, 1H), 3.17 (d, J=4.9 Hz, 1H), 2.93 (s, 3H), 2.13 (s, 3H), 1.18 (d, J=6.7 Hz, 3H). ESMS(M+1)=477.28. Chiral HPLC (Chiralpak IC, 4.6×250 mm; 50% hexane/30% ethanol/20% methanol/0.1% diethylamine). Rt=6.773 mins.; 95.1% ee.

Compound 394: (7S)-7-Ethyl-2-(((1-((6-fluoro-5-methoxypyridin-3-yl)methyl)-1H-pyrazol-4-yl)methyl)amino)-4,8-dimethyl-7,8-dihydropteridin-6(5H)-one The compound was prepared by general procedure Method A via reaction of intermediates A-8 and B-84 to provide the title compound; 59% yield. 1H NMR (300 MHz, CDCl$_3$) δ 7.55 (s, 2H), 7.45 (s, 1H), 7.33 (s, 1H), 7.10 (d, J=9.6 Hz, 1H), 5.25 (d, J=16.2 Hz, 2H), 5.15 (s, 2H), 4.34 (d, J=5.6 Hz, 2H), 3.99 (dd, J=6.4, 3.6 Hz, 1H), 3.76 (s, 3H), 2.98 (s, 3H), 2.16 (s, 3H), 2.01-1.66 (m, 1H), 0.81 (t, J=7.4 Hz, 3H). ESMS(M+1)=441.3. Chiral HPLC (Chiralpak IC, 4.6×250 mm; 50% hexane/30% ethanol/20% methanol/0.1% diethylamine). Rt=11.614 mins.; 96.7% ee.

Compound 391: (S)-7-cyclopropyl-2-(((1-((6-fluoropyridin-3-yl)methyl)-1H-pyrazol-4-yl)methyl)amino)-4,8-dimethyl-7,8-dihydropteridin-6(5H)-one The compound was prepared by general procedure Method A via reaction of intermediates A-6 and B-53 to provide the title compound; 1H NMR (300 MHz, CDCl$_3$) δ 8.84 (s, 1H), 8.11 (dt, J=2.6, 0.9 Hz, 1H), 7.65 (ddd, J=8.3, 7.6, 2.6 Hz, 1H), 7.53 (d, J=0.7 Hz, 1H), 7.46-7.35 (m, 1H), 6.98-6.84 (m, 1H), 5.49 (s, 1H), 5.26 (s, 2H), 4.44 (dd, J=5.6, 1.7 Hz, 2H), 3.29 (d, J=9.1 Hz, 1H), 3.14 (s, 3H), 2.26 (s, 3H), 1.38-1.13 (m, 1H), 1.07-0.90 (m, 1H), 0.76-0.63 (m, 1H), 0.63-0.38 (m, 2H); ESMS(M+1)=423.34.

Compound 389: (7S)-7-Ethyl-2-(((1-((6-fluoropyridin-3-yl)methyl)-1H-pyrazol-4-yl)methyl)amino)-4,8-dimethyl-7,8-dihydropteridin-6(5H)-one The compound was prepared by general procedure Method A via reaction of intermediates A-8 and B-53 to provide the title compound; 13% yield. 1H NMR (300 MHz, CDCl$_3$) δ 8.99 (s, 1H), 8.04 (d, J=2.7 Hz, 1H), 7.65-7.50 (m, 1H), 7.45 (s, 1H), 7.31 (s, 1H), 6.82 (dd, J=8.4, 2.9 Hz, 1H), 5.18 (s, 2H), 4.92 (t, J=5.7 Hz, 1H), 4.34 (d, J=5.8 Hz, 2H), 3.97 (dd, J=6.4, 3.8 Hz, 1H), 2.97 (s, 3H), 2.15 (s, 3H), 1.98-1.79 (m, 1H), 1.79-1.64 (m, 1H), 0.82 (t, J=7.5 Hz, 3H). ESMS(M+1)=411.31. Chiral HPLC (Chiralpak IC, 4.6×250 mm; 50% hexane/30% ethanol/20% methanol/0.1% diethylamine). Rt=11.481 mins.; 93.7% ee.

Compound 395: (7S)-8-Ethyl-4,7-dimethyl-2-(((1-((6-(trifluoromethyl)pyridin-3-yl)methyl)-1H-pyrazol-4-yl)methyl)amino)-7,8-dihydropteridin-6(5H)-one The compound was prepared by general procedure Method A via reaction of intermediates A-44 and B-52 to provide the title product. 1H NMR (300 MHz, Methanol-d4) δ 8.53 (s, 1H), 7.87-7.61 (m, 3H), 7.52 (s, 1H), 5.45 (s, 2H), 4.40 (s, 2H), 4.22-3.85 (m, 3H), 2.17 (s, 3H), 1.42-0.98 (m, 6H). ESMS(M+1)=461.52. Chiral HPLC (Chiralpak IC, 4.6×250 mm; 50% hexane/30% ethanol/20% methanol/0.1% diethylamine) Rt 6.831 mins.; 98% ee.

Compound 396: (7S)-7-Cyclopropyl-4,8-dimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one The compound was prepared by general procedure Method A via reaction of intermediates A-6 and B-89 to provide the title product. 1H NMR (300 MHz, DMSO-d6) δ 9.82 (s, 1H), 7.68 (s, 1H), 7.41 (s, 1H), 6.59 (d, J=7.8 Hz, 2H), 5.44 (s, 2H), 4.22 (dd, J=6.0, 3.3 Hz, 2H), 3.88 (s, 3H), 3.39-3.26 (d, 1H), 3.02 (s, 3H), 2.14 (s, 3H), 1.01-0.73 (m, 1H), 0.64-0.23 (m, 4H). ESMS(M+1)=476.55. Analytical SFC (AD-H column, 4.6×100 mm; 40% isopropanol (5 mM ammonia)/60% CO$_2$, isocratic) Rt 1.061 mins. (98% ee); [a,]$_D$=+54.7° (C=1, methanol).

Compound 397: (7S)-7-Isopropyl-4,8-dimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one The compound was prepared by general procedure Method A by reaction of intermediates A-9 and B-89 to provide the title product. 1H NMR (300 MHz, CDCl$_3$) δ 8.97 (s, 1H), 7.43 (s, 1H), 7.25 (s, 1H), 6.41 (s, 1H), 5.23 (s, 2H), 4.88 (d, J=5.9 Hz, 1H), 4.33 (d, J=5.8 Hz, 2H), 3.79 (d, J=4.4 Hz, 1H), 3.77 (s, 3H), 3.01 (s, 3H), 2.14 (s, 4H), 0.98 (d, J=7.0 Hz, 3H), 0.84 (d, J=6.9 Hz, 3H). ESMS(M+1)=478.57. Chiral HPLC (ChiralPAK IC column; 20% Methanol/30% ethanol/50% hexanes, isocratic) Rt 5.24 mins., 98% ee.

Compound 398: 4',8'-dimethyl-2'-(((1-((6-(trifluoromethyl)pyridin-3-yl)methyl)-1H-pyrazol-4-yl)methyl)amino)-5',8'-dihydro-6'H-spiro[cyclobutane-1,7'-pteridin]-6'-one The compound was prepared by general procedure Method A via reaction of intermediates A-17 and B-52 to provide the title product. 1H NMR (300 MHz, CDCl$_3$) δ 8.45 (s, 1H), 7.58 (t, J=7.0 Hz, 2H), 7.42 (d, J=10.9 Hz, 2H), 5.27 (s, 2H), 4.31 (s, 2H), 3.14 (s, 3H), 2.75-2.27 (m, 4H), 2.08 (s, 3H), 1.95 (q, J=9.3, 8.8 Hz, 0H), 1.87-1.67 (m, 1H). ESMS(M+1)=473.27.

Compound 239: 4',8'-dimethyl-2'-(((1-((6-(trifluoromethyl)pyridin-3-yl)methyl)-1H-pyrazol-4-yl)methyl)amino)-5',8'-dihydro-6'H-spiro[cyclopropane-1,7'-pteridin]-6'-one The compound was prepared by general procedure Method A via reaction of intermediates A-16 and B-52 to provide the title product, 53% yield. 1H NMR (300 MHz, Methanol-d4) δ 8.28 (s, 1H), 8.05 (d, J=8.6 Hz, 1H), 7.55 (s, 1H), 7.16 (dd, J=13.5, 5.8 Hz, 2H), 5.55 (s, 2H), 4.64 (d, J=2.4 Hz, 2H), 4.00 (dq, J=14.4, 7.2 Hz, 1H), 3.91-3.75 (m, 2H), 3.56 (dq, J=14.0, 6.9 Hz, 1H), 2.20-1.91 (m, 3H), 1.70 (s, 3H), 1.21 (t, J=7.0 Hz, 6H), 0.77 (t, J=7.3 Hz, 3H); ESMS (M+1)=459.41.

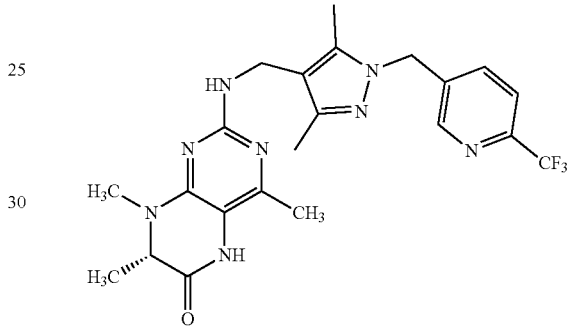

Compound 212: (7S)-2-(((3,5-Dimethyl-1-((6-(trifluoromethyl)pyridin-3-yl)methyl)-1H-pyrazol-4-yl)methyl)amino)-4,7,8-trimethyl-7,8-dihydropteridin-6(5H)-one The compound was prepared by general procedure Method A of A-2 and B-82 to provide the title compound. 1H NMR (300 MHz, CDCl$_3$) δ 8.52-8.45 (m, 1H), 7.73-7.54 (m, 2H), 5.31 (s, 2H), 4.31 (s, 2H), 4.06 (q, J=6.8 Hz, 1H), 3.08 (d, J=1.1 Hz, 3H), 2.26 (s, 3H), 2.22 (d, J=5.1 Hz, 6H), 1.39 (d, J=6.8 Hz, 3H). ESMS(M+1)=475.39.

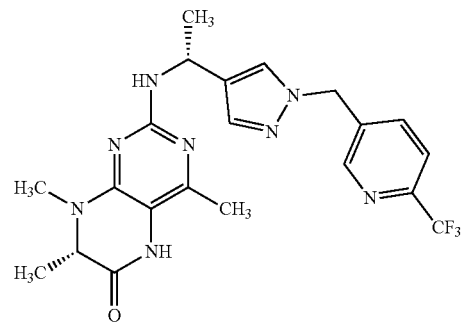

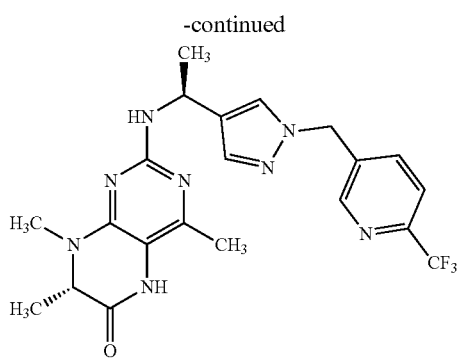

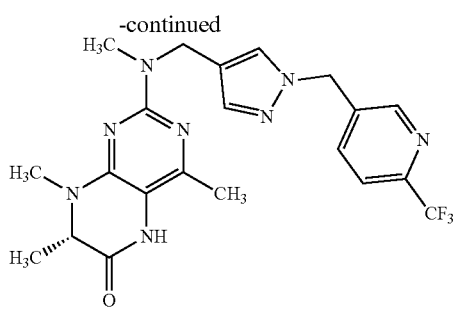

Compound 403

Compound 216 and Compound 217: (7S)-4,7,8-Trimethyl-2-(((S)-1-(1-((6-(trifluoromethyl)pyridin-3-yl)methyl)-1H-pyrazol-4-yl)ethyl)amino)-7,8-dihydropteridin-6(5H)-one and (7S)-4,7,8-Trimethyl-2-(((R)-1-(1-((6-(trifluoromethyl)pyridin-3-yl)methyl)-1H-pyrazol-4-yl)ethyl)amino)-7,8-dihydropteridin-6(5H)-one The compounds were prepared by general procedure Method A via reaction of A-2 and B-99 to provide a mixture of diastereomers (Compound 214). The pair diastereomers were separated by SFC (AD-H column, 10×250 mm; 40% EtOH(0.2% diethylamine), 60% CO2):

Diastereomer A: SFC(Rt 0.627 mins.; 99.2% ee); 1H NMR (300 MHz, DMSO-d6) δ 9.81 (s, 1H), 8.62 (d, J=1.9 Hz, 1H), 7.95-7.79 (m, 2H), 7.75 (s, 1H), 7.43 (s, 1H), 6.46 (d, J=8.7 Hz, 1H), 5.44 (s, 2H), 5.01 (q, J=7.3, 6.8 Hz, 1H), 3.99 (q, J=6.7 Hz, 1H), 2.92 (s, 3H), 2.12 (s, 3H), 1.37 (d, J=6.8 Hz, 3H), 1.17 (d, J=6.8 Hz, 3H); ESMS(M+1)=461.34.

Diastereomer B: SFC (Rt 0.814 mins.; 99.4% ee); 1H NMR (300 MHz, DMSO-d6) δ 9.80 (s, 1H), 8.63 (d, J=1.3 Hz, 1H), 7.97-7.80 (m, 2H), 7.75 (s, 1H), 7.42 (s, 1H), 6.46 (d, J=8.7 Hz, 1H), 5.44 (s, 2H), 5.17-4.91 (m, 1H), 3.98 (q, J=6.8 Hz, 1H), 2.92 (s, 3H), 2.12 (s, 3H), 1.38 (d, J=6.9 Hz, 3H), 1.19 (d, J=6.8 Hz, 3H); ESMS(M+1)=461.39.

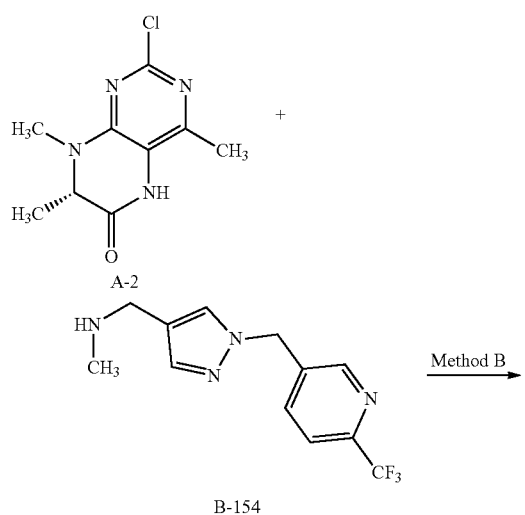

Compound 403: (7S)-4,7,8-trimethyl-2-(methyl((1-((6-(trifluoromethyl)pyridin-3-yl)methyl)-1H-pyrazol-4-yl)methyl)amino)-7,8-dihydropteridin-6(5H)-one A solution of (7S)-2-chloro-4,7,8-trimethyl-5,7-dihydropteridin-6-one (A-2; 696.2 mg, 3.010 mmol) and N-methyl-1-[1-[[6-(trifluoromethyl)-3-pyridyl]methyl]pyrazol-4-yl]methanamine (Trifluoroacetic Acid (2)) (B-154; 1.5 g, 3.010 mmol) in n-BuOH (10.44 mL) was heated in microwave at 165° C. for 30 min. The crude reaction mixture was diluted with EtOAc, washed with saturated NaHCO3 solution, dried over MgSO4, filtered, and evaporated in vacuo. The crude product was purified by column chromatography (SiO2) eluting with a gradient of dichloromethane to 20% MeOH/DCM. The desired fractions were collected and evaporated to afford the title product, wt. 624 mg, 52.2% yield) 1H NMR (300 MHz, DMSO-d6) δ 9.84 (s, 1H), 8.63 (s, 1H), 8.06-7.72 (m, 3H), 7.43 (s, 1H), 5.46 (s, 2H), 4.73-4.40 (m, 2H), 4.02 (q, J=6.7 Hz, 1H), 2.97 (s, 6H), 2.17 (s, 3H), 1.20 (d, J=6.8 Hz, 3H). ESMS (M+1)=461.34; Chiral HPLC (ChiralPAK IC column; 20% Methanol/30% ethanol/50% hexanes, isocratic) Rt 5.410 mins. (87% ee).

2E. Preparation of Compounds of Table 8

Compound 246: (7S)-4,7,8-trimethyl-2-((trans-3-(3,4,5-trifluorophenoxy)cyclobutyl)amino)-7,8-dihydropteridin-6(5H)-one (7S)-2-Chloro-4,7,8-trimethyl-5,7-dihydropteridin-6-one (A-2) (2.492 g, 10.99 mmol), 3-(3,4,5-trifluorophenoxy)cyclobutanamine hydrochloride (B-101) (2.899 g, 11.43 mmol) and t-BuXPhos palladium(II) phenethylamine chloride (377.3 mg, 0.5495 mmol) were taken into tBuOH (40 mL) and degassed by bubbling nitrogen. Sodium t-butoxide (19 mL of 2 M, 38 mmol)) was added to the reaction and the reaction was stirred at room temperature for 2 hours under a nitrogen atmosphere. Water (100 ml) was added to the reaction and extracted with ethyl acetate (3×100 ml). The combined extracts were dried over sodium sulfate, filtered, and evaporated in vacuo to afford the crude product that was purified by column chromatography (SiO2) eluting with a gradient of 0 to 20% Methanol in dichloromethane. The desired fractions were evaporated in vacuo and converted to a hydrochloride salt. Wt. 3.9 g. 1H NMR (300 MHz, DMSO-d6) δ 9.84 (s, 1H), 6.93-6.81 (m, 2H), 6.79 (d, J=7.1 Hz, 1H), 4.83 (s, 1H), 4.39 (dd, J=13.4, 6.7 Hz, 1H), 4.00 (q, J=6.8 Hz, 1H), 2.93 (s, 3H), 2.43-2.27 (m, 4H), 2.12 (s, 3H), 1.18 (d, J=6.8 Hz, 3H); ESMS(M+1)=408.3. Chiral HPLC (IC column; 10% methanol/10% ethanol/80% hexane (0.1% diethylamine): Rt 10.023 mins., 96% ee. [α]=+57.2 (c=0.5, methanol).

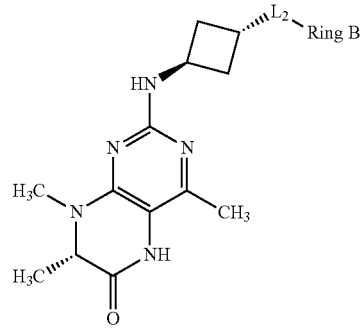

TABLE 8

| Comp # | L$_2$-Ring B | M + 1 | Synthetic Method |
|---|---|---|---|
| Comp 242 | 4-F-phenyl-O- | 372.28 | B |
| Comp 246 | 3,4,5-triF-phenyl-O- | 408.34 | A |
| Comp 248 | 3,4-diF-phenyl-O- | 390.29 | B |
| Comp 262 | 5-F-pyridin-3-yl-O- | 420.22 | B |
| Comp 276 | 5-F-pyrimidin-2-yl-O- | 374.26 | B |
| Comp 287 | 3-F-4-OMe-phenyl-O- | 420.22 | A |
| Comp 291 | 2,3,4-triF-phenyl-O- | 408.21 | A |

TABLE 8-continued

| Comp # | L$_2$-Ring B | M + 1 | Synthetic Method |
|---|---|---|---|
| Comp 292 | 2,4,5-triF-phenyl-O- | 408.42 | A |
| Comp 295 | 2,4-diF-phenyl-O- | 390.15 | A |
| Comp 315 | 5-CF$_3$-pyridin-3-yl-O- | 423.17 | A |
| Comp 324 | 6-CF$_3$-pyridin-3-yl-O- | 423.24 | A |
| Comp 326 | 4-OCF$_3$-phenyl-O- | 438.28 | A |
| Comp 333 | 2-CF$_3$-pyrimidin-5-yl-O- | 424.23 | A |
| Comp 335 | 2-CF$_3$-pyridin-4-yl-O- | 423.24 | A |
| Comp 339 | 4-Me-phenyl-O- | 368.38 | B |
| Comp 340 | 4-CF$_3$-phenyl-O- | 422.53 | B |
| Comp 342 | 4-OMe-phenyl-O- | 384.37 | B |
| Comp 344 | 2-OMe-4-F-phenyl-O- | 402.3 | B |
| Comp 347 | 6-OCH$_2$CF$_3$-pyridin-3-yl-O- | 453.27 | A |

TABLE 8-continued

| Comp # | L₂-Ring B | M + 1 | Synthetic Method |
|---|---|---|---|
| Comp 350 | 3-fluoro-4-methoxyphenoxy | 402.23 | B |
| Comp 352 | 2,3-dimethoxyphenoxy (H₃C-O, CH₃-O) | 414.28 | B |
| Comp 354 | 2-fluoro-4-methoxyphenoxy | 402.26 | B |
| Comp 357 | (6-fluoropyridin-3-yl)oxy | 373.31 | B |
| Comp 359 | 3-fluoro-4-(trifluoromethoxy)phenoxy | 456.31 | B |
| Comp 361 | (6-(difluoromethoxy)pyridin-3-yl)oxy | 421.18 | B |
| Comp 370 | 4-fluoro-3-methoxyphenoxy | 402.36 | B |
| Comp 303 | (4-fluorophenyl)thio | 388.17 | A |
| Comp 317 | (4-(trifluoromethyl)phenyl)thio | 438.2 | A |
| Comp 329 | (3,4,5-trifluorophenyl)thio | 424.23 | A |

Compound 242: (7S)-2-((trans 3-(4-fluorophenoxy)cyclobutyl)amino)-4,7,8-trimethyl-7,8-dihydropteridin-6(5H)-one The compound was prepared by procedure Method B via reaction of intermediates A-2 and B-100 to provide the title product, 138 mg (59% yield). 1H NMR (300 MHz, Methanol-d4) δ 7.00 (t, J=8.7 Hz, 2H), 6.90-6.73 (m, 2H), 4.87 (dd, J=10.4, 6.1 Hz, 1H), 4.68-4.50 (m, 1H), 4.32 (q, J=6.8 Hz, 1H), 3.23 (s, 3H), 2.73-2.53 (m, 4H), 2.36 (s, 3H), 1.54 (d, J=6.9 Hz, 3H).

Compound 246: (7S)-4,7,8-trimethyl-2-((trans-3-(3,4,5-trifluorophenoxy)cyclobutyl)amino)-7,8-dihydropteridin-6(5H)-one The compound was prepared by procedure Method A via reaction of intermediates A-2 and B-101 to provide the title product, 22.2 g (90.7% yield); 1H NMR (300 MHz, DMSO-d6) δ 9.82 (s, 1H), 6.85 (dd, J=10.0, 6.0 Hz, 2H), 6.77 (d, J=6.9 Hz, 1H), 4.91-4.74 (m, 1H), 4.39 (dd, J=13.1, 6.5 Hz, 1H), 4.00 (q, J=6.7 Hz, 1H), 2.93 (s, 3H), 2.47-2.23 (m, 4H), 2.13 (s, 3H), 1.19 (d, J=6.8 Hz, 3H); ESMS=408.3 (M+1); 96% ee (Column: IC column; 10% MeOH-10% EtOH/80% Hexans-0.1% diethylamine)

Compound 248: (7S)-2-((trans 3-(3,4-difluorophenoxy)cyclobutyl)amino)-4,7,8-trimethyl-7,8-dihydropteridin-6(5H)-one The compound was prepared by procedure Method B via reaction of intermediates A-2 and B-102 to provide the title product, 65 mg (63% yield); 1H NMR (300 MHz, Methanol-d4) δ 7.17 (dd, J=19.5, 9.2 Hz, 1H), 6.78 (ddd, J=12.3, 6.6, 2.9 Hz, 1H), 6.69-6.53 (m, 1H), 4.69-4.50 (m, 1H), 4.32 (q, J=6.9 Hz, 1H), 3.24 (s, 3H), 2.76-2.51 (m, 4H), 2.35 (s, 3H), 1.53 (t, J=9.2 Hz, 3H); ESMS(M+H)=390.29.

Compound 262: (7S)-2-((trans-3-((5-fluoropyridin-3-yl)oxy)cyclobutyl)amino)-4,7,8-trimethyl-7,8-dihydropteridin-6(5H)-one The compound was prepared by procedure Method B via reaction of intermediates A-2 and B-103 to provide the title product, 91 mg (27.6% yield) 1H NMR (300 MHz, Methanol-d4) δ 8.68 (s, 1H), 8.57 (d, J=1.9 Hz, 1H), 8.19 (d, J=9.8 Hz, 1H), 4.79-4.63 (m, 1H), 4.38-4.25 (m, 1H), 3.25 (s, 3H), 2.78 (s, 4H), 2.37 (d, J=6.7 Hz, 3H), 1.54 (dd, J=9.2, 5.5 Hz, 3H). ESMS (M+H)=373.23.

Compound 276: (7S)-2-((trans-3-((5-fluoropyrimidin-2-yl)oxy)cyclobutyl)amino)-4,7,8-trimethyl-7,8-dihydropteridin-6(5H)-one The compound was prepared by procedure Method B via reaction of intermediates A-2 and B-155 to provide the title product, 4.5% yield. 1H NMR (300 MHz, CDCl₃) δ 8.30 (s, 2H), 7.92 (s, 1H), 5.30-5.16 (m, 1H), 4.89 (d, J=6.3 Hz, 1H), 4.60-4.46 (m, 1H), 4.00 (q, J=6.8 Hz, 1H), 2.96 (s, 3H), 2.58 (ddtd, J=9.5, 7.9, 4.0, 1.6 Hz, 2H), 2.44-2.29 (m, 2H), 2.13 (s, 3H), 1.32 (d, J=6.8 Hz, 3H). ESMS (M+1)=374.26.

Compound 287: (7S)-2-((trans-3-(3,5-difluoro-4-methoxyphenoxy)cyclobutyl)amino)-4,7,8-trimethyl-7,8-dihydropteridin-6(5H)-one The compound was prepared by procedure Method A via reaction of intermediates A-2 and B-104 to provide the title product, 219 mg (84% yield); 1H NMR (300 MHz, CDCl₃) δ 9.57 (s, 1H), 6.36-6.15 (m, 2H), 5.15 (d, J=5.9 Hz, 1H), 4.64 (ddd, J=10.7, 7.0, 4.0 Hz, 1H), 4.52-4.34 (m, 1H), 3.98 (q, J=6.8 Hz, 1H), 3.81 (s, 3H), 2.93 (d, J=12.3 Hz, 3H), 2.50

(ddd, J=12.4, 6.7, 3.7 Hz, 2H), 2.41-2.21 (m, 2H), 2.17 (s, 3H), 1.31 (d, J=6.8 Hz, 3H); ESMS (M+H)=420.22.

Compound 291: (7S)-4,7,8-trimethyl-2-((trans 3-(2,3,4-trifluorophenoxy)cyclobutyl)amino)-7,8-dihydropteridin-6(5H)-one The compound was prepared by procedure Method A reaction of intermediates A-2 and B-106 to provide the title product. 1H NMR (300 MHz, CDCl$_3$) δ 9.03 (s, 1H), 6.76 (tdd, J=9.7, 8.2, 2.5 Hz, 1H), 6.51-6.30 (m, 1H), 4.97 (d, J=5.8 Hz, 1H), 4.83-4.67 (m, 1H), 4.58-4.39 (m, 1H), 3.99 (q, J=6.8 Hz, 1H), 2.96 (s, 3H), 2.65-2.47 (m, 2H), 2.41-2.26 (m, 2H), 2.16 (s, 3H), 1.32 (d, J=6.9 Hz, 3H); ESMS (M+H)=408.21.

Compound 292: (7S)-4,7,8-trimethyl-2-((trans 3-(2,4,5-trifluorophenoxy)cyclobutyl)amino)-7,8-dihydropteridin-6(5H)-one The compound was prepared by procedure Method A via reaction of intermediates A-2 and B-107 to provide the title product. 1H NMR (300 MHz, Methanol-d4) δ 7.17 (td, J=10.6, 7.6 Hz, 1H), 6.90 (dt, J=11.9, 7.8 Hz, 1H), 5.48 (s, 1H), 4.90-4.84 (m, 1H), 4.66-4.47 (m, 1H), 4.07 (dt, J=10.6, 4.8 Hz, 1H), 3.06 (d, J=5.1 Hz, 3H), 2.67-2.35 (m, 4H), 2.18 (s, 3H), 1.32 (t, J=5.8 Hz, 3H); ESMS (M+H)=408.42.

Compound 295: (7S)-4,7,8-trimethyl-2-((trans-3-(2,4-drifluorophenoxy)cyclobutyl)amino)-7,8-dihydropteridin-6(5H)-one The compound was prepared by procedure Method A via reaction of intermediates A-2 and B-108 to provide the title product. 1H NMR (300 MHz, CDCl$_3$) δ 8.37 (s, 1H), 6.94-6.81 (m, 1H), 6.82-6.66 (m, 2H), 5.01 (d, J=4.3 Hz, 1H), 4.92-4.76 (m, 1H), 4.67-4.49 (m, 1H), 4.16-4.00 (m, 1H), 3.06 (s, 3H), 2.77-2.56 (m, 2H), 2.41 (ddd, J=13.9, 6.2, 4.5 Hz, 2H), 2.23 (s, 3H), 1.41 (d, J=6.9 Hz, 3H); ESMS (M+H)=390.15.

Compound 315: (7S)-4,7,8-trimethyl-2-((trans-3-((5-(trifluoromethyl)pyridin-3-yl)oxy)cyclobutyl)amino)-7,8-dihydropteridin-6(5H)-one The compound was prepared by procedure Method A via reaction of intermediates A-2 and B-110 to provide the title product. 345 mg (55% yield); 1H NMR (400 MHz, Methanol-d4) δ 9.00 (s, 1H), 8.89 (d, J=2.4 Hz, 1H), 8.47 (s, 1H), 5.39-5.27 (m, 1H), 4.79-4.66 (m, 1H), 4.33 (q, J=6.9 Hz, 1H), 3.25 (s, 3H), 2.91-2.65 (m, 4H), 2.37 (s, 3H), 1.54 (d, J=6.9 Hz, 3H); ESMS (M+H)=423.17.

Compound 324: (7S)-4,7,8-trimethyl-2-((trans-3-((6-(trifluoromethyl)pyridin-3-yl)oxy)cyclobutyl)amino)-7,8-dihydropteridin-6(5H)-one The compound was prepared by procedure Method A via reaction of intermediates A-2 and B-112 to provide the title product. 664 mg (68% yield); 1H NMR (400 MHz, Methanol-d4) δ 8.36 (d, J=2.7 Hz, 1H), 7.82 (d, J=8.7 Hz, 1H), 7.55 (dd, J=8.7, 2.7 Hz, 1H), 5.19-5.06 (m, 1H), 4.73-4.60 (m, 1H), 4.34 (q, J=6.9 Hz, 1H), 3.26 (s, 3H), 2.85-2.60 (m, 4H), 2.39 (s, 3H), 1.54 (d, J=6.9 Hz, 3H); ESMS (M+H)=423.24.

Compound 326: (7S)-4,7,8-trimethyl-2-((trans-3-(4-(trifluoromethoxy)phenoxy)-cyclobutyl)amino)-7,8-dihydropteridin-6(5H)-one The compound was prepared by procedure Method A via reaction of intermediates A-2 and B-113 to provide the title product. 309 mg (61% yield); 1H NMR (400 MHz, CDCl$_3$) δ 8.50 (s, 1H), 7.05 (d, J=8.9 Hz, 2H), 6.71 (t, J=6.3 Hz, 2H), 4.86 (d, J=6.0 Hz, 1H), 4.78-4.69 (m, 1H), 4.46 (dt, J=13.8, 6.9 Hz, 1H), 4.03-3.91 (m, 1H), 2.54 (ddd, J=13.7, 7.2, 3.3 Hz, 2H), 2.39-2.28 (m, 2H), 2.15 (s, 3H), 1.79 (s, 1H), 1.32 (d, J=6.8 Hz, 3H); ESMS (M+H)=438.28.

Compound 333: (7S)-4,7,8-trimethyl-2-((trans-3-((2-(trifluoromethyl)pyrimidin-5-yl)oxy)cyclobutyl)amino)-7,8-dihydropteridin-6(5H)-one The compound was prepared by procedure Method A via reaction of intermediates A-2 and B-115 to provide the title product. 234 mg (99% yield); 1H NMR (400 MHz, CDCl$_3$) δ 8.97 (s, 1H), 8.42 (s, 2H), 7.08 (s, 1H), 5.05 (s, 1H), 4.63 (d, J=6.1 Hz, 1H), 4.28-4.11 (m, 1H), 3.15 (s, 3H), 2.67 (s, 4H), 2.36 (s, 3H), 1.52 (d, J=6.7 Hz, 3H); ESMS (M+H)=424.23.

Compound 335: (7S)-4,7,8-trimethyl-2-((trans-3-((2-(trifluoromethyl)pyridin-4-yl)oxy)cyclobutyl)amino)-7,8-dihydropteridin-6(5H)-one The compound was prepared by procedure Method A via reaction of intermediates A-2 and B-116 to provide the title product. 314 mg (91% yield); 1H NMR (400 MHz, CDCl$_3$) δ 9.26 (s, 1H), 8.51 (d, J=5.6 Hz, 1H), 7.10 (d, J=2.3 Hz, 1H), 6.83 (dd, J=5.6, 2.3 Hz, 1H), 5.07 (d, J=5.9 Hz, 1H), 4.97-4.86 (m, 1H), 4.63-4.44 (m, 1H), 4.06 (q, J=6.8 Hz, 1H), 3.04 (d, J=5.7 Hz, 3H), 2.64 (ddt, J=14.0, 7.2, 3.4 Hz, 2H), 2.47 (dt, J=31.8, 12.1 Hz, 2H), 2.25 (s, 3H), 1.39 (d, J=6.8 Hz, 3H); ESMS (M+H)=423.24.

Compound 339: (7S)-4,7,8-trimethyl-2-((trans-3-(p-tolyloxy)cyclobutyl)amino)-7,8-dihydropteridin-6(5H)-one The compound was prepared by procedure Method B via reaction of intermediate A-2 and B-117 to provide the title product. 204 mg (64% yield); 1H NMR (400 MHz, Methanol-d4) δ 7.05 (d, J=8.2 Hz, 2H), 6.70 (d, J=8.3 Hz, 2H), 4.57 (dd, J=14.0, 7.2 Hz, 1H), 4.28 (q, J=6.9 Hz, 1H), 3.22 (s, 3H), 2.57 (dd, J=10.6, 4.7 Hz, 4H), 2.28 (d, J=13.2 Hz, 3H), 2.25 (s, 3H), 1.52 (d, J=6.9 Hz, 3H); ESMS (M+H)=368.38.

Compound 340: (7S)-4,7,8-trimethyl-2-((trans-3-(4-(trifluoromethyl)phenoxy)cyclobutyl)amino)-7,8-dihydropteridin-6(5H)-one The compound was prepared by procedure Method B via reaction of intermediates A-2 and B-118 to provide the title product. 141 mg (66% yield); 1H NMR (400 MHz, Methanol-d4) δ 7.57 (d, J=8.5 Hz, 2H), 6.98 (d, J=8.5 Hz, 2H), 5.04-4.90 (m, 1H), 4.61 (p, J=7.1 Hz, 1H), 4.29 (q, J=6.9 Hz, 1H), 3.22 (d, J=4.2 Hz, 3H), 2.64 (ddd, J=6.4, 4.1, 1.5 Hz, 4H), 2.31 (s, 3H), 1.52 (d, J=7.0 Hz, 3H); ESMS (M+H)=422.53.

Compound 342: (7S)-2-((trans-3-(4-methoxyphenoxy)cyclobutyl)amino)-4,7,8-trimethyl-7,8-dihydropteridin-6(5H)-one The compound was prepared by procedure Method B via reaction of intermediates A-2 and B-119 to provide the title product. 131 mg (64% yield); 1H NMR (400 MHz, Methanol-d4) δ 6.78 (dd, J=29.6, 7.8 Hz, 4H), 4.57 (s, 1H), 4.27 (d, J=6.5 Hz, 1H), 3.73 (s, 3H), 3.21 (s, 3H), 2.71-2.38 (m, 4H), 2.30 (s, 3H), 1.52 (d, J=6.3 Hz, 3H); ESMS (M+H)=384.37.

Compound 344: (7S)-2-((trans-3-(4-fluoro-2-methoxyphenoxy)cyclobutyl)amino)-4,7,8-trimethyl-7,8-dihydropteridin-6(5H)-one The compound was prepared by procedure Method B via reaction of intermediates A-2 and B-120 to provide the title product. 112 mg (59% yield); 1H NMR (400 MHz, Methanol-d4) δ 6.87-6.67 (m, 2H), 6.57 (ddd, J=8.8, 8.3, 2.9 Hz, 1H), 4.87-4.84 (m, 1H), 4.66-4.52 (m, 1H), 4.33-4.23 (m, 1H), 3.84 (s, 3H), 3.23 (s, 3H), 2.70-2.57 (m, 2H), 2.51 (ddd, J=18.7, 12.5, 7.2 Hz, 2H), 2.30 (d, J=2.4 Hz, 3H), 1.52 (d, J=6.9 Hz, 3H); ESMS (M+H)=402.3.

Compound 347: (7S)-4,7,8-trimethyl-2-((trans-3-((6-(2,2,2-trifluoroethoxy)pyridin-3-yl)oxy)cyclobutyl)amino)-7,8-dihydropteridin-6(5H)-one The compound was prepared by procedure Method A via reaction of intermediates A-2 and B-121 to provide the title product. 170 mg (81% yield); 1H NMR (400 MHz, CDCl$_3$) δ 9.57 (s, 1H), 7.65-7.56 (m, 1H), 7.16 (ddd, J=8.9, 3.0, 1.6 Hz, 1H), 6.77 (dd, J=8.9, 0.9 Hz, 1H), 5.12 (d, J=5.8 Hz, 1H), 4.88-4.74 (m, 1H), 4.74-4.57 (m, 2H), 4.59-4.47 (m, 1H), 4.09-3.97 (m, 1H), 3.01 (d, J=1.3 Hz, 3H), 2.70-2.49 (m, 2H), 2.45-2.35 (m, 2H), 2.24 (d, J=1.3 Hz, 3H), 1.40-1.31 (m, 3H); ESMS (M+H)=453.27.

Compound 350: (7S)-2-((trans-3-(3-fluoro-4-methoxyphenoxy)cyclobutyl)amino)-4,7,8-trimethyl-7,8-dihydropteridin-6(5H)-one The compound was prepared by procedure Method B via reaction of intermediate A-2 and trans-3-(3-fluoro-4-methoxyphenoxy)cyclobutan-1-amine hydrochloride (Pharmablock) to provide the title product, 127 mg (75% yield); 1H NMR (400 MHz, Methanol-d4) δ 7.06-6.94 (m, 1H), 6.68-6.60 (m, 1H), 6.56 (ddd, J=9.0, 2.9, 1.6 Hz, 1H), 4.62-4.52 (m, 1H), 4.33-4.24 (m, 1H), 3.80 (s, 3H), 3.22 (s, 3H), 2.62-2.49 (m, 4H), 2.30 (d, J=3.4 Hz, 3H), 1.55-1.48 (m, 3H); ESMS (M+H)=402.23.

Compound 352: (7S)-2-((trans-3-(3,4-dimethoxyphenoxy)cyclobutyl)amino)-4,7,8-trimethyl-7,8-dihydropteridin-6(5H)-one The compound was prepared by procedure Method B via reaction of intermediates A-2 and B-122 to provide the title product. 2.69 g (97% yield); 1H NMR (400 MHz, DMSO-d6) δ 12.76 (s, 1H), 10.50 (s, 1H), 8.37 (d, J=48.2 Hz, 1H), 6.83 (d, J=8.8 Hz, 1H), 6.50 (t, J=4.8 Hz, 1H), 6.39-6.19 (m, 1H), 4.87-4.71 (m, 1H), 4.62-4.41 (m, 1H), 4.30 (q, J=6.9 Hz, 1H), 3.71 (d, J=15.7 Hz, 3H), 3.68 (s, 3H), 3.15 (d, J=14.3 Hz, 3H), 2.29 (s, 3H), 1.39 (t, J=7.1 Hz, 3H); ESMS (M+H)=414.28.

Compound 354: (7S)-2-((trans-3-(2-fluoro-4-methoxyphenoxy)cyclobutyl)amino)-4,7,8-trimethyl-7,8-dihydropteridin-6(5H)-one The compound was prepared by procedure Method B via reaction of intermediates A-2 and B-123 to provide the title product. 185 mg (83% yield); 1H NMR (400 MHz, Methanol-d4) δ 6.86 (t, J=9.2 Hz, 1H), 6.72 (dt, J=20.4, 10.2 Hz, 1H), 6.63 (ddd, J=9.0, 2.9, 1.5 Hz, 1H), 4.88-4.83 (m, 1H), 4.65-4.56 (m, 1H), 4.28 (q, J=6.9 Hz, 1H), 3.74 (s, 3H), 3.23 (s, 3H), 2.67-2.58 (m, 2H), 2.57-2.44 (m, 2H), 2.30 (s, 3H), 1.52 (d, J=7.0 Hz, 3H); ESMS (M+H)=402.26.

Compound 357: (7S)-2-((trans-3-((6-fluoropyridin-3-yl)oxy)cyclobutyl)amino)-4,7,8-trimethyl-7,8-dihydropteridin-6(5H)-one The compound was prepared by procedure Method B via reaction of intermediates A-2 and B-124 to provide the title product. 124 mg (45% yield); 1H NMR (400 MHz, Methanol-d4) δ 7.73 (dd, J=3.0, 1.6 Hz, 1H), 7.49-7.39 (m, 1H), 6.99 (dd, J=8.9, 3.1 Hz, 1H), 4.98-4.88 (m, 1H), 4.61 (p, J=7.0 Hz, 1H), 4.35-4.23 (m, 1H), 3.22 (s, 3H), 2.67-2.56 (m, 4H), 2.31 (s, 3H), 1.51 (d, 7.0 Hz, 3H); ESMS (M+H)=373.31.

Compound 359: (7S)-2-((trans-3-(3-fluoro-4-(trifluoromethoxy)phenoxy)cyclobutyl) amino)-4,7,8-trimethyl-7,8-dihydropteridin-6(5H)-one The compound was prepared by procedure Method B via reaction of intermediates A-2 and B-125 to provide the title product. 171 mg (53% yield); 1H NMR (400 MHz, Methanol-d4) δ 7.30 (td, J=9.0, 1.0 Hz, 1H), 6.84-6.78 (m, 1H), 6.75-6.65 (m, 1H), 4.97-4.85 (m, 1H), 4.66-4.55 (m, 1H), 4.34-4.24 (m, 1H), 3.22 (s, 3H), 2.62 (dt, J=6.4, 5.1 Hz, 4H), 2.30 (d, J=3.6 Hz, 3H), 1.52 (dd, J=6.9, 3.6 Hz, 3H); ESMS (M+H)=456.31.

Compound 361: (7S)-2-((trans-3-((6-(difluoromethoxy)pyridin-3-yl)oxy)cyclobutyl)amino)-4,7,8-trimethyl-7,8-dihydropteridin-6(5H)-one Prepared by reaction of intermediates A-2 and B-126 to provide the title product, 161 mg (64% yield); 1H NMR (400 MHz, Methanol-d4) δ 7.77 (d, J=2.9 Hz, 1H), 7.39 (dd, J=8.6, 2.8 Hz, 1H), 7.28 (T, J=73.5 Hz, 1H), 6.92 (d, J=8.9 Hz, 1H), 4.97-4.88 (m, 1H), 4.59 (dt, J=14.4, 7.1 Hz, 1H), 4.33-4.23 (m, 1H), 3.22 (s, 3H), 2.81-2.50 (m, 4H), 2.31 (s, 3H), 1.52 (d, J=6.9 Hz, 3H); ESMS (M+H)=421.18.

Compound 370: (7S)-2-((trans-3-(4-fluoro-3-methoxyphenoxy)cyclobutyl)amino)-4,7,8-trimethyl-7,8-dihydropteridin-6(5H)-one The compound was prepared by procedure Method B via reaction of intermediates A-2 and B-127 to provide the title product. 161 mg (70% yield); 1H NMR (400 MHz, Methanol-d4) δ 6.96 (dd, J=11.2, 8.9 Hz, 1H), 6.58 (dd, J=7.2, 2.9 Hz, 1H), 6.30 (dt, J=8.9, 3.1 Hz, 1H), 4.57 (dd, J=13.8, 7.2 Hz, 1H), 4.31-4.24 (m, 1H), 3.83 (s, 3H), 3.22 (s, 3H), 2.61-2.54 (m, 4H), 2.30 (s, 3H), 1.52 (d, J=6.9 Hz, 3H); ESMS (M+H)=402.36.

Compound 303: (7S)-2-((trans-3-((4-fluorophenyl)thio)cyclobutyl)amino)-4,7,8-trimethyl-7,8-dihydropteridin-6(5H)-one The compound was prepared by procedure Method A via reaction of intermediates A-2 and B-109 to provide the title product. 1H NMR (400 MHz, Methanol-d4) δ 7.39-7.29 (m, 2H), 7.12-7.02 (m, 2H), 4.60 (p, J=7.5 Hz, 1H), 4.28 (q, J=6.9 Hz, 1H), 3.96-3.82 (m, 1H), 3.21 (s, 3H), 2.67-2.52 (m, 2H), 2.41 (ddd, J=11.9, 7.9, 3.7 Hz, 2H), 2.28 (d, J=3.1 Hz, 3H), 1.51 (d, J=6.9 Hz, 3H); ESMS(M+1)=388.17.

Compound 317: (7S)-4,7,8-trimethyl-2-((trans-3-((4-(trifluoromethyl)phenyl)thio)-cyclobutyl)amino)-7,8-dihydropteridin-6(5H)-one The compound was prepared by procedure Method A via reaction of intermediates A-2 and B-111 to provide the title product. 1H NMR (400 MHz, CDCl₃) δ 7.88 (s, 1H), 7.43 (d, J=8.2 Hz, 2H), 7.17 (d, J=8.3 Hz, 2H), 4.83 (d, J=6.8 Hz, 1H), 4.67-4.57 (m, 1H), 4.03-3.96 (m, 1H), 3.93-3.83 (m, 1H), 2.96 (s, 3H), 2.54-2.35 (m, 4H), 2.13 (s, 3H), 1.32 (d, J=6.8 Hz, 3H). ESMS(M+1)=438.2.

Compound 329: (7S)-4,7,8-trimethyl-2-((trans-3-((3,4,5-trifluorophenyl)thio)-cyclobutyl)amino)-7,8-dihydropteridin-6(5H)-one The compound was prepared by procedure Method A via reaction of intermediates A-2 and B-114 to provide the title product. 1H NMR (400 MHz, Methanol-d4) δ 7.10-6.92 (m, 2H), 4.68 (p, J=7.5 Hz, 1H), 4.30 (q, J=6.9 Hz, 1H), 4.09-3.97 (m, 1H), 3.23 (s, 3H), 2.82-2.63 (m, 2H), 2.52-2.35 (m, 2H), 2.33 (s, 3H), 1.53 (d, J=6.9 Hz, 3H); ESMS (M+1)=424.23.

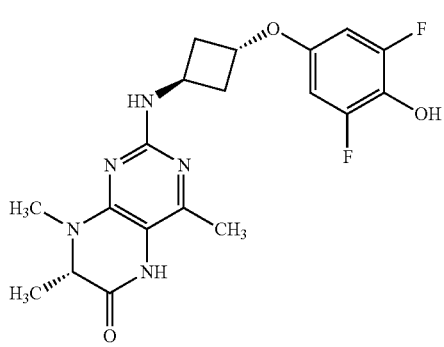 [SMILES: Cc1nc(N[C@H]2C[C@H](Oc3cc(F)c(O)c(F)c3)C2)nc2c1NC(=O)[C@H](C)N2C]

Compound 349: (7S)-2-((trans-3-(3,5-difluoro-4-hydroxyphenoxy)cyclobutyl)amino)-4,7,8-trimethyl-7,8-dihydropteridin-6(5H)-one A 1 M solution of Boron tribromide (1.9 ml, 1.9 mmol) was added to Compound 287 (105 mg, 0.24 mmol) and stirred at room temperature for 16 hours. Methanol was added ot the mixture then evaporated in vacup to provide the crude product. The crude was purified by reverse phase chromatography to provide 5.5 mg of the title product. 1H NMR (400 MHz, Methanol-d4) δ 6.50-6.37 (m, 2H), 4.80-4.72 (m, 1H), 4.62-4.51 (m, 1H), 4.29 (q, J=6.9 Hz, 1H), 3.22 (d, J=6.2 Hz, 3H), 2.64-2.45 (m, 4H), 2.33-2.28 (m, 3H), 1.52 (d, J=7.0 Hz, 3H). ESMS(M+1)=406.18.

2F. Preparation of Compounds of Table 9A

2F. Preparation of Compounds Table 9A

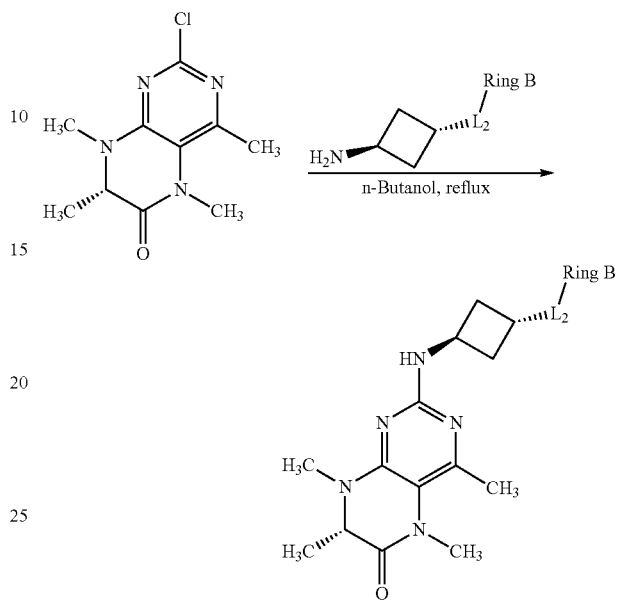

Compound 253: (7S)-4,5,7,8-tetramethyl-2-((trans-3-(3,4,5-trifluorophenoxy)cyclobutyl)amino)-7,8-dihydropteridin-6(5H)-one (7S)-2-chloro-4,5,7,8-tetramethyl-7H-pteridin-6-one (A-3) (2.15 g, 8.94 mmol) and trans-3-(3,4,5-trifluorophenoxy)cyclobutan-1-amine hydrochloride (B-101) (2.25 g, 8.89 mmol) was taken into 20 ml of n-butanol and refluxed for 20 hours. The reaction was evaporated in vacuo to give the crude residue. The crude was dissolved in dichloromethane (a flocculent material seen in the solution) and filtered over a plug of silica gel eluting with 3% methanol in dichloromethane. The filtrate was evaporated in vacuo to afford an oil that turned into a crunchy foam, wt 2.1 g. 1H (CDCl₃, 300 MHz) δ 6.44-6.38 (m, 2H), 5.37 (br s, 1H), 4.76-4.54 (m, 1H), 4.58-4.54 (m, 1H), 4.0 (q, J=6.9 Hz, 1H), 3.30 (s, 3H), 3.02 (s, 3H), 2.64-2.55 (m, 2H), 2.49-2.37 (m, 2H), 2.37 (s, 3H), 1.21 (d, J=6.9 Hz, 3H). Chiral HPLC (ChiralPak IB column; 25% EtOH/hexanes; isocratic): Rt 10.283 mins. (94% ee).

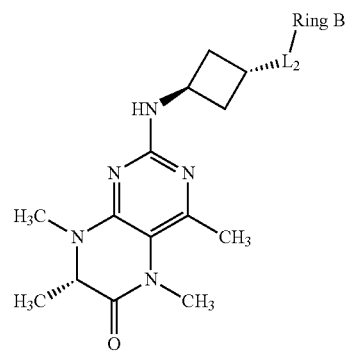

TABLE 9A
| Compound # | L₂-Ring B | M + 1 |
|---|---|---|
| Comp 353 | 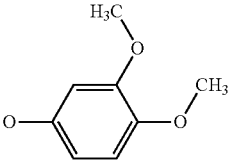 | 428.31 |
| Comp 343 | 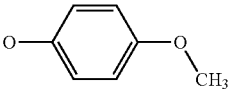 | 398.37 |
| Comp 355 | 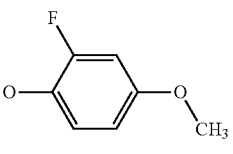 | 416.36 |
| Comp 351 | 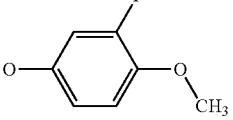 | 416.29 |
| Comp 338 | 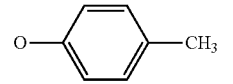 | 382.38 |
| Comp 358 |  | 387.32 |
| Comp 345 | 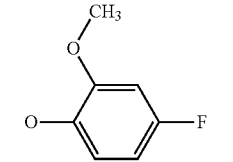 | 416.29 |
| Comp 346 | 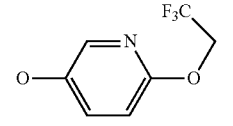 | 467.33 |
| Comp 250 |  | 386.33 |
| Comp 274 | 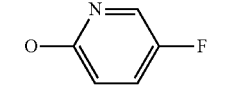 | 388.36 |
| Comp 314 | 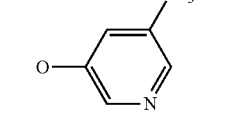 | 437.17 |
| Comp 325 | 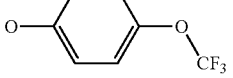 | 452.28 |
| Comp 362 | 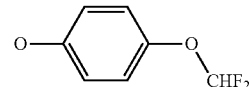 | 435.21 |
| Comp 373 | 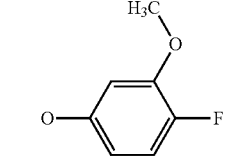 | 416.31 |
| Comp 337 | 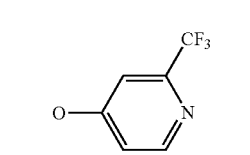 [SMILES: Oc1ccnc(C(F)(F)F)c1] | 437.33 |
| Comp 334 | 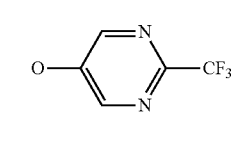 [SMILES: Oc1cnc(C(F)(F)F)nc1] | 438.28 |
| Comp 323 | 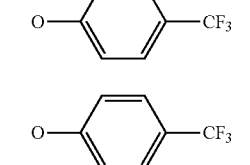 | 437.29 |
| Comp 341 | 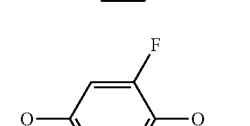 | 436.33 |
| Comp 360 | 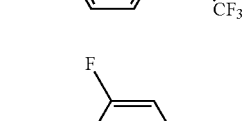 | 470.32 |
| Comp 296 | 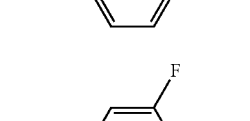 | 404.2 |
| Comp 252 | 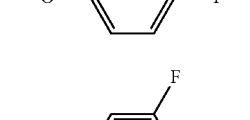 | 404.38 |
| Comp 253 | 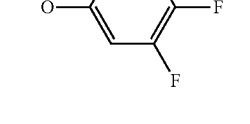 | 422.22 |
| Comp 293 | 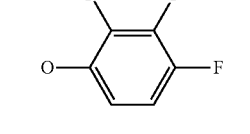 | 422.2 |

TABLE 9A-continued

| Compound # | L₂-Ring B | M + 1 |
|---|---|---|
| Comp 294 | 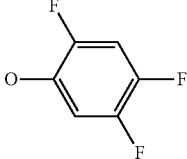 | 422.2 |
| Comp 307 |  | 402.17 |
| Comp 320 |  | 452.2 |
| Comp 330 | 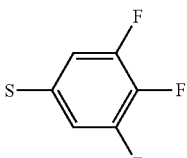 | 438.23 |

Compound 353: (7S)-2-((trans-3-(3,4-dimethoxyphenoxy)cyclobutyl)amino)-4,5,7,8-tetramethyl-7,8-dihydropteridin-6(5H)-one The compound was prepared by reaction of intermediates A-3 and B-122 to provide the title product. 1H NMR (400 MHz, Methanol-d4) δ 6.83 (d, J=8.8 Hz, 1H), 6.52 (d, J=2.8 Hz, 1H), 6.31 (dd, J=8.7, 2.8 Hz, 1H), 4.84-4.79 (m, 1H), 4.60 (p, J=7.0 Hz, 1H), 4.28 (q, J=7.0 Hz, 1H), 3.80 (s, 3H), 3.76 (s, 3H), 3.32 (d, J=3.3 Hz, 3H), 3.22 (s, 3H), 2.64-2.53 (m, 4H), 2.48 (s, 3H), 1.37 (d, J=7.0 Hz, 3H); ESMS(M+H)=428.31.

Compound 343: (7S)-2-((trans-3-(4-methoxyphenoxy)cyclobutyl)amino)-4,5,7,8-tetramethyl-7,8-dihydropteridin-6(5H)-one The compound was prepared by reaction of intermediates A-3 and B-119 to provide the title product. 1H NMR (400 MHz, Methanol-d4) δ 6.86-6.80 (m, 2H), 6.78-6.72 (m, 2H), 4.84-4.76 (m, 1H), 4.60 (p, J=7.0 Hz, 1H), 4.28 (q, J=7.0 Hz, 1H), 3.73 (s, 3H), 3.34-3.31 (m, 3H), 3.21 (s, 3H), 2.54 (tdd, J=8.7, 7.9, 3.3 Hz, 4H), 2.48 (s, 3H), 1.36 (d, J=7.0 Hz, 3H); ESMS(M+H)=398.37.

Compound 355: (7S)-2-((trans-3-(2-fluoro-4-methoxyphenoxy)cyclobutyl)amino)-4,5,7,8-tetramethyl-7,8-dihydropteridin-6(5H)-one The compound was prepared by reaction of intermediates A-3 and B-123 to provide the title product. 1H NMR (400 MHz, Methanol-d4) δ 6.85 (t, J=9.3 Hz, 1H), 6.70 (dd, J=12.9, 2.9 Hz, 1H), 6.66-6.52 (m, 1H), 4.66-4.52 (m, 1H), 4.27 (q, J=7.0 Hz, 1H), 3.73 (s, 3H), 3.34-3.31 (m, 3H), 3.22 (s, 3H), 2.66-2.49 (m, 4H), 2.48 (s, 3H), 1.37 (d, J=7.0 Hz, 3H); ESMS(M+H)=416.36.

Compound 351: (7S)-2-((trans-3-(3-fluoro-4-methoxyphenoxy)cyclobutyl)amino)-4,5,7,8-tetramethyl-7,8-dihydropteridin-6(5H)-one The compound was prepared by reaction of intermediate A-3 and (trans)-3-(4-fluoro-3-methoxyphenoxy)cyclobutan-1-amine hydrochloride to provide the title product. 1H NMR (400 MHz, Methanol-d4) δ 6.98 (t, J=9.3 Hz, 1H), 6.68-6.60 (m, 1H), 6.61-6.48 (m, 1H), 4.83-4.77 (m, 1H), 4.59 (p, J=7.0 Hz, 1H), 4.28 (q, J=7.0 Hz, 1H), 3.80 (s, 3H), 3.34-3.31 (m, 3H), 3.21 (s, 3H), 2.58 (dt, J=8.3, 4.9 Hz, 4H), 2.48 (s, 3H), 1.37 (d, J=7.0 Hz, 3H); ESMS(M+H)=416.29.

Compound 338: (7S)-4,5,7,8-tetramethyl-2-((trans-3-(p-tolyloxy)cyclobutyl)amino)-7,8-dihydropteridin-6(5H)-one The compound was prepared by reaction of intermediates A-3 and B-117 to provide the title product. 1H NMR (400 MHz, Methanol-d4) δ 7.11-7.00 (m, 2H), 6.77-6.64 (m, 2H), 4.60 (p, J=7.0 Hz, 1H), 4.28 (q, J=7.0 Hz, 1H), 3.33-3.31 (m, 3H), 3.22 (s, 3H), 2.63-2.51 (m, 4H), 2.48 (s, 3H), 2.25 (s, 3H), 1.36 (t, J=5.9 Hz, 3H); ESMS(M+H)=382.38.

Compound 358: (7S)-2-((trans 3-((6-fluoropyridin-3-yl)oxy)cyclobutyl)amino)-4,5,7,8-tetramethyl-7,8-dihydropteridin-6(5H)-one The compound was prepared by reaction of intermediates A-3 and B-124 to provide the title product. 1H NMR (400 MHz, Methanol-d4) δ 7.73 (dd, J=2.8, 1.7 Hz, 1H), 7.53-7.40 (m, 1H), 6.99 (dd, J=8.9, 2.9 Hz, 1H), 4.98-4.92 (m, 1H), 4.64 (p, J=7.1 Hz, 1H), 4.29 (q, J=7.0 Hz, 1H), 3.34 (s, 3H), 3.23 (s, 3H), 2.73-2.57 (m, 4H), 2.49 (s, 3H), 1.37 (d, J=7.0 Hz, 3H); ESMS(M+H)=387.32.

Compound 345: (7S)-2-((trans-3-(4-fluoro-2-methoxyphenoxy)cyclobutyl)amino)-4,5,7,8-tetramethyl-7,8-dihydropteridin-6(5H)-one The compound was prepared by reaction of intermediates A-3 and B-120 to provide the title product. 1H NMR (400 MHz, Methanol-d4) δ 6.84-6.67 (m, 2H), 6.57 (td, J=8.5, 2.9 Hz, 1H), 4.68-4.55 (m, 1H), 4.34-4.22 (m, 1H), 3.83 (d, J=7.4 Hz, 3H), 3.34-3.30 (m, 3H), 3.23 (s, 2H), 2.71-2.50 (m, 4H), 2.48 (d, J=2.4 Hz, 3H), 1.37 (d, J=7.0 Hz, 3H); ESMS(M+H)=416.29.

Compound 346: (7S)-4,5,7,8-tetramethyl-2-((trans-3-((6-(2,2,2-trifluoroethoxy)pyridin-3-yl)oxy)cyclobutyl)amino)-7,8-dihydropteridin-6(5H)-one The compound was prepared by reaction of intermediates A-3 and B-121 to provide the title product. 1H NMR (400 MHz, Methanol-d4) δ 7.71 (d, J=3.0 Hz, 1H), 7.33 (dd, J=8.9, 3.0 Hz, 1H), 6.84 (d, J=9.0 Hz, 1H), 4.76 (q, J=8.8 Hz, 2H), 4.63 (p, J=7.0 Hz, 1H), 4.29 (q, J=7.0 Hz, 1H), 3.36-3.32 (m, 3H), 3.23 (d, J=4.5 Hz, 3H), 2.71-2.53 (m, 4H), 2.49 (s, 3H), 1.37 (d, J=7.0 Hz, 3H); ESMS(M+H)=467.33.

Compound 250: (7S)-2-((trans-3-(4-fluorophenoxy)cyclobutyl)amino)-4,5,7,8-tetramethyl-7,8-dihydropteridin-6(5H)-one The compound was prepared by reaction of intermediates A-3 and B-109 to provide the title product. 1H NMR (300 MHz, Methanol-d4) δ 7.07-6.95 (m, 2H), 6.88-6.77 (m, 2H), 4.95-4.83 (m, 1H), 4.70-4.57 (m, 1H), 4.32 (q, J=6.9 Hz, 1H), 3.37-3.33 (m, 3H), 3.24 (s, 3H), 2.72-2.56 (m, 4H), 2.53 (s, 3H), 1.39 (d, J=7.0 Hz, 3H); ESMS(M+H)=386.33.

Compound 274: (S)-2-((trans-3-((5-fluoropyrimidin-2-yl)oxy)cyclobutyl)amino)-4,5,7,8-tetramethyl-7,8-dihydropteridin-6(5H)-one The compound was prepared by reaction of intermediates A-3 and B-155 to provide the title product, 5.2% yield. 1H NMR (300 MHz, CDCl$_3$) δ 8.39 (s, 2H), 5.31 (dq, J=7.5, 4.2, 3.7 Hz, 1H), 4.94 (d, J=6.3 Hz, 1H), 4.64 (q, J=7.5, 7.0 Hz, 1H), 4.01 (q, J=6.9 Hz, 1H), 3.30 (s, 3H), 3.01 (s, 3H), 2.75-2.59 (m, 2H), 2.55-2.40 (m, 2H), 2.35 (s, 3H), 1.21 (d, J=6.9 Hz, 3H); ESMS (M+1)=388.36.

Compound 314 (7S)-4,5,7,8-tetramethyl-2-((trans-3-((5-(trifluoromethyl)pyridin-3-yl)oxy)cyclobutyl)amino)-7,8-dihydropteridin-6(5H)-one The compound was prepared by reaction of intermediates A-3 and B-110 to provide the title product. 1H NMR (400 MHz, Methanol-d4) δ 8.96 (s, 1H), 8.85 (d, J=2.5 Hz, 1H), 8.42 (s, 1H), 5.36-5.22 (m, 1H), 4.78-4.68 (m, 1H), 4.32 (q, J=7.0 Hz, 1H), 3.34 (s, 3H), 3.24 (s, 3H), 2.87-2.68 (m, 4H), 2.52 (s, 3H), 1.38 (d, J=7.0 Hz, 3H); ESMS(M+H)=437.17.

Compound 325: (7S)-4,5,7,8-tetramethyl-2-((trans-3-(4-(trifluoromethoxy)phenoxy)-cyclobutyl)amino)-7,8-dihydropteridin-6(5H)-one The compound was prepared by reaction of intermediates A-3 and B-113 to provide the title product. 1H NMR (400 MHz, Methanol-d4) δ 7.19 (d, J=8.5 Hz, 2H), 6.93-6.86 (m, 2H), 4.99-4.87 (m, 1H), 4.70-4.56 (m, 1H), 4.36-4.25 (m, 1H), 3.33 (d, J=6.8 Hz, 3H), 3.23 (s, 3H), 2.76-2.55 (m, 4H), 2.52 (s, 3H), 1.38 (d, J=7.0 Hz, 3H); ESMS(M+H)=452.28.

Compound 362: (7S)-2-((trans-3-((6-(difluoromethoxy)pyridin-3-yl)oxy)cyclobutyl)amino)-4,5,7,8-tetramethyl-7,8-dihydropteridin-6(5H)-one The compound was prepared by reaction of intermediates A-3 and B-126 to provide the title product. 1H NMR (400 MHz, Methanol) δ 7.78 (t, J=5.7 Hz, 1H), 7.38 (ddd, J=77.7, 69.1, 67.0 Hz, 2H), 6.91 (dt, J=8.9, 1.4 Hz, 1H), 4.97-4.90 (m, 1H), 4.70-4.54 (m, 1H), 4.34-4.21 (m, 1H), 3.34-3.29 (m, 3H), 3.22 (s, 3H), 2.70-2.55 (m, 4H), 2.48 (d, J=3.5 Hz, 3H), 1.37 (d, J=6.6 Hz, 2H); ESMS(M+H)=435.21.

Compound 373: (7S)-2-((trans-3-(4-fluoro-3-methoxyphenoxy)cyclobutyl)amino)-4,5,7,8-tetramethyl-7,8-dihydropteridin-6(5H)-one The compound was prepared by reaction of intermediates A-3 and B-127 to provide the title product. 1H NMR (300 MHz, Methanol-d4) δ 6.94 (t, J=9.3 Hz, 1H), 6.65-6.49 (m, 1H), 6.30 (dd, J=6.1, 2.4 Hz, 1H), 4.97 (d, J=35.2 Hz, 4H), 4.85 (s, 1H), 4.58 (s, 1H), 4.28 (d, J=5.6 Hz, 1H), 3.83 (s, 3H), 3.34 (s, 3H), 3.22 (s, 3H), 2.56 (d, J=19.1 Hz, 4H), 2.49 (s, 3H), 1.38 (d, J=5.5 Hz, 3H); ESMS(M+H)=416.31.

Compound 337: (7S)-4,5,7,8-tetramethyl-2-((trans-3-((2-(trifluoromethyl)pyridin-4-yl)oxy)cyclobutyl)amino)-7,8-dihydropteridin-6(5H)-one The compound was prepared by reaction of intermediates A-3 and B-116 to provide the title product. 1H NMR (400 MHz, Methanol-d4) δ 8.51 (d, J=5.8 Hz, 1H), 7.28 (d, J=2.4 Hz, 1H), 7.15-7.05 (m, 1H), 5.11 (ddd, J=23.4, 13.9, 11.1 Hz, 2H), 4.67 (p, J=7.1 Hz, 1H), 4.30 (q, J=7.0 Hz, 1H), 3.37-3.32 (m, 3H), 3.23 (s, 3H), 2.82-2.67 (m, 4H), 2.67 (s, 3H), 2.50 (d, J=4.3 Hz, 3H), 1.38 (dd, J=6.9, 3.2 Hz, 3H); ESMS(M+H)=437.33.

Compound 334: (7S)-4,5,7,8-tetramethyl-2-((trans-3-((2-(trifluoromethyl)pyrimidin-5-yl)oxy)cyclobutyl)amino)-7,8-dihydropteridin-6(5H)-one The compound was prepared by reaction of intermediates A-3 and B-115 to provide the title product. 1H NMR (400 MHz, Methanol-d4) δ 8.55 (s, 2H), 5.17 (p, J=5.2 Hz, 1H), 4.69 (p, J=7.1 Hz, 1H), 4.30 (q, J=7.0 Hz, 1H), 3.34 (s, 3H), 3.24 (s, 3H), 2.78-2.67 (m, 4H), 2.50 (s, 3H), 1.38 (d, J=7.0 Hz, 3H); ESMS(M+H)=438.28.

Compound 323: (7S)-4,5,7,8-tetramethyl-2-((trans-3-((6-(trifluoromethyl)pyridin-3-yl)oxy)cyclobutyl)amino)-7,8-dihydropteridin-6(5H)-one The compound was prepared by reaction of intermediates A-3 and B-112 to provide the title product. 1H NMR (400 MHz, Methanol-d4) δ 8.37 (d, J=2.7 Hz, 1H), 7.83 (d, J=8.8 Hz, 1H), 7.61-7.50 (m, 1H), 5.21-5.10 (m, 1H), 4.76-4.61 (m, 1H), 4.38-4.26 (m, 1H), 3.36 (s, 3H), 3.25 (s, 3H), 2.86-2.61 (m, 4H), 2.55 (s, 3H), 1.39 (d, J=7.0 Hz, 3H); ESMS(M+H)=437.29.

Compound 341: (7S)-4,5,7,8-tetramethyl-2-((trans-3-(4-(trifluoromethyl)phenoxy)-cyclobutyl)-amino)-7,8-dihydropteridin-6(5H)-one The compound was prepared by reaction of intermediates A-3 and B-118 to provide the title product. 1H NMR (400 MHz, Methanol-d4) δ 7.57 (d, J=8.7 Hz, 2H), 6.98 (d, J=8.6 Hz, 2H), 4.98 (p, J=5.2 Hz, 1H), 4.64 (p, J=7.1 Hz, 1H), 4.29 (q, J=7.0 Hz, 1H), 3.32 (d, J=5.4 Hz, 3H), 3.22 (s, 3H), 2.66-2.59 (m, 4H), 2.49 (s, 3H), 1.37 (d, J=7.0 Hz, 3H); ESMS(M+H)=436.33.

Compound 360: (7S)-2-((trans 3-(3-fluoro-4-(trifluoromethoxy)phenoxy)cyclobutyl)amino)-4,5,7,8-tetramethyl-7,8-dihydropteridin-6(5H)-one The compound was prepared by reaction of intermediates A-3 and B-125 to provide the title product. 1H NMR (400 MHz, Methanol-d4) δ 7.31 (td, J=9.0, 1.0 Hz, 1H), 6.88-6.77 (m, 1H), 6.73 (tdd, J=9.1, 2.9, 1.6 Hz, 1H), 4.91 (p, J=5.1 Hz, 1H), 4.69-4.54 (m, 1H), 4.34-4.24 (m, 1H), 3.33-3.31 (m, 3H), 3.31 (dd, J=3.3, 1.6 Hz, 3H), 3.22 (d, J=6.4 Hz, 3H), 2.70-2.57 (m, 4H), 2.48 (d, J=4.1 Hz, 3H), 1.37 (dd, J=7.0, 2.8 Hz, 3H); ESMS(M+H)=470.32.

Compound 296: (7S)-2-((trans-3-(2,4-difluorophenoxy)cyclobutyl)amino)-4,5,7,8-tetramethyl-7,8-dihydropteridin-6(5H)-one The compound was prepared by reaction of intermediates A-3 and B-108 to provide the title product. 1H NMR (300 MHz, Methanol-d4) δ 7.10-6.77 (m, 3H), 4.91 (td, J=6.5, 3.2 Hz, 1H), 4.72-4.53 (m, 1H), 4.29 (q, J=7.0 Hz, 1H), 3.32 (d, J=3.1 Hz, 3H), 3.23 (s, 3H), 2.74-2.52 (m, 4H), 2.48 (s, 3H), 1.37 (d, J=7.0 Hz, 3H); ESMS(M+H)=404.2.

Compound 252: (7S)-2-((trans-3-(3,4-difluorophenoxy)cyclobutyl)amino)-4,5,7,8-tetramethyl-7,8-dihydropteridin-6(5H)-one The compound was prepared by reaction of intermediates A-3 and B-102 to provide the title product. 1H NMR (300

MHz, Methanol-d4) δ 7.17 (dd, J=19.5, 9.3 Hz, 1H), 6.85-6.70 (m, 1H), 6.67-6.57 (m, 1H), 4.94-4.83 (m, 1H), 4.66-4.53 (m, 1H), 4.32 (q, J=6.9 Hz, 1H), 3.37-3.33 (m, 3H), 3.24 (s, 3H), 2.71-2.57 (m, 4H), 2.52 (s, 3H), 1.38 (d, J=7.0 Hz, 3H); ESMS(M+H)=404.38.

Compound 253: (7S)-4,5,7,8-tetramethyl-2-((trans-3-(3,4,5-trifluorophenoxy)cyclobutyl)-amino)-7,8-dihydropteridin-6(5H)-one The compound was prepared by reaction of intermediates A-3 and B-101 to provide the title product. 1H NMR (300 MHz, DMSO-d6) δ 7.01 (d, J=6.9 Hz, 1H), 6.93-6.78 (m, 2H), 4.84 (dt, J=6.7, 3.2 Hz, 1H), 4.42 (q, J=7.8, 6.9 Hz, 1H), 4.02 (q, J=6.8 Hz, 1H), 3.18 (s, 3H), 2.92 (s, 3H), 2.49-2.31 (m, 4H), 2.27 (s, 3H), 1.05 (d, J=6.8 Hz, 3H); ESMS(M+H)=422.22.

Compound 293: (7S)-4,5,7,8-tetramethyl-2-((trans-3-(2,3,4-trifluorophenoxy)cyclobutyl)-amino)-7,8-dihydropteridin-6(5H)-one The compound was prepared by reaction of intermediates A-3 and B-106 to provide the title product. 1H NMR (300 MHz, Methanol-d4) δ 7.08-6.91 (m, 1H), 6.79-6.66 (m, 1H), 4.95 (dt, J=10.9, 5.4 Hz, 1H), 4.71-4.57 (m, 1H), 4.35-4.22 (m, 1H), 3.38-3.33 (m, 3H), 3.24 (s, 3H), 2.75-2.56 (m, 4H), 2.50 (s, 3H), 1.38 (d, J=7.0 Hz, 3H); ESMS(M+H)=422.2.

Compound 294: (7S)-4,5,7,8-tetramethyl-2-((trans-3-(2,4,5-trifluorophenoxy)-cyclobutyl)amino)-7,8-dihydropteridin-6(5H)-one The compound was prepared by reaction of intermediates A-3 and B-107 to provide the title product. 1H NMR (300 MHz, Methanol-d4) δ 7.26-7.09 (m, 1H), 6.94 (dt, J=11.8, 7.8 Hz, 1H), 4.93 (dd, J=10.3, 5.4 Hz, 1H), 4.72-4.55 (m, 1H), 4.29 (q, J=7.0 Hz, 1H), 3.36-3.32 (m, 3H), 3.23 (s, 3H), 2.72-2.57 (m, 4H), 2.49 (s, 3H), 1.37 (d, J=7.0 Hz, 3H); ESMS(M+H)=422.2.

Compound 307: (7S)-2-((trans-3-((4-fluorophenyl)thio)cyclobutyl)amino)-4,5,7,8-tetramethyl-7,8-dihydropteridin-6(5H)-one The compound was prepared by reaction of intermediates A-3 and B-109 to provide the title product. 1H NMR (300 MHz, Methanol-d4) δ 7.43-7.26 (m, 2H), 7.14-7.00 (m, 2H), 4.62 (p, J=7.6 Hz, 1H), 4.29 (q, J=7.0 Hz, 1H), 3.98-3.80 (m, 1H), 3.31 (s, 3H), 3.21 (s, 3H), 2.62 (ddd, J=23.7, 13.4, 8.3 Hz, 2H), 2.46 (s, 3H), 2.45-2.34 (m, 2H), 1.36 (d, J=7.0 Hz, 3H); ESMS(M+1)=402.17.

Compound 320: (7S)-4,5,7,8-tetramethyl-2-((trans-3-((4(trifluoromethyl)phenyl)thio)-cyclobutyl)-amino)-7,8-dihydropteridin-6(5H)-one The compound was prepared by reaction of intermediates A-3 and B-111 to provide the title product. 1H NMR (400 MHz, Methanol-d4) δ 7.55 (d, J=8.3 Hz, 2H), 7.34 (t, J=8.5 Hz, 2H), 5.07 (d, J=61.3 Hz, 3H), 4.72 (p, J=7.4 Hz, 1H), 4.34-4.21 (m, 1H), 4.17-4.01 (m, 1H), 3.33 (s, 3H), 3.21 (s, 3H), 2.85-2.69 (m, 2H), 2.52-2.47 (m, 4H), 2.47-2.38 (m, 1H), 1.37 (d, J=7.0 Hz, 3H); ESMS(M+1)=452.2.

Compound 330: (7S)-4,5,7,8-tetramethyl-2-((trans-3-((3,4,5-trifluorophenyl)thio)-cyclobutyl)amino)-7,8-dihydropteridin-6(5H)-one The compound was prepared by reaction of intermediates A-3 and B-114 to provide the title product. 1H NMR (400 MHz, Methanol-d4) δ 7.10-6.95 (m, 2H), 4.71 (p, J=7.5 Hz, 1H), 4.39-4.26 (m, 1H), 4.14-3.98 (m, 1H), 3.35 (s, 3H), 3.25 (s, 3H), 2.88-2.68 (m, 2H), 2.52 (d, J=11.4 Hz, 3H), 2.50-2.38 (m, 2H), 1.39 (d, J=6.9 Hz, 3H); ESMS(M+1)=438.23.

2G. Preparation of Compounds of Table 9B

General Procedure for Compounds Prepared in Table 9B

Compound 246 (115 mg, 0.28 mmol), an alkyl halide (0.31 mmol), and potassium carbonate (150 mg, 1.08 mmol) were taken into DMF (5 mL) and stirred at room temperature for 18 hours. TFA (125 μL, 1.622 mmol) was added. Purification by reverse MPLC: 100 g C18 column, eluting with 10-100% acetonitrile in water (0.1% TFA), desired fractions were combined and dried to provide a product. The recovered the product was neutralized by passing through the product from PL-HCO3 MPSPE cartridge (500 mg/6 mL tube capacity 0.9 mmol) to provide the desired product.

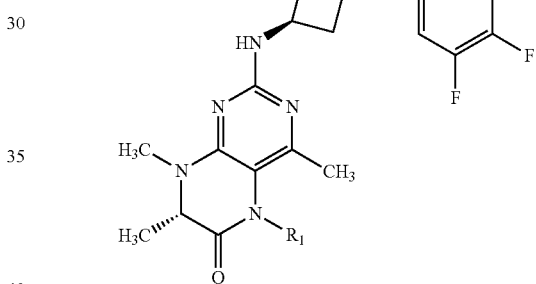

TABLE 9B

| Compound # | $R_1$ |
|---|---|
| 312 | Et |
| 381 | —CH₂CH₂F |
| 313 | —CH₂CF₃ |
| 327 | —CD₃ |
| 328 | —CD₂CD₃ |

Compound 312: (7S)-5-ethyl-4,7,8-trimethyl-2-((trans-3-(3,4,5-trifluorophenoxy)-cyclobutyl)amino)-7,8-dihydropteridin-6(5H)-one 1H NMR (300 MHz, CDCl₃) δ 6.48-6.36 (m, 2H), 4.76 (tt, J=7.0, 3.9 Hz, 1H), 4.57 (td, J=8.0, 5.8 Hz, 1H), 4.21 (dq, J=14.4, 7.2 Hz, 1H), 3.99 (q, J=6.9 Hz, 1H), 3.60 (dd, J=14.0, 7.0 Hz, 1H), 3.02 (s, 3H), 2.70-2.54 (m, 2H), 2.47 (td, J=6.3, 3.7 Hz, 2H), 2.36 (s, 3H), 1.25-1.07 (m, 6H); ESMS (M+H)=436.13.

Compound 381: (7S)-5-(2-fluoroethyl)-4,7,8-trimethyl-2-((trans-3-(3,4,5-trifluorophenoxy)-cyclobutyl)-amino)-7,8-dihydropteridin-6(5H)-one 1H NMR (300 MHz, CDCl₃) δ 6.42 (ddt, J=9.6, 5.7, 1.0 Hz, 2H), 5.09 (d, J=6.1 Hz, 1H), 4.81-4.42 (m, 5H), 4.09-

3.76 (m, 2H), 3.02 (s, 3H), 2.70-2.40 (m, 4H), 2.35 (s, 3H), 1.21 (d, J=6.9 Hz, 3H); ESMS (M+H)=454.09.

Compound 313: (7S)-4,7,8-trimethyl-5-(2,2,2-trifluoroethyl)-2-((trans-3-(3,4,5-trifluorophenoxy)cyclobutyl)-amino)-7,8-dihydropteridin-6(5H)-one 1H NMR (300 MHz, CDCl₃) δ 6.43 (ddt, J=9.5, 5.7, 1.0 Hz, 2H), 5.19 (dq, J=15.6, 9.1 Hz, 1H), 5.03 (s, 1H), 4.76 (tt, J=7.1, 3.8 Hz, 1H), 4.58 (td, J=8.1, 5.7 Hz, 2H), 4.24-4.02 (m, 2H), 3.03 (s, 3H), 2.63 (dddd, J=12.4, 7.9, 3.9, 2.0 Hz, 2H), 2.53-2.39 (m, 2H), 2.34 (s, 3H), 1.21 (d, J=7.0 Hz, 3H); ESMS (M+H)=490.19.

Compound 327: (7S)-4,7,8-trimethyl-5-(methyl-d3)-2-((trans-3-(3,4,5-trifluorophenoxy)-cyclobutyl)-amino)-7,8-dihydropteridin-6(5H)-one 1H NMR (400 MHz, CDCl₃) δ 6.46-6.37 (m, 2H), 4.76 (tt, J=7.0, 3.8 Hz, 1H), 4.57 (q, J=7.6 Hz, 1H), 4.11-4.00 (m, 1H), 3.06 (d, J=1.1 Hz, 3H), 2.61 (td, J=8.7, 4.3 Hz, 2H), 2.50 (s, 2H), 2.41 (d, J=1.1 Hz, 3H), 1.26 (dd, J=7.0, 1.1 Hz, 3H); ESMS (M+H)=425.24.

Compound 328: (7S)-5-(ethyl-d5)-4,7,8-trimethyl-2-((trans-3-(3,4,5-trifluorophenoxy)-cyclobutyl)amino)-7,8-dihydropteridin-6(5H)-one 1H NMR (400 MHz, CDCl₃) δ 6.46-6.37 (m, 2H), 4.77 (dq, J=6.8, 3.5 Hz, 1H), 4.58 (td, J=8.0, 5.8 Hz, 1H), 4.01 (q, J=6.9 Hz, 1H), 3.05 (s, 3H), 2.69-2.56 (m, 2H), 2.55-2.42 (m, 2H), 2.39 (s, 3H), 1.23 (d, J=6.9 Hz, 3H); ESMS (M+H)=441.22.

2I. Preparation of Compounds of Table 10

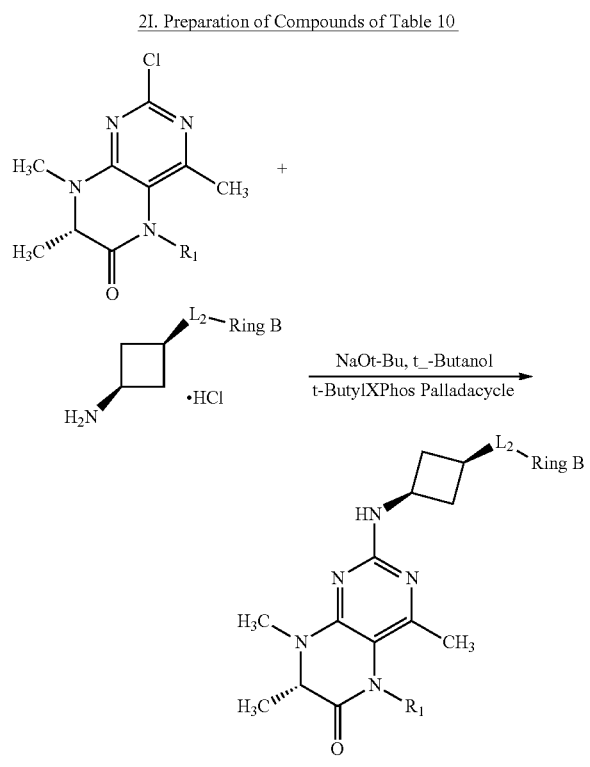

2I. Preparation of Compounds of Table 10

TABLE 10

| Compound # | L₂-Ring B | R₁ | M + 1 | Synthetic Method |
|---|---|---|---|---|
| Comp 243 | O—(4-F-phenyl) | H | 372.28 | B |
| Comp 247 | O—(3,4,5-triF-phenyl) | H | 408.29 | B |
| Comp 304 | S—(4-F-phenyl) | H | 388.2 | A |
| Comp 305 | S—(4-F-phenyl) | Me | 402.22 | B |
| Comp 321 | S—(4-CF₃-phenyl) | H | 438.16 | A |
| Comp 322 | S—(4-CF₃-phenyl) | Me | 450.98 | B |
| Comp 332 | S—(3,4,5-triF-phenyl) | H | 424.19 | A |
| Comp 331 | S—(3,4,5-triF-phenyl) | Me | 438.23 | B |
| Comp 336 | S—(4-OCF₃-phenyl) | H | 454.26 | A |
| Comp 348 | S—(4-OCF₃-phenyl) | Me | 468.3 | B |

Compound 243: (7S)-2-((cis-3-(4-fluorophenoxy)cyclobutyl)amino)-4,7,8-trimethyl-7,8-dihydropteridin-6(5H)-one The compound was prepared by procedure Method B via reaction of intermediates A-2 and B-128 to provide the title compound. 1H NMR (300 MHz, Methanol-d4) δ 7.00 (t, J=8.7 Hz, 2H), 6.85 (dd, J=9.0, 4.3 Hz, 2H), 4.57-4.41 (m, 1H), 4.38-4.13 (m, 2H), 3.26 (d, J=11.7 Hz, 3H), 3.05 (dd, J=6.7, 4.2 Hz, 2H), 2.35 (s, 3H), 2.24 (dd, J=18.8, 8.5 Hz, 2H), 1.55 (d, J=6.9 Hz, 3H); ESMS(M+1)=372.28.

Compound 247: (7S)-4,7,8-trimethyl-2-((cis-3-(3,4,5-trifluorophenoxy)cyclobutyl)amino)-7,8-dihydropteridin-6(5H)-one The compound was prepared by procedure Method B via reaction of intermediates A-2 and B-129 to provide the title compound. 1H NMR (300 MHz, Methanol-d4) δ 6.73-6.56 (m, 2H), 4.51 (p, J=6.9 Hz, 1H), 4.30 (q, J=6.9 Hz, 1H), 4.18 (dd, J=16.0, 8.1 Hz, 1H), 3.26 (s, 3H), 3.12-2.90 (m, 2H), 2.30 (s, 3H), 2.21 (dt, J=12.3, 8.5 Hz, 2H), 1.53 (d, J=6.9 Hz, 3H), 0.60-0.58 (m, 1H); ESMS(M+1)=408.29.

Compound 304: (7S)-2-((cis-3-((4-fluorophenyl)thio)cyclobutyl)amino)-4,7,8-trimethyl-7,8-dihydropteridin-6(5H)-one The compound was prepared by by procedure Method A via reaction of intermediates A-2 and B-130 to provide the title product. 1H NMR (300 MHz, Methanol-d4) δ 7.41-7.23 (m, 2H), 7.05 (t, J=8.6 Hz, 2H), 4.46-4.22 (m, 2H), 3.63 (d, J=11.9 Hz, 3H), 3.62-3.46 (m, 1H), 3.24 (s, 3H), 2.99-2.78 (m, 2H), 2.32 (s, 3H), 2.11 (dd, J=20.3, 9.2 Hz, 2H), 1.52 (d, J=6.8 Hz, 3H).

Compound 305: (7S)-2-((cis-3-((4-fluorophenyl)thio)cyclobutyl)amino)-4,5,7,8-tetramethyl-7,8-dihydropteridin-6(5H)-one The compound was prepared by procedure Method B via reaction of intermediates A-3 and B-130 to provide the title product. 1H NMR (300 MHz, Methanol-d4) δ 7.35 (dd, J=8.5, 5.3 Hz, 2H), 7.06 (t, J=8.7 Hz, 2H), 4.48-4.33 (m, 1H), 4.30 (q, J=6.9 Hz, 1H), 3.70-3.49 (m, 1H), 3.32 (s, 3H), 3.24 (s, 3H), 2.98-2.82 (m, 2H), 2.50 (s, 3H), 2.21-2.04 (m, 2H), 1.37 (d, J=6.9 Hz, 3H).

Compound 321: (7S)-4,7,8-trimethyl-2-((cis-3-((4-(trifluoromethyl)phenyl)thio)cyclobutyl)amino)-7,8-dihydropteridin-6(5H)-one The compound was prepared by procedure Method A via reaction of intermediates A-2 and B-131 to provide the title product. 1H NMR (400 MHz, CDCl₃) δ 8.12 (s, 1H), 7.43 (d, J=8.2 Hz, 2H), 7.25-7.20 (m, 2H), 5.02 (s, 1H), 4.42-4.29 (m, 1H), 4.05-3.94 (m, 1H), 3.61-3.43 (m, 1H), 2.98 (s, 3H), 2.96-2.89 (m, 2H), 2.14 (s, 3H), 2.02-1.89 (m, 4H), 1.33 (d, J=6.9 Hz, 3H).

Compound 322: (7S)-4,5,7,8-tetramethyl-2-((cis-3-((4-(trifluoromethyl)phenyl)thio)cyclobutyl)amino)-7,8-dihydropteridin-6(5H)-one The compound was prepared by procedure Method B via reaction of intermediates A-3 and B-131 to provide the title product. 1H NMR (400 MHz, Methanol-d4) δ 7.55 (d, J=8.3 Hz, 2H), 7.37 (t, J=8.7 Hz, 2H), 4.93 (s, 4H), 4.47 (p, J=8.5 Hz, 1H), 4.29 (q, J=7.0 Hz, 1H), 3.88-3.71 (m, 1H), 3.35-3.31 (m, 3H), 3.26 (s, 3H), 3.11-2.94 (m, 2H), 2.48 (s, 3H), 2.28-2.12 (m, 2H), 1.37 (d, J=7.0 Hz, 3H).

Compound 332: (7S)-4,7,8-trimethyl-2-((cis-3-((3,4,5-trifluorophenyl)thio)cyclobutyl)amino)-7,8-dihydropteridin-6(5H)-one The compound was prepared by procedure Method A via reaction of intermediates A-2 and B-132 to provide the title product. 1H NMR (400 MHz, Methanol-d4) δ 7.12-7.00 (m, 2H), 4.49-4.36 (m, 1H), 4.30 (q, J=6.9 Hz, 1H), 3.80-3.65 (m, 1H), 3.25 (s, 3H), 3.00 (dt, J=11.3, 7.2 Hz, 2H), 2.30 (s, 3H), 2.14 (dd, J=20.2, 9.1 Hz, 2H), 1.52 (d, J=6.9 Hz, 3H).

Compound 331: (7S)-4,5,7,8-tetramethyl-2-((cis-3-((3,4,5-trifluorophenyl)thio)cyclobutyl)amino)-7,8-dihydropteridin-6(5H)-one The compound was prepared by procedure Method B via reaction of intermediates A-3 and B-132 to provide the title product. 1H NMR (400 MHz, Methanol-d4) δ 7.05 (dd, J=7.8, 6.7 Hz, 2H), 4.57-4.42 (m, 1H), 4.40-4.26 (m, 1H), 3.87-3.69 (m, 1H), 3.35 (s, 3H), 3.27 (d, J=12.2 Hz, 3H), 3.03 (s, 2H), 2.54 (s, 3H), 2.29-2.12 (m, 2H), 1.40 (d, J=6.8 Hz, 3H).

Compound 336: (7S)-4,7,8-trimethyl-2-((cis-3-((4-(trifluoromethoxy)phenyl)thio)cyclobutyl)amino)-7,8-dihydropteridin-6(5H)-one The compound was prepared by procedure Method A via reaction of intermediates A-2 and B-133 to provide the title product. 1H NMR (400 MHz, CDCl₃) δ 9.70 (s, 1H), 7.26 (dd, J=11.7, 4.8 Hz, 2H), 7.10 (d, J=8.7 Hz, 2H), 5.15 (d, J=7.7 Hz, 1H), 4.43-4.27 (m, 1H), 4.02 (q, J=6.8 Hz, 1H), 3.55-3.39 (m, 1H), 2.97 (d, J=23.2 Hz, 3H), 2.90 (tt, J=27.9, 13.9 Hz, 2H), 2.24 (s, 3H), 1.95 (dd, J=20.7, 9.3 Hz, 2H), 1.36 (d, J=6.8 Hz, 3H).

Compound 348: (7S)-4,5,7,8-tetramethyl-2-((cis-3-((4-(trifluoromethoxy)phenyl)thio)cyclobutyl)amino)-7,8-dihydropteridin-6(5H)-one The compound was prepared by procedure Method B via reaction of intermediates A-3 and B-133 to provide the title product. 1H NMR (400 MHz, Methanol-d4) δ 7.45-7.28 (m, 2H), 7.26-7.11 (m, 2H), 4.47-4.34 (m, 1H), 4.29 (q, J=7.0 Hz, 1H), 3.69 (tt, J=9.3, 7.4 Hz, 1H), 3.33-3.31 (m, 4H), 3.24 (s, 3H), 3.05-2.86 (m, 2H), 2.46 (s, 3H), 2.24-2.06 (m, 2H), 1.37 (d, J=7.0 Hz, 3H).

2J. Preparation of Compounds of Table 11

The compounds were prepared in a similar manner as those for the compounds of Table 10 above.

TABLE 11

| Compound # | R₅ | Method |
|---|---|---|
| 240 | 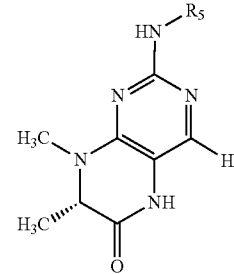 | B |

TABLE 11-continued

| Compound # | R5 | Method |
|---|---|---|
| 241 | (trans-cyclobutyl-O-4-fluorophenyl) | B |
| 249 | (trans-cyclobutyl-O-3,4,5-trifluorophenyl) | B |
| 251 | (trans-cyclobutyl-O-3,4-difluorophenyl) | B |

Compound 240: (7S)-2-((trans-3-(4-fluorophenoxy)cyclobutyl)amino)-7,8-dimethyl-7,8-dihydropteridin-6(5H)-one The compound was prepared by procedure Method B via reaction of intermediate A-1 and B-100 to provide the title product. 1H NMR (300 MHz, Methanol-d4) δ 7.24 (s, 1H), 7.06-6.94 (m, 2H), 6.87-6.75 (m, 2H), 4.87-4.78 (m, 1H), 4.51 (s, 1H), 4.33 (q, J=6.9 Hz, 1H), 3.23 (s, 3H), 2.58 (dd, J=12.1, 6.5 Hz, 4H), 1.56 (d, J=6.9 Hz, 3H); ESMS(M+1)=358.28.

Compound 241: (7S)-2-((cis-3-(4-fluorophenoxy)cyclobutyl)amino)-7,8-dimethyl-7,8-dihydropteridin-6(5H)-one The compound was prepared by procedure Method B via reaction of intermediate A-1 and B-128 to provide the title product. 1H NMR (300 MHz, Methanol-d4) δ 7.23 (s, 1H), 6.99 (t, J=8.7 Hz, 2H), 6.84 (dd, J=9.1, 4.3 Hz, 2H), 4.50 (p, J=6.8 Hz, 1H), 4.34 (q, J=6.8 Hz, 1H), 4.14 (s, 1H), 3.25 (d, J=9.2 Hz, 3H), 3.04 (d, J=5.4 Hz, 2H), 2.19 (dd, J=19.0, 8.7 Hz, 2H), 1.57 (d, J=6.9 Hz, 3H); ESMS(M+1)=358.29.

Compound 249: (7S)-7,8-dimethyl-2-((trans-3-(3,4,5-trifluorophenoxy)cyclobutyl)amino)-7,8-dihydropteridin-6(5H)-one The compound was prepared by procedure Method B via reaction of intermediate A-1 and B-101 to provide the title product. 1H NMR (300 MHz, EtOD) δ 7.23 (s, 1H), 6.70-6.54 (m, 2H), 4.85 (dd, J=8.7, 3.5 Hz, 1H), 4.53 (s, 1H), 4.34 (q, J=6.9 Hz, 1H), 3.24 (s, 3H), 2.61 (dd, J=6.9, 5.4 Hz, 4H), 1.57 (d, J=7.0 Hz, 3H); ESMS(M+1)=394.29.

Compound 251: (7S)-4,7,8-trimethyl-2-((trans-3-(3,4-difluorophenoxy)cyclobutyl)amino)-7,8-dihydropteridin-6(5H)-one The compound was prepared by procedure Method B via reaction of intermediate A-1 and B-102 to provide the title product. 1H NMR (300 MHz, Methanol-d4) δ 7.23 (s, 1H), 7.16 (dd, J=19.4, 9.3 Hz, 1H), 6.76 (ddd, J=12.3, 6.6, 2.8 Hz, 1H), 6.62 (dd, J=6.4, 2.6 Hz, 1H), 4.86 (d, J=5.0 Hz, 1H), 4.55 (d, J=22.0 Hz, 1H), 4.34 (q, J=6.7 Hz, 1H), 3.24 (s, 3H), 2.60 (t, J=5.9 Hz, 4H), 1.57 (d, J=6.8 Hz, 3H); ESMS(M+1)=376.24.

2K. Preparation of Compounds of Table 12

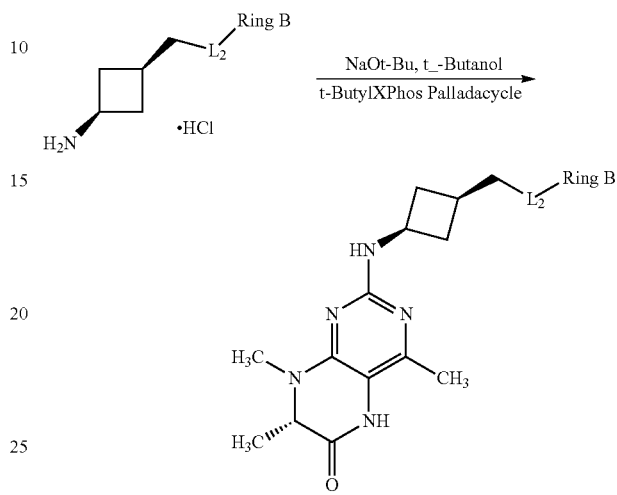

TABLE 12

| Compound | L2-RingB | M + 1 |
|---|---|---|
| Comp 257 | O-(2,3,4-trifluorophenyl) | 422.29 |
| Comp 271 | O-(3,4-difluorophenyl) | 404.29 |
| Comp 261 | O-(4-fluorophenyl) | 386.33 |
| Comp 277 | O-(2-cyano-4-fluorophenyl) | 411.31 |
| Comp 263 | O-(5-fluoropyridin-3-yl) | 387.32 |
| Comp 270 | O-(6-fluoropyridin-3-yl) | 387.36 |

TABLE 12-continued

| Compound | L₂-RingB | M + 1 |
|---|---|---|
| Comp 275 | (pyrazole with N-attachment and CF₃) | 410.27 |

Compound 257: (7S)-4,7,8-Trimethyl-2-((cis-3-((3,4,5-trifluorophenoxy)methyl)cyclobutyl)-amino)-7,8-dihydropteridin-6(5H)-one The compound was prepared by general procedure Method A via reaction of intermediates A-2 and B-134 to afford the title product. 1H NMR (300 MHz, Methanol-d4) δ 6.72 (dt, J=13.5, 6.7 Hz, 2H), 4.46-4.37 (m, 1H), 4.31 (q, J=6.9 Hz, 1H), 3.95 (d, J=5.1 Hz, 2H), 3.26 (s, 3H), 2.66-2.45 (m, 3H), 2.34 (s, 3H), 2.09-1.91 (m, 2H), 1.54 (d, J=6.9 Hz, 3H); ESMS(M+1)=422.29.

Compound 271: (7S)-2-((cis-3-((3,4-difluorophenoxy)methyl)cyclobutyl)amino)-4,7,8-trimethyl-7,8-dihydropteridin-6(5H)-one The compound was prepared by general procedure Method A via reaction of intermediates A-2 and B-138 to afford the title product. 1H NMR (300 MHz, Methanol-d4) δ 7.25-7.05 (m, 1H), 6.93-6.79 (m, 1H), 6.77-6.61 (m, 1H), 4.47-4.33 (m, 1H), 4.28 (dd, J=13.8, 6.9 Hz, 1H), 3.93 (d, J=4.4 Hz, 2H), 3.24 (s, 3H), 2.68-2.43 (m, 3H), 2.32 (d, J=16.1 Hz, 3H), 2.05-1.88 (m, 2H), 1.52 (d, J=6.0 Hz, 3H); ESMS(M+1)=404.29.

Compound 261: (7S)-2-((cis-3-((4-fluorophenoxy)methyl)cyclobutyl)amino)-4,7,8-trimethyl-7,8-dihydropteridin-6(5H)-one The compound was prepared by general procedure Method A via reaction of intermediates A-2 and B-135 to afford the title product. 1H NMR (300 MHz, Methanol-d4) δ 5.51-5.30 (m, 4H), 2.90-2.81 (m, 1H), 2.76 (q, J=7.0 Hz, 1H), 2.40 (d, J=5.4 Hz, 2H), 1.71 (s, 3H), 1.14-0.92 (m, 3H), 0.78 (s, 3H), 0.54-0.39 (m, 2H), −0.01 (d, J=6.9 Hz, 3H); ESMS(M+1)=386.33.

Compound 277: 5-fluoro-2-((cis-3-(((7S)-4,7,8-trimethyl-6-oxo-5,6,7,8-tetrahydropteridin-2-yl)amino)cyclobutyl)methoxy)benzonitrile The compound was prepared by general procedure Method A via reaction of intermediates A-2 and B-140 to afford the title product. 1H NMR (300 MHz, CDCl₃) δ 8.66 (s, 1H), 7.29-7.20 (m, 2H), 6.91 (dd, J=9.0, 4.1 Hz, 1H), 4.92 (d, J=7.8 Hz, 1H), 4.49-4.30 (m, 1H), 4.08 (dt, J=10.0, 5.0 Hz, 1H), 4.02 (d, J=5.5 Hz, 2H), 3.05 (s, 3H), 2.79-2.42 (m, 4H), 2.23 (s, 3H), 1.95-1.74 (m, 2H), 1.40 (d, J=6.9 Hz, 3H); ESMS(M+1)=411.31.

Compound 263: (7S)-2-((cis-3-(((5-fluoropyridin-3-yl)oxy)methyl)cyclobutyl)amino)-4,7,8-trimethyl-7,8-dihydropteridin-6(5H)-one The compound was prepared by general procedure Method A via reaction of intermediates A-2 and B-136 to afford the title product. 1H NMR (300 MHz, Methanol-d4) δ 8.66 (s, 2H), 8.30 (d, J=9.6 Hz, 1H), 4.44 (d, J=25.4 Hz, 1H), 4.32 (s, 3H), 3.27 (s, 3H), 2.66 (s, 3H), 2.35 (s, 4H), 2.10 (d, J=5.1 Hz, 2H), 1.54 (d, J=6.4 Hz, 3H).

Compound 270: (7S)-2-((cis-3-(((6-fluoropyridin-3-yl)oxy)methyl)cyclobutyl)amino)-4,7,8-trimethyl-7,8-dihydropteridin-6(5H)-one The compound was prepared by general procedure Method A via reaction of intermediates A-2 and B-137 to afford the title product. 1H NMR (300 MHz, Methanol-d4) δ 7.82 (d, J=1.0 Hz, 1H), 7.63-7.45 (m, 1H), 6.98 (dd, J=8.8, 2.6 Hz, 1H), 4.38 (dd, J=15.4, 7.7 Hz, 1H), 4.35-4.20 (m, 1H), 4.03 (d, J=4.5 Hz, 2H), 3.25 (s, 3H), 2.72-2.47 (m, 3H), 2.30 (s, 3H), 1.99 (dd, J=17.5, 9.0 Hz, 2H), 1.52 (d, J=6.8 Hz, 3H); ESMS(M+1)=387.36.

Compound 275: (7S)-4,7,8-trimethyl-2-((cis-3-((5-(trifluoromethyl)-1H-pyrazol-1-yl)methyl)cyclobutyl)amino)-7,8-dihydropteridin-6(5H)-one The compound was prepared by general procedure Method A via reaction of intermediates A-2 and B-139 to afford the title product. 1H NMR (300 MHz, CDCl₃) δ 9.62 (s, 1H), 7.36 (d, J=1.2 Hz, 1H), 6.47 (d, J=2.0 Hz, 1H), 4.94 (d, J=7.5 Hz, 1H), 4.28 (dt, J=14.8, 7.4 Hz, 1H), 4.15 (d, J=5.9 Hz, 2H), 3.98 (dd, J=16.7, 10.0 Hz, 1H), 2.98 (s, 3H), 2.62-2.38 (m, 3H), 2.20 (s, 3H), 1.72-1.50 (m, 2H), 1.32 (t, J=9.9 Hz, 3H); ESMS(M+1)=410.27.

2L. Preparation of Compounds of Table 13

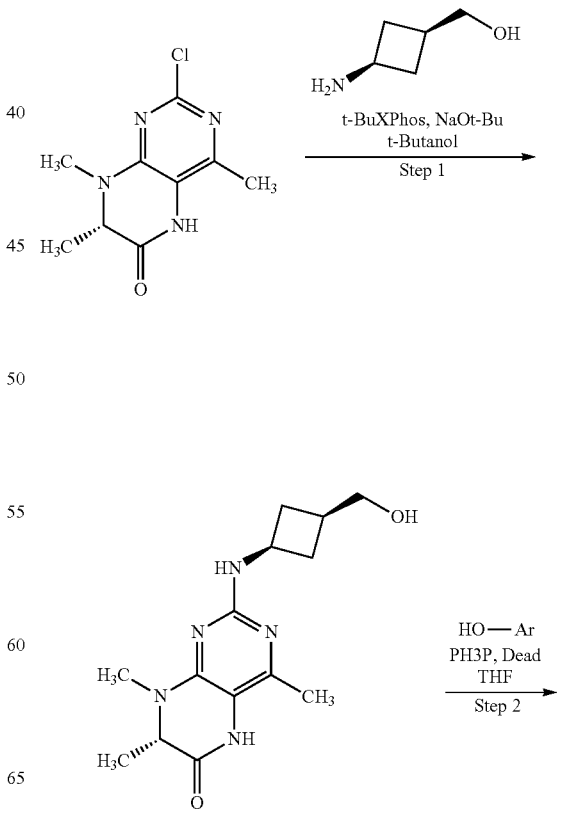

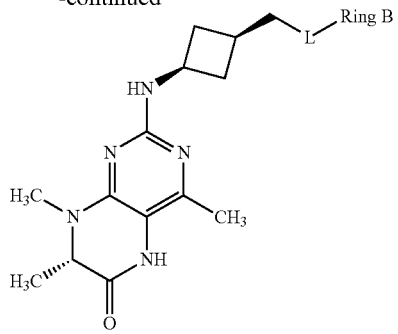

Compound 284: (7S)-2-((cis-3-((3,5-difluoro-4-methoxyphenoxy)methyl)cyclobutyl)amino)-4,7,8-trimethyl-7,8-dihydropteridin-6(5H)-one Step 1: (7S)-2-((cis-3-(hydroxymethyl)cyclobutyl)amino)-4,7,8-trimethyl-7,8-dihydropteridin-6(5H)-one (7S)-2-chloro-4,7,8-trimethyl-5,7-dihydropteridin-6-one (2.96 g, 13.05 mmol), cis-3-aminocyclobutyl)methanol hydrochloride (1.796 g, 13.05 mmol) and tBuXPhos palladacycle (358.5 mg, 0.5220 mmol) were taken into t-butanol (50 mL) and degassed. A 2M solution of sodium t-butoxide (23 mL, 45.70 mmol) was added to the mixture under nitrogen. After stirring at room temperature for 2 hours, ethyl acetate (100 ml) and water was added to the reaction mixture. The organic layers separated and the aqueous extracted with ethyl acetate (3×50 ml). The combined extracts were dried over anhydrous sodium sulfate, filtered, and evaporated in vacuo to afford the crude product. The crude product was purified by column chromatography (SiO$_2$) eluting with a gradient of 0-20% methanol in dichloromethane to afford 1.07 g (25% yield) of the title product. 1H NMR (300 MHz, CDCl$_3$) δ 9.30 (s, 1H), 9.01 (s, 1H), 5.04 (t, J=10.9 Hz, 1H), 4.39-4.24 (m, 1H), 4.05 (q, J=6.8 Hz, 1H), 3.60 (d, J=5.9 Hz, 2H), 3.04 (s, 3H), 2.87-2.57 (m, 2H), 2.59-2.40 (m, 3H), 2.23 (s, 4H), 1.79-1.58 (m, 2H), 1.38 (d, J=6.8 Hz, 3H). ESMS(M+1)=292.24.

Step 2: (7S)-2-((cis-3-((3,5-difluoro-4-methoxyphenoxy)methyl)cyclobutyl)amino)-4,7,8-trimethyl-7,8-dihydropteridin-6(5H)-one A mixture of (7S)-2-((cis-3-(hydroxymethyl)cyclobutyl)amino)-4,7,8-trimethyl-7,8-dihydropteridin-6(5H)-one (160 mg, 0.5 mmol), 3,5-difluoro-4-methoxyphenol (166 mg, 1.04 mmol), and triphenylphosphine 272 mg, 1.04 mmol) was taken into 5 ml of THF. Diethylazodicarboxylate (1.038 mmol) was added to the mixture dropwise then heated to 50° C. for 12 hours. The reaction was evaporated in vacuo and the resulting residue purified by column chromatography (C18 MPLC; 0-100% acetonitrile/water(0.1% TFA)). The desired fractions were lyophilized to provide 45 mg (18% yield) of the title product. 1H NMR (300 MHz, Methanol-d4) δ 6.66-6.50 (m, 2H), 4.46-4.34 (m, 1H), 4.28 (q, J=6.9 Hz, 1H), 3.92 (d, J=5.3 Hz, 2H), 3.84 (s, 3H), 3.22 (d, J=12.4 Hz, 3H), 2.63-2.43 (m, 3H), 2.29 (s, 3H), 1.96 (dd, J=17.7, 9.0 Hz, 2H), 1.52 (d, J=6.9 Hz, 3H); ESMS(M+1)=434.26.

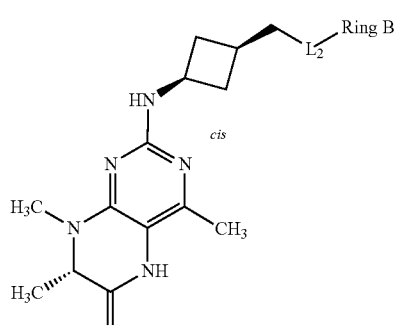

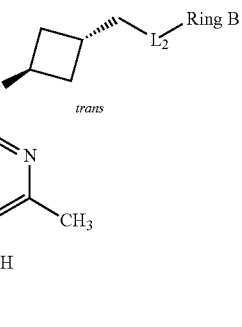

TABLE 13

| Comp # | L$_2$-Ring B | M + 1 |
|---|---|---|
| Comp 284 | ![3,5-difluoro-4-methoxyphenoxy] | 434.26 |
| Comp 282 | ![2-chloro-4-fluorophenoxy] | 420.18 |
| Comp 281 | ![2,3-difluorophenoxy with F] | 422.2 |
| Comp 285 | ![3,4,5-trifluorophenoxy] | 422.37 |
| Comp 258 (trans) | ![3,4,5-trifluorophenoxy] | |

TABLE 13-continued

| Comp # | L₂-Ring B | M + 1 |
|---|---|---|
| Comp 367 | 3-fluoro-2-chloro-5-pyridyloxy | 421.26 |
| Comp 369 (trans) | 4-(trifluoromethyl)-2-pyridyloxy | 437.29 |
| Comp 366 | 5-chloro-3-pyridyloxy | 403.25 |
| Comp 365 | 2-methyl-4-(trifluoromethyl)-6-pyridyloxy | 451.29 |
| Comp 364 | 6-(trifluoromethyl)-3-pyridyloxy | 437.29 |
| Comp 363 | 5-(trifluoromethyl)-3-pyridyloxy | 437.29 |
| Comp 356 | 5-(trifluoromethyl)-2-pyridyloxy | 437.29 |
| Comp 283 | 3-ethynylphenoxy | 392.18 |
| Comp 280 | 3,4,5-trimethoxyphenoxy | 458.17 |
| Comp 279 | 4-fluoro-1H-pyrazol-1-yl (N–N linked) | 360.17 |

Compounds 282, 281, 285, 258, 367, 369, 366, 365, 364, 363, 356, 283, 280, and 279 were prepared in a similar manner by reaction of either (7S)-2-((trans-3-(hydroxymethyl)cyclobutyl)amino)-4,7,8-trimethyl-7,8-dihydropteridin-6(5H)-one or (7S)-2-((cis-3-(hydroxymethyl)cyclobutyl)amino)-4,7,8-trimethyl-7,8-dihydropteridin-6(5H)-one (see Compound 284, Step 1) and a phenol or pyrazole derivative as reported in the procedure for Compound 284.

Compound 282: (7S)-2-((cis-3-((2-chloro-4-fluorophenoxy)methyl)cyclobutyl)amino)-4,7,8-trimethyl-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 2-chloro-4-fluorophenol to provide the title product. 1H NMR (300 MHz, Methanol-d4) δ 7.17 (dd, J=8.2, 2.8 Hz, 1H), 7.09-6.92 (m, 2H), 4.43-4.33 (m, 1H), 4.28 (q, J=7.0 Hz, 1H), 4.01 (d, J=4.8 Hz, 2H), 3.22 (d, J=10.9 Hz, 3H), 2.66-2.51 (m, 3H), 2.29 (s, 3H), 2.12-1.96 (m, 2H), 1.52 (d, J=6.9 Hz, 3H); ESMS(M+1)=420.18.

Compound 281: (7S)-4,7,8-trimethyl-2-((cis-3-((2,3,4-trifluorophenoxy)methyl)cyclobutyl)-amino)-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 2,3,4-trifluorophenol to provide the title product. 1H NMR (300 MHz, Methanol-d4) δ 7.08-6.94 (m, 1H), 6.95-6.80 (m, 1H), 4.37 (d, J=8.0 Hz, 1H), 4.29 (dd, J=13.9, 6.9 Hz, 1H), 4.05 (d, J=4.9 Hz, 2H), 3.25 (s, 3H), 2.68-2.51 (m, 3H), 2.29 (s, 3H), 1.97 (d, J=8.3 Hz, 2H), 1.52 (d, J=6.9 Hz, 3H). ESMS(M+1)=422.2.

Compound 285: (7S)-4,7,8-trimethyl-2-((cis-3-((2,4,5-trifluorophenoxy)methyl)cyclobutyl)-amino)-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 2,4,5-trifluorophenol to provide the title product. 1H NMR (300 MHz, Methanol-d4) δ 7.14 (ddt, J=15.6, 12.0, 7.8 Hz, 2H), 4.47-4.34 (m, 1H), 4.29 (q, J=6.9 Hz, 1H), 4.02 (d, J=5.2 Hz, 2H), 3.24 (s, 3H), 2.70-2.43 (m, 4H), 2.29 (s, 3H), 2.06-1.88 (m, 2H), 1.52 (d, J=6.9 Hz, 3H). ESMS(M+1)=422.37.

Compound 258: (7S)-4,7,8-trimethyl-2-((trans-3-((3,4,5-trifluorophenoxy)methyl)-cyclobutyl)amino)-7,8-dihydropteridin-6(5H)-one The compound was prepared by reaction of (7S)-2-((trans-3-(hydroxymethyl)cyclobutyl)amino)-4,7,8-trimethyl-7,8-dihydropteridin-6(5H)-one and 3,4,5-trifluorophenol to provide the title product. 1H NMR (300 MHz, Methanol-d4) δ 6.72 (dt, J=13.5, 6.7 Hz, 2H), 4.46-4.37 (m, 1H), 4.31 (q, J=6.9 Hz, 1H), 3.95 (d, J=5.1 Hz, 2H), 3.26 (s, 3H), 2.66-2.45 (m, 3H), 2.34 (s, 3H), 2.09-1.91 (m, 2H), 1.54 (d, J=6.9 Hz, 3H); ESMS (M+1)=422.34

Compound 367: (7S)-2-((cis-3-(((6-chloro-5-fluoro-pyridin-3-yl)oxy)methyl)cyclobutyl)amino)-4,7,8-trimethyl-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 3-hydroxy-5-fluoro-6-chloropyridine to provide the title product. 1H NMR (400 MHz, CDCl$_3$) δ 9.04 (s, 1H), 7.86 (t, J=6.2 Hz, 1H), 6.98 (dd, J=9.4, 2.5 Hz, 1H), 4.87 (d, J=7.5 Hz, 1H), 4.39-4.23 (m, 1H), 4.05-3.92 (m, 1H), 3.90 (t, J=5.0 Hz, 2H), 2.95 (d, J=12.5 Hz, 3H), 2.60-2.48 (m, 2H), 2.48-2.34 (m, 1H), 2.17 (s, 3H), 1.80-1.62 (m, 2H), 1.31 (d, J=6.8 Hz, 3H). ESMS (M+1)=421.26.

Compound 369: (7S)-4,7,8-trimethyl-2-((trans-3-(((4-(trifluoromethyl)pyridin-2-yl)oxy)methyl)cyclobutyl)amino)-7,8-dihydropteridin-6(5H)-one The compound was prepared by reaction of (7S)-2-((trans-3-(hydroxymethyl)cyclobutyl)amino)-4,7,8-trimethyl-7,8-dihydropteridin-6(5H)-one and 2-hydroxy-4-trifluoromethylpyridine to provide the title product. 1H NMR (400 MHz, Methanol-d4) δ 8.36 (d, J=5.3 Hz, 1H), 7.20 (d, J=5.3 Hz, 1H), 7.06 (s, 1H), 4.57 (p, J=7.8 Hz, 1H), 4.48 (d, J=6.8 Hz, 2H), 4.29 (q, J=6.9 Hz, 1H), 3.22 (s, 3H), 2.78 (dd, J=8.7, 4.5 Hz, 1H), 2.42 (ddd, J=11.9, 9.1, 5.1 Hz, 2H), 2.36-2.31 (m, 1H), 2.30 (s, 3H), 1.52 (d, J=6.9 Hz, 3H). ESMS(M+1)=437.29.

Compound 366: (7S)-2-((cis-3-(((5-chloropyridin-3-yl)oxy)methyl)cyclobutyl)amino)-4,7,8-trimethyl-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 3-hydroxy-5-chloropyridine to provide the title product. 1H NMR (400 MHz, Methanol-d4) δ 8.36 (d, J=5.3 Hz, 1H), 7.20 (d, J=5.3 Hz, 1H), 7.06 (s, 1H), 4.57 (p, J=7.8 Hz, 1H), 4.48 (d, J=6.8 Hz, 2H), 4.29 (q, J=6.9 Hz, 1H), 3.22 (s, 3H), 2.78 (dd, J=8.7, 4.5 Hz, 1H), 2.42 (ddd, J=11.9, 9.1, 5.1 Hz, 2H), 2.36-2.31 (m, 1H), 2.30 (s, 3H), 1.52 (d, J=6.9 Hz, 3H). ESMS(M+1)=403.25.

Compound 365: (7S)-4,7,8-trimethyl-2-((cis-3-(((6-methyl-4-(trifluoromethyl)pyridin-2-yl)oxy)methyl)cyclobutyl)amino)-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 6-methyl-4-(trifluoromethyl)pyridin-2-ol to provide the title product. 1H NMR (400 MHz, Methanol-d4) δ 7.60-7.45 (m, 1H), 7.05 (s, 1H), 6.85 (s, 1H), 4.48-4.15 (m, 4H), 3.25 (d, J=8.5 Hz, 3H), 2.73-2.52 (m, 3H), 2.51 (s, 3H), 2.34 (s, 3H), 2.10-1.90 (m, 2H), 1.53 (d, J=6.9 Hz, 3H). ESMS(M+1)=451.29.

Compound 364: (7S)-4,7,8-trimethyl-2-((cis-3-(((6-(trifluoromethyl)pyridin-3-yl)oxy)methyl)cyclobutyl)amino)-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 6-(trifluoromethyl)pyridin-3-ol to provide the title product. 1H NMR (400 MHz, CDCl$_3$) δ 9.17 (s, 1H), 8.30 (s, 1H), 7.50 (t, J=14.0 Hz, 1H), 7.24-7.11 (m, 1H), 4.89 (d, J=7.3 Hz, 1H), 4.38-4.23 (m, 1H), 3.97 (dd, J=16.4, 5.4 Hz, 3H), 2.95 (d, J=13.4 Hz, 3H), 2.67-2.31 (m, 4H), 2.17 (s, 3H), 1.71 (d, J=7.8 Hz, 2H), 1.31 (d, J=6.3 Hz, 3H). ESMS(M+1)=437.29.

Compound 363: (7S)-4,7,8-trimethyl-2-((cis-3-(((5-(trifluoromethyl)pyridin-3-yl)oxy)methyl)cyclobutyl)amino)-7,8-dihydropteridin-6(5H)-one The compound was prepared by reaction of(7S)-2-((cis-3-(hydroxymethyl)cyclobutyl)amino)-4,7,8-trimethyl-7,8-dihydropteridin-6(5H)-one and 5-(trifluoromethyl)pyridin-3-ol to provide the title product. 1H NMR (400 MHz, Methanol-d4) δ 8.56 (s, 1H), 8.50 (s, 1H), 7.73 (d, J=24.0 Hz, 1H), 4.43 (s, 1H), 4.27 (t, J=14.7 Hz, 1H), 4.17 (s, 2H), 3.25 (s, 3H), 2.62 (s, 3H), 2.31 (s, 3H), 2.04 (s, 2H), 1.53 (d, J=5.1 Hz, 3H). ESMS(M+1)=437.29.

Compound 356: (7S)-4,7,8-trimethyl-2-((cis-3-(((5-(trifluoromethyl)pyridin-2-yl)oxy)methyl)cyclobutyl)amino)-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 5-(trifluoromethyl)pyridin-2-ol to provide the title product. 1H NMR (400 MHz, Methanol-d4) δ 8.47 (d, J=6.1 Hz, 1H), 7.44 (d, J=4.3 Hz, 2H), 4.47 (t, J=5.8 Hz, 2H), 4.46-4.40 (m, 1H), 4.31 (q, J=6.9 Hz, 1H), 3.25 (d, J=7.2 Hz, 3H), 2.63 (t, J=5.9 Hz, 2H), 2.33 (s, 3H), 2.05 (d, J=8.1 Hz, 2H), 1.53 (d, J=6.9 Hz, 3H). ESMS(M+1)=437.29.

Compound 283: (7S)-2-((cis-3-((3-ethynylphenoxy)methyl)cyclobutyl)amino)-4,7,8-trimethyl-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 3-ethynylphenol to provide the title product. 1H NMR (300 MHz, Methanol-d4) δ 7.23 (t, J=7.9 Hz, 1H), 7.01 (dd, J=8.1, 5.0 Hz, 2H), 6.94 (dd, J=8.3, 2.4 Hz, 1H), 4.36 (dd, J=14.8, 6.9 Hz, 1H), 4.29 (q, J=6.9 Hz, 1H), 3.97 (d, J=5.2 Hz, 2H), 3.45 (s, 1H), 3.22 (d, J=13.4 Hz, 3H), 2.63-2.50 (m, 3H), 2.29 (s, 3H), 1.98 (dd, J=17.1, 8.6 Hz, 2H), 1.52 (d, J=6.9 Hz, 3H). ESMS(M+1)=392.18.

Compound 280: (7S)-4,7,8-trimethyl-2-((cis-3-((3,4,5-trimethoxyphenoxy)methyl)-cyclobutyl)amino)-7,8-dihydropteridin-6(5H)-one The compound was prepared by reaction of (7S)-2-((cis-3-(hydroxymethyl)cyclobutyl)amino)-4,7,8-trimethyl-7,8-dihydropteridin-6(5H)-one and 3,4,5-timethoxyphenol to provide the title product. 1H NMR (300 MHz, Methanol-d4) δ 6.22 (s, 2H), 4.45-4.33 (m, 1H), 4.28 (q, J=6.9 Hz, 1H), 3.94 (d, J=5.3 Hz, 2H), 3.80 (s, 6H), 3.68 (s, 3H), 3.24 (s, 3H), 2.68-2.46 (m, 3H), 2.29 (s, 3H), 1.98 (dd, J=17.0, 8.0 Hz, 2H), 1.52 (d, J=6.9 Hz, 3H). ESMS(M+1)=458.17.

Compound 279. (7S)-2-((cis-3-((4-fluoro-1H-pyrazol-1-yl)methyl)cyclobutyl)amino)-4,7,8-trimethyl-7,8-dihydropteridin-6(5H)-one The compound was prepared by reaction (7S)-2-((cis-3-(hydroxymethyl)cyclobutyl)amino)-4,7,8-trimethyl-7,8-dihydropteridin-6(5H)-one and 4-fluoro-1H-pyrazole to provide the title product. 1H NMR (300 MHz, Methanol-d4) δ 7.63 (d, J=4.4 Hz, 1H), 7.35 (d, J=4.0 Hz, 1H), 4.38-4.22 (m, 3H), 4.19-4.14 (m, 1H), 4.11 (d, J=5.9 Hz, 2H), 3.22 (s, 3H), 2.61-2.39 (m, 4H), 2.29 (s, 3H), 1.96-1.73 (m, 3H), 1.51 (d, J=6.9 Hz, 3H); ESMS(M+1)=360.17.

Compound 286: (7S)-2-((cis-3-(((4-fluorobenzyl)oxy)methyl)cyclobutyl)amino)-4,7,8-trimethyl-7,8-dihydropteridin-6(5H)-one The compound was prepared by procedure Method A via reaction of intermediates A-2 and B-157 to provide the title product, 21.5% yield. 1H NMR (300 MHz, CDCl₃) δ 7.49 (s, 1H), 7.37-7.24 (m, 2H), 7.11-6.98 (m, 2H), 4.79 (d, J=7.8 Hz, 1H), 4.32 (q, J=8.1 Hz, 1H), 4.07 (q, J=6.8 Hz, 1H), 3.44 (d, J=6.1 Hz, 2H), 3.05 (s, 3H), 2.55 (qd, J=7.5, 3.8 Hz, 2H), 2.37-2.24 (m, 1H), 2.19 (s, 3H), 1.64 (dt, J=16.3, 5.3 Hz, 2H), 1.40 (d, J=6.8 Hz, 3H); ESMS (M+1)=400.28.

Compound 288: (7S)-2-((cis-3-(((4-fluorobenzyl)oxy)methyl)cyclobutyl)amino)-7,8-dimethyl-7,8-dihydropteridin-6(5H)-one The compound was prepared by procedure Method A via reaction of intermediates A-1 and B-157 to provide the title product, 55% yield. 1H NMR (300 MHz, CDCl₃) δ 7.43-7.25 (m, 5H), 7.10-6.98 (m, 2H), 4.49 (s, 2H), 4.29 (q, J=8.0, 7.6 Hz, 1H), 4.09 (q, J=6.8 Hz, 1H), 3.47 (d, J=6.2 Hz, 2H), 3.08 (s, 3H), 2.64-2.49 (m, 2H), 2.41-2.24 (m, 1H), 1.71 (p, J=8.9 Hz, 2H), 1.45 (d, J=6.9 Hz, 3H); ESMS (M+1)=386.41.

TABLE 14

| Compound # | R₁ | R₆ | R₅ | Method |
|---|---|---|---|---|
| 254 | H | Me | (3,4,5-trifluorobenzyl ether cyclobutyl) | A |
| 255 | Me | Me | (3,4,5-trifluorobenzyl ether cyclobutyl) | B |
| 256 | H | H | (3,4,5-trifluorobenzyl ether cyclobutyl) | A |
| 265 | H | H | (3,4-difluorobenzyl ether cyclobutyl) | A |
| 289 | H | H | (3,4,5-trifluorobenzyl ether cyclobutyl, alt stereo) | A |
| 264 | H | Me | (3,4-difluorobenzyl ether cyclobutyl) | A |
| 266 | Me | Me | (3,4-difluorobenzyl ether cyclobutyl) | B |

TABLE 14-continued

| Compound # | R₁ | R₆ | R₅ | Method |
|---|---|---|---|---|
| 290 | H | Me | (structure) | A |

Compound 254: (7S)-4,7,8-trimethyl-2-((trans-3-((3,4,5-trifluorobenzyl)oxy)cyclobutyl)amino)-7,8-dihydropteridin-6(5H)-one The compound was prepared by procedure Method A via reaction of intermediates A-2 and B-202 to provide the title product. 1H NMR (300 MHz, CDCl₃) δ 7.05-6.91 (m, 2H), 4.56-4.42 (m, 1H), 4.40-4.31 (m, 3H), 4.31-4.16 (m, 2H), 4.09 (q, J=6.9 Hz, 1H), 3.05 (s, 3H), 2.56-2.40 (m, 2H), 2.33-2.13 (m, 5H), 2.13-1.98 (m, 1H), 1.41 (d, J=6.9 Hz, 3H); ESMS(M+1)=422.34.

Compound 255: (7S)-4,5,7,8-tetramethyl-2-((trans-3-((3,4,5-trifluorobenzyl)oxy)cyclobutyl)amino)-7,8-dihydropteridin-6(5H)-one The compound was prepared by procedure Method B via reaction of intermediates A-3 and B-202 to provide the title product. 1H NMR (300 MHz, CDCl₃) δ 7.05-6.93 (m, 2H), 4.91 (d, J=6.2 Hz, 1H), 4.57-4.44 (m, 1H), 4.40-4.31 (m, 2H), 4.24 (ddd, J=6.8, 5.7, 3.4 Hz, 1H), 4.01 (q, J=6.9 Hz, 1H), 3.30 (s, 3H), 3.01 (s, 3H), 2.56-2.41 (m, 2H), 2.35 (s, 3H), 2.22 (ddt, J=12.8, 7.1, 3.8 Hz, 2H), 1.21 (d, J=6.9 Hz, 3H); ESMS(M+1)=436.34.

Compound 256: (7S)-7,8-dimethyl-2-((trans-3-((3,4,5-trifluorobenzyl)oxy)cyclobutyl)amino)-7,8-dihydropteridin-6(5H)-one The compound was prepared by procedure Method A via reaction of intermediates A-1 and B-202 to provide the title product. 1H NMR (300 MHz, CDCl₃) δ 7.39 (s, 1H), 7.06-6.94 (m, 2H), 4.55-4.41 (m, 1H), 4.41-4.20 (m, 3H), 4.11 (q, J=6.8 Hz, 1H), 3.09 (s, 3H), 2.56-2.39 (m, 2H), 2.40-2.23 (m, 2H), 1.48 (d, J=6.9 Hz, 3H); ESMS(M+1)=408.3.

Compound 265: (7S)-2-((trans-3-((3,4-difluorobenzyl)oxy)cyclobutyl)amino)-7,8-dimethyl-7,8-dihydropteridin-6(5H)-one The compound was prepared by procedure Method A via reaction of intermediates A-1 and B-201 to provide the title product. 1H NMR (300 MHz, CDCl₃) δ 7.38 (d, J=3.0 Hz, 1H), 7.28-7.01 (m, 3H), 4.48 (td, J=7.9, 5.8 Hz, 1H), 4.46-4.36 (m, 2H), 4.29 (ddd, J=8.6, 6.9, 4.5 Hz, 1H), 4.11 (dd, J=6.9, 1.3 Hz, 1H), 3.09 (s, 3H), 2.55-2.40 (m, 2H), 2.39-2.24 (m, 2H), 1.48 (d, J=6.8 Hz, 3H); ESMS(M+1)=390.29.

Compound 289: (S)-7,8-dimethyl-2-((cis-3-methyl-3-((3,4,5-trifluorobenzyl)oxy)cyclobutyl)amino)-7,8-dihydropteridin-6(5H)-one The compound was prepared by procedure Method A via reaction of intermediates A-1 and B-203 to provide the title product. 1H NMR (300 MHz, CDCl₃) δ 7.32 (s, 1H), 6.96-6.85 (m, 2H), 4.25 (dd, J=13.2, 1.1 Hz, 3H), 4.01 (q, J=8.9, 7.9 Hz, 2H), 3.64-3.56 (m, 1H), 2.99 (s, 3H), 2.97-2.80 (m, 1H), 2.43 (tt, J=9.3, 2.8 Hz, 2H), 2.26 (ddt, J=9.1, 7.1, 2.3 Hz, 1H), 2.06 (q, J=9.4 Hz, 2H), 1.86-1.73 (m, 1H), 1.37 (t, J=3.5 Hz, 5H), 1.28 (d, J=0.9 Hz, 1H); ESMS(M+1)=422.37.

Compound 264: (7S)-2-((trans-3-((3,4-difluorobenzyl)oxy)cyclobutyl)amino)-4,7,8-trimethyl-7,8-dihydropteridin-6(5H)-one The compound was prepared by procedure Method A via reaction of intermediates A-2 and B-201 to provide the title product. 1H NMR (300 MHz, CDCl₃) δ 7.82 (s, 1H), 7.24-7.02 (m, 3H), 4.88 (d, J=6.2 Hz, 1H), 4.55-4.33 (m, 3H), 4.31-4.17 (m, 1H), 4.08 (q, J=6.9 Hz, 1H), 3.05 (d, J=1.0 Hz, 3H), 2.57-2.40 (m, 2H), 2.33-1.96 (m, 5H), 1.41 (dd, J=6.8, 1.0 Hz, 3H); ESMS(M+1)=404.33.

Compound 266: (7S)-2-((trans-3-((3,4-difluorobenzyl)oxy)-cyclobutyl)amino)-4,5,7,8-tetramethyl-7,8-dihydropteridin-6(5H)-one The compound was prepared by procedure Method B via reaction of intermediates A-3 and B-201 to provide the title product. 1H NMR (300 MHz, CDCl₃) δ 7.27-7.03 (m, 3H), 4.51 (t, J=6.7 Hz, 1H), 4.43-4.18 (m, 3H), 4.01 (q, J=6.8 Hz, 1H), 3.30 (s, 3H), 3.01 (s, 3H), 2.55-2.41 (m, 2H), 2.36 (s, 3H), 2.30-2.16 (m, 2H), 1.21 (d, J=6.9 Hz, 3H); ESMS(M+1)=418.39.

Compound 290: (7S)-4,7,8-trimethyl-2-((cis-3-methyl-3-((3,4,5-trifluorobenzyl)oxy)cyclobutyl)amino)-7,8-dihydropteridin-6(5H)-one The compound was prepared by procedure Method A via reaction of intermediates A-2 and B-203 to provide the title product. ESMS(M+1)=436.41.

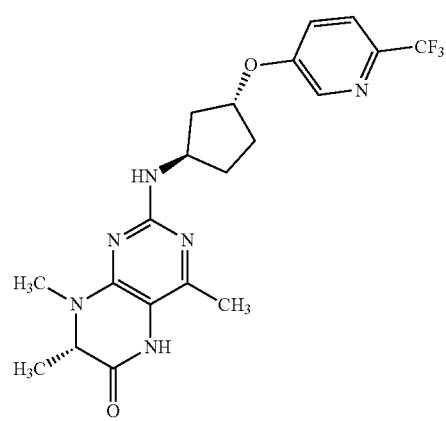

-continued

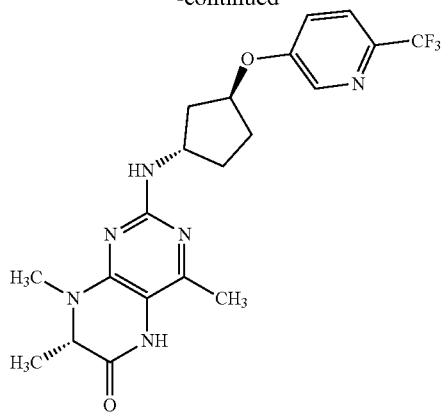

Compound 376 and 377

(7S)-4,7,8-trimethyl-2-((trans-3-((6-(trifluoromethyl)pyridin-3-yl)oxy)cyclopentyl)amino)-7,8-dihydropteridin-6(5H)-one and (7S)-4,7,8-trimethyl-2-(((1S,3S)-3-((6-(trifluoromethyl)pyridin-3-yl)oxy)cyclopentyl)amino)-7,8-dihydropteridin-6(5H)-one The compounds were prepared by procedure Method B via reaction of A-2 and B-142 to provide the title product as a mixture of trans diastereomers (Compound 375). The trans diastereomers were separated by SFC (Column: Chiralpak IB, 10×250 mm; 20% methanol(0.2% diethylamine)/800% CO₂, isocratic, flow rate: 10 ml/min) to provide the individual diastereomers that were arbitrarily assigned:

Peak A: Rt 0.604 mins. (88% ee); 1H NMR (300 MHz, CDCl₃) δ 8.35 (d, J=2.8 Hz, 1H), 7.61 (s, 1H), 7.31-7.19 (m, 1H), 4.94 (tt, J=5.8, 2.7 Hz, 1H), 4.79 (d, J=6.6 Hz, 1H), 4.48 (q, J=6.8 Hz, 1H), 4.06 (q, J=6.8 Hz, 1H), 3.00 (s, 3H), 2.47-2.26 (m, 3H), 2.24 (s, 3H), 2.01-1.84 (m, 2H), 1.70-1.55 (m, 1H), 1.39 (d, J=6.9 Hz, 3H). ESMS(M+1)=437.29.

Peak B: Rt 0.963 mins. (89.2% ee) 1H NMR (300 MHz, CDCl₃) δ 8.35 (d, J=2.8 Hz, 1H), 7.62 (s, 1H), 7.31-7.20 (m, 1H), 4.94 (dq, J=5.9, 2.9 Hz, 1H), 4.78 (d, J=6.6 Hz, 1H), 4.48 (q, J=6.8 Hz, 1H), 4.06 (q, J=6.8 Hz, 1H), 3.01 (s, 3H), 2.48-2.20 (m, 6H), 2.03-1.85 (m, 2H), 1.62 (ddd, J=13.4, 7.4, 4.3 Hz, 1H), 1.39 (d, J=6.8 Hz, 3H). ESMS(M+1)=437.29.

Compound 259: (7S)-4,7,8-trimethyl-2-((cis-3-(3,4,5-trifluorophenoxy)cyclopentyl)amino)-7,8-dihydropteridin-6(5H)-one The compound was prepared by procedure Method B via reaction of intermediate A-2 and B-143 to provide the title compound as a mixture of trans diastereomers, 46% yield. 1H NMR (300 MHz, Methanol-d4) δ 6.85-6.71 (m, 2H), 4.57-4.45 (m, 1H), 4.32 (q, J=6.8 Hz, 1H), 3.27 (s, 3H), 2.60-2.42 (m, 1H), 2.33 (s, 3H), 2.28-2.15 (m, 1H), 2.11-2.00 (m, 2H), 1.98-1.82 (m, 2H), 1.54 (d, J=6.9 Hz, 3H).

Compound 260: (7S)-4,7,8-trimethyl-2-((trans-3-(3,4,5-trifluorophenoxy)cyclopentyl)amino)-7,8-dihydropteridin-6(5H)-one The compound was prepared by procedure Method B via reaction of intermediate A-2 and B-141 to provide the title compound as a mixture of trans diastereomers, 55% yield. The diastereomer were separated by chiral HPLC (Chiralpak IF column, 4.6×250 mm; 15% ethanol/15% methanol/70% hexanes (0.2% diethylamine), isocratic) to provide each individual trans-diastereomer: Compound 267: (S)-4,7,8-trimethyl-2-(((1R,3R)-3-(3,4,5-trifluorophenoxy)cyclopentyl)amino)-7,8-dihydropteridin-6(5H)-one Peak A: Rt 6.57 mins.; 99% ee. 1H NMR (300 MHz, CDCl₃) δ 9.14 (s, 1H), 6.48-6.26 (m, 2H), 4.71 (t, J=8.5 Hz, 1H), 4.65 (td, J=5.9, 2.8 Hz, 1H), 4.45-4.30 (m, 1H), 4.02 (dq, J=17.9, 6.9 Hz, 1H), 2.37-2.20 (m, 2H), 2.16 (s, 3H), 2.14-2.04 (m, 1H), 1.88-1.68 (m, 2H), 1.59-1.39 (m, 1H), 1.31 (dd, J=6.8, 2.3 Hz, 3H); ESMS(M+1)=422.34.

Compound 268: (S)-4,7,8-trimethyl-2-(((1S,3S)-3-(3,4,5-trifluorophenoxy)cyclopentyl)amino)-7,8-dihydropteridin-6(5H)-one Peak B: Rt 10.219 mins.; 99% ee. 1H NMR (300 MHz, CDCl₃) δ 9.04 (s, 1H), 6.49-6.29 (m, 2H), 4.71 (t, J=10.2 Hz, 1H), 4.65 (td, J=5.9, 2.8 Hz, 1H), 4.49-4.25 (m, 1H), 4.13-3.90 (m, 2H), 2.23 (ddd, J=15.1, 10.6, 5.2 Hz, 2H), 2.15 (d, J=4.9 Hz, 4H), 2.11 (dd, J=14.6, 6.3 Hz, 1H), 1.89-1.68 (m, 2H), 1.59-1.42 (m, 1H), 1.32 (d, J=6.8 Hz, 3H); ESMS (M+1)=422.38.

Compound 269: (7S)-4,5,7,8-tetramethyl-2-((trans-3-(3,4,5-trifluorophenoxy)cyclopentyl)amino)-7,8-dihydropteridin-6(5H)-one The compound was prepared by procedure Method B via reaction of intermediates A-3 and B-141 to provide the title compound as a mixture of trans diastereomers. 1H NMR (300 MHz, Methanol-d4) δ 6.77-6.65 (m, 2H), 4.94 (d, J=1.9 Hz, 1H), 4.61-4.48 (m, 1H), 4.32 (q, J=6.9 Hz, 1H), 3.34 (d, J=5.1 Hz, 3H), 3.23 (s, 3H), 2.52 (s, 3H), 2.42-2.20 (m, 4H), 2.06 (ddd, J=20.5, 13.7, 6.8 Hz, 1H), 1.97-1.65 (m, 2H), 1.39 (dd, J=6.9, 1.3 Hz, 3H); ESMS(M+1)=404.29. The diastereomers were separated by SFC (AD-H, 4.6×100 mm column, 10% methanol(0.2% diethylamine)/90% CO₂, Isocratic) to provide each individual trans diastereomers.

Compound 272: (S)-4,5,7,8-tetramethyl-2-(((1R,3R)-3-(3,4,5-trifluorophenoxy)cyclopentyl)amino)-7,8-dihydropteridin-6(5H)-one Peak A: Rt 0.488 mins.; 99.2% de. 1H NMR (300 MHz, CDCl₃) δ 6.54-6.39 (m, 2H), 4.80-4.65 (m, 2H), 4.45 (dd, J=14.0, 7.0 Hz, 1H), 4.00 (q, J=6.9 Hz, 1H), 3.29 (s, 3H), 2.99 (s, 3H), 2.44-2.10 (m, 6H), 1.95-1.76 (m, 2H), 1.57 (ddd, J=10.8, 7.7, 5.9 Hz, 1H), 1.20 (d, J=6.9 Hz, 3H); ESMS(M+1)=436.31.

Compound 273: (S)-4,5,7,8-tetramethyl-2-(((1S,3S)-3-(3,4,5-trifluorophenoxy)cyclopentyl)amino)-7,8-dihydropteridin-6(5H)-one Peak B: Rt 0.553 mins.; 96.8% de. 1H NMR (300 MHz, CDCl₃) δ 6.49-6.30 (m, 2H), 4.66 (ddd, J=20.7, 15.2, 10.6 Hz, 2H), 4.46-4.28 (m, 1H), 3.93 (q, J=6.9 Hz, 1H), 3.21 (s, 3H), 2.91 (s, 3H), 2.26 (s, 3H), 2.25-1.99 (m, 4H), 1.79 (ddd, J=21.3, 8.4, 4.2 Hz, 2H), 1.59-1.41 (m, 1H), 1.11 (d, J=6.6 Hz, 3H); ESMS(M+1)=436.29.

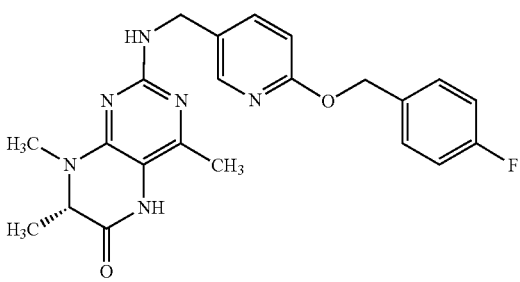 [SMILES: Cc1nc(NCc2ccc(OCc3ccc(F)cc3)nc2)nc2c1NC(=O)[C@H](C)N2C]

Compound 57: (7S)-2-(((6-((4-fluorobenzyl)oxy)pyridin-3-yl)methyl)amino)-4,7,8-trimethyl-7,8-dihydropteridin-6(5H)-one The compound was prepared by general procedure Method A via reaction of intermediates A-2 and B-144 to provide the title product. 1H NMR (400 MHz, CDCl$_3$) δ 8.19-8.07 (m, 1H), 7.72-7.58 (m, 1H), 7.43 (q, J=5.2 Hz, 2H), 7.06 (t, J=9.0 Hz, 2H), 6.86-6.65 (m, 1H), 5.32 (q, J=3.9, 2.9 Hz, 2H), 4.49 (q, J=6.8, 3.6 Hz, 2H), 4.07 (q, J=6.1 Hz, 1H), 3.04 (d, J=3.0 Hz, 3H), 2.30-2.11 (m, 3H), 1.39 (dd, J=7.5, 3.7 Hz, 3H). ESMS(M+1)=423.26.

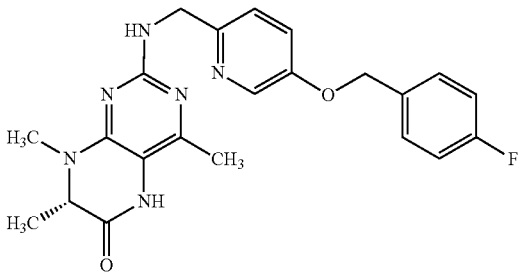 [SMILES: Cc1nc(NCc2ccc(OCc3ccc(F)cc3)cn2)nc2c1NC(=O)[C@H](C)N2C]

Compound 70: (S)-2-(((5-((4-fluorobenzyl)oxy)pyridin-2-yl)methyl)amino)-4,7,8-trimethyl-7,8-dihydropteridin-6(5H)-one The compound was prepared by by procedure Method B via a reaction with intermediate A-2 and B-145 to provide the title product. 1H NMR (300 MHz, CDCl$_3$) δ 9.09 (s, 1H), 8.29 (dd, J=2.9, 0.7 Hz, 1H), 7.39 (dd, J=8.5, 5.4 Hz, 2H), 7.31-7.23 (m, 1H), 7.19 (dd, J=8.6, 2.8 Hz, 1H), 7.07 (t, J=8.6 Hz, 2H), 5.62 (t, J=5.7 Hz, 1H), 5.04 (s, 2H), 4.65 (dd, J=5.8, 4.1 Hz, 2H), 4.04 (q, J=6.9 Hz, 1H), 2.99 (s, 4H), 2.25 (s, 3H), 1.38 (d, J=6.8 Hz, 3H); ESMS(M+1)=423.12.

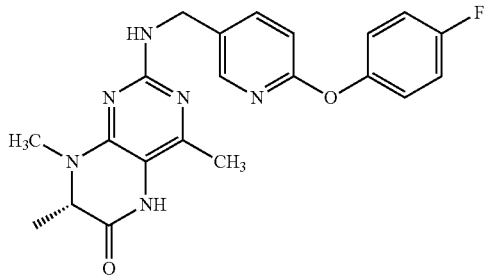 [SMILES: Cc1nc(NCc2ccc(Oc3ccc(F)cc3)nc2)nc2c1NC(=O)[C@H](C)N2C]

Compound 54: (7S)-2-(((6-(4-fluorophenoxy)pyridin-3-yl)methyl)amino)-4,7,8-trimethyl-7,8-dihydropteridin-6(5H)-one The compound was prepared by reaction of intermediate A-2 and (6-(4-fluorophenoxy)pyridin-3-yl)methanamine via Method B procedure to provide the title product. 1H NMR (400 MHz, Methanol-d4) δ 8.44 (s, 1H), 8.37-8.16 (m, 1H), 7.27 (dt, J=15.3, 8.1 Hz, 4H), 7.17-6.98 (m, 1H), 4.72 (s, 2H), 4.31 (d, J=5.8 Hz, 1H), 3.21 (s, 3H), 2.33 (s, 3H), 1.63-1.39 (m, 3H); ESMS(M+1)=409.13.

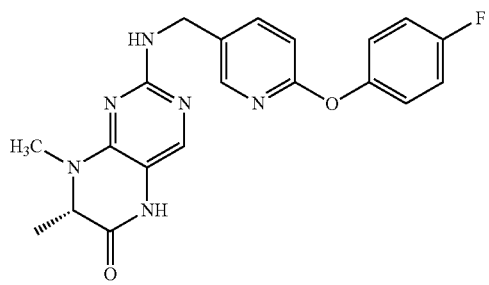 [SMILES: C[C@H]1C(=O)Nc2cnc(NCc3ccc(Oc4ccc(F)cc4)nc3)nc2N1C]

Compound 56: (7S)-2-(((6-(4-fluorophenoxy)pyridin-3-yl)methyl)amino)-7,8-dimethyl-7,8-dihydropteridin-6(5H)-one The compound was prepared by reaction of intermediate A-1 and (6-(4-fluorophenoxy)pyridin-3-yl)methanamine via procedure Method B to provide the title product. 1H NMR (300 MHz, Methanol-d4) δ 8.16 (d, J=2.4 Hz, 1H), 7.87 (dd, J=8.5, 2.5 Hz, 1H), 7.18-7.05 (m, 4H), 6.94 (d, J=8.5 Hz, 1H), 4.60 (s, 2H), 4.32 (q, J=6.9 Hz, 1H), 3.23 (s, 3H), 1.56 (d, J=6.9 Hz, 3H); ESMS(M+1)=395.22.

Compound 143: (S)-4,7,8-trimethyl-2-(((6-(4-(trifluoromethyl)-1H-pyrazol-1-yl)pyridin-3-yl)methyl)amino)-7,8-dihydropteridin-6(5H)-one The compound was prepared by procedure A via reaction of intermediates A-2 and B-148 to provide the title product. 1H NMR (300 MHz, Methanol-d4) δ 8.95 (s, 1H), 8.47 (s, 1H), 8.08-7.89 (m, 3H), 4.58 (s, 2H), 4.05 (q, J=6.8 Hz, 1H), 3.01 (s, 3H), 2.18 (s, 3H), 1.31 (d, J=6.8 Hz, 3H); ESMS (M+1)=433.35

Compound 371: (7S)-2-(((S)-1-benzylpyrrolidin-3-yl)amino)-4,7,8-trimethyl-7,8-dihydropteridin-6(5H)-one The compound was prepared by procedure Method B via reaction of intermediate A-2 and (S)-1-benzylpyrrolidin-3-amine to provide the title product. 1H NMR (400 MHz, Methanol-d4) δ 7.40-7.16 (m, 5H), 4.50-4.39 (m, 1H), 4.06 (q, J=6.8 Hz, 1H), 3.64 (s, 2H), 3.03 (s, 3H), 2.94 (dd, J=9.8, 7.0 Hz, 1H), 2.73 (dd, J=14.8, 8.7 Hz, 1H), 2.57 (dd, J=15.7, 8.2 Hz, 1H), 2.47 (dd, J=9.9, 5.1 Hz, 1H), 2.32 (ddd, J=14.0, 8.6, 5.7 Hz, 1H), 2.16 (s, 3H), 1.67 (ddd, J=13.4, 8.3, 5.8 Hz, 1H), 1.31 (d, J=6.8 Hz, 3H); ESMS(M+1)=367.33.

Compound 372: (7S)-2-(((R)-1-benzylpyrrolidin-3-yl)amino)-4,7,8-trimethyl-7,8-dihydropteridin-6(5H)-one The compound was prepared by procedure Method B via reaction of intermediate A-2 and (R)-1-benzylpyrrolidin-3- amine to provide the title product. 1H NMR (400 MHz, Methanol-d4) δ 7.38-7.20 (m, 5H), 4.44 (ddt, J=10.0, 6.9, 5.1 Hz, 1H), 4.05 (q, J=6.8 Hz, 1H), 3.64 (s, 2H), 3.03 (s, 3H), 2.93 (dd, J=9.9, 7.0 Hz, 1H), 2.78-2.68 (m, 1H), 2.57 (dd, J=15.4, 8.3 Hz, 1H), 2.46 (dd, J=9.9, 5.0 Hz, 1H), 2.38-2.26 (m, 1H), 2.16 (s, 3H), 1.68 (ddd, J=13.3, 8.2, 6.1 Hz, 1H), 1.32 (d, J=6.8 Hz, 3H). ESMS(M+1)=367.33.

Compound 374: (7S)-2-(((S)-1-(4-fluorobenzyl) pyrrolidin-3-yl)amino)-4,7,8-trimethyl-7,8-dihydropteridin-6(5H)-one The compound was prepared by procedure Method B via reaction of intermediate A-2 and (S)-1-(4-fluorobenzyl)pyrrolidin-3-amine to provide the title product. 1H NMR (300 MHz, Methanol-d4) δ 7.35 (s, 2H), 7.04 (dd, J=8.3, 7.2 Hz, 2H), 4.44 (s, 1H), 4.13-3.99 (m, 1H), 3.61 (s, 2H), 3.02 (d, J=0.8 Hz, 3H), 2.91 (s, 1H), 2.71 (d, J=6.1 Hz, 1H), 2.60-2.37 (m, 2H), 2.27 (d, J=13.6 Hz, 1H), 2.15 (d, J=1.6 Hz, 3H), 1.67 (s, 1H), 1.31 (dd, J=6.6, 1.7 Hz, 3H); ESMS(M+1)=385.27.

Compound 278: (7S)-4,7,8-trimethyl-2-((2-(phenoxymethyl)cyclopropyl)-amino)-7,8-dihydropteridin-6(5H)-one The compound was prepared by procedure Method B via reaction of intermediate A-2 and 2-(phenoxymethyl)cyclopropan-1-amine to provide the title product. 1H NMR (300 MHz, Methanol-d4) δ 7.37-7.20 (m, 2H), 6.97 (d, J=6.6 Hz, 3H), 4.30 (q, J=6.9 Hz, 1H), 4.22-4.12 (m, 1H), 3.89-3.74 (m, 1H), 3.24 (d, J=1.4 Hz, 3H), 2.86-2.73 (m, 1H), 2.34 (s, 2H), 1.53 (dd, J=6.9, 1.2 Hz, 3H), 1.06 (dd, J=13.1, 5.3 Hz, 2H); ESMS(M+1)=354.37.

2N. Preparation of Compounds 401, 402, 404-408

2N. Preparation of Compounds 401, 402, 404-408

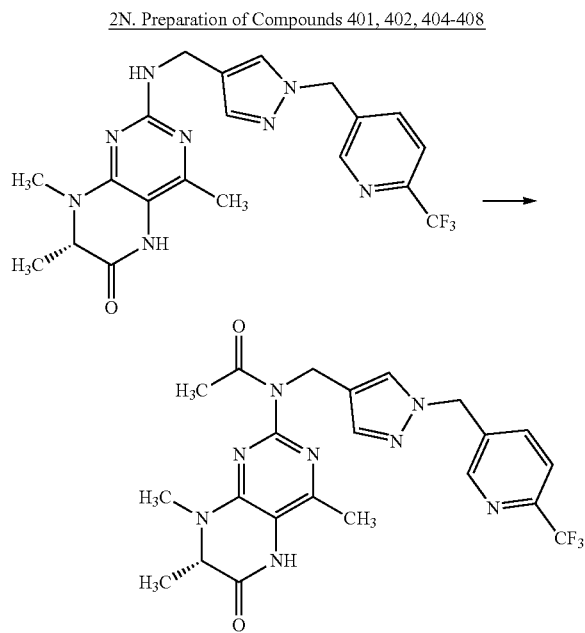

Compound 405: (7S)—N-((1-((6-(trifluoromethyl) pyridin-3-yl)methyl)-1H-pyrazol-4-yl)methyl)-N-(4, 7,8-trimethyl-6-oxo-5,6,7,8-tetrahydropteridin-2-yl) acetamide To a solution of (7R)-4,7,8-trimethyl-2-[[1-[[6-(trifluoromethyl)-3-pyridyl]methyl]pyrazol-4-yl]methylamino]-5,7-dihydropteridin-6-one (250 mg, 0.5600 mmol) in anhydrous THF (3.750 mL) was added acetyl acetate (87 mg, 80 µL, 0.8400 mmol) and DIEA (217 mg, 290 µL, 1.680 mmol), the mixture was sealed in a microwave tube and heated at 100° C. for 24 hrs in a heating bath. The solvent was removed by evaporation, the residue was purified by silica gel column (40 g) in ISCO eluting with DCM, 20% MeOH/DCM. The desired fractions were collected and evaporated. The resulting material was dried over 50° C. vacuum for over night. chiral HPLC (Column: ChiralPak IC,), ee>99.9% (206.0 mg, 74.55% yield) 1H NMR (300 MHz, DMSO-d6) δ 10.30 (s, 1H), 8.66-8.52 (m, 1H), 7.94-7.77 (m, 2H), 7.74 (d, J=0.8 Hz, 1H), 7.35 (d, J=0.7 Hz, 1H), 5.42 (s, 2H), 4.93-4.80 (m, 2H), 4.17 (q, J=6.8 Hz, 1H), 2.98 (s, 3H), 2.28 (s, 3H), 2.24 (s, 3H), 1.26 (d, J=6.8 Hz, 3H). ESMS (M+1) 489.3.

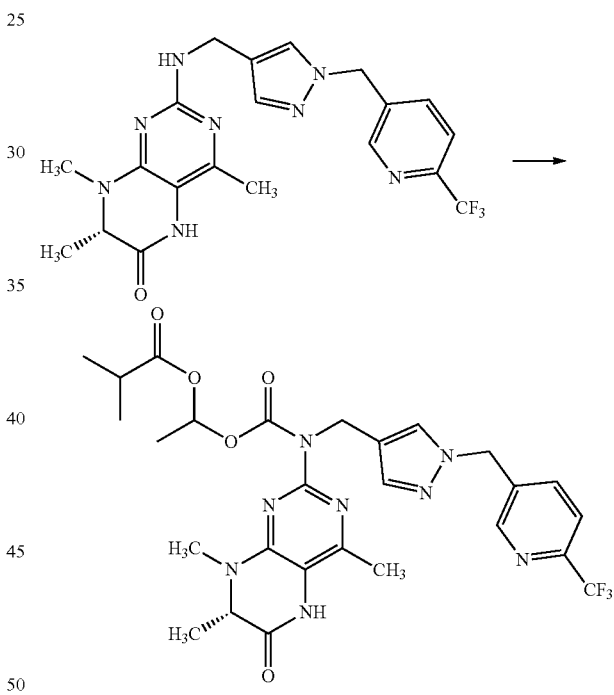

Compound 408: 1-((((1-((6-(trifluoromethyl)pyridin-3-yl)methyl)-1H-pyrazol-4-yl)methyl)((7S)-4,7,8-trimethyl-6-oxo-5,6,7,8-tetrahydropteridin-2-yl) carbamoyl)oxy)ethyl isobutyrate To a solution of (7S)-4,7,8-trimethyl-2-[[1-[[6-(trifluoromethyl)-3-pyridyl]methyl]pyrazol-4-yl]methylamino]-5,7-dihydropteridin-6-one (200 mg, 0.4480 mmol) in anhydrous THF (2 mL) was added 1-(4-nitrophenoxy) carbonyloxyethyl 2-methylpropanoate (161.4 mg, 0.5376 mmol) and DIEA (2 eq); the mixture was sealed in a microwave tube and heated in heating bath at 110° C. for 24 hrs. UPLC showed desired Mw was found, evaporated the solvent, the residue was purified by column chromatography (SiO₂) eluting with a gradient of dichloromethane to 20% methanol in dichloromethane. The desired fractions were collected and evaporated, the pure product was dried on vacuum for overnight to provide the title product. (232.5 mg, 0.3816 mmol, 85.16%) 1H NMR (300 MHz, DMSO-d6) δ 8.58 (d, J=1.2 Hz, 1H), 7.97-7.72 (m, 3H), 7.40 (s, 1H), 6.74 (qd, J=5.5, 1.6 Hz, 1H), 5.45 (s, 2H), 4.87-4.61 (m, 2H), 4.16 (q, J=6.8 Hz, 1H), 2.96 (s, 3H), 2.51-2.39 (m, 1H), 2.26 (s, 3H), 1.39 (d, J=5.5 Hz, 3H), 1.31-1.21 (m, 3H), 1.09-0.96 (m, 6H). ESMS (M+1)=605.41.

General Procedures for Preparation of Compounds 406 and 402

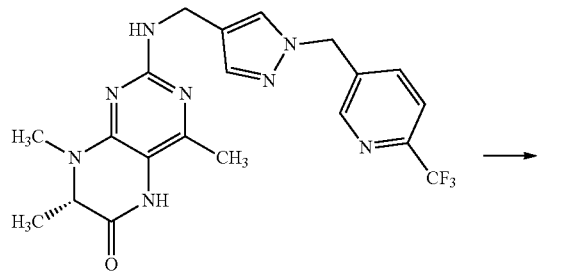

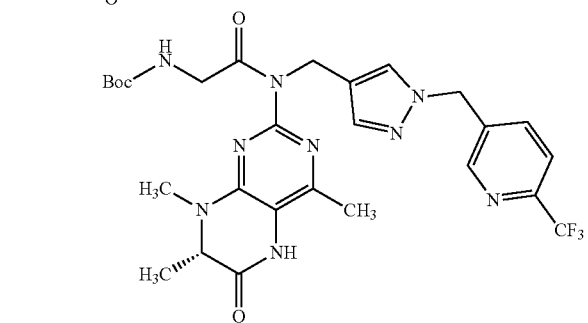

tert-butyl (7S)-(2-oxo-2-(((1-((6-(trifluoromethyl)pyridin-3-yl)methyl)-1H-pyrazol-4-yl)methyl)(4,7,8-trimethyl-6-oxo-5,6,7,8-tetrahydropteridin-2-yl)amino)ethyl)carbamate To the solution of (S)-4,7,8-trimethyl-2-(((1-((6-(trifluoromethyl)pyridin-3-yl)methyl)-1H-pyrazol-4-yl)methyl)amino)-7,8-dihydropteridin-6(5H)-one (180 mg, 0.4032 mmol) and DIPEA (140 μL, 0.8038 mmol) in THF was added (4-nitrophenyl) 2-(tert-butoxycarbonylamino)acetate and DIPEA (140 μL, 0.8038 mmol). After microwaved at 130° C. for 2h, LCMS indicated desired product. After concentration, the product was purified by silica gel chromatography to give the product (185 mg, 0.3037 mmol, 75.32%) 1H NMR (300 MHz, CDCl3) δ 8.55 (d, J=1.8 Hz, 1H), 8.30 (s, 1H), 7.76-7.61 (m, 2H), 7.58 (d, J=6.0 Hz, 2H), 5.50 (t, J=5.1 Hz, 1H), 5.33 (d, J=5.9 Hz, 3H), 5.10 (s, 2H), 4.57-4.34 (m, 2H), 4.19 (q, J=6.8 Hz, 1H), 3.13 (s, 3H), 2.36 (s, 3H), 1.48 (d, J=6.9 Hz, 3H), 1.45 (s, 9H). ESMS (M+1)=604.37.

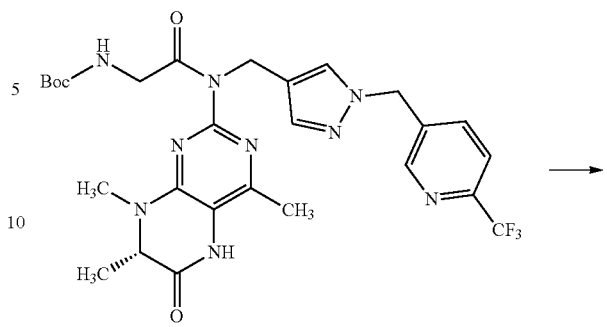

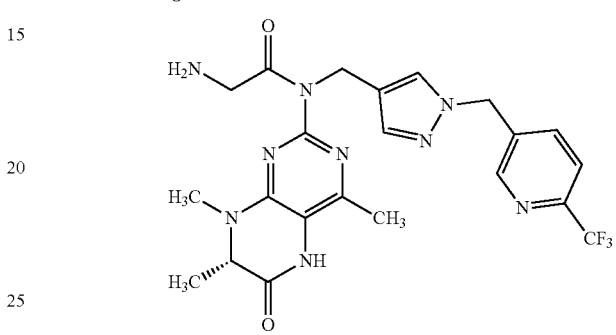

Compound 406: (7S)-2-amino-N-((1-((6-(trifluoromethyl)pyridin-3-yl)methyl)-1H-pyrazol-4-yl)methyl)-N-(4,7,8-trimethyl-6-oxo-5,6,7,8-tetrahydropteridin-2-yl)acetamide To a solution of tert-butyl (S)-(2-oxo-2-(((1-((6-(trifluoromethyl)pyridin-3-yl)methyl)-1H-pyrazol-4-yl)methyl)(4,7,8-trimethyl-6-oxo-5,6,7,8-tetrahydropteridin-2-yl)amino)ethyl)carbamate (173 mg, 0.2840 mmol) in MeOH (0.5 mL) was added HCl (1 mL of 4 M, 4.000 mmol) in dioxane (1 mL). The reaction was stirred for 1 h at RT. LCMS indicated completion of reaction. Removed the solvent, the product was triturated by ether. (160 mg, 0.2740 mmol, 96.47%) 1H NMR (300 MHz, Methanol-d4) δ 8.45 (s, 1H), 7.98 (s, 1H), 7.89 (d, J=8.5 Hz, 1H), 7.77 (d, J=8.1 Hz, 1H), 7.63 (d, J=4.8 Hz, 1H), 5.57-5.35 (m, 3H), 5.16 (d, J=3.3 Hz, 2H), 4.35 (d, J=18.0 Hz, 3H), 3.64 (q, J=1.2 Hz, 2H), 3.19 (d, J=3.5 Hz, 3H), 2.51-2.34 (m, 3H), 1.52 (t, J=6.7 Hz, 3H). ESMS (M+1)=504.38.

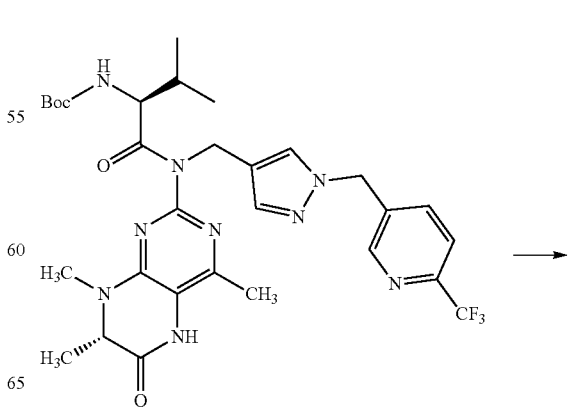

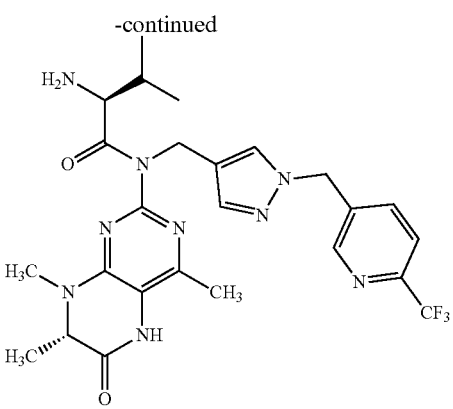

Compound 402: (S)-2-amino-3-methyl-N-((1-((6-(trifluoromethyl)pyridin-3-yl)methyl)-1H-pyrazol-4-yl)methyl)-N—((S)-4,7,8-trimethyl-6-oxo-5,6,7,8-tetrahydropteridin-2-yl)butanamide Prepared in a similar manner as described above to give product HCl salt. (41 mg, 0.06629 mmol, 67.94% yield) 1H NMR (300 MHz, Methanol-d4) δ 8.49-8.32 (m, 1H), 7.81 (d, J=2.7 Hz, 2H), 7.76 (d, J=8.1 Hz, 1H), 7.59 (s, 1H), 5.45 (s, 2H), 5.19-5.00 (m, 3H), 4.25 (q, J=6.8 Hz, 1H), 3.14 (d, J=2.3 Hz, 3H), 2.36 (s, 3H), 2.04 (dt, J=12.7, 7.0 Hz, 1H), 1.42 (dd, J=6.9, 4.3 Hz, 3H), 0.87 (d, J=6.9 Hz, 3H), 0.77 (d, J=6.8 Hz, 3H). ESMS (M+1)=546.25.

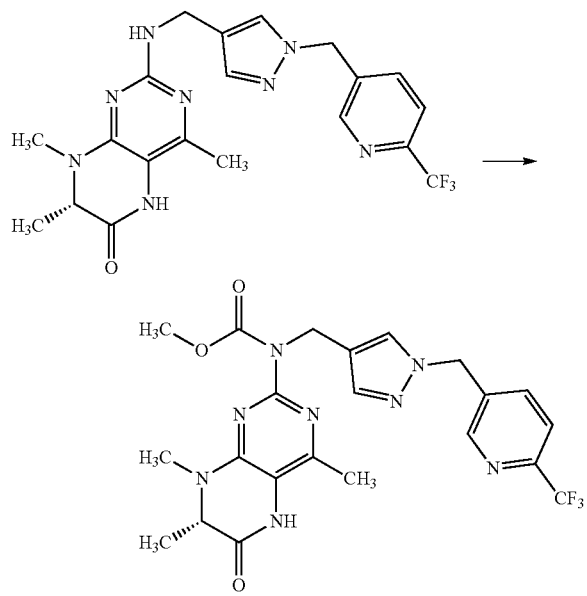

Compound 407: methyl (7S)-((1-((6-(trifluoromethyl)pyridin-3-yl)methyl)-1H-pyrazol-4-yl)methyl)(4,7,8-trimethyl-6-oxo-5,6,7,8-tetrahydropteridin-2-yl)carbamate At 0° C., methyl carbonochloridate (158.8 mg, 129.8 µL, 1.680 mmol) was added dropwise to the solution of (S)-4,7,8-trimethyl-2-(((1-((6-(trifluoromethyl)pyridin-3-yl)methyl)-1H-pyrazol-4-yl)methyl)amino)-7,8-dihydropteridin-6(5H)-one (500 mg, 1.120 mmol) and DIPEA (361.9 mg, 487.7 µL, 2.800 mmol) in THF. After stirred over the weekend and reaction went to completion. After concentration, the crude product was purified by silica gel chromatography to give the product (10% yield). 1H NMR (300 MHz, CDCl$_3$) δ 8.83 (s, 1H), 8.54 (s, 1H), 7.75-7.60 (m, 2H), 7.54 (d, J=9.0 Hz, 2H), 5.33 (d, J=9.6 Hz, 2H), 5.04-4.72 (m, 2H), 4.16 (q, J=6.9 Hz, 1H), 3.79 (s, 3H), 3.07 (s, 3H), 2.36 (s, 3H), 1.45 (d, J=6.9 Hz, 3H). ESMS (M+1)=505.33.

Compounds 401 and 404

These compounds were prepared similarly as described above for Compounds 402, 406, 407 and 408

Compound 401: (7S)-3-cyclohexyl-1-((1-((6-(trifluoromethyl)pyridin-3-yl)methyl)-1H-pyrazol-4-yl)methyl)-1-(4,7,8-trimethyl-6-oxo-5,6,7,8-tetrahydropteridin-2-yl)urea 1H NMR (300 MHz, Methanol-d4) δ 8.52 (d, J=1.7 Hz, 1H), 7.87-7.67 (m, 3H), 7.57 (s, 1H), 5.45 (s, 2H), 5.19 (s, 2H), 4.19 (q, J=6.8 Hz, 1H), 3.79-3.62 (m, 1H), 3.11 (s, 3H), 2.32 (s, 3H), 1.95 (d, J=12.0 Hz, 2H), 1.84-1.68 (m, 2H), 1.61 (s, 2H), 1.54-1.20 (m, 6H); ESMS (M+1)=572.32.

Compound 404: (7S)-6-acetamido-2-amino-N-((1-((6-(trifluoromethyl)pyridin-3-yl)methyl)-1H-pyrazol-4-yl)methyl)-N—((S)-4,7,8-trimethyl-6-oxo-5,6,7,8-tetrahydropteridin-2-yl)hexanamide 1H NMR (300 MHz, Methanol-d4) δ 8.38 (d, J=4.3 Hz, 1H), 7.97 (s, 1H), 7.85 (d, J=8.3 Hz, 1H), 7.72 (dt, J=8.2, 4.8 Hz, 1H), 7.59 (d, J=5.7 Hz, 1H), 5.44 (s, 2H), 4.72-4.45 (m, 1H), 4.33 (t, J=6.3 Hz, 1H), 3.61 (m, 2H), 3.15 (d, J=3.4 Hz, 3H), 3.09 (s, 2H), 2.41 (d, J=2.3 Hz, 3H), 2.10-1.87 (m, 3H), 1.88-1.59 (m, 2H), 1.50 (dd, J=6.9, 2.8 Hz, 3H), 1.33 (d, J=22.9 Hz, 4H); ESMS (M+1)=617.51.

2O. Preparation of Compounds 297, 299, 300, 301, 302, 306, 308, 309, 316, 318, and 319

Compound 308

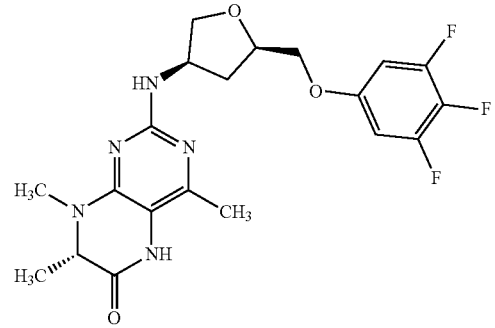

Compound 309

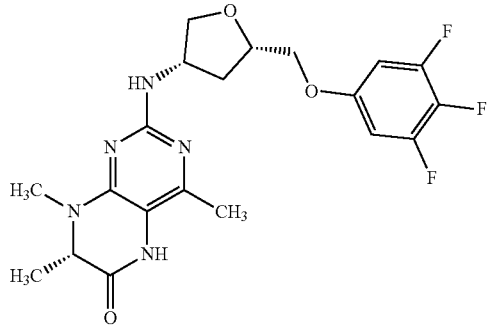

Compounds 308 & 309: (7S)-4,7,8-trimethyl-2-(((3S,5S)-5-((3,4,5-trifluorophenoxy)methyl)tetrahydrofuran-3-yl)amino)-7,8-dihydropteridin-6(5H)-one and (7S)-4,7,8-trimethyl-2-(((3R,5R)-5-((3,4,5-trifluorophenoxy)methyl)-tetrahydrofuran-3-yl)amino)-7,8-dihydropteridin-6(5H)-one These compounds were prepared in 3 steps.

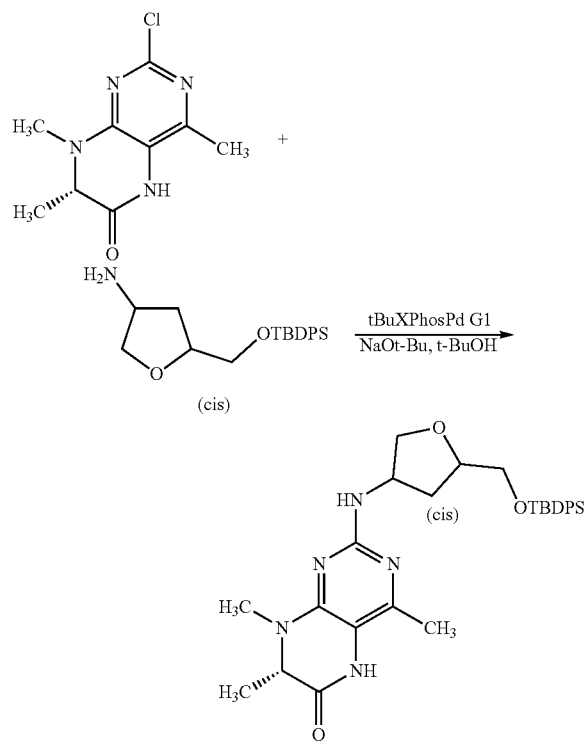

Step 1: (7S)-2-((cis-5-(((tert-butyldiphenylsilyl)oxy)methyl)tetrahydrofuran-3-yl)amino)-4,7,8-trimethyl-7,8-dihydropteridin-6(5H)-one To a mixture of (7S)-2-chloro-4,7,8-trimethyl-5,7-dihydropteridin-6-one (191.1 mg, 0.8429 mmol), (cis)-5-[[tert-butyl(diphenyl)silyl]oxymethyl]tetrahydrofuran-3-amine (333 mg, 0.8429 mmol) and tBuXPhos Pd G1 (23 mg, 0.03349 mmol) in tBuOH (5 mL) was added sodium t-butoxide (1.1 mL of 2 M, 2.11 mmol)) under nitrogen. The reaction was stirred at room temperature for 30 min. Water (50 ml) was added to the reaction and extracted with ethyl acetate (3×50 ml). The combined organic extracts were dried over anhydrous sodium sulfate, filtered and evaporated in vacuo. The resulting residue was purified by column chromatography (SiO$_2$) eluting with a gradient of 10-100% ethyl acetate in hexanes. The desired fractions were evaporated to afford the title product as a mixture of cis isomers, wt. 282 mg (61% yield). 1H NMR (400 MHz, CDCl$_3$) δ 7.61-7.53 (m, 4H), 7.35-7.20 (m, 6H), 4.81 (t, J=6.8 Hz, 1H), 4.47-4.36 (m, 1H), 3.99-3.82 (m, 3H), 3.67-3.53 (m, 3H), 2.86 (s, 3H), 2.25 (dt, J=12.9, 7.7 Hz, 1H), 2.04 (d, J=3.1 Hz, 3H), 1.68-1.56 (m, 1H), 1.25 (dd, J=6.9, 1.4 Hz, 3H), 0.95 (s, 9H). ESMS (M+1)=546.31.

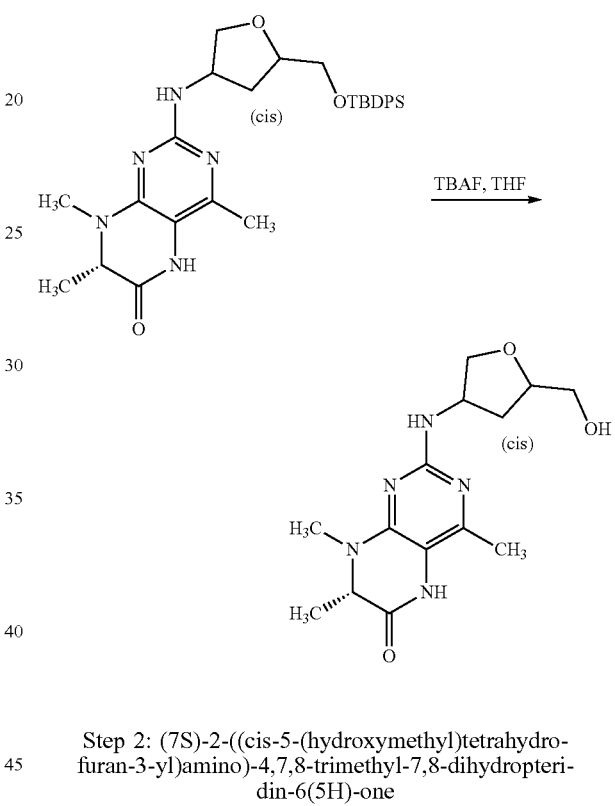

Step 2: (7S)-2-((cis-5-(hydroxymethyl)tetrahydrofuran-3-yl)amino)-4,7,8-trimethyl-7,8-dihydropteridin-6(5H)-one To a solution of (7S)-2-((cis-5-(((tert-butyldiphenylsilyl)oxy)methyl)tetrahydrofuran-3-yl)amino)-4,7,8-trimethyl-7,8-dihydropteridin-6(5H)-one (279 mg, 0.5045 mmol) in THF (6 mL) was added tetrabutylammonium fluoride (757.4 μL of 1 M, 0.7574 mmol). The reaction was stirred at room temperature for 12 hours. The reaction was evaporated in vacuo and 20 ml of brine was added to the residue followed by extraction with ethyl acetate (2×30 ml) and dichloromethane (2×10 ml). The combined organic extracts were dried over MgSO4, filtered, and evaporated. The crude product was purified by column chromatography (SiO$_2$) eluting with a gradient of d0-10% methanol in dichloromethane. The desired fractions were evaporated in vacuo to afford the title product as a mixture of cis isomers, wt. 234 mg (92% yield). 1H NMR (400 MHz, CDCl$_3$) δ 5.65 (s, 1H), 4.52 (d, J=4.0 Hz, 1H), 4.15-4.09 (m, 3H), 4.04 (dt, J=7.1, 3.5 Hz, 1H), 3.93 (ddd, J=9.2, 5.2, 4.1 Hz, 1H), 3.86-3.74 (m, 3H), 3.59 (dd, J=11.8, 4.7 Hz, 1H), 3.42-3.34 (m, 9H), 3.03 (s, 3H), 2.45-2.30 (m, 1H), 2.24 (s, 3H), 1.75-1.62 (m, 10H), 1.38 (dd, J=6.8, 0.7 Hz, 4H), 1.27 (dt, J=14.3, 7.1 Hz, 9H), 1.00 (t, J=7.3 Hz, 13H). ESMS (M+1)=308.0.

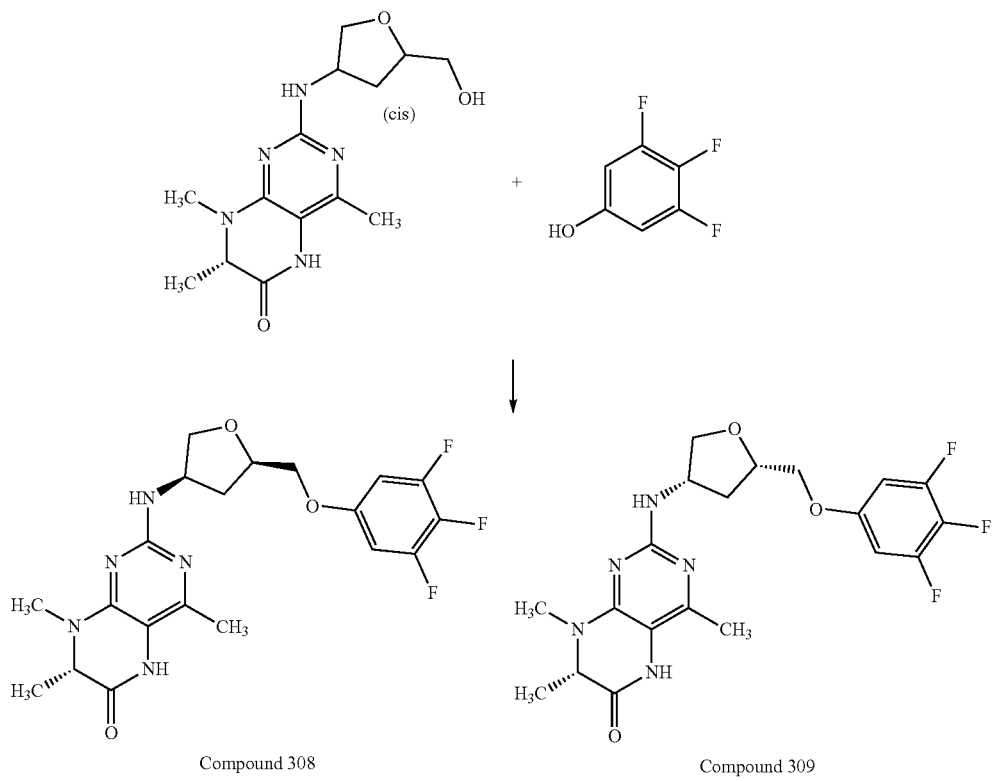

Compound 308  Compound 309

Step 3: (Compounds 308 & 309). (7S)-4,7,8-trimethyl-2-(((3S,5S)-5-((3,4,5-trifluorophenoxy)methyl)tetrahydrofuran-3-yl)amino)-7,8-dihydropteridin-6(5H)-one and (7S)-4,7,8-trimethyl-2-(((3R,5R)-5-((3,4,5-trifluorophenoxy)methyl)tetrahydrofuran-3-yl)amino)-7,8-dihydropteridin-6(5H)-one To a solution of the cis diastereomers (7S)-2-[[(cis)-5-(hydroxymethyl)tetrahydrofuran-3-yl]amino]-4,7,8-trimethyl-5,7-dihydropteridin-6-one (150 mg, 0.3 mmol), 3,4,5-trifluorophenol (133 mg, 0.9 mmol) and triphenylphosphine (196 mg, 0.75 mmol) in THF (4 mL) at room temperature was added diethyl azodicarboxylate (340 µL, 0.75 mmol). The reaction was stirred at 50° C. for 12 hours. The reaction was evaporated in vacuo, and the residue purified by reverse phase chromatography to afford the title product, wt. 74 mg (48% yield); ESMS (M+1)=438.19.

The cis diastereomers were separated by SFC (Column: Chiralpak IC, 10×250 mm; 40% methanol(0.2% diethylamine)/60% $CO_2$, isocratic, 10 ml/min) and the cis isomers arbitrarily assigned.

Peak A: Rt 2.867 mins. (99% ee); 1H NMR (300 MHz, $CDCl_3$) δ 7.88 (s, 1H), 6.71-6.52 (m, 2H), 5.31 (d, J=7.7 Hz, 1H), 4.54 (dd, J=7.2, 3.4 Hz, 1H), 4.39-4.22 (m, 1H), 4.05 (dd, J=12.7, 5.6 Hz, 1H), 3.92-3.74 (m, 3H), 2.99 (s, 3H), 2.51-2.33 (m, 1H), 2.15 (s, 3H), 1.76 (ddd, J=9.6, 5.3, 3.8 Hz, 1H), 1.35 (t, J=8.5 Hz, 3H). ESMS (M+1)=438.14.

Peak B: Rt 3.773 mins. (99% ee); 1H NMR (300 MHz, $CDCl_3$) δ 8.00 (s, 1H), 6.70-6.51 (m, 2H), 5.25 (d, J=8.0 Hz, 1H), 4.53 (ddt, J=11.7, 7.9, 3.8 Hz, 1H), 4.38-4.19 (m, 1H), 4.10-4.01 (m, 1H), 3.88 (ddd, J=6.9, 5.2, 1.8 Hz, 2H), 3.81 (dd, J=9.1, 2.7 Hz, 1H), 2.98 (s, 3H), 2.16 (s, 3H), 1.75 (ddd, J=13.2, 5.4, 4.0 Hz, 1H), 1.33 (d, J=6.9 Hz, 3H). ESMS (M+1)=438.19.

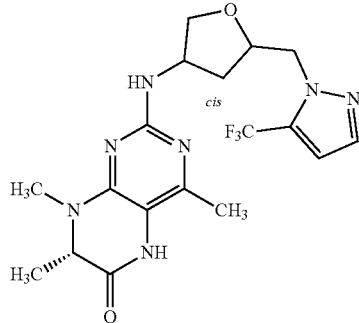

Compound 306

Compound 306: (7S)-4,7,8-trimethyl-2-((cis-5-((5-(trifluoromethyl)-1H-pyrazol-1-yl)methyl)-tetrahydrofuran-3-yl)amino)-7,8-dihydropteridin-6(5H)-one Diethyl azodicarboxylate (0.15 ml, 0.32 mmol) was added dropwise to a solution of (7S)-2-[[(cis)-5-(hydroxymethyl)tetrahydrofuran-3-yl]amino]-4,7,8-trimethyl-5,7-dihydropteridin-6-one (80 mg, 0.16 mmol), 3-(trifluoromethyl)-1H-pyrazole (65 mg, 0.48 mmol), and triphenylphosphine (84 mg, 0.32 mmol) in THF (2 ml). The reaction was stirred at 50° C. for 12 hours then evaporated in vacuo. The crude product was purified by preparative reverse phase HPLC (C18 column) to afford the title product as a mixture of cis diastereomers, wt 26 mg. 1H NMR (300 MHz, Methanol-d4) δ 7.80 (d, J=1.3 Hz, 1H), 6.59 (d, J=2.3 Hz, 1H), 4.55-4.47 (m, 1H), 4.41 (dd, J=8.4, 3.8 Hz, 2H), 4.36-4.23 (m, 2H), 4.01-3.91 (m, 1H), 3.89-3.80 (m, 1H), 3.24 (s, 3H), 2.52 (dt, J=7.0, 5.5 Hz, 1H), 2.30 (s, 3H), 1.90-1.68 (m, 1H), 1.52 (d, J=6.9 Hz, 3H); ESMS (M+1)=426.26.

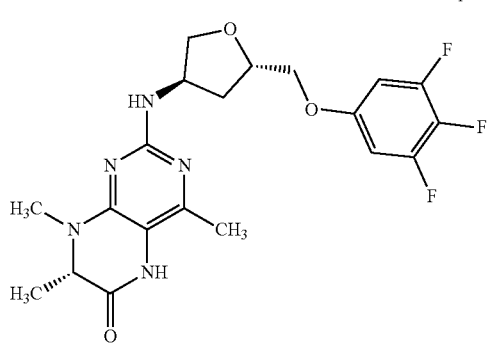

Compound 301

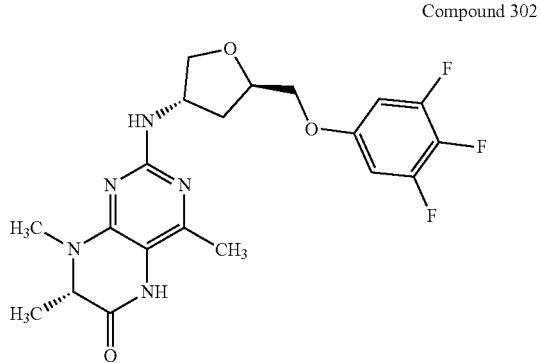

Compound 302

Compounds 301 and 302: (7S)-4,7,8-trimethyl-2-(((3R,5S)-5-((3,4,5-trifluorophenoxy)methyl)tetrahydrofuran-3-yl)amino)-7,8-dihydropteridin-6(5H)-one and (7S)-4,7,8-trimethyl-2-(((3R,5S)-5-((3,4,5-trifluorophenoxy)methyl)tetrahydrofuran-3-yl)amino)-7,8-dihydropteridin-6(5H)-one These compounds were prepared in 3 steps by the same method described for Compounds 308 and 309 via reaction of A-2 and (trans)-5-[[tert-butyl(diphenyl)silyl]-oxymethyl] tetrahydrofuran-3-amine as the initial reactants to provide a mixture of trans isomers (Compound 299) that were separated by SFC (Column: Chiralpak IC, 10×250 mm; 40% ethanol(0.2% diethylamine)/60% CO$_2$, isocratic, 10 ml/min) to provide the trans isomers that were arbitrarily assigned.

Peak A: Rt 0.570 mins. (99% ee); 1H NMR (400 MHz, CDCl$_3$) δ 8.09 (s, 1H), 6.55-6.41 (m, 2H), 4.97 (s, 1H), 4.57-4.45 (m, 1H), 4.38 (dt, J=7.9, 5.8 Hz, 1H), 4.13 (dd, J=9.1, 5.5 Hz, 1H), 4.01 (q, J=6.9 Hz, 1H), 3.88 (ddd, J=15.4, 9.8, 4.7 Hz, 2H), 3.65 (dd, J=9.1, 4.0 Hz, 1H), 2.98 (s, 3H), 2.15 (s, 3H), 2.08-1.95 (m, 2H), 1.34 (d, J=6.9 Hz, 3H). ESMS (M+1)=438.19.

Peak B: Rt 0.856 mins. (99% ee); 1H NMR (400 MHz, CDCl$_3$) δ 9.18 (s, 1H), 6.70 (s, 1H), 6.55-6.40 (m, 2H), 4.50 (d, J=5.2 Hz, 1H), 4.47-4.35 (m, 1H), 4.21-4.10 (m, 1H), 4.08 (q, J=6.9 Hz, 1H), 3.94 (dd, J=10.0, 3.4 Hz, 1H), 3.85 (dd, J=9.9, 5.2 Hz, 1H), 3.70 (dd, J=9.2, 4.3 Hz, 1H), 3.06 (s, 3H), 2.27 (s, 3H), 2.20-2.02 (m, 2H), 1.43 (d, J=6.9 Hz, 3H). ESMS (M+1)=438.23.

Compound 297: (7S)-2-((trans-4-(4-fluorophenoxy) tetrahydrofuran-3-yl)amino)-4,7,8-trimethyl-7,8-dihydropteridin-6(5H)-one The compound was prepared by procedure Method A via reaction of intermediates A-2 and B-156 to provide the title product as a mixture of trans isomers, 10% yield. 1H NMR-1H NMR (300 MHz, Methanol-d4) δ 6.98 (ddd, J=13.7, 9.2, 3.4 Hz, 5H), 4.96-4.86 (m, 1H), 4.63 (s, 1H), 4.33-4.15 (m, 3H), 4.01-3.78 (m, 2H), 3.05 (d, J=5.4 Hz, 3H), 2.31 (s, 3H), 1.50 (dd, J=6.9, 2.0 Hz, 3H); ESMS (M+1)=388.22.

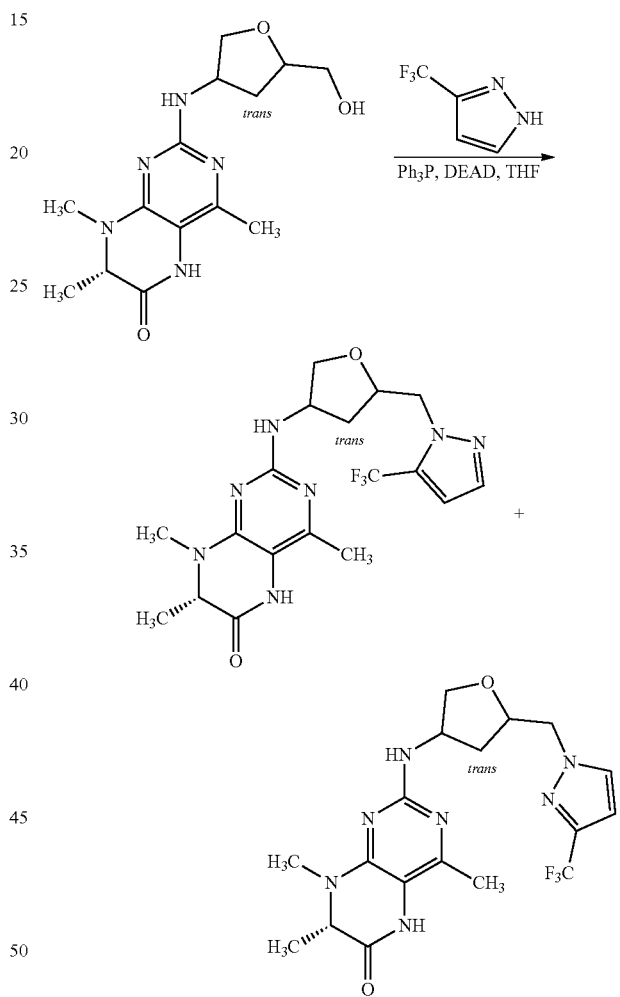

Compound 300, 316, 318, and 319: (7S)-4,7,8-trimethyl-2-(trans-(5-((5-(trifluoromethyl)-1H-pyrazol-1-yl)methyl)tetrahydrofuran-3-yl)amino)-7,8-dihydropteridin-6(5H)-one and (7S)-4,7,8-trimethyl-2-((trans-5-((3-(trifluoromethyl)-1H-pyrazol-1-yl) methyl)tetrahydrofuran-3-yl)amino)-7,8-dihydropteridin-6(5H)-one The compound was prepared by reaction of (7S)-2-((trans-5-(hydroxymethyl)tetrahydrofuran-3-yl)amino)-4,7,8-trimethyl-7,8-dihydropteridin-6(5H)-one and 3-(trifluoromethyl)-1H-pyrazole under the Mitsunobu conditions run for Compound 306 to afford a mixture of trans diastereomers as well as regioisomers (Compound 300) based on the 1H NMR. The mixture was separated by SFC (Chiralpak IC column (50% CO2/50% methanol(0.2% diethylamine), isocratic); 12 ml/min to afford Peak A (Compound 318):

Rt 5.33 mins. (>99% ee); 1H NMR (400 MHz, CDCl$_3$) δ 7.57 (s, 1H), 7.51 (s, 1H), 6.46 (d, J=2.1 Hz, 1H), 4.81 (s, 1H), 4.49-4.27 (m, 3H), 4.18 (dd, J=14.2, 5.9 Hz, 1H), 4.03-3.93 (m, 2H), 3.59 (dd, J=9.1, 3.9 Hz, 1H), 2.96 (d, J=8.9 Hz, 3H), 2.11 (s, 3H), 1.88 (dt, J=31.8, 13.1 Hz, 1H), 1.33 (d, J=6.8 Hz, 3H); ESMS (M+1)=426.18.

Peak B (Compound 319):

Rt 7.15 mins. (>99% ee); 1H NMR (400 MHz, CDCl$_3$) δ 7.46 (d, J=8.9 Hz, 2H), 6.55 (d, J=1.3 Hz, 1H), 4.57-4.38 (m, 3H), 4.25 (ddd, J=19.1, 14.1, 6.0 Hz, 3H), 3.61 (dd, J=9.3, 3.9 Hz, 2H), 2.97 (d, J=3.7 Hz, 3H), 2.11 (d, J=4.6 Hz, 3H), 1.33 (d, J=6.9 Hz, 3H); ESMS (M+1)=426.14.

Peak C & D (Compound 316):

Rt 9.95 mins. (2 peaks observed, not separable); 1H NMR (400 MHz, CDCl$_3$) δ 7.73 (s, 1H), 7.49 (d, J=15.1 Hz, 1H), 6.51 (d, J=36.2 Hz, 1H), 4.76 (s, 1H), 4.61-4.41 (m, 1H), 4.45-4.26 (m, 3H), 4.19 (td, J=13.1, 5.0 Hz, 1H), 3.68-3.51 (m, 1H), 2.95 (d, J=4.7 Hz, 3H), 2.12 (s, 3H), 1.98-1.83 (m, 3H), 1.32 (d, J=6.8 Hz, 3H); ESMS (M+1)=426.18.

2P. Preparation of Compounds

The following compounds were prepared in a similar manner as those described above for the compounds of Tables 1-14.

Compound 127: (7S)-2-(((1-((R)-1-(4,4-difluorocyclohexyl)pyrrolidin-3-yl)-1H-pyrazol-4-yl)methyl)amino)-4,7,8-trimethyl-7,8-dihydropteridin-6(5H)-one The compound was prepared by procedure Method A via reaction of intermediates A-2 and B-160 to provide the title product. 1H NMR (300 MHz, Methanol-d4) δ 7.69 (s, 1H), 7.44 (s, 1H), 4.37 (s, 3H), 4.07 (q, J=6.8 Hz, 2H), 3.07 (s, 3H), 3.05-2.82 (m, 3H), 2.71 (td, J=8.5, 6.3 Hz, 1H), 2.49-2.23 (m, 3H), 2.18 (s, 3H), 2.15-1.49 (m, 11H), 1.33 (d, J=6.8 Hz, 3H); ESMS(M+1)=475.3.

Compound 142: (7S)-2-(((1-((S)-1-(4,4-difluorocyclohexyl)pyrrolidin-3-yl)-1H-pyrazol-4-yl)methyl)amino)-4,7,8-trimethyl-7,8-dihydropteridin-6(5H)-one The compound was prepared by procedure Method A via reaction of intermediates A-2 and B-161 to provide the title product. 1H NMR (300 MHz, Methanol-d4) δ 7.69 (s, 1H), 7.44 (s, 1H), 4.51-4.21 (m, 2H), 4.07 (q, J=6.8 Hz, 1H), 3.39-3.21 (m, 2H), 3.12-2.77 (m, 6H), 2.69 (td, J=8.5, 6.4 Hz, 1H), 2.50-2.23 (m, 2H), 2.22-1.48 (m, 12H), 1.33 (d, J=6.8 Hz, 3H). ESMS(M+1)=475.24.

Compound 169: (7S)-2-(((6-((1-(4-fluorophenyl)pyrrolidin-3-yl)oxy)pyridin-3-yl)methyl)amino)-4,7,8-trimethyl-7,8-dihydropteridin-6(5H)-one The compound was prepared by procedure Method A via reaction of intermediates B-147 and A-2 to provide the title product. 1H NMR (300 MHz, Methanol-d4) δ 8.14 (s, 1H), 7.68 (d, J=7.3 Hz, 1H), 6.89 (d, J=8.5 Hz, 2H), 6.72 (d, J=8.4 Hz, 1H), 6.52 (s, 2H), 5.59 (s, 1H), 4.50 (d, J=27.5 Hz, 3H), 4.06 (d, J=6.4 Hz, 1H), 3.65 (s, 1H), 3.48-3.32 (m, 5H), 3.04 (s, 3H), 2.47-2.06 (m, 5H), 1.33 (d, J=6.5 Hz, 3H); ESMS (M+1)=478.45.

Compound 170: (7S)-2-(((1-((R)-1-(4-fluorophenyl)pyrrolidin-3-yl)-1H-pyrazol-4-yl)methyl)amino)-4,7,8-trimethyl-7,8-dihydropteridin-6(5H)-one The compound was prepared by procedure Method A via reaction of intermediates A-2 and B-163 to provide the title product. 1H NMR (300 MHz, Methanol-d4) δ 7.53 (d, J=35.2 Hz, 2H), 6.93 (s, 2H), 6.57 (s, 2H), 5.49 (s, 1H), 5.05 (s, 1H), 4.36 (s, 2H), 4.04 (s, 1H), 3.83-3.39 (m, 4H), 3.03 (s, 3H), 2.46 (d, J=34.0 Hz, 2H), 2.16 (s, 2H), 1.31 (s, 3H); ESMS(M+1)=451.48.

Compound 171: (7S)-2-(((1-((S)-1-(4-fluorophenyl)pyrrolidin-3-yl)-1H-pyrazol-4-yl)methyl)amino)-4,7,8-trimethyl-7,8-dihydropteridin-6(5H)-one The compound was prepared by procedure Method A via reaction of intermediates A-2 and B-162 to provide the title product. 1H NMR (300 MHz, Methanol-d4) δ 7.53 (d, J=35.2 Hz, 2H), 6.93 (s, 2H), 6.57 (s, 2H), 5.49 (s, 1H), 5.05 (s, 1H), 4.36 (s, 2H), 4.04 (s, 1H), 3.83-3.39 (m, 4H), 3.03 (s, 3H), 2.46 (d, J=34.0 Hz, 2H), 2.16 (s, 2H), 1.31 (s, 3H); ESMS(M+1)=451.48.

Compound 219: (7S)-2-(((1-(((S)-1-(3,5-difluorophenyl)pyrrolidin-2-yl)methyl)-1H-pyrazol-4-yl)methyl)amino)-4,7,8-trimethyl-7,8-dihydropteridin-6(5H)-one The compound was prepared by procedure Method A via reaction of intermediate A-2 and B-200 to provide the title product, 50 mg (22.6% yield) of title compound. 1H NMR (300 MHz, Methanol-d4) δ 7.79 (s, 1H), 7.68 (s, 1H), 6.40 (ddd, J=11.3, 6.6, 2.1 Hz, 3H), 4.63 (s, 2H), 4.58-4.30 (m, 4H), 3.75-3.43 (m, 3H), 2.49 (s, 3H), 2.42-2.03 (m, 4H), 1.97-1.48 (m, 6H). ESMS(M+1)=483.44.

Compound 244: (7S)-2-((1-benzylazetidin-3-yl)amino)-4,7,8-trimethyl-7,8-dihydropteridin-6(5H)-one The compound was prepared by procedure Method B via reaction of intermediate A-2 and 1-benzyl-3-aminoazetidine to provide the title product. 1H NMR (300 MHz, CDCl$_3$) δ 7.41-7.24 (m, 5H), 4.52-4.42 (m, 1H), 4.07-3.96 (m, 1H), 3.94-3.72 (m, 4H), 3.44-3.35 (m, 1H), 3.12-3.07 (m, 3H), 2.91-2.79 (m, 2H), 2.28 (dd, J=7.6, 4.7 Hz, 2H), 1.43 (dd, J=6.9, 3.9 Hz, 3H); ESMS(M+1)=353.33.

Compound 245: (7S)-2-((1-benzylazetidin-3-yl)amino)-7,8-dimethyl-7,8-dihydropteridin-6(5H)-one The compound was prepared by procedure Method B via reaction of intermediate A-1 and 1-benzyl-3-aminoazetidine to provide the title product. 1H NMR (300 MHz, CDCl$_3$) δ 7.44-7.21 (m, 6H), 4.46 (ddd, J=11.1, 7.6, 4.8 Hz, 1H), 4.10-3.79 (m, 4H), 3.68-3.47 (m, 1H), 3.47-3.23 (m, 1H), 3.10 (s, 3H), 2.99-2.88 (m, 2H), 1.48 (dq, J=6.5, 3.7 Hz, 3H); ESMS(M+1)=339.33.

Compound 298: 3,4,5-trifluoro-N-(cis-3-(((S)-4,7,8-trimethyl-6-oxo-5,6,7,8-tetrahydropteridin-2-yl)amino)cyclopentyl)benzamide The compound was prepared by procedure Method A via reaction of intermediates A-2 and B-159 to provide the title product. ESMS (M+1)=449.28.

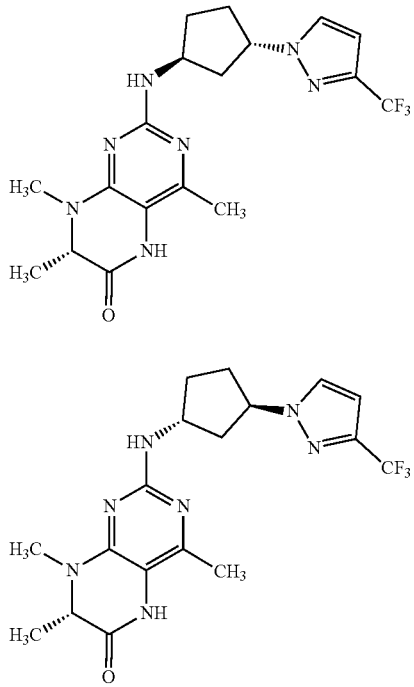

Compound 310

Compound 311

Compounds 310 and 311: (7S)-4,7,8-trimethyl-2-(((1S,3S)-3-(3-(trifluoromethyl)-1H-pyrazol-1-yl)cyclopentyl)amino)-7,8-dihydropteridin-6(5H)-one and (7S)-4,7,8-trimethyl-2-(((1R,3R)-3-(3-(trifluoromethyl)-1H-pyrazol-1-yl)cyclopentyl)amino)-7,8-dihydropteridin-6(5H)-one The compound was prepared by procedure Method A via reaction of intermediates A-2 and B-158 to provide the title products as a mixture of trans diastereomers. The diastereomers were separated by chiral HPLC (Chiralpak AD-H column; 85% hexanes/7.5% ethanol/7.5% methanol(0.2% diethylamine), isocratic, 20 ml/min) and arbitrarily assigned as Peak A and B.

Peak A: Rt 6.486 mins. (>99% ee); 1H NMR (300 MHz, CDCl$_3$) δ 8.60 (s, 1H), 7.48 (dq, J=1.9, 1.0 Hz, 1H), 6.55-6.47 (m, 1H), 4.94-4.70 (m, 2H), 4.57 (q, J=6.5 Hz, 1H), 4.08 (q, J=6.9 Hz, 1H), 3.05 (s, 3H), 2.62-2.31 (m, 3H), 2.28-2.05 (m, 5H), 1.65 (dddd, J=13.8, 9.0, 5.7, 2.4 Hz, 1H), 1.41 (d, J=6.8 Hz, 3H); ESMS (M+1)=410.18.

Peak B: Rt 10.216 mins. (>99% ee); 1H NMR (300 MHz, CDCl$_3$) δ 8.45 (s, 1H), 7.49 (dq, J=2.2, 1.0 Hz, 1H), 6.51 (dd, J=2.3, 0.7 Hz, 1H), 4.87 (dt, J=12.9, 6.6 Hz, 2H), 4.63-4.50 (m, 1H), 4.08 (q, J=6.9 Hz, 1H), 3.05 (s, 3H), 2.63-2.30 (m, 3H), 2.28-2.11 (m, 6H), 1.72-1.57 (m, 1H), 1.41 (d, J=6.8 Hz, 3H). ESMS (M+1)=410.18

Preparation of Compound 409. (7S)-2-(((1-((6-chloropyridin-3-yl)methyl)-1H-pyrazol-4-yl)methyl)amino)-7-isopropyl-4,8-dimethyl-7,8-dihydropteridin-6(5H)-one

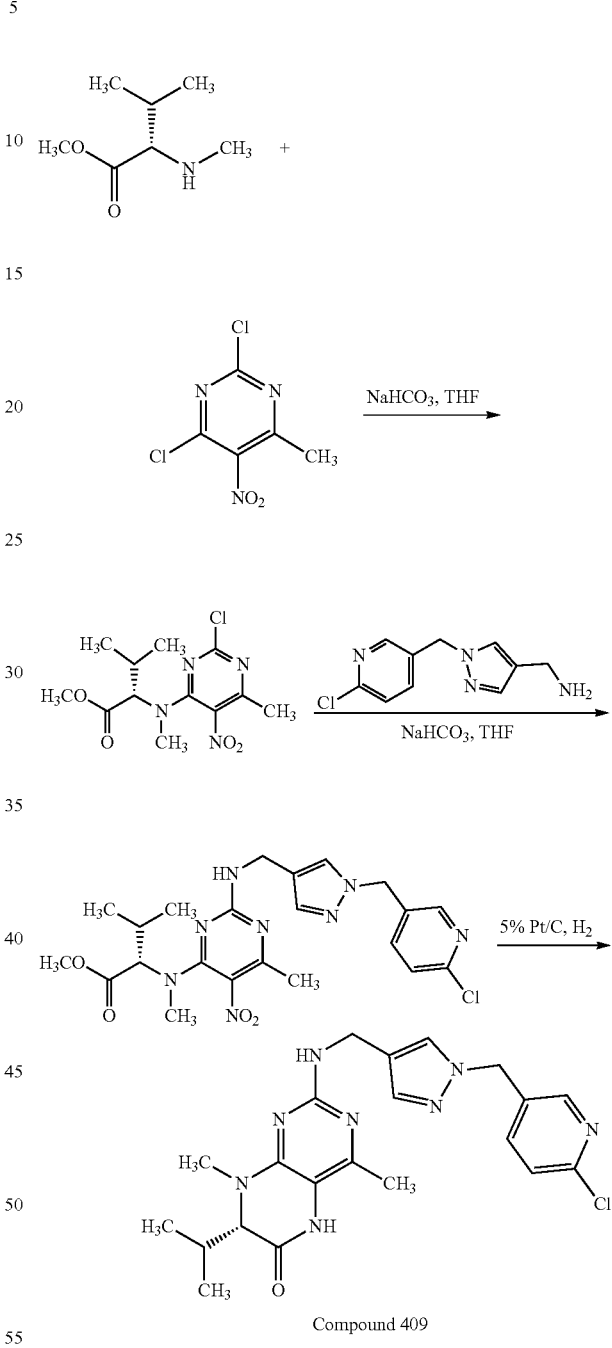

Compound 409

Step A: Methyl N-(2-chloro-6-methyl-5-nitropyrimidin-4-yl)-N-methyl-L-valinate A flask with 2,4-Dichloro-6-methyl-5-nitropyrimidine (10 g, 48.1 mmol), methyl methyl-L-valinate hydrochloride (9.61 g, 53 mmol), and sodium bicarbonate (20.2 g, 240.4 mmol) in cyclohexane (100 ml) was equipped with a Dean Stark trap and heated to reflux. The hot reaction mixture was filtered through Celite hot. The filtrate was evaporated in vacuo to afford the title product, wt. 15.5 g that was used without further purification. 1H NMR (300 MHz, CDCl$_3$) δ 4.99 (d, J=10.5 Hz, 1H), 3.77 (s, 3H), 2.95 (s, 3H), 2.49 (s, 3H), 2.45-2.23 (m, 1H), 1.10 (d, J=6.6 Hz, 3H), 0.99 (d, J=6.7 Hz, 3H); ESMS (M+1)=317.04.

Step B: Methyl N-(2-(((1-((6-chloropyridin-3-yl) methyl)-1H-pyrazol-4-yl)methyl)amino)-6-methyl-5-nitropyrimidin-4-yl)-N-methyl-L-valinate Methyl N-(2-chloro-6-methyl-5-nitropyrimidin-4-yl)-N-methyl-L-valinate (12 g, 37.9 mmol), (1-((6-chloropyridin-3-yl)methyl)-1H-pyrazol-4-yl)methanamine (B-67; 16.54 g, 49.3 mmol), and sodium bicarbonate (9.88 g, 118 mmol) were taken into 120 ml of tetrahydrofuran and refluxed for 6 hours. The reaction was filtered through Celite and the filtrated evaporated in vacuo to afford a yellow oil. The curde product was filtered through a silica gel plug eluting with ethyl acetate. The collected fractions were evaporated in vacuo to afford 19 g of the title product as a yellow oil. ESMS (M+1)=503.23.

Step C: (S)-2-(((1-((6-chloropyridin-3-yl)methyl)-1H-pyrazol-4-yl)methyl)amino)-7-isopropyl-4,8-dimethyl-7,8-dihydropteridin-6(5H)-one hydrochloride Methyl N-(2-(((1-((6-chloropyridin-3-yl)methyl)-1H-pyrazol-4-yl)methyl)amino)-6-methyl-5-nitropyrimidin-4-yl)-N-methyl-L-valinate (19 g, 37.9 mmol) was dissolved in 200 ml of methanol and 5% Pt/C (1.5 g, 0.384 mmol) was added to the solution and the mixture placed on the Parr shaker under 58 psi of hydrogen. After 5 hours, the reaction was filtered through Celite and the colorless filtrate evaporated in vacuo to afford the crude product. The crude product was purified by column chromatography (SiO$_2$, 330 g) eluting with a gradient of dichloromethane to 20% methanol in dichloromethane. The desired fractions were combined and evaporated to provide the product as a white foam, wt. 13 g (77% yield). The product was dissolved in 100 ml of methanol and treated with 1N HCl in diethyl ether (36 ml) and stirred for 30 minutes. The solvent was removed in vacuum and the resulting foam was triturated with 150 ml of t-butylmethyl ether and stirred for 30 minutes. The resulting material was collected by vacuum filtration and the filter cake dried at 50° C. overnight to provide the title product, wt. 13 g. [α]$_D$=+60.0° (c=1.0, MeOH). Chiral HPLC(Chiralpak IC column, 20% MeOH/30% EtOH/50% hexanes (0.1% diethylamine), isocratic): Rt 10.646 minutes (>98% ee). 1H NMR (300 MHz, DMSO-d6) δ 12.78 (s, 1H), 10.53 (s, 1H), 8.31 (d, J=2.1 Hz, 1H), 7.94 (s, 1H), 7.84 (s, 1H), 7.70 (dd, J=8.2, 2.5 Hz, 1H), 7.50 (d, J=8.2 Hz, 2H), 5.35 (s, 2H), 4.49-4.34 (m, 2H), 4.16 (d, J=3.8 Hz, 1H), 3.18 (s, 3H), 2.35-2.10 (m, 4H), 1.01 (d, J=6.9 Hz, 3H), 0.77 (d, J=6.9 Hz, 3H). ESMS (M+1)=441.26.

2Q. Preparations of Compounds

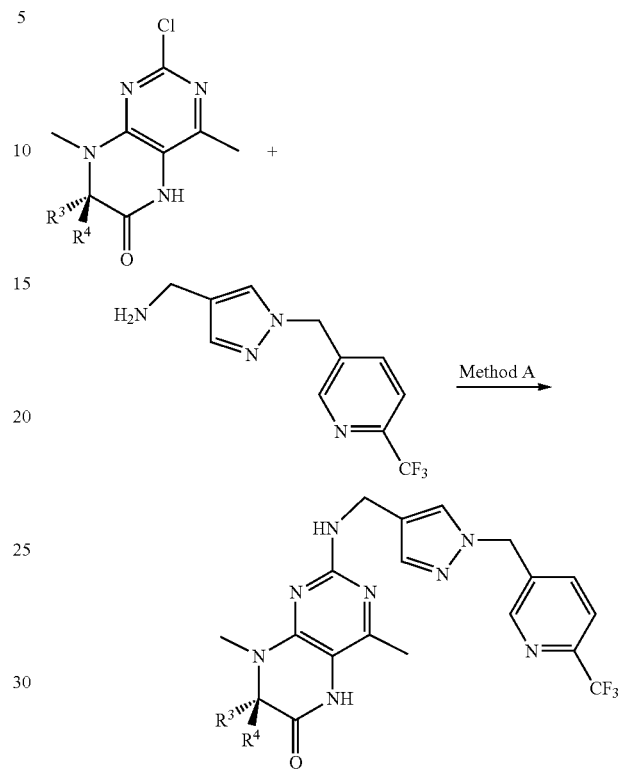

Table 15 provides certain compounds prepared by Method A procedure by reaction of Intermediate A-# and B-52 (See procedure for compound 46), and $^1$H NMR data are also provided for certain compounds.

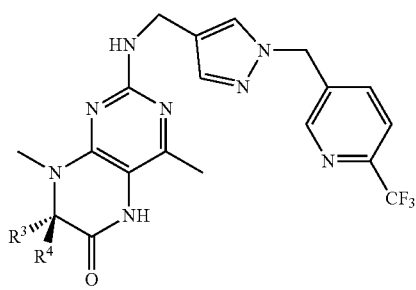

TABLE 15

| Compound No. | R$^3$ | R$^4$ | Intermediate A-# | Op rotation | M + 1 |
|---|---|---|---|---|---|
| 436 | —C(CH$_3$)$_3$ | H | A-55 | +54.6°<br>c = 0.5<br>CHCl$_3$ | 489.27 |
| 495 | —CH$_2$CF$_3$ | H | A-57 | +18.24°<br>c = 0.5<br>MeOH | 515.28 |
| 498 | —(R)—CH(OCH$_3$)CH$_3$ | H | A-59 | +72.6°<br>c = 0.5<br>MeOH | 491.32 |

TABLE 15-continued

| Compound No. | R³ | R⁴ | Intermediate A-# | Op rotation | M + 1 |
|---|---|---|---|---|---|
| 563 | —CH₂CH(CH₃)₂ | H | A-60 | 80.4 c = 0.5 CHCl3 | 489.52 |
| 589 | —CH₂CH₂OCH₃ | H | A-62 | +87.0° c = 1.0 MeOH | 491.07 |
| 590 | —CH₂OtBu | H | A-63 | 38.2 c = 0.5 CHCl3 | 519.06 |
| 604 | —CH₂OH | H | * | 38.2 c = 0.5 CHCl3 | 463.61 |
| 600 | Spiro-oxetan3-yl | | | | 475.26 |
| 601 | 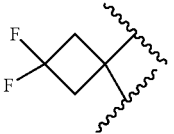 [SMILES: *C1(*)CC(F)(F)C1] | | A-65 | | 509.25 |
| 661 | 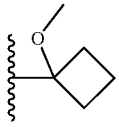 | H | A-66 | 78.0 c = 0.5 MeOH | 517.22 |
| 665 | 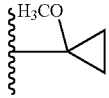 | H | A-68 | 61.0 c = 0.5 CHCl3 | 503.26 |
| 726 | —C(CH₃)₂OH | H | A-61 | +61.6 c = 0.5 MeOH | 491.29 |
| 742 | (R)—CH(OtBu)CH₃ | H | A-74 | 142.2 c = 0.5 CHCl₃ | 533.46 |
| 744 | (R)—CH(OH)CH₃ | H | ** | 32.2 c = 0.5 CHCl₃ | |
| 703 | —CH₂OCH₃ | —CH₃ | A-69 | | 491.2 |
| 707 | —CH₃ | —CH₂OCH₃ | A-70 | −43.3 c = 0.5 MeOH | 491.25 |
| 662 | 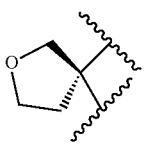 | | A-67 | +28.3° c = 1.0 MeOH | 489.26 |
| 663 | 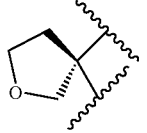 | | A-67 | −27° c = 1.0 MeOH | 489.22 |

*Compound 604 was prepared by deprotection of Compound 590 in 4 M HCl in dioxane and methanol at 65° C.
**Compound 744 was prepared by deprotection of Compound 742 in a similar manner.

Compound 436. (7S)-7-(tert-butyl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, Chloroform-d) δ 8.67 (s, 1H), 8.52 (d, J=1.7 Hz, 1H), 7.63-7.52 (m, 2H), 7.48 (s, 1H), 7.37 (s, 1H), 5.28 (s, 2H), 5.20 (d, J=12.9 Hz, 1H), 4.37 (d, J=5.7 Hz, 2H), 3.62 (s, 1H), 3.13 (s, 3H), 2.15 (s, 3H), 0.92 (s, 9H).

Compound 495. (S)-4,8-dimethyl-7-(2,2,2-trifluoroethyl)-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, DMSO-d6) δ 10.04 (s, 1H), 8.62 (d, J=1.9 Hz, 1H), 7.88-7.78 (m, 2H), 7.75 (s, 1H), 7.42 (s, 1H), 6.60 (t, J=6.0 Hz, 1H), 5.44 (s, 2H), 4.40 (dd, J=6.0, 4.0 Hz, 1H), 4.23 (d, J=6.0 Hz, 2H), 2.99 (s, 3H), 2.84-2.70 (m, 1H), 2.13 (s, 3H).

Compound 498. (S)-7-((R)-1-methoxyethyl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, DMSO-d6) δ 9.90 (s, 1H), 8.63 (s, 1H), 7.92-7.82 (m, 2H), 7.76 (d, J=0.8 Hz, 1H), 7.43 (d, J=0.8 Hz, 1H), 6.58 (t, J=6.0 Hz, 1H), 5.44 (s, 2H), 4.24 (d, J=6.0 Hz, 2H), 3.92 (dd, J=5.9, 0.9 Hz, 1H), 3.47 (p, J=6.2 Hz, 1H), 3.16 (s, 3H), 3.08 (s, 3H), 2.12 (s, 3H), 1.08 (d, J=6.3 Hz, 3H).

Compound 563. (S)-7-isobutyl-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, Chloroform-d) δ 8.61 (s, 1H), 7.87 (s, 1H), 7.75-7.62 (m, 2H), 7.57 (d, J=0.7 Hz, 1H), 7.50-7.38 (m, 1H), 5.37 (s, 2H), 4.91 (d, J=6.1 Hz, 1H), 4.45 (d, J=5.8 Hz, 2H), 4.01 (dd, J=7.4, 5.9 Hz, 1H), 3.07 (s, 3H), 2.22 (s, 3H), 1.80 (dp, J=12.9, 6.6 Hz, 1H), 1.61 (ddd, J=7.9, 5.6, 1.4 Hz, 2H), 0.99 (d, J=6.4 Hz, 3H), 0.94 (d, J=6.6 Hz, 3H).

Compound 589. (S)-7-(2-methoxyethyl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, Chloroform-d) δ 9.10 (s, 1H), 8.62-8.54 (m, 1H), 7.71-7.61 (m, 1H), 7.55 (d, J=0.7 Hz, 1H), 7.42 (d, J=0.8 Hz, 1H), 5.33 (d, J=17.3 Hz, 1H), 4.91 (t, J=5.9 Hz, 1H), 4.43 (d, J=5.8 Hz, 1H), 4.15 (dd, J=7.3, 4.2 Hz, 1H), 3.42 (ddd, J=7.6, 5.6, 3.6 Hz, 1H), 3.21 (s, 2H), 3.05 (s, 2H), 2.24 (s, 2H), 2.26-2.05 (m, 1H), 2.07-1.87 (m, 0H).

Compound 590. (S)-7-(tert-butoxymethyl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, Chloroform-d) δ 8.66-8.47 (m, 2H), 7.66 (d, J=1.4 Hz, 2H), 7.56 (d, J=0.7 Hz, 1H), 7.43 (d, J=0.8 Hz, 2H), 5.36 (s, 2H), 4.93 (t, J=5.8 Hz, 1H), 4.44 (d, J=5.8 Hz, 2H), 4.08 (t, J=3.2 Hz, 1H), 3.70 (dd, J=3.2, 2.0 Hz, 2H), 3.08 (s, 3H), 2.21 (s, 3H), 1.04 (d, J=1.1 Hz, 9H).

Compound 604. (S)-7-(hydroxymethyl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, Methanol-d$_4$) δ 8.53 (s, 1H), 7.85-7.75 (m, 2H), 7.73 (s, 1H), 7.54 (s, 1H), 5.45 (s, 2H), 4.41 (s, 2H), 4.06 (t, J=2.8 Hz, 1H), 3.99-3.81 (m, 2H), 3.11 (s, 3H), 2.15 (s, 3H).

Compound 600. 4',8'-dimethyl-2'-(((1-((6-(trifluoromethyl)pyridin-3-yl)methyl)-1H-pyrazol-4-yl)methyl)amino)-5',8'-dihydro-6'H-spiro[oxetane-3,7'-pteridin]-6'-one $^1$H NMR (400 MHz, Chloroform-d) δ 8.67-8.50 (m, 2H), 7.83-7.63 (m, 2H), 7.58 (s, 1H), 7.44 (s, 1H), 5.38 (s, 2H), 5.30 (d, J=7.1 Hz, 2H), 4.92 (t, J=6.5 Hz, 3H), 4.46 (d, J=5.8 Hz, 2H), 3.50 (s, 3H), 2.26 (s, 3H).

Compound 601. 3,3-difluoro-4',8'-dimethyl-2'-(((1-((6-(trifluoromethyl)pyridin-3-yl)methyl)-1H-pyrazol-3-yl)methyl)amino)-5',8'-dihydro-6'H-spiro[cyclobutane-1,7'-pteridin]-6'-one $^1$H NMR (300 MHz, Chloroform-d) δ 8.96 (s, 1H), 8.59 (d, J=1.9 Hz, 1H), 7.74-7.64 (m, 2H), 7.57 (d, J=0.7 Hz, 1H), 7.44 (d, J=0.8 Hz, 1H), 5.38 (s, 2H), 4.97 (t, J=5.8 Hz, 1H), 4.45 (d, J=5.8 Hz, 2H), 3.62-3.38 (m, 2H), 3.24 (s, 3H), 3.19-3.03 (m, 1H), 2.28 (s, 3H).

Compound 661. 7-(1-methoxycyclobutyl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (400 MHz, DMSO) δ 9.91 (s, 1H), 8.63 (s, 1H), 7.85 (dt, J=8.1, 7.0 Hz, 2H), 7.74 (s, 1H), 7.42 (s, 1H), 6.49 (s, 1H), 5.44 (s, 2H), 4.23 (d, J=6.0 Hz, 2H), 4.20 (s, 1H), 3.09 (s, 3H), 3.06 (s, 3H), 2.27-2.17 (m, 1H), 2.17-2.05 (m, 5H), 2.01-1.91 (m, 1H), 1.77-1.63 (m, 1H), 1.55 (dt, J=9.1, 8.0 Hz, 1H).

Compound 665. 7-(1-methoxycyclopropyl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, Chloroform-d) δ 8.61 (s, 1H), 8.24 (s, 1H), 7.67 (d, J=1.5 Hz, 2H), 7.57 (d, J=2.0 Hz, 1H), 7.44 (s, 1H), 5.37 (s, 2H), 4.88 (d, J=6.0 Hz, 1H), 4.46 (d, J=5.7 Hz, 2H), 3.70 (d, J=1.9 Hz, 1H), 3.19 (d, J=1.8 Hz, 3H), 3.17 (d, J=1.9 Hz, 3H), 2.24 (d, J=1.8 Hz, 3H), 1.13-0.87 (m, 3H), 0.86-0.72 (m, 1H)

Compound 726. (S)-7-(2-hydroxypropan-2-yl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (400 MHz, DMSO-d6) δ 9.84 (s, 1H), 8.64 (s, 1H), 7.87 (d, J=7.4 Hz, 1H), 7.83 (d, J=9.7 Hz, 1H), 7.76 (s, 1H), 7.43 (s, 1H), 6.52 (s, 1H), 5.44 (s, 2H), 4.69 (s, 1H), 4.24 (d, J=6.1 Hz, 2H), 3.79 (s, 1H), 3.19-3.09 (m, 3H), 2.09 (s, 3H), 1.16 (d, J=16.2 Hz, 3H), 0.89 (d, J=23.9 Hz, 3H).

Compound 742. (S)-7-((S)-1-(tert-butoxy)ethyl)-4,8-dimethyl-2-(((1-((6-(trifluoromethyl)pyridin-3-yl)methyl)-1H-pyrazol-4-yl)methyl)amino)-7,8-dihydropteridin-6(5H)-one ¹H NMR (300 MHz, Chloroform-d) δ 8.61 (s, 1H), 7.75-7.61 (m, 3H), 7.57 (s, 1H), 7.43 (s, 1H), 5.37 (s, 2H), 4.84 (s, 1H), 4.46 (d, J=5.8 Hz, 2H), 3.93 (t, J=6.0 Hz, 1H), 3.58-3.43 (m, 2H), 3.33-3.13 (m, 3H), 2.20 (d, J=1.1 Hz, 3H), 1.36-1.20 (m, 3H), 1.15-0.96 (m, 9H).

Compound 744. (S)-7-((R)-1-hydroxyethyl)-4,8-dimethyl-2-(((1-((6-(trifluoromethyl)pyridin-3-yl)methyl)-1H-pyrazol-4-yl)methyl)amino)-7,8-dihydropteridin-6(5H)-one 1H NMR (300 MHz, Methanol-d₄) δ 8.59 (s, 1H), 7.93 (d, J=8.2 Hz, 2H), 7.84 (d, J=8.4 Hz, 1H), 7.69 (d, J=9.0 Hz, 1H), 5.55 (d, J=4.0 Hz, 2H), 4.60 (d, J=2.0 Hz, 2H), 4.21 (dt, J=12.5, 3.4 Hz, 2H), 3.46-3.39 (m, 3H), 2.33 (d, J=1.8 Hz, 3H), 1.36 (d, J=6.4 Hz, 3H).

Compound 703. 7-(methoxymethyl)-4,7,8-trimethyl-2-(((1-((6-(trifluoromethyl)pyridin-3-yl)methyl)-1H-pyrazol-4-yl)methyl)amino)-7,8-dihydropteridin-6(5H)-one ¹H NMR (400 MHz, DMSO-d6) δ 9.80 (s, 1H), 8.63 (s, 1H), 7.89-7.80 (m, 2H), 7.75 (s, 1H), 7.45 (d, J=22.5 Hz, 1H), 6.49 (s, 1H), 5.44 (s, 2H), 4.23 (d, J=6.0 Hz, 2H), 3.73-3.61 (m, 1H), 3.55 (t, J=12.0 Hz, 1H), 3.20 (d, J=6.4 Hz, 3H), 2.97 (d, J=4.0 Hz, 3H), 2.15-2.05 (m, 3H), 1.32 (s, 3H).

Compound 707. 7-(methoxymethyl)-4,7,8-trimethyl-2-(((1-((6-(trifluoromethyl)pyridin-3-yl)methyl)-1H-pyrazol-4-yl)methyl)amino)-7,8-dihydropteridin-6(5H)-one ¹H NMR (400 MHz, DMSO-d6) δ 9.86 (s, 1H), 8.63 (s, 1H), 7.86 (dt, J=9.8, 8.1 Hz, 2H), 7.76 (s, 1H), 7.43 (s, 1H), 6.59 (s, 1H), 5.45 (s, 2H), 4.24 (d, J=6.0 Hz, 2H), 3.66 (d, J=10.0 Hz, 1H), 3.55 (d, J=10.1 Hz, 1H), 3.19 (s, 3H), 3.00 (d, J=15.7 Hz, 3H), 2.11 (s, 3H), 1.34 (s, 3H).

Compound 662. 4',8'-dimethyl-2'-(((1-((6-(trifluoromethyl)pyridin-3-yl)methyl)-1H-pyrazol-4-yl)methyl)amino)-4,5,5',8'-tetrahydro-2H,6'H-spiro[furan-3,7'-pteridin]-6'-one ¹H NMR (400 MHz, Chloroform-d) δ 8.44 (s, 1H), 7.52 (t, J=1.8 Hz, 2H), 7.41 (s, 1H), 7.28 (s, 1H), 5.22 (s, 2H), 4.74 (t, J=5.8 Hz, 1H), 4.29 (d, J=5.8 Hz, 2H), 4.12 (d, J=9.9 Hz, 1H), 4.05 (dd, J=8.5, 3.4 Hz, 1H), 3.99 (s, 0H), 3.73 (q, J=8.5 Hz, 1H), 3.29 (q, J=7.1 Hz, 1H), 2.96 (s, 3H), 2.45 (ddd, J=13.4, 7.6, 3.4 Hz, 1H), 2.10 (s, 3H), 1.02 (dt, J=37.1, 7.1 Hz, 2H).

Compound 663. 4',8'-dimethyl-2'-(((1-((6-(trifluoromethyl)pyridin-3-yl)methyl)-1H-pyrazol-4-yl)methyl)amino)-4,5,5',8'-tetrahydro-2H,6'H-spiro[furan-3,7'-pteridin]-6'-one ¹H NMR (400 MHz, Chloroform-d) δ 8.60 (s, 1H), 7.68 (t, J=1.9 Hz, 2H), 7.57 (s, 1H), 7.43 (s, 1H), 5.38 (s, 2H), 4.86 (t, J=5.8 Hz, 1H), 4.45 (d, J=5.7 Hz, 2H), 4.32-4.05 (m, 3H), 3.91 (q, J=8.5 Hz, 1H), 3.12 (d, J=1.5 Hz, 3H), 2.62 (ddd, J=13.5, 7.7, 3.6 Hz, 1H), 2.22 (d, J=1.7 Hz, 3H), 1.34-1.21 (m, 2H).

Compound 497. (7S)-7-ethyl-8-isopropyl-2-(((1-((6-(trifluoromethyl)pyridin-3-yl)methyl)-1H-pyrazol-4-yl)methyl)amino)-7,8-dihydropteridin-6(5H)-one

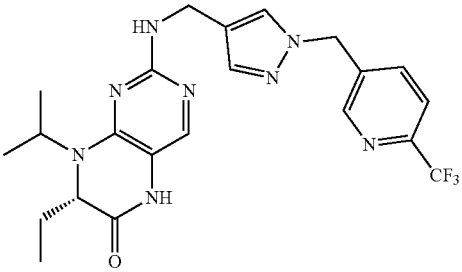 [SMILES: CC[C@H]1C(=O)Nc2cnc(NCc3cnn(Cc4ccc(C(F)(F)F)nc4)c3)nc2N1C(C)C]

Compound 497. (7S)-7-ethyl-8-isopropyl-2-(((1-((6-(trifluoromethyl)pyridin-3-yl)methyl)-1H-pyrazol-4-yl)methyl)amino)-7,8-dihydropteridin-6(5H)-one was prepared by the general procedure for Method A (see Compound 46) via reaction of Intermediate A-76 and B-52 to afford the title product. 1H NMR (300 MHz, DMSO-d6) δ 10.33 (s, 1H), 8.63 (s, 1H), 7.96-7.81 (m, 2H), 7.76 (s, 1H), 7.43 (s, 1H), 7.35 (s, 1H), 7.01 (s, 1H), 5.45 (s, 2H), 4.43-4.20 (m, 3H), 4.11 (dd, J=6.7, 2.9 Hz, 1H), 1.88-1.54 (m, 2H), 1.34-1.17 (m, 6H), 0.78 (t, J=7.4 Hz, 3H). ESI-MS m/z calc. 474.21033, found 475.37 (M+1)⁺; 473.37 (M−1)+; [α]D=+136.56° (c=1.0, MeOH). Chiral HPLC (IC column, 2×250 mm; 20% methanol/30% ethanol/50% hexanes (0.1% diethylamine)): Rt 8.2 mins. (97% ee).

Example 2R

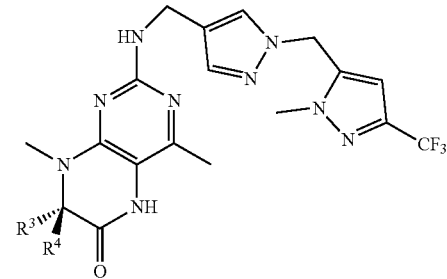

Table 16 shows certain compounds prepared by Method A by reaction of Intermediate A-# and B-89 (See procedure for compound 46). ¹H NMR data for certain compounds are also provided.

TABLE 16

| Compound No. | R³ | R⁴ | Int. A-# | [α]$_D$ | M + 1 |
|---|---|---|---|---|---|
| 656 | H₃CO⤴ | H | A-59 | +74.7°<br>c = 0.5<br>CHCl₃ | 493.35 |

TABLE 16-continued

| Compound No. | R³ | R⁴ | Int. A-# | [α]_D | M + 1 |
|---|---|---|---|---|---|
| 666 | H₃CO-cyclopropyl | H | A-68 | +60.7° c = 0.5 CHCl₃ | 506.27 |
| 670 | O-cyclobutyl | H | A-66 | +95.8° c = 0.5 CHCl₃ | 520.23 |
| 678 | —CH₂CH₂OCH₃ | H | A-62 | +90.3° c = 0.5 MeOH | 493.95 |
| 704 | —CH₂OCH₃ | CH₃ | A-69 |  | 494.26 |
| 709 | —CH₃ | CH₂OCH₃ | A-70 | −31.5 c = 0.5 MeOH | 494.31 |

Compound 656. (S)-7-((R)-1-methoxyethyl)-4,8-dimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one ¹H NMR (300 MHz, Chloroform-d) δ 7.52 (s, 1H), 7.47 (d, J=4.7 Hz, 1H), 6.50 (s, 1H), 5.83 (s, 1H), 5.54 (s, 1H), 5.32 (d, J=3.9 Hz, 2H), 4.41-4.20 (m, 2H), 3.84 (d, J=27.0 Hz, 4H), 3.47 (p, J=6.4 Hz, 1H), 3.23 (d, J=7.1 Hz, 3H), 3.07 (s, 2H), 2.37 (s, 3H), 1.22 (dd, J=6.3, 3.6 Hz, 3H).

Compound 666. 7-(1-methoxycyclopropyl)-4,8-dimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one ¹H NMR (300 MHz, Chloroform-d) δ 8.13 (s, 1H), 7.53 (d, J=2.0 Hz, 1H), 7.34 (d, J=2.2 Hz, 1H), 6.51 (s, 1H), 5.32 (d, J=2.1 Hz, 2H), 4.84 (d, J=6.1 Hz, 1H), 4.52-4.35 (m, 2H), 3.87 (d, J=2.1 Hz, 3H), 3.70 (d, J=2.2 Hz, 1H), 2.23 (d, J=2.2 Hz, 3H), 1.41-1.17 (m, 2H), 1.10-0.85 (m, 2H).

Compound 670. 7-(1-methoxycyclobutyl)-4,8-dimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one ¹H NMR (400 MHz, DMSO-d6) δ9.92 (s, 1H), 7.67 (s, 1H), 7.40 (s, 1H), 6.57 (s, 1H), 6.51 (s, 1H), 5.44 (s, 2H), 4.21 (d, J=5.5 Hz, 3H), 3.87 (s, 3H), 3.09 (s, 3H), 3.06 (s, 2H), 2.21 (s, 1H), 2.10 (s, 4H), 1.96 (d, J=20.0 Hz, 1H), 1.70 (dd, J=10.0, 4.6 Hz, 1H), 1.62-1.44 (m, 1H).

Compound 678. (S)-7-(2-methoxyethyl)-4,8-dimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one ¹H NMR (300 MHz, Methanol-d₄) δ 7.62 (s, 1H), 7.51 (s, 1H), 6.48 (s, 1H), 5.57-5.30 (m, 3H), 4.83 (s, 3H), 4.38 (s, 2H), 4.16 (dd, J=6.1, 4.0 Hz, 1H), 3.84 (s, 3H), 3.14-2.99 (m, 6H), 2.21-1.89 (m, 5H).

Compound 704. 7-(methoxymethyl)-4,7,8-trimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one ¹H NMR (400 MHz, DMSO-d6-d6) δ 9.88 (s, 1H), 7.68 (s, 1H), 7.41 (s, 1H), 6.59 (s, 2H), 5.45 (s, 2H), 4.23 (d, J=6.0 Hz, 2H), 3.89 (d, J=8.3 Hz, 3H), 3.66 (d, J=10.0 Hz, 1H), 3.55 (d, J=10.0 Hz, 1H), 3.20 (s, 3H), 2.98 (s, 3H), 2.11 (s, 3H), 1.40-1.29 (m, 3H).

Compound 709. 7-(methoxymethyl)-4,7,8-trimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one ¹H NMR (400 MHz, DMSO-d6) δ 9.79 (s, 1H), 7.67 (s, 1H), 7.40 (s, 1H), 6.58 (s, 1H), 6.48 (s, 1H), 5.44 (s, 2H), 4.21 (d, J=6.1 Hz, 2H), 3.87 (s, 3H), 3.65 (d, J=10.0 Hz, 1H), 3.54 (d, J=10.1 Hz, 1H), 3.19 (s, 3H), 2.96 (s, 3H), 2.10 (s, 3H), 1.32 (s, 3H).

Example 2S

Table 17 shows certain compounds prepared by the Method A procedure by reaction of Intermediate A-# and B-39 (See procedure for compound 46). ¹H NMR data are also provided for certain compounds.

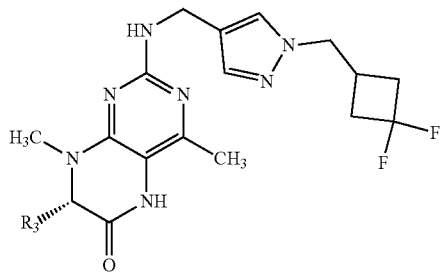

TABLE 17

| Comp. No. | R₃ = | [α]_D | M + 1 |
|---|---|---|---|
| 728 | H₃CO- | +112.1° c = 0.5 MeOH | 436.13 |

TABLE 17-continued

| Comp. No. | $R_3 =$ | $[\alpha]_D$ | M + 1 |
|---|---|---|---|
| 727 | —iPr | +107.9°<br>c = 0.5<br>MeOH | 420.16 |

Compound 728. (S)-2-(((1-((3,3-difluorocyclobutyl)methyl)-1H-pyrazol-4-yl)methyl)amino)-7-((R)-1-methoxyethyl)-4,8-dimethyl-7,8-dihydropteridin-6(5H)-one $^1$H NMR (300 MHz, Methanol-d$_4$) δ 7.59 (s, 1H), 7.47 (s, 1H), 4.39 (s, 2H), 4.19 (d, J=5.2 Hz, 2H), 4.04-3.87 (m, 1H), 3.69-3.45 (m, 1H), 2.60 (d, J=7.2 Hz, 3H), 2.35 (d, J=7.1 Hz, 2H), 2.24-2.06 (m, 3H), 1.19 (d, J=6.4 Hz, 3H).

Compound 727. (S)-2-(((1-((3,3-difluorocyclobutyl)methyl)-1H-pyrazol-4-yl)methyl)amino)-7-isopropyl-4,8-dimethyl-7,8-dihydropteridin-6(5H)-one $^1$H NMR (300 MHz, Methanol-d$_4$) δ 7.58 (s, 1H), 7.46 (s, 1H), 4.38 (s, 2H), 4.19 (d, J=3.8 Hz, 2H), 3.96-3.85 (m, 1H), 3.14 (s, 3H), 2.72-2.47 (m, 3H), 2.46-2.08 (m, 6H), 1.03 (d, J=7.0 Hz, 3H), 0.87 (d, J=6.9 Hz, 3H).

Example 2T

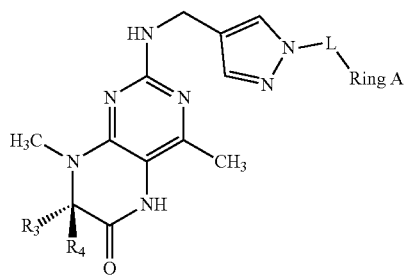

Table 18 provides certain compounds that were prepared by the Method A procedure by reaction of Intermediates A-# and B-# (See procedure for Compound 46). $^1$H NMR data are also provided for certain compounds.

TABLE 18

| Comp. No. | L-Ring A | $R_3 =$ | $R_4 =$ | Int A | Int B | $[\alpha]_D$ | M + 1 |
|---|---|---|---|---|---|---|---|
| 417 | pyridine-CH$_2$, OCHF$_2$ | —Et | —H | A-8 | B-166 | +36.6°<br>c = 0.5<br>CHCl$_3$ | 459.27 |
| 421 | pyridine-CH$_2$, F | —cPr | —H | A-6 | B-53 | +29.2°<br>c = 0.5<br>CHCl$_3$ | 423.29 |
| 422 | pyridine-CH$_2$, OCHF$_2$ | —iPr | —H | A-9 | B-166 | +43.4°<br>c = 0.5<br>CHCl$_3$ | 473.41 |
| 423 | pyridine-CH$_2$, Me, F | —iPr | —H | A-9 | B-54 | +36.7°<br>c = 0.5<br>CHCl$_3$ | 439.55 |
| 425 | pyridine-CH$_2$, Me, F | —iPr | —H | A-9 | B-169 | +49°<br>c = 0.55<br>CHCl$_3$ | 439.19 |
| 427 | pyridine-CH$_2$, CF$_3$ | —Et | —H | A-8 | B-52 | | 447.34 |

TABLE 18-continued

| Comp. No. | L-Ring A | R₃ = | R₄ = | Int A | Int B | [α]_D | M + 1 |
|---|---|---|---|---|---|---|---|
| 429 | pyridine-CH₂- with 6-OMe | —iPr | —H | A-9 | B-64 | +47.4° c = 0.5 CHCl₃ | 437.39 |
| 433 | pyridine-CH₂- with 6-OCH₂CF₃ | —Et | —H | A-8 | B-83 | 68 c = 0.5 MeOH | 491.46 |
| 435 | pyridine-CH₂- with 6-OCH₂CF₃ | —cPr | —H | A-6 | B-83 | 36.88 c = 1.0 MeOH | 503.57 |
| 437 | pyridine-CH₂- with 6-F | —tBu | —H | A-55 | B-53 | +54.6° c = 0.5 CHCl₃ | 439.24 |
| 439 | pyridine-CH₂- with 6-CF₃ | CH₂CH₂OH | —H | A-25 | B-52 |  | 463.5 |
| 440 | pyridine-CH₂- with 6-cyclopropyl | —Et | —H | A-8 | B-171 | 59.3 c = 0.5 CHCl₃ | 433.38 |
| 441 | pyridine-CH₂- with 6-cyclopropyl | —cPr | —H | A-6 | B-171 | 47.1 c = 0.5 CHCl₃ | 445.4 |
| 442 | pyridine-CH₂- with 6-cyclopropyl | —iPr | —H | A-9 | B-171 | 62.4 c = 0.5 CHCl₃ | 447.34 |
| 444 | pyridine-CH₂CH₂- with 6-CF₃ | —CH₃ | —H | A-2 | B-172 | 41.35 c = 0.5 MeOH | 461.47 |
| 447 | pyridine-CH₂- with 2-CF₃ (4-linked) | —iPr | —H | A-9 | B-71 | 68.3 c = 1 MeOH | 475.48 |

TABLE 18-continued

| Comp. No. | L-Ring A | $R_3$ = | $R_4$ = | Int A | Int B | $[\alpha]_D$ | M + 1 |
|---|---|---|---|---|---|---|---|
| 448 | (pyridine with NMe₂) | —iPr | —H | A-9 | CA | 56.8 c = 0.5 CHCl₃ | 450.53 |
| 449 | (3,4,5-trifluorophenyl) | —iPr | —H | A-9 | B-23 | 78.3 c = 0.5 CHCl₃ | 460.44 |
| 450 | (3,5-difluoro-4-methoxyphenyl) | —iPr | —H | A-9 | B-20 | 74.3 c = 0.5 CHCl₃ | 472.42 |
| 454 | (5-fluoropyridin-2-yl) | —iPr | —H | A-9 | B-174 | 88.16 c = 0.5 MeOH | 425.45 |
| 455 | (2-CF₃-pyridin-4-yl) | —cPr | —H | A-6 | B-71 | 41.3 c = 41.3 MeOH | 473.45 |
| 456 | (3,4,5-trifluorophenyl) | —cPr | —H | A-6 | B-23 | 34.5 c = 0.5 CHCl₃ | 458.46 |
| 457 | (3,5-difluoro-4-methoxyphenyl) | —cPr | —H | A-6 | B-20 | 28.2 c = 0.5 CHCl₃ | 470.48 |
| 466 | (pyridine with NMe₂) | —cPr | —H | A-6 | CA | 47.9 c = 0.5 CHCl₃ | 448.51 |
| 467 | (4-OCF₃-phenyl) | —iPr | —H | A-9 | B-175 | | 489.49 |
| 468 | (6-CF₃-pyridin-3-yl) | —CH₃ | —H | A-2 | B-176 | 83.14 c = 0.35 MeOH | 433.38 |

TABLE 18-continued
| Comp. No. | L-Ring A | R₃ = | R₄ = | Int A | Int B | [α]_D | M + 1 |
|---|---|---|---|---|---|---|---|
| 469 | 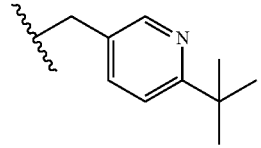 [SMILES: *Cc1ccc(C(C)(C)C)nc1] | —iPr | —H | A-9 | B-177 | 72.7 c = 0.5 CHCl₃ | 463.5 |
| 470 | 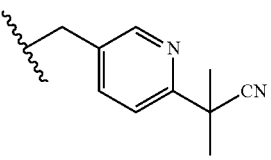 [SMILES: *Cc1ccc(C(C)(C)C#N)nc1] | —iPr | —H | A-9 | B-178 | 73.4 c = 0.5 CHCl₃ | 474.44 |
| 479 | 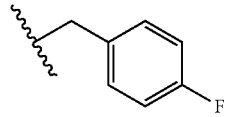 | —iPr | —H | A-9 | B-2 | 74.00 c = 0.5 MeOH | 424.46 |
| 480 | 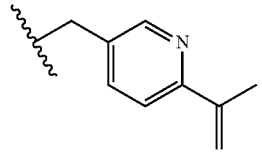 [SMILES: *Cc1ccc(C(=C)C)nc1] | —iPr | —H | A-9 | B-179 | | 447.43 |
| 492 | 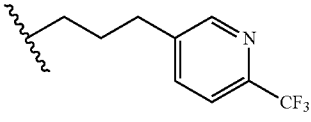 [SMILES: *CCCc1ccc(C(F)(F)F)nc1] | —CH₃ | —H | A-2 | B-183 | 30.7 c = MeOH | 475.34 |
| 500 | 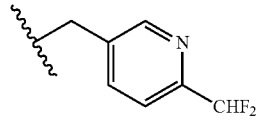 | —iPr | —H | A-9 | B-182 | 68.8 c = 0.5 CHCl₃ | 457.33 |
| 501 | 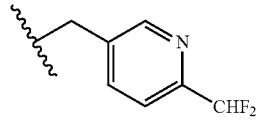 | —cPr | —H | A-6 | B-182 | 47 c = 0.5 CHCl₃ | 455.36 |
| 510 | 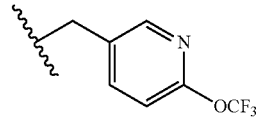 [SMILES: *Cc1ccc(OC(F)(F)F)nc1] | —iPr | —H | A-9 | B-184 | | 491.07 |
| 511 | 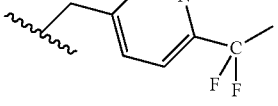 | —iPr | —H | A-9 | B-185 | 67.9 c = 0.5 CHCl₃ | 471.33 |
| 516 | 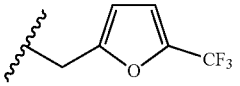 [SMILES: *Cc1ccc(C(F)(F)F)o1] | —Et | —H | A-8 | B-93 | 54.8 c = 0.5 CHCl₃ | 450.35 |
| 518 | 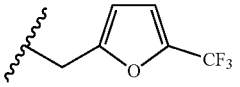 [SMILES: *Cc1ccc(C(F)(F)F)o1] | —iPr | —H | A-9 | B-93 | 72.6 c = 0.5 CHCl₃ | 464.31 |

TABLE 18-continued

| Comp. No. | L-Ring A | R_3 = | R_4 = | Int A | Int B | $[\alpha]_D$ | M + 1 |
|---|---|---|---|---|---|---|---|
| 565 | 5-(pyridyl)methyl, 2-OCF_3 | (R) H_3CO,,,/CH_3 | —H | A-59 | B-184 | 62.6 c = 0.5 CHCl_3 | 507.35 |
| 658 | 4-F-benzyl | (R) H_3CO,,,/CH_3 | —H | A-59 | B-2 |  | 440.25 |
| 659 | 3,4,5-triF-benzyl | (R) H_3CO,,,/CH_3 | —H | A-59 | B-23 |  | 476.25 |
| 668 | 3,4,5-triF-benzyl | H_3CO-cyclobutyl | —H | A-66 | B-23 | 75.6 c = 1 MeOH | 502.23 |
| 729 | 3,4,5-triF-benzyl | H_3C, HO, CH_3 | —H | A-61 | B-23 | +50.2° c = 0.5 MeOH | 476.3 |
| 741 | 3,4,5-triF-benzyl | CH_2OtBu | —H | A-63 | B-23 | +51.5° c = 0.5 MeOH | 504.47 |
| 705 | 3,4,5-triF-benzyl | —CH_2OCH_3 | —CH_3 | A-69 | B-23 | +50.3° c = 0.5 MeOH | 476.26 |
| 708 | 3,4,5-triF-benzyl | —CH_3 | CH_2OCH_3 | A-70 | B-23 | −48.1° c = 0.5 MeOH | 476.26 |
| 747 | 5-(pyridyl)methyl, 2-CF_3 | (S) CH_2OtBu | —H | A-72 | B-23 |  | 517.24 |

TABLE 18-continued

| Comp. No. | L-Ring A | R₃ = | R₄ = | Int A | Int B | [α]$_D$ | M + 1 |
|---|---|---|---|---|---|---|---|
| 746 | (3,5-difluoro-4-methoxybenzyl) | (S)-CH(CH₂OtBu)- | —H | A-72 | B-20 | 51.52 c = 0.5 MeOH | |

Compound 417. (7S)-2-(((1-((6-(difluoromethoxy)pyridin-3-yl)methyl)-1H-pyrazol-4-yl)methyl)amino)-7-ethyl-4,8-dimethyl-7,8-dihydropteridin-6(5H)-one $^1$H NMR (300 MHz, Chloroform-d) δ 8.08 (d, J=2.5 Hz, 1H), 7.59 (dd, J=8.5, 2.5 Hz, 1H), 7.52 (s, 1H), 7.36 (s, 1H), 7.61-7.19 (t, 1H), 6.87 (d, J=8.5 Hz, 1H), 5.23 (s, 2H), 4.82 (d, J=5.8 Hz, 1H), 4.40 (d, J=5.7 Hz, 2H), 4.06 (dd, J=6.4, 3.7 Hz, 1H), 3.04 (s, 3H), 2.17 (s, 3H), 1.96 (dtd, J=15.2, 7.6, 3.9 Hz, 1H), 1.83 (dt, J=14.3, 7.1 Hz, 1H), 0.88 (t, J=7.6 Hz, 3H).

Compound 421. (7S)-7-cyclopropyl-2-(((1-((6-fluoropyridin-3-yl)methyl)-1H-pyrazol-4-yl)methyl)amino)-4,8-dimethyl-7,8-dihydropteridin-6(5H)-one $^1$H NMR (300 MHz, Chloroform-d) δ 8.84 (s, 1H), 8.11 (dt, J=2.6, 0.9 Hz, 1H), 7.65 (ddd, J=8.3, 7.6, 2.6 Hz, 1H), 7.53 (d, J=0.7 Hz, 1H), 7.46-7.35 (m, 1H), 6.98-6.84 (m, 1H), 5.49 (s, 1H), 5.26 (s, 2H), 4.44 (dd, J=5.6, 1.7 Hz, 2H), 3.29 (d, J=9.1 Hz, 1H), 3.14 (s, 3H), 2.26 (s, 3H), 1.38-1.13 (m, 1H), 1.07-0.90 (m, 1H), 0.76-0.63 (m, 1H), 0.63-0.38 (m, 2H)

Compound 422. (7S)-2-(((1-((6-(difluoromethoxy)pyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 8.36 (s, 1H), 8.10 (d, J=2.4 Hz, 1H), 7.61 (dd, J=8.5, 2.5 Hz, 1H), 7.54 (s, 1H), 7.38 (s, 1H), 7.25 (d, J=21.3 Hz, 1H), 6.89 (d, J=8.5 Hz, 1H), 5.25 (s, 2H), 4.91 (d, J=5.8 Hz, 1H), 4.42 (d, J=5.7 Hz, 2H), 3.89 (d, J=4.3 Hz, 1H), 3.11 (s, 3H), 2.33-2.23 (m, 1H), 2.21 (s, 3H), 1.07 (dd, J=6.9, 1.8 Hz, 3H), 0.97-0.89 (m, 4H).

Compound 423. (7S)-2-(((1-((6-fluoro-4-methylpyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 7.97 (s, 1H), 7.78 (s, 1H), 7.52 (s, 1H), 6.70 (m, 1H), 5.27 (s, 2H), 4.81 (t, J=5.7 Hz, 1H), 4.41 (d, J=5.7 Hz, 2H), 3.89 (d, J=4.3 Hz, 1H), 3.11 (s, 3H), 2.38-2.27 (m, 3H), 2.26-2.19 (m, 1H), 2.19 (s, 3H), 1.08 (d, J=6.9 Hz, 3H), 0.99-0.81 (m, 3H).

Compound 425. (7S)-2-(((1-((5-fluoro-6-methylpyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 8.23 (d, J=1.5 Hz, 1H), 7.54 (s, 1H), 7.42 (s, 1H), 7.17 (dd, J=9.7, 1.9 Hz, 1H), 5.95-5.52 (m, 1H), 5.27 (s, 2H), 4.45 (d, J=5.7 Hz, 2H), 3.92 (d, J=4.3 Hz, 1H), 3.15 (s, 3H), 2.52 (d, J=2.9 Hz, 3H), 2.38-2.26 (m, 1H), 2.25 (s, 3H), 1.09 (d, J=7.0 Hz, 3H), 0.93 (d, J=6.9 Hz, 3H).

Compound 427. (7S)-7-ethyl-8-methyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, Chloroform-d) δ 8.65-8.54 (m, 1H), 7.74-7.61 (m, 2H), 7.59 (s, 1H), 7.50 (s, 1H), 7.36 (s, 1H), 6.54 (s, 1H), 5.38 (s, 2H), 4.47 (d, J=5.7 Hz, 2H), 4.13 (dd, J=6.0, 3.4 Hz, 1H), 3.09 (s, 3H), 2.13-1.78 (m, 2H), 0.89 (d, J=7.5 Hz, 3H).

Compound 429. (7S)-7-isopropyl-2-(((1-((6-methoxypyridin-3-yl)methyl)-1H-pyrazol-4-yl)methyl)amino)-4,8-dimethyl-7,8-dihydropteridin-6(5H)-one $^1$H NMR (300 MHz, Chloroform-d) δ 8.02-7.95 (m, 1H), 7.42 (d, J=0.7 Hz, 1H), 7.38 (dd, J=8.6, 2.5 Hz, 1H), 7.31-7.23 (m, 1H), 6.63 (dd, J=8.5, 0.7 Hz, 1H), 5.46 (s, 1H), 5.10 (s, 2H), 4.33 (d, J=5.5 Hz, 2H), 3.85 (s, 3H), 3.82-3.75 (m, 1H), 3.03 (s, 3H), 2.16 (s, 4H), 0.99 (d, J=7.0 Hz, 3H), 0.84 (d, J=6.9 Hz, 3H).

Compound 433. (7S)-7-ethyl-4,8-dimethyl-2-(((1-((6-(2,2,2-trifluoroethoxy)pyridin-3-yl)methyl)-1H-pyrazol-4-yl)methyl)amino)-7,8-dihydropteridin-6(5H)-one $^1$H NMR (300 MHz, DMSO-d6) δ 9.89 (s, 1H), 8.12 (d, J=2.3 Hz, 1H), 7.73-7.63 (m, 2H), 7.37 (s, 1H), 6.94 (d, J=8.5 Hz, 1H), 6.60 (t, J=5.8 Hz, 1H), 5.24 (s, 2H), 4.96 (q, J=9.1 Hz, 2H), 4.22 (d, J=6.0 Hz, 2H), 4.01 (dd, J=6.5, 3.7 Hz, 1H), 2.97 (s, 3H), 2.12 (s, 3H), 1.89-1.59 (m, 2H), 0.74 (t, J=7.4 Hz, 3H).

Compound 435. (7S)-7-cyclopropyl-4,8-dimethyl-2-(((1-((6-(2,2,2-trifluoroethoxy)pyridin-3-yl)methyl)-1H-pyrazol-4-yl)methyl)amino)-7,8-dihydropteridin-6(5H)-one $^1$H NMR (300 MHz, DMSO-d6) δ 9.81 (s, 1H), 8.12 (d, J=2.4 Hz, 1H), 7.73-7.62 (m, 2H), 7.38 (d, J=0.8 Hz, 1H), 6.94 (dd, J=8.5, 0.7 Hz, 1H), 6.56 (t, J=6.1 Hz, 1H), 5.24 (s, 2H), 4.96 (q, J=9.1 Hz, 2H), 4.22 (dd, J=6.1, 3.32 (d, J=7.0 Hz, 1H), 2.6 Hz, 2H), 3.02 (s, 3H), 2.14 (s, 3H), 0.83 (ddt, J=12.9, 8.0, 3.9 Hz, 1H), 0.63-0.25 (m, 4H).

Compound 437. (7S)-7-(tert-butyl)-2-(((1-((6-fluoropyridin-3-yl)methyl)-1H-pyrazol-4-yl)methyl)amino)-4,8-dimethyl-7,8-dihydropteridin-6(5H)-one $^1$H NMR (300 MHz, Chloroform-d) δ 8.14 (d, J=2.5 Hz, 1H), 7.78 (s, 1H), 7.73-7.59 (m, 1H), 7.55 (s, 1H), 7.40 (s, 1H), 6.92 (dd, J=8.4, 3.0 Hz, 1H), 5.27 (s, 2H), 4.90 (s, 1H), 4.44 (d, J=5.8 Hz, 2H), 3.71 (s, 1H), 3.21 (s, 3H), 2.20 (s, 3H), 1.01 (s, 9H).

Compound 439. (S)-7-(2-hydroxyethyl)-4-methyl-2-(((1-((6-(trifluoromethyl)pyridin-3-yl)methyl)-1H-pyrazol-4-yl)methyl)amino)-7,8-dihydropteridin-6(5H)-one ¹H NMR (300 MHz, DMSO-d6) δ 9.90 (s, 1H), 8.65 (d, J=1.9 Hz, 1H), 7.93-7.83 (m, 2H), 7.80 (s, 1H), 7.46 (s, 1H), 6.94 (brs, 1H), 5.45 (s, 2H), 4.61 (t, J=5.1 Hz, 1H), 4.24 (d, J=5.9 Hz, 2H), 4.11-3.98 (m, 1H), 3.53 (m, 2H), 2.14 (s, 3H), 1.93-1.85 (m, 2H).

Compound 440. (7S)-7-(2-hydroxyethyl)-4-methyl-2-(((1-((6-(trifluoromethyl)pyridin-3-yl)methyl)-1H-pyrazol-4-yl)methyl)amino)-7,8-dihydropteridin-6(5H)-one ¹H NMR (300 MHz, Chloroform-d) δ 8.35 (d, J=2.3 Hz, 1H), 7.73 (s, 1H), 7.52 (s, 1H), 7.41 (dd, J=8.1, 2.4 Hz, 1H), 7.35 (s, 1H), 7.11 (d, J=8.0 Hz, 1H), 5.22 (s, 2H), 4.86 (s, 1H), 4.41 (d, J=5.7 Hz, 2H), 4.08 (dd, J=6.4, 3.7 Hz, 1H), 3.06 (s, 3H), 2.19 (s, 3H), 2.10-1.94 (m, 2H), 1.91-1.80 (m, 1H), 1.01 (d, J=5.4 Hz, 3H), 0.90 (td, J=7.3, 2.2 Hz, 4H).

Compound 441. (7S)-7-cyclopropyl-2-(((1-((6-cyclopropylpyridin-3-yl)methyl)-1H-pyrazol-4-yl)methyl)amino)-4,8-dimethyl-7,8-dihydropteridin-6(5H)-one ¹H NMR (300 MHz, Chloroform-d) δ 8.39-8.27 (m, 1H), 7.81 (s, 1H), 7.53 (d, J=0.8 Hz, 1H), 7.41 (dd, J=8.1, 2.4 Hz, 1H), 7.11 (dd, J=8.1, 0.8 Hz, 1H), 5.22 (s, 2H), 4.85 (d, J=6.0 Hz, 1H), 4.49-4.34 (m, 2H), 3.30 (d, J=9.0 Hz, 1H), 3.13 (s, 3H), 2.23 (s, 3H), 2.10-1.96 (m, 1H), 1.07-0.94 (m, 5H), 0.78-0.44 (m, 3H).

Compound 442. (7S)-2-(((1-((6-cyclopropylpyridin-3-yl)methyl)-1H-pyrazol-4-yl)methyl)amino)-7-isopropyl-4,8-dimethyl-7,8-dihydropteridin-6(5H)-one ¹H NMR (300 MHz, Chloroform-d) δ 8.34 (d, J=2.3 Hz, 1H), 7.54-7.49 (m, 1H), 7.40 (dd, J=8.1, 2.4 Hz, 1H), 7.35 (s, 2H), 7.11 (dd, J=8.1, 0.9 Hz, 1H), 5.22 (s, 2H), 5.04 (s, 1H), 4.41 (d, J=5.7 Hz, 2H), 3.89 (d, J=4.3 Hz, 1H), 3.11 (s, 3H), 2.21 (m, 4H), 2.12-1.94 (m, 1H), 1.07 (d, J=7.0 Hz, 3H), 1.05-0.97 (m, 4H), 0.92 (d, J=7.0 Hz, 3H).

Compound 444. (7S)-4,7,8-trimethyl-2-(((1-(2-(6-(trifluoromethyl)pyridin-3-yl)ethyl)-1H-pyrazol-4-yl)methyl)amino)-7,8-dihydropteridin-6(5H)-one ¹H NMR (300 MHz, DMSO-d6) δ 10.34 (s, 1H), 8.46 (s, 1H), 7.76 (brs, 3H), 7.57 (s, 1H), 7.41 (s, 1H), 4.38 (t, J=6.9 Hz, 2H), 4.30 (d, J=4.9 Hz, 2H), 4.23 (q, J=6.8 Hz, 1H), 3.21 (t, J=6.9 Hz, 2H), 3.09 (s, 3H), 2.22 (s, 3H), 1.35 (d, J=6.9 Hz, 3H).

Compound 447. (S)-7-isopropyl-4,8-dimethyl-2-(((1-((2-(trifluoromethyl)pyridin-4-yl)methyl)-1H-pyrazol-4-yl)methyl)amino)-7,8-dihydropteridin-6(5H)-one ¹H NMR (300 MHz, Methanol-d₄) δ 8.65 (s, 1H), 7.88 (s, 1H), 7.65 (s, 1H), 7.51 (s, 1H), 7.39 (s, 1H), 5.51 (s, 2H), 4.56 (s, 2H), 4.15 (s, 1H), 3.28 (s, 3H), 2.29 (s, 3H), 1.11 (d, J=5.8 Hz, 3H), 0.88 (d, J=5.7 Hz, 3H).

Compound 448. (S)-2-(((1-((2-(dimethylamino)pyridin-4-yl)methyl)-1H-pyrazol-4-yl)methyl)amino)-7-isopropyl-4,8-dimethyl-7,8-dihydropteridin-6(5H)-one ¹H NMR (300 MHz, Chloroform-d) δ 8.11 (dd, J=5.2, 0.8 Hz, 2H), 7.55 (d, J=0.8 Hz, 1H), 7.39 (d, J=0.8 Hz, 1H), 6.31 (dd, J=5.1, 1.4 Hz, 1H), 6.26 (dd, J=1.5, 0.8 Hz, 1H), 5.17 (s, 2H), 4.81 (t, J=5.7 Hz, 1H), 4.43 (d, J=5.7 Hz, 2H), 3.89 (d, J=4.4 Hz, 1H), 3.11 (s, 3H), 3.06 (s, 7H), 2.63 (s, 5H), 2.30-2.21 (m, 1H), 2.20 (s, 3H), 1.07 (d, J=7.0 Hz, 3H), 0.97-0.91 (m, 3H).

Compound 449. (S)-7-isopropyl-4,8-dimethyl-2-(((1-(3,4,5-trifluorobenzyl)-1H-pyrazol-4-yl)methyl)amino)-7,8-dihydropteridin-6(5H)-one ¹H NMR (300 MHz, Methanol-d₄) δ 7.85 (s, 1H), 7.65 (s, 1H), 7.03 (dd, J=8.4, 6.4 Hz, 2H), 5.36 (s, 2H), 4.60 (s, 2H), 4.21 (d, J=3.5 Hz, 1H), 3.34 (s, 3H), 2.36 (s, 3H), 1.17 (d, J=6.7 Hz, 3H), 0.95 (d, J=6.7 Hz, 3H).

Compound 450. (S)-2-(((1-(3,5-difluoro-4-methoxybenzyl)-1H-pyrazol-4-yl)methyl)amino)-7-isopropyl-4,8-dimethyl-7,8-dihydropteridin-6(5H)-one ¹H NMR (300 MHz, Methanol-d₄) δ 7.83 (s, 1H), 7.63 (s, 1H), 6.89 (d, J=8.7 Hz, 2H), 5.31 (s, 2H), 4.59 (s, 2H), 4.21 (d, J=3.3 Hz, 1H), 3.98 (s, 3H), 3.33 (s, 3H), 2.35 (s, 3H), 1.17 (d, J=6.5 Hz, 3H), 0.94 (d, J=6.4 Hz, 3H).

Compound 454. (S)-2-(((1-((5-fluoropyridin-2-yl)methyl)-1H-pyrazol-4-yl)methyl)amino)-7-isopropyl-4,8-dimethyl-7,8-dihydropteridin-6(5H)-one ¹H NMR (300 MHz, DMSO-d6) δ 10.10 (s, 1H), 8.51 (d, J=2.9 Hz, 1H), 7.73 (s, 1H), 7.71-7.60 (m, 1H), 7.42 (s, 1H), 7.14 (dd, J=8.7, 4.5 Hz, 1H), 5.37 (s, 2H), 4.30 (d, J=5.9 Hz, 2H), 3.97 (d, J=4.2 Hz, 1H), 2.16 (s, 3H), 0.96 (d, J=6.9 Hz, 3H), 0.77 (d, J=6.8 Hz, 3H).

Compound 455. (S)-7-cyclopropyl-4,8-dimethyl-2-(((1-((2-(trifluoromethyl)pyridin-4-yl)methyl)-1H-pyrazol-4-yl)methyl)amino)-7,8-dihydropteridin-6(5H)-one ¹H NMR (300 MHz, Methanol-d₄) δ 8.65 (d, J=5.1 Hz, 1H), 7.84 (d, J=0.8 Hz, 1H), 7.64 (d, J=0.8 Hz, 1H), 7.50 (s, 1H), 7.39 (d, J=5.1 Hz, 1H), 5.50 (s, 2H), 4.56 (s, 2H), 3.63 (d, J=9.0 Hz, 1H), 3.33 (s, 3H), 2.31 (s, 3H), 1.24-1.00 (m, 1H), 0.83-0.51 (m, 3H).

Compound 456. (S)-7-cyclopropyl-4,8-dimethyl-2-(((1-(3,4,5-trifluorobenzyl)-1H-pyrazol-4-yl)methyl)amino)-7,8-dihydropteridin-6(5H)-one ¹H NMR (300 MHz, Methanol-d₄) δ 7.79 (d, J=0.8 Hz, 1H), 7.59 (d, J=0.8 Hz, 1H), 7.07-6.87 (m, 2H), 5.30 (d, J=1.0 Hz, 2H), 4.54 (s, 2H), 3.63 (d, J=9.0 Hz, 1H), 3.34 (d, J=3.9 Hz, 3H), 2.31 (s, 3H), 1.22-1.02 (m, 1H), 0.83-0.53 (m, 3H).

Compound 457. (S)-7-cyclopropyl-2-(((1-(3,5-difluoro-4-methoxybenzyl)-1H-pyrazol-4-yl)methyl)amino)-4,8-dimethyl-7,8-dihydropteridin-6(5H)-one $^1$H NMR (300 MHz, Methanol-d$_4$) δ 7.76 (s, 1H), 7.58 (d, J=0.8 Hz, 1H), 6.93-6.75 (m, 2H), 5.25 (s, 2H), 4.53 (s, 2H), 3.92 (t, J=1.0 Hz, 3H), 3.63 (d, J=9.0 Hz, 1H), 2.30 (s, 3H), 1.19-1.01 (m, 0H), 0.84-0.48 (m, 3H).

Compound 466. (S)-7-cyclopropyl-2-(((1-((2-(dimethylamino)pyridin-4-yl)methyl)-1H-pyrazol-4-yl)methyl)amino)-4,8-dimethyl-7,8-dihydropteridin-6(5H)-one $^1$H NMR (300 MHz, Methanol-d$_4$) δ 7.90 (s, 1H), 7.83 (d, J=6.3 Hz, 1H), 7.65 (s, 1H), 6.98 (s, 1H), 6.62 (d, J=6.4 Hz, 1H), 5.45 (s, 2H), 4.57 (s, 2H), 3.64 (d, J=8.2 Hz, 1H), 3.36 (s, 3H), 2.32 (s, 3H), 1.12 (s, 1H), 0.81-0.54 (m, 5H).

Compound 467. (S)-7-isopropyl-4,8-dimethyl-2-(((1-(4-(trifluoromethoxy)benzyl)-1H-pyrazol-4-yl)methyl)amino)-7,8-dihydropteridin-6(5H)-one $^1$H NMR (400 MHz, DMSO-d6) δ 10.14 (s, 1H), 7.72 (s, 1H), 7.42 (s, 1H), 7.32 (s, 4H), 5.31 (s, 2H), 4.30 (d, J=5.7 Hz, 2H), 3.99 (s, 1H), 3.09 (s, 3H), 2.16 (s, 4H), 0.97 (d, J=6.9 Hz, 3H), 0.76 (d, J=6.9 Hz, 3H).

Compound 468. (S)-4,7,8-trimethyl-2-(((1-(6-(trifluoromethyl)pyridin-3-yl)-1H-pyrazol-4-yl)methyl)amino)-7,8-dihydropteridin-6(5H)-one $^1$H NMR (300 MHz, DMSO-d6) δ 9.87 (s, 1H), 9.25 (d, J=2.5 Hz, 1H), 8.60 (s, 1H), 8.44 (dd, J=8.6, 2.6 Hz, 1H), 8.03 (d, J=8.6 Hz, 1H), 7.84 (s, 1H), 6.77 (t, J=6.0 Hz, 1H), 4.34 (dd, J=5.9, 2.3 Hz, 2H), 4.01 (q, J=6.7 Hz, 1H), 2.96 (s, 3H), 2.15 (s, 3H), 1.20 (d, J=6.8 Hz, 3H).

Compound 469. (S)-2-(((1-((6-(tert-butyl)pyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 8.50-8.42 (m, 1H), 7.61 (d, J=9.2 Hz, 1H), 7.54 (d, J=0.7 Hz, 1H), 7.48 (dd, J=8.2, 2.4 Hz, 1H), 7.43-7.37 (m, 1H), 7.33 (dd, J=8.3, 0.9 Hz, 1H), 5.26 (s, 2H), 4.81 (s, 1H), 4.42 (d, J=5.7 Hz, 2H), 3.90 (d, J=4.3 Hz, 1H), 3.12 (s, 3H), 2.24 (td, J=7.0, 4.5 Hz, 1H), 2.19 (s, 3H), 1.37 (s, 9H), 1.08 (d, J=7.0 Hz, 3H), 0.92 (d, J=7.0 Hz, 3H).

Compound 470. (S)-2-(5-((4-(((7-isopropyl-4,8-dimethyl-6-oxo-5,6,7,8-tetrahydropteridin-2-yl)amino)methyl)-1H-pyrazol-1-yl)methyl)pyridin-2-yl)-2-methylpropanenitrile $^1$H NMR (300 MHz, Chloroform-d) δ 8.73 (s, 1H), 8.48 (d, J=1.7 Hz, 1H), 7.71-7.52 (m, 3H), 7.42 (s, 1H), 5.29 (s, 2H), 4.99 (s, 1H), 4.43 (d, J=5.7 Hz, 2H), 3.89 (d, J=4.3 Hz, 1H), 3.12 (s, 4H), 2.22 (s, 5H), 1.75 (s, 6H), 1.07 (d, J=7.0 Hz, 3H), 0.92 (d, J=7.0 Hz, 3H).

Compound 479. (S)-2-(((1-(4-fluorobenzyl)-1H-pyrazol-4-yl)methyl)amino)-7-isopropyl-4,8-dimethyl-7,8-dihydropteridin-6(5H)-one $^1$H NMR (300 MHz, DMSO-d6) δ 9.83 (s, 1H), 7.68-7.60 (m, 1H), 7.37 (d, J=0.8 Hz, 1H), 7.31-7.22 (m, 2H), 7.14 (t, J=8.9 Hz, 1H), 6.48 (t, J=6.1 Hz, 1H), 5.23 (s, 2H), 4.21 (d, J=6.1 Hz, 2H), 3.91-3.77 (m, 1H), 3.01 (s, 3H), 2.10 (s, 3H), 0.93 (d, J=6.9 Hz, 3H), 0.75 (d, J=6.9 Hz, 3H).

Compound 480. (S)-7-isopropyl-4,8-dimethyl-2-(((1-((6-(prop-1-en-2-yl)pyridin-3-yl)methyl)-1H-pyrazol-4-yl)methyl)amino)-7,8-dihydropteridin-6(5H)-one $^1$H NMR (300 MHz, Chloroform-d) δ 8.39 (d, J=2.3 Hz, 1H), 7.91 (s, 1H), 7.44 (s, 1H), 7.40 (dd, J=7.1, 1.6 Hz, 1H), 7.30 (s, 1H), 5.82-5.72 (m, 1H), 5.24 (p, J=1.6 Hz, 1H), 5.19 (s, 2H), 4.34 (d, J=5.7 Hz, 2H), 3.81 (d, J=4.3 Hz, 1H), 3.03 (s, 2H), 2.12 (d, J=1.5 Hz, 4H), 0.99 (d, J=7.0 Hz, 2H), 0.87-0.81 (m, 3H)

Compound 492. (S)-4,7,8-trimethyl-2-(((1-(3-(6-(trifluoromethyl)pyridin-3-yl)propyl)-1H-pyrazol-4-yl)methyl)amino)-7,8-dihydropteridin-6(5H)-one $^1$H NMR (300 MHz, DMSO-d6) δ 10.09 (s, 1H), 8.60 (d, J=2.0 Hz, 1H), 7.90 (dd, J=8.1, 2.1 Hz, 1H), 7.80 (dd, J=8.1, 0.8 Hz, 1H), 7.64 (s, 1H), 7.38 (s, 1H), 7.13 (s, 1H), 4.28 (dd, J=5.8, 1.9 Hz, 2H), 4.16-4.07 (m, 3H), 3.03 (s, 3H), 2.65 (t, J=7.7 Hz, 2H), 2.18 (s, 3H), 2.13-1.95 (m, 2H), 1.26 (d, J=6.9 Hz, 3H).

Compound 500. (S)-2-(((1-((6-(difluoromethyl)pyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 9.27 (s, 1H), 8.56-8.47 (m, 1H), 7.72-7.57 (m, 2H), 7.56-7.49 (m, 1H), 7.44 (s, 1H), 6.61 (t, J=55.4 Hz, 1H), 5.81 (s, 1H), 5.33 (s, 2H), 4.43 (d, J=5.7 Hz, 2H), 3.88 (d, J=4.3 Hz, 1H), 3.11 (s, 3H), 2.25 (s, 4H), 1.06 (d, J=7.0 Hz, 3H), 0.91 (d, J=6.9 Hz, 3H).

Compound 501. (S)-7-cyclopropyl-2-(((1-((6-(difluoromethyl)pyridin-3-yl)methyl)-1H-pyrazol-4-yl)methyl)amino)-4,8-dimethyl-7,8-dihydropteridin-6(5H)-one $^1$H NMR (300 MHz, Chloroform-d) δ 9.24 (s, 1H), 8.26 (s, 1H), 7.46-7.32 (m, 2H), 7.30 (s, 1H), 7.17 (s, 1H), 6.37 (t, J=55.4 Hz, 1H), 5.08 (s, 2H), 4.93 (s, 1H), 4.19 (dd, J=5.7, 1.7 Hz, 2H), 3.03 (d, J=8.9 Hz, 1H), 2.87 (s, 3H), 2.02 (s, 3H), 0.74 (dtd, J=13.1, 8.4, 5.1 Hz, 1H), 0.52-0.13 (m, 4H).

Compound 510. (S)-7-isopropyl-4,8-dimethyl-2-(((1-((6-(trifluoromethoxy)pyridin-3-yl)methyl)-1H-pyrazol-4-yl)methyl)amino)-7,8-dihydropteridin-6(5H)-one $^1$H NMR (300 MHz, Methanol-d$_4$) δ 8.17 (d, J=2.4 Hz, 1H), 7.76 (dd, J=8.4, 2.5 Hz, 1H), 7.68 (s, 1H), 7.51 (s, 1H), 7.10 (d, J=8.5 Hz, 1H), 5.48 (d, J=0.6 Hz, 1H), 5.35 (s, 2H), 4.39 (s, 2H), 3.89 (d, J=4.5 Hz, 1H), 3.11 (s, 3H), 2.15 (s, 4H), 1.01 (d, J=6.9 Hz, 3H), 0.84 (d, J=6.9 Hz, 3H).

Compound 511. (S)-2-(((1-((6-(1,1-difluoroethyl)pyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 8.52 (s, 1H), 8.10 (s, 1H), 7.56 (s, 1H), 7.41 (s, 1H), 5.33 (s, 2H), 4.85 (t, J=5.8

Hz, 1H), 4.44 (d, J=5.8 Hz, 2H), 3.89 (d, J=4.4 Hz, 1H), 3.11 (s, 3H), 2.33-2.23 (m, 1H), 2.20 (s, 3H), 2.02 (t, J=18.6 Hz, 3H), 1.08 (d, J=6.9 Hz, 3H), 0.94 (s, 3H). [

Compound 516. (S)-7-ethyl-4,8-dimethyl-2-(((1-((5-(trifluoromethyl)furan-2-yl)methyl)-1H-pyrazol-4-yl)methyl)amino)-7,8-dihydropteridin-6(5H)-one $^1$H NMR (300 MHz, Chloroform-d) δ 7.42 (d, J=0.7 Hz, 1H), 7.35 (d, J=0.8 Hz, 1H), 6.65 (dq, J=3.6, 1.2 Hz, 1H), 6.27 (dq, J=2.5, 0.8 Hz, 1H), 5.19 (s, 2H), 5.04-4.90 (m, 1H), 4.33 (d, J=5.8 Hz, 2H), 3.96 (dd, J=6.4, 3.8 Hz, 1H), 2.97 (s, 3H), 2.15 (s, 3H), 1.95-1.67 (m, 2H), 0.82 (t, J=7.5 Hz, 3H).

Compound 518. (S)-7-isopropyl-4,8-dimethyl-2-(((1-((5-(trifluoromethyl)furan-2-yl)methyl)-1H-pyrazol-4-yl)methyl)amino)-7,8-dihydropteridin-6(5H)-one $^1$H NMR (300 MHz, Chloroform-d) δ 9.42 (s, 1H), 7.51 (d, J=3.3 Hz, 1H), 7.43 (d, J=2.6 Hz, 1H), 6.73 (td, J=3.2, 1.5 Hz, 1H), 6.35 (t, J=3.6 Hz, 1H), 5.27 (d, J=3.7 Hz, 2H), 5.05 (s, 1H), 4.42 (t, J=4.3 Hz, 2H), 3.86 (t, J=3.7 Hz, 1H), 3.10 (d, J=3.2 Hz, 3H), 2.23 (d, J=0.9 Hz, 4H), 1.06 (dd, J=6.6, 2.8 Hz, 3H), 1.01-0.77 (m, 3H).

Compound 565. (S)-7-((R)-1-methoxyethyl)-4,8-dimethyl-2-(((1-((6-(trifluoromethoxy)pyridin-3-yl)methyl)-1H-pyrazol-4-yl)methyl)amino)-7,8-dihydropteridin-6(5H)-one $^1$H NMR (300 MHz, Chloroform-d) δ 8.21 (dd, J=2.5, 0.8 Hz, 1H), 7.82 (s, 1H), 7.65 (dd, J=8.4, 2.5 Hz, 1H), 7.55 (d, J=0.8 Hz, 1H), 7.41 (d, J=0.8 Hz, 1H), 7.00 (d, J=8.4 Hz, 1H), 5.29 (s, 2H), 4.86 (t, J=5.7 Hz, 1H), 4.44 (d, J=5.8 Hz, 2H), 3.95 (d, J=6.0 Hz, 1H), 3.58 (p, J=6.2 Hz, 1H), 3.31 (s, 3H), 3.19 (s, 3H), 2.22 (s, 3H), 1.40-1.27 (m, 7H), 1.24 (d, J=6.4 Hz, 3H).

Compound 658. (S)-2-(((1-(4-fluorobenzyl)-1H-pyrazol-4-yl)methyl)amino)-7-((R)-1-methoxyethyl)-4,8-dimethyl-7,8-dihydropteridin-6(5H)-one $^1$H NMR (400 MHz, DMSO-d6) δ 7.76 (d, J=0.8 Hz, 1H), 7.45 (d, J=0.7 Hz, 1H), 7.30-7.25 (m, 2H), 7.20-7.12 (m, 2H), 5.27 (s, 2H), 4.47-4.33 (m, 2H), 4.30 (d, J=4.0 Hz, 1H), 3.71 (qd, J=6.5, 4.0 Hz, 1H), 3.24 (s, 3H), 3.19 (s, 3H), 3.10 (qd, J=7.3, 4.8 Hz, 1H), 2.24 (s, 3H), 1.21-1.15 (m, 4H).

Compound 659. (S)-7-((R)-1-methoxyethyl)-4,8-dimethyl-2-(((1-(3,4,5-trifluorobenzyl)-1H-pyrazol-4-yl)methyl)amino)-7,8-dihydropteridin-6(5H)-one $^1$H NMR (300 MHz, Methanol-d4) δ 7.77 (s, 1H), 7.05-6.89 (m, 2H), 5.32 (d, J=14.7 Hz, 2H), 4.53 (s, 2H), 4.23 (d, J=3.9 Hz, 1H), 3.89 (d, J=19.8 Hz, 1H), 3.78 (d, J=8.2 Hz, 2H), 2.38 (2, 5H), 1.28 (d, J=6.5 Hz, 6H).

Compound 668. 7-(1-methoxycyclobutyl)-4,8-dimethyl-2-(((1-(3,4,5-trifluorobenzyl)-1H-pyrazol-4-yl)methyl)amino)-7,8-dihydropteridin-6(5H)-one $^1$H NMR (400 MHz, DMSO-d6) δ 9.91 (s, 1H), 7.69 (s, 1H), 7.41 (s, 1H), 7.12 (dd, J=8.7, 6.8 Hz, 2H), 6.50 (s, 1H), 5.26 (s, 2H), 4.29-4.12 (m, 3H), 3.09 (s, 3H), 3.06 (s, 3H), 2.28-2.17 (m, 1H), 2.12 (d, J=12.7 Hz, 5H), 1.97 (dd, J=19.0, 9.2 Hz, 1H), 1.68 (ddd, J=20.4, 9.4, 5.5 Hz, 1H), 1.56 (dt, J=9.1, 8.0 Hz, 1H).

Compound 729. (S)-7-(2-hydroxypropan-2-yl)-4,8-dimethyl-2-(((1-(3,4,5-trifluorobenzyl)-1H-pyrazol-4-yl)methyl)amino)-7,8-dihydropteridin-6(5H)-one $^1$H NMR (400 MHz, DMSO-d6) δ 9.87 (s, 1H), 7.71 (s, 1H), 7.43 (s, 1H), 7.13 (dd, J=8.7, 6.8 Hz, 2H), 6.59 (s, 1H), 5.26 (s, 2H), 4.70 (s, 1H), 4.25 (d, J=4.1 Hz, 2H), 3.81 (s, 1H), 3.20-3.07 (m, 4H), 2.14 (d, J=32.3 Hz, 3H), 1.18 (s, 3H), 0.92 (s, 3H).

Compound 741. (S)-7-(tert-butoxymethyl)-4,8-dimethyl-2-(((1-(3,4,5-trifluorobenzyl)-1H-pyrazol-4-yl)methyl)amino)-7,8-dihydropteridin-6(5H)-one $^1$H NMR (300 MHz, Chloroform-d) δ 8.03 (d, J=106.2 Hz, 1H), 7.46 (s, 1H), 7.32 (s, 1H), 6.86-6.54 (m, 2H), 5.42 (s, 1H), 5.10 (s, 2H), 4.37 (d, J=5.7 Hz, 2H), 4.01 (t, J=3.0 Hz, 1H), 3.63 (t, J=3.4 Hz, 2H), 3.14-2.94 (m, 3H), 2.22-2.03 (m, 3H), 1.07-0.87 (m, 9H).

Compound 746. (S)-7-((S)-1-(tert-butoxy)ethyl)-2-(((1-(3,5-difluoro-4-methoxybenzyl)-1H-pyrazol-4-yl)methyl)amino)-4,8-dimethyl-7,8-dihydropteridin-6(5H)-one $^1$H NMR (400 MHz, Chloroform-d) δ 7.52 (d, J=14.9 Hz, 2H), 6.80-6.69 (m, 2H), 5.18 (s, 2H), 4.49 (dd, J=5.4, 2.8 Hz, 2H), 4.12 (pd, J=7.4, 6.4, 4.2 Hz, 1H), 4.02-3.95 (m, 4H), 3.29 (s, 3H), 2.37 (s, 3H), 1.24 (d, J=6.4 Hz, 3H), 1.06 (s, 9H).

Compound 747. (S)-7-((S)-1-(tert-butoxy)ethyl)-4,8-dimethyl-2-(((1-(3,4,5-trifluorobenzyl)-1H-pyrazol-4-yl)methyl)amino)-7,8-dihydropteridin-6(5H)-one $^1$H NMR (400 MHz, CDCl$_3$) δ 7.54 (d, J=0.7 Hz, 1H), 7.50 (d, J=0.8 Hz, 1H), 6.82-6.70 (m, 2H), 5.16 (d, J=0.9 Hz, 2H), 4.42 (t, J=4.0 Hz, 2H), 4.05 (tt, J=6.9, 3.4 Hz, 1H), 3.96 (d, J=2.1 Hz, 1H), 3.24 (s, 3H), 2.26 (s, 3H), 1.18 (d, J=6.4 Hz, 3H), 0.96 (s, 9H).

Example 2U

Table 19 provides certain compounds that were prepared by the Method B procedure by reaction of Intermediates A-# and B-# (See procedure for Compound 1). $^1$H NMR data for certain compounds are also provided.

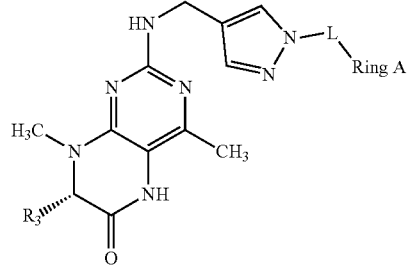

TABLE 19

| Comp. No. | L-Ring A | R₃ = | Int A | Int B | [α]_D | M + 1 |
|---|---|---|---|---|---|---|
| 414 | 5-(6-chloropyridin-3-yl)methyl | —iPr | A-9 | B-67 | +61.2 c = 1 MeOH | 441.26 |
| 415 | 5-fluoropyridin-3-yl methyl | —iPr | A-9 | B-78 | | 425.45 |
| 418 | 2-chloro-6-(trifluoromethyl)pyridin-3-yl methyl | —CH₃ | A-2 | B-167 | | 481.28 |
| 424 | 6-chloro-5-fluoropyridin-3-yl methyl | —iPr | A-9 | B-168 | | 459.31 |
| 426 | 6-chloro-5-fluoropyridin-3-yl methyl | —Et | A-8 | B-168 | | 445.36 |
| 431 | 6-cyanopyridin-3-yl methyl | —iPr | A-9 | B-170 | | 432.43 |
| 432 | 6-chloropyridin-3-yl methyl | —Et | A-8 | B-67 | +45.2 c = 0.5 MeOH | 427.25 |
| 434 | 6-chloropyridin-3-yl methyl | —cPr | A-6 | B-67 | +33 c = 1.0 MeOH | 439.32 |
| 438 | 6-chloropyridin-3-yl methyl | —tBu | A-55 | B-67 | +79.2 c = 1.0 CHCl₃ | 455.22 |
| 443 (R₁ = Me) | 6-(trifluoromethyl)pyridin-3-yl methyl | CH₂CH₂OH | A-56 | B-52 | +46.3 c = 0.55 MeOH | 491.28 |
| 445 (R₁ = Me) | 6-chloropyridin-3-yl methyl | CH₂CH₂OH | A-56 | B-67 | +46.9 c = 0.55 MeOH | 457.05 |

TABLE 19-continued

| Comp. No. | L-Ring A | R₃ = | Int A | Int B | [α]$_D$ | M + 1 |
|---|---|---|---|---|---|---|
| 446 | pyridine with Cl | —iPr | A-9 | CA | +78.7 C = 1.0 CHCl₃ | 441.39 |
| 608 | pyridine with Cl | —cPr | A-6 | CA | +44.7 c = 0.5 CHCl₃ | 439.46 |
| 499 | pyridine with Cl | H₃CO,,,,CH₃ | A-59 | B-67 | +68.9 c = 0.6 MeOH | 457.33 |
| 491 | thiazole with Cl | iPr | A-9 | B-181 | +48.5 c = 1, MeOH | 447.34 |
| 517 | oxazole with iPr | —iPr | A-9 | B-186 | +77.8 c = 0.5 CHCl₃ | 439.32 |
| 513 | oxazole with iPr | —Et | A-8 | B-186 | +72.5 c = 0.5 CHCl₃ | 477.25 |
| 550 | pyridine with Cl | isobutyl | A-60 | B-67 | +91.4 c = 0.5 CHCl₃ | 455.26 |

Compound 414. (7S)-2-(((1-((6-chloropyridin-3-yl)methyl)-1H-pyrazol-4-yl)methyl)amino)-7-isopropyl-4,8-dimethyl-7,8-dihydropteridin-6(5H)-one $^1$H NMR (300 MHz, DMSO-d6) δ 12.73 (s, 1H), 10.52 (s, 1H), 8.31 (d, J=2.1 Hz, 1H), 7.91 (s, 1H), 7.84 (s, 1H), 7.70 (dd, J=8.2, 2.5 Hz, 1H), 7.50 (d, J=8.0 Hz, 2H), 5.35 (s, 2H), 4.41 (d, J=5.7 Hz, 2H), 4.16 (d, J=3.7 Hz, 1H), 3.18 (s, 3H), 2.35-2.12 (m, 4H), 1.01 (d, J=6.9 Hz, 3H), 0.77 (d, J=6.9 Hz, 3H).

Compound 415. (7S)-2-(((1-((5-fluoropyridin-3-yl)methyl)-1H-pyrazol-4-yl)methyl)amino)-7-isopropyl-4,8-dimethyl-7,8-dihydropteridin-6(5)-one $^1$H NMR (300 MHz, Methanol-d$_4$) δ 8.96 (t, J=2.3 Hz, 1H), 8.68 (d, J=1.5 Hz, 1H), 8.28 (dd, J=8.7, 2.1 Hz, 1H), 8.00 (s, 1H), 7.69 (s, 1H), 5.66 (s, 2H), 4.59 (d, J=2.1 Hz, 2H), 4.19 (d, J=3.9 Hz, 1H), 2.46-2.34 (m, 0H), 2.33 (s, 3H), 1.14 (d, J=6.9 Hz, 3H), 0.92 (d, J=6.9 Hz, 3H).

Compound 418. (7S)-2-(((1-((2-chloro-6-(trifluoromethyl)pyridin-3-yl)methyl)-1H-pyrazol-4-yl)methyl)amino)-4,7,8-trimethyl-7,8-dihydropteridin-6(5H)-one $^1$H NMR (300 MHz, DMSO-d6) δ 9.85 (s, 1H), 7.94 (d, J=7.9 Hz, 1H), 7.78 (s, 1H), 7.54-7.43 (m, 2H), 6.65 (t, J=6.1 Hz, 1H), 5.49 (s, 2H), 4.24 (d, J=6.2 Hz, 2H), 4.00 (q, J=6.7 Hz, 1H), 2.94 (s, 3H), 2.13 (s, 3H), 1.18 (d, J=6.8 Hz, 3H).

Compound 424. (7S)-2-(((1-((6-chloro-5-fluoropyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 8.13 (d, J=2.0 Hz, 1H), 7.67 (s, 1H), 7.57 (s, 1H), 7.41 (s, 1H), 7.31 (dd, J=8.4, 2.1 Hz, 1H), 5.29 (s, 2H), 4.82 (t, J=5.8 Hz, 1H), 4.44 (d, J=5.8 Hz, 2H), 3.90 (d, J=4.3 Hz, 1H), 3.12 (s, 3H), 2.24 (td, J=6.9, 4.4 Hz, 1H), 2.19 (s, 3H), 1.64 (s, 6H), 1.08 (d, J=7.0 Hz, 3H), 0.93 (d, J=6.9 Hz, 3H).

Compound 426. (7S)-2-(((1-((6-chloro-5-fluoropyridin-3-yl)methyl)-1H-pyrazol-4-yl)methyl)amino)-7-ethyl-4,8-dimethyl-7,8-dihydropteridin-6(5H)-one $^1$H NMR (300 MHz, Chloroform-d) δ 8.16-8.05 (m, 1H), 7.54 (s, 1H), 7.39 (d, J=0.8 Hz, 1H), 7.29 (d, J=8.5 Hz, 1H), 5.27 (s, 2H), 4.84 (d, J=5.9 Hz, 1H), 4.42 (d, J=5.8 Hz, 2H), 4.06 (dd, J=6.4, 3.7 Hz, 1H), 3.05 (s, 3H), 2.18 (s, 3H), 1.97 (dqd, J=15.3, 7.8, 4.0 Hz, 1H), 1.83 (dt, J=14.3, 7.1 Hz, 1H), 0.93-0.86 (m, 3H).

Compound 431. (7S)-5-((4-(((7-isopropyl-4,8-dimethyl-6-oxo-5,6,7,8-tetrahydropteridin-2-yl)amino)methyl)-1H-pyrazol-1-yl)methyl)picolinonitrile $^1$H NMR (300 MHz, Methanol-d$_4$) δ 8.51 (d, J=1.7 Hz, 1H), 7.96-7.75 (m, 3H), 7.62 (s, 1H), 5.49 (s, 2H), 4.54 (s, 2H), 4.15 (d, J=3.8 Hz, 1H), 3.27 (s, 3H), 2.43-2.29 (m, 1H), 2.29 (s, 3H), 1.11 (d, J=7.0 Hz, 3H), 0.88 (d, J=6.9 Hz, 3H).

Compound 432. (7S)-2-(((1-((6-chloropyridin-3-yl)methyl)-1H-pyrazol-4-yl)methyl)amino)-7-ethyl-4,8-dimethyl-7,8-dihydropteridin-6(5H)-one $^1$H NMR (300 MHz, DMSO-d6) δ 9.83 (s, 1H), 8.30 (d, J=2.5 Hz, 1H), 7.75-7.62 (m, 2H), 7.47 (dd, J=8.2, 0.8 Hz, 1H), 7.39 (d, J=0.8 Hz, 1H), 6.50 (t, J=6.1 Hz, 1H), 5.31 (s, 2H), 4.21 (d, J=6.0 Hz, 2H), 3.99 (dd, J=6.6, 3.8 Hz, 1H), 2.96 (s, 3H), 2.11 (s, 3H), 1.89-1.53 (m, 2H), 0.74 (t, J=7.4 Hz, 3H)

Compound 434. (7S)-2-(((1-((6-chloropyridin-3-yl)methyl)-1H-pyrazol-4-yl)methyl)amino)-7-cyclopropyl-4,8-dimethyl-7,8-dihydropteridin-6(5H)-one $^1$H NMR (300 MHz, DMSO-d6) δ 10.17 (s, 1H), 8.30 (d, J=2.4 Hz, 1H), 7.78 (s, 1H), 7.68 (dd, J=8.3, 2.5 Hz, 1H), 7.55-7.42 (m, 3H), 5.34 (s, 2H), 4.33 (dd, J=5.7, 2.8 Hz, 2H), 3.52 (d, J=8.9 Hz, 1H), 3.13 (s, 3H), 2.20 (s, 3H), 1.09-0.86 (m, 1H), 0.68-0.32 (m, 4H).

Compound 438. (7S)-7-(tert-butyl)-2-(((1-((6-chloropyridin-3-yl)methyl)-1H-pyrazol-4-yl)methyl)amino)-4,8-dimethyl-7,8-dihydropteridin-6(5H)-one $^1$H NMR (300 MHz, Chloroform-d) δ 8.60 (s, 1H), 8.26-8.16 (m, 1H), 7.46 (d, J=0.7 Hz, 1H), 7.41 (dd, J=8.3, 2.5 Hz, 1H), 7.31 (d, J=0.8 Hz, 1H), 7.20 (d, J=0.8 Hz, 1H), 5.17 (s, 2H), 4.88 (t, J=5.8 Hz, 1H), 4.35 (d, J=5.8 Hz, 2H), 3.61 (s, 1H), 3.12 (s, 3H), 2.14 (s, 3H), 0.92 (s, 9H).

Compound 443. (7S)-7-(2-hydroxyethyl)-4,5,8-trimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 Hz, Chloroform-d) δ 7.45 (s, 1H), 6.94 (brs, 1H), 5.46 (s, 2H), 4.60 (t, J=5.0 Hz, 1H), 4.26 (dd, J=6.1, 2.3 Hz, 2H), 4.07 (dd, J=7.7, 5.8 Hz, 1H), 3.43-3.31 (m, 1H), 3.17 (s, 3H), 2.99 (s, 3H), 2.27 (s, 3H), 1.79-1.32 (m, 2H).

Compound 445. (7S)-2-(((1-((6-chloropyridin-3-yl)methyl)-1H-pyrazol-4-yl)methyl)amino)-7-(2-hydroxyethyl)-4,5,8-trimethyl-7,8-dihydropteridin-6(5H)-one $^1$H NMR (300 MHz, DMSO-d6) δ 8.31 (d, J=2.5 Hz, 1H), 7.74 (s, 1H), 7.68 (dd, J=8.3, 2.5 Hz, 1H), 7.49 (d, J=8.3 Hz, 1H), 7.41 (s, 1H), 6.84 (t, J=6.0 Hz, 1H), 5.32 (s, 2H), 4.64-4.54 (m, 1H), 4.23 (dd, J=6.0, 2.3 Hz, 2H), 4.04 (dd, J=7.7, 5.8 Hz, 1H), 3.17 (s, 3H), 2.97 (s, 3H), 2.25 (s, 3H), 1.76-1.38 (m, 2H).

Compound 446. (7S)-2-(((1-((2-chloropyridin-4-yl)methyl)-1H-pyrazol-4-yl)methyl)amino)-7-isopropyl-4,8-dimethyl-7,8-dihydropteridin-6(5H)-one $^1$H NMR (300 MHz, CDCl3) δ 8.35 (dd, J=5.2, 0.7 Hz, 1H), 7.87 (s, 1H), 7.59 (d, J=0.7 Hz, 1H), 7.43 (d, J=0.8 Hz, 1H), 7.06 (dq, J=1.6, 0.8 Hz, 1H), 6.97 (ddt, J=5.1, 1.5, 0.7 Hz, 1H), 5.28 (s, 2H), 4.86 (t, J=5.8 Hz, 1H), 4.47 (d, J=5.8 Hz, 2H), 3.90 (d, J=4.4 Hz, 1H), 3.13 (s, 3H), 2.25 (qd, J=7.0, 4.4 Hz, 1H), 2.20 (s, 3H), 1.31-1.17 (m, 1H), 1.08 (d, J=7.0 Hz, 3H), 0.93 (d, J=6.9 Hz, 3H)

Compound 608. (S)-2-(((1-((2-chloropyridin-4-yl)methyl)-1H-pyrazol-4-yl)methyl)amino)-7-cyclopropyl-4,8-dimethyl-7,8-dihydropteridin-6(5H)-one $^1$H NMR (300 MHz, Chloroform-d) δ 8.35 (dd, J=5.1, 0.7 Hz, 1H), 8.07 (s, 1H), 7.64-7.54 (m, 1H), 7.48-7.37 (m, 1H), 7.05 (dd, J=1.6, 0.8 Hz, 1H), 6.97 (dd, J=5.2, 1.5 Hz, 1H), 5.28 (s, 2H), 4.89 (t, J=5.8 Hz, 1H), 4.56-4.35 (m, 2H), 3.30 (d, J=9.0 Hz, 1H), 3.15 (s, 3H), 2.25 (s, 3H), 1.09-0.94 (m, 1H), 0.77-0.43 (m, 4H).

Compound 499. (S)-2-(((1-((6-chloropyridin-3-yl)methyl)-1H-pyrazol-4-yl)methyl)amino)-7-((R)-1-methoxyethyl)-4,8-dimethyl-7,8-dihydropteridin-6(5H)-one $^1$H NMR (300 MHz, DMSO-d6) δ 9.89 (s, 1H), 8.30 (d, J=2.4 Hz, 1H), 7.76-7.62 (m, 2H), 7.47 (d, J=8.2 Hz, 1H), 7.40 (s, 1H), 6.55 (t, J=6.0 Hz, 1H), 5.31 (s, 2H), 4.23 (d, J=6.0 Hz, 2H), 3.91 (d, J=5.8 Hz, 1H), 3.47 (p, J=6.3 Hz, 1H), 3.16 (s, 3H), 3.08 (s, 3H), 2.12 (s, 3H), 1.08 (d, J=6.4 Hz, 3H).

Compound 491. (S)-2-(((1-((2-chlorothiazol-5-yl)methyl)-1H-pyrazol-4-yl)methyl)amino)-7-isopropyl-4,8-dimethyl-7,8-dihydropteridin-6(5H)-one $^1$H NMR (300 MHz, DMSO-d6) δ 10.39 (s, 1H), 7.91 (br, 1H), 7.77 (s, 1H), 7.66 (d, J=1.0 Hz, 1H), 7.47 (s, 1H), 5.53 (s, 2H), 4.34 (d, J=5.7 Hz, 2H), 4.10 (d, J=4.0 Hz, 1H), 3.15 (s, 3H), 2.27-2.10 (m, 1H), 2.20 (s, 3H), 0.99 (d, J=6.9 Hz, 3H), 0.77 (d, J=6.9 Hz, 3H).

Compound 517. (S)-7-isopropyl-2-(((1-((2-isopropyloxazol-5-yl)methyl)-1H-pyrazol-4-yl)methyl)amino)-4,8-dimethyl-7,8-dihydropteridin-6(5H)-one $^1$H NMR (300 MHz, Chloroform-d) δ 9.30 (s, 1H), 7.49-7.37 (m, 2H), 7.35 (t, J=1.0 Hz, 1H), 5.07 (d, J=1.0 Hz, 2H), 4.88 (t, J=5.7 Hz, 1H), 4.33 (d, J=5.7 Hz, 2H), 3.78 (d, J=4.4 Hz, 1H), 3.03 (s, 3H), 3.02-2.87 (m, 1H), 2.15 (s, 4H), 1.24 (d, J=7.0 Hz, 6H), 0.98 (d, J=7.0 Hz, 3H), 0.84 (d, J=6.9 Hz, 3H).

Compound 513. (S)-7-ethyl-2-(((1-((2-isopropyloxazol-5-yl)methyl)-1H-pyrazol-4-yl)methyl)amino)-4,8-dimethyl-7,8-dihydropteridin-6(5H)-one $^1$H NMR (400 MHz, Methanol-d4) δ 7.11-6.99 (m, 2H), 4.23-4.16 (m, 1H), 4.14 (d, J=3.8 Hz, 1H), 4.09-3.97 (m, 1H), 3.48 (s, 2H), 3.26 (s, 3H), 2.88-2.77 (m, 2H), 2.40-2.31 (m, 1H), 2.30 (s, 3H), 2.13-1.99 (m, 2H), 1.10 (t, J=7.5 Hz, 3H), 1.07-0.97 (m, 1H), 0.88 (d, J=6.9 Hz, 3H).

Compound 550. (S)-2-(((1-((6-chloropyridin-3-yl)methyl)-1H-pyrazol-4-yl)methyl)amino)-7-isobutyl-4,8-dimethyl-7,8-dihydropteridin-6(5H)-one $^1$H NMR (300 MHz, Chloroform-d) δ 8.37 (s, 1H), 8.34-8.25 (m, 1H), 7.54 (d, J=0.8 Hz, 1H), 7.50 (dd, J=8.2, 2.5 Hz, 1H), 7.39 (d, J=0.8 Hz, 1H), 7.31 (dd, J=8.2, 0.7 Hz, 1H), 5.27 (s, 2H), 4.88 (t, J=5.7 Hz, 1H), 4.50-4.37 (m, 2H), 4.01 (dd, J=7.6, 5.8 Hz, 1H), 3.06 (s, 3H), 2.23 (s, 3H), 1.88-1.72 (m, 1H), 1.60 (ddd, J=8.1, 5.6, 1.9 Hz, 2H), 0.96 (dd, J=17.4, 6.5 Hz, 6H)

Example 2V

The examples in Table 20 were prepared by Method A procedure by reaction of Intermediates A-9 and B-# (See procedure for Compound 46)

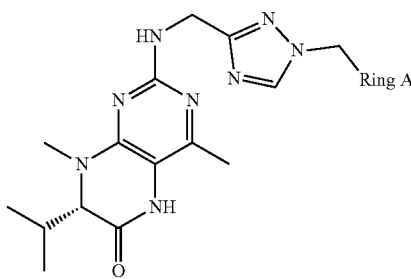

TABLE 20

| Comp. No. | Ring A | Int A | Int B | [α]$_D$ | M + 1 |
|---|---|---|---|---|---|
| 488 | ![3,5-difluoro-4-methoxyphenyl] | A-9 | B-187 | +31.76 c = 0.5 MeOH | 473.33 |
| 489 | ![4-OCF3 phenyl] | A-9 | B-188 | +13.54 c = 0.5 MeOH | 491.29 |
| 490 | ![3,4,5-trifluorophenyl] | A-9 | B-189 | +20.18 c = 0.5 | 461.31 |

Compound 488. (S)-2-(((1-(3,5-difluoro-4-methoxy-benzyl)-1H-1,2,4-triazol-3-yl)methyl)amino)-7-isopropyl-4,8-dimethyl-7,8-dihydropteridin-6(5H)-one $^1$H NMR (400 MHz, DMSO-d6) δ 10.56 (s, 1H), 8.61 (s, 1H), 7.12-6.98 (m, 2H), 5.39-5.27 (m, 2H), 4.65-4.51 (m, 2H), 4.11 (t, J=10.1 Hz, 1H), 3.90 (s, 3H), 3.57 (s, 1H), 3.02 (s, 3H), 2.26-2.16 (m, 4H), 0.99 (d, J=6.9 Hz, 3H), 0.74 (t, J=12.3 Hz, 3H).

Compound 489. (S)-7-isopropyl-4,8-dimethyl-2-(((1-(4-(trifluoromethoxy)benzyl)-1H-1,2,4-triazol-3-yl)methyl)amino)-7,8-dihydropteridin-6(5H)-one $^1$H NMR (400 MHz, DMSO-d6) δ 10.56 (s, 1H), 8.65 (s, 1H), 7.43-7.33 (m, 4H), 5.41 (s, 2H), 4.64-4.47 (m, 2H), 4.12 (d, J=3.7 Hz, 1H), 3.03 (d, J=22.2 Hz, 3H), 2.29-2.21 (m, 3H), 2.21-2.14 (m, 1H), 1.00 (t, J=7.2 Hz, 3H), 0.75 (dd, J=19.6, 6.8 Hz, 3H).

Compound 490. (S)-7-isopropyl-4,8-dimethyl-2-(((1-(3,4,5-trifluorobenzyl)-1H-1,2,4-triazol-3-yl)methyl)amino)-7,8-dihydropteridin-6(5H)-one $^1$H NMR (400 MHz, DMSO-d6) δ 8.62 (s, 1H), 8.23 (d, J=7.8 Hz, 1H), 7.25 (d, J=8.6 Hz, 1H), 5.38 (s, 1H), 4.61-4.52 (m, 2H), 4.13 (dd, J=10.1, 6.9 Hz, 3H), 3.06 (s, 1H), 3.02 (s, 2H), 2.30 (s, 2H), 2.24 (d, J=6.8 Hz, 3H), 1.02-0.99 (m, 3H), 0.78 (dd, J=16.0, 6.9 Hz, 3H).

Example 2W

Table 21 provides certain compounds that were prepared by Method A procedure by reaction of Intermediates A-9 and B-# (See procedure for Compound 46). $^1$H NMR data for certain compounds are also provided.

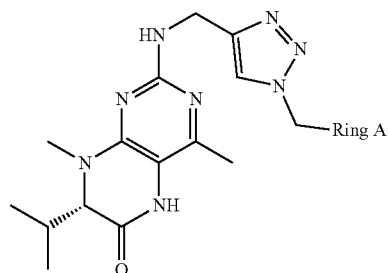

TABLE 21

| Comp. No. | Ring A | Int A | Int B | [α]$_D$ | M + 1 |
|---|---|---|---|---|---|
| 451 | ![3,5-difluoro-4-methoxyphenyl] | A-9 | B-193 | | 473.29 |
| 452 | ![3,4,5-trifluorophenyl] | A-9 | B-192 | +24.9 c = 0.5 MeOH | 461.36 |

Compound 451. (S)-2-(((1-(3,5-difluoro-4-methoxy-benzyl)-1H-1,2,3-triazol-4-yl)methyl)amino)-7-isopropyl-4,8-dimethyl-7,8-dihydropteridin-6(5H)-one $^1$H NMR (400 MHz, DMSO-d6) δ 10.57 (s, 1H), 8.11 (s, 2H), 7.20-7.00 (m, 2H), 5.54 (s, 2H), 4.71-4.48 (m, 2H), 4.14 (t, J=17.3 Hz, 1H), 3.87 (d, J=27.8 Hz, 3H), 3.12 (s, 3H), 2.31-2.13 (m, 4H), 1.05 (t, J=31.1 Hz, 3H), 0.75 (d, J=6.9 Hz, 3H).

Compound 452. (S)-7-isopropyl-4,8-dimethyl-2-(((1-(3,4,5-trifluorobenzyl)-1H-1,2,3-triazol-4-yl)methyl)amino)-7,8-dihydropteridin-6(5H)-one $^1$H NMR (400 MHz, DMSO-d6) δ 10.57 (s, 1H), 8.13 (s, 1H), 7.29 (dd, J=8.5, 6.8 Hz, 2H), 5.56 (d, J=19.2 Hz, 2H), 4.77-4.46 (m, 2H), 4.12 (t, J=27.2 Hz, 2H), 3.36-2.92 (m, 4H), 2.37-1.91 (m, 4H), 1.05 (t, J=31.4 Hz, 3H), 0.76 (t, J=9.4 Hz, 2H).

Example 2X

Table 22 provides certain compounds that were prepared by Method A procedure by reaction of Intermediates A-9 and B-# (See procedure for Compound 46). $^1$H NMR data are also provided for certain compounds.

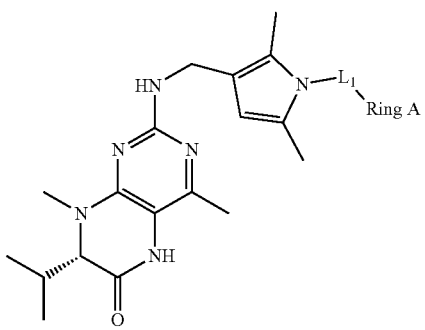

TABLE 22

| Comp. No. | Ring A | Int A | Int B | [α]$_D$ | M + 1 |
|---|---|---|---|---|---|
| 453 | 4-CF3-phenyl | A-9 | CA | +45.3 c = 0.5 MeOH | 487.2 |
| 508 | 4-F-phenyl | A-9 | CA | +24.9 c = 0.5 MeOH | 451.12 |

Compound 453. (S)-2-(((2,5-dimethyl-1-(4-(trifluoromethyl)phenyl)-1H-pyrrol-3-yl)methyl)amino)-7-isopropyl-4,8-dimethyl-7,8-dihydropteridin-6(5H)-one $^1$H NMR (300 MHz, Methanol-d$_4$) δ 7.91-7.75 (m, 2H), 7.48-7.32 (m, 2H), 5.94 (d, J=1.1 Hz, 1H), 4.33 (d, J=1.1 Hz, 2H), 3.91 (d, J=4.5 Hz, 1H), 3.35 (s, 1H), 3.17 (s, 3H), 2.16 (s, 4H), 2.01 (d, J=7.9 Hz, 6H), 1.04 (d, J=7.0 Hz, 3H), 0.89 (d, J=6.9 Hz, 3H).

Compound 508. (S)-2-(((1-(4-fluorobenzyl)-2,5-dimethyl-1H-pyrrol-3-yl)methyl)amino)-7-isopropyl-4,8-dimethyl-7,8-dihydropteridin-6(5H)-one $^1$H NMR (300 MHz, Methanol-d$_4$) δ 7.11-6.69 (m, 4H), 5.83 (d, J=1.0 Hz, 1H), 5.02 (d, J=1.2 Hz, 3H), 4.28 (d, J=2.1 Hz, 2H), 3.90 (d, J=4.5 Hz, 1H), 3.35-3.32 (m, 2H), 3.16 (s, 3H), 2.35-1.98 (m, 9H), 1.03 (d, J=7.0 Hz, 3H), 0.88 (d, J=6.9 Hz, 3H).

Scheme for Synthesis of Compound 430

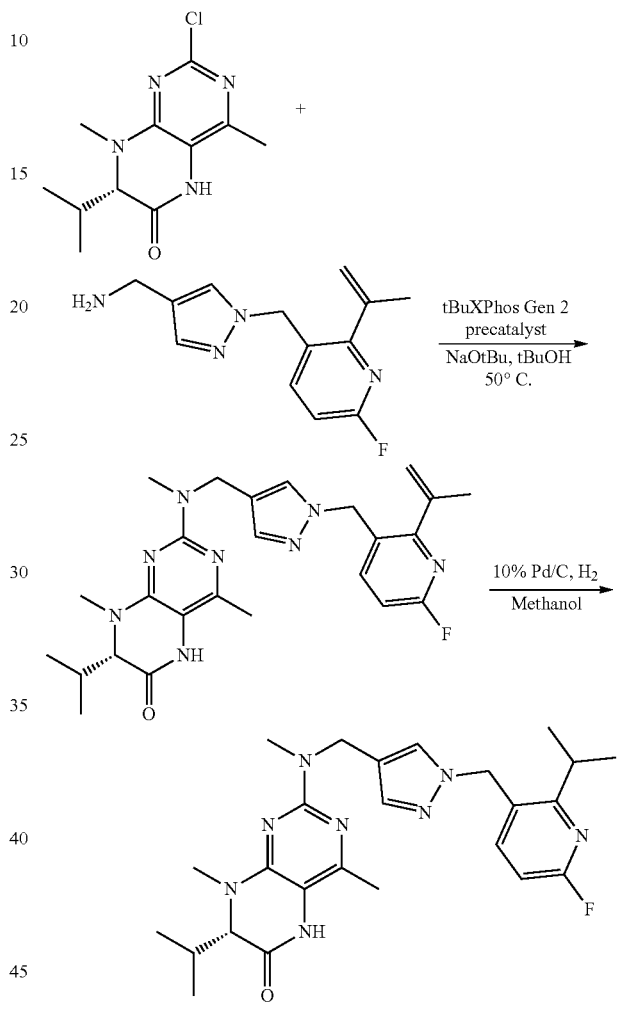

Compound 430

Compound 430. (7S)-2-(((1-((6-fluoro-2-isopropylpyridin-3-yl)methyl)-1H-pyrazol-4-yl)methyl)(methyl)amino)-7-isopropyl-4,8-dimethyl-7,8-dihydropteridin-6(5H)-one The compound was prepared in two steps.

Step 1. (7S)-2-(((1-((6-fluoro-2-(prop-1-en-2-yl)pyridin-3-yl)methyl)-1H-pyrazol-4-yl)methyl)(methyl)amino)-7-isopropyl-4,8-dimethyl-7,8-dihydropteridin-6(5H)-one This compound was prepared by the general procedure (Method B; see Compound 46) via reaction of A-9 and B-208 to provide the title product that was used without further purification. ESI-MS m/z 465.39 (M+1)$^+$.

Step 2. (7S)-2-(((1-((6-fluoro-2-isopropylpyridin-3-yl)methyl)-1H-pyrazol-4-yl)methyl)(methyl)amino)-7-isopropyl-4,8-dimethyl-7,8-dihydropteridin-6(5H)-one In a flask was placed the product from Step 1 (95 mg, 0.186 mmol) and 10% Pd/C (50 mg) in 10 ml of methanol and charged with a hydrogen balloon. The reaction was stirred at room temperature for 14 hours. The reaction was filtered through celite and the filtrate evaporated. The crude product was purified by column chromatography (SiO$_2$, 40 g) eluting with a gradient of 0-20% methanol in dichloromethane. The desired fractions were collected to provide the title product (52 mg, 57% yield). 1H NMR (300 MHz, DMSO-d6) δ 9.84 (s, 1H), 7.67-7.51 (m, 2H), 7.38 (d, J=0.7 Hz, 1H), 6.93 (dd, J=8.3, 3.5 Hz, 1H), 6.51 (t, J=6.0 Hz, 1H), 5.35 (s, 2H), 4.21 (d, J=6.1 Hz, 2H), 3.84 (d, J=4.6 Hz, 1H), 3.49-3.19 (m, 2H), 3.01 (s, 3H), 2.09 (s, 3H), 1.04 (d, J=6.6 Hz, 6H), 0.93 (d, J=6.9 Hz, 3H), 0.75 (d, J=6.9 Hz, 3H). ESI-MS m/z calc. 466.2605, found 467.51 (M+1)$^+$; [α]$_D$=+86.86 (c=1, MeOH). Chiral HPLC (ChiralPAK IC column, 5×250 mm; 50% hexanes/30% ethanol/20% methanol (0.1% diethylamine) Rt 6.202 mins (96% ee).

Example 2Y

General scheme and procedure for examples in Table 23:

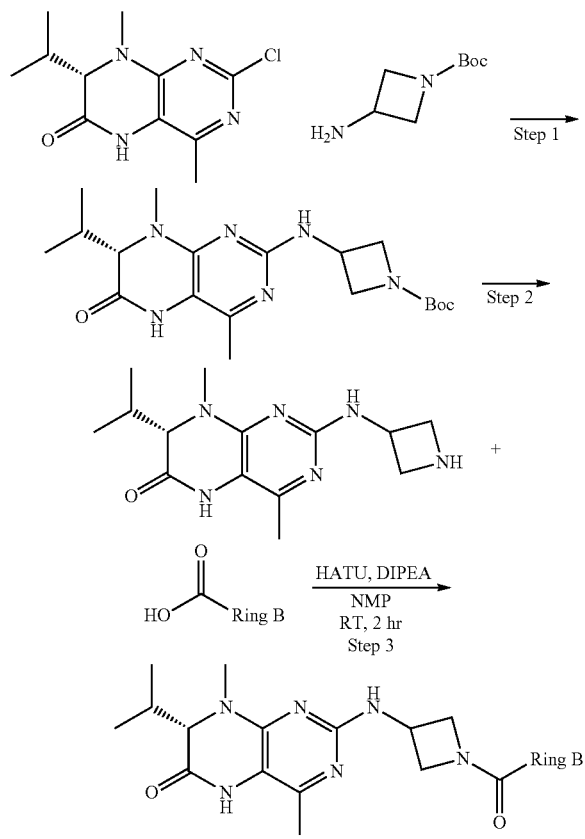

Step 1: tert-Butyl (S)-3-((2-isopropyl-1,5-dimethyl-3-oxo-1,2,3,4-tetrahydropyrido[3,4-b]pyrazin-7-yl)amino)azetidine-1-carboxylate (7S)-2-Chloro-7-isopropyl-4,8-dimethyl-5,7-dihydropteridin-6-one (6.6 g, 25.91 mmol) and tert-butyl 3-aminoazetidine-1-carboxylate (4.9 g, 28.45 mmol) were taken into t-butanol (70 mL) and THF (65 mL). Sodium tert-butoxide (12.5 g, 130 mmol) was added to the solution and the mixture was degassed for 20 mins. by bubbling nitrogen in the solution. tButylXPhos palladacycle (Gen 1; 900 mg, 1.3 mmol) was added to the mixture and heated for 1.5 hours at 50° C. The reaction was quenched with saturated ammonium chloride (80 ml) and extracted with ethyl acetate 3×100 ml). The organic layer was collected combined and Pd scavenger (2 g) was added and stirred overnight at room temperature. The mixture was filtered and the solvent evaporated in vacuo. The resulting material was triturated with 5% dichloromethane/methyl t-butyl ether (25 ml), filtered and and dried under vacuum at 40° C. to afford the title product (9.7 g, 95% yield). $^1$H NMR (400 MHz, Methanol-d4) δ 4.56 (tt, J=7.6, 5.5 Hz, 1H), 4.20 (dd, J=13.4, 8.1 Hz, 2H), 3.91 (d, J=4.4 Hz, 1H), 3.86 (dd, J=8.6, 5.4 Hz, 2H), 3.12 (s, 3H), 2.21 (tt, J=10.0, 2.7 Hz, 1H), 2.16 (s, 3H), 1.44 (s, 9H), 1.03 (d, J=7.0 Hz, 3H), 0.86 (d, J=6.9 Hz, 3H). ESMS (M+1) =391.26.

Step 2: (S)-7-(azetidin-3-ylamino)-2-isopropyl-1,5-dimethyl-1,4-dihydropyrido[3,4-b]pyrazin-3(2H)-one tert-Butyl (S)-3-((2-isopropyl-1,5-dimethyl-3-oxo-1,2,3,4-tetrahydropyrido[3,4-b]pyrazin-7-yl)amino)azetidine-1-carboxylate (7.36 g, 18.42 mmol) was dissolved in 20 ml of dichloromethane. Trifluoroacetic acid (10 ml) was added to the solution and stirred at room temperature for 14 hours. The reaction was concentrated to give a residue that was dissolved in dichloromethane (30 ml) and triturated by slow addition of diethyl ether. The precipitate was collected by filtration and dried in a vacuum oven at 50° C. to afford the tittle product as a TFA salt (9 g, 98% yield). 1H NMR (400 MHz, Methanol-d4) δ 5.01 (p, J=7.6 Hz, 1H), 4.46-4.31 (m, 2H), 4.19 (ddd, J=16.9, 10.2, 5.6 Hz, 3H), 3.26 (s, 3H), 2.40-2.24 (m, 4H), 1.11 (d, J=7.0 Hz, 3H), 0.89 (d, J=6.9 Hz, 3H). ESI-MS m/z calc. 290.18552, found 291.26 (M+1)$^+$.

Step 3: Procedure for Formation of Amide Derivatives in Table Below

To a solution of (7S)-2-(azetidin-3-ylamino)-7-isopropyl-4,8-dimethyl-5,7-dihydropteridin-6-one (bis TFA salt) (50 mg, 0.1 mmol), the carboxylic acid (0.1 mmol), and HATU (55 mg, 0.15 mmol) in NMP (1 mL) at room temperature was added DIPEA (67 mL, 0.4 mmol). The reaction was allowed to stir for 2 hours at room temperature. The reaction mixture was diluted to 2 mL total volume with DMSO and submitted for automated purification (Ortho 2 method). The solvent was removed under reduced pressure to afford the amide.

Table 23 provides certain compounds that were prepared via the general procedure reported above. $^1$H NMR data are also provided for certain compounds.

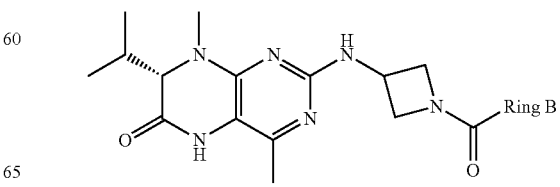

| Comp. No. | Ring B | [α]_D | M + 1 |
|---|---|---|---|
| 496 | 3,4,5-trifluorophenyl | +95.95 c = 1.05 MeOH | 449.33 |
| 542 | 3,5-difluoro-4-methoxyphenyl | | 461.26 |
| 543 | 4,4-difluorocyclohexyl | | 437.31 |
| 544 | (3,4,5-trifluorophenyl)methyl | | 463.24 |
| 545 | 6-(trifluoromethyl)pyridin-3-yl | | 464.28 |
| 548 | 4-fluorophenyl | | 413.27 |
| 549 | 6-chloropyridin-3-yl | | 430.25 |
| 594 | (6-(trifluoromethyl)pyridin-3-yl)methyl | | 477.87 |
| 595 | (3-(trifluoromethyl)-1H-pyrazol-1-yl)methyl | | 466.87 |
| 596 | 1-methyl-3-(trifluoromethyl)-1H-pyrazol-5-yl | | 467.3 |
| 597 | 1-methyl-5-(trifluoromethyl)-1H-pyrazol-3-yl | | 467.3 |
| 605 | oxazol-4-yl | | 386.26 |
| 606 | (3,3-difluorocyclobutyl)methyl | | 423.35 |
| 607 | 6-(trifluoromethoxy)pyridin-3-yl | | 477.92 |
| 609 | 1-methyl-3-(trifluoromethyl)-1H-pyrazol-4-yl | | 467.3 |
| 610 | 2-methyloxazol-4-yl | | 400.33 |
| 611 | tetrahydro-2H-pyran-2-yl | | 403.36 |
| 612 | (2-(trifluoromethyl)phenoxy)methyl | | 493.3 |
| 613 | 2-methylthiazol-4-yl | | 470.27 |
| 614 | 1-(difluoromethyl)-1H-pyrazol-3-yl | | 435.36 |

-continued

| Comp. No. | Ring B | [α]_D | M + 1 |
|---|---|---|---|
| 615 | 5-(2,2,2-trifluoroethoxy)pyridin-2-yl | | 494.36 |
| 616 | 2,4-difluorobenzyl | | 445.33 |
| 617 | 1,2,5-oxadiazol-3-yl | | 387.27 |
| 618 | 4-fluorobenzyl | | 427.31 |
| 619 | 5-isopropylisoxazol-3-yl | | 428.37 |
| 620 | 5-methylisoxazol-3-yl | | 400.33 |
| 621 | 5-(trifluoromethyl)furan-2-yl | | 453.31 |
| 622 | 4-(trifluoromethyl)phenyl | | 463.34 |
| 623 | norbornan-2-ylmethyl | | 427.38 |
| 626 | 3,4-difluorobenzyl | | 445.26 |
| 627 | (S)-1-phenylethyl | | 423.35 |

-continued

| Comp. No. | Ring B | [α]_D | M + 1 |
|---|---|---|---|
| 628 | 2,5-dimethylthiazol-4-yl | | 445.28 |
| 629 | 3,5-difluorobenzyl | | 445.33 |
| 630 | 2-chlorothiazol-4-yl | | 436.22 |
| 631 | pyrazin-2-yl | | 397.36 |
| 632 | 2,3-difluorobenzyl | | 445.33 |
| 633 | 2-chlorothiazol-5-yl | | 436.29 |
| 634 | (S)-methoxy(phenyl)methyl | | 439.39 |
| 635 | 3-(trifluoromethyl)phenyl | | 463.34 |
| 636 | tetrahydrofuran-2-yl | | 389.38 |
| 637 | 5-methyltetrahydrofuran-2-yl | | 403.36 |

-continued

| Comp. No. | Ring B | [α]_D | M + 1 |
|---|---|---|---|
| 638 | 2-methyltetrahydrofuran-2-yl | | 403.36 |
| 639 | bicyclo[2.2.1]heptan-2-yl (norbornyl) | | 413.39 |
| 640 | pyrimidin-2-yl | | 397.29 |
| 641 | 1-phenylethyl | | 423.35 |
| 642 | tetrahydrofuran-2-yl | | 389.38 |
| 699 | 3-(trifluoromethyl)bicyclo[1.1.1]pentan-1-yl | | 453.3 |

Compound 496. (S)-7-isopropyl-4,8-dimethyl-2-((1-(3,4,5-trifluorobenzoyl)azetidin-3-yl)amino)-7,8-dihydropteridin-6(5H)-one $^1$H NMR (400 MHz, Methanol-d4) δ 7.47 (dd, J=8.2, 6.7 Hz, 2H), 4.76-4.62 (m, 2H), 4.55-4.42 (m, 1H), 4.39-4.28 (m, 1H), 4.17-4.06 (m, 1H), 3.92 (d, J=4.4 Hz, 1H), 3.11 (s, 3H), 2.28-2.17 (m, 1H), 2.16 (s, 3H), 1.02 (d, J=7.0 Hz, 3H), 0.85 (d, J=6.9 Hz, 3H).

Compound 542. (S)-2-((1-(3,5-difluoro-4-methoxybenzoyl)azetidin-3-yl)amino)-7-isopropyl-4,8-dimethyl-7,8-dihydropteridin-6(5H)-one $^1$H NMR (400 MHz, Methanol-d4) δ 7.37-7.25 (m, 2H), 4.74-4.61 (m, 2H), 4.46 (s, 1H), 4.35 (s, 1H), 4.11 (d, J=7.2 Hz, 1H), 4.03 (s, 3H), 3.93 (d, J=4.4 Hz, 1H), 3.12 (s, 3H), 2.29-2.19 (m, 1H), 2.17 (s, 3H), 1.03 (d, J=7.0 Hz, 3H), 0.86 (d, J=6.9 Hz, 3H).

Compound 543. (S)-2-((1-(4,4-difluorocyclohexane-1-carbonyl)azetidin-3-yl)amino)-7-isopropyl-4,8-dimethyl-7,8-dihydropteridin-6(5H)-one $^1$H NMR (400 MHz, Methanol-d4) δ 4.66 (ddd, J=12.9, 7.6, 5.3 Hz, 1H), 4.57 (td, J=8.3, 4.8 Hz, 1H), 4.32-4.23 (m, 1H), 4.18 (td, J=8.9, 5.3 Hz, 1H), 3.98 (d, J=4.2 Hz, 1H), 3.93 (dd, J=10.3, 5.4 Hz, 1H), 3.16 (s, 3H), 2.43 (t, J=9.7 Hz, 1H), 2.24 (ddd, J=9.8, 9.3, 4.9 Hz, 1H), 2.20 (s, 3H), 2.09 (d, J=7.7 Hz, 2H), 1.93-1.66 (m, 6H), 1.05 (d, J=7.0 Hz, 3H), 0.87 (d, J=6.9 Hz, 3H).

Compound 544. (S)-7-isopropyl-4,8-dimethyl-2-((1-(2-(3,4,5-trifluorophenyl)acetyl)azetidin-3-yl)amino)-7,8-dihydropteridin-6(5H)-one $^1$H NMR (400 MHz, Methanol-d4) δ 7.11-7.01 (m, 2H), 4.67 (dq, J=7.3, 5.4 Hz, 1H), 4.58 (td, J=8.3, 4.4 Hz, 1H), 4.36-4.27 (m, 1H), 4.25-4.16 (m, 1H), 4.02-3.92 (m, 2H), 3.52 (s, 2H), 3.14 (d, J=5.0 Hz, 3H), 2.24 (tdd, J=6.9, 5.7, 1.9 Hz, 1H), 2.20 (s, 3H), 1.05 (d, J=7.0 Hz, 3H), 0.87 (d, J=6.9 Hz, 3H).

Compound 545. (S)-7-isopropyl-4,8-dimethyl-2-((1-(6-(trifluoromethyl)nicotinoyl)azetidin-3-yl)amino)-7,8-dihydropteridin-6(5H)-one $^1$H NMR (400 MHz, Methanol-d4) δ 8.98 (d, J=1.5 Hz, 1H), 8.29 (dd, J=8.1, 1.7 Hz, 1H), 7.92 (d, J=8.1 Hz, 1H), 4.83-4.63 (m, 6H), 4.59-4.51 (m, 1H), 4.38 (dd, J=14.0, 8.8 Hz, 1H), 4.20 (dd, J=10.7, 5.3 Hz, 1H), 3.98 (d, J=4.2 Hz, 1H), 3.15 (s, 3H), 2.32-2.21 (m, 1H), 2.20 (s, 3H), 1.04 (d, J=7.0 Hz, 3H), 0.86 (d, J=6.9 Hz, 3H).

Compound 548. (S)-2-((1-(4-fluorobenzoyl)azetidin-3-yl)amino)-7-isopropyl-4,8-dimethyl-7,8-dihydropteridin-6(5H)-one $^1$H NMR (400 MHz, Methanol-d4) δ 7.72 (dd, J=8.6, 5.5 Hz, 2H), 7.19 (t, J=8.7 Hz, 2H), 4.77-4.58 (m, 2H), 4.55-4.41 (m, 1H), 4.33 (d, J=5.1 Hz, 1H), 4.14 (dd, J=10.4, 4.8 Hz, 1H), 3.94 (d, J=4.3 Hz, 1H), 3.12 (s, 3H), 2.28-2.19 (m, 1H), 2.18 (s, 3H), 1.03 (d, J=6.9 Hz, 3H), 0.86 (d, J=6.9 Hz, 3H).

Compound 549. (S)-2-((1-(6-chloronicotinoyl)azetidin-3-yl)amino)-7-isopropyl-4,8-dimethyl-7,8-dihydropteridin-6(5H)-one $^1$H NMR (400 MHz, Methanol-d4) δ 8.66 (d, J=2.1 Hz, 1H), 8.07 (dd, J=8.3, 2.3 Hz, 1H), 7.55 (d, J=8.3 Hz, 1H), 4.80-4.63 (m, 2H), 4.51 (dd, J=14.5, 8.6 Hz, 1H), 4.44-4.29 (m, 1H), 4.16 (dd, J=10.5, 4.9 Hz, 1H), 3.97 (d, J=4.2 Hz, 1H), 3.14 (s, 3H), 2.30-2.21 (m, 1H), 2.19 (s, 3H), 1.04 (d, J=6.9 Hz, 3H), 0.86 (d, J=6.9 Hz, 3H).

Compound 594. (S)-7-isopropyl-4,8-dimethyl-2-((1-(2-(6-(trifluoromethyl)pyridin-3-yl)acetyl)azetidin-3-yl)amino)-7,8-dihydropteridin-6(5H)-one $^1$H NMR (400 MHz, DMSO-d6) δ 9.99 (s, 1H), 8.62 (s, 1H), 7.94 (d, J=8.3 Hz, 1H), 7.85 (d, J=8.0 Hz, 1H), 7.16 (s, 1H), 4.51 (s, 2H), 4.10 (d, J=7.5 Hz, 2H), 3.90 (s, 1H), 3.81 (s, 1H), 3.63 (s, 2H), 3.06-2.95 (m, 3H), 2.12 (s, 4H), 0.95 (d, J=6.9 Hz, 3H), 0.76 (d, J=6.8 Hz, 3H).

Compound 595. (S)-7-isopropyl-4,8-dimethyl-2-((1-(2-(3-(trifluoromethyl)-1H-pyrazol-1-yl)acetyl)azetidin-3-yl)amino)-7,8-dihydropteridin-6(5H)-one $^1$H NMR (400 MHz, DMSO-d6) δ 9.99 (s, 1H), 7.91 (s, 1H), 7.18 (s, 1H), 6.74 (s, 1H), 5.11-4.92 (m, 2H), 4.53 (s, 1H), 4.41 (t, J=7.4 Hz, 1H), 4.16 (t, J=8.1 Hz, 1H), 4.01 (s, 1H), 3.89 (dd, J=15.7, 4.6 Hz, 2H), 3.02 (m, 3H), 2.13 (s, 4H), 0.95 (d, J=6.8 Hz, 3H), 0.77 (d, J=6.8 Hz, 3H).

Compound 596. (S)-7-isopropyl-4,8-dimethyl-2-((1-(1-methyl-3-(trifluoromethyl)-1H-pyrazole-5-carbonyl)azetidin-3-yl)amino)-7,8-dihydropteridin-6(5H)-one $^1$H NMR (400 MHz, DMSO-d6) δ 9.93 (s, 1H), 7.13 (s, 1H), 7.04 (t, J=5.8 Hz, 1H), 4.67-4.49 (m, 2H), 4.36-4.14 (m, 2H), 4.08 (s, 2H), 4.05-3.96 (m, 1H), 3.87 (d, J=4.3 Hz, 1H), 3.02 (s, 3H), 2.11 (s, 3H), 0.94 (d, J=6.8 Hz, 3H), 0.76 (d, J=6.8 Hz, 3H).

Compound 597. (S)-7-isopropyl-4,8-dimethyl-2-((1-(1-methyl-5-(trifluoromethyl)-1H-pyrazole-3-carbonyl)azetidin-3-yl)amino)-7,8-dihydropteridin-6(5H)-one $^1$H NMR (400 MHz, DMSO-d6) δ 9.95 (s, 1H), 7.21 (s, 1H), 7.13 (s, 1H), 4.72 (t, J=7.8 Hz, 1H), 4.56 (d, J=5.5 Hz, 1H), 4.45-4.19 (m, 2H), 4.02 (s, 3H), 3.98-3.81 (m, 2H), 3.03 (s, 3H), 2.12 (s, 4H), 0.94 (d, J=4.7 Hz, 3H), 0.77 (d, J=6.7 Hz, 3H).

Compound 605. (S)-7-isopropyl-4,8-dimethyl-2-((1-(oxazole-4-carbonyl)azetidin-3-yl)amino)-7,8-dihydropteridin-6(5H)-one $^1$H NMR (400 MHz, DMSO-d6) δ 9.93 (s, 1H), 8.64 (s, 1H), 8.48 (s, 1H), 7.08 (d, J=5.5 Hz, 1H), 4.71 (dd, J=11.9, 5.0 Hz, 1H), 4.54 (s, 1H), 4.29 (ddd, J=29.4, 15.3, 8.7 Hz, 2H), 4.04-3.80 (m, 2H), 3.00 (d, J=7.0 Hz, 3H), 2.11 (s, 4H), 0.94 (d, J=6.5 Hz, 3H), 0.76 (d, J=6.8 Hz, 3H).

Compound 606. (S)-2-((1-(2-(3,3-difluorocyclobutyl)acetyl)azetidin-3-yl)amino)-7-isopropyl-4,8-dimethyl-7,8-dihydropteridin-6(5H)-one $^1$H NMR (400 MHz, DMSO-d6) δ 9.92 (s, 1H), 6.99 (d, J=6.1 Hz, 1H), 4.54-4.38 (m, 1H), 4.33 (td, J=7.9, 3.3 Hz, 1H), 4.04 (t, J=7.6 Hz, 1H), 3.97-3.81 (m, 2H), 3.81-3.66 (m, 1H), 3.01 (s, 3H), 2.77-2.58 (m, 2H), 2.46-2.16 (m, 5H), 2.16-2.03 (m, 4H), 0.93 (d, J=6.9 Hz, 3H), 0.75 (d, J=6.9 Hz, 3H).

Compound 607. (S)-7-isopropyl-4,8-dimethyl-2-((1-(6-(trifluoromethoxy)nicotinoyl)azetidin-3-yl)amino)-7,8-dihydropteridin-6(5H)-one $^1$H NMR (400 MHz, DMSO-d6) δ 9.92 (s, 1H), 8.61 (d, J=1.8 Hz, 1H), 8.23 (dd, J=8.5, 2.3 Hz, 1H), 7.36 (d, J=8.6 Hz, 1H), 7.04 (s, 1H), 4.58 (dd, J=19.2, 11.1 Hz, 2H), 4.31 (t, J=7.2 Hz, 1H), 4.25-4.14 (m, 1H), 4.01 (dd, J=10.0, 5.1 Hz, 1H), 3.87 (d, J=4.3 Hz, 1H), 3.01 (s, 3H), 2.11 (d, J=12.7 Hz, 4H), 0.93 (d, J=6.8 Hz, 3H), 0.75 (d, J=6.8 Hz, 3H).

Compound 609. (S)-7-isopropyl-4,8-dimethyl-2-((1-(1-methyl-3-(trifluoromethyl)-1H-pyrazole-4-carbonyl)azetidin-3-yl)amino)-7,8-dihydropteridin-6(5H)-one $^1$H NMR (400 MHz, DMSO-d6) δ 9.92 (s, 1H), 8.31 (s, 1H), 7.07 (s, 1H), 4.49 (dd, J=16.4, 8.5 Hz, 2H), 4.20 (s, 1H), 4.08 (d, J=13.4 Hz, 1H), 3.99-3.82 (m, 4H), 3.01 (s, 3H), 2.12 (d, J=11.6 Hz, 4H), 0.94 (d, J=6.9 Hz, 3H), 0.75 (d, J=6.9 Hz, 3H).

Compound 610. (S)-7-isopropyl-4,8-dimethyl-2-((1-(2-methyloxazole-4-carbonyl)azetidin-3-yl)amino)-7,8-dihydropteridin-6(5H)-one $^1$H NMR (400 MHz, DMSO-d6) δ 9.92 (s, 1H), 8.46 (s, 1H), 7.06 (d, J=5.4 Hz, 1H), 4.69 (t, J=7.3 Hz, 1H), 4.63-4.44 (m, 1H), 4.37-4.13 (m, 2H), 3.89 (dd, J=14.6, 5.2 Hz, 2H), 3.01 (s, 3H), 2.43 (s, 3H), 2.12 (d, J=11.1 Hz, 4H), 0.94 (d, J=6.8 Hz, 3H), 0.76 (d, J=6.8 Hz, 3H).

Compound 611. (7S)-7-isopropyl-4,8-dimethyl-2-((1-(tetrahydro-2H-pyran-2-carbonyl)azetidin-3-yl)amino)-7,8-dihydropteridin-6(5H)-one $^1$H NMR (400 MHz, DMSO-d6) δ 9.91 (s, 1H), 7.01 (dd, J=10.8, 5.2 Hz, 1H), 4.55-4.33 (m, 2H), 4.16-3.96 (m, 2H), 3.87 (d, J=4.2 Hz, 2H), 3.79-3.66 (m, 1H), 3.01 (s, 3H), 2.10 (s, 4H), 1.76 (s, 1H), 1.64 (d, J=6.6 Hz, 1H), 1.47 (d, J=8.9 Hz, 3H), 0.93 (d, J=6.9 Hz, 3H), 0.75 (d, J=6.8 Hz, 3H).

Compound 612. (S)-7-isopropyl-4,8-dimethyl-2-((1-(2-(2-(trifluoromethyl)phenoxy)acetyl)azetidin-3-yl)amino)-7,8-dihydropteridin-6(5H)-one $^1$H NMR (400 MHz, DMSO-d6) δ 9.92 (s, 1H), 7.61 (t, J=8.2 Hz, 2H), 7.18-6.96 (m, 3H), 4.77 (s, 2H), 4.58-4.38 (m, 2H), 4.15 (t, J=8.4 Hz, 1H), 4.02 (d, J=3.0 Hz, 1H), 3.85 (dd, J=13.8, 4.7 Hz, 2H), 3.00 (s, 3H), 2.11 (d, J=11.9 Hz, 4H), 0.93 (d, J=6.6 Hz, 3H), 0.75 (d, J=6.9 Hz, 3H).

Compound 613. (S)-7-isopropyl-4,8-dimethyl-2-((1-(2-(trifluoromethyl)thiazole-4-carbonyl)azetidin-3-yl)amino)-7,8-dihydropteridin-6(5H)-one $^1$H NMR (400 MHz, DMSO-d6) δ 9.92 (s, 1H), 8.69 (s, 1H), 7.05 (d, J=5.9 Hz, 1H), 4.82-4.66 (m, 1H), 4.54 (d, J=7.0 Hz, 1H), 4.44-4.25 (m, 2H), 3.97 (dd, J=14.7, 9.6 Hz, 1H), 3.86 (d, J=4.5 Hz, 1H), 3.00 (d, J=4.3 Hz, 3H), 2.22-1.97 (m, 4H), 0.93 (d, J=6.3 Hz, 3H), 0.81-0.68 (m, 3H).

Compound 614. (S)-2-((1-(1-(difluoromethyl)-1H-pyrazole-3-carbonyl)azetidin-3-yl)amino)-7-isopropyl-4,8-dimethyl-7,8-dihydropteridin-6(5H)-one $^1$H NMR (400 MHz, DMSO-d6) δ 9.92 (s, 1H), 8.33 (d, J=2.4 Hz, 1H), 7.87 (t, J=58.9 Hz, 2H), 7.07 (d, J=5.5 Hz, 1H), 6.85 (d, J=2.6 Hz, 1H), 4.70 (t, J=7.7 Hz, 1H), 4.64-4.46 (m, 1H), 4.43-4.19 (m, 2H), 4.02-3.81 (m, 2H), 3.01 (s, 3H), 2.22-2.00 (m, 4H), 0.94 (dd, J=6.8, 2.1 Hz, 3H), 0.76 (d, J=6.1 Hz, 3H).

Compound 615. (S)-7-isopropyl-4,8-dimethyl-2-((1-(6-(2,2,2-trifluoroethoxy)nicotinoyl)azetidin-3-yl)amino)-7,8-dihydropteridin-6(5H)-one $^1$H NMR (400 MHz, DMSO-d6) δ 9.92 (s, 1H), 8.48 (d, J=1.7 Hz, 1H), 8.03 (dd, J=8.6, 2.3 Hz, 2H), 7.11-6.95 (m, 3H), 5.05 (dd, J=18.1, 9.0 Hz, 2H), 4.58 (d, J=9.0 Hz, 3H), 4.28 (s, 1H), 4.19 (s, 1H), 4.04-3.94 (m, 2H), 3.87 (d, J=4.3 Hz, 1H), 3.00 (d, J=3.9 Hz, 4H), 2.11 (d, J=12.9 Hz, 4H), 0.93 (d, J=6.9 Hz, 3H), 0.75 (d, J=6.8 Hz, 3H).

Compound 616. (S)-2-((1-(2-(2,4-difluorophenyl)acetyl)azetidin-3-yl)amino)-7-isopropyl-4,8-dimethyl-7,8-dihydropteridin-6(5H)-one $^1$H NMR (400 MHz, DMSO-d6) δ 9.92 (s, 1H), 7.33 (dd, J=15.5, 8.5 Hz, 1H), 7.19 (td, J=10.1, 2.5 Hz, 1H), 7.03 (t, J=7.6 Hz, 2H), 4.59-4.33 (m, 2H), 4.16-3.97 (m, 2H), 3.93-3.70 (m, 2H), 3.45 (s, 2H), 3.02 (s, 3H), 2.12 (d, J=12.1 Hz, 4H), 0.94 (d, J=6.9 Hz, 3H), 0.76 (d, J=6.9 Hz, 3H).

Compound 617. (S)-2-((1-(1,2,5-oxadiazole-3-carbonyl)azetidin-3-yl)amino)-7-isopropyl-4,8-dimethyl-7,8-dihydropteridin-6(5H)-one $^1$H NMR (400 MHz, DMSO-d6) δ 9.93 (s, 1H), 7.05 (d, J=5.5 Hz, 1H), 4.63-4.44 (m, 2H), 4.22 (dt, J=12.8, 8.3 Hz, 2H), 3.89 (dd, J=10.2, 4.8 Hz, 2H), 3.00 (d, J=4.2 Hz, 3H), 2.12 (d, J=13.0 Hz, 4H), 0.93 (d, J=6.9 Hz, 3H), 0.75 (d, J=6.9 Hz, 3H).

Compound 618. (S)-2-((1-(2-(4-fluorophenyl)acetyl)azetidin-3-yl)amino)-7-isopropyl-4,8-dimethyl-7,8-dihydropteridin-6(5H)-one $^1$H NMR (400 MHz, DMSO-d6) δ 9.92 (s, 1H), 7.26 (dd, J=8.3, 5.8 Hz, 2H), 7.11 (t, J=8.8 Hz, 2H), 7.02 (d, J=5.8 Hz, 1H), 4.44 (ddd, J=15.3, 12.1, 6.6 Hz, 2H), 4.14-3.93 (m, 2H), 3.87 (d, J=4.4 Hz, 1H), 3.77 (td, J=9.4, 5.3 Hz, 1H), 3.41 (s, 2H), 3.00 (d, J=2.5 Hz, 3H), 2.12 (d, J=15.1 Hz, 4H), 0.94 (d, J=6.9 Hz, 3H), 0.75 (d, J=6.9 Hz, 3H).

Compound 619. (S)-7-isopropyl-2-((1-(5-isopropylisoxazole-3-carbonyl)azetidin-3-yl)amino)-4,8-dimethyl-7,8-dihydropteridin-6(5H)-one $^1$H NMR (400 MHz, DMSO-d6) δ 9.93 (s, 1H), 7.07 (d, J=6.0 Hz, 1H), 6.53 (s, 1H), 4.72-4.49 (m, 2H), 4.37-4.22 (m, 2H), 4.04-3.83 (m, 2H), 3.14 (td, J=14.0, 7.1 Hz, 1H), 3.00 (d, J=5.0 Hz, 3H), 2.11 (s, 4H), 1.26 (d, J=6.9 Hz, 6H), 0.94 (dd, J=6.8, 2.0 Hz, 3H), 0.76 (d, J=6.8 Hz, 3H).

Compound 620. (S)-7-isopropyl-4,8-dimethyl-2-((1-(3-methylisoxazole-5-carbonyl)azetidin-3-yl)amino)-7,8-dihydropteridin-6(5H)-one $^1$H NMR (400 MHz, DMSO-d6) δ 9.93 (s, 1H), 7.08 (d, J=6.0 Hz, 1H), 6.89 (s, 1H), 4.69 (dd, J=11.1, 5.3 Hz, 1H), 4.64-4.52 (m, 1H), 4.31 (dd, J=16.7, 9.1 Hz, 2H), 3.96 (dd, J=10.1, 5.1 Hz, 1H), 3.87 (d, J=4.4 Hz, 1H), 3.01 (s, 3H), 2.29 (s, 3H), 2.11 (s, 4H), 0.94 (d, J=5.8 Hz, 3H), 0.76 (d, J=6.6 Hz, 3H).

Compound 621. (S)-7-isopropyl-4,8-dimethyl-2-((1-(5-(trifluoromethyl)furan-2-carbonyl)azetidin-3-yl)amino)-7,8-dihydropteridin-6(5H)-one $^1$H NMR (400 MHz, DMSO-d6) δ 10.04 (s, 1H), 7.41 (d, J=2.8 Hz, 1H), 7.21 (d, J=3.2 Hz, 2H), 4.71 (d, J=5.0 Hz, 1H), 4.61 (s, 1H), 4.45-4.24 (m, 2H), 4.08-3.85 (m, 2H), 3.03 (s, 3H), 2.12 (d, J=11.6 Hz, 4H), 0.94 (d, J=6.7 Hz, 3H), 0.76 (d, J=6.6 Hz, 3H).

Compound 622. (S)-7-isopropyl-4,8-dimethyl-2-((1-(4-(trifluoromethyl)benzoyl)azetidin-3-yl)amino)-7,8-dihydropteridin-6(5H)-one $^1$H NMR (400 MHz, DMSO-d6) δ 10.05 (s, 1H), 7.83 (s, 3H), 7.27 (s, 1H), 4.65-4.46 (m, 2H), 4.33 (s, 1H), 4.18 (s, 1H), 4.09-3.99 (m, 1H), 3.92 (d, J=3.4 Hz, 1H), 3.03 (s, 3H), 2.13 (s, 4H), 0.94 (d, J=6.8 Hz, 3H), 0.75 (d, J=6.9 Hz, 3H).

Compound 623. (7S)-2-((1-(2-(bicyclo[2.2.1]heptan-2-yl)acetyl)azetidin-3-yl)amino)-7-isopropyl-4,8-dimethyl-7,8-dihydropteridin-6(5H)-one $^1$H NMR (400 MHz, DMSO-d6) δ 10.00 (s, 1H), 7.14 (s, 1H), 4.46 (d, J=5.7 Hz, 1H), 4.32 (td, J=7.9, 3.6 Hz, 1H), 4.05 (t, J=8.7 Hz, 1H), 4.01-3.86 (m, 2H), 3.82-3.69 (m, 1H), 3.03 (s, 3H), 2.13 (d, J=10.8 Hz, 5H), 2.07-1.69 (m, 5H), 1.52-1.24 (m, 4H), 1.21-0.87 (m, 7H), 0.75 (d, J=6.9 Hz, 3H).

Compound 626. (S)-2-((1-(2-(3,4-difluorophenyl)acetyl)azetidin-3-yl)amino)-7-isopropyl-4,8-dimethyl-7,8-dihydropteridin-6(5H)-one $^1$H NMR (400 MHz, DMSO-d6) δ 9.92 (s, 1H), 7.32 (ddd, J=16.5, 15.8, 10.1 Hz, 2H), 7.13-6.98 (m, 2H), 4.57-4.37 (m, 2H), 4.15-3.94 (m, 2H), 3.87 (d, J=4.4 Hz, 1H), 3.78 (td, J=9.5, 5.1 Hz, 1H), 3.43 (s, 2H), 3.00 (t, J=2.6 Hz, 3H), 2.24-1.96 (m, 4H), 0.94 (d, J=6.9 Hz, 3H), 0.76 (d, J=6.9 Hz, 3H).

Compound 627. (S)-7-isopropyl-4,8-dimethyl-2-((1-((R)-2-phenylpropanoyl)azetidin-3-yl)amino)-7,8-dihydropteridin-6(5H)-one $^1$H NMR (400 MHz, DMSO-d6) δ 9.90 (d, J=4.5 Hz, 1H), 7.38-7.16 (m, 4H), 6.97 (dd, J=19.8, 5.8 Hz, 1H), 4.54-4.37 (m, 1H), 4.35 (dd, J=13.0, 6.6 Hz, 1H), 4.07 (t, J=6.7 Hz, 1H), 4.03-3.91 (m, 1H), 3.90-3.60 (m, 3H), 2.97 (d, J=18.1 Hz, 3H), 2.08 (d, J=6.7 Hz, 4H), 1.26 (d, J=6.9 Hz, 3H), 0.93 (dd, J=6.7, 4.2 Hz, 3H), 0.74 (t, J=7.1 Hz, 3H).

Compound 628. (S)-2-((1-(2-(2,5-dimethylthiazol-4-yl)acetyl)azetidin-3-yl)amino)-7-isopropyl-4,8-dimethyl-7,8-dihydropteridin-6(5H)-one $^1$H NMR (400 MHz, DMSO-d6) δ 9.93 (s, 1H), 7.04 (d, J=3.9 Hz, 1H), 4.42 (ddd, J=13.0, 9.7, 5.6 Hz, 2H), 4.12-3.92 (m, 2H), 3.88 (d, J=4.3 Hz, 1H), 3.76 (dd, J=15.6, 6.4 Hz, 1H), 3.42 (s, 2H), 3.02 (s, 3H), 2.29 (s, 3H), 2.12 (d, J=12.8 Hz, 4H), 0.94 (d, J=6.9 Hz, 3H), 0.76 (d, J=6.9 Hz, 3H).

Compound 629. (S)-2-((1-(2-(3,5-difluorophenyl)acetyl)azetidin-3-yl)amino)-7-isopropyl-4,8-dimethyl-7,8-dihydropteridin-6(5H)-one $^1$H NMR (400 MHz, DMSO-d6) δ 9.92 (s, 1H), 7.23-6.82 (m, 3H), 4.57-4.35 (m, 2H), 4.18-3.98 (m, 2H), 3.80 (ddd, J=18.1, 14.3, 4.8 Hz, 2H), 3.00 (d, J=5.8 Hz, 3H), 2.24-1.98 (m, 4H), 0.93 (d, J=6.9 Hz, 3H), 0.76 (d, J=6.9 Hz, 3H).

Compound 630. (S)-2-((1-(2-chlorothiazole-4-carbonyl)azetidin-3-yl)amino)-7-isopropyl-4,8-dimethyl-7,8-dihydropteridin-6(5H)-one $^1$H NMR (400 MHz, DMSO-d6) δ 9.96 (s, 1H), 8.28 (s, 1H), 7.11 (s, 1H), 4.72 (t, J=8.6 Hz, 1H), 4.63-4.49 (m, 1H), 4.44-4.20 (m, 2H), 4.02-3.83 (m, 2H), 3.02 (s, 3H), 2.13 (d, J=9.7 Hz, 4H), 0.94 (d, J=6.4 Hz, 3H), 0.76 (d, J=6.8 Hz, 3H).

Compound 631. (S)-7-isopropyl-4,8-dimethyl-2-((1-(pyrazine-2-carbonyl)azetidin-3-yl)amino)-7,8-dihydropteridin-6(5H)-one $^1$H NMR (400 MHz, DMSO-d6) δ 9.92 (s, 1H), 9.11 (s, 1H), 8.79 (d, J=1.1 Hz, 1H), 8.70 (d, J=1.4 Hz, 1H), 7.08 (d, J=5.6 Hz, 1H), 4.79 (t, J=8.7 Hz, 1H), 4.64-4.48 (m, 1H), 4.48-4.24 (m, 2H), 4.08-3.95 (m, 1H), 3.87 (d, J=4.4 Hz, 1H), 3.01 (s, 3H), 2.11 (s, 4H), 0.93 (dd, J=6.8, 2.4 Hz, 3H), 0.76 (d, J=5.8 Hz, 3H).

Compound 632. (S)-2-((1-(2-(2,3-difluorophenyl)acetyl)azetidin-3-yl)amino)-7-isopropyl-4,8-dimethyl-7,8-dihydropteridin-6(5H)-one $^1$H NMR (400 MHz, DMSO-d6) δ 9.93 (s, 1H), 7.31 (dd, J=16.2, 8.2 Hz, 1H), 7.22-6.96 (m, 2H), 4.45 (dd, J=11.0, 7.4 Hz, 2H), 4.17-3.98 (m, 2H), 3.89-3.74 (m, 2H), 3.54 (s, 2H), 3.02 (s, 3H), 2.12 (d, J=12.0 Hz, 4H), 0.94 (d, J=6.9 Hz, 3H), 0.76 (d, J=6.9 Hz, 3H).

Compound 633. (S)-2-((1-(2-chlorothiazole-5-carbonyl)azetidin-3-yl)amino)-7-isopropyl-4,8-dimethyl-7,8-dihydropteridin-6(5H)-one $^1$H NMR (400 MHz, DMSO-d6) δ 9.93 (s, 1H), 8.04 (s, 1H), 7.08 (s, 1H), 4.71 (d, J=6.7 Hz, 1H), 4.61 (s, 1H), 4.30 (d, J=9.0 Hz, 2H), 4.01 (s, 1H), 3.87 (d, J=4.4 Hz, 1H), 3.01 (s, 3H), 2.12 (d, J=10.2 Hz, 4H), 0.93 (d, J=6.7 Hz, 3H), 0.76 (d, J=6.8 Hz, 3H).

Compound 634. (S)-7-isopropyl-2-((1-((R)-2-methoxy-2-phenylacetyl)azetidin-3-yl)amino)-4,8-dimethyl-7,8-dihydropteridin-6(5H)-one $^1$H NMR (400 MHz, DMSO-d6) δ 9.91 (s, 1H), 7.45-7.23 (m, 4H), 7.02 (dd, J=8.9, 6.0 Hz, 1H), 4.79 (d, J=3.4 Hz, 1H), 4.59-4.33 (m, 2H), 4.21-3.99 (m, 2H), 3.99-3.73 (m, 2H), 3.28 (s, 3H), 2.98 (d, J=10.0 Hz, 3H), 2.09 (d, J=2.8 Hz, 4H), 0.93 (d, J=6.8 Hz, 3H), 0.75 (dd, J=6.8, 2.4 Hz, 3H).

Compound 635. (S)-7-isopropyl-4,8-dimethyl-2-((1-(3-(trifluoromethyl)benzoyl)azetidin-3-yl)amino)-7,8-dihydropteridin-6(5H)-one $^1$H NMR (400 MHz, DMSO-d6) δ 9.92 (s, 1H), 7.90 (t, J=8.2 Hz, 2H), 7.70 (t, J=7.8 Hz, 1H), 7.04 (d, J=4.0 Hz, 1H), 4.54 (s, 2H), 4.31 (s, 1H), 4.17 (s, 1H), 3.99 (s, 1H), 3.87 (d, J=4.3 Hz, 1H), 3.00 (d, J=3.2 Hz, 3H), 2.11 (d, J=11.8 Hz, 4H), 0.93 (d, J=6.8 Hz, 3H), 0.75 (d, J=6.9 Hz, 3H).

Compound 636. (S)-7-isopropyl-4,8-dimethyl-2-((1-((R)-tetrahydrofuran-2-carbonyl)azetidin-3-yl)amino)-7,8-dihydropteridin-6(5H)-one $^1$H NMR (400 MHz, DMSO-d6) δ 9.91 (s, 1H), 7.00 (d, J=5.1 Hz, 1H), 4.44 (dd, J=17.0, 8.1 Hz, 2H), 4.31 (dd, J=13.0, 5.7 Hz, 1H), 4.07 (dd, J=19.7, 12.9 Hz, 2H), 3.87 (d, J=4.4 Hz, 1H), 3.82-3.61 (m, 3H), 3.01 (s, 3H), 2.22-1.68 (m, 9H), 0.93 (d, J=6.9 Hz, 3H), 0.75 (d, J=6.9 Hz, 3H).

Compound 637. (7S)-7-isopropyl-4,8-dimethyl-2-((1-(5-methyltetrahydrofuran-2-carbonyl)azetidin-3-yl)amino)-7,8-dihydropteridin-6(5H)-one $^1$H NMR (400 MHz, DMSO-d6) δ 9.97 (s, 1H), 7.11 (s, 1H), 4.47 (s, 2H), 4.26 (dd, J=13.1, 6.2 Hz, 1H), 4.09 (s, 2H), 3.99-3.85 (m, 2H), 3.77 (dd, J=9.7, 5.2 Hz, 1H), 3.03 (s, 3H), 2.23-1.81 (m, 8H), 1.39 (ddd, J=20.4, 15.1, 8.5 Hz, 1H), 1.25-1.07 (m, 3H), 0.94 (d, J=6.9 Hz, 3H), 0.76 (d, J=6.9 Hz, 3H).

Compound 638. (7S)-7-isopropyl-4,8-dimethyl-2-((1-(2-methyltetrahydrofuran-2-carbonyl)azetidin-3-yl)amino)-7,8-dihydropteridin-6(5H)-one $^1$H NMR (400 MHz, DMSO-d6) δ 9.96 (s, 1H), 7.08 (s, 1H), 4.64-4.40 (m, 2H), 4.12 (ddd, J=26.6, 13.0, 7.1 Hz, 2H), 3.95-3.58 (m, 4H), 3.03 (s, 3H), 2.29 (dd, J=11.8, 5.2 Hz, 1H), 2.13 (d, J=13.2 Hz, 4H), 1.91-1.67 (m, 2H), 1.67-1.53 (m, 1H), 1.29 (d, J=3.1 Hz, 3H), 0.94 (d, J=6.9 Hz, 3H), 0.76 (d, J=6.9 Hz, 3H).

Compound 639. (7S)-2-((1-(bicyclo[2.2.1]heptane-2-carbonyl)azetidin-3-yl)amino)-7-isopropyl-4,8-dimethyl-7,8-dihydropteridin-6(5H)-one $^1$H NMR (400 MHz, DMSO-d6) δ 9.95 (s, 1H), 7.05 (d, J=17.3 Hz, 1H), 4.57-4.27 (m, 2H), 4.17-3.64 (m, 5H), 3.02 (d, J=2.4 Hz, 3H), 2.66 (t, J=11.8 Hz, 1H), 2.44-2.34 (m, 1H), 2.14 (d, J=22.1 Hz, 5H), 1.69-1.08 (m, 9H), 0.94 (d, J=6.9 Hz, 3H), 0.76 (d, J=6.8 Hz, 3H).

Compound 640. (S)-7-isopropyl-4,8-dimethyl-2-((1-(pyrimidine-2-carbonyl)azetidin-3-yl)amino)-7,8-dihydropteridin-6(5H)-one $^1$H NMR (400 MHz, DMSO-d6) δ 9.92 (s, 1H), 8.92 (dd, J=4.9, 1.7 Hz, 1H), 7.62 (td, J=4.9, 1.3 Hz, 1H), 7.08 (d, J=4.9 Hz, 1H), 4.56 (dt, J=12.4, 6.6 Hz, 2H), 4.37-4.15 (m, 2H), 4.04-3.93 (m, 1H), 3.87 (d, J=4.3 Hz, 1H), 3.01 (s, 3H), 2.12 (d, J=11.6 Hz, 4H), 0.93 (d, J=6.2 Hz, 3H), 0.75 (d, J=6.9 Hz, 3H).

Compound 641. (S)-7-isopropyl-4,8-dimethyl-2-((1-((S)-2-phenylpropanoyl)azetidin-3-yl)amino)-7,8-dihydropteridin-6(5H)-one $^1$H NMR (400 MHz, DMSO-d6) δ 9.93 (d, J=7.8 Hz, 1H), 7.38-7.14 (m, 4H), 7.02 (d, J=19.7 Hz, 1H), 4.54-4.38 (m, 1H), 4.34 (dd, J=13.2, 6.5 Hz, 1H), 4.04 (dt, J=17.6, 9.2 Hz, 2H), 3.84 (ddd, J=15.3, 8.9, 5.1 Hz, 2H), 3.68 (dt, J=13.8, 6.1 Hz, 2H), 2.98 (d, J=12.2 Hz, 3H), 2.09 (d, J=7.0 Hz, 4H), 1.26 (dd, J=6.9, 2.3 Hz, 3H), 0.93 (d, J=6.8, 3.1 Hz, 3H), 0.75 (dd, J=6.7, 4.3 Hz, 3H).

Compound 642. (S)-7-isopropyl-4,8-dimethyl-2-((1-((S)-tetrahydrofuran-2-carbonyl)azetidin-3-yl)amino)-7,8-dihydropteridin-6(5H)-one $^1$H NMR (400 MHz, DMSO-d6) δ 9.95 (s, 1H), 7.06 (s, 1H), 4.45 (d, J=5.6 Hz, 2H), 4.30 (d, J=5.7 Hz, 1H), 4.20-4.03 (m, 2H), 3.88 (d, J=3.7 Hz, 1H), 3.83-3.63 (m, 2H), 3.01 (d, J=10.2 Hz, 3H), 2.22-1.68 (m, 8H), 0.94 (d, J=6.9 Hz, 3H), 0.76 (d, J=6.8 Hz, 3H).

Compound 699. (S)-7-isopropyl-4,8-dimethyl-2-((1-(3-(trifluoromethyl)bicyclo[1.1.1]pentane-1-carbonyl)azetidin-3-yl)amino)-7,8-dihydropteridin-6(5H)-one $^1$H NMR (400 MHz, Methanol-d4) δ 4.70-4.60 (m, 2H), 4.37-4.23 (m, 2H), 4.03-3.94 (m, 1H), 3.92 (d, J=4.3 Hz, 1H), 3.12 (s, 3H), 2.29 (s, 6H), 2.21 (dd, J=11.6, 6.8 Hz, 1H), 2.17 (s, 3H), 2.03 (s, 1H), 1.03 (d, J=6.9 Hz, 3H), 0.86 (d, J=6.9 Hz, 3H).

Compound 592. (7S)-2-((1-((4-fluorophenyl)sulfonyl)azetidin-3-yl)amino)-7-isopropyl-4,8-dimethyl-7,8-dihydropteridin-6(5H)-one

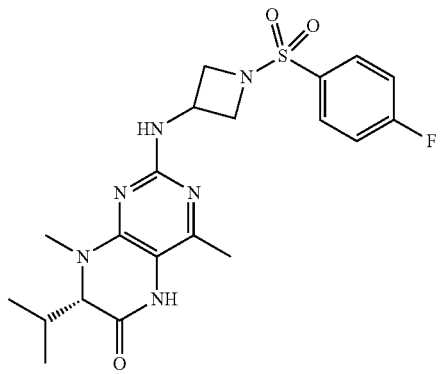

Compound 592

(7S)-7-(azetidin-3-ylamino)-2-isopropyl-1,5-dimethyl-1,4-dihydropyrido[3,4-b]pyrazin-3(2H)-one (prepared in step 2 of scheme for Table H) (200 mg, 0.495 mmol) was taken into dichloromethane (4 ml) and diisopropylethylamine (0.35 μL, 1.98 mmol). 4-Fluorobenzenesulfonyl chloride (106 mg, 0.545 mmol) was added ot the mixture and stirred at room temperature for 2 hours. The reaction was quenched with 5 ml of saturated sodium bicarbonate and stirred for 30 mins. The layers were separated with phase separator cartridge and the solvent removed under reduced pressure. The crude product was purified by column chromatography (SiO$_2$, 80 g) eluting with a gradient of 0-20% methanol in dichloromethane. The desired fractions were evaporated in vacuo to afford the title product (124 mg, 56% yield). 1H NMR (400 MHz, Methanol-d4) δ 7.98-7.88 (m, 2H), 7.39 (t, J=8.7 Hz, 2H), 4.51-4.37 (m, 1H), 4.09 (td, J=7.6, 4.3 Hz, 2H), 3.89 (d, J=4.4 Hz, 1H), 3.62 (dd, J=14.6, 6.4 Hz, 2H), 3.07 (s, 3H), 2.24-2.12 (m, 1H), 2.11 (s, 3H), 1.01 (d, J=7.0 Hz, 3H), 0.83 (d, J=6.9 Hz, 3H). ESI-MS m/z calc. 448.16928, found 449.29 (M+1)$^+$.

Compound 564. (7S)-3-((7-isopropyl-4,8-dimethyl-6-oxo-5,6,7,8-tetrahydropteridin-2-yl)amino)-N-(3,4,5-trifluorophenyl)azetidine-1-carboxamide

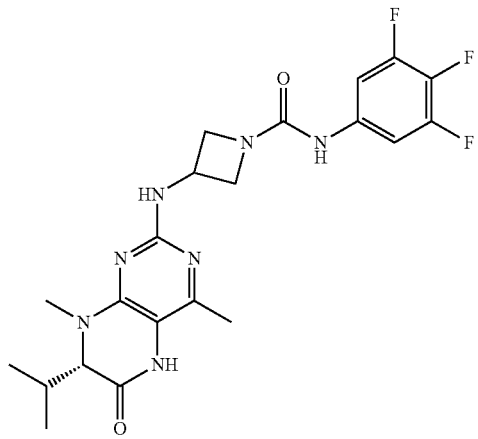

Compound 564

1,2,3-trifluoro-5-isocyanatobenzene (38 mg, 0.22 mmol) was added to a solution of (7S)-7-(azetidin-3-ylamino)-2-isopropyl-1,5-dimethyl-1,4-dihydropyrido[3,4-b]pyrazin-3(2H)-one (82 mg, 0.158 mmol) and diisopropylethylamine (0.14 μL, 0.79 mmol) in NMP (2 ml). The reaction was heated at 50° C. for 1 hour. The reaction was purified by preparative reverse phase HPLC (C18 column; 10-90% acetonitrile/water (HCl). The relevant fraction were evaporated to provide the title product as the hydrochloride salt (27 mg, 29% yield). 1H NMR (400 MHz, Methanol-d4) δ 7.21 (dddd, J=10.2, 9.1, 3.9, 2.3 Hz, 2H), 4.82-4.68 (m, 1H), 4.40-4.04 (m, 1H), 3.53-3.34 (m, 1H), 3.31-3.27 (m, 3H), 3.23 (d, J=5.9 Hz, 1H), 2.33-2.24 (m, 3H), 1.14-0.77 (m, 6H). ESI-MS m/z calc. 463.19437, found 464.24 (M+1)$^+$.

Example 2Z

Reaction Scheme for Examples in Table 24.

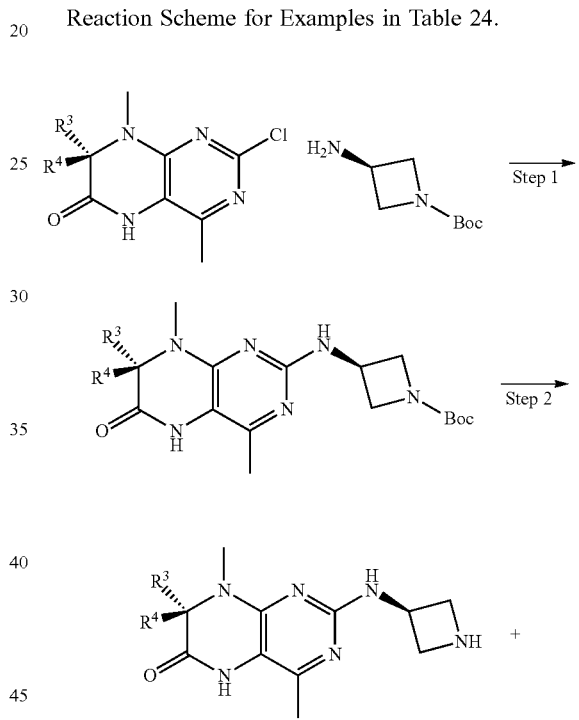

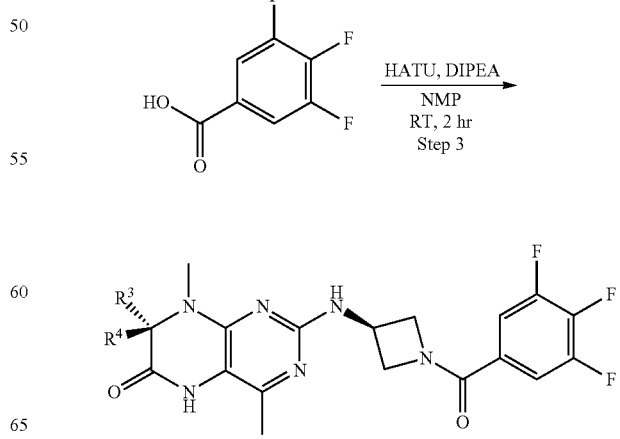

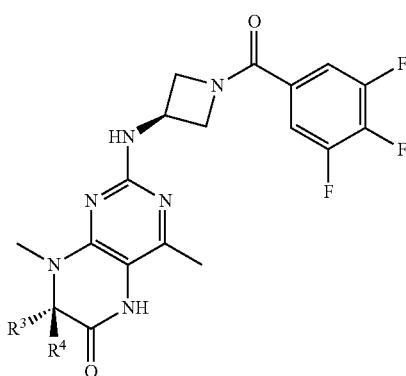

The following examples of Table 24 were prepared from various Intermediates A-# via the general procedure reported for Table 23.

TABLE 24

| Comp. No. | R³ | R⁴ | Int A | [α]$_D$ | M + 1 |
|---|---|---|---|---|---|
| 568 | —(R)—CH(OCH₃)CH₃ | H | A-59 | | 465.27 |
| 675 | H₃CO-cyclobutyl | H | A-66 | +96.7 c = 0.86 MeOH | 491.2 |
| 721 | —CH₂OCH₃ | —CH₃ | A-69 | +37.6 c = 0.76 MeOH | 465.28 |
| 722 | —CH₃ | —CH₂OCH₃ | A-70 | −29.3 c = 0.86 MeOH | 465.32 |
| 739 | —Et | H | A-8 | | 435.38 |
| 740 | —CH₃ | H | A-2 | | 435.38 |

Compound 568. (S)-7-((R)-1-methoxyethyl)-4,8-dimethyl-2-((1-(3,4,5-trifluorobenzoyl)azetidin-3-yl)amino)-7,8-dihydropteridin-6(5H)-one ¹H NMR (400 MHz, Methanol-d4) δ 7.52-7.41 (m, 2H), 4.76-4.60 (m, 2H), 4.54-4.41 (m, 1H), 4.39-4.29 (m, 1H), 4.19-4.06 (m, 1H), 3.97 (d, J=5.4 Hz, 1H), 3.64-3.52 (m, 1H), 3.26 (s, 3H), 3.17 (s, 3H), 2.18 (s, 3H), 1.18 (d, J=6.4 Hz, 3H).

Compound 675. 7-(1-methoxycyclobutyl)-4,8-dimethyl-2-((1-(3,4,5-trifluorobenzoyl)azetidin-3-yl)amino)-7,8-dihydropteridin-6(5H)-one ¹H NMR (400 MHz, DMSO-d6) δ 10.00 (s, 1H), 7.65-7.37 (m, 2H), 7.06 (s, 1H), 4.71-4.47 (m, 2H), 4.42-4.12 (m, 3H), 4.02 (dt, J=12.2, 6.1 Hz, 1H), 3.08 (d, J=14.3 Hz, 6H), 2.28-2.19 (m, 1H), 2.19-2.07 (m, 5H), 2.04-1.84 (m, 1H), 1.70 (ddd, J=15.0, 9.6, 5.2 Hz, 1H), 1.64-1.45 (m, 1H).

Compound 721. 7-(methoxymethyl)-4,7,8-trimethyl-2-((1-(3,4,5-trifluorobenzoyl)azetidin-3-yl)amino)-7,8-dihydropteridin-6(5H)-one ¹H NMR (400 MHz, DMSO-d6) δ 10.50 (s, 2H), 7.69-7.38 (m, 4H), 4.68 (s, 5H), 4.34 (d, J=23.6 Hz, 5H), 4.09 (d, J=9.9 Hz, 2H), 3.67 (s, 4H), 3.22 (s, 6H), 3.11 (s, 6H), 2.25 (s, 6H), 1.46 (s, 6H), 8.36-7.85 (m, 1H).

Compound 722. 7-(methoxymethyl)-4,7,8-trimethyl-2-((1-(3,4,5-trifluorobenzoyl)azetidin-3-yl)amino)-7,8-dihydropteridin-6(5H)-one ¹H NMR (400 MHz, DMSO-d6) δ 3.22 (s, 3H), 3.11 (s, 3H), 2.25 (s, 3H), 1.46 (s, 3H), 3.72-3.60 (m, 2H), 10.50 (s, 1H), 8.10 (s, 1H), 7.69-7.21 (m, 2H), 4.68 (s, 2H), 4.36 (s, 2H).

Compound 739. (S)-7-ethyl-4,8-dimethyl-2-((1-(3,4,5-trifluorobenzoyl)azetidin-3-yl)amino)-7,8-dihydropteridin-6(5H)-one ¹H NMR (400 MHz, Methanol-d4) δ 7.51-7.41 (m, 2H), 4.76-4.59 (m, 2H), 4.47 (s, 1H), 4.33 (s, 1H), 4.18-4.00 (m, 2H), 3.06 (s, 2H), 2.17 (s, 2H), 1.99-1.74 (m, 2H), 0.84 (t, J=7.5 Hz, 3H).

Compound 740. (S)-4,7,8-trimethyl-2-((1-(3,4,5-trifluorobenzoyl)azetidin-3-yl)amino)-7,8-dihydropteridin-6(5H)-one ¹H NMR (400 MHz, Methanol-d4) δ 7.53-7.42 (m, 2H), 4.75-4.59 (m, 2H), 4.47 (d, J=7.2 Hz, 1H), 4.32 (s, 1H), 4.18-4.00 (m, 2H), 3.04 (s, 3H), 2.18 (s, 3H), 1.33 (d, J=6.9 Hz, 3H).

Compound 509

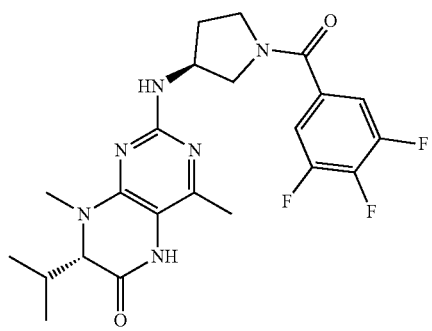 [SMILES: Cc1nc(N[C@H]2CCN(C(=O)c3cc(F)c(F)c(F)c3)C2)nc2c1NC(=O)[C@H](C(C)C)N2C]

(7S)-7-Isopropyl-4,8-dimethyl-2-(((S)-1-(3,4,5-trifluorobenzoyl)pyrrolidin-3-yl)amino)-7,8-dihydropteridin-6(5H)-one The compound was prepared via the same general 3 step procedure recorded for Table H examples to provide the title compound. ¹H NMR (400 MHz, Methanol-d4) δ 7.37 (dt, J=14.3, 7.3 Hz, 2H), 4.63-4.53 (m, 0.5H), 4.49-4.40 (m, 0.5H), 3.96 (dd, J=21.8, 4.3 Hz, 1.5H), 3.81 (ddd, J=28.9, 12.9, 6.6 Hz, 1H), 3.66 (dt, J=11.7, 4.8 Hz, 1H), 3.63-3.53 (m, 1H), 3.48 (dd, J=10.9, 4.7 Hz, 0.5H), 3.19 (s, 1.5H), 3.09 (s, 1.5H), 2.19 (d, J=19.8 Hz, 5H), 2.13-1.95 (m, 1H), 1.03 (dd, J=24.9, 7.0 Hz, 3H), 0.86 (dd, J=22.6, 6.9 Hz, 3H); ESI-MS m/z 463.29 (M+1)⁺.

Compound 541

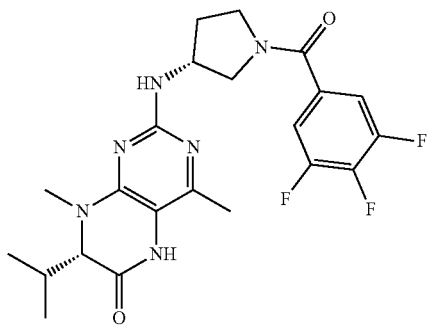 [SMILES: Cc1nc(N[C@@H]2CCN(C(=O)c3cc(F)c(F)c(F)c3)C2)nc2c1NC(=O)[C@H](C(C)C)N2C]

(7S)-7-Isopropyl-4,8-dimethyl-2-(((R)-1-(3,4,5-trifluorobenzoyl)pyrrolidin-3-yl)amino)-7,8-dihydropteridin-6(5H)-one This compound was prepared via the same general 3 step procedure recorded for Table H examples to provide the title compound. $^1$H NMR (400 MHz, Methanol-d4) δ 7.36 (dt, J=14.9, 7.4 Hz, 2H), 4.62-4.51 (m, 0.5H), 4.48-4.40 (m, 0.5H), 4.00-3.75 (m, 2.5H), 3.71-3.50 (m, 2H), 3.43 (dd, J=10.8, 5.0 Hz, 0.5H), 3.18 (s, 1.5H), 3.07 (s, 1.5H), 2.38-2.12 (m, 5H), 2.11-1.95 (m, 1H), 1.03 (dd, J=10.3, 7.0 Hz, 3H), 0.86 (dd, J=11.6, 6.9 Hz, 3H); ESI-MS m/z 463.24 (M+1)$^+$.

Example 2AA

General Scheme and Procedure for Examples in Table 25:
General Procedure for Examples in Table 25:

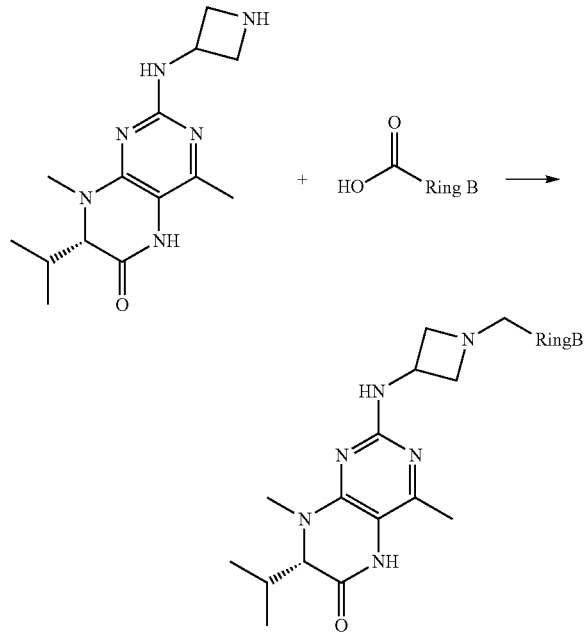

Sodium triacetoxyborohydride (184 mg, 0.87 mmol) was added to a solution of (7S)-2-(azetidin-3-ylamino)-7-isopropyl-4,8-dimethyl-7,8-dihydropteridin-6(5H)-one trifluoroacetic acid (300 mg, 0.579 mmol), 3,4,5-trifluorobenzaldehyde (102 mg, 0.64 mmol), and acetic acid (65 μL, 1.157 mmol) in dichloromethane (3 ml) and stirred at room temperature for 12 hours. The reaction was quenched with saturated sodium bicarbonate (3 ml). The organic layer was separated and the aqueous extracted with 10 ml of dichloromethane. The combined organic layers were dried and evaporated to afford the crude product. The product was purified by reverse phase chromatography (C18, 100 g column) eluting with 5-90% acetonitrile/water (0.1% TFA). The desired fractions were evaporated and neutralized to afford the desired product.

The following examples of Table 25 were prepared by the general procedure described above.

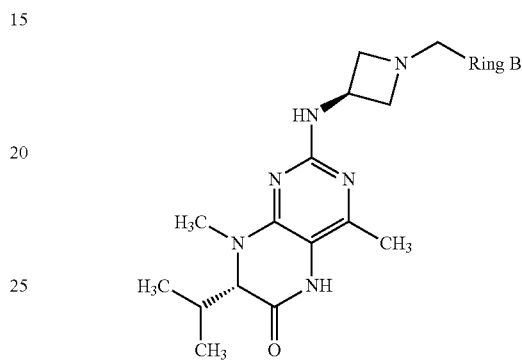

TABLE 25

| Comp. No. | Ring B | M + 1 |
|---|---|---|
| 591 | 3,4,5-trifluorophenyl | 435.29 |
| 603 | 2-OCH₃, 4-F phenyl | 429.3 |
| 649 | 6-CF₃ pyridin-3-yl | 450.2 |
| 650 | 4-CF₃ phenyl | 449.25 |

Compound 591. (S)-7-isopropyl-4,8-dimethyl-2-((1-(3,4,5-trifluorobenzyl)azetidin-3-yl)amino)-7,8-dihydropteridin-6(5H)-one $^1$H NMR (400 MHz, Methanol-d4) δ 7.15-7.04 (m, 2H), 4.58 (p, J=7.0 Hz, 1H), 3.91 (d, J=4.4 Hz, 1H), 3.76 (dd, J=11.6, 5.4 Hz, 2H), 3.67 (s, 2H), 3.14-3.03 (m, 5H), 2.28-2.16 (m, 1H), 2.15 (s, 3H), 1.02 (d, J=7.0 Hz, 3H), 0.85 (d, J=6.9 Hz, 3H).

Compound 603. (S)-2-((1-(4-fluoro-2-methoxybenzyl)azetidin-3-yl)amino)-7-isopropyl-4,8-dimethyl-7,8-dihydropteridin-6(5H)-one ¹H NMR (400 MHz, Methanol-d4) δ 7.21 (t, J=7.5 Hz, 1H), 6.81-6.71 (m, 1H), 6.63 (td, J=8.3, 2.3 Hz, 1H), 4.53 (p, J=7.0 Hz, 1H), 3.89 (d, J=4.3 Hz, 1H), 3.83 (s, 3H), 3.71 (d, J=2.8 Hz, 2H), 3.65 (s, 2H), 3.13-3.02 (m, 5H), 2.20 (dt, J=6.9, 5.6 Hz, 1H), 2.14 (s, 3H), 1.02 (d, J=6.9 Hz, 3H), 0.85 (d, J=6.9 Hz, 3H)

Compound 649. (S)-7-isopropyl-4,8-dimethyl-2-((1-((6-(trifluoromethyl)pyridin-3-yl)methyl)azetidin-3-yl)amino)-7,8-dihydropteridin-6(5H)-one ¹H NMR (400 MHz, Methanol-d4) δ 8.65 (s, 1H), 7.98 (d, J=8.0 Hz, 1H), 7.79 (d, J=8.1 Hz, 1H), 4.59 (p, J=7.0 Hz, 1H), 3.90 (d, J=4.4 Hz, 1H), 3.81 (s, 2H), 3.76 (ddd, J=9.8, 5.1, 2.5 Hz, 2H), 3.14-3.05 (m, 5H), 2.25-2.16 (m, 1H), 2.15 (s, 4H), 1.02 (d, J=7.0 Hz, 3H), 0.85 (d, J=6.9 Hz, 3H)

Compound 650. (S)-7-isopropyl-4,8-dimethyl-2-((1-(4-(trifluoromethyl)benzyl)azetidin-3-yl)amino)-7,8-dihydropteridin-6(5H)-one ¹H NMR (400 MHz, Methanol-d4) δ 7.62 (d, J=8.2 Hz, 2H), 7.50 (d, J=8.1 Hz, 2H), 4.59 (p, J=7.0 Hz, 1H), 3.90 (d, J=4.4 Hz, 1H), 3.82-3.69 (m, 4H), 3.17-2.98 (m, 5H), 2.29-2.09 (m, 5H), 1.02 (d, J=7.0 Hz, 3H), 0.85 (d, J=6.9 Hz, 3H).

Example 2BB

General Scheme and Procedure for Examples in Table 26: General Procedure for Examples in Table 26.

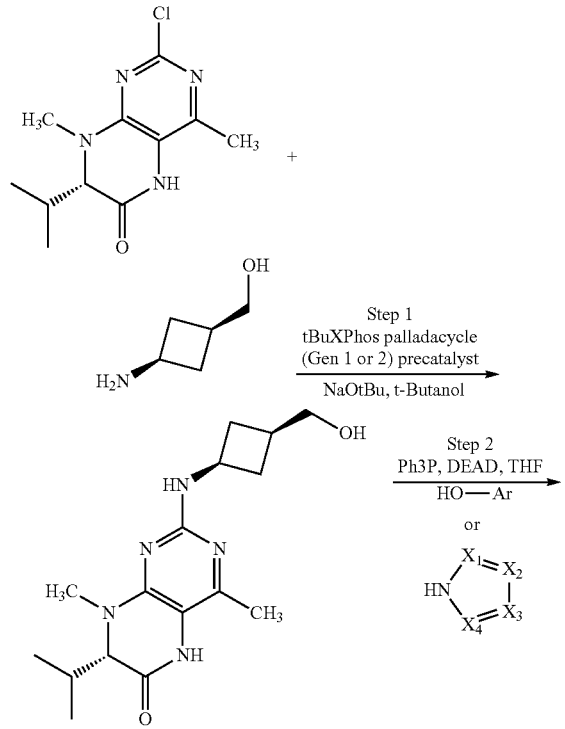

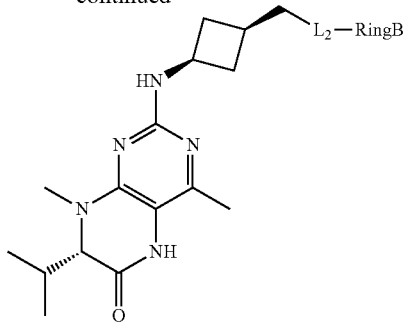

Step 1: (7S)-2-((cis-3-(hydroxymethyl)cyclobutyl) amino)-7-isopropyl-4,8-dimethyl-7,8-dihydropteridin-6(5H)-one A mixture of (S)-2-chloro-7-isopropyl-4,8-dimethyl-7,8-dihydropteridin-6(5H)-one (5 g, 19.5 mmol), cis-(3-aminocyclobutyl)methanol hydrochloride (2.95 g, 21.4 mmol), and sodium tert-butoxide (8.07 g, 84 mmol) were taken into t-butanol (80 ml) and dioxane (75 ml) and stirred for 20 mins until most of the solids were dissolved. The mixture was purged with nitrogen for 15 minutes. tBuXPhos palladacycle (Gen 1) (260 mg, 0.4 mmol) was added to the mixture then purged with nitrogen for 10 minutes. The reaction was stirred at 60° C. for 1 hour. The reaction mixture was evaporated in vacuo and the resulting residue was taken into 100 ml of water and extracted with dichloromethane (2×80 ml). The extracts were combined, washed with brine, dried over anhydrous sodium sulfate, filtered, and evaporated in vacuo to afford the crude product. The product was purified by column chromatography (120 g SiO₂ column) eluting with a gradient of dichloromethane to 20% methanol. The desired fractions were combined and evaporated to afford a light green solid, 3.5 g. The solid was dissolved in dichloromethane (30 ml), added MP-TMP resin (1.5 g) and stirred for 12 hours. This was filtered through Celite and the filtrate evaporated in vacuo. The resulting solid was washed with heptanes and filtered to afford 3.4 g (55% yield) of the product as a white solid. 1H NMR (300 MHz, CDCl₃) δ 5.55 (s, 1H), 4.32 (dd, J=15.7, 8.1 Hz, 1H), 3.97-3.85 (m, 1H), 3.63 (d, J=5.9 Hz, 2H), 3.15 (s, 3H), 2.62-2.44 (m, 2H), 2.31-2.15 (m, 4H), 1.81-1.62 (m, 2H), 1.08 (d, J=6.9 Hz, 3H), 0.93 (d, J=6.9 Hz, 3H). ESI-MS m/z 320.09 (M+1)⁺; $[\alpha]^D$=+258.98 (c=1.0, CHCl3) at 22.3° C.

Step 2: General Procedure

A mixture of (7S)-2-((cis-3-(hydroxymethyl)cyclobutyl) amino)-7-isopropyl-4,8-dimethyl-7,8-dihydropteridin-6 (5H)-one (1 equiv), triphenyl phosphine (2.1 equiv), and the heterocycle (hydroxy heterocycle, pyrazole, or imidazole derivative; 1.6 equiv) was taken into THF (25 vol equiv). Diethylazodicarboxylate (2.1 equiv) was added to the mixture dropwise at room temperature then heated to 50° C. for 2 hours. The crude products were purified by preparative reverse phase HPLC (C18 column) eluting with 10-95% acetonitrile/water (0.5 mMHCl) to provide the products described in Table 26.

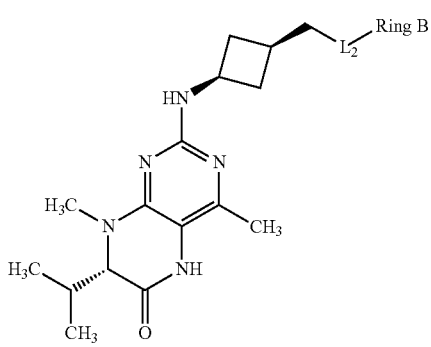
TABLE 26
| Comp. No. | L2-Ring B | [α]D | M + 1 |
|---|---|---|---|
| 551 | O—pyridine—CF3 (5-O, 2-CF3) | +37.8 c = 1.0 DMSO | 465.27 |
| 570 | O—pyridine—Cl | | 431.28 |
| 571 | O—pyridine—CH3 | | 411.25 |
| 572 | O—pyridine—CN | | 422.23 |
| 573 | O—pyridine—OCH3 | | 427.24 |
| 574 | O—pyridine—F | | 415.28 |
| 575 | O—pyrazole(N-CH3, CF3) | | 468.21 |
| 580 | O—benzodioxole | | 440.33 |
| 581 | pyrazole-cyclopropyl, CF3 | | 478.26 |
TABLE 26-continued
| Comp. No. | L2-Ring B | [α]D | M + 1 |
|---|---|---|---|
| 582 | pyrazole-CH3, CF3 | | 452.22 |
| 583 | pyrazole-Cl | | 404.23 |
| 584 | pyrazole-NH2, CF3 | | 453.3 |
| 585 | pyrazole-CF3, NH2 | | 453.3 |
| 598 | O—pyridine—OCF3 | | 481.23 |
| 679 | imidazole-CF3 | | 438.31 |
| 680 | imidazole-CF3 | | 438.31 |
| 690 | pyrazole-CF3 | | 438.56 |
| 693 | O—pyrazole-N-CH3 | | 400.23 |

TABLE 26-continued

| Comp. No. | L₂-Ring B | [α]_D | M + 1 |
|---|---|---|---|
| 694 | 3-fluoro-2-cyano-5-oxy-pyridine | | 440.24 |
| 685 | 4-chloro-3-cyano-1H-1,2,4-triazol-1-yl | | 430.15 |
| 696 | 2-acetyl-5-oxy-pyridine | | 439.26 |

Compound 551. (S)-7-isopropyl-4,8-dimethyl-2-((cis-3-(((6-(trifluoromethyl)pyridin-3-yl)oxy)methyl)cyclobutyl)amino)-7,8-dihydropteridin-6(5H)-one ¹H NMR (400 MHz, Methanol-d4) δ 8.40 (d, J=2.7 Hz, 1H), 7.78 (t, J=7.4 Hz, 1H), 7.69-7.63 (m, 1H), 4.53-4.33 (m, 1H), 4.17 (dd, J=4.2, 2.2 Hz, 3H), 3.35-3.30 (m, 1H), 3.29 (d, J=6.3 Hz, 3H), 2.71-2.56 (m, 3H), 2.34 (d, J=8.5 Hz, 3H), 2.14-1.98 (m, 2H), 1.11 (d, J=6.9 Hz, 3H), 0.89 (d, J=6.9 Hz, 3H)

Compound 570. (S)-2-((cis-3-(((6-chloropyridin-3-yl)oxy)methyl)cyclobutyl)amino)-7-isopropyl-4,8-dimethyl-7,8-dihydropteridin-6(5H)-one 1H NMR (400 MHz, Methanol-d₄) δ 8.09 (d, J=3.0 Hz, 1H), 7.50 (dd, J=8.8, 3.1 Hz, 1H), 7.39 (d, J=8.8 Hz, 1H), 4.50-4.32 (m, 1H), 4.08 (d, J=5.0 Hz, 2H), 3.28 (s, 3H), 2.71-2.53 (m, 3H), 2.36 (dd, J=7.0, 3.1 Hz, 0H), 2.32 (s, 3H), 2.08-1.94 (m, 2H), 1.11 (d, J=6.9 Hz, 3H), 0.89 (d, J=6.9 Hz, 3H).

Compound 571. (S)-7-isopropyl-4,8-dimethyl-2-((cis-3-(((6-methylpyridin-3-yl)oxy)methyl)cyclobutyl)amino)-7,8-dihydropteridin-6(5H)-one ¹H NMR (400 MHz, Methanol-d₄) δ 8.46 (d, J=2.8 Hz, 1H), 8.16 (dd, J=9.0, 2.8 Hz, 1H), 7.84 (d, J=9.0 Hz, 1H), 4.46 (p, J=8.1 Hz, 1H), 4.22 (d, J=4.7 Hz, 2H), 4.15 (d, J=3.8 Hz, 1H), 3.28 (s, 3H), 2.72 (s, 3H), 2.64 (tt, J=6.2, 1.4 Hz, 2H), 2.40-2.32 (m, 1H), 2.31 (s, 3H), 2.14-1.92 (m, 2H), 1.11 (d, J=7.0 Hz, 3H), 0.89 (d, J=6.9 Hz, 3H).

Compound 572. 5-((cis-3-(((S)-7-isopropyl-4,8-dimethyl-6-oxo-5,6,7,8-tetrahydropteridin-2-yl)amino)cyclobutyl)methoxy)picolinonitrile ¹H NMR (400 MHz, Methanol-d₄) δ 8.39 (dd, J=2.9, 0.6 Hz, 1H), 7.82 (dd, J=8.7, 0.6 Hz, 1H), 7.53 (dd, J=8.7, 2.9 Hz, 1H), 4.48-4.35 (m, 1H), 4.15 (t, J=4.7 Hz, 3H), 3.28 (s, 3H), 2.65-2.57 (m, 3H), 2.35 (dd, J=7.0, 3.9 Hz, 0H), 2.31 (s, 3H), 2.11-1.94 (m, 2H), 1.11 (d, J=7.0 Hz, 3H), 0.89 (d, J=6.9 Hz, 3H).

Compound 573. (S)-7-isopropyl-2-((cis-3-(((6-methoxypyridin-3-yl)oxy)methyl)cyclobutyl)amino)-4,8-dimethyl-7,8-dihydropteridin-6(5H)-one ¹H NMR (400 MHz, Methanol-d₄) δ 7.95 (dd, J=3.2, 0.6 Hz, 1H), 7.87 (dd, J=9.3, 3.1 Hz, 1H), 7.23 (dd, J=9.3, 0.6 Hz, 1H), 4.52-4.36 (m, 1H), 4.15 (d, J=3.8 Hz, 1H), 4.05 (s, 3H), 3.28 (s, 3H), 2.69-2.56 (m, 2H), 2.35 (dt, J=7.0, 3.5 Hz, 1H), 2.31 (s, 3H), 2.03 (dtd, J=10.3, 8.9, 7.2 Hz, 2H), 1.11 (d, J=7.0 Hz, 3H), 0.89 (d, J=6.9 Hz, 3H).

Compound 574. (S)-2-((cis-3-(((6-fluoropyridin-3-yl)oxy)methyl)cyclobutyl)amino)-7-isopropyl-4,8-dimethyl-7,8-dihydropteridin-6(5H)-one ¹H NMR (400 MHz, Methanol-d₄) δ 7.88-7.74 (m, 1H), 7.55 (ddd, J=9.0, 6.4, 3.2 Hz, 1H), 7.00 (ddd, J=8.9, 3.1, 0.5 Hz, 1H), 4.39 (d, J=7.6 Hz, 1H), 4.15 (d, J=3.8 Hz, 1H), 4.04 (d, J=5.3 Hz, 2H), 3.28 (s, 3H), 2.67-2.57 (m, 2H), 2.39-2.33 (m, 0H), 2.30 (s, 3H), 2.08-1.95 (m, 2H), 1.11 (d, J=7.0 Hz, 3H), 0.89 (d, J=6.9 Hz, 3H).

Compound 575. (S)-7-isopropyl-4,8-dimethyl-2-((cis-3-(((1-methyl-5-(trifluoromethyl)-1H-pyrazol-4-yl)oxy)methyl)cyclobutyl)amino)-7,8-dihydropteridin-6(5H)-one ¹H NMR (400 MHz, Methanol-d₄) δ 7.39 (d, J=0.9 Hz, 1H), 4.39-4.28 (m, 1H), 4.14 (d, J=3.8 Hz, 1H), 4.00 (d, J=5.5 Hz, 2H), 3.89 (q, J=0.9 Hz, 3H), 3.27 (s, 3H), 2.61-2.49 (m, 2H), 2.40-2.33 (m, 1H), 2.30 (s, 3H), 1.96 (dtd, J=10.7, 3.8, 1.7 Hz, 2H), 1.11 (d, J=7.0 Hz, 3H), 0.89 (d, J=6.9 Hz, 3H)

Compound 580. (S)-2-((cis-3-((benzo[d][1,3]dioxol-5-yloxy)methyl)cyclobutyl)amino)-7-isopropyl-4,8-dimethyl-7,8-dihydropteridin-6(5H)-one ¹H NMR (400 MHz, Chloroform-d) δ 8.62 (s, 1H), 6.67-6.54 (m, 1H), 6.46-6.37 (m, 1H), 6.24 (dd, J=8.5, 2.5 Hz, 1H), 5.83 (s, 2H), 4.77 (d, J=7.8 Hz, 1H), 4.36-4.22 (m, 1H), 3.78 (dd, J=6.2, 5.1 Hz, 3H), 3.03 (s, 3H), 2.59-2.42 (m, 2H), 2.44-2.29 (m, 1H), 2.22-2.13 (m, 1H), 2.12 (s, 3H), 1.72-1.59 (m, 2H), 0.98 (d, J=7.0 Hz, 3H), 0.84 (d, J=6.9 Hz, 3H).

Compound 581. (S)-2-((cis-3-((3-cyclopropyl-5-(trifluoromethyl)-1H-pyrazol-1-yl)methyl)cyclobutyl)amino)-7-isopropyl-4,8-dimethyl-7,8-dihydropteridin-6(5H)-one ¹H NMR (400 MHz, Chloroform-d) δ 6.30 (2s, 1H), 4.39-4.24 (m, 3H), 4.19 (dd, J=6.8, 4.4 Hz, 2H), 3.26 (s, 3H), 2.59-2.48 (m, 1H), 2.34 (dt, J=7.0, 3.5 Hz, 1H), 2.29 (s, 3H), 1.98-1.83 (m, 2H), 1.29 (q, J=7.0 Hz, 3H), 1.10 (d, J=6.9 Hz, 3H), 0.97-0.91 (m, 1H), 0.88 (d, J=6.9 Hz, 3H), 0.80-0.63 (m, 2H).

Compound 582. (S)-7-isopropyl-4,8-dimethyl-2-((cis-3-((3-methyl-5-(trifluoromethyl)-1H-pyrazol-1-yl)methyl)cyclobutyl)amino)-7,8-dihydropteridin-6(5H)-one ¹H NMR (400 MHz, Methanol-d₄) δ 6.57, 6.31 (2s, 1H), 4.34-4.28 (m, 1H), 4.21 (dd, J=10.1, 6.4 Hz, 2H), 4.13 (d, J=3.8 Hz, 1H), 3.25 (s, 3H), 2.59-2.48 (2s, 3H), 2.31-2.23 (m, 4H), 1.96-1.80 (m, 2H), 1.10 (d, J=7.0 Hz, 3H), 0.88 (d, J=7.0 Hz, 3H).

Compound 583. (S)-2-((cis-3-((3-chloro-1H-pyrazol-1-yl)methyl)cyclobutyl)amino)-7-isopropyl-4,8-dimethyl-7,8-dihydropteridin-6(5H)-one $^1$H NMR (400 MHz, Methanol-d$_4$) δ 7.66 (d, J=2.4 Hz, 1H), 6.27 (d, J=2.4 Hz, 1H), 4.31 (q, J=7.9 Hz, 1H), 4.24 (d, J=6.3 Hz, 1H), 4.18-4.10 (m, 2H), 3.27-3.17 (m, 3H), 2.59-2.47 (m, 2H), 2.38-2.32 (m, 1H), 2.29 (d, J=2.6 Hz, 3H), 1.93-1.79 (m, 1H), 1.10 (dd, J=7.0, 2.2 Hz, 3H), 0.92-0.80 (m, 3H).

Compound 584. (S)-2-((cis-3-((3-amino-5-(trifluoromethyl)-1H-pyrazol-1-yl)methyl)cyclobutyl)amino)-7-isopropyl-4,8-dimethyl-7,8-dihydropteridin-6(5H)-one $^1$H NMR (400 MHz, Methanol-d$_4$) δ 6.84 (s, 1H), 4.39 (d, J=8.0 Hz, 0H), 4.35 (s, 1H), 4.14 (d, J=3.7 Hz, 1H), 3.27 (d, J=3.8 Hz, 3H), 2.69-2.50 (m, 3H), 2.41-2.32 (m, 1H), 2.31 (s, 3H), 2.04-1.91 (m, 2H), 1.26 (t, J=7.1 Hz, 1H), 1.10 (d, J=6.9 Hz, 3H), 0.88 (dd, J=6.9, 2.0 Hz, 3H).

Compound 585. (S)-2-((cis-3-((5-amino-3-(trifluoromethyl)-1H-pyrazol-1-yl)methyl)cyclobutyl)amino)-7-isopropyl-4,8-dimethyl-7,8-dihydropteridin-6(5H)-one $^1$H NMR (400 MHz, Methanol-d$_4$) δ 4.30 (dt, J=15.7, 8.2 Hz, 1H), 4.18-4.10 (m, 1H), 4.04 (d, J=6.0 Hz, 1H), 3.26 (d, J=5.6 Hz, 3H), 2.64-2.43 (m, 1H), 2.34 (dq, J=10.2, 3.5 Hz, 0H), 2.28 (s, 2H), 1.95-1.78 (m, 2H), 1.10 (dd, J=7.1, 1.9 Hz, 3H), 0.88 (dd, J=7.1, 2.1 Hz, 3H).

Compound 598. (S)-7-isopropyl-4,8-dimethyl-2-((cis-3-(((6-(trifluoromethoxy)pyridin-3-yl)oxy)methyl)cyclobutyl)amino)-7,8-dihydropteridin-6(5H)-one $^1$H NMR (400 MHz, Methanol-d$_4$) δ 8.08-7.85 (m, 1H), 7.54 (dd, J=8.9, 3.1 Hz, 1H), 7.13 (d, J=8.9 Hz, 1H), 4.50-4.30 (m, 1H), 4.15 (d, J=3.9 Hz, 1H), 4.07 (d, J=5.3 Hz, 2H), 3.28 (s, 3H), 2.73-2.52 (m, 2H), 2.36 (td, J=7.0, 3.9 Hz, 1H), 2.30 (s, 3H), 2.02 (ddd, J=9.8, 5.8, 3.5 Hz, 2H), 1.11 (d, J=6.9 Hz, 3H), 0.89 (d, J=6.9 Hz, 3H).

Compound 679. (S)-7-isopropyl-4,8-dimethyl-2-((cis-3-((5-(trifluoromethyl)-1H-imidazol-1-yl)methyl)cyclobutyl)amino)-7,8-dihydropteridin-6(5H)-one $^1$H NMR (400 MHz, Methanol-d$_4$) δ 9.42 (s, 1H), 8.37 (s, 1H), 4.48 (d, J=6.0 Hz, 3H), 4.15 (d, J=3.5 Hz, 1H), 3.27 (s, 3H), 2.67 (d, J=13.6 Hz, 3H), 2.31 (s, 4H), 2.03 (dt, J=13.9, 8.1 Hz, 2H), 1.11 (d, J=6.8 Hz, 3H), 0.89 (d, J=6.7 Hz, 3H).

Compound 680. (S)-7-isopropyl-4,8-dimethyl-2-((cis-3-((4-(trifluoromethyl)-1H-imidazol-1-yl)methyl)cyclobutyl)amino)-7,8-dihydropteridin-6(5H)-one $^1$H NMR (400 MHz, Methanol-d$_4$) δ 9.31 (d, J=1.4 Hz, 1H), 8.42 (t, J=1.4 Hz, 1H), 4.44 (d, J=7.0 Hz, 1H), 4.16 (d, J=3.7 Hz, 1H), 3.28 (d, J=1.7 Hz, 3H), 2.65 (dddd, J=20.3, 18.3, 10.0, 4.2 Hz, 2H), 2.32 (d, J=1.7 Hz, 3H), 2.08-1.93 (m, 1H), 1.38-1.21 (m, 3H), 1.10 (d, J=6.9 Hz, 3H), 0.89 (dd, J=6.9, 1.6 Hz, 3H).

Compound 690. (S)-7-isopropyl-4,8-dimethyl-2-((cis-3-((3-(trifluoromethyl)-1H-pyrazol-1-yl)methyl)cyclobutyl)amino)-7,8-dihydropteridin-6(5H)-one $^1$H NMR (400 MHz, Methanol-d$_4$) δ 7.58 (dd, J=2.0, 0.8 Hz, 1H), 6.74 (d, J=2.0 Hz, 1H), 4.31 (d, J=6.7 Hz, 3H), 4.14 (d, J=3.8 Hz, 1H), 3.32 (s, 3H), 3.25 (s, 3H), 2.61-2.50 (m, 2H), 2.34 (dd, J=7.0, 3.8 Hz, 0H), 2.29 (s, 3H), 1.92 (dtd, J=11.4, 9.0, 6.3 Hz, 2H), 1.10 (d, J=6.9 Hz, 3H), 0.88 (d, J=6.9 Hz, 3H).

Compound 693. (S)-7-isopropyl-4,8-dimethyl-2-((cis-3-(((1-methyl-1H-pyrazol-5-yl)oxy)methyl)cyclobutyl)amino)-7,8-dihydropteridin-6(5H)-one $^1$H NMR (400 MHz, Methanol-d$_4$) δ 7.57 (t, J=2.4 Hz, 1H), 5.86 (dq, J=2.6, 1.5 Hz, 1H), 4.40 (t, J=7.7 Hz, 1H), 4.17-4.14 (m, 2H), 4.13 (s, 1H), 3.80 (d, J=1.1 Hz, 3H), 3.28 (s, 3H), 2.65-2.50 (m, 3H), 2.35 (ddd, J=14.6, 7.3, 4.2 Hz, 1H), 2.31 (s, 3H), 2.07-1.85 (m, 2H), 1.11 (d, J=7.0 Hz, 3H), 0.89 (d, J=6.9 Hz, 3H).

Compound 694. 3-fluoro-5-((cis-3-(((S)-7-isopropyl-4,8-dimethyl-6-oxo-5,6,7,8-tetrahydropteridin-2-yl)amino)cyclobutyl)methoxy)picolinonitrile $^1$H NMR (400 MHz, Methanol-d$_4$) δ 8.27 (dd, J=2.4, 1.0 Hz, 1H), 7.49 (dd, J=11.0, 2.4 Hz, 1H), 4.39 (d, J=9.7 Hz, 1H), 4.16 (dd, J=6.3, 4.3 Hz, 3H), 3.29 (s, 3H), 2.69-2.55 (m, 4H), 2.34 (td, J=7.0, 3.9 Hz, 1H), 2.29 (s, 3H), 2.02 (q, J=7.5, 6.2 Hz, 2H), 1.11 (d, J=7.0 Hz, 3H), 0.89 (d, J=6.9 Hz, 3H).

Compound 695. 5-chloro-2-((cis-3-(((S)-7-isopropyl-4,8-dimethyl-6-oxo-5,6,7,8-tetrahydropteridin-2-yl)amino)cyclobutyl)methyl)-2H-1,2,3-triazole-4-carbonitrile 1H NMR (400 MHz, Methanol-d4) δ 4.59 (d, J=6.9 Hz, 2H), 4.37 (q, J=8.2 Hz, 1H), 4.14 (d, J=3.8 Hz, 1H), 3.26 (s, 3H), 2.78-2.67 (m, 1H), 2.59 (dddd, J=11.5, 6.1, 4.8, 2.1 Hz, 2H), 2.39-2.33 (m, 0H), 2.30 (s, 3H), 1.95 (dtd, J=11.8, 9.2, 6.3 Hz, 2H), 1.10 (d, J=6.9 Hz, 3H), 0.88 (d, J=6.9 Hz, 3H).

Compound 696. (S)-2-((cis-3-(((6-acetylpyridin-3-yl)oxy)methyl)cyclobutyl)amino)-7-isopropyl-4,8-dimethyl-7,8-dihydropteridin-6(5H)-one $^1$H NMR (400 MHz, Methanol-d$_4$) δ 8.47 (d, J=2.8 Hz, 1H), 8.24 (dd, J=9.1, 2.8 Hz, 1H), 8.05 (d, J=9.1 Hz, 1H), 4.53-4.43 (m, 1H), 4.28 (d, J=4.6 Hz, 1H), 4.16 (dd, J=11.6, 4.3 Hz, 2H), 3.28 (s, 3H), 2.64 (q, J=5.5, 4.2 Hz, 4H), 2.35 (dd, J=7.0, 3.9 Hz, 0H), 2.31 (s, 3H), 2.06 (ddt, J=14.7, 8.2, 3.5 Hz, 2H), 1.67 (s, 2H), 1.11 (d, J=6.9 Hz, 3H), 0.89 (d, J=6.9 Hz, 3H).

Example 2CC

General Scheme and Procedure for Examples in Table 27:

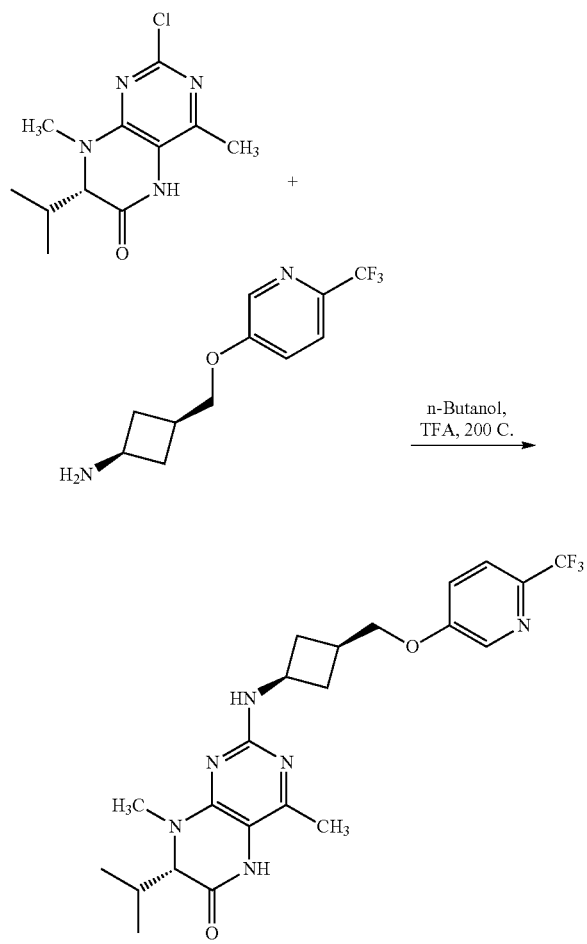

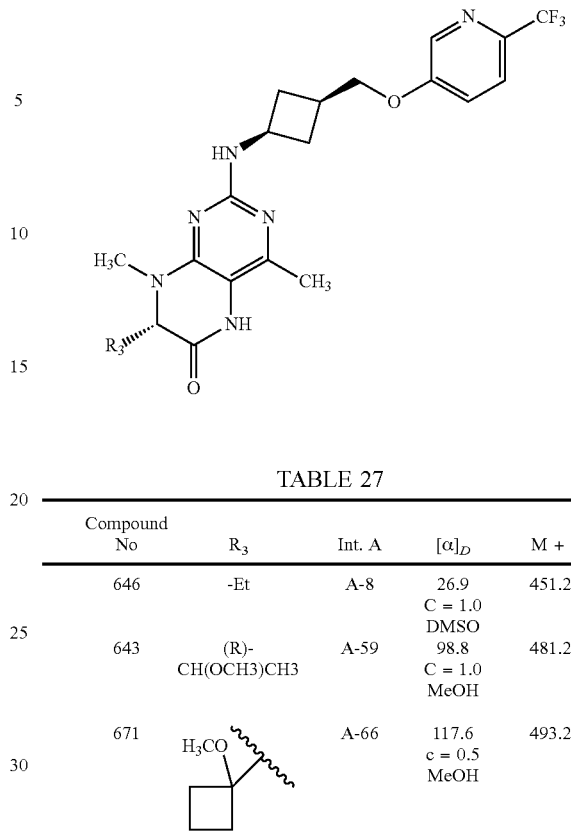

TABLE 27

| Compound No | R₃ | Int. A | [α]$_D$ | M + 1 |
|---|---|---|---|---|
| 646 | -Et | A-8 | 26.9<br>C = 1.0<br>DMSO | 451.22 |
| 643 | (R)-CH(OCH3)CH3 | A-59 | 98.8<br>C = 1.0<br>MeOH | 481.25 |
| 671 | 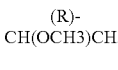 | A-66 | 117.6<br>c = 0.5<br>MeOH | 493.27 |
| 551 | (CH₃)₂CH— | B-213 | 39.7<br>c = 1.04<br>meOH | 465.47 |

General Procedure for Examples in Table 27:

Compound 646

A mixture of (7S)-2-chloro-7-ethyl-4,8-dimethyl-5,7-dihydropteridin-6-one (81 mg, 0.34 mmol), 3-[[6-(trifluoromethyl)-3-pyridyl]oxymethyl]cyclobutanamine hydrochloride (79 mg, 0.28 mmol) and TFA (40 µL, 0.56 mmol) in n-BuOH (1 mL) was heated at 150° C. for 90 minutes using the microwave reactor. The reaction was evaporated in vacuo and the crude product purified by reverse phase chromatography eluting with a gradient of 5-90% acetonitrile/water (5 mM HCl). Evaporation of the desired fractions afforded the product as the HCl salt (56 mg, 41% yield). $^1$H NMR (400 MHz, Methanol-d$_4$) δ 8.37 (d, J=2.8 Hz, 1H), 7.74 (d, J=8.7 Hz, 1H), 7.55 (dd, J=8.8, 2.8 Hz, 1H), 4.49-4.36 (m, 1H), 4.32 (dd, J=5.8, 3.4 Hz, 1H), 4.15 (d, J=4.8 Hz, 2H), 3.25 (s, 3H), 2.71-2.52 (m, 3H), 2.31 (s, 3H), 2.10-1.90 (m, 4H), 0.86 (t, J=7.4 Hz, 3H). ESI-MS m/z 451.22 (M+1)$^+$.

Examples prepared by general procedure described above via reaction of Intermediate A-# and B-195 are provided in Table 27.

Compound 646. (S)-7-ethyl-4,8-dimethyl-2-((cis-3-(((6-(trifluoromethyl)pyridin-3-yl)oxy)methyl)cyclobutyl)amino)-7,8-dihydropteridin-6(5H)-one $^1$H NMR (400 MHz, Methanol-d$_4$) δ 8.37 (d, J=2.8 Hz, 1H), 7.74 (d, J=8.7 Hz, 1H), 7.55 (dd, J=8.8, 2.8 Hz, 1H), 4.49-4.36 (m, 1H), 4.32 (dd, J=5.8, 3.4 Hz, 1H), 4.15 (d, J=4.8 Hz, 2H), 3.25 (s, 3H), 2.71-2.52 (m, 3H), 2.31 (s, 3H), 2.10-1.90 (m, 4H), 0.86 (t, J=7.4 Hz, 3H).

Compound 643. (S)-7-((R)-1-methoxyethyl)-4,8-dimethyl-2-((cis-3-(((6-(trifluoromethyl)pyridin-3-yl)oxy)methyl)cyclobutyl)amino)-7,8-dihydropteridin-6(5H)-one $^1$H NMR (400 MHz, Chloroform-d) δ 9.49 (s, 1H), 8.35 (d, J=2.8 Hz, 1H), 7.58 (d, J=8.7 Hz, 1H), 7.25 (dd, J=8.6, 2.8 Hz, 1H), 5.00 (d, J=7.6 Hz, 1H), 4.49-4.30 (m, 1H), 4.01 (d, J=5.7 Hz, 2H), 3.90 (d, J=6.2 Hz, 1H), 3.53 (p, J=6.3 Hz, 1H), 3.27 (s, 3H), 3.16 (s, 3H), 2.61 (ddd, J=11.7, 9.1, 6.8 Hz, 2H), 2.49 (tdd, J=9.2, 6.9, 4.5 Hz, 1H), 2.22 (s, 3H), 1.77 (qd, J=9.1, 4.1 Hz, 2H), 1.20 (d, J=6.4 Hz, 3H).

Compound 671. 7-(1-methoxycyclobutyl)-4,8-dimethyl-2-((trans-3-((6-(trifluoromethyl)pyridin-3-yl)oxy)cyclobutyl)amino)-7,8-dihydropteridin-6(5H)-one $^1$H NMR (400 MHz, DMSO-d6) δ 9.90 (s, 1H), 8.44 (d, J=2.8 Hz, 1H), 7.83 (d, J=8.7 Hz, 1H), 7.59 (dd, J=8.5, 2.7

Hz, 1H), 6.51 (s, 1H), 4.31-4.17 (m, 2H), 4.11 (d, J=5.5 Hz, 2H), 3.10 (s, 3H), 3.06 (s, 3H), 2.40 (t, J=6.0 Hz, 3H), 2.29-2.19 (m, 1H), 2.17-2.05 (m, 5H), 1.98 (dd, J=18.9, 9.0 Hz, 1H), 1.86-1.63 (m, 3H), 1.63-1.50 (m, 1H).

Compound 750. (1s,3s)-3-(((2-(trifluoromethyl)pyrimidin-5-yl)oxy)methyl)cyclobutan-1-amine $^1$H NMR (300 MHz, Methanol-d4) δ 8.61 (s, 2H), 4.20 (d, J=5.5 Hz, 2H), 3.73 (tt, J=8.7, 7.6 Hz, 1H), 2.77-2.60 (m, 1H), 2.57-2.40 (m, 2H), 2.24-1.94 (m, 2H); ESI-MS m/z calc. 247.09, found 248.17 (M+1)$^+$; Retention time: 0.58 minutes Example 2DD General Scheme and Procedure for Examples in Table 28:

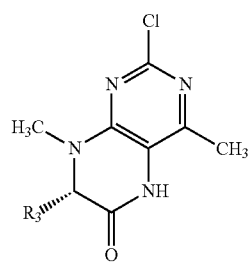

+

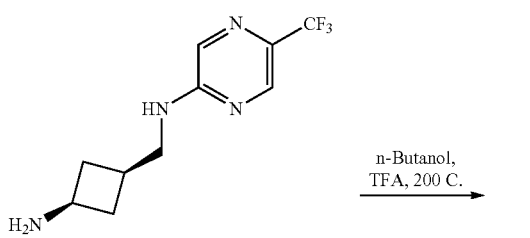

n-Butanol, TFA, 200 C.

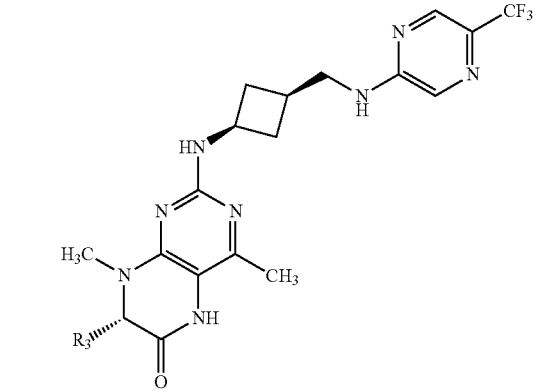

General Procedure for Examples in Table 28:

The examples in Table 28 were prepared by the same procedure described for Table 27 via reaction of an intermediate A-# and Intermediate B-211

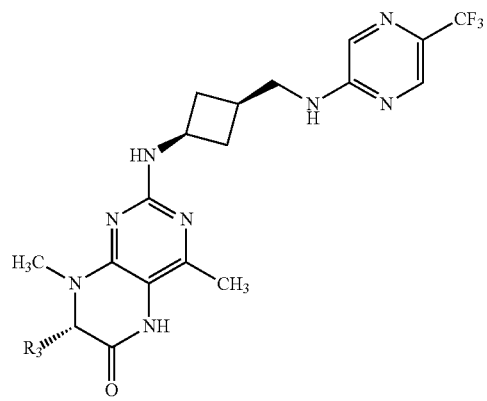

TABLE 28

| Compound No. | R$_3$ | [α]$_D$ | M + 1 |
|---|---|---|---|
| 714 | —CH3 | 11.1 c = 1.0 DMSO | 437.21 |
| 713 | —Et | 24.2 c = 1.0 DMSO | 451.22 |
| 712 | (R)—CH(OCH3)CH$_3$ | 33.8 c = 1.0 DMSO | 481.21 |
| 711 | -iPr | 36.6 c = 1.0 DMSO | 465.22 |

Compound 714. (S)-4,7,8-trimethyl-2-((cis-3-(((5-(trifluoromethyl)pyrazin-2-yl)amino)methyl)cyclobutyl)amino)-7,8-dihydropteridin-6(5H)-one $^1$H NMR (400 MHz, Methanol-d$_4$) δ 8.25 (d, J=1.3 Hz, 1H), 8.22 (d, J=1.1 Hz, 1H), 4.30 (q, J=6.9 Hz, 1H), 3.54 (d, J=6.8 Hz, 2H), 3.24 (s, 3H), 2.69-2.57 (m, 2H), 2.32 (s, 3H), 1.91 (qt, J=9.3, 2.1 Hz, 2H), 1.52 (d, J=7.0 Hz, 3H).

Compound 713. (S)-7-ethyl-4,8-dimethyl-2-((cis-3-(((5-(trifluoromethyl)pyrazin-2-yl)amino)methyl)cyclobutyl)amino)-7,8-dihydropteridin-6(5H)-one $^1$H NMR (400 MHz, Methanol-d$_4$) δ 8.23 (s, 1H), 8.18 (d, J=1.3 Hz, 1H), 4.39-4.26 (m, 2H), 3.52 (d, J=6.8 Hz, 2H), 3.23 (s, 3H), 2.68-2.53 (m, 2H), 2.44 (tt, J=9.4, 7.1 Hz, 1H), 2.30 (s, 3H), 2.11-1.99 (m, 2H), 1.89 (ddt, J=11.2, 6.8, 4.6 Hz, 2H), 0.86 (t, J=7.5 Hz, 3H).

Compound 712. (S)-7-((R)-1-methoxyethyl)-4,8-dimethyl-2-((cis-3-(((5-(trifluoromethyl)pyrazin-2-yl)amino)methyl)cyclobutyl)amino)-7,8-dihydropteridin-6(5H)-one $^1$H NMR (400 MHz, Methanol-d$_4$) δ 8.26 (d, J=1.2 Hz, 1H), 8.23 (s, 1H), 4.39 (t, J=8.1 Hz, 1H), 4.22 (d, J=3.9 Hz, 1H), 3.78 (tt, J=6.4, 3.2 Hz, 1H), 3.54 (d, J=6.8 Hz, 2H), 3.33 (s, 3H), 3.29 (s, 3H), 2.72-2.58 (m, 2H), 2.31 (s, 3H), 1.92 (dq, J=11.4, 8.8 Hz, 2H), 1.28 (d, J=6.5 Hz, 3H)

Compound 711. (S)-7-isopropyl-4,8-dimethyl-2-((cis-3-(((5-(trifluoromethyl)pyrazin-2-yl)amino)methyl)cyclobutyl)amino)-7,8-dihydropteridin-6(5H)-one $^1$H NMR (400 MHz, Methanol-d$_4$) δ 8.23 (t, J=1.0 Hz, 1H), 8.17 (d, J=1.3 Hz, 1H), 4.37 (q, J=8.2 Hz, 1H), 4.14 (d, J=3.8 Hz, 1H), 3.52 (d, J=6.7 Hz, 2H), 3.27 (s, 3H), 2.69-2.57 (m, 2H), 2.52-2.44 (m, 1H), 2.34 (dt, J=7.0, 3.5 Hz, 1H), 2.30 (s, 3H), 1.89 (dtd, J=11.7, 9.3, 6.0 Hz, 2H), 1.10 (d, J=7.0 Hz, 3H), 0.88 (d, J=6.9 Hz, 3H).

Example 2EE

General Scheme and Procedure for Examples in Table 29:
General Procedure for Examples in Table 29:

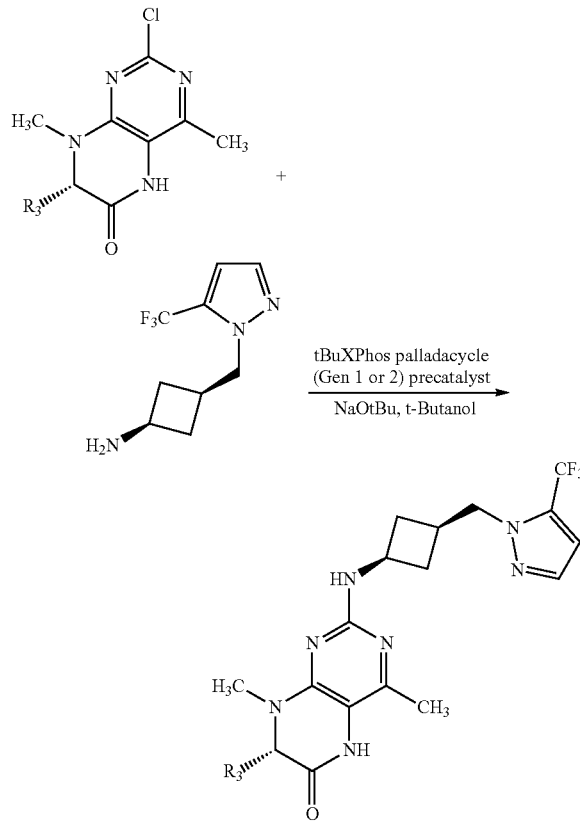

(S)-2-((cis-3-(hydroxymethyl)cyclobutyl)amino)-7-isopropyl-4,8-dimethyl-7,8-dihydropteridin-6(5H)-one A mixture of (S)-2-chloro-7-isopropyl-4,8-dimethyl-7,8-dihydropteridin-6(5H)-one (1.17 g, 4.55 mmol), cis-3-((5-(trifluoromethyl)-1H-pyrazol-1-yl)methyl)cyclobutan-1-amine hydrochloride (1.16 g, 21.4 mmol), and a 2M solution of sodium tert-butoxide (8.07 g, 84 mmol) in THF were taken into t-butanol (35 ml) and stirred for 20 mins until most of the solids were dissolved. The mixture was purged with nitrogen for 15 minutes. tBuXPhos palladacycle (Gen 1) (150 mg, 0.22 mmol) was added to the mixture, then purged with nitrogen for 10 minutes. The reaction was stirred at 60° C. for 1 hour. The reaction mixture was evaporated in vacuo and the resulting residue was taken into 100 ml of water and extracted with dichloromethane (2×80 ml). The extracts were combined, washed with brine, dried over anhydrous sodium sulfate, filtered, and evaporated in vacuo to afford the crude product. The product was purified by column chromatography (120 g SiO$_2$ column) eluting with a gradient of dichloromethane to 20% methanol. The desired fractions were combined and evaporated, 3.5 g. The resulting material was dissolved in dichloromethane (30 ml), added MP-TMP resin (1.5 g) and stirred for 12 hours. This was filtered through Celite and the filtrate evaporated in vacuo. The resulting material was washed with heptanes and filtered to afford 3.4 g (55% yield) of the product.

Table 29 provides examples prepared by general procedure described above via reaction of Intermediate A-# and B-139.

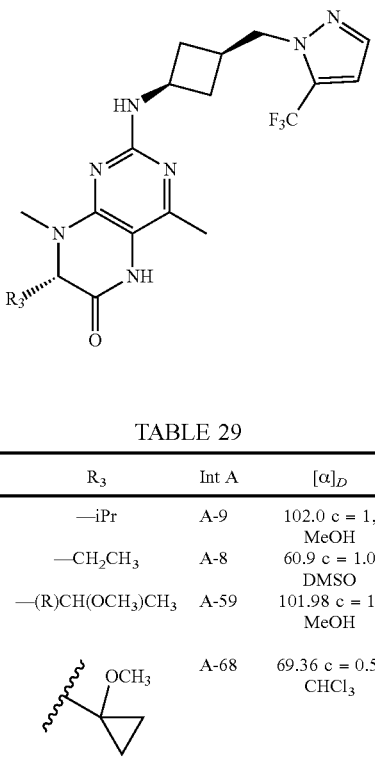

TABLE 29

| Comp. No. | R$_3$ | Int A | [α]$_D$ | M + 1 |
|---|---|---|---|---|
| 512 | —iPr | A-9 | 102.0 c = 1, MeOH | 438.35 |
| 593 | —CH$_2$CH$_3$ | A-8 | 60.9 c = 1.0 DMSO | 424.3 |
| 588 | —(R)CH(OCH$_3$)CH$_3$ | A-59 | 101.98 c = 1, MeOH | 454.33 |
| 676 | ⟜OCH$_3$ (cyclopropyl) | A-68 | 69.36 c = 0.5, CHCl$_3$ | 466.29 |
| 723 | —CH$_2$OtBu | A-63 | 42.2 c = 0.5 CHCl3 | 482.46 |
| 743 | —CH2OH | ** | 13.8 c = 0.5 MeOH | 426.4 |

** Compound was prepared by deprotection of the t-butyl ether of Compound 723

Compound 512. (S)-7-isopropyl-4,8-dimethyl-2-((cis-3-((5-(trifluoromethyl)-1H-pyrazol-1-yl)methyl)cyclobutyl)amino)-7,8-dihydropteridin-6(5H)-one $^1$H NMR (400 MHz, CDCl3) δ 8.87 (s, 1H), 7.40 (d, J=1.2 Hz, 1H), 6.51 (d, J=2.0 Hz, 1H), 4.91 (d, J=7.2 Hz, 1H), 4.41-4.27 (m, 1H), 4.21 (d, J=6.0 Hz, 2H), 3.87 (d, J=4.3 Hz, 1H), 3.10 (s, 3H), 2.67-2.43 (m, 3H), 2.28-2.22 (m, 1H), 2.21 (d, J=5.7 Hz, 3H), 1.79-1.55 (m, 2H), 1.07 (d, J=6.9 Hz, 3H), 0.92 (d, J=6.9 Hz, 3H).

Compound 593. (S)-7-ethyl-4,8-dimethyl-2-((cis-3-((5-(trifluoromethyl)-1H-pyrazol-1-yl)methyl)cyclobutyl)amino)-7,8-dihydropteridin-6(5H)-one $^1$H NMR (400 MHz, Chloroform-d) δ 9.31 (s, 1H), 7.39 (d, J=2.3 Hz, 1H), 6.50 (d, J=2.3 Hz, 1H), 5.03 (d, J=7.5 Hz, 1H), 4.30 (q, J=7.6 Hz, 1H), 4.19 (d, J=5.9 Hz, 2H), 4.04 (dd, J=6.5, 3.7 Hz, 1H), 3.04 (s, 3H), 2.55 (p, J=7.8 Hz, 3H), 2.21 (s, 3H), 1.95 (ddp, J=11.1, 7.4, 3.7 Hz, 1H), 1.83 (dt, J=14.2, 7.1 Hz, 1H), 1.65 (tdd, J=11.8, 9.0, 5.1 Hz, 2H), 0.89 (t, J=7.5 Hz, 3H).

Compound 588. (S)-7-((R)-1-methoxyethyl)-4,8-dimethyl-2-((cis-3-((5-(trifluoromethyl)-1H-pyrazol-1-yl)methyl)cyclobutyl)amino)-7,8-dihydropteridin-6(5H)-one $^1$H NMR (400 MHz, Chloroform-d) δ 9.11 (s, 1H), 7.39 (dt, J=2.2, 0.9 Hz, 1H), 6.50 (d, J=2.2 Hz, 1H), 5.14 (d, J=8.1 Hz, 1H), 4.31 (dq, J=11.0, 7.7, 7.1 Hz, 1H), 4.20 (s, 1H), 4.12 (qd, J=7.1, 0.9 Hz, 1H), 3.92 (dd, J=6.1, 1.0 Hz, 1H), 3.63-3.51 (m, 1H), 3.28 (d, J=1.0 Hz, 3H), 3.17 (d, J=0.9 Hz, 3H), 2.66-2.46 (m, 3H), 2.22 (s, 3H), 1.75-1.59 (m, 2H), 1.27 (dd, J=7.2, 1.0 Hz, 1H), 1.25-1.11 (m, 3H).

Compound 676. 7-(1-methoxycyclopropyl)-4,8-dimethyl-2-((cis-3-((5-(trifluoromethyl)-1H-pyrazol-1-yl)methyl)cyclobutyl)amino)-7,8-dihydropteridin-6(5H)-one $^1$H NMR (300 MHz, Chloroform-d) δ 7.41 (s, 1H), 6.52 (d, J=1.9 Hz, 1H), 4.93 (s, 1H), 4.43-4.28 (m, 1H), 4.22 (d, J=5.5 Hz, 2H), 3.79-3.59 (m, 1H), 3.23-3.18 (m, 3H), 3.17 (d, J=1.7 Hz, 3H), 2.68-2.44 (m, 3H), 2.22 (d, J=3.7 Hz, 3H), 1.77-1.55 (m, 3H), 1.41-1.10 (m, 4H), 0.84-0.64 (m, 1H).

Compound 723. (S)-7-(tert-butoxymethyl)-4,8-dimethyl-2-((cis-3-((5-(trifluoromethyl)-1H-pyrazol-1-yl)methyl)cyclobutyl)amino)-7,8-dihydropteridin-6(5H)-one $^1$H NMR (300 MHz, Chloroform-d) δ 8.01 (s, 1H), 7.40 (d, J=2.4 Hz, 1H), 6.52 (d, J=2.4 Hz, 1H), 4.83 (s, 1H), 4.30 (d, J=13.7 Hz, 1H), 4.21 (d, J=5.6 Hz, 2H), 4.08 (t, J=3.3 Hz, 1H), 3.70 (d, J=3.2 Hz, 2H), 3.08 (s, 4H), 2.58 (t, J=6.5 Hz, 3H), 2.17 (d, J=2.0 Hz, 3H), 1.05 (s, 10H).

Compound 743. (S)-7-(hydroxymethyl)-4,8-dimethyl-2-(((1s,3R)-3-((5-(trifluoromethyl)-1H-pyrazol-1-yl)methyl)cyclobutyl)amino)-7,8-dihydropteridin-6(5H)-one $^1$H NMR (300 MHz, Methanol-d$_4$) δ 7.76 (s, 1H), 6.58 (d, J=2.3 Hz, 1H), 4.35 (d, J=7.8 Hz, 1H), 4.32-4.17 (m, 2H), 4.11-3.85 (m, 2H), 3.81-3.51 (m, 3H), 3.25 (s, 3H), 2.71-2.40 (m, 3H), 2.29 (s, 3H), 1.89 (q, J=10.8, 9.1 Hz, 2H).

Example 2FF

General Scheme and Procedure for Examples in Table 30:

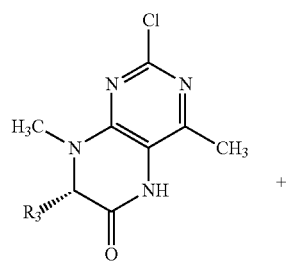

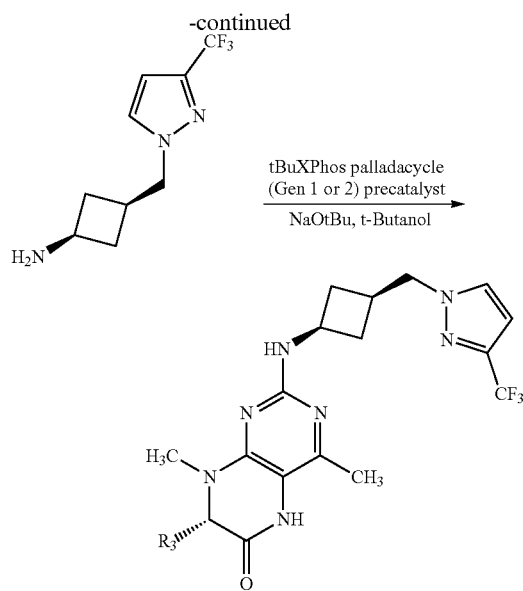

General Procedure for Examples in Table 30:
The examples in Table 30 were prepared by the same procedure that was reported for Table 29 via reaction of Intermediate A-# and B-210.

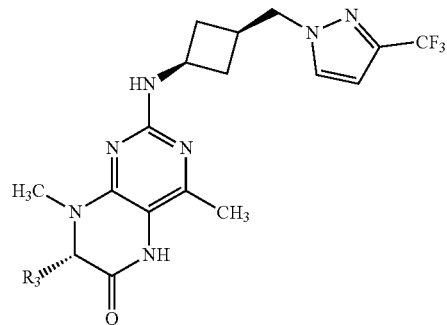

TABLE 30

| Comp. No. | R$_3$ | Int A | [α]$_D$ | M + 1 |
|---|---|---|---|---|
| 690 | iPr | A-9 | 42.3 c = 1.0 DMSO | 438.56 |
| 691 | (R)—CH(OCH$_3$)CH$_3$ | A-59 | | 454.55 |
| 692 | —Et | A-8 | 15.6 c = 1.0 DMSO | 424.21 |
| 698 | —CH$_3$ | A-2 | 7.3 c = 1.0 DMSO | 410.26 |

Compound 690. (S)-7-isopropyl-4,8-dimethyl-2-((cis-3-((3-(trifluoromethyl)-1H-pyrazol-1-yl)methyl)cyclobutyl)amino)-7,8-dihydropteridin-6(5H)-one $^1$H NMR (400 MHz, Methanol-d$_4$) δ 7.58 (dd, J=2.0, 0.8 Hz, 1H), 6.74 (d, J=2.0 Hz, 1H), 4.31 (d, J=6.7 Hz, 3H), 4.14 (d, J=3.8 Hz, 1H), 3.32 (s, 3H), 3.25 (s, 3H), 2.61-2.50 (m, 2H), 2.34 (dd, J=7.0, 3.8 Hz, 0H), 2.29 (s, 3H), 1.92 (dtd, J=11.4, 9.0, 6.3 Hz, 2H), 1.10 (d, J=6.9 Hz, 3H), 0.88 (d, J=6.9 Hz, 3H).

1143

Compound 691. (S)-7-((R)-1-methoxyethyl)-4,8-dimethyl-2-((cis-3-((3-(trifluoromethyl)-1H-pyrazol-1-yl)methyl)cyclobutyl)amino)-7,8-dihydropteridin-6(5H)-one $^1$H NMR (400 MHz, Methanol-d$_4$) δ 7.58 (dd, J=2.0, 0.8 Hz, 1H), 6.74 (dd, J=2.0, 0.8 Hz, 1H), 4.37 (d, J=3.7 Hz, 1H), 4.32 (d, J=6.6 Hz, 3H), 4.21 (d, J=3.9 Hz, 1H), 3.88-3.73 (m, 2H), 3.31 (s, 3H), 3.27 (s, 2H), 2.62-2.47 (m, 2H), 2.30 (s, 3H), 1.33-1.28 (m, 3H)

Compound 692. (S)-7-ethyl-4,8-dimethyl-2-((cis-3-((3-(trifluoromethyl)-1H-pyrazol-1-yl)methyl)cyclobutyl)amino)-7,8-dihydropteridin-6(5H)-one $^1$H NMR (400 MHz, Methanol-d$_4$) δ7.90-7.49 (m, 1H), 6.66 (dd, J=62.4, 2.2 Hz, 1H), 4.40-4.18 (m, 4H), 3.22 (s, 3H), 2.73-2.46 (m, 3H), 2.30 (s, 3H), 2.15-1.84 (m, 4H), 0.85 (t, J=7.5 Hz, 3H)

Compound 698. (S)-4,7,8-trimethyl-2-((cis-3-((3-(trifluoromethyl)-1H-pyrazol-1-yl)methyl)cyclobutyl)amino)-7,8-dihydropteridin-6(5H)-one $^1$H NMR (400 MHz, Methanol-d$_4$) δ7.82-7.50 (m, 1H), 6.65 (dd, J=61.9, 2.2 Hz, 1H), 4.37-4.23 (m, 4H), 3.22 (s, 3H), 2.69-2.44 (m, 3H), 2.29 (s, 3H), 1.90 (dddd, J=18.0, 11.4, 5.2, 2.0 Hz, 2H), 1.51 (d, J=7.0 Hz, 3H).

Example 2GG

General Scheme and Procedure for Examples in Table 31: General Procedure for Examples in Table 31:

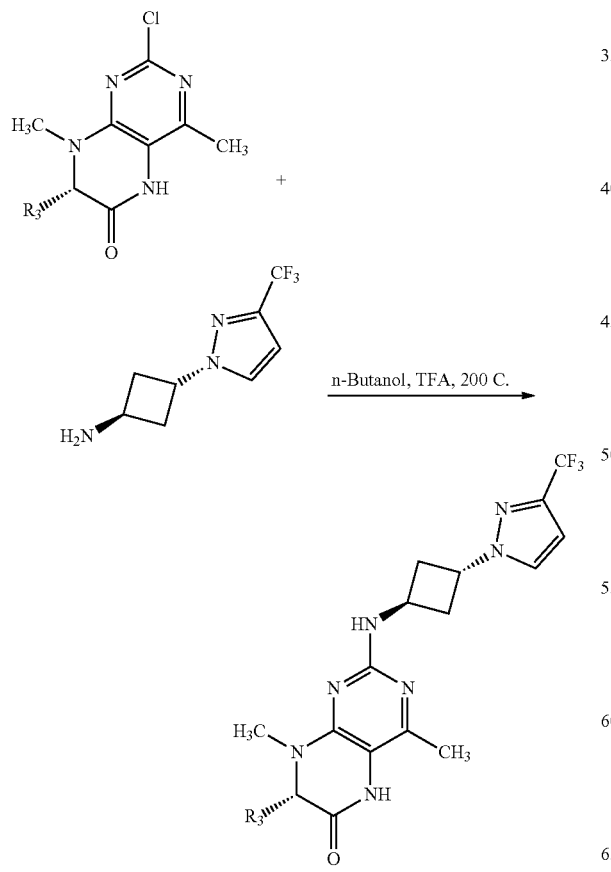

1144

The examples in Table 31 were prepared by the same procedure that was reported for Table 28 via reaction of Intermediate A-# and B-197b.

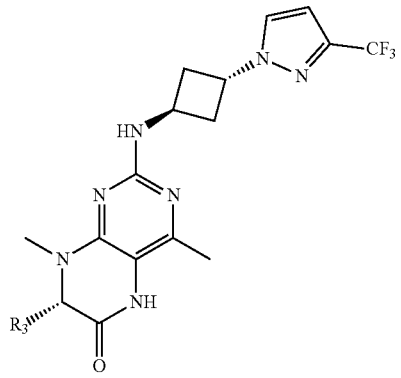

TABLE 31

| Comp. No. | R$_3$ | Int A | [α]$_D$ | M + 1 |
|---|---|---|---|---|
| 730 | -iPr | A-9 | | 424.28 |
| 731 | —(R)—CH(OCH3)CH3 | A-59 | | 440.34 |

Compound 730. (S)-7-isopropyl-4,8-dimethyl-2-((trans-3-(3-(trifluoromethyl)-1H-pyrazol-1-yl)cyclobutyl)amino)-7,8-dihydropteridin-6(5H)-one $^1$H NMR (400 MHz, Methanol-d$_4$) δ 7.67 (s, 1H), 6.82 (s, 1H), 5.17 (td, J=8.7, 4.5 Hz, 1H), 4.79-4.67 (m, 0H), 4.15 (d, J=3.8 Hz, 1H), 3.27 (s, 3H), 3.04 (dtt, J=11.0, 5.7, 2.8 Hz, 2H), 2.83-2.69 (m, 2H), 2.42-2.34 (m, 0H), 2.32 (s, 3H), 1.11 (d, J=7.0 Hz, 3H), 0.89 (d, J=6.9 Hz, 3H).

Compound 731. (S)-7-((R)-1-methoxyethyl)-4,8-dimethyl-2-((trans-3-(3-(trifluoromethyl)-1H-pyrazol-1-yl)cyclobutyl)amino)-7,8-dihydropteridin-6(5H)-one $^1$H NMR (400 MHz, Methanol-d$_4$) δ 7.71-7.62 (m, 1H), 6.80-6.70 (m, 1H), 5.19 (tt, J=9.3, 5.6 Hz, 1H), 4.80-4.72 (m, 0H), 4.23 (d, J=3.9 Hz, 1H), 3.79 (dt, J=6.6, 3.3 Hz, 1H), 3.34 (s, 3H), 3.29 (s, 3H), 3.05 (ddt, J=8.4, 5.3, 3.2 Hz, 1H), 2.83-2.71 (m, 2H), 2.34 (s, 3H), 1.29 (d, J=6.5 Hz, 3H).

Example 2HH

General Scheme and Procedure for Examples in Table 32:

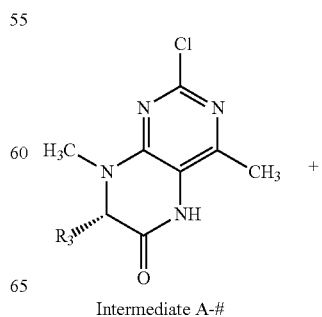

Intermediate A-#

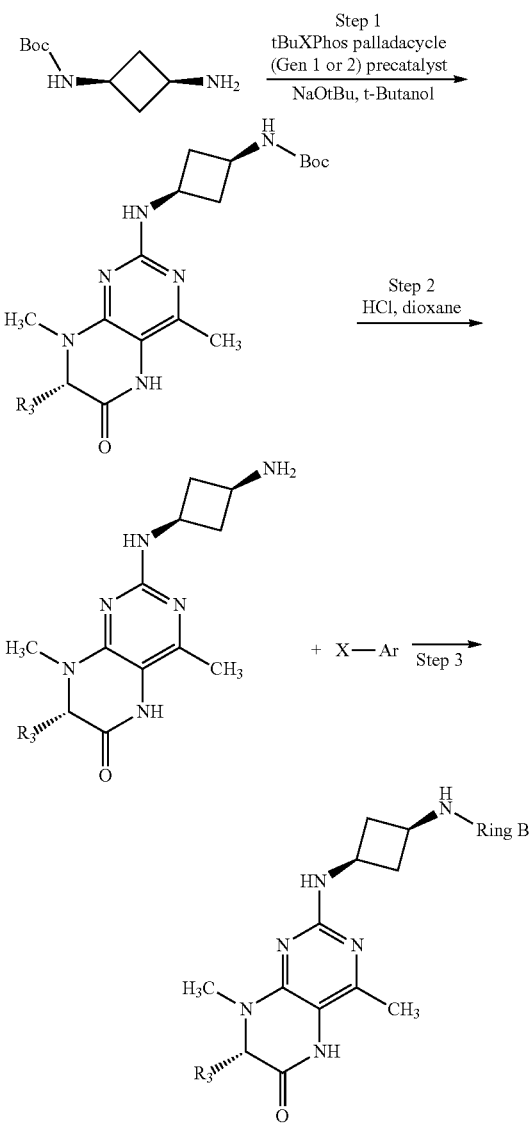

Step 1. tert-Butyl (cis-3-(((7S)-7-isopropyl-4,8-dimethyl-6-oxo-5,6,7,8-tetrahydropteridin-2-yl)amino)cyclobutyl)carbamate A THF solution of sodium tert-butoxide (2 M solution; 17 ml, 33.4 mmol) was added to a mixture of (7S)-2-chloro-7-isopropyl-4,8-dimethyl-5,7-dihydropteridin-6-one (2.446 g, 9.507 mmol), tert-butyl (trans-3-aminocyclobutyl)carbamate (1.773 g, 9.517 mmol) and tBuXPhoS (Gen 1; 261.4 mg, 0.3806 mmol) in 40 ml of tert-butanol under a nitrogen. The reaction was stirred for 30 mins. at 50 C. The reaction was quenched with ice cooled ammonium chloride (200 ml) and extracted with ethyl acetate (3×100 ml). The extracts were combined, dried over anhydrous sodium sulfate, and filtered. The filtrate was stirred with TMT scavenger resin to remove Pd, filtered, and evaporated in vacuo. The crude product was purified by column chromatography (SiO2) eluting with a gradient of dichloromethane to 10% methanol. The relevant fractions were combined and evaporated in vacuo to afford the title product (2.5 g, 64.9% yield). 1H NMR (400 MHz, CDCl$_3$) δ 7.96 (s, 1H), 4.77 (d, J=7.1 Hz, 1H), 4.69 (d, J=7.6 Hz, 1H), 4.23-3.96 (m, 2H), 3.89 (d, J=4.2 Hz, 2H), 3.12 (s, 3H), 2.86 (d, J=5.5 Hz, 2H), 2.29-2.21 (m, 1H), 2.19 (s, 3H), 2.07 (s, 1H), 1.83-1.60 (m, 3H), 1.46 (s, 9H), 1.28 (dd, J=7.5, 6.7 Hz, 1H), 1.08 (d, J=6.9 Hz, 3H), 0.93 (t, J=7.1 Hz, 3H). ESI-MS m/z 405.35 (M+1).

Step 2. (7S)-2-((cis-3-aminocyclobutyl)amino)-7-isopropyl-4,8-dimethyl-7,8-dihydropteridin-6(5H)-one dihydrochloride $^{tert}$-Butyl (trans-3-(((7S)-7-isopropyl-4,8-dimethyl-6-oxo-5,6,7,8-tetrahydropteridin-2-yl)amino)cyclobutyl)carbamate (2.17 g, 5.36 mmol) was dissolved in methanol (30 ml). A 4 M solution of hydrogen chloride (11 ml, 44 mmol) in dioxane was added to the solution and the mixture heated to 50 C for 30 minutes. The reaction was evaporated in vacuo and the resulting solid was washed with heptanes, filtered, and dried under vacuum at 50 C to afford the title product as a white solid, 2.31 g (quantitative yield). 1H NMR (400 MHz, Methanol-d4) δ 4.43-4.26 (m, 1H), 4.15 (d, J=3.8 Hz, 1H), 3.58 (ddd, J=22.7, 16.2, 7.5 Hz, 1H), 3.28 (s, 3H), 2.98-2.81 (m, 2H), 2.38-2.31 (m, 1H), 2.30 (d, J=3.5 Hz, 3H), 2.25 (d, J=8.7 Hz, 1H), 1.11 (d, J=7.0 Hz, 3H), 0.89 (d, J=6.9 Hz, 3H). ESI-MS m/z 305.22 (M+1)$^+$.

Step 3. General Procedure

A mixture of (7S)-2-((trans-3-aminocyclobutyl)amino)-7-isopropyl-4,8-dimethyl-7,8-dihydropteridin-6(5H)-one dihydrochloride (1 equiv), a halogen substituted aromatic or heteroaromatic ring (1.1 equiv), and diisopropylethylamine (5 equiv) was taken into 2 ml of isopropanol and heated in a microwave tube for 1 hour at 250 C. The reaction was evaporated in vacuo and purified by prep column chromatography (C18) eluting with 0 to 100% acetonitrile/water (TFA modifier).

Examples prepared by the general procedure described above via reaction of Intermediate A-1 (R$_3$=Me) or A-9 (R$_3$=iPr) are provided in Table 32.

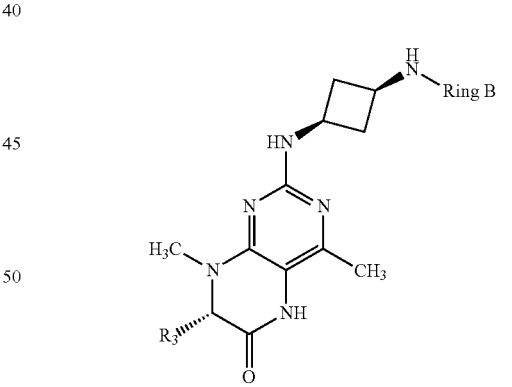

TABLE 32

| Comp. No. | Ring B | R3 | [α]$_D$ | M + 1 |
|---|---|---|---|---|
| 485 | ![3,4,5-trifluorophenyl] | Me | | 407.29 |

TABLE 32-continued

| Comp. No. | Ring B | R3 | [α]_D | M + 1 |
|---|---|---|---|---|
| 527 | pyrimidine-CF3 | iPr | 41.9 c = 1.0 DMSO | 451.33 |
| 528 | pyrimidine-CF3 | iPr | 18.9 c = 1.0 DMSO | 451.4 |
| 532 | pyridine-CF3 | iPr | 27.6 c = 1.0 DMSO | 449.87 |
| 534 | pyridine-CF3 | iPr | | 449.91 |
| 536 | trifluorophenyl-CH2 | iPr | 36.1 c = 1.0 DMSO | 448.91 |
| 539 | pyrimidine-CF3-CH2 | iPr | | 451.25 |
| 552 | pyrimidine-CF3-CH2 | iPr | 18.1 c = 1.0 DMSO | 423.71 |
| 556 | pyridazine-CF3 | iPr | | 451.22 |
| 561 | pyridine-CF3 | iPr | | 450.21 |
| 562 | pyridine-CF3 | Me | | 421.87 |
| 569 | N-methyl-triazole-CF3 | iPr | | 454.28 |
| 576 | pyridine-OCF3 | iPr | | 465.87 |
| 577 | pyridine-OCF3 | Me | | 437.9 |
| 586 | pyridine-CF3 | iPr | 88.7 c = 1.0 DMSO | 450.28 |
| 602 | pyrazine-CN | iPr | 53.2 c = 1.0 | 407.97 |
| 715 | pyridine-F-CN | iPr | | 425.29 |
| 716 | pyridine-CN | iPr | 22.6 c = 1.0 DMSO | 407.29 |
| 717 | pyrimidine-CN | iPr | 6.2 c = 1.0 DMSO | 408.3 |
| 732 | pyridine-F | iPr | | 400.31 |
| 733 | pyridazine-OCH3 | iPr | | 412.35 |
| 734 | pyrimidine-CF3 | iPr | | 451.32 |

Compound 485. (S)-4,7,8-trimethyl-2-((cis-3-((3,4,5-trifluorophenyl)amino)cyclobutyl)amino)-7,8-dihydropteridin-6(5H)-one $^1$H NMR (400 MHz, Methanol-d4) δ 6.40-6.26 (m, 2H), 4.30 (q, J=6.9 Hz, 1H), 4.21 (dd, J=16.1, 8.1 Hz, 1H), 3.72-3.59 (m, 1H), 3.26 (s, 3H), 2.95 (dq, J=10.7, 7.2 Hz, 2H), 2.30 (s, 3H), 1.96 (dd, J=19.6, 8.9 Hz, 2H), 1.53 (d, J=7.0 Hz, 3H).

Compound 527. (S)-7-isopropyl-4,8-dimethyl-2-((cis-3-((4-(trifluoromethyl)pyrimidin-2-yl)amino)cyclobutyl)amino)-7,8-dihydropteridin-6(5H)-one $^1$H NMR (400 MHz, Methanol-d4) δ 8.57 (d, J=5.4 Hz, 1H), 7.04 (d, J=5.4 Hz, 1H), 4.37-4.19 (m, 2H), 4.16 (d, J=3.8 Hz, 1H), 3.30 (d, J=3.5 Hz, 3H), 3.05-2.83 (m, 2H), 2.41-2.33 (m, 1H), 2.34-2.28 (m, 3H), 2.22-2.08 (m, 2H), 1.11 (d, J=7.0 Hz, 3H), 0.89 (d, J=6.9 Hz, 3H).

Compound 528. (S)-7-isopropyl-4,8-dimethyl-2-((cis-3-((6-(trifluoromethyl)pyrimidin-4-yl)amino)cyclobutyl)amino)-7,8-dihydropteridin-6(5H)-one $^1$H NMR (400 MHz, Methanol-d4) δ 8.69 (s, 1H), 7.08 (s, 1H), 4.42 (dd, J=22.5, 14.8 Hz, 1H), 4.37-4.22 (m, 1H), 4.16 (d, J=3.8 Hz, 1H), 3.29 (s, 3H), 3.00 (dt, J=12.3, 6.3 Hz, 2H), 2.35 (ddd, J=12.3, 6.2, 3.1 Hz, 1H), 2.31 (s, 3H), 2.26-2.15 (m, 2H), 1.11 (d, J=7.0 Hz, 3H), 0.89 (d, J=6.9 Hz, 3H).

Compound 532. (S)-7-isopropyl-4,8-dimethyl-2-((cis-3-((6-(trifluoromethyl)pyridin-2-yl)amino)cyclobutyl)amino)-7,8-dihydropteridin-6(5H)-one $^1$H NMR (400 MHz, Methanol-d4) δ 7.56 (t, J=7.9 Hz, 1H), 6.90 (d, J=7.2 Hz, 1H), 6.68 (d, J=8.5 Hz, 1H), 4.19 (dt, J=12.0, 5.3 Hz, 2H), 4.14 (t, J=4.4 Hz, 1H), 3.29 (s, 3H), 3.04-2.84 (m, 2H), 2.40-2.30 (m, 1H), 2.30 (s, 3H), 2.08-1.90 (m, 2H), 1.11 (d, J=7.0 Hz, 3H), 0.89 (d, J=6.9 Hz, 3H).

Compound 534. (S)-7-isopropyl-4,8-dimethyl-2-((cis-3-((5-(trifluoromethyl)pyridin-2-yl)amino)cyclobutyl)amino)-7,8-dihydropteridin-6(5H)-one $^1$H NMR (400 MHz, Methanol-d4) δ 8.26 (s, 1H), 8.05 (dd, J=9.5, 1.9 Hz, 1H), 7.15 (d, J=9.4 Hz, 1H), 4.42-4.29 (m, 1H), 4.16 (d, J=3.8 Hz, 1H), 4.11 (td, J=8.5, 4.3 Hz, 1H), 3.19-3.03 (m, 2H), 2.35 (ddd, J=13.4, 6.7, 3.6 Hz, 1H), 2.32-2.29 (m, 3H), 2.29-2.18 (m, 3H), 1.11 (d, J=7.0 Hz, 3H), 0.89 (d, J=6.9 Hz, 3H).

Compound 536. (S)-7-isopropyl-4,8-dimethyl-2-((cis-3-((3,4,5-trifluorobenzyl)amino)cyclobutyl)amino)-7,8-dihydropteridin-6(5H)-one $^1$H NMR (400 MHz, Methanol-d4) δ 7.49-7.36 (m, 2H), 4.40 (p, J=8.4 Hz, 1H), 4.18 (s, 2H), 4.16 (d, J=3.8 Hz, 1H), 3.69 (p, J=8.3 Hz, 1H), 3.28 (s, 3H), 2.98-2.84 (m, 2H), 2.51-2.42 (m, 2H), 2.38-2.33 (m, 1H), 2.31 (d, J=2.9 Hz, 3H), 1.11 (d, J=7.0 Hz, 3H), 0.89 (d, J=6.9 Hz, 3H).

Compound 539. (S)-7-isopropyl-4,8-dimethyl-2-((cis-3-((2-(trifluoromethyl)pyrimidin-4-yl)amino)cyclobutyl)amino)-7,8-dihydropteridin-6(5H)-one $^1$H NMR (400 MHz, Methanol-d4) δ 8.16 (s, 1H), 6.79 (d, J=6.4 Hz, 1H), 4.42 (s, 1H), 4.29 (dd, J=16.0, 8.1 Hz, 1H), 4.16 (d, J=3.8 Hz, 1H), 2.98 (s, 2H), 2.41-2.32 (m, 1H), 2.31 (s, 3H), 2.17 (dd, J=17.0, 8.3 Hz, 2H), 1.11 (d, J=7.0 Hz, 3H), 0.89 (d, J=6.9 Hz, 3H).

Compound 552. (S)-4,7,8-trimethyl-2-((cis-3-((6-(trifluoromethyl)pyrimidin-4-yl)amino)cyclobutyl)amino)-7,8-dihydropteridin-6(5H)-one $^1$H NMR (400 MHz, Methanol-d4) δ 8.64 (s, 1H), 7.02 (s, 1H), 4.52-4.35 (m, 1H), 4.35-4.29 (m, 1H), 4.29-4.20 (m, 1H), 3.27 (s, 3H), 2.99 (dt, J=11.0, 6.8 Hz, 2H), 2.33 (s, 3H), 2.18 (dd, J=19.0, 9.2 Hz, 2H), 1.53 (d, J=6.9 Hz, 3H).

Compound 556. (S)-7-isopropyl-4,8-dimethyl-2-((cis-3-((6-(trifluoromethyl)pyridazin-3-yl)amino)cyclobutyl)amino)-7,8-dihydropteridin-6(5H)-one $^1$H NMR (400 MHz, Methanol-d4) δ 7.87 (d, J=9.6 Hz, 1H), 7.45 (d, J=9.6 Hz, 1H), 4.34 (p, J=8.7 Hz, 1H), 4.20 (dd, J=14.9, 7.5 Hz, 1H), 4.17 (t, J=3.2 Hz, 1H), 3.30 (s, 3H), 3.17-3.01 (m, 2H), 2.42-2.34 (m, 1H), 2.32 (d, J=4.0 Hz, 3H), 2.28-2.15 (m, 2H), 1.12 (d, J=7.0 Hz, 3H), 0.89 (d, J=6.9 Hz, 3H).

Compound 561. (S)-7-isopropyl-4,8-dimethyl-2-((cis-3-((4-(trifluoromethyl)pyridin-2-yl)amino)cyclobutyl)amino)-7,8-dihydropteridin-6(5H)-one $^1$H NMR (400 MHz, Methanol-d4) δ 8.08 (d, J=6.8 Hz, 1H), 7.40 (d, J=0.7 Hz, 1H), 7.11 (dd, J=6.8, 1.5 Hz, 1H), 4.46-4.31 (m, 1H), 4.15 (dd, J=10.4, 4.6 Hz, 1H), 4.14-4.03 (m, 1H), 3.30 (s, 3H), 3.20-3.03 (m, 2H), 2.39 (ddd, J=10.1, 9.0, 3.3 Hz, 1H), 2.32 (s, 3H), 2.28-2.18 (m, 1H), 1.11 (d, J=7.0 Hz, 3H), 0.89 (d, J=6.9 Hz, 3H).

Compound 562. (S)-4,7,8-trimethyl-2-((cis-3-((5-(trifluoromethyl)pyridin-2-yl)amino)cyclobutyl)amino)-7,8-dihydropteridin-6(5H)-one $^1$H NMR (400 MHz, Methanol-d4) δ 8.26 (s, 1H), 7.98 (dd, J=9.4, 2.1 Hz, 1H), 7.09 (t, J=11.5 Hz, 1H), 4.40-4.26 (m, 2H), 4.14 (p, J=8.4 Hz, 1H), 3.26 (d, J=4.0 Hz, 3H), 3.14-2.98 (m, 2H), 2.32 (s, 3H), 2.27-2.14 (m, 2H), 1.53 (d, J=7.0 Hz, 3H).

Compound 569. (S)-7-isopropyl-4,8-dimethyl-2-((cis-3-((1-methyl-3-(trifluoromethyl)-1H-1,2,4-triazol-5-yl)amino)cyclobutyl)amino)-7,8-dihydropteridin-6(5H)-one $^1$H NMR (400 MHz, Methanol-d$_4$) δ 4.18 (d, J=8.2 Hz, 1H), 4.15 (d, J=3.8 Hz, 1H), 4.00 (tt, J=8.9, 7.2 Hz, 1H), 3.64 (s, 3H), 3.29 (s, 3H), 2.95 (tdd, J=7.2, 5.7, 4.1 Hz, 2H), 2.35 (dd, J=7.2, 4.1 Hz, 0H), 2.30 (s, 3H), 2.20-2.01 (m, 1H), 1.11 (d, J=6.9 Hz, 3H), 0.89 (d, J=6.9 Hz, 3H).

Compound 576. (S)-7-isopropyl-4,8-dimethyl-2-((cis-3-((5-(trifluoromethoxy)pyridin-2-yl)amino)cyclobutyl)amino)-7,8-dihydropteridin-6(5H)-one $^1$H NMR (400 MHz, Methanol-d$_4$) δ 8.05 (d, J=2.6 Hz, 1H), 7.99-7.84 (m, 1H), 7.14 (dd, J=9.9, 0.7 Hz, 1H), 4.40-4.25 (m, 1H), 4.16 (d, J=3.8 Hz, 1H), 4.04 (ddd, J=8.7, 7.1, 1.5 Hz, 1H), 3.29 (s, 3H), 3.13-2.97 (m, 2H), 2.41-2.33 (m, 1H), 2.31 (s, 3H), 2.23 (ddd, J=11.8, 6.0, 2.8 Hz, 1H), 1.11 (d, J=7.0 Hz, 3H), 0.89 (d, J=6.9 Hz, 3H).

Compound 577. (S)-4,7,8-trimethyl-2-((cis-3-((5-(trifluoromethoxy)pyridin-2-yl)amino)cyclobutyl)amino)-7,8-dihydropteridin-6(5H)-one $^1$H NMR (400 MHz, Methanol-d$_4$) δ 8.05 (d, J=2.6 Hz, 1H), 7.99-7.82 (m, 1H), 7.11 (d, J=9.8 Hz, 1H), 4.35-4.24 (m, 2H), 4.11-4.01 (m, 1H), 3.27 (s, 3H), 3.08 (dt, J=11.2, 6.9 Hz, 2H), 2.32 (s, 3H), 2.26-2.15 (m, 2H), 1.53 (d, J=6.9 Hz, 3H).

Compound 586. (S)-7-isopropyl-4,8-dimethyl-2-((cis-3-((6-(trifluoromethyl)pyridin-3-yl)amino)cyclobutyl)amino)-7,8-dihydropteridin-6(5H)-one $^1$H NMR (400 MHz, Methanol-$d_4$) δ 7.96 (d, J=2.7 Hz, 1H), 7.49 (d, J=8.6 Hz, 1H), 6.99 (dd, J=8.6, 2.7 Hz, 1H), 4.23 (tt, J=9.0, 7.3 Hz, 1H), 3.90 (d, J=4.4 Hz, 1H), 3.69 (tt, J=8.5, 7.0 Hz, 1H), 3.14 (s, 3H), 3.00-2.84 (m, 2H), 2.22 (qd, J=7.0, 4.5 Hz, 1H), 2.17 (s, 3H), 1.84 (dddd, J=11.7, 10.3, 8.8, 4.4 Hz, 1H), 1.03 (d, J=7.0 Hz, 3H), 0.86 (d, J=6.9 Hz, 3H).

Compound 602. 5-((cis-3-(((S)-7-isopropyl-4,8-dimethyl-6-oxo-5,6,7,8-tetrahydropteridin-2-yl)amino)cyclobutyl)amino)pyrazine-2-carbonitrile $^1$H NMR (400 MHz, Methanol-$d_4$) δ 8.33 (d, J=1.4 Hz, 1H), 7.98 (d, J=1.4 Hz, 1H), 4.32-4.19 (m, 2H), 4.15 (d, J=3.8 Hz, 1H), 3.29 (s, 3H), 3.03-2.90 (m, 2H), 2.35 (dd, J=7.0, 3.8 Hz, 0H), 2.31 (s, 3H), 2.19-1.95 (m, 1H), 1.11 (d, J=7.0 Hz, 3H), 0.89 (d, J=7.0 Hz, 3H).

Compound 715. 5-fluoro-6-((cis-3-(((S)-7-isopropyl-4,8-dimethyl-6-oxo-5,6,7,8-tetrahydropteridin-2-yl)amino)cyclobutyl)amino)nicotinonitrile $^1$H NMR (400 MHz, Methanol-$d_4$) δ 8.22 (d, J=3.0 Hz, 1H), 7.78 (dd, J=7.9, 3.0 Hz, 1H), 4.35-4.18 (m, 2H), 4.15 (d, J=3.8 Hz, 1H), 3.31 (s, 3H), 2.94 (dt, J=12.6, 6.6 Hz, 2H), 2.37 (s, 0H), 2.30 (s, 3H), 2.17-2.04 (m, 2H), 1.11 (d, J=6.9 Hz, 3H), 0.89 (d, J=6.9 Hz, 3H).

Compound 716. 6-((cis-3-(((S)-7-isopropyl-4,8-dimethyl-6-oxo-5,6,7,8-tetrahydropteridin-2-yl)amino)cyclobutyl)amino)nicotinonitrile $^1$H NMR (400 MHz, Methanol-$d_4$) δ 8.46 (d, J=2.0 Hz, 1H), 8.00 (d, J=9.5 Hz, 1H), 7.12 (d, J=9.5 Hz, 1H), 4.40-4.28 (m, 1H), 4.15 (dd, J=6.7, 2.6 Hz, 1H), 4.14-4.04 (m, 1H), 3.12-3.02 (m, 2H), 2.31 (s, 3H), 2.28-2.19 (m, 1H), 1.11 (d, J=7.0 Hz, 3H), 0.89 (d, J=6.9 Hz, 3H).

Compound 717. 2-((cis-3-(((S)-7-isopropyl-4,8-dimethyl-6-oxo-5,6,7,8-tetrahydropteridin-2-yl)amino)cyclobutyl)amino)pyrimidine-5-carbonitrile $^1$H NMR (400 MHz, Methanol-$d_4$) δ 8.59 (s, 1H), 8.53 (s, 1H), 4.37-4.18 (m, 2H), 4.15 (d, J=3.8 Hz, 1H), 3.28 (s, 3H), 2.97-2.84 (m, 2H), 2.34 (td, J=7.0, 3.9 Hz, 0H), 2.30 (s, 3H), 2.16-2.05 (m, 2H), 1.11 (d, J=7.0 Hz, 3H), 0.89 (d, J=6.9 Hz, 3H).

Compound 732. (S)-2-((cis-3-((5-fluoropyridin-2-yl)amino)cyclobutyl)amino)-7-isopropyl-4,8-dimethyl-7,8-dihydropteridin-6(5H)-one $^1$H NMR (400 MHz, Methanol-$d_4$) δ 7.99-7.93 (m, 2H), 7.15-7.08 (m, 1H), 4.33 (m, 2H), 3.64-3.54 (m, 1H), 3.27 (d, J=1.4 Hz, 5H), 3.16-3.00 (m, 3H), 2.29 (s, 3H), 1.11 (dd, J=6.9, 1.8 Hz, 3H), 0.90 (d, J=2.3 Hz, 3H).

Compound 733. (S)-7-isopropyl-2-((cis-3-((5-methoxypyridin-2-yl)amino)cyclobutyl)amino)-4,8-dimethyl-7,8-dihydropteridin-6(5H)-one $^1$H NMR (400 MHz, Methanol-$d_4$) δ 7.78-7.62 (m, 1H), 7.37 (dd, J=37.2, 2.8 Hz, 1H), 7.02 (dd, J=19.0, 9.7 Hz, 0H), 4.44-4.22 (m, 1H), 4.16 (t, J=3.1 Hz, 1H), 3.98 (q, J=8.0 Hz, 1H), 3.76 (t, J=7.4 Hz, 1H), 3.28 (s, 3H), 3.11 (s, 2H), 2.93 (d, J=6.5 Hz, 1H), 2.30 (d, J=1.6 Hz, 3H), 1.11 (d, J=6.8 Hz, 3H), 0.88 (d, J=2.0 Hz, 3H)

Compound 734. (S)-7-isopropyl-4,8-dimethyl-2-((cis-3-((5-(trifluoromethyl)pyrimidin-2-yl)amino)cyclobutyl)amino)-7,8-dihydropteridin-6(5H)-one $^1$H NMR (400 MHz, Methanol-$d_4$) δ 8.57 (s, 2H), 4.37-4.19 (m, 2H), 4.15 (d, J=3.8 Hz, 1H), 3.29 (s, 3H), 3.02-2.89 (m, 2H), 2.42-2.32 (m, 1H), 2.31 (s, 3H), 2.21-2.06 (m, 2H), 1.11 (d, J=7.0 Hz, 3H), 0.89 (d, J=6.9 Hz, 3H).

Example 2II

General Scheme and Procedure for Examples in Table 33:

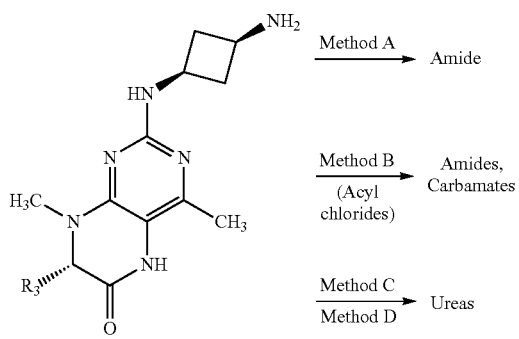

Amide Formation (Methods A-D).

Method A.

Diisopropylethylamine (4 equiv) was added to a solution of (7S)-2-((cis-3-aminocyclobutyl)amino)-7-isopropyl-4,8-dimethyl-7,8-dihydropteridin-6(5H)-one dihydrochloride (1 equiv), carboxylic acid derivative (1.5 equiv), and HATU (1.5 equiv) in NMP (2 ml) and stirred at room temperature. The reaction was purified by reverse chromatography (C18) eluting with acetonitrile/water (TFA modifier).

Method B.

An acid chloride or chloroformate derivative (1.3 equiv) was added to a solution of (7S)-2-((cis-3-aminocyclobutyl)amino)-7-isopropyl-4,8-dimethyl-7,8-dihydropteridin-6(5H)-one dihydrochloride (1 equiv) in pyridine (1 ml) and stirred at room temperature for 1 hour. The reaction was evaporated in vacuo and the residue purified by reverse chromatography (C18) eluting with acetonitrile/water (TFA modifier).

Method C.

A solution of phosgene (15% w/w, 800 µL) in toluene was added to a mixture of (7S)-2-((cis-3-aminocyclobutyl)amino)-7-isopropyl-4,8-dimethyl-7,8-dihydropteridin-6(5H)-one dihydrochloride and diisopropylethylamine (0.5 ml, 2.89 mmol) in dichloromethane (4 ml) and the reaction as stirred for 30 mins. The reaction was evaporated in vacuo to afford the crude isocyante derivative. The amine (3 equuiv) was added to a solution of the isocyante (1 equiv) and diisopropylethylamine (7 equiv) in dichloromethane (3 ml) and heated at 50 C overnight. Reaction was evaporated in vacuo and purified by reverse phase chromatography (C18) eluting with acetonitrile/water (0.5% TFA)

Method D.

1-fluoro-4-isocyantobenzene (35 µL, 0.31 mmol) was added to a solution of (7S)-2-((cis-3-aminocyclobutyl)

amino)-7-isopropyl-4,8-dimethyl-7,8-dihydropteridin-6 (5H)-one dihydrochloride (91 mg, 0.25 mmol) and diisopropylethylamine (175 μL, 1.02 mmol) in isopropanol (2 ml). The reaction stirred at room temperature for 1 hour then evaporated in vacupo and the residue was purified by reverse phase chromatography (C18) eluting with acetonitrile/water (0.5% TFA). To afford 67 mg of the desired product.

Table 33 examples were prepared by the general procedure described above via reaction of (7S)-2-((cis-3-aminocyclobutyl)amino)-7-isopropyl-4,8-dimethyl-7,8-dihydropteridin-6(5H)-one (R$_3$=iPr) or (7S)-2-((cis-3-aminocyclobutyl)amino)-7-methyl-4,8-dimethyl-7,8-dihydropteridin-6(5H)-one (R$_3$=CH$_3$) and one of the following: acyl chloride, sulfonyl chloride, chloroformate or isocyante.

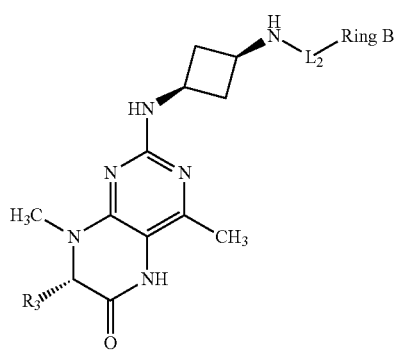

TABLE 33

| Comp. No. | L$_2$-Ring B | R$_3$ | [α]$_D$ | M + 1 |
|---|---|---|---|---|
| 475 | | Me | | 435.29 |
| 514 | | iPr | 34.5 c = 1.0 DMSO | 477.25 |
| 553 | | iPr | 35 c = 1.0 DMSO | 480.84 |
| 559 | | iPr | | 491.81 |

TABLE 33-continued

| Comp. No. | L$_2$-Ring B | R$_3$ | [α]$_D$ | M + 1 |
|---|---|---|---|---|
| 481 | | Me | 20.1 c = 1.0 DMSO | 471.27 |
| 458 | | Me | 19.4 c = 1.0 DMSO | 414.17 |
| 460 | | Me | | 450.37 |
| 462 | | Me | 18.9 c = 1.0 DMSO | 431.34 |
| 464 | | Me | 15.4 c = 1.0 DMSO | 415.28 |
| 472 | | Me | | 450.28 |
| 484 | | Me | | 451.14 |
| 473 | | Me | 19.3 c = 1.0 DMSO | 465.33 |
| 477 | | Me | 18.1 c = 1.0 DMSO | 450.32 |
| 525 | | iPr | 30.2 c = 1.0 DMSO | 452.39 |

TABLE 33-continued

| Comp. No. | L₂-Ring B | R₃ | [α]_D | M + 1 |
|---|---|---|---|---|
| 526 | -C(=O)-NH-cyclohexyl-CF₂ (HN-cyclohexyl-gem-difluoro, acyl linker) | iPr | 31.5 c = 1.0 DMSO | 466.44 |
| 538 | | iPr | | 480.35 |

Compound 475. 3,4,5-trifluoro-N-(cis-3-(((S)-4,7,8-trimethyl-6-oxo-5,6,7,8-tetrahydropteridin-2-yl)amino)cyclobutyl)benzamide $^1$H NMR (400 MHz, Methanol-d4) δ 8.78 (d, J=6.6 Hz, 1H), 7.74-7.59 (m, 2H), 4.31 (q, J=6.9 Hz, 1H), 4.27-4.16 (m, 2H), 3.26 (s, 3H), 2.97-2.79 (m, 2H), 2.32 (s, 3H), 2.25-2.11 (m, 2H), 1.53 (d, J=7.0 Hz, 3H).

Compound 514. N-(cis-3-(((S)-7-isopropyl-4,8-dimethyl-6-oxo-5,6,7,8-tetrahydropteridin-2-yl)amino)cyclobutyl)-2-(3,4,5-trifluorophenyl)acetamide $^1$H NMR (400 MHz, Methanol-d4) δ 7.11-6.99 (m, 2H), 4.23-4.16 (m, 1H), 4.14 (d, J=3.8 Hz, 1H), 4.09-3.97 (m, 1H), 3.48 (s, 2H), 3.26 (s, 3H), 2.88-2.77 (m, 2H), 2.40-2.31 (m, 1H), 2.30 (s, 3H), 2.13-1.99 (m, 2H), 1.10 (t, J=7.5 Hz, 3H), 1.07-0.97 (m, 1H), 0.88 (d, J=6.9 Hz, 3H).

Compound 553

$^1$H NMR (400 MHz, Methanol-d4) δ 7.79 (dd, J=2.3, 0.9 Hz, 1H), 6.62 (d, J=2.3 Hz, 1H), 4.92 (s, 2H), 4.20 (dd, J=15.9, 8.1 Hz, 1H), 4.14 (t, J=4.2 Hz, 1H), 4.07 (dd, J=9.0, 7.5 Hz, 1H), 3.27 (s, 3H), 2.92-2.76 (m, 2H), 2.42-2.30 (m, 1H), 2.30 (s, 3H), 2.17-1.97 (m, 2H), 1.11 (d, J=7.0 Hz, 3H), 0.88 (d, J=6.9 Hz, 3H).

Compound 559. N-(cis-3-(((S)-7-isopropyl-4,8-dimethyl-6-oxo-5,6,7,8-tetrahydropteridin-2-yl)amino)cyclobutyl)-2-(6-(trifluoromethyl)pyridin-3-yl)acetamide $^1$H NMR (400 MHz, Methanol-d4) δ 8.61 (t, J=7.3 Hz, 1H), 7.97 (dd, J=8.1, 1.5 Hz, 1H), 7.77 (d, J=8.1 Hz, 1H), 4.14 (q, J=3.8 Hz, 1H), 4.04 (td, J=9.1, 4.5 Hz, 1H), 3.64 (d, J=10.1 Hz, 2H), 3.27 (d, J=5.6 Hz, 3H), 2.94-2.69 (m, 2H), 2.43-2.30 (m, 1H), 2.29 (s, 3H), 2.12-1.94 (m, 2H), 1.10 (d, J=7.0 Hz, 3H), 0.88 (d, J=6.9 Hz, 3H).

Compound 481. 3,4,5-trifluoro-N-(cis-3-(((S)-4,7,8-trimethyl-6-oxo-5,6,7,8-tetrahydropteridin-2-yl)amino)cyclobutyl)benzenesulfonamide $^1$H NMR (400 MHz, Methanol-d4) δ 7.74-7.50 (m, 2H), 4.27 (q, J=6.9 Hz, 1H), 4.13-3.99 (m, 1H), 3.68-3.52 (m, 1H), 3.20 (s, 3H), 2.73-2.56 (m, 2H), 2.27 (s, 3H), 1.96-1.81 (m, 2H), 1.50 (d, J=6.9 Hz, 3H).

Compound 458. 1-(4-fluorophenyl)-3-(cis-3-(((S)-4,7,8-trimethyl-6-oxo-5,6,7,8-tetrahydropteridin-2-yl)amino)cyclobutyl)urea $^1$H NMR (Methanol-d4) δ 7.41-7.27 (m, 2H), 6.98 (t, J=8.5 Hz, 2H), 4.30 (d, J=6.7 Hz, 1H), 4.13 (s, 1H), 4.04-3.90 (m, 1H), 3.24 (s, 3H), 2.84 (d, J=3.5 Hz, 2H), 2.30 (s, 3H), 2.07-1.94 (m, 2H), 1.52 (d, J=6.7 Hz, 3H)

Compound 460. 1-(2,3,4-trifluorophenyl)-3-(cis-3-(((S)-4,7,8-trimethyl-6-oxo-5,6,7,8-tetrahydropteridin-2-yl)amino)cyclobutyl)urea $^1$H NMR (400 MHz, Methanol-d4) δ 7.66 (dddd, J=9.4, 8.1, 5.2, 2.6 Hz, 1H), 7.03 (tdd, J=10.3, 8.2, 2.4 Hz, 1H), 4.30 (q, J=6.9 Hz, 1H), 4.22-4.07 (m, 1H), 4.07-3.92 (m, 1H), 3.25 (s, 3H), 2.92-2.78 (m, 2H), 2.31 (s, 3H), 2.09-1.93 (m, 2H), 1.53 (d, J=7.0 Hz, 3H).

Compound 462. 1-(6-chloropyridin-3-yl)-3-(cis-3-(((S)-4,7,8-trimethyl-6-oxo-5,6,7,8-tetrahydropteridin-2-yl)amino)cyclobutyl)urea $^1$H NMR (300 MHz, Methanol-d4) δ 8.50 (s, 1H), 7.95 (s, 1H), 7.42 (d, J=6.9 Hz, 1H), 4.41-3.93 (m, 3H), 3.25 (s, 3H), 2.85 (s, 2H), 2.66 (s, 1H), 2.31 (s, 3H), 2.03 (s, 2H), 1.52 (s, 3H).

Compound 464. 4-fluorophenyl (cis-3-(((S)-4,7,8-trimethyl-6-oxo-5,6,7,8-tetrahydropteridin-2-yl)amino)cyclobutyl)carbamate $^1$H NMR (400 MHz, DMSO-d6) δ 12.66 (s, 1H), 10.49 (s, 1H), 8.38 (s, 3H), 8.18 (s, 1H), 4.66 (d, J=6.2 Hz, 1H), 4.30 (q, J=6.8 Hz, 1H), 3.73 (t, J=10.8 Hz, 1H), 3.57 (s, 1H), 2.27 (s, 3H), 1.41 (d, J=6.9 Hz, 3H).

Compound 472. 1-(3,4,5-trifluorophenyl)-3-(cis-3-(((S)-4,7,8-trimethyl-6-oxo-5,6,7,8-tetrahydropteridin-2-yl)amino)cyclobutyl)urea $^1$H NMR (400 MHz, Methanol-d4) δ 7.24-7.10 (m, 2H), 4.37-4.21 (m, 1H), 4.14 (dd, J=15.8, 7.9 Hz, 1H), 3.99 (dt, J=16.4, 4.5 Hz, 1H), 3.25 (s, 3H), 2.85 (ddd, J=14.6, 7.1, 3.8 Hz, 2H), 2.31 (s, 3H), 2.02 (dt, J=16.9, 5.1 Hz, 2H), 1.53 (d, J=6.9 Hz, 3H).

Compound 484. 3,4,5-trifluorophenyl (cis-3-(((S)-4,7,8-trimethyl-6-oxo-5,6,7,8-tetrahydropteridin-2-yl)amino)cyclobutyl)carbamate $^1$H NMR (400 MHz, Methanol-d4) δ 7.08-6.79 (m, 2H), 4.30 (q, J=6.9 Hz, 1H), 4.23-4.04 (m, 1H), 3.99-3.77 (m, 1H), 3.25 (s, 3H), 2.85 (dt, J=11.1, 7.1 Hz, 2H), 2.30 (s, 3H), 2.10 (dd, J=19.6, 9.0 Hz, 2H), 1.53 (d, J=7.0 Hz, 3H).

Compound 473. 1-(6-(trifluoromethyl)pyridin-3-yl)-3-(cis-3-(((S)-4,7,8-trimethyl-6-oxo-5,6,7,8-tetrahydropteridin-2-yl)amino)cyclobutyl)urea $^1$H NMR (400 MHz, Methanol-d4) δ 8.70 (d, J=2.5 Hz, 1H), 8.14-8.04 (m, 1H), 7.69 (d, J=8.6 Hz, 1H), 4.30 (q, J=6.9 Hz, 1H), 4.24-4.12 (m, 1H), 4.11-3.95 (m, 1H), 3.26 (s, 3H), 2.92-2.79 (m, 2H), 2.31 (s, 3H), 2.07 (dtd, J=10.4, 9.1, 1.4 Hz, 2H), 1.53 (d, J=7.0 Hz, 3H).

Compound 477. 1-(2,4,5-trifluorophenyl)-3-(cis-3-(((S)-4,7,8-trimethyl-6-oxo-5,6,7,8-tetrahydropteridin-2-yl)amino)cyclobutyl)urea $^1$H NMR (400 MHz, Methanol-d4) δ 8.08-7.87 (m, 1H), 7.17 (td, J=10.5, 7.3 Hz, 1H), 4.30 (q, J=6.9 Hz, 1H), 4.22-4.10 (m, 1H), 4.08-3.89 (m, 1H), 3.25 (s, 3H), 2.92-2.77 (m, 2H), 2.31 (s, 3H), 2.10-1.94 (m, 2H), 1.53 (d, J=7.0 Hz, 3H).

Compound 525. 4,4-difluoro-N-(cis-3-(((S)-7-isopropyl-4,8-dimethyl-6-oxo-5,6,7,8-tetrahydropteridin-2-yl)amino)cyclobutyl)piperidine-1-carboxamide ¹H NMR (400 MHz, Methanol-d4) δ 4.37-4.27 (m, 1H), 4.20 (d, J=3.8 Hz, 1H), 4.03-3.89 (m, 1H), 3.77-3.68 (m, 4H), 3.51 (dd, J=14.3, 8.5 Hz, 4H), 3.26 (s, 3H), 2.92-2.76 (m, 2H), 2.40 (s, 3H), 2.34 (dtd, J=10.8, 6.9, 3.5 Hz, 1H), 2.21-2.05 (m, 6H), 1.93 (ddd, J=19.6, 13.6, 5.8 Hz, 4H), 1.12 (d, J=6.9 Hz, 3H), 0.89 (dd, J=6.8, 4.0 Hz, 3H).

Compound 526. 1-(4,4-difluorocyclohexyl)-3-(cis-3-(((S)-7-isopropyl-4,8-dimethyl-6-oxo-5,6,7,8-tetrahydropteridin-2-yl)amino)cyclobutyl)urea ¹H NMR (400 MHz, Methanol-d4) δ 4.30-4.21 (m, 1H), 4.14 (t, J=3.9 Hz, 1H), 3.92 (dt, J=14.9, 6.2 Hz, 1H), 3.81 (t, J=9.7 Hz, 1H), 3.61 (t, J=9.6 Hz, 1H), 3.25 (s, 3H), 3.02-2.88 (m, 2H), 1.92 (ddd, J=14.3, 9.9, 6.9 Hz, 9H), 1.72-1.58 (m, 2H), 1.56-1.45 (m, 2H), 1.09 (d, J=7.0 Hz, 3H), 0.87 (dd, J=14.9, 6.9 Hz, 3H).

Compound 538. 1-(4,4-difluorocyclohexyl)-3-(cis-3-(((S)-7-isopropyl-4,8-dimethyl-6-oxo-5,6,7,8-tetrahydropteridin-2-yl)amino)cyclobutyl)-1-methylurea ¹H NMR (400 MHz, Methanol-d4) δ 4.15 (d, J=3.8 Hz, 1H), 4.09 (d, J=8.5 Hz, 1H), 4.04-3.91 (m, 1H), 3.27 (s, 3H), 2.89-2.77 (m, 2H), 2.75 (s, 3H), 2.41-2.31 (m, 1H), 2.29 (s, 3H), 2.05 (dddd, J=13.1, 9.2, 7.9, 5.0 Hz, 4H), 1.94-1.71 (m, 4H), 1.65 (d, J=9.3 Hz, 2H), 1.11 (d, J=7.0 Hz, 3H), 0.89 (d, J=6.9 Hz, 3H).

Example 2JJ

General Scheme and Procedure for Examples in Table 34:

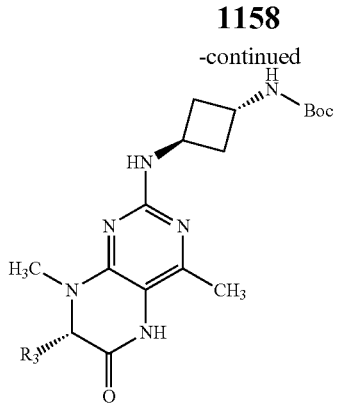

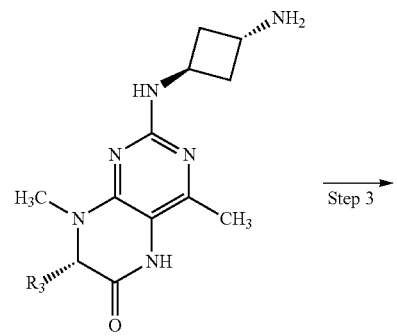

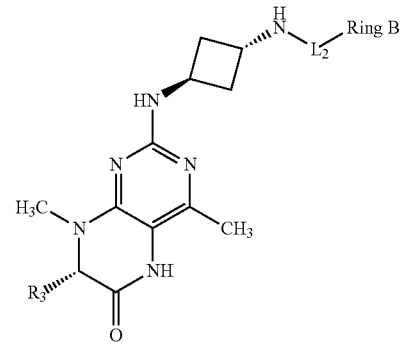

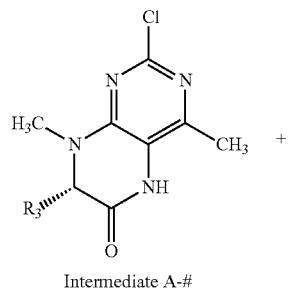

Intermediate A-#

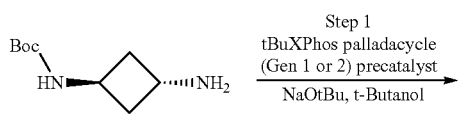

Step 1
tBuXPhos palladacycle
(Gen 1 or 2) precatalyst
NaOtBu, t-Butanol

Step 1.

tert-Butyl (trans-3-(((7S)-7-isopropyl-4,8-dimethyl-6-oxo-5,6,7,8-tetrahydropteridin-2-yl)amino)cyclobutyl)carbamate and tert-Butyl (trans-3-(((7S)-7-methyl-4,8-dimethyl-6-oxo-5,6,7,8-tetrahydropteridin-2-yl)amino) cyclobutyl)carbamate were prepared and deprotected to (7S)-2-((trans-3-aminocyclobutyl)amino)-7-isopropyl-4,8-dimethyl-7,8-dihydropteridin-6(5H)-one dihydrochloride and (7S)-2-((trans-3-aminocyclobutyl)amino)-7-methyl-4,8-dimethyl-7,8-dihydropteridin-6(5H)-one dihydrochloride via the same procedure as described for scheme and Table 32.

The examples in Table 34 were prepared via the same procedures described for Table 33.

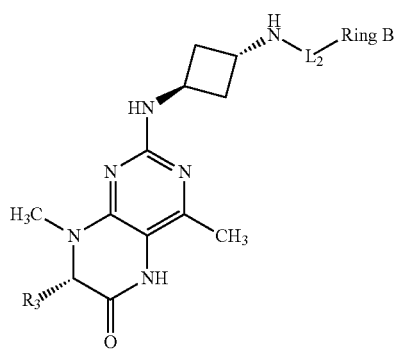

TABLE 34

| Comp. No. | L2-Ring B | R3 | Op rotation | M + 1 |
|---|---|---|---|---|
| 476 | 3,4,5-trifluorophenyl ketone | Me | 14.5 c = 1.0 DMSO | 435.29 |
| 515 | 3,4,5-trifluorobenzyl ketone | iPr | | 477.28 |
| 554 | 3-CF3-pyrazol-1-yl methyl ketone | iPr | | 480.87 |
| 560 | 6-CF3-pyridin-3-yl methyl ketone | iPr | | 491.81 |
| 482 | 2,3,4,5-tetrafluorophenyl sulfonyl | Me | | 471.2 |
| 459 | 4-fluoroanilide | Me | | 414.2 |
| 461 | 2,3,4-trifluoroanilide | Me | | 450.14 |

TABLE 34-continued

| Comp. No. | L2-Ring B | R3 | Op rotation | M + 1 |
|---|---|---|---|---|
| 463 | 6-chloropyridin-3-yl amide | Me | | 431.27 |
| 465 | 4-fluorophenyl ester | Me | | 415.28 |
| 474 | 3,4,5-trifluoroanilide | Me | | 450.32 |
| 483 | 3,4,5-trifluorophenyl ester | Me | | 451.14 |
| 471 | 6-CF3-pyridin-3-yl amide | Me | | 465.29 |
| 478 | 2,4,5-trifluoroanilide | Me | | 450.32 |
| 523 | 4,4-difluoropiperidinyl amide | iPr | | 452.39 |
| 524 | 4,4-difluorocyclohexyl amide | iPr | | 466.44 |
| 537 | N-methyl-4,4-difluorocyclohexyl amide | iPr | | 480.24 |

Compound 476. 3,4,5-trifluoro-N-(trans-3-(((S)-4,7,8-trimethyl-6-oxo-5,6,7,8-tetrahydropteridin-2-yl)amino)cyclobutyl)benzamide ¹H NMR (400 MHz, Methanol-d4) δ 8.87 (d, J=6.3 Hz, 1H), 7.76-7.60 (m, 2H), 4.65-4.48 (m, 2H), 4.30 (q, J=6.9 Hz, 1H), 3.25 (s, 3H), 2.65-2.48 (m, 4H), 2.33 (s, 3H), 1.53 (d, J=6.9 Hz, 3H).

Compound 515. N-(trans-3-(((S)-7-isopropyl-4,8-dimethyl-6-oxo-5,6,7,8-tetrahydropteridin-2-yl)amino)cyclobutyl)-2-(3,4,5-trifluorophenyl)acetamide ¹H NMR (400 MHz, Methanol-d4) δ 7.15-6.99 (m, 2H), 4.50 (p, J=6.4 Hz, 1H), 4.41-4.31 (m, 1H), 4.15 (d, J=3.8 Hz, 1H), 3.51 (s, 2H), 3.26 (s, 3H), 2.53-2.40 (m, 4H), 2.37-2.31 (m, 1H), 2.31 (d, J=4.2 Hz, 3H), 1.15-1.06 (m, 3H), 0.89 (d, J=6.9 Hz, 3H).

Compound 554. N-(trans-3-(((S)-7-isopropyl-4,8-dimethyl-6-oxo-5,6,7,8-tetrahydropteridin-2-yl)amino)cyclobutyl)-2-(3-(trifluoromethyl)-1H-pyrazol-1-yl)acetamide ¹H NMR (400 MHz, Methanol-d4) δ 7.80 (dd, J=2.3, 0.9 Hz, 1H), 6.62 (d, J=2.1 Hz, 1H), 4.95 (s, 2H), 4.52 (p, J=6.5 Hz, 1H), 4.45-4.35 (m, 1H), 4.15 (d, J=3.8 Hz, 1H), 3.27 (s, 3H), 2.50 (dd, J=11.4, 6.1 Hz, 4H), 2.36 (ddd, J=10.0, 8.8, 5.0 Hz, 1H), 2.31 (d, J=5.0 Hz, 3H), 1.11 (d, J=7.0 Hz, 3H), 0.89 (d, J=6.9 Hz, 3H).

Compound 560. N-(trans-3-(((S)-7-isopropyl-4,8-dimethyl-6-oxo-5,6,7,8-tetrahydropteridin-2-yl)amino)cyclobutyl)-2-(6-(trifluoromethyl)pyridin-3-yl)acetamide ¹H NMR (400 MHz, Methanol-d4) δ 8.64 (d, J=1.8 Hz, 1H), 7.98 (dd, J=8.1, 1.5 Hz, 1H), 7.78 (d, J=8.1 Hz, 1H), 4.56-4.44 (m, 1H), 4.42-4.32 (m, 1H), 4.14 (d, J=3.8 Hz, 1H), 3.76-3.63 (m, 2H), 3.26 (s, 3H), 2.47 (dd, J=10.3, 6.6 Hz, 4H), 2.40-2.31 (m, 1H), 2.30 (s, 3H), 1.78-1.54 (m, 2H), 1.09 (dd, J=10.6, 5.1 Hz, 3H), 0.89 (t, J=7.7 Hz, 3H).

Compound 482. 3,4,5-trifluoro-N-(trans-3-(((S)-4,7,8-trimethyl-6-oxo-5,6,7,8-tetrahydropteridin-2-yl)amino)cyclobutyl)benzenesulfonamide ¹H NMR (400 MHz, Methanol-d4) δ 7.70-7.54 (m, 2H), 4.42-4.32 (m, 1H), 4.28 (q, J=6.9 Hz, 1H), 3.95 (p, J=6.8 Hz, 1H), 3.20 (s, 3H), 2.32 (td, J=6.8, 2.6 Hz, 4H), 2.29 (d, J=6.9 Hz, 3H), 1.51 (d, J=6.9 Hz, 3H)

Compound 459. 1-(4-fluorophenyl)-3-(trans-3-(((S)-4,7,8-trimethyl-6-oxo-5,6,7,8-tetrahydropteridin-2-yl)amino)cyclobutyl)urea ¹H NMR (400 MHz, DMSO-d6) δ 12.66 (s, 1H), 10.49 (s, 1H), 8.38 (s, 3H), 8.18 (s, 1H), 4.66 (d, J=6.2 Hz, 1H), 4.30 (q, J=6.8 Hz, 1H), 3.73 (t, J=10.8 Hz, 1H), 3.57 (s, 1H), 2.27 (s, 3H), 1.41 (d, J=6.9 Hz, 3H).

Compound 461. 1-(2,3,4-trifluorophenyl)-3-(trans-3-(((S)-4,7,8-trimethyl-6-oxo-5,6,7,8-tetrahydropteridin-2-yl)amino)cyclobutyl)urea ¹H NMR (400 MHz, Methanol-d4) δ 7.66 (dddd, J=9.4, 8.1, 5.2, 2.6 Hz, 1H), 7.03 (tdd, J=10.2, 8.2, 2.4 Hz, 1H), 4.52-4.42 (m, 1H), 4.40-4.17 (m, 2H), 3.24 (s, 3H), 2.53-2.39 (m, 4H), 2.32 (s, 3H), 1.53 (d, J=7.0 Hz, 3H).

Compound 463. 1-(6-chloropyridin-3-yl)-3-(trans-3-(((S)-4,7,8-trimethyl-6-oxo-5,6,7,8-tetrahydropteridin-2-yl)amino)cyclobutyl)urea ¹H NMR (300 MHz, Methanol-d4) δ 8.45 (d, J=2.4 Hz, 1H), 7.93 (dd, J=8.7, 2.8 Hz, 1H), 7.37 (d, J=8.7 Hz, 1H), 4.53-4.40 (m, 1H), 4.33 (dq, J=17.6, 6.9 Hz, 2H), 3.24 (s, 3H), 2.47 (t, J=6.7 Hz, 4H), 2.31 (s, 3H), 1.52 (d, J=6.9 Hz, 3H).

Compound 465. 4-fluorophenyl (trans-3-(((S)-4,7,8-trimethyl-6-oxo-5,6,7,8-tetrahydropteridin-2-yl)amino)cyclobutyl)carbamate ¹H NMR (400 MHz, DMSO-d6) δ 12.66 (s, 1H), 10.49 (s, 1H), 8.38 (s, 3H), 8.18 (s, 1H), 4.66 (d, J=6.2 Hz, 1H), 4.30 (q, J=6.8 Hz, 1H), 3.73 (t, J=10.8 Hz, 1H), 3.57 (s, 1H), 2.27 (s, 3H), 1.41 (d, J=6.9 Hz, 3H).

Compound 474. 1-(3,4,5-trifluorophenyl)-3-(trans-3-(((S)-4,7,8-trimethyl-6-oxo-5,6,7,8-tetrahydropteridin-2-yl)amino)cyclobutyl)urea ¹H NMR (400 MHz, Methanol-d4) δ 7.27-7.11 (m, 2H), 4.43 (s, 1H), 4.31 (dt, J=20.7, 7.1 Hz, 2H), 3.23 (s, 3H), 2.46 (dd, J=11.4, 4.4 Hz, 4H), 2.31 (s, 3H), 1.52 (d, J=6.9 Hz, 3H).

Compound 483. 3,4,5-trifluorophenyl (trans-3-(((S)-4,7,8-trimethyl-6-oxo-5,6,7,8-tetrahydropteridin-2-yl)amino)cyclobutyl)carbamate ¹H NMR (400 MHz, Methanol-d4) δ 7.07-6.89 (m, 2H), 4.48 (dd, J=12.4, 6.7 Hz, 1H), 4.35-4.28 (m, 1H), 4.27-4.19 (m, 1H), 3.25 (s, 3H), 2.59-2.41 (m, 4H), 2.31 (s, 3H), 1.53 (d, J=7.0 Hz, 3H).

Compound 471. 1-(6-(trifluoromethyl)pyridin-3-yl)-3-(trans-3-(((S)-4,7,8-trimethyl-6-oxo-5,6,7,8-tetrahydropteridin-2-yl)amino)cyclobutyl)urea ¹H NMR (400 MHz, Methanol-d4) δ 8.70 (d, J=2.5 Hz, 1H), 8.17-8.02 (m, 1H), 7.69 (d, J=8.6 Hz, 1H), 4.48 (p, J=6.4 Hz, 1H), 4.42-4.34 (m, 1H), 4.34-4.23 (m, 1H), 3.25 (d, J=4.8 Hz, 3H), 2.49 (t, J=6.8 Hz, 4H), 2.32 (s, 3H), 1.53 (d, J=7.0 Hz, 3H).

Compound 478. 1-(2,4,5-trifluorophenyl)-3-(trans-3-(((S)-4,7,8-trimethyl-6-oxo-5,6,7,8-tetrahydropteridin-2-yl)amino)cyclobutyl)urea ¹H NMR (400 MHz, Methanol-d4) δ 8.15-7.91 (m, 1H), 7.18 (td, J=10.6, 7.3 Hz, 1H), 4.56-4.39 (m, 1H), 4.40-4.24 (m, 2H), 3.24 (s, 3H), 2.58-2.36 (m, 4H), 2.32 (s, 3H), 1.53 (d, J=7.0 Hz, 3H).

Compound 523. 4,4-difluoro-N-(trans-3-(((S)-7-isopropyl-4,8-dimethyl-6-oxo-5,6,7,8-tetrahydropteridin-2-yl)amino)cyclobutyl)piperidine-1-carboxamide ¹H NMR (400 MHz, Methanol-d4) δ 4.40 (s, 1H), 4.31 (dd, J=14.5, 6.7 Hz, 1H), 4.14 (d, J=3.9 Hz, 1H), 3.57-3.47 (m, 4H), 3.26 (s, 3H), 2.65 (s, 2H), 2.50-2.39 (m, 4H), 2.35-2.31 (m, 1H), 2.30 (s, 3H), 1.94 (ddd, J=19.6, 13.7, 5.8 Hz, 4H), 1.11 (d, J=7.0 Hz, 3H), 0.89 (d, J=6.9 Hz, 3H).

Compound 524. 1-(4,4-difluorocyclohexyl)-3-(trans-3-(((S)-7-isopropyl-4,8-dimethyl-6-oxo-5,6,7,8-tetrahydropteridin-2-yl)amino)cyclobutyl)urea ¹H NMR (400 MHz, Methanol-d4) δ 4.39 (s, 1H), 4.32-4.22 (m, 1H), 4.14 (d, J=3.8 Hz, 1H), 3.63 (t, J=9.7 Hz, 1H), 3.32 (dd, J=3.3, 1.7 Hz, 1H), 3.26 (s, 3H), 2.46-2.32 (m, 4H), 2.29 (s, 3H), 2.00 (t, J=11.9 Hz, 2H), 1.86 (ddd, J=28.9, 12.5, 4.0 Hz, 4H), 1.62-1.37 (m, 2H), 1.11 (d, J=7.0 Hz, 3H), 0.89 (d, J=6.9 Hz, 3H).

Compound 537. 1-(4,4-difluorocyclohexyl)-3-(trans-3-(((S)-7-isopropyl-4,8-dimethyl-6-oxo-5,6,7,8-tetrahydropteridin-2-yl)amino)cyclobutyl)-1-methylurea ¹H NMR (400 MHz, Methanol-d4) δ 4.45-4.32 (m, 2H), 4.17 (d, J=11.7 Hz, 1H), 4.14 (s, 1H), 3.25 (d, J=4.9 Hz, 3H), 2.77 (s, 3H), 2.45 (dddd, J=13.9, 11.3, 7.6, 3.3 Hz, 4H), 2.36-2.31 (m, 1H), 2.30 (s, 3H), 2.17-2.05 (m, 2H), 2.01-1.91 (m, 1H), 1.89-1.74 (m, 3H), 1.67 (s, 2H), 1.11 (d, J=7.0 Hz, 3H), 0.89 (d, J=6.9 Hz, 3H).

Example 2KK

General Scheme and Procedure for Preparation of Examples in Table 35

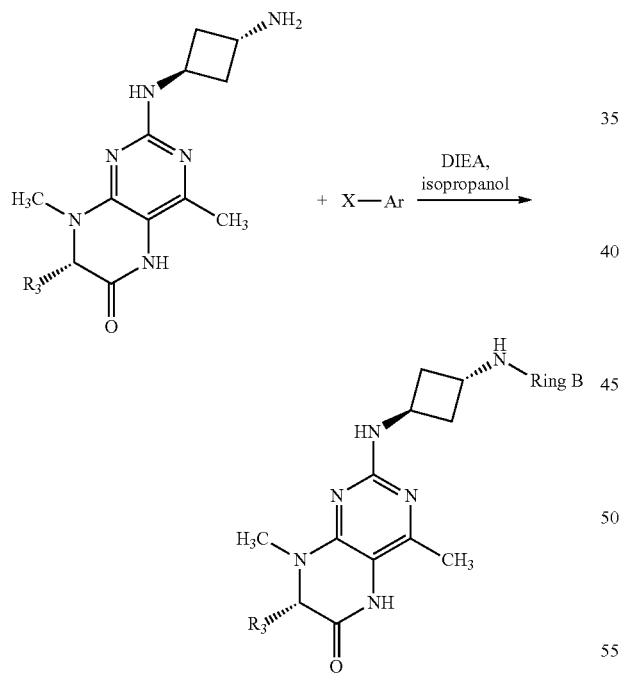

General Procedure.

A mixture of (7S)-2-((trans-3-aminocyclobutyl)amino)-7-isopropyl-4,8-dimethyl-7,8-dihydropteridin-6(5H)-one dihydrochloride (1 equiv), a halogen substituted aromatic or heteroaromatic ring (1.1 equiv), and diisopropylethylamine (5 equiv) was taken into 2 ml of isopropanol and heated in a microwave tube for 1 hour at 150 C. The reaction was evaporated in vacuo and purified by prep column chromatography (C18) eluting with 0 to 100% acetonitrile/water (TFA modifier).

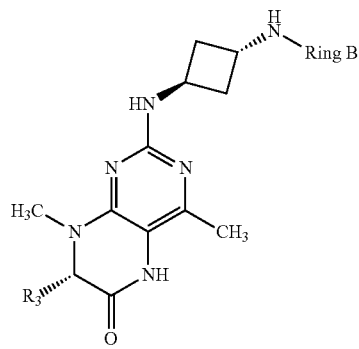

TABLE 35

| Comp. No. | Ring B | $R_3$ | $[\alpha]_D$ | M + 1 |
|---|---|---|---|---|
| 486 | 3,4,5-trifluorophenyl | Me | | 407.36 |
| 529 | 4-CF₃-pyrimidin-2-yl | iPr | | 451.4 |
| 530 | 4-CF₃-pyrimidin-2-yl (isomer) | iPr | 42.0 c = 1.0 DMSO | 451.4 |
| 531 | 6-CF₃-pyridin-2-yl | iPr | | 449.87 |
| 533 | 5-CF₃-pyridin-2-yl | iPr | | 449.71 |
| 535 | 3,4,5-trifluorobenzyl | iPr | | 448.91 |
| 540 | 2-CF₃-pyrimidin-4-yl | iPr | | 451.25 |
| 555 | 6-CF₃-pyridazin-3-yl | iPr | 47.4 c = 1.0 DMSO | 451.25 |

TABLE 35-continued

| Comp. No. | Ring B | R₃ | [α]_D | M + 1 |
|---|---|---|---|---|
| 558 | pyrazine-CF₃ | iPr | 39.4 c = 1.0 DMSO | 451.18 |
| 579 | pyrazine-CF₃ | Me | 15.6 c = 1.0 DMSO | 422.9 |
| 587 | pyridine-CF₃ | iPr | 25.0 c = 1.0 DMSO | 450.28 |

Compound 486. (S)-4,7,8-trimethyl-2-((trans-3-((3,4,5-trifluorophenyl)amino)cyclobutyl)amino)-7,8-dihydropteridin-6(5H)-one ¹H NMR (400 MHz, Methanol-d4) δ 6.37-6.28 (m, 2H), 4.61-4.49 (m, 1H), 4.29 (q, J=6.9 Hz, 1H), 4.02-3.92 (m, 1H), 3.23 (s, 3H), 2.58-2.36 (m, 4H), 2.31 (s, 3H), 1.52 (d, J=7.0 Hz, 3H).

Compound 529. (S)-7-isopropyl-4,8-dimethyl-2-((trans-3-((4-(trifluoromethyl)pyrimidin-2-yl)amino)cyclobutyl)amino)-7,8-dihydropteridin-6(5H)-one ¹H NMR (400 MHz, Methanol-d4) δ 8.56 (d, J=5.3 Hz, 1H), 7.03 (d, J=5.3 Hz, 1H), 4.57 (dd, J=12.0, 6.1 Hz, 2H), 4.15 (d, J=3.8 Hz, 1H), 3.27 (s, 3H), 2.58 (dd, J=11.4, 6.3 Hz, 4H), 2.38-2.34 (m, 1H), 2.32 (d, J=3.1 Hz, 3H), 1.11 (d, J=7.0 Hz, 3H), 0.89 (d, J=6.9 Hz, 3H).

Compound 530. (S)-7-isopropyl-4,8-dimethyl-2-((trans-3-((6-(trifluoromethyl)pyrimidin-4-yl)amino)cyclobutyl)amino)-7,8-dihydropteridin-6(5H)-one ¹H NMR (400 MHz, Methanol-d4) δ 8.61 (s, 1H), 7.04 (s, 1H), 4.62 (dt, J=13.9, 7.5 Hz, 2H), 4.15 (d, J=3.8 Hz, 1H), 3.28 (s, 3H), 2.71-2.45 (m, 4H), 2.36 (ddd, J=8.5, 8.1, 4.2 Hz, 1H), 2.32 (s, 3H), 1.11 (d, J=7.0 Hz, 3H), 0.89 (d, J=6.9 Hz, 3H).

Compound 531. (S)-7-isopropyl-4,8-dimethyl-2-((trans-3-((6-(trifluoromethyl)pyridin-2-yl)amino)cyclobutyl)amino)-7,8-dihydropteridin-6(5H)-one ¹H NMR (400 MHz, Methanol-d4) δ 7.56 (t, J=7.9 Hz, 1H), 6.89 (t, J=8.3 Hz, 1H), 6.67 (d, J=8.6 Hz, 1H), 4.49 (dd, J=12.3, 6.7 Hz, 2H), 4.14 (d, J=3.8 Hz, 1H), 3.26 (d, J=6.9 Hz, 3H), 2.57-2.44 (m, 4H), 2.39-2.32 (m, 1H), 2.30 (d, J=3.5 Hz, 3H), 1.11 (d, J=7.0 Hz, 3H), 0.89 (d, J=6.9 Hz, 3H).

Compound 533. (S)-7-isopropyl-4,8-dimethyl-2-((trans-3-((5-(trifluoromethyl)pyridin-2-yl)amino)cyclobutyl)amino)-7,8-dihydropteridin-6(5H)-one ¹H NMR (400 MHz, Methanol-d4) δ 8.25 (s, 1H), 8.04 (dd, J=9.5, 2.1 Hz, 1H), 7.20 (d, J=9.4 Hz, 1H), 4.77-4.62 (m, 1H), 4.49-4.36 (m, 1H), 4.16 (d, J=3.8 Hz, 1H), 3.28 (d, J=6.5 Hz, 3H), 2.75 (td, J=14.0, 7.5 Hz, 2H), 2.65 (ddt, J=11.9, 7.8, 3.8 Hz, 2H), 2.36 (dt, J=5.1, 3.0 Hz, 1H), 2.32 (s, 3H), 1.11 (d, J=7.0 Hz, 3H), 0.89 (d, J=6.9 Hz, 3H).

Compound 535. (S)-7-isopropyl-4,8-dimethyl-2-((trans-3-((3,4,5-trifluorobenzyl)amino)cyclobutyl)amino)-7,8-dihydropteridin-6(5H)-one ¹H NMR (400 MHz, Methanol-d4) δ 7.50-7.34 (m, 2H), 4.79-4.67 (m, 1H), 4.19 (s, 2H), 4.16 (d, J=3.8 Hz, 1H), 4.08-3.94 (m, 1H), 3.28 (s, 3H), 2.85-2.76 (m, 2H), 2.67-2.59 (m, 2H), 2.37-2.32 (m, 1H), 2.32 (d, J=6.8 Hz, 3H), 1.11 (d, J=7.0 Hz, 3H), 0.89 (d, J=6.9 Hz, 3H).

Compound 540. (S)-7-isopropyl-4,8-dimethyl-2-((trans-3-((2-(trifluoromethyl)pyrimidin-4-yl)amino)cyclobutyl)amino)-7,8-dihydropteridin-6(5H)-one ¹H NMR (400 MHz, Methanol-d4) δ 8.18 (s, 1H), 6.87 (d, J=5.7 Hz, 1H), 4.75 (s, 1H), 4.60 (s, 1H), 4.15 (d, J=3.8 Hz, 1H), 3.27 (s, 3H), 2.70-2.53 (m, 4H), 2.38-2.32 (m, 1H), 2.32 (s, 3H), 1.11 (d, J=7.0 Hz, 3H), 0.89 (d, J=6.9 Hz, 3H).

Compound 555. (S)-7-isopropyl-4,8-dimethyl-2-((trans-3-((6-(trifluoromethyl)pyridazin-3-yl)amino)cyclobutyl)amino)-7,8-dihydropteridin-6(5H)-one ¹H NMR (400 MHz, Methanol-d4) δ 7.89 (d, J=9.6 Hz, 1H), 7.52 (d, J=9.6 Hz, 1H), 4.69 (p, J=7.2 Hz, 1H), 4.53-4.39 (m, 1H), 4.15 (d, J=3.8 Hz, 1H), 3.29 (d, J=7.5 Hz, 3H), 2.87-2.58 (m, 4H), 2.37 (ddd, J=11.2, 9.3, 6.2 Hz, 1H), 2.32 (s, 3H), 1.11 (d, J=7.0 Hz, 3H), 0.89 (d, J=6.9 Hz, 3H).

Compound 558. (S)-7-isopropyl-4,8-dimethyl-2-((trans-3-((5-(trifluoromethyl)pyrazin-2-yl)amino)cyclobutyl)amino)-7,8-dihydropteridin-6(5H)-one ¹H NMR (400 MHz, Methanol-d4) δ 8.25 (d, J=0.5 Hz, 1H), 8.15 (d, J=0.8 Hz, 1H), 4.62 (dd, J=13.7, 6.8 Hz, 1H), 4.54-4.41 (m, 1H), 4.16 (d, J=3.8 Hz, 1H), 3.28 (s, 3H), 2.72-2.51 (m, 4H), 2.40-2.34 (m, 1H), 2.32 (s, 3H), 1.11 (d, J=7.0 Hz, 3H), 0.89 (d, J=6.9 Hz, 3H)

Compound 579. (S)-4,7,8-trimethyl-2-((trans-3-((5-(trifluoromethyl)pyrazin-2-yl)amino)cyclobutyl)amino)-7,8-dihydropteridin-6(5H)-one ¹H NMR (400 MHz, Methanol-d₄) δ 8.40-8.18 (m, 1H), 8.16 (d, J=1.3 Hz, 1H), 4.61 (t, J=7.1 Hz, 1H), 4.48 (dtd, J=7.2, 3.4, 1.8 Hz, 1H), 4.30 (q, J=6.9 Hz, 1H), 3.25 (s, 3H), 2.75-2.49 (m, 3H), 2.33 (s, 3H), 1.53 (d, J=7.0 Hz, 3H)

Compound 587. (S)-7-isopropyl-4,8-dimethyl-2-((trans-3-((6-(trifluoromethyl)pyridin-3-yl)amino)cyclobutyl)amino)-7,8-dihydropteridin-6(5H)-one ¹H NMR (400 MHz, Methanol-d₄) δ 7.98 (d, J=2.7 Hz, 1H), 7.50 (d, J=8.7 Hz, 1H), 6.97 (dd, J=8.6, 2.7 Hz, 1H), 4.61 (t, J=7.1 Hz, 1H), 4.13 (d, J=3.8 Hz, 1H), 4.08 (s, 1H), 3.25 (s, 3H), 2.69-2.41 (m, 4H), 2.32 (s, 3H), 1.11 (d, J=6.9 Hz, 3H), 0.89 (d, J=6.9 Hz, 3H).

Example 2LL

General Scheme and Procedure for Preparation of Examples in Table 36

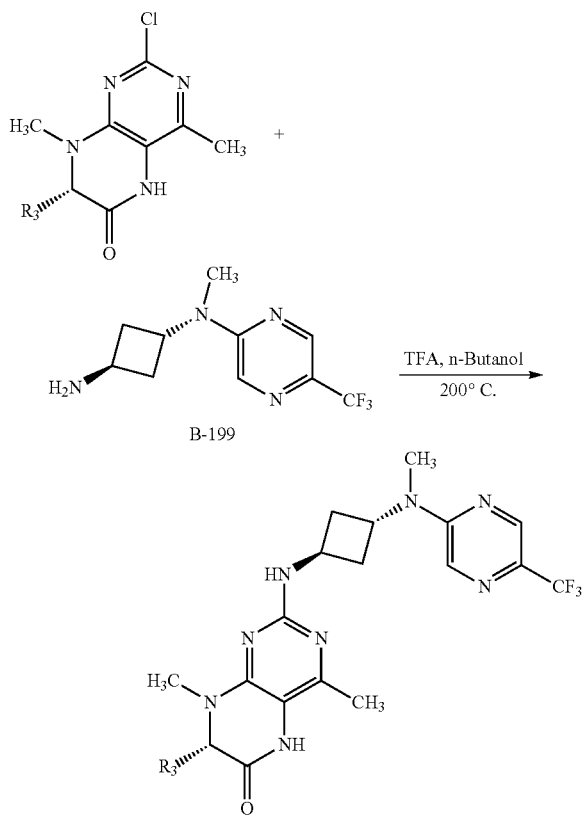

General Procedure for Examples in Table 36

The compounds were prepared via reaction of Intermediate A-# (1 equiv) and trans-N1-methyl-N1-(5-(trifluoromethyl)pyrazin-2-yl)cyclobutane-1,3-diamine hydrochloride (B-199) (1.2 equiv) via the procedure described for examples in Table 27 to provide the desired products.

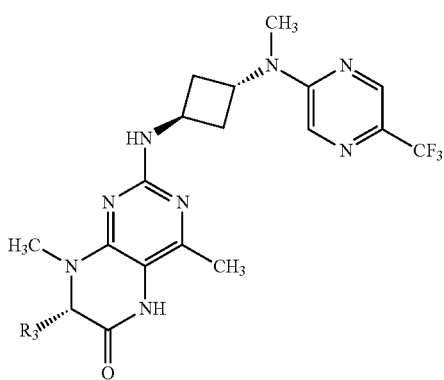

TABLE 36

| Comp. No. | $R_3$ | Int A | $[\alpha]_D$ | M + 1 |
|---|---|---|---|---|
| 655 | iPr | A-9 | 81.2 c = 1.0 DMSO | 465.32 |
| 681 | (R)—CH(OCH3)CH3 | A-59 | 49.7 c = 1.0 DMSO | 481.34 |

TABLE 36-continued

| Comp. No. | $R_3$ | Int A | $[\alpha]_D$ | M + 1 |
|---|---|---|---|---|
| 682 | Et | A-8 | 33.3 c = 1.0 DMSO | 451.57 |
| 683 | Me | A-2 | 9.9 c = 1.0 DMSO | 437.56 |

Compound 655. (7S)-7-isopropyl-4,8-dimethyl-2-((trans-3-(methyl(5-(trifluoromethyl)pyrazin-2-yl)amino)cyclobutyl)amino)-7,8-dihydropteridin-6(5H)-one $^1$H NMR (400 MHz, Chloroform-d) δ 8.90 (s, 1H), 8.38 (s, 1H), 8.00 (d, J=1.4 Hz, 1H), 5.16-4.94 (m, 2H), 4.35 (td, J=8.1, 4.2 Hz, 1H), 3.89 (d, J=4.4 Hz, 1H), 3.19 (s, 3H), 3.12 (s, 3H), 2.64 (dtd, J=11.9, 7.5, 3.7 Hz, 2H), 2.43 (d, J=3.0 Hz, 1H), 2.23 (s, 3H), 1.08 (d, J=6.9 Hz, 3H), 0.94 (d, J=6.9 Hz, 3H)

Compound 681. (S)-7-((R)-1-methoxyethyl)-4,8-dimethyl-2-((trans-3-(methyl(5-(trifluoromethyl)pyrazin-2-yl)amino)cyclobutyl)amino)-7,8-dihydropteridin-6(5H)-one $^1$H NMR (400 MHz, Methanol-d$_4$) δ 8.37 (dd, J=1.5, 0.8 Hz, 1H), 8.27-8.15 (m, 1H), 5.28-5.14 (m, 1H), 4.39 (d, J=8.4 Hz, 1H), 4.23 (d, J=3.9 Hz, 1H), 3.80 (qd, J=6.5, 3.9 Hz, 1H), 3.33 (s, 3H), 3.29 (s, 3H), 3.23 (s, 3H), 2.88-2.67 (m, 2H), 2.53 (dq, J=10.1, 6.4, 5.3 Hz, 2H), 2.34 (s, 3H), 1.29 (d, J=6.5 Hz, 3H).

Compound 682. (S)-7-ethyl-4,8-dimethyl-2-((trans-3-(methyl(5-(trifluoromethyl)pyrazin-2-yl)amino)cyclobutyl)amino)-7,8-dihydropteridin-6(5H)-one $^1$H NMR (400 MHz, Methanol-d$_4$) δ8.37 (s, 1H), 8.19 (d, J=1.3 Hz, 1H), 5.23 (p, J=8.2 Hz, 1H), 4.43 (ddt, J=16.9, 8.5, 4.2 Hz, 1H), 4.34 (dd, J=5.8, 3.4 Hz, 1H), 3.24 (2s, 6H), 2.90-2.76 (m, 2H), 2.54 (tt, J=7.9, 3.5 Hz, 2H), 2.35 (s, 3H), 2.05 (tdd, J=21.1, 10.7, 5.3 Hz, 2H), 0.87 (t, J=7.4 Hz, 3H).

Compound 683. (S)-4,7,8-trimethyl-2-((trans-3-(methyl(5-(trifluoromethyl)pyrazin-2-yl)amino)cyclobutyl)amino)-7,8-dihydropteridin-6(5H)-one $^1$H NMR (400 MHz, Methanol-d$_4$) δ 8.36 (s, 1H), 8.18 (d, J=1.3 Hz, 1H), 5.23 (t, J=8.2 Hz, 1H), 4.42 (td, J=8.4, 7.7, 4.1 Hz, 1H), 4.32 (q, J=6.9 Hz, 1H), 3.23 (s, 3H), 2.87-2.74 (m, 2H), 2.54 (tt, J=8.5, 3.7 Hz, 2H), 2.36 (s, 3H), 1.54 (d, J=6.9 Hz, 3H).

Example 2MM

General Scheme and Procedure for Preparation of Examples in Table 37

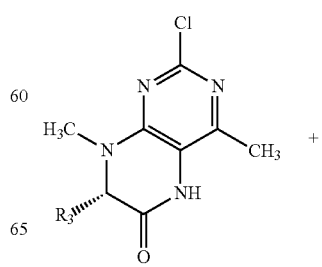

-continued

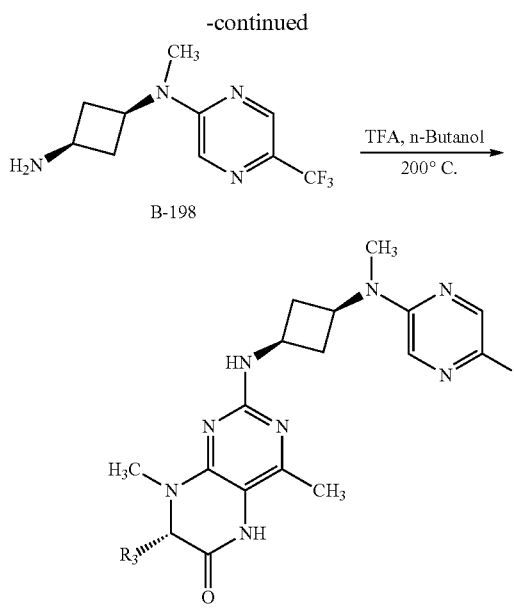

General Procedure for Examples in Table 37

The compounds were prepared via reaction of Intermediate A-# (1 equiv) and cis-N1-methyl-N1-(5-(trifluoromethyl)pyrazin-2-yl)cyclobutane-1,3-diamine hydrochloride (B-198) (1.2 equiv) via the procedure described for examples in Table 27 to provide the desired products.

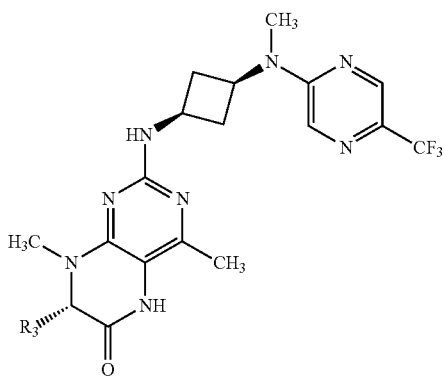

TABLE 37

| Comp. No. | $R_3$ | Int A | $[\alpha]_D$ | M + 1 |
|---|---|---|---|---|
| 652 | iPr | A-9 | 76.2 c = 10 DMSO | 465.27 |
| 653 | Me | A-2 | 40.2 c = 1.0 DMSO | 437.22 |
| 651 | (R)—CH(OCH3)CH3 | A-59 | 65.2 c = 1.0 DMSO | 481.34 |
| 654 | Et | A-8 | | 451.32 |

Compound 652. (S)-7-isopropyl-4,8-dimethyl-2-((cis-3-(methyl(5-(trifluoromethyl)pyrazin-2-yl)amino)cyclobutyl)amino)-7,8-dihydropteridin-6(5H)-one $^1$H NMR (400 MHz, Chloroform-d) δ 9.28 (s, 1H), 8.37 (d, J=1.3 Hz, 1H), 8.03 (d, J=1.4 Hz, 1H), 4.96 (d, J=7.1 Hz, 1H), 4.52 (tt, J=9.5, 7.2 Hz, 1H), 4.21 (dtd, J=8.9, 7.1, 1.8 Hz, 1H), 3.88 (d, J=4.4 Hz, 1H), 2.86 (dtt, J=11.7, 5.7, 1.6 Hz, 2H), 2.23 (s, 3H), 2.08 (dtd, J=11.5, 9.3, 2.1 Hz, 2H), 1.07 (d, J=7.0 Hz, 3H), 0.93 (d, J=7.0 Hz, 3H).

Compound 653. (S)-4,7,8-trimethyl-2-((cis-3-(methyl(5-(trifluoromethyl)pyrazin-2-yl)amino)cyclobutyl)amino)-7,8-dihydropteridin-6(5H)-one $^1$H NMR (400 MHz, Chloroform-d) δ 8.40 (s, 1H), 8.16 (s, 1H), 8.05 (d, J=1.5 Hz, 1H), 4.87 (d, J=7.1 Hz, 1H), 4.54 (tt, J=9.6, 7.2 Hz, 1H), 4.31-4.17 (m, 1H), 4.09 (q, J=6.8 Hz, 1H), 3.14 (s, 3H), 3.07 (s, 3H), 2.88 (dt, J=11.5, 6.9 Hz, 2H), 2.24 (s, 3H), 2.16-2.04 (m, 2H), 1.42 (d, J=6.8 Hz, 3H).

Compound 651. (S)-7-((R)-1-methoxyethyl)-4,8-dimethyl-2-((cis-3-(methyl(5-(trifluoromethyl)pyrazin-2-yl)amino)cyclobutyl)amino)-7,8-dihydropteridin-6(5H)-one $^1$H NMR (400 MHz, Chloroform-d) δ 8.96 (s, 1H), 8.47-8.31 (m, 1H), 8.04 (d, J=1.4 Hz, 1H), 5.09 (d, J=7.1 Hz, 1H), 4.54 (tt, J=9.6, 7.2 Hz, 1H), 4.22 (dtd, J=8.9, 7.1, 1.8 Hz, 1H), 3.95 (d, J=6.1 Hz, 1H), 3.58 (p, J=6.3 Hz, 1H), 3.20 (s, 3H), 3.13 (s, 3H), 2.92-2.83 (m, 2H), 2.25 (s, 3H), 2.10 (dtd, J=13.1, 10.8, 10.1, 2.9 Hz, 2H), 1.25 (d, J=6.4 Hz, 3H).

Compound 654. (7S)-7-ethyl-4,8-dimethyl-2-((cis-3-(methyl(5-(trifluoromethyl)pyrazin-2-yl)amino)cyclobutyl)amino)-7,8-dihydropteridin-6(5H)-one $^1$H NMR (400 MHz, Chloroform-d) δ 8.44-8.34 (m, 1H), 8.21 (s, 1H), 8.05 (d, J=1.5 Hz, 1H), 4.88 (d, J=7.2 Hz, 1H), 4.54 (tt, J=9.5, 7.2 Hz, 1H), 4.34-4.19 (m, 1H), 4.08 (dd, J=6.5, 3.8 Hz, 1H), 3.14 (s, 3H), 3.09 (s, 3H), 2.92-2.79 (m, 2H), 2.22 (s, 3H), 2.17-1.77 (m, 4H), 0.92 (t, J=7.5 Hz, 3H)

Example 2NN

General Procedure for Examples in Table 38

The compounds were prepared via reaction of Intermediate A-# (1 equiv) and cis-N1-(5-(trifluoromethyl)pyrazin-2-yl)cyclobutane-1,3-diamine hydrochloride, B-209 (1.2 equiv) via the procedure described for examples in Table L to provide the desired products.

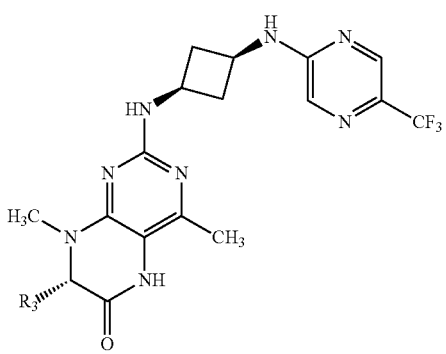

TABLE 38

| Comp. No. | R3 | Int A | [α]D | M + 1 |
|---|---|---|---|---|
| 557 | iPr | A-9 | 72.4 c = 1.0 DMSO | 451.22 |
| 578 | Me | A-2 | 14.9 c = 1.0 DMSO | 422.9 |
| 647 | (R)-CH(OCH3)CH3 | A-59 | 39.5 c = 1.0 DMSO | 467.24 |
| 648 | -Et | A-8 | | 435.19 |
| 672 | 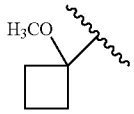 | A-66 | | 493.27 |

Compound 557. (S)-7-isopropyl-4,8-dimethyl-2-((cis-3-((5-(trifluoromethyl)pyrazin-2-yl)amino)cyclobutyl)amino)-7,8-dihydropteridin-6(5H)-one $^1$H NMR (400 MHz, Methanol-d4) δ 8.27 (d, J=0.6 Hz, 1H), 7.99 (d, J=1.2 Hz, 1H), 4.33-4.18 (m, 2H), 4.16 (d, J=3.8 Hz, 1H), 3.29 (s, 3H), 3.03-2.85 (m, 2H), 2.38-2.31 (m, 1H), 2.31 (s, 3H), 2.16-2.00 (m, 2H), 1.11 (d, J=7.0 Hz, 3H), 0.89 (d, J=6.9 Hz, 3H).

Compound 578. (S)-4,7,8-trimethyl-2-((cis-3-((5-(trifluoromethyl)pyrazin-2-yl)amino)cyclobutyl)amino)-7,8-dihydropteridin-6(5H)-one $^1$H NMR (400 MHz, Methanol-d$_4$) δ 8.31 (s, 1H), 8.28-8.13 (m, 1H), 4.41-4.26 (m, 2H), 4.20 (tt, J=8.7, 7.2 Hz, 1H), 3.27 (s, 3H), 3.10-2.91 (m, 2H), 2.33 (s, 3H), 2.22 (dtt, J=10.6, 7.1, 1.8 Hz, 2H), 1.53 (d, J=6.9 Hz, 3H).

Compound 647. (S)-7-((R)-1-methoxyethyl)-4,8-dimethyl-2-((cis-3-((5-(trifluoromethyl)pyrazin-2-yl)amino)cyclobutyl)amino)-7,8-dihydropteridin-6(5H)-one $^1$H NMR (400 MHz, Methanol-d$_4$) δ 8.35-8.20 (m, 1H), 8.04 (d, J=1.3 Hz, 1H), 4.34-4.27 (m, 1H), 4.23 (d, J=3.9 Hz, 1H), 3.79 (tt, J=6.5, 3.2 Hz, 1H), 3.35 (s, 3H), 3.29 (s, 3H), 2.99 (dddd, J=12.8, 7.0, 5.7, 1.7 Hz, 2H), 2.31 (d, J=8.0 Hz, 3H), 2.21-2.04 (m, 2H), 1.29 (d, J=6.5 Hz, 3H)

Compound 648. (S)-7-ethyl-4,8-dimethyl-2-((cis-3-((5-(trifluoromethyl)pyrazin-2-yl)amino)cyclobutyl)amino)-7,8-dihydropteridin-6(5H)-one $^1$H NMR (400 MHz, Methanol-d$_4$) δ 8.28 (s, 1H), 7.91 (d, J=1.5 Hz, 1H), 4.33 (dd, J=5.7, 3.4 Hz, 1H), 4.23 (q, J=8.7, 7.3 Hz, 2H), 3.25 (s, 3H), 2.97 (t, J=5.7 Hz, 2H), 2.30 (s, 3H), 2.11-1.99 (m, 1H), 0.86 (dd, J=7.5, 3.2 Hz, 3H).

Compound 672. 7-(1-methoxycyclobutyl)-4,8-dimethyl-2-((cis-3-((5-(trifluoromethyl)pyrazin-2-yl)amino)cyclobutyl)amino)-7,8-dihydropteridin-6(5H)-one $^1$H NMR (400 MHz, DMSO-d6) δ 9.91 (s, 1H), 6.94-6.79 (m, 2H), 6.69 (d, J=6.8 Hz, 1H), 4.84 (td, J=6.6, 3.3 Hz, 1H), 4.39 (dd, J=13.2, 6.4 Hz, 1H), 4.21 (s, 1H), 3.10 (s, 3H), 3.06 (d, J=4.5 Hz, 3H), 2.40 (dd, J=13.8, 9.7 Hz, 1H), 2.37-2.28 (m, 2H), 2.23 (dd, J=9.0, 3.5 Hz, 1H), 2.18-2.05 (m, 5H), 1.98 (dd, J=18.6, 8.9 Hz, 1H), 1.70 (ddd, J=20.2, 10.2, 4.7 Hz, 1H), 1.56 (dt, J=9.0, 7.9 Hz, 1H).

Example 200

General Procedure for Examples in Table 39

The compounds were prepared via reaction of Intermediate A-# (1 equiv) and cis-N1-(5-(trifluoromethyl)pyrazin-2-yl)cyclobutane-1,3-diamine hydrochloride, B-212 (1.2 equiv) via the procedure described for examples in Table L to provide the desired products.

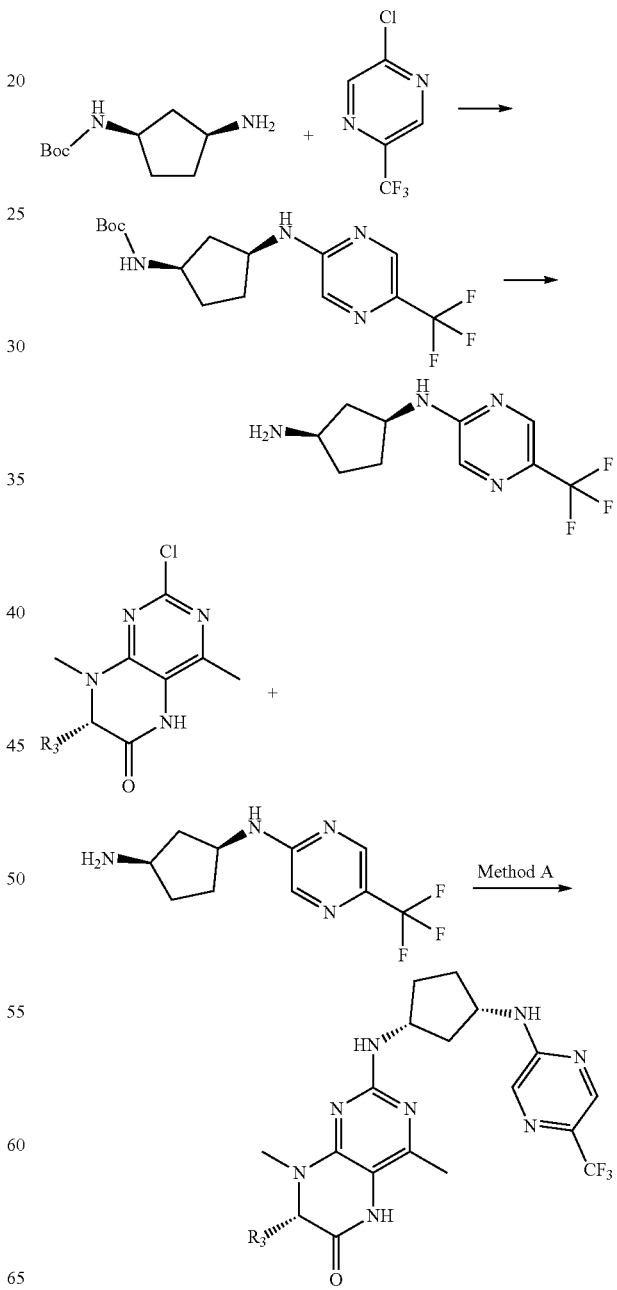

TABLE 39

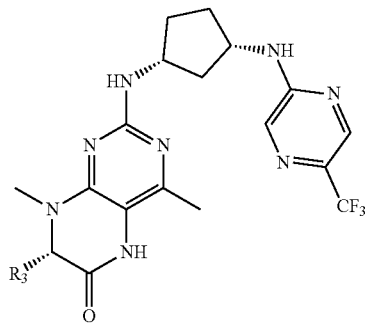

| Comp. No. | R₃ | Int A | [α]$_D$ | M + 01 |
|---|---|---|---|---|
| 738 | -Et | A-8 | | 451.29 |
| 737 | —CH3 | A-2 | | 437.29 |
| 736 | (R)-CH(OCH3)CH3 | A-59 | | 481.31 |
| 735 | iPr | A-9 | 76.9 c = 1.0 MeOH | 465.45 |

Compound 738. (S)-7-ethyl-4,8-dimethyl-2-(((1R,3S)-3-((5-(trifluoromethyl)pyrazin-2-yl)amino)cyclopentyl)amino)-7,8-dihydropteridin-6(5H)-one $^1$H NMR (400 MHz, Methanol-d$_4$) δ 8.29-8.22 (m, 1H), 8.20 (d, J=1.4 Hz, 1H), 4.51-4.42 (m, 1H), 4.33 (dt, J=6.4, 3.3 Hz, 2H), 3.26 (s, 3H), 2.69 (dt, J=14.2, 7.4 Hz, 1H), 2.31 (s, 3H), 2.23-2.18 (m, 1H), 2.12-2.00 (m, 2H), 1.92-1.86 (m, 2H), 1.71 (dt, J=13.7, 6.9 Hz, 1H), 0.91-0.83 (m, 3H).

Compound 737. (S)-4,7,8-trimethyl-2-(((1R,3S)-3-((5-(trifluoromethyl)pyrazin-2-yl)amino)cyclopentyl)amino)-7,8-dihydropteridin-6(5H)-one $^1$H NMR (400 MHz, Methanol-d$_4$) δ8.28-8.21 (m, 1H), 8.18 (d, J=1.3 Hz, 1H), 4.44 (qd, J=6.9, 4.3 Hz, 1H), 4.36-4.25 (m, 2H), 3.26 (s, 3H), 2.73-2.64 (m, 1H), 2.32 (s, 3H), 2.20 (td, J=6.6, 4.4 Hz, 2H), 1.93-1.86 (m, 2H), 1.75-1.67 (m, 1H), 1.53 (dd, J=7.0, 2.0 Hz, 3H).

Compound 736. (S)-7-((R)-1-methoxyethyl)-4,8-dimethyl-2-(((1R,3S)-3-((5-(trifluoromethyl)pyrazin-2-yl)amino)cyclopentyl)amino)-7,8-dihydropteridin-6(5H)-one $^1$H NMR (400 MHz, Methanol-d$_4$) δ 8.31-8.22 (m, 1H), 8.11 (d, J=1.3 Hz, 1H), 4.46-4.41 (m, 1H), 4.35-4.29 (m, 1H), 4.23 (d, J=3.9 Hz, 1H), 3.79 (qd, J=6.4, 3.9 Hz, 1H), 3.35 (s, 3H), 3.30 (s, 3H), 2.74-2.64 (m, 1H), 2.31 (s, 3H), 2.24-2.16 (m, 2H), 1.94-1.85 (m, 2H), 1.68 (dt, J=13.7, 7.1 Hz, 1H), 1.29 (d, J=6.5 Hz, 3H).

Compound 735. (S)-7-isopropyl-4,8-dimethyl-2-(((1R,3S)-3-((5-(trifluoromethyl)pyrazin-2-yl)amino)cyclopentyl)amino)-7,8-dihydropteridin-6(5H)-one $^1$H NMR (400 MHz, Methanol-d$_4$) δ 8.24 (t, J=1.0 Hz, 1H), 8.21 (d, J=1.3 Hz, 1H), 4.44 (p, J=6.8 Hz, 1H), 4.36-4.29 (m, 1H), 4.15 (d, J=3.8 Hz, 1H), 3.29 (s, 3H), 2.69 (dt, J=13.4, 7.4 Hz, 1H), 2.35 (ddd, J=10.9, 7.0, 3.6 Hz, 1H), 2.31 (s, 3H), 2.25-2.16 (m, 2H), 1.96-1.84 (m, 2H), 1.72 (dt, J=13.6, 6.9 Hz, 1H), 1.11 (d, J=7.0 Hz, 3H), 0.90 (d, J=6.9 Hz, 3H).

Example 2PP

General Scheme and Procedure for Preparation of Examples in Table 40

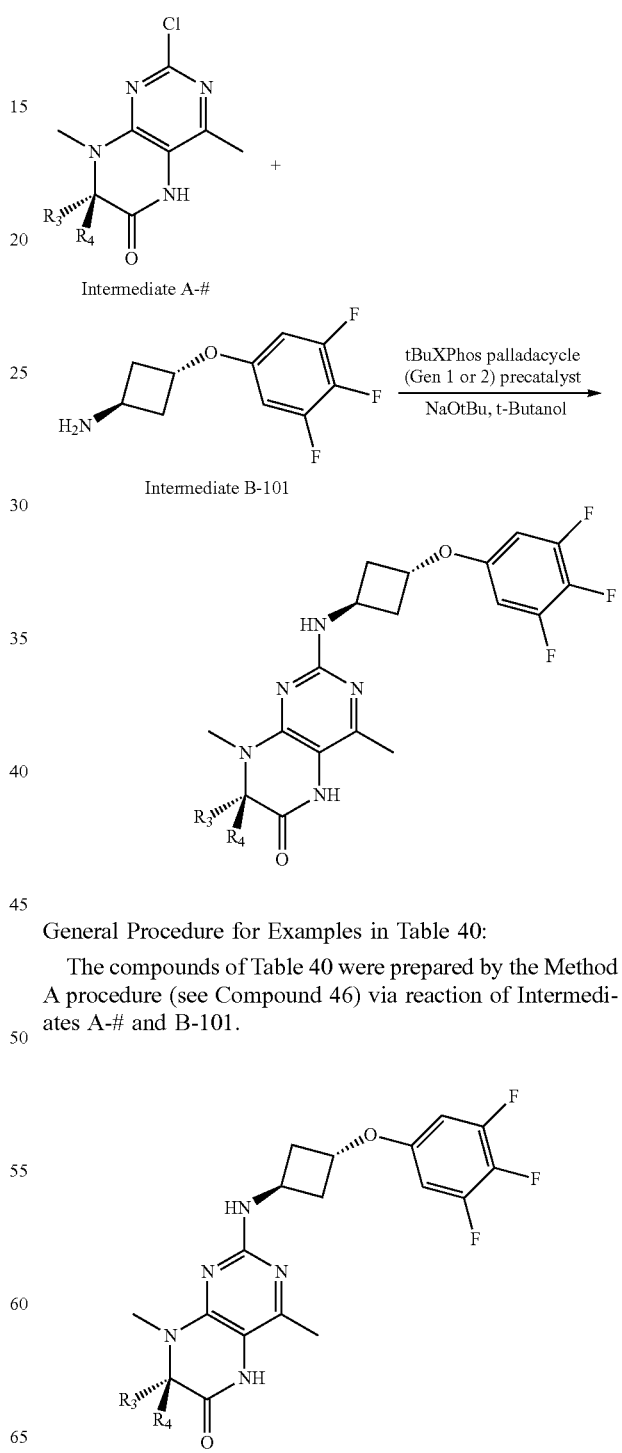

General Procedure for Examples in Table 40:

The compounds of Table 40 were prepared by the Method A procedure (see Compound 46) via reaction of Intermediates A-# and B-101.

TABLE 40

| Comp. No. | R3 = <br> R4 = | [α]D | M + 1 |
|---|---|---|---|
| 745 | R3 = (S)-CH(OtBu)CH3 <br> R4 = H | | 494.35 |
| 720 | R3 = —CH3 <br> R4 = —CH2OCH3 | −45.9 c = 0.5 MeOH | 452.27 |
| 719 | R3 = —CH2OCH3 <br> R4 = —CH3 | 46.8 c = 0.7 MeOH | 452.27 |
| 677 | R3 = —CH2OH <br> R4 = H | 43.6 c = 0.5 DMSO | 424.8 |
| 674 | R3 = —CH2OtBu <br> R4 = H | 46.4 c = 0.5 CHCl3 | 480.43 |
| 667 | R3 = H3CO-cyclobutyl <br> R4 = H | 9.6 c = 0.5 MeOH | 478.19 |
| 599 | R3 = (R)-CH(OCH3)CH3 <br> R4 = H | 63.9 c = 1.0 DMSO | 452.31 |

Compound 745. (S)-7-((S)-1-(tert-butoxy)ethyl)-4,8-dimethyl-2-(((1r,3S)-3-(3,4,5-trifluorophenoxy)cyclobutyl)amino)-7,8-dihydropteridin-6(5H)-one ¹H NMR (400 MHz, Chloroform-d) δ 6.43 (dd, J=9.2, 5.7 Hz, 2H), 4.79 (p, J=5.2 Hz, 1H), 4.59 (d, J=6.3 Hz, 1H), 4.21-4.07 (m, 3H), 4.04 (d, J=2.1 Hz, 2H), 3.29 (s, 3H), 2.61 (s, 4H), 2.37 (s, 3H), 1.27 (d, J=6.4 Hz, 3H), 1.10 (s, 9H).

Compound 720. 7-(methoxymethyl)-4,7,8-trimethyl-2-((trans-3-(3,4,5-trifluorophenoxy)cyclobutyl)amino)-7,8-dihydropteridin-6(5H)-one ¹H NMR (400 MHz, DMSO-d6) δ 9.80 (s, 1H), 6.90-6.77 (m, 2H), 6.66 (s, 1H), 4.83 (td, J=6.8, 3.5 Hz, 1H), 4.38 (q, J=6.8 Hz, 1H), 3.60 (dd, J=45.4, 10.0 Hz, 2H), 3.20 (s, 3H), 2.47-2.01 (m, 7H), 1.33 (s, 3H), 1.29-1.15 (m, 3H).

Compound 719. 7-(methoxymethyl)-4,7,8-trimethyl-2-((trans-3-(3,4,5-trifluorophenoxy)cyclobutyl)amino)-7,8-dihydropteridin-6(5H)-one ¹H NMR (400 MHz, DMSO-d6) δ 9.80 (s, 1H), 6.91-6.77 (m, 2H), 6.66 (d, J=6.9 Hz, 1H), 4.84 (td, J=6.7, 3.4 Hz, 1H), 4.38 (q, J=6.9 Hz, 1H), 3.66 (d, J=10.1 Hz, 1H), 3.54 (d, J=10.0 Hz, 1H), 3.20 (s, 3H), 2.96 (s, 3H), 2.47-2.29 (m, 4H), 2.10 (s, 3H), 1.33 (s, 3H), 1.27-1.12 (m, 3H).

Compound 677. (S)-7-(hydroxymethyl)-4,8-dimethyl-2-((trans-3-(3,4,5-trifluorophenoxy)cyclobutyl)amino)-7,8-dihydropteridin-6(5H)-one ¹H NMR (300 MHz, DMSO-d6) δ 6.96-6.75 (m, 2H), 6.62 (d, J=6.9 Hz, 1H), 4.97 (t, J=5.3 Hz, 1H), 4.39 (d, J=6.6 Hz, 1H), 3.97 (t, J=2.7 Hz, 1H), 3.70 (dd, J=11.8, 6.9 Hz, 2H), 3.17 (dd, J=5.2, 1.7 Hz, 1H), 2.99 (d, J=1.7 Hz, 3H), 2.47-2.22 (m, 4H), 2.08 (d, J=1.7 Hz, 3H).

Compound 674. (S)-7-(tert-butoxymethyl)-4,8-dimethyl-2-((trans-3-(3,4,5-trifluorophenoxy)cyclobutyl)amino)-7,8-dihydropteridin-6(5H)-one ¹H NMR (300 MHz, Chloroform-d) δ 8.93 (s, 1H), 6.41 (dd, J=9.4, 5.6 Hz, 2H), 5.04 (d, J=6.2 Hz, 1H), 4.75 (tt, J=7.4, 4.0 Hz, 1H), 4.55 (ddd, J=13.5, 6.7, 3.8 Hz, 1H), 4.09 (q, J=3.1 Hz, 1H), 3.71 (d, J=3.6 Hz, 2H), 3.09 (s, 3H), 2.59 (ddt, J=15.3, 7.3, 3.4 Hz, 2H), 2.42 (dt, J=13.3, 6.3 Hz, 2H), 2.21 (d, J=2.9 Hz, 3H), 1.05 (d, J=3.3 Hz, 9H).

Compound 667. 7-(1-methoxycyclobutyl)-4,8-dimethyl-2-(((trans-3-(3,4,5-trifluorophenoxy)cyclobutyl)amino)-7,8-dihydropteridin-6(5H)-one ¹H NMR (400 MHz, DMSO-d6) δ 9.91 (s, 1H), 6.94-6.79 (m, 2H), 6.69 (d, J=6.8 Hz, 1H), 4.84 (td, J=6.6, 3.3 Hz, 1H), 4.39 (dd, J=13.2, 6.4 Hz, 1H), 4.21 (s, 1H), 3.10 (s, 3H), 3.06 (d, J=4.5 Hz, 3H), 2.40 (dd, J=13.8, 9.7 Hz, 1H), 2.37-2.28 (m, 2H), 2.23 (dd, J=9.0, 3.5 Hz, 1H), 2.18-2.05 (m, 5H), 1.98 (dd, J=18.6, 8.9 Hz, 1H), 1.70 (ddd, J=20.2, 10.2, 4.7 Hz, 1H), 1.56 (dt, J=9.0, 7.9 Hz, 1H).

Compound 599. (S)-7-((R)-1-methoxyethyl)-4,8-dimethyl-2-((trans-3-(3,4,5-trifluorophenoxy)cyclobutyl)amino)-7,8-dihydropteridin-6(5H)-one ¹H NMR (400 MHz, Chloroform-d) δ 9.25 (s, 1H), 6.48-6.24 (m, 2H), 5.11 (d, J=6.1 Hz, 1H), 4.74 (tt, J=7.1, 4.0 Hz, 1H), 4.56 (td, J=8.1, 5.7 Hz, 1H), 3.94 (d, J=6.1 Hz, 1H), 3.57 (p, J=6.3 Hz, 1H), 3.30 (s, 3H), 3.18 (s, 3H), 2.59 (ddt, J=12.4, 8.4, 4.2 Hz, 2H), 2.51-2.39 (m, 2H), 2.25 (s, 3H), 1.25 (dd, J=12.1, 4.0 Hz, 6H).

Example 2QQ

General Scheme and Procedure for Preparation of Examples in Table 41

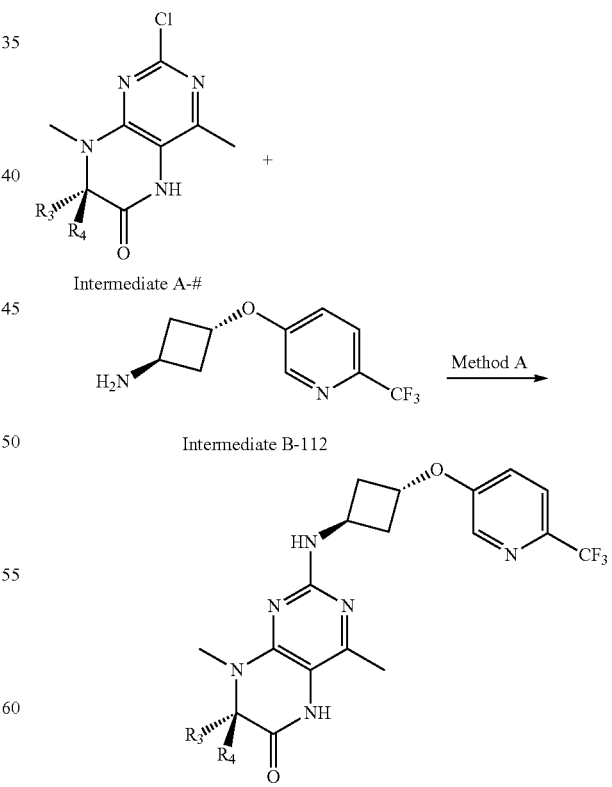

Procedure for the examples in Table 41 were prepared by the Method A procedure (see Compound 46) via reaction of Intermediates A-# and B-112.

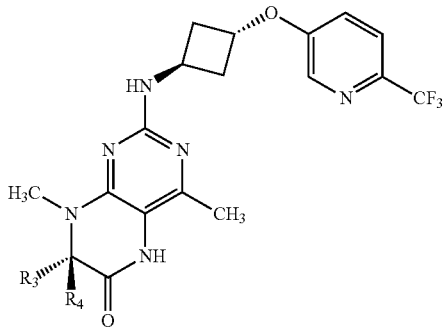

TABLE 41

| Comp. No. | R₃ | R₄ | Int A | [α]$_D$ | M + 1 |
|---|---|---|---|---|---|
| 748 | —CH₃ | H | A-3 (R₁ = CH₃) | | 437.29 |
| 725 | CH₂OtBu | H | A-63 (R₁ = H) | | 495.47 |
| | | | A-66 | 119.1 | |
| 669 | ⤳—[1-methoxycyclobutyl] | H | (R₁ = H) | c = 1.0 MeOH 36.8 | 507.27 |
| 685 | -iPr | H | A-9 (R₁ = H) | c = 1.0 DMSO 40.0 | 451.22 |
| 684 | -(R)-CH(OCH₃)CH₃ | H | A-59 (R₁ = H) | c = 1.0 DMSO 23.8 | 467.28 |
| 686 | —CH₂CH₃ | H | A-8 (R₁ = H) | c = 1.0 DMSO 52.4 | 437.21 |
| 724 | —CH₂OCH₃ | —CH₃ | A-69 (R₁ = H) | c = 0.5 MeOH | 467.3 |

Compound 748. (7S)-4,5,7,8-tetramethyl-2-((trans-3-(((6-(trifluoromethyl)pyridin-3-yl)oxy)cyclobutyl)amino)-7,8-dihydropteridin-6(5H)-one ¹H NMR (400 MHz, Methanol-d4) δ 8.37 (d, J=2.7 Hz, 1H), 7.83 (d, J=8.8 Hz, 1H), 7.61-7.50 (m, 1H), 5.21-5.10 (m, 1H), 4.76-4.61 (m, 1H), 4.38-4.26 (m, 1H), 3.36 (s, 3H), 3.25 (s, 3H), 2.86-2.61 (m, 4H), 2.55 (s, 3H), 1.39 (d, J=7.0 Hz, 3H).

Compound 725. (S)-7-(tert-butoxymethyl)-4,8-dimethyl-2-((trans-3-((6-(trifluoromethyl)pyridin-3-yl)oxy)cyclobutyl)amino)-7,8-dihydropteridin-6(5H)-one ¹H NMR (300 MHz, Chloroform-d) δ 8.31 (d, J=3.0 Hz, 1H), 7.61 (d, J=8.6 Hz, 1H), 7.17 (dd, J=8.8, 2.9 Hz, 1H), 5.20-5.00 (m, 1H), 4.95 (tt, J=7.0, 4.0 Hz, 1H), 4.59 (dd, J=12.0, 6.1 Hz, 1H), 4.09 (t, J=3.2 Hz, 1H), 3.71 (d, J=3.4 Hz, 2H), 3.08 (d, J=4.2 Hz, 2H), 2.75-2.57 (m, 2H), 2.57-2.36 (m, 3H), 2.21 (d, J=2.9 Hz, 3H), 1.05 (d, J=4.3 Hz, 9H).

Compound 669. 7-(1-methoxycyclobutyl)-4,8-dimethyl-2-((trans-3-(((6-(trifluoromethyl)pyridin-3-yl)oxy)methyl)cyclobutyl)amino)-7,8-dihydropteridin-6(5H)-one ¹H NMR (400 MHz, DMSO-d6) δ 9.92 (s, 1H), 8.38 (d, J=2.8 Hz, 1H), 7.82 (d, J=8.7 Hz, 1H), 7.45 (dd, J=8.5, 2.7 Hz, 1H), 6.75 (s, 1H), 5.02 (s, 1H), 4.52-4.37 (m, 1H), 4.22 (s, 1H), 3.10 (s, 3H), 3.06 (s, 3H), 2.44-2.34 (m, 1H), 2.22 (d, J=3.8 Hz, 1H), 2.18-2.06 (m, 5H), 1.99 (d, J=9.4 Hz, 1H), 1.79-1.62 (m, 1H), 1.61-1.45 (m, 1H).

Compound 685. (S)-7-isopropyl-4,8-dimethyl-2-((trans-3-(((6-(trifluoromethyl)pyridin-3-yl)oxy)cyclobutyl)amino)-7,8-dihydropteridin-6(5H)-one ¹H NMR (400 MHz, DMSO-d6) δ 9.92 (s, 1H), 8.38 (d, J=2.8 Hz, 1H), 7.82 (d, J=8.7 Hz, 1H), 7.45 (dd, J=8.5, 2.7 Hz, 1H), 6.75 (s, 1H), 5.02 (s, 1H), 4.52-4.37 (m, 1H), 4.22 (s, 1H), 3.10 (s, 3H), 3.06 (s, 3H), 2.44-2.34 (m, 1H), 2.22 (d, J=3.8 Hz, 1H), 2.18-2.06 (m, 5H), 1.99 (d, J=9.4 Hz, 1H), 1.79-1.62 (m, 1H), 1.61-1.45 (m, 1H).

Compound 684. (S)-7-((R)-1-methoxyethyl)-4,8-dimethyl-2-((trans-3-((6-(trifluoromethyl)pyridin-3-yl)oxy)cyclobutyl)amino)-7,8-dihydropteridin-6(5H)-one ¹H NMR (300 MHz, Methanol-d₄) δ 8.31 (d, J=2.9 Hz, 1H), 7.75 (dd, J=8.9, 2.1 Hz, 1H), 7.44 (dd, J=8.7, 2.9 Hz, 1H), 5.13-5.01 (m, 1H), 4.68 (q, J=7.0 Hz, 1H), 4.23 (dd, J=3.9, 2.0 Hz, 1H), 3.79 (qd, J=6.5, 3.9 Hz, 1H), 3.32 (s, 3H), 3.29 (s, 3H), 2.70 (dq, J=7.4, 4.2 Hz, 4H), 2.33 (d, J=2.1 Hz, 3H), 1.29 (dd, J=6.5, 2.1 Hz, 3H)

Compound 686. (S)-7-ethyl-4,8-dimethyl-2-((trans-3-((6-(trifluoromethyl)pyridin-3-yl)oxy)cyclobutyl)amino)-7,8-dihydropteridin-6(5H)-one ¹H NMR (300 MHz, Methanol-d₄) δ 8.31 (d, J=2.7 Hz, 1H), 7.80-7.70 (m, 1H), 7.44 (dd, J=8.7, 2.8 Hz, 1H), 5.09 (t, J=5.4 Hz, 1H), 4.72-4.60 (m, 1H), 4.41-4.24 (m, 1H), 3.25 (s, 3H), 2.79-2.59 (m, 4H), 2.33 (d, J=1.5 Hz, 3H), 2.15-1.84 (m, 2H), 0.93-0.79 (m, 3H).

Compound 724. 7-(methoxymethyl)-4,7,8-trimethyl-2-((trans-3-((6-(trifluoromethyl)pyridin-3-yl)oxy)cyclobutyl)amino)-7,8-dihydropteridin-6(5H)-one ¹H NMR (400 MHz, DMSO-d6) δ 9.82 (s, 1H), 8.38 (d, J=2.8 Hz, 1H), 7.83 (d, J=8.7 Hz, 1H), 7.46 (dd, J=8.6, 2.8 Hz, 1H), 6.72 (s, 1H), 5.02 (s, 1H), 4.53-4.24 (m, 1H), 3.66 (d, J=10.0 Hz, 1H), 3.54 (d, J=10.1 Hz, 1H), 3.20 (s, 3H), 2.93 (d, J=31.5 Hz, 3H), 2.45-2.31 (m, 1H), 2.09 (d, J=7.1 Hz, 3H), 1.29 (d, J=36.9 Hz, 2H).

Example 2RR

General Scheme and Procedure for Preparation of Examples in Table 42

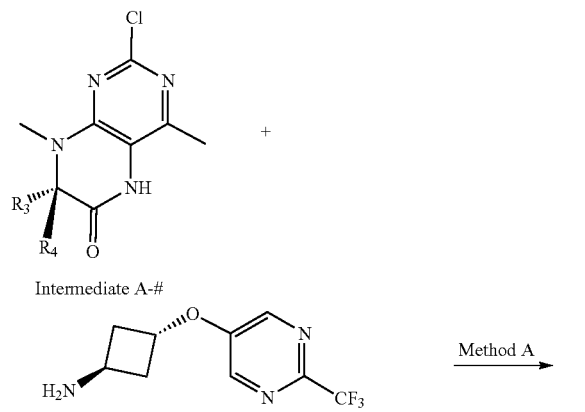

Intermediate A-#

Intermediate B-115

Method A

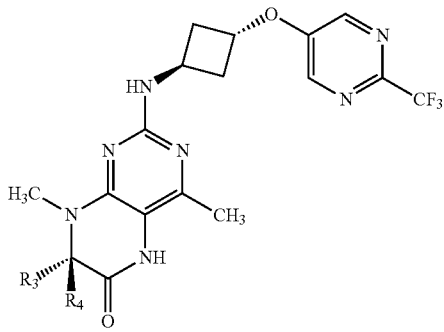

The examples in Table 42 were prepared by the Method A procedure (see Compound 46) via reaction of Intermediates A-# and B-115.

TABLE 42

| Appl. No. | $R_3 =$<br>$R_4 =$ | Int A | $[\alpha]_D$ | M + 1 |
|---|---|---|---|---|
| 645 | $R_3$ = Et<br>$R_4$ = H | A-8 | 19.8<br>c = 1.0<br>DMSO | 438.18 |
| 644 | $R_3$ = iPr<br>$R_4$ = H | A-9 | 30.3<br>c = 1.0<br>DMSO | 452.22 |

TABLE 42-continued

| Appl. No. | $R_3 =$<br>$R_4 =$ | Int A | $[\alpha]_D$ | M + 1 |
|---|---|---|---|---|
| 657 | $R_3$ = (R)-CH(OCH$_3$)CH$_3$<br>DMSO<br>$R_4$ = H | A-59 | 43.9<br>c = 1.0 | 468.29 |
| 718 | $R_3$ = H$_3$CO-cyclobutyl<br>$R_4$ = H | A-66 | 96.8<br>c = 0.5<br>MeOH | 494.31 |
| 710 | $R_3$ = —CH$_3$<br>$R_4$ = —CH$_2$OCH$_3$ | A-70 | −31.5<br>c = 0.6<br>MeOH | 468.25 |
| 706 | $R_3$ = —CH$_2$OCH$_3$<br>$R_4$ = —CH$_3$ | A-69 | 45.8<br>c = 0.7<br>MeOH | 468.25 |

Compound 645. (S)-7-ethyl-4,8-dimethyl-2-((trans-3-((2-(trifluoromethyl)pyrimidin-5-yl)oxy)cyclobutyl)amino)-7,8-dihydropteridin-6(5H)-one $^1$H NMR (400 MHz, Methanol-d$_4$) δ 8.55 (s, 2H), 5.17 (t, J=5.3 Hz, 1H), 4.67 (t, J=7.2 Hz, 1H), 4.33 (dd, J=5.8, 3.4 Hz, 1H), 3.23 (s, 3H), 2.73 (dp, J=7.3, 2.2 Hz, 4H), 2.32 (s, 3H), 2.13-1.93 (m, 2H), 0.86 (td, J=7.4, 2.9 Hz, 3H).

Compound 644. (S)-7-isopropyl-4,8-dimethyl-2-((cis-3-((2-(trifluoromethyl)pyrimidin-5-yl)oxy)cyclobutyl)amino)-7,8-dihydropteridin-6(5H)-one $^1$H NMR (400 MHz, Methanol-d$_4$) δ 8.56 (s, 2H), 5.18 (td, J=6.0, 3.0 Hz, 1H), 4.68 (q, J=7.1 Hz, 1H), 4.16 (d, J=3.8 Hz, 1H), 3.27 (s, 3H), 2.74 (qd, J=7.0, 6.4, 2.3 Hz, 4H), 2.33 (s, 3H), 1.11 (d, J=7.0 Hz, 3H), 0.89 (d, J=6.9 Hz, 3H)

Compound 657. (S)-7-((R)-1-methoxyethyl)-4,8-dimethyl-2-((trans-3-((2-(trifluoromethyl)pyrimidin-5-yl)oxy)cyclobutyl)amino)-7,8-dihydropteridin-6(5H)-one $^1$H NMR (400 MHz, Chloroform-d) δ 9.75 (s, 2H), 8.40 (s, 2H), 6.84 (s, 1H), 5.02 (tt, J=7.0, 3.8 Hz, 1H), 4.63 (ddt, J=14.0, 7.9, 6.0 Hz, 1H), 3.96 (d, J=5.6 Hz, 1H), 3.68-3.56 (m, 1H), 3.29 (s, 3H), 3.21 (s, 3H), 2.72-2.52 (m, 3H), 2.29 (s, 3H), 1.25 (d, J=6.4 Hz, 3H).

Compound 718. 7-(1-methoxycyclobutyl)-4,8-dimethyl-2-((trans-3-((2-(trifluoromethyl)pyrimidin-5-yl)oxy)cyclobutyl)amino)-7,8-dihydropteridin-6(5H)-one $^1$H NMR (400 MHz, DMSO-d6) δ 9.92 (s, 2H), 8.66 (s, 4H), 6.74 (d, J=7.1 Hz, 2H), 5.12 (d, J=6.9 Hz, 2H), 4.46 (d, J=7.2 Hz, 1H), 4.21 (s, 2H), 3.10 (s, 6H), 2.28-2.18 (m, 2H), 3.06 (s, 6H), 2.10 (s, 11H), 1.98 (s, 2H), 1.75-1.61 (m, 1H), 1.55 (d, J=9.4 Hz, 2H), 1.27-1.22 (m, 2H), 1.21-1.10 (m, 4H).

Compound 710. 7-(methoxymethyl)-4,7,8-trimethyl-2-((trans-3-((2-(trifluoromethyl)pyrimidin-5-yl)oxy)cyclobutyl)amino)-7,8-dihydropteridin-6(5H)-one $^1$H NMR (400 MHz, DMSO-d6) δ 9.83 (s, 1H), 8.66 (s, 2H), 6.75 (s, 1H), 5.21-5.04 (m, 1H), 4.45 (q, J=7.2 Hz, 1H), 3.66 (d, J=10.0 Hz, 1H), 3.55 (d, J=10.1 Hz, 1H), 3.20 (s, 3H), 2.97 (s, 3H), 2.11 (s, 3H), 1.33 (s, 3H).

Compound 706. 7-(methoxymethyl)-4,7,8-trimethyl-2-((trans-3-((2-(trifluoromethyl)pyrimidin-5-yl)oxy)cyclobutyl)amino)-7,8-dihydropteridin-6(5H)-one ¹H NMR (400 MHz, DMSO-d6) δ 9.79 (s, 1H), 7.67 (s, 1H), 7.40 (s, 1H), 6.58 (s, 1H), 6.48 (s, 1H), 5.44 (s, 2H), 4.21 (d, J=6.1 Hz, 2H), 3.87 (s, 3H), 3.65 (d, J=10.0 Hz, 1H), 3.54 (d, J=10.1 Hz, 1H), 3.19 (s, 3H), 2.96 (s, 3H), 2.10 (s, 3H), 1.32 (s, 3H).

Example 2SS

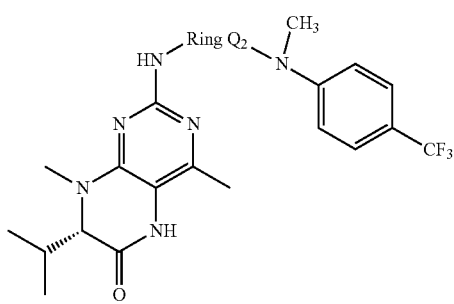

The following compounds in Table 43 were prepared by reaction of Intermediates A-9 and Intermediate B-# via Method A procedure.

TABLE 43

| Compound # | Ring Q2 | Intermediate B | [α]_D | M + 1 |
|---|---|---|---|---|
| Compound 502 | | B-204 | 34.9 c = 1.0 MeOH | 477.38 |
| Compound 503 | | B-205 | −24.2 c = 1.0 MeOH | 477.33 |
| Compound 504 | | B-206 | 165.3 c = 1.0 MeOH | 477.29 |
| Compound 505 | | B-207 | 98.8 c = 1.0 MeOH | 477.29 |

Compound 502. (S)-7-isopropyl-4,8-dimethyl-2-(((1S,3R)-3-(methyl(4-(trifluoromethyl)phenyl)amino)cyclopentyl)amino)-7,8-dihydropteridin-6(5H)-one ¹H NMR (400 MHz, Methanol-d4) δ 7.81 (s, 4H), 4.46 (dq, J=16.1, 8.1 Hz, 2H), 4.15 (d, J=3.8 Hz, 1H), 3.34-3.28 (m, 2H), 3.26 (s, 3H), 2.50 (d, J=18.8 Hz, 1H), 2.43-2.33 (m, 1H), 2.32 (d, J=5.2 Hz, 3H), 2.23-1.89 (m, 5H), 1.10 (d, J=7.0 Hz, 3H), 0.88 (d, J=6.9 Hz, 3H).

Compound 503. (S)-7-isopropyl-4,8-dimethyl-2-(((1S,3S)-3-(methyl(4-(trifluoromethyl)phenyl)amino)cyclopentyl)amino)-7,8-dihydropteridin-6(5H)-one ¹H NMR (400 MHz, Methanol-d4) δ 7.99 (t, J=15.0 Hz, 2H), 7.92 (d, J=8.7 Hz, 2H), 4.72-4.53 (m, 2H), 4.15 (d, J=3.8 Hz, 1H), 33.32 (s, 3H), 3.30 (s, 3H), 2.56-2.32 (m, 3H), 2.31 (d, J=5.8 Hz, 3H), 2.22-2.00 (m, 2H), 1.77 (ddt, J=13.0, 10.1, 7.5 Hz, 1H), 1.10 (d, J=7.0 Hz, 3H), 0.88 (d, J=6.9 Hz, 3H).

Compound 504. (S)-7-isopropyl-4,8-dimethyl-2-(((1R,3R)-3-(methyl(4-(trifluoromethyl)phenyl)amino)cyclopentyl)amino)-7,8-dihydropteridin-6(5H)-one ¹H NMR (400 MHz, Methanol-d4) δ 7.78 (t, J=10.6 Hz, 4H), 4.68-4.54 (m, 2H), 4.15 (d, J=3.8 Hz, 1H), 3.28 (d, J=8.2 Hz, 3H), 3.21 (s, 3H), 2.45-2.33 (m, 2H), 2.31 (s, 3H), 2.15 (d, J=7.7 Hz, 1H), 2.08-1.87 (m, 2H), 1.78 (ddt, J=13.1, 10.0, 7.5 Hz, 1H), 1.11 (d, J=7.0 Hz, 3H), 0.89 (d, J=6.9 Hz, 3H).

Compound 505. (S)-7-isopropyl-4,8-dimethyl-2-(((1R,3S)-3-(methyl(4-(trifluoromethyl)phenyl)amino)cyclopentyl)amino)-7,8-dihydropteridin-6(5H)-one ¹H NMR (400 MHz, Methanol-d4) δ 7.82 (s, 4H), 4.53-4.35 (m, 2H), 4.15 (d, J=3.8 Hz, 1H), 3.26 (d, J=4.3 Hz, 6H), 2.49 (d, J=14.7 Hz, 1H), 2.24-1.90 (m, 5H), 1.11 (d, J=7.0 Hz, 3H), 0.89 (d, J=6.9 Hz, 3H)

Example 2TT

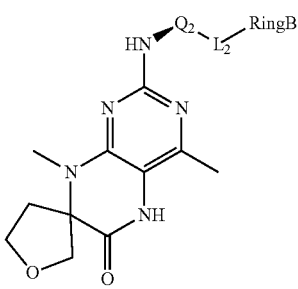

The following compounds of Table 44 were prepared by reaction of Intermediates A-67 and Intermediate B-# via Method A procedure.

| Comp. No. | Q₂—L₂-Ring | Intermediate B | M + 1 |
|---|---|---|---|
| 687 | cyclobutyl-NH-pyrazine-CF₃ | B-209 | 465.32 |
| 688 | cyclobutyl-CH₂-pyrazoline-CF₃ | B-210 | 452.22 |
| 689 | cyclobutyl-O-pyridine-CF₃ | B-112 | 465.54 |
| 697 | cyclobutyl-CH₂-O-pyridine-CF₃ | B-195 | 479.27 |

Compound 687. 4',8'-dimethyl-2'-((cis-3-((5-(trifluoromethyl)pyrazin-2-yl)amino)cyclobutyl)amino)-4,5,5',8'-tetrahydro-2H,6'H-spiro[furan-3,7'-pteridin]-6'-one ¹H NMR (400 MHz, Chloroform-d) δ 8.36 (s, 1H), 7.89 (d, J=1.4 Hz, 1H), 7.78 (s, 1H), 5.19 (d, J=6.9 Hz, 1H), 4.91 (d, J=7.2 Hz, 1H), 4.33-4.24 (m, 2H), 4.22-4.13 (m, 3H), 3.91 (q, J=8.6 Hz, 1H), 3.14 (s, 4H), 3.04 (dtd, J=9.8, 7.2, 2.9 Hz, 2H), 2.62 (ddd, J=13.5, 7.7, 3.5 Hz, 1H), 2.22 (s, 3H), 1.85 (qd, J=8.8, 2.8 Hz, 2H).

Compound 688. 4',8'-dimethyl-2'-((trans-3-((5-(trifluoromethyl)-1H-pyrazol-1-yl)methyl)cyclobutyl)amino)-4,5,5',8'-tetrahydro-2H,6'H-spiro[furan-3,7'-pteridin]-6'-one ¹H NMR (400 MHz, Methanol-d4) δ 7.75 (dd, J=2.3, 1.0 Hz, 1H), 6.58 (d, J=2.3 Hz, 1H), 4.30-4.24 (m, 4H), 4.22-4.14 (m, 2H), 3.87-3.76 (m, 1H), 3.25 (d, J=1.2 Hz, 3H), 2.66-2.59 (m, 1H), 2.56-2.49 (m, 2H), 2.30 (s, 3H), 1.88 (qd, J=8.9, 2.6 Hz, 2H).

Compound 689. 4',8'-dimethyl-2'-((trans-3-((6-(trifluoromethyl)pyridin-3-yl)oxy)cyclobutyl)amino)-4,5,5',8'-tetrahydro-2H,6'H-spiro[furan-3,7'-pteridin]-6'-one 1H NMR (400 MHz, Methanol-d4) δ 8.30 (d, J=2.8 Hz, 1H), 7.75 (d, J=8.7 Hz, 1H), 7.43 (dd, J=8.7, 2.8 Hz, 1H), 5.07 (t, J=5.2 Hz, 1H), 4.64 (t, J=7.2 Hz, 1H), 4.30-4.12 (m, 4H), 3.83 (td, J=9.3, 7.3 Hz, 1H), 3.25 (s, 3H), 2.68 (dd, J=7.2, 5.2 Hz, 4H), 2.62-2.58 (m, OH), 2.46-2.36 (m, 1H), 2.32 (s, 3H).

Compound 697. 4',8'-dimethyl-2'-((cis-3-(((6-(trifluoromethyl)pyridin-3-yl)oxy)methyl)cyclobutyl)amino)-4,5,5',8'-tetrahydro-2H,6'H-spiro[furan-3,7'-pteridin]-6'-one ¹H NMR (400 MHz, Methanol-d4) δ 8.37 (d, J=2.8 Hz, 1H), 7.75 (d, J=8.7 Hz, 1H), 7.55 (dd, J=8.8, 2.8 Hz, 1H), 4.41 (t, J=8.2 Hz, 1H), 4.26 (q, J=3.8, 2.7 Hz, 1H), 4.20-4.14 (m, 3H), 3.84 (td, J=9.2, 7.3 Hz, 1H), 3.28 (s, 3H), 2.67-2.58 (m, 4H), 2.45-2.37 (m, 1H), 2.32 (s, 3H), 2.04 (qd, J=7.9, 7.4, 3.8 Hz, 2H).

Example 2UU

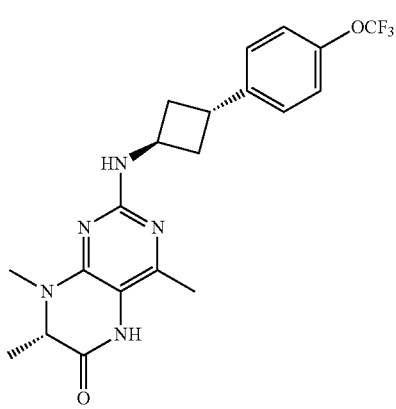

Compound 506

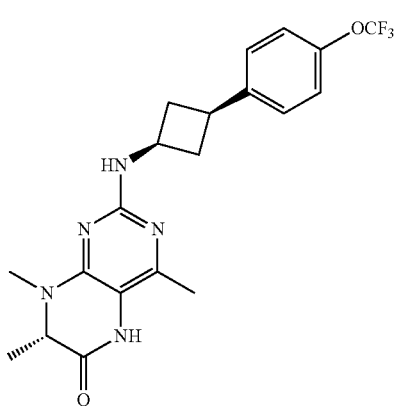

Compound 507

Compound 506 and 507. (7S)-4,7,8-trimethyl-2-(((trans)-3-(4-(trifluoromethoxy)phenyl)cyclo-butyl)amino)-7,8-dihydropteridin-6(5H)-one and (7S)-4,7,8-trimethyl-2-(((cis)-3-(4-(trifluoromethoxy)phenyl)cyclo-butyl)amino)-7,8-dihydropteridin-6(5H)-one Compound 503 and Compound 504 were prepared by reaction of Intermediate A-2 (220 mg, 0.975 mmol) and 3-(4-(trifluoromethoxy)phenyl)cyclobutan-1-amine hydrochloride (261 mg, 0.975 mmol) by the Method B procedure (see Compound 1) that provided a mixture of the cis:trans isomers. The isomers were separated by SFC (OJ-H column, 20×250 mm; 20% methanol (5 mM ammonia)/80% CO2, Isocratic; 80 ml/min): Peak A Rt 0.506 mins and Peak B (cis) Rt 0.653 mins.

Compound 506: Peak A (trans isomer), 37 mg; 1H NMR (400 MHz, CDCl3) δ 8.33 (s, 1H), 7.38-7.31 (m, 2H), 7.21 (t, J=10.7 Hz, 2H), 5.04 (d, J=6.3 Hz, 1H), 4.58-4.43 (m, 1H), 4.09 (q, J=6.9 Hz, 1H), 3.73-3.58 (m, 1H), 3.06 (d, J=5.2 Hz, 3H), 2.59 (dddd, J=10.9, 7.8, 6.1, 3.2 Hz, 2H), 2.50-2.35 (m, 2H), 2.24 (s, 3H), 1.41 (d, J=6.9 Hz, 3H). ESI-MS m/z calc. 421.17255, found 422.28 (M+1)$^+$;

Compound 507: Peak B (cis isomer), 89 mg; 1H NMR (400 MHz, CDCl3) δ 9.34 (s, 1H), 7.24 (d, J=8.6 Hz, 2H), 7.15 (d, J=8.1 Hz, 2H), 5.48 (s, 1H), 4.51-4.31 (m, 1H), 4.09 (q, J=6.8 Hz, 1H), 3.33-3.17 (m, 1H), 3.08 (s, 3H), 2.96-2.76 (m, 2H), 2.29 (s, 3H), 2.01 (td, J=11.7, 2.5 Hz, 2H), 1.43 (d, J=6.9 Hz, 3H). ESI-MS m/z calc. 421.17255, found 422.28 (M+1)$^+$

Example 2VV

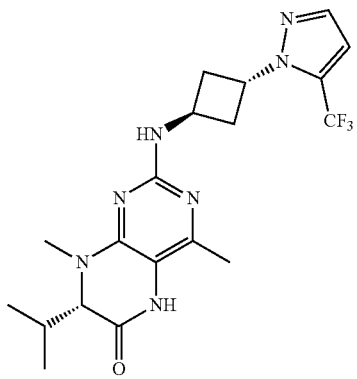 [SMILES: Cc1nc(N[C@H]2C[C@H](n3nccc3C(F)(F)F)C2)nc2c1NC(=O)[C@H](C(C)C)N2C]

Compound 673. (7S)-7-isopropyl-4,8-dimethyl-2-((trans-3-(5-(trifluoromethyl)-1H-pyrazol-1-yl)cyclobutyl)amino)-7,8-dihydropteridin-6(5H)-one The compound was prepared by Method A (Compound 46) procedure by reaction of Intermediates A-9 and B-197a to provide the title product. 1H NMR (400 MHz, Chloroform-d) δ 8.43 (s, 1H), 7.43 (q, J=1.1 Hz, 1H), 6.46 (d, J=2.3 Hz, 1H), 4.99-4.77 (m, 2H), 4.51 (tt, J=8.5, 4.7 Hz, 1H), 3.81 (dd, J=4.4, 1.6 Hz, 1H), 3.03 (d, J=1.1 Hz, 3H), 2.96-2.81 (m, 2H), 2.50 (ddd, J=13.4, 8.6, 4.9 Hz, 2H), 2.19-2.13 (m, 1H), 2.13 (t, J=1.4 Hz, 3H), 1.04-0.91 (m, 3H), 0.84 (d, J=6.9 Hz, 3H). ESI-MS m/z calc. 423.19943, found 424.3 (M+1)$^+$; [α]=67.3° (c=1.0, DMSO).

Example 2WW

The following compounds were prepared by the same procedure described for Compound 409 via the same scheme:

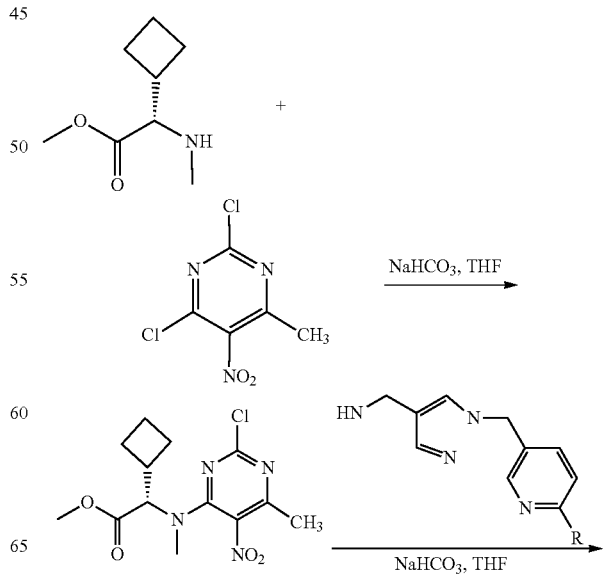

-continued

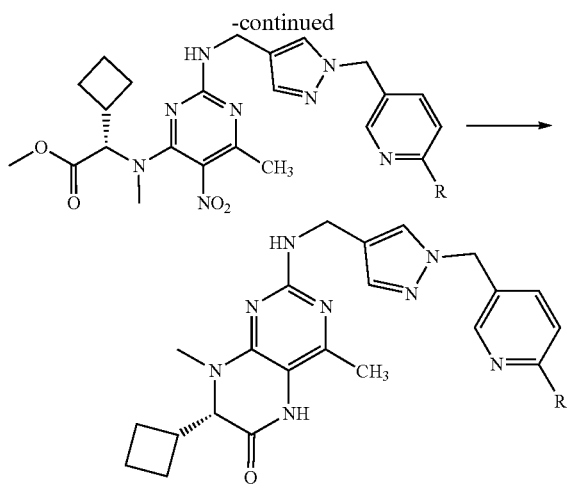

Compound 567 (R=CF3). (7S)-7-cyclobutyl-4,8-dimethyl-2-(((1-((6-(trifluoromethyl)pyridin-3-yl)methyl)-1H-pyrazol-4-yl)methyl)amino)-7,8-dihydropteridin-6(5H)-one 1H NMR (300 MHz, Chloroform-d) δ 8.61 (s, 1H), 7.83 (s, 1H), 7.75-7.62 (m, 2H), 7.57 (d, J=0.7 Hz, 1H), 7.44 (d, J=0.7 Hz, 1H), 5.37 (s, 2H), 4.87 (d, J=5.9 Hz, 1H), 4.57-4.35 (m, 2H), 3.86 (d, J=7.9 Hz, 1H), 3.09 (s, 3H), 2.67 (h, J=8.0 Hz, 1H), 2.21 (s, 3H), 2.05 (qd, J=8.9, 3.3 Hz, 3H), 1.99-1.60 (m, 3H). ESI-MS m/z 487.23 (M+1)+; Chiral HPLC (ChiralPAK IC Column; Method: 20% methanol/30% ethanol/50% hexanes): Rt (95% ee); [α]=62.4° (c=1.0, CHCl₃) @ 22.7° C.

Compound 566 (R=Cl). (7S)-2-(((1-((6-chloropyridin-3-yl)methyl)-1H-pyrazol-4-yl)methyl)amino)-7-cyclobutyl-4,8-dimethyl-7,8-dihydropteridin-6(5H)-one 1H NMR (300 MHz, Chloroform-d) δ 8.30 (d, J=2.5 Hz, 1H), 7.55 (s, 1H), 7.51 (dd, J=8.5, 2.9 Hz, 2H), 7.39 (s, 1H), 7.33 (s, 0H), 5.27 (s, 2H), 4.85 (s, 1H), 4.43 (d, J=5.8 Hz, 2H), 3.87 (d, J=7.9 Hz, 1H), 3.09 (s, 3H), 2.65 (p, J=8.3 Hz, 1H), 2.20 (s, 3H), 2.14-1.99 (m, 3H), 1.99-1.74 (m, 3H). ESI-MS m/z 453.41 (M+1)+; Chiral HPLC (ChiralPAK IC Column; Method: 20% methanol/30% ethanol/50% hexanes): Rt (98% ee); [α]=133.76° (c=1.0, CHCl₃)@22.7° C.

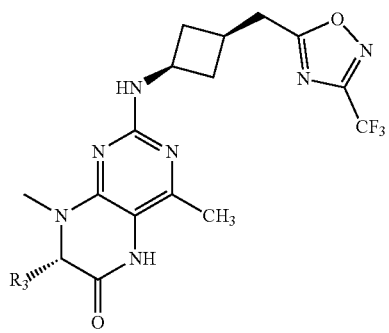

Compound 660 (R3=iPr). (S)-7-isopropyl-4,8-dimethyl-2-(((1s,3R)-3-((3-(trifluoromethyl)-1,2,4-oxadiazol-5-yl)methyl)cyclobutyl)amino)-7,8-dihydropteridin-6(5H)-one The compound was prepared by Method B (Compound 1) procedure by reaction of A-9 and B-173 to provide the title product. 1H NMR (400 MHz, Methanol-d4) δ 4.38 (p, J=8.2 Hz, 1H), 4.14 (d, J=3.8 Hz, 1H), 3.27 (s, 3H), 3.22 (d, J=7.2 Hz, 2H), 2.79-2.64 (m, 2H), 2.64-2.54 (m, 1H), 2.34 (dt, J=6.9, 3.5 Hz, 0H), 2.30 (s, 3H), 1.93 (dtd, J=10.9, 9.0, 5.9 Hz, 2H), 1.11 (d, J=7.0 Hz, 3H), 0.89 (d, J=6.9 Hz, 3H); ESI-MS m/z calc. 439.19437, found 440.33.

Compound 664 (R₃=—(R)—CH(OCH₃)CH₃. (S)-7-((R)-1-methoxyethyl)-4,8-dimethyl-2-(((1s,3R)-3-((3-(trifluoromethyl)-1,2,4-oxadiazol-5-yl)methyl)cyclobutyl)amino)-7,8-dihydropteridin-6(5H)-one The compound was prepared by Method B (Compound 1) procedure by reaction of A-59 and B-173 to provide the title product. 1H NMR (400 MHz, Methanol-d4) δ 4.40 (q, J=8.2 Hz, 1H), 4.23 (d, J=3.8 Hz, 1H), 3.79 (qd, J=6.4, 3.7 Hz, 1H), 3.34 (s, 3H), 3.29 (s, 3H), 3.23 (d, J=7.3 Hz, 2H), 2.71 (tt, J=7.5, 3.8 Hz, 2H), 2.60 (dt, J=9.3, 7.4 Hz, 1H), 2.32 (s, 3H), 2.01-1.90 (m, 2H), 1.28 (d, J=6.5 Hz, 3H). ESI-MS m/z calc. 455.18927, found 456.27. [α]=36.0° (c=1.0, DMSO) @ 23° C.

Compound 428. (S)-4,7,8-trimethyl-2-(((1-((6-(trifluoromethyl)pyridin-3-yl)methyl)-1H-imidazol-4-yl)methyl)amino)-7,8-dihydropteridin-6(5H)-one The compound was prepared by Method A (Compound 46) procedure by reaction of Intermediates A-1 and B-180 to provide the title product. 1H NMR (300 MHz, Methanol-d4) δ 8.57 (s, 1H), 8.44 (s, 1H), 7.75 (dd, J=12.1, 7.0 Hz, 2H), 7.43 (s, 1H), 7.32 (d, J=15.5 Hz, 0H), 5.61 (d, J=28.3 Hz, 2H), 4.65 (q, J=16.0 Hz, 1H), 4.25 (d, J=6.9 Hz, 1H), 4.12 (s, 1H), 3.09 (d, J=18.5 Hz, 3H), 2.20 (d, J=22.5 Hz, 3H), 1.43 (dd, J=40.0, 6.9 Hz, 3H); ESI-MS m/z 447.29.

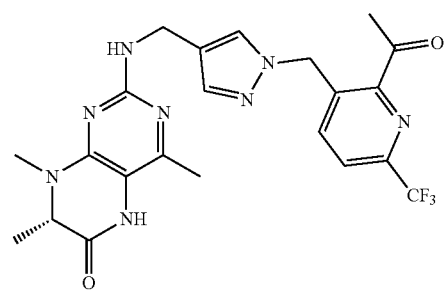 [SMILES: CC(=O)c1nc(C(F)(F)F)ccc1Cn1cc(CNc2nc(C)c3c(n2)N(C)[C@@H](C)C(=O)N3)cn1]

Compound 413. (7S)-2-(((1-((2-acetyl-6-(trifluoromethyl)pyridin-3-yl)methyl)-1H-pyrazol-4-yl)methyl)amino)-4,7,8-trimethyl-7,8-dihydropteridin-6(5H)-one Mixture of 1-(3-((4-(aminomethyl)-1H-pyrazol-1-yl)methyl)-6-(trifluoromethyl)pyridin-2-yl)ethan-1-one hydrochloride (814 mg, 2.432 mmol), (7S)-2-chloro-4,7,8-trimethyl-5,7-dihydropteridin-6-one (500 mg, 2.206 mmol) and NaOtBu (742.0 mg, 7.721 mmol) was taken into t-butanol (10 mL) and heated to 35° C. The reaction was purged by bubbling nitrogen for 30 mins. tBuXPhosPd palladcycle (Gen 1; 31 mg, 0.04514 mmol) was added the reaction. The reaction was purged with nitrogen for 5 mins. then heated at 50° C. for 45 minutes. The t-butanol was removed in vacuo and the residues was dissolved dichloromethane (20 ml) plus some methanol and filtered through celite. The filtrate was evaporated in vacuo and the residue purified by column chromatography (SiO$_2$; 40 g) eluting with a gradient of dichloromethane to 20% methanol in dichloromethane. The desired fractions were evaporated in vacuo to afford the the product (500 mg, 45% yield). 1H NMR (400 MHz, CDCl3) δ 7.78-7.67 (m, 2H), 7.60 (s, 1H), 7.54 (s, 1H), 7.23 (d, J=8.2 Hz, 1H), 5.77 (s, 2H), 4.88 (t, J=5.5 Hz, 1H), 4.56-4.39 (m, 2H), 4.10 (q, J=6.8 Hz, 1H), 3.07 (s, 3H), 2.80 (s, 3H), 2.23 (s, 3H), 1.42 (d, J=6.9 Hz, 3H). ESI-MS m/z 489.14 (M+1; [α]D=+43.71°, 9.7 mg in 1 mL of MeOH, temp=20.6° C.

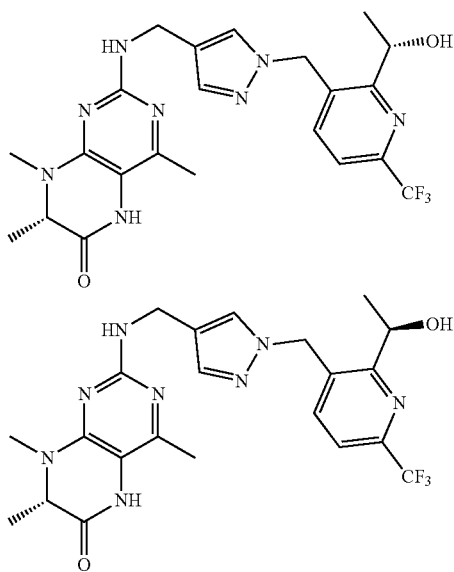

Compound 419 & Compound 420. (7S)-2-(((1-((2-((S)-1-hydroxyethyl)-6-(trifluoromethyl)pyridin-3-yl)methyl)-1H-pyrazol-4-yl)methyl)amino)-4,7,8-trimethyl-7,8-dihydropteridin-6(5H)-one and (7S)-2-(((1-((2-((R)-1-hydroxyethyl)-6-(trifluoromethyl)pyridin-3-yl)methyl)-1H-pyrazol-4-yl)methyl)amino)-4,7,8-trimethyl-7,8-dihydropteridin-6(5H)-one (7S)-2-(((1-((2-acetyl-6-(trifluoromethyl)pyridin-3-yl)methyl)-1H-pyrazol-4-yl)methyl)amino)-4,7,8-trimethyl-7,8-dihydropteridin-6(5H)-one (310 mg, 0.6219 mmol) was dissolved in methanol (10 ml) and cooled to 0° C. Sodium borohydride (25 mg, 0.6608 mmol) was added and warmed to room temperature over 2 hours. The reaction was evaporated in vacuo to afford a residue that was dissolved in to water and extracted with dichloromethane (2×25 ml). The extracts were combined, dried over anhydrous sodium sulfate, filtered, and evaporated in vacuo to afford the crude product. The crude was purified by column chromatography (SiO$_2$; 12 g) eluting with a gradient of dichloromethane to 20% methanol. The desired fractions were combined and evaporated in vacuo to provide 230 mg desired product as a mixture of enantiomers. The enantiomers were separated by SFC (AD-H column; 20% isopropanol/80% CO2 (5 mM ammonia), isocratic) to provide enantiomers A and B.

Enantiomer A: 1H NMR (300 MHz, CDCl3) δ 7.94 (s, 1H), 7.57 (t, J=4.0 Hz, 2H), 7.48-7.35 (m, 2H), 5.42 (s, 2H), 5.14 (q, J=6.4 Hz, 1H), 4.90 (t, J=5.7 Hz, 1H), 4.55-4.35 (m, 2H), 4.09 (q, J=6.9 Hz, 1H), 3.05 (s, 3H), 2.22 (s, 3H), 1.50-1.32 (m, 6H), 1.23 (d, J=6.1 Hz, 1H). ESI-MS m/z 491.26 (M+1); [α]$_D$=48.3°, 10 mg in 1 mL of MeOH, temp=19.5° C.

Enantiomer B: 1H NMR (300 MHz, CDCl3) δ 7.63 (s, 1H), 7.58 (t, J=4.0 Hz, 2H), 7.42 (d, J=7.1 Hz, 2H), 5.42 (s, 2H), 5.14 (q, J=6.5 Hz, 1H), 4.93 (s, 1H), 4.52-4.35 (m, 2H), 4.09 (q, J=6.9 Hz, 1H), 3.05 (s, 3H), 2.22 (s, 3H), 1.43 (dd, J=8.9, 6.7 Hz, 6H). ESI-MS m/z 491.26 (M+1)$^+$; [α]$_D$=37.38°, 10 mg in 1 mL of MeOH, temp=21.2° C.

Compound 416. (7S)-2-(((1-((2-(2-hydroxypropan-2-yl)-6-(trifluoromethyl)pyridin-3-yl)methyl)-1H-pyrazol-4-yl)methyl)amino)-4,7,8-trimethyl-7,8-dihydropteridin-6(5H)-one (7S)-2-(((1-((2-acetyl-6-(trifluoromethyl)pyridin-3-yl)methyl)-1H-pyrazol-4-yl)methyl)amino)-4,7,8-trimethyl-7,8-dihydropteridin-6(5H)-one (184 mg, 0.3692 mmol) was dissolved in THF (5 mL) and cooled to −78° C. under N2. Methyl magnesium chloride (400 µL of 3 M, 1.200 mmol) was added to the solution dropwise. After the addition, the reaction was warmed to room temperature over 2 hours. The reaction was quenched by the addition of an ammonium chloride solution then extracted with ethyl acetate. The organic layer was dried over anhydrous sodium sulfate, filtered, and evaporated in vacuo. The crude product was purified by column chromatography (SiO2; 12 g) eluting with a gradient of dichloromethane to 20% methanol. The desired fractions were combined and evaporated to afford the desired product (102 mg, 46% yield). 1H NMR (300 MHz, DMSO) δ 12.64 (s, 1H), 10.50 (s, 1H), 8.03-7.82 (m, 2H), 7.70 (d, J=8.1 Hz, 1H), 7.54 (s, 1H), 7.15 (d, J=8.0 Hz, 1H), 5.85 (s, 2H), 4.43 (d, J=5.7 Hz, 2H), 4.31 (q, J=6.8 Hz, 1H), 3.21-3.07 (m, 4H), 2.26 (s, 3H), 1.56 (s, 6H), 1.41 (d, J=6.9 Hz, 3H). ESI-MS m/z 505.3 (M+1); [α]$_D$=+13.2°, c=1.0, MeOH.

Compound 412. (S)-2-(((3-bromo-1-((6-(trifluoromethyl)pyridin-3-yl)methyl)-1H-pyrazol-4-yl)methyl)amino)-4,7,8-trimethyl-7,8-dihydropteridin-6(5H)-one The compound was prepared by Method B (Compound 1) procedure by reaction of Intermediates A-1 and B-164 to provide the title product. 1H NMR (300 MHz, Chloroform-d) δ 8.89 (s, 1H), 8.66-8.49 (m, 1H), 7.87-7.55 (m, 2H), 7.38 (s, 1H), 5.29 (s, 2H), 5.03 (t, J=6.0 Hz, 1H), 4.51-4.20 (m, 2H), 4.04 (q, J=6.8 Hz, 1H), 3.01 (s, 3H), 2.23 (s, 3H), 1.38 (d, J=6.8 Hz, 3H). ESI-MS m/z calc. 524.08954, found 525.36 (M+1)$^+$. Chiral HPLC (ChiralPAK IC column; 20% methanol/30% ethanol/50% hexanes) Rt 6.241 mins. (98% ee). [α]$_D$=+13.2° c.=0.585, CHCl3.

Example 2XX

Synthesis of the Radioligand Used in the WFS1 Binding Displacement Assay (7S)-4,7,8-trimethyl-2-(((1-((6-(trifluoromethyl)pyridin-3-yl)methyl)-1H-pyrazol-4-yl-3-tritio)methyl)amino)-7,8-dihydropteridin-6(5H)-one 10% Palladium on Carbon (1.0 mg) was added to a Tritium reaction vessel, followed by a solution of (S)-2-(((3- bromo-1-((6-(trifluoromethyl)pyridin-3-yl)methyl)-1H-pyrazol-4-yl)methyl)amino)-4,7,8-trimethyl-7,8-dihydropteridin-6(5H)-one (1.0 mg) in DMF (0.3 mL) and DIEA(0.1 ml). The vessel was attached to the Tritium line and pressurized to 0.5 atm with Tritium gas at −200° C. The solution was stirred for 1 hour at room temperature, cooled to −200° C. and excess gas removed. The reaction flask was rinsed with 4×5 mL CH30H passing each of the methanol washes through a celite pad. The combined methanol washes was removed under vacuum. Crude yield: 30 mCi. The material was purified by semi-prep reverse phase HPLC. Mobile phase was removed under vacuum and the product was re-dissolved in absolute Ethanol. Yield: 15 mCi, purity >99%. The Specific Activity was determined to be 19.9 Ciimmol by Mass Spec.

Example 2YY

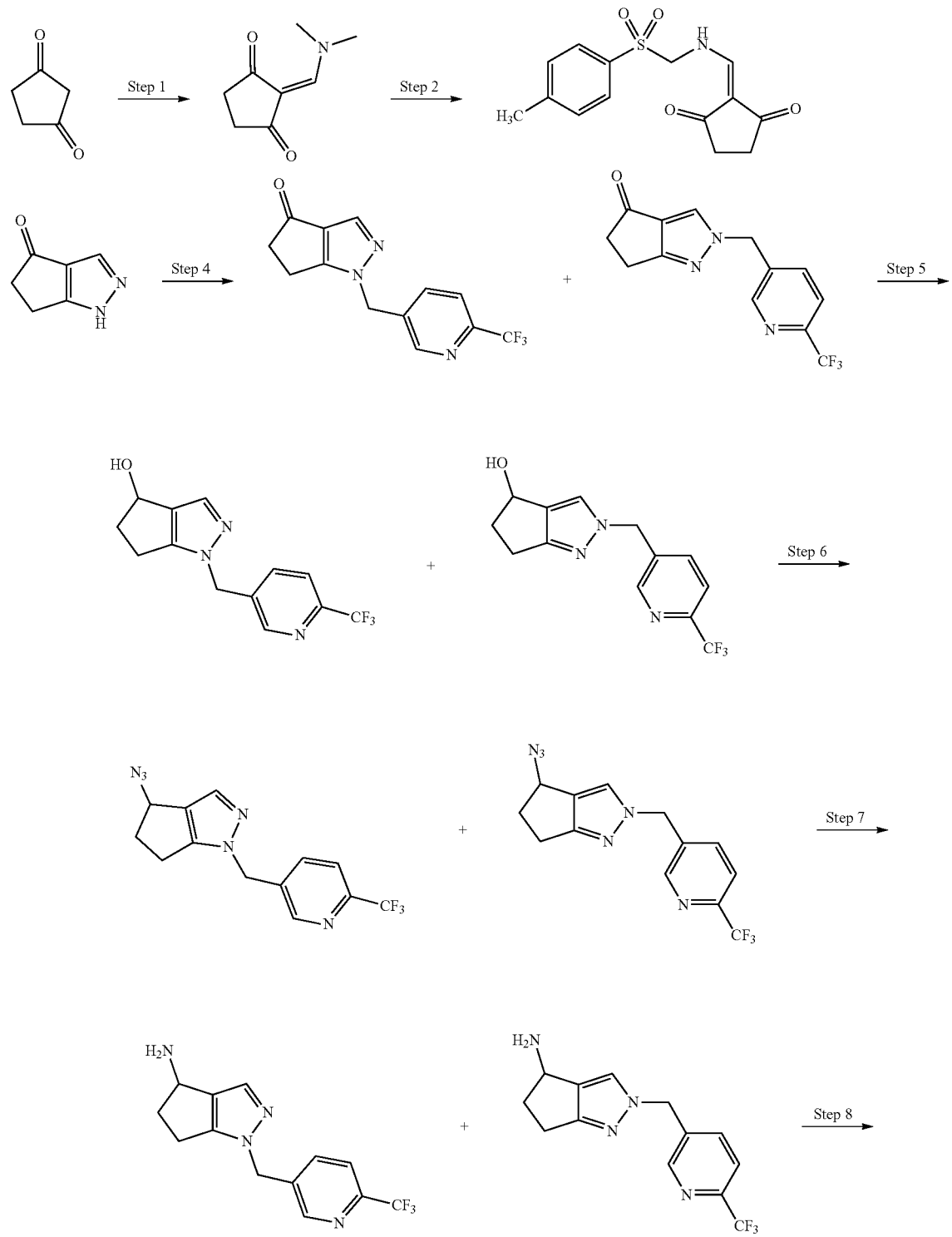

-continued

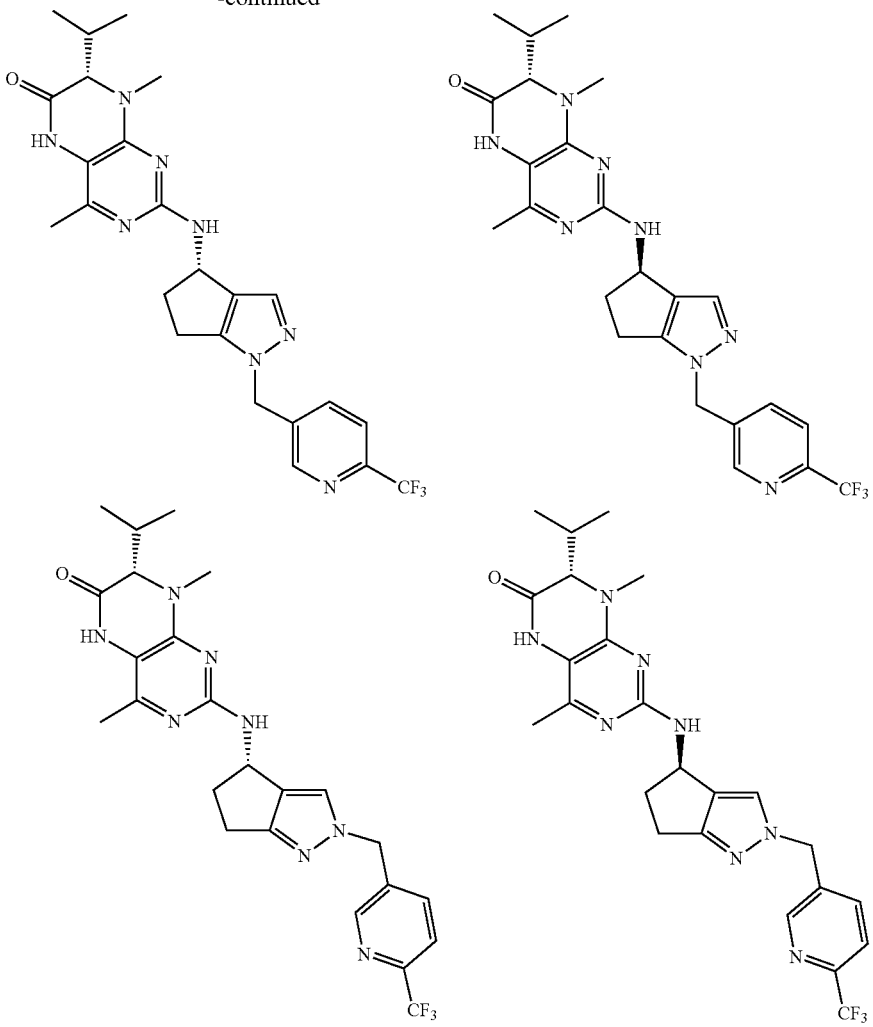

Step 1: 2-((Dimethylamino)methylene)cyclopentane-1,3-dione

Cyclopentane-1,3-dione (10 g, 101.9 mmol) and 1,1-dimethoxy-N,N-dimethyl-methanamine (16 g, 134.3 mmol) were taken into dichloromethane (90 mL) and stirred at room temperature for hr. The reaction was evaporated in vacuo and the residue was triturated with cyclohexane (2×25 mL) to afford a pale yellow solid of the desired product (18 g) $^1$H NMR (300 MHz, Chloroform-d) δ 7.44 (s, 1H), 3.72 (s, 3H), 3.36 (s, 3H), 2.50 (s, 4H). ESI-MS m/z calc. 153.07898, found 154.11 (M+1).

Step 2: 2-(((Tosylmethyl)amino)methylene)cyclopentane-1,3-dione 2-((Dimethylamino)methylene)cyclopentane-1,3-dione (18 g, 110%) and 4-methylbenzenesulfonohydrazide (19.93 g, 107.0 mmol) were taken into methanol and stirred at room temperature for 1 hr. The reaction was evaporated in vacuo to provide the desired product as a yellow solid that was washed with hexanes and filtered to provide the desired product (25.5 g, 82%). $^1$H NMR (300 MHz, Chloroform-d) δ 7.86-7.80 (m, 1H), 7.80-7.75 (m, 1H), 7.38 (d, J=8.1 Hz, 1H), 7.29 (d, J=2.7 Hz, 2H), 2.73 (s, 3H), 2.47 (s, 1H), 2.40 (s, 3H). ESI-MS m/z calc. 294.0674, found 295.12 (M+1)$^+$.

Step 3: 5,6-Dihydrocyclopenta[c]pyrazol-4(1H)-one

A mixture of 2-(((Tosylmethyl)amino)methylene)cyclopentane-1,3-dione (5 g, 2 mmol), HCl (20 mL, 37% aqueous) and n-BuOH (40 mL) was stirred at 110° C. for 12 h. The black reaction mixture was concentrated in vacuo to afford the dark crude product which was purified by MPLC (SiO2; 40 g) eluting with a gradient of 0-10% methanol in dichloromethane. The relevant fractions were combined and evaporated in vacuo to afford the product as a yellow solid (1.2 g, 48%). $^1$H NMR (300 MHz, Chloroform-d) δ 7.78 (s, 1H), 3.06 (d, J=0.9 Hz, 4H). ESI-MS m/z calc. 122.04801, found 123.06 (M+1)$^+$.

Step 4: 1-((6-(Trifluoromethyl)pyridin-3-yl)methyl)-5,6-dihydrocyclopenta[c]pyrazol-4(1H)-one & 2-((6-(Trifluorometh paladl)pyridin-3-yl)methyl)-5,6-dihydrocyclopenta[c]pyrazol-4(2H)-one 5,6-Dihydrocyclopenta[c]pyrazol-4(1H)-one (1.15 g, 9.357 mmol), 5-(chloromethyl)-2-(trifluoromethyl)pyridine (2.1 g, 10.74 mmol), and K$_2$CO$_3$ (2.5 g, 31.2 mmol) were taken into acetonitrile (20 mL). The mixture was heated to reflux for 3 hours. After cooling to room temperature, the reaction mixture was diluted with water (40 m L) and extracted with ethyl acetate (3×15 ml). The combined organic extracts were dried over magnesium sulfate, filtered, and evaporated in vacuo. The crude product was purified by column chromatography (SiO$_2$) eluting with a gradient of 0-10% methanol in dichloromethane. The relevant fractions were combined and evaporated in vacuo to provide the title product (as a mixture of regioisomers) as a yellow crystalline solid (2.56 g, 96%). $^1$H NMR (300 MHz, Chloroform-d) δ 8.71 (d, J=2.1 Hz, 1H), 7.86-7.75 (m, 2H), 7.71 (dd, J=8.2, 0.9 Hz, 1H), 5.45 (s, 2H), 3.10-3.01 (m, 2H), 3.00-2.93 (m, 2H). ESI-MS m/z calc. 281.0776, found 282.2 (M+1)$^+$.

Step 5: 1-((6-(Trifluoromethyl)pyridin-3-yl)methyl)-1,4,5,6-tetrahydrocyclopenta[c]pyrazol-4-ol & 2-((6-(trifluoromethyl)pyridin-3-yl)methyl)-2,4,5,6-tetrahydrocyclopenta[c]pyrazol-4-ol The mixture of regioisomers from Step 4 (1 g, 3.556 mmol) was dissolved in methanol. Sodium borohydride (134.5 mg, 142.3 µL, 3.556 mmol) was added to the solution and stirred at room temperature for 1 hr. The reaction was evaporated in vacuo. The residue was dissolved in dichloromethane and washed with water. The organic layer was dried over sodium sulfate, filtered, and evaporated in vacuo. The crude product was purified by column chromatography (SiO2; 40 g) eluting with a gradient of 0-100% ethyl acetate in hexanes followed by 2-5% methanol in dichloromethane. The relevant fractions were combined and evaporated to provide the title product (as a mixture of regioisomers) as a light brown solid (0.76 g, 75%). The $^1$H NMR showed two isomers, but LCMS only showed one peak. $^1$H NMR (300 MHz, Chloroform-d) δ 8.51 (dd, J=5.0, 2.0 Hz, 1H), 7.64 (ddd, J=6.3, 4.3, 2.3 Hz, 1H), 7.57 (dt, J=8.2, 1.1 Hz, 1H), 7.27 (d, J=19.8 Hz, 1H), 5.23 (d, J=18.0 Hz, 2H), 5.16-4.99 (m, 1H), 2.85 (dddd, J=13.7, 10.8, 5.9, 2.0 Hz, 1H), 2.79-2.64 (m, 1H), 2.63-2.40 (m, 1H), 2.40-2.18 (m, 1H), 2.17-2.00 (m, 1H). ESI-MS m/z calc. 283.09326, found 284.13 (M+1)$^+$; Retention time: 0.66 minutes.

Step 6: 4-azido-1-((6-(trifluoromethyl)pyridin-3-yl) methyl)-1,4,5,6-tetrahydrocyclopenta[c]pyrazole & 4-azido-2-((6-(trifluoromethyl)pyridin-3-yl)methyl)-2,4,5,6-tetrahydrocyclopenta[c]pyrazole The product from Step 5 (0.76 g, 2.683 mmol) was taken into THF (10 ml) and cooled to 0° C. DBU (490 µL, 3.277 mmol) and DPPA (886.1 mg, 693.9 µL, 3.220 mmol) were added to the solution and stirred at room temperature for 3 hours. The reaction was evaporated in vacuo. The resulting residue was dissolved in dichloromethane and washed with water. The organic layer was dried over Na$_2$SO$_4$ and concentrated to give the crude product which was purified by column chromatography (SiO2; 12 g) eluting with a gradient of 0-8% methanol in dichloromethane. The relevant fractions were combined and evaporated to give the desired product (as a mixture of regioisomers) as clear light yellow liquid (650 mg, 78%). The $^1$H NMR shows a mixture of regioisomers. 1H NMR (300 MHz, Chloroform-d) δ 8.73-8.58 (m, 1H), 7.80-7.64 (m, 2H), 7.44 (d, J=21.8 Hz, 1H), 5.37 (d, J=18.6 Hz, 2H), 4.81 (ddd, J=17.4, 6.6, 2.6 Hz, 1H), 3.05-2.89 (m, 1H), 2.89-2.39 (m, 3H). ESI-MS m/z calc. 308.09973, found 309.13 (M+1)$^+$; Retention time: 0.83 minutes Step 7: 1-((6-(trifluoromethyl)pyridin-3-yl)methyl)-1,4,5,6-tetrahydrocyclopenta[c]pyrazol-4-amine & 2-((6-(trifluoromethyl)pyridin-3-yl)methyl)-2,4,5,6-tetrahydrocyclopenta[c]pyrazol-4-amine Water (1 ml, 55.5 mmol) was added to a solution of the two regiosmers from Step 6 (4-azido-1-((6-(trifluoromethyl) pyridin-3-yl)methyl)-1,4,5,6-tetrahydrocyclopenta[c]pyrazole & 4-azido-2-((6-(trifluoromethyl)pyridin-3-yl)methyl)-2,4,5,6-tetrahydrocyclopenta[c]pyrazole) (0.650 g, 2.11 mmol) and triphenylphosphine (0.98 g, 3.736 mmol) in THF (10 ml). The reaction was stirred at room temperature for 16 hours. The reaction was evaporated in vacuo. The residue was dissolved in 2N HCl (5 ml) and washed with ethyl acetate (2×10 mL). The aqueous layer was basified with 2N sodium hydroxide and extracted with dichloromethane (3×5 ml). The combined organic layer was dried over anhydrous sodium sulfate, filtered, and evaporated to provide the product as a mixture of regioisomers as a light yellow oil (591 mg, 99%). $^1$H NMR (300 MHz, Chloroform-d) δ 8.62 (d, J=2.9 Hz, 1H), 7.79-7.60 (m, 2H), 7.36 (s, 1H), 7.24 (s, OH), 5.32 (d, J=16.5 Hz, 2H), 4.46-4.27 (m, 1H), 3.06-2.44 (m, 3H), 2.30-1.96 (m, 1H). ESI-MS m/z calc. 282.10922, found 282.92 (M+1)$^+$.

Step 8

The following final products were prepared to give Compound 519, 520, 521, 522. These compounds were prepared by reaction of (7S)-2-chloro-7-isopropyl-4,8-dimethyl-5,7-dihydropteridin-6-one (A-3; 250 mg, 0.9815 mmol) and the mixture of the regioisomers from Step 7 (1-((6-(trifluoromethyl)pyridin-3-yl)methyl)-1,4,5,6-tetrahydrocyclopenta[c] pyrazol-4-amine & 2-((6-(trifluoromethyl)pyridin-3-yl) methyl)-2,4,5,6-tetrahydrocyclopenta[c]pyrazol-4-amine (305 mg, 1.081 mmol) via the Method A procedure to afford the product as a mixture of enantiomers of each regioisomer (130 mg, 26%)

Chiral HPLC showed four peaks: R & S enantiomers of each regioisomer and each isomer with R, S enantiomers. Chiral HPLC (Chiral PAK IC column; method 20% methanol/30% ethanol/50% hexanes, isocratic; in 25 mins.). The four isomers were separated by SFC chromatography (IA column, 10×250 mm; 30% Ethanol (5 mM Ammonia)/70% CO2, isocratic, 15 ml/min) Peaks A and B are pairs of diastereomers of the one regioisomer. Peaks C and D are another pair of diastereomers of the other regioisomer. This was determined by 1H NMR based on the proton shift of the pyrazole: higher field proton shift (7.2 ppm) for the peaks A and B; lower field pyrazole proton shift (7.4 ppm) for peaks C & D.

Compound 519 (Isomer A) and Compound 520 (Isomer B)

(S)-7-isopropyl-4,8-dimethyl-2-(((S)-1-((6-(trifluoromethyl)pyridin-3-yl)methyl)-1,4,5,6-tetrahydrocyclopenta[c]pyrazol-4-yl)amino)-7,8-dihydropteridin-6(5H)-one and (S)-7-isopropyl-4,8-dimethyl-2-(((R)-1-((6-(trifluoromethyl)pyridin-3-yl)methyl)-1,4,5,6-tetrahydrocyclopenta[c]pyrazol-4-yl)amino)-7,8-dihydropteridin-6(5H)-one Compound 519 (Isomer A)

Isomer A (26 mg, 20%) 1H NMR (300 MHz, Chloroform-d) δ 8.69 (s, 1H), 8.52 (d, J=2.0 Hz, 1H), 7.72-7.52 (m, 2H), 7.15 (s, 1H), 5.25 (s, 2H), 5.22 (d, J=6.8 Hz, 3H), 3.81 (d, J=4.4 Hz, 1H), 3.04 (s, 3H), 2.81 (ddt, J=14.9, 8.1, 3.7 Hz, 2H), 2.64 (ddd, J=15.0, 9.4, 5.9 Hz, 1H), 2.27-2.03 (m, 6H), 0.99 (d, J=6.9 Hz, 3H), 0.85 (d, J=6.9 Hz, 3H), 0.83-0.59 (m, 4H). ESI-MS m/z calc. 500.22598, found 501.54 (M+1)+.

Chiral HPLC (Chiral PAK IC column; 20% methanol/30% ethanol/50% hexanes, isocratic, 25 mins): Rt 6.934 mins (98% ee); [α]=28.5° (c=0.5, CHCl3) @ 22.2° C.

Compound 520 (Isomer B)

Isomer B (28.5 mg, 22%) 1H NMR (300 MHz, Chloroform-d) δ 8.99 (s, 1H), 8.59 (s, 1H), 7.68 (q, J=8.3 Hz, 2H), 7.24 (s, 1H), 5.62 (s, 1H), 5.32 (d, J=10.2 Hz, 3H), 3.91 (d, J=4.3 Hz, 1H), 3.14 (s, 3H), 2.91 (tdd, J=12.5, 8.7, 4.9 Hz, 2H), 2.73 (dt, J=14.9, 8.5 Hz, 1H), 2.40-2.07 (m, 5H), 1.27 (s, 1H), 1.21 (dd, J=6.1, 4.0 Hz, 1H), 1.08 (d, J=6.9 Hz, 7H), 0.94 (d, J=6.9 Hz, 3H). ESI-MS m/z calc. 500.22598, found 501.36 (M+1)+.

Chiral HPLC (Chiral PAK IC column; 20% methanol/30% ethanol/50% hexanes, isocratic, 25 mins): Rt 6.45 mins (98% ee); [α]=135.1° (c=0.5, CHCl3) @ 22.2° C.

Compound 521 (Isomer C) and Compound 522 (Isomer D)

(S)-7-isopropyl-4,8-dimethyl-2-(((S)-2-((6-(trifluoromethyl)pyridin-3-yl)methyl)-2,4,5,6-tetrahydrocyclopenta[c]pyrazol-4-yl)amino)-7,8-dihydropteridin-6(5H)-one and (S)-7-isopropyl-4,8-dimethyl-2-(((R)-2-((6-(trifluoromethyl)pyridin-3-yl)methyl)-2,4,5,6-tetrahydrocyclopenta[c]pyrazol-4-yl)amino)-7,8-dihydropteridin-6(5H)-one Compound 521 (Isomer C)

Isomer C (7S)-7-isopropyl-4,8-dimethyl-2-[[2-[[6-(trifluoromethyl)-3-pyridyl]methyl]-5,6-dihydro-4H-cyclopenta[c]pyrazol-4-yl]amino]-5,7-dihydropteridin-6-one (24.5 mg, 19%) 1H NMR (300 MHz, Chloroform-d) δ 8.78 (s, 1H), 8.59 (s, 1H), 7.88-7.58 (m, 2H), 7.34 (s, 1H), 5.44 (s, 1H), 5.29 (s, 2H), 5.26 (s, 1H), 4.34-4.09 (m, 1H), 3.89 (d, J=4.4 Hz, 1H), 3.14 (s, 3H), 3.01 (p, J=7.3, 6.7 Hz, 1H), 2.75 (ddd, J=14.5, 8.4, 5.1 Hz, 1H), 2.55 (ddd, J=14.8, 8.6, 4.7 Hz, 1H), 2.41 (tt, J=8.9, 4.0 Hz, 1H), 2.23 (s, 4H), 1.07 (d, J=6.9 Hz, 3H), 0.93 (d, J=6.8 Hz, 3H). ESI-MS m/z calc. 500.22598, found 501.27 (M+1)+; Chiral HPLC (Chiral PAK IC column; 20% methanol/30% ethanol/50% hexanes, isocratic, 25 mins): Rt 7.436 mins (98% ee); [α]=31° (c=0.5, CHCl3) @ 22.2° C.

Compound 522 (Isomer D)

Isomer D (7S)-7-isopropyl-4,8-dimethyl-2-[[2-[[6-(trifluoromethyl)-3-pyridyl]methyl]-5,6-dihydro-4H-cyclopenta[c]pyrazol-4-yl]amino]-5,7-dihydropteridin-6-one (31 mg, 24%) 1H NMR (300 MHz, Chloroform-d) δ 8.76 (s, 1H), 8.58 (s, 1H), 7.81-7.57 (m, 2H), 7.31 (s, 1H), 5.39-5.22 (m, 5H), 4.32-4.11 (m, 1H), 3.87 (d, J=4.4 Hz, 1H), 3.12 (s, 3H), 3.03 (qd, J=8.3, 5.1 Hz, 1H), 2.74 (ddd, J=14.2, 8.7, 4.9 Hz, 1H), 2.55 (ddd, J=14.9, 8.7, 5.0 Hz, 1H), 2.39 (ddt, J=13.7, 9.2, 4.7 Hz, 1H), 2.21 (s, 4H), 1.17 (d, J=6.1 Hz, 3H), 1.05 (d, J=6.9 Hz, 3H). ESI-MS m/z calc. 500.22598, found 501.27 (M+1)+; Chiral HPLC (Chiral PAK IC column; 20% methanol/30% ethanol/50% hexanes, isocratic, 25 mins): Rt 7.407 mins (98% ee); [α]=114.1° (c=0.5, CHCl3) @ 22.2° C.

Example 2ZZ

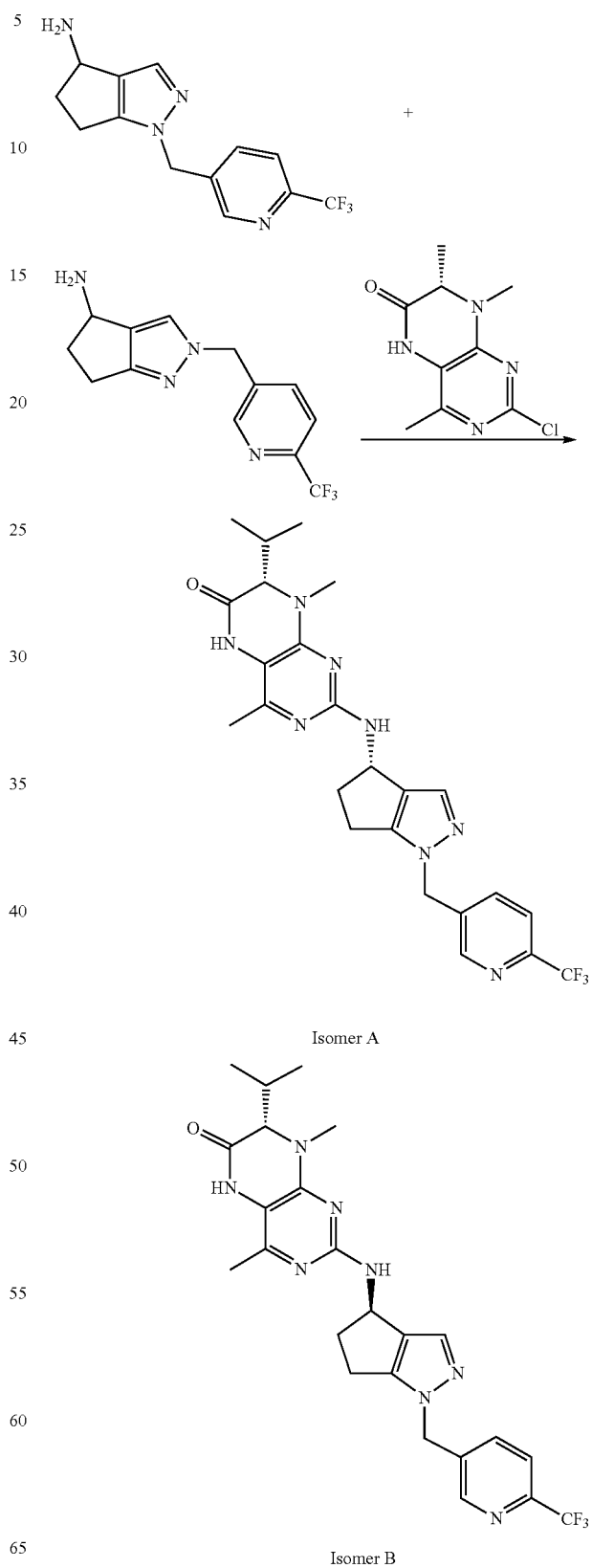

Isomer A

Isomer B

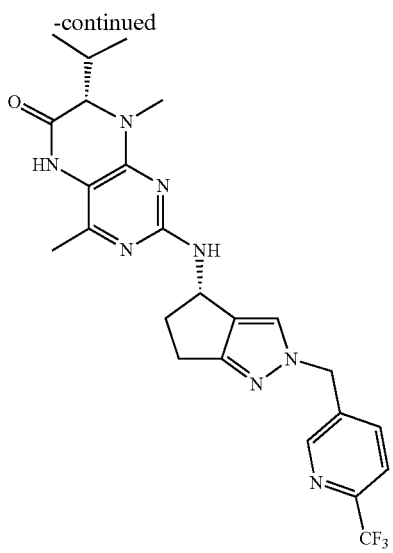

Isomer C

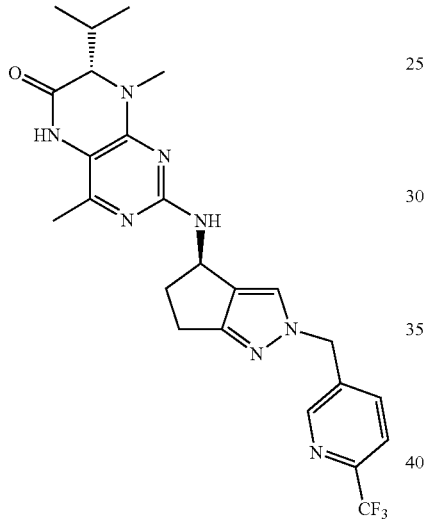

Isomer D

Compounds 546, 547, 624, and 625

These compounds were prepared by reaction of A-2 (390 mg, 1.72 mmol) and a mixture of regioisomers (1-((6-(trifluoromethyl)pyridin-3-yl)methyl)-1,4,5,6-tetrahydrocyclopenta[c]pyrazol-4-amine & 2-((6-(trifluoromethyl)pyridin-3-yl)methyl)-2,4,5,6-tetrahydrocyclopenta[c]pyrazol-4-amine (585 mg, 2.073 mmol) via the Method A procedure reported for Compound 46.

The product was a mixture of 2 regioisomers each as a pair of diastereomers. Chiral HPLC (Chiral PAK IC column; 20% methanol/30% ethanol/50% hexanes, isocratic, 25 mins).

The mixture was separated by SFC (IA column, 20×250 mm; 30% ethanol (0.2% diethylamine)/70% CO2, isocratic, 80 ml/min) to provide an inseparable mixture of Peaks A & B and clean separation of Peak C and Peak D. Peaks A & B were subjected to preparative chiral HPLC (IC column, 20×250 mm; 70% hexanes/30% ethanol/methanol (0.2% diethylamine, Isocratic, 20 ml/min) to provide clean separation of Peak A and B.

Isomer A & B: (7S)-4,7,8-trimethyl-2-(((S)-1-((6-(trifluoromethyl)pyridin-3-yl)methyl)-1,4,5,6-tetrahydrocyclopenta[c]pyrazol-4-yl)amino)-7,8-dihydropteridin-6(5H)-one and (7S)-4,7,8-trimethyl-2-(((R)-1-((6-(trifluoromethyl)pyridin-3-yl)methyl)-1,4,5,6-tetrahydrocyclopenta[c]pyrazol-4-yl)amino)-7,8-dihydropteridin-6(5H)-one Isomer A; Compound 624

Isomer A: 1H NMR (300 MHz, Chloroform-d) δ 8.61 (d, J=1.9 Hz, 1H), 7.69 (qd, J=8.8, 8.1, 2.2 Hz, 3H), 7.23 (s, 1H), 5.34 (s, 2H), 5.33-5.26 (m, 1H), 4.88 (d, J=7.6 Hz, 1H), 4.10 (q, J=6.8 Hz, 1H), 3.06 (s, 3H), 3.02-2.83 (m, 2H), 2.74 (ddd, J=15.2, 9.3, 6.1 Hz, 1H), 2.29 (dd, J=8.4, 5.3 Hz, 1H), 2.22 (s, 3H), 1.42 (d, J=6.9 Hz, 3H). ESI-MS m/z calc. 472.1947, found 473.12 (M+1). Chiral HPLC (AD-H column, 70% hexanes/15% methanol/15% ethanol (0.2% diethylamine)): Rt 6.754 mins. (98% ee).

Isomer B; Compound 625

Isomer B: 1H NMR (300 MHz, Chloroform-d) δ 8.61 (s, 1H), 7.79-7.62 (m, 3H), 7.23 (s, 1H), 5.33 (d, J=8.7 Hz, 3H), 4.88 (d, J=7.6 Hz, 1H), 4.09 (q, J=6.8 Hz, 1H), 3.06 (s, 3H), 2.98-2.86 (m, 1H), 2.91-2.65 (m, 2H), 2.34-2.16 (m, 1H), 2.23 (s, 3H), 1.42 (d, J=6.8 Hz, 3H). ESI-MS m/z calc. 472.1947, found 473.07 (M+1)$^+$. Chiral HPLC (AD-H column, 70% hexanes/15% methanol/15% ethanol (0.2% diethylamine)): Rt 7.103 mins (98% ee).

Isomer C & D: (7S)-4,7,8-trimethyl-2-(((S)-2-((6-(trifluoromethyl)pyridin-3-yl)methyl)-2,4,5,6-tetrahydrocyclopenta[c]pyrazol-4-yl)amino)-7,8-dihydropteridin-6(5H)-one and (7S)-4,7,8-trimethyl-2-(((R)-2-((6-(trifluoromethyl)pyridin-3-yl)methyl)-2,4,5,6-tetrahydrocyclopenta[c]pyrazol-4-yl)amino)-7,8-dihydropteridin-6(5H)-one Isomer C; Compound 546

Isomer C: 1H NMR (300 MHz, Chloroform-d) δ 9.31 (s, 1H), 8.52 (d, J=1.9 Hz, 1H), 7.78-7.48 (m, 2H), 7.27 (s, 1H), 5.23 (s, 2H), 5.23-5.10 (m, 2H), 4.96 (d, J=7.4 Hz, 1H), 3.99 (q, J=6.8 Hz, 1H), 2.98 (s, 4H), 2.67 (ddd, J=14.1, 8.6, 5.0 Hz, 1H), 2.49 (ddd, J=15.4, 8.8, 5.0 Hz, 1H), 2.31 (dq, J=9.1, 4.5 Hz, 1H), 2.18 (s, 3H), 1.32 (d, J=6.8 Hz, 3H). ESI-MS m/z calc. 472.1947, found 473.36 (M+1)$^+$. Chiral HPLC (Chiral PAK IC column, 20% methanol/30% ethanol/50% hexanes; 20 mins, Isocratic): Rt 9.265 mins (95% ee). [α]=14.8° (c=0.5), CHCl3@20.8° C.

Isomer D; Compound 547

Isomer D: 1H NMR (300 MHz, Chloroform-d) δ 9.21 (s, 1H), 8.52 (d, J=1.9 Hz, 1H), 7.70-7.52 (m, 2H), 7.25 (s, 1H), 5.23 (s, 2H), 5.18 (dt, J=7.4, 3.9 Hz, 1H), 4.89 (d, J=7.5 Hz, 1H), 3.99 (q, J=6.8 Hz, 1H), 3.08-2.87 (m, 4H), 2.76-2.57 (m, 1H), 2.49 (ddd, J=15.4, 8.7, 5.2 Hz, 1H), 2.30 (ddt, J=13.4, 9.1, 4.8 Hz, 1H), 2.18 (s, 3H), 1.32 (d, J=6.9 Hz, 3H). ESI-MS m/z calc. 472.1947, found 473.36 (M+1)$^+$. Chiral HPLC(Chiral PAK IC column, 20% methanol/30% ethanol/50% hexanes; 20 mins, Isocratic): Rt 9.973 mins (95% ee). [α]=86.6° (c=0.5, CHCl3) @ 22.2° C.

Example 2AAA

Scheme for the Preparation of Compound 494.

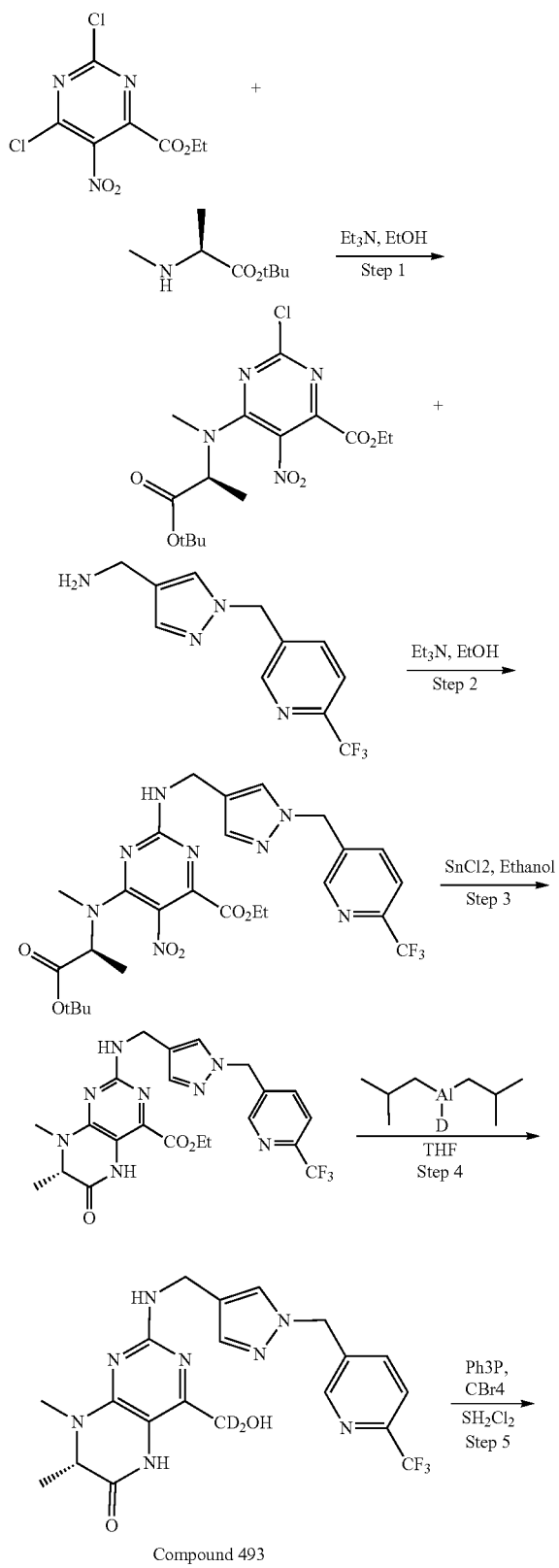

Compound 493

Compound 494. (7S)-7,8-dimethyl-4-(methyl-d3)-2-(((1-((6-(trifluoromethyl)pyridin-3-yl)methyl)-1H-pyrazol-4-yl)methyl)amino)-7,8-dihydropteridin-6(5H)-one Step 1: Ethyl (S)-6-((1-(tert-butoxy)-1-oxopropan-2-yl)(methyl)amino)-2-chloro-5-nitro-pyrimidine-4-carboxylate Ethyl 4-2,6-dichloro-5-nitro-pyrimidine-4-carboxylate ((5 g, 18.8 mmol) and tert-butyl methyl-L-alaninate hydrochloride (4.05 g, 20.67 mmol) were taken into 95% ethanol (50 ml) and triethylamine (2.6 ml, 18.8 mmol) and stirred at room temperature for 2 hours. The reaction was poured into water and extracted with ethyl acetate (3×100 ml). The combined extracts were dried over anhydrous magnesium sulfate, filtered, and evaporated in vacuo to provide the title product (5.5 g, 75.3% yield). 1H NMR (400 MHz, DMSO-d6) δ 4.87 (q, J=7.0 Hz, 1H), 4.37 (q, J=7.1 Hz, 2H), 2.86 (s, 3H), 1.46 (d, J=7.1 Hz, 3H), 1.40 (s, 9H), 1.28 (t, J=7.1 Hz, 3H).

Step 2: Ethyl (S)-6-((1-(tert-butoxy)-1-oxopropan-2-yl)(methyl)amino)-5-nitro-2-(((1-((6-(trifluoromethyl)pyridin-3-yl)methyl)-1H-pyrazol-4-yl)methyl)amino)pyrimidine-4-carboxylate (1-((6-(Trifluoromethyl)pyridin-3-yl)methyl)-1H-pyrazol-4-yl)methanamine hydrochloride (935 mg, 3.2 mmol) was added to a solution of Ethyl (7S)-6-((1-(tert-butoxy)-1-oxopropan-2-yl)(methyl)amino)-2-chloro-5-nitro-pyrimidine-4-carboxylate (1 g, 2.57 mmol) and triethylamine (1.1 ml, 7.8 mmol) in ethanol (40 ml) and heated at reflux for 3 hours. The reaction was cooled to room temperature and poured into water and extracted with ethyl acetate (3×100 ml). The combined extracts was dried over magnesium sulfate, filtered, and evaporated in vacuo to provide the title product as a yellow solid (1.56 g, 99.6% yield). 1H NMR (300 MHz, Chloroform-d) δ 8.63 (s, 1H), 7.69 (t, J=1.3 Hz, 2H), 7.53 (s, 1H), 7.45 (d, J=11.4 Hz, 1H), 5.38 (s, 2H), 4.78

(d, J=7.5 Hz, 1H), 4.50-4.35 (m, 4H), 2.92 (s, 3H), 1.51 (s, 3H), 1.43 (s, 9H), 1.40 (d, J=7.1 Hz, 3H). ESI-MS m/z 609.5 (M+1)+.

Step 3: Ethyl (S)-7,8-dimethyl-6-oxo-2-(((1-((6-(trifluoromethyl)pyridin-3-yl)methyl)-1H-pyrazol-4-yl)methyl)amino)-5,6,7,8-tetrahydropteridine-4-carboxylate Tin(II) chloride (1.6 g, 8.44 mmol) was added to a solution of ethyl (7S)-6-((1-(tert-butoxy)-1-oxopropan-2-yl)(methyl)amino)-5-nitro-2-(((1-((6-(trifluoromethyl)pyridin-3-yl)methyl)-1H-pyrazol-4-yl)methyl)amino)pyrimidine-4-carboxylate in ethanol (40 ml) and heated to reflux. After 1 hour, an additional tin(II) chloride (1 g) was added to the reaction and refluxed for 2 hours. The reaction was evaporated in vacuo and the residue taken into water and basified with 1 M sodium hydroxide. The mixture was extracted with ethyl acetate (2×40 ml). The combined extracts was dried over anhydrous magnesium sulfate, filtered, and evaporated. The crude product was purified by column chromatography (SiO$_2$; 40 g) eluting with a gradient of 0-10% methanol in dichloromethane. Evaporation of the relevant fractions provided the title product as a yellow solid(0.93 g, 72% yield). 1H NMR (300 MHz, Chloroform-d) δ 8.58 (d, J=1.7 Hz, 1H), 7.65 (d, J=1.5 Hz, 2H), 7.61-7.49 (m, 1H), 7.44 (s, 1H), 5.36 (s, 2H), 5.03 (t, J=5.8 Hz, 1H), 4.14 (q, J=6.9 Hz, 1H), 3.09 (s, 3H), 1.47 (d, J=6.9 Hz, 3H), 1.41 (t, J=7.1 Hz, 3H). ESI-MS m/z calc. 504.1845, found 505.33 (M+1)+. [α]=58.8° (c=1.0, CHCl3) @ 22.5° C. Chiral HPLC (ChiralPAK IC column; 20% methanol/30% ethanol/50% hexanes, Isocratic, 25 mins.) Rt25.869 mins. (96.6% ee).

Step 4: Compound 493. (7S)-4-(hydroxymethyl-d2)-7,8-dimethyl-2-(((1-((6-(trifluoromethyl)pyridin-3-yl)methyl)-1H-pyrazol-4-yl)methyl)amino)-7,8-dihydropteridin-6(5H)-one A 0.7 M solution of diisobutyl aluminum deuteride (4 ml, 2.8 mmol) in toluene was added dropwise to a solution of (ethyl (S)-7,8-dimethyl-6-oxo-2-(((1-((6-(trifluoromethyl)pyridin-3-yl)methyl)-1H-pyrazol-4-yl)methyl)amino)-5,6,7,8-tetrahydropteridine-4-carboxylate (410 mg, 0.81 mmol) in THF (10 ml) and stirred at room temperature for 1 hour. Water (1 ml) was slowly added to the reaction. Ethyl acetate (10 ml) was added and the mixture was filtered through Celite. The filtrate was evaporated in vacuo to afford a yellow solid which was purified by column chromatography (SiO2) eluting with a gradient of 0-10% methanol in dichloromethane. Evaporation of the desired fractions afforded the title product as a yellow solid (350 mg, 91% yield). 1H NMR (300 MHz, Chloroform-d) δ 8.55 (d, J=1.9 Hz, 1H), 7.74-7.59 (m, 3H), 7.54 (s, 1H), 7.45 (s, 1H), 5.36 (s, 2H), 5.11 (t, J=5.8 Hz, 1H), 4.41 (d, J=5.8 Hz, 2H), 4.05 (q, J=6.8 Hz, 1H), 3.46 (s, 1H), 3.03 (s, 3H), 1.40 (d, J=6.8 Hz, 3H). ESI-MS m/z calc. 464.18652, found 464.52 (M+1)+; [α]=50.72° (c=0.75, acetone) @ 23° C.

Step 5: (7S)-4-(bromomethyl-d2)-7,8-dimethyl-2-(((1-((6-(trifluoromethyl)pyridin-3-yl)methyl)-1H-pyrazol-4-yl)methyl)amino)-7,8-dihydropteridin-6(5H)-one HBr (5 ml of 33% w/w) was added to a solution of (7S)-4-(hydroxymethyl-d2)-7,8-dimethyl-2-(((1-((6-(trifluoromethyl)pyridin-3-yl)methyl)-1H-pyrazol-4-yl)methyl)amino)-7,8-dihydropteridin-6(5H)-one (500 mg, 0.99 mmol) in acetic acid (2 ml) and heated at 110° C. for 1 hour. The reaction was evaporated in vacuo to afford the crude product as a dark solid (188 mg) which was used immediately in Step 6.

Step 6: Compound 494. (7S)-7,8-dimethyl-4-(methyl-d3)-2-(((1-((6-(trifluoromethyl)pyridin-3-yl)methyl)-1H-pyrazol-4-yl)methyl)amino)-7,8-dihydropteridin-6(5H)-one Sodium borodeuteride (12 mg, 0.29 mmol) was added to a solution of (7S)-4-(bromomethyl-d2)-7,8-dimethyl-2-(((1-((6-(trifluoromethyl)pyridin-3-yl)methyl)-1H-pyrazol-4-yl)methyl)amino)-7,8-dihydropteridin-6(5H)-one (75 mg) in DMSO-d6 (3 ml) and stirred overnight at room temperature. The crude reaction material was filtered and purified by reverse phase HPLC (C18; 10-95% acetonitrile in water, 0.5 mM HCl) to provide the product. The compound was neutralized by dissolving in dichloromethane and filtering through a PL-HCO3 cartridge and the filtrate evaporated to give the title product (17.5 mg, 28% yield). 1H NMR (300 MHz, Chloroform-d) δ 8.57 (d, J=1.8 Hz, 1H), 7.81-7.71 (m, 2H), 7.57-7.49 (m, 1H), 7.42 (d, J=0.8 Hz, 1H), 5.34 (s, 2H), 4.49-4.31 (m, 2H), 4.03 (q, J=6.9 Hz, 1H), 3.01 (s, 3H), 1.43-1.31 (m, 3H). ESI-MS m/z calc. 449.19788, found 449.41 (M+1)+. Chiral HPLC (ChiralPAK IC column; 20% methanol/30% ethanol/50% hexanes): Rt 7.885 mins. (82% ee).

Example 2BBB

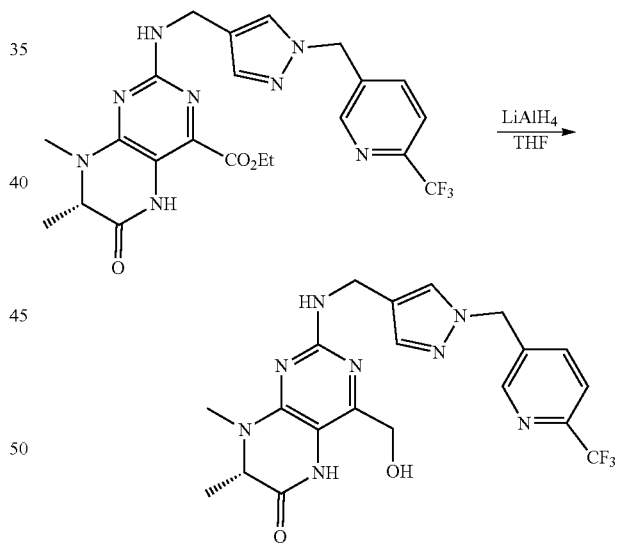

Compound 487

Compound 487 (7S)-4-(hydroxymethyl)-7,8-dimethyl-2-(((1-((6-(trifluoromethyl)pyridin-3-yl)methyl)-1H-pyrazol-4-yl)methyl)amino)-7,8-dihydropteridin-6(5H)-one A 2M solution of lithium aluminum hydride (300 mL, 0.6 mmol) in THF was added dropwise to a solution of ethyl (S)-7,8-dimethyl-6-oxo-2-(((1-((6-(trifluoromethyl)pyridin-3-yl)methyl)-1H-pyrazol-4-yl)methyl)amino)-5,6,7,8-tetrahydropteridine-4-carboxylate(see Compound 494, Step 3;

252 mg, 0.5 mmol) in 5 ml of THF and stirred at room temperature for 1 hour. The reaction was quenched by the addition the dropwise addition of water (1 ml). Ethyl acetate (10 ml) was added to the mixture followed by filtration through celite. The filtrate was evaporated in vacuo to afford a crude product which was purified by column chromatography ($SiO_2$; 12 g) eluting with a gradient of 0-10% methanol in dichloromethane. The relevant fractions were evaporated to afford the title product (152 mg (65% yield). 1H NMR (300 MHz, Methanol-d4/CDCl3) δ 8.71 (s, 1H), 8.01-7.87 (m, 2H), 7.79 (s, 1H), 7.71 (s, 1H), 5.59 (s, 2H), 4.86-4.67 (m, 2H), 4.59 (s, 2H), 4.26 (q, J=6.9 Hz, 1H), 3.55 (t, J=1.1 Hz, 1H), 3.24 (t, J=1.0 Hz, 3H), 1.58 (dt, J=6.9, 1.2 Hz, 3H). ESI-MS m/z calc. 462.17395, found 463.37 $(M+1)^+$; [α]=36.7° (c=1.0, THF) @ 22.7° C. Chiral HPLC (AD-H column, 6×250 mm; 50% isopropanol (0.2% diethylamine)/500% hexanes, Isocratic; 1 ml/min) Rt 6.611 mins. (95% ee).

Example 2CCC

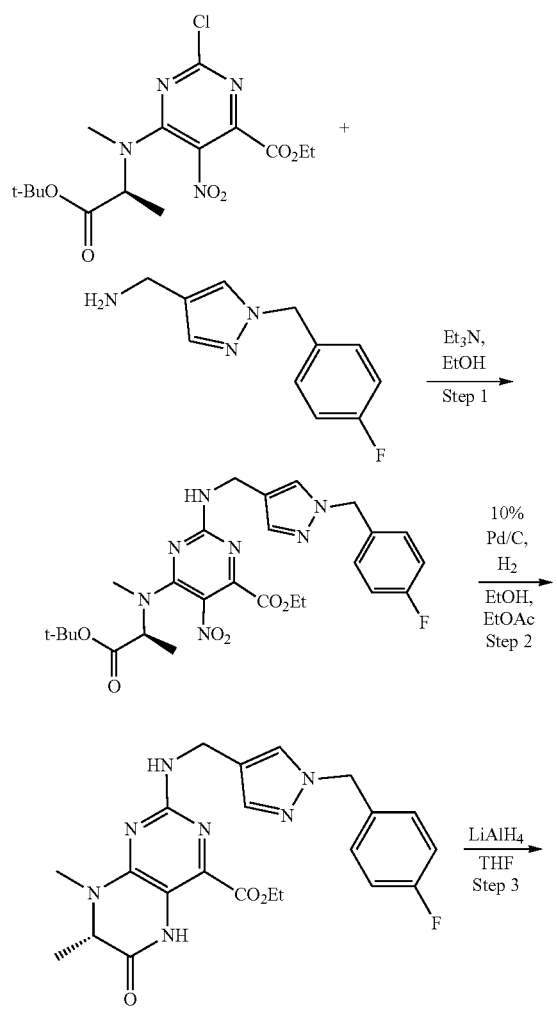

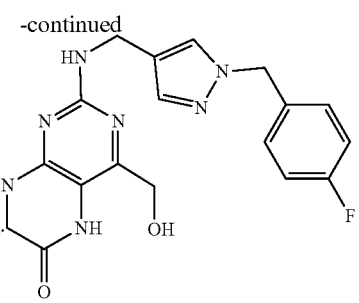

Compound 410

Compound 410. (7S)-2-(((1-(4-fluorobenzyl)-1H-pyrazol-4-yl)methyl)amino)-4-(hydroxymethyl)-7,8-dimethyl-7,8-dihydropteridin-6(5H)-one Step 1: Ethyl (S)-6-((1-(tert-butoxy)-1-oxopropan-2-yl)(methyl)amino)-2-(((1-(4-fluorobenzyl)-1H-pyrazol-4-yl)methyl)amino)-5-nitropyrimidine-4-carboxylate (1-(4-fluorobenzyl)-1H-pyrazol-4-yl)methanamine (2.64 g, 12.86 mmol) was added to a solution of ethyl (7S)-6-((1-(tert-butoxy)-1-oxopropan-2-yl)(methyl)amino)-2-chloro-5-nitro-pyrimidine-4-carboxylate (2.5 g, 6.43 mmol) and triethylamine (2.7 ml, 19.3 mmol) in ethanol (100 ml) and heated at reflux for 3 hours. The reaction was cooled to room temperature. The reaction mixture was poured into water (100 ml) and extracted with ethyl acetate (3×150 ml). The combined extracts were dried over magnesium sulfate, filtered, and evaporated in vacuo to provide the title product that was used immediately without purification.

Step 2: Ethyl (S)-2-(((1-(4-fluorobenzyl)-1H-pyrazol-4-yl)methyl)amino)-7,8-dimethyl-6-oxo-5,6,7,8-tetrahydropteridine-4-carboxylate Ethyl (S)-6-((1-(tert-butoxy)-1-oxopropan-2-yl)(methyl)amino)-2-(((1-(4-fluorobenzyl)-1H-pyrazol-4-yl)methyl)amino)-5-nitropyrimidine-4-carboxylate (3.5 g, 6.63 mmol) was placed Parr bottle and dissolved in ethanol (50 ml) and ethyl acetate (25 ml). 10% Pd/C (300 mg) was placed in the solution and the was placed on the Parr shaker and charged with 50 psi of hydrogen for 20 hours. The reaction was filtered through celite and the filtrate evaporated. The resulting crude product was purified by column chromatography ($SiO_2$) eluting with 0-20% methanol in dichloromethane. The desired fractions were combined and evaporated to afford 633 mg (21% yield) of the title product. 1H NMR (400 MHz, DMSO-d6) δ 9.67 (s, 1H), 7.68 (s, 1H), 7.42 (s, 1H), 7.32-7.21 (m, 2H), 7.14 (t, J=8.9 Hz, 2H), 7.07 (s, 1H), 5.23 (s, 2H), 4.30 (q, J=7.1 Hz, 2H), 3.33 (s, 2H), 3.01 (s, 3H), 1.30 (m, 6H). ESI-MS m/z calc. 453.19247, found 454.3 $(M+1)^+$.

Step 3: Compound 410. (7S)-2-(((1-(4-fluorobenzyl)-1H-pyrazol-4-yl)methyl)amino)-4-(hydroxymethyl)-7,8-dimethyl-7,8-dihydropteridin-6(5H)-one A 1M solution of lithium aluminum hydride (1.5 mL, 1.5 mmol) in THF was added dropwise to a solution of ethyl (S)-2-(((1-(4-fluorobenzyl)-1H-pyrazol-4-yl)methyl)amino)-7,8-dimethyl-6-oxo-5,6,7,8-tetrahydropteridine-4-carboxylate (700 mg, 1.45 mmol) in THF (20 ml). The reaction was stirred at room temperature for 2 hours. The reaction was quenched by the addition of methanol and water and extracted with ethyl acetate. The combined extracts were dried over magnesium sulfate, filtered, and evaporated. The crude was purified be column chromatography (SiO$_2$, 12 g) eluting with a gradient of 0-20% methanol in dichloromethane. The desired fractions were combined and evaporated in vacuo to provide the title product (208.0 mg, 33% yield). 1H NMR (400 MHz, DMSO-d6) δ 9.68 (br, 1H), 7.69 (s, 1H), 7.40 (s, 1H), 7.26 (dd, J=8.5, 5.5 Hz, 2H), 7.15 (t, J=8.7 Hz, 2H), 5.51 (br, 1H), 5.24 (s, 2H), 4.43 (s, 2H), 4.26 (d, J=5.9 Hz, 2H), 4.07 (m, 1H), 3.00 (s, 3H), 1.26 (d, J=6.8 Hz, 3H). ESI-MS m/z calc. 411.18192, found 412.14 (M+1)$^+$.

Example 2DDD: Synthesis of Compound 136B (R-isomer of Compound 136): (7R)-4,7,8-trimethyl-2-[[1-[[6-(trifluoromethyl)-3-pyridyl]methyl]pyrazol-4-yl]methylamino]-5,7-dihydropteridin-6-one Compound 136B was made with same route as Compound 136 but with the corresponding R starting material A-2. (13.3 g, 84%)$^1$H NMR (300 MHz, DMSO) δ 9.83 (s, 1H), 8.63 (s, 1H), 7.94-7.79 (m, 2H), 7.76 (s, 1H), 7.43 (s, 1H), 6.61 (s, 1H), 5.44 (s, 2H), 4.23 (d, J=6.2 Hz, 2H), 4.00 (q, J=6.8 Hz, 1H), 2.94 (s, 3H), 2.13 (s, 3H), 1.19 (d, J=6.8 Hz, 3H).

Example 2EEE: Synthesis of Compound 1B (R-isomer of Compound 1): (7R)-2-[[1-[(4-fluorophenyl)methyl]pyrazol-4-yl]methylamino]-4,5,7,8-tetramethyl-7H-pteridin-6-one Compound 1B was separated from the racemic mixture in the preparation of Compound 1 above using SFC separation. $^1$H NMR (300 MHz, MeOD) δ 7.66 (s, 1H), 7.51 (s, 1H), 7.24 (dd, J=8.6, 5.4 Hz, 2H), 7.05 (dd, J=12.1, 5.4 Hz, 2H), 5.26 (s, 2H), 4.46 (s, 2H), 4.18 (q, J=6.9 Hz, 1H), 3.30 (s, 3H), 3.13 (s, 3H), 2.39 (s, 3H), 1.27 (d, J=7.0 Hz, 3H).

Example 2FFF: Synthesis of Compound 42B (R-isomer of Compound 42): (R)-7,8-dimethyl-2-(((1-(3,4,5-trifluorobenzyl)-1H-pyrazol-4-yl)methyl)amino)-7,8-dihydropteridin-6(5H)-one Compound 42B was separated from the racemic mixture in the preparation of Compound 42 above using SFC separation. $^1$H NMR (300 MHz, Chloroform-d) δ 7.49 (s, 1H), 7.38 (s, 1H), 7.28 (s, 1H), 6.72 (dd, J=7.8, 6.3 Hz, 2H), 5.11 (s, 2H), 4.38 (d, J=5.5 Hz, 2H), 3.97 (q, J=6.8 Hz, 1H), 3.00 (s, 3H), 1.35 (d, J=6.8 Hz, 3H).

Example 2GGG: Synthesis of Compound 46B (R-isomer of Compound 46): (R)-2-(((1-(3,5-difluoro-4-methoxybenzyl)-1H-pyrazol-4-yl)methyl)amino)-4,7,8-trimethyl-7,8-dihydropteridin-6(5H)-one Compound 46B was separated from the racemic mixture in the preparation of Compound 46 above using SFC separation. $^1$H NMR (300 MHz, Chloroform-d) δ 7.54 (d, J=0.7 Hz, 1H), 7.41-7.34 (m, 1H), 6.73 (dt, J=8.4, 0.8 Hz, 2H), 5.31 (s, 1H), 5.17 (s, 2H), 4.89 (t, J=5.9 Hz, 1H), 4.44 (d, J=5.7 Hz, 2H), 4.15-3.94 (m, 4H), 3.05 (s, 3H), 2.23 (s, 3H), 1.41 (d, J=6.9 Hz, 3H).

Example 2HHH: Synthesis of Compound 405B (R-isomer of Compound 405): N-[[1-[[6-(trifluoromethyl)-3-pyridyl]methyl]pyrazol-4-yl]methyl]-N-[(7R)-4,7,8-trimethyl-6-oxo-5,7-dihydropteridin-2-yl]acetamide Compound 405B was prepared from Compound 136B. To a solution of (7R)-4,7,8-trimethyl-2-[[1-[[6-(trifluoromethyl)-3-pyridyl]methyl]pyrazol-4-yl]methylamino]-5,7-dihydropteridin-6-one (250 mg, 0.560 mmol) in anhydrous THF (3.7 mL) was added acetyl acetate (approximately 87 mg, 80.06 µL, 0.84 mmol) and DIEA (approximately 217 mg, 293 µL, 1.68 mmol), the mixture was sealed in a microwave tube and heated at 100° C. for 24 hrs. The solvent was removed by evaporation, the residue was purified by silica gel column (40 g) in ISCO eluting with DCM, 20% MeOH/DCM. The desired fractions were collected and evaporated. The off white solid was dried over 50° C. vacuum for overnight. (206 mg, 75%). First eluting peak SFC: 20% MeOH: 30% EtOH: 50% Hexanes (ChiralPac IC)
$^1$H NMR (300 MHz, DMSO-d6) δ 10.30 (s, 1H), 8.66-8.52 (m, 1H), 7.94-7.77 (m, 2H), 7.74 (d, J=0.8 Hz, 1H), 7.35 (d, J=0.7 Hz, 1H), 5.42 (s, 2H), 4.93-4.80 (m, 2H), 4.17 (q, J=6.8 Hz, 1H), 2.98 (s, 3H), 2.28 (s, 3H), 2.24 (s, 3H), 1.26 (d, J=6.8 Hz, 3H).

Example 2III: Synthesis of Other Compounds of Table 46

The compounds of Table 46 described herein were prepared in a similar manner as described above for other compounds having R-stereochemistry at the carbon to which R$^3$ and R$^4$ are bound (for example, using a respective R-isomer intermediate(s) or by chiral separation (e.g., SFC separation)).

Compound 9B. (R)-7-ethyl-2-(((1-(4-fluorobenzyl)-1H-pyrazol-4-yl)methyl)amino)-8-methyl-7,8-dihydropteridin-6(5H)-one/

1H NMR (300 MHz, MeOD) δ 7.66 (s, 1H), 7.51 (s, 1H), 7.24 (dd, J=8.6, 5.4 Hz, 2H), 7.05 (dd, J=12.1, 5.4 Hz, 2H), 5.26 (s, 2H), 4.46 (s, 2H), 4.18 (q, J=6.9 Hz, 1H), 3.30 (s, 3H), 3.13 (s, 3H), 2.39 (s, 3H), 1.27 (d, J=7.0 Hz, 3H). [3], 1H NMR (300 MHz, Methanol-d4) ?7.57 (s, 1H), 7.44 (s, 1H), 7.23-7.12 (m, 2H), 7.05-6.92 (m, 2H), 5.20 (s, 2H), 4.34 (s, 2H), 3.99 (q, J=6.9 Hz, 1H), 3.22 (s, 3H), 2.96 (s, 3H), 2.27 (s, 3H), 1.10 (d, J=6.9 Hz, 3H). M+1 410.215.

Compound 14B. (R)-4,5,7,8-tetramethyl-2-(((1-(3,4,5-trifluorobenzyl)-1H-pyrazol-4-yl)methyl)amino)-7,8-dihydropteridin-6(5H)-one

M+1 446.19.

Compound 19B. (R)-5,7-diethyl-2-(((1-(4-fluorobenzyl)-1H-pyrazol-4-yl)methyl)amino)-8-methyl-7,8-dihydropteridin-6(5H)-one

M+1 424.23.

Compound 22B. (R)-8-ethyl-2-(((1-(4-fluorobenzyl)-1H-pyrazol-4-yl)methyl)amino)-5,7-dimethyl-7,8-dihydropteridin-6(5H)-one 1H NMR (300 MHz, DMSO-d6) δ 7.63 (d, J=1.5 Hz, 2H), 7.37 (d, J=0.8 Hz, 1H), 7.26 (dd, J=8.5, 5.7 Hz, 2H), 7.14 (t, J=8.9 Hz, 2H), 6.72 (t, J=6.0 Hz, 1H), 5.24 (s, 2H), 4.35-4.14 (m, 3H), 3.97-3.80 (m, 1H), 3.16 (s, 3H), 3.13-3.01 (m, 1H), 1.22 (d, J=6.7 Hz, 3H), 1.12 (t, J=7.1 Hz, 3H). [2], 1H NMR (300 MHz, CDCl3) δ 7.45 (d, J=4.9 Hz, 2H), 7.27 (s, 1H), 7.16-7.09 (m, 2H), 7.02-6.89 (m, 2H), 5.15 (s, 2H), 4.93 (t, J=5.1 Hz, 1H), 4.32 (t, J=7.3 Hz, 2H), 4.09 (dd, J=14.4, 7.6 Hz, 1H), 3.93 (dq, J=14.4, 7.2 Hz, 1H), 3.18 (s, 3H), 3.01 (tt, J=12.2, 6.1 Hz, 1H), 1.28 (d, J=6.8 Hz, 3H), 1.16-1.06 (m, 3H). M+1 410.3.

Compound 23B. (R)-5,8-dimethyl-7-propyl-2-(((1-(3,4,5-trifluorobenzyl)-1H-pyrazol-4-yl)methyl)amino)-7,8-dihydropteridin-6(5H)-one $^1$H NMR (300 MHz, Methanol-d4) δ 7.67 (d, J=0.8 Hz, 1H), 7.56-7.48 (m, 2H), 6.98-6.86 (m, 2H), 5.26 (d, J=1.0 Hz, 2H), 4.40 (s, 2H), 4.19 (dd, J=5.8, 4.2 Hz, 1H), 3.26 (s, 3H), 3.06 (s, 3H), 1.89-1.71 (m, 2H), 1.35-1.09 (m, 2H), 0.87 (t, J=7.3 Hz, 3H). M+1 460.19.

Compound 24B. (R)-2-(((1-(4-fluorobenzyl)-1H-pyrazol-4-yl)methyl)amino)-5,8-dimethyl-7-propyl-7,8-dihydropteridin-6(5H)-one $^1$H NMR (300 MHz, Methanol-d4) δ 7.65-7.58 (m, 1H), 7.49 (d, J=6.0 Hz, 2H), 7.23 (dd, J=8.6, 5.4 Hz, 2H), 7.10-6.97 (m, 2H), 5.25 (s, 2H), 4.37 (s, 2H), 4.25-4.15 (m, 1H), 3.26 (s, 3H), 3.05 (s, 3H), 1.87-1.75 (m, 2H), 1.20 (s, 2H), 0.87 (t, J=7.3 Hz, 3H). [2], 1H NMR (300 MHz, Methanol-d4) δ 7.61 (d, J=0.8 Hz, 1H), 7.53-7.44 (m, 2H), 7.28-7.17 (m, 2H), 7.10-6.97 (m, 2H), 5.25 (s, 2H), 4.37 (s, 2H), 4.19 (dd, J=5.7, 4.2 Hz, 1H), 3.26 (s, 3H), 3.05 (s, 3H), 1.90-1.70 (m, 2H), 1.18 (dtt, J=9.1, 7.3, 6.0 Hz, 2H), 0.87 (t, J=7.3 Hz, 3H). M+1 424.275.

Compound 27B. (R)-2-(((1-(4-fluorobenzyl)-1H-pyrazol-4-yl)methyl)amino)-5,7,8-trimethyl-7,8-dihydropteridin-6(5H)-one $^1$H NMR (300 MHz, CDCl3) δ 7.45 (s, 2H), 7.28 (s, 1H), 7.17-7.05 (m, 2H), 7.02-6.86 (m, 2H), 5.15 (s, 2H), 5.00 (s, 1H), 4.39-4.30 (m, 2H), 4.05 (q, J=6.8 Hz, 1H), 3.18 (s, 3H), 2.94 (s, 3H), 1.27 (d, J=7.7 Hz, 3H). M+1 396.14.

Compound 30B. (R)-5,8-diethyl-2-(((1-(4-fluorobenzyl)-1H-pyrazol-4-yl)methyl)amino)-7-methyl-7,8-dihydropteridin-6(5H)-one $^1$H NMR (300 MHz, CDCl3) δ 7.48 (s, 1H), 7.45 (d, J=4.0 Hz, 1H), 7.27 (s, 1H), 7.15-7.06 (m, 2H), 6.99-6.88 (m, 2H), 5.15 (s, 2H), 4.95 (dd, J=17.0, 3.5 Hz, 1H), 4.32 (t, J=7.3 Hz, 2H), 4.19-3.60 (m, 4H), 3.14-2.92 (m, 1H), 1.25 (t, J=6.9 Hz, 3H), 1.14 (dt, J=14.2, 5.4 Hz, 6H). M+1 424.27.

Compound 31B. (R)-5,8-diethyl-7-methyl-2-(((1-(3,4,5-trifluorobenzyl)-1H-pyrazol-4-yl)methyl)amino)-7,8-dihydropteridin-6(5H)-one 1H NMR (300 MHz, CDCl3) δ 7.49 (d, J=5.9 Hz, 1H), 7.45 (d, J=10.3 Hz, 1H), 7.33 (s, 1H), 6.77-6.67 (m, 2H), 5.12 (s, 2H), 4.97 (d, J=5.2 Hz, 1H), 4.36 (t, J=5.6 Hz, 2H), 4.10 (q, J=6.8 Hz, 1H), 4.00-3.62 (m, 3H), 3.04 (dq, J=14.1, 7.1 Hz, 1H), 1.26 (t, J=7.7 Hz, 3H), 1.14 (dd, J=13.5, 7.1 Hz, 6H). M+1 460.28.

Compound 32B. (R)-7-ethyl-2-(((1-(4-fluorobenzyl)-1H-pyrazol-4-yl)methyl)amino)-8-isopropyl-5-methyl-7,8-dihydropteridin-6(5H)-one $^1$H NMR (300 MHz, CDCl3) δ 7.41 (d, J=6.8 Hz, 1H), 7.40 (s, 1H), 7.31 (s, 1H), 7.17-7.05 (m, 2H), 7.01-6.86 (m, 2H), 5.80 (s, 1H), 5.14 (s, 2H), 4.65 (d, J=33.9 Hz, 1H), 4.51-4.39 (m, 1H), 4.36 (t, J=6.0 Hz, 2H), 4.15 (dt, J=11.3, 5.7 Hz, 1H), 3.18 (s, 3H), 1.85 (dqd, J=15.0, 7.6, 3.4 Hz, 1H), 1.74-1.53 (m, 1H), 1.33-1.20 (m, 6H), 0.77 (t, J=7.5 Hz, 3H). [2], 1H NMR (300 MHz, CDCl3) δ 7.44 (s, 2H), 7.27 (s, 1H), 7.17-7.09 (m, 2H), 7.00-6.89 (m, 2H), 5.15 (s, 2H), 4.96 (s, 1H), 4.44 (dt, J=13.7, 6.8 Hz, 1H), 4.34 (d, J=5.6 Hz, 2H), 4.13 (dd, J=7.6, 3.4 Hz, 1H), 3.20 (s, 3H), 1.81 (dtt, J=15.1, 7.5, 3.8 Hz, 1H), 1.69-1.57 (m, 1H), 1.25 (t, J=6.5 Hz, 6H), 0.78 (t, J=7.5 Hz, 4H). M+1 438.345

Compound 36B. (R)-7-ethyl-8-isopropyl-5-methyl-2-(((1-(3,4,5-trifluorobenzyl)-1H-pyrazol-4-yl)methyl)amino)-7,8-dihydropteridin-6(5H)-one $^1$H NMR (300 MHz, CDCl3) δ 7.46 (d, J=3.8 Hz, 1H), 7.45 (s, 1H), 7.32 (s, 1H), 6.76-6.69 (m, 2H), 5.12 (s, 2H), 5.05 (s, 1H), 4.46 (dd, J=13.7, 6.9 Hz, 1H), 4.37 (d, J=5.7 Hz, 2H), 4.14 (dd, J=7.6, 3.4 Hz, 1H), 3.20 (s, 3H), 1.82 (tdd, J=15.1, 7.6, 3.4 Hz, 1H), 1.72-1.56 (m, 1H), 1.26 (t, J=6.5 Hz, 6H), 0.78 (t, J=7.5 Hz, 3H). M+1 474.24

Compound 51B. (R)-5-ethyl-8-isopropyl-7-methyl-2-(((1-(3,4,5-trifluorobenzyl)-1H-pyrazol-4-yl)methyl)amino)-7,8-dihydropteridin-6(5H)-one $^1$H NMR (300 MHz, CDCl3) δ 7.54 (s, 1H), 7.45 (d, J=10.6 Hz, 1H), 7.33 (s, 1H), 6.76-6.67 (m, 2H), 5.12 (s, 2H), 5.00 (t, J=5.5 Hz, 1H), 4.54 (dq, J=13.2, 6.6 Hz, 1H), 4.35 (t, J=5.8 Hz, 2H), 4.18 (q, J=6.7 Hz, 1H), 3.87 (dq, J=14.3, 7.1 Hz, 1H), 3.77-3.58 (m, 1H), 1.19 (m, 12H). M+1 474.34.

Compound 52B. (R)-5-ethyl-2-(((1-(4-fluorobenzyl)-1H-pyrazol-4-yl)methyl)amino)-8-isopropyl-7-methyl-7,8-dihydropteridin-6(5H)-one $^1$H NMR (300 MHz, CDCl3) δ 7.52 (s, 1H), 7.44 (s, 1H), 7.27 (s, 1H), 7.15-7.06 (m, 2H), 6.98-6.88 (m, 2H), 5.15 (s, 2H), 5.01 (t, J=5.1 Hz, 1H), 4.54 (hept, J=6.8 Hz, 1H), 4.33 (d, J=5.6 Hz, 2H), 4.24-4.08 (m, 1H), 3.93-3.76 (m, 1H), 3.68 (dq, J=14.2, 7.1 Hz, 1H), 2.62 (s, 1H), 1.29-1.07 (m, 12H). M+1 438.32.

Compound 186B. (R)-7-ethyl-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, DMSO-d6) δ 9.94 (s, 1H), 8.63 (s, 1H), 7.87 (td, J=7.8, 1.5 Hz, 2H), 7.77 (s, 1H), 7.43 (s, 1H), 6.70 (s, 1H), 5.45 (s, 2H), 4.24 (d, J=5.9 Hz, 2H), 4.03 (dd, J=6.5, 3.7 Hz, 1H), 2.98 (s, 3H), 2.12 (s, 3H), 1.86-1.61 (m, 2H), 0.74 (t, J=7.4 Hz, 3H). M+1 461.47.

Compound 177B. (R)-4,5,7,8-tetramethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, DMSO-d6) δ 8.63 (s, 1H), 7.95-7.82 (m, 2H), 7.78 (s, 1H), 7.44 (s, 1H), 6.89 (t, J=6.4 Hz, 1H), 5.45 (s, 2H), 4.25 (dd, J=5.8, 2.9 Hz, 2H), 4.02 (q, J=6.8 Hz, 1H), 3.18 (s, 3H), 2.91 (s, 3H), 2.27 (s, 3H), 1.04 (d, J=6.9 Hz, 3H). [3]. $^1$H NMR (300 MHz, DMSO-d6) δ 8.63 (s, 1H), 7.95-7.82 (m, 2H), 7.78 (s, 1H), 7.44 (s, 1H), 6.87 (t, J=6.1 Hz, 1H), 5.45 (s, 2H), 4.25 (dd, J=6.0, 2.7 Hz, 2H), 4.02 (q, J=6.8 Hz, 1H), 3.18 (s, 3H), 2.91 (s, 3H), 2.27 (s, 3H), 1.04 (d, J=5.8 Hz, 3H). M+1 461.315.

Compound 187B. (R)-4,7,8-trimethyl-2-(((1-((3-(trifluoromethyl)pyridin-4-yl)methyl)-1H-pyrazol-4-yl)methyl)amino)-7,8-dihydropteridin-6(5H)-one

M+1 447.28.

Compound 220B. (R)-4,8-dimethyl-7-propyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, DMSO-d6) δ 9.87 (s, 1H), 8.70-8.54 (m, 1H), 7.86 (qd, J=8.1, 1.5 Hz, 2H), 7.76 (s, 1H), 7.42 (s, 1H), 6.59 (t, J=5.8 Hz, 1H), 5.45 (s, 2H), 4.22 (d, J=6.0 Hz, 2H), 4.00 (dd, J=6.8, 4.0 Hz, 1H), 2.96 (s, 3H), 2.11 (s, 3H), 1.83-1.48 (m, 2H), 1.27-1.05 (m, 2H), 0.83 (t, J=7.3 Hz, 3H). M+1 447.28.

Compound 386B. (R)-7-cyclopropyl-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, DMSO-d6) δ 9.87 (brs, 1H), 8.63 (d, J=2.3 Hz, 1H), 7.96-7.81 (m, 2H), 7.78 (s, 1H), 7.44 (s, 1H), 6.67 (d, J=6.2 Hz, 1H), 5.45 (s, 2H), 4.24 (dd, J=5.8, 3.1 Hz, 2H), 3.32 (d, J=9.0 Hz, 1H), 3.03 (s, 3H), 2.14 (s, 3H), 0.83 (m, 1H), 0.62-0.27 (m, 4H). M+1 473.23.

Compound 396B. (R)-7-cyclopropyl-4,8-dimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one $^1$H NMR (300 MHz, DMSO-d6) δ 9.82 (s, 1H), 7.68 (s, 1H), 7.41 (s, 1H), 6.61 (t, J=6.1 Hz, 1H), 6.58 (s, 1H), 5.44 (s, 2H), 4.22 (dd, J=6.0, 3.3 Hz, 2H), 3.88 (s, 3H), 3.32 (d, J=4.5 Hz, 1H), 3.02 (s, 3H), 2.14 (s, 3H), 0.83 (ddt, J=13.2, 8.1, 4.0 Hz, 1H), 0.63-0.27 (m, 4H). M+1 476.55.

Compound 421B. (R)-7-cyclopropyl-2-(((1-((6-fluoropyridin-3-yl)methyl)-1H-pyrazol-4-yl)methyl)amino)-4,8-dimethyl-7,8-dihydropteridin-6(5H)-one $^1$H NMR (300 MHz, Chloroform-d) δ 8.84 (s, 1H), 8.11 (dt, J=2.6, 0.9 Hz, 1H), 7.65 (ddd, J=8.3, 7.6, 2.6 Hz, 1H), 7.53 (d, J=0.7 Hz, 1H), 7.46-7.35 (m, 1H), 6.98-6.84 (m, 1H), 5.49 (s, 1H), 5.26 (s, 2H), 4.44 (dd, J=5.6, 1.7 Hz, 2H), 3.29 (d, J=9.1 Hz, 1H), 3.14 (s, 3H), 2.26 (s, 3H), 1.38-1.13 (m, 1H), 1.07-0.90 (m, 1H), 0.76-0.63 (m, 1H), 0.63-0.38 (m, 2H). M+1 423.29.

Compound 422B. (R)-2-(((1-((6-(difluoromethoxy)pyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 8.36 (s, 1H), 8.10 (d, J=2.4 Hz, 1H), 7.61 (dd, J=8.5, 2.5 Hz, 1H), 7.54 (s, 1H), 7.38 (s, 1H), 7.25 (d, J=21.3 Hz, 1H), 6.89 (d, J=8.5 Hz, 1H), 5.25 (s, 2H), 4.91 (d, J=5.8 Hz, 1H), 4.42 (d, J=5.7 Hz, 2H), 3.89 (d, J=4.3 Hz, 1H), 3.11 (s, 3H), 2.33-2.23 (m, 1H), 2.21 (s, 3H), 1.07 (dd, J=6.9, 1.8 Hz, 3H), 0.97-0.89 (m, 4H). M+1 473.41.

Compound 423B. (R)-2-(((1-((6-fluoro-4-methylpyridin-3-yl)methyl)-1H-pyrazol-4-yl)methyl)amino)-7-isopropyl-4,8-dimethyl-7,8-dihydropteridin-6(5H)-one $^1$H NMR (300 MHz, Chloroform-d) δ 7.97 (s, 1H), 7.78 (s, 1H), 7.52 (s, 1H), 6.70 (m, 1H), 5.27 (s, 2H), 4.81 (t, J=5.7 Hz, 1H), 4.41 (d, J=5.7 Hz, 2H), 3.89 (d, J=4.3 Hz, 1H), 3.11 (s, 3H), 2.38-2.27 (m, 3H), 2.26-2.19 (m, 1H), 2.19 (s, 3H), 1.08 (d, J=6.9 Hz, 3H), 0.99-0.81 (m, 3H). M+1 439.37.

Compound 445B. (R)-2-(((1-((6-chloropyridin-3-yl)methyl)-1H-pyrazol-4-yl)methyl)amino)-7-(2-hydroxyethyl)-4,5,8-trimethyl-7,8-dihydropteridin-6(5H)-one $^1$H NMR (300 MHz, DMSO-d6) δ 8.31 (d, J=2.5 Hz, 1H), 7.74 (s, 1H), 7.68 (dd, J=8.3, 2.5 Hz, 1H), 7.49 (d, J=8.2 Hz, 1H), 7.42 (s, 1H), 6.87 (s, 1H), 5.32 (s, 2H), 4.64-4.55 (m, 1H), 4.24 (dd, J=6.2, 2.2 Hz, 2H), 4.05 (dd, J=7.7, 5.8 Hz, 1H), 3.17 (s, 3H), 2.98 (s, 3H), 2.26 (s, 3H), 1.79-1.38 (m, 2H). M+1 457.1.

Compound 495B. (R)-4,8-dimethyl-7-(2,2,2-trifluoroethyl)-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, DMSO-d6) δ 10.04 (s, 1H), 8.62 (d, J=1.9 Hz, 1H), 7.88-7.79 (m, 2H), 7.75 (s, 1H), 7.42 (s, 1H), 6.60 (t, J=6.0 Hz, 1H), 5.44 (s, 2H), 4.40 (dd, J=6.0, 4.0 Hz, 1H), 4.23 (d, J=6.0 Hz, 2H), 2.99 (s, 3H), 2.80-2.70 (m, 1H), 2.13 (s, 3H). M+1 515.28.

Compound 497B. (R)-7-ethyl-8-isopropyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, DMSO) δ 10.26 (s, 1H), 8.62 (s, 1H), 7.94-7.78 (m, 2H), 7.75 (s, 1H), 7.42 (s, 1H), 7.36 (s, 1H), 6.82 (s, 1H), 5.45 (s, 2H), 4.42-4.29 (m, 1H), 4.26 (d, J=5.9 Hz, 2H), 4.07 (dd, J=7.1, 3.2 Hz, 1H), 1.85-1.53 (m, 2H), 1.26 (dd, J=6.8, 3.6 Hz, 6H), 0.78 (t, J=7.4 Hz, 3H). M+1 475.37.

Compound 589B. (R)-7-(2-methoxyethyl)-4,8-dimethyl-2-(((1-((6-(trifluoromethyl)pyridin-3-yl)methyl)-1H-pyrazol-4-yl)methyl)amino)-7,8-dihydropteridin-6(5H)-one $^1$H NMR (300 MHz, Chloroform-d) δ 9.13 (s, 1H), 8.68-8.50 (m, 1H), 7.65 (t, J=1.2 Hz, 2H), 7.55 (d, J=0.7 Hz, 1H), 7.42 (d, J=0.7 Hz, 1H), 5.35 (s, 2H), 4.92 (t, J=5.8 Hz, 1H), 4.43 (d, J=5.8 Hz, 2H), 4.15 (dd, J=7.2, 4.2 Hz, 1H), 3.50-3.29 (m, 2H), 3.20 (s, 3H), 3.05 (s, 3H), 2.24 (s, 3H), 2.21-1.79 (m, 2H). M+1 491.07.

Compound 678B. (R)-7-(2-methoxyethyl)-4,8-dimethyl-2-(((1-((1-methyl-3-(trifluoromethyl)-1H-pyrazol-5-yl)methyl)-1H-pyrazol-4-yl)methyl)amino)-7,8-dihydropteridin-6(5H)-one $^1$H NMR (300 MHz, Methanol-d4) δ 7.62 (s, 1H), 7.51 (s, 1H), 6.48 (s, 1H), 5.42 (s, 2H), 4.83 (s, 3H), 4.38 (s, 2H), 4.16 (dd, J=6.6, 4.0 Hz, 1H), 3.84 (s, 3H), 3.07 (d, J=14.6 Hz, 6H), 2.22-1.89 (m, 5H). M+1 494.04.

Compound 204B. (R)-4-((4-(((4,7,8-trimethyl-6-oxo-5,6,7,8-tetrahydropteridin-2-yl)amino)methyl)-1H-pyrazol-1-yl)methyl)picolinonitrile $^1$H NMR (300 MHz, Chloroform-d) δ 8.57 (d, J=5.2 Hz, 1H), 7.52 (s, 1H), 7.40 (s, 1H), 7.30 (s, 1H), 7.23-7.10 (m, 1H), 5.45 (s, 1H), 5.26 (s, 2H), 4.47-4.31 (m, 2H), 4.00 (q, J=6.7 Hz, 1H), 2.99 (s, 3H), 2.86 (s, 3H), 2.17 (s, 3H), 1.34 (d, J=6.8 Hz, 3H). M+1 404.36.

Compound 677B. (R)-7-(hydroxymethyl)-4,8-dimethyl-2-(((1r,3R)-3-(3,4,5-trifluorophenoxy)cyclobutyl)amino)-7,8-dihydropteridin-6(5H)-one

M+1 424.14.

Example 2JJJ: Synthesis of 4,8-dimethyl-7-methylene-2-(((1-((6-(trifluoromethyl)pyridin-3-yl)methyl)-1H-pyrazol-4-yl)methyl)amino)-7,8-dihydropteridin-6(5H)-one (Compound 749)

An oven dried flask was charged with (7S)-7-(hydroxymethyl)-4,8-dimethyl-2-[[1-[[6-(trifluoromethyl)-3-pyridiyl]methylamino]-5,7-dihydropteridin-6-one (25 mg, 0.05360 mmol) dissolved in dichloromethane (2 mL) under an atmosphere of nitrogen was added 55 mg (0.08178 mmol) of Martin's sulfurane (diphenyl-bis[2,2,2-trifluoro-1-phenyl-1-(trifluoromethyl)ethoxy]-λ4}-sulfane). The resulting suspension was stirred at ambient temperature for 1 h. The reaction was still cloudy. Another 0.5 eq sulfurane reagent was added, and the solution slowly turned clear and blue. After 30 mins, it turned yellow. LCMS indicated 80% done. Another 0.5 eq sulfurane was added. The reaction was stirred for 20 mins and turned yellow again. The crude product was loaded directly onto silica gel column (MeOH/DCM 0-50%) to provide desired product as white solid.

$^1$H NMR (400 MHz, CDCl$_3$/Methanol-d$_4$) δ 8.26 (s, 1H), 7.47 (d, J=8.5 Hz, 1H), 7.24 (d, J=8.3 Hz, 1H), 7.30 (s, 1H), 7.24 (d, J=13.7 Hz, 1H), 5.17 (s, 1H), 5.12 (s, 2H), 4.35 (s, 1H), 4.16 (s, 2H), 3.10 (s, 3H), 1.99 (s, 3H). ESI-MS m/z 444.1634, found 445.36 (M+1)+; 443.46 (M−1)+; Retention time: 0.69 minutes.

Example 2KKK: Synthesis of (S)-2-(((1-(3,3-difluorocyclobutyl)-1H-pyrazol-4-yl)methyl)amino)-7-ethyl-4,8-dimethyl-7,8-dihydropteridin-6(5H)-one (Compound 795)

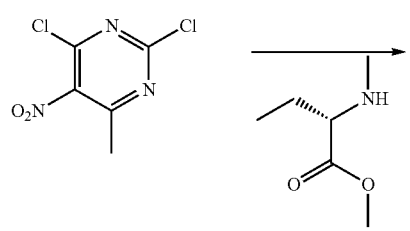

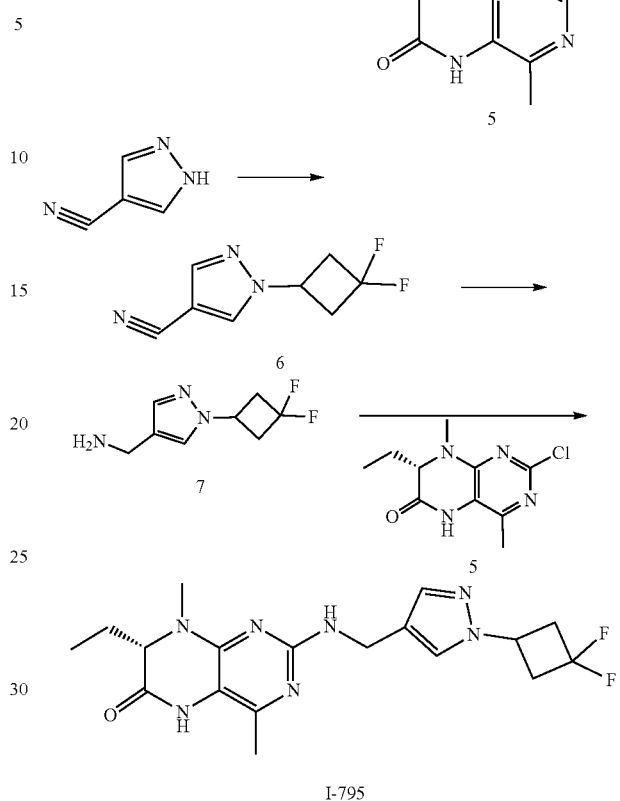

I-795

Formation of (S)-2-chloro-7-ethyl-4,8-dimethyl-7,8-dihydropteridin-6(5H)-one (5)

A suspension of 2,4-dichloro-6-methyl-5-nitro-pyrimidine (26.0 g, 125.0 mmol), methyl (2S)-2-(methylamino)butanoate (HCl salt) (23.1 g, 137.5 mmol) and NaHCO$_3$ (52.5 g, 625.0 mmol) in cyclohexane (400 mL) was equipped with a dean-stark trap. The mixture was heated to reflux for 3 h, (4 mL water accumulated in DS trap). Lcms showed desired product. Hot filtered this solution through celite and washed the cake with hot cyclohexane. The filtrate was concentrated in vacuo. $^1$H NMR shows pure desired product 3, with approximately 5% undesired regioisomer (19:1 ratio) to afford 37 grams of desired product as a yellow oil.

The oil was dissolved in 300 mL of THF, and added platinum (6.5 g of 3% w/w, 0.9996 mmol). The mixture was placed on a parr shaker and mixed overnight at 50 psi hydrogen. LCMS still shows some hydroxy-intermediate. To the mixture was added bis[(E)-1-methyl-3-oxo-but-1-enoxy]-oxo-vanadium (approximately 3.314 g, 12.50 mmol) and the mixture was placed again into a parr shaker and shaken at 50 psi for 2 more hours. The catalyst was filtered off and the resulting filtrate was concentrated in vacuo. The residue was dissolved in chloroform (200 mL) and filtered through a plug of florisil. The plug was eluted with 50% EtOAc/dichloromethane. The filtrate was concentrated in vacuo to a solid containing black impurities. The mixture was diluted with TBME 500 mL and stirred for 1 hour, filtered, and washed with TBME twice to afford 23 grams of product as a white solid: [α]$_D$=+47.1°, 100 mg in 10 mL of CHCl$_3$, temp 20.9° C.; $^1$H NMR (300 MHz, d6-DMSO) δ 10.41 (s, 1H), 4.21 (dd, J=6.1, 3.8 Hz, 1H), 3.01 (s, 3H), 2.24 (s, 3H), 1.93-1.66 (m, 2H), 0.75 (t, J=7.5 Hz, 3H); ESI-MS m/z calc. 240.08, found 241.17 (M+1)$^+$; 239.17 (M−1)$^−$; Retention time: 0.6 minutes.

Formation of 1-(3,3-difluorocyclobutyl)-1H-pyrazole-4-carbonitrile (6)

Step 1: To a solution of 1H-pyrazole-4-carbonitrile (10.0 g, 107.4 mmol) in dichloromethane (80 mL) was added pyridine (17.4 mL, 215.1 mmol). The mixture was cooled (0° C.). A separate mixture of trifluoromethylsulfonyl trifluoromethanesulfonate (20 mL, 118.9 mmol) in dichloromethane (20 mL) was slowly added to the first mixture, keeping internal temperature below 30° C. The mixture was stirred at this temperature for 30 minutes. The mixture was quenched with aqueous saturated NH$_4$Cl solution (100 mL). Split layers and wash organic layer with sat NaHCO$_3$ (100 mL), water, brine (100 mL each), dry, filter and remove solvent under reduced pressure. Added water (50 mL) to the residue and agitated for 60 minutes. Filtered resulting solid and dried o/n under vacuum to afford 18.5 grams of desired product: $^1$H NMR (400 MHz, CDCl$_3$) δ 8.60-8.41 (m, 1H), 8.14 (s, 1H); ESI-MS m/z calc. 224.98198, Retention time: minutes.

Step 2: To a solution of 3,3-difluorocyclobutanol (1.06 g, 9.81 mmol) in acetonitrile (10 m L) was added Cs$_2$CO$_3$ (3.5 g, 10.74 mmol). The mixture was cooled to 0° C. A solution of the previous intermediate-1-(trifluoromethylsulfonyl)pyrazole-4-carbonitrile (2.0 g, 8.9 mmol) in acetonitrile (10 mL) was slowly added to reaction mixture keeping temperature below 30° C. The mixture was warmed to room temperature and stirred for 30 minutes. Filtered solids and remove solvent under reduced pressure. Partition residue between dichloromethane and water (30 mL each). Split layers and washed organic with brine, dry, filter and remove solvent under reduced pressure. The resulting residue was purified via silica gel chromatography (Isco 80 g gold gradient 0-100% EtOAc/heptanes) product elutes about 35-40% EA/Hep and only visible under all wavelength to afford 1.38 grams of desired product: $^1$H NMR (400 MHz, CDCl$_3$) δ 7.90 (d, J=4.3 Hz, 2H), 4.88-4.66 (m, 1H), 3.42-3.08 (m, 4H).

Formation of (1-(3,3-difluorocyclobutyl)-1H-pyrazol-4-yl)methanamine (7)

To a solution of 1-(3,3-difluorocyclobutyl)pyrazole-4-carbonitrile, 6, (4.4 g, 22.82 mmol) in MeOH (30 mL) was added 7N ammonia in methanol (30 mL). Washed Raney nickel (750 mg, 12.78 mmol) with water (~4×10 mL) than added to reaction mixture. Put on Parr shaker and pressurized to 50 psi hydrogen and allowed to react for 4 hours. Filtered through Celite and removed solvent under reduced pressure. Stripped from diethyl ether (3×100 mL) and placed on vacuum overnight to afford 4.6 grams of desired product: $^1$H NMR (400 MHz, CDCl$_3$) δ 7.52 (s, 1H), 7.40 (s, 1H), 4.67 (dq, J=14.6, 7.3 Hz, 1H), 4.09-3.63 (m, 2H), 3.38-2.95 (m, 4H); ESI-MS m/z calc. 187.09, found 188.12 (M+1)$^+$; Retention time: 0.51 minutes. Used in next step without further purification.

Formation of (S)-2-(((1-(3,3-difluorocyclobutyl)-1H-pyrazol-4-yl)methyl)amino)-7-ethyl-4,8-dimethyl-7,8-dihydropteridin-6(5H)-one (I-795)

To (7S)-2-chloro-7-ethyl-4,8-dimethyl-5,7-dihydropteridin-6-one, 5, (1.94 g, 8.05 mmol), [1-(3,3-difluorocyclobutyl)pyrazol-4-yl]methanamine, 7, (1.51 g, 8.05 mmol), (tBuXPhos Pd G1) (200 mg, 0.29 mmol) in tBuOH (50.77 mL) under nitrogen was added NaOtBu (approximately 15.1 mL of 2 M, 30.18 mmol). The mixture was stirred for 20 minutes. The mixture was diluted with aqueous saturated NH$_4$Cl solution and extracted with dichloromethane (3×), dried, stirred with TMP resin. The solution was evaporated and purified by silica gel chromatography (0 to 20% MeOH in dichloromethane) to afford 3.05 g of desired product: [α]$_D$=34.31 (c 0.51, MeOH); $^1$H NMR (400 MHz, CDCl$_3$) δ 8.15 (s, 1H), 7.56 (s, 1H), 7.44 (s, 1H), 4.83 (t, J=5.7 Hz, 1H), 4.72-4.55 (m, 1H), 4.43 (d, J=5.8 Hz, 2H), 4.08 (dd, J=6.5, 3.7 Hz, 1H), 3.36-3.08 (m, 7H), 3.08 (d, J=6.1 Hz, 3H), 2.23 (s, 3H), 2.09-1.91 (m, 1H), 1.92-1.80 (m, 1H), 0.92 (t, J=7.5 Hz, 3H); ESI-MS m/z calc. 391.19, found 392.23 (M+1)$^+$; Retention time: 0.69 minutes; Chiral HPLC ee >99.5%.

Example 2LLL: Synthesis of (S)-7-isopropyl-4,8-dimethyl-2-(((1s,3R)-3-(((2-(trifluoromethyl)pyrimidin-5-yl)oxy)methyl)cyclobutyl)amino)-7,8-dihydropteridin-6(5H)-one (Compound 1417)

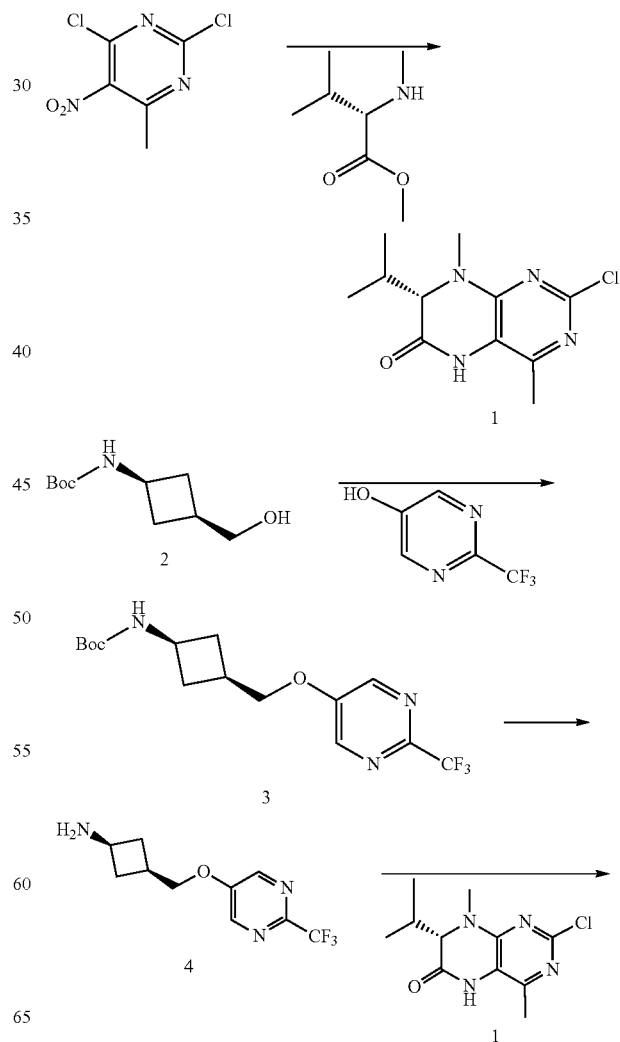

-continued

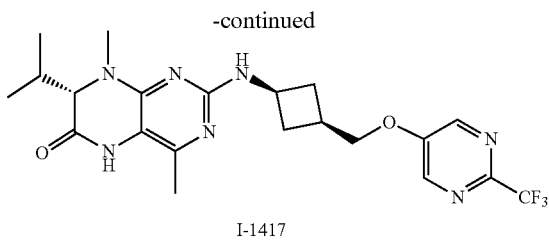

I-1417

Formation of (S)-2-chloro-7-isopropyl-4,8-dimethyl-7,8-dihydropteridin-6(5H)-one (1)

To a 2-L round bottom flas was added 2,4-dichloro-6-methyl-5-nitro-pyrimidine (55.0 g, 256.5 mmol), NaHCO$_3$ (108.4 g, 1.290 mol), and cyclohexane (600 mL). Let stir to dissolve pyrimidine (5 min), then added methyl (2S)-3-methyl-2-(methylamino)butanoate (Hydrochloride salt) (49.0 g, 256.2 mmol). The flask was equipped with a Dean-Stark trap and the reaction was heated to 110° C. LC-MS (UPLC_CSH_C18_5 to95_ACN_TFA_1p4 min) showed reaction complete after 2.5h. The mixture was stirred for another 30 min, filtered reaction hot through Celite and washed solid with 1 L hot cyclohexane. Concentrated mixture to a yellow oil. 1H NMR showed pure. In a 2-L Parr bottle was added platinum (13.34 g of 3% w/w, 2.051 mmol). Dissolved oil in THF (550 mL) and added to Parr bottle under N2. The bottle was placed on a Parr shaker under 50 psi of H2. The Parr shaker was refilled to 50 psi several times. Let go overnight. LC-MS showed small amt of dechlorinated intermediate. Added bis[(E)-1-methyl-3-oxo-but-1-enoxy]-oxo-vanadium (1.36 g, 5.129 mmol) and placed the bottle on the Parr shaker under 50 psi of H2. The Parr shaker was refilled to 50 psi three times. After 5h, no more consumption of H2. Filtered rxn through Florisil and eluted with EtOAc/DCM (1:1) until no more material was detected by UV (~4 L). Concentrated filtrate. Yellow solid. Stirred resulting solid with MTBE (1 L) for 2h. Filtered and washed white solid with MTBE (2×250 mL). Dried under vacuum in funnel.

Optical rotation: CHCl$_3$, 100 mg/10 mL conc, $[\alpha]_D$=118.12°, temp=22.8° C. Chiral HPLC: AD-H column, 4.6 mm×250 mm, 40% EtOH/hex isocratic gradient, 20 min run, >99% ee. (7S)-2-chloro-7-isopropyl-4,8-dimethyl-5,7-dihydropteridin-6-one (57.75 g, 88%). $^1$H NMR (300 MHz, Chloroform-d) δ 9.32 (s, 1H), 3.96 (d, J=4.1 Hz, 1H), 2.35 (s, 3H), 2.32-2.18 (m, 1H), 1.08 (d, J=6.9 Hz, 3H), 0.92 (d, J=6.9 Hz, 3H). ESI-MS m/z calc. 254.09, found 255.12 (M+1)$^+$; Retention time: 0.63 minutes.

Formation of tert-butyl ((1s,3s)-3-(((2-(trifluoromethyl)pyrimidin-5-yl)oxy)methyl)-cyclobutyl)carbamate (3)

To cis-tert-butyl N-[3-(hydroxymethyl)cyclobutyl]carbamate (5.8 g, 28.82 mmol) and triphenylphosphane (9.1 g, 34.7 mmol) in THF (80 mL) at room temp was added ethyl (NE)-N-ethoxycarbonyliminocarbamate (15.8 mL of 40% w/w, 34.69 mmol), followed by 2-(trifluoromethyl)pyrimidin-5-ol (5 g, 30.47 mmol). The reaction mixture was stirred at room temperature for 1 h. THF was removed, added 100 mL DCM, washed with 2 N NaOH twice. The organic phase was concentrated in vacuo. The resulting residue was purified by silica gel chromatography using EtOAc/heptanes to afford 8.17 grams of desired product: $^1$H NMR (400 MHz, Chloroform-d) δ 8.51 (s, 2H), 4.72 (s, 1H), 4.11 (d, J=5.5 Hz, 2H), 2.67-2.41 (m, 3H), 1.84-1.74 (m, 1H).

Formation of (1s,3s)-3-(((2-(trifluoromethyl)pyrimidin-5-yl)oxy)methyl)cyclobutan-1-amine (4)

To tert-butyl N-[3-[[2-(trifluoromethyl)pyrimidin-5-yl]oxymethyl]cyclobutyl]carbamate, 3, (8.17 g, 23.51 mmol) in Methanol (20 mL) was added hydrogen chloride (27 mL of 4 M solution, 108.0 mmol) in dioxane at room temperature. Stir at 50° C. for 30 minutes. The organics were evaporated and the resulting residue was washed with ether-heptane to afford 6.5 g of desired product as HCl salt: $^1$H NMR (300 MHz, Methanol-d4) δ 8.61 (s, 2H), 4.20 (d, J=5.5 Hz, 2H), 3.73 (tt, J=8.7, 7.6 Hz, 1H), 2.77-2.60 (m, 1H), 2.57-2.40 (m, 2H), 2.24-1.94 (m, 2H); ESI-MS m/z calc. 247.09, found 248.17 (M+1)$^+$; Retention time: 0.58 minutes.

Formation of (S)-7-isopropyl-4,8-dimethyl-2-(((1s,3R)-3-(((2-(trifluoromethyl)pyrimidin-5-yl)oxy)methyl)cyclobutyl)amino)-7,8-dihydropteridin-6(5H)-one (I-1417)

To (7S)-2-chloro-7-isopropyl-4,8-dimethyl-5,7-dihydropteridin-6-one, 1, (1.43 g, 5.56 mmol), 3-[[2-(trifluoromethyl)pyrimidin-5-yl]oxymethyl]cyclobutanamine, 4, (Hydrochloride salt) (1.57 g, 5.52 mmol), (tBuXPhos Pd G1) (200 mg, 0.2913 mmol) in $^t$BuOH (30 mL) under an atmosphere of nitrogen was added NaOtBu (12.5 mL of 2 M, 25.00 mmol). The mixture was stirred for 20 minutes then diluted into 80 mL of aqueous saturated NH$_4$Cl solution. The mixture was extracted with dichloromethane (3×60 mL), dried, stirred with TMP resin. The organic phase was concentrated in vacuo and purified by silica gel chromatography (0 to 20% MeOH/DCM gradient) to afford 2.62 grams of desired product: $[\alpha]_D$=39.69 (c 1.04, MeOH); $^1$H NMR (400 MHz, CDCl$_3$) δ 8.52 (s, 2H), 7.69 (s, 1H), 4.82 (d, J=7.5 Hz, 1H), 4.43 (dd, J=16.3, 8.8 Hz, 1H), 4.14 (d, J=5.7 Hz, 2H), 3.90 (d, J=4.3 Hz, 1H), 3.14 (s, 3H), 2.74-2.60 (m, 2H), 2.62-2.50 (m, 1H), 2.32-2.20 (m, 1H), 2.19 (s, 3H), 1.94-1.75 (m, 2H), 1.30 (s, 2H), 1.08 (d, J=7.0 Hz, 3H), 0.93 (d, J=6.9 Hz, 3H). ESI-MS m/z calc. 465.21, found 466.27 (M+1)$^+$; Retention time: 0.79 minutes.

Example 3: PLK1 Inhibition Assay

Compounds were screened for their ability to inhibit Plk1 using a radioactive-phosphate incorporation assay. Assays were carried out in a mixture of 25 mM HEPES (pH 7.5), 10 mM MgCl$_2$, 25 mM NaCl, and 2 mM DTT. Final substrate concentrations were 20 μM [γ-33P]ATP (35mCi 33P ATP/mmol ATP, Perkin Elmer/Sigma Chemicals) and 9 uM Sam68 protein. Assays were carried out at room temperature in the presence of 15 nM Plk1. An assay stock buffer solution was prepared containing all of the reagents listed above, with the exception of ATP and the test compound of interest. 0.75 μL of DMSO stock containing serial dilutions of the test compound (typically starting from a final concentration of 10 μM with 2-fold serial dilutions—final DMSO concentration 1.5%) was placed in a 384 well plate followed by addition of 25 μL [γ-33P]ATP (final concentration 20 μM). The reaction was initiated by addition of 25 μL of the assay stock buffer solution.

The reaction was stopped after 45 minutes by the addition of 25 μL 30% trichloroacetic acid (TCA) containing 10 mM cold ATP. The entire quenched reaction was transferred to a 384-well glass fiber filter plate (Millipore, Cat no. MZFB- NOW50). The plate was washed with 3×5% TCA. After drying, 40 µL of Ultima Gold liquid scintillation cocktail (Perkin Elmer) was added to the well prior to scintillation counting in a PerkinElmer TopCount.

After removing mean background values for all of the data points, Ki(app) data were calculated from non-linear regression analysis of the initial rate data using the Prism software package (GraphPad Prism, GraphPad Software, San Diego Calif., USA). The data is summarized in Table 45.

Example 4: Colo 205 Reporter Assay

The compounds of the invention described herein were screened using the assay procedure for β-catenin-TCF-mediated reporter transcription activity described below.

In cells with activated WNT signaling, we have found that induction of ER Stress by the mechanism of these compounds results in a rapid reduction in the activity of this reporter gene and that the activity in the assay correlates with the activity of these compounds as inducers of ER Stress and the UPR, and all other measures of specific activity of these compounds, including calcium release, viability, and displacement of radiolabeled version of these compounds from their specific binding site in cells.

Reporter cell lines were generated by stably transfecting cells of cancer cell lines (e.g., colon cancer) with a plasmid reporter construct (From SABiosciences, a QIAGEN company) that includes TCF/LEF promoter driving expression of the firefly luciferase gene. TCF/LEF reporter constructs were made in which TCF/LEF promoter, a promoter with optimal number of TCF/LEF binding sites designed by SABiosceinces, was linked upstream of the firefly luciferase gene. This construct could also include a puromycin resistance gene as a selectable marker. This construct could also be used to stably transfect Colo 205 cells, a colon cancer cell line having a mutated APC gene that causes a constitutively active β-catenin. A control cell line was generated using another plasmid construct containing the luciferase gene under the control of a CMV basal promoter which is not activated by β-catenin.

Colo 205 Cultured cells with a stably transfected reporter construct were plated at approximately 10,000 cells per well into 384 well multi-well plates for twenty four hours. The testing compounds were then added to the wells in 2-fold serial dilutions using a twenty micromolar top concentration. A series of control wells for each cell type received only compound solvent. Five hours after the addition of compound, reporter activity for luciferase was assayed, by addition of the SteadyGlo luminescence reagent (Promega). The reporter luminescence activity was measured using Pherastar plate reader (BMG Labtech). Readings were normalized to DMSO only treated cells, and normalized activities were then used in the IC50 calculations. The Colo 205 reporter assay data are summarized in Table 45: A<0.3 µM; 0.3 µM≤B<1.0 µM; 1.0 µM≤C<5.0 µM; D≥5.0 µM.

TABLE 45

PLK1 and Colo 205 Reporter Assay Data

| Comp. # | PLK1 - 33P.ENZ - CB 10 Ki (uM) | TCF reporter Colo205 IC$_{50}$ (uM) | Comp. # | TCF reporter Colo205 IC$_{50}$ (uM) |
|---|---|---|---|---|
| 1 | >4 | A | 410 | |
| 2 | >4 | A | 412 | A |
| 3 | >4 | A | 413 | A |
| 4 | >4 | A | 414 | A |
| 5 | >4 | B | 415 | A |
| 6 | >4 | B | 416 | A |
| 7 | >4 | B | 417 | A |
| 8 | >4 | B | 418 | A |
| 9 | >4 | A | 419 | A |
| 10 | — | D | 420 | A |
| 11 | — | D | 421 | A |
| 12 | — | B | 422 | A |
| 13 | — | D | 423 | A |
| 14 | >4 | A | 424 | A |
| 15 | >4 | A | 425 | A |
| 16 | — | A | 426 | A |
| 17 | — | A | 427 | B |
| 18 | — | A | 428 | D |
| 19 | >4 | B | 429 | A |
| 20 | — | B | 430 | A |
| 21 | — | A | 431 | A |
| 22 | >4 | A | 432 | A |
| 23 | >4 | A | 433 | A |
| 24 | >4 | B | 434 | A |
| 25 | — | A | 435 | A |
| 26 | — | A | 436 | A |
| 27 | — | B | 437 | A |
| 28 | — | A | 438 | A |
| 29 | — | A | 439 | D |
| 30 | >4 | A | 440 | A |
| 31 | — | A | 441 | A |
| 32 | >4 | B | 442 | A |
| 33 | — | B | 443 | B |
| 34 | >4 | B | 444 | B |
| 35 | — | A | 445 | B |
| 36 | — | A | 446 | A |
| 37 | — | A | 447 | A |
| 38 | — | A | 448 | A |
| 39 | — | — | 449 | A |
| 40 | — | C | 450 | A |
| 41 | — | B | 451 | A |
| 42 | — | A | 452 | A |
| 43 | — | D | 453 | A |
| 44 | >4 | A | 454 | A |
| 45 | — | A | 455 | A |
| 46 | >4 | A | 456 | A |
| 47 | >4 | A | 457 | A |
| 48 | >4 | A | 458 | B |
| 49 | — | A | 459 | D |
| 50 | >4 | D | 460 | A |
| 51 | >4 | A | 461 | C |
| 52 | — | B | 462 | C |
| 53 | — | A | 463 | D |
| 54 | >4 | A | 464 | B |
| 55 | — | A | 465 | B |
| 56 | — | A | 466 | A |
| 57 | — | A | 467 | A |
| 58 | — | A | 468 | A |
| 59 | — | D | 469 | A |
| 60 | — | D | 470 | A |
| 61 | — | A | 471 | D |
| 62 | — | D | 472 | A |
| 63 | — | A | 473 | A |
| 64 | — | A | 474 | C |
| 65 | — | A | 475 | C |
| 66 | — | A | 476 | C |
| 67 | — | A | 477 | A |
| 68 | — | A | 478 | C |
| 69 | — | A | 479 | A |
| 70 | — | B | 480 | A |
| 71 | — | B | 481 | B |
| 72 | — | A | 482 | D |
| 73 | — | A | 483 | C |
| 74 | — | B | 484 | C |
| 75 | — | A | 485 | A |
| 76 | — | D | 486 | C |

TABLE 45-continued

PLK1 and Colo 205 Reporter Assay Data

| Comp. # | PLK1 - 33P.ENZ - CB 10 Ki (uM) | TCF reporter Colo205 IC$_{50}$ (uM) | Comp. # | TCF reporter Colo205 IC$_{50}$ (uM) |
|---|---|---|---|---|
| 77 | — | A | 487 | B |
| 78 | — | A | 488 | C |
| 79 | — | A | 489 | D |
| 80 | — | A | 490 | D |
| 81 | — | A | 491 | A |
| 82 | — | B | 492 | B |
| 83 | — | A | 493 | C |
| 84 | — | A | 494 | A |
| 85 | — | A | 495 | A |
| 86 | — | A | 496 | A |
| 87 | — | A | 497 | B |
| 88 | — | A | 498 | A |
| 89 | — | A | 499 | A |
| 90 | — | A | 500 | A |
| 91 | — | A | 501 | A |
| 92 | — | A | 502 | C |
| 93 | — | B | 503 | C |
| 94 | — | A | 504 | B |
| 95 | — | A | 505 | C |
| 96 | — | A | 506 | B |
| 97 | — | A | 507 | A |
| 98 | — | C | 508 | B |
| 99 | — | D | 509 | B |
| 100 | — | C | 510 | A |
| 101 | — | A | 511 | A |
| 102 | — | C | 512 | A |
| 103 | — | A | 513 | A |
| 104 | — | A | 514 | A |
| 105 | — | A | 515 | A |
| 106 | — | A | 516 | A |
| 107 | — | A | 517 | A |
| 108 | — | B | 518 | A |
| 109 | — | C | 519 | C |
| 110 | — | B | 520 | D |
| 111 | — | B | 521 | C |
| 112 | >4 | A | 522 | A |
| 113 | >4 | A | 523 | D |
| 115 | — | C | 524 | D |
| 116 | >4 | A | 525 | D |
| 117 | — | A | 526 | D |
| 118 | — | D | 527 | B |
| 119 | — | C | 528 | A |
| 120 | — | B | 529 | C |
| 121 | — | C | 530 | D |
| 122 | — | A | 531 | B |
| 123 | — | A | 532 | B |
| 124 | — | B | 533 | B |
| 125 | — | C | 534 | A |
| 126 | — | C | 535 | A |
| 127 | — | B | 536 | A |
| 128 | — | C | 537 | C |
| 129 | — | B | 538 | C |
| 130 | — | D | 539 | B |
| 131 | — | C | 540 | C |
| 132 | — | B | 541 | B |
| 133 | — | A | 542 | A |
| 134 | — | A | 543 | C |
| 135 | — | A | 544 | A |
| 136 | >4 | A | 545 | B |
| 137 | — | A | 546 | D |
| 138 | >4 | A | 547 | C |
| 139 | — | C | 548 | B |
| 140 | — | A | 549 | C |
| 141 | — | A | 550 | A |
| 142 | — | B | 551 | A |
| 143 | — | B | 552 | D |
| 144 | — | A | 553 | B |
| 145 | — | A | 554 | C |
| 146 | — | A | 555 | C |
| 147 | — | A | 556 | A |
| 148 | — | B | 557 | A |
| 149 | — | A | 558 | C |
| 150 | — | A | 559 | C |
| 151 | — | A | 560 | D |
| 152 | — | A | 561 | A |
| 153 | — | A | 562 | B |
| 154 | — | A | 563 | A |
| 155 | — | A | 564 | C |
| 156 | — | A | 565 | A |
| 157 | — | A | 566 | A |
| 158 | — | A | 567 | A |
| 159 | — | B | 568 | A |
| 160 | >4 | A | 569 | C |
| 161 | — | B | 570 | A |
| 162 | — | D | 571 | B |
| 163 | — | C | 572 | A |
| 164 | — | C | 573 | A |
| 165 | — | D | 574 | A |
| 166 | — | D | 575 | A |
| 167 | — | A | 576 | A |
| 168 | — | A | 577 | B |
| 169 | — | A | 578 | A |
| 170 | — | A | 579 | C |
| 171 | — | A | 580 | B |
| 172 | — | A | 581 | A |
| 173 | — | C | 582 | B |
| 174 | — | A | 583 | A |
| 175 | — | A | 584 | D |
| 176 | — | B | 585 | B |
| 177 | — | A | 586 | A |
| 178 | — | C | 587 | B |
| 179 | — | A | 588 | A |
| 180 | — | A | 589 | A |
| 181 | — | A | 590 | B |
| 182 | — | A | 591 | A |
| 183 | — | A | 592 | D |
| 184 | — | A | 593 | A |
| 185 | — | B | 594 | C |
| 186 | — | A | 595 | B |
| 187 | — | A | 596 | A |
| 188 | — | A | 597 | C |
| 189 | — | A | 598 | A |
| 190 | — | B | 599 | A |
| 191 | — | C | 600 | C |
| 192 | >4 | A | 601 | B |
| 193 | — | B | 602 | B |
| 194 | — | A | 603 | B |
| 195 | — | B | 604 | C |
| 196 | — | B | 605 | D |
| 197 | — | A | 606 | B |
| 198 | — | C | 607 | A |
| 199 | — | A | 608 | A |
| 200 | — | B | 609 | C |
| 201 | — | B | 610 | D |
| 202 | — | D | 611 | D |
| 203 | — | A | 612 | A |
| 204 | — | D | 613 | B |
| 205 | — | B | 614 | C |
| 206 | — | A | 615 | B |
| 207 | — | A | 616 | B |
| 208 | — | A | 617 | D |
| 209 | — | A | 618 | B |
| 210 | — | A | 619 | C |
| 211 | — | B | 620 | D |
| 212 | — | D | 621 | B |
| 213 | — | A | 622 | A |
| 214 | — | D | 623 | B |
| 215 | — | A | 624 | D |
| 216 | — | D | 625 | D |
| 217 | — | D | 626 | A |
| 218 | — | A | 627 | C |
| 219 | — | A | 628 | D |
| 220 | — | A | 629 | A |
| 221 | >4 | A | 630 | C |
| 222 | — | D | 631 | D |
| 223 | >4 | A | 632 | B |

TABLE 45-continued

PLK1 and Colo 205 Reporter Assay Data

| Comp. # | PLK1 - 33P.ENZ - CB 10 Ki (uM) | TCF reporter Colo205 IC$_{50}$ (uM) | Comp. # | TCF reporter Colo205 IC$_{50}$ (uM) | Comp. # | PLK1 - 33P.ENZ - CB 10 Ki (uM) | TCF reporter Colo205 IC$_{50}$ (uM) | Comp. # | TCF reporter Colo205 IC$_{50}$ (uM) |
|---|---|---|---|---|---|---|---|---|---|
| 224 | >4 | A | 633 | C | 297 | — | D | 710 | C |
| 225 | — | D | 634 | D | 298 | — | C | 711 | A |
| 226 | — | A | 635 | A | 299 | — | B | 712 | A |
| 227 | — | B | 636 | D | 300 | — | D | 713 | A |
| 228 | — | C | 637 | D | 301 | — | A | 714 | A |
| 229 | >4 | A | 638 | D | 302 | — | C | 715 | C |
| 230 | — | B | 639 | C | 303 | — | B | 716 | A |
| 231 | — | A | 640 | D | 304 | — | B | 717 | C |
| 232 | — | A | 641 | D | 305 | — | B | 718 | A |
| 233 | — | A | 642 | D | 306 | — | C | 719 | A |
| 234 | >4 | B | 643 | A | 307 | — | C | 720 | B |
| 235 | — | A | 644 | A | 308 | — | C | 721 | C |
| 236 | — | A | 645 | A | 309 | — | B | 722 | C |
| 237 | — | B | 646 | A | 310 | — | C | 723 | A |
| 238 | — | A | 647 | A | 311 | >4 | A | 724 | B |
| 239 | — | A | 648 | A | 312 | — | A | 725 | A |
| 240 | — | C | 649 | A | 313 | — | D | 726 | C |
| 241 | — | D | 650 | A | 314 | — | B | 727 | A |
| 242 | — | A | 651 | C | 315 | — | A | 728 | A |
| 243 | — | C | 652 | B | 316 | — | D | 729 | A |
| 244 | — | D | 653 | D | 317 | — | B | 730 | C |
| 245 | — | D | 655 | A | 318 | — | D | 731 | D |
| 246 | >4 | A | 656 | A | 319 | — | D | 732 | C |
| 247 | >4 | C | 657 | A | 320 | — | C | 733 | D |
| 248 | — | A | 658 | A | 321 | — | B | 734 | B |
| 249 | — | A | 659 | A | 322 | — | B | 735 | A |
| 250 | — | B | 660 | A | 323 | — | A | 736 | B |
| 251 | — | B | 661 | A | 324 | — | A | 737 | C |
| 252 | — | A | 662 | B | 325 | — | B | 738 | B |
| 253 | >4 | A | 663 | C | 326 | — | A | 739 | B |
| 254 | >4 | A | 664 | B | 327 | — | A | 740 | B |
| 255 | — | A | 665 | B | 328 | — | A | 741 | B |
| 256 | — | B | 666 | B | 329 | — | A | 742 | C |
| 257 | — | A | 667 | A | 330 | — | B | 743 | C |
| 258 | — | C | 668 | A | 331 | — | A | 744 | B |
| 259 | — | D | 669 | A | 332 | — | A | 745 | B |
| 260 | — | B | 670 | A | 333 | — | A | 746 | B |
| 261 | — | A | 671 | A | 334 | — | B | 747 | B |
| 262 | — | C | 672 | A | 335 | >4 | A | 748 | A |
| 263 | — | B | 673 | B | 336 | — | B | 749 | C |
| 264 | — | A | 674 | A | 337 | — | B | 795 | A |
| 265 | — | B | 675 | B | 338 | — | C | 1417 | A |
| 266 | — | B | 676 | A | 339 | — | B | — | — |
| 267 | >4 | A | 677 | A | 340 | — | A | — | — |
| 268 | >4 | B | 678 | A | 341 | — | A | — | — |
| 269 | — | A | 679 | B | 342 | — | C | — | — |
| 270 | — | B | 680 | B | 343 | — | D | — | — |
| 271 | — | A | 681 | B | 344 | — | B | — | — |
| 272 | — | A | 682 | A | 345 | — | B | — | — |
| 273 | — | A | 683 | B | 346 | — | B | — | — |
| 274 | — | D | 684 | A | 347 | — | A | — | — |
| 275 | >4 | A | 685 | A | 348 | — | C | — | — |
| 276 | — | D | 686 | A | 349 | — | D | — | — |
| 277 | — | A | 687 | B | 350 | — | B | — | — |
| 278 | — | C | 688 | A | 351 | — | C | — | — |
| 279 | — | B | 689 | B | 352 | — | C | — | — |
| 280 | — | A | 690 | A | 353 | — | D | — | — |
| 281 | — | A | 691 | A | 354 | — | C | — | — |
| 282 | — | A | 692 | B | 355 | — | C | — | — |
| 283 | — | A | 693 | D | 356 | — | B | — | — |
| 284 | — | A | 694 | A | 357 | — | C | — | — |
| 285 | — | A | 695 | A | 358 | — | C | — | — |
| 286 | — | A | 696 | B | 359 | — | A | — | — |
| 287 | — | A | 697 | B | 360 | — | A | — | — |
| 288 | — | B | 698 | B | 361 | — | A | — | — |
| 289 | — | D | 699 | C | 362 | — | B | — | — |
| 290 | — | D | 703 | B | 363 | — | A | — | — |
| 291 | — | A | 704 | A | 364 | — | A | — | — |
| 292 | — | A | 705 | A | 365 | — | A | — | — |
| 293 | — | A | 706 | B | 366 | — | A | — | — |
| 294 | — | A | 707 | B | 367 | — | A | — | — |
| 295 | — | A | 708 | A | 369 | — | D | — | — |
| 296 | — | A | 709 | B | 370 | — | A | — | — |

TABLE 45-continued

PLK1 and Colo 205 Reporter Assay Data

| Comp. # | PLK1 - 33P.ENZ - CB 10 Ki (uM) | TCF reporter Colo205 IC$_{50}$ (uM) | Comp. # | TCF reporter Colo205 IC$_{50}$ (uM) |
|---|---|---|---|---|
| 371 | — | D | — | |
| 372 | — | D | — | |
| 373 | — | B | — | |
| 374 | — | D | — | |
| 375 | — | A | — | |
| 376 | — | C | — | |
| 377 | — | A | — | |
| 381 | — | B | — | |
| 382 | — | A | — | |
| 383 | — | A | — | |
| 384 | — | A | — | |
| 385 | — | A | — | |
| 386 | — | A | — | |
| 387 | — | A | — | |
| 388 | — | A | — | |
| 389 | — | A | — | |
| 390 | — | A | — | |
| 394 | — | A | — | |
| 395 | — | A | — | |
| 396 | — | A | — | |
| 397 | — | A | — | |
| 398 | — | A | — | |
| 400 | — | A | — | |
| 401 | — | D | — | |
| 402 | — | D | — | |
| 403 | — | D | — | |
| 404 | — | D | — | |
| 405 | — | D | — | |
| 406 | — | D | — | |
| 407 | — | D | — | |
| 408 | — | A | — | |
| 409 | — | A | — | |

Example 5

Colo 205 reporter assay data has also been obtained for certain R-isomers of Formula (I) wherein R$^4$ is —H or -D, and wherein the carbon to which R$^3$ and R$^4$ are attached (C2 carbon of Formula (X)) has R stereochemistry; such epimeric compounds are represented using the suffix "B" attached to the Compound described herein having the S stereochemistry at the carbon to which R$^3$ and R$^4$ are attached:

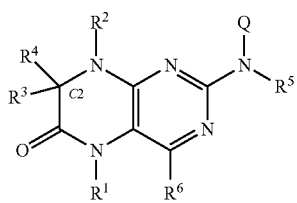

These assay data for the R-stereoisomers are summarized in Table 46 below, where A<0.3 µM; 0.3 µM≤B<1.0 µM; 1.0 µM≤C<5.0 µM; D≥5.0 µM.

TABLE 46

Colo 205 Reporter Assay Data

| Compound No. | R-isomer at C2 (Corresponding to C2 S-isomer) | TCF reporter Co10205 IC$_{50}$ (µM)* |
|---|---|---|
| I-866 | 1B | B |
| I-1634 | 9B | D |
| I-1229 | 14B | A |
| I-987 | 19B | A |
| I-860 | 22B | A |
| I-1348 | 23B | A |
| I-984 | 24B | B |
| I-809 | 27B | B |
| I-985 | 30B | A |
| I-1349 | 31B | A |
| I-1146 | 32B | B |
| I-1465 | 36B | A |
| I-1463 | 51B | A |
| I-1144 | 52B | B |
| I-896 | 42B | B |
| I-1205 | 46B | A |
| I-1635 | 186B | C* |
| I-1363 | 177B | B* |
| I-1636 | 136B | C* |
| I-1637 | 187B | C* |
| I-1638 | 220B | C* |
| I-1639 | 386B | C* |
| I-1640 | 405B | D* |
| I-1498 | 396B | B* |
| I-1641 | 421B | D* |
| I-1642 | 422B | C* |
| I-1643 | 423B | C* |
| I-1644 | 445B | C* |
| I-1645 | 495B | C* |
| I-1646 | 497B | D* |
| I-1647 | 589B | C* |
| I-1648 | 678B | D* |
| I-1649 | 204B | D* |
| I-1650 | 677B | C* |

Example 6: HepG2 XBP1 Reporter Assay

HepG2 hepatoma cells were transduced with a retrovirus encoding the cDNA for unspliced (u) XBP1, which contains a non-processed intron, fused to the cDNA for firefly luciferase. Upon induction of ER stress, the non-processed intron of XBP1(u) is spliced out by active IRE1alpha endonuclease. The resulting spliced (s) XBP1 is now in frame with luciferase which causes the production of active luciferase protein, resulting in bioluminescence HepG2 XBP1(u)-Luc cells were plated Colo 205 Cultured cells with a stably transfected reporter construct were plated at approximately 30,000 cells per well into 96 well multi-well plates for twenty four hours. The testing compounds were then added to the wells in 3-fold serial dilutions using a twenty seven micromolar top concentration. A series of control wells for each cell type received only compound solvent. Six hours after the addition of compound, reporter activity for luciferase was assayed, by addition of the SteadyGlo luminescence reagent (Promega). The reporter luminescence activity was measured using Pherastar plate reader (BMG Labtech). Readings was normalized to DMSO only treated cells, and normalized activities were then used in the IC50 calculations. The HepG2 XBP1 reporter assay data are summarized in Table 47: A<0.6 µM; 0.6 µM≤B<2.0 µM; 2.0 µM≤C<10.0 µM; D≥10.0 µM.

TABLE 47

| Comp. No. | Calcium Flux[A] | Radioligand Displacement[B] | HepG2 XBP1 Reporter[C] | Hek293 empty vector viability[D] | Hek293 WFS1 viability[D] | HepG2 viability[E] | HepG2 WFS1 KO viability[E] |
|---|---|---|---|---|---|---|---|
| 170 | A | B | A | D | A | A | — |
| 388 | A | A | A | D | A | — | — |
| 122 | A | A | A | D | A | — | — |
| 254 | B | B | A | — | — | — | — |
| 149 | A | B | A | D | A | A | — |
| 332 | B | B | A | D | A | — | — |
| 292 | A | A | A | — | — | — | — |
| 311 | A | B | A | D | A | D | — |
| 386 | B | B | A | D | A | — | — |
| 430 | B | A | A | D | A | A | D |
| 418 | A | A | A | D | A | A | D |
| 416 | B | A | A | D | A | A | D |
| 154 | A | A | A | D | A | — | — |
| 324 | A | A | A | D | A | — | — |
| 335 | B | A | A | D | A | C | — |
| 424 | B | A | A | D | A | A | D |
| 80 | B | A | A | D | A | — | — |
| 186 | B | B | A | D | A | — | — |
| 412 | B | A | A | D | B | C | D |
| 356 | B | C | A | D | A | D | — |
| 188 | B | B | A | D | A | — | — |
| 385 | B | A | A | D | A | — | — |
| 160 | B | B | A | D | A | — | — |
| 397 | B | B | A | D | A | — | — |
| 409 | B | A | A | D | A | A | D |
| 423 | B | B | A | D | A | A | D |
| 96 | A | A | A | D | B | C | D |
| 310 | C | C | A | D | B | D | — |
| 421 | B | B | A | D | B | B | D |
| 207 | B | B | A | D | A | — | — |
| 396 | B | B | A | D | A | — | — |
| 329 | B | B | A | D | A | — | — |
| 83 | A | A | B | D | A | — | — |
| 395 | B | B | B | D | A | — | — |
| 174 | B | B | B | D | A | — | — |
| 384 | B | B | B | D | A | A | — |
| 136 | B | B | B | D | A | B | D |
| 9 | B | B | B | D | B | D | D |
| 415 | B | A | B | D | A | B | D |
| 398 | B | B | B | D | A | B | — |
| 425 | B | B | B | D | B | B | D |
| 7 | B | B | B | D | B | C | D |
| 376 | B | B | B | D | B | — | — |
| 383 | B | A | B | D | A | A | — |
| 142 | B | B | B | D | B | — | — |
| 6 | B | B | B | D | B | C | D |
| 427 | B | A | B | D | B | D | D |
| 377 | A | A | B | D | A | — | — |
| 94 | B | B | B | D | A | — | — |
| 307 | B | B | B | D | B | C | — |
| 237 | B | B | B | D | B | D | — |
| 305 | B | B | C | D | B | D | — |
| 357 | B | B | C | D | B | C | — |
| 420 | C | B | C | D | B | B | D |
| 8 | C | C | C | D | B | C | D |
| 419 | C | B | C | D | B | C | D |
| 143 | C | B | C | D | B | — | — |
| 173 | C | C | C | D | B | — | — |
| 128 | C | D | C | D | C | C | D |
| 164 | C | B | C | D | C | D | D |
| 121 | B | B | C | D | C | D | D |
| 247 | C | B | D | D | D | C | D |
| 115 | C | C | D | D | C | D | D |
| 125 | C | B | D | D | C | C | D |
| 163 | C | D | D | D | D | D | D |
| 139 | C | C | D | D | D | D | D |
| 222 | C | C | D | D | D | D | D |
| 428 | D | D | D | D | D | D | D |
| 405 | D | D | D | D | D | D | — |
| 403 | D | D | D | D | D | D | — |
| 1 | A | B | — | D | A | A | D |
| 272 | B | B | — | D | A | A | — |
| 253 | A | A | — | D | A | B | — |
| 257 | B | B | — | D | A | C | — |
| 258 | B | B | — | D | B | C | — |

TABLE 47-continued

| Comp. No. | Calcium Flux[A] | Radioligand Displacement[B] | HepG2 XBP1 Reporter[C] | Hek293 empty vector viability[D] | Hek293 WFS1 viability[D] | HepG2 viability[E] | HepG2 WFS1 KO viability[E] |
|---|---|---|---|---|---|---|---|
| 4 | A | B | — | D | A | C | — |
| 251 | B | B | — | D | B | D | — |
| 46 | A | A | — | D | A | — | — |
| 246 | D | B | — | D | A | — | — |
| 77 | B | B | — | D | B | — | — |
| 250 | B | B | — | D | B | — | — |
| 684 | A | A | — | — | — | — | — |
| 686 | A | A | — | — | — | — | — |
| 711 | A | A | — | — | — | — | — |
| 685 | A | A | — | — | — | — | — |
| 551 | A | A | — | — | — | — | — |
| 643 | A | A | — | — | — | — | — |
| 716 | B | A | — | — | — | — | — |
| 677 | — | B | — | — | — | — | — |
| 717 | C | B | — | — | — | — | — |
| 723 | B | B | — | — | — | — | — |
| 216 | D | D | — | — | — | — | — |
| 795 | A | B | A | — | — | — | — |
| 1417 | A | B | A | — | — | — | — |

[A]Scale for Calcium Flux Assay Data A < 0.6 μM; 0.6 μM ≤ B < 2.0 μM; 2.0 μM ≤ C < 10.0 μM; D ≥ 10.0 μM.
[B]Scale for Radioligand Displacement Assay Data: A < 0.06 μM; 0.06 μM ≤ B < 0.6 μM; 0.6 μM ≤ C < 3.0 μM; D ≥ 3.0 μM.
[C]Scale for HepG2 XBP1 Reporter Data: A < 0.6 μM; 0.6 μM ≤ B < 2.0 μM; 2.0 μM ≤ C < 10.0 μM; D ≥ 10.0 μM.
[D]Scale for Hek293 empty vector and WFS1 over-expressing cell data: A < 0.06 μM; 0.06 μM ≤ B < 0.6 μM; 0.6 μM ≤ C < 3.0 μM; D ≥ 3.0 μM.
[E]Scale for HepG2 parental and WFS1 knockout cell data: A < 0.5 μM; 0.5 μM ≤ B < 2.0 μM; 2.0 μM ≤ C < 10.0 μM; D ≥ 10.0 μM.

Example 7: Calcium Flux Assay

Compounds described herein induced ER stress by causing intracellular calcium flux. Calcium flux was measured in Colo-205 cells using the FLIPR® Calcium 5 Assay Kit according to manufacture's protocol (Molecular Devices, Cat. # R8186) on a FLIPR3 system (Molecular Devices). Calcium flux is measured over 36 minutes. The Colo-205 calcium flux assay data are summarized in Table 47: A<0.6 μM; 0.6 μM≤B<2.0 μM; 2.0 μM≤C<10.0 μM; D≥10.0 μM.

Example 8: Membrane Extraction Protocol

Cell pellets were re-suspended in 15 times packed cellular volume in 4° C. hypotonic lysis buffer (10 mM HEPES, pH 7.5 containing 1×Protease inhibitor, 0.5 mM EDTA and 2 mM DTT). Re-suspended cells were homogenized with 6-8 strokes in a dounce homogenizer kept on ice. Lysates were centrifuged at 500×G for 15 minutes at 4° C. without brake to decelerate rotor. Following centrifugation, remove the supernatant to a fresh tube and place on ice (Supernatant 1). Repeat the above steps on the lysed cell pellet using 0.5 the original volume of hypotonic lysis buffer and remove the 500×G supernatant (Supernatant 2) and combine with Supernatant 1. Transfer the combined supernatants to a 45-Ti ultracentrifuge tube and centrifuge at 100,000×G for 30 minutes. Following ultracentrifugation, carefully remove the supernatant and discard. Resuspend the 100,000×G pellet in cold resuspension buffer (10 mM HEPES, pH 7.5, 300 mM NaCl containing 1× Protease inhibitor, 1×EDTA and 2 mM DTT). Centrifuge sample at 500×G for 10 minutes with no brake and remove any cloudy, flocculent material. Resuspend pellet in resuspension buffer to approximately 2 mg/mL of protein concentration for use in radioligand binding assay and immunoblotting.

Example 9: Radioligand Displacement Assay

Radiolabeled Compound 136 (tritiated Compound 136) was shown to specifically bind cellular membrane extracts which over-express WFS1. The binding affinities of compounds were determined by measuring the competitive displacement of a tritiated Compound 136 probe from purified HEK293 membranes over-expressing WFS-1. The data for the radioligand displacement assay are summarized in Table 47: A<0.06 μM; 0.06 μM≤B<0.6 μM; 0.6 μM≤C<3.0 μM; D≥3.0 μM.

The assay was performed in 50 μl assay volume containing a final concentration of 20 mM HEPES, pH 7.5, 300 mM NaCl, 1 mM DTT, 0.5% DMSO, 0.15 g/mL purified membrane, and tritiated Compound 136 probe at Kd. The probe Kd was determined by titrating tritiated probe under the standard assay conditions plus and minus excess unlabeled probe and fitting the resulting data to a "One site-Total and nonspecific binding" model in Graphpad Prism, version 6.0, San Diego, Calif., US. Initially, 0.25 μl of compound dissolved in DMSO at varying concentrations was dispensed to a 384 well plate. Membrane and probe were both prepared at 2× their final concentration in 1× assay buffer as described above. 25 μL of membrane was added to the wells and incubated for 10 minutes. 25 μL of diluted probe was then added to the wells. The assay was incubated for 90 minutes at room temperature. The entire assay volume was then transferred to Millipore GF/B 384-well plates pretreated with 15 μL 0.5% PEI. The filter plates were washed 3× with 75 μL 25 mM TRIS, ph7.5, 0.1% BSA and then dried overnight. Following addition of 45 μL UltimaGold scintillant, the samples were counted in a Perkin Elmer Topcount. The radioactivity remaining is a measure of bound probe. From the bound probe vs concentration of compound titration curve, the IC50 is determined by fitting the data to a standard 3 parameter IC50 model using either Graphpad Prism, version 6.0, San Diego, Calif., US, or using GeneData Analyzer, Basel, Switzerland.

Example 10. WFS1 Knockout, Knockdown, and Over-Expression Studies

10A. Materials and Experiments

Creation of Cells Stably Over-Expressing WFS1

WFS1 cDNA is amplified from clone RC202901 (Origene Technologies) with primers 5'-TCC GCG GCC CCA AGC TTA TCG CCA TGG ACT CCA ACA CTG C-3' (SEQ ID NO: 1), 5'-GAT GGG CCC AGA TCT CGA GTC AGG CCG CCG ACA GGA ATG-3' (SEQ ID NO: 2) and cloned into a retroviral mammalian expression vector pCLPCX using HD Infusion (CLONTECH) at Hind3-Xho1 sites using standard procedures. The resulting clone is identified as pCLPCX_WFS1.

HEK293 (ATCC, catalog # CRL-1573) cells are plated in 10 cm dishes (Corning, product #430167) into 10 mL of complete DMEM cell culture media [DMEM (Life Technologies, product #11960-051) media supplemented with 10% FBS (Hyclone, catalog # SH30071.03), antimycotic/antibiotic (Life Technologies, product #15240-062), and Glutamax (Life Technologies, product #35050-061)] at $3 \times 10^6$ cells per dish. Cells are allowed to attach and grow overnight at 37° C. in humidified 5% $CO_2$. Cells are co-transfected with pVSV-G, pCMV-Gag/Pol and pCLPCX_WFS1 using Fugene 6 (Promega, catalog #E2691) according to manufacturer's protocol. Separately, cells are co-transfected with pVSV-G, pCMV-Gag/Pol and pCLPCX to produce control retrovirus. Cell culture media containing retrovirus (viral supernatant) is collected at 48 and 72 hours following transfection, filtered through a 0.4 uM filter, and stored at −80° C.

HEK293 cells are plated in 6 well plates (Corning, product #3516) in 2 mL of complete DMEM cell culture media at $1 \times 10^5$ cells well and allowed to attach and grow overnight at 37° C. in humidified 5% $CO_2$. The following day, the media is replaced with viral supernatant to which 10 ug/ml of Polybrene® (Santa Cruz Biotech, catalog # sc-134220) is added. Viral supernatant is replaced 24 hours later with complete DMEM media. Transduced cells are selected in complete DMEM cell culture media containing 1 microgram/mL of puromycin (Life Technologies, catalog #A1113803).

Creation of Cells with Stable Knockdown of WFS1

Colo-205 (ATCC, catalog #CCL-222), HepG2 (ATCC, catalog #HB-8065), CFPAC1 (ATCC, catalog #CRL-1918), or DU4475 (ATCC, catalog #HTB-123) cells are plated in 10 mL of complete DMEM cell culture media [DMEM (Life Technologies, product #11960-051) media supplemented with 10% FBS (Hyclone, catalog # SH30071.03), antimycotic/antibiotic (Life Technologies, product #15240-062), and Glutamax (Life Technologies, product #35050-061)] at $3 \times 10^6$ cells per 10 cm cell culture plate (Corning, product #430167). Cells are allowed to attach and grow overnight at 37° C. in humidified 5% CO2. Cells are transduced by addition of $1 \times 10^6$ infectious units of lentivirus encoding WFS1 shRNA (Santa Cruz Biotech, catalog # sc-61804-V) or a non-targeting control shRNA (Santa Cruz Biotech, catalog # sc-108080) and 10 ug/ml of Polybrene® (Santa Cruz Biotech, catalog # sc-134220) to the cell culture media. After 48 hours transduced cells are selected by the addition of 1 microgram/mL of puromycin (Life Technologies, catalog # A1113803) to the cell culture media.

Creation of Cells with WFS1 Knockout by CRISPR/Cas9

A double cleavage strategy was employed to remove large fragments from the WFS1 locus. Suitable target sites in WFS1 exon 8 were first selected using CRISPR design software to rank suitable target sites and computationally predict off-target sites for each intended target. Six top guide RNA sequences are identified and screened for activity using the Surveyor Mutation Detection Kit (Integrated DNA Technologies). Then, the best 2 guide RNAs were cloned into GeneArt OFP CRISPR nuclease vectors (Thermofisher, Cat #A21174) separately and co-transfected into HepG2 cells using nucleofection (4D Nucleofector X, Lonza). Cells were sorted by FACS 48 hrs later to enrich for the OFP positive cell population. The OFP positive cell population were plated into 96-well plates at 0.5-5 cells/well to isolate clonal cell lines. After allowing cells to expand for 2-3 weeks, plates were inspected for presence of colonies. When colonies became more than 70% confluent, they were dissociated with trypsin and were further expanded. Cell clones with homozygous double cleavage of WFS1 exon 8 were detected with PCR and confirmed with DNA sequencing.

Determination of Cellular WFS1 Protein Levels

Cell lysates are prepared either by whole cell lysis with cold Lysis Buffer (20 mM Tris-HCl (pH 7.5), 150 mM NaCl, 1 mM Na2EDTA, 1 mM EGTA, 1% Triton, 2.5 mM sodium pyrophosphate, 1 mM beta-glycerophosphate, 1 mM Na3VO4, 1 µg/ml leupeptin, 0.05% SDS) or by membrane extraction using Mem-PER™ Plus Membrane Protein Extraction Kit (Life Technologies, catalog #89842). Protein content of cell lysates is determined using the BCA assay (Life Technologies Cat #23225). Twenty micrograms of protein are loaded onto Nupage 3-8% TA gels (Life Technologies, catalog #EA0375BOX) and subjected to electrophoresis in Tris-Acetate SDS running buffer (Life Technologies, catalog # LA0041) approximately 1.5 hours. Protein is transferred to nitrocellulose membranes via wet transfer in Tris-glycine transfer buffer (Life Technologies, catalog #LC3675) containing 0.2% SDS and 10% methanol. Nitrocellulose membranes were blocked in Odyssey® blocking buffer (Li-Cor Bioscience, catalog #927-40000) for at least 1 hour. Wfs1 protein (i.e. wolframin) was detected by immunoblotting with anti-WFS1 antibody (Abcam, catalog # ab176909) diluted in Odyssey blocking buffer overnight at 4° C. Membranes were washed 3 times in TBST (50 mM Tris, 150 mM NaCl, 0.05% Tween 20) at room temperature and then immunoblotted with anti-rabbit antibody conjugated with IRDye 800 (Li-Cor Bioscience catalog #926-32211) for 1 hour at room temperature while rocking gently. Membranes were imaged on the ODYSSEY® CLx Imaging System (Li-Cor Bioscience). Wolframin has a predicted kDa of ~110 kD.

Determination of Compound Effects on In Vitro Cell Viability

HEK293 cells containing empty pCLPCx vector (HEK293 empty), HEK293 cells stably over-expression WFS1 (HEK293 WFS1), HepG2, and HepG2 cells where WFS1 was depleted via CRISPR/Cas9 (HepG2 WFS1 KO) cells were plated into 96-well black plates (Corning, product #3904) in 100 microliters of complete DMEM cell culture media [DMEM (Life Technologies, product #11960-051) media supplemented with 10% FBS (Hyclone, catalog #SH30071.03), antimycotic/antibiotic (Life Technologies, product #15240-062), and Glutamax (Life Technologies, product #35050-061)] at 1,000 (HEK293) or 5,000 (HepG2) cells per well. Cells were allowed to attach and grow overnight, after which compounds are added at various concentrations. Cell viability was assessed 96 hrs after compound addition with CellTiter-Glo reagent (Promega, catalog #G7570) according to manufacturer's protocol and measurement on a Pherastar luminescence plate reader (BMG Labtech).

10B. Results and Discussions

Knockout of WFS1 by CRISPR/Cas9 Blocks the Ability of Compounds to Cause Calcium Flux, Induce ER Stress Markers, Induce Global Gene Expression Changes, and Inhibit Cell Viability.

Figure 2:
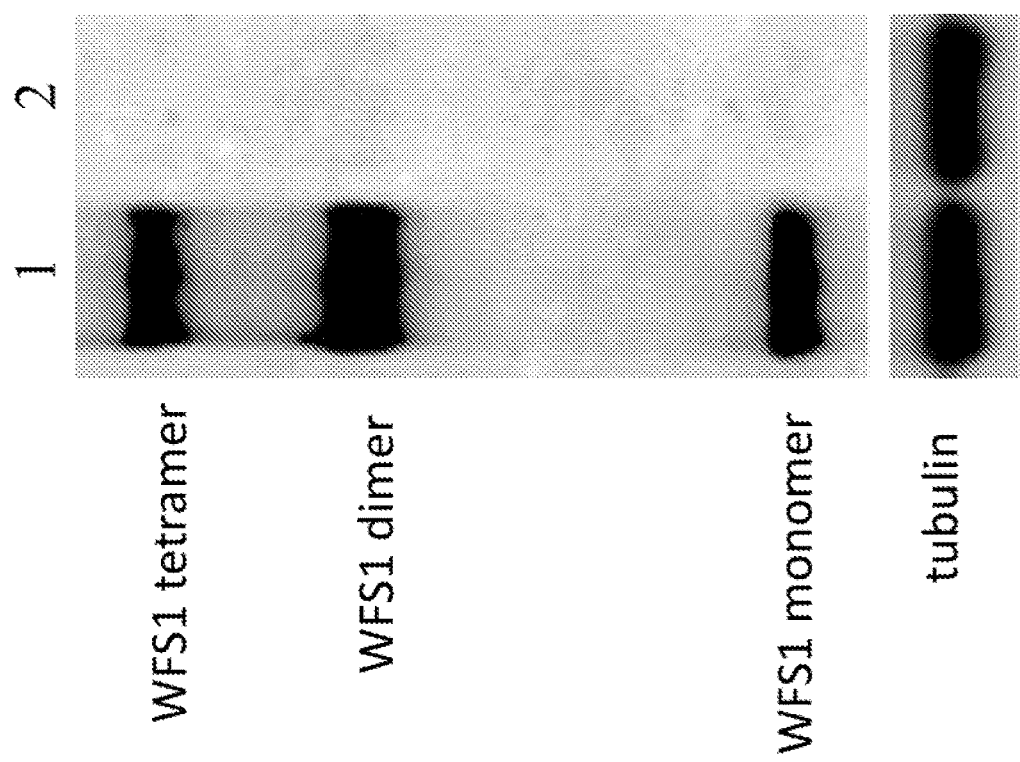
FIG. 2 is an immunoblot showing the WFS1 and tubulin protein levels in parental HepG2 cells and HepG2 cells where WFS1 is knocked out by CRISPR/Cas9.

CRISPR/Cas9 was used to create HepG2 cells with a WFS1 gene deletion. Compared to parental HepG2 cells (FIG. 2, lane 1), HepG2 cells subjected to WFS1 gene deletion (FIG. 2, lane 2) have a complete absence of WFS1 protein expression. FIG. 2 also shows the presence of monomeric and multimeric forms of WFS1, all of which are absent in the WFS1 gene deleted cells. There was no difference in tubulin protein levels between parental HepG2 and HepG2 WFS1 knockout cells (FIG. 2, lanes 1 and 2, respectively).

Figure 5A:
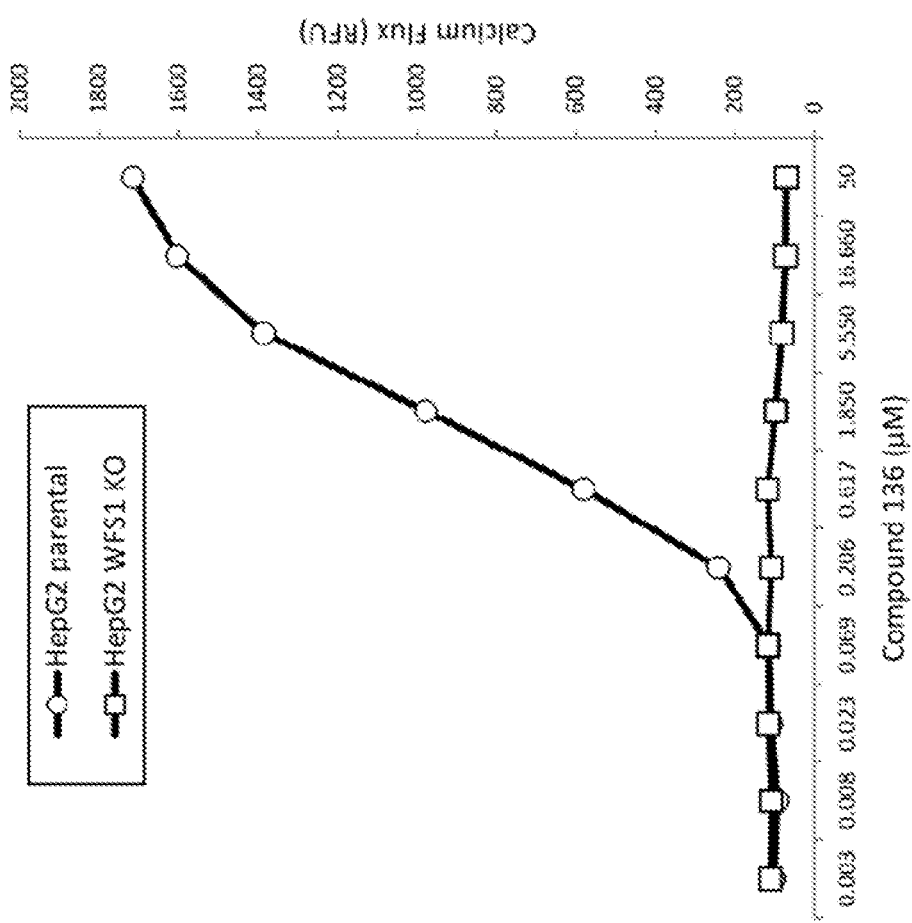
FIG. 5A is a graph showing the degree of calcium flux induced by Compound 136 in HepG2 cells, where levels of WFS1 protein have been altered by either knockout (KO) or over-expression.

Compounds described herein showed induction of calcium flux, as shown in FIG. 5A and exemplified by induction of luciferase in HepG2 cells containing an XBP1-Luc reporter (Table 47). In order to determine whether WFS1 is involved in compound induced calcium flux, parental HepG2 cells and HepG2 cells with CRISPR/Cas9 mediated WFS1 knockout (KO) were subjected to increasing concentrations of Compound 136 and intracellular calcium levels were measured after 30 minutes of compound addition. Depletion of WFS1 from HepG2 cells completely eliminated Compound 136 ability to induce calcium flux as compared to parental HepG2 cells (FIG. 5A), suggesting WFS1 expression level relates to the ability of the compounds to induce calcium flux.

Figure 6:
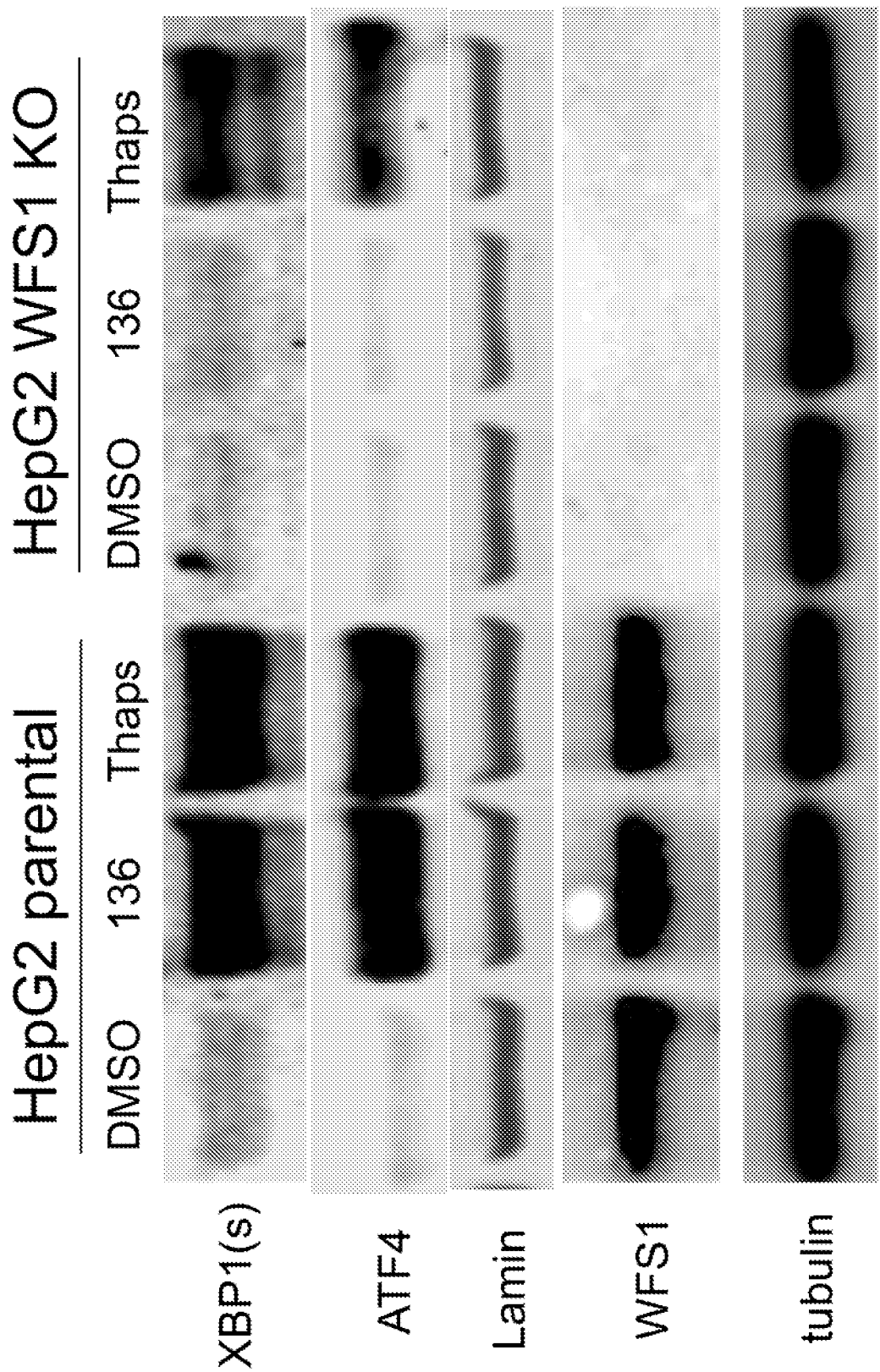
FIG. 6 is an immunoblot showing WFS1, ATF4, XBP1(s), lamin, and tubulin protein levels in either parental HepG2 cells or HepG2 cells where WFS1 is knocked out by CRISPR/Cas9 after 6 hours of exposure to either Compound 136 or thapsigargin.
Figure 7:
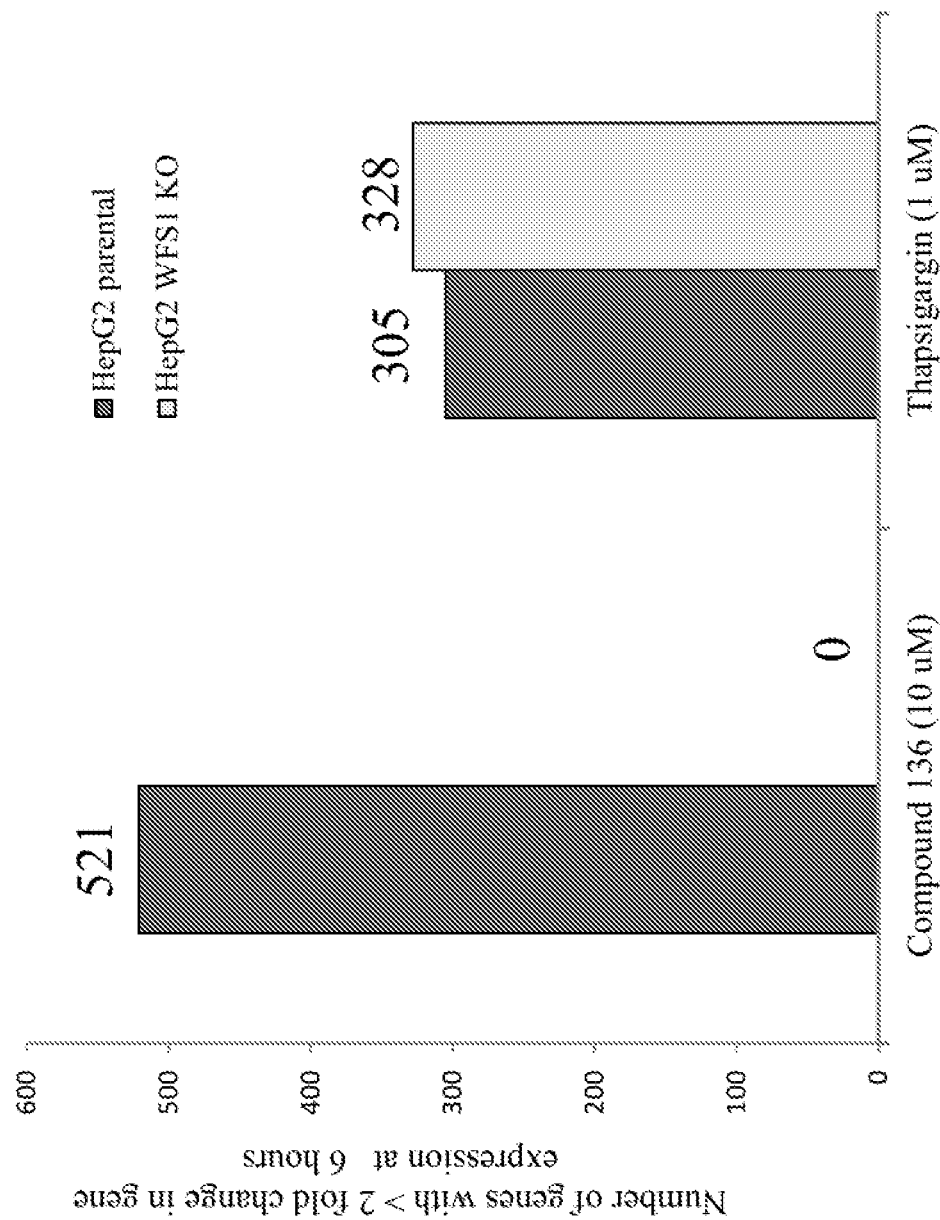
FIG. 7 is a graph depicting the number of genes whose expression changes more than 2 fold in either parental HepG2 cells or HepG2 cells where WFS1 is knocked out by CRISPR/Cas9 after 6 hours of exposure to either Compound 136 or thapsigargin.

Also, in order to determine whether WFS1 is involved in compound induced ER stress, parental HepG2 cells and HepG2 cells with CRISPR/Cas9 mediated WFS1 knockout (KO) were exposed to Compound 136 or thapsigargin for 6 hours after which time cell lysates were prepared and subjected to immunoblotting. FIG. 6 shows that WFS1 depletion prevents the induction of the ER stress marker proteins XBP1(s) and ATF4 by Compound 136. In contrast, depletion of WFS1 had a much lesser effect on thapsigargin (thaps) induced XBP1(s) and ATF4. These results further indicate that WFS1 expression level relates to the ability of the compounds to induce calcium flux. Further, depletion of WFS1 from HepG2 cells prevented Compound 136 from causing changes in global gene expression after 6 hours of exposure (FIG. 7). In contrast WFS1 depletion had no effect on thapsigargin induced changes in global gene expression (FIG. 7.)

To determine the effect of WFS1 depletion on compound mediated inhibition of cell viability, parental HepG2 cells and HepG2 cells where WFS1 was deleted by CRISPR/Cas9 were exposed to increasing concentrations of either Compound 136 or Compound 253 for 96 hours after which time viability was determined using Cell Titer Glo reagent (Promega). Depletion of WFS1 from HepG2 cells resulted in a greater than 100 fold shift in IC50 for Compound 136 and a greater than 5 fold shift in IC50 for Compound 253, suggesting that WFS1 is required for compounds described herein to inhibit cell viability (Table 47 and Table 48). The IC50s for the viability of both the HepG2 parental and WFS1 knockout cells are summarized in Table 47: A<0.5 µM; 0.5 µM≤B<2.0 µM; 2.0 µM≤C<10.0 µM; D≥10.0 µM.

TABLE 48

| Cell Line | Compound 136 IC$_{50}$ (µM) | | Compound 253 IC$_{50}$ (µM) | |
|---|---|---|---|---|
| HepG2 parental | 0.33 | A | 0.64 | B |
| HepG2 WFS1 KO | >27 | D | 4.4 | C |

Figure 3:
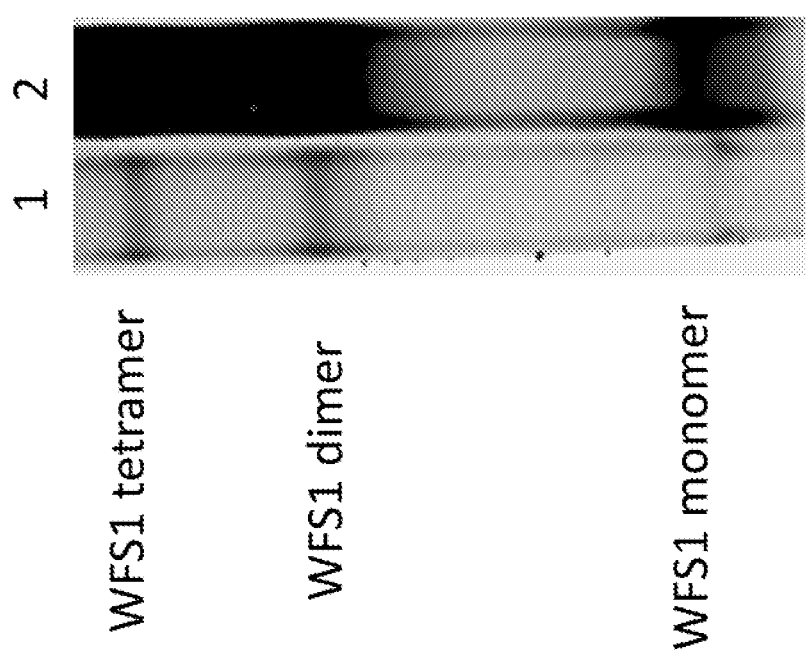
FIG. 3 is an immunoblot showing the WFS1 protein levels in Hek293 cells transduced with an empty control retrovirus (pCLPCX) and Hek293 cells transduced with a retrovirus encoding the full length WFS1 cDNA.
Figure 5B:
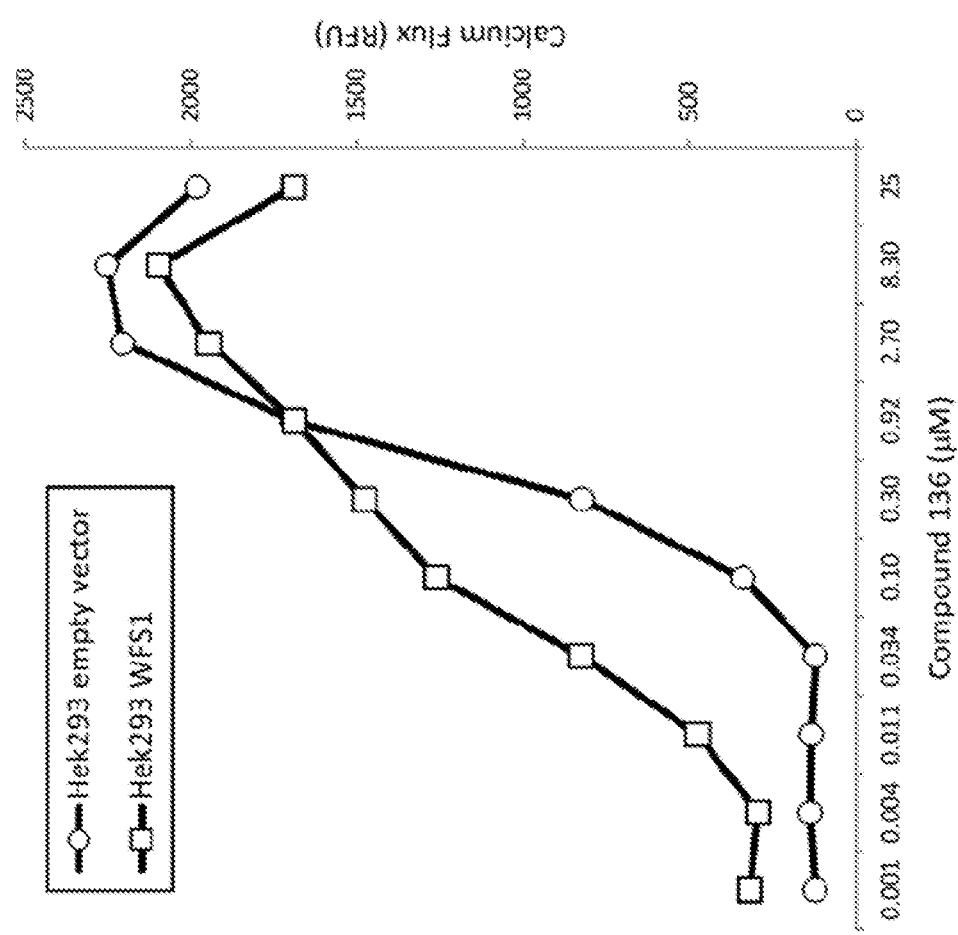
FIG. 5B is a graph showing the degree of calcium flux induced by Compound 136 in Hek293 cells, where levels of WFS1 protein have been altered by either knockout (KO) or over-expression.

To determine the effect of WFS1 over-expression on compound mediated effects on calcium flux and cell viability, Hek293 cells were transduced with either an empty retroviral vector or a retroviral vector expressing full length WFS1 cDNA. Hek293 cells transduced with the WFS1 encoding retrovirus expressed greater than 100 times the amount of WFS1 protein than empty vector Hek293 cells (FIG. 3). The effect of WFS1 over-expression on the induction of calcium flux induced by Compound 136 is shown in FIG. 5B. Over-expression of WFS1 resulted in approximately 10 fold reduction in the EC50 of Compound 136, suggesting that WFS1 is involved in the mechanism of action for the compounds described herein.

Further, the effect of WFS1 over-expression on the inhibition of cell viability by Compounds 136 and 253 is shown in Table 49 (below). Over-expression of WFS1 in Hek293 cells results in greater than a 1000 fold reduction in the IC50 of both of these of compounds, suggesting that WFS1 alone is sufficient to impart sensitivity of non-responder cells to the compounds described herein. The IC50s for the viability of both the Hek293 empty vector and WFS1 over-expressing cells are summarized in Table 47: A<0.06 µM; 0.06 µM≤B<0.6 µM; 0.6 µM≤C<3.0 µM; D≥3.0 µM.

TABLE 49

| Cell Line | Compound 136 IC$_{50}$ (µM) | | Compound 253 IC$_{50}$ (µM) | |
|---|---|---|---|---|
| Hek293 empty vector | >27 | D | 15 | D |
| Hek293 WFS1 over-expressor | 0.03 | A | 0.012 | A |

Figure 4:
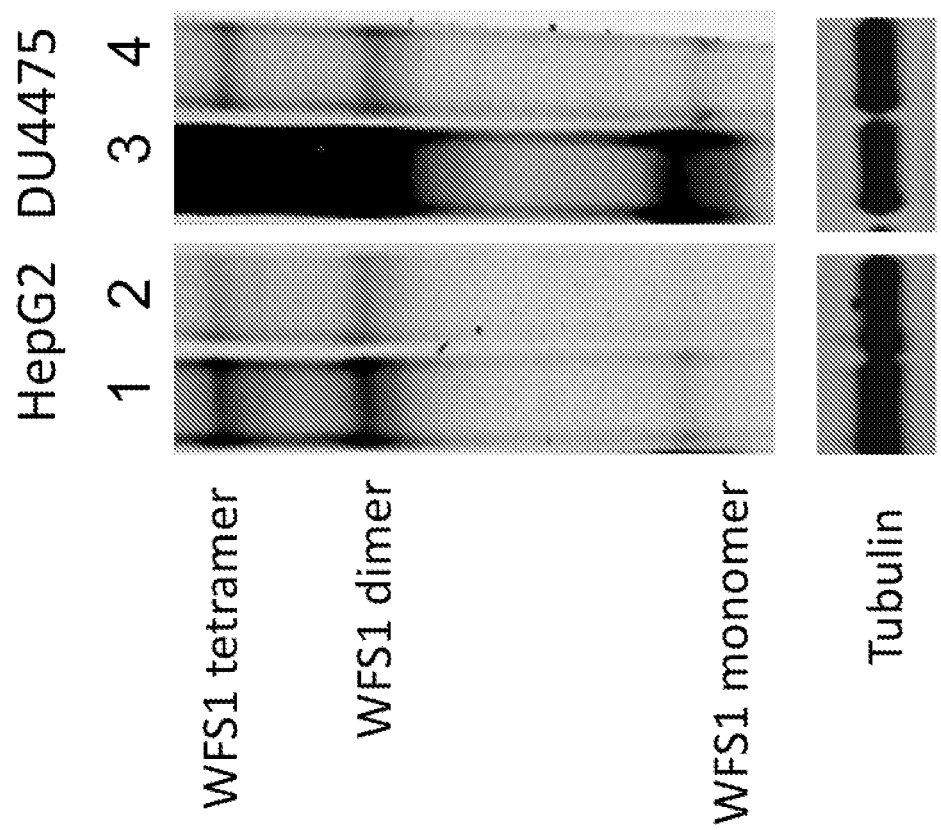
FIG. 4 is an immunoblot showing WFS1 and tubulin protein levels in HepG2 and DU4475 cancer cells expressing either negative control shRNA or shRNA targeting WFS1.

Knockdown of WFS1 by RNAi Reduced Ability of Compounds to Inhibit TCF/LEF Reporter Activity and Cell Viability Transduction of HepG2 (FIG. 4), DU4475 (FIG. 4), and Colo-205 (not shown) cells with a lentivirus encoding a shRNA targeting WFS1 resulted in a greater than 75% reduction of WFS1 protein levels when compared to cells transduced with lentivirus encoding a non-targeting control shRNA as determined by immunoblot (FIG. 4). Stable knockdown of WFS1 protein levels in DU4475 and Colo-205 cells containing the TC-Luc reporter resulted in a 5 to 7 fold increase in the IC$_{50}$ for Compound 253 and Compound 136 in blocking TCF reporter activity as compared to control cells (Table 50). Furthermore, knockdown of WFS1 protein levels in DU4475, Colo-205, and HepG2 cells resulted in a greater than 50 fold increase in the IC$_{50}$ for Compound 253 and Compound 136 in reducing cell viability as compared to control cells (Table 51). These results suggest that WFS1 is involved in the inhibition of TCF reporter activity and viability of the tested compounds.

TABLE 50

Expression of shRNA targeting WFS1
reduces ability of Compound 253 and
Compound 136 to inhibit TCF reporter activity.

| Cell Line | Compound 136 IC$_{50}$ ((μM) | Compound 253 IC$_{50}$ ((μM) |
|---|---|---|
| Colo-205 Control shRNA | 0.1 +/− 0.02 | 0.2 +/− 0.03 |
| Colo-205 WFS1 shRNA | 0.7 +/− 0.2 | 1.5 +/− 0.7 |
| DU4475 Control shRNA | 0.09 +/− 0.01 | 0.2 +/− 0.03 |
| DU4475 WFS1 shRNA | 0.7 +/− 0.1 | 1.0 +/− 0.1 |

TABLE 51

Expression of shRNA targeting WFS1
reduces ability of Compound 253 and
Compound 136 to inhibit cell viability.

| Cell Line | Compound 136 IC$_{50}$ (μM) | Compound 253 IC$_{50}$ (μM) |
|---|---|---|
| Colo-205 Control shRNA | 0.05 +/− 0.02 | 0.14 +/− 0.14 |
| Colo-205 WFS1 shRNA | >9.0 +/− 0 | >9.0 +/− 0 |
| DU4475 Control shRNA | 0.08 +/− 0.01 | 0.1 +/− 0.01 |
| DU4475 WFS1 shRNA | 6.1 +/− 2.5 | 7.8 +/− 2.3 |
| HepG2 Control shRNA | 0.26 | 0.20 |
| HepG2 WFS1 shRNA | 2.2 | 17 |

Binding capacity of Compound 136 to cellular membrane extracts correlates with levels of WFS1 protein.

Figure 8:
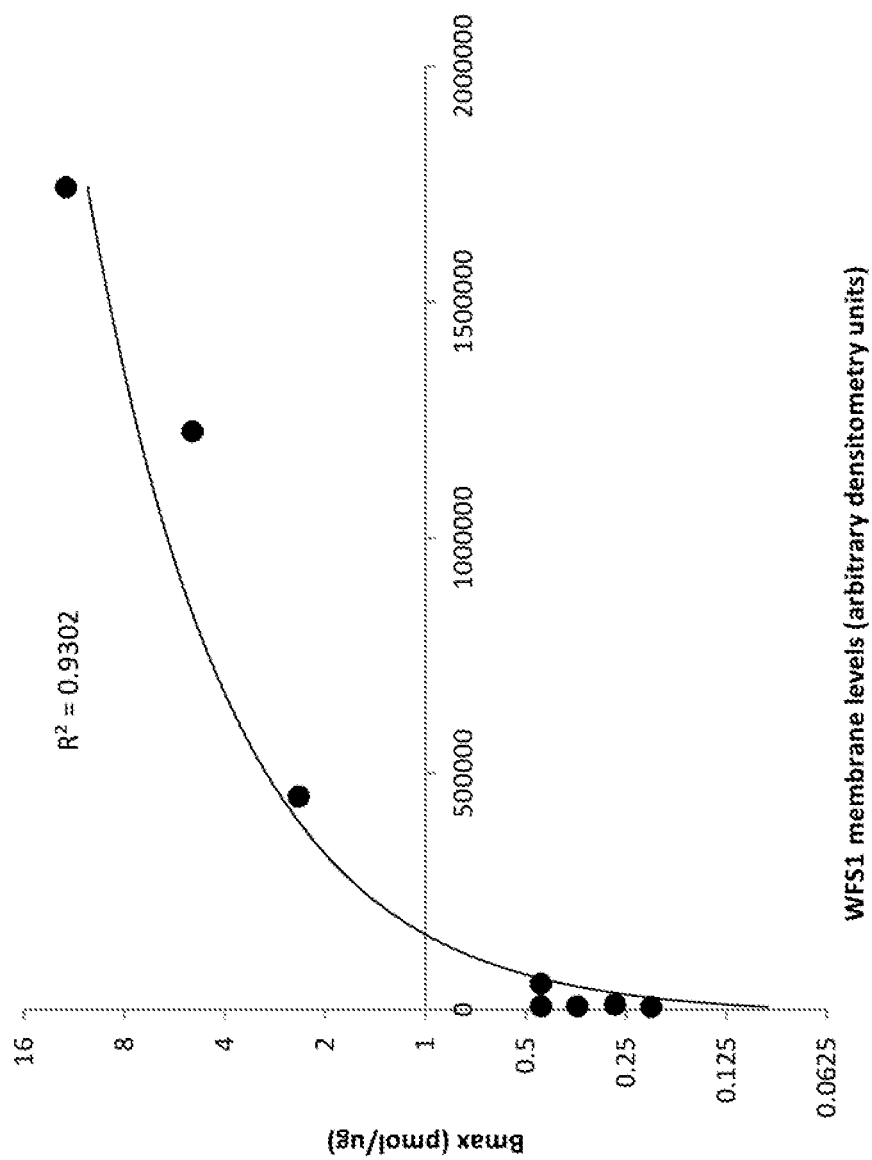
FIG. 8 is a graph showing the degree of binding of radiolabeled Compound 136 to membrane lysates from cells with varying degrees of WFS1 protein expression.

The binding affinity of radiolabeled Compound 136 to cell membranes derived from cells expressing different levels of WFS1 as determined by immunoblotting is shown in FIG. 8. As the figure shows, the Bmax (pg/mol) of Compound 136 correlates with the level of WFS1 protein in cellular membrane. This correlation is consistent with Compound 136 and the compounds described herein directly binding to WFS1 or a WFS1 associated complex or a protein complex in tight stoichiometry with WFS1.

Example 11. In Vivo Inhibition of TCF/LEF Reporter Activity in Tumors

Determination of Compound Effects on In Vivo Tumor TCF/LEF Reporter Activity

Colo205-TCF/LEF-Luciferase (Luc) tumor cells were expanded in complete DMEM cell culture media [DMEM (Life Technologies, product #11960-051) media supplemented with 10% FBS (Hyclone, catalog # SH30071.03), antimycotic/antibiotic (Life Technologies, product #15240-062), and Glutamax (Life Technologies, product #35050-061)] with 1 ug/ml puromycin. After reaching confluency/high density, the loosely attached cells in media were transferred from the flask to 50 ml conical tubes. Tumor cells adhered to plastic were detached with trypsin and combined with cells in the conical tubes. The tumor cells were triturated, counted, and pelleted by centrifugation. Cell pellets were resuspended in 0.9% injectable saline (6×10^7 cells/ml). A 50 ul volume (3×10^6 cells) was injected subcutaneously in the flanks of 4-6 wk old female nu/nu mice (Charles River Laboratories). Approximately 13-16 days after implantation, tumors between 200-500 mm^3 were selected (based on caliper measurements and applying the formula volume=width×length×0.54) and randomized into groups of n=4. Mice were dosed by oral gavage with compound dissolved in 1:3:5:1 EtOH:DMSO:PEG-400:H$_2$O at a rate of 10 ml/kg or 1:3:5:1 EtOH:DMSO:PEG-400:H$_2$O alone (Vehicle Control). Tumors were collected from mice euthanized by CO$_2$ inhalation and snap frozen in liquid nitrogen. Tumors were stored in a −80 degrees C. freezer until they were processed.

Tumors were thawed on ice and homogenized in cold Lysis Buffer (20 mM Tris-HCl (pH 7.5), 150 mM NaCl, 1 mM Na2EDTA, 1 mM EGTA, 1% Triton, 2.5 mM sodium pyrophosphate, 1 mM beta-glycerophosphate, 1 mM Na3VO4, 1 μg/ml leupeptin, 0.05% SDS) using a closed tissue grinder system (Fisher Scientific, Cat #02-542-09) on ice according to manufacturer's instructions. For 100 mg of tumor, 500 uL of Lysis Buffer was used. Tumor lysate was transferred to a pre-chilled microcentrifuge tube and centrifuged at 10,000×g for 10 minutes at 4 degrees C. Supernatant was transferred to a new pre-chilled microcentrifuge tube and was used immediately for analysis of protein content and luciferase activity.

Protein content of tumor lysate supernatant was determined using the BCA assay (Life Technologies Cat #23225). Luciferase activity of tumor lysate supernatant was determined by addition of Steady-Glo luminescence reagent (Promega, Cat # E2550) according to manufacturer's instructions and measurement on a Pherastar luminescence plate reader (BMG Labtech). Luciferase activity was normalized to protein content.

The in vivo inhibition of TCF/LEF reporter activity in Colo-205 tumors are summarized in Table 53.

TABLE 53

In Vivo Inhibition of TCF/LEF Reporter Activity in Colo-205 Tumors.

| Comp. # | Percent Remaining Activity at 8 hrs after Dosing | Comp. # | Percent Remaining Activity at 8 hrs after Dosing | Comp. # | Percent Remaining Activity at 8 hrs after Dosing |
|---|---|---|---|---|---|
| Comp 1 | 32% | Comp 149 | 17% | Comp 384 | 14% |
| Comp 4 | 23% | Comp 324 | 16% | Comp 385 | 25% |
| Comp 42 | 20% | Comp 332 | 51% | Comp 386 | 19% |
| Comp 46 | 20% | Comp 154 | 24% | Comp 398 | 83% |
| Comp 246 | 18% | Comp 155 | 17% | Comp 388 | 13% |
| Comp 253 | 15% | Comp 160 | 18% | Comp 395 | 19% |
| Comp 272 | 14% | Comp 335 | 18% | Comp 396 | 23% |
| Comp 77 | 30% | Comp 174 | 22% | Comp 397 | 23% |
| Comp 80 | 34% | Comp 186 | 23% | Comp 257 | 30% |
| Comp 122 | 16% | Comp 207 | 18% | Comp 383 | 36% |
| Comp 136 | 24% | Comp 377 | 33% | Comp 188 | 15% |
| Comp 14 | 33% | Comp 223 | 39% | Comp 63 | 9% |
| Comp 135 | 43% | Comp 229 | 49% | Comp 409 | 27% |
| Comp 414 | 27% | Comp 416 | 22% | Comp 420 | 28% |
| Comp 421 | 23% | Comp 423 | 70% | Comp 425 | 29% |
| Comp 431 | 29% | Comp 434 | 26% | Comp 436 | 16% |
| Comp 437 | 20% | Comp 443 | 100% | Comp 445 | 98% |
| Comp 447 | 76% | Comp 449 | 22% | Comp 450 | 32% |
| Comp 455 | 63% | Comp 466 | 101% | Comp 491 | 41% |
| Comp 496 | 17% | Comp 499 | 31% | Comp 500 | 43% |
| Comp 501 | 53% | Comp 511 | 52% | Comp 513 | 90% |
| Comp 517 | 93% | Comp 518 | 21% | Comp 522 | 91% |
| Comp 528 | 28% | Comp 542 | 22% | Comp 545 | 51% |
| Comp 549 | 30% | Comp 551 | 20% | Comp 556 | 62% |
| Comp 557 | 20% | Comp 565 | 68% | Comp 578 | 47% |

TABLE 53-continued

In Vivo Inhibition of TCF/LEF Reporter Activity in Colo-205 Tumors.

| Comp. # | Percent Remaining Activity at 8 hrs after Dosing | Comp. # | Percent Remaining Activity at 8 hrs after Dosing | Comp. # | Percent Remaining Activity at 8 hrs after Dosing |
|---|---|---|---|---|---|
| Comp 589 | 94% | Comp 602 | 57% | Comp 643 | 22% |
| Comp 656 | 51% | Comp 658 | 62% | Comp 678 | 75% |

Example 12. In Vivo Efficacy

Female immune deficient mice (Charles River, 4-6 wks age) were anesthetized with Ketamine-Xylazine (140 mg/kg-14 mg/kg ip) and shaved. Puralube eye ointment was applied to the eyes to prevent desiccation of the corneas. Betadine and 7000 ethanol was applied to the shaved location to sterilize the skin at the location of the incision. The animals were placed in a biosafety cabinet for the duration of the surgery. Using scissors, an 8 to 10 mm incision was made in the lateral flank of the skin. A tumor fragment weighing between 50 and 150 mg was placed under the skin at the incision site using forceps, and staples were used to close the incision. The staples were removed 5 to 7 days after surgery. Starting approximately two weeks after implantation, animals were weighed, and tumors were measured using caliper twice weekly. Tumor volume was calculated using the formula: volume=length×width$^2$×0.52.

Compound administration began when xenografts reached approximately 100-300 mm3 and continued until control xenografts reached 10% of the animal's body weight. Test compounds were administered orally by gastric gavage. Percent tumor growth inhibition (% TGI) was calculated on the indicated treatment day. Percent TGI is defined as: [1-(del T/del C)]×100%, where del T is the final minus initial average volumes of the treated group, and del C is the final minus initial average volumes of the control group. Table 54 shows efficacies of multiple testing compounds against the non-small cell lung cancer (NSCLC) adenocarcinoma line OD33966 in nu/nu mice. The tested compounds were administered orally. Vehicle control consisted of either 0.5% methylcellulose/0.1% sodium lauryl sulfate or 20% captisol. Tumor volumes were determined by caliper measurement twice a week.

TABLE 54

In vivo efficacy for the NSCLC Patient Derived Xenograft OD33966

| Compound # | Dose | Treatment day | % TGI* |
|---|---|---|---|
| Compound 1 | 200 mpk bid | 19 | 94.53 |
| Compound 42 | 100 mpk qd | 14 | 79.63 |
| Compound 46 | 100 mpk qd | 14 | 93.26 |
| Compound 246 | 100 mpk qd | 11 | 82.57 |
| Compound 253 | 100 mpk qd | 14 | 96.60 |
| Compound 272 | 100 mpk qd | 14 | 77.91 |
| Compound 77 | 100 mpk qd | 14 | 98.45 |
| Compound 83 | 100 mpk qd | 14 | 97.25 |
| Compound 94 | 100 mpk qd | 14 | 94.52 |
| Compound 136 | 100 mpk qd | 14 | 106.65 |
| Compound 405 | 100 mpk qd | 12 | 91.03 |
| Compound 403 | 100 mpk qd | 12 | 102.84 |

*[1-(del T/del C)] × 100%

Table 55 shows efficacy of Compound 136 against various tumorXenograft models. As shown in Table 55, Compound 136 inhibits growth of tumor xenografts derived from multiple cancer types. Tumors were engrafted in either SCID or nude mice. Compound 136 was administered orally once a day (QD) at 100 mg/kg. Vehicle control consisted of 0.500 methylcellulose/0.1% sodium lauryl sulfate. Tumor volumes were determined by caliper measurement twice a week. TGL: tumor growth inhibition at end of treatment. CR: complete regression (majority response on treatment is that tumors become undetectable), PR: partial regression (majority response on treatment is that tumors shrink by at least 330%).

TABLE 55

In vivo efficacy of Compound 136 in various tumor Xenografts

| Tumor type | Model name | Treatment duration | % TGI* | Body weight change at end of treatment |
|---|---|---|---|---|
| Multiple myeloma | NCI-H929 | 21 days | >100% (CR) | +1.8% |
| Multiple myeloma | OPM2 | 21 days | >100% (CR) | −0.9% |
| Non-small cell lung | OD33966 | 21 days | >100% (PR) | +4.5% |
| Non-small cell lung | OD26749 | 21 days | >100% (CR) | −0.1% |
| Non-small cell lung | LXFL 625 | 21 days | >100% (CR) | +3.7% |
| Non-small cell lung | LXFL 529 | 21 days | >100% (CR) | +5.5% |
| Non-small cell lung | LXFL 2207 | 21 days | >100% (PR) | +1.5% |
| Breast | DU4475 | 14 days | 99% | |
| Melanoma | MEXF 1765 | 21 days | >100% (CR) | +9.8% |
| Bladder | BXF 1036 | 21 days | >100% (PR) | +5.5% |
| Kidney | RXF 631 | 21 days | 89% | +6.2% |

Example 13. Assessment of Monotherapy Response in Multiple Panels of Cancer Cell Lines This study was performed to identify candidate gene expression markers which could predict in vitro response to Compound 136.

TABLE 56

Abbreviations

| Abbreviation | Term |
|---|---|
| AML | Acute myeloid leukemia |
| ATPlite | Adenosine triphosphate luciferase |
| BH | Benjamini-Hochberg |
| DNA | Deoxyribonucleic acid |
| FDR | False discovery rate |
| GI | Growth inhibition |
| NSCLC | Non-small cell lung cancer |
| CORD | Oncology responder ID |

TABLE 57

Bladder cancer cell line list

| CELL LINE | TUMOR TYPE |
| --- | --- |
| 5637 | Bladder |
| T-24 | Bladder |
| RT4 | Bladder |
| RT-112 | Bladder |
| J82 | Bladder |
| SCaBER | Bladder |
| HT-1197 | Bladder |
| SW780 | Bladder |
| UM-UC-3 | Bladder |
| TCCSUP | Bladder |

TABLE 58

428 Cancer Cell Line List

| CELL LINE | TUMOR TYPE |
| --- | --- |
| 22RV1 | prostate |
| 5637 | bladder |
| 59M | ovary |
| 769-P | kidney |
| 786-0 | kidney |
| A101D | skin |
| A2058 | skin |
| A253 | head/neck |
| A2780 | ovary |
| A3/KAW | DLBCL |
| A375 | skin |
| A4-Fuk | DLBCL |
| A498 | kidney |
| A549 | NSCLC |
| A673 | bone |
| A704 | kidney |
| ACC-MESO-1 | mesothelioma |
| ACHN | kidney |
| AGS | gastric |
| AN3-CA | endometrium |
| AsPC-1 | pancreas |
| AU565 | breast |
| BEN | NSCLC |
| BICR 16 | head/neck |
| BICR 22 | head/neck |
| BICR 31 | head/neck |
| BICR 56 | head/neck |
| BT-20 | breast |
| BT-474 | breast |
| BT-549 | breast |
| BxPC-3 | pancreas |
| C2BBe1 | colorectal |
| C32 | skin |
| C3A | liver |
| CA46 | burkitt lymphoma |
| Caki-1 | kidney |
| CAKI-2 | kidney |
| CAL-120 | breast |
| CAL-12T | NSCLC |
| CAL-148 | breast |
| CAL-27 | head/neck |
| CAL-54 | kidney |
| CAL-85-1 | breast |
| Calu-1 | NSCLC |
| Calu-3 | NSCLC |
| Calu-6 | NSCLC |
| CAMA-1 | breast |
| Caov-3 | ovary |
| Caov-4 | ovary |
| CAPAN-2 | pancreas |
| CCK-81 | colorectal |
| CCRF-CEM | T cell ALL |
| CEM-Cl | T cell ALL |
| CESS | AML |
| CFPAC-1 | pancreas |

TABLE 58-continued

428 Cancer Cell Line List

| CELL LINE | TUMOR TYPE |
| --- | --- |
| ChaGo-K-1 | NSCLC |
| CHL-1 | skin |
| CHP-126 | neuroblastoma |
| CHP-212 | neuroblastoma |
| CJM | skin |
| CL-11 | colorectal |
| CL-34 | colorectal |
| CL-40 | colorectal |
| COLO-201 | colorectal |
| COLO-205 | colorectal |
| COLO-320 | colorectal |
| COLO-320-DM | colorectal |
| COLO-320-HSR | colorectal |
| COLO-668 | SCLC |
| COLO-677 | multiple myeloma |
| COLO-678 | colorectal |
| COLO-679 | skin |
| COLO-684 | endometrium |
| COLO-699 | skin |
| COLO-741 | colorectal |
| COLO-783 | skin |
| COLO-792 | skin |
| COLO-800 | skin |
| COLO-818 | skin |
| COLO-829 | skin |
| COLO-849 | skin |
| COLO-858 | skin |
| COR-L105 | NSCLC |
| COR-L23 | NSCLC |
| COV362 | ovary |
| COV644 | ovary |
| CW-2 | colorectal |
| Daoy | medulloblastoma |
| Daudi | burkitt lymphoma |
| DB | DLBCL |
| DBTRG-05MG | glioma |
| Detroit562 | head/neck |
| DK-MG | glioma |
| DLD-1 | colorectal |
| DMS-114 | SCLC |
| DMS-273 | SCLC |
| DU-145 | prostate |
| DU-4475 | breast |
| DV-90 | NSCLC |
| EBC-1 | NSCLC |
| EC-GI-10 | esophageal |
| ECC10 | gastric |
| EFO-21 | ovary |
| EFO-27 | ovary |
| EPLC-272H | NSCLC |
| FaDu | head/neck |
| FTC-238 | thyroid |
| G-361 | skin |
| G-401 | soft tissue |
| G-402 | soft tissue |
| GA-10 | burkitt lymphoma |
| GCIY | gastric |
| GSS | gastric |
| H4 | glioma |
| H9 | cutaneous T cell lymphoma |
| HARA | NSCLC |
| HCC1438 | NSCLC |
| HCC2157 | breast |
| HCT-116 | colorectal |
| HCT-15 | colorectal |
| HEC-1 | endometrium |
| HEC-1-A | endometrium |
| HEC-1-B | endometrium |
| HEC-151 | endometrium |

TABLE 58-continued

428 Cancer Cell Line List

| CELL LINE | TUMOR TYPE |
|---|---|
| HEC-251 | endometrium |
| HEC-265 | endometrium |
| HEC-50B | endometrium |
| HEC-59 | endometrium |
| HEL 92.1.7 | AML |
| Hep 3B 2.1-7 | liver |
| Hep G2 | liver |
| Hey-A8 | ovary |
| HGC-27 | gastric |
| HH | cutaneous T cell lymphoma |
| HL-60 | AML |
| HLC-1 | NSCLC |
| HLE | liver |
| HLF | liver |
| HMC-1-8 | NSCLC |
| HMCB | skin |
| HOP-62 | NSCLC |
| HPAF-II | pancreas |
| HRT-18G | colorectal |
| Hs 294T | skin |
| Hs 739.T | breast |
| Hs 746T | gastric |
| Hs 852.T | skin |
| HSC-2 | head/neck |
| HSC-3 | head/neck |
| HSC-4 | head/neck |
| HT-144 | skin |
| HT-29 | colorectal |
| HuCCT1 | bile duct |
| HuH-1 | liver |
| HuH-28 | bile duct |
| HUH-6-clone5 | liver |
| HuH-7 | liver |
| HuNS1 | multiple myeloma |
| HuP-T3 | pancreas |
| HUTU-80 | gastric |
| IA-LM | NSCLC |
| IGR-1 | skin |
| IGR-37 | skin |
| IGR-39 | skin |
| IGROV-1 | ovary |
| IM-95 | gastric |
| INA-6 | multiple myeloma |
| Ishikawa | endometrium |
| IST-MES1 | mesothelioma |
| IST-MES2 | mesothelioma |
| IST-SL2 | SCLC |
| JAR | endometrium |
| Jeko-1 | mantle cell lymphoma |
| JHH-1 | liver |
| JHH-2 | liver |
| JHH-5 | liver |
| JHH-6 | liver |
| JHH-7 | liver |
| JHOC-5 | ovary |
| JHOS-2 | ovary |
| JHUEM-1 | endometrium |
| JHUEM-2 | endometrium |
| JHUEM-3 | endometrium |
| JHUEM-7 | endometrium |
| JIMT-1 | breast |
| JL-1 | mesothelioma |
| JM1 | B cell lymphoma |
| JU77 | mesothelioma |
| JVM-2 | mantle cell lymphoma |
| K-562 | CML |
| KASUMI-1 | AML |
| KATO III | gastric |
| KE-39 | gastric |
| KE-97 | multiple myeloma |
| KELLY | neuroblastoma |
| KG-1 | AML |
| Ki-JK | ALCL |
| KLE | endometrium |
| KLM-1 | pancreas |
| KMM-1 | multiple myeloma |
| KM5-11 | multiple myeloma |
| KM5-20 | multiple myeloma |
| KM5-34 | multiple myeloma |
| KN5-62 | NSCLC |
| KN5-81 | glioma |
| KP-2 | pancreas |
| KP-3 | pancreas |
| KP-4 | pancreas |
| KP-N-5I9s | neuroblastoma |
| KS-1 | glioma |
| KYM-1 | soft tissue |
| KYSE-180 | esophageal |
| KYSE-30 | esophageal |
| KYSE-510 | esophageal |
| KYSE-70 | esophageal |
| LC-1sq | NSCLC |
| LCLC-97TM1 | NSCLC |
| Li-7 | liver |
| LK-2 | NSCLC |
| LMSU | gastric |
| LO68 | mesothelioma |
| LOU-NH91 | NSCLC |
| LoVo | colorectal |
| LS-123 | colorectal |
| LS-411N | colorectal |
| LS-513 | colorectal |
| LU-134-A | SCLC |
| LU-135 | SCLC |
| LU-65 | NSCLC |
| LU-99 | NSCLC |
| LUDLU-1 | NSCLC |
| LXF-289 | NSCLC |
| MC116 | B cell lymphoma |
| MCAS | ovary |
| MCF7 | breast |
| MDA-MB-175-VII | breast |
| MDA-MB-231 | breast |
| MDA-MB-361 | breast |
| MDA-MB-435S | skin |
| MDA-MB-436 | breast |
| MDA-MB-453 | breast |
| MDA-MB-468 | breast |
| MEL-JUSO | skin |
| MES-SA | endometrium |
| MeWo | skin |
| MFE-280 | endometrium |
| MFE-296 | endometrium |
| MG-63 | bone |
| MIA PaCa-2 | pancreas |
| Mino | mantle cell lymphoma |
| MKN1 | gastric |
| MKN45 | gastric |
| MKN7 | gastric |
| MKN74 | gastric |
| MM.1S | multiple myeloma |
| MOLT-4 | T cell ALL |
| Molt3 | T cell ALL |
| MOR-CPR | NSCLC |
| MPP-89 | mesothelioma |
| MSTO-211H | mesothelioma |
| MV-4-11 | AML |

TABLE 58-continued

428 Cancer Cell Line List

| CELL LINE | TUMOR TYPE |
|---|---|
| Namalwa | burkitt lymphoma |
| NB1 | neuroblastoma |
| NCC-StC-K140 | gastric |
| NCI-H292 | NSCLC |
| NCI-H322 | NSCLC |
| NCI-H345 | SCLC |
| NCI-H446 | SCLC |
| NCI-H460 | NSCLC |
| NCI-H520 | NSCLC |
| NCI-H596 | NSCLC |
| NCI-H69 | SCLC |
| NCI-H747 | colorectal |
| NCI-H929 | multiple myeloma |
| NCI-SNU-1 | gastric |
| NH-6 | neuroblastoma |
| NU-DHL-1-epst | DLBCL |
| NUGC-3 | gastric |
| NUGC-4 | gastric |
| OAW-42 | ovary |
| OC-316 | ovary |
| OCUM-1 | gastric |
| ONS-76 | medulloblastoma |
| OV56 | ovary |
| OV90 | ovary |
| OVCAR-3 | ovary |
| OVCAR-4 | ovary |
| OVCAR-5 | ovary |
| OVCAR-8 | ovary |
| OVISE | ovary |
| OVSAHO | ovary |
| OVTOKO | ovary |
| PA-1 | ovary |
| PANC-08-13 | pancreas |
| Panc 02.03 | pancreas |
| Panc 02.13 | pancreas |
| Panc 03.27 | pancreas |
| Panc 04.03 | pancreas |
| Panc 05.04 | pancreas |
| PC-3 | prostate |
| PCM6 | multiple myeloma |
| PE-CA-PJ15 | head/neck |
| PE-CA-PJ41-cl D2 | head/neck |
| Pfeiffer | DLBCL |
| PK-1 | pancreas |
| PK-45H | pancreas |
| PLC/PRF/5 | liver |
| PSN1 | pancreas |
| Raji | burkitt lymphoma |
| RCM-1 | colorectal |
| REC-1 | mantle cell lymphoma |
| REH | B cell ALL |
| RERF-GC-1B | gastric |
| RERF-LC-Ad2 | NSCLC |
| RERF-LC-AI | NSCLC |
| RERF-LC-MS | NSCLC |
| RH-41 | soft tissue |
| RKO | colorectal |
| RL | non-Hodgkins B cell lymphoma |
| RL95-2 | endometrium |
| RPMI-7951 | skin |
| RPMI-8226 | multiple myeloma |
| RS4-11 | B cell ALL |
| RT4 | bladder |
| RVH-421 | skin |
| SBC-5 | SCLC |
| SC-1 | non-Hodgkins B cell lymphoma |
| SCC-15 | head/neck |
| SF126 | glioma |
| SH-10-TC | gastric |
| SH-4 | skin |
| SHP-77 | SCLC |
| SJSA-1 | bone |
| SK-BR-3 | breast |
| SK-HEP-1 | liver |
| SK-LU-1 | NSCLC |
| SK-MEL-1 | skin |
| SK-MEL-24 | skin |
| SK-MEL-28 | skin |
| SK-MEL-3 | skin |
| SK-MEL-30 | skin |
| SK-MEL-31 | skin |
| SK-MEL-5 | skin |
| SK-MES-1 | NSCLC |
| SK-N-AS | neuroblastoma |
| SK-N-BE-2 | neuroblastoma |
| SK-N-DZ | neuroblastoma |
| SK-N-FI | neuroblastoma |
| SK-OV-3 | ovary |
| SNB-75 | glioma |
| SNG-II | endometrium |
| SNG-M | endometrium |
| SNU-1197 | colorectal |
| SNU-16 | gastric |
| SNU-175 | colorectal |
| SNU-182 | liver |
| SNU-283 | colorectal |
| SNU-308 | bile duct |
| SNU-324 | pancreas |
| SNU-387 | liver |
| SNU-398 | liver |
| SNU-407 | colorectal |
| SNU-423 | liver |
| SNU-449 | liver |
| SNU-478 | bile duct |
| SNU-620 | gastric |
| SNU-685 | endometrium |
| SNU-8 | ovary |
| SNU-81 | colorectal |
| SNU-878 | liver |
| SNU-C2B | colorectal |
| SNU-C4 | colorectal |
| SNU-C5 | colorectal |
| SU-DHL-1-epst | ALCL |
| SU-DHL-10-epst | DLBCL |
| SU-DHL-16-epst | non-Hodgkins B cell lymphoma |
| SU-DHL-2-epst | B cell lymphoma |
| SU-DHL-5-epst | DLBCL |
| SU-DHL-7-epst | DLBCL |
| SU-DHL-8-epst | DLBCL |
| SU.86.86 | pancreas |
| SUIT-2 | pancreas |
| SUM159PT | breast |
| SUP-B15 | B cell ALL |
| SUP-T1 | T cell ALL |
| SW1088 | glioma |
| SW1116 | colorectal |
| SW1271 | SCLC |
| SW1417 | colorectal |
| SW1573 | NSCLC |
| SW1990 | pancreas |
| SW48 | colorectal |
| SW480 | colorectal |
| SW579 | thyroid |

TABLE 58-continued

428 Cancer Cell Line List

| CELL LINE | TUMOR TYPE |
|---|---|
| SW620 | colorectal |
| SW756 | endometrium |
| SW837 | colorectal |
| SW900 | NSCLC |
| SW948 | colorectal |
| T-24 | bladder |
| T3M-10 | NSCLC |
| T3M-4 | pancreas |
| T47D | breast |
| TCCSUP | bladder |
| TE-10 | esophageal |
| TE-11 | esophageal |
| TE-14 | esophageal |
| TE-159.T | soft tissue |
| TE-4 | esophageal |
| TE-5 | esophageal |
| TE-6 | esophageal |
| TE-8 | esophageal |
| TE-9 | esophageal |
| TEN | endometrium |
| Toledo | DLBCL |
| TOV-21G | ovary |
| U-2-OS | bone |
| U-87 MG | glioma |
| U266B1 | multiple myeloma |
| UWB1.289 | ovary |
| VMRC-LCD | NSCLC |
| WM-115 | skin |
| WM-266-4 | skin |
| WSU-FSCCL | non-Hodgkins B cell lymphoma |
| YD-10B | head/neck |
| YD-38 | head/neck |
| YH-13 | glioma |
| YMB-1 | breast |

Cell Culture Methods

Cells were removed from liquid nitrogen storage, thawed and expanded in appropriate growth media. Once expanded, cells were seeded in 384-well tissue culture treated plates at 500 cells per well. After 24 hours, cells were treated for either 0 hours or treated for 96 hours with Compound 136 (at the concentrations of 100 nM and 2 uM). At the end of either 0 hours or 96 hours, cell status was analyzed using ATPLite (Perkin Elmer) to assess the biological response of cells to drug combinations.

Growth Inhibition

In this study, growth inhibition (GI) was used as the primary endpoint. ATP monitoring was performed using ATPLite, which allows for the monitoring of cytocidal, cytostatic and proliferative effects of drugs on cells.

a. Univariate Gene Expression Analysis

Analyses of the transcript expression level and synergy value correlations were undertaken in both an unbiased and biased manner. The unbiased course involved choosing any genes with p values less than 0.06 or 0.1 after multiple test correction. Other genes were added in a biased manner, taking into consideration biological function and relationship to relevant pathways.

I. Results

The Association Between WFS1 Gene Expression and Response to Compound 136

Figure 9:
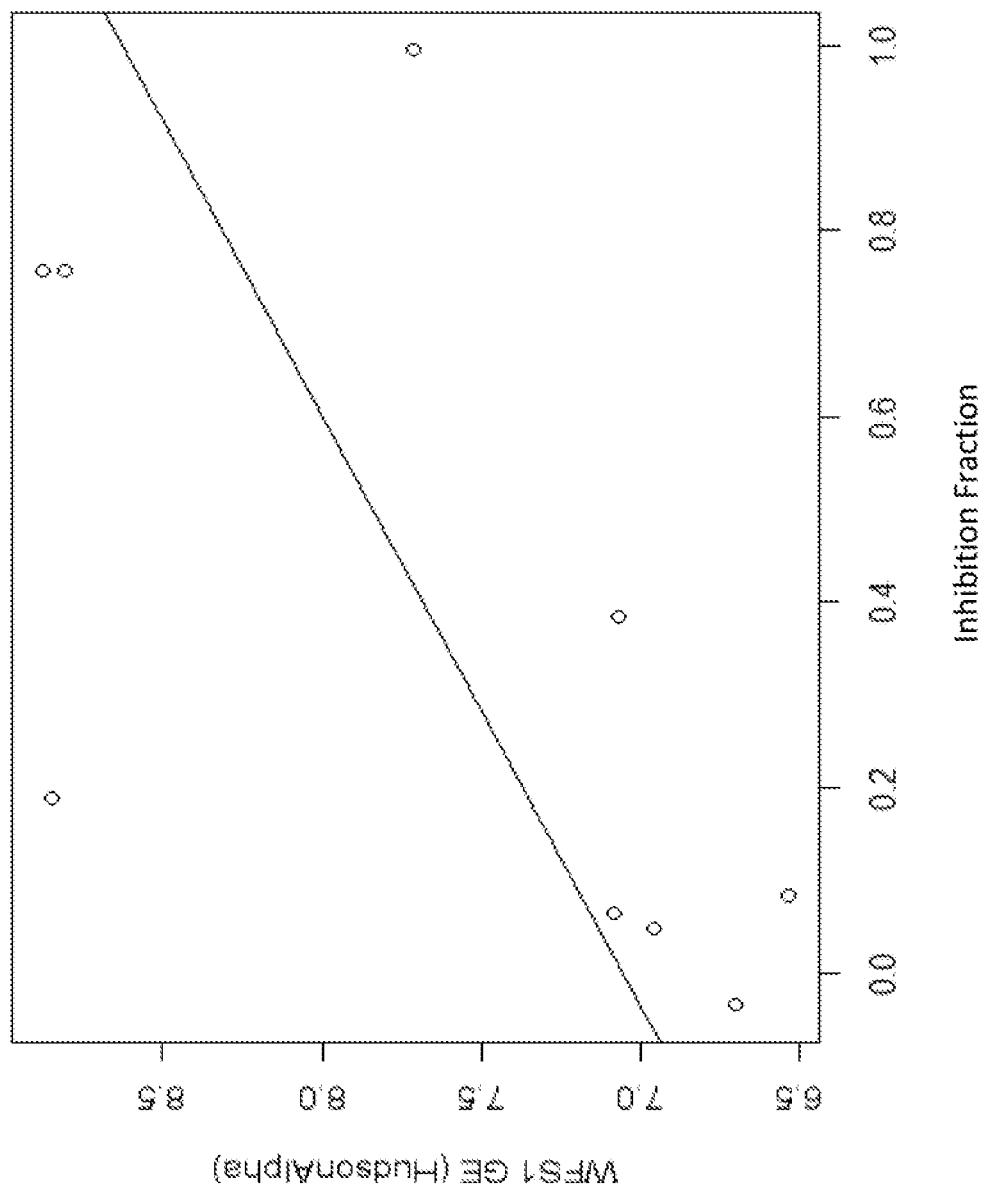
FIG. 9 is a graph showing association between WFS1 gene expression and response to Compound 136 in a panel of bladder cancer cell lines.

The relationship between WFS1 gene expression and response to Compound 136 was evaluated in a panel of 9 bladder cancer cell lines (Table 57). Response to Compound 136 was associated with response (FIG. 9) and the association was statistically significant (Spearman rho 0.68, p-value 0.048).

Figure 10:
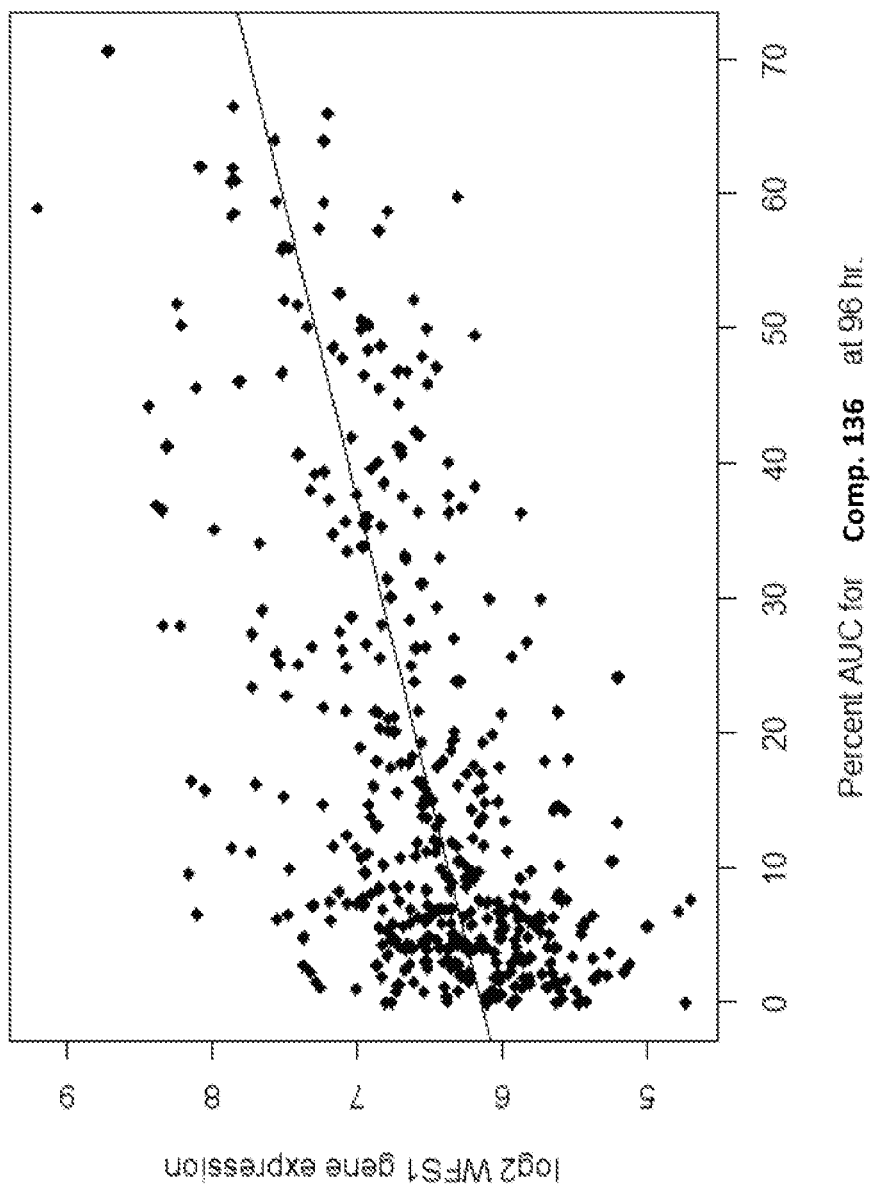
FIG. 10 is a graph showing association between WFS1 gene expression and response to Compound 136 in a panel of 428 cancer cell lines.

In addition, the relationship between response to Compound 136 and response was further assessed in a panel of 428 cancer cell lines (Table 58). As expected, WFS1 gene expression was associated with response to Compound 136 at 2 µM (FIG. 10) and this association was statistically significant (Spearman rho 0.42, p value 0.0056).

Figure 11:
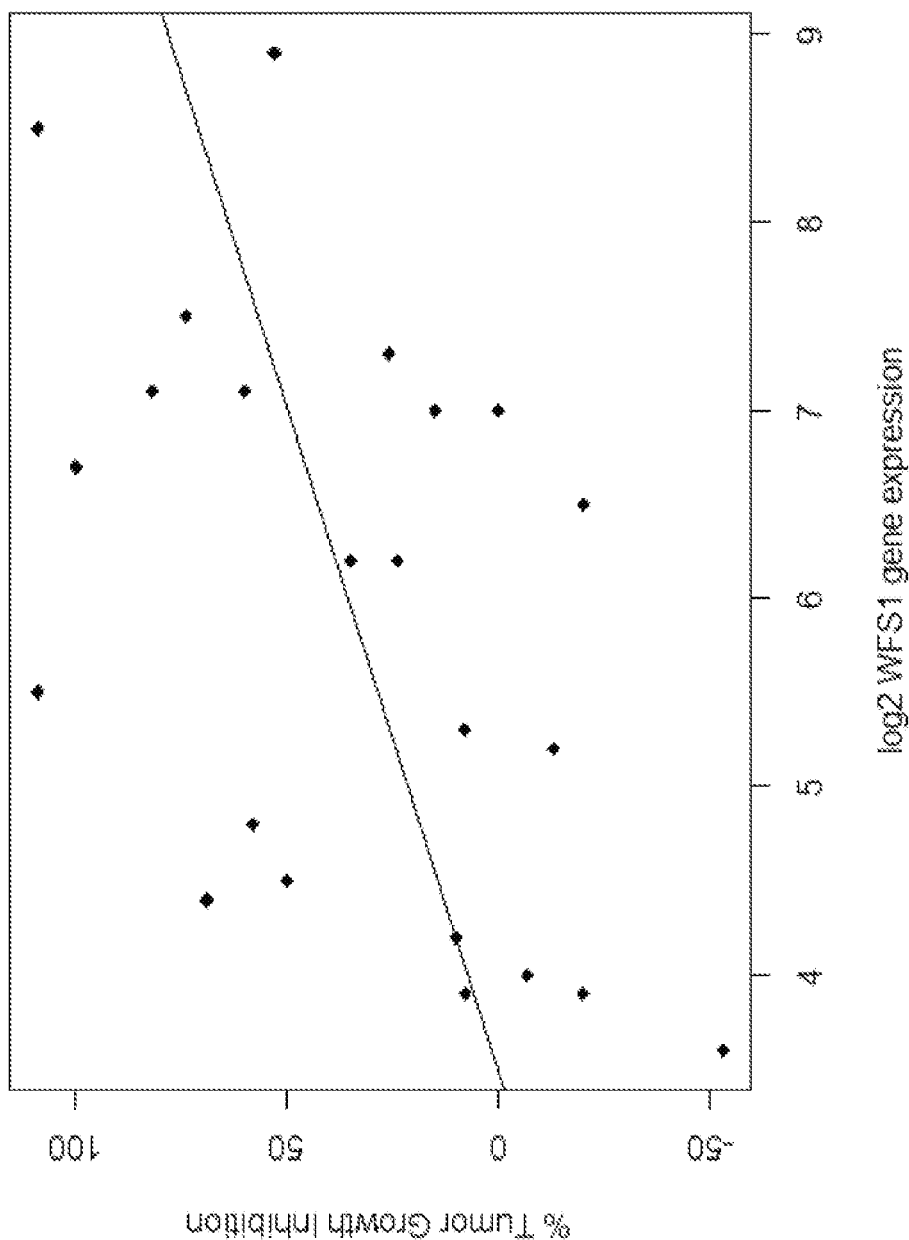
FIG. 11 is a graph showing association between WFS1 gene expression and response to Compound 136 in a panel of 23 patient-derived lung xenografts.

Finally, an in vivo study was run to evaluate the relationship between WFS1 expression in patient derived xenografts (PDX). To do this, the 10 lung PDX models with the highest WFS1 gene expression and the 10 lung PDX models with the lowest WFS1 gene expression were selected from the Oncotest compendium. There was a strong association between WFS1 gene expression and response to Compound 136 in PDX models (FIG. 11).

CONCLUSIONS

WFS1 was predictive of response to Compound 136 as a single agent in cancer cell lines and in patient-derived xenografts. The WFS1 expression/Compound response relationship was held in the experiments using PDX model systems.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C. American Chemical Society, 1997.

We claim:

1. A compound of formula I:

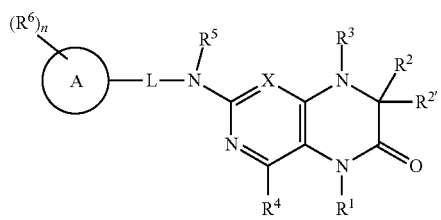

or a pharmaceutically acceptable salt thereof, wherein:

Ring A is selected from a 3-8 membered saturated or partially unsaturated monocyclic carbocyclic ring, phenyl, indanyl, a 4-8 membered saturated or partially unsaturated monocyclic heterocyclic ring having 1-2 heteroatoms independently selected from nitrogen, oxygen, or sulfur, a 8-12 membered saturated or partially unsaturated bicyclic heterocyclic ring having 1-2 heteroatoms independently selected from nitrogen, oxygen, or sulfur, a 5-8 membered saturated or partially unsaturated bridged bicyclic carbocyclic ring, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

L is a covalent bond or a $C_{1-6}$ bivalent straight or branched saturated or unsaturated hydrocarbon chain wherein one to three methylene units of the chain are independently and optionally replaced with -Cy-, —O—, —C(R)$_2$—, —CH(R)—, —CH(OR)—, —CR(OR)—, —C(D)$_2$-, —C(F)$_2$—, —N(R)—, —N(R)C(O)—, —C(O)N(R)—, —N(R)C(O)O—, —OC(O)N(R)—, —N(R)C(O)N(R)—, —N(R)S(O)$_2$—, —S(O)$_2$N(R)—, —C(O)—, —OC(O)—, —C(O)O—, —S—, —S(O)—, —S(O)$_2$—, or —Si(R)$_2$—, wherein -Cy- is an optionally substituted bivalent group selected from phenylenyl, cyclopropylenyl, cyclobutylenyl, cyclopentylenyl, cyclohexylenyl, furylenyl, tetrahydrofurylenyl, azetidylenyl, pyrrolidylenyl, piperidylenyl, triazolylenyl, pyrrolylenyl, pyrazolylenyl, pyridylenyl, 2,4,5,6-tetrahydrocyclopenta[c]pyrazolylenyl, or thiazolylenyl;

$R^1$ is hydrogen;

each of $R^2$ and $R^{2'}$ is independently hydrogen, $R^D$, or an optionally substituted group selected from $C_{1-6}$ aliphatic, a 3-8 membered saturated or partially unsaturated monocyclic carbocyclic ring, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or $R^2$ and $R^{2'}$ are optionally taken together to form =CH$_2$ or =CH—(C$_{1-3}$ aliphatic);

$R^3$ is hydrogen, $R^D$, or an optionally substituted $C_{1-6}$ aliphatic group; or $R^4$ is $R^D$, —CD$_2$OH, or an optionally substituted $C_{1-3}$ aliphatic group;

$R^5$ is hydrogen, —C(O)R, —C(O)OR, —C(O)NR$_2$, an optionally substituted 3-8 membered saturated or partially unsaturated monocyclic carbocyclic ring, or a $C_{1-3}$ aliphatic group;

each of $R^6$ is independently halogen, —CN, —NO$_2$, —C(O)R, —C(O)OR, —C(O)NR$_2$, —NR$_2$, —NRC(O)R, —NRC(O)OR, —NRS(O)$_2$R, —OR, —P(O)R$_2$, —SR, —SF$_5$, —S(CF$_3$)$_5$, —S(O)R, —S(O)$_2$R, —S(O)(NH)R, —C(=NR)—OR, —O—C(=NR)—R, or R; or two $R^6$ groups are optionally taken together to form =O;

each R is independently hydrogen or an optionally substituted group selected from $C_{1-6}$ aliphatic, a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur;

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups;

$R^D$ is a $C_{1-4}$ aliphatic group wherein one or more hydrogens are replaced by deuterium;

X is N or CH; and n is 0, 1, 2, 3, 4 or 5.

2. The compound of claim 1, wherein Ring A is a 3-8 membered saturated or partially unsaturated monocyclic carbocyclic ring.

3. The compound of claim 1, wherein Ring A is phenyl.

4. The compound of claim 1, wherein Ring A is a 4-8 membered saturated or partially unsaturated monocyclic heterocyclic ring having 1-2 heteroatoms independently selected from nitrogen, oxygen, or sulfur.

5. The compound of claim 1, wherein Ring A is a 5-6 membered monocyclic heteroaromatic ring having 1-4 heteroatoms independently selected from nitrogen, oxygen, or sulfur.

6. The compound of claim 1, wherein Ring A is

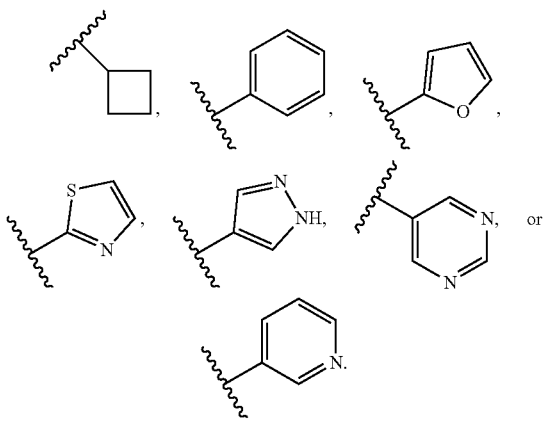

7. The compound of claim 1, wherein L is a $C_{1-6}$ bivalent straight or branched saturated or unsaturated hydrocarbon chain wherein one to three methylene units of the chain are independently and optionally replaced with -Cy-, —O—, —C(R)$_2$—, —CH(R)—, —CH(OR)—, —CR(OR)—, —C(D)$_2$—, —C(F)$_2$—, —N(R)—, —N(R)C(O)—, —C(O)N(R)—, —N(R)C(O)O—, —OC(O)N(R)—, —N(R)C(O)N(R)—, —N(R)S(O)$_2$—, —S(O)$_2$N(R)—, —C(O)—, —OC(O)—, —C(O)O—, —S—, —S(O)—, —S(O)$_2$—, or —Si(R)$_2$—.

8. The compound of claim 1, wherein L is a covalent bond.

9. The compound of claim 1, wherein L is a $C_{1-6}$ bivalent straight or branched saturated or unsaturated hydrocarbon chain wherein one to three methylene units of the chain are independently and optionally replaced with -Cy-, —O—, —C(R)$_2$—, —CH(R)—, —CH(OR)—, —CR(OR)—, —C(D)$_2$—, —C(F)$_2$—, —N(R)—, —N(R)C(O)—, —C(O)N(R)—, —C(O)—, —OC(O)—, or —C(O)O—.

10. The compound of claim 9, wherein -Cy- is an optionally substituted bivalent group selected from cyclopropylenyl, cyclobutylenyl, cyclopentylenyl, or cyclohexylenyl.

11. The compound of claim 9, wherein -Cy- is an optionally substituted bivalent group selected from furylenyl, triazolylenyl, pyrrolylenyl, pyrazolylenyl, pyridylenyl, or thiazolylenyl.

12. The compound of claim 1, wherein each of $R^2$ and $R^{2'}$ is independently hydrogen, $R^D$, or an optionally substituted group selected from $C_{1-6}$ aliphatic, a 3-8 membered saturated or partially unsaturated monocyclic carbocyclic ring, or a 4-8 membered saturated or partially unsaturated monocyclic heterocyclic ring having 1-2 heteroatoms independently selected from nitrogen, oxygen, or sulfur.

13. The compound of claim 1, wherein $R^2$ and $R^{2'}$ taken together form =CHCH$_3$.

14. The compound of claim 1, wherein $R^2$ is $C_{1-6}$ aliphatic substituted by 1-3 halogen, —OH, —OCH$_3$, or —OC(CH$_3$)$_3$.

15. The compound of claim 1, wherein $R^2$ is a 3-8 membered saturated or partially unsaturated monocyclic carbocyclic ring substituted by 1-3 halogen, —OH, —OCH$_3$, or —OC(CH$_3$)$_3$.

16. The compound of claim 1, wherein $R^2$ is a 4-8 membered saturated or partially unsaturated monocyclic heterocyclic ring having 1-2 heteroatoms independently selected from nitrogen, oxygen, or sulfur, substituted by 1-3 halogen, —OH, —OCH$_3$, or —OC(CH$_3$)$_3$.

17. The compound of claim 1, wherein $R^2$ is unsubstituted $C_{1-6}$ aliphatic.

18. The compound of claim 1, wherein $R^3$ is hydrogen or an optionally substituted $C_{1-6}$ aliphatic group.

19. The compound of claim 1, wherein $R^3$ is $C_{1-6}$ aliphatic substituted by

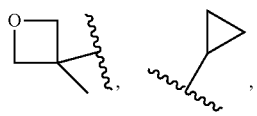

or —OCH$_3$.

20. The compound of claim 1, wherein $R^5$ is hydrogen, —C(O)R, —C(O)OR, or a $C_{1-3}$ aliphatic group.

21. The compound claim 1, wherein $R^5$ is a 3-8 membered saturated or partially unsaturated monocyclic carbocyclic ring.

22. The compound of claim 1, wherein $R^5$ is

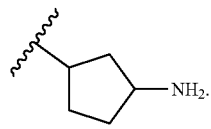 [SMILES: *C1CCC(N)C1]

23. The compound of claim 1, wherein each of $R^6$ is independently halogen, —CN, —NO$_2$, —C(O)R, —C(O)OR, —C(O)NR$_2$, —NR$_2$, —NRC(O)R, —NRC(O)OR, —NRS(O)$_2$R, —OR, —P(O)R$_2$, —SR, —S(O)R, —S(O)$_2$R, —S(O)(NH)R, or R.

24. The compound of claim 1, wherein one or more $R^6$ is —NR$_2$.

25. The compound of claim 1, wherein each R of the —NR$_2$ group is independently optionally substituted $C_{1-6}$ aliphatic.

26. The compound of claim 25, wherein each R of the —NR$_2$ group is independently

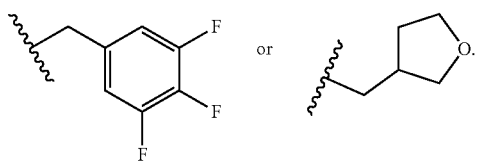 [SMILES: *Cc1cc(F)c(F)c(F)c1 ; *CC1CCOC1]

27. The compound of claim 1, wherein one or more $R^6$ is —C(=NR)—OR.

28. The compound of claim 27, wherein the one or more $R^6$ is —C(=NH)—OC(CH$_3$)$_3$.

29. The compound of claim 1, wherein one or more $R^6$ is —NO$_2$.

30. The compound of claim 1, wherein one or more $R^6$ is $C_{1-6}$ aliphatic substituted by 1-5 halogen or —OH.

31. The compound of claim 1, wherein one or more $R^6$ is —C(O)—R.

32. The compound of claim 31, wherein the one or more $R^6$ is —C(O)—CH$_2$OCH$_2$CF$_3$ or —C(O)—CH$_2$CH$_2$OCH$_2$CF$_3$.

33. The compound of claim 1, wherein X is N.

34. The compound of claim 1, wherein n is 1, 2, 3, 4 or 5.

35. The compound of claim 1, wherein X is N, $R^3$ is methyl, $R^4$ is methyl, and $R^5$ is hydrogen.

36. The compound of claim 1, of one of formula VI-a, VI-b, VI-c, or VI-d:

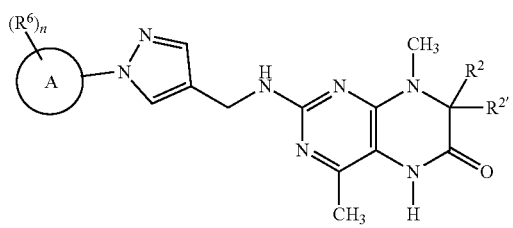

VI-a

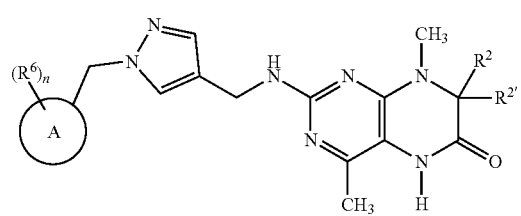

VI-b

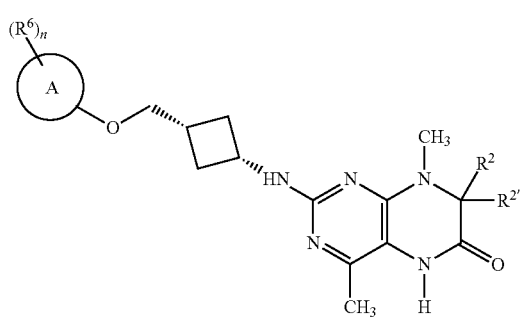

VI-c

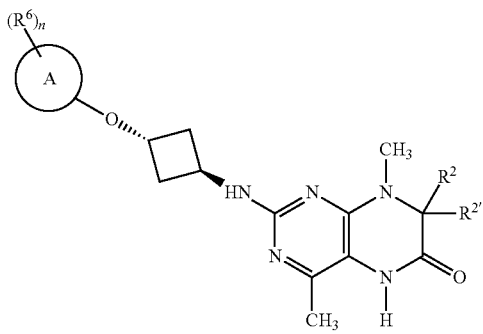

VI-d or a pharmaceutically acceptable salt thereof.

37. The compound of claim 36, wherein:

$R^2$ is unsubstituted $C_{1-6}$ aliphatic, or $R^D$;

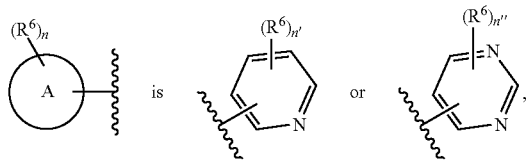

wherein one of $R^6$ is —CF$_3$; n' is 1, 2, 3, or 4; and n" is 1, 2, or 3;

or

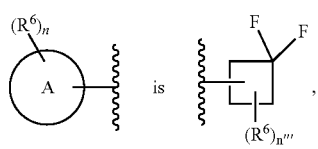

wherein n''' is 0, 1, 2, or 3.

38. The compound of claim 37, wherein $R^2$ is —CH$_3$, —CH$_2$CH$_3$, or —CH(CH$_3$)$_2$, wherein one or more hydrogens are optionally replaced by deuterium.

39. The compound of claim 37, wherein

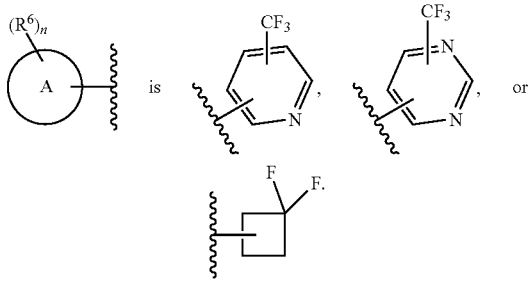

40. A pharmaceutical composition comprising the compound of claim 1, or a pharmaceutically acceptable salt thereof, and a pharmaceutically acceptable carrier, adjuvant, or vehicle.

41. The compound of claim 1, wherein L is:
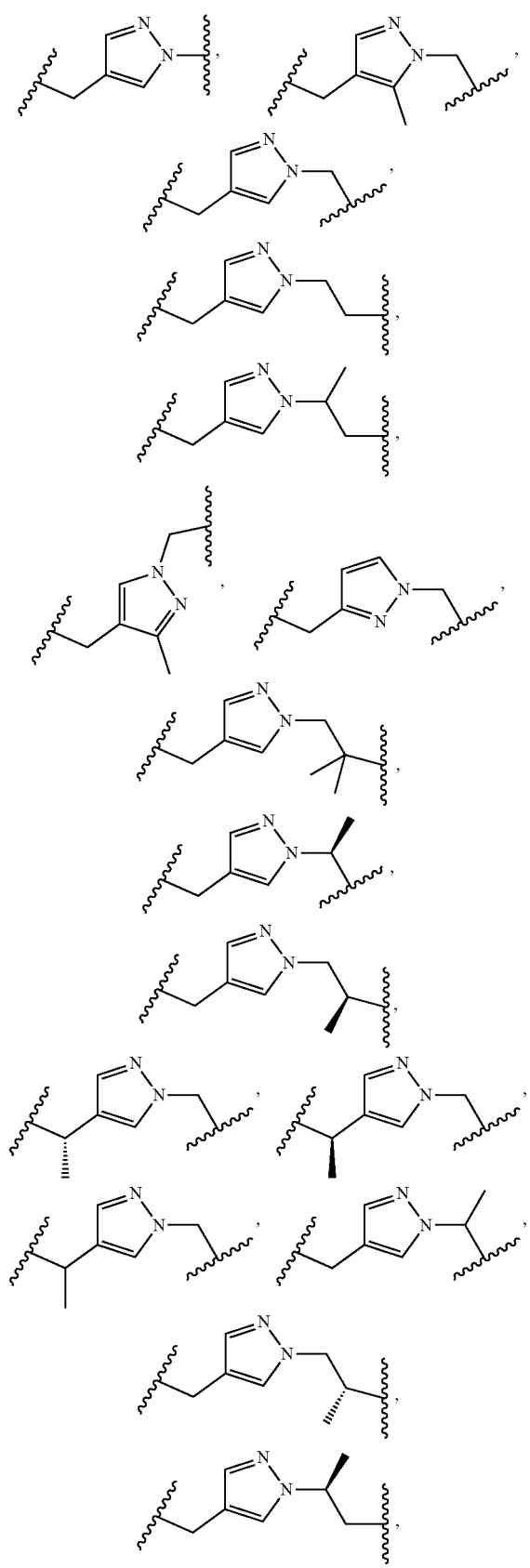
-continued
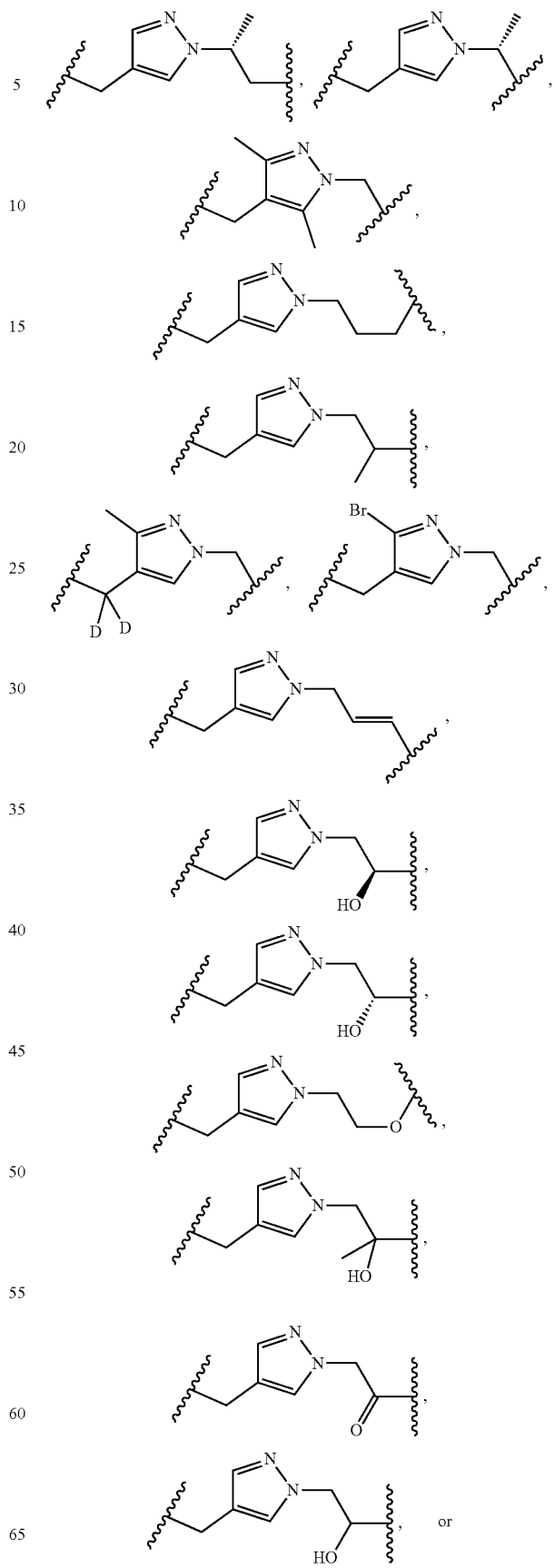
or -continued
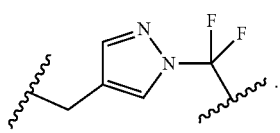
42. The compound of claim 1, wherein L is:
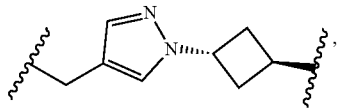
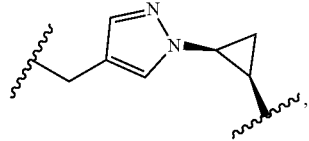
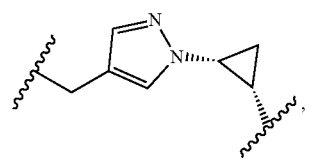
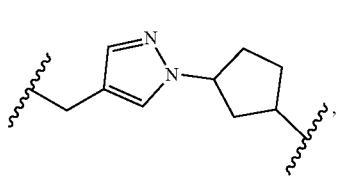
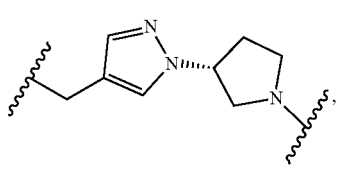
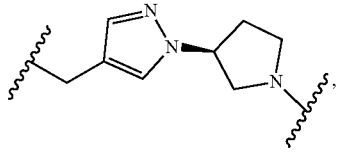
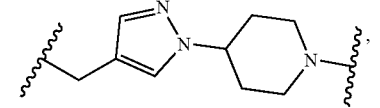
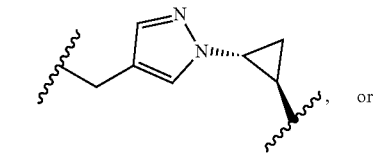
, or
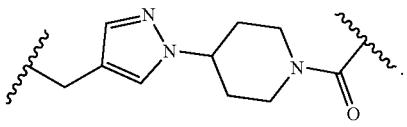
.
43. The compound of claim 1, wherein L is:
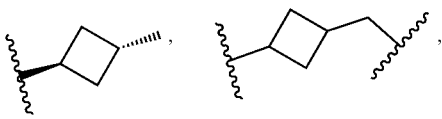
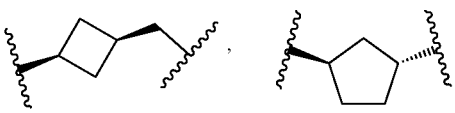
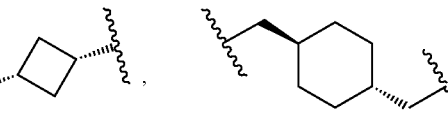
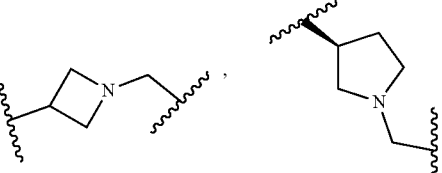
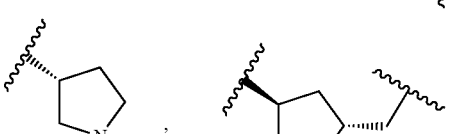
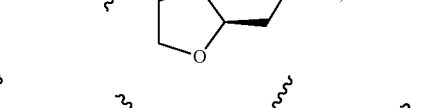
or
.
44. The compound of claim 1, wherein L is:
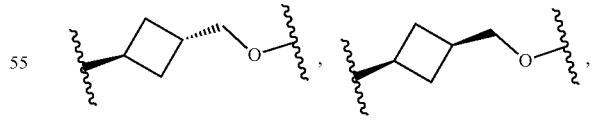
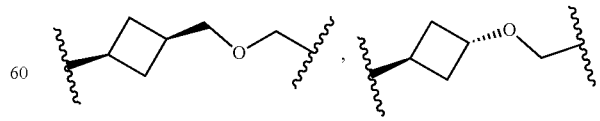
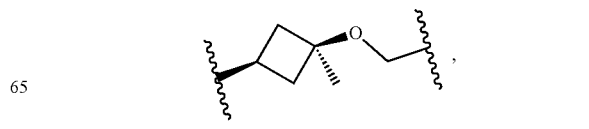

1257
-continued
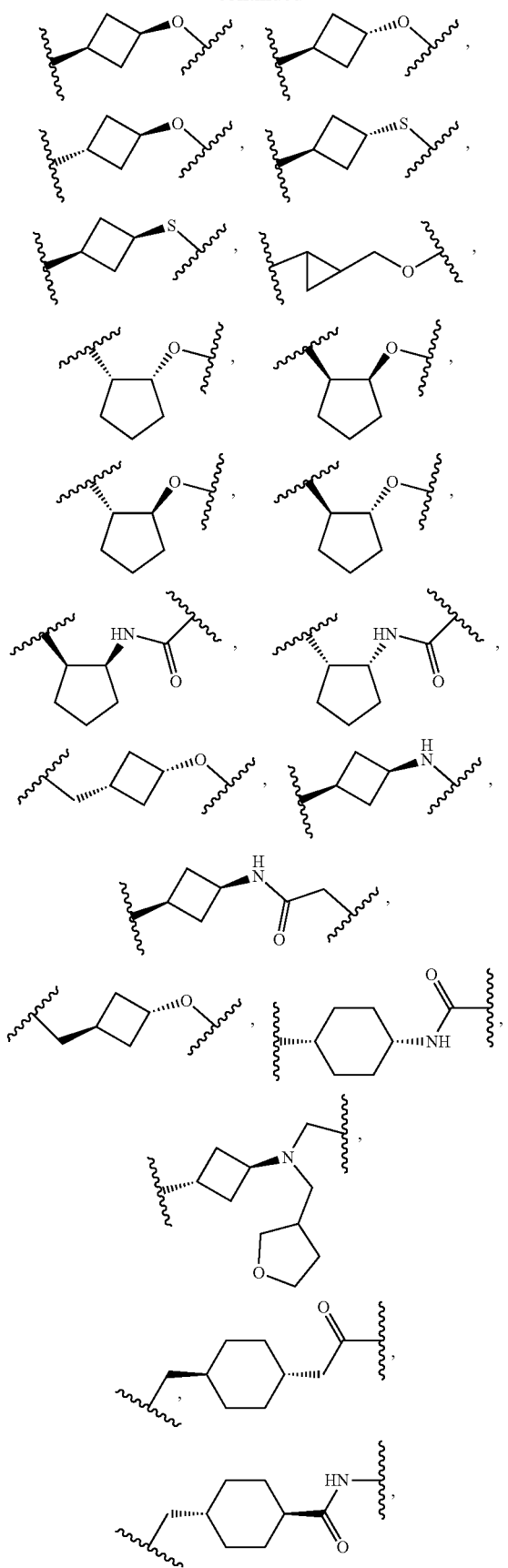
1258
-continued
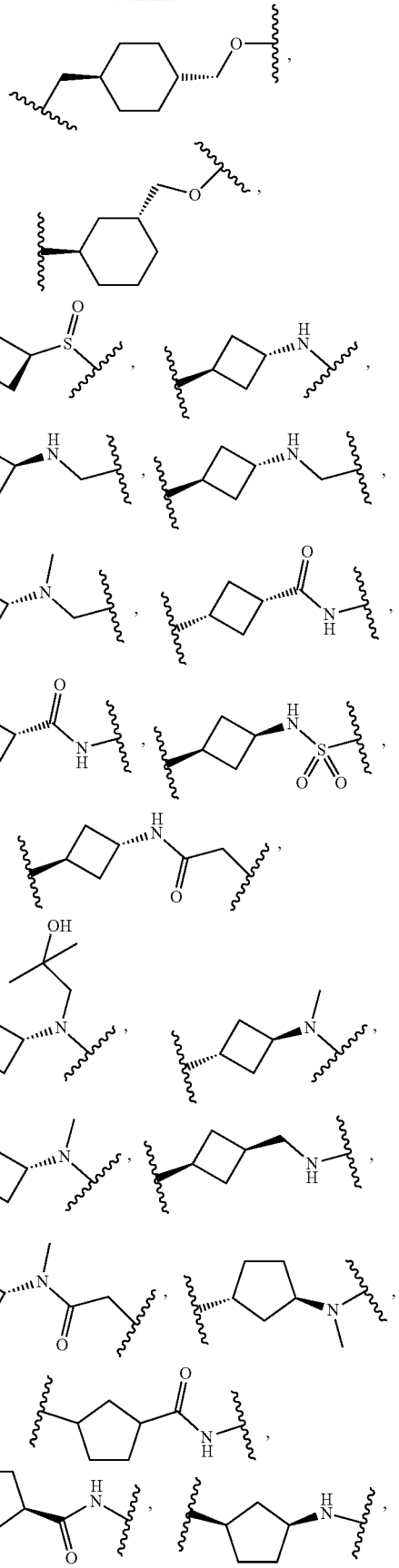

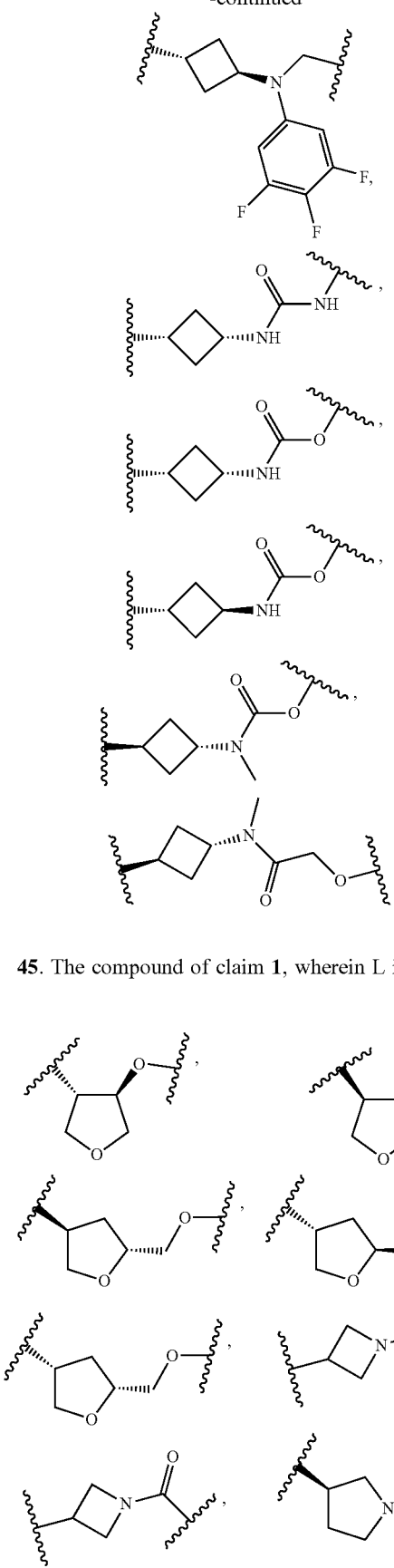
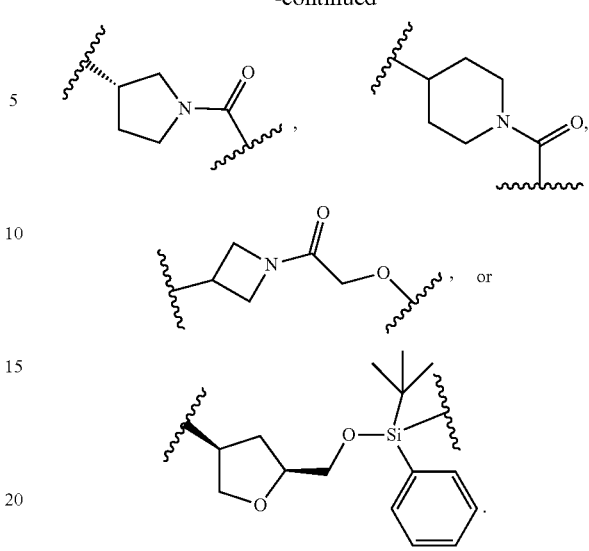
46. The compound of claim 1, wherein L is:
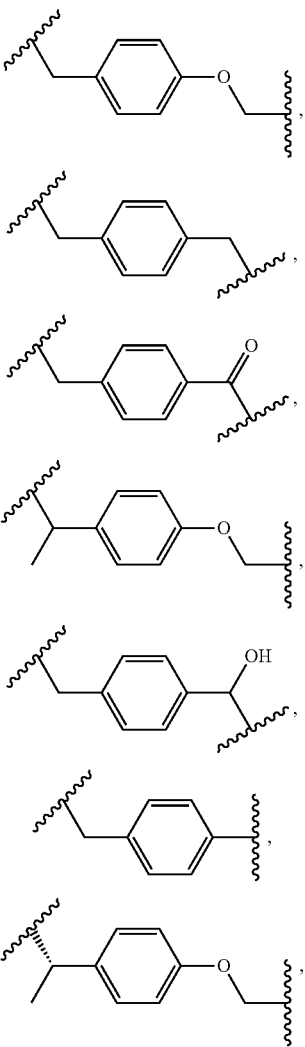
45. The compound of claim 1, wherein L is:

1261
-continued
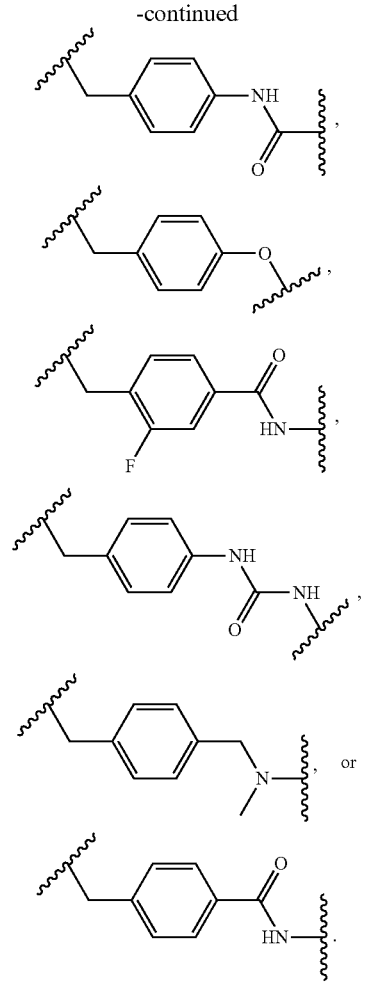
47. The compound of claim 1, wherein L is:
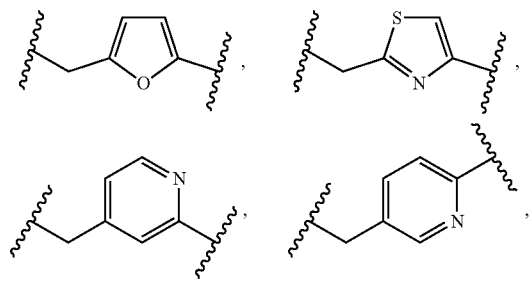
1262
-continued
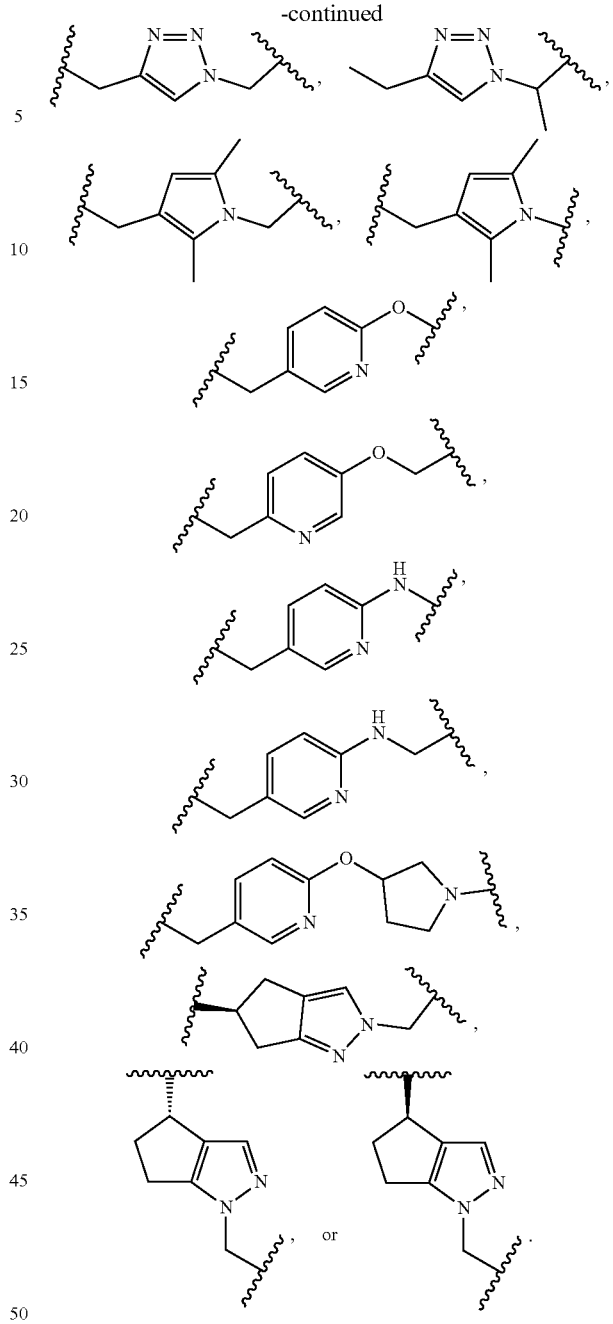
48. The compound of claim 1, wherein $R^4$ is $R^D$.
* * * * *